US012772965B2

(12) United States Patent
Hering et al.

(10) Patent No.: US 12,772,965 B2
(45) Date of Patent: Oct. 27, 2026

(54) GENETICALLY MODIFIED CELLS, TISSUES, AND ORGANS FOR TREATING DISEASE

(71) Applicant: REGENTS OF THE UNIVERSITY OF MINNESOTA, Minneapolis, MN (US)

(72) Inventors: Bernhard J. Hering, Minnetonka, MN (US); Christopher Burlak, Minnetrista, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 1059 days.

(21) Appl. No.: 17/365,643

(22) Filed: Jul. 1, 2021

(65) Prior Publication Data

US 2022/0061279 A1 Mar. 3, 2022

Related U.S. Application Data

(63) Continuation of application No. PCT/US2020/012271, filed on Jan. 3, 2020.

(60) Provisional application No. 62/788,044, filed on Jan. 3, 2019.

(51) Int. Cl.

| | |
|---|---|
| ***A01K 67/0278*** | (2024.01) |
| ***C07K 14/705*** | (2006.01) |
| ***C12N 15/85*** | (2006.01) |
| ***C12N 15/877*** | (2010.01) |

(52) U.S. Cl.

CPC .... *A01K 67/0278* (2013.01); *C07K 14/70539* (2013.01); *C12N 15/8509* (2013.01); *C12N 15/8778* (2013.01); *A01K 2217/072* (2013.01); *A01K 2227/108* (2013.01); *A01K 2267/01* (2013.01); *A01K 2267/025* (2013.01)

(58) Field of Classification Search

CPC .......... A01K 67/0278; C07K 14/70539; C12N 15/8509

See application file for complete search history.

(56) References Cited

U.S. PATENT DOCUMENTS

| | | | |
|---|---|---|---|
| 6,639,122 | B1 | 10/2003 | Tu |
| 7,141,656 | B2 | 11/2006 | Rhode |
| 2002/0198144 | A1 | 12/2002 | Wong |

FOREIGN PATENT DOCUMENTS

| | | | |
|---|---|---|---|
| WO | 9728191 | W | 8/1997 |
| WO | 2016094679 | A1 | 6/2016 |
| WO | 2016210280 | A1 | 12/2016 |

OTHER PUBLICATIONS

Hryhorowicz, et al., Mol Biotechnol (2017) 59: 435-444 (Year: 2017).*

Schnieke et al., Science (1997) 278(5346): 2130-2133 (Year: 1997).*

Cencic, R., "Protospacer adjacent motif (PAM)-distal sequences engage CRISPR Cas9 DNA target cleavage", PLoS One. Oct. 2, 2014;9(10):e109213. doi: 10.1371/journal.pone.0109213.

Huan, J., "Mhc class II derived recombinant T cell receptor ligands protect DBA/1LacJ mice from collagen-induced arthritis" J Immunol. Jan. 15, 2008;180(2):1249-57. doi: 10.4049/jimmunol.180.2.1249.

International Search Report issued Jun. 26, 2020 in PCT/US2020/012271.

Pascolo, S. et al., "HLA-A2.1-restricted education and cytolytic activity of CD8(+) T lymphocytes from beta2 microglobulin (beta2m) HLA-A2.1 monochain transgenic H-2Db beta2m double knockout mice" J Exp Med. Jun. 16, 1997;185(12):2043-51. doi: 10.1084/jem.185.12.2043.

Supplemental European Search Report in EP Application No. 20736106 issued Aug. 25, 2022.

Tai, H. C., et al., "Long-term survival of HLA-DR15+ pig skin in SCID mice after reconstitution with human peripheral blood mononuclear cells and under short-term immunosuppression" Transplant Proc. Mar. 2008;40(2):570-3. doi: 10.1016/j.transproceed.2008.02.006.

Tu, C., et al., "Human leukocyte antigen-DR matching improved skin graft survival from transgenic pigs to accommodate SCID mice reconstituted with human peripheral blood mononuclear cells" Transplant Proc. Mar. 2008;40 (2):578-80. doi: 10.1016/j.transproceed.2007.12.018.

Weiss, E. H., et al., "HLA-E/human beta2-microglobulin transgenic pigs: protection against xenogeneic human anti-pig natural killer cell cytotoxicity" Transplantation. Jan. 15, 2009;87(1):35-43. doi: 10.1097/TP.0b013e318191c784.

Zachary, A. A., et al., "HLA Mismatching Strategies for Solid Organ Transplantation—A Balancing Act" Front Immunol. Dec. 7, 2016;7:575. doi: 10.3389/fimmu.2016.00575.

* cited by examiner

*Primary Examiner* — Evelyn Y Pyla
*Assistant Examiner* — Katherine R Small
(74) *Attorney, Agent, or Firm* — Greenberg Traurig, LLP

(57) ABSTRACT

Genetically modified cells, tissues, and organs for treating or preventing diseases are disclosed. Also disclosed are methods of making the genetically modified cells and non-human animals.

9 Claims, 25 Drawing Sheets

Specification includes a Sequence Listing.

Native HLA-DR3

Beta chain linked peptide

Alpha chain linked peptide

WT

GGTA1 KO

Piglet 114-1 forward sequence (SEQ ID NO: 93)

GCGGCGAGTCATGTTCGACTTCGACGGGGACGAAATCTTTCACGTGGACATGGCCAAAAAGAAACCGTGTGGCGCCTGGAAGAGTTCGGAAGAT
TCGCCTCTTTCGAGGCCCAAGGCGCCCTGGCCAATATCGCTGTGGACAAAGCCAACCTGGAAATCATGACCAAGCGCAGCAACTACACCCCAATCAC
CAACGTGCCACCTGAAGTGACCGTGCTGACAAACAGCCCAGTGGAACTGCGCGAGCCCAACGTGCTGATCTGCTTCATCGACAAGTTCACCCCACC
AGTGGTCAACGTGACCTGGCTGAGAAACGGCAAGCCAGTGACAACCGGCGTGTCCGAGACAGTGTTTCTGCCAAGAGAGGACCACCTGTTCCGCA
AGTTCCACTACCTGCCATTTCTGCCGTCGACTGAGGATGTGTACGACTGCAGAGTCGAGCACTGGGGACTCGACGAGCCACTGCTGAAGCACTGGG
AGTTTGACGCCCCATCTCCACTGCCAGAAACCACCGAGAATGTCGTGTGTGCCCTGGGCCTGACAGTGGGACTCGTGGGAATCATCATCGGCACCAT
CTTCATCATCAAGGGCCTGCGCAAAAGCAACGCCGCTGAAAGAAGAGGCCCACTCTGAACGCGTTCTAGAAATAAAAGATCCTTATTTTCATTGGATC
TGTGTGTTGGTTTTTTGTGTGGCTAACAAGAGGCTGTGCTCTGAGGGCTGCGGCTCCTCTTATAGACTCGAGCTAGGTAAGTGAGCGGGAC

FIG. 15A

Piglet 114-1 reverse sequence (SEQ ID NO: 94)

CCCGACCAAGAGCGGCGAGTTCATGTTCGACTTCGACGGGGACGAAATCTTTCACGTGGACATGGCCAAAAAAGAAACCCGTGTGGCGCTGGAA
GAGTTCGGAAGATTCGCCTCTTTCGAGGCCCAAGGCGCCTGGGCCAATATCGCTGTGGACAAAGCCAACCTGGAAATCATGACCAAGCGGCAGCAA
CTTACACACCCCCCATCACCAACGTGCCACTGAAGTGACCGTGCTGACAAACAGCCCAGTGGAACTGCGCGAGCCCAACGTGCTGATCTGCTTCATC
GACAAGTTCACCCCACCAGTGGTCAACGTGACCTGGCTGAGAAACGGCAAGCCAGTGACAACCGGCGTGTCCGAGACAGTGTTTCTGCCAAGAGA
GGACCACCTGTTCCGCAAGTTCCACTACCTGCCATTTCTGCCGTCGACTGAGGATGTGTACGACTGCAGAGTCGAGCACTGGGGACTCGACGAGCCA
CTGCTGAAGCACTGGGAGTTTGACGCCCCATCTCCACTGCCAGAAACCACCGAGAATGTCGTGTGTGCCCTGGGCCTGACAGTGGGACTCGTGGGA
ATCATCATCGGCACCATCTTCATCATCAAGGGCCTGCGCAAAAGCAACGCCGCTGAAAGAAGAGGCCCACTCTGAACGCGTTCTAGAAATAAAAGAT
CCTTATTTTCATTGGATCTGTGTGTTGGTTTTTTGTGTGGCTAGCAAGAGGCTGTGCTCTGGGGCTCCGGCTCCTCAGAGAGCCTCGGCTAGGTAGG
GGAGCGGGACTCTGGTTTGGGGGAGGGCCGGCGGTTTGGCGGGGGATGGGTGCTTGAGGTGGTCTGACCGGTAGCGGGGGTCGCCTTCCCTAG
CGGGAAGTCGGGAGCATATCGTTTGTTACGCTGGAAGGGGAAGAGGTGGTGAGAGGCAGGCGGGAGTGCGGCCCGCCCTGCGGCAACCGGAGG
GGGAGGGAGAAGGGAGCGGAAAAGCCTGGAATACGGACGGAGCCATTGCTCCCGCAGAGGGAGGAGCGCTTCCTGCTCTTCTCTTGTCACTGATT
GGCCGCTCTCCTCCCGCCGTGT

FIG. 15B

Piglet 114-2 forward sequence (SEQ ID NO: 95)
CCAGGGCGCGAGTCATGTTCGACTTCGACGGGGACGAAATCTTTCACGTGGACATGGCCAAAAAAGAAACCGTGTGGCGCCTGGAAGAGTTCGG
AAGATTCGCCTCTTTCGAGGCCCAAGGCGCCCTGGCCAATATCGCTGTGGACAAAGCCAACCTGGAAATCATGACCAAGCGCAGCAACTACACCCC
AATCACCAACGTGCCACCTGAAGTGACCGTGCTGACAAACAGCCCAGTGGAACTGCGCGAGCCCAACGTGCTGATCTGCTTCATCGACAAGTTCAC
CCCACCAGTGGTCAACGTGACCTGGCTGAGAAACGGCAAGCCAGTGACAACCGGCGTGTCCGAGACAGTGTTTCTGCCAAGAGAGGACCACCTG
TTCCGCAAGTTCCACTACCTGCCATTTCTGCCGTCGACTGAGGATGTGTACGACTGCAGAGTCGAGCACTGGGGACTCGACGAGCCACTGCTGAAG
CACTGGGAGTTTGACGCCCCATCTCCACTGCCAGAAACCACCGAGAATGTCGTGTGTGCCCTGGGCCTGACAGTGGGACTCGTGGGAATCATCATC
GGCACCATCTTCATCATCAAGGGCCTGCGCAAAAGCAACGCCGCTGAAAGAAGAGGCCCACTCTGAACGCGTTCTAGAAATAAAAGATCCTTATTT
TCATTGGATCTGTGTGTTGGTTTTTTTGTGTGGCTAGCAAGAGGCTGTGCTCTGGGGCTCCGGCTCCTCAGAGAGCCTCGGCTAGGTAGGGGGAG
CGGGACTCTGGTTTGGGGGGAGGGCCGGCGGTTTGCGGGGGGATGGGTGCTTTGAGAGGTGGTTCTGACCGGTAGCCGGGGGGTCGCCTTCCC
TAGCGGGAAGTCGGGAGCATATCGTTTGTTACGCTGGAGGGGAAGAGGGTGGGTGGGGAGGCAGGCGGGAGTGCGGCCCGCTCTGCGGCACG
AGGGGAGAGGGGAGAAGGAGCCGAAGCCTG

FIG. 16A

Piglet 114-2 reverse sequence (SEQ ID NO: 96)
CCCGACCAAGAGCGGCGGAGTCATGTCGACTCGACGGGGACGAAATCTTTCACGTGGACATGGCCAAAAAAGAAACCGTGTGGCGCTGGAAGA
GTCGGAAGATTCGCTCTTTCGAGGCCAAGGGCGCCTGGCCAATATCGCTGTGGACAAAGCCCAACCTGGAAATTCATGAACCAGGGGCGAGACAA
TATCACACCCCCACAATCACAACGTGCCACTGAAGTGACCGTGCTGACAAACAGCCCAGTGGAACTGCGCGAGCCCAACGTGCTGATCTGCTTCAT
CGACAAGTTCACCCCACCCAGTGGTCAACGTGACCTGGCTGAGAAACGGCAAGCCAGTGACAACCGGCGTGTCCGAGACAGTGTTTCTGCCAAG
AGAGGACCACCTGTTCCGCAAGTTCCACTACCTGCCATTTCTGCCGTCGACTGAGGATGTGTACGACTGCAGAGTCGAGCACTGGGGACTCGACGA
GCCACTGCTGAAGCACTGGGAGTTTGACGCCCCATCTCCACTGCCAGAAACCACCGAGAATGTCGTGTGTGCCCTGGGCCTGACAGTGGGACTCG
TGGGAATCATCATCGGCACCATCTTCATCATCAAGGGCCTGCGCAAAAGCAACGCCGCTGAAAGAAGAGGCCCACTCTGAACGCGTTCTAGAAATA
AAAGATCCTTATTTTCATTGGATCTGTGTGTTGGTTTTTTGTGTGGCTAGCAAGAGGCTGTGCTCTGGGGCTCCGGCTCCTCAGAGAGCCTCGGCTA
GGTAGGGGAGCGGGACTCTGGTTTGGGGGAGGGCCGGCGGTTTGGCGGGGGATGGGTGCTTGAGGTGGTCTGACCGGTAGCGGGGGTCGCCT
TCCCTAGCGGGAAGTCGGGAGCATATCGTTTGTTACGCTGGAAGGGGAAGAGGTGGTGAGAGGCAGGCGGGAGTGCGGCCCGCCCTGCGGCAA
CCGGAGGGGGAGGGAGAAGGGAGCGGAAAAGCCTGGAATACGGACGGAGCCATTGCTCCCGCAGAGGGAGGAGCGCTTCCTGCTCTTCTCTTG
TCACTGATTGGCCGCTCTCCTCCCGCCGTGTG

FIG. 16B

GENETICALLY MODIFIED CELLS, TISSUES, AND ORGANS FOR TREATING DISEASE

CROSS REFERENCE

This application is a continuation of International Application No. PCT/US2020/012271, filed Jan. 3, 2020, which claims the benefit of U.S. Provisional Patent Application No. 62/788,044, filed Jan. 3, 2019, all of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Jul. 1, 2021, is named 199830722301_SL.txt and is 559,854 bytes in size.

BACKGROUND OF THE DISCLOSURE

There is a shortage of organs, tissues or cells available for transplantation in recipients such as humans. Xenotransplantation or allotransplantation of organs, tissues, or cells into humans has the potential to fulfill this need and help hundreds of thousands of people every year. Non-human animals can be chosen as organ donors based on their anatomical and physiological similarities to humans. Additionally, xenotransplantation has implications not only in humans, but also in veterinary applications. However, unmodified wild-type non-human animal tissues can be rejected by recipients, such as humans, by the immune system. Rejection is believed to be caused at least in part by antibodies binding to the tissues and cell-mediated immunity leading to graft loss. For example, pig grafts can be rejected by cellular mechanisms mediated by adaptive immune cells.

INCORPORATION BY REFERENCE

All publications, patents, and patent applications herein are incorporated by reference to the same extent as if each individual publication, patent, or patent application was specifically and individually indicated to be incorporated by reference. In the event of a conflict between a term herein and a term in an incorporated reference, the term herein controls.

SUMMARY

In one aspect provided herein is a genetically modified animal comprising an exogenous nucleic acid molecule comprising a nucleic acid sequence comprising, a first polynucleotide encoding a β chain of a MHC molecule or a fragment thereof, and/or a second polynucleotide encoding an α chain of the MHC molecule or a fragment thereof.

In some embodiments, the β chain or the fragment thereof and the α chain or the fragment thereof form a peptide binding groove. In some embodiments, the genetically modified animal further comprises a third polynucleotide encoding a peptide derived from the MHC molecule, wherein the peptide is capable of binding the peptide binding groove, to generate a functional MHC-peptide complex. In some embodiments, the (a), (b) or both (a) and (b) lack a functional transmembrane domain. In some embodiments, the nucleic acid sequence comprises from 5'-3', the third polynucleotide, the first polynucleotide, and the second polynucleotide.

In some embodiments, the nucleic acid sequence encodes a single chain MHC chimeric peptide comprising covalently linked in a sequence (a) the peptide derived from the MHC molecule, (b) the β chain of the MHC molecule or fragment thereof, and (c) the α chain of the MHC molecule or fragment thereof, wherein the β chain and the α chain form a peptide binding groove, and wherein the peptide derived from the MHC molecule is capable of binding the peptide binding groove, to generate a functional MHC-peptide complex.

In some embodiments, the genetically modified animal further comprises a regulatory sequence operatively linked to the nucleic acid sequence. In some embodiments, the nucleic acid sequence further comprises in frame a first linker polynucleotide encoding a first linker peptide, wherein the first linker polynucleotide is interposed between the first polynucleotide and the second polynucleotide. In some embodiments, the nucleic acid sequence further comprises in frame a second linker polynucleotide encoding a second linker peptide interposed between the second polynucleotide and the third polynucleotide. In some embodiments, the first linker peptide is cleavable. In some embodiments, the second linker peptide is cleavable. In some embodiments, the first linker peptide is linked between the C-terminus of a β2 domain of the β chain and the N-terminus of an α1 domain of the α chain.

In some embodiments, the second linker peptide is linked between the C-terminus of the peptide derived from the MHC molecule and the N-terminus of the β chain of the MHC molecule or fragment thereof. In some embodiments, the exogenous nucleic acid molecule is inserted into an insertion site into the genetically modified animal's genome. In some embodiments, the insertion site is located in a safe harbor site, a PERV site or a gene encoding a GGTA1, a NOD-like receptor family CARD domain containing 5 (NLRC5), a putative cytidine monophosphatase-N-acetylneuraminic acid hydroxylase-like protein (CMAH), a beta-1,4-N-acetylgalactosaminyltransferase (B4GALNT2), cytidine monophospho-N-acetylneuraminic acid (CMP-N-NeuAc) hydrolase in the genetically modified animal's genome. In some embodiments, the safe harbor site is in ROSA26 gene. In some embodiments, the genetically modified animal further comprises a disruption in one or more genes, wherein the one or more genes encoding a NOD-like receptor family CARD domain containing 5 (NLRC5), a putative cytidine monophosphatase-N-acetylneuraminic acid hydroxylase-like protein (CMAH), a beta-1,4-N-acetylgalactosaminyltransferase (B4GALNT2) or a combination thereof.

In some embodiments, the genetically modified animal further comprises an exogenous polynucleotide, (HLA-E), human leukocyte antigen G (HLA-G), or β-2-microglobulin (B2M). In some embodiments, the genetically modified animal comprises exogenous polynucleotide encoding HLA-G, wherein the HLA-G is HLA-G1, HLA-G2, HLA-G3, HLA-G4, HLA-G5, HLA-G6, or HLA-G7. In some embodiments, the HLA-G is HLA-G1. In some embodiments, the genetically modified animal is a member of the Laurasiatheria superorder. In some embodiments, the genetically modified animal is an ungulate. In some embodiments, the genetically modified animal is a pig. In some embodiments, the genetically modified animal is a non-human primate. In some embodiments, the genetically modified animal is fetus.

In some embodiments, the first linker peptide comprises a sequence set forth in SEQ ID NO 2. In some embodiments, the second linker peptide comprises a sequence set forth in SEQ ID NO 1. In some embodiments, the MHC molecule is MHC class II molecule selected from the group consisting of HLA-DP, HLA-DQ, and HLA-DR. In some embodiments, the MHC class II molecule is HLA-DR and the βchain is HLA-DR1, HLA-DR2, HLA-DR3, HLA-DR4, or HLA-DR5. In some embodiments, the MHC class II molecule is HLA-DR3 and the β chain is encoded by HLA-DRB1*03 or HLA-DRB1*04 allele. In some embodiments, the MHC molecule is HLA-DR and the α chain of the MHC class II molecule is encoded by HLA-DRA010202 allele.

In some embodiments, the peptide derived from a MHC class II molecule comprises a sequence from the β chain of the MHC class II molecule. In some embodiments, the peptide derived from a MHC class II molecule comprises a sequence from a hypervariable region of the β chain of the MHC class II molecule. In some embodiments, the peptide derived from a MHC class II molecule is at least 8 to 30 amino acids in length. In some embodiments, the peptide derived from a MHC class II molecule comprises a sequence selected from Table 1. In some embodiments, the nucleic acid sequence is at least 95% identical to SEQ ID NO 3.

In one aspect provided herein is a population of genetically modified animals comprising two or more animals of any one of aspects above. In some embodiments, at least two or more animals have identical phenotypes. In some embodiments, at least two or more animals have identical genotypes.

Provided herein is a pancreas or pancreatic islet isolated from said genetically modified animal of any one of aspects above.

Provided herein is a genetically modified cell, tissue, or organ isolated from said genetically modified animal of any one of aspects above. In some embodiments, the cell is an islet cell, or a kidney cell. In some embodiments, the cell is a stem cell. In some embodiments, the tissue is a solid organ transplant. In some embodiments, the tissue is all or a portion of a liver. In some embodiments, the tissue is all or a portion of a kidney.

Provided herein is a genetically modified cell, tissue, or organ of any one of aspects above, for use in treating a condition or transplanting to a subject in need thereof to treat a condition in said subject, wherein the subject expresses the MHC molecule, wherein said subject is tolerized to the genetically modified cell, tissue, or organ by use of a vaccine.

Provided herein is a genetically modified cell comprising an exogenous nucleic acid molecule comprising a nucleic acid sequence comprising, a first polynucleotide encoding a β chain of a MHC molecule or a fragment thereof, and/or a second polynucleotide encoding an α chain of the MHC molecule or a fragment thereof. In some embodiments, the β chain or the fragment thereof and the α chain or the fragment thereof form a peptide binding groove. In some embodiments, the genetically modified cell further comprises a third polynucleotide encoding a peptide derived from the MHC molecule, wherein the peptide is capable of binding the peptide binding groove, to generate a functional MHC-peptide complex. In some embodiments, the nucleic acid sequence comprises from 5'-3' the third polynucleotide, the first polynucleotide, and the second polynucleotide. In some embodiments, the nucleic acid sequence encodes a single chain chimeric peptide comprising covalently linked in a sequence (a) the peptide derived from the MHC molecule, (b) the β chain of the MHC molecule or fragment thereof, and (c) the α chain of the MHC molecule or fragment thereof, wherein the β chain and the chain form a peptide binding groove, and wherein the peptide derived from the MHC molecule is capable of binding the peptide binding groove, to generate a functional MHC-peptide complex.

In some embodiments, the genetically modified cell further comprises a regulatory sequence operatively linked to the nucleic acid sequence. In some embodiments, the nucleic acid sequence further comprises in frame a first linker polynucleotide encoding a first linker peptide interposed between the first polynucleotide and the second polynucleotide. In some embodiments, the nucleic acid sequence further comprises in frame a second linker polynucleotide encoding a second linker peptide interposed between the second polynucleotide and the third polynucleotide. In some embodiments, the first linker peptide is linked between the C-terminus of a β2 domain of the β chain and the N-terminus of an α1 domain of the α chain. In some embodiments, the second linker peptide is linked between the C-terminus of the peptide derived from the MHC molecule and the N-terminus of the β chain of the MHC molecule or fragment thereof. In some embodiments, the first linker peptide is cleavable.

In some embodiments, the second linker peptide is cleavable. In some embodiments, the exogenous nucleic acid molecule is inserted into an insertion site into the genetically modified animal's genome. In some embodiments, the insertion site is located in a safe harbor site, a PERV site, or a gene encoding a NOD-like receptor family CARD domain containing 5 (NLRC5), a GGTA1, a putative cytidine monophosphatase-N-acetylneuraminic acid hydroxylase-like protein (CMAH), a beta-1,4-N-acetylgalactosaminyltransferase (B4GALNT2) the genetically modified animal's genome. In some embodiments, the safe harbor site is in ROSA26 gene.

In some embodiments, the genetically modified cell further comprises a disruption in one or more genes, wherein the one or more genes encoding a GGTA1, NOD-like receptor family CARD domain containing 5 (NLRC5), a putative cytidine monophosphatase-N-acetylneuraminic acid hydroxylase-like protein (CMAH), a beta-1,4-N-acetylgalactosaminyltransferase (B4GALNT2) or a combination thereof. In some embodiments, the genetically modified cell further comprises an exogenous polynucleotide, (HLA-E), human leukocyte antigen G (HLA-G), or β-2-microglobulin (B2M). In some embodiments, the genetically modified cell comprising exogenous polynucleotide encoding HLA-G, wherein the HLA-G is HLA-G1, HLA-G2, HLA-G3, HLA-G4, HLA-G5, HLA-G6, or HLA-G7. In some embodiments, the HLA-G is HLA-G1.

In some embodiments, the genetically modified non-human cell is from a member of the Laurasiatheria superorder. In some embodiments, the member of the Laurasiatheria superorder is an ungulate. In some embodiments, the ungulate is a pig. In some embodiments, the genetically modified cell is a pancreatic, kidney, eye, liver, small bowel, lung, or heart cell. In some embodiments, the genetically modified cell is a pancreatic cell. In some embodiments, the pancreatic cell is a pancreatic β cell. In some embodiments, the genetically modified cell is a spleen, liver, peripheral blood, lymph nodes, thymus, or bone marrow cell. In some embodiments, the genetically modified cell is a porcine cell. In some embodiments, the genetically modified cell is from an embryotic tissue, a non-human fetal animal, perinatal non-human animal, neonatal non-human animal, preweaning non-human animal, young adult non-human animal, or adult non-human animal. In some embodiments, the first linker peptide comprises a sequence set forth in SEQ ID NO: 2. In some embodiments, the second linker peptide comprises a sequence set forth in SEQ ID NO: 1.

In some embodiments, the MHC molecule is MHC class II molecule selected from the group consisting of HLA-DP, HLA-DQ, and HLA-DR. In some embodiments, the MHC class II molecule is HLA-DR and the β chain is HLA-DR1, HLA-DR2, HLA-DR3, HLA-DR4, or HLA-DR5. In some embodiments, the MHC class II molecule is HLA-DR3 and the β chain is encoded by HLA-DRB1*03 or HLA-DRB1*04 allele. In some embodiments, the MHC molecule is HLA-DR and the α chain of the MHC class II molecule is encoded by HLA-DRA010202 allele. In some embodiments, the peptide derived from a MHC class II molecule comprises a sequence from the β chain of the MHC class II molecule.

In some embodiments, the peptide derived from a MHC class II molecule comprises a sequence from a hypervariable region of the β chain of the MHC class II molecule. In some embodiments, the peptide derived from a MHC class II molecule is at least 8 to 30 amino acids in length. In some embodiments, the peptide derived from a MHC class II molecule comprises a sequence selected from Table 1. In some embodiments, the nucleic acid sequence is at least 95% identical to SEQ ID NO: 3.

Provided herein is a solid organ transplant comprising the genetically modified cell of any one of aspects above.

Provided herein is an embryo comprising the genetically modified cell of any one of aspects above.

Provided herein is a genetically modified cell of any one of aspects above for use in treating a condition or for use in transplantation in a subject, wherein the subject expresses the MHC molecule.

Provided herein is a tissue or organ comprising said genetically modified cell described above.

Provided herein is a pancreas or pancreatic islet comprising said genetically modified cell of any one of aspects above.

Provided herein is a pharmaceutical composition comprising said genetically modified cell of any one of aspects above, and a pharmaceutically acceptable excipient.

In some embodiments, the pharmaceutical composition is formulated for administration via a subcutaneous, intravenous, intradermal, intraperitoneal, oral, intramuscular, intracerebroventricular, intranasal, intracranial, intracelial, intracerebellar, intrathecal, transdermal, pulmonary, or topical administration route.

In some embodiments, the pharmaceutical composition is formulated for administration via intravenous administration route. In some embodiments, the pharmaceutical composition is contained in a delivery device selected from the group consisting of a syringe, a blunt tip syringe, a catheter, an inhaler, a nebulizer, a nasal spray pump, a nasal irrigation pump or nasal lavage pump, and an implantable pump. In some embodiments, he pharmaceutical composition has a shelf life of at least 2 days, 2 weeks, 1 month to 2 years at room temperature. In some embodiments, the pharmaceutical composition has a shelf life of at least 2 days, 2 weeks, 1 month to 2 years at 4° C.

In one aspect provided herein is a tolerizing regimen for transplantation comprising an effective amount of a composition comprising the genetically modified cell described above. In some embodiments, said genetically modified cell is an apoptotic cell. In some embodiments, said genetically modified cell is a fixed cell. In some embodiments, the tolerizing regimen of any one of aspects above, further comprises a non-fixed cell. In some embodiments, said fixed cell and said non-fixed cell are genetically identical. In some embodiments, said fixed cell is fixed by a chemical and/or said fixed cell induces anergy of immune cells in said subject. In some embodiments, said genetically modified cell is an 1-Ethyl-3-(3-dimethylaminopropyl) carbodiimide (ECDI)-fixed cell.

In one aspect provided herein is as method for treating a condition in a subject in need thereof comprising (a) transplanting to the subject, said genetically modified cell described above, or said cell, tissue or organ described above; and/or (b) administering a tolerizing regimen of aspects above to said subject.

Provided herein is a method for treating a condition in a subject in need thereof comprising, (a) administering a tolerizing regimen of any one of aspects above to said subject, and (b) transplanting a genetically modified cell, tissue, or organ comprising a genetically modified cell of any one of aspects above to said subject. In some embodiments, the subject expresses the MHC molecule. In some embodiments, the method further comprises administering to said subject an effective amount of one or more immunomodulatory molecules. In some embodiments, the one or more immunomodulatory molecules inhibit T cell activation, B cell activation, and/or dendritic cell activation in the subject.

In some embodiments, the one or more immunomodulatory molecules is an anti-CD40 agent, anti-CD40L agent, a B-cell depleting or modulating agent, an mTOR inhibitor, a TNF-alpha inhibitor, a IL-6 inhibitor, a nitrogen mustard alkylating agent, a complement C3 or C5 inhibitor, IFNγ, an NFκB inhibitor, vitamin D3, cobalt protoporphyrin, insulin B9-23, a cluster of differentiation protein, alpha lanti-trypsin inhibitor, dehydroxymethylepoxyquinomycin (DHMEQ), or any combination thereof. In some embodiments, the NF-κB inhibitor is curcumin, triptolide, Bay-117085, or a combination thereof. In some embodiments, the anti-CD40 agent is CD40 siRNA. In some embodiments, the anti-CD40 agent is a CD40 binding peptide inhibitor, anti-CD40 monoclonal antibody, a Fab' anti-CD40 monoclonal antibody fragment, FcR-engineered, Fc silent anti-CD40 monoclonal domain antibody.

In some embodiments, the anti CD40L agent is an anti-CD40 L monoclonal antibody, a Fab' anti-CD40L monoclonal antibody fragment CDP7657, a FcR-engineered, Fc silent anti-CD40L monoclonal domain antibody, a Fab' anti-CD40L antibody, CD-40 binding peptides or an Fc-engineered anti-CD40L antibody. In some embodiments, said tolerizing regimen comprises from or from about 0.001 to 1.0 endotoxin unit per kg bodyweight of said subject. In some embodiments, said tolerizing regimen comprises from or from about 1 to 10 aggregates per μl. In some embodiments, the tolerizing regimen is provided prior to, concurrently with, or after the transplanting. In some embodiments, said tolerizing regimen is administered 7 days before said transplantation and 1 day after said transplantation. In some embodiments, said tolerizing regimen is provided intravenously. In some embodiments, said transplanted cell, tissue, or organ survives for at least 7 days after the transplanting. In some embodiments, said transplanting is xenotransplanting.

In some embodiments, a first dose of the one or more immunomodulatory molecule is administered about 8 days before said transplantation. In some embodiments, said subject is a human subject. In some embodiments, said subject is a non-human animal. In some embodiments, is type 1 diabetes, type 2 diabetes, surgical diabetes, cystic fibrosis-related diabetes, and/or mitochondrial diabetes.

Provided herein is a method for tolerizing a recipient to a graft comprising providing to said recipient said tolerizing regimen of any one of aspects above.

In one aspect provided herein is an isolated nucleic acid molecule comprising a nucleic acid sequence comprising, a first polynucleotide encoding a β chain of a MHC molecule or a fragment thereof, and/or a second polynucleotide encoding an α chain of the MHC molecule or a fragment thereof. In some embodiments, the β chain or the fragment thereof and the α chain or the fragment thereof form a peptide binding groove. In some embodiments, the isolated nucleic acid molecule further comprises a third polynucleotide encoding a peptide derived from the MHC molecule, wherein the peptide is capable of binding the peptide binding groove, to generate a functional MHC-peptide complex. In some embodiments, the (a), (b) or both (a) and (b) lack a functional transmembrane domain. In some embodiments, the nucleic acid sequence comprises from 5'-3', the third polynucleotide, the first polynucleotide, and the second polynucleotide.

In some embodiments, the nucleic acid sequence encodes a single chain chimeric peptide comprising covalently linked in a sequence (a) the peptide derived from the MHC molecule, (b) the β chain of the MHC molecule or fragment thereof, and (c) the α chain of the MHC molecule or fragment thereof, wherein the β chain and the α chain form a peptide binding groove, and wherein the peptide derived from the MHC molecule is capable of binding the peptide binding groove, to generate a functional MHC-peptide complex. In some embodiments, the isolated nucleic acid molecule further comprises a regulatory sequence operatively linked to the nucleic acid sequence.

In some embodiments, the nucleic acid sequence further comprises in frame a first linker polynucleotide encoding a first linker peptide, wherein the first linker polynucleotide is interposed between the first polynucleotide and the second polynucleotide. In some embodiments, the nucleic acid sequence further comprises in frame a second linker polynucleotide encoding a second linker peptide interposed between the second polynucleotide and the third polynucleotide. In some embodiments, the first linker peptide is cleavable. In some embodiments, the second linker peptide is cleavable. In some embodiments, the first linker peptide is linked between the C-terminus of a β2 domain of the β chain and the N-terminus of an α1 domain of the α chain. In some embodiments, the second linker peptide is linked between the C-terminus of the peptide derived from the MHC molecule and the N-terminus of the β chain of the MHC molecule or fragment thereof.

In some embodiments, the first linker peptide comprises a sequence set forth in SEQ ID NO: 2. In some embodiments, the second linker peptide comprises a sequence set forth in SEQ ID NO: 1. In some embodiments, the MHC molecule is MHC class II molecule selected from the group consisting of HLA-DP, HLA-DQ, and HLA-DR. In some embodiments, the MHC class II molecule is HLA-DR and the β chain is HLA-DR1, HLA-DR2, HLA-DR3, HLA-DR4, or HLA-DR5.

In some embodiments, the MHC class II molecule is HLA-DR3 and the β chain is encoded by HLA-DRB1*03 or HLA-DRB1*04 allele. In some embodiments, the MHC molecule is HLA-DR and the α chain of the MHC class II molecule is encoded by HLA-DRA010202 allele. In some embodiments, the peptide derived from a MHC class II molecule comprises a sequence from the β chain of the MHC class II molecule. In some embodiments, the peptide derived from a MHC class II molecule comprises a sequence from a hypervariable region of the β chain of the MHC class II molecule. In some embodiments, the peptide derived from a MHC class II molecule is at least 8 to 30 amino acids in length.

In some embodiments, the peptide derived from a MHC class II molecule comprises a sequence selected from Table 1. In some embodiments, the nucleic acid sequence is at least 95% identical to SEQ ID NO: 3. In some embodiments, the nucleic acid sequence is at least 95% identical to SEQ ID NO: 4. In some embodiments, the isolated nucleic acid molecule further comprises: a first flanking sequence homologous to a first genome sequence upstream of an insertion site, said first flanking sequence located upstream of the nucleic acid sequence; and a second flanking sequence homologous to a second genome sequence downstream of the insertion site, said second flanking sequence located downstream of the nucleic acid sequence.

In some embodiments, said first flanking sequence, said second flanking sequence, or both comprise at least 50 nucleotides.

In some embodiments, said first flanking sequence, said second flanking sequence, or both comprise at least 100 nucleotides. In some embodiments, said first flanking sequence, said second flanking sequence, or both comprise at least 500 nucleotides. In some embodiments, the insertion site is in ROSA26 genomic locus. In some embodiments, the insertion site is in gene encoding for a glycoprotein galactosyltransferase alpha 1,3 (GGTA1), a putative cytidine monophosphate-N-acetylneuraminic acid hydroxylase-like protein (CMAH), a β1,4 N-acetylgalactosaminyltransferase (B4GALNT2), a C-X-C motif chemokine 10 (CXCL10), a MHC class I polypeptide-related sequence A (MICA), a MHC class I polypeptide-related sequence B (MICB), a transporter associated with antigen processing 1 (TAP1), a NOD-like receptor family CARD domain containing 5 (NLRC5). In some embodiments, he first flanking sequence comprises a nucleic acid sequence that is at least 95% identical to SEQ ID NO: 3. In some embodiments, the second flanking sequence comprises a nucleic acid sequence that is at least 95% identical to SEQ ID NO: 4.

Provided herein is a vector comprising the isolated nucleic acid molecule of any one of aspects above.

Provided herein is a host cell comprising the isolated nucleic acid described above; or the vector above.

Provided herein is a kit comprising a first container comprising the isolated nucleic acid molecule of any one of aspects above. In some embodiments, the isolated nucleic acid molecule is in a lyophilized form or a solution form. In some embodiments, the kit further comprises a second container comprising a cell for generating a genetically modified cell. In some embodiments, the kit further comprises, a reconstitution solution, diluent, a culture medium, or a combination thereof. In some embodiments, the kit further comprises instructions of introducing the nucleic acid in the genome of the cell to generate the genetically modified cell.

Provided herein is a kit for transplantation comprising, (a) the genetically modified cell of any one of aspects above, (b) the tolerizing regimen of any one of aspects above, or (c) the cell, tissue or organ of any one of aspects above. In some embodiments, the kit further comprises one or more immunomodulatory agent.

Provided herein is a method for making a genetically modified animal of any one of aspects above, comprising: (a) obtaining a fetal fibroblast cell from an animal comprising, (i) the isolated nucleic acid molecule described above or (ii) a disruption in one or more gene encoding GGTA1, NLRC5, CMAH, or B4GALNT2, b) genetically modifying said fetal fibroblast using CRISPR/Cas by (i) disrupting one or more gene encoding GGTA1, NLRC5, CMAH, or B4GALNT2 in the fetal fibroblast cell comprising the isolated nucleic acid molecule disclosed above, or (ii) inserting the isolated nucleic acid molecule of any one of aspects above in the fetal fibroblast cell comprising the disruption in the gene encoding GGTA1, NLRC5, CMAH, or B4GALNT2, c) transferring a nucleus of the fetal fibroblast cell to an enucleated oocyte of the animal to generate an embryo, and d) transferring the embryo into a surrogate animal of the same species and growing the embryo to the genetically modified animal in the surrogate animal. In some embodiments, the fetal fibroblast cell further comprises an exogenous nucleotide sequence encoding a human β2-microglobulin polypeptide, an exogenous nucleotide sequences encoding a human leukocyte antigen E (HLA-E) polypeptide, or a combination thereof.

Provided herein is a method for making a genetically modified cell, the method comprising genetically modifying a cell to express an exogenous single chain MHC chimeric peptide using CRISPR/Cas. In some embodiments, the genetically modifying comprises inserting the isolated nucleic acid molecule of aspects above in an insertion site into the genome of the cell. In some embodiments, the insertion site is in a safe harbor site. In some embodiments, the safe harbor site is ROSA 26 gene. In some embodiments, the insertion site is a PERV site. In some embodiments, the insertion site is in a gene encoding a glycoprotein galactosyltransferase alpha 1,3 (GGTA1), a putative cytidine monophosphate-N-acetylneuraminic acid hydroxylase-like protein (CMAH), a β1,4 N-acetylgalactosaminyltransferase (B4GALNT2), a C-X-C motif chemokine 10 (CXCL10), a MHC class I polypeptide-related sequence A (MICA), a MHC class I polypeptide-related sequence B (MICB), a transporter associated with antigen processing 1 (TAP1), or a NOD-like receptor family CARD domain containing 5 (NLRC5). In some embodiments, the inserting reduces expression of the gene.

Provided herein is a method for making a genetically modified animal comprising the steps of: (a) inducing a fusion of a genetically modified cell with one or more oocyte, under conditions suitable for forming a reconstructed embryo, wherein the one or more oocytes are zona pellucida free, and enucleated, (b) activating the reconstructed embryo, (c) culturing the activated reconstructed embryo of step (b), until greater than 2-cell developmental stage, and (d) implanting the cultured embryo into a surrogate and growing the embryo to the genetically modified animal in the surrogate. In some embodiments, the method further comprises forming an aggregate of at least two activated reconstructed embryo prior to step (c), wherein the at least two activated reconstructed embryos are genetically identical. In some embodiments, the culturing of step (c) is done until formation of a blastocyst. In some embodiments, the zona pellucida is removed by physical manipulation, chemical treatment and enzymatic digestion. In some embodiments, the enucleation is by physical removal or chemical expulsion.

In some embodiments, the physical removal is by bisection. In some embodiments, the fusion is by chemical fusion, electrofusion or biofusion. In some embodiments, the electrofusion is induced by application of an electrical pulse. In some embodiments, the electrofusion is by chamber fusion or electrode fusion. In some embodiments, the electrofusion comprises the step of delivering one or more electrical pulses to the genetically engineered donor cell together with the one or more oocyte. In some embodiments, the chemical fusion or biofusion is accomplished by exposing the genetically engineered donor cell together with the one or more oocyte to a fusion agent. In some embodiments, the fusion agents are selected from the group consisting of polyethylene glycol (PEG), trypsin, dimethylsulfoxide (DMSO), lectins, agglutinin, viruses, and Sendai virus.

In some embodiments, the activating is by treating with an effective amount of an activating agent. In some embodiments, the activating agent is Thimerosal, dithiothreitol, or a combination thereof. In some embodiments, the genetically modified donor cell is a somatic cell selected from epithelial cells, neural cells, epidermal cells, keratinocytes, hematopoietic cells, melanocytes, chondrocytes, lymphocytes (B and T lymphocytes), erythrocytes, macrophages, monocytes, mononuclear cells, fibroblasts, cardiac muscle cells, and other muscle cells. In some embodiments, the genetically modified cell is a fibroblast cell. In some embodiments, the genetically modified cell is a fetal fibroblast cell. In some embodiments, the genetically modified cell has been modified by insertion, deletion or modification of one or more desired gene.

Provided herein is a method for making a genetically modified animal comprising, (a) inducing a fusion of a genetically modified cell of aspects above with one or more oocyte, under conditions suitable for forming a reconstructed embryo, wherein the one or more oocytes are zona pellucida free, and enucleated and wherein the genetically engineered porcine fetal fibroblast comprises an exogenous nucleic acid molecule expressing MHC molecule, (b) activating the reconstructed embryo, (c) culturing the activated reconstructed embryo of step (b), until greater than 2-cell developmental stage, and (d) implanting the cultured embryo into a surrogate and growing the embryo to the genetically modified animal in the surrogate.

In some embodiments, the method further comprises forming an aggregate of at least two activated reconstructed embryo prior to step (c), wherein the at least two activated reconstructed embryos are genetically identical.

Provided herein is a method for generating a genetically modified embryonic stem cell comprising, (a) inducing a fusion of a genetically modified donor cell with one or more oocyte, under conditions suitable for forming a reconstructed embryo, wherein the one or more oocytes are zona pellucida free, and enucleated, (b) activating the reconstructed embryo, (c) culturing the activated reconstructed embryo of step (b), until formation of a blastocyst, (d) isolating an inner cell mass of the blastocyst, and (e) culturing the inner cell mass to generate the genetically modified embryonic stem cell.

In some embodiments, the method of aspects above, further comprising forming an aggregate of at least two activated reconstructed embryo prior to step (c), wherein the at least two activated reconstructed embryos are genetically identical.

Provided herein is a genetically modified cell comprising an (a) an exogenous nucleic acid sequence encoding a β chain of a MHC molecule; and/or (b) an exogenous nucleic acid sequence encoding an α chain of the MHC molecule. In some embodiments, the β chain, and the α chain form a functional MHC complex, wherein the functional MHC complex comprises a peptide binding groove.

In some embodiments, the genetically modified cell further comprises an exogenous nucleic acid sequence encoding a peptide derived from a MHC molecule, wherein the peptide derived from a MHC molecule is capable of binding the peptide binding groove, thereby forming a functional peptide-MHC complex.

Provided herein is a genetically modified animal that is a member of the Laurasiatheria superorder or is a non-human primate comprising: (a) an exogenous nucleic acid sequence encoding a β chain of a MHC molecule; and/or (b) an exogenous nucleic acid sequence encoding an α chain of the MHC molecule.

In some embodiments, the β chain, and the α chain form a functional MHC complex, wherein the functional MHC complex comprises a peptide binding groove.

In some embodiments, the genetically modified cell further comprises an exogenous nucleic acid sequence encoding a peptide derived from a MHC molecule, wherein the peptide derived from a MHC molecule is capable of binding the peptide binding groove, thereby forming a functional peptide-MHC complex.

Provided herein is a single chain MHC (scMHC) chimeric peptide comprising, (a) a peptide derived from a MHC molecule, (b) a β chain of the MHC molecule or fragment thereof, and (c) an αchain of the MHC molecule or fragment thereof; wherein the β chain and the α chain form a peptide binding groove, and wherein the peptide derived from the MHC molecule is capable of binding the peptide binding groove, to generate a functional MHC-peptide complex. In some embodiments, (b), (c) or both (b) and (c) lack a functional transmembrane domain. In some embodiments, the scMHC chimeric peptide further comprises a first linker peptide, wherein the first linker peptide is linked between the C-terminus of a α2 domain of the β chain and the N-terminus of an α1 domain of the α chain.

In some embodiments, the scMHC chimeric peptide further comprises a second linker peptide wherein the second linker peptide is linked between the C-terminus of (a) and N-terminus of (b). In some embodiments, the first linker peptide comprises a sequence set forth in SEQ ID NO 2. In some embodiments, the second linker peptide comprises a sequence set forth in SEQ ID NO 1. In some embodiments, the MHC molecule is MHC class II molecule selected from the group consisting of HLA-DP, HLA-DQ, and HLA-DR. In some embodiments, the MHC class II molecule is HLA-DR and the β chain is HLA-DR1, HLA-DR2, HLA-DR3, HLA-DR4, or HLA-DR5. In some embodiments, the MHC class II molecule is HLA-DR3 and the β chain is encoded by HLA-DRB1*03 or HLA-DRB1*04 allele.

In some embodiments, the MHC molecule is HLA-DR and the α chain of the MHC class II molecule is encoded by HLA-DRA010202 allele. In some embodiments, the peptide derived from a MHC class II molecule comprises a sequence from the β chain of the MHC class II molecule. In some embodiments, the peptide derived from a MHC class II molecule comprises a sequence from a hypervariable region of the β chain of the MHC class II molecule. In some embodiments, the peptide derived from a MHC class II molecule is at least 8 to 30 amino acids in length. In some embodiments, the peptide derived from a MHC class II molecule comprises a sequence selected from Table 1. In some embodiments, the scMHC chimeric peptide is recombinant. In some embodiments, the scMHC chimeric peptide is soluble.

Provided herein is a method of making a genetically modified animal, comprising, (a) obtaining a fetal fibroblast cell from an animal comprising; (i) the isolated nucleic acid molecule of aspects above, b) transferring a nucleus of the fetal fibroblast cell to an enucleated oocyte of the animal to generate an embryo, and c) transferring the embryo into a surrogate animal of the same species and growing the embryo to the genetically modified animal in the surrogate animal.

Provided herein is a method of making a genetically modified cell, comprising, (a) obtaining a fetal fibroblast cell from an animal, b) genetically modifying said fetal fibroblast using CRISPR/Cas by inserting the isolated nucleic acid molecule of aspects above in the fetal fibroblast cell, c) transferring a nucleus of the fetal fibroblast cell to an enucleated oocyte of the animal to generate an embryo, and d) transferring the embryo into a surrogate animal of the same species and growing the embryo to the genetically modified animal in the surrogate animal.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A shows expression of the native form of the alpha and beta chain assembled to form the HLA-DR molecule comprising a peptide binding region or peptide binding groove. FIG. 2B shows expression of the alpha and beta chain, where both the alpha and beta chain comprise a functional transmembrane region. The beta chain of the HLA-DR molecule has a peptide (tolerogenic peptide) linked to the N terminus via a flexible linker allowing it to assemble in the peptide binding region formed by the alpha and beta chain. FIG. 2C illustrates expression of the alpha and beta chain, where both the alpha and beta chains comprise a transmembrane region. The alpha chain of the HLA-DR molecule has a peptide linked to the N terminus via a flexible linker allowing it to assemble in the peptide binding region. FIG. 2D shows beta chain scHLA-DR molecule. The molecule shows expression of the alpha and beta chain where the alpha chain lacks a transmembrane region and the beta chain comprise a transmembrane region. The C-terminus of alpha chain is linked to the N-terminus of beta chain with a flexible linker, and the alpha and the beta chain assemble to form a peptide binding region. FIG. 2E shows alpha chain scHLA-DR molecule. The molecule shows expression of the alpha chain and the beta chain, where the alpha chain comprise a transmembrane region and the beta chain lacks a transmembrane region. The N-terminus of alpha chain is linked to the C-terminus of the beta chain with a flexible linker, and the alpha and the beta chain assemble to form a peptide binding region. FIG. 2F shows expression of the beta chain scHLA-DR with an N-terminal flexible linker and peptide. The molecule shows expression of the alpha and beta chain where the alpha chain lacks a transmembrane region and the beta chain comprises a transmembrane region. The C-terminus of alpha chain is linked to the N-terminus of beta chain with a flexible linker, and the alpha and the beta chain assemble to form a peptide binding region. The alpha chain of the HLA-DR molecule has a peptide linked to the N terminus via a flexible linker allowing it to assemble in the peptide binding region. FIG. 2G shows expression of the alpha chain scHLA-DR with an N-terminal flexible linker and peptide. The molecule shows expression of the alpha chain and the beta chain, where the alpha chain comprise a transmembrane region and the beta chain lacks a transmembrane region. The N-terminus of alpha chain is linked to the C-terminus of the beta chain with a flexible linker, and the alpha and the beta chain assemble to form a peptide binding region. The beta chain of the HLA-DR molecule has a peptide (tolerogenic peptide) linked to the N terminus via a flexible linker allowing it to assemble in the peptide binding region formed by the alpha and beta chain. The peptides (tolerogenic peptides or cognate peptide) can be derived from MHC class I or the MHC class II DR molecule (i.e. from the polypeptide encoding the beta chain or the alpha chain). The flexible linker can be continuous or have a thrombin or thrombin-like cleavage domain to allow cleavage of the peptide. One or more peptides can be linked each with the aforementioned cleavage domains such that the expression of one or more versions of FIG. 2A, FIG. 2D, or FIG. 2E, along with the co-expression of version illustrated in FIG. 2B, FIG. 2C, FIG. 2F, or FIG. 2G can be done. The various version of HLA-DR molecule can include a single or multiple peptide expression construct where cleavage domains allow the release of peptides individually. The result being the purposeful loading of a unique peptide derived from one expression construct where it is cleaved and released to be bound by a neighboring construct.

FIG. 6A shows immunofluorescence staining of stem-like cell markers in ICM colonies derived from bi-oocyte fusion cloned embryos: Expressions of pluripotency markers (Nanog, Oct4) are shown in green at passage 5. Scale bars=20x. FIG. 6B shows real time RT-PCR analysis of stem cell markers Oct4, Sox2 and Nanog gene after 5 culture passages.

FIG. 8A shows FACS analysis on CRISPR/Cas9 sgRNA for GGTA1 transfected and wild type non transfected cells. FIG. 8B shows PCR amplification of sorted GGTA1 KO cells (Lane 1) and WT fetal fibroblast cells (Lane 2). PCR product (586 bp). FIG. 8C shows Sanger sequencing depicts GGTA1 sgRNA cut site and single nucleotide deletion in GGTA1 KO cells for comparison of sequence alignment with WT genomic DNA. FIG. 8D shows TIDE analysis for major induced mutations in the projected editing site frequency in a single cell population of GGTA1 KO fetal fibroblast cells in comparison to WT cells.

FIG. 9A shows immunofluorescence analysis of GGTA1 KO in comparison with WT cells. WT Cells and GGTA1 KO cells are stained with DAPI and AF647 conjugated labelling for IB4 lectin staining. GGTA1 KO cells. Magnification 20×. FIG. 9B shows Karyotype analysis of wild type fetal cells and FIG. 9C shows Karyotype analysis of GGTA1 KO fetal cells.

FIG. 10A shows differential staining of GGTA1 KO blastocyst produced by BOF cloning. Blue color (Hoechst 33342) and pink color (propidium iodide) indicate ICM and TE cells, respectively. Magnification 20×. FIG. 10B shows relative gene expression for Klf4, Oct4, Nanog, Igf2, Dnmt1, Bax, Bcl-xl and ASF1 genes in GGTA1 KO blastocysts compared to WT blastocysts. All genes were normalized with the ACTB gene. All values indicate non-significant difference within each gene expression, significance calculated at ($p<0.05$).

FIG. 12A shows threshold and scatter control in the top panel and genetically modified cells with positive staining with PE anti-human HLA-DR Antibody L243 (1:100) in the bottom panel. FIG. 12B shows cytometry sorting of genetically modified porcine fibroblast cells expressing chimeric HLA-DR molecule in a population of porcine fibroblast cells transfected with a plasmid construct expressing HLA-DR transgene.

FIG. 13A shows DAPI staining on HLA-DR transfected cells. FIG. 13B shows fluorescence image showing presence of transgenic HLA-DR3 on transfected fetal cells and stained for PE anti-human HLA-DR Antibody. FIG. 13C shows merged image of DAPI and HLA-DR staining. FIG. 13D shows DAPI staining on non-transfected fetal cells. FIG. 13E shows absence of HLA-DR3 expression when non transfected cells are stained for PE anti-human HLA-DR Antibody. FIG. 13F shows merged image of both DAPI and PE anti-human HLA-DR Antibody staining. Magnification 40×

FIGS. 15A-15B show sanger sequencing results of DNA isolated from a genetically modified pig (piglet 114-1) subjected to PCR amplification of the HLA-DR transgene. FIG. 15A shows the forward sequence obtained by sanger sequencing of the amplicon using the forward primer. FIG.

15B shows the reverse sequence obtained by sanger sequencing of the amplicon using the reverse primer.

FIGS. 16A-16B shows sanger sequencing results of DNA isolated from a genetically modified pig (piglet 114-2) subjected to PCR amplification of the HLA-DR transgene. FIG. 16A shows the forward sequence obtained by sanger sequencing of the amplicon using the forward primer. FIG. 16B shows the reverse sequence obtained by sanger sequencing of the amplicon using the reverse primer.

Figure 17:
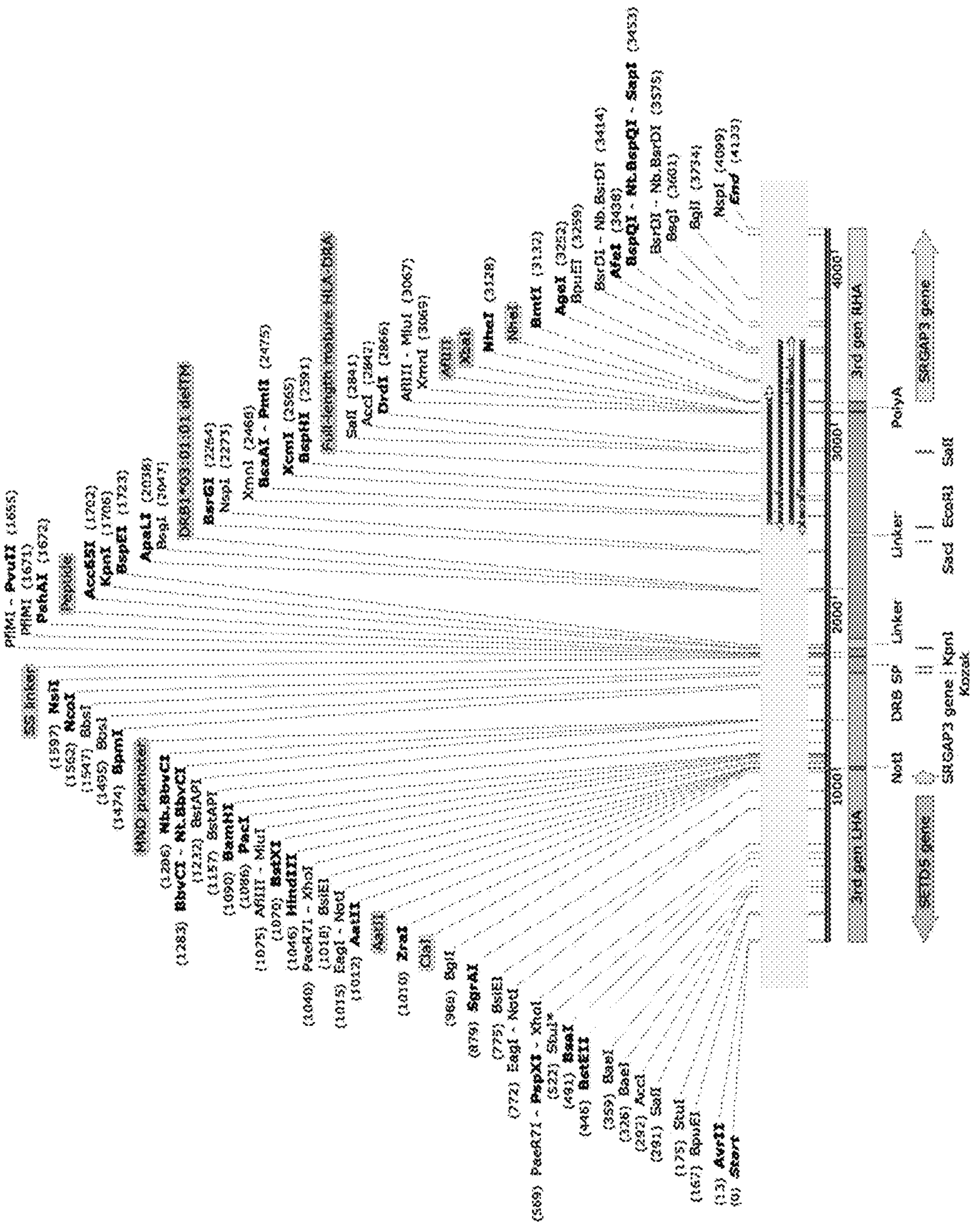

FIG. 17 shows alignment of HLA-DR transgene sequences obtained from genetically modified pig (piglet 114-1 and piglet 114-2) with the HLA-DR transgene sequence in the plasmid construct encoding single chain HLA-DR chimeric peptide.

DETAILED DESCRIPTION OF THE DISCLOSURE

The following description and examples illustrate embodiments of the invention in detail. It is to be understood that this invention is not limited to the particular embodiments described herein and as such can vary. Those of skill in the art will recognize that there are numerous variations and modifications of this invention, which are encompassed within its scope.

Graft rejection can be prevented by methods tempering the immune response, including those described herein. For example, one method described herein to prevent transplantation rejection or prolong the time to transplantation rejection without or with minimal immunosuppressive drug use, an animal, e.g., a donor non-human animal, could be altered, e.g., genetically. Subsequently, the cells, organs, and/or tissues of the altered animal, e.g., a donor non-human animal, can be harvested and used in allografts or xenografts. Alternatively, cells can be extracted from an animal, e.g., a human or non-human animal (including but not limited to primary cells) or cells can be previously extracted animal cells, e.g., cell lines. These cells can be used to create a genetically altered cell.

Transplant rejection (e.g., T cells-mediated transplant rejection) can be prevented by chronic immunosuppression. However, immunosuppression is costly and associated with the risk of serious side effects. To circumvent the need for chronic immunosuppression, a multifaceted, T cell-targeted rejection prophylaxis was developed (FIG. 1) that

- i) utilizes genetically modified grafts lacking functional expression of MHC class I, thereby interfering with activation of $CD8^+$ T cells with direct specificity and precluding cytolytic effector functions of these $CD8^+$ T cells,
- ii) interferes with B cell (and other APC)-mediated priming and memory generation of anti-donor T cells using induction immunotherapy comprising antagonistic anti-CD40 mAbs (and depleting anti-CD20 mAbs and a mTOR inhibitor), and/or
- iii) depletes anti-donor T cells with indirect specificity via peritransplant infusions of apoptotic donor cell vaccines.

Described herein are genetically modified non-human animals (such as non-human primates or a genetically modified animal that is member of the Laurasiatheria superorder, e.g., ungulates) and organs, tissues, or cells isolated therefrom, tolerizing vaccines, and methods for treating or preventing a disease in a recipient in need thereof by transplantation of an organ, tissue, or cell isolated from a non-human animal. An organ, tissue, or cell isolated from a non-human animal (such as non-human primates or a genetically modified animal that is member of the Laurasiatheria superorder, e.g., ungulates) can be transplanted into a recipient in need thereof from the same species (an allotransplant) or a different species (a xenotransplant). A recipient can be tolerized with a tolerizing vaccine and/or one or more immunomodulatory agents (e.g., an antibody). In embodiments involving xenotransplantation the recipient can be a human. Suitable diseases that can be treated are any in which an organ, tissue, or cell of a recipient is defective or injured, (e.g., a heart, lung, liver, vein, skin, or pancreatic islet cell) and a recipient can be treated by transplantation of an organ, tissue, or cell isolated from a non-human animal.

In one aspect, disclosed herein are genetically modified non-human animals and cells comprising an exogenous nucleic acid sequence encoding for a MHC molecule. In some embodiments, the MHC molecule is a MHC class I molecule. In some embodiments, the MHC molecule is a MHC class II molecule. In some embodiments, the MHC molecule is HLA-DR. For example, the genetically modified cells, or genetically modified non-human animal, and the cells, tissues and organs derived therefrom comprises a transgene comprising a nucleic acid sequence encoding a MHC molecule (e.g., single chain chimeric MHC molecule), a α chain of a MHC molecule or a fragment thereof, or a β chain of a MHC molecule or a fragment thereof, or a peptide derived from a MHC molecule. In some embodiments, the transgene can further comprise a polynucleotide encoding a peptide derived from a MHC molecule capable of binding the peptide binding groove for presentation to a T cell. In some embodiments, the genetically modified non-human animals and cells can further comprise one or more additional genetic modifications, such as any of the genetic modifications (e.g., knock-ins, knock-outs, gene disruptions, etc.) disclosed herein. For example, in some embodiments, the genetically modified cells, or genetically modified non-human animal, and the cells, tissues and organs derived therefrom can further comprise one or more transgenes encoding ICP47, CD46, CD55, CD59, HLA-E, HLA-G (e.g., HLA-G1, HLA-G2, HLA-G3, HLA-G4, HLA-G5, HLA-G6, or HLA-G7), B2M, any functional fragments thereof, and/or any combination thereof.

Definitions

The term "about" in relation to a reference numerical value and its grammatical equivalents as used herein can include the numerical value itself and a range of values plus or minus 10% from that numerical value. For example, the amount "about 10" includes 10 and any amounts from 9 to 11. For example, the term "about" in relation to a reference numerical value can also include a range of values plus or minus 10%, 9%, 8%, 7%, 6%, 5%, 4%, 3%, 2%, or 1% from that value.

The term "non-human animal" and its grammatical equivalents as used herein includes all animal species other than humans, including non-human mammals, which can be a native animal or a genetically modified non-human animal. A non-human mammal includes, an ungulate, such as an even-toed ungulate (e.g., pigs, peccaries, hippopotamuses, camels, llamas, chevrotains (mouse deer), deer, giraffes, pronghorn, antelopes, goat-antelopes (which include sheep, goats and others), or cattle) or an odd-toed ungulate (e.g., horse, tapirs, and rhinoceroses), a non-human primate (e.g., a monkey, or a chimpanzee), a Canidae (e.g., a dog) or a cat. A non-human animal can be a member of the Laurasiatheria superorder. The Laurasiatheria superorder can include a group of mammals as described in Waddell et al., *Towards*

*Resolving the Interordinal Relationships of Placental Mammals*. Systematic Biology 48 (1): 1-5 (1999). Members of the Laurasiatheria superorder can include Eulipotyphla (hedgehogs, shrews, and moles), Perissodactyla (rhinoceroses, horses, and tapirs), Carnivora (carnivores), Cetartiodactyla (artiodactyls and cetaceans), Chiroptera (bats), and Pholidota (pangolins). A member of Laurasiatheria superorder can be an ungulate described herein, e.g., an odd-toed ungulate or even-toed ungulate. An ungulate can be a pig. A member can be a member of Carnivora, such as a cat, or a dog. In some cases, a member of the Laurasiatheria superorder can be a pig.

The term "pig" and its grammatical equivalents as used herein can refer to an animal in the genus *Sus*, within the Suidae family of even-toed ungulates. For example, a pig can be a wild pig, a domestic pig, mini pigs, a *Sus scrofa* pig, a *Sus scrofa domesticus* pig, or inbred pigs.

The term "transgene" and its grammatical equivalents as used herein can refer to a gene or genetic material that can be transferred into an organism. For example, a transgene can be a stretch or segment of DNA containing a gene that is introduced into an organism. The gene or genetic material can be from a different species. The gene or genetic material can be synthetic. When a transgene is transferred into an organism, the organism can then be referred to as a transgenic organism. A transgene can retain its ability to produce RNA or polypeptides (e.g., proteins) in a transgenic organism. A transgene can comprise a polynucleotide encoding a protein or a fragment (e.g., a functional fragment) thereof. The polynucleotide of a transgene can be an exogenous polynucleotide. A fragment (e.g., a functional fragment) of a protein can comprise at least or at least about 5%, 10%, 20%, 30%, 40%, 50%, 60%, 70%, 80%, 90%, 95%, or 99% of the amino acid sequence of the protein. A fragment of a protein can be a functional fragment of the protein. A functional fragment of a protein can retain part or all of the function of the protein.

The term "exogenous nucleic acid sequence" can refer to a gene or genetic material that was transferred into a cell or animal that originated outside of the cell or animal. An exogenous nucleic acid sequence can by synthetically produced. An exogenous nucleic acid sequence can be from a different species, or a different member of the same species. An exogenous nucleic acid sequence can be another copy of an endogenous nucleic acid sequence.

The term "genetic modification" and its grammatical equivalents as used herein can refer to one or more alterations of a nucleic acid, e.g., the nucleic acid within an organism's genome. For example, genetic modification can refer to alterations, additions, and/or deletion of genes. A genetically modified cell can also refer to a cell with an added, deleted and/or altered gene. A genetically modified cell can be from a genetically modified non-human animal. A genetically modified cell from a genetically modified non-human animal can be a cell isolated from such genetically modified non-human animal. A genetically modified cell from a genetically modified non-human animal can be a cell originated from such genetically modified non-human animal.

The term "gene knock-out" or "knock-out" can refer to any genetic modification that reduces the expression of the gene being "knocked out." Reduced expression can include no expression. The genetic modification can include a genomic disruption.

The term "islet" or "islet cells" and their grammatical equivalents as used herein can refer to endocrine (e.g., hormone-producing) cells present in the pancreas of an organism. For example, islet cells can comprise different types of cells, including, but not limited to, pancreatic α cells, pancreatic β cells, pancreatic δ cells, pancreatic F cells, and/or pancreatic ε cells. Islet cells can also refer to a group of cells, cell clusters, or the like.

The term "condition" condition and its grammatical equivalents as used herein can refer to a disease, event, or change in health status.

The term "diabetes" and its grammatical equivalents as used herein can refer to is a disease characterized by high blood sugar levels over a prolonged period. For example, the term "diabetes" and its grammatical equivalents as used herein can refer to all or any type of diabetes, including, but not limited to, type 1, type 2, cystic fibrosis-related, surgical, gestational diabetes, and mitochondrial diabetes. In some cases, diabetes can be a form of hereditary diabetes.

The term "phenotype" and its grammatical equivalents as used herein can refer to a composite of an organism's observable characteristics or traits, such as its morphology, development, biochemical or physiological properties, phenology, behavior, and products of behavior. Depending on the context, the term "phenotype" can sometimes refer to a composite of a population's observable characteristics or traits.

The term "disrupting" and its grammatical equivalents as used herein can refer to a process of altering a gene, e.g., by deletion, insertion, mutation, rearrangement, or any combination thereof. For example, a gene can be disrupted by knockout. Disrupting a gene can be partially reducing or completely suppressing expression (e.g., mRNA and/or protein expression) of the gene. Disrupting can also include inhibitory technology, such as shRNA, siRNA, microRNA, dominant negative, or any other means to inhibit functionality or expression of a gene or protein.

The term "gene editing" and its grammatical equivalents as used herein can refer to genetic engineering in which one or more nucleotides are inserted, replaced, or removed from a genome. For example, gene editing can be performed using a nuclease (e.g., a natural-existing nuclease or an artificially engineered nuclease).

The term "transplant rejection" and its grammatical equivalents as used herein can refer to a process or processes by which an immune response of an organ transplant recipient mounts a reaction against the transplanted material (e.g., cells, tissues, and/or organs) sufficient to impair or destroy the function of the transplanted material.

The term "hyperacute rejection" and its grammatical equivalents as used herein can refer to rejection of a transplanted material or tissue occurring or beginning within the first 24 hours after transplantation. For example, hyperacute rejection can encompass but is not limited to "acute humoral rejection" and "antibody-mediated rejection".

The term "negative vaccine", "tolerizing vaccine" and their grammatical equivalents as used herein, can be used interchangeably. A tolerizing vaccine can tolerize a recipient to a graft or contribute to tolerization of the recipient to the graft if used under the cover of appropriate immunotherapy. This can help to prevent transplantation rejection.

The term "recipient", "subject" and their grammatical equivalents as used herein, can be used interchangeably. A recipient or a subject can be a human or non-human animal. A recipient or a subject can be a human or non-human animal that will receive, is receiving, or has received a transplant graft, a tolerizing vaccine, and/or other composition disclosed in the application. A recipient or subject can also be in need of a transplant graft, a tolerizing vaccine and/or other composition disclosed in the application. In some cases, a recipient can be a human or non-human animal that will receive, is receiving, or has received a transplant graft.

The phrases “translationally fused” and “in frame” are interchangeably used herein to refer to polynucleotides which are covalently linked to form a single continuous open reading frame spanning the length of the coding sequences of the linked polynucleotides. Such polynucleotides can be covalently linked directly or preferably indirectly through a spacer or linker region. Thus, according to some embodiments, the nucleic acid sequence further includes an in-frame linker polynucleotide. This linker polynucleotide encodes a linker peptide and is interposed between two polynucleotides to be fused or linked.

The linker peptide is selected of an amino acid sequence which is inherently flexible, such that the polypeptides encoded by the first and said second polynucleotides independently and natively fold following expression thereof, thus facilitating the formation of a functional MHC complex and or a functional MHC-peptide complex.

Some numerical values disclosed throughout are referred to as, for example, “X is at least or at least about 100; or 200 [or any numerical number].” This numerical value includes the number itself and all of the following:

i) X is at least 100;
ii) X is at least 200;
iii) X is at least about 100; and
iv) X is at least about 200.

All these different combinations are contemplated by the numerical values disclosed throughout. All disclosed numerical values should be interpreted in this manner, whether it refers to an administration of a therapeutic agent or referring to days, months, years, weight, dosage amounts, etc., unless otherwise specifically indicated to the contrary.

The ranges disclosed throughout are sometimes referred to as, for example, “X is administered on or on about day 1 to 2; or 2 to 3 [or any numerical range].” This range includes the numbers themselves (e.g., the endpoints of the range) and all of the following:

i) X being administered on between day 1 and day 2;
ii) X being administered on between day 2 and day 3;
iii) X being administered on between about day 1 and day 2;
iv) X being administered on between about day 2 and day 3;
v) X being administered on between day 1 and about day 2;
vi) X being administered on between day 2 and about day 3;
vii) X being administered on between about day 1 and about day 2; and
viii) X being administered on between about day 2 and about day 3.

All these different combinations are contemplated by the ranges disclosed throughout. All disclosed ranges should be interpreted in this manner, whether it refers to an administration of a therapeutic agent or referring to days, months, years, weight, dosage amounts, etc., unless otherwise specifically indicated to the contrary.

The terms “and/or” and “any combination thereof” and their grammatical equivalents as used herein, can be used interchangeably. These terms can convey that any combination is specifically contemplated. Solely for illustrative purposes, the following phrases “A, B, and/or C” or “A, B, C, or any combination thereof” can mean “A individually; B individually; C individually; A and B; B and C; A and C; and A, B, and C.”

The term “or” can be used conjunctively or disjunctively, unless the context specifically refers to a disjunctive use.

Genetically Modified Non-Human Animals

Provided herein are genetically modified non-human animals that can be donors of cells, tissues, and/or organs for transplantation. A genetically modified non-human animal can be any desired species. For example, a genetically modified non-human animal described herein can be a genetically modified non-human mammal. A genetically modified non-human mammal can be a genetically modified ungulate, including a genetically modified even-toed ungulate (e.g., pigs, peccaries, hippopotamuses, camels, llamas, chevrotains (mouse deer), deer, giraffes, pronghorn, antelopes, goat-antelopes (which include sheep, goats and others), or cattle) or a genetically modified odd-toed ungulate (e.g., horse, tapirs, and rhinoceroses), a genetically modified non-human primate (e.g., a monkey, or a chimpanzee) or a genetically modified Canidae (e.g., a dog). A genetically modified non-human animal can be a member of the Laurasiatheria superorder. A genetically modified non-human animal can be a non-human primate, e.g., a monkey, or a chimpanzee. If a non-human animal is a pig, the pig can be at least or at least about 1, 5, 50, 100, or 300 pounds, e.g., the pig can be or be about between 5 pounds to 50 pounds; 25 pounds to 100 pounds; or 75 pounds to 300 pounds. In some cases, a non-human animal is a pig that has given birth at least one time.

A genetically modified non-human animal can be of any age. For example, the genetically modified non-human animal can be a fetus; from or from about 1 day to 1 month; from or from about 1 month to 3 months; from or from about 3 months to 6 months; from or from about 6 months to 9 months; from or from about 9 months to 1 year; from or from about 1 year to 2 years. A genetically modified non-human animal can be a non-human fetal animal, perinatal non-human animal, neonatal non-human animal, preweaning non-human animal, young adult non-human animal, or an adult non-human animal.

A genetically modified non-human animal can survive for at least a period of time after birth. For example, the genetically modified non-human animal can survive for at least 1 day, 2 days, 3 days, 1 week, 2 weeks, 3 weeks, 1 month, 2 months, 4 months, 8 months, 1 year, 2 years, 5 years, or 10 years after birth. Multiple genetically modified animals (e.g., a pig) can be born in a litter. A litter of genetically modified animal can have at least 30%, 50%, 60%, 80%, or 90% survival rate, e.g., number of animals in a litter that survive after birth divided by the total number of animals in the litter.

The genetically modified non-human animal of the instant disclosure comprises an exogenous nucleic acid sequence encoding for a MHC molecule. In some embodiments, the MHC molecule is a MHC class I molecule. In some embodiments, the MHC molecule is a MHC class II molecule. In some embodiments, the MHC molecule is HLA-DR. For example, genetically modified non-human animal comprises a transgene comprising a nucleic acid sequence encoding a MHC molecule (e.g., single chain chimeric MHC molecule), a $\alpha$ chain of a MHC molecule or a fragment thereof, or a $\beta$ chain of a MHC molecule or a fragment thereof, or a peptide derived from a MHC molecule. In some embodiments, the transgene can further comprise a polynucleotide encoding a peptide derived from a MHC molecule capable of binding the peptide binding groove for presentation to a T cell. In some embodiments, the genetically modified non-human animal further comprises one or more additional genetic modifications, such as any of the genetic modifications (e.g., knock-ins, knock-outs, gene disruptions, etc.) described herein. For example, in some embodiments, the genetically modified non-human animal, can further comprise one or more transgenes encoding ICP47, CD46, CD55, CD59, HLA-E, HLA-G (e.g., HLA-G1, HLA-G2, HLA-G3, HLA-G4, HLA-G5, HLA-G6, or HLA-G7), B2M, any functional fragments thereof, and/or any combination thereof.

For example, in some embodiments a genetically modified non-human animal can further comprise reduced expression of one or more genes compared to a non-genetically modified counterpart animal. The reduction of expression of a gene can result from mutations on one or more alleles of the gene. For example, a genetically modified animal can comprise a mutation on two or more alleles of a gene. In some cases, such genetically modified animal can be a diploid animal.

A genetically modified non-human animal can comprise one or more transgenes or one or more exogenous nucleic acid sequences. In some case, a genetically modified non-human animal comprises two or more transgenes. Exemplary transgenes contemplated in the present disclosure are discussed below. A genetically modified non-human animal can comprise reduced expression of one or more genes compared to a non-genetically modified counterpart animal. A genetically modified non-human animal can comprise reduced expression of two or more genes compared to a non-genetically modified counterpart animal. A genetically modified animal can have a genomic disruption in at least one gene selected from a group consisting of a component of an MHC I-specific enhanceosome, a transporter of an MHC I-binding peptide, a natural killer (NK) group 2D ligand, a CXC chemokine receptor (CXCR) 3 ligand, MHC II transactivator (CIITA), C3, an endogenous gene not expressed in a human, and any combination thereof.

In some cases, a genetically modified animal has reduced expression of a gene in comparison to a non-genetically modified counterpart animal. In some cases, a genetically modified animal survives at least 22 days after birth. In other cases, a genetically modified animal can survive at least or at least about 23 to 30, 25 to 35, 35 to 45, 45 to 55, 55 to 65, 65 to 75, 75 to 85, 85 to 95, 95 to 105, 105 to 115, 115 to 225, 225 to 235, 235 to 245, 245 to 255, 255 to 265, 265 to 275, 275 to 285, 285 to 295, 295 to 305, 305 to 315, 315 to 325, 325 to 335, 335 to 345, 345 to 355, 355 to 365, 365 to 375, 375 to 385, 385 to 395, or 395 to 400 days after birth.

A non-genetically modified counterpart animal can be an animal substantially identical to the genetically modified animal but without genetic modification in the genome. For example, a non-genetically modified counterpart animal can be a wild-type animal of the same species as the genetically modified animal.

A genetically modified non-human animal can provide cells, tissues or organs for transplanting to a recipient or subject in need thereof. A recipient or subject in need thereof can be a recipient or subject known or suspected of having a condition. The condition can be treated, prevented, reduced, eliminated, or augmented by the methods and compositions disclosed herein. The recipient can exhibit low or no immuno-response to the transplanted cells, tissues or organs. The transplanted cells, tissues or organs can be non-recognizable by CD8+ T cells, NK cells, or CD4+ T cells of the recipient (e.g., a human or another animal). The genes whose expression is reduced can include MHC molecules, regulators of MHC molecule expression, and genes differentially expressed between the donor non-human animal and the recipient (e.g., a human or another animal). The reduced expression can be mRNA expression or protein expression of the one or more genes. For example, the reduced expression can be protein expression of the one or more genes. Reduced expression can also include no expression. For example, an animal, cell, tissue or organ with reduced expression of a gene can have no expression (e.g., mRNA and/or protein expression) of the gene. Reduction of expression of a gene can inactivate the function of the gene. In some cases, when expression of a gene is reduced in a genetically modified animal, the expression of the gene is absent in the genetically modified animal.

A genetically modified non-human animal can comprise reduced expression of one or more MHC molecules compared to a non-genetically modified counterpart animal. For example, the non-human animal can be an ungulate, e.g., a pig, with reduced expression of one or more swine leukocyte antigen (SLA) class I and/or SLA class II molecules.

A genetically modified non-human animal can comprise reduced expression of any genes that regulate major histocompatibility complex (MHC) molecules (e.g., MHC I molecules and/or MHC II molecules) compared to a non-genetically modified counterpart animal. Reducing expression of such genes can result in reduced expression and/or function of MHC molecules (e.g., MHC I molecules and/or MHC II molecules). In some cases, the one or more genes whose expression is reduced in the non-human animal can comprise one or more of the following: components of an MHC I-specific enhanceosome, transporters of a MHC I-binding peptide, natural killer group 2D ligands, CXC chemical receptor (CXCR) 3 ligands, complement component 3 (C3), and major histocompatibility complex II transactivator (CIITA). In some cases, the component of a MHC I-specific enhanceosome can be NLRC5. In some cases, the component of a MHC I-specific enhanceosome can also comprise regulatory factor X (RFX) (e.g., RFX1), nuclear transcription factor Y (NFY), and cAMP response element-binding protein (CREB). In some instances, the transporter of a MHC I-binding peptide can be Transporter associated with antigen processing 1 (TAP1). In some cases, the natural killer (NK) group 2D ligands can comprise MICA and MICB. For example, the genetically modified non-human animal can comprise reduced expression of one or more of the following genes: NOD-like receptor family CARD domain containing 5 (NLRC5), Transporter associated with antigen processing 1 (TAP1), C-X-C motif chemokine 10 (CXCL10), MHC class I polypeptide-related sequence A (MICA), MHC class I polypeptide-related sequence B (MICB), complement component 3 (C3), and CIITA. A genetically modified animal can comprise reduced expression of one or more of the following genes: a component of an MHC I-specific enhanceosome (e.g., NLRC5), a transporter of an MHC I-binding peptide (TAP1), and C3.

A genetically modified non-human animal can comprise reduced expression compared to a non-genetically modified counterpart of one or more genes expressed at different levels between the non-human animal and a recipient receiving a cell, tissue, or organ from the non-human animal. For example, the one or more genes can be expressed at a lower level in a human than in the non-human animal. In some cases, the one or more genes can be endogenous genes of the non-human animal. The endogenous genes are in some cases genes not expressed in another species. For example, the endogenous genes of the non-human animal can be genes that are not expressed in a human. For example, in some cases, homologs (e.g., orthologs) of the one or more genes do not exist in a human. In another example, homologs (e.g., orthologs) of the one or more genes whose expression can be reduced can exist in a human but are not expressed.

In some cases, a non-human animal can be a pig, and the recipient can be a human. The one or more genes with reduced gene expression or comprising a disruption can be any genes expressed in a pig but not in a human. For example, the one or more genes with reduced expression can comprise glycoprotein galactosyltransferase alpha 1, 3 (GGTA1), putative cytidine monophosphate-N-acetyl-neuraminic acid hydroxylase-like protein (CMAH), and β1,4 N-acetylgalactosaminyltransferase (B4GALNT2).

The genetically modified non-human animal can comprise reduced expression compared to a non-genetically modified counterpart of one or more of any of the genes disclosed herein, including NLRC5, TAP1, CXCL10, MICA, MICB, C3, CIITA, GGTA1, CMAH, and B4GALNT2.

A genetically modified non-human animal can comprise one or more genes whose expression is reduced, e.g., where genetic expression is reduced. The one or more genes whose expression is reduced include but are not limited to NOD-like receptor family CARD domain containing 5 (NLRC5), Transporter associated with antigen processing 1 (TAP1), Glycoprotein galactosyltransferase alpha 1,3 (GGTA1), Putative cytidine monophosphate-N-acetylneuraminic acid hydroxylase-like protein (CMAH), C-X-C motif chemokine 10 (CXCL10), MHC class I polypeptide-related sequence A (MICA), MHC class I polypeptide-related sequence B (MICB), class II major histocompatibility complex transactivator (CIITA), Beta-1,4-N-Acetyl-Galactosaminyl Transferase 2 (B4GALNT2), complemental component 3 (C3), and/or any combination thereof.

A genetically modified non-human animal can comprise 1, 2, 3, 4, 5, 6, 7, 8, 9, 10, 11, 12, 13, 14, 15, 16, 17, 18, 19, 20 or more genes whose expression is disrupted. Exemplary disrupted genes contemplated in the disclosure are discussed in sections below. For illustrative purposes, and not to limit various combinations a person of skill in the art can envision, a genetically modified non-human animal can have NLRC5 and TAP1 individually disrupted. A genetically modified non-human animal can also have both NLRC5 and TAP1 disrupted. A genetically modified non-human animal can also have NLRC5 and TAP1, and in addition to one or more of the following GGTA1, CMAH, CXCL10, MICA, MICB, B4GALNT2, or CIITA genes disrupted; for example, "NLRC5, TAP1, and GGTA1" or "NLRC5, TAP1, and CMAH" can be disrupted. A genetically modified non-human animal can also have NLRC5, TAP1, GGTA1, and CMAH disrupted. Alternatively, a genetically modified non-human animal can also have NLRC5, TAP1, GGTA1, B4GALNT2, and CMAH disrupted. In some cases, a genetically modified non-human animal can have C3 and GGTA1 disrupted. In some cases, a genetically modified non-human animal can have reduced expression of NLRC5, C3, GGTA1, B4GALNT2, CMAH, and CXCL10. In some cases, a genetically modified non-human animal can have reduced expression of TAP1, C3, GGTA1, B4GALNT2, CMAH, and CXCL10. In some cases, a genetically modified non-human animal can have reduced expression of NLRC5, TAP1, C3, GGTA1, B4GALNT2, CMAH, and CXCL10. A α4GALNT2 gene can be a Gal2-2 or Gal 2-1.

Lack of MHC class I expression on transplanted human cells can cause the passive activation of natural killer (NK) cells (Ohlen et al., 1989). Lack of MHC class I expression could be due to NLRC5, TAP1, or B2M gene deletion. NK cell cytotoxicity can be overcome by the expression of the human MHC class 1 gene, HLA-E, can stimulate the inhibitory receptor CD94/NKG2A on NK cells to prevent cell killing (Weiss et al., 2009; Lilienfeld et al., 2007; Sasaki et al., 1999). Successful expression of the HLA-E gene can be dependent on co-expression of the human B2M (beta 2 microglobulin) gene and a cognate peptide (Weiss et al., 2009; Lilienfeld et al., 2007; Sasaki et al., 1999; Pascasova et al., 1999). A nuclease mediated break in the stem cell DNA can allow for the insertion of one or multiple genes via homology directed repair. The HLA-E and hB2M genes in series can be integrated in the region of the nuclease mediated DNA break thus preventing expression of the target gene (for example, NLRC5) while inserting the transgenes.

Expression levels of genes can be reduced to various extents. For example, expression of one or more genes can be reduced by or by about 100%. In some cases, expression of one or more genes can be reduced by or by about 99%, 95%, 90%, 85%, 80%, 75%, 70%, 65%, 60%, 55%, or 50% of normal expression, e.g., compared to the expression of non-modified controls. In some cases, expression of one or more genes can be reduced by at least or to at least about 99% to 90%; 89% to 80%, 79% to 70%; 69% to 60%; 59% to 50% of normal expression, e.g., compared to the expression of non-modified controls. For example, expression of one or more genes can be reduced by at least or at least about 90% or by at least or at least about 90% to 99% of normal expression.

Expression can be measured by any known method, such as quantitative PCR (qPCR), including but not limited to PCR, real-time PCR (e.g., Sybr-green), and/or hot PCR. In some cases, expression of one or more genes can be measured by detecting the level of transcripts of the genes. For example, expression of one or more genes can be measured by Northern blotting, nuclease protection assays (e.g., RNase protection assays), reverse transcription PCR, quantitative PCR (e.g., real-time PCR such as real-time quantitative reverse transcription PCR), in situ hybridization (e.g., fluorescent in situ hybridization (FISH)), dot-blot analysis, differential display, serial analysis of gene expression, subtractive hybridization, microarrays, nanostring, and/or sequencing (e.g., next-generation sequencing). In some cases, expression of one or more genes can be measured by detecting the level of proteins encoded by the genes. For example, expression of one or more genes can be measured by protein immunostaining, protein immunoprecipitation, electrophoresis (e.g., SDS-PAGE), Western blotting, bicinchoninic acid assay, spectrophotometry, mass spectrometry, enzyme assays (e.g., enzyme-linked immunosorbent assays), immunohistochemistry, flow cytometry, and/or immunoctyochemistry. Expression of one or more genes can also be measured by microscopy. The microscopy can be optical, electron, or scanning probe microscopy. Optical microscopy can comprise use of bright field, oblique illumination, cross-polarized light, dispersion staining, dark field, phase contrast, differential interference contrast, interference reflection microscopy, fluorescence (e.g., when particles, e.g., cells, are immunostained), confocal, single plane illumination microscopy, light sheet fluorescence microscopy, deconvolution, or serial time-encoded amplified microscopy. Expression of MHC I molecules can also be detected by any methods for testing expression as described herein.

Exemplary Disrupted Genes

Genetically modified non-human animal or genetically modified cells, and cells, organs, and/or tissues derived from a genetically modified animal, having different combinations of disrupted genes are contemplated herein. Genetically modified cells, organs, and/or tissues that are less susceptible to rejection when transplanted into a recipient are described herein. For example, disrupting (e.g., reducing expression of) certain genes, such as NLRC5, TAP1, GGTA1, B4GALNT2, CMAH, CXCL10, MICA, MICB, C3, and/or CIITA, cytidine monophospho-N-acetylneuraminic acid (CMP-N-NeuAc) hydrolase, or a PERV region can increase the likelihood of graft survival. In some cases, at least two genes are disrupted. For example, GGTA1-10 and Gal2-2 can be disrupted. In some cases, GGTA1-10, Gal2-2, and NLRC5-6 can be disrupted. In other cases, NLRC5-6 and Gal2-2 can be disrupted.

In some cases, the disruptions are not limited to solely these genes. It is contemplated that genetic homologues (e.g., any mammalian version of the gene) of the genes within this application are covered. For example, genes that are disrupted can exhibit a certain identity and/or homology to genes disclosed herein, e.g., cytidine monophospho-N-acetylneuraminic acid (CMP-N-NeuAc) hydrolase, NLRC5, TAP1, GGTA1, B4GALNT2, CMAH, CXCL10, MICA, MICB, C3, and/or CIITA. Therefore, it is contemplated that a gene that exhibits at least or at least about 50%, 55%, 60%, 65%, 70%, 75%, 80%, 85%, 90%, 95%, 99%, or 100% homology (at the nucleic acid or protein level) can be disrupted, e.g., a gene that exhibits at least or at least about from 50% to 60%; 60% to 70%; 70% to 80%; 80% to 90%; or 90% to 99% homology. It is also contemplated that a gene that exhibits at least or at least about 50%, 55%, 60%, 65%, 70%, 75%, 80%, 85%, 90%, 99%, or 100% identity (at the nucleic acid or protein level) can be disrupted, e.g., a gene that exhibits at least or at least about from 50% to 60%; 60% to 70%; 70% to 80%; 80% to 90%; or 90% to 99% identity. Some genetic homologues are known in the art, however, in some cases, homologues are unknown. However, homologous genes between mammals can be found by comparing nucleic acid (DNA or RNA) sequences or protein sequences using publicly available databases such as NCBI BLAST.

Gene suppression can also be done in a number of ways. For example, gene expression can be reduced by knock out, altering a promoter of a gene, and/or by administering interfering RNAs (knockdown). This can be done at an organism level or at a tissue, organ, and/or cellular level. If one or more genes are knocked down in a non-human animal, cell, tissue, and/or organ, the one or more genes can be reduced by administrating RNA interfering reagents, e.g., siRNA, shRNA, or microRNA. For example, a nucleic acid which can express shRNA can be stably transfected into a cell to knockdown expression. Furthermore, a nucleic acid which can express shRNA can be inserted into the genome of a non-human animal, thus knocking down a gene with in a non-human animal.

Disruption methods can also comprise overexpressing a dominant negative protein. This method can result in overall decreased function of a functional wild-type gene. Additionally, expressing a dominant negative gene can result in a phenotype that is similar to that of a knockout and/or knockdown.

In some cases, a stop codon can be inserted or created (e.g., by nucleotide replacement), in one or more genes, which can result in a nonfunctional transcript or protein (sometimes referred to as knockout). For example, if a stop codon is created within the middle of one or more genes, the resulting transcription and/or protein can be truncated, and can be nonfunctional. However, in some cases, truncation can lead to an active (a partially or overly active) protein. In some cases, if a protein is overly active, this can result in a dominant negative protein, e.g., a mutant polypeptide that disrupts the activity of the wild-type protein.

This dominant negative protein can be expressed in a nucleic acid within the control of any promoter. For example, a promoter can be a ubiquitous promoter. A promoter can also be an inducible promoter, tissue specific promoter, and/or developmental specific promoter.

The nucleic acid that codes for a dominant negative protein can then be inserted into a cell or non-human animal. Any known method can be used. For example, stable transfection can be used. Additionally, a nucleic acid that codes for a dominant negative protein can be inserted into a genome of a non-human animal.

One or more genes in a non-human animal can be knocked out using any method known in the art. For example, knocking out one or more genes can comprise deleting one or more genes from a genome of a non-human animal. Knocking out can also comprise removing all or a part of a gene sequence from a non-human animal. It is also contemplated that knocking out can comprise replacing all or a part of a gene in a genome of a non-human animal with one or more nucleotides. Knocking out one or more genes can also comprise inserting a sequence in one or more genes thereby disrupting expression of the one or more genes. For example, inserting a sequence can generate a stop codon in the middle of one or more genes. Inserting a sequence can also shift the open reading frame of one or more genes. In some cases, knock out can be performed in a first exon of a gene. In other cases, knock out can be performed in a second exon of a gene.

Knockout can be done in any cell, organ, and/or tissue in a non-human animal. For example, knockout can be whole body knockout, e.g., expression of one or more genes is reduced in all cells of a non-human animal. Knockout can also be specific to one or more cells, tissues, and/or organs of a non-human animal. This can be achieved by conditional knockout, where expression of one or more genes is selectively reduced in one or more organs, tissues or types of cells. Conditional knockout can be performed by a Cre-lox system, where cre is expressed under the control of a cell, tissue, and/or organ specific promoter. For example, one or more genes can be knocked out (or expression can be reduced) in one or more tissues, or organs, where the one or more tissues or organs can include brain, lung, liver, heart, spleen, pancreas, small intestine, large intestine, skeletal muscle, smooth muscle, skin, bones, adipose tissues, hairs, thyroid, trachea, gall bladder, kidney, ureter, bladder, aorta, vein, esophagus, diaphragm, stomach, rectum, adrenal glands, bronchi, ears, eyes, retina, genitals, hypothalamus, larynx, nose, tongue, spinal cord, or ureters, uterus, ovary, testis, and/or any combination thereof. One or more genes can also be knocked out (or expression can be reduced) in one types of cells, where one or more types of cells include trichocytes, keratinocytes, gonadotropes, corticotropes, thyrotropes, somatotropes, lactotrophs, chromaffin cells, parafollicular cells, glomus cells melanocytes, nevus cells, merkel cells, odontoblasts, cementoblasts corneal keratocytes, retina muller cells, retinal pigment epithelium cells, neurons, glias (e.g., oligodendrocyte astrocytes), ependymocytes, pinealocytes, pneumocytes (e.g., type I pneumocytes, and type II pneumocytes), clara cells, goblet cells, G cells, D cells, Enterochromaffin-like cells, gastric chief cells, parietal cells, foveolar cells, K cells, D cells, I cells, goblet cells, paneth cells, enterocytes, microfold cells, hepatocytes, hepatic stellate cells (e.g., Kupffer cells from mesoderm), cholecystocytes, centroacinar cells, pancreatic stellate cells, pancreatic α cells, pancreatic β cells, pancreatic δ cells, pancreatic F cells, pancreatic ε cells, thyroid (e.g., follicular cells), parathyroid (e.g., parathyroid chief cells), oxyphil cells, urothelial cells, osteoblasts, osteocytes, chondroblasts, chondrocytes, fibroblasts, fibrocytes, myoblasts, myocytes, myosatellite cells, tendon cells, cardiac muscle cells, lipoblasts, adipocytes, interstitial cells of cajal, angioblasts, endothelial cells, mesangial cells (e.g., intraglomerular mesangial cells and extraglomerular mesangial cells), juxtaglomerular cells, macula densa cells, stromal cells, interstitial cells, telocytes simple epithelial cells, podocytes, kidney proximal tubule brush border cells, sertoli cells, leydig cells, granulosa cells, peg cells, germ cells, spermatozoon ovums, lymphocytes, myeloid cells, endothelial progenitor cells, endothelial stem cells, angioblasts, mesoangioblasts, pericyte mural cells, and/or any combination thereof.

Conditional knockouts can be inducible, for example, by using tetracycline inducible promoters, development specific promoters. This can allow for eliminating or suppressing expression of a gene/protein at any time or at a specific time. For example, with the case of a tetracycline inducible promoter, tetracycline can be given to a non-human animal any time after birth. If a non-human animal is a being that develops in a womb, then promoter can be induced by giving tetracycline to the mother during pregnancy. If a non-human animal develops in an egg, a promoter can be induced by injecting, or incubating in tetracycline. Once tetracycline is given to a non-human animal, the tetracycline will result in expression of cre, which will then result in excision of a gene of interest.

A cre/lox system can also be under the control of a developmental specific promoter. For example, some promoters are turned on after birth, or even after the onset of puberty. These promoters can be used to control cre expression, and therefore can be used in developmental specific knockouts.

It is also contemplated that any combinations of knockout technology can be combined. For example, tissue specific knockout can be combined with inducible technology, creating a tissue specific, inducible knockout. Furthermore, other systems such developmental specific promoter, can be used in combination with tissues specific promoters, and/or inducible knockouts.

In some cases, gene editing can be useful to design a knockout. For example, gene editing can be performed using a nuclease, including CRISPR associated proteins (Cas proteins, e.g., Cas9), Zinc finger nuclease (ZFN), Transcription Activator-Like Effector Nuclease (TALEN), and maganucleases. Nucleases can be naturally existing nucleases, genetically modified, and/or recombinant. For example, a CRISPR/Cas system can be suitable as a gene editing system.

It is also contemplated that less than all alleles of one or more genes of a non-human animal can be knocked out. For example, in diploid non-human animals, it is contemplated that one of two alleles are knocked out. This can result in decreased expression and decreased protein levels of genes. Overall decreased expression can be less than or less than about 99%, 95%, 90%, 85%, 80%, 75%, 70%, 65%, 60%, 55%, 50%, 45%, 40%, 35%, 30%, 25%, or 20%; e.g., from or from about 99% to 90%; 90% to 80%; 80% to 70%; 70% to 60%; 60% to 50%; 50% to 40%; 40% to 30%, or 30% to 20%; compared to when both alleles are functioning, for example, not knocked out and/or knocked down. Additionally, overall decrease in protein level can be the same as the decreased in overall expression. Overall decrease in protein level can be about or less than about 99%, 95%, 90%, 80%, 70%, 60%, 50%, 40%, 30%, or 20%, e.g., from or from about 99% to 90%; 90% to 80%; 80% to 70%; 70% to 60%; 60% to 50%; 50% to 40%; 40% to 30%, or 30% to 20%; compared to when both alleles are functioning, for example, not knocked out and/or knocked down. However, it is also contemplated that all alleles of one or more genes in a non-human animal can be knocked out.

Knockouts of one or more genes can be verified by genotyping. Methods for genotyping can include sequencing, restriction fragment length polymorphism identification (RFLPI), random amplified polymorphic detection (RAPD), amplified fragment length polymorphism detection (AFLPD), PCR (e.g., long range PCR, or stepwise PCR), allele specific oligonucleotide (ASO) probes, and hybridization to DNA microarrays or beads. For example, genotyping can be performed by sequencing. In some cases, sequencing can be high fidelity sequencing. Methods of sequencing can include Maxam-Gilbert sequencing, chain-termination methods (e.g., Sanger sequencing), shotgun sequencing, and bridge PCR. In some cases, genotyping can be performed by next-generation sequencing. Methods of next-generation sequencing can include massively parallel signature sequencing, colony sequencing, pyrosequencing (e.g., pyrosequencing developed by 454 Life Sciences), single-molecule rea-time sequencing (e.g., by Pacific Biosciences), Ion semiconductor sequencing (e.g., by Ion Torrent semiconductor sequencing), sequencing by synthesis (e.g., by Solexa sequencing by Illumina), sequencing by ligation (e.g., SOLID sequencing by Applied Biosystems), DNA nanoball sequencing, and heliscope single molecule sequencing. In some cases, genotyping of a non-human animal herein can comprise full genome sequencing analysis. In some cases, knocking out of a gene in an animal can be validated by sequencing (e.g., next-generation sequencing) a part of the gene or the entire gene. For example, knocking out of NLRC5 gene in a pig can be validated by next generation sequencing of the entire NLRC5.

In some embodiments, the genetically modified animal and the genetically modified cells disclosed herein can comprise a disruption in a PERV site. Methods for disrupting a PERV site are known in the art. For example, see Yang et al. Science 27 Nov. 2015: Vol. 350, Issue 6264, pp. 1101-1104, the contents of which are incorporated herein in its entirety.

Transgenes

Provided herein are genetically modified cells, or genetically modified non-human animal, and the cells, tissues and organs derived therefrom comprising a transgene comprising a nucleic acid sequence encoding a MHC molecule (e.g., single chain chimeric MHC molecule), a $\alpha$ chain of a MHC molecule or a fragment thereof, or a $\beta$ chain of a MHC molecule or a fragment thereof, or a peptide derived from a MHC molecule. In some embodiments, the transgene can further comprise a polynucleotide encoding a peptide derived from a MHC molecule capable of binding the peptide binding groove for presentation to a T cell. In some embodiments, the genetically modified cells, or genetically modified non-human animal, and the cells, tissues and organs derived therefrom can further comprise one or more transgenes encoding ICP47, CD46, CD55, CD59, HLA-E, HLA-G (e.g., HLA-G1, HLA-G2, HLA-G3, HLA-G4, HLA-G5, HLA-G6, or HLA-G7), B2M, any functional fragments thereof, and/or any combination thereof. Genetically modified non-human animal or genetically modified cells, and cells, organs, and/or tissues derived from a genetically modified animal, having one or more or different combinations of transgenes are also contemplated herein. Genetically modified cells, organs, and/or tissues that are less susceptible to rejection when transplanted into a recipient are described herein. Transgenes or exogenous nucleic acid sequences, can be useful for overexpressing endogenous genes at higher levels than without the transgenes. Additionally, exogenous nucleic acid sequences can be used to express exogenous genes. Transgenes can also encompass other types of genes, for example, a dominant negative gene.

A transgene of protein X can refer to a transgene comprising an exogenous nucleic acid sequence encoding protein X. As used herein, in some cases, a transgene encoding protein X can be a transgene encoding 100% or about 100% of the amino acid sequence of protein X. In some cases, a transgene encoding protein X can encode the full or partial amino sequence of protein X. For example, the transgene can encode at least or at least about 99%, 95%, 90%, 80%, 70%, 60%, 50%, 40%, 30%, 20%, 10%, or 5%, e.g., from or from about 99% to 90%; 90% to 80%; 80% to 70%; 70% to 60%; or 60% to 50%; of the amino acid sequence of protein X. Expression of a transgene can ultimately result in a functional protein, e.g., a partially or fully functional protein. As discussed above, if a partial sequence is expressed, the ultimate result can be in some cases a nonfunctional protein or a dominant negative protein. A nonfunctional protein or dominant negative protein can also compete with a functional (endogenous or exogenous) protein. A transgene can also encode an RNA (e.g., mRNA, shRNA, siRNA, or microRNA). In some cases, where a transgene encodes for an mRNA, this can in turn be translated into a polypeptide (e.g., a protein). Therefore, it is contemplated that a transgene can encode for protein. A transgene can, in some instances, encode a protein or a portion of a protein. Additionally, a protein can have one or more mutations (e.g., deletion, insertion, amino acid replacement, or rearrangement) compared to a wild-type polypeptide. A protein can be a natural polypeptide or an artificial polypeptide (e.g., a recombinant polypeptide). A transgene can encode a fusion protein formed by two or more polypeptides.

Where a transgene, or exogenous nucleic acid sequence, encodes for an mRNA based on a naturally occurring mRNA (e.g., an mRNA normally found in another species), the mRNA can comprise one or more modifications in the 5' or 3' untranslated regions. The one or more modifications can comprise one or more insertions, on or more deletions, or one or more nucleotide changes, or a combination thereof. The one or more modifications can increase the stability of the mRNA. The one or more modifications can remove a binding site for an miRNA molecule, such as an miRNA molecule that can inhibit translation or stimulate mRNA degradation. For example, an mRNA encoding for a HLA-G and/or HLA-DR protein can be modified to remove a biding site for an miR148 family miRNA. Removal of this binding site can increase mRNA stability.

Transgenes can be placed into an organism, cell, tissue, or organ, in a manner which produces a product of the transgene. For example, disclosed herein is a non-human animal comprising one or more transgenes. One or more transgenes can be in combination with one or more disruptions as described herein. A transgene can be incorporated into a cell. For example, a transgene can be incorporated into an organism's germ line. When inserted into a cell, a transgene can be either a complementary DNA (cDNA) segment, which is a copy of messenger RNA (mRNA), or a gene itself residing in its original region of genomic DNA (with or without introns).

A transgene can comprise a polynucleotide encoding a protein of a species and expressing the protein in an animal of a different species. For example, a transgene can comprise a polynucleotide encoding a human protein. Such a polynucleotide can be used express the human protein (e.g., CD47) in a non-human animal (e.g., a pig). In some cases, the polynucleotide can be synthetic, e.g., different from any native polynucleotide in sequence and/or chemical characteristics.

The polynucleotide encoding a protein of species X can be optimized to express the protein in an animal of a species Y. There may be codon usage bias (e.g., differences in the frequency of occurrence of synonymous codons in coding DNA). A codon can be a series of nucleotides (e.g., a series of 3 nucleotides) that encodes a specific amino acid residue in a polypeptide chain or for the termination of translation (stop codons). Different species may have different preference in the DNA codons. The optimized polynucleotide can encode a protein of species X, in some cases with codons of a species Y, so that the polynucleotide can express the protein more efficiently in the species Y, compared to the native gene encoding the protein of species X. In some cases, an optimized polynucleotide can express a protein at least 5%, 10%, 20%, 40%, 80%, 90%, 1.5 folds, 2 folds, 5 folds, or 10 folds more efficiently in species Y than a native gene of species X encoding the same protein. Methods for making gene disruption are described, for example, in WO2017218714A1 and WO2016094679A1, the teachings of which are incorporated herein in their entireties. For example, see Tables 4-9, of WO2017218714A1, which describes exemplary sequences for making gRNA constructs targeting genes for disruption and EXAMPLES 1-9 which describe making the genetic disruption using the gRNA constructs.

Transgene Encoding MHC Molecule

Provided herein are methods to generate a genetically modified cell and a genetically modified animal expressing an exogenous functional MHC molecule or MHC complex comprising a peptide binding groove, and in some embodiments, further expressing a peptide capable of binding the peptide binding groove to form a functional MHC-peptide complex. The term "MHC complex" or "MHC molecule" as used herein refers to MHC heterodimer will be understood to include the MHC α chain and MHC β chain associated together to form a peptide binding groove.

Accordingly, in some embodiments, a genetically modified cell, genetically modified non-human animal or cells, organs or tissues disclosed herein comprise a transgene comprising a polynucleotide encoding a β chain of a MHC molecule or a fragment thereof. In some embodiments, a genetically modified cell, genetically modified non-human animal or cells, organs or tissues disclosed herein comprise a transgene comprising a polynucleotide encoding a α chain of a MHC molecule or a fragment thereof. In some embodiments, a genetically modified cell, genetically modified non-human animal or cells, organs or tissues disclosed herein comprise a transgene comprising a polynucleotide encoding an α chain of a MHC molecule or a fragment thereof, and a polynucleotide encoding a β chain of a MHC molecule or a fragment thereof. In some embodiments, the β chain and the α chain form a functional MHC complex (i.e., a MHC heterodimer or a MHC molecule) wherein the functional MHC complex comprises a peptide binding grove. In some embodiments, the β chain and/or the α chain lacks a functional transmembrane domain. In some embodiments, the genetically modified cells or non-human animals further comprises a transgene comprising a polynucleotide encoding a peptide derived from a MHC molecule. In some embodiments, the peptide derived from a MHC molecule can bind to the peptide binding groove such that it forms a functional MHC-peptide complex. In some embodiments, a polynucleotide encoding the β chain and a polynucleotide α chain are translationally fused.

In some embodiments, a polynucleotide encoding a β chain or fragment thereof is translationally fused upstream of a polynucleotide encoding a α chain or fragment thereof. In some embodiments, the polynucleotide encoding a peptide derived from a MHC molecule is translationally fused to the polynucleotide encoding the β chain or the polynucleotide encoding the α chain. In some embodiments, the polynucleotide encoding a peptide derived from a MHC molecule is translationally fused upstream to the polynucleotide encoding the β chain. In some embodiments, a transgene comprises translationally fused in a sequence from 5'-3', a polynucleotide encoding a β chain or fragment thereof and a polynucleotide encoding a α chain or fragment thereof. In some embodiments, a transgene comprises translationally fused in a sequence from 5'-3', a polynucleotide encoding a peptide derived from a MHC molecule, a polynucleotide encoding a β chain or fragment thereof and a polynucleotide encoding a α chain or fragment thereof. In related embodiments, a transgene encodes a single chain MHC chimeric polypeptide comprising a β chain or fragment thereof and a α chain or fragment thereof, which upon expression folds in a functional MHC molecule. In some embodiments, a single chain MHC chimeric polypeptide further comprises a peptide derived from a MHC molecule covalently linked to a β chain or a α chain, which upon expression folds in a functional MHC-peptide complex. In some embodiments, the single chain MHC chimeric polypeptide further comprises a peptide that can bind in the peptide binding groove of the MHC molecule and can thereby be presented by the MHC molecule, such that it generates a tolerogenic response towards the genetically engineered cell or a cell, tissue or organ isolated from a genetically modified animal upon transplantation. In some embodiments, a transgene encodes a single chain MHC chimeric polypeptide comprising covalently linked in a sequence a peptide derived from a MHC molecule, a β chain of MHC molecule or a fragment thereof, and a α chain of a MHC molecule or a fragment thereof.

The term "single chain MHC chimeric peptide" or "scMHC chimeric peptide" as used herein means a single polypeptide, the amino acid sequence of which is derived at least in part from two or more different naturally occurring proteins or protein chain sections, in this case at least a α chain of a MHC molecule or a fragment thereof and a β chain of a MHC molecule or a fragment thereof. It is contemplated that upon expression the scMHC chimeric peptide folds to form a functional MHC molecule comprising a peptide binding groove. Accordingly, the term "fragment thereof" as used herein, with regards to a α chain or β chain part of a peptide chain is meant, a fragment which still exhibits the desired functional characteristics of the full-length peptide it is derived from, i.e., forming a functional MHC molecule forming a peptide binding groove. In some embodiments, the scMHC chimeric peptide further comprises a peptide derived from a MHC molecule. In related embodiments, upon expression the scMHC chimeric peptide folds to form the MHC-peptide complex where the peptide derived from MHC molecule binds the peptide binding groove formed by association of the α chain or a fragment thereof and the β chain or a fragment thereof.

The phrases "translationally fused" and "in frame" are interchangeably used herein to refer to polynucleotides which are covalently linked to form a single continuous open reading frame spanning the length of the coding sequences of the linked polynucleotides. Such polynucleotides can be covalently linked directly or preferably indirectly through a spacer or linker region. Thus, according to some embodiments a transgene further comprises an in-frame linker polynucleotide. This linker polynucleotide encodes a linker peptide (e.g., a first linker peptide or a second linker peptide). In some embodiments, a transgene comprises a first linker polynucleotide encoding a first linker peptide interposed between the polynucleotide encoding a β chain of MHC molecule or a fragment thereof, and a polynucleotide encoding a α chain of a MHC molecule or a fragment thereof. In some embodiments, a transgene further comprises a second linker polynucleotide encoding a second linker peptide interposed between a polynucleotide encoding a peptide derived from a MHC molecule and a polynucleotide encoding a β chain or a polynucleotide encoding a α chain. In some embodiments, a linker peptide is cleavable. In some embodiments, a linker peptide is non-cleavable.

The linker peptide linked between a β chain of MHC molecule or a fragment thereof, and a α chain of a MHC molecule or a fragment thereof is selected of an amino acid sequence which is inherently flexible, such that the polypeptides encoded by the first and said second polynucleotides independently and natively fold following expression thereof, thus facilitating the formation of a functional MHC molecule. The linker peptide linked between a peptide derived from a MHC molecule and a β chain of a MHC molecule or a fragment thereof, or a αchain of a MHC molecule or a fragment thereof is selected of an amino acid sequence which is inherently flexible, such that the peptide derived from MHC molecule independently and natively fold following expression thereof and bind a peptide binding groove, thus facilitating the formation of a functional single chain (sc) human MHC-peptide complex. In some embodiments, a first linker peptide is linked between the C-terminus of a β2 domain of the β chain and the N-terminus of an α1 domain of the α chain. In some embodiments, a second linker peptide is linked between the C-terminus of a peptide derived from a MHC molecule and a N-terminus of a β chain of the MHC molecule or fragment thereof or N-terminus of a α chain of the MHC molecule or fragment thereof.

It is to be understood that the disclosure is not limited in its application to the details of construction and the arrangement of the components set forth in the following description or illustrated in the drawings described in the Examples section. The disclosure is capable of other embodiments or of being practiced or carried out in various ways. Also, it is to be understood that the phraseology and terminology employed herein is for the purpose of description and should not be regarded as limiting.

In some embodiments, a first linker peptide comprises a sequence that is at least about 50%, 60%, 70%, 80%, 90%, 95%, 98%, 99% or 100% identical to a sequence selected from SEQ ID NO 1 or SEQ ID NO: 2. In some embodiments, a second linker peptide comprises a sequence that is at least about 50%, 60%, 70%, 80%, 90%, 95%, 98%, 99% or 100% identical to a sequence selected from SEQ ID NO 1 or SEQ ID NO: 2. In some embodiments, a transgene encoding a single chain MHC chimeric polypeptide comprises a sequence that is at least about 50%, 60%, 70%, 80%, 90%, 95%, 98%, 99% or 100% identical to a sequence selected from SEQ ID NO: 3, or SEQ ID NO: 4.

MHC Molecules

In some embodiments, the MHC molecule is MHC class I. In some embodiments, the MHC molecule is MHC class II. The term "MHC molecule" refers to a molecule comprising Major Histocompatibility Complex (MHC) glycoprotein protein sequences. The term "MHC" as used herein will be understood to refer to the Major Histocompatibility Complex, which is defined as a set of gene loci specifying major histocompatibility complex glycoprotein antigens including the human leukocyte antigen (HLA). The term "HLA" as used herein will be understood to refer to Human Leukocyte Antigens, which is defined as the major histocompatibility antigens found in humans. As used herein, "HLA" is the human form of "MHC" and therefore can be used interchangeably. Examples of HLA proteins that can be encoded by transgene of instant disclosure and claimed inventive concept(s) include, but are not limited to, an HLA class I α chain, an HLA class II α chain and an HLA class II β chain. Non-limiting examples of HLA class II α and/or β proteins that can be encoded by a transgene of the present disclosure and claimed inventive concept(s) include, but are not limited to, those encoded at the following gene loci: HLA-DRA; HLA-DRB1; HLA-DRB3,4,5; HLA-DQA; HLA-DQB; HLA-DPA; and HLA-DPB. In some embodiments, the MHC class II molecule is HLA-DP, HLA-DQ or HLA-DR. In some embodiments, a β chain of a MHC molecule is HLA-DR1, HLA-DR2, HLA-DR3, HLA-DR4, or HLA-DR5. In some embodiments, the MHC molecule is human MHC molecule.

In general, the major function of MHC molecules is to bind antigenic peptides and display them on the surface of cells. The glycoproteins (MHC molecules) encoded by the MHC have been extensively studied in both the human and murine systems and their nucleic acid and protein sequences are well known in the art. Many of the histocompatibility proteins have been isolated and characterized. For a general review of MHC glycoprotein structure and function, see Fundamental Immunology, 3d Ed., W. E. Paul, ed., (Ravens Press N.Y. 1993).

In mice, Class I molecules are encoded by the K, D and Qa regions of the MHC. Class II molecules are encoded by the I-A and I-E subregions. The isolated antigens encoded by the murine I-A and I-E subregions have been shown to consist of two noncovalently bonded peptide chains: an α chain of 32-38 kd and a β chain of 26-29 kd. A third, invariant, 31 kd peptide is noncovalently associated with these two peptides, but it is not polymorphic and does not appear to be a component of the antigens on the cell surface. The α and β chains of a number of allelic variants of the I-A region have been cloned and sequenced.

The human Class I proteins (MHC class I molecules) have also been studied (Bjorkman, P. J., et al., (1987) Nature 329:506-512). These are found to consist of a 44 kd subunit MHC class I heavy chain and a 12 kd β2-microglobulin subunit which is common to all antigenic specificities. Further work has resulted in a detailed picture of the 3-D structure of HLA-A2, a Class I human antigen.

Structurally, MHC class I molecules are heterodimers comprised of two noncovalently bound polypeptide chains, a larger "MHC class I heavy chain (a)" and a smaller "light" chain ((β-2-microglobulin). The polymorphic, polygenic heavy chain (45 kDa), is encoded within the MHC on chromosome six. Chromosome 6 has three loci, HLA-A, HLA-B, and HLA-C, the first two of which have a large number of alleles encoding MHC class I heavy chain alloantigens, HLA-A, HLA-B respectively. In some embodiments, a transgene comprises a polynucleotide encoding for a MHC class I heavy chain (α chain) (e.g., HLA-A, HLA-B and HLA-C) or a fragment thereof. MHC class I heavy chain (α chain) (e.g., HLA-A, HLA-B and HLA-C) is subdivided into three extracellular domains (designated α1, α2, and α3), one intracellular domain, and one transmembrane domain. The two outermost extracellular domains, α1 and α2, together form the groove that binds antigenic peptide. Thus, interaction with the TCR occurs at this region of the protein. The 3rd extracellular domain of the molecule contains the recognition site for the CD8 protein on the CTL; this interaction serves to stabilize the contact between the T cell and the APC. In some embodiments, a transgene comprises a polynucleotide encoding for α1, α2, α3 domain, intracellular domain, or transmembrane domain. In some embodiments, the transgene encodes a MHC class I heavy chain (α chain) that lacks a transmembrane domain.

The invariant light chain (12 kDa), encoded outside the MHC on chromosome 15, consists of a single, extracellular polypeptide. In some embodiments, a transgene encodes a MHC class I light chain (chain). The terms "MHC class I light chain", "B-2-microglobulin", and "B2m" may be used interchangeably herein. In some embodiments, the transgene encodes a MHC class I light chain (β chain) that lacks a transmembrane domain. Association of the class I heavy and light chains is required for expression of MHC class I molecules on cell membranes. In this picture, the β2-microglobulin protein and α3 domain of the heavy chain are associated. In some embodiments, α chain or a fragment thereof and the β chain or a fragment thereof, that is encoded by a transgene associate to form a peptide binding groove. Accordingly, the MHC class I molecule as disclosed herein can refer to a MHC class I heterodimer, comprising a MHC class I heavy chain (e.g., HLA-A, HLA-B, or HLA-C), a MHC class I light chain or portions thereof or regions thereof. In some embodiments, the transgene encodes entire MHC class I heavy chain. In some embodiments, the MHC class I molecule can be domains of MHC class I heavy chain (α1, α2, or α3). In some embodiments, the MHC class I molecule can comprise sequence from the α1, α2, or α3 region of the MHC class I heavy chain. The α1 and α2 domains of the heavy chain comprise the hypervariable region which forms the antigen-binding sites to which the peptide is bound.

In some embodiments, a MHC molecule is a MHC class II molecule. MHC class II glycoproteins, HLA-DR, HLA-DQ, and HLA-DP (encoded by alleles at the HLA-DR, DP, and DQ loci) have a domain structure, including antigen binding sites, similar to that of Class I. MHC class II molecules are heterodimers, consist of two nearly homologous subunits; a and βchains, both of which are encoded in the MHC. Accordingly, in some embodiments, the MHC class II molecule refers to a heterodimer of MHC class II α chain and MHC class II β chain (e.g., HLA-DQ, HLA-DR, HLA-DP). In some embodiments, the MHC class II molecule can be a subunit of the heterodimer. In some embodiments, a transgene comprises a polynucleotide encoding a MHC class II α chain (e.g., HLA-DPA, HLA-DQA, or HLA-DRA). In some embodiments, a transgene comprises a polynucleotide encoding a MHC class II β chain (e.g., HLA-DPB, HLA-DQB, or HLA-DRB), or domains thereof. In some embodiments, a transgene comprises a polynucleotide encoding a MHC class II α chain and a polynucleotide encoding a MHC class II β chain. In some embodiments, the β chain is HLA-DRB.

The β chain is encoded by four gene loci in human (HLA-DRB1, HLA-DRB3, HLA-DRB4 and HLA-DRB4), however no more than 3 functional loci are present in a single individual, and no more than two on a single chromosome. In some embodiments, the β chain is encoded by HLA-DRB1, HLA-DRB3, HLA-DRB4 or HLA-DRB4 gene locus. In some embodiments, the β chain is encoded by HLA-DRB1*03 or HLA-DRB1*04. The HLA-DRB1 locus is ubiquitous and encodes a very large number of functionally variable gene products (HLA-DR1 to HLA-DR17). The HLA-DRB3 locus encodes the HLA-DR52 specificity, is moderately variable and is variably associated with certain HLA-DRB1 types. The HLA-DRB4 locus encodes the HLA-DR53. In some embodiments, the β chain is selected from HLA-DR1, HLA-DR2, HLA-DR3, HLA-DR4, or HLA-DR5.

In some embodiments, a transgene encodes an entire MHC class II β chain and/or MHC class II α chain or large portions thereof. For instance, a transgene can encode an extracellular domain from an MHC class II subunit of about 90-100 residues (e.g., β1 and 2 and/or α1 and α2 of class II molecules). Each chain in Class II molecules consist of globular domains, referred to as α1, α2, β1, and B2. All except the α1 domain are stabilized by intrachain disulfide bonds typical of molecules in the immunoglobulin superfamily. Each chain in a class II molecule contains two external domains: the 33-kDa α chain contains α1 and α2 external domains, while the 28-kDa β chain contains β1 and B2 external domains. The membrane-proximal α2 and β2 domains, like the membrane-proximal 3rd extracellular domain of class I heavy chain molecules, bear sequence homology to the immunoglobulin-fold domain structure. The membrane-distal domain of a class II molecule is composed of the α1 and β1 domains, which form an antigen-binding cleft for processed peptide antigen. Accordingly, in some embodiments, α chain or a fragment thereof and the β chain or a fragment thereof, that is encoded by a transgene associate to form a peptide binding groove. The N-terminal portions of the α and β chains, the α1 and β1 domains, contain hypervariable regions which are thought to comprise the majority of the antigen-binding sites (see, Brown et al., Nature 364:33-39 (1993)).

Polynucleotides encoding a α chain or a fragment thereof and/or a β chain or fragment thereof can be obtained from a variety of sources including polymerase chain reaction (PCR) amplification of publicly available MHC chain sequences. In some embodiments, a transgene encodes a MHC class molecule that is matched to a recipient of a transplant. In some embodiments, a transgene encodes a MHC molecule that is mismatched to a recipient of a transplant. In some embodiments, the MHC molecule of a recipient is matched with the MHC molecule of a donor of a transplant. Sequences of MHC glycoproteins and genes encoding the glycoproteins are known in the art. In some embodiments, wherein the MHC molecule is matched with a subject (e.g., a recipient or a donor of a transplant or a subject in need of treatment), the MHC molecule can be determined, for example, by conventional methods of HLA-typing or tissue typing known in the arts. Non limiting examples of methods that can be employed for selection of a MHC molecule include serological methods, cellular methods and DNA typing methods. Serology is used to identify the HLA proteins on the surface of cells. A complement dependent cytotoxicity test or microlymphocytotoxicity assay can be used for serological identification of MHC molecules. Peripheral blood lymphocytes (PBLs) express MHC class I antigens and are used for the serologic typing of HLA-A, HLA-B, and HLA-C. MHC class II typing is done with B lymphocytes isolated from PBLs because these cells express class II molecules. HLA typing is performed in multiwell plastic trays with each well containing a serum of known HLA specificity.

Lymphocytes are plated in the well and incubated, and complement (rabbit serum as a source) is added to mediate the lysis of antibody-bound lymphocytes (See. Terasaki Pi, Nature. 1964). Cellular assays such as the mixed lymphocyte culture (MLC) measure the differences in class II proteins between individuals. This may be accomplished in a number of ways, all of which are known to those skilled in the art, e.g., subtyping may be accomplished by mixed lymphocyte response (MLR) typing and by primed lymphocyte testing (PLT). Both methods are described in Weir and Blackwell, eds., Handbook of Experimental Immunology, which is incorporated herein by reference. It may also be accomplished by analyzing DNA restriction fragment length polymorphism (RFLP) using DNA probes that are specific for the MHC locus being examined. Methods for preparing probes for the MHC loci are known to those skilled in the art. See, e.g., Gregersen et al. (1986), Proc. Natl. Acad. Sci. USA 79:5966, which is incorporated herein by reference. High resolution selection of a MHC molecule can be done by DNA typing methods. Different HLA alleles defined by DNA typing can specify HLA proteins which are indistinguishable using serologic typing. For example, an individual carrying the DRB1*040101 allele would have the same serologic type (DR4) as an individual carrying the DRB1*0412 allele. Thus, DRB1*040101 and DRB1*0412 are splits of the broad specificity DR4. These splits are identified by DNA typing.

Sequences of transgene encoding a MHC molecule can be obtained by sequencing of genomic DNA of the locus, or cDNA to mRNA encoded within the locus. The DNA which is sequenced includes the section encoding the hypervariable regions of the MHC encoded polypeptide. Techniques for identifying specifically desired DNA with a probe, for amplification of the desired region are known in the art, and include, for example, the polymerase chain reaction (PCR) technique. Live lymphocytes are not required for DNA typing and DNA is easily extracted from any nucleated cell, although peripheral blood lymphocytes are the usual source. DNA is easily stored, allowing repeat sample testing and amplifying desired MHC sequences when required. The polymerase chain reaction (PCR)-based technology is used for clinical HLA typing. The first method developed uses sequence-specific oligonucleotide probe (SSOP). For HLA class II typing, the variable exon sequences encoding the first amino terminal domains of the DRB1 and DQB1 genes are amplified from genomic DNA. Based on the HLA sequence database, a panel of synthetic oligonucleotide sequences corresponding to variable regions of the gene are designed and used as SSOP in hybridization with the amplified PCR products.

As an alternative method, polymorphic DNA sequences can be used as amplification primers, and in this case only alleles containing sequences complementary to these primers will anneal to the primers and amplification will proceed. This second strategy of DNA typing is called the sequence-specific primer (SSP) method. Actual DNA sequencing of amplified products of multiple HLA loci is increasingly used as clinical HLA typing. HLA alleles are designated by the locus followed by an asterisk (*), a two-digit number corresponding to the antigen specificity, and the assigned allele number. For example, HLA-A*0210 represents the tenth HLA-A2 allele within the serologically defined HLA-A2 antigen family. Methods for HLA typing and identification of MHC molecules expressed in a donor of transplant and a potential recipient at the protein or DNA level are described for example, in Altaf et al World J Transplant. 2017, Erlich H. A. et al. Immunity, Vol. 14, 347-356, April 2001, Dunckley H, Methods Mol Biol. 2012. US20090069190A1, US20110117553A1. One of skill in the art can determine the protein product once the gene sequence of MHC molecule is determined by DNA typing methods. In some embodiments, the amplified DNA sequences can be easily be translationally fused to generate a transgene encoding a single chain MHC chimeric MHC molecule using standard molecular biology techniques such as PCR.

Peptides Derived from MHC Molecule

In some embodiments, the transgene comprises a polynucleotide encoding a peptide derived from a MHC molecule.

As such, the sequences of amino acid residues in the peptide will be identical to or substantially identical to a polypeptide sequence in the MHC molecule. Thus, "a peptide derived from a MHC molecule" refers to a peptide that has a sequence "from a region in an MHC molecule" (e.g., the hypervariable region), and is a peptide that has a sequence either identical to or substantially identical to the naturally occurring MHC amino acid sequence of the region. In some embodiments, the MHC molecule is MHC class II molecule. Thus, "a peptide derived from a MHC class II molecule" refers to a peptide that has a sequence "from a region in an MHC class II molecule" (e.g., the hypervariable region), and is a peptide that has a sequence either identical to or substantially identical to the naturally occurring MHC amino acid sequence of the region. Accordingly, "a peptide derived from a MHC class II molecule of a recipient" refers to a peptide that has a sequence "from a region in an MHC class II molecule of a recipient" (e.g., the hypervariable region), and is a peptide that has a sequence either identical to or substantially identical to the naturally occurring MHC amino acid sequence of the region in the recipient. It is understood that MHC class II molecule of a recipient refers to the MHC class II molecule that is expressed in the recipient.

In some embodiments, the MHC molecule is MHC class I molecule. Thus, "a peptide derived from a MHC class I molecule" refers to a peptide that has a sequence "from a region in an MHC class I molecule" (e.g., the hypervariable region), and is a peptide that has a sequence either identical to or substantially identical to the naturally occurring MHC amino acid sequence of the region. Accordingly, "a peptide derived from a MHC class I molecule of a recipient" refers to a peptide that has a sequence "from a region in an MHC class I molecule of a recipient" (e.g., the hypervariable region), and is a peptide that has a sequence either identical to or substantially identical to the naturally occurring MHC amino acid sequence of the region in the recipient. It is understood that MHC class I molecule of a recipient refers to the MHC class I molecule that is expressed in the recipient.

Accordingly, "a peptide derived from a MHC class I molecule of a donor" refers to a peptide that has a sequence "from a region in an MHC class I molecule of a donor" (e.g., the hypervariable region), and is a peptide that has a sequence either identical to or substantially identical to the naturally occurring MHC amino acid sequence of the region in the donor. In some embodiments, the peptide derived from a MHC class I molecule can comprise a sequence from the hypervariable region of the MHC class I molecule. It is understood that MHC class I molecule of a donor refers to the MHC class I molecule that is expressed in the donor. In some embodiments, the MHC class I molecule of the donor is mismatched with the MHC class I molecule of the recipient of the transplant. In some embodiments, the peptide derived from a MHC class I molecule will comprise a sequence from the hypervariable region of the MHC class I molecule.

As used herein a "hypervariable region" of an MHC molecule is a region of the molecule in which polypeptides encoded by different alleles at the same locus have high sequence variability or polymorphism. The polymorphism is typically concentrated in the α1 and α2 domains of in Class I molecules and in the α1 and β1 domains of Class II molecules. The number of alleles and degree of polymorphism among alleles may vary at different loci. For instance, in HLA-DR molecules all the polymorphism is attributed to the β chain and the α chain is relatively invariant. For HLA-DQ, both the α and β chains are polymorphic. In some embodiments, a peptide derived from a MHC molecule comprises a sequence that is at least about 50%, 60%, 70%, 80%, 90%, 95%, 99%, or 100% identical to a sequence selected from Table 1

Peptides Derived from MHC-Class I Molecule

In some embodiments, the peptide derived from a MHC molecule is derived from a MHC class I molecule. The human Class I proteins (MHC class I molecules) have also been studied (Bjorkman, P. J., et al., (1987) Nature 329:506-512). These are found to consist of a 44 kd subunit MHC class I heavy chain and a 12 kd β2-microglobulin subunit which is common to all antigenic specificities. Further work has resulted in a detailed picture of the 3-D structure of HLA-A2, a Class I human antigen.

Structurally, MHC class I molecules are heterodimers comprised of two noncovalently bound polypeptide chains, a larger "MHC class I heavy chain (α)" and a smaller "light" chain ((B-2-microglobulin). The polymorphic, polygenic heavy chain (45 kDa), is encoded within the MHC on chromosome six. Chromosome 6 has three loci, HLA-A, HLA-B, and HLA-C, the first two of which have a large number of alleles encoding MHC class I heavy chain alloantigens, HLA-A, HLA-B respectively. MHC class I heavy chain (α) (e.g., HLA-A, HLA-B and HLA-C) is subdivided into three extracellular domains (designated α1, α2, and α3), one intracellular domain, and one transmembrane domain. The two outermost extracellular domains, α1 and α2, together form the groove that binds antigenic peptide. Thus, interaction with the TCR occurs at this region of the protein. The 3rd extracellular domain of the molecule contains the recognition site for the CD8 protein on the CTL; this interaction serves to stabilize the contact between the T cell and the APC.

The invariant light chain (12 kDa), encoded outside the MHC on chromosome 15, consists of a single, extracellular polypeptide. The terms "MHC class I light chain", "β-2-microglobulin", and "B2m" may be used interchangeably herein. Association of the class I heavy and light chains is required for expression of MHC class I molecules on cell membranes. In this picture, the β2-microglobulin protein and α3 domain of the heavy chain are associated. Accordingly, the MHC class I molecule as disclosed herein can refer to a MHC class I heterodimer, a MHC class I heavy chain (e.g., HLA-A, HLA-B, or HLA-C), a MHC class I light chain or portions thereof or regions thereof. In some embodiments, the peptide can be derived from a MHC class I heavy chain e.g., HLA-A, or HLA-B. In some embodiments, the peptide can comprise sequence from the α1, α2, or α3 region of the MHC class I heavy chain. The α1 and α2 domains of the heavy chain comprise the hypervariable region which forms the antigen-binding sites to which the peptide is bound. In some embodiments, a peptide can be derived from a α1 or α2 domains of the MHC class I heavy chain. In some embodiments, the peptide derived from a MHC class I molecule can comprise sequence from a hypervariable region of a MHC class I molecule.

Peptide Derived from MHC-Class II Molecule

In some embodiments, the peptide derived from a MHC molecule is derived from a MHC class II molecule. MHC class II glycoproteins, HLA-DR, HLA-DQ, and HLA-DP (encoded by alleles at the HLA-DR, DP, and DQ loci) have a domain structure, including antigen binding sites, similar to that of Class I. MHC class II molecules are heterodimers, consist of two nearly homologous subunits; a and β chains, both of which are encoded in the MHC. Accordingly, in some embodiments, the peptide derived from MHC class II molecule is derived from a MHC class II α chain (e.g., HLA-DPA, HLA-DQA, or HLA-DRA), or MHC class II β chain (e.g., HLA-DPB, HLA-DQB, or HLA-DRB), or domains thereof. In some embodiments, the peptide derived from MHC class II molecule is derived from HLA-DRB.

The HLA-DRB is encoded by four gene loci in human (HLA-DRB1, HLA-DRB3, HLA-DRB4 and HLA-DRB4), however no more than 3 functional loci are present in a single individual, and no more than two on a single chromosome. In some embodiments, the HLA-DRB is encoded by HLA-DRB1, HLA-DRB3, HLA-DRB4 or HLA-DRB4 gene locus. In some embodiments, the HLA-DRB is encoded by HLA-DRB1*03 or HLA-DRB1*04. The HLA-DRB1 locus is ubiquitous and encodes a very large number of functionally variable gene products (HLA-DR1 to HLA-DR17). The HLA-DRB3 locus encodes the HLA-DR52 specificity, is moderately variable and is variably associated with certain HLA-DRB1 types. The HLA-DRB4 locus encodes the HLA-DR53. In some embodiments, the peptide derived from a MHC class II molecule is derived from HLA-DR1, HLA-DR2, HLA-DR3, HLA-DR4, or HLA-DR5. In some embodiments, the peptide derived from HLA-DR3 can comprise a sequence that is at least about 50%, 60%, 70%, 80%, 90%, 95%, 99%, or 100% identical to a sequence selected from Table 1

In some embodiments, the peptide derived from a MHC class II molecule can be derived from a globular domain e.g., α1, α2, β1, or B2. The peptides derived from MHC class II molecule can comprise the entire subunit (a or β chain) or large portions thereof. For instance, the peptides can comprise an extracellular domain from an MHC class II subunit of about 90-100 residues (e.g., β1 and B2 or α1 and α2 of class II molecules). The N-terminal portions of the α and βchains, the α1 and β1 domains, contain hypervariable regions which are thought to comprise the majority of the antigen-binding sites (see, Brown et al., Nature 364:33-39 (1993)). Accordingly, the peptides derived from MHC class II molecule can comprise a sequence from hypervariable region of the MHC class II molecule (e.g., the α1 and β1 domains of the α and β chains subunits respectively).

In some embodiments the peptides are derived from hypervariable regions of the α or βchain of an MHC Class II molecule associated with the deleterious immune response. In this way, the ability of antigen presenting cells (APC) to present the target antigen (e.g., autoantigen or allergen) is inhibited.

The methods for obtaining sequences of MHC molecule are disclosed above. The amino acid sequences of peptides capable of binding MHC complex are currently known, and others can be determined through routine experimentation well known to those skilled in the art (see, e.g., Rammensee et al., (1995) Immunogenetics 41:178-228). For example, if the peptide antigen has been isolated it is possible to identify its sequence by techniques such as Edman degradation (Nelson et al., (1992) Proc. Natl. Acad. Sci. USA 89:7380-7383) and mass spectrometric methods (see, e.g., Cox et al., (1994) Science 264:716-719). In addition, whether a given peptide of interest is capable of binding a peptide bindiong groove of a MHC molecule can be determined by scanning the sequence of a peptide of interest with the respective consensus-motif of the restricting MHC-complex (see, e.g., WO96/27387). In general, consensus-motifs of MHC-ligands are allele-specific (i.e., the motif of peptides bound, for example, to HLA-A2.1 is different from the motif of peptides which bind to HLA-B2701). Such motifs summarize invariant features contained within such peptides including, for example, length and position of the invariant amino acid positions. Consensus motifs have been identified for the ligands of MHC class I complex and MHC class II complex and methods for the identification of such motifs have been described. These include, for example, pool sequencing (Falk et al., (1991) Nature 351:290-296; Falk et al., 0 94) Immunogenetics 39:230-242) as well as the use of phage display libraries (e.g., Hammer et al., (1992) J. Exp. Med. 179:1007-1013); selected motifs are specifically disclosed by Rammensee et al., (1995) Immunogenetics 41:178-228. Methods for the prediction of the binding affinity of a given peptide to MHC complex are known in the art (see for example, WO1998059244A1). In some embodiments, the peptides predicted to bind MHC class II complex of the recipient of a transplant with a high affinity are preferred in the methods disclosed herein. For instance, once the sequence of an polypeptide of a MHC molecule is obtained, for example from a publically available sequences (e.g., IPD-MHC (http://www.ebi.ac.uk/ipd/mhc/) or IPD-IMGT/HLA (https://www.ebi.ac.uk/ipd/imgt/hla/)) by PCR amplification from the genomic DNA of a subject, the peptides that are capable of binding the MHC molecule can be determined, for example, by a in silico prediction tool. A variety of MHC class II complex binding prediction tools are publicly available and will be known to those skilled in the art. Non limiting examples include; ARB, PROPRED, SVMHC, SYFPEITHI, RANKPEP, SMM-align, SVRMHC, MHC2PRED and MHCPRED; see WANG P et al, PLOS Comput Biol. 2008. In some embodiments, the MHC class II binding peptides (e.g., peptides derived from MHC class II or peptides derived from MHC class I molecule can be predicted using the publicly available The Immune Epitope Database and Analysis Resource (IEDB). Cells comprising a variety of MHC genes are readily available, for instance, they may be obtained from the American Type Culture Collection ("Catalogue of Cell Lines and Hybridomas," 6th edition (1988) Rockville, Md., U.S.A. Standard techniques can be used to screen cDNA libraries to identify sequences encoding the desired sequences (see, Sambrook et al., Molecular Cloning—A Laboratory Manual, Cold Spring Harbor Laboratory, Cold Spring Harbor, N.Y., 1989, which is incorporated herein by reference).

The biochemical approach, involves the fractionation of the MHC complex bound peptides by chromatography, assaying the fractions for immunological activity and sequencing the individual peptides in the active fractions can also be used, e.g, WO1994004171A1. The peptides predicted to bind MHC molecule can be tested in an HLA-Binding assay, e.g., ProImmune REVEAL® MHC Class II, Creative Biolabs SIAT®, see Salvat R. et al. J Vis Exp. 2014.

In some embodiments, the peptide derived from MHC molecule comprises at least 10, 11, 12, 13, 14, 15, 16, 17, 18, 19, 20, 21, 22, 23, 24, 25, 26, 27, 28, 29, 30 or more amino acid residues.

Binding to MHC Molecule

In aspects of the present disclosure, the peptide derived from a MHC molecule are capable of binding the peptide binding groove of the MHC molecule to generate a MHC-peptide complex. As used herein, the term "capable of binding the peptide binding groove" means a peptide is capable of selectively binding within the cleft formed by the α and β chains of a specified MHC molecule to form an MHC-peptide antigen complex. For MHC class II complexes, the peptides are typically 10-25 amino acids in length, and more typically 13-18 residues in length, although longer and shorter ones may bind effectively. As used herein, the term "selectively binding" means capable of binding in the electro- and stereospecific manner of an antibody to antigen or ligand to receptor. With respect to a peptide capable of binding a peptide binding groove, selective binding entails the non-covalent binding of specific side chains of the peptide within the binding pockets present in the MHC binding cleft in order to form an MHC-peptide complex (see, e.g., Brown et al., (1993) Nature 364:33-39; Stern et al., (1994) Nature 368:215-221; Stern and Wiley (1992) CeU 68:465-477).

Nucleic Acid Construct

The disclosure also pertains to an isolated nucleic acid molecule (RNA, mRNA, cDNA or genomic DNA) comprising a transgene disclosed herein. In some embodiments, the nucleic acid construct further includes a first cis acting regulatory sequence. The cis acting regulatory sequence can include a promoter sequence and additional transcriptional or a translational enhancer sequences all of which serve for facilitating the expression of the nucleic acid sequence when introduced into a host cell. In some cases, the nucleic acid construct is inserted into a DNA vector (i.e., DNA expression vector) capable of expressing the MHC complex in a desired cell, typically a eukaryotic or prokaryotic cell. The nucleic acid molecule can include or be fused to operably linked control elements such as a promoter, leader and/or optional enhancer sequences, to augment expression of the MHC complex in the cell. Alternatively, the nucleic acid segment can be optimized for use in a cell-free translation system if desired. In some embodiments, the nucleic acid molecule is for CRISPR/Cas mediated integration into a specific genomic locus. Homologous recombination can permit site-specific integration of a transgene. Accordingly, in some embodiments, the nucleic acid molecule comprises a first flanking sequence homologous to a genome sequence upstream of a select insertion site, said first flanking sequence located upstream of a transgene. In some embodiments, the nucleic acid molecule comprises a second flanking sequence homologous to a genome sequence downstream of a select insertion site, said second flanking sequence located downstream of a transgene. Vector comprising the isolated nucleic acid construct are also contemplated in the present disclosure. In some embodiments, the first flanking sequence comprises a sequence that is at least about 50%, 60%, 70%, 80%, 90%, 95%, 98%, 99% or 100% identical to sequence set forth in SEQ ID NO: 5. In some embodiments, the first flanking sequence comprises a sequence that is at least about 50%, 60%, 70%, 80%, 90%, 95%, 98%, 99% or 100% identical to sequence set forth in SEQ ID NO: 6.

In some embodiments, an isolated nucleic acid molecule comprises a sequence that is at least about 50%, 60%, 70%, 80%, 90%, 95%, 98%, 99% or 100% identical to a sequence selected from SEQ ID NO: 3, or SEQ ID NO: 4.

The genetically modified non-human animals and cells can also comprise one or more additional genetic modifications, such as any of the genetic modifications (e.g., knock-ins, knock-outs, gene disruptions, etc.) disclosed herein. For example, the genetically modified cells, or genetically modified non-human animal, and the cells, tissues and organs derived therefrom can further comprise one or more additional transgenes encoding ICP47, CD46, CD55, CD59, HLA-E, HLA-G (e.g., HLA-G1, HLA-G2, HLA-G3, HLA-G4, HLA-G5, HLA-G6, or HLA-G7), B2M, any functional fragments thereof, and/or any combination thereof. The disclosure is not limited to the exemplified modification and contemplates various combinations of the transgenes and gene disruptions disclosed herein.

Human Leukocyte Antigen G (HLA-G)

In some embodiments, the genetically modified cells, or genetically modified non-human animal, and the cells, tissues and organs derived therefrom can further comprise a transgene encoding HLA-G. The HLA-G can be a potent immuno-inhibitory and tolerogenic molecule. HLA-G expression in a human fetus can enable the human fetus to elude the maternal immune response. Neither stimulatory functions nor responses to allogeneic HLA-G have been reported to date. HLA-G can be a non-classical HLA class I molecule. It can differ from classical MHC class I molecules by its genetic diversity, expression, structure, and function. HLA-G can be characterized by a low allelic polymorphism. Expression of HLA-G can be restricted to trophoblast cells, adult thymic medulla, and stem cells. However, HLA-G neo-expression may be induced in pathological conditions such as cancers, multiple sclerosis, inflammatory diseases, or viral infections.

Seven isoforms of HLA-G have been identified. The different isoforms can be products of alternative splicing. Four of these can be membrane bound (HLA-G1 to G4), and 3 can be soluble isoforms (HLA-G5 to G7). HLA-G1 and HLA-G5 isoforms present the typical structure of the classical HLA class I molecules formed by a 3 globular domain (α1-α3) heavy-chain, noncovalently associated to β-2-microglobulin (B2M) and a nonapeptide. The truncated isoforms lack 1 or 2 domains, although they all contain the α1 domain, and they are all B2M-free isoforms.

HLA-G can exert an immuno-inhibitory function through direct binding to inhibitory receptors, e.g., ILT2/CD85j/LILRB1, ILT4/CD85d/LILRB2, or KIR2DL4/CD158d.

ILT2 can be expressed by B cells, some T cells, some NK cells, and monocytes/dendritic cells. ILT4 can be myeloid-specific and its expression can be restricted to monocytes/dendritic cells. KIR2DL4 can be a specific receptor for HLA-G. It can be expressed by the $CD56^{bright}$ subset of NK cells. ILT2 and ILT4 receptors can bind a wide range of classical HLA molecules through the α3 domain and B2M. However, HLA-G can be their ligand of highest affinity.

ILT2-HLA-G interaction can mediate the inhibition of, for example: i) NK and antigen-specific CD8+ T cell cytolytic function, ii) alloproliferative response of CD4+ T cells, and iii) maturation and function of dendritic cells. ILT2-HLA-G interaction can impede both naïve and memory B cell function in vitro and in vivo. HLA-G can inhibit B cell proliferation, differentiation, and Ig secretion in both T cell-dependent and -independent models of B cell activation. HLA-G can act as a negative B cell regulator in modulating B cell Ab secretion. HLA-G can also induce the differentiation of regulatory T cells, which can then inhibit allogeneic responses themselves may participate in the tolerance of allografts. The expression of HLA-G by tumor cells can enable the escape of immunosurveillance mediated by host T lymphocytes and NK cells. Thus, the expression of HLA-G by malignant cells may prevent tumor immune eradication by inhibiting the activity of tumor-infiltrating NK cells, cytotoxic T lymphocytes (CTLs), and antigen presenting cells (APCs). The HLA-G structure variation, particularly its monomeric/multimeric status and its association with B2M, can play a role in the biological function of HLA-G, its regulation and its interactions with the inhibitory receptors ILT2 and ILT4.

ILT2 and ILT4 inhibitory receptors may have a higher affinity for HLA-G multimers than monomeric structures. HLA-G1 and HLA-G5 (HLA-G1/5) can form dimers through disulphide bonds between unique cysteine residues at positions 42 (Cys42-Cys42), within the α1 domain. Dimers of B2M-associated HLA-G1 may bind ILT2 and ILT4 with higher affinity than monomers. This increased affinity of dimers may be due to an oblique orientation that exposes the ILT2— and ILT4-binding sites of the α3 domain, making it more accessible to the receptors. Both ILT2 and ILT4 can bind the HLA-G α3 domain at the level of F195 and Y197 residues.

ILT2 and ILT4 bind differently to their HLA-G isoforms. ILT2 may recognize only B2M-associated HLA-G structures, whereas ILT4 may recognize both B2M-associated and B2M-free HLA-G heavy chains. B2M-free heavy chains have been detected at the cell surface and in culture supernatants of HLA-G-expressing cells. Furthermore, B2M-free HLA-G heavy chains may be the main structure produced by human villous trophoblast cells. The presence of (B2M-free) α1-α3 structures (HLA-G2 and G-6 isoforms) was shown in the circulation of human heart transplant recipients and may be associated with better allograft acceptance. The α1-α3 structure may bind only to ILT4 but not ILT2. However, α1-α3 dimers (with dimerization of α1-α3 monomers achieved through disulfide bonds between two free cysteines in position 42) may be tolerogenic in vivo in an allogeneic murine skin transplantation model. An (α1-α3) x2 synthetic molecule may inhibit the proliferation of tumor cell lines that did not express ILT4. This may indicate the existence of yet unknown receptors for HLA-G.

Accordingly, in some embodiments, genetically modified non-human animals and cells comprises an exogenous nucleic acid sequence encoding for an HLA-G protein.

In some embodiments, a genetically modified non-human animal, cells, tissues or organs can further comprise one or more transgenes comprising one or more polynucleotide inserts. The polynucleotide inserts can encode one or more proteins or functional fragments thereof. For example, a non-human genetically modified animal can comprise one or more exogenous nucleic acid sequences encoding one or more proteins or functional fragments thereof. In some cases, a non-human animal can comprise one or more transgenes comprising one or more polynucleotide inserts encoding proteins that can reduce expression and/or function of MHC molecules (e.g., MHC I molecules and/or MHC II molecules). The one or more transgenes can comprise one or more polynucleotide inserts encoding MHC I formation suppressors, regulators of complement activations, inhibitory ligands for NK cells, B7 family members, CD47, serine protease inhibitors, galectins, and/or any fragments thereof. In some cases, the MHC I formation suppressors can be infected cell protein 47 (ICP47). In some cases, regulators of complement activation can comprise cluster of differentiation 46 (CD46), cluster of differentiation 55 (CD55), and cluster of differentiation 59 (CD59). In some cases, inhibitory ligands for NK cells can comprise leukocyte antigen E (HLA-E), human leukocyte antigen G (HLA-G), and β-2-microglobulin (B2M). An inhibitory ligand for NK cells can be an isoform of HLA-G, e.g., HLA-G1, HLA-G2, HLA-G3, HLA-G4, HLA-G5, HLA-G6, or HLA-G7. For example, inhibitory ligand for NK cells can be HLA-G1. A transgene of HLA-G (e.g., HLA-G1, HLA-G2, HLA-G3, HLA-G4, HLA-G5, HLA-G6, or HLA-G7) can refer to a transgene comprising a nucleotide sequence encoding HLA-G (e.g., HLA-G1, HLA-G2, HLA-G3, HLA-G4, HLA-G5, HLA-G6, or HLA-G7). As used herein, in some cases, a transgene encoding HLA-G (e.g., HLA-G1, HLA-G2, HLA-G3, HLA-G4, HLA-G5, HLA-G6, or HLA-G7) can be a transgene encoding 100% or about 100% of the amino acid sequence of HLA-G (e.g., HLA-G1, HLA-G2, HLA-G3, HLA-G4, HLA-G5, HLA-G6, or HLA-G7). In other cases, a transgene encoding HLA-G (e.g., HLA-G1, HLA-G2, HLA-G3, HLA-G4, HLA-G5, HLA-G6, or HLA-G7) can be a transgene encoding the full or partial sequence of HLA-G (e.g., HLA-G1, HLA-G2, HLA-G3, HLA-G4, HLA-G5, HLA-G6, or HLA-G7). For example, the transgene can encode at least or at least about 99%, 95%, 90%, 80%, 70%, 60%, or 50% of the amino acid sequence of HLA-G (e.g., HLA-G1, HLA-G2, HLA-G3, HLA-G4, HLA-G5, HLA-G6, or HLA-G7). For example, the transgene can encode 90% of the HLA-G amino acid sequence. A transgene can comprise polynucleotides encoding a functional (e.g., a partially or fully functional) HLA-G (e.g., HLA-G1, HLA-G2, HLA-G3, HLA-G4, HLA-G5, HLA-G6, or HLA-G7). In some cases, the one or more transgenes can comprise one or more polynucleotide inserts encoding one or more of ICP47, CD46, CD55, CD59, HLA-E, HLA-G (e.g., HLA-G1, HLA-G2, HLA-G3, HLA-G4, HLA-G5, HLA-G6, or HLA-G7), and B2M. The HLA-G genomic DNA sequence can have 8 exons by which alternative splicing results in 7 isoforms. The HLA-G1 isoform can exclude exon 7. The HLA-G2 isoform can exclude exon 3 and 7. Translation of intron 2 or intron 4 can result secreted isoforms due to the loss of the transmembrane domain expression. In some cases, B7 family members can comprise CD80, CD86, programed death-ligand 1 (PD-L1), programed death-ligand 2 (PD-L2), CD275, CD276, V-set domain containing T cell activation inhibitor 1 (VTCN1), platelet receptor Gi24, natural cytotoxicity triggering receptor 3 ligand 1 (NR3L1), and HERV-H LTR-associating 2 (HHLA2). For example, a α7 family member can be PD-L1 or PD-L2. In some cases, a serine protease inhibitor can be serine protease inhibitor 9 (Spi9). In some cases, galectins can comprise galectin-1, galectin-2, galectin-3, galectin-4, galectin-5, galectin-6, galectin-7, galectin-8, galectin-9, galectin-10, galectin-11, galectin-12, galectin-13, galectin-14, and galectin-15. For example, a galectin can be galectin-9.

In some embodiments, a genetically modified non-human animal or cells, tissues and organs derived therefrom or a genetically modified cell of the present disclosure can further comprise reduced expression of one or more genes and one or more transgenes disclosed herein. In some cases, a genetically modified non-human animal can comprise reduced expression of one or more of NLRC5, TAP1, CXCL10, MICA, MICB, C3, CIITA, GGTA1, CMAH, and B4GALNT2, and one or more transgenes comprising one or more polynucleotide inserts encoding one or more of ICP47, CD46, CD55, CD59, HLA-E, HLA-G (e.g., HLA-G1, HLA-G2, HLA-G3, HLA-G4, HLA-G5, HLA-G6, or HLA-G7), B2M, PD-L1, PD-L2, CD47, Spi9, and galectin-9. In some cases, a genetically modified non-human animal can comprise reduced expression GGTA1, CMAH, and B4GALNT2, and exogenous polynucleotides encoding HLA-G (e.g., HLA-G1, HLA-G2, HLA-G3, HLA-G4, HLA-G5, HLA-G6, or HLA-G7), CD47 (e.g., human CD47), PD-L1 (e.g., human PD-L1), and PD-L2 (e.g., human PD-L2). In some cases, a genetically modified non-human animal can comprise reduced expression GGTA1, CMAH, and B4GALNT2, and exogenous polynucleotides encoding HLA-E, CD47 (e.g., human CD47), PD-L1 (e.g., human PD-L1), and PD-L2 (e.g., human PD-L2). In some cases, a genetically modified non-human animal can comprise reduced expression NLRC5, C3, CXC10, GGTA1, CMAH, and B4GALNT2, and exogenous polynucleotides encoding HLA-G (e.g., HLA-G1, HLA-G2, HLA-G3, HLA-G4, HLA-G5, HLA-G6, or HLA-G7), CD47 (e.g., human CD47), PD-L1 (e.g., human PD-L1), and PD-L2 (e.g., human PD-L2). In some cases, a genetically modified non-human animal can comprise reduced expression TAP1, C3, CXC10GGTA1, CMAH, and B4GALNT2, and exogenous polynucleotides encoding HLA-G (e.g., HLA-G1, HLA-G2, HLA-G3, HLA-G4, HLA-G5, HLA-G6, or HLA-G7), CD47 (e.g., human CD47), PD-L1 (e.g., human PD-L1), and PD-L2 (e.g., human PD-L2). In some cases, a genetically modified non-human animal can comprise reduced expression NLRC5, C3, CXC10, GGTA1, CMAH, and B4GALNT2, and exogenous polynucleotides encoding HLA-E, CD47 (e.g., human CD47), PD-L1 (e.g., human PD-L1), and PD-L2 (e.g., human PD-L2). In some cases, a genetically modified non-human animal can comprise reduced expression TAP1, C3, CXC10, GGTA1, CMAH, and B4GALNT2, and exogenous polynucleotides encoding HLA-E. In some cases, a genetically modified non-human animal can comprise reduced expression of GGTA1 and a transgene comprising one or more polynucleotide inserts encoding HLA-E. In some cases, a genetically modified non-human animal can comprise reduced expression of GGTA1 and a transgene comprising one or more polynucleotide inserts encoding HLA-G (e.g., HLA-G1, HLA-G2, HLA-G3, HLA-G4, HLA-G5, HLA-G6, or HLA-G7). In some cases, a genetically modified non-human animal can comprise a transgene comprising one or more polynucleotide inserts encoding HLA-G (e.g., HLA-G1, HLA-G2, HLA-G3, HLA-G4, HLA-G5, HLA-G6, or HLA-G7) inserted adjacent to a Rosa26 promoter, e.g., a porcine Rosa26 promoter. In some cases, a genetically modified non-human animal can comprise reduced expression of NLRC5, C3, GGTA1, CMAH, and B4GALNT2, and transgenes comprising polynucleotides encoding proteins or functional fragments thereof, where the proteins comprise HLA-G1, Spi9, PD-L1, PD-L2, CD47, and galectin-9. In some cases, a genetically modified non-human animal can comprise reduced expression of TAP1, C3, GGTA1, CMAH, and B4GALNT2, and transgenes comprising polynucleotides encoding proteins or functional fragments thereof, where the proteins comprise HLA-G1, Spi9, PD-L1, PD-L2, CD47, and galectin-9. In some cases, a genetically modified non-human animal can comprise reduced expression of NLRC5, TAP1, C3, GGTA1, CMAH, and B4GALNT2, and transgenes comprising polynucleotides encoding proteins or functional fragments thereof, where the proteins comprise HLA-G1, Spi9, PD-L1, PD-L2, CD47, and galectin-9. In some cases, a genetically modified non-human animal can comprise reduced protein expression of NLRC5, C3, GGTA1, and CXCL10, and transgenes comprising polynucleotides encoding proteins or functional fragments thereof, where the protein comprise HLA-G1 or HLA-E. In some cases, a genetically modified non-human animal can comprise reduced protein expression of TAP1, C3, GGTA1, and CXCL10, and transgenes comprising polynucleotides encoding proteins or functional fragments thereof, where the protein comprise HLA-G1 or HLA-E. In some cases, a genetically modified non-human animal can comprise reduced protein expression of NLRC5, TAP1, C3, GGTA1, and CXCL10, and transgenes comprising polynucleotides encoding proteins or functional fragments thereof, where the protein comprise HLA-G1 or HLA-E. In some cases, CD47, PD-L1, and PD-L2 encoded by the transgenes herein can be human CD47, human PD-L1 and human PD-L2.

A genetically modified non-human animal and a genetically modified cell can comprise a transgene inserted in a locus in the genome of the animal. In some cases, the transgene is inserted in a safe harbor site, e,g. ROSA26. In some cases, a transgene can be inserted adjacent to the promoter of or inside a targeted gene. In some cases, insertion of the transgene can reduce the expression of the targeted gene. The targeted gene can be a gene whose expression is reduced disclosed herein. For example, a transgene can be inserted adjacent to the promoter of or inside one or more of NLRC5, TAP1, CXCL10, MICA, MICB, C3, CIITA, GGTA1, CMAH, and B4GALNT2. In some cases, a transgene can be inserted adjacent to the promoter of or inside GGTA1. In some cases, a transgene (e.g., a CD47 transgene) can be inserted adjacent to a promoter that allows the transgene to selectively expression in certain types of cells. For example, a CD47 transgene can be inserted adjacent to promoter that allows the CD47 transgene to selectively express in blood cells and splenocytes. One of such promoters can be GGTA1 promoters.

A non-human animal can comprise 1, 2, 3, 4, 5, 6, 7, 8, 9, 10, 11, 12, 13, 14, 15, 16, 17, 18, 19, 20, or more transgenes. For example, in addition to a transgene encoding a MHC molecule, a non-human animal and a cell can comprise one or more transgene comprising ICP47, CD46, CD55, CD59, HLA-E, HLA-G (e.g., HLA-G1, HLA-G2, HLA-G3, HLA-G4, HLA-G5, HLA-G6, or HLA-G7), B2M, Spi9, PD-L1, PD-L2, CD47, galectin-9, any functional fragments thereof, or any combination thereof.

A combination of transgenes and gene disruptions can be used. A non-human animal can comprise one or more reduced genes and one or more transgenes. For example, one or more genes whose expression is reduced can comprise any one of NLRC5, TAP1, GGTA1, B4GALNT2, CMAH, CXCL10, MICA, MICB, C3, CIITA, and/or any combination thereof, and one or more transgene can comprise ICP47, CD46, CD55, CD 59, any functional fragments thereof, and/or any combination thereof. For example, solely to illustrate various combinations, one or more genes whose expression is disrupted can comprise NLRC5 and one or more transgenes comprise a nucleic acid sequence encoding a MHC molecule (e.g., single chain chimeric MHC molecule), a $\alpha$ chain or a fragment thereof, or a $\beta$ chain or a fragment thereof, or a peptide derived from a MHC molecule. One or more genes whose expression is disrupted can also comprise TAP1, and one or more transgenes comprise a nucleic acid sequence encoding a MHC molecule (e.g., single chain chimeric MHC molecule), a $\alpha$ chain or a fragment thereof, or a $\beta$ chain or a fragment thereof, or a peptide derived from a MHC molecule. One or more genes whose expression is disrupted can also comprise NLRC5 and TAP1, and one or more transgenes comprise a nucleic acid sequence encoding a MHC molecule (e.g., single chain chimeric MHC molecule), a $\alpha$ chain or a fragment thereof, or a $\beta$ chain or a fragment thereof, or a peptide derived from a MHC molecule. One or more genes whose expression is disrupted can also comprise NLRC5, TAP1, and GGTA1, and one or more transgenes comprise a nucleic acid sequence encoding a MHC molecule (e.g., single chain chimeric MHC molecule), a $\alpha$ chain or a fragment thereof, or a $\beta$ chain or a fragment thereof, or a peptide derived from a MHC molecule. One or more genes whose expression is disrupted can also comprise NLRC5, TAP1, B4GALNT2, and CMAH, and one or more transgenes comprise a nucleic acid sequence encoding a MHC molecule (e.g., single chain chimeric MHC molecule), a α chain or a fragment thereof, or a β chain or a fragment thereof, or a peptide derived from a MHC molecule. One or more genes whose expression is disrupted can also comprise NLRC5, TAP1, GGTA1, B4GALNT2, and CMAH, and one or more transgenes comprise a nucleic acid sequence encoding a MHC molecule (e.g., single chain chimeric MHC molecule), a α chain or a fragment thereof, or a β chain or a fragment thereof, or a peptide derived from a MHC molecule.

In some cases, a first exon of a gene is genetically modified. For example, one or more first exons of a gene that can be genetically modified can be a gene selected from a group consisting of NLRC5, TAP1, GGTA1, B4GALNT2, CMAH, CXCL10, MICA, MICB, C3, CIITA, cytidine monophospho-N-acetylneuraminic acid (CMP-N-NeuAc) hydrolase, or a PERV site and any combination thereof. In other cases, a second exon of a gene is targeted. Transgenes that can be used and are specifically contemplated can include those genes that exhibit a certain identity and/or homology to genes disclosed herein, for example, a nucleic acid sequence encoding a MHC molecule (e.g., single chain chimeric MHC molecule), a α chain of a MHC molecule or a fragment thereof, or a β chain of a MHC molecule or a fragment thereof, or a peptide derived from a MHC molecule, ICP47, CD46, CD55, CD59, HLA-E, HLA-G (e.g., HLA-G1, HLA-G2, HLA-G3, HLA-G4, HLA-G5, HLA-G6, or HLA-G7), B2M, Spi9, PD-L1, PD-L2, CD47, galectin-9, any functional fragments thereof, and/or any combination thereof. Therefore, it is contemplated that if gene that exhibits at least or at least about 60%, 70%, 80%, 90%, 95%, 98%, or 99% homology, e.g., at least or at least about 99% to 90%; 90% to 80%; 80% to 70%; 70% to 60% homology; (at the nucleic acid or protein level), it can be used as a transgene. It is also contemplated that a gene that exhibits at least or at least about 60%, 65%, 70%, 75%, 80%, 85%, 90%, 95%, 98%, or 99%, identity e.g., at least or at least about 99% to 90%; 90% to 80%; 80% to 70%; 70% to 60% identity; (at the nucleic acid or protein level) can be used as a transgene.

A non-human animal can also comprise 1, 2, 3, 4, 5, 6, 7, 8, 9, 10, 11, 12, 13, 14, 15, 16, 17, 18, 19, 20, or more dominant negative transgenes. Expression of a dominant negative transgenes can suppress expression and/or function of a wild type counterpart of the dominant negative transgene. Thus, for example, a non-human animal comprising a dominant negative transgene X, can have similar phenotypes compared to a different non-human animal comprising an X gene whose expression is reduced. One or more dominant negative transgenes can be dominant negative NLRC5, dominant negative TAP1, dominant negative GGTA1, dominant negative CMAH, dominant negative B4GALNT2, dominant negative CXCL10, dominant negative MICA, dominant negative MICB, dominant negative CIITA, dominant negative C3, or any combination thereof.

Also provided is a non-human animal comprising one or more transgenes that encodes one or more nucleic acids that can suppress genetic expression, e.g., can knockdown a gene. RNAs that suppress genetic expression can comprise, but are not limited to, shRNA, siRNA, RNAi, and microRNA. For example, siRNA, RNAi, and/or microRNA can be given to a non-human animal to suppress genetic expression. Further, a non-human animal can comprise one or more transgene encoding shRNAs. shRNA can be specific to a particular gene. For example, a shRNA can be specific to any gene described in the application, including but not limited to, NLRC5, TAP1, GGTA1, B4GALNT2, CMAH, CXCL10, MICA, MICB, B4GALNT2, CIITA, C3, and/or any combination thereof.

When transplanted to a subject, cells, tissues, or organs from the genetically modified non-human animal can trigger lower immune responses (e.g., transplant rejection) in the subject compared to cells, tissues, or organs from a non-genetically modified counterpart. In some cases, the immune responses can include the activation, proliferation and cytotoxicity of T cells (e.g., CD8+ T cells and/or CD4+ T cells) and NK cells. Thus, phenotypes of genetically modified cells disclosed herein can be measured by co-culturing the cells with NK cells, T cells (e.g., CD8+ T cells or CD4+ T cells), and testing the activation, proliferation and cytotoxicity of the NK cells or T cells. In some cases, the T cells or NK cells activation, proliferation and cytotoxicity induced by the genetically modified cells can be lower than that induced by non-genetically modified cells. In some cases, phenotypes of genetically modified cells herein can be measured by Enzyme-Linked ImmunoSpot (ELISPOT) assays.

One or more transgenes can be from different species. For example, one or more transgenes can comprise a human gene, a mouse gene, a rat gene, a pig gene, a bovine gene, a dog gene, a cat gene, a monkey gene, a chimpanzee gene, or any combination thereof. For example, a transgene can be from a human, having a human genetic sequence. One or more transgenes can comprise human genes. In some cases, one or more transgenes are not adenoviral genes.

A transgene can be inserted into a genome of a non-human animal in a random or site-specific manner. For example, a transgene can be inserted to a random locus in a genome of a non-human animal. These transgenes can be fully functional if inserted anywhere in a genome. For instance, a transgene can encode its own promoter or can be inserted into a position where it is under the control of an endogenous promoter. Alternatively, a transgene can be inserted into a gene, such as an intron of a gene or an exon of a gene, a promoter, or a non-coding region. A transgene can be integrated into a first exon of a gene.

Sometimes, more than one copy of a transgene can be inserted into more than a random locus in a genome. For example, multiple copies can be inserted into a random locus in a genome. This can lead to increased overall expression than if a transgene was randomly inserted once. Alternatively, a copy of a transgene can be inserted into a gene, and another copy of a transgene can be inserted into a different gene. A transgene can be targeted so that it could be inserted to a specific locus in a genome of a non-human animal.

Expression of a transgene can be controlled by one or more promoters. A promoter can be a ubiquitous, tissue-specific promoter or an inducible promoter. Expression of a transgene that is inserted adjacent to a promoter can be regulated. For example, if a transgene is inserted near or next to a ubiquitous promoter, the transgene will be expressed in all cells of a non-human animal. Some ubiquitous promoters can be a CAGGS promoter, an hCMV promoter, a PGK promoter, an SV40 promoter, or a Rosa26 promoter.

A promoter can be endogenous or exogenous. For example, one or more transgenes can be inserted adjacent to an endogenous or exogenous Rosa26 promoter. Further, a promoter can be specific to a non-human animal. For example, one or more transgenes can be inserted adjacent to a porcine Rosa26 promoter.

Tissue specific promoter (which can be synonymous with cell-specific promoters) can be used to control the location of expression. For example, one or more transgenes can be inserted adjacent to a tissue-specific promoter. Tissue-specific promoters can be a FABP promoter, a Lck promoter, a CamKII promoter, a CD19 promoter, a Keratin promoter, an Albumin promoter, an aP2 promoter, an insulin promoter, an MCK promoter, an MyHC promoter, a WAP promoter, or a Col2A promoter. For example, a promoter can be a pancreas-specific promoter, e.g., an insulin promoter.

Inducible promoters can be used as well. These inducible promoters can be turned on and off when desired, by adding or removing an inducing agent. It is contemplated that an inducible promoter can be a Lac, tac, trc, trp, araBAD, phoA, recA, proU, cst-1, tetA, cadA, nar, PL, cspA, T7, VHB, Mx, and/or Trex.

A non-human animal or cells as described herein can comprise a transgene encoding insulin. A transgene encoding insulin can be a human gene, a mouse gene, a rat gene, a pig gene, a cattle gene, a dog gene, a cat gene, a monkey gene, a chimpanzee gene, or any other mammalian gene. For example, a transgene encoding insulin can be a human gene. A transgene encoding insulin can also be a chimeric gene, for example, a partially human gene.

Expression of transgenes can be measured by detecting the level of transcripts of the transgenes. For example, expression of transgenes can be measured by Northern blotting, nuclease protection assays (e.g., RNase protection assays), reverse transcription PCR, quantitative PCR (e.g., real-time PCR such as real-time quantitative reverse transcription PCR), in situ hybridization (e.g., fluorescent in situ hybridization (FISH)), dot-blot analysis, differential display, Serial analysis of gene expression, subtractive hybridization, microarrays, nanostring, and/or sequencing (e.g., next-generation sequencing). In some cases, expression of transgenes can be measured by detecting proteins encoded by the genes. For example, expression of one or more genes can be measured by protein immunostaining, protein immunoprecipitation, electrophoresis (e.g., SDS-PAGE), Western blotting, bicinchoninic acid assay, spectrophotometry, mass spectrometry, enzyme assays (e.g., enzyme-linked immunosorbent assays), immunohistochemistry, flow cytometry, and/or immunocytochemistry. In some cases, expression of transgenes can be measured by microscopy. The microscopy can be optical, electron, or scanning probe microscopy. In some cases, optical microscopy comprises use of bright field, oblique illumination, cross-polarized light, dispersion staining, dark field, phase contrast, differential interference contrast, interference reflection microscopy, fluorescence (e.g., when particles, e.g., cells, are immunostained), confocal, single plane illumination microscopy, light sheet fluorescence microscopy, deconvolution, or serial time-encoded amplified microscopy.

Insertion of transgenes can be validated by genotyping. Methods for genotyping can include sequencing, restriction fragment length polymorphism identification (RFLPI), random amplified polymorphic detection (RAPD), amplified fragment length polymorphism detection (AFLPD), PCR (e.g., long range PCR, or stepwise PCR), allele specific oligonucleotide (ASO) probes, and hybridization to DNA microarrays or beads. In some cases, genotyping can be performed by sequencing. In some cases, sequencing can be high fidelity sequencing. Methods of sequencing can include Maxam-Gilbert sequencing, chain-termination methods (e.g., Sanger sequencing), shotgun sequencing, and bridge PCR. In some cases, genotyping can be performed by next-generation sequencing. Methods of next-generation sequencing can include massively parallel signature sequencing, colony sequencing, pyrosequencing (e.g., pyrosequencing developed by 454 Life Sciences), single-molecule rea-time sequencing (e.g., by Pacific Biosciences), Ion semiconductor sequencing (e.g., by Ion Torrent semiconductor sequencing), sequencing by synthesis (e.g., by Solexa sequencing by Illumina), sequencing by ligation (e.g., SOLID sequencing by Applied Biosystems), DNA nanoball sequencing, and heliscope single molecule sequencing. In some cases, genotyping of a non-human animal herein can comprise full genome sequencing analysis.

In some cases, insertion of a transgene in an animal can be validated by sequencing (e.g., next-generation sequencing) a part of the transgene or the entire transgene. For example, insertion of a transgene adjacent to a Rosa26 promoter in a pig can be validated by next generation sequencing of Rosa exons 1 to 4

Populations of Non-Human Animals

Provided herein is a single non-human animal and also a population of non-human animals. A population of non-human animals can be genetically identical. A population of non-human animals can also be phenotypical identical. A population of non-human animals can be both phenotypical and genetically identical.

Further provided herein is a population of non-human animals, which can be genetically modified. For example, a population can comprise at least or at least about 2, 5, 10, 50, 100, or 200, non-human animals as disclosed herein. The non-human animals of a population can have identical phenotypes. For example, the non-human animals of a population can be clones. A population of non-human animal can have identical physical characteristics. The non-human animals of a population having identical phenotypes can comprise a same transgene(s). The non-human animals of a population having identical phenotypes can also comprise a same gene(s) whose expression is reduced. The non-human animals of a population having identical phenotypes can also comprise a same gene(s) whose expression is reduced and comprise a same transgene(s). A population of non-human animals can comprise at least or at least about 2, 5, 10, 50, 100, or 200, non-human animals having identical phenotypes. For example, the phenotypes of any particular litter can have the identical phenotype (e.g., in one example, anywhere from 1 to about 20 non-human animals). The non-human animals of a population can be pigs having identical phenotypes.

The non-human animals of a population can have identical genotypes. For example, all nucleic acid sequences in the chromosomes of non-human animals in a population can be identical. The non-human animals of a population having identical genotypes can comprise a same transgene(s). The non-human animals of a population having identical genotypes can also comprise a same gene(s) whose expression is reduced. The non-human animals of a population having identical genotypes can also comprise a same gene(s) whose expression is reduced and comprise a same transgene(s). A population of non-human animals can comprise at least or at least about 2, 5, 50, 100, or 200 non-human animals having identical genotypes. The non-human animals of a population can be pigs having identical genotypes.

Cells from two or more non-human animals with identical genotypes and/or phenotypes can be used in a tolerizing vaccine or a tolerizing regimen. In some cases, a tolerizing vaccine or tolerizing regimen disclosed herein can comprise a plurality of the cells (e.g., genetically modified cells) from two or more non-human animals (e.g., pigs) with identical genotypes and/or phenotypes. A method for immunotolerizing a recipient to a graft can comprise administering to the recipient a tolerizing vaccine or tolerizing regimen comprising a plurality of cells (e.g., genetically modified cells) from two or more non-human animals with identical genotypes or phenotypes.

Cells from two or more non-human animals with identical genotypes and/or phenotypes can be used in transplantation. In some cases, a graft (e.g., xenograft or allograft) can comprise a plurality of cells from two or more non-human animals with identical genotypes and/or phenotypes. In embodiments of the methods described herein, e.g., a method for treating a disease in a subject in need thereof, can comprise transplanting a plurality of cells (e.g., genetically modified cells) from two or more non-human animals with identical genotypes and/or phenotypes.

Populations of non-human animals can be generated using any method known in the art. In some cases, populations of non-human animals can be generated by breeding. For example, inbreeding can be used to generate a phenotypically or genetically identical non-human animal or population of non-human animals. Inbreeding, for example, sibling to sibling or parent to child, or grandchild to grandparent, or great grandchild to great grandparent, can be used. Successive rounds of inbreeding can eventually produce a phenotypically or genetically identical non-human animal. For example, at least or at least about 2, 3, 4, 5, 10, 20, 30, 40, or 50 generations of inbreeding can produce a phenotypically and/or a genetically identical non-human animal. It is thought that after 10-20 generations of inbreeding, the genetic make-up of a non-human animal is at least 99% pure. Continuous inbreeding can lead to a non-human animal that is essentially isogenic, or close to isogenic as a non-human animal can be without being an identical twin.

Breeding can be performed using non-human animals that have the same genotype. For example, the non-human animals have the same gene(s) whose expression is reduced and/or carry the same transgene(s). Breeding can also be performed using non-human animals having different genotypes. Breeding can be performed using a genetically modified non-human animal and non-genetically modified non-human animal, for example, a genetically modified female pig and a wild-type male pig, or a genetically modified male pig and a wild-type female pig. All these combinations of breeding can be used to produce a non-human animal of desire.

Populations of genetically modified non-human animals can also be generated by cloning. For example, the populations of genetically modified non-human animal cells can be asexually producing similar populations of genetically or phenotypically identical individual non-human animals. Cloning can be performed by various methods, such as twinning (e.g., splitting off one or more cells from an embryo and grow them into new embryos), somatic cell nuclear transfer, or artificial insemination. More details of the methods are provided throughout the disclosure.

Genetically Modified Cells

Disclosed herein are one or more genetically modified cells that can be used to treat or prevent disease. These genetically modified cells can be from genetically modified non-human animals. For example, genetically modified non-human animals as disclosed above can be processed so that one or more cells are isolated to produce isolated genetically modified cells. These isolated cells can also in some cases be further genetically modified cells. However, a cell can be modified ex vivo, e.g., outside an animal using modified or non-modified human or non-human animal cells. For example, cells (including human and non-human animal cells) can be modified in culture. It is also contemplated that a genetically modified cell can be used to generate a genetically modified non-human animal described herein. In some cases, the genetically modified cell can be isolated from a genetically modified animal. In some cases, the genetically modified cell can be derived from a cell from a non-genetically modified animal. Isolation of cells can be performed by methods known in the art, including methods of primary cell isolation and culturing. It is specifically contemplated that a genetically modified cell is not extracted from a human.

Therefore, anything that can apply to the genetically modified non-human animals including the various methods of making as described throughout can also apply herein. For example, all the genes that are disrupted and the transgenes that are overexpressed are applicable in making genetically modified cells used herein. Further, any methods for testing the genotype and expression of genes in the genetically modified non-human animals described throughout can be used to test the genetic modification of the cells.

A genetically modified cell can be from a member of the Laurasiatheria superorder or a non-human primate. Such genetically modified cell can be isolated from a member of the Laurasiatheria superorder or a non-human primate. Alternatively, such genetically modified cell can be originated from a member of the Laurasiatheria superorder or a non-human primate. For example, the genetically modified cell can be made from a cell isolated from a member of the Laurasiatheria superorder or a non-human primate, e.g., using cell culturing or genetic modification methods.

Genetically modified cells, e.g., cells from a genetically modified animal or cells made ex vivo, can be analyzed and sorted. In some cases, genetically modified cells can be analyzed and sorted by flow cytometry, e.g., fluorescence-activated cell sorting. For example, genetically modified cells expressing a transgene can be detected and purified from other cells using flow cytometry based on a label (e.g., a fluorescent label) recognizing the polypeptide encoded by the transgene.

In some cases, genetically modified cells can reduce, inhibit, or eliminate an immune response. For example, a genetic modification can decrease cellular effector function, decrease proliferation, decrease, persistence, and/or reduce expression of cytolytic effector molecules such as Granzyme B and CD107alpha in an immune cell. An immune cell can be a monocyte and/or macrophage. In some cases, T cell-derived cytokines, such as IFN-g, can activate macrophages via secretion of IFN-gamma. In some cases, T cell activation is inhibited and may cause a macrophage to also be inhibited.

Stem cells, including, non-human animal and human stem cells can be used. Stem cells do not have the capability to generating a viable human being. For example, stem cells can be irreversibly differentiated so that they are unable to generate a viable human being. Stem cells can be pluripotent, with the caveat that the stem cells cannot generate a viable human. As discussed above, the genetically modified cells comprise a transgene comprising a nucleic acid sequence encoding a MHC molecule (e.g., single chain chimeric MHC molecule), a $\alpha$ chain of a MHC molecule or a fragment thereof, or a $\beta$ chain of a MHC molecule or a fragment thereof, or a peptide derived from a MHC molecule. In some embodiments, the transgene can further comprise a polynucleotide encoding a peptide derived from a MHC molecule capable of binding the peptide binding groove for presentation to a T cell. In some embodiments, the genetically modified cells, can further comprise one or more transgenes encoding ICP47, CD46, CD55, CD59, HLA-E, HLA-G (e.g., HLA-G1, HLA-G2, HLA-G3, HLA- G4, HLA-G5, HLA-G6, or HLA-G7), B2M, any functional fragments thereof, and/or any combination thereof.

As discussed above in the section regarding the genetically modified non-human animals, in some embodiments, the genetically modified cells can further comprise one or more genes whose expression is reduced. The same genes as disclosed above for the genetically modified non-human animals can be disrupted. For example, a genetically modified cell comprising one or more genes whose expression is disrupted, e.g., reduced, where the one or more genes comprise NLRC5, TAP1, GGTA1, B4GALNT2, CMAH, CXCL10, MICA, MICB, C3, CIITA and/or any combination thereof. Further, the genetically modified cell can comprise one or more transgenes comprising one or more polynucleotide inserts. The genetically modified cell can comprise an exogenous nucleic acid sequence encoding a β chain of a MHC molecule; and/or an exogenous nucleic acid sequence encoding an α chain of the MHC molecule. In some embodiments, the β chain and the α chain form a functional MHC complex comprising a peptide binding groove. The genetically modified cell can further comprise an exogenous nucleic acid sequence encoding for a peptide derived from a MHC molecule capable of binding the peptide binding groove for presentation to a T cell. For example, a genetically modified cell can comprise one or more transgenes comprising one or more polynucleotide inserts of ICP47, CD46, CD55, CD 59, HLA-E, HLA-G (e.g., HLA-G1, HLA-G2, HLA-G3, HLA-G4, HLA-G5, HLA-G6, or HLA-G7), B2M, Spi9, PD-L1, PD-L2, CD47, galectin-9, any functional fragments thereof, or any combination thereof. A genetically modified cell can comprise one or more reduced genes and one or more transgenes. For example, one or more genes whose expression is reduced can comprise any one of NLRC5, TAP1, GGTA1, B4GALNT2, CMAH, CXCL10, MICA, MICB, CIITA, cytidine monophospho-N-acetylneuraminic acid (CMP-N-NeuAc) hydrolase, and/or any combination thereof, and one or more transgene can comprise ICP47, CD46, CD55, CD 59, HLA-E, HLA-G (e.g., HLA-G1, HLA-G2, HLA-G3, HLA-G4, HLA-G5, HLA-G6, or HLA-G7), B2M, Spi9, PD-L1, PD-L2, CD47, galectin-9, any functional fragments thereof, and/or any combination thereof. In some cases, a genetically modified cell can comprise reduced expression of NLRC5, C3, GGTA1, CMAH, and B4GALNT2, and transgenes comprising polynucleotides encoding proteins or functional fragments thereof, where the proteins comprise HLA-G1, Spi9, PD-L1, PD-L2, CD47, and galectin-9. In some cases, a genetically modified cell can comprise reduced expression of TAP1, C3, GGTA1, CMAH, and B4GALNT2, and transgenes comprising a nucleic acid sequence encoding a MHC molecule (e.g., single chain chimeric MHC molecule), a α chain of a MHC molecule or a fragment thereof, or a β chain of a MHC molecule or a fragment thereof, or a peptide derived from a MHC molecule. In some embodiments, the transgene can further comprise a polynucleotide encoding a peptide derived from a MHC molecule capable of binding the peptide binding groove for presentation to a T cell. In some cases, a genetically modified cell can comprise reduced expression of NLRC5, TAP1, C3, GGTA1, CMAH, and B4GALNT2, and transgenes comprising a nucleic acid sequence encoding a MHC molecule (e.g., single chain chimeric MHC molecule), a α chain of a MHC molecule or a fragment thereof, or a β chain of a MHC molecule or a fragment thereof, or a peptide derived from a MHC molecule. In some embodiments, the transgene can further comprise a polynucleotide encoding a peptide derived from a MHC molecule capable of binding the peptide binding groove for presentation to a T cell.

As discussed above in the section regarding the genetically modified non-human animals, the genetically modified cell can comprise 1, 2, 3, 4, 5, 6, 7, 8, 9, 10, 11, 12, 13, 14, 15, 16, 17, 18, 19, 20 or more disrupted genes. A genetically modified cell can also comprise 1, 2, 3, 4, 5, 6, 7, 8, 9, 10, 11, 12, 13, 14, 15, 16, 17, 18, 19, 20, or more transgenes.

As discussed in detail above, a genetically modified cell, e.g., porcine cell, can also comprise dominant negative transgenes and/or transgenes expressing one or more knockdown genes. Also as discussed above, expression of a transgene can be controlled by one or more promoters.

A genetically modified cell can be one or more cells from tissues or organs, the tissues or organs including brain, lung, liver, heart, spleen, pancreas, small intestine, large intestine, skeletal muscle, smooth muscle, skin, bones, adipose tissues, hairs, thyroid, trachea, gall bladder, kidney, ureter, bladder, aorta, vein, esophagus, diaphragm, stomach, rectum, adrenal glands, bronchi, ears, eyes, retina, genitals, hypothalamus, larynx, nose, tongue, spinal cord, or ureters, uterus, ovary and testis. For example, a genetically modified cell, e.g., porcine cell, can be from brain, heart, liver, skin, intestine, lung, kidney, eye, small bowel, or pancreas. In some cases, a genetically modified cell can be from a pancreas. More specifically, pancreas cells can be islet cells. Further, one or more cells can be pancreatic α cells, pancreatic β cells, pancreatic δ cells, pancreatic F cells (e.g., PP cells), or pancreatic δ cells. For example, a genetically modified cell can be pancreatic β cells. Tissues or organs disclosed herein can comprise one or more genetically modified cells. The tissues or organs can be from one or more genetically modified animals described in the application, e.g., pancreatic tissues such as pancreatic islets from one or more genetically modified pigs.

A genetically modified cell, e.g., porcine cell, can comprise one or more types of cells, where the one or more types of cells include Trichocytes, keratinocytes, gonadotropes, corticotropes, thyrotropes, somatotropes, lactotrophs, chromaffin cells, parafollicular cells, glomus cells melanocytes, nevus cells, Merkel cells, odontoblasts, cementoblasts corneal keratocytes, retina Muller cells, retinal pigment epithelium cells, neurons, glias (e.g., oligodendrocyte astrocytes), ependymocytes, pinealocytes, pneumocytes (e.g., type I pneumocytes, and type II pneumocytes), clara cells, goblet cells, G cells, D cells, ECL cells, gastric chief cells, parietal cells, foveolar cells, K cells, D cells, I cells, goblet cells, paneth cells, enterocytes, microfold cells, hepatocytes, hepatic stellate cells (e.g., Kupffer cells from mesoderm), cholecystocytes, centroacinar cells, pancreatic stellate cells, pancreatic α cells, pancreatic β cells, pancreatic δ cells, pancreatic F cells (e.g., PP cells), pancreatic δ cells, thyroid (e.g., follicular cells), parathyroid (e.g., parathyroid chief cells), oxyphil cells, urothelial cells, osteoblasts, osteocytes, chondroblasts, chondrocytes, fibroblasts, fibrocytes, myoblasts, myocytes, myosatellite cells, tendon cells, cardiac muscle cells, lipoblasts, adipocytes, interstitial cells of cajal, angioblasts, endothelial cells, mesangial cells (e.g., intraglomerular mesangial cells and extraglomerular mesangial cells), juxtaglomerular cells, macula densa cells, stromal cells, interstitial cells, telocytes simple epithelial cells, podocytes, kidney proximal tubule brush border cells, sertoli cells, leydig cells, granulosa cells, peg cells, germ cells, spermatozoon ovums, lymphocytes, myeloid cells, endothelial progenitor cells, endothelial stem cells, angioblasts, mesoangioblasts, and pericyte mural cells. A genetically modified cell can potentially be any cells used in cell therapy. For example, cell therapy can be pancreatic β cells supplement or replacement to a disease such as diabetes.

A genetically modified cell, e.g., porcine cell, can be from (e.g., extracted from) a non-human animal. One or more cells can be from a mature adult non-human animal. However, one or more cells can be from a fetal or neonatal tissue.

Depending on the disease, one or more cells can be from a transgenic non-human animal that has grown to a sufficient size to be useful as an adult donor, e.g., an islet cell donor. In some cases, non-human animals can be past weaning age. For example, non-human animals can be at least or at least about six months old. In some cases, non-human animals can be at least or at least about 18 months old. A non-human animal in some cases, survive to reach breeding age. For example, islets for xenotransplantation can be from neonatal (e.g., age 3-7 days) or pre-weaning (e.g., age 14 to 21 days) donor pigs. One or more genetically modified cells, e.g., porcine cells, can be cultured cells. For example, cultured cells can be from wild-type cells or from genetically modified cells (as described herein). Furthermore, cultured cells can be primary cells. Primary cells can be extracted and frozen, e.g., in liquid nitrogen or at −20° C. to −80° C. Cultured cells can also be immortalized by known methods, and can be frozen and stored, e.g., in liquid nitrogen or at −20° C. to −80° C.

Genetically modified cells, e.g., porcine cells, as described herein can have a lower risk of rejection, when compared to when a wild-type non-genetically modified cell is transplanted.

Disclosed herein is a nucleic acid construct comprising a nucleic acid sequence encoding a β chain of a MHC molecule; and/or a nucleic acid sequence encoding an α chain of the MHC molecule. In some embodiments, the β chain and the α chain form a functional MHC complex comprising a peptide binding groove. In some embodiments, the β chain, the α chain or both lack a functional transmembrane domain. In some embodiments, the nucleic acid construct can further comprise a nucleic acid sequence encoding for a peptide derived from a MHC molecule capable of binding the peptide binding groove for presentation to a T cell. Disclosed herein is a vector comprising a polynucleotide sequence of ICP47, CD46, CD55, CD59, HLA-E, HLA-G (e.g., HLA-G1, HLA-G2, HLA-G3, HLA-G4, HLA-G5, HLA-G6, or HLA-G7), B2M, Spi9, PD-L1, PD-L2, CD47, galectin-9, any functional fragments thereof, or any combination thereof. These vectors can be inserted into a genome of a cell (by transfection, transformation, viral delivery, or any other known method). These vectors can encode ICP47, CD46, CD55, CD59, HLA-E, HLA-G (e.g., HLA-G1, HLA-G2, HLA-G3, HLA-G4, HLA-G5, HLA-G6, or HLA-G7), B2M Spi9, PD-L1, PD-L2, CD47, and/or galectin-9 proteins or functional fragments thereof.

Vectors contemplated include, but not limited to, plasmid vectors, artificial/mini-chromosomes, transposons, and viral vectors.

Guide RNA sequences can be used in targeting one or more genes in a genome of a non-human animal. For example, guide RNA sequence can target a single gene in a genome of non-human animal. In some cases, guide RNA sequences can target one or more target sites of each of one or more genes in a genome of a non-human animal.

Genetically modified cells can also be leukocytes, lymphocytes, B lymphocytes, or any other cell such as islet cells, islet beta cells, or hepatocytes. These cells can be fixed or made apoptotic by any method disclosed herein, e.g., by ECDI fixation.

A genetically modified cells can be derived (e.g., retrieved) from a non-human fetal animal, perinatal non-human animal, neonatal non-human animal, preweaning non-human animal, young adult non-human animal, adult non-human animal, or any combination thereof. In some cases, a genetically modified non-human animal cell can be derived from an embryonic tissue, e.g., an embryonic pancreatic tissue. For example, a genetically modified cell can be derived (e.g., retrieved) from an embryonic pig pancreatic tissue from embryonic day 42 (E42).

The term "fetal animal" and its grammatical equivalents can refer to any unborn offspring of an animal. The term "perinatal animal" and its grammatical equivalents can refer to an animal immediately before or after birth. For example, a perinatal period can start from 20th to 28th week of gestation and ends 1 to 4 weeks after birth. The term "neonatal animal" and its grammatical equivalents can refer to any new born animals. For example, a neonatal animal can be an animal born within a month. The term "preweaning non-human animal" and its grammatical equivalents can refer to any animal before being withdrawn from the mother's milk.

Genetically modified non-human animal cells and cells, tissues or organs derived from a genetically modified non-human animal can be formulated into a pharmaceutical composition. For example, the genetically modified non-human animal cells can be combined with a pharmaceutically acceptable excipient. An excipient that can be used is saline. The pharmaceutical composition can be used to treat patients in need of transplantation.

A genetically modified cell can comprise reduced expression of any genes, and/or any transgenes disclosed herein. Genetic modification of the cells can be done by using any of the same method as described herein for making the genetically modified animals. In some cases, a method of making a genetically modified cell originated from a non-human animal can comprise reducing expression of one or more genes and/or inserting one or more transgenes. The reduction of gene expression and/or transgene insertion can be performed using any methods described in the application, e.g., gene editing.

Genetically Modified Cells Derived from Stem Cells

Genetically modified cells can be a stem cell. The genetically modified stem cell cells, and the cells, tissues and organs derived upon their differentiation comprises a transgene comprising a nucleic acid sequence encoding a MHC molecule (e.g., single chain chimeric MHC molecule), a α chain of a MHC molecule or a fragment thereof, or a β chain of a MHC molecule or a fragment thereof, or a peptide derived from a MHC molecule. In some embodiments, the transgene can further comprise a polynucleotide encoding a peptide derived from a MHC molecule capable of binding the peptide binding groove for presentation to a T cell. In some embodiments, the genetically modified stem cells and the cells, tissues and organs derived upon their differentiation can further comprise one or more transgenes encoding ICP47, CD46, CD55, CD59, HLA-E, HLA-G (e.g., HLA-G1, HLA-G2, HLA-G3, HLA-G4, HLA-G5, HLA-G6, or HLA-G7), B2M, any functional fragments thereof, and/or any combination thereof. These genetically modified stem cells can be used to make a potentially unlimited supply of cells that can be subsequently processed into fixed or apoptotic cells by the methods disclosed herein. As discussed above, stem cells are not capable of generating a viable human being.

The production of hundreds of millions of insulin-producing, glucose-responsive pancreatic beta cells from human pluripotent stem cells provides an unprecedented cell source for cell transplantation therapy in diabetes. Other human stem cell-(embryonic, pluripotent, placental, induced pluripotent, etc.) derived cell sources for cell transplantation therapy in diabetes and in other diseases are being developed.

These stem cell-derived cellular grafts are subject to rejection. The rejection can be mediated by CD8+ T cells. In Type 1 diabetic recipients, human stem cell-derived functional beta cells are subject to rejection and autoimmune recurrence. Both are thought to be mediated by CD8+ T cells.

To interfere with activation and effector function of these allo-reactive and auto-reactive CD8+ T cells, established molecular methods of gene modification, including CRISPR/Cas9 gene targeting, can be used to mutate the NLRC5, TAP1, and/or B2M genes in human stem cells for the purpose of preventing cell surface expression of functional MHC class I in the stem cell-derived, partially or fully differentiated cellular graft. Thus, transplanting human stem cell-derived cellular grafts lacking functional expression of MHC class I can minimize the requirements of immunosuppression otherwise required to prevent rejection and autoimmune recurrence.

However, lack of MHC class I expression on transplanted human cells will likely cause the passive activation of natural killer (NK) cells (Ohlen et al, 1989). NK cell cytotoxicity can be overcome by the expression of the human MHC class 1 gene, HLA-E, which stimulates the inhibitory receptor CD94/NKG2A on NK cells to prevent cell killing (Weiss et al., 2009; Lilienfeld et al., 2007; Sasaki et al., 1999). Successful expression of the HLA-E gene was dependent on co-expression of the human B2M (beta 2 microglobulin) gene and a cognate peptide (Weiss et al., 2009; Lilienfeld et al., 2007; Sasaki et al., 1999; Pascasova et al., 1999). A nuclease mediated break in the stem cell DNA allows for the insertion of one or multiple genes via homology directed repair. The HLA-E and hB2M genes in series can be integrated in the region of the nuclease mediated DNA break thus preventing expression of the target gene (for example, NLRC5) while inserting the transgenes.

To further minimize, if not eliminate, the need for maintenance immunosuppression in recipients of stem cell derived cellular grafts lacking functional expression of MHC class I, recipients of these grafts can also be treated with tolerizing apoptotic donor cells disclosed herein.

The methods for the production of insulin-producing pancreatic beta cells (Pagliuca et al., 2014) can potentially be applied to non-human (e.g., pig) primary isolated pluripotent, embryonic stem cells or stem-like cells (Goncalves et al., 2014; Hall et al. V. 2008). However, the recipient of these insulin-producing pancreatic beta cells likely has an active immune response that threatens the success of the graft. To overcome antibody-mediated and CD8+ T cell immune attack, the donor animal can be genetically modified before isolation of primary non-human pluripotent, embryonic stem cells or stem-like cells to prevent the expression of the GGTA1, CMAH, B4GalNT2, or MHC class I-related genes as disclosed throughout the application. The pluripotent, embryonic stem cells or stem-like cells isolated from genetically modified animals could then be differentiated into millions of insulin-producing pancreatic beta cells.

Xenogeneic stem cell-derived cell transplants can be desirable in some cases. For example, the use of human embryonic stem cells may be ethically objectionable to the recipient. Therefore, human recipients may feel more comfortable receiving a cellular graft derived from non-human sources of embryonic stem cells.

Non-human stem cells may include pig stem cells. These stem cells can be derived from wild-type pigs or from genetically engineered pigs. If derived from wild-type pigs, genetic engineering using established molecular methods of gene modification, including CRISP/Cas9 gene targeting, may best be performed at the stem cell stage. Genetic engineering may be targeted to disrupt expression of NLRC5, TAP1, and/or B2M genes to prevent functional expression of MHC class I. Disrupting genes such as NLRC5, TAP1, and B2M in the grafts can cause lack of functional expression of MHC class I on graft cells including on islet beta cells, thereby interfering with the post-transplant activation of autoreactive CD8+ T cells. Thus, this can protect the transplant, e.g., transplanted islet beta cells, from the cytolytic effector functions of autoreactive CD8+ T cells.

However, as genetic engineering of stem cells may alter their potential for differentiation, an approach can be to generate stem cell lines from genetically engineered pigs, including those pigs, in whom the expression of NLRC5, TAP1, and/or B2M genes has been disrupted.

Generation of stem cells from pigs genetically modified to prevent the expression also of the GGTA1, CMAH, B4GalNT2 genes or modified to express transgenes that encode for MHC molecule, and in some embodiments, further encode complement regulatory proteins CD46, CD55, or CD59, as disclosed throughout the application, could further improve the therapeutic use of the insulin-producing pancreatic beta cells or other cellular therapy products. Likewise, the same strategy as described herein can be used in other methods and compositions described throughout.

Like in recipients of human stem cell-derived cellular grafts lacking functional expression of MHC class I, the need for maintenance immunosuppression in recipients of pig stem cell-derived grafts can be further minimized by peritransplant treatments with tolerizing apoptotic donor cells.

Tolering Regimen (Tolerizing Vaccines)

Traditionally, vaccines are used to confer immunity to a host. For example, injecting an inactivated virus with adjuvant under the skin can lead to temporary or permanent immunity to the active and/or virulent version of the virus. This can be referred to as a positive vaccine. However, inactivated cells (e.g., cells from a donor or an animal genetically different from the donor) that are injected intravenously can result in tolerance of donor cells or cells with similar cellular markers. This can be referred to as a tolerizing vaccine (also referred to as a negative vaccine). The inactive cells can be injected without an adjuvant. Alternatively, the inactive cells can be injected with an adjuvant. These tolerizing vaccines can be advantageous in transplantation, for example, in xenotransplantation, by tolerizing a recipient and preventing rejection. Tolerization can be conferred to a recipient without the use of immunosuppressive therapies. However, in some cases, other immunosuppressive therapies in combination with tolerizing vaccines can decrease transplantation rejection.

A donor can provide xenografts for transplantation (e.g., islets), as well as cells (e.g., splenocytes) as a tolerizing vaccine. The tolerizing vaccine cells can be apoptotic cells (e.g., by ECDI fixation) and administered to the recipient before (e.g., the first vaccine, on day 7 before the transplantation) and after the transplantation (e.g., the booster vaccine, on day 1 after the transplantation). The tolerizing vaccine can provide transient immunosuppression that extends the time of survival of the transplanted grafts (e.g., islets).

Tolerizing vaccines can comprise the genetically modified cell disclosed herein. This can minimize or eliminate cell-mediated immunity and cell-dependent antibody-mediated immunity to organ, tissue, cell, and cell line grafts (e.g., xenografts) from animals that are genotypically identical with the apoptotic cell vaccine donor animal, or from animals that have undergone additional genetic modifications (e.g., suppression of NLRC5, TAP1, MICA, MICB, CXCL10, C3, CIITA genes or expression of transgenes comprising two or more polynucleotide inserts of a MHC molecule with or without tolerogenic peptide, ICP47, CD46, CD55, HLA-E, HLA-G (e.g., HLA-G1, HLA-G2, HLA-G3, HLA-G4, HLA-G5, HLA-G6, or HLA-G7), B2M, CD59, or any functional fragments thereof), but are genotypically similar to the donor animal from which the apoptotic cell vaccine is derived; ii) apoptotic stem cell (e.g., embryonic, pluripotent, placental, induced pluripotent, etc.)-derived donor cells (e.g., leukocytes, lymphocytes, T lymphocytes, B lymphocytes, red blood cells, graft cells, or any other donor cell) for minimizing or eliminating cell-mediated immunity and cell-dependent antibody-mediated immunity to organ, tissue, cell, and cell line grafts (e.g., xenografts) from animals that are genotypically identical with the apoptotic cell vaccine donor animal or from animals that have undergone additional genetic modifications (e.g., suppression of GGTA1, NLRC5, TAP1, MICA, MICB, CXCL10, C3, CIITA, cytidine monophospho-N-acetylneuraminic acid (CMP-N-NeuAc) hydrolase genes or expression of transgenes comprising a nucleic acid sequence encoding a MHC molecule (e.g., single chain chimeric MHC molecule), a α chain or a fragment thereof, or a β chain or a fragment thereof, or a peptide derived from a MHC molecule. In some embodiments, the β chain and the α chain form a functional MHC complex comprising a peptide binding groove. In some embodiments, the β chain, the α chain or both lack a functional transmembrane domain. In some embodiments, the transgene can further comprise a nucleic acid sequence encoding for a peptide derived from a MHC molecule capable of binding the peptide binding groove for presentation to a T cell. The cells further comprising one or more additional transgene inserts of ICP47, CD46, CD55, HLA-E, HLA-G (e.g., HLA-G1, HLA-G2, HLA-G3, HLA-G4, HLA-G5, HLA-G6, or HLA-G7), B2M, CD59, or any functional fragments thereof), but are genotypically similar to the donor animal from which the apoptotic stem cell-derived cell vaccine is derived; iii) apoptotic stem cell (e.g., embryonic, pluripotent, placental, induced pluripotent, etc.)-derived donor cells (leukocytes, lymphocytes, T lymphocytes, B lymphocytes, red blood cells, graft cells such as functional islet beta cells, or any other donor cell) for minimizing or eliminating cell-mediated immunity and cell-dependent antibody-mediated immunity to organ, tissue, cell, and cell grafts (e.g., allografts) that are genotypically identical with the human stem cell line or to grafts (e.g., allografts) derived from the same stem cell line that have undergone genetic modifications (e.g., suppression of GGTA1, NLRC5, TAP1, MICA, MICB, CXCL10, C3, CIITA, cytidine monophospho-N-acetylneuraminic acid (CMP-N-NeuAc) hydrolase genes) but are otherwise genotypically similar to the apoptotic human stem cell-derived donor cell vaccine; iv) apoptotic donor cells, where the cells are made apoptotic by UV irradiation, gamma-irradiation, or other methods not involving incubation in the presence of ECDI. In some cases, tolerizing vaccine cells can be administered, e.g., infused (in some cases repeatedly infused) to a subject in need thereof. Tolerizing vaccines can be produced by disrupting (e.g., reducing expression) one or more genes from a cell. For example, genetically modified cells as described throughout the application can be used to make a tolerizing vaccine. For example, the genetically modified cells comprising a transgene comprising a nucleic acid sequence encoding a MHC molecule (e.g., single chain chimeric MHC molecule), a α chain of a MHC molecule or a fragment thereof, or a β chain of a MHC molecule or a fragment thereof, or a peptide derived from a MHC molecule can be used to make a tolerizing regimen or tolerizing vaccine. In some embodiments, the transgene can further comprise a polynucleotide encoding a peptide derived from a MHC molecule capable of binding the peptide binding groove for presentation to a T cell. In some embodiments, the genetically modified cells of the tolerizing regimen can further comprise one or more transgenes encoding ICP47, CD46, CD55, CD59, HLA-E, HLA-G (e.g., HLA-G1, HLA-G2, HLA-G3, HLA-G4, HLA-G5, HLA-G6, or HLA-G7), B2M, any functional fragments thereof, and/or any combination thereof. For example, in some embodiments, cells used for tolerizing regimen can have one or more genes that can be disrupted (e.g., reduced expression) including glycoprotein galactosyltransferase alpha 1, 3 (GGTA1), putative cytidine monophosphate-N-acetylneuraminic acid hydroxylase-like protein (CMAH), B4GALNT2, and/or any combination thereof. For example, a cell can have disrupted GGTA1 only, or disrupted CMAH only, or disrupted B4GALNT2 only. A cell can also have disrupted GGTA1 and CMAH, disrupted GGTA1 and B4GALNT2, or disrupted CMAH and B4GALNT2. A cell can have disrupted GGTA1, CMAH, and B4GALNT2. In some cases, the disrupted gene does not include GGTA1. A cell can also express NLRC5 (endogenously or exogenously), while GGTA1 and/or CMAH are disrupted. A cell can also have disrupted C3. A cell can also have a disrupted PERV site.

In some cases, tolerization may comprise administration of a genetically modified graft. A graft can be a cell, tissue, organ, or a combination. In some cases, immunosuppression is combined with a vaccine or tolerizing graft. In some cases, expression of HLA-G1 on a graft and an MHC or HLA class I deficiency of a graft may have tolerogenic activity independent from administration of a vaccine.

When administered in a subject, a cell of a tolerizing vaccine can have a circulation half-life. A cell of a tolerizing vaccine can have a circulation half-life of at least or at least about 0.1, 0.5, 1, 2, 3, 4, 5, 6, 7, 8, 9, 10, 12, 18, 24, 36, 48, 60, or 72 hours. For example, the circulation half-life of the tolerizing vaccine can be from or from about 0.1 to 0.5; 0.5 to 1.0; 1.0 to 2.0; 1.0 to 3.0; 1.0 to 4.0; 1.0 to 5.0; 5 to 10; 10 to 15; 15 to 24; 24 to 36; 36 to 48; 48 to 60; or 60 to 72 hours. A cell in a tolerizing vaccine can be treated to enhance its circulation half-life. Such treatment can include coating the cell with a protein, e.g., CD47. A cell treated to enhance its circulation half-life can be a non-apoptotic cell. A cell treated to enhance its circulation half-life can be an apoptotic cell. Alternatively, a cell in a tolerizing vaccine can be genetically modified (e.g., insertion of a transgene such as CD47 in its genome) to enhance its circulation half-life. A cell genetically modified to enhance its circulation half-life can be a non-apoptotic cell. A cell genetically modified to enhance its circulation half-life can be an apoptotic cell.

A tolerizing vaccine can have both one or more disrupted genes (e.g., reduced expression) and one or more transgenes. Any genes and/or transgenes as described herein can be used.

A cell that comprises one or more disrupted genes (e.g., reduced expression) can be used as, or be a part of, a tolerizing vaccine. In other words, a cell that comprises one or more disrupted genes can be or can be made into a tolerizing vaccine.

A tolerizing vaccine can have the same genotype and/or phenotype as cells, organs, and/or tissues used in transplantation. Sometimes, the genotype and/or phenotype of a tolerizing vaccine and a transplant are different. A tolerizing vaccine used for a transplant recipient can comprise cells from the transplant graft donor. A tolerizing vaccine used for a transplant recipient can comprise cells that are genetically and/or phenotypically different from the transplant graft. In some cases, a tolerizing vaccine used for a transplant recipient can comprise cells from the transplant graft donor and cells that are genetically and/or phenotypically different from the transplant graft. The cells that are genetically and/or phenotypically different from the transplant graft can be from an animal of the same species of the transplant graft donor.

A source of cells for a tolerizing vaccine can be from a human or non-human animal.

Cells as disclosed throughout the application can be made into a tolerizing vaccine. For example, a tolerizing vaccine can be made of one or more transplanted cells disclosed herein. Alternatively, a tolerizing vaccine can be made of one or more cells that are different from any of the transplanted cells. For example, the cells made into a tolerizing vaccine can be genotypically and/or phenotypically different from any of the transplanted cells. However in some cases, the tolerizing vaccine will express NLRC5 (endogenously or exogenously). A tolerizing vaccine can promote survival of cells, organs, and/or tissues in transplantation. A tolerizing vaccine can be derived from non-human animals that are genotypically identical or similar to donor cells, organs, and/or tissues. For example, a tolerizing vaccine can be cells derived from pigs (e.g., apoptotic pig cells) that are genotypically identical or similar to donor pig cells, organs, and/or tissues. Subsequently, donor cells, organs, and/or tissues can be used in allografts or xenografts.

A tolerizing vaccine can comprise non-human animal cells (e.g., non-human mammalian cells). For example, non-human animal cells can be from a pig, a cat, a cow, a deer, a dog, a ferret, a gaur, a goat, a horse, a mouse, a mouflon, a mule, a rabbit, a rat, a sheep, or a primate. Specifically, non-human animal cells can be porcine cells. A tolerizing vaccine can also comprise genetically modified non-human animal cells. For example, genetically modified non-human animal cells can be dead cells (e.g., apoptotic cells). A tolerizing vaccine can also comprise any genetically modified cells disclosed herein. Treatment of cells to make a tolerizing vaccine A tolerizing vaccine can comprise cells treated with a chemical. In some cases, the treatment can induce apoptosis of the cells. Without being bound by theory, the apoptotic cells can be picked up by host antigen presenting cells (e.g., in the spleen) and presented to host immune cells (e.g., T cells) in a non-immunogenic fashion that leads to induction of anergy in the immune cells (e.g., T cells).

Tolerizing vaccines can comprise apoptotic cells and non-apoptotic cells. An apoptotic cell in a tolerizing vaccine can be genetically identical to a non-apoptotic cell in the tolerizing vaccine. Alternatively, an apoptotic cell in a tolerizing vaccine can be genetically different from a non-apoptotic cell in the tolerizing vaccine. Tolerizing vaccines can comprise fixed cells and non-fixed cells. A fixed cell in a tolerizing vaccine can be genetically identical to a non-fixed cell in the tolerizing vaccine. Alternatively, a fixed cell in a tolerizing vaccine can be genetically different from a non-fixed cell in the tolerizing vaccine. In some cases, the fixed cell can be a 1-ethyl-3-(3-dimethylaminopropyl)-carbodiimide (ECDI)-fixed cell.

Cells in a tolerizing vaccine can be fixed using a chemical, e.g., ECDI. The fixation can make the cells apoptotic. A tolerizing vaccine, cells, kits and methods disclosed herein can comprise ECDI and/or ECDI treatment. For example, a tolerizing vaccine can be cells, e.g., the genetically modified cell as disclosed herein, that are treated with 1-ethyl-3-(3-dimethylaminopropyl)-carbodiimide (ECDI). In other words, the genetically modified cells as described throughout can be treated with ECDI to create a tolerizing vaccine. A tolerizing vaccine can then be used in transplantation to promote survival of cells, organs, and/or tissues that are transplanted. It is also contemplated that ECDI derivatives, functionalized ECDI, and/or substituted ECDI can also be used to treat the cells for a tolerizing vaccine. In some cases, cells for a tolerizing vaccine can be treated with any suitable carbodiimide derivatives, e.g., ECDI, N,N'diisopropylcarbodiimide (DIC), N,N'-dicyclohexylcarbodiimide (DCC), and other carbodiimide derivatives understood by those in the art.

Cells for tolerizing vaccines can also be made apoptotic methods not involving incubation in the presence of ECDI, e.g., other chemicals or irradiation such as UV irradiation or gamma-irradiation.

ECDI can chemically cross-link free amine and carboxyl groups, and can effectively induce apoptosis in cells, organs, and/or tissues, e.g., from animal that gave rise to both a tolerizing vaccine and a donor non-human animal. In other words, the same genetically modified animal can give rise to a tolerizing vaccine and cells, tissues and/or organs that are used in transplantation. For example, the genetically modified cells as disclosed herein can be treated with ECDI. This ECDI fixation can lead to the creation of a tolerizing vaccine.

Genetically modified cells that can be used to make a tolerizing vaccine can be derived from: a spleen (including splenic B cells), liver, peripheral blood (including peripheral blood B cells), lymph nodes, thymus, bone marrow, or any combination thereof. For example, cells can be spleen cells, e.g., porcine spleen cells. In some cases, cells can be expanded ex-vivo. In some cases, cells can be derived from fetal, perinatal, neonatal, preweaning, and/or young adult, non-human animals. In some cases, cells can be derived from an embryo of a non-human animal.

Cells in a tolerizing vaccine can also be derived from one or more donor non-human animals. In some cases, cells can be derived from the same donor non-human animal. Cells can be derived from one or more recipient non-human animals. In some cases, cells can be derived from two or more non-human animals (e.g., pig).

A tolerizing vaccine can comprise from or from about 0.001 and about 5.0, e.g., from or from about 0.001 and 1.0, endotoxin unit per kg bodyweight of a prospective recipient. For example, a tolerizing vaccine can comprise from or from about 0.01 to 5.0; 0.01 to 4.5; 0.01 to 4.0, 0.01 to 3.5; 0.01 to 3.0; 0.01 to 2.5; 0.01 to 2.0; 0.01 to 1.5; 0.01 to 1.0; 0.01 to 0.9; 0.01 to 0.8; 0.01 to 0.7; 0.01 to 0.6; 0.01 to 0.5; 0.01 to 0.4; 0.01 to 0.3; 0.01 to 0.2; or 0.01 to 0.1 endotoxin unit per kg bodyweight of a prospective recipient.

A tolerizing vaccine can comprise from or from about 1 to 100 aggregates, per μl. For example, a tolerizing vaccine can comprise from or from about 1 to 5; 1 to 10, or 1 to 20 aggregate per μl. A tolerizing vaccine can comprise at least or at least about 1, 5, 10, 20, 50, or 100 aggregates.

A tolerizing vaccine can trigger a release from or from about 0.001 μg/ml to 10.0 μg/ml, e.g., from or from about 0.001 μg/ml to 1.0 μg/ml, IL-1 beta when about 50,000 frozen to thawed human peripheral blood mononuclear cells are incubated with about 160,000 cells of the tolerizing vaccine (e.g., pig cells). For example, a tolerizing vaccine triggers a release of from or from about 0.001 to 10.0; 0.001 to 5.0; 0.001 to 1.0; 0.001 to 0.8; 0.001 to 0.2; or 0.001 to 0.1 μg/ml IL-1 beta when about 50,000 frozen to thawed human peripheral blood mononuclear cells are incubated with about 160,000 cell of the tolerizing vaccine (e.g., pig cells). A tolerizing vaccine can trigger a release of from or from about 0.001 to 2.0 μg/ml, e.g., from or from about 0.001 to 0.2 μg/ml, IL-6 when about 50,000 frozen to thawed human peripheral blood mononuclear cells are incubated with about 160,000 cells of the tolerizing vaccine (e.g., pig cells). For example, a tolerizing vaccine can trigger a release of from or from about 0.001 to 2.0; 0.001 to 1.0; 0.001 to 0.5; or 0.001 to 0.1 μg/ml IL-6 when about 50,000 frozen to thawed human peripheral blood mononuclear cells are incubated with about 160,000 cells of the tolerizing vaccine (e.g., pig cells).

A tolerizing vaccine can comprise more than or more than about 60%, e.g., more than or more than about 85%, Annexin V positive, apoptotic cells after a 4 hour or after about 4 hours post-release incubation at 37° C. For example, a tolerizing vaccine comprises more than 60%, 70%, 80%, 90%, or 99% Annexin V positive, apoptotic cells after about a 4 hour post-release incubation at 37° C.

A tolerizing vaccine can include from or from about 0.01% to 10%, e.g., from or from about 0.01% to 2%, necrotic cells. For example, a tolerizing vaccine includes from or from about 0.01% to 10%; 0.01% to 7.5%, 0.01% to 5%; 0.01% to 2.5%; or 0.01% to 1% necrotic cells.

Administering a tolerizing vaccine comprising ECDI-treated cells, organs, and/or tissues before, during, and/or after administration of donor cells can induce tolerance for cells, organs, and/or tissues in a recipient (e.g., a human or a non-human animal). ECDI-treated cells can be administered by intravenous infusion.

Tolerance induced by infusion of a tolerizing vaccine comprising ECDI-treated splenocytes is likely dependent on synergistic effects between an intact programmed death 1 receptor-programmed death ligand 1 signaling pathway and $CD4^{+}CD25^{+}Foxp3^{+}$ regulatory T cells.

Cells in a telorizing vaccine can be made into apoptotic cells (e.g., tolerizing vaccines) not only by ECDI fixation, but also through other methods. For example, any of the genetically modified cells as disclosed throughout, e.g., non-human cells animal cells or human cells (including stem cells), can be made apopototic by exposing the genetically modified cells to UV irradiation. The genetically modified cells can also be made apopototic by exposing it to gamma-irradiation. Other methods, not involving ECDI are also comtemplated, for example, by EtOH fixation.

Cells in a tolerizing vaccine, e.g., ECDI-treated cells, antigen-coupled cells, and/or epitope-coupled cells can comprise donor cells (e.g., cells from the donor of transplant grafts). Cells in a tolerizing vaccine, e.g., ECDI-treated cells, antigen-coupled cells, and/or epitope-coupled cells can comprise recipient cells (e.g., cells from the recipient of transplant grafts). Cells in a tolerizing vaccine, e.g., ECDI-treated cells, antigen-coupled cells, and/or epitope-coupled cells can comprise third party (e.g., neither donor nor recipient) cells. In some cases, third party cells are from a non-human animal of the same species as a recipient and/or donor. In other cases, third party cells are from a non-human animal of a different species as a recipient and/or donor.

ECDI-treatment of cells can be performed in the presence of one or more antigens and/or epitopes. ECDI-treated cells can comprise donor, recipient and/or third party cells. Likewise, antigens and/or epitopes can comprise donor, recipient and/or third party antigens and/or epitopes. In some cases, donor cells are coupled to recipient antigens and/or epitopes (e.g., ECDI-induced coupling). For example, soluble donor antigen derived from genetically engineered and genotypically identical donor cells (e.g., porcine cells) is coupled to recipient peripheral blood mononuclear cells with ECDI and the ECDI-coupled cells are administered via intravenous infusion.

In some cases, recipient cells are coupled to donor antigens and/or epitopes (e.g., ECDI-induced coupling). In some cases, recipient cells are coupled to third party antigens and/or epitopes (e.g., ECDI-induced coupling). In some cases, donor cells are coupled to recipient antigens and/or epitopes (e.g., ECDI-induced coupling). In some cases, donor cells are coupled to third party antigens and/or epitopes (e.g., ECDI-induced coupling). In some cases, third party cells are coupled to donor antigens and/or epitopes (e.g., ECDI-induced coupling). In some cases, third party cells are coupled to recipient antigens and/or epitopes (e.g., ECDI-induced coupling). For example, soluble donor antigen derived from genetically engineered and genotypically identical donor cells (e.g., porcine cells) is coupled to polystyrene nanoparticles with ECDI and the ECDI-coupled cells are administered via intravenous infusion.

Tolerogenic potency of any of these tolerizing cell vaccines can be further optimized by coupling to the surface of cells one or more of the following: IFN-g, NF-κB inhibitors (such as curcumin, triptolide, Bay-117085), vitamin D3, siCD40, cobalt protoporphyrin, insulin B9-23, or other immunomodulatory molecules that modify the function of host antigen-presenting cells and host lymphocytes.

These apoptotic cell vaccines can also be complemented by donor cells engineered to display on their surface molecules (such as FasL, PD-L1, galectin-9, CD8alpha) that trigger apoptotic death of donor-reactive cells.

Tolerizing vaccines dislosed herein can increase the duration of survival of a transplant (e.g., a xenograft or an allograft transplant) in a recipient. Tolerizing vaccines disclosed herein can also reduce or eliminate need for immunosupression following transplantation. Xenograft or allograft transplant can be an organ, tissue, cell or cell line. Xenograft transplants and tolerizing vaccines can also be from different species. Alternatively, xenograft transplants and the tolerizing vaccines can be from the same species. For example, a xenograft transplant and a tolerizing vaccine can be from substantially genetically identical individuals (e.g., the same individual).

In some cases, a tolerizing vaccine or negative vaccine can produce synergistic effects in a subject administered a tolerizing or negative vaccine. In other cases, a tolerizing or negative vaccine can produce antagonistic effects in a subject administered a tolerizing or negative vaccine.

The ECDI fixed cells can be formulated into a pharmaceutical composition. For example, the ECDI fixed cells can be combined with a pharmaceutically acceptable excipient. An excipient that can be used is saline. An excipient that can be used is phosphate buffered saline (PBS). The pharmaceutical compositions can be then used to treat patients in need of transplantation.

Method of Making Genetically Modified Non-Human Animals

In order to make a genetically modified non-human animal as described above, various techniques can be used. Disclosed herein are a few examples to create genetically modified animals. It is to be understood that the methods disclosed herein are simply examples, and are not meant to limiting in any way.

Gene Disruption

Gene disruption can be performed by any methods described above, for example, by knockout, knockdown, RNA interference, dominant negative, etc. A detailed description of the methods is disclosed above in the section regarding genetically modified non-human animals.

CRISPR/Cas System

Methods described herein can take advantage of a CRISPR/Cas system. For example, double-strand breaks (DSBs) can be generated using a CRISPR/Cas system, e.g., a type II CRISPR/Cas system. A Cas enzyme used in the methods disclosed herein can be Cas9, which catalyzes DNA cleavage. Enzymatic action by Cas9 derived from *Streptococcus pyogenes* or any closely related Cas9 can generate double stranded breaks at target site sequences which hybridize to 20 nucleotides of a guide sequence and that have a protospacer-adjacent motif (PAM) following the 20 nucleotides of the target sequence.

A vector can be operably linked to an enzyme-coding sequence encoding a CRISPR enzyme, such as a Cas protein. Cas proteins that can be used herein include class 1 and class 2. Non-limiting examples of Cas proteins include Cas1, Cas1B, Cas2, Cas3, Cas4, Cas5, Cas5d, Cas5t, Cas5h, Cas5a, Cas6, Cas7, Cas8, Cas9 (also known as Csn1 or Csx12), Cas10, Csy1, Csy2, Csy3, Csy4, Cse1, Cse2, Cse3, Cse4, Cse5e, Csc1, Csc2, Csa5, Csn1, Csn2, Csm1, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx1S, Csf1, Csf2, CsO, Csf4, Csd1, Csd2, Cst1, Cst2, Csh1, Csh2, Csa1, Csa2, Csa3, Csa4, Csa5, C2c1, C2c2, C2c3, Cpf1, CARF, DinG, homologues thereof, or modified versions thereof. An unmodified CRISPR enzyme can have DNA cleavage activity, such as Cas9. A CRISPR enzyme can direct cleavage of one or both strands at a target sequence, such as within a target sequence and/or within a complement of a target sequence. For example, a CRISPR enzyme can direct cleavage of one or both strands within about 1, 2, 3, 4, 5, 6, 7, 8, 9, 10, 15, 20, 25, 50, 100, 200, 500, or more base pairs from the first or last nucleotide of a target sequence. A vector that encodes a CRISPR enzyme that is mutated to with respect, to a corresponding wild-type enzyme such that the mutated CRISPR enzyme lacks the ability to cleave one or both strands of a target polynucleotide containing a target sequence can be used.

Cas9 can refer to a polypeptide with at least or at least about 50%, 60%, 70%, 80%, 90%, 91%, 92%, 93%, 94%, 95%, 96%, 97%, 98%, 99%, or 100% sequence identity and/or sequence homology to a wild type exemplary Cas9 polypeptide (e.g., Cas9 from *S. pyogenes*). Cas9 can refer to a polypeptide with at most or at most about 50%, 60%, 70%, 80%, 90%, 91%, 92%, 93%, 94%, 95%, 96%, 97%, 98%, 99%, or 100% sequence identity and/or sequence homology to a wild type exemplary Cas9 polypeptide (e.g., from *S. pyogenes*). Cas9 can refer to the wild type or a modified form of the Cas9 protein that can comprise an amino acid change such as a deletion, insertion, substitution, variant, mutation, fusion, chimera, or any combination thereof.

*S. pyogenes* Cas9 (SpCas9) can be used as a CRISPR endonuclease for genome engineering. However, others can be used. In some cases, a different endonuclease may be used to target certain genomic targets. In some cases, synthetic SpCas9-derived variants with non-NGG PAM sequences may be used. Additionally, other Cas9 orthologues from various species have been identified and these "non-SpCas9s" can bind a variety of PAM sequences that could also be useful for the present invention. For example, the relatively large size of SpCas9 (approximately 4 kb coding sequence) can lead to plasmids carrying the SpCas9 cDNA that may not be efficiently expressed in a cell. Conversely, the coding sequence for *Staphylococcus aureus* Cas9 (SaCas9) is approximately 1 kilo base shorter than SpCas9, possibly allowing it to be efficiently expressed in a cell. Similar to SpCas9, the SaCas9 endonuclease is capable of modifying target genes in mammalian cells in vitro and in mice in vivo. In some cases, a Cas protein may target a different PAM sequence. In some cases, a target gene, such as NLRC5, may be adjacent to a Cas9 PAM, 5'-NGG, for example. In other cases, other Cas9 orthologs may have different PAM requirements. For example, other PAMs such as those of *S. thermophilus* (5'-NNAGAA for CRISPR1 and 5'-NGGNG for CRISPR3) and *Neisseria meningiditis* (5'-NNNNGATT) may also be found adjacent to a target gene, such as NLRC5. A transgene of the present invention may be inserted adjacent to any PAM sequence from any Cas, or Cas derivative, protein. In some cases, a PAM can be found every, or about every, 8 to 12 base pairs in a genome. A PAM can be found every 1 to 15 basepairs in a genome. A PAM can also be found every 5 to 20 basepairs in a genome. In some cases, a PAM can be found every 5,6,7,8,9,10,11,12, 13,14,15,16,17,18,19,20, or more basepairs in a genome. A PAM can be found at or between every 5-100 base pairs in a genome.

For example, for a *S. pyogenes* system, a target gene sequence can precede (i.e., be 5' to) a 5'-NGG PAM, and a 20-nt guide RNA sequence can base pair with an opposite strand to mediate a Cas9 cleavage adjacent to a PAM. In some cases, an adjacent cut may be or may be about 3 base pairs upstream of a PAM. In some cases, an adjacent cut may be or may be about 10 base pairs upstream of a PAM. In some cases, an adjacent cut may be or may be about 0-20 base pairs upstream of a PAM. For example, an adjacent cut can be next to, 1,2,3,4,5,6,7,8,9,10,11,12,13,14,15,16,17,18, 19,20,21,22,23,24,25,26,27,28, 29, or 30 base pairs upstream of a PAM. An adjacent cut can also be downstream of a PAM by 1 to 30 base pairs.

Alternatives to *S. pyogenes* Cas9 may include RNA-guided endonucleases from the Cpf1 family that display cleavage activity in mammalian cells. Unlike Cas9 nucleases, the result of Cpf1-mediated DNA cleavage is a double-strand break with a short 3' overhang. Cpf1's staggered cleavage pattern may open up the possibility of directional gene transfer, analogous to traditional restriction enzyme cloning, which may increase the efficiency of gene editing. Like the Cas9 variants and orthologues described above, Cpf1 may also expand the number of sites that can be targeted by CRISPR to AT-rich regions or AT-rich genomes that lack the NGG PAM sites favored by SpCas9.

A vector that encodes a CRISPR enzyme comprising one or more nuclear localization sequences (NLSs) can be used. For example, there can be or be about 1, 2, 3, 4, 5, 6, 7, 8, 9, 10 NLSs used. A CRISPR enzyme can comprise the NLSs at or near the ammo-terminus, about or more than about 1, 2, 3, 4, 5, 6, 7, 8, 9, 10 NLSs at or near the carboxy-terminus, or any combination of these (e.g., one or more NLS at the ammo-terminus and one or more NLS at the carboxy terminus). When more than one NLS is present, each can be selected independently of others, such that a single NLS can be present in more than one copy and/or in combination with one or more other NLSs present in one or more copies.

CRISPR enzymes used in the methods can comprise at most 6 NLSs. An NLS is considered near the N- or C-terminus when the nearest amino acid to the NLS is within about 50 amino acids along a polypeptide chain from the N- or C-terminus, e.g., within 1, 2, 3, 4, 5, 10, 15, 20, 25, 30, 40, or 50 amino acids.

Guide RNA

As used herein, the term "guide RNA" and its grammatical equivalents can refer to an RNA which can be specific for a target DNA and can form a complex with Cas protein. An RNA/Cas complex can assist in "guiding" Cas protein to a target DNA.

A method disclosed herein also can comprise introducing into a cell or embryo at least one guide RNA or nucleic acid, e.g., DNA encoding at least one guide RNA. A guide RNA can interact with a RNA-guided endonuclease to direct the endonuclease to a specific target site, at which site the 5' end of the guide RNA base pairs with a specific protospacer sequence in a chromosomal sequence.

A guide RNA can comprise two RNAs, e.g., CRISPR RNA (crRNA) and transactivating crRNA (tracrRNA). A guide RNA can sometimes comprise a single-chain RNA, or single guide RNA (sgRNA) formed by fusion of a portion (e.g., a functional portion) of crRNA and tracrRNA. A guide RNA can also be a dualRNA comprising a crRNA and a tracrRNA. Furthermore, a crRNA can hybridize with a target DNA.

As discussed above, a guide RNA can be an expression product. For example, a DNA that encodes a guide RNA can be a vector comprising a sequence coding for the guide RNA. A guide RNA can be transferred into a cell or organism by transfecting the cell or organism with an isolated guide RNA or plasmid DNA comprising a sequence coding for the guide RNA and a promoter. A guide RNA can also be transferred into a cell or organism in other way, such as using virus-mediated gene delivery.

A guide RNA can be isolated. For example, a guide RNA can be transfected in the form of an isolated RNA into a cell or organism. A guide RNA can be prepared by in vitro transcription using any in vitro transcription system known in the art. A guide RNA can be transferred to a cell in the form of isolated RNA rather than in the form of plasmid comprising encoding sequence for a guide RNA.

A guide RNA can comprise three regions: a first region at the 5' end that can be complementary to a target site in a chromosomal sequence, a second internal region that can form a stem loop structure, and a third 3' region that can be single-stranded. A first region of each guide RNA can also be different such that each guide RNA guides a fusion protein to a specific target site. Further, second and third regions of each guide RNA can be identical in all guide RNAs.

A first region of a guide RNA can be complementary to sequence at a target site in a chromosomal sequence such that the first region of the guide RNA can base pair with the target site. In some cases, a first region of a guide RNA can comprise from or from about 10 nucleotides to 25 nucleotides (i.e., from 10 nts to 25nts; or from about 10nts to about 25 nts; or from 10 nts to about 25nts; or from about 10 nts to 25 nts) or more. For example, a region of base pairing between a first region of a guide RNA and a target site in a chromosomal sequence can be or can be about 10, 11, 12, 13, 14, 15, 16, 17, 18, 19, 20, 22, 23, 24, 25, or more nucleotides in length. Sometimes, a first region of a guide RNA can be or can be about 19, 20, or 21 nucleotides in length.

A guide RNA can also comprise a second region that forms a secondary structure. For example, a secondary structure formed by a guide RNA can comprise a stem (or hairpin) and a loop. A length of a loop and a stem can vary. For example, a loop can range from or from about 3 to 10 nucleotides in length, and a stem can range from or from about 6 to 20 base pairs in length. A stem can comprise one or more bulges of 1 to 10 or about 10 nucleotides. The overall length of a second region can range from or from about 16 to 60 nucleotides in length. For example, a loop can be or can be about 4 nucleotides in length and a stem can be or can be about 12 base pairs.

A guide RNA can also comprise a third region at the 3' end that can be essentially single-stranded. For example, a third region is sometimes not complementarity to any chromosomal sequence in a cell of interest and is sometimes not complementarity to the rest of a guide RNA. Further, the length of a third region can vary. A third region can be more than or more than about 4 nucleotides in length. For example, the length of a third region can range from or from about 5 to 60 nucleotides in length.

A guide RNA can target any exon or intron of a gene target. In some cases, a guide can target exon 1 or 2 of a gene, in other cases; a guide can target exon 3 or 4 of a gene. A composition can comprise multiple guide RNAs that all target the same exon or in some cases, multiple guide RNAs that can target different exons. An exon and an intron of a gene can be targeted.

A guide RNA can target a nucleic acid sequence of or of about 20 nucleotides. A target nucleic acid can be less than or less than about 20 nucleotides. A target nucleic acid can be at least or at least about 5, 10, 15, 16, 17, 18, 19, 20, 21, 22, 23, 24, 25, 30, or anywhere between 1-100 nucleotides in length. A target nucleic acid can be at most or at most about 5, 10, 15, 16, 17, 18, 19, 20, 21, 22, 23, 24, 25, 30, 40, 50, or anywhere between 1-100 nucleotides in length. A target nucleic acid sequence can be or can be about 20 bases immediately 5' of the first nucleotide of the PAM. A guide RNA can target a nucleic acid sequence. A target nucleic acid can be at least or at least about 1-10, 1-20, 1-30, 1-40, 1-50, 1-60, 1-70, 1-80, 1-90, or 1-100.

A guide nucleic acid, for example, a guide RNA, can refer to a nucleic acid that can hybridize to another nucleic acid, for example, the target nucleic acid or protospacer in a genome of a cell. A guide nucleic acid can be RNA. A guide nucleic acid can be DNA. The guide nucleic acid can be programmed or designed to bind to a sequence of nucleic acid site-specifically. A guide nucleic acid can comprise a polynucleotide chain and can be called a single guide nucleic acid. A guide nucleic acid can comprise two polynucleotide chains and can be called a double guide nucleic acid. A guide RNA can be introduced into a cell or embryo as an RNA molecule. For example, a RNA molecule can be transcribed in vitro and/or can be chemically synthesized. An RNA can be transcribed from a synthetic DNA molecule, e.g., a gBlocks® gene fragment. A guide RNA can then be introduced into a cell or embryo as an RNA molecule. A guide RNA can also be introduced into a cell or embryo in the form of a non-RNA nucleic acid molecule, e.g., DNA molecule. For example, a DNA encoding a guide RNA can be operably linked to promoter control sequence for expression of the guide RNA in a cell or embryo of interest. A RNA coding sequence can be operably linked to a promoter sequence that is recognized by RNA polymerase III (Pol III).

Plasmid vectors that can be used to express guide RNA include, but are not limited to, px330 vectors and px333 vectors. In some cases, a plasmid vector (e.g., px333 vector) can comprise at least two guide RNA-encoding DNA sequences. A px333 vector can be used, for example, to introduce transgene disclosed herein.

A DNA sequence encoding a guide RNA can also be part of a vector. Further, a vector can comprise additional expression control sequences (e.g., enhancer sequences, Kozak sequences, polyadenylation sequences, transcriptional termination sequences, etc.), selectable marker sequences (e.g., antibiotic resistance genes), origins of replication, and the like. A DNA molecule encoding a guide RNA can also be linear. A DNA molecule encoding a guide RNA can also be circular.

When DNA sequences encoding an RNA-guided endonuclease and a guide RNA are introduced into a cell, each DNA sequence can be part of a separate molecule (e.g., one vector containing an RNA-guided endonuclease coding sequence and a second vector containing a guide RNA coding sequence) or both can be part of a same molecule (e.g., one vector containing coding (and regulatory) sequence for both an RNA-guided endonuclease and a guide RNA).

Guide RNA can target a gene in a non-human animal or a cell. In some cases, guide RNA can target a safe harbor gene e.g., ROSA26. In some cases a guide RNA can target a PERV site. In some cases, guide RNA can target a pig NLRC5 gene. In some cases, guide RNA can be designed to target pig NLRC5, GGTA1, cytidine monophospho-N-acetylneuraminic acid (CMP-N-NeuAc) hydrolase or CMAH gene. In some cases, at least two guide RNAs are introduced. At least two guide RNAs can each target two genes. For example, in some cases, a first guide RNA can target GGTA1 and a second guide RNA can target Gal2-2. In some cases, a first guide RNA can target NLRC5 and a second guide RNA can target Gal2-2. In other cases, a first guide RNA can target GGTA1-10 and a second guide RNA can target Gal2-2.

A guide nucleic acid can comprise one or more modifications to provide a nucleic acid with a new or enhanced feature. A guide nucleic acid can comprise a nucleic acid affinity tag. A guide nucleic acid can comprise synthetic nucleotide, synthetic nucleotide analog, nucleotide derivatives, and/or modified nucleotides.

In some cases, a gRNA can comprise modifications. A modification can be made at any location of a gRNA. More than one modification can be made to a single gRNA. A gRNA can undergo quality control after a modification. In some cases, quality control may include PAGE, HPLC, MS, or any combination thereof.

A modification of a gRNA can be a substitution, insertion, deletion, chemical modification, physical modification, stabilization, purification, or any combination thereof.

A gRNA can also be modified by 5'adenylate, 5' guanosine-triphosphate cap, 5'$N^7$-Methylguanosine-triphosphate cap, 5'triphosphate cap, 3'phosphate, 3'thiophosphate, 5'phosphate, 5'thiophosphate, Cis-Syn thymidine dimer, trimers, C12 spacer, C3 spacer, C6 spacer, dSpacer, PC spacer, rSpacer, Spacer 18, Spacer 9,3'-3' modifications, 5'-5' modifications, abasic, acridine, azobenzene, biotin, biotin BB, biotin TEG, cholesteryl TEG, desthiobiotin TEG, DNP TEG, DNP-X, DOTA, dT-Biotin, dual biotin, PC biotin, psoralen C2, psoralen C6, TINA, 3'DABCYL, black hole quencher 1, black hole quencer 2, DABCYL SE, dT-DABCYL, IRDye QC-1, QSY-21, QSY-35, QSY-7, QSY-9, carboxyl linker, thiol linkers, 2'deoxyribonucleoside analog purine, 2'deoxyribonucleoside analog pyrimidine, ribonucleoside analog, 2'-O-methyl ribonucleoside analog, sugar modified analogs, wobble/universal bases, fluorescent dye label, 2'fluoro RNA, 2'O-methyl RNA, methylphosphonate, phosphodiester DNA, phosphodiester RNA, phosphothioate DNA, phosphorothioate RNA, UNA, pseudouridine-5'-triphosphate, 5-methylcytidine-5'-triphosphate, or any combination thereof.

In some cases, a modification is permanent. In other cases, a modification is transient. In some cases, multiple modifications are made to a gRNA. A gRNA modification may alter physio-chemical properties of a nucleotide, such as their conformation, polarity, hydrophobicity, chemical reactivity, base-pairing interactions, or any combination thereof.

A modification can also be a phosphorothioate substitute. In some cases, a natural phosphodiester bond may be susceptible to rapid degradation by cellular nucleases and; a modification of internucleotide linkage using phosphorothioate (PS) bond substitutes can be more stable towards hydrolysis by cellular degradation. A modification can increase stability in a gRNA. A modification can also enhance biological activity. In some cases, a phosphorothioate enhanced RNA gRNA can inhibit RNase A, RNase TI, calf serum nucleases, or any combinations thereof. These properties can allow the use of PS-RNA gRNAs to be used in applications where exposure to nucleases is of high probability in vivo or in vitro. For example, phosphorothioate (PS) bonds can be introduced between the last 3-5 nucleotides at the 5'- or 3'-end of a gRNA which can inhibit exonuclease degradation. In some cases, phosphorothioate bonds can be added throughout an entire gRNA to reduce attack by endonucleases.

Homologous Recombination

Homologous recombination can also be used for any of the relevant genetic modifications as disclosed herein. Homologous recombination can permit site-specific modifications in endogenous genes and thus novel modifications can be engineered into a genome. For example, the ability of homologous recombination (gene conversion and classical strand breakage/rejoining) to transfer genetic sequence information between DNA molecules can render targeted homologous recombination and can be a powerful method in genetic engineering and gene manipulation.

Cells that have undergone homologous recombination can be identified by a number of methods. For example, a selection method can detect an absence of an immune response against a cell, for example by a human anti-gal antibody. A selection method can also include assessing a level of clotting in human blood when exposed to a cell or tissue. Selection via antibiotic resistance can be used for screening.

Making Transgenic Non-Human Animals

Random Insertion

One or more transgenes of the methods described herein can be inserted randomly to any locus in a genome of a cell. These transgenes can be functional if inserted anywhere in a genome. For instance, a transgene can encode its own promoter or can be inserted into a position where it is under the control of an endogenous promoter. Alternatively, a transgene can be inserted into a gene, such as an intron of a gene or an exon of a gene, a promoter, or a non-coding region. A transgene can be integrated into a first exon of a gene.

A DNA encoding a transgene sequences can be randomly inserted into a chromosome of a cell. A random integration can result from any method of introducing DNA into a cell known to one of skill in the art. This can include, but is not limited to, electroporation, sonoporation, use of a gene gun, lipotransfection, calcium phosphate transfection, use of dendrimers, microinjection, use of viral vectors including adenoviral, AAV, and retroviral vectors, and/or group II ribozymes.

A DNA encoding a transgene can also be designed to include a reporter gene so that the presence of the transgene or its expression product can be detected via activation of the reporter gene. Any reporter gene known in the art can be used, such as those disclosed above. By selecting in cell culture those cells in which a reporter gene has been activated, cells can be selected that contain a transgene.

A DNA encoding a transgene can be introduced into a cell via electroporation. A DNA can also be introduced into a cell via lipofection, infection, or transformation. Electroporation and/or lipofection can be used to transfect fibroblast cells.

Expression of a transgene can be verified by an expression assay, for example, qPCR or by measuring levels of RNA. Expression level can be indicative also of copy number. For example, if expression levels are extremely high, this can indicate that more than one copy of a transgene was integrated in a genome. Alternatively, high expression can indicate that a transgene was integrated in a highly transcribed area, for example, near a highly expressed promoter. Expression can also be verified by measuring protein levels, such as through Western blotting.

Site Specific Insertion

Inserting one or more transgenes in any of the methods disclosed herein can be site-specific. For example, one or more transgenes can be inserted adjacent to a promoter, for example, adjacent to or near a Rosa26 promoter.

Modification of a targeted locus of a cell can be produced by introducing DNA into cells, where the DNA has homology to the target locus. DNA can include a marker gene, allowing for selection of cells comprising the integrated construct. Homologous DNA in a target vector can recombine with a chromosomal DNA at a target locus. A marker gene can be flanked on both sides by homologous DNA sequences, a 3' recombination arm, and a 5' recombination arm.

A variety of enzymes can catalyze insertion of foreign DNA into a host genome. For example, site-specific recombinases can be clustered into two protein families with distinct biochemical properties, namely tyrosine recombinases (in which DNA is covalently attached to a tyrosine residue) and serine recombinases (where covalent attachment occurs at a serine residue). In some cases, recombinases can comprise Cre, fC31 integrase (a serine recombinase derived from *Streptomyces* phage fC31), or bacteriophage derived site-specific recombinases (including Flp, lambda integrase, bacteriophage HK022 recombinase, bacteriophage R4 integrase and phage TP901-1 integrase).

Expression control sequences can also be used in constructs. For example, an expression control sequence can comprise a constitutive promoter, which is expressed in a wide variety of cell types. For example, among suitable strong constitutive promoters and/or enhancers are expression control sequences from DNA viruses (e.g., SV40, polyoma virus, adenoviruses, adeno-associated virus, pox viruses, CMV, HSV, etc.) or from retroviral LTRs. Tissue-specific promoters can also be used and can be used to direct expression to specific cell lineages. While experiments discussed in the Examples below will be conducted using a Rosa26 gene promoter, other Rosa26-related promoters capable of directing gene expression can be used to yield similar results, as will be evident to those of skill in the art. Therefore, the description herein is not meant to be limiting, but rather disclose one of many possible examples. In some cases, a shorter Rosa26 5'-upstream sequences, which can nevertheless achieve the same degree of expression, can be used. Also useful are minor DNA sequence variants of a Rosa26 promoter, such as point mutations, partial deletions or chemical modifications.

A Rosa26 promoter is expressible in mammals. For example, sequences that are similar to the 5' flanking sequence of a pig Rosa26 gene, including, but not limited to, promoters of Rosa26 homologues of other species (such as human, cattle, mouse, sheep, goat, rabbit and rat), can also be used.

A Rosa26 gene can be sufficiently conserved among different mammalian species and other mammalian Rosa26 promoters can also be used.

The CRISPR/Cas system can be used to perform site specific insertion. For example, a nick on an insertion site in the genome can be made by CRISPR/Cas to facilitate the insertion of a transgene at the insertion site.

The methods described herein, can utilize techniques which can be used to allow a DNA or RNA construct entry into a host cell include, but are not limited to, calcium phosphate/DNA coprecipitation, microinjection of DNA into a nucleus, electroporation, bacterial protoplast fusion with intact cells, transfection, lipofection, infection, particle bombardment, sperm mediated gene transfer, or any other technique known by one skilled in the art.

Certain aspects disclosed herein can utilize vectors. Any plasmids and vectors can be used as long as they are replicable and viable in a selected host. Vectors known in the art and those commercially available (and variants or derivatives thereof) can be engineered to include one or more recombination sites for use in the methods. Vectors that can be used include, but not limited to eukaryotic expression vectors such as pFastBac, pFastBacHT, pFastBacDUAL, pSFV, and pTet-Splice (Invitrogen), pEUK-C1, pPUR, pMAM, pMAMneo, pBI101, pBI121, pDR2, pCMVEBNA, and pYACneo (Clontech), pSVK3, pSVL, pMSG, pCH110, and pKK232-8 (Pharmacia, Inc.), p3'SS, pXT1, pSG5, pPbac, pMbac, pMClneo, and pOG44 (Stratagene, Inc.), and pYES2, pAC360, pBlueBa-cHis A, B, and C, pVL1392, pBlueBac111, pCDM8, pcDNA1, pZeoSV, pcDNA3, pREP4, pCEP4, and pEBVHis (Invitrogen, Corp.), and variants or derivatives thereof.

These vectors can be used to express a gene, e.g., a transgene, or portion of a gene of interest. A gene of portion or a gene can be inserted by using known methods, such as restriction enzyme-based techniques.

Making a Similar Genetically Modified Non-Human Animal Using Cell Nuclear Transfer An alternative method of making a genetically modified non-human animal can be by cell nuclear transfer. A method of making genetically modified non-human animals can comprise a) producing a cell with reduced expression of one or more genes and/or comprise exogenous polynucleotides disclosed herein; b) providing a second cell and transferring a nucleus of the resulting cell from a) to the second cell to generate an embryo generating an embryo; c) growing the embryo into the genetically modified non-human animal. A cell in this method can be an enucleated cell. The cell of a) can be made using any methods, e.g., gene disruption and/or insertion described herein or known in the art.

This method can be used to make a similar genetically modified non-human animal disclosed herein. For example, a method of making a genetically modified non-human animal can comprise: a) producing a cell comprising a transgene encoding a MHC molecule (e.g., single chain chimeric MHC molecule), a $\alpha$ chain or a fragment thereof, or a $\beta$ chain or a fragment thereof, or a peptide derived from a MHC molecule, in some embodiments, further comprising reduced expression of NLRC5, TAP1 and/or C3; b) providing a second cell and transferring a nucleus of the resulting cell from a) to the second cell to generate an embryo; and c) growing the embryo to the genetically modified non-human animal. A cell in this method can be an enucleated cell.

Cells used in this method can be from any disclosed genetically modified cells as described herein. For example, transgenes are not limited to comprising a transgene encoding a MHC molecule (e.g., single chain chimeric MHC molecule), a $\alpha$ chain or a fragment thereof, or a $\beta$ chain or a fragment thereof, or a peptide derived from a MHC molecule. Other combinations of gene disruptions and transgenes can be found throughout disclosure herein. For example, a method can comprise providing a first cell from any non-human animal disclosed herein; providing a second cell; transferring a nucleus of the first cell of a) to the second cell of b); generating an embryo from the product of c); and growing the embryo to the genetically modified non-human animal.

A cell of a) in the methods disclosed herein can be a zygote. The zygote can be formed by joining: i) of a sperm of a wild-type non-human animal and an ovum of a wild-type non-human animal; ii) a sperm of a wild-type non-human animal and an ovum of a genetically modified non-human animal; iii) a sperm of a genetically modified non-human animal and an ovum of a wild-type non-human animal; and/or iv) a sperm of a genetically modified non-human animal and an ovum of a genetically modified non-human animal. A non-human animal can be a pig.

One or more genes in a cell of a) in the methods disclosed herein can be disrupted by generating breaks at desired locations in the genome. For example, breaks can be double-stranded breaks (DSBs). DSBs can be generated using a nuclease comprising Cas (e.g., Cas9), ZFN, TALEN, and maganuclease. Nuclease can be a naturally-existing or a modified nuclease. A nucleic acid encoding a nuclease can be delivered to a cell, where the nuclease is expressed. Cas9 and guide RNA targeting a gene in a cell can be delivered to the cell. In some cases, mRNA molecules encoding Cas9 and guide RNA can be injected into a cell. In some cases, a plasmid encoding Cas9 and a different plasmid encoding guide RNA can be delivered into a cell (e.g., by infection). In some cases, a plasmid encoding both Cas9 and guide RNA can be delivered into a cell (e.g., by infection).

As described above, following DSBs, one or more genes can be disrupted by DNA repairing mechanisms, such as homologous recombination (HR) and/or nonhomologous end-joining (NHEJ). A method can comprise inserting one or more transgenes to a genome of the cell. Transgene can comprise a nucleic acid sequence encoding a MHC molecule (e.g., single chain chimeric MHC molecule), a $\alpha$ chain or a fragment thereof, or a $\beta$ chain or a fragment thereof, or a peptide derived from a MHC molecule. In some embodiments, the transgene can further comprise a polynucleotide encoding a peptide derived from a MHC molecule capable of binding the peptide binding groove for presentation to a T cell. One or more transgenes can comprise ICP47, CD46, CD55, CD59, HLA-E, HLA-G (e.g., HLA-G1, HLA-G2, HLA-G3, HLA-G4, HLA-G5, HLA-G6, or HLA-G7), B2M, any functional fragments thereof, and/or any combination thereof. The methods provided herein can comprise inserting one or more transgenes where the one or more transgenes can be any transgene in any non-human animal or genetically modified cell disclosed herein.

Also disclosed herein are methods of making a non-human animal using a cell from a genetically modified non-human animal. A cell can be from any genetically modified non-human animal disclosed herein. A method can comprise: a) providing a cell from a genetically identified non-human animal; b) providing a cell; c) transferring a nucleus of the cell of a) to the cell of b); c) generating an embryo from the product of c); and d) growing the embryo to the genetically modified non-human animal. A cell of this method can be an enucleated cell.

Further, cells of a) in the methods can be any cell from a genetically modified non-human animal. For example, a cell of a) in methods disclosed herein can be a somatic cell, such as a fibroblast cell or a fetal fibroblast cell.

An enucleated cell in the methods can be any cell from an organism. For example, an enucleated cell is a porcine cell. An enucleated cell can be an ovum, for example, an enucleated unfertilized ovum.

Genetically modified non-human animal disclosed herein can be made using any suitable techniques known in the art. For example, these techniques include, but are not limited to, microinjection (e.g., of pronuclei), sperm-mediated gene transfer, electroporation of ova or zygotes, and/or nuclear transplantation, or bi-oocyte fusion.

A method of making similar genetically modified non-human animals can comprise a) disrupting one or more genes in a cell, b) generating an embryo using the resulting cell of a); and c) growing the embryo into the genetically modified non-human animal.

A cell of a) in the methods disclosed herein can be a somatic cell. There is no limitation on a type or source of a somatic cell. For example, it can be from a pig or from cultured cell lines or any other viable cell. A cell can also be a dermal cell, a nerve cell, a cumulus cell, an oviduct epithelial cell, a fibroblast cell (e.g., a fetal fibroblast cell), or hepatocyte. A cell of a) in the methods disclosed herein can be from a wild-type non-human animal, a genetically modified non-human animal, or a genetically modified cell. Furthermore, a cell of b) can be an enucleated ovum (e.g., an enucleated unfertilized ovum).

Enucleation can also be performed by known methods. For example, metaphase II oocytes can be placed in either HECM, optionally containing or containing about 7-10 micrograms per milliliter cytochalasin B, for immediate enucleation, or can be placed in a suitable medium (e.g., an embryo culture medium such as CRlaa, plus 10% estrus cow serum), and then enucleated later (e.g., not more than 24 hours later or 16-18 hours later). Enucleation can also be accomplished microsurgically using a micropipette to remove the polar body and the adjacent cytoplasm. Oocytes can then be screened to identify those of which have been successfully enucleated. One way to screen oocytes can be to stain the oocytes with or with about 3-10 microgram per milliliter 33342 Hoechst dye in suitable holding medium, and then view the oocytes under ultraviolet irradiation for less than 10 seconds. Oocytes that have been successfully enucleated can then be placed in a suitable culture medium, for example, CRlaa plus 10% serum. The handling of oocytes can also be optimized for nuclear transfer.

The embryos generated herein can be transferred to surrogate non-human animals (e.g., pigs) to produce offspring (e.g., piglets). For example, the embryos can be transferred to the oviduct of recipient gilts on the day or 1 day after estrus e.g., following mid-line laparotomy under general anesthesia. Pregnancy can be diagnosed, e.g., by ultrasound. Pregnancy can be diagnosed after or after about 28 days from the transfer. The pregnancy can then checked at or at about 2-week intervals by ultrasound examination. All of the microinjected offspring (e.g., piglets) can be delivered by natural birth. Information of the pregnancy and delivery (e.g., time of pregnancy, rates of pregnancy, number of offspring, survival rate, etc.) can be documented. The genotypes and phenotypes of the offspring can be measured using any methods described through the application such as sequencing (e.g., next-generation sequencing). Sequencing can also be Zas 258 sequencing. Sequencing products can also be verified by electrophoresis of the amplification product. Cultured cells can be used immediately for nuclear transfer (e.g., somatic cell nuclear transfer), embryo transfer, and/or inducing pregnancy, allowing embryos derived from stable genetic modifications give rise to offspring (e.g., piglets). Such approach can reduce time and cost, e.g., months of costly cell screening that may result in genetically modified cells fail to produce live and/or healthy piglets.

Embryo growing and transferring can be performed using standard procedures used in the embryo growing and transfer industry. For example, surrogate mothers can be used. Embryos can also be grown and transferred in culture, for example, by using incubators. In some cases, an embryo can be transferred to an animal, e.g., a surrogate animal, to establish a pregnancy.

It can be desirable to replicate or generate a plurality of genetically modified non-human animals that have identical genotypes and/or phenotypes disclosed herein. For example, a genetically modified non-human animal can be replicated by breeding (e.g., selective breeding). A genetically modified non-human animal can be replicated by nuclear transfer (e.g., somatic cell nuclear transfer) or introduction of DNA into a cell (e.g., oocytes, sperm, zygotes or embryonic stem cells). These methods can be reproduced a plurality of times to replicate or generate a plurality of a genetically modified non-human animal disclosed herein. In some cases, cells can be isolated from the fetuses of a pregnant genetically modified non-human animal. The isolated cells (e.g., fetal cells) can be used for generating a plurality of genetically modified non-human animals similar or identical to the pregnant animal. For example, the isolated fetal cells can provide donor nuclei for generating genetically modified animals by nuclear transfer, (e.g., somatic cell nuclear transfer).

The method of making a genetically modified non-human animal of the present disclosure can include bi-oocyte fusion. For example, the a method for making a genetically modified animal comprising the steps of: (a) inducing a fusion of a genetically modified cell of the present disclosure with one or more oocyte, under conditions suitable for forming a reconstructed embryo, wherein the one or more oocytes are zona pellucida free, and enucleated, (b) activating the reconstructed embryo, (c) culturing the activated reconstructed embryo, until greater than 2-cell developmental stage; and (d) implanting the cultured embryo into a surrogate and growing the embryo to the genetically modified animal in the surrogate. In some embodiments, the genetically modified cell comprises a transgene comprising a nucleic acid sequence encoding a MHC molecule (e.g., single chain chimeric MHC molecule), a α chain or a fragment thereof, or a β chain or a fragment thereof, or a peptide derived from a MHC molecule. The transgene can further comprise a polynucleotide encoding a peptide derived from a MHC molecule capable of binding the peptide binding groove for presentation to a T cell. In some embodiments, the genetically modified cell can further comprise one or more additional transgenes e.g., ICP47, CD46, CD55, CD59, HLA-E, HLA-G (e.g., HLA-G1, HLA-G2, HLA-G3, HLA-G4, HLA-G5, HLA-G6, or HLA-G7), B2M, any functional fragments thereof, and/or any combination thereof.

A "reconstructed embryo" is an embryo made by the fusion of an enucleated oocyte with a genetically modified donor somatic or embryonic stem(ES) or embryonic germ (EG) cell. Methods of bio-oocyte fusion are described in Examples herein. The term "enucleated oocyte" as used herein can refer to an oocyte which has had its nucleus, or its chromosomes removed. Typically, a needle can be placed into an oocyte and the nucleus and/or chromosomes can be aspirated into the needle. The needle can be removed from the oocyte without rupturing the plasma membrane. This enucleation technique is well known to a person of ordinary skill in the art. See, e.g., U.S. Pat. Nos. 4,994,384; 5,057,420; and Willadsen, 1986, Nature 320:63-65. The oocyte can be enucleated by means of manual bisection. Oocyte bisection may be carried out by any method known to those skilled in the art. In one preferred embodiment, the bisection is carried out using a microsurgical blade as described in WO98/29532 which is incorporated by reference herein. If the oocyte is obtained in an immature state (e.g. as with current bovine techniques), an enucleated oocyte is prepared from an oocyte that has been matured for greater than 24 hours, preferably matured for greater than 36 hours, more preferably matured for greater than 48 hours, and most preferably matured for about 53 hours.

The term "electrical pulses" as used herein can refer to subjecting a nuclear donor and recipient oocyte to electric current. For nuclear transfer, a nuclear donor and recipient oocyte can be aligned between electrodes and subjected to electrical current. Electrical current can be alternating current or direct current. The term "activation" can refer to any materials and methods useful for stimulating a cell to divide before, during, and after a nuclear transfer step. Examples of components that are useful for non-electrical activation include ethanol; inositol trisphosphate (IP3); divalent ions (e.g., addition of Ca2+ and/or Sr2+); microtubule inhibitors (e.g., cytochalasin B); ionophores for divalent ions (e.g., the α3+ionophore ionomycin); protein kinase inhibitors (e.g., 6-dimethylaminopurine (DMAP)); protein synthesis inhibitors (e.g., cyclohexamide); phorbol esters such as phorbol 12-myristate 13-acetate (PMA); and thapsigargin. It is also known that temperature change and mechanical techniques are also useful for non-electrical activation. The invention includes any activation techniques known in the art. See, e.g., U.S. Pat. No. 5,496,720, entitled "Parthenogenic Oocyte Activation," issued on Mar. 5, 1996, Susko-Parrish et al., and Wakayama et al. (1998) Nature 394:369-374. The zona pellucida can be removed by any means known in the art such as, without limitation, treatment with acidic Tyrode's solution or pronase or by physical manipulation by means of a micro-needle, laser, or the like. he term "fusion agent" as used herein can refer to any compound or biological organism that can increase the probability that portions of plasma membranes from different cells will fuse when a nuclear donor is placed adjacent to a recipient oocyte. In preferred embodiments fusion agents are selected from the group consisting of polyethylene glycol (PEG), trypsin, dimethylsulfoxide (DMSO), lectins, agglutinin, viruses, and Sendai virus. These examples are not meant to be limiting and other fusion agents known in the art are applicable and included herein.

Methods of Use

Cells, organs, and/or tissues can be extracted from a non-human animal as described herein. Cells, organs, and/or tissues can be genetically altered ex vivo and used accordingly. These cells, organs, and/or tissues can be used for cell-based therapies. These cells, organs, and/or tissues can be used to treat or prevent disease in a recipient (e.g., a human or non-human animal). Surprisingly, the genetic modifications as described herein can help prevent rejection. Additionally, cells, organs, and/or tissues can be made into tolerizing vaccines to also help tolerize the immune system to transplantation. Further, tolerizing vaccines can temper the immune system, including, abrogating autoimmune responses.

Disclosed herein are methods for treating a disease in a subject in need thereof can comprise administering a tolerizing vaccine to the subject; administering a pharmaceutical agent that inhibits T cell activation to the subject; and transplanting a genetically modified cell to the subject. The pharmaceutical agent that inhibits T cell activation can be an antibody. The antibody can be an anti-CD40 antibody disclosed herein. The anti-CD40 antibody can be an antagonistic antibody. The anti-CD40 antibody can be an anti-CD40 antibody that specifically binds to an epitope within the amino acid sequence: EPPTACREKQYLINSQCCSLCQPGQKLVSDCTEFTETECLPCGESEFLDTWNRETHCHQHKYCDP NLGLRVQQKGTSETDTICTCEEGWHCTSEACESCV (SEQ ID NO: 61). The anti-CD40 antibody can be an anti-CD40 antibody that specifically binds to an epitope within the amino acid sequence: EKQYLINSQCCSLCQPGQKLVSDCTEFTETECL (SEQ ID NO: 62). The anti-CD40 antibody can be a Fab' anti-CD40L monoclonal antibody fragment CDP7657. The anti-CD-40 antibody can be a FcR-engineered, Fc silent anti-CD40L monoclonal domain antibody. The cell transplanted to the subject can be any genetically modified cell described throughout the application. The tissue or organ transplanted to the subject can comprise one or more of the genetically modified cells. In some cases, the methods can further comprise administering one or more immunosuppression agent described in the application, such as further comprising providing to the recipient one or more of a B-cell depleting antibody, an mTOR inhibitor, a TNF-alpha inhibitor, a IL-6 inhibitor, a nitrogen mustard alkylating agent (e.g., cyclophosphamide), and a complement C3 or C5 inhibitor.

Also disclosed herein are methods for treating a disease, comprising transplanting one or more cells to a subject in need thereof. The one or more cells can be any genetically modified cells disclosed herein. In some cases, the methods can comprise transplanting a tissue or organ comprising the one or more cells (e.g., genetically modified cells) to the subject in need thereof.

Described herein are methods of treating or preventing a disease in a recipient (e.g., a human or non-human animal) comprising transplanting to the recipient (e.g., a human or non-human animal) one or more cells (including organs and/or tissues) derived from a genetically modified non-human animal comprising one or more genes with reduced expression. One or more cells can be derived from a genetically modified non-human animal as described throughout.

The methods disclosed herein can be used for treating or preventing disease including, but not limited to, diabetes, cardiovascular diseases, lung diseases, liver diseases, skin diseases, or neurological disorders. For example, the methods can be used for treating or preventing Parkinson's disease or Alzheimer's disease. The methods can also be used for treating or preventing diabetes, including type 1, type 2, cystic fibrosis related, surgical diabetes, gestational diabetes, mitochondrial diabetes, or combination thereof. In some cases, the methods can be used for treating or preventing hereditary diabetes or a form of hereditary diabetes. Further, the methods can be used for treating or preventing type 1 diabetes. The methods can also be used for treating or preventing type 2 diabetes. The methods can be used for treating or preventing pre-diabetes.

For example, when treating diabetes, genetically modified splenocytes can be fixed with ECDI and given to a recipient. Further, genetically modified pancreatic islet cells can be grafted into the same recipient to produce insulin. Genetically modified splenocytes and pancreatic islet cells can be genetically identical and can also be derived from the same genetically modified non-human animal.

Provided herein include i) genetically modified cells, tissues or organs for use in administering to a subject in need thereof to treat a condition in the subject; ii) a tolerizing vaccine for use in immunotolerizing the subject to a graft, where the tolerizing vaccine comprise a genetically modified cell, tissue, or organ; iii) one or more pharmaceutical agents for use in inhibiting T cell activation, B cell activation, dendritic cell activation, or a combination thereof in the subject; or iv) any combination thereof.

Also provided herein include genetically modified cells, tissues or organs for use in administering to a subject in need thereof to treat a condition in the subject. The subject can have been or become tolerized to the genetically modified cell, tissue or organ by use of a tolerizing vaccine. Further, the subject can be administered one or more pharmaceutical agents that inhibit T cell activation, B cell activation, dendritic cell activation, or a combination thereof.

Transplantation

The methods disclosed herein can comprise transplanting. Transplanting can be autotransplanting, allotransplanting, xenotransplanting, or any other transplanting. For example, transplanting can be xenotransplanting. Transplanting can also be allotransplanting.

"Xenotransplantation" and its grammatical equivalents as used herein can encompass any procedure that involves transplantation, implantation, or infusion of cells, tissues, or organs into a recipient, where the recipient and donor are different species. Transplantation of the cells, organs, and/or tissues described herein can be used for xenotransplantation in into humans. Xenotransplantation includes but is not limited to vascularized xenotransplant, partially vascularized xenotransplant, unvascularized xenotransplant, xenodressings, xenobandages, and nanostructures.

"Allotransplantation" and its grammatical equivalents as used herein can encompass any procedure that involves transplantation, implantation, or infusion of cells, tissues, or organs into a recipient, where the recipient and donor are the same species. Transplantation of the cells, organs, and/or tissues described herein can be used for allotransplantation in into humans. Allotransplantation includes but is not limited to vascularized allotransplant, partially vascularized allotransplant, unvascularized allotransplant, allodressings, allobandages, and allostructures.

After treatment (e.g., any of the treatment as disclosed herein), transplant rejection can be improved as compared to when one or more wild-type cells is transplanted into a recipient. For example, transplant rejection can be hyperacute rejection. Transplant rejection can also be acute rejection. Other types of rejection can include chronic rejection. Transplant rejection can also be cell-mediated rejection or T cell-mediated rejection. Transplant rejection can also be natural killer cell-mediated rejection.

In some cases, a subject is sensitized to major histocompatibility complex (MHC) or human leukocyte antigen (HLA). For example, a subject may have a positive result on a panel reactive antibody (PRA) screen. In some cases, a subject may have a calculated PRA (cPRA) score from 0.1 to 100%. A cPRA score can be or can be about from 0.1 to 10%, 5% to 30%, 10% to 50%, 20% to 80%, 40% to 90%, 50% to 100%. In some cases, a subject with a positive PRA screen may be transplanted with the genetically modified cells of the invention.

In some cases, a subject may have a quantification performed of their PRA level by a single antigen bead (SAB) test. An SAB test can identify MHC or HLA for which a subject has antibodies to.

"Improving" and its grammatical equivalents as used herein can mean any improvement recognized by one of skill in the art. For example, improving transplantation can mean lessening hyperacute rejection, which can encompass a decrease, lessening, or diminishing of an undesirable effect or symptom.

The disclosure describes methods of treatment or preventing diabetes or prediabetes. For example, the methods include but are not limited to, administering one or more pancreatic islet cell(s) from a donor non-human animal described herein to a recipient, or a recipient in need thereof. The methods can be transplantation or, in some cases, xenotransplantation. The donor animal can be a non-human animal. A recipient can be a primate, for example, a non-human primate including, but not limited to, a monkey. A recipient can be a human and in some cases, a human with diabetes or pre-diabetes. In some cases, whether a patient with diabetes or pre-diabetes can be treated with transplantation can be determined using an algorithm, e.g., as described in *Diabetes Care* 2015; 38:1016-1029, which is incorporated herein by reference in its entirety.

The methods can also include methods of xenotransplantation where the transgenic cells, tissues and/or organs, e.g., pancreatic tissues or cells, provided herein are transplanted into a primate, e.g., a human, and, after transplant, the primate requires less or no immunosuppressive therapy. Less or no immunosuppressive therapy includes, but is not limited to, a reduction (or complete elimination of) in dose of the immunosuppressive drug(s)/agent(s) compared to that required by other methods; a reduction (or complete elimination of) in the number of types of immunosuppressive drug(s)/agent(s) compared to that required by other methods; a reduction (or complete elimination of) in the duration of immunosuppression treatment compared to that required by other methods; and/or a reduction (or complete elimination of) in maintenance immunosuppression compared to that required by other methods.

The methods disclosed herein can be used for treating or preventing disease in a recipient (e.g., a human or non-human animal). A recipient can be any non-human animal or a human. For example, a recipient can be a mammal. Other examples of recipient include but are not limited to primates, e.g., a monkey, a chimpanzee, a bamboo, or a human. If a recipient is a human, the recipient can be a human in need thereof. The methods described herein can also be used in non-primate, non-human recipients, for example, a recipient can be a pet animal, including, but not limited to, a dog, a cat, a horse, a wolf, a rabbit, a ferret, a gerbil, a hamster, a chinchilla, a fancy rat, a guinea pig, a canary, a parakeet, or a parrot. If a recipient is a pet animal, the pet animal can be in need thereof. For example, a recipient can be a dog in need thereof or a cat in need thereof.

Transplanting can be by any transplanting known to the art. Graft can be transplanted to various sites in a recipient. Sites can include, but not limited to, liver subcapsular space, splenic subcapsular space, renal subcapsular space, omentum, bursa omentalis, gastric or intestinal submucosa, vascular segment of small intestine, venous sac, testis, brain, spleen, or cornea. For example, transplanting can be subcapsular transplanting. Transplanting can also be intramuscular transplanting. Transplanting can be intraportal transplanting.

Transplanting can be of one or more cells, tissues, and/or organs from a human or non-human animal. For example, the tissue and/or organs can be, or the one or more cells can be from, a brain, heart, lungs, eye, stomach, pancreas, kidneys, liver, intestines, uterus, bladder, skin, hair, nails, ears, glands, nose, mouth, lips, spleen, gums, teeth, tongue, salivary glands, tonsils, pharynx, esophagus, large intestine, small intestine, rectum, anus, thyroid gland, thymus gland, bones, cartilage, tendons, ligaments, suprarenal capsule, skeletal muscles, smooth muscles, blood vessels, blood, spinal cord, trachea, ureters, urethra, hypothalamus, pituitary, pylorus, adrenal glands, ovaries, oviducts, uterus, vagina, mammary glands, testes, seminal vesicles, penis, lymph, lymph nodes or lymph vessels. The one or more cells can also be from a brain, heart, liver, skin, intestine, lung, kidney, eye, small bowel, or pancreas. The one or more cells are from a pancreas, kidney, eye, liver, small bowel, lung, or heart. The one or more cells can be from a pancreas. The one or more cells can be pancreatic islet cells, for example, pancreatic β cells. Further, the one or more cells can be pancreatic islet cells and/or cell clusters or the like, including, but not limited to pancreatic α cells, pancreatic β cells, pancreatic δ cells, pancreatic F cells (e.g., PP cells), or pancreatic ε cells. In one instance, the one or more cells can be pancreatic α cells. In another instance, the one or more cells can be pancreatic β cells.

As discussed above, a genetically modified non-human animal can be used in xenograft (e.g., cells, tissues and/or organ) donation. Solely for illustrative purposes, genetically modified non-human animals, e.g., pigs, can be used as donors of pancreatic tissue, including but not limited to, pancreatic islets and/or islet cells. Pancreatic tissue or cells derived from such tissue can comprise pancreatic islet cells, or islets, or islet-cell clusters. For example, cells can be pancreatic islets which can be transplanted. More specifically, cells can be pancreatic β cells. Cells also can be insulin-producing. Alternatively, cells can be islet-like cells. Islet cell clusters can include any one or more of α, β, δ, PP or ε cells. A disease to be treated by methods and compositions herein can be diabetes. Transplantable grafts can be pancreatic islets and/or cells from pancreatic islets. A modification to a transgenic animal can be to the pancreatic islets or cells from pancreatic islets. In some cases, pancreatic islets or cells from a pancreatic islet can be porcine. In some cases, cells from a pancreatic islet include pancreatic β cells.

Donor non-human animals can be at any stage of development including, but not limited to, embryonic, fetal, neonatal, young and adult. For example, donor cells islet cells can be isolated from adult non-human animals. Donor cells, e.g., islet cells, can also be isolated from fetal or neonatal non-human animals. Donor non-human animals can be under the age of 10, 9, 8, 7, 6, 5, 4, 3, 2, or 1 year(s). For example, islet cells can be isolated from a non-human animal under the age of 6 years. Islet cells can also be isolated from a non-human animal under the age of 3 years. Donors can be non-human animals and can be any age from or from about 0 (including a fetus) to 2; 2 to 4; 4 to 6; 6 to 8; or 8 to 10 years. A non-human animal can be older than or than about 10 years. Donor cells can be from a human as well.

Islet cells can be isolated from non-human animals of varying ages. For example, islet cells can be isolated from or from about newborn to 2 year old non-human animals. Islets cells can also be isolated from or from about fetal to 2 year old non-human animals. Islets cells can be isolated from or from about 6 months old to 2 year old non-human animals. Islets cells can also be isolated from or from about 7 months old to 1 year old non-human animals. Islets cells can be isolated from or from about 2-3 year old non-human animals. In some cases, non-human animals can be less than 0 years (e.g., a fetus or embryo). In some cases, neonatal islets can be more hearty and consistent post-isolation than adult islets, can be more resistant to oxidative stress, can exhibit significant growth potential (likely from a nascent islet stem cell subpopulation), such that they can have the ability to proliferate post-transplantation and engraftment in a transplantation site.

With regards to treating diabetes, neonatal islets can have the disadvantage that it can take them up to or up to about 4-6 weeks to mature enough such that they produce significant levels of insulin, but this can be overcome by treatment with exogenous insulin for a period sufficient for the maturation of the neonatal islets. In xenograft transplantation, survival and functional engraftment of neo-natal islets can be determined by measuring donor-specific c-peptide levels, which are easily distinguished from any recipient endogenous c-peptide.

As discussed above, adult cells can be isolated. For example, adult non-human animal islets, e.g., adult porcine cells, can be isolated. Islets can then be cultured for or for about 1-3 days prior to transplantation in order to deplete the preparation of contaminating exocrine tissue. Prior to treatment, islets can be counted, and viability assessed by double fluorescent calcein-AM and propidium iodide staining. Islet cell viability >75% can be used. However, cell viability greater than or greater than about 40%, 50%, 60%, 70%, 80%, 90%, 95%, 99% can be used. For example, cells that exhibit viability from or from about 40% to 50%; 50% to 60%; 60% to 70%; 70% to 80%; 80% to 90%; 90% to 95%, or 90% to 100% can be used. Additionally, purity can be greater than or greater than about 80% islets/whole tissue. Purity can also be at least or at least about 40%, 50%, 60%, 70%, 80%, 90%, 95%, or 99% islets/whole tissue. For example, purity can be from or can be from about 40% to 50%; 50% to 60%; 60% to 70%; 70% to 80%; 80% to 90%; 90% to 100%; 90% to 95%, or 95% to 100%.

Functional properties of islets, including glucose-stimulated insulin secretion as assed by dynamic perifusion and viability, can be determined in vitro prior to treatment (Balamurugan, 2006). For example, non-human animal islet cells, e.g., transgenic porcine islet cells can be cultured in vitro to expand, mature, and/or purify them so that they are suitable for grafting.

Islet cells can also be isolated by standard collagenase digestion of minced pancreas. For example, using aseptic techniques, glands can be distended with tissue dissociating enzymes (a mixture of purified enzymes formulated for rapid dissociation of a pancreas and maximal recovery of healthy, intact, and functional islets of Langerhans, where target substrates for these enzymes are not fully identified, but are presumed to be collagen and non-collagen proteins, which comprise intercellular matrix of pancreatic acinar tissue) (1.5 mg/ml), trimmed of excess fat, blood vessels and connective tissue, minced, and digested at 37 degree C. in a shaking water bath for 15 minutes at 120 rpm. Digestion can be achieved using lignocaine mixed with tissue dissociating enzymes to avoid cell damage during digestion. Following digestion, the cells can be passed through a sterile 50 mm to 1000 mm mesh, e.g., 100 mm, 200 mm, 300 mm, 400 mm, 500 mm, 600 mm, 700 mm, 800 mm, 900 mm, or 1000 mm mesh into a sterile beaker. Additionally, a second digestion process can be used for any undigested tissue.

Islets can also be isolated from the adult pig pancreas (Brandhorst et al., 1999). The pancreas is retrieved from a suitable source pig, peri-pancreatic tissue is removed, the pancreas is divided into the splenic lobe and in the duodenal/connecting lobe, the ducts of each lobes are cannulated, and the lobes are distended with tissue dissociating enzymes. The pancreatic lobes are placed into a Ricordi chamber, the temperature is gradually increased to 28 to 32° C., and the pancreatic lobes are dissociated by means of enzymatic activity and mechanical forces. Liberated islets are separated from acinar and ductal tissue using continuous density gradients. Purified pancreatic islets are cultured for or for about 2 to 7 days, subjected to characterization, and islet products meeting all specifications are released for transplantation (Korbutt et al., 2009).

Donor cells, organs, and/or tissues before, after, and/or during transplantation can be functional. For example, transplanted cells, organs, and/or tissues can be functional for at least or at least about 1, 5, 10, 20, 30 days after transplantation. Transplanted cells, organs, and/or tissues can be functional for at least or at least about 1, 2, 3, 4, 5, 6, 7, 8, 9, 10, 11, or 12 months after transplantation. Transplanted cells, organs, and/or tissues can be functional for at least or at least about 1, 2, 3, 4, 5, 6, 7, 8, 9, 10, 15, 20, 25, or 30 years after transplantation. In some cases, transplanted cells, organs, and/or tissues can be functional for up to the lifetime of a recipient. This can indicate that transplantation was successful. This can also indicate that there is no rejection of the transplanted cells, tissues, and/or organs.

Further, transplanted cells, organs, and/or tissues can function at 100% of its normal intended operation. Transplanted cells, organs, and/or tissues can also function at least or at least about 50, 60, 65, 70, 75, 80, 85, 90, 95, 99, or 100% of its normal intended operation, e.g., from or from about 50 to 60; 60 to 70; 70 to 80; 80 to 90; 90 to 100%. In certain instances, the transplanted cells, organs, and/or tissues can function at greater 100% of its normal intended operation (when compared to a normal functioning non-transplanted cell, organ, or tissue as determined by the American Medical Association). For example, the transplanted cells, organs, and/or tissues can function at or at about 110, 120, 130, 140, 150, 175, 200% or greater of its normal intended operation, e.g., from or from about 100 to 125; 125 to 150; 150 to 175; 175 to 200%.

In certain instances, transplanted cells can be functional for at least or at least about 1 day. Transplanted cells can also functional for at least or at least about 7 days. Transplanted cells can be functional for at least or at least about 14 days. Transplanted cells can be functional for at least or at least about 21 days. Transplanted cells can be functional for at least or at least about 28 days. Transplanted cells can be functional for at least or at least about 60 days.

Another indication of successful transplantation can be the days a recipient does not require immunosuppressive therapy. For example, after treatment (e.g., transplantation) provided herein, a recipient can require no immunosuppressive therapy for at least or at least about 1, 5, 10, 100, 365, 500, 800, 1000, 2000, 4000 or more days. This can indicate that transplantation was successful. This can also indicate that there is no rejection of the transplanted cells, tissues, and/or organs.

In some cases, a recipient can require no immunosuppressive therapy for at least or at least about 1 day. A recipient can also require no immunosuppressive therapy for at least or at least about 7 days. A recipient can require no immunosuppressive therapy for at least or at least about 14 days. A recipient can require no immunosuppressive therapy for at least or at least about 21 days. A recipient can require no immunosuppressive therapy for at least or at least about 28 days. A recipient can require no immunosuppressive therapy for at least or at least about 60 days. Furthermore, a recipient can require no immunosuppressive therapy for at least or at least about 1, 2, 3, 4, 5, 6, 7, 8, 9, 10, 15, 20, 30, 40, or 50 years, e.g., for at least or at least about 1 to 2; 2 to 3; 3 to 4; 4 to 5; 1 to 5; 5 to 10; 10 to 15; 15 to 20; 20 to 25; 25 to 50 years.

Another indication of successful transplantation can be the days a recipient requires reduced immunosuppressive therapy. For example, after the treatment provided herein, a recipient can require reduced immunosuppressive therapy for at least or at least about 1, 5, 10, 50, 100, 200, 300, 365, 400, 500 days, e.g., for at least or at least about 1 to 30; 30 to 120; 120 to 365; 365 to 500 days. This can indicate that transplantation was successful. This can also indicate that there is no or minimal rejection of the transplanted cells, tissues, and/or organs.

For example, a recipient can require reduced immunosuppressive therapy for at least or at least about 1 day. A recipient can also require reduced immunosuppressive therapy for at least 7 days. A recipient can require reduced immunosuppressive therapy for at least or at least about 14 days. A recipient can require reduced immunosuppressive therapy for at least or at least about 21 days. A recipient can require reduced immunosuppressive therapy for at least or at least about 28 days. A recipient can require reduced immunosuppressive therapy for at least or at least about 60 days. Furthermore, a recipient can require reduced immunosuppressive therapy for at least or at least about 1, 2, 3, 4, 5, 6, 7, 8, 9, 10, 15, 20, 30, 40, or 50 years, e.g., for at least or at least about 1 to 2; 2 to 3; 3 to 4; 4 to 5; 1 to 5; 5 to 10; 10 to 15; 15 to 20; 20 to 25; 25 to 50 years.

"Reduced" and its grammatical equivalents as used herein can refer to less immunosuppressive therapy compared to a required immunosuppressive therapy when one or more wild-type cells is transplanted into a recipient.

A donor (e.g., a donor for a transplant graft and/or a cell in a tolerizing vaccine) can be a mammal. A donor of allografts can be an unmodified human cell, tissue, and/or organ, including but not limited to pluripotent stem cells. A donor of xenografts can be any cell, tissue, and/or organ from a non-human animal, such as a mammal. In some cases, the mammal can be a pig.

The methods herein can further comprise treating a disease by transplanting one or more donor cells to an immunotolerized recipient (e.g., a human or a non-human animal).

Kits

Provided herein are kits comprising the isolated nucleic acid molecule of the present disclosure or a vector comprising the isolated nucleic acid molecule disclosed above. In some embodiments, the isolated nucleic acid is in a lyophilized or a solution form. In some embodiments, the kit further comprises a cell of generating a genetically modified cell using methods disclosed herein. In some embodiments, the kit further comprises instructions for insertion of the isolated nucleic molecule into the genome of a cell. The kit is intended for use in generation of genetically modified cell using methods disclosed herein.

In another embodiment of the disclosure, an article of manufacture which contains the pharmaceutical composition in a solution form or in a lyophilized form or a kit comprising an article of manufacture is provided. The kit of the instant disclosure can be contemplated for use in transplantation of a transplant in a recipient. In some embodiments, the kit comprises a third container comprising one or more immunomodulatory molecules. In some embodiments, kits of the disclosure include a formulation of nanoparticle compositions disclosed herein or nanoparticle compositions disclosed herein packaged for use in combination with the co-administration of a second compound (such as an anti-inflammatory agent, immunomodulating agent, anti-tumor agent, a natural product, a hormone or antagonist, an anti-angiogenesis agent or inhibitor, a apoptosis-inducing agent, a chelator, or anti-CD40 agent) or a pharmaceutical composition thereof. The components of the kit may be pre-complexed or each component may be in a separate distinct container prior to administration to a patient.

In some embodiments, the kits can comprise a container comprising a diluent, a reconstitution solution, and/or a culture medium. The kit can comprise instructions for diluting the composition or for its reconstitution and/or use. The article of manufacture comprises a container. Suitable containers include, for example, bottles, vials (e.g. dual chamber vials), syringes (such as dual chamber syringes) and test tubes. The container may be formed from a variety of materials such as glass or plastic. The container holds the lyophilized formulation and a label on, or associated with, the container may indicate directions for reconstitution and/or use. The label may further indicate that the formulation is useful transformation of cells or intended for subcutaneous administration. The container holding the formulation may be a multi-use vial. The article of manufacture may further include other materials desirable from a commercial and user standpoint, including other buffers, diluents, filters, needles, syringes, and package inserts with instructions for use.

The components of the kits may be provided in one or more liquid solutions, preferably, an aqueous solution, more preferably, a sterile aqueous solution. The components of the kit may also be provided as solids, which may be converted into liquids by addition of suitable solvents, which are preferably provided in another distinct container.

The containers of a kit may be a vial, test tube, flask, bottle, syringe, or any other means of enclosing a solid or liquid. Usually, when there is more than one component, the kit will contain a second vial or additional container, which allows for separate dosing. The kit may also contain another container for a pharmaceutically acceptable liquid. Preferably, a kit will contain apparatus (e.g., one or more needles, syringes, eye droppers, pipette, etc.), which enables administration of the nanoparticle of the disclosure which are components of the present kit.

In some embodiments, the kit disclosed herein further comprises the transplant. In some embodiment, the transplant is cell, tissue or organ transplant. In some embodiments, the transplant is genetically modified. In some embodiments, the transplant is a is a kidney, liver, heart, lung, pancreas, islet cell, small bowel, bone marrow, hematopoietic stem cell, embryonic or induced pluripotent stem cell-derived islet beta cell, embryonic or induced pluripotent stem cell-derived islet, embryonic or induced pluripotent stem cell-derived hepatocyte or a combination thereof. In some embodiments, the transplant can be autologous, allograft, or a xenograft. In some embodiments, the transplant can be genetically modified.

EXAMPLES

Example 1: Construction of a Transgene Encoding Single Chain MHC (HLA-DR) Chimeric Polypeptide MHC class II matching between donor and recipient limits the activation of CD4+ T cells with direct and indirect donor specificities and promotes the generation of CD4+ T cells with potent regulatory properties that actively suppress alloreactive CD8+ cytotoxic T cell responses and modulate dendritic cells (DC). Without wishing to be bound by theory, it may be possible that because of the propensity of MHC class II molecules to present themselves as peptides the peri-transplant infusions of ADL (including numerous splenic and/or ex vivo expanded, MHC class II expressing B cells) causes a substantial increase of shared MHC class II molecule complexes presenting their MHC class II peptides on the surface of host antigen presenting cells including spleen marginal zone macrophages and possibly also liver sinusoidal endothelial cells. These complexes, also referred to as "T-Lo" or "Suppress Me" complexes, are involved in the thymic differentiation of thymus-derived tTregs and, after being transferred from antigen presenting cells to activated T cells by trogozytosis, provide strong activation signals to pre-existing tTregs. It is well known that tTregs exported to the periphery exhibit a TCR repertoire skewed toward self-recognition. Activation of tTregs profoundly increases their regulatory potency. Treg cells have been shown to trigger the generation of Trl regulatory cells.

If one MHC class II allele is matched between porcine donor and human recipient, host tTreg activation may be accomplished by graft expression of T-Lo complexes. Whenever the microenvironment of the accepted xenograft changes from quiescent to inflammatory, MHC class II antigen expression is upregulated, leading to increased expression of T-Lo complexes by the graft. The sustained activation of tTregs is also facilitated by the persistent expression of T-Lo complexes on host APC and their transfer to host Teff that are indirectly primed by mismatched MHC-class II peptides presented by host MHC class II.

The shared self MHC class II peptide self MHC class II T-Lo complexes can spread tolerance when expressed on peripheral antigen presenting cells through T-Lo-specific tTregs, which could inhibit-via linked suppression- and convert-via infectious tolerance-Teff that recognize mismatched donor antigens on the same APC. Without wishing to be bound by theory, sharing of one HLA class II allele between transgenic porcine donors and human porcine xenograft recipients will promote the presentation of HLA class II peptide HLA class II molecule complexes on host immune cells, leading to activation and expansion of CD4+ Tregs and Trl-like cells, thereby resulting in induction of immune tolerance towards the porcine xenograft.

Provided below are methods for generating genetically modified cells and genetically modified animals expressing a transgene encoding a single chain MHC chimeric polypeptide (scMHC chimeric peptide) in which a MHC molecule is covalently linked to a peptide derived from the MHC molecule. The transgene encodes a single chain MHC chimeric polypeptide in which α chain of the MHC molecule, chain of the MHC molecule and a peptide derived from the MHC molecule are functionally fused in a single chain. The chimeric polypeptide folds such that the α chain of the MHC molecule and the β chain of the MHC molecule form a peptide binding groove in which the peptide derived from the MHC molecule binds to form a functional MHC-peptide complex (FIG. 2). The methods below exemplifies generation of a genetically modified cell and animal expressing the single chain MHC chimeric polypeptide. The example illustrates expression of a single chain MHC chimeric polypeptide wherein the α chain and the β chain is from HLA-DR which fold to form a HLA-DR MHC molecule.

Figure 1:
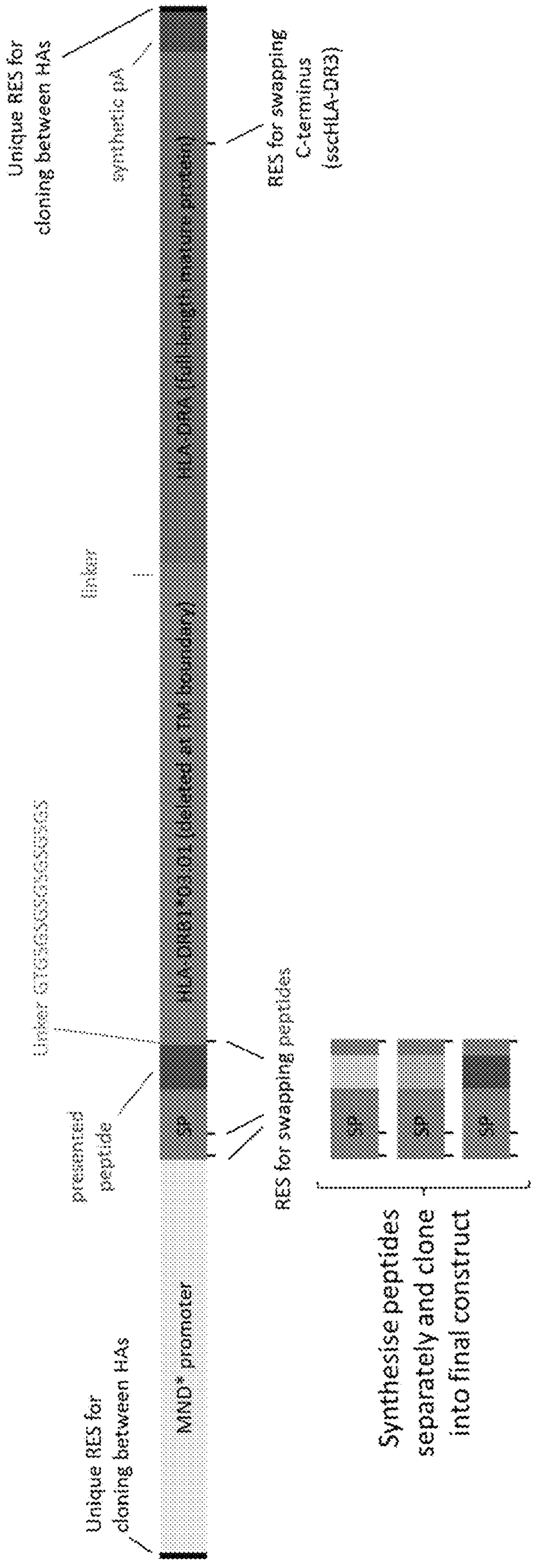
FIG. 1 shows design of a single chain HLA-DR polypeptide (scHLA-DR) with an intact tolerogenic peptide. 4 different peptides that originate from the DR3 molecule derived from the NCBI algorithm for antigneic peptide analysis will be tested. The small MND promoter is chosen and GS linkers have been incorporated. Other promoters such as those from beta actin, EFlalpha can be also be used. Several restriction enzyme sites for future modifications have been included. The flexible linker comprises a sequence of GTGSGSGSGSGSGSGS (SEQ ID NO: 1) or GGGGSGGGG (SEQ ID NO: 2).
Figure 2A:
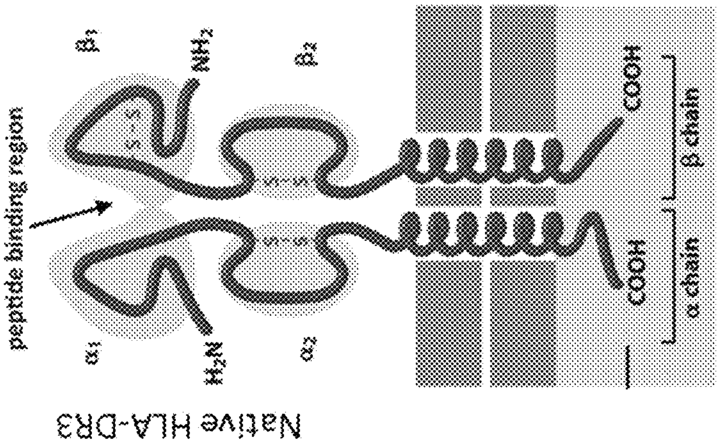
FIGS. 2A-2G shows exemplary HLA-DR molecule comprising an alpha chain and a beta chain which assemble to form a peptide binding region. The present disclosure encompasses the expression of HLA-DR molecule in various forms as illustrated in FIGS. 2A-2G, in a genetically modified cell or genetically modified animal.
Figure 2B:
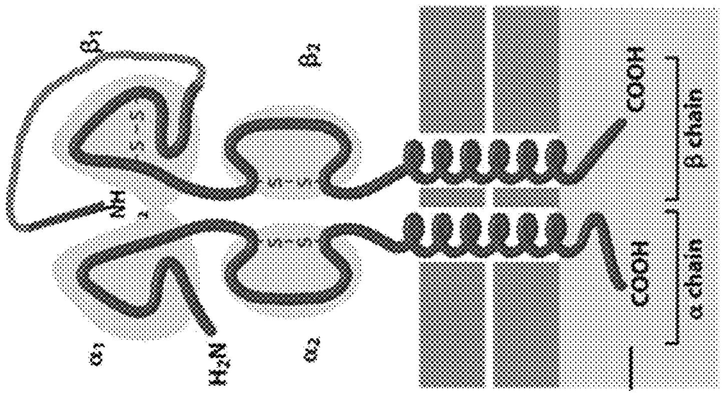
Figure 2C:
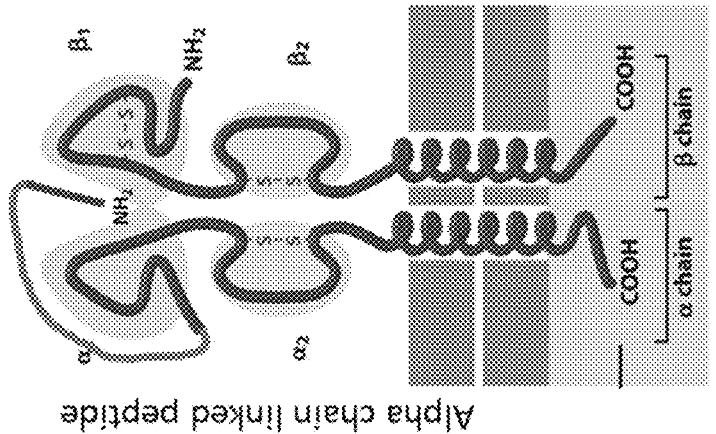
Figure 2D:
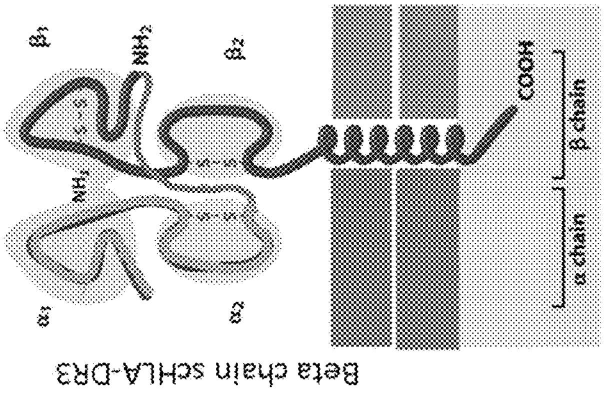
Figure 2E:
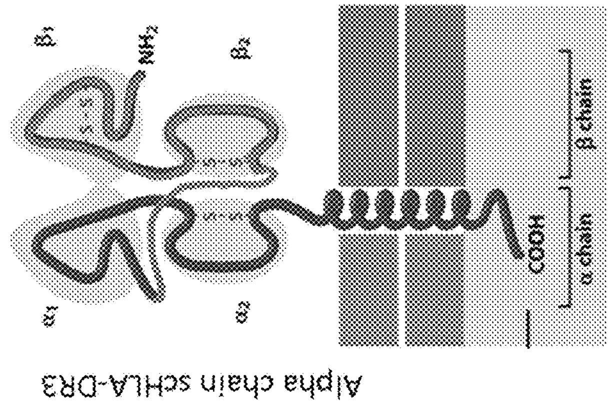
Figure 2F:
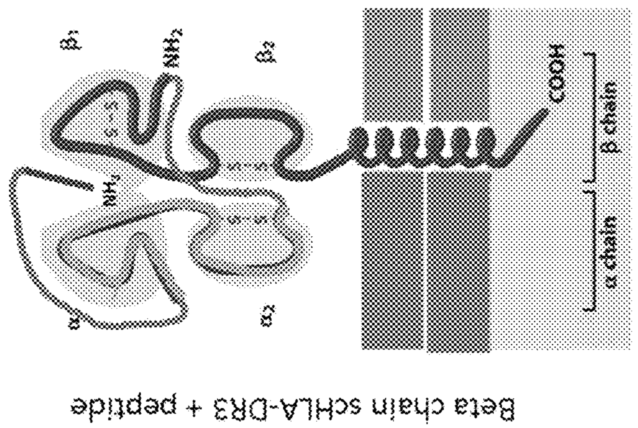
Figure 2G:
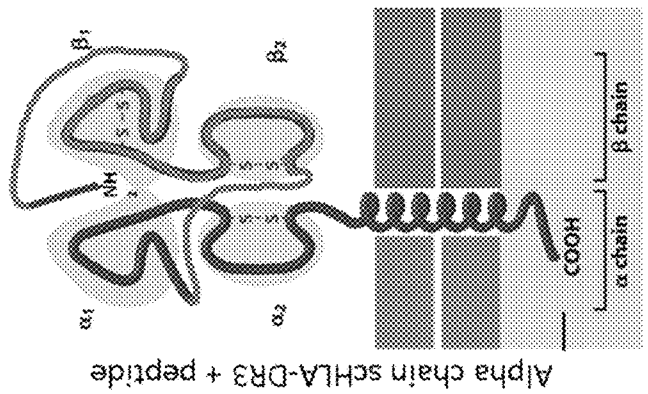

The sequence of a nucleic acid construct for the scMHC peptide (HLA-DR transgene construct) to produce the single chain HLA-DR molecule covalently linked with a cognate peptide was optimized and modified to improve gene expression and delivery (FIG. 1). Linker 1 was added to be a GT(GS)7 linker to improve successful association of the peptide in the binding grove. Gene expression was under the MND promoter and a synthetic polyA sequence was incorporated (FIG. 1). The construct is synthesized with a restriction enzyme site that allows the inclusion of linker 1 and one of 4 peptides to be covalently linked and presented in the final folded protein or no peptide. A first round of synthesis generated the 5 MND HLA-DR transgene constructs. (Exemplary sequence is provided In Table 9)

A subsequent round of cloning generated these 5 constructs inserted between the ROSA26 homology arms for knock in into a ROSA26 insertion site of a cell (Exemplary sequence is provided in Table 9). The ROSA26 homology arms were designed for homologous recombination of the transgene in exon 1 of ROSA26. The left flanking homologous arm of the HLA-DR transgene cassette was designed to include a 500 basepair (bp) sequence spanning the promoter and exon 1 and a 500 bp sequence located at the 3' end to exon 1 was selected for design of the right flanking homologous arm.

Primers used to amplify the 500 bp fragments by PCR and the resulting amplicon sequenced by NGS.

The mRNA for HLA-DRA010202 for the alpha chain and mRNA for HLA-DRB010301 for the beta chain was used in the single peptide expression construct with a covalently linked peptide at the 5' end of the beta chain mRNA. One of 4 potential peptides from the DRB010301 AA sequence was derived from the Immune Epitope Database provided by the NIH (Table 1).

The natural expression of the alpha and beta chains occurs independently and each have their own transmembrane domain. To express a single chimeric peptide of the alpha and beta chains the transmembrane domain of the alpha chain is removed and replaced by a 30 AA linker sequence that allows the folding of the functional peptide binding domain of the alpha chain with the entirety of the beta chain including one of the cognate peptide candidates. The 4 constructs, differing only by cognate peptide, will be flanked by 500 bp arms specific for the ROSA26 site designed and validated by sequence analysis prior to transfection. The final successful chimeric DR/peptide expression construct can also be designed for alternative insertion site. The insertion of chimeric DR/peptide will be evaluated at the ROSA26 site for cell surface expression using the BD Melody cell sorter. Sorted cells will be used for functional analysis.

Table 1 shows exemplary cognate peptides derived from a MHC molecule that bind the peptide binding groove of the MHC molecule. The cognate peptides were derived from the entire HLA-DR3 peptide beta chain excluding the signal sequence. The percentile rank indicates the predicted affinity of the peptide for the proposed peptide binding groove of the HLA-DR folded molecule.

| HLA-DRB1*03:01 | Start | End | Peptide | Percentile Rank |
|---|---|---|---|---|
| 1 | 153 | 167 | WTFQTLVMLETVPRS (SEQ ID NO: 63) | 0.59 |
| 2 | 111 | 125 | HHNLLVCSVSGFYPG (SEQ ID NO: 64) | 1.39 |
| 3 | 37 | 51 | NVRFDSDVGEFRAVT (SEQ ID NO: 65) | 2.11 |
| 4 | 81 | 95 | HNYGVVESFTVQRRV (SEQ ID NO: 66) | 2.46 |

guide RNA

The ZiFiT Targeter tool version 4.2 (http://zifit.partners.org/ZiFiT/) was used to design guide RNA (gRNA) specific for exon 1 of the porcine ROSA26 locus. The gRNA sequence GCCGGGGCCGCCTAGAGAAG (SEQ ID NO: 67) targeted a PAM site proximal to the start codon and promoter while maintaining a high efficiency of DNA cleavage. Chemically synthesized gRNAs targeting GGTA1 and ROSA26 were obtained from Synthego and reconstituted in 20 nM concentration nuclease free water, as per instructions provided with the Guide-it sgRNA In Vitro Transcription Kit (#632635, Takara BioTech).

Cell Culture, Electroporation and Flow Sorting

Cryopreserved pig fetal fibroblasts (PFF) were allowed to thaw at 37° C., washed twice with complete 10% Dulbecco's Modified Eagle's Medium (DMEM) (Life Technologies), and 2×106 cells per petri dish were subsequently placed in 10% complete DMEM media. Media was changed every 48 hours to allow for at least 70% confluence. Cells were detached by Tryple Express (Life Technologies) and prepared for transfection, as per the Amaxa™ 4D-Nucleofector™ Protocol. In summary, 5×105 cells were suspended in 75 μL transfection buffer prepared by mixing 82 μL Nucleofector™ Solution and 18 μL Nucleofector™ Supplement provided in the kit, as per manufacturer instructions. The remaining 25 μL of transfection buffer was used to mix gRNA, Cas9 endonuclease (Aldevron) and HL-DR transgene template prior to incubation at room temperature for 10 minutes. Following incubation, gRNA: Cas9 complex was mixed with PFF cells and transferred to Nucleocuvette™ cuvettes. Cells were subsequently transfected by electroporation using program CM-137, according to manufacturer instructions. Following transfection, cuvettes were kept at 37° C. for 10 minutes to allow for cell recovery prior to being transferred to petri dishes. Media was changed 48 hours after transfection. After successfully attaining 70% confluence, cells were sorted by FC. Briefly, cells were detached by Tryple Express and stained with 1 μg of IB4-APC (Biolegend), 9 μL of PE anti-human HLA-DR in 100 μL of flow buffer composed of DMEM 1% BSA containing 1 mM CaCl2, prior to incubation for 30 minutes at 4° C. in the absence of light. Identical temperature incubation and centrifugation steps were performed with unstained cells. After washing twice with flow buffer in a 15 mL tube, cells were suspended in 300 μL flow buffer and loaded into the BD FACSAria II (BD Biosciences) under aseptic conditions for flow sorting. A 130 μm nozzle was used to sort the porcine fibroblast cells.

DNA Isolation

In this experiment, DNA obtained from sections of transgenic pig tail were isolated using the QIAmp Fast DNA Tissue Kit (#51404, Qiagen). In addition, DNA obtained from flow sorted cells was isolated using the QIAmp DNA Micro Kit (#56304, Qiagen). Following flow sorting, 1000 sorted cells were removed and suspended in 100 μL 1× phosphate buffered saline (PBS), prior to the addition of 10 μL PBA [PBS+1% BSA? 5% below], 100 μL Buffer AL, and proteinase K, all provided in the kit, as per manufacturer instructions. Following 15 minutes incubation at room temperature, DNA obtained from flow sorted cells was eluted in 20 μL Buffer AE, also provided in the kit, and sorted cells were stored at −20° C. for future use.

Example 2: Analysis of the HLA-DR-Expressing Cell Line and DR Cognate Peptide The surface expression of cells post transfection for the expression of the chimeric HLA-DR3 molecule was analyzed by flow cytometry. Cells positive for chimeric HLA-DR3 molecule were reserved for DNA isolation and sanger sequence analysis of the junction site where the insertion region begins and the template ends. Sorted porcine HLA-DR3$^+$ positive cells will be lysed for protein isolation to be further validated by western blot. The physical characteristics of the genetically modified cells will meet the following criteria: (a) Positive anti-DR3$^+$ antibody binding by flow cytometry, (b) Homologous DNA sequence of inserted gene to the original template at the specific insertion site, and (c) correct size and specific protein band identified by immunoblotting.

Example 3: Exemplary Sites for Gene Insertion for the Transgene

The ROSA 26 gene site has a constitutively active endogenous promoter and has proven to accept additions of DNA without disruption to cell viability in mice and humans, and pigs. However, to create the best genetics for porcine donor the following additional strategies will be to incorporated in the porcine genome the proposed novel transgenes.

Target an additional site for gene addition and/or "Stack" genes in one site with the same or multiple promoters. Therefore, reducing the transfection burden on the cells through targeting the GGTA1 gene (or other genes where mutation has a desirable phenotype such as NLRC5, CMAH, or B4GalNT2) with the HLA-DR3 transgene or others will both mutate the target gene and express a new desirable immune-regulatory phenotype. 500 bp homology arms specific to the gene are designed thereby knocking out a known antigen while inserting the desired transgene. The insertion of the transgene with disrupt the expression of the gene in which it is inserted. This will also simplify the selection of genetically engineered cells by allowing to select for transgene expression in the first round of cell culture. This method will comprise the following steps:

i) Sequencing of the flanking regions of the target gene (e.g., ROSA26 or GGTA1) in select porcine cells.
ii) Generation of the proposed transgene construct (e.g., chimeric MHC polypeptide) targeting one of the genes to be deleted (e.g., GGTA1). Additional target sites will follow the same sequencing strategy.
iii) Incorporation of the transgene into unique pig cells at the new GGTA1 targeting site identified by Gal2-2 synthetic guide RNA.
iv) The HLA-DR gene insertion can occur in only one allele of a gene (e.g. ROSA26) and if gene expression is sufficient then the second allele of gene (e.g., ROSA26) can be targeted for expression of a second transgene (e.g., HLA-G1).

v) To address proper expression and folding of the chimeric HLA-DR3 while preventing accumulation of improperly folded protein, the spacing around the signal sequence in the construct can be modified, the spacing between elements can be lengthened to enhance folding, and the space linking the peptide to the 5' end of the beta allele can be changed.

vi) Exemplary cognate peptides in Table 1 were determined using an algorithm designed around the affinity of amino acids in the binding groove for the amino acids that compose the antigenic peptide. Additional peptide can be designed and used in the construct using similar approach. Alternatively, the transgene templates that vary by each peptide can be combined to either add or synergize the effects of individual cognate peptide antigens.

Example 4: Exemplary Methods to Make a Genetically Modified Animal Expressing the HLA-DR Molecule The HLA-DR porcine donor will express a very unique protein on the cell surface that combines by three molecule being expressed as a single chimeric polypeptide. The HLA-DRB (beta chain of MHC molecule) and HLA-DRA (alpha chain of MHC molecule) normally associate in the presence of a cognate peptide to form a cognate peptide-MHC complex. We designed and developed a construct so that these three molecules are expressed together and can be inserted as one transgene into the genome of an animal. The generation of a genetically modified cells and animal expressing a transgene encoding a MHC molecule (such as chimeric HLA-DR molecule covalently linked with its cognate peptide) is summarized in the following steps:

LA-DR3 allele was sequenced from Genbank comprised of the HLA-DRB1*03:01 up to the transmembrane domain and then directly connected in frame to the HLA-DRA full length sequence with the transmembrane domain intact.

A dsDNA template that contains the MND promoter, a signal peptide, a cognate peptide liked to the HLA-DRB1*03:01/HLA-DRA, a synthetic polyA tail, and flanked at the 5' and 3' ends by 500 bp domains homologous to each side of the CRISPR directed Cas9 cut site was designed The cells were electroporated to allow the entry of the ROSA26 targeting CRISPR guides and recombinant Cas9 to cut the DNA in the presence of the dsDNA repair template described above.

Cells positive for an HLA-DR specific antibody are sorted away from non-expressing cells.

HLA-DR positive cells are then used as nuclear donors for SCNT where they are fused with enucleated oocytes to form embryos. SCNT was performed as described by Whitworth et al. Biology of Reproduction 91 (3): 78, 1-13, (2014). The SCNT was performed using in vitro matured oocytes (DeSoto Biosciences Inc., St. Seymour, TN). Cumulus cells were removed from the oocytes by pipetting in 0.1% hyaluronidase. Only oocytes with normal morphology and a visible polar body were selected for SCNT. Oocytes were incubated in manipulation media (Ca-free NCSU-23 with 5% FBS) containing 5 μg/mL bisbenzimide and 7.5 g/mL cytochalasin B for 15 min. Oocytes were enucleated by removing the first polar body plus metaphase II plate. A single cell was injected into each enucleated oocyte, fused, and activated simultaneously by two DC pulses of 180 V for 50 usec (BTX cell electroporator, Harvard Apparatus, Hollison, MA, USA) in 280 mM Mannitol, 0.1 mM CaCl2, and 0.05 mM MgCl2. Activated embryos were placed back in NCSU-23 medium with 0.4% bovine serum albumin (BSA) and cultured at 38.5° C., 5% $CO_2$ in a humidified atmosphere for less than 1 hour, and transferred into the surrogate pigs.

On day 5-6 of embryo development 20-60 embryos are implanted via minimally invasive surgical embryo transfer in matrix-synchronized "in heat" surrogate sows directly into the uterine horn and with a milking motion evenly distributed throughout. The horn is placed into a natural position to encourage a natural movement of fluid and embryos.

Approximately 50% of pregnancies are successful by ultrasound at day30 post embryo transfer. Those liters are often comprised of 3-7 piglets born by cesarean section. Ear notches for identity and tail clips are collected and used to determine the genomic presence of the transgene.

The ear and tail pieces are macerated and digested in collagenase IV to release fibroblasts from the tissue. Tissue fragments are cultured for several days to 70-80% culture plate confluence. The DNA is isolated from the fibroblasts and PCR primers specific for a region inside the DR3 gene that could only be amplified if the gene was inserted.

Example 5: Immunological Characterization

Analysis of the Functional Implications of a Natural Human DR3 Homolog in Porcine Donors on Mechanisms of Tolerance.

Peripheral blood leucocytes (PBL) obtained from 20 different donor pigs will be serotyped with anti-HLA DR3 or anti-HLA DR4 specific antibody to identify donor pigs that express the homolog of human HLA-DR3 or HLA-DR4, the common alleles expressed in >30% of patients with type 1 diabetes. The DR sequence of the HLA-DR3 serotyped donor pigs will be sequenced using Sanger sequencing technology. To determine the effect of DR3 matching in induction of tolerance, we will analyze the proliferation of PBLs from RM with and without a human homolog of DR3. Briefly PBLs from Rhesus Macaque (RM) expressing DR03a or DR04 will be stimulated with donor pigs that express human homolog of HLA-DR3 in a CFSE MLR. Proliferation of CD4+, CD8+ and CD20+ lymphocytes will be analyzed by flow cytometry. To determine whether ECDI fixed B cells from the pigs with human homolog of DR3 can induce the expansion of regulatory T cells that promote long term tolerance we will coculture RM PBL from DR03a+ and DR04+ animals with ECDI fixed donor PBLs for 7 days and analyze the expansion of Trl (CD4+CD49b+Lag3+) and Treg (CD4+CD25+CD127low).

Analysis of the Effects of Transgenic Expression of HLA-DR3 in Porcine Donors on Mechanisms of Tolerance.

To determine the effect of DR3 matching in induction of tolerance, we will analyze the proliferation of PBLs from patients with type 1 diabetes with and without HLA-DR3. Briefly PBLs from patients with type 1 diabetes expressing DR03a or DR04 will be stimulated with transgenic pig PBLs that express chimeric HLA-DR3 with covalently linked cognate peptide in a CFSE MLR. Proliferation of CD4+, CD8+ and CD20+ lymphocytes will be analyzed by flow cytometry. To determine whether ECDI fixed B cells from the HLA-DR3 transgenic pig PBL can induce the expansion of regulatory T cells that promote long term tolerance we will coculture TID PBL from DR03a+ and DR04+individuals with ECDI fixed donor PBLs for 7 days and analyze the expansion of Trl (CD4+CD49b+Lag3+) and Treg (CD4+CD25+CD127low). The frequency of the individual TCR specific clones will be enumerated before and after exposure to the ECDI-fixed B cells using flurochome labeled HLA- DR3 tetramers loaded with the cognate peptide and HLA-DR3 tetramers loaded with irrelevant peptide will serve as controls.

Example 6: Exemplary Methods for Making a Genetically Engineered Porcine Organ Donor Procurement and maturation of oocytes, enucleation and fusion of the oocytes with genetically engineered cells, and culture of embryos before implantation are critical steps in development of genetically modified animal. Exemplary method includes:

i) Validation of oocytes for use in the production of embryos by somatic cell nuclear transfer (SCNT) or Bi-oocyte fusion (BOF).
ii) Embryo production by SCNT or BOF
iii) In vitro embryo development and analysis of embryo for genetically engineered targets and viability at day 0 through day 7.
iv) Utilize qualified embryos for embryo transfer to surrogate to generate pregnancies and grow to genetically modified piglets as donors for genetically modified cell, tissue and organs for xenotransplantion.

Oocyte Selection

Validation of Porcine Oocytes for Cloning.

Selecting oocytes that are most likely to develop is crucial for both assisted human reproductive technology and animal embryo technologies involving IVM oocytes. Characterizing ovarian oocytes in a non-invasive and non-perturbing manner for selection of oocytes prior to culture has become of prime importance. A non-limiting exemplary method includes zinc supplementation in in vitro medium to increase the oocyte quality and production efficiency of cloned pigs. Zinc can be supplemented in oocyte maturation media, then test them for oocyte quality and embryo developmental rates.

Glucose-6-phosphate (G6PDH) enzyme activity can be measured as readout of increased developmental competence and as a simple test for porcine oocyte viability. In mouse model, Brilliant Cresyl Blue dye (BCB) staining can be used as an efficient method for oocyte selection, but the competence of the BCB+ oocytes may vary with oocyte diameter, animal sexual maturity and gonadotropin stimulation. In this test, staining of immature cumulus-oocyte complexes (COCs) with BCB was selected for further maturation. Oocytes stained blue (BCB+, low G6PDH activity) are characterized by higher developmental competence or superior quality when compared with colorless oocytes of reduced quality (BCB negative/high activity of G6PDH). The BCB test is a very useful tool for the selection of superior quality oocytes in. Validation of oocyte for use in production of embryos will include the following:

i) Screen commercially available oocytes (Desoto Inc.) and in-house isolated oocytes for maturation traits beneficial to cloning.
ii) Selection of Immature oocytes based on Glucose-6-phosphate (G6PDH) enzyme activity by using BCB staining.
iii) Evaluation of the maturation efficiency of BCB+ oocytes using standard nutritive media, highly enriched stem cell media, while testing the impact of follicular fluid on development.
iv) Measurement of the oxygen consumption rate among selected oocytes to determine if the Seahorse technology is beneficial to confirm BCB selection and validate final oocytes
v) Supplementation of zinc in in vitro oocyte maturation media Completion of steps described above will select viable oocytes, enhance maturation and assess the utility of validation markers for selection of higher quality oocytes for for use in the production of embryos by somatic cell nuclear transfer (SCNT) or Bi-oocyte fusion (BOF).

Bi-Oocyte Fusion Cloning (BOF)

Exemplary steps for Bi-Oocyte fusion cloning will include;

i) Micro scalpel excision of oocyte nucleus and/or chemical (demecolcine) expulsion of nuclei combined with
ii) Electro fusion of bisected and enucleated oocytes with wild-type or genetically engineered cells (e.g., porcine fibroblasts cells expressing HLA-DR3 transgene and/or comprising a genetic disruption in one or more gene encoding NLRC5, CMAH, GGTA1) followed by
iii) Phenotypic and genomic analysis of fusion products.

Great improvements have been made in nuclear transfer (NT) techniques, following critical investigations on the use of different donor cell types, cell cycle, stage of passaging cells, variation in maturation stage of the recipient oocytes, epigenetic modifications of oocytes, and variations in fusion and activation protocols. These alterations have also led to a substantial increase in the efficiency of production of cloned embryos. A zona free cloning or "handmade cloning" HMC approach is an alternative to the micromanipulation based SCNT. Electro fusion can be performed either through chamber fusion or microelectrode fusion. The fusion efficiency can be higher with the zona free cloning method. In mammalian SCNT, activation is a crucial step to progress reconstructed embryos into the interphase of mitotic division. Addition of thimerosal will induce complete activation of porcine oocytes. Activation will induce train of Ca2+ spikes in the oocytes and followed by incubation with dithiothreitol (DTT), it can stimulate pronuclear formation. The combined thimerosal/dithiothreitol (DTT) chemical incubation will induce full activation of oocytes that supports development to the blastocyst.

Treatment of Vitamin C and Latrunculin A in porcine embryos can enhance epigenetic reprogramming and produce viable embryos for pregnancy. By inducing the somatic cell into a totipotent state, the stem cell is able to give rise to the rest of the cells in the body. The efficiency of zona free BOF cloning is increased by optimizing the electrofusion and activation procedure, to improve the developmental competence of zona free BOF cloning to produce superior quality transferable embryos to create porcine organ donors. The zona free BOF cloning method disclosed here will increase the developmental rate of blastocysts and overall quality of embryos. Embryos will be analyzed and validated and then used for embryo transfer for into surrogates for generation of genetically modified animal production. The data shown in Tables 2-6 will be used as a guide for optimization of BOF to generate genetically modified embryos for use in producing the genetically engineered animal.

TABLE 2

Rate of embryo development derived from demecolcine assisted enucleation (DAOE), and Random handmade enucleation (RHE).

| Groups | Reconstructed Embryos (n) | Fusion Rate n (%) | Cleave Rate n (%) | Blastocyst Development Rate n (%) |
|---|---|---|---|---|
| Demecolcine assisted enucleation | 147 | 127 (85 ± 1.5) a | 122 (96 ± 2.0) a | 51 (42 ± 1.5) a |
| Random handmade enucleation | 75 | 60 (83 ± 1.5) a | 51 (82 ± 1.5) b | 16 (33 ± 1.1) b |

Values are mean ± SEM Data from 3 trials. Values having different superscripts with in same column differ significantly ($p < 0.05$).

TABLE 3

Effect of DC pulse on fusion and cleavage efficiency of oocyte bisection cloned embryos on 6 V AC current applied.

| Group | DC Parameter | Reconstructed Embryos (n) | Fusion rate n (%) | Cleavage rate n (%) |
|---|---|---|---|---|
| Group A | 1.2 kV/cm for 20 µs single pulse | 65 | 62 (93.0 ± 1.0) a | 45 (73.0 ± 2.0) a |
| Group B | 2.0 kV/cm for 80 µs single pulse | 68 | 65 (91 ± 0.5) a | 43 (67.0 ± 1.0) b |
| Group C | 1.0 kV/cm for 9 µs single pulse | 131 | 125 (96 ± 3.0) a | 96 (79 ± 2.0) a |

Values are mean ± SEM Data from 3 trials. Values having different superscripts with in same column differ significantly ($p < 0.05$).

TABLE 4

Effect of single and double step fusion efficiency on in vitro developmental competence of oocyte bisected cloned pig embryos.

| Fusion Method | Reconstructed Embryos (n) | Fusion rate n (%) | Cleavage Rate n (%) | Blastocyst Development Rate n (%) |
|---|---|---|---|---|
| Single-step | 135 | 131 (96 ± 1.0) a | 118 (90 ± 2.6) a | 52 (39 ± 4.0) a |
| Double-step | 111 | 95 (84 ± 1.0) b | 78 (81 ± 1.6) b | 27 (25 ± 1.6) b |

Values are mean ± SEM Data from 4 trials. Values having different superscripts with in same column differ significantly ($p < 0.05$).

TABLE 5

Effect of holding time between electrofusion and activation on in vitro developmental competence of oocyte bisection cloned embryos of pigs. Interval refers to the period of time between fusion and activation.

| Interval (h) | Embryos Cultured (n) | 2-4 Cell Stage n (%) | Blastocyst Development Rate n (%) |
|---|---|---|---|
| 0 | 95 | 76 (80 ± 1.1) | 25 (28 ± 1.5) a |
| 1 | 108 | 95 (89 ± 0.5) | 42 (39 ± 1.0) a |
| 4 | 121 | 97 (81 ± 1.6) | 7 (6 ± 1.5) b |

Values are mean ± SEM Data from 4 trials. Values having different superscripts with in same column differ significantly ($p < 0.05$).

TABLE 6

Blastocyst development of oocyte bisected cloned sow and gilt embryos

| | No. of Activated Oocytes (n) | Cleave Rate n (%) | Blastocyst Development Rate n (%) |
|---|---|---|---|
| Sow | 142 | 121 (88 ± 1.0) a | 52 (37 ± 1.6) a |
| Gilt | 107 | 76 (71 ± 1.6) b | 25 (23 ± 1.6) b |

Values are mean ± SEM Data from 4 trials. Values having different superscripts with in same column differ significantly ($p < 0.05$).

Development of Embryo

Figure 4:
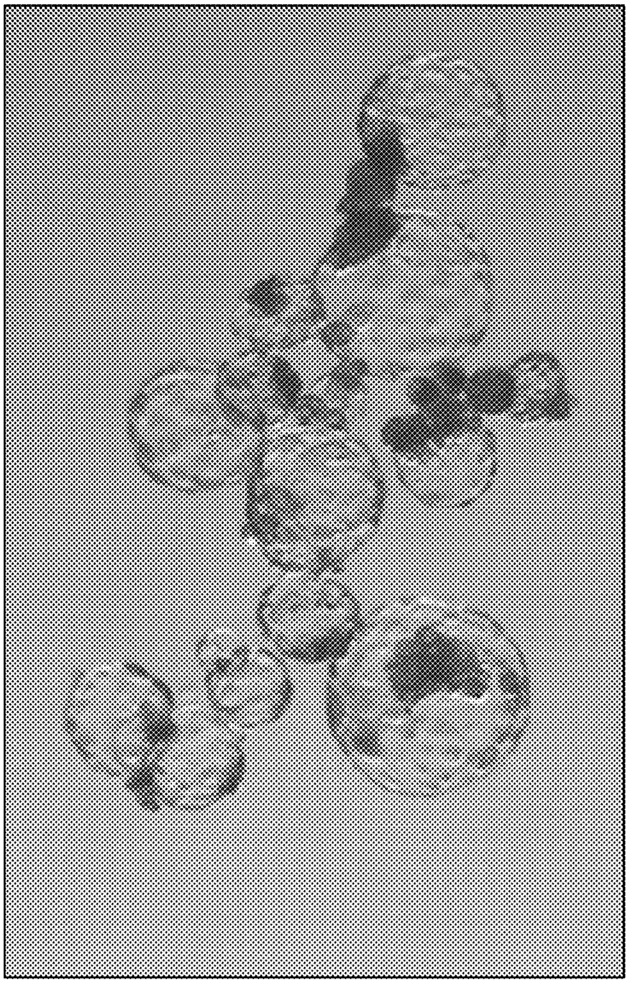
FIG. 4 shows blastocysts produced by bi-oocyte fusion cultured to day 7.
Figure 5:
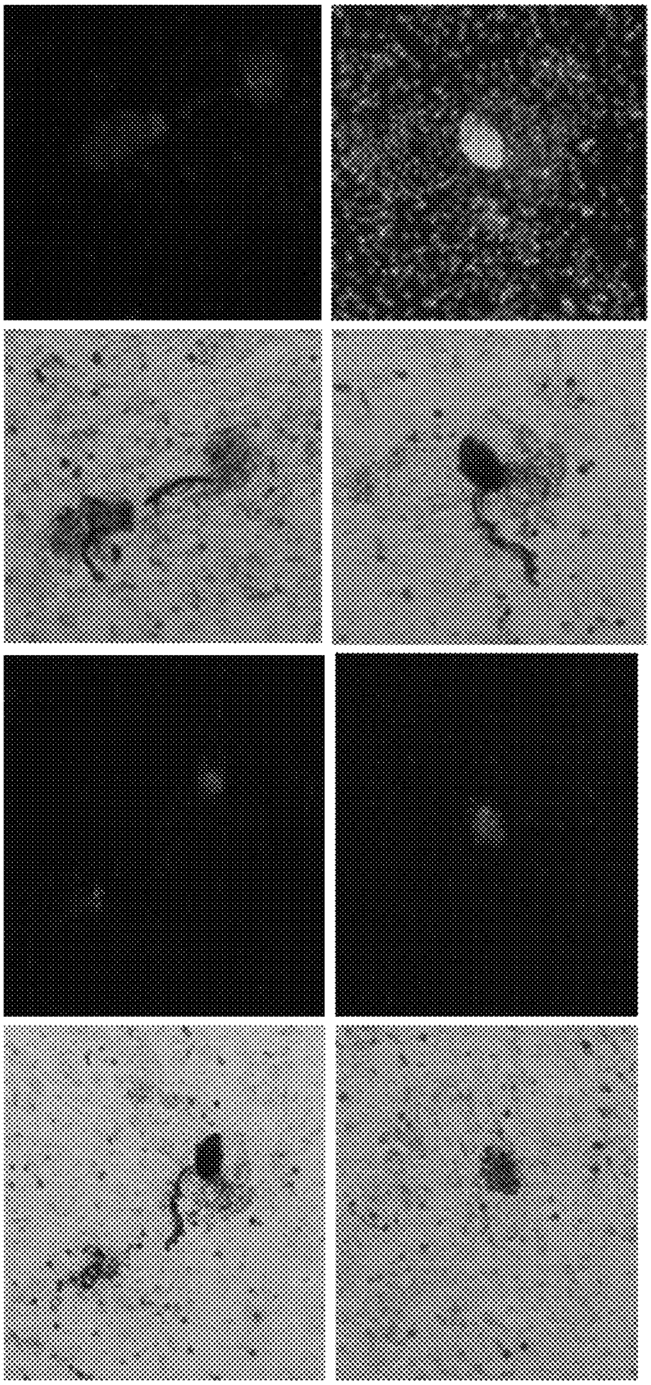
FIG. 5 shows immunofluorescence staining of pluripotency markers in embryonic stem cell colonies derived from embryos produced by bi-oocyte fusion: Expressions of pluripotency markers (Tra 1-60, Tra 1-81) are shown in green at passage 5. Nuclei are stained with DAPI (blue). Scale bars=20×
Figure 6B:
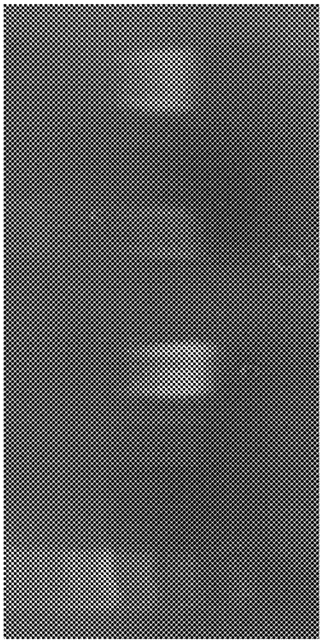
FIGS. 6A-6B shows characterization of ICM derived from bi-oocyte fusion.
Figure 6A:
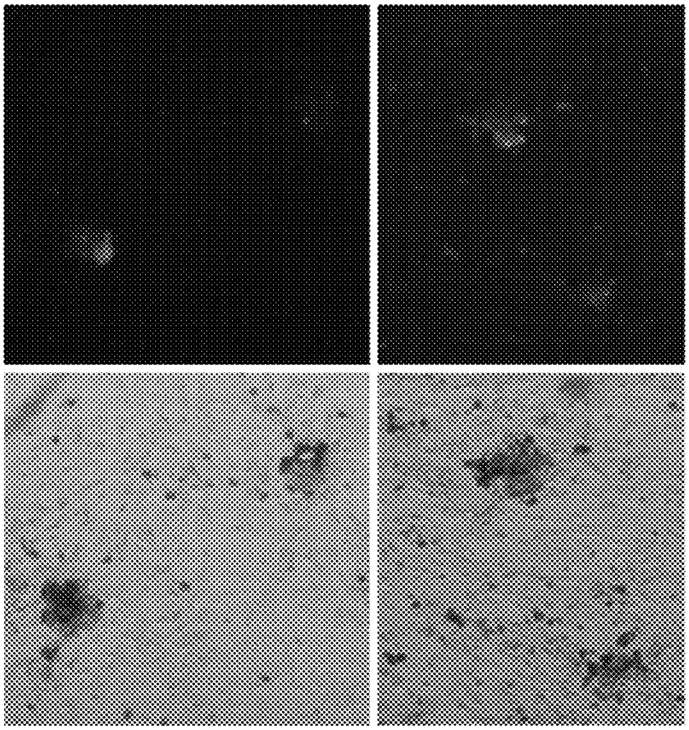

The generation of genetically modified embryos can be improved through a novel method of electrofusion and subsequent development to day 1-7 embryos in culture conditions. Genetically engineered embryos produced by BOF method and cultured in culture to day 7 result in development to blastocyst stage (FIG. 4). Additionally, developing genetically engineered embryos in culture contain within them a transient cluster of cells inside the blastocyst called the "inner cell mass" (ICM). The ICM is composed of stem cells that give rise to all terminal cell lines in the developing pig. The ICM was isolated and stem-like cells that proliferate in vitro and express stem like cell markers were cultured (FIGS. 5 and 6). The ICM (Dark masses in FIG. 4) were placed on a feeder layer porcine fibroblast where they increase in size and spread out onto the feeder layer). The ICM as an indicator of development and durability and consistency of the genetic engineering process.

Embryo Developmental Efficiency

Apoptosis is a cellular process that plays a vital role in mammalian reproduction and development. Normal preimplantation embryos undergo spontaneous apoptosis to eliminate cells that are abnormal, detrimental, or superfluous, and to regulate embryo cell numbers. Perhaps apoptosis has a similar role in in vitro produced embryos, which are frequently mosaic. In human embryos, apoptosis removed only genetically damaged cells and concurrently enabled normal developing cells to proliferate. In vitro embryos are frequently mosaic, leading researchers to believe apoptosis plays a similar role in these systems. Use of Trichostatin A (TSA), a histone deacetylase inhibitor, in cloning protocols might enhance cloning efficiency by inducing apoptosis of abnormal cells in cloned embryos. Assessment of TSA utility is conducted through the analysis of the expression of apoptosis and pluripotency-related genes, namely Bcl-xl, Bax, Caspase 3, Oct4, and Nanog. The goal is to improve the blastocyst quality, selection and transfer for successful implantation to make live cloned piglets. Biomarkers tested for non-invasive embryo selection included: cumulus cell-related genome marker COX2, steroidogenic acute regulatory protein STAR, pentraxin 3 PTX3, and sCD146. CD146 is involved in embryo implantation and is the membrane-bound form of sCD146 and sCD146 is a recently discovered biomarker for in vitro fertilized embryo development in humans. sCD146 is a non-invasive biomarker selection for in vitro porcine cloned embryo development by using anti-sCD146 antibody for immunocytochemical staining, ELISA and western blotting.

Aggregation Improves Cloning Efficiency and Embryo Quality

Embryo aggregation can improve the developmental competence and quality of cloned pig embryos. After aggregation, the quality of genetically embryos will be determined as compared to wild type as a sample of the total embryos produced based on the following assays:

Blast development efficiency, Measure apoptosis, Measure Karyotype, Embryo development efficiency, Size, Rate, Markers of pluripotency, Methylation pattern, Multi blast culture to enrich development, Soluble CD146 (sCD146) non-invasive biomarker for embryo selection, Follicular fluid/cumulus free DNA biomolecular marker to measure embryo quality cox2/PTX3/ASF1A/PCK1 gene expression quantification.

Release Testing

Genetically engineered embryos generated by methods outlined above will undergo testing to determine whether specifications for release into next stage for embryo transfer. Assays to be included and specifications will be as follows:

Minimum 20% blast development rate if measured to day 7, Micrometer size threshold, Phenotypic cell surface markers expressed as the result of Genetic Engineering, Potential presence of soluble CD146 (sCD146) non-invasive biomarker for embryo selection, Potential DNA biomolecular marker present in culture to measure embryo quality, Verify potential of cox2/PTX3/BCL2L11/ASFIA/PCK1 embryo gene expression from representative embryos from individual batch, and Viral testing through VDL or MVS: PERV A, B, and C, CMV, PCV2, PPV, PRRS Cell, Fetus, and Piglet Release Genetically engineered cells generated by methods outlined above will undergo testing to determine whether fetal fibroblast cells meet specifications for release into the next step of SCNT or bi-oocyte fusion (BOF), or in the case of genetically modified piglets, release into next step for generation of genetically modified cells, tissue and organs for transplantation. Assays to be included and specifications will be as follows:

i) Positive selection of each batch of transfected cells with a flow sorter using an anti-HLA-DR antibody. The specification is to collect a minimum of 1,000 genetically-engineered cells per batch.
ii) One to 4 days after sort, secondary validation by flow cytometry of sorted cells using anti-HLA-DR antibody. The specification is a minimum percentage of HLA-DR-positive cells of 80%.
iii) Two to 4 days after sort, Sanger sequencing of sorted cells. The specifications are i) positive PCR for an HLA-DR amplicon and ii) demonstration of high-fidelity HLA-DR sequence from said amplicon.
iv) Additionally, at 0 to 4 days after sort, genomic DNA is isolated for next generation sequencing of the HLA-DR genes at the insertion site. The specification is a high-fidelity copy of the original gene template with no mutations, insertions, or deletions at critical signaling or protein folding domains. This criteria may come after SCNT as high fidelity sequencing may take longer than 2 weeks.
v) Within one week of sort, as few as 100,000 cells solubilized in a gentle non-reducing detergent buffer to assess the presence of HLA-DR by immune-blotting with anti-HLA-DR antibodies. Meeting this specification can be required for validation of the specific homology recombination directed template used for the generation of transfected cells but not for the release of each batch of transfected cells for embryo production.
vi) Sanger sequencing with primers specific for the genes targeted for deletion or insertion (e.g., GGTA1, Rosa26, CMAH, NLRC5, B4GalNT2) will be performed.

In summary, transfected porcine cells, sorted cells, fetal cells, or neonatal piglet cells will be qualified if the following specifications for demonstration of HLA-DR3 gene expression, deletion of target genes, and ability to grow in culture are met.

Figure 3:
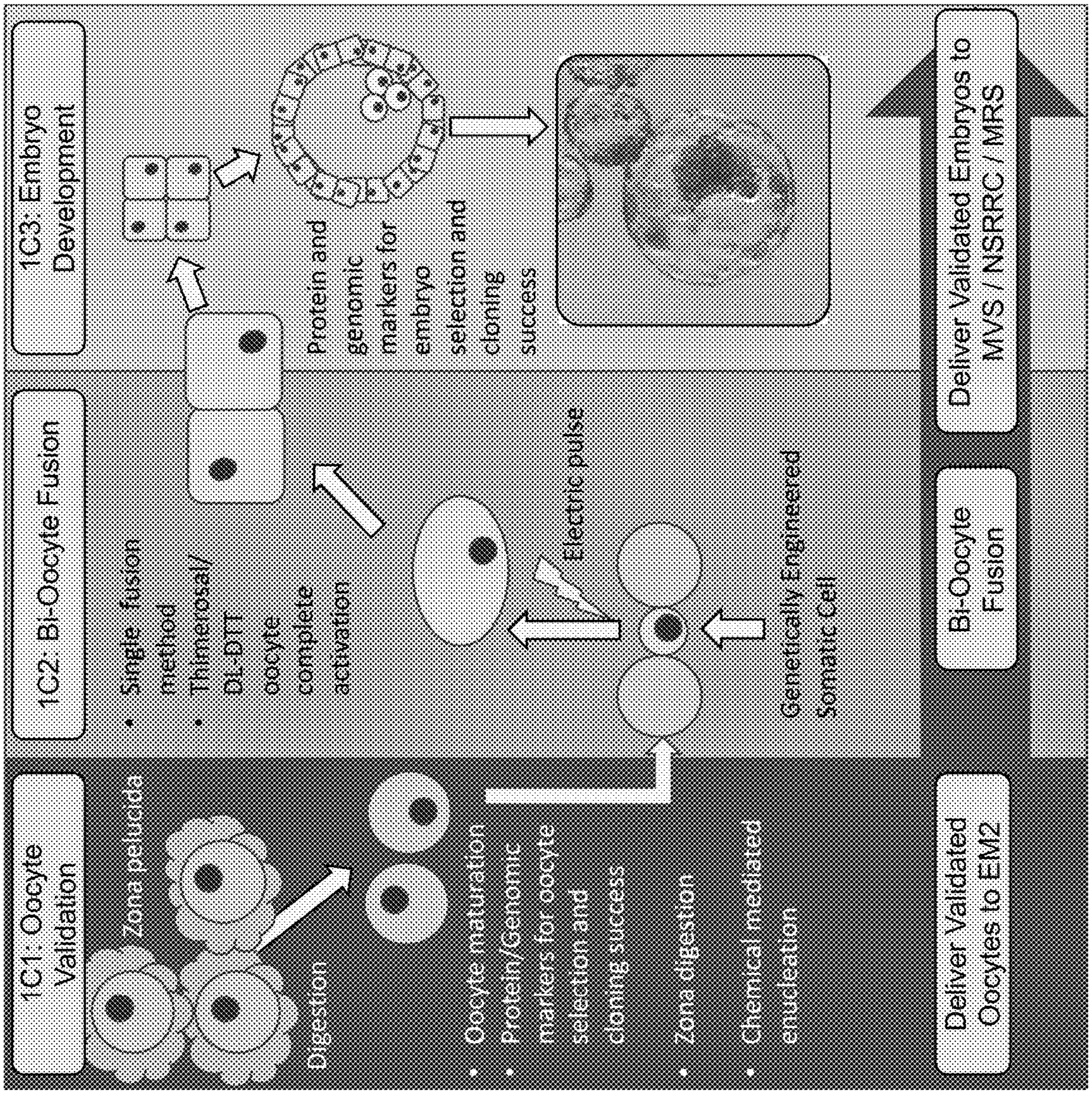
FIG. 3 shows the process of bi-oocyte fusion. The method for embryo generation and development using BOF includes oocyte selection, bi-oocyte fusion cloning, embryo development in culture. Collectively, these steps will enhance the quality of genetically engineered embryos thereby increasing the rate and volume of porcine organ donors produced.

Genetically engineered cells or embryos will be used for embryo transfer. Embryo transfer of validated embryos will test the viability of new gene modifications to establish pregnancy, develop to full term, and to produce porcine donors for cells, tissues or organ transplants (e.g., islet/kidney transplant). Genetically engineered embryos will be obtained by methods outlined above (e.g. FIG. 3).

Exemplary Method for Production of Genetically Modified Porcine Donor of Cells, Tissues and Organs for Transplantation Will Entail the Following Steps:

i) Deliver 5-30 embryos in culture for up to 36 embryo transfer. provided embryos pass validation by methods described above.
ii) Tissue and blood samples collected at the time of fetus retrieval or birth will be used to evaluate genetics of neonates. DNA samples from each fetus or piglet will be sequenced at the target gene sites for evidence of mutation as compared to founder pig samples. The phenotype of tissue and blood cells will reflect the genetic changes of each piglet tested. Other markers of embryo development as described above will be tested as necessary to monitor developmental success.

iii) Continued observation and maintenance of developing piglets will be done. Depending on the number of piglets per litter(s) a piglet/pig possessing the desired gene mutations will be sacrificed after skin fibroblast testing at birth and test all the organs relevant to transplantation or cells of interest to present studies. Alternatively, blood samples will be taken and peripheral blood mononuclear cells analyzed for gene mutations and their impact on human and NHP immune cells, antibody binding, and complement deposition.

The methods described above will deliver genetically modified piglets as donors for islets, kidneys, and vaccines for transplantation.

Somatic Cell Nuclear Transfer (SCNT)

SCNT was performed as described by Whitworth et al. Biology of Reproduction 91 (3): 78, 1-13, (2014). The SCNT was performed using in vitro matured oocytes (DeSoto Biosciences Inc., St. Seymour, TN). Cumulus cells were removed from the oocytes by pipetting in 0.1% hyaluronidase. Only oocytes with normal morphology and a visible polar body were selected for SCNT. Oocytes were incubated in manipulation media (Ca-free NCSU-23 with 5% FBS) containing 5 g/mL bisbenzimide and 7.5 μg/mL cytochalasin B for 15 min. Oocytes were enucleated by removing the first polar body plus metaphase II plate. A single cell was injected into each enucleated oocyte, fused, and activated simultaneously by two DC pulses of 180 V for 50 usec (BTX cell electroporator, Harvard Apparatus, Hollison, MA, USA) in 280 mM Mannitol, 0.1 mM $CaCl_2$), and 0.05 mM $MgCl_2$. Activated embryos were placed back in NCSU-23 medium with 0.4% bovine serum albumin (BSA) and cultured at 38.5° C., 5% $CO_2$ in a humidified atmosphere for less than 1 hour, and transferred into the surrogate pigs.

While some embodiments have been shown and described herein, such embodiments are provided by way of example only. Numerous variations, changes, and substitutions will now occur to those skilled in the art without departing from the invention. It should be understood that various alternatives to the embodiments of the invention described herein will be employed in practicing the invention.

Example 7 Bi-Oocyte Fusion Cloning (BOF)

Exemplary method for the activation of porcine cytoplast-fibroblast fused constructs developed to α-1,3-galactosyltransferase (GGTA1) knockout (KO) blastocysts by the zona free bi-oocyte fusion (BOF) cloning is provided below. The Examples demonstrate that the bi-oocyte method disclosed herein has successfully used DAOE to produce BOF embryos, and in doing so, concluded that DAOE is superior to mechanical enucleation for pre-implantation development of embryos. For the purpose of electrofusion, membranes to be fused must be placed parallel to the electrodes. This is generally accomplished by employing both an AC alignment pulse and manual alignment. For effective fusion, parameters such as pulse duration, pulse length, number of pulses, fusion medium constituents and fusion chamber configuration etc. are disclosed. During conventional nuclear transfer, the donor cell is held close to the cytoplast by the zona pellucida. However, in zona-free SCNT, stereomicroscopic control of the floating somatic cell is difficult due to its small and transparent nature. The somatic cell's orientation with the cytoplast following application of AC current is inefficient, therefore, phytohemagglutinin aided gluing of the surface of the cytoplast is required, creating a bond strong enough to keep the majority of the somatic cell-cytoplast pairs together, even in the fusion medium. The Examples disclosed herein demonstrate that fusion, cleavage and blastocyst development rates were all significantly higher for the single-step method (96%, 90%, and 39%, respectively), than those obtained for the double-step fusion method (84%, 81%, and 25%, respectively). The holding time interval between electrofusion and activation can affect the remodeling and reprogramming of donor nuclei and the subsequent development of nuclear transfer embryos. The Examples herein demonstrate that cleavage rates associated with 0, 1-and 4-hour holding times were similar, however, the overall blastocyst development rate for the 1-hour holding time was significantly higher (42%) than that obtained for 0-hour (25%) and 4-hour (7%) holding times. The observed increase in blastocyst development rate can be attributed to electrofusion conditions and an appropriate holding time following electrofusion used in the methods herein.

Further the Examples demonstrate that the observed cleavage and blastocyst development rate was significantly higher in sow-derived oocytes (88% and 37%, respectively) than that of gilt-derived oocytes (71% and 23%, respectively). GGTA1 KO pigs were successfully generated using the CRISPR/Cas9 gene editing system in PFF followed by FACS analysis for selection of the a-Gal negative population and subsequent Bi-oocyte fusion method as disclosed herein. WT cells and GGTA1 KO cells used in bi-oocyte fusion method were compared in terms of cleavage rate and blastocyst developmental rate. WT and GGTA1 KO cells showed similar cleavage (91.95% and 90.28%, respectively) and blastocyst development rates (41.10% and 38%, respectively). Cloned embryos obtained by methods disclosed herein exhibited similar levels of expression of pluripotent genes, Klf4, Oct4 and Nanog, differentiation related marker, Igf2, apoptosis markers, Bcl-xl and Bax, modulator of DNA methylation, Dnmt1, and cellular reprogramming factor, ASF1.

Material and Methods

Animal Care and Chemicals

Animal experiments in this study were approved according to Institutional Animal Care and Use Committee (IACUC) protocols. Except where otherwise indicated, all chemicals were purchased from Sigma Chemicals Co. (St. Louis, MO).

Preparation of Porcine Fetal Cell Culture

Porcine fetal fibroblast (PFF) cells used during the duration of these experiments were isolated from Mangalista male fetuses 35 days after insemination. PFFs were cultured in Dulbecco's modified eagle medium (DMEM; Gibco) supplemented with 15% (vol/vol) fetal bovine serum (FBS; Gibco) and 1% Glutamax™-I (Gibco) at 38° C. in a 5% $CO_2$ incubator.

sgRNA Design

Targeted synthetic single guide RNAs (sgRNAs) within the porcine GGTA1 gene were purchased from Synthego and designed according to manufacturer protocol. The GGTA1 sgRNA sequence was designed targeting the first translated exon.

GGTA1 sgRNA: 5' GCTGCTTGTCTCAACTGTAA 3' (SEQ ID NO: 68).

Transfection of GGTA1 sgRNA Gene

Prior to nucleofection, PFF cells were thawed and cultured for 48 hours until reaching 70 to 80% confluency. Approximately 5×106 cells were subjected to nucleofection using the SE Cell Line 4D-Nucleofector™ X Kit (Lonza, Allendale, NJ, USA) for primary mammalian cell lines according to the manufacturer's protocols. Briefly, 5×106 cells were suspended in 100 μl Nucleofector™ SE solution at room temperature. Synthego synthesized GGTA1 sgRNA (150 μM) and sNLS-SpCas9-Snls Nuclease (10 μg/μl) were mixed in a 3:1 ratio. Following sgRNA synthesis, ribonucleoproteins (RNPs) were incubated for 10 minutes at room temperature. Nucleofection was performed after 10 minutes on a 4D-Nucleofector™ Transfection System (Lonza) using program CM-137.

Selection of GGTA1 KO Cells

Figure 8A:
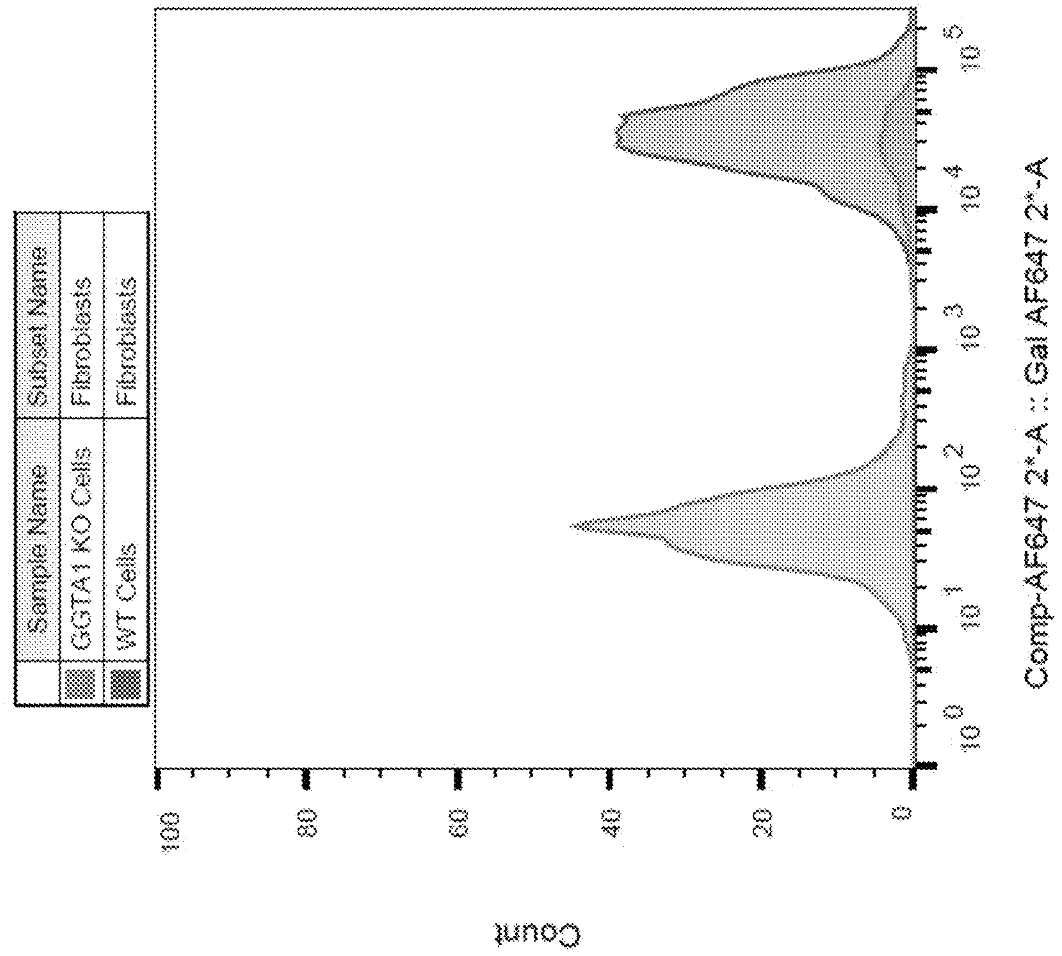
FIGS. 8A-8D shows CRISPR/Cas 9 mediated GGTA1 KO in the PFFs.

At day 7 post-transfection, PFFs were sorted for GGTA1 KO by flow cytometry (FC) (FIG. 8A). Approximately 5×106 cells were incubated with AF-647 conjugated Isolectin GS-IB4 (3 μg/mL cell suspension; isolated from Griffonia simplicifolia, Thermo-Fisher Scientific) for 1 hour on ice. Incubated cells were then washed in 4 ml of phosphate buffered saline (PBS) and cell pellets were made by centrifugation at 1000 rpm for 5 minutes. After centrifugation, cell pellets were resuspended in 0.5 ml of PBS. Sorting of GGTA1 KO cells was accomplished by fluorescence-activated cell sorting (FACS) analysis on a BD FACSMelody Cell Sorter (BD Biosciences) with WT cells as a positive control and an additional unstained control.

Sequencing and TIDE Analysis for GGTA1 KO Cells

Figure 8B:
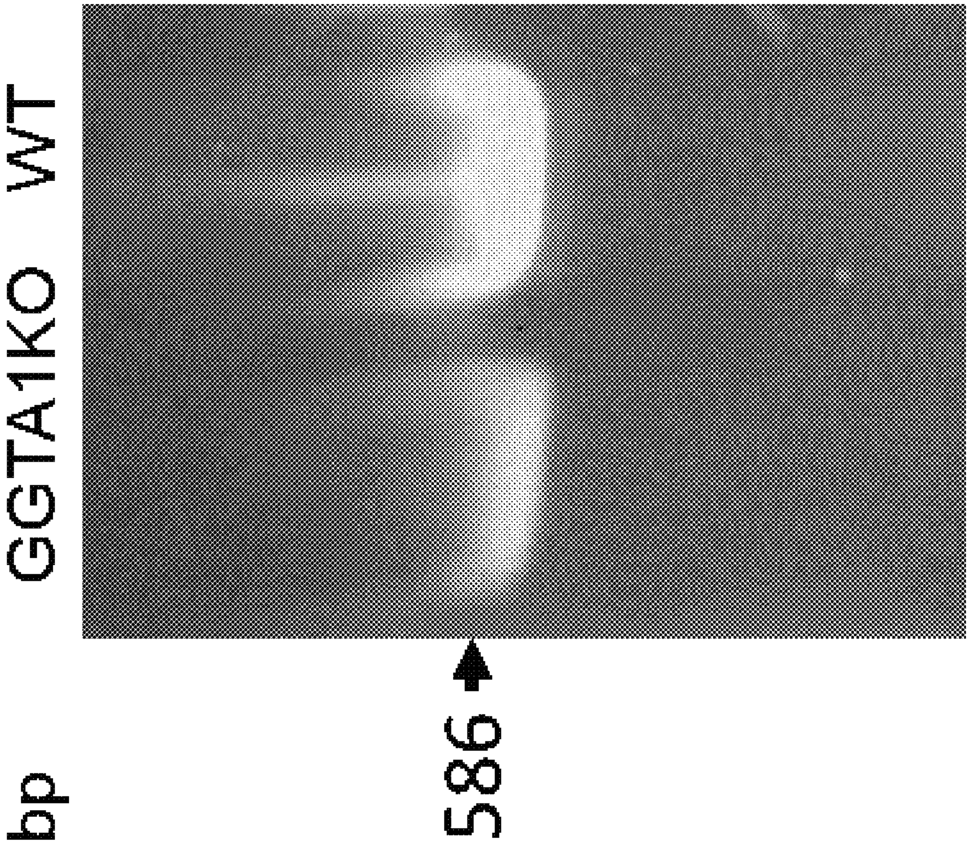
Figure 8C:
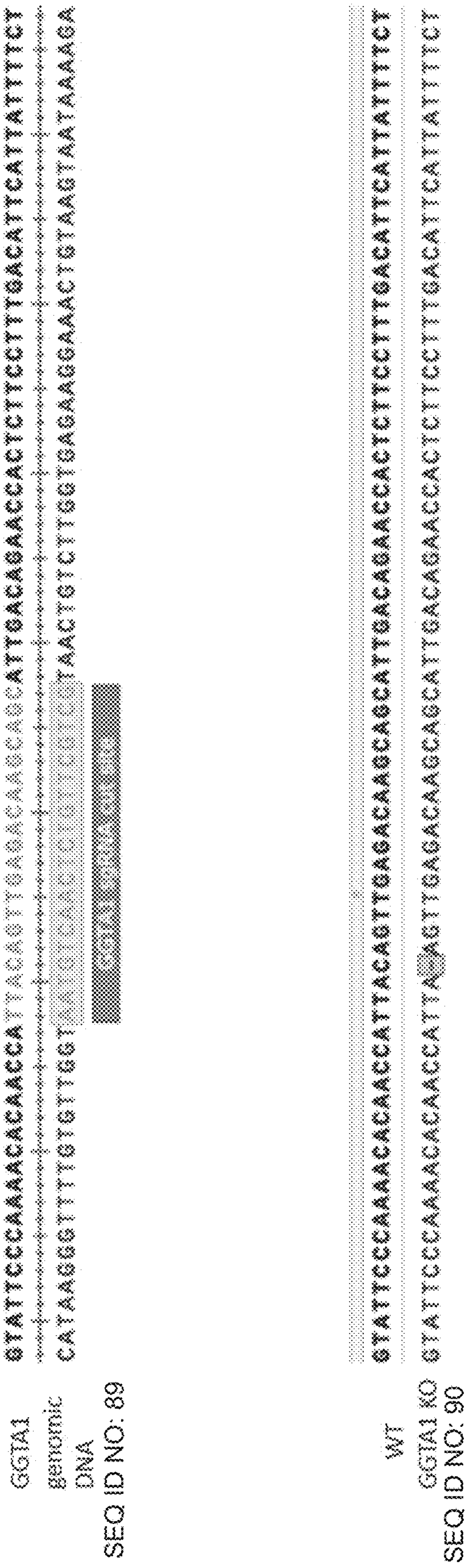
Figure 8D:
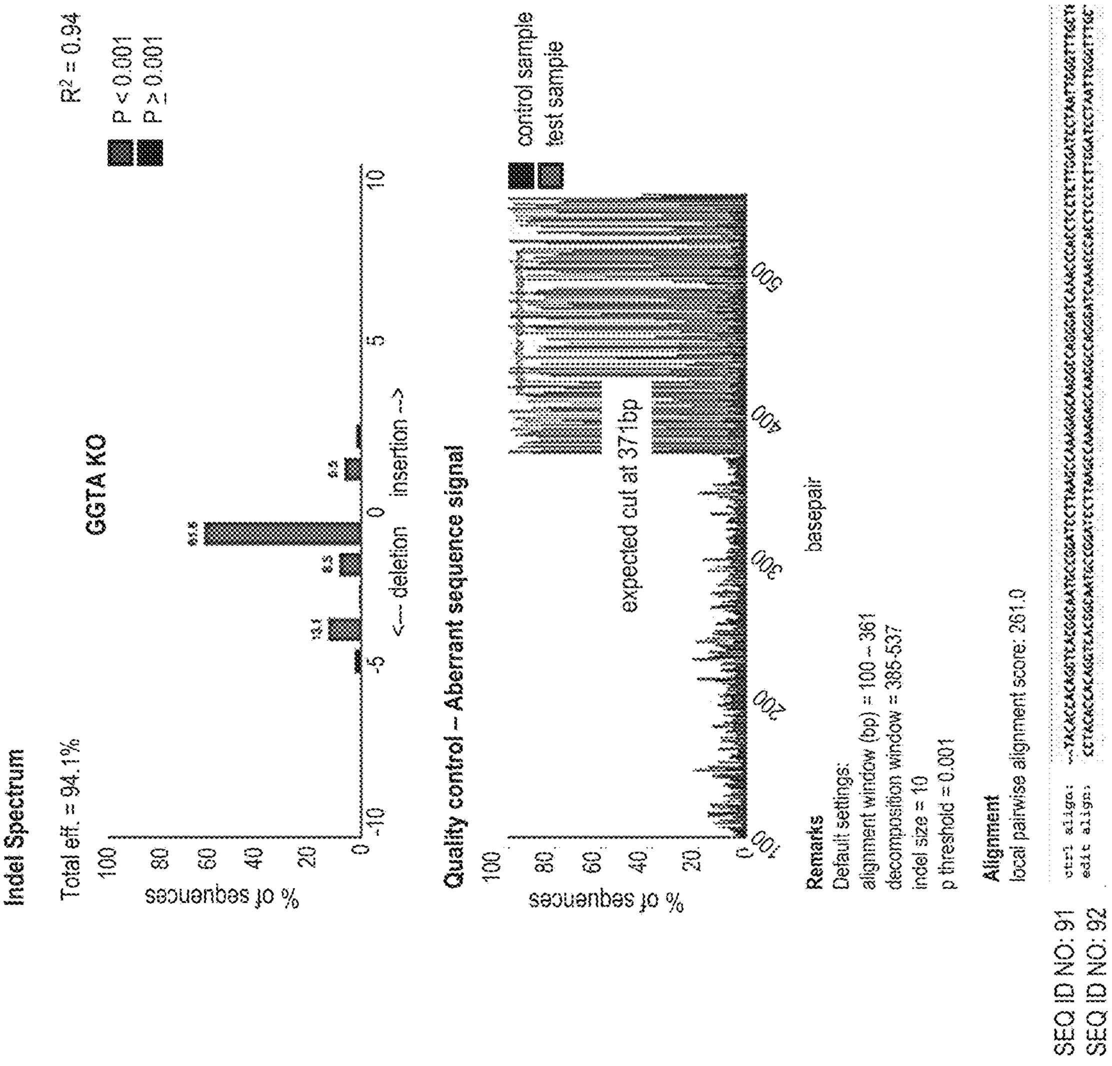
Figure 9A:
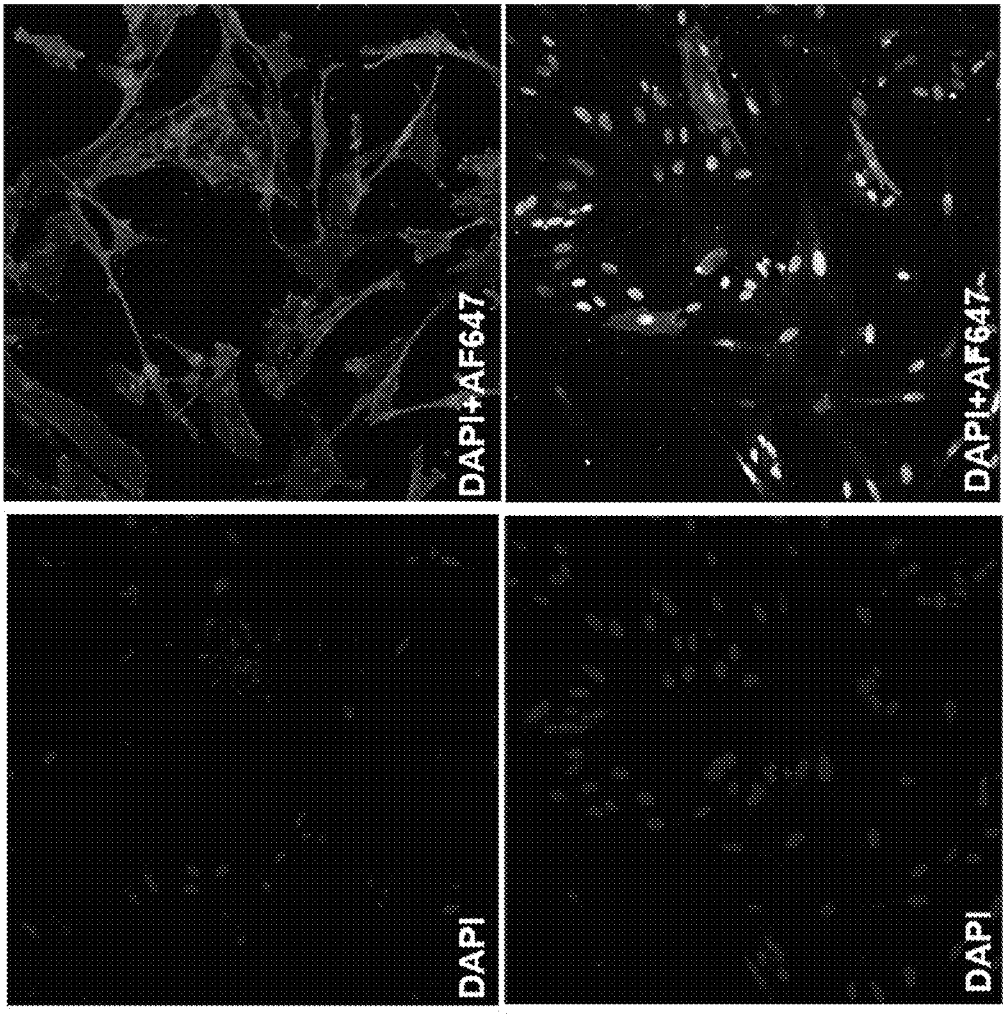
FIGS. 9A-9C shows phenotypic analysis of GGTA1 KO cells.
Figure 9B:
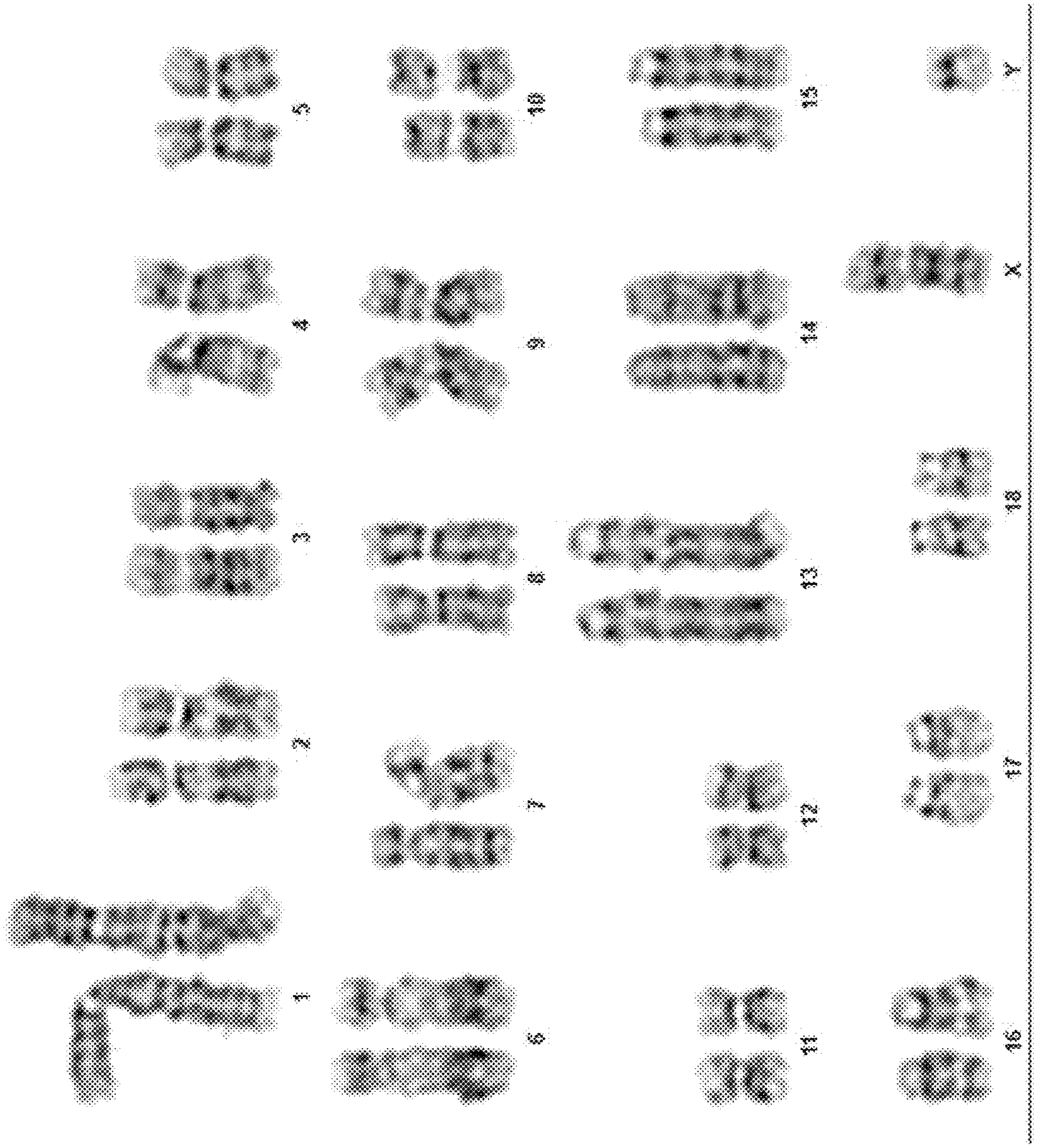
Figure 9C:
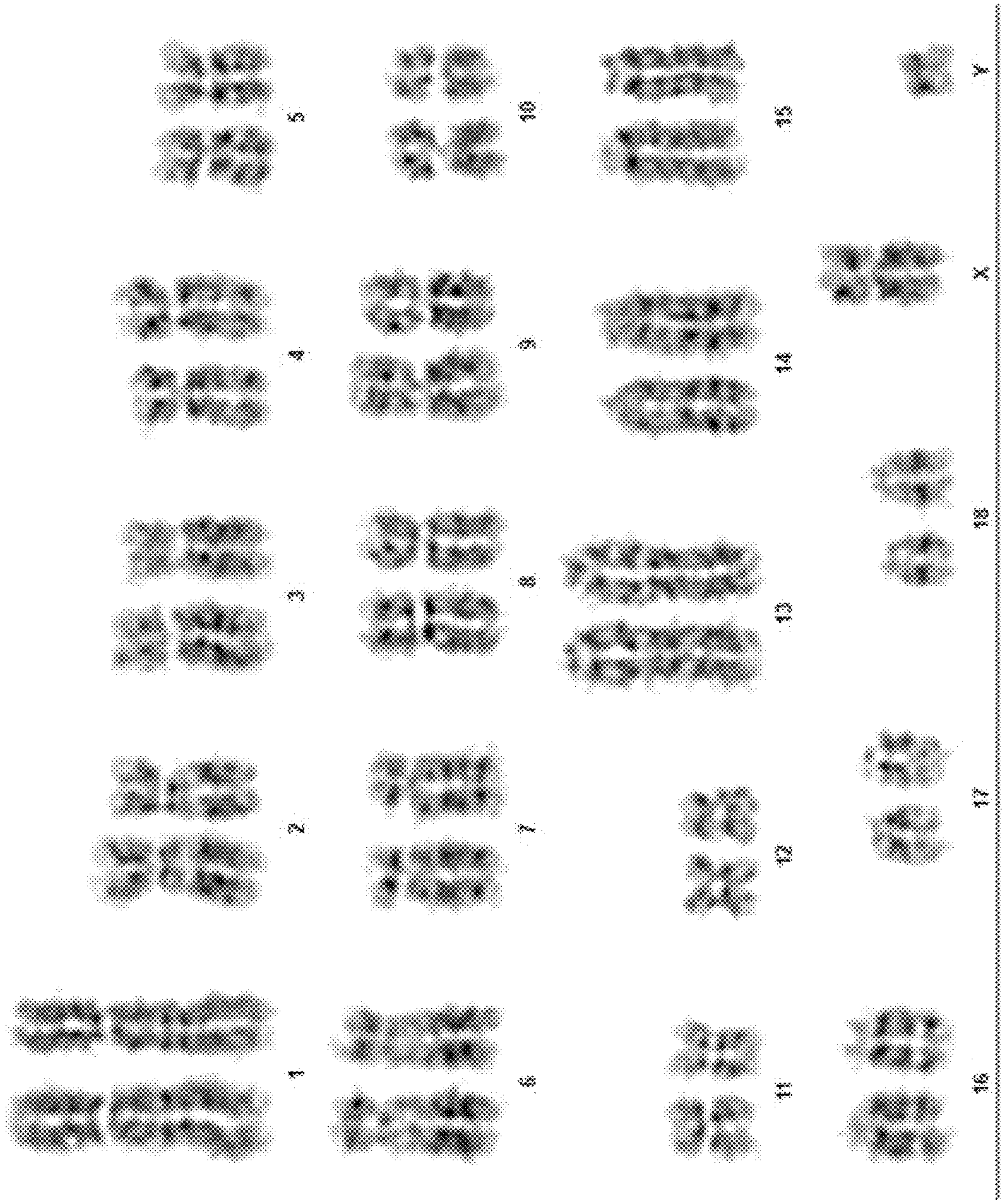

Isolation of DNA was performed using the QIAmp DNA Micro Kit (Qiagen) to detect mutations in GGTA1 KO fetal fibroblasts. PCR fragments around the cut site region were amplified by forward and reverse sequencing (FIG. 8B):

Forward 5' CCTTAGCGCTCGTTGACTATTC 3' (SEQ ID NO: 69);

Reverse 5' TTTCTTTG CTTTTTAGGGCCGC 3' (SEQ ID NO: 70).

The amplicon, measuring approximately 586 bp, was subsequently sent for Sanger sequencing using the primers shown in Table 8. TIDE analysis was performed as previously described in order to analyze the incidence of major induced mutations in the projected editing site frequency in a single cell population when compared with the WT population.

TABLE 8

Primer Sequences and PCR Product Sizes

| Genes | Primer sequence (5'-3') | PCR Product Size (bp) | Tm (° C.) | Reference/Sequence Accession # |
|---|---|---|---|---|
| Klf4 | CCATGGGCCAAACTACCCAC (SEQ ID NO: 71) | 81 | 60 | NM_001031782.2 |
| Klf4 | GGCATGAGCTCTTGGTAATGG (SEQ ID NO: 72) | 81 | 59 | NM_001031782.2 |
| Nanog | CCACTGGCCAAGGAATAGC (SEQ ID NO: 73) | 88 | 60 | NM_001129971.1 |
| Nanog | CAGGCATCCTTGGTGGTAGG (SEQ ID NO: 74) | 88 | 60 | NM_001129971.1 |
| Oct4 | GCTCACTTTGGGGGTTCTCT (SEQ ID NO: 75) | 80 | 59 | NM_001113060 |
| Oct4 | TGAAACTGAGCTGCAAAGC (SEQ ID NO: 76) | 80 | 59 | NM_001113060 |
| Bcl-xl | GTTGACTTTCTCTCCTACAAG (SEQ ID NO: 77) | 277 | 62 | Hwang_et_al. |
| Bcl-xl | GGTACCTCAGTTCAAACTCAT (SEQ ID NO: 78) | 277 | 62 | Hwang_et_al. |
| Bax-a | ACTGGACAGTAACATGGAG (SEQ ID NO: 79) | 294 | 63 | Hwang_et_al. |
| Bax-a | GTCCCAAAGTAGGAGAGGAG (SEQ ID NO: 80) | 294 | 63 | Hwang_et_al. |
| Dnmt1 | TTCTCACTGCCTGACGATGT (SEQ ID NO: 81) | 79 | 59 | NM_001032355.1 |
| Dnmt1 | CCTTCACGCATTCCTTTTCTG (SEQ ID NO: 82) | 79 | 59 | NM_001032355.1 |
| Igf2 | GGCATCGTGGAAGAGTGCT (SEQ ID NO: 83) | 128 | 60 | X56094.1 |
| Igf2 | CTGGGGAAGTTGTCCGGAAG (SEQ ID NO: 84) | 128 | 60 | X56094.1 |
| ASF1A | AGTTCGAGATCACCTTCGAGTG (SEQ ID NO: 85) | 431 | 60 | XM_003121238.3 |
| ASF1A | ACTGCTCTCTGG ATCTTCCAGT (SEQ ID NO: 86) | 431 | 60 | XM_003121238.3 |

TABLE 8-continued

Primer Sequences and PCR Product Sizes

| Genes | Primer sequence (5'-3') | PCR Product Size (bp) | Tm (° C.) | Reference/Sequence Accession # |
|---|---|---|---|---|
| ACTB | AGATCGTGCGGGACATCAAG (SEQ ID NO: 87) | 93 | | DQ452569. |
| ACTB | GCGGCAGTGGCCATCTC (SEQ ID NO: 88) | 93 | | DQ452569. |
| GGTA1 | CCTTAGCGCTCGTTGACTATTC (SEQ ID NO: 69) | 586 | 56 | NM_001031782.2 |
| GGTA1 | TTTCTTTGCTTTTTAGGGCCGC (SEQ ID NO: 70) | 586 | 56 | NM_001031782.2 |
| GGTA1 (TIDE) | CCTTAGCGCTCGTTGACTATTC (SEQ ID NO: 69) | | 56 | NM_001031782.2 |

Immunofluorescence Staining

For Gal epitope staining, GGTA1 KO and WT positive control cells were incubated in 4% paraformaldehyde for 30 minutes at 4° C. After fixation, cells were further incubated in AF-647 conjugated Isolectin GS-IB4 (3 μg/mL cell suspension; isolated from Griffonia simplicifolia, Thermo-Fisher Scientific) for 30 minutes 4° C. Following incubation, cells were washed with PBS a total of four times each.

Differential Staining

Differential staining was performed. Briefly, on day 7, blastocysts were subjected to anti-Bovine Serum antibody produced in rabbit (Sigma, B3759) at a 1:4 dilution in PZM culture media containing 3 mg/ml of bovine serum albumin (BSA) (PZM-3) for 30 minutes. Blastocysts were washed in PZM-3 and then placed into a 1:9 dilution in PZM-3 of complement sera from guinea pig (Sigma-Aldrich, S1639) containing 5 mg/mL propidium iodide and 40 mg/mL Hoechst 33342 for 15 minutes. Blastocysts were rinsed in DPBS containing 0.1% BSA and mounted on glass slides. Images were taken using an Olympus Fluo View 2000 confocal inverted microscope.

Karyotyping

Cytogenetic analyses were performed using the Cytogenomics Shared Resource at the University of Minnesota.

RNA Extraction and Reverse Transcription

Gene expression analysis was performed for both WT and GGTA1 KO cells. For each group, 20 blastocysts were pooled. Each analysis was repeated three times, where each repetition was done by duplicate. Embryos were washed two times in PBS to eliminate any remaining culture media from the blastocysts. RNA was isolated using the PicoPure™ RNA Isolation Kit (Applied Biosystems, Thermo-Fisher Scientific, Lithuania) according to manufacturer's instructions. Samples were subjected to DNase treatment using the RNase-Free DNase Set (Qiagen, 79254) for genomic DNA digestion. RNA concentration and purity at the absorbance ratio 260/280 nm were determined on a NanoDrop 2000c Spectrophotometer (Thermo-Fisher Scientific). The range of the extracted RNA was between 30 and 65 ng/μl.

The QuantiTect® Reverse Transcription Kit (Qiagen) was used for reverse transcription (RT) according to the manufacturer's instructions. Amplification of complementary DNA (cDNA) was performed in 20 μL final volumes containing 2 μl of genomic DNA (gDNA) wipeout, up to 500 ng of template RNA, and RNase-free water, followed by incubation at 42° C. for 2 minutes. Following incubation, samples were placed immediately on ice. To further carry out the RT reaction, 1 μl of reverse transcriptase, 4 μl of 5x Quantiscript RT Buffer, and 1 μl RT Primer Mix were added. RT was carried out in a C1000 Touch™ Thermal Cycler (Bio-Rad) at 42° C. for 1 hour. The RT reaction was then inactivated at 95° C. for 3 minutes and finally maintained at 4° C.

Gene Expression Analysis

Real-time PCR was performed in accordance with the minimum information for publication of quantitative real-time PCR experiments (MIQE) guidelines. Quantitative PCR was applied using SYBR-Green with a CFX96 Touch™ Real-Time PCR Detection System (Bio-Rad) according to the manufacturer's instructions. Messenger RNA (mRNA) levels of Klf4, Oct4, Nanog, Igf2, Bax, Bcl-xl, Dnmt1, and ASF1 were measured and normalized with ACTB. PCR was carried out in a total volume of 20 μL contained 10 μl master mix, 1 μl of each primer (10 mmol/μl), 1 μl cDNA template (500 ng), and 7 μl nuclease free water.

All PCR reactions were initiated at 95° C. for 30 seconds, followed by 39 cycles of 95° C. for 15 seconds, 60° C. for 20 seconds, and 72° C. for 30 seconds. Reactions were terminated at around 10 minutes at 72° C. All tests were conducted in duplicate and the final product's identity was confirmed by melting curve analysis.

Primer Design

Primers used for expression analysis were designed using the online PrimerQuest tool (Integrated DNA Technologies) based on available sequences obtained from the NCBI GenBank database. Primers and products sizes are shown (Table 8).

Oocyte Collection and IVM

Sow cumulus-oocyte complexes (COCs) were obtained from a commercial supplier (DeSoto Biosciences, Inc., Seymour, TN). Gilt ovaries were obtained from a local slaughter house (MRS, Glencoe). Immature oocytes were aspirated from follicles measuring between 2 and 6 mm with an 18-gauge needle attached to a 10-ml syringe. Oocytes with 3 to 4 layers of cumulus cells and evenly dark cytoplasm were selected for maturation. Maturation of oocytes was accomplished according to established protocol with the following modifications. COCs were matured in groups of 50 in 500 μL of M199 supplemented with 5 μg/mL of porcine follicle-stimulating hormone (pFSH), 40 ng/mL fibroblast growth factor-2 (FGF2), 20 ng/mL leukemia inhibition factor (LIF), 20 ng/mL insulin-like growth factor-1 (IGF1), 10% (v/v) FBS, 10% (v/v) pig follicular fluid, 0.8 mM sodium pyruvate and 50 μg/mL gentamicin at 38.50C in a humidified 5% $CO_2$ incubator for between 41 and 44 hours.

Enucleation Followed by Bi-Oocyte Fusion Cloning

Figure 7:
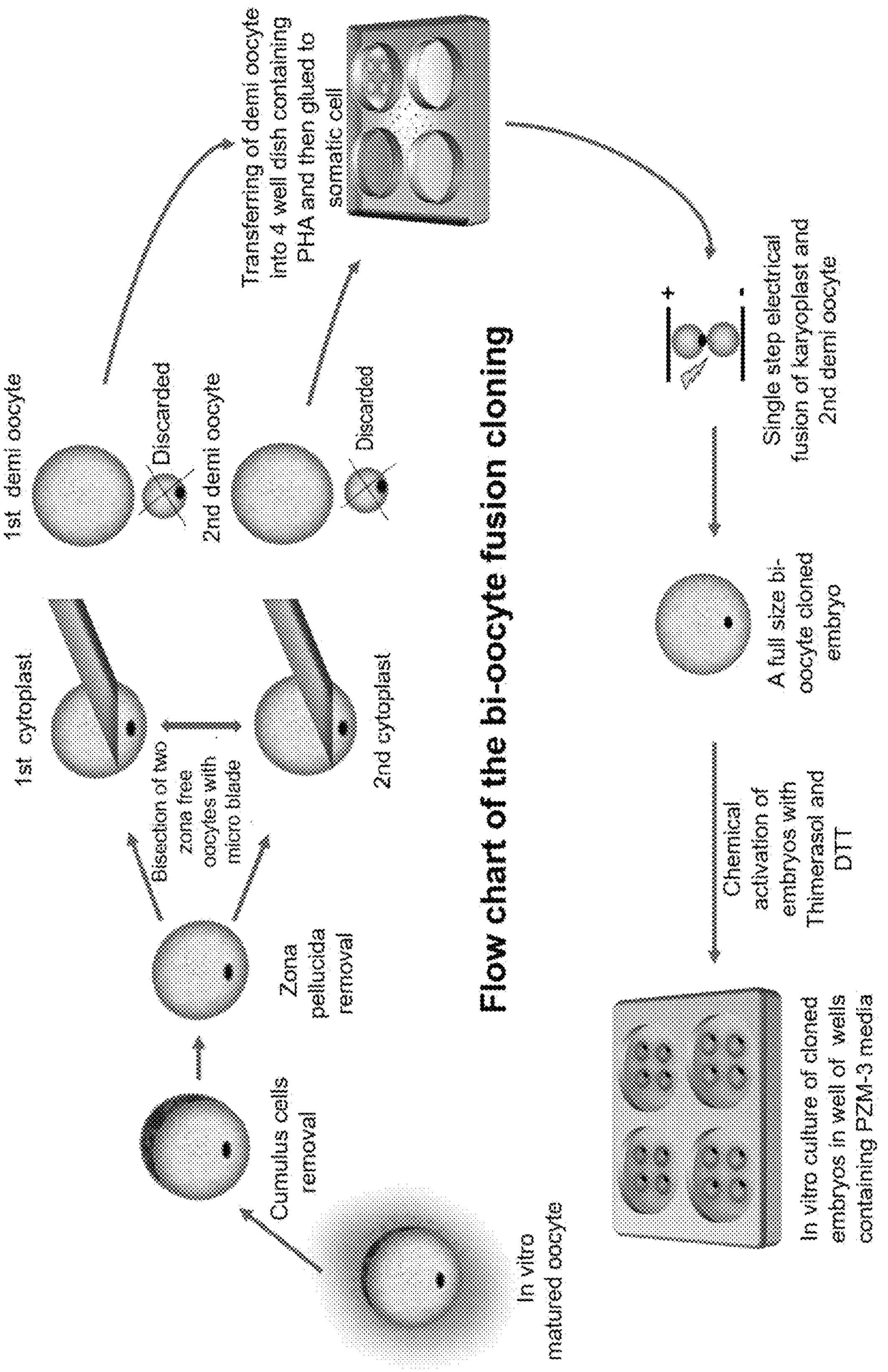
FIG. 7 shows a flow chart summarizing steps involved in bi-oocyte fusion cloning.

DAOE was performed. After 41 hours maturation in vitro, COCs were further cultured for 45 minutes in the media supplemented with 0.4 μg/mL demecolcine. The following steps for BOF cloning are summarized in a flow chart (FIG. 7). Cumulus cells were removed by pipetting in 1 mg/ml hyaluronidase dissolved in HEPES-buffered tissue culture medium 199 (TCM-199). From this point, all steps were performed on a heated stage adjusted to 390C, except where otherwise indicated.

The procedures for BOC and HMC were performed. Zona pellucida of oocytes were partially digested by 3 mg/ml pronase dissolved in 30% BSA in HEPES-buffered TCM-199 Medium (T30) (Thermo-Fisher Scientific). Upon observing the occurrence of partial lyses of zonae pellucidae and slight deformation of oocytes, oocytes were picked up and washed quickly in T20 drops. Oocytes were then lined up in a 35 mm dish containing 20% BSA in HEPES-buffered TCM-199 Medium (T20) (Thermo-Fisher Scientific) supplemented with 2.5 μg/mL cytochalasin B (CB). Using finely drawn, fire-polished glass pipettes, oocytes were rotated to find either a light extrusion cone and/or a strongly attached polar body (PB) on the surface, and oocyte bisection was performed with a micro blade ((Ultra-Sharp Splitting Blades, Bioniche, USA)) under a stereo microscope. Following enucleation, bisected oocytes were rested in T20 in a 5% $CO_2$ incubator at 38.5° C. for between 20 and 30 minutes.

Oocyte Bisection Enucleation without Demecolcine Treatment or Random Enucleation All steps performed were similar to procedure described above, with the exception that demecolcine pre-incubation was omitted.

Fusion and Activation

Fusion was attempted according to both the double-step fusion method, and the single-step fusion method. Enucleated demi-cytoplasts were immersed in phytohemagglutinin (0.5 mg/ml in T20) for 3 to 4 seconds and transferred into T20-containing, low-density donor cells. Each demi-cytoplast was then allowed to stick to one rounded, medium sized cell by gently rolling the demi-cytoplast over it. Demi-cytoplast-donor cell pairs were transferred to fusion medium (0.3 M D-mannitol, 0.1 mM MgSO4, 0.1 mM CaCl2 supplemented with 0.01% (w/v) poly-vinyl alcohol (PVA) for equilibration. The couplets and the remaining demi-cytoplasts were then transferred away from the positive and negative poles, respectively, of the fusion chamber using a Model ECM 2001 BTX Microslide™ with a 0.5 mm gap (BTX, San Diego, CA). A single-step fusion protocol was subsequently followed, wherein a demi-cytoplast and a couplet were picked using fine-pulled Unopette® capillary pipettes (Becton Dickinson, NJ) with an inner diameter of 100 to 120 μm. Initially, the couplet was expelled and aligned with a 6 V AC pulse using an ECM 2001 Electro Cell Manipulator (BTX), where the somatic cell was facing the negative electrode. Immediately after alignment, the demi-cytoplast was introduced into the fusion chamber closest to the somatic cell. Once the somatic cell was sandwiched between the demi-cytoplasts, a single DC pulse was applied, and triplets were then rested in T20 for 1 to 2 hours at 38.5° C. Following incubation, reconstructs were activated by combined thimerosal/DTT treatment. Oocytes were treated with 200 μM thimerosal (Sigma, T8784) for 10 minutes followed by treatment with 8 mM DTT for 30 minutes. Following activation, embryos were transferred to 700 μl PZM-3 medium supplemented with 3 mg/ml of fatty acid free BSA in a well of the well (WOW) system.

Experimental Design

All of the experiments conducted in this study were performed keeping all parameters constant except the variable intended to be tested, in order to achieve better understanding of each parameter.

Experiment 1

The efficiency of DAOE and oriented random handmade enucleation (RHE), was tested in three replicates using a total of 147 oocytes. After 41 hours of maturation, oocytes were subjected to demecolcine incubation. Oocyte bisection was performed for selected oocytes where either an extrusion cone and/or a strongly attached PB were detected after partial pronase digestion.

The efficiency and reliability of enucleation without demecolcine treatment was also investigated in three replicates using a total of 75 oocytes. After 41 hours of in vitro maturation, oocyte bisection was performed in selected matured oocytes where either an extrusion cone and/or a strongly attached PB were detected after partial pronase digestion.

Experiment 2

For electrofusion of oocyte-fibroblast-oocyte triplets, pulse amplitude and number of pulses given were compared according to the following: Group A (1.2 kV/cm for 20 μs, single pulse), Group B (2.0 kV/cm for 80 μs single pulse), Group C (1.0 kV/cm for 9 μs, single pulse). Cleavage rate was determined at day 2 of culture.

Experiment 3

Two different fusion methods were compared in this experiment. In the first method, a single donor cell was sandwiched between two demi-cytoplasts, after which electrofusion was carried out in a single-step. The second method was comprised of a two-step protocol where the first step included fusion of a single somatic cell with an enucleated demi-cytoplast after which the pair was fused with another demi-cytoplast in the second step.

Experiment 4

Fused reconstructs were incubated for 0, 1 and 4 hours at 38.5° C. in a humidified 5% $CO_2$ incubator in air after electrofusion in T20 for genomic reprogramming of the donor cell. Developmental competence was compared in terms of blastocyst development rate.

Experiment 5

Difference in developmental competence between sow- and gilt-derived oocytes were investigated through zona-free oocyte bisection cloning after demecolcine treatment, followed by activation in thimerosal/DTT.

Example 8 Effect of Demecolcine-Assisted Oocyte Enucleation on Embryo Development to Blastocyst Stage Fusion rates were similar for DAOE and RHE. Overall efficiency, cleavage rate, and blastocyst development rate were significantly higher ($p<0.05$) in the DAOE group, as compared to the RHE group (Table 2) followed by thimerosal/DTT chemical activation.

Example 9 DC Pulse Effect on Fusion and Cleavage Efficiency of Oocyte Bisected Cloned Embryos Similar fusion rates were found for groups A, B, and C. The cleavage rate was significantly higher ($p<0.05$) for group C, compared to group A and group B (Table 3) with a voltage of 6 V. Based on these results, the electrofusion parameter of a single pulse of 1.0 kV/cm for a 9 μs duration was subsequently used for further experiments.

Example 10 Single-Step Fusion Efficiency on Blastocyst Development Competency

Fusion, cleavage and blastocyst development rates were all significantly higher ($p<0.05$) for the single-step fusion method when compared to the double-step fusion method (Table 4).

Example 11 Effect of Differential Holding Time Interval Between Electro-Fusion and Activation on In Vitro Developmental Competence of Cloned Embryos Cleavage rates for oocytes subjected to 0, 1- and 4-hour incubation were similar, however, the overall blastocyst development rate was significantly higher ($p<0.05$) for oocytes incubated for 1 hour, as compared to 0 and 4-hour holding times (Table 5).

Example 12 In Vitro Developmental Competence of Sow-and Gilt-Oocyte Derived Blastocysts Cleavage and blastocyst development rates were significantly higher ($p<0.05$) for sow-derived oocytes subjected to BOF cloning followed by activation in thimerosal/DTT, as compared to gilt-derived oocytes (Table 6).

Example 13 Generation of GGTA1 KO Cells

PFFs were isolated from day 35 fetuses bred from male Mangalista pigs. CRISPR/Cas9 GGTA1 sgRNA transfected into PFFs by nucleofection. After 7 days in culture, sorting was performed on WT and GGTA1 KO cells by AF-647 Isolectin GS-IB4 staining. Specific gene product (586 bp) was isolated by PCR amplification and sequencing confirmed the single nucleotide deletion in GGTA1 KO compared to WTs. TIDE analysis for major induced mutations in the projected editing site frequency in a single cell population of GGTA1 KO fetal fibroblast cells in comparison to WT cells. Comparison of GGTA1 KO cells to WT cells by FACS showed no a-Gal expression on the cells. Karyotyping analysis was performed on WT and KO cells to rule out any chromosomal abnormality and no aberrant chromosomal rearrangements were detected in either GGTA1 KO or WT cells.

Figure 10A:
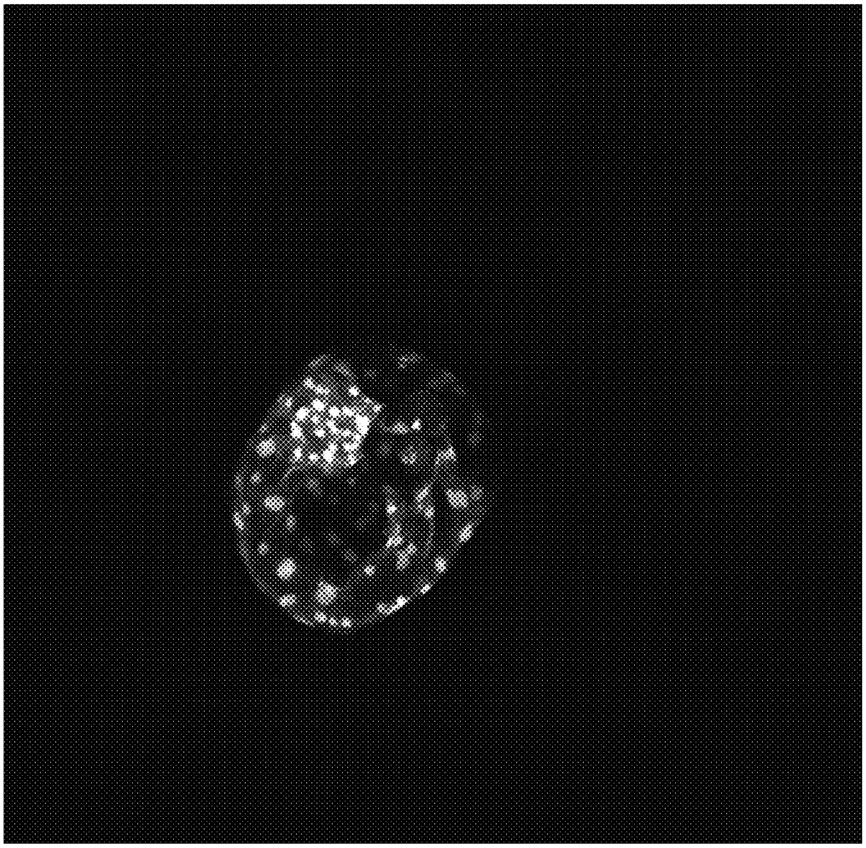
FIGS. 10A-10B shows production of GGTA1 KO blastocysts. Day-7 GGTA1 KO porcine blastocysts produced by BOF cloning are shown in FIG. 4 above.

Example 14 Production of GGTA1 KO Embryos, Gene Expression Pattern, and Embryo Quality Evaluation Comparison of in vitro production efficiency for WT and GGTA1 KO embryos is shown in Table 7. Blastocyst development rates for GGTA1 KO cells (38±1.76) were comparable to the rate of blastocyst development for WT cells (41.1±0.67). As shown in FIG. 4, GGTA1 KO blastocysts generated at day 7 show a proper developmental appearance. In addition, differential staining of GGTA1 KO blastocyst produced by BOF cloning (FIG. 10A), demonstrated by blue color (Hoechst 33342) and pink color (propidium iodide), are indicative of inner cell mass (ICM) and trophectoderm (TE) cells, respectively.

Figure 10B:
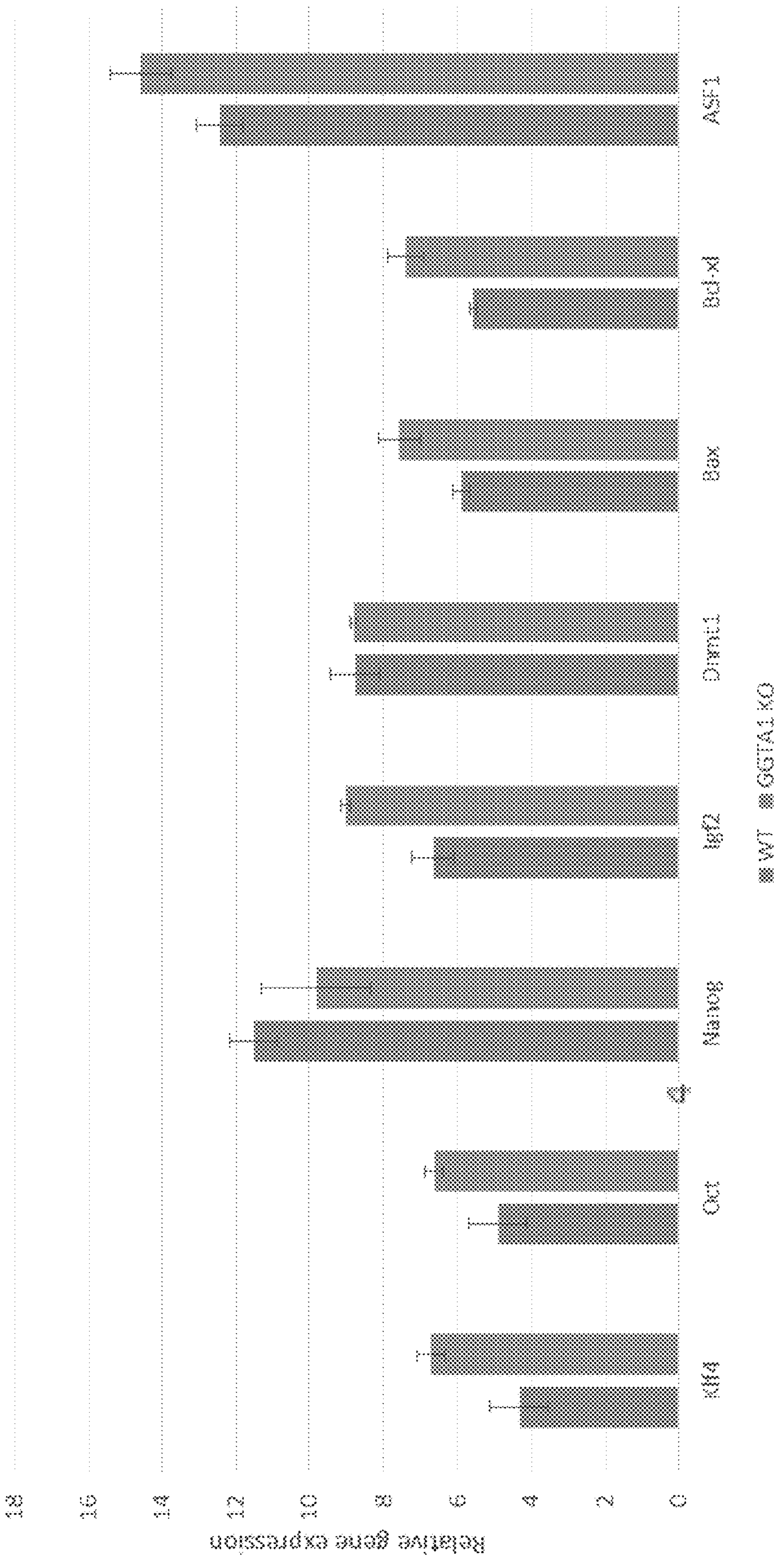
Figure 11:
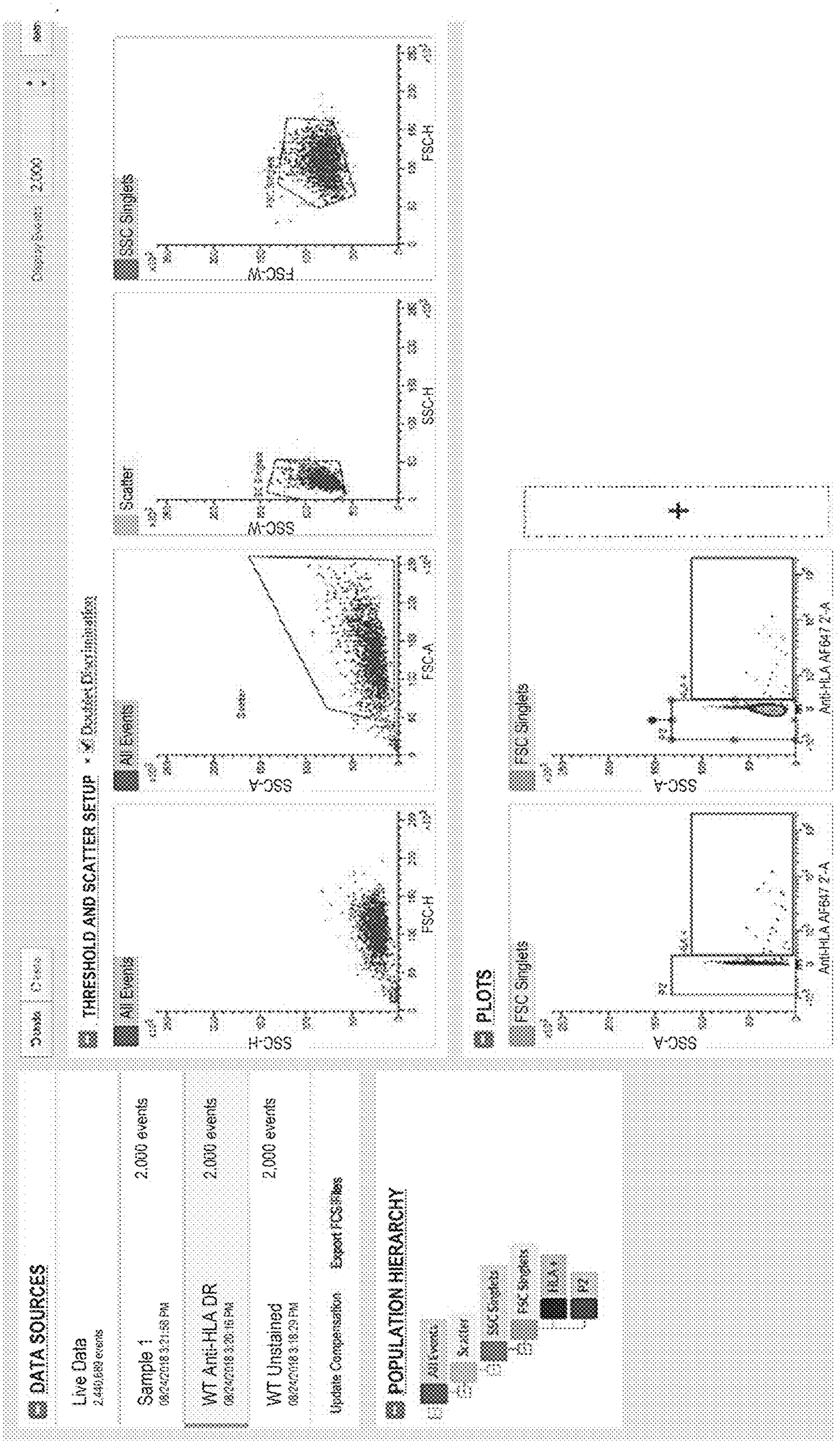
FIG. 11 shows flow cytometry results of genetically modified pig fibroblast cells confirming surface expression of chimeric HLA-DR molecule. The top panel shows threshold and scatter control. The bottom panel shows genetically modified cells with positive staining with PE anti-human HLA-DR Antibody L243 (1:100).
Figure 12A:
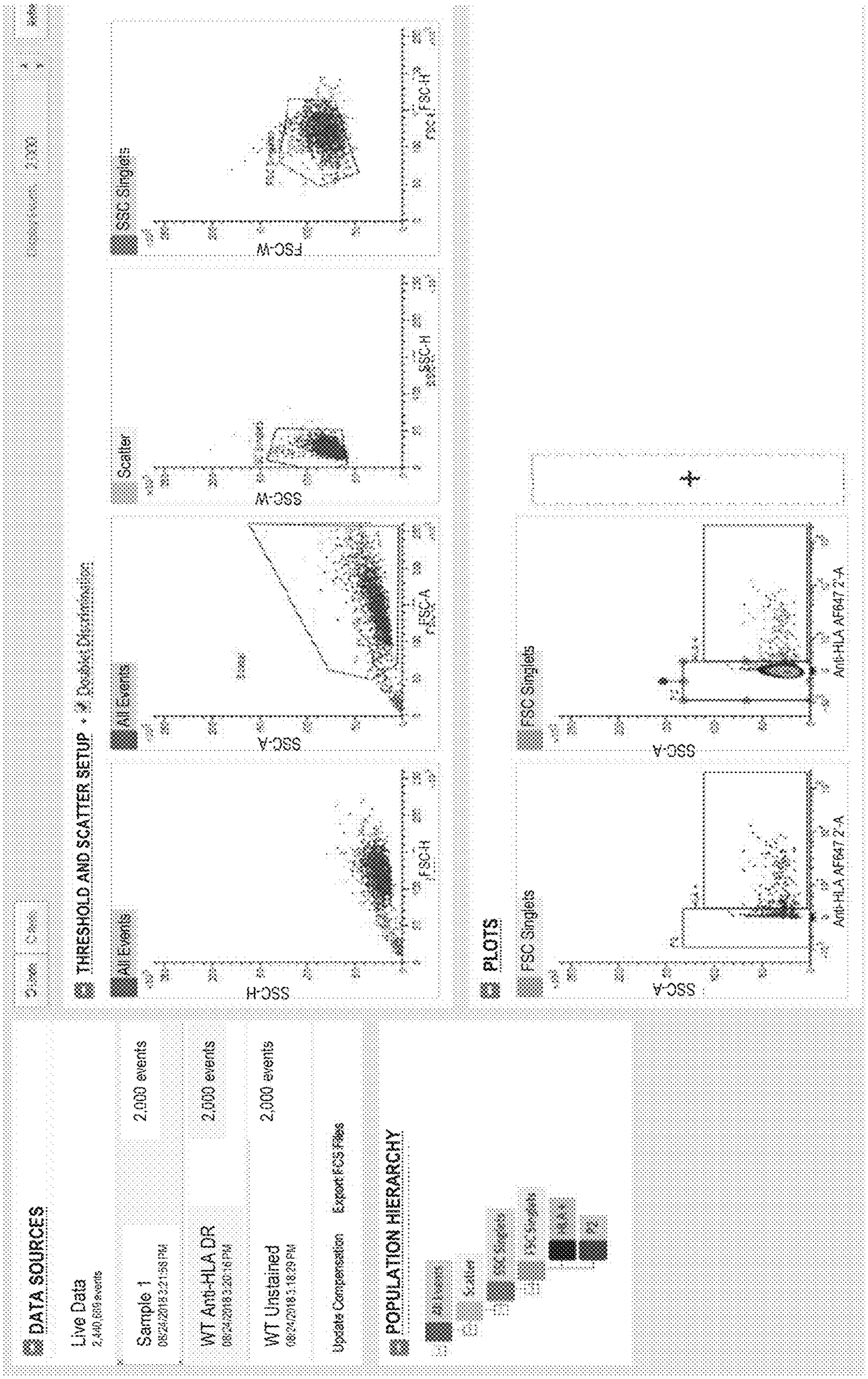
FIGS. 12A-12B shows flow cytometry results of genetically modified pig fibroblast cells confirming surface expression of chimeric HLA-DR molecule.
Figure 12B:
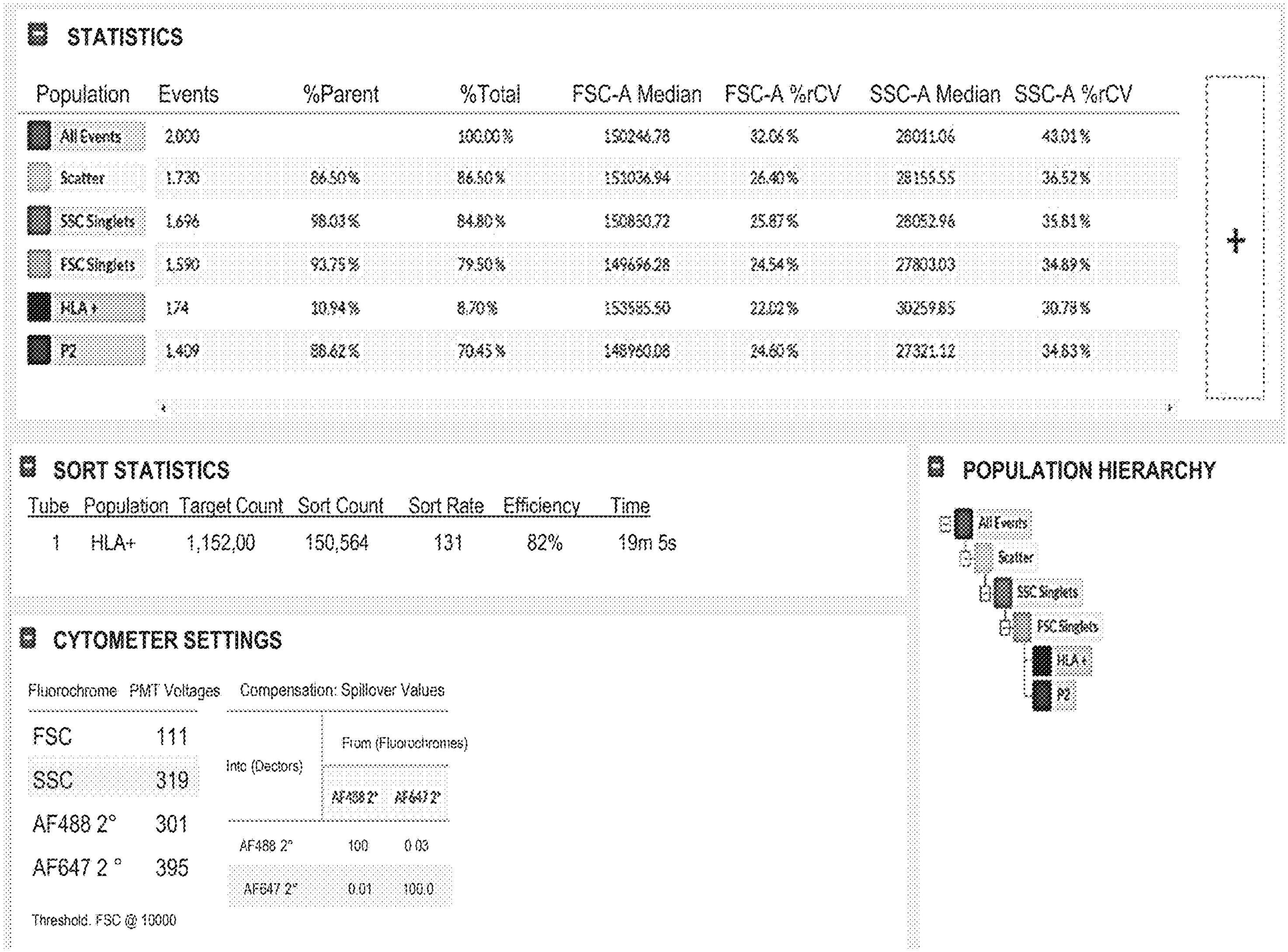
Figure 13A:
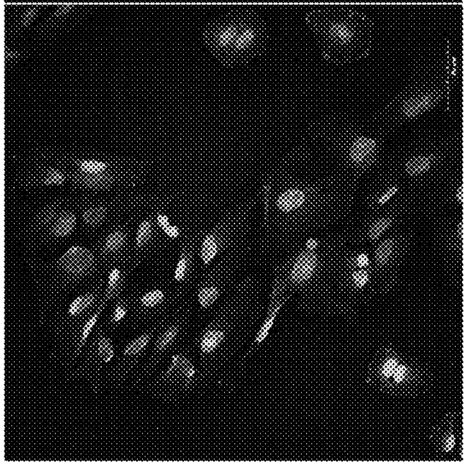
FIGS. 13A-13F show immunostaining analysis confirming expression of HLA-DR in HLA-DR transgenic fibroblast cells and absence of expression in non transgenic wild type fetal fibroblast cells using PE anti-human HLA-DR Antibody L243 (1:100).
Figure 13B:
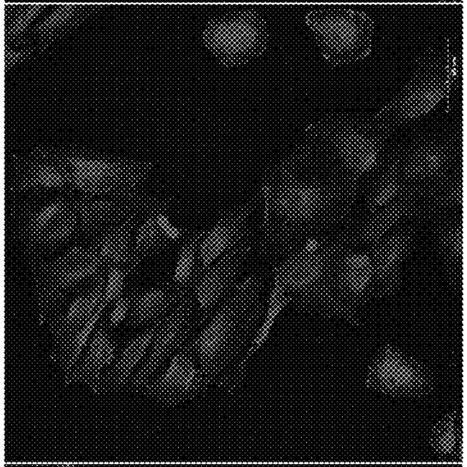
Figure 13C:
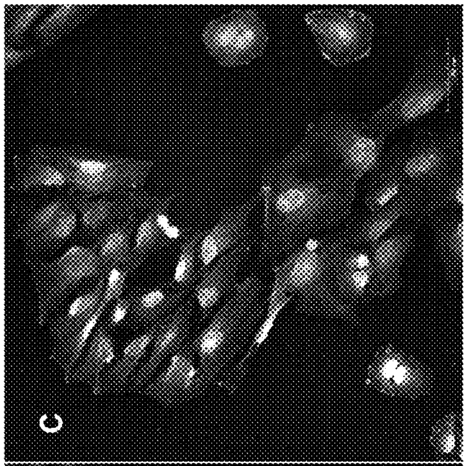
Figure 13D:
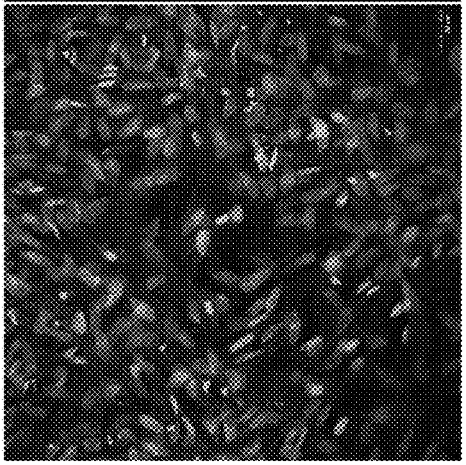
Figure 13E:
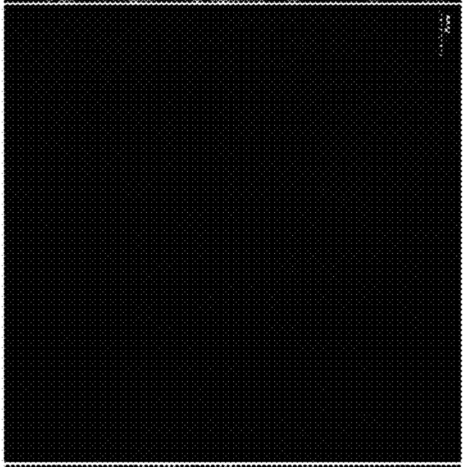
Figure 13F:
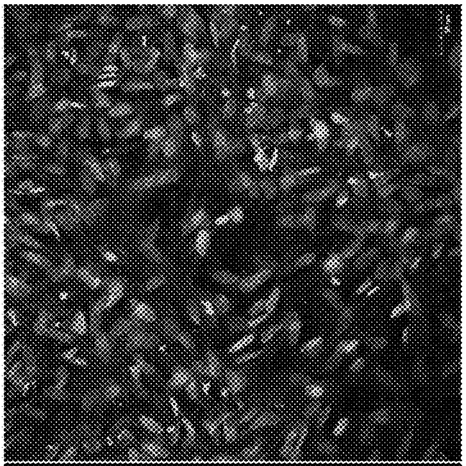
Figure 14:
FIG. 14 shows a genetically modified pig expressing HLA-DR transgene. Ear clippings and tail skin samples were taken and analyzed to confirm genotype of the pig by sequencing.

Accordingly, in order to compare cellular reprogramming between WT and GGTA1 KO blastocysts, the following parameters were assessed (FIG. 10B): relative expression levels of pluripotency genes Klf4, Oct4 and Nanog, the differentiation related marker, Igf2, two apoptosis markers, Bcl-xl and Bax, a key modulator of DNA methylation, Dnmt1, and cellular reprogramming factor, ASF1. Non-significant mRNA levels were observed for Klf4, Oct4, Nanog, Igf2, Dnmt1, Bax, Bcl-xl and ASF1 genes in GGTA1 KO blastocysts, as compared to WT blastocysts.

TABLE 9

| lists sequences for the disclosure | |
|---|---|
| SEQ ID NO: 1 | Exemplary Linker sequence<br>GTGSGSGSGSGSGSGS |
| SEQ ID NO: 2 | Exemplary Linker sequence<br>GGGGSGGGG |
| SEQ ID NO: 3 | Exemplary nucleic acid sequence of transgene encoding single chain MHC chimeric protein of the disclosure |

ATGGTGTGCCTGAGACTGCCAGGCGGATCATGCATGGCTGTGCTGACCGTGACACTGATGGTGCTGTCCTCTCCAC
TGGCTCTGGCCAGCAGCCACCACAACCTGCTCGTGTGTAGCGTGTCCGGATTCTACCCAGGTGGTACCGGCAGCGG
ATCAGGTTCCGGAAGTGGTAGCGGATCTGGAAGCGGAAGCGGAGATACAAGACCCCGCTTCCTGGAATACTCTACC
AGCGAGTGCCACTTCTTCAACGGCACAGAGAGAGTGCGCTACCTGGACCGCTACTTCCACAATCAAGAGGAAAACG
TGCGCTTCGACAGCGACGTGGGAGAGTTTAGAGCCGTGACAGAACTGGGACGCCCAGACGCCGAATACTGGAACTC
CCAGAAGGACCTGCTGGAACAGAAACGAGGCCGCGTGGACAACTACTGCAGGCACAATTATGGCGTGGTGGAATCC
TTCACCGTGCAGAGGCGAGTGCACCCCAAAGTGACAGTGTACCCCAGCAAGACCCAGCCACTGCAGCACCACAATC
TGCTCGTGTGTAGCGTGTCCGGCTTCTACCCAGGCTCTATCGAAGTGCGCTGGTTCCGCAACGGCCAAGAAGAGAA
AACAGGCGTCGTGTCCACCGGACTGATCCACAACGGCGACTGGACCTTTCAGACCCTCGTGATGCTCGAAACAGTG
CCCAGATCCGGCGAGGTGTACACATGCCAGGTGGAACACCCAAGCGTGACAAGCCCACTGACCGTCGAGTGGAGAG
CTCGGAGTGAAAGCGCCCAGTCTAAAGGCGGCGGAGGATCTGGTGGCGGCGGAATCAAAGAGGAGCACGTCATCAT
CCAGGCCGAATTCTATCTGAACCCCGACCAGAGCGGCGAGTTCATGTTCGACTTCGACGGGGACGAAATCTTTCAC
GTGGACATGGCCAAAAAAGAAACCGTGTGGCGCCTGGAAGAGTTCGGAAGATTCGCCTCTTTCGAGGCCCAAGGCG
CCCTGGCCAATATCGCTGTGGACAAAGCCAACCTGGAAATCATGACCAAGCGCAGCAACTACACCCCAATCACCAA
CGTGCCACCTGAAGTGACCGTGCTGACAAACAGCCCAGTGGAACTGCGCGAGCCCAACGTGCTGATCTGCTTCATC
GACAAGTTCACCCCACCAGTGGTCAACGTGACCTGGCTGAGAAACGGCAAGCCAGTGACAACCGGCGTGTCCGAGA
CAGTGTTTCTGCCAAGAGAGGACCACCTGTTCCGCAAGTTCCACTACCTGCCATTTCTGCCGTCGACTGAGGATGT
GTACGACTGCAGAGTCGAGCACTGGGGACTCGACGAGCCACTGCTGAAGCACTGGGAGTTTGACGCCCCATCTCCA
CTGCCAGAAACCACCGAGAATGTCGTGTGTGCCCTGGGCCTGACAGTGGGACTCGTGGGAATCATCATCGGCACCA
TCTTCATCATCAAGGGCCTGCGCAAAAGCAACGCCGCTGAAAGAAGAGGCCCACTCTGA

TABLE 9-continued lists sequences for the disclosure

SEQ ID NO: 4 Exemplary nucleic acid sequence of transgene encoding single chain MHC chimeric protein of the disclosure TGCAATAGGGACCCTAGGACGAGAGGAAAAGCGTCCAGGAACATTCTTGGAGGGGGGAGATCGAGGGCCCCAGAGC
GACCAGAGTTGTCACAAGGCCGCGCGAACGGGGGTGGGGGTGGGGTTTGGGGAGGGGAAAAAAAAGTGTGCTGTGT
ATTTTGAGGAGGGCGGCGAGAGGCCTATTCTCAAGTAAAAGGTAAACGTGGAGTAGGCAGTTCACAGGAAAAGGGG
TGAAGAGGCGTGGGGGGAGGGGAAACGTCCTGACCCAGGAAAGACATGAAAAGGGTAGTGGGGTCGACTAGATTAA
GGAGGGGGCCTCTCCGCCTGGGAAAGAGGGGTACAGTGGTGTGGGGGGGCGAGGGGGGATGGGAAGGGGCAGCATC
CTCCTGCTGAGAGCCGGGGGAGGGCCAGGCCCACGTCCCGAGAGCAAGCGCGAGGAGACGGAGGAGGTGACCCTTC
CCTCCCCCGGGGCCCGGTGGTGAGGGGAGGTCTCTCTTTTCTGTCGCACCCTTACCTTGTCCCAGGCCTGGGCCCG
GGCTGCGGCGCACGGCACTCCCGGTAGGCAGCAGGACTCGAGTTAGGCCCAGCGCGGCGCCACGGCGTTTCCTGGC
CGGGAATGGCCCGTGCCCGTGAGGTGGGGGTGGGGGGCAAAAAGGCGGAGCGAGCCAAAGGCGGTGAGGGGGGAGG
GCCAGGGAAGGAGGGGGGGGCCGGCACTACTGTGTTGGCGGACTGGCGGGACTGGGGCTGCGTGAGTCTCTGAGCG
CAGGCGGGCGGCGGCCGCCCCTCCCCCGGCGGCGGCGGCGGCGGCGGCGGCGGCGGCAGCAGCTCACTCAGCCCGC
TGCCCGAGCGGAAACGCCACTGACCGCACGGGGATTCCCAGCGCCGGCGCCAGGGGCACCCGGGACACGCCCCCTC
CCGCCGCGCCATTGGCCCCTCCGCCCACCGTCTCGCACCCATTGCCAGCTCCCCGCCAATCAGCGGAAGCCGCCGG
GGCCGCCTAGAGATCGATGACGTCGCGGCCGCATCGATCACGAGACTAGCCTCGAGAAGCTTGATATCGAATTCCA
CGGGGTTGGACGCGTCTTAATTAAGGATCCAAGGTCAGGAACAGAGAAACAGGAGAATATGGGCCAAACAGGATAT
CTGTGGTAAGCAGTTCCTGCCCCGGCTCAGGGCCAAGAACAGTTGGAACAGCAGAATATGGGCCAAACAGGATATC
TGTGGTAAGCAGTTCCTGCCCCGGCTCAGGGCCAAGAACAGATGGTCCCCAGATGCGGTCCCGCCCTCAGCAGTTT
CTAGAGAACCATCAGATGTTTCCAGGGTGCCCCAAGGACCTGAAATGACCCTGTGCCTTATTTGAACTAACCAATC
AGTTCGCTTCTCGCTTCTGTTCGCGCGCTTCTGCTCCCCGAGCTCTATATAAGCAGAGCTCGTTTAGTGAACCGTC
AGATCGCCTGGAGACGCCATCCACGCTGTTTTGACCTCCATAGAAGACACCGACTCTAGAGGATCGATCCCCCGGG
CTGCAGGAATTCAAGCGAGAAGACAAGGGCAGAAAGGCCACCATGGTGTGCCTGAGACTGCCAGGCGGATCATGCA
TGGCTGTGCTGACCGTGACACTGATGGTGCTGTCCTCTCCACTGGCTCTGGCCAGCAGCCACCACAACCTGCTCGT
GTGTAGCGTGTCCGGATTCTACCCAGGTGGTACCGGCAGCGGATCAGGTTCCGGAAGTGGTAGCGGATCTGGAAGC
GGAAGCGGAGATACAAGACCCCGCTTCCTGGAATACTCTACCAGCGAGTGCCACTTCTTCAACGGCACAGAGAGAG
TGCGCTACCTGGACCGCTACTTCCACAATCAAGAGGAAAACGTGCGCTTCGACAGCGACGTGGGAGAGTTTAGAGC
CGTGACAGAACTGGGACGCCCAGACGCCGAATACTGGAACTCCCAGAAGGACCTGCTGGAACAGAAACGAGGCCGC
GTGGACAACTACTGCAGGCACAATTATGGCGTGGTGGAATCCTTCACCGTGCAGAGGCGAGTGCACCCCAAAGTGA
CAGTGTACCCCAGCAAGACCCAGCCACTGCAGCACCACAATCTGCTCGTGTGTAGCGTGTCCGGCTTCTACCCAGG
CTCTATCGAAGTGCGCTGGTTCCGCAACGGCCAAGAAGAGAAAACAGGCGTCGTGTCCACCGGACTGATCCACAAC
GGCGACTGGACCTTTCAGACCCTCGTGATGCTCGAAACAGTGCCCAGATCCGGCGAGGTGTACACATGCCAGGTGG
AACACCCAAGCGTGACAAGCCCACTGACCGTCGAGTGGAGAGCTCGGAGTGAAAGCGCCCAGTCTAAAGGCGGCGG
AGGATCTGGTGGCGGCGGAATCAAAGAGGAGCACGTCATCATCCAGGCCGAATTCTATCTGAACCCCGACCAGAGC
GGCGAGTTCATGTTCGACTTCGACGGGGACGAAATCTTTCACGTGGACATGGCCAAAAAAGAAACCGTGTGGCGCC
TGGAAGAGTTCGGAAGATTCGCCTCTTTCGAGGCCCAAGGCGCCCTGGCCAATATCGCTGTGGACAAAGCCAACCT
GGAAATCATGACCAAGCGCAGCAACTACACCCCAATCACCAACGTGCCACCTGAAGTGACCGTGCTGACAAACAGC
CCAGTGGAACTGCGCGAGCCCAACGTGCTGATCTGCTTCATCGACAAGTTCACCCCACCAGTGGTCAACGTGACCT
GGCTGAGAAACGGCAAGCCAGTGACAACCGGCGTGTCCGAGACAGTGTTTCTGCCAAGAGAGGACCACCTGTTCCG
CAAGTTCCACTACCTGCCATTTCTGCCGTCGACTGAGGATGTGTACGACTGCAGAGTCGAGCACTGGGGACTCGAC
GAGCCACTGCTGAAGCACTGGGAGTTTGACGCCCCATCTCCACTGCCAGAAACCACCGAGAATGTCGTGTGTGCCC
TGGGCCTGACAGTGGGACTCGTGGGAATCATCATCGGCACCATCTTCATCATCAAGGGCCTGCGCAAAAGCAACGC
CGCTGAAAGAAGAGGCCCACTCTGAACGCGTTCTAGAAATAAAAGATCCTTATTTTCATTGGATCTGTGTGTTGGT
TTTTTGTGTGGCTAGCAAGAGGCTGTGCTCTGGGGCTCCGGCTCCTCAGAGAGCCTCGGCTAGGTAGGGGAGCGGG
ACTCTGGTTTGGGGGAGGGCCGGCGGTTTGGCGGGGGATGGGTGCTTGAGGTGGTCTGACCGGTAGCGGGGGTCGC
CTTCCCTAGCGGGAAGTCGGGAGCATATCGTTTGTTACGCTGGAAGGGGAAGAGGTGGTGAGAGGCAGGCGGGAGT
GCGGCCCGCCCTGCGGCAACCGGAGGGGGAGGGAGAAGGGAGCGGAAAAGCCTGGAATACGGACGGAGCCATTGCT
CCCGCAGAGGGAGGAGCGCTTCCTGCTCTTCTCTTGTCACTGATTGGCCGCTTCTCCTCCCGCCGTGTGTGAAAAC
ACAAATGGCGTGTTTTGGTTGGAGTAAAGCTCCTGTCAGTTACAGCCTCGGGAGTGCGCAGCCTCCCAGGAACTCT
CGCATTGCCCCCTGGGTGGGTAGGTAGGTGGGGTGGAGAGAGCTGCACAGGCGGGCGCTGTCGGCCTCCTGCGGGG
GGAGGGGAGGGTCAGTGAAAGTGGCTCCCGCGCGGGCGTCCTGCCACCCTCCCCTCCGGGGGAGTCGGTTTACCCG
CCGCCTGCTCGGCTTTGGTATCTGATTGGCTGCTGAAGTCCTGGGAACGGCCCCTTGTTATTGGCTTGGGTCCCAA
ATGAGCGAAACCACTACGCGAGTCGGCAGGGAGGCGGTCTTTGGTACGGCCCTCCCCGAGGCCAGCGCCGCAGTGT
CTGGCCCCTCGCCCCTGCGCAACGTGGCAGGAAGCGCGCGCAGGAGGCGGGGGCGGGCTGCCGGGCCGAGGCTTCT
GGGTGGTGGTGACTGCGGCTCCGCCCTGGGCGTCCGCCGCCTGAAGGACGAGACTAGCTCTCTACCTGCTCTCGGA
CCCGTGGGGGTGGGGGGTGGAGGAAGGAGTGGGGGGTCGGTCCTGCTGGCT
TGTGGGTGGGAGGCGCATGTTCTCCAAAAACCCGCGCGAGCTGCAATCCTGAG SEQ ID NO: 5 Exemplary sequence of a first flanking sequence located upstream of a transgene (left Rosa 26 homology arms)

TGCAATAGGGACCCTAGGACGAGAGGAAAAGCGTCCAGGAACATTCTTGGAGGGGGGAGATCGAGGGCCCCAGAGC
GACCAGAGTTGTCACAAGGCCGCGCGAACGGGGGTGGGGGTGGGGTTTGGGGAGGGGAAAAAAAAGTGTGCTGTGT
ATTTTGAGGAGGGCGGCGAGAGGCCTATTCTCAAGTAAAAGGTAAACGTGGAGTAGGCAGTTCACAGGAAAAGGGG
TGAAGAGGCGTGGGGGGAGGGGAAACGTCCTGACCCAGGAAAGACATGAAAAGGGTAGTGGGGTCGACTAGATTAA
GGAGGGGGCCTCTCCGCCTGGGAAAGAGGGGTACAGTGGTGTGGGGGGGCGAGGGGGGATGGGAAGGGGCAGCATC
CTCCTGCTGAGAGCCGGGGGAGGGCCAGGCCCACGTCCCGAGAGCAAGCGCGAGGAGACGGAGGAGGTGACCCTTC
CCTCCCCCGGGGCCCGGTGGTGAGGGGAGGTCTCTCTTTTCTGTCGCACCCTTACCTTGTCCCAGGCCTGGGCCCG
GGCTGCGGCGCACGGCACTCCCGGTAGGCAGCAGGACTCGAGTTAGGCCCAGCGCGGCGCCACGGCGTTTCCTGGC
CGGGAATGGCCCGTGCCCGTGAGGTGGGGGTGGGGGGCAAAAAGGCGGAGCGAGCCAAAGGCGGTGAGGGGGGAGG
GCCAGGGAAGGAGGGGGGGGCCGGCACTACTGTGTTGGCGGACTGGCGGGACTGGGGCTGCGTGAGTCTCTGAGCG
CAGGCGGGCGGCGGCCGCCCCTCCCCCGGCGGCGGCGGCGGCGGCGGCGGCGGCGGCAGCAGCTCACTCAGCCCGC
TGCCCGAGCGGAAACGCCACTGACCGCACGGGGATTCCCAGCGCCGGCGCCAGGGGCACCCGGGACACGCCCCCTC
CCGCCGCGCCATTGGCCCCTCCGCCCACCGTCTCGCACCCATTGCCAGCTCCCCGCCAATCAGCGGAAGCCGCCGG
GGCCGCCTAGAG

TABLE 9-continued lists sequences for the disclosure

SEQ ID NO: 6 Exemplary sequence of a second flanking sequence located downstream of a transgene (right ROSA26 homology arm)

AAGAGGCTGTGCTCTGGGGCTCCGGCTCCTCAGAGAGCCTCGGCTAGGTAGGGGAGCGGGACTCTGGTTTGGGGGA
GGGCCGGCGGTTTGGCGGGGGATGGGTGCTTGAGGTGGTCTGACCGGTAGCGGGGTCGCCTTCCCTAGCGGGAAG
TCGGGAGCATATCGTTTGTTACGCTGGAAGGGGAAGAGGTGGTGAGAGGCAGGCGGGAGTGCGGCCCGCCCTGCGG
CAACCGGAGGGGGAGGGAGAAGGGAGCGGAAAAGCCTGGAATACGGACGGAGCCATTGCTCCCGCAGAGGGAGGAG
CGCTTCCTGCTCTTCTCTTGTCACTGATTGGCCGCTTCTCCTCCCGCCGTGTGTGAAAACACAAATGGCGTGTTTT
GGTTGGAGTAAAGCTCCTGTCAGTTACAGCCTCGGGAGTGCGCAGCCTCCCAGGAACTCTCGCATTGCCCCCTGGG
TGGGTAGGTAGGTGGGGTGGAGAGAGCTGCACAGGCGGGCGCTGTCGGCCTCCTGCGGGGGGAGGGGAGGGTCAGT
GAAAGTGGCTCCCGCGCGGGCGTCCTGCCACCCTCCCCTCCGGGGGAGTCGGTTTACCCGCCGCCTGCTCGGCTTT
GGTATCTGATTGGCTGCTGAAGTCCTGGGAACGGCCCCTTGTTATTGGCTTGGGTCCCAAATGAGCGAAACCACTA
CGCGAGTCGGCAGGGAGGCGGTCTTTGGTACGGCCCTCCCCGAGGCCAGCGCCGCAGTGTCTGGCCCCTCGCCCCT
GCGCAACGTGGCAGGAAGCGCGCGCAGGAGGCGGGGGCGGGCTGCCGGGCCGAGGCTTCTGGGTGGTGGTGACTGC
GGCTCCGCCCTGGGCGTCCGCCGCCTGAAGGACGAGACTAGCTCTCTACCTGCTCTCGGACCCGTGGGGGTGGGGG
GTGGAGGAAGGAGTGGGGGGTCGGTCCTGCTGGCTTGTGGGTGGGAGGCGCATGTTCTCCAAAAACCCGCGCGAGC
TGCAATCCTGAG

SEQ ID NO: 7 NLRC5 Genomic Sequence

TGGAAACAACATGAACACTGTGAGCTCCCGGGAGTTCAGTCAGATCCACTGAGGTAGTGGCCGGGTCCAGCGGCCT
TGCCTAACTTGGCAGTCCCCACCCGCTGCATCCTTAGATCTGGCTTTGTCCCTTACACAGGACAGCCCAGGCCTGT
GATCCCCAAGGTCAGGCTAACGCTACCTGGACCTGGGCTCTAAGACCTGGGAAGCTACAGGAGGGGTGAGCCAGTT
CCCAGATTGGGAAAACTGAGGCTTGAGGCGAGAGGATAGTCATCCACAAGCCTCGTGGCTAAATCCCTGGCTTGGC
CCAGGGCCCTGGACCTCAGGCCACTGGGCTGATCAGTGCTTGTATGCTTTCCTCATCGCACTTGTTTGGAAGACAT
TCCCTGGTTTAGCTGCTCTGGGATGGTAATCTATAAATACATACTTTGTTTAAAAAATTAATAAATTAAATCTTGG
ACCAGCATGAGGGCATCTGGCCAGCCACATGGCATATGACATGGACATTTGCCACGTCTCAAATATGGACTGCCCA
TCACATGTAGTGCTAGGACCCATGCCAACAACCCACAGGCCACACTGCAGGTTTCATGCAATGTCACATGGAACGC
TGCCACGNNNNNNNNNNNNNNNNNNNNNNNNNNNNNNNNNNNNNNNNNNNNNNNNNNNNNNNNNNNNNNN
NNNNNNNNNNNNNNNNNNNNNNNNNTCACGCCACGACATCCTCACTGTGCTGCATATTCCCGACTGGTCA
TGCATGTCATGTGTGATGGAGGGTGGTCTGTTGGCCATANNNNNNNNNNNNNNNNNNNNNNNNNNNNNNN
NNNNNNNNNNNNNNNNNNNNNNNNNNNNNNNNNNNNNNNNNNNNNNNNNNNNNNNNNTCTGAAGACCGTG
CCTGGAAAACGGCGTCTCTCCCTCCCGGAACAGTGTGCCGGGACAGCCAGCTGAGGCTCTTTTCCTGAGCCCTCTA
TCCTGGGGGATGGAAGCGGACATCACTTGGCTGTATTGGAAGGGTCTTGCGGGGGCCGTCAAGCATCCCAGGGGAC
CTGTGGCTGATGGTCGAAGAAAGCAAAGTCCAGCCTGGGCTCCCGGCTCTGCAGATGCTGGGCCGTGTCCTGGGGG
ATGGGGTTATTCCACAGGCTGCGGGGCACAGAGACAGACATTCAGCACTGGGAGCTGTTCACTTGTCCTTGTCTCT
ACCCTCTGTCCAACCCACAGATGGGGAAACTGAGGCCCCAAAGGGGAAGAGCTGTTCCCAGAGTTACCTGGCAGGT
AGGAGCAGGTGTTAGACCAGCATGGCTACCTTAGGGAGATGGTATCCCCCATGCCCACCCCAACTTCTTCCACTCA
CTCTTCTTCCCTGGAAGCTAGTGATGCCAGCTGGGCCATGCTCATATGACACATTGTGCAAATAAGGAGAAAGCCC
CCCCCTTTATTTCTTTTTGTTTTTTTTTTTTTTACCATTTCTTGGGCCGCTCCCGCGGCATATGGAGATTCCCAGG
CTAGGGGTCGAATCGGAGCTGTAGCCGCCAGCCTACGCCAGAGCCACAGCAACTCGGGATCCGAGCTGCATCTGCG
ACCTGCACCACAGCTCATGGCAACGCCGGATCGTTAACCCACTGAGCAGGGCCAGGGATCGAACCCGCAACCTCAT
GGTTCCTAGTTGGATTCATTAACCACTGTGCCACGATGGGAACTCTGAAAGCTCCCCCTTTTTAGACACTTTATTT
CTATCTTCTGAAACTGTCATACTGAGTTTTATAGAGCGAGACCNCCCCCTTTTTAAGACACTTTATTTCTATCTTC
TGAAACTGTCGTAATATACTGAGTTTTATAGAGCGAGACCCTTCACTACTACCAGAAACCTAACACGTCAACGGTG
TGAACAGTGTCCTTTAGATGCAAGGCCTTGGTACAGTGTGCAGCCTGTGCAACTGTACGTGGTGGCTGTGATTACA
GTTATCATTTTAAGCACTTGCTATGTGCCAGGCATTGTACTCAGTGCTTTGTAGAATCATTTAGTCTGCAGAGCGC
CCATCTAAGGCTGATATGATCATTGTCTCCAGTTTACAAATGAGGAAACCGAGGTTCAGGGAGGTTGAGTTACTGA
GGCAAAGTTACACAGTCAGCAACCAGTAGAGCTGGGATTTGATCCAGGTCTGCTGGCTGCCACATTCCTGGTGGAG
TGGGCCAAATCTCCTTTGATAATCCCCAATCCAGGAGTTCCTGTTGTGGCGCAGCAGAAATGAATCCGACTAGTAA
CCATAAGGTTGCAGGTTCAATCCCTGGTCTTGCTCAGTGGGTTAAGGATCTGGCGTTGCTATGAGCTGTGGTGTAG
GTTGAAGATGCACCTCAGATCCCACAATGCTGTGGCTATGGCGTAGGCTGGCGGATGTAGCTCTGATTGGACCCCT
AGCCTGGGAATCTCCATATGCTGCAGGTGCGGCCCTAAAAAAGCAATAAATAAGTAAATAGATAACCCTCAACCCA
GGTCCTGCCTCCTCCTACAGAAAGTTCCTTTGCATTGTAGAGGCTGCTGTGGCCCCCACCTCCCACCATCCTCGCC
CCTGCAAGTCCTGTTACCGAATGACTTGGATGCCAGAGCCCTGAGCCAGCCCTTCAGCCAGGAGCCAGGCTCCATG
AG

SEQ ID NO: 8 NLRC5 cDNA Sequence

GGGCCTGTCCTATGGAAAGAACCTGCAAGTCCAGCACAGGGGCTTGGCCGGGAACCCATGAGACCCCCTCTGGGGA
CATCCTAGGACATCTGTGATGAATCAGGAAGCAGGGCTGGCTCCTCATGGACCCCATTAGTCGCCACCTGGGCACC
AAGAACCTGTGGGGATGGCTCGTGAGGCTGCTCTGCAAACACTCAGAATGGCTGAGTGCCAAGGTGAAGTTCTTCC
TCCCCAACATGGACCTGGGTGCCAGGAACGAGGCCTCAGACCCCACACAGAGGGTCGTCCTACAACTCAGAAAACT
GCGTACCCAGAGTCAGATCACCTGGCAGGCGTTCATCCACTGTGTGTGCATGGAGCTGGACGTGCCGCTGGACCTG
GAGGTACTGCTGCTGAGCACCTGGGGCCACGGAGAAGGGCTCCCCAGTCAGCTGGAAGCTGATGAGGAGCACCCAC
CTGAGTCTCAGCCCCACTCTGGCCTCAAGCGGCCACATCAGAGCTGTGGGCCCTCCCCTCGCCCAAAGCAGTGCAG
GAAGCAGCAGCGAGAACTGGCCAAGAGGTACCTGCAGCTGCTGAGAACGTTTGCCCAGCAGCGTTACGACAGCAGG
AGCCCTGGGCCAGGACAGCCGGTCGCCTGCCACCGAACCTACATCCCGCCCATCTTGCAATGGAACCGAGCCTCTG
TGCCCTTCGACACTCAGGAGGGGACTGTTGCAGGGGGCCCCAAGGCAGAAGATGGCACGGATGTGAGCATTCGGGA
CCTCTTCAGTGCCAAAGCCAACAAGGGCCCGAGAGTCACGGTGCTTCTGGGAAAGGCGGGCATGGGCAAGACCACG
CTGGCCCACCGGCTCTGCCAAGAGTGGGCCGATGGTCAGCTGGAGCGCTTCCAGGCCCTGTTCCTTTTCGAATTCC
GCCAGCTCAACCTGATCACAAACTTCCTGATGCTGCCACAGCTCCTTTTTGATCTGTACCTGAGGCCCGAGGCGGG
CCCAGAGGCAGTCTTCCAGTACCTGGAGGAGAATGCTAATAAAATCCTGCTCATCTTTGATGGGCTGGACGAGGTC
CTCCACCCCGGCTCCAGCAAGGAGGCTGCAGATCCTGAGGCCTCGGCGTCAGCCCTCACCCTCTTCTCCCGCCTCT
GCCATGGGACCCTCCTGCCCGGCTGCTGGGTCATGACCACCTCCCGTCCAGGGAAGCTGCCCGCCTGCCTGCCCAC
AGAGGTGGTCACGGTCAGCATGTGGGGCTTTGACGGACCACGGGTGGAGGAGTACGTGAGCCGCTTCTTCAGCGAC
CAGCCAGTCCAGGAGGCGGCCCTCGCGGAGCTGCGGGCCAGCTGGCATCTCTGGAGCATGTGTGTGGTGCCCGCGC
TGTGCCAGGTCGCCTGCCTCTGCCTCCACCATCTGCTCCCAGGCCGCTCTCCAGGCCAGTCTGCAGCCCTCCTGCC
CACCGTGACCCAGAGCTACGTGCAGATGGTGCTTTCCCTCAGCCCCCAAGGGTTCCTGCCTGCCGAGTCCCTGATG

TABLE 9-continued lists sequences for the disclosure

GGCCTCGGGGAGGTGGCCCTGTGGGGCCTGGAGACGGGGAAGGTTGTCTTCACTGCAGGAGACATCCCTCCACCCA
CGATGGCCTTCGCGGCGGCCCTCGGCCTGCTCACCTCCTTCTGTGTGTACACGGAACCCGGGCACCAGGAGACAGG
CTACGTCTTCACCCACCTCAGCCTGCAGCAGTTTTTGGCTGCCCTGCACCTGATGGCCAGCCCCAAGGTGGACAGA
GACACACTTGCCCAACATGTCACCCTCAATTCTCGCTGGGTGCTGCGGACCAAAGCTAGGCTGGGCCTCTTAGACC
ACCACCTTCCCACCTTTCTGGCCGGCCTGGCCTCCTGCGCCTGCCACCCCTTCCTCACACCCCTGGCACAGCAGGA
GGAGGTGTGGGTGCGTGCCAGGCAGGCGGCAGTCATGCAAGCCTTGGAGAAGTTGGCCACTCGCAAGCTGACGGGG
CCAAAGCTGATAGAGCTATGTCACTGCGTGGCTGAGACACAGAAGCCGGAGCTGGCCAGCCTCGTGGCCCAGAGCC
TCCCCCATCACCTCTCCTTCCGCAACTTTCTGCTGACCTATGCCGACCTGGCTGCCCTGACCAACATCCTCGGGCA
CAGGGATGCCCCCATCCACCTGGATTTTGAGGGCTGCCCCTTGGAGCCACACTGTCCTGAAGCCCTGGCAGGCTGC
GAGCAGGTGGAGAATCTCAGCTTTAAGAGCAGGAAGTGTGGGGATGCCTTTGCTGAAGCCCTCTCCAGGAGTTTGC
CAACAATGGGGAGCCTGAAGAAGCTGGGGTTGTCAGGAAGTAGGATCACTGCCCGAGGCATCAGCCACCTGGTGCG
GGCTTTGCCCCTCTGTCCACAGCTGGAAGAGGTCAGCTTTCAGGACAACCAGCTCAAGGACGGGGAGGTCCTGAAC
ATCGTGGAAATACTTCCCCACCTGCCGCAGCTCCGGATGCTTGACCTGAGCCGCAACAGTGTCTCCGTGTCAACTC
TCCTCTCCTTGACAAAGGTGGCAGTCACGTACCCTACCATTAGGAAGCTGCAGGTCAGGGAGACAGACCTCGTCTT
CCTTCTCTCCCCACCTACAGAGATGACCACAGAGCTACAAAGAGACCCAGACCTACAGGAAAATGCCAGCCAGAGG
AAAGAGGCTCAGAGGAGAAGCCTGGAGCTCAGGCTCCAGAAGTGTCAGCTCAGTGTCTATGATGTGAAGCTGCTCC
TCGCCCAGCTCCGGATGGGTCCACAGCTGGATGAAGTGGACCTCTCAGGGAACCAGCTGGAAGATGAAGGCTGTCA
ACTGGTGGCAGAGGCTGCGCCCCAGCTGCACATTGCCAGGAAGCTGGACCTCAGCGACAATGGGCTTTCTGTGGCT
GGGATGCAACGTGTGCTGAGTGCAGTGAGAACCTGCCGGACCCTGGCAGAGCTACACATCAGTCTGCTGCACAAAA
CCGTGGTGCTCATGTTTGCCCCAGAACCAGAGGAGCAGGAGGGGATCCAGAAGAGGCTGACACATTGTGGCCTGCA
AGCCCAGCACCTTGAGCAGCTCTGCAAAGCGCTGGGAGGAAGTTGCCACCTCAAGTACCTCGATTTATCAGGCAAT
GCTCTGGGGGACGAAGGTGTGGCCCTGCTGGCTCAGCTGCTCCCCGGGCTTGGTGCCCTGCAGCTGCTGAACCTCA
GTGAGAACGGTTTGTCCCTGGATGCTGTGTTCAGTTTGACCCAGTGCTTCTCTACAGTGCGGTGGCTTCAGCGCTT
GGACTTCAGCTCTGAGAGCCAGCACGTCATCCTGAGCGGTGACAGCAGAGGCAGGCATCTCTTGGCTGGCGGATCT
TTGCCAGAGTTTCAAGCTGGAGCCCAGTTCTTGGGGTTCCGTCAGCGCCGCATCCCCAGGAGCTTCTGCCTCAAGG
AGTGTCAGCTGGAGCCCCCGAGCCTCTCCCGCCTCTGTGAGACTCTGGAGAAGTGCCCGGGGCCTCTGGAAGTCGA
ATTGTTCTGCAAGGTCCTGAGTGACCAGAGCCTGGAGACCCTGCTGCATCACCTTCCCCGGCTCCCCCAACTAAGC
CTGCTGCAGCTGAGCCAGACGGGACTGTCCCAAAGGAGCCCCCTCCTGCTGGCCGACCTCTTCAGCCTGTACCCAC
GGGTTCAGAAGGTGGATCTCAGGTCCCTCCATCACATGACTCTGCACTTCAGGTTTAGCGAGGAGCAGGAAGGCGG
ATGCTGTGGCAGGTTCACAGGCTGTGGCCTCAGCCAGGAGCACATGGAGCCGCTGTGTTGGTCGCTGAGCAAGTGT
GAGGACCTCAGCCAACTGGACCTCTCCGCCAACCTGCTGGGTGATGACGGGCTCAGGTCCCTCCTGGAATGTCTCC
CTCAGGTGCCCATCTCCGGTTCGCTTGATCTGAGTCACAACGGCATCTCTCAGGAAAGTGCCCTCCGCCTGGTGGA
AACCCTTCCCTCCTGCCCACGTGTCCGGGAGGCCTCGGTGAACCCGGGCTCCAAGCAGACCTTCTGGATTCACTTC
TCCCGAAAGGAGGAGGCTAGGAAGACACTAAGGCTGAGTGAGTGCAGCTTCAGGCCAGAGCACGTGCCCAGACTGG
CCACCGGCCTGAGCCAGGCCCTGCAGCTGACAGAGCTCACGTTGAACCAGGGCTGCCTGGGCCTGGAGCAGCTGAC
TATCCTCCTGGGCCTGCTGAAGTGGCCGGCGGGGCTGCTGACTCTCAGGGTAGAGGAGCCGTGGGTGGGCAGAGCC
GGAGTGCTCACCCTGCTGGAAGTCCGTGCCCACGCCTCAGGCAACGTCACTGAAATAAGCATCTCTGAGACCCAGG
AGCAGCTCTGTATGCAGCTGGAATTTCCCCATCAGGAGAACCCAGAAGCCGTGGCCCTCAGGTTGGCTCATTGTGA
TCTCGGGACCCACCACAGCCTCCTTGTCAGGGAGCTAATGGAGACATGCGCCAGGCTGCGGCAGCTCAGCTTGTCC
CAGGTGAAGCTCTGCAAGGCCAGCTCTCTGCTGCTGCAAAGCCTCCTGCTGTCCCTCTCTGAGCTGAAGAACTTCC
GGCTGACCTCCAGCTGTGTGAGCTCTGATGGGCTAGCCCACCTGACATTTGGTCTGAGCCATTGTCACCACCTGGA
GGAGCTGGACTTGTCTAACAATCAATTTGGCAAGGAGGACACCAAGGTGCTGATGGGAGCCCTTGAGGGCAAATGC
TGGCTGAAGAGGCTTGACCTCAGCCACTTGCCTCTGAGCAGCTCCACCCTGGCCGCGCTCATTCAAGGACTGAGCC
ACATGAGCCTCCTGCAGAGCCTCCGTCTAAGCAGGAGCGGCGTTGATGACATCGGCTGCTGCCACCTCTCCGAGGC
GCTCAGAGCTGCCACCAGCTTGGTGGAGCTGGGCTTGAGCCACAACCAGATCGGAGACGCCGGTGCCCAGCACTTA
GCTGCCATCCTGCCAGGGCTGCCTGAGCTCAGGAAGATAGACCTCTCAGCCAATGGCATCGGCCCGGCAGGGGGAG
TGCGGTTGGCGGAGTCCCTCACCCTTTGCGAGCACCTGGAGGAGCTGATGCTTGACTACAATGCTCTGGGAGATCT
CACAGCCCTGGGGCTGGCCCGAGGGTTGCCTCAGCACCTGAGGGTCCTGCACCTGCGGTCCAGCCACCTGGGCCCA
GAGGGGGCGCTGAGCCTGGGCCAGGCACTGGATGGATGCCCATACGTGGAAGAGATCAACTTGGCCGAGAACAGCC
TGGCTGGAGGGATCCCACATTTCTGTCAGGGGCTCCCGATGCTCCGGCAGATAGACCTGATGTCATGTGAGATTGA
CAACCAGACTGCCAAGCCCCTCGCCGCCAGCTTCGTGCTCTGCCCAGCCCTGGAAGAAATCATGCTGTCCTGGAAT
CTGCTCGGTGACGAGGCAGCTGCTGAGCTGGCCCAGGTCCTGCCGCGGATGGGCCGACTGAAGAGAGTGGACCTGG
AGAAGAATCGGATCACAGCTCACGGAGCCTGGCTCCTGGCTGAAGGGCTGGCTCAGGGCTCTGGCATCCAAGTCAT
TCGCCTGTGGAATAACCCCATCCCCCAGGACACGGCCCAGCATCTGCAGAGCCGGGAGCCCAGGCTGGACTTTGCT
TTCTTCGACCATCAGCCACAGGTCCCCTGGGATGCTTGACGGCCCCCGCAAGACCCTTCCAATACAGCCAAGTGAT
GTCCGCTTCCATCCCCCAGGATAGAGGGCTCAGGAAAAGAGCCTCAGCTGGCTGTCCCGGCACACTGTTCCGGGAG
GGAGAGACGCCGTTTTCCAGGCACGGTCTTCAGAATGGACTTTATGGGCGACAAAGAGCCTACCATGGCCAACAGA
CCACCCTCCATCACACATGACATGCATGACCAGTCGGGAATATGCAGCACAGTGAGGATGTCGTGGCGTGATGCAA
GACACAGAAGGTTGCACGTGGCAGCGTTCCATGTGACATTGCATGAAACCTGCAGTGTGGCCTGTGGGTTGTTGGC
GTGGGTCCTAGCACTACATGTGATGGGCAGTCCATATTTGAGACGTGGCAAATGTCCGTGTCATATGCCATGTGGC
TGGCCAGATGCCCTCATGCTGGTCCAAGATTTAATTTATTAATTTTTTAAACAAAGTATGTATTTATAGATTACCT
TTCCAGAGCAGCTAAACCAGGGAATGTCTTCCAAACAAGTGCGATGAGGAAAGCATACAAGCACTGATCAGCCCAG
TGGCCTGAGGTCCAGGGCCCTGGGCCAAGCCAGGGATTTAGCCACGAGGCTTGTGGATGACTATCCTCTCGCCTCA
AGCCTCAGTTTTCCCAATCTGGGAACTGGCTCACCCCTCCCGTAGCTTCCCAGGTCTTAGAGCCCAGGTCCAGGTA
GCGTTAGCCTGACCTTGGGGATCACAGGCCTGGGCTGTCCTGTGTAAGGGACAAAGCCAGATCTAAGGATGCAGCG
GGTGGGGACTGCCAAGTTAGGCAAGGCCGCTGGACCCGGCCACTACCTCAGTGGATCTGACTGAACTCCCGGGAGC
TCACAGTGTTCATGTTGTTTCCAAGAAGGCCCAAGGATTGTGAGCCAAGTTTGATCAATAAATGTGAGTGATCTTC
CGGCCTCTAAAAAAAAAAAAAAAAAAA

SEQ ID NO: 9 NLRC5 Protein Sequence
MDPISRHLGTKNLWGWLVRLLCKHSEWLSAKVKFFLPNMDLGARNEASDPTQRVVLQLRKLRTQSQITWQAFIHCV
CMELDVPLDLEVLLLSTWGHGEGLPSQLEADEEHPPESQPHSGLKRPHQSCGPSPRPKQCRKQQRELAKRYLQLLR
TFAQQRYDSRSPGPGQPVACHRTYIPPILQWNRASVPFDTQEGTVAGGPKAEDGTDVSIRDLFSAKANKGPRVTVL
LGKAGMGKTTLAHRLCQEWADGQLERFQALFLFEFRQLNLITNFLMLPQLLEDLYLRPEAGPEAVFQYLEENANKI
LLIFDGLDEVLHPGSSKEAADPEASASALTLFSRLCHGTLLPGCWVMTTSRPGKLPACLPTEVVTVSMWGEDGPRV
EEYVSRFFSDQPVQEAALAELRASWHLWSMCVVPALCQVACLCLHHLLPGRSPGQSAALLPTVTQSYVQMVLSLSP
QGFLPAESLMGLGEVALWGLETGKVVFTAGDIPPPTMAFAAALGLLTSFCVYTEPGHQETGYVFTHLSLQQFLAAL
HLMASPKVDRDTLAQHVTLNSRWVLRTKARLGLLDHHLPTFLAGLASCACHPFLTPLAQQEEVWVRARQAAVMQAL TABLE 9-continued lists sequences for the disclosure EKLATRKLTGPKLIELCHCVAETQKPELASLVAQSLPHHLSFRNFLLTYADLAALTNILGHRDAPIHLDFEGCPLE
PHCPEALAGCEQVENLSFKSRKCGDAFAEALSRSLPTMGSLKKLGLSGSRITARGISHLVRALPLCPQLEEVSFQD
NQLKDGEVLNIVEILPHLPQLRMLDLSRNSVSVSTLLSLTKVAVTYPTIRKLQVRETDLVFLLSPPTEMTTELQRD
PDLQENASQRKEAQRRSLELRLQKCQLSVYDVKLLLAQLRMGPQLDEVDLSGNQLEDEGCQLVAEAAPQLHIARKL
DLSDNGLSVAGMQRVLSAVRTCRTLAELHISLLHKTVVLMFAPEPEEQEGIQKRLTHCGLQAQHLEQLCKALGGSC
HLKYLDLSGNALGDEGVALLAQLLPGLGALQLLNLSENGLSLDAVESLTQCESTVRWLQRLDESSESQHVILSGDS
RGRHLLAGGSLPEFQAGAQFLGFRQRRIPRSFCLKECQLEPPSLSRLCETLEKCPGPLEVELFCKVLSDQSLETLL
HHLPRLPQLSLLQLSQTGLSQRSPLLLADLESLYPRVQKVDLRSLHHMTLHFRFSEEQEGGCCGRFTGCGLSQEHM
EPLCWSLSKCEDLSQLDLSANLLGDDGLRSLLECLPQVPISGSLDLSHNGISQESALRLVETLPSCPRVREASVNP
GSKQTFWIHFSRKEEARKTLRLSECSFRPEHVPRLATGLSQALQLTELTLNQGCLGLEQLTILLGLLKWPAGLLTL
RVEEPWVGRAGVLTLLEVRAHASGNVTEISISETQEQLCMQLEFPHQENPEAVALRLAHCDLGTHHSLLVRELMET
CARLRQLSLSQVKICKASSLLLQSLLLSLSELKNFRLTSSCVSSDGLAHLTFGLSHCHHLEELDLSNNQFGKEDTK
VLMGALEGKCWLKRLDLSHLPLSSSTLAALIQGLSHMSLLQSLRLSRSGVDDIGCCHLSEALRAATSLVELGLSHN
QIGDAGAQHLAAILPGLPELRKIDLSANGIGPAGGVRLAESLTLCEHLEELMLDYNALGDLTALGLARGLPQHLRV
LHLRSSHLGPEGALSLGQALDGCPYVEEINLAENSLAGGIPHFCQGLPMLRQIDLMSCEIDNQTAKPLAASFVLCP
ALEEIMLSWNLLGDEAAAELAQVLPRMGRLKRVDLEKNRITAHGAWLLAEGLAQGSGIQVIRLWNNPIPQDTAQHL
QSREPRLDFAFFDHQPQVPWDA SEQ ID NO: 10 TAP1 Genomic Sequence
GTCTGAGAAGAGCTTCACTCAGGAGCATCTGACCCACCAGGAGCCTGCAACATGGTCCAATAGCGCCCCTTATTAG
CCATGAGCTGCTGGTGGGTTCCCTCCTCAACAATGGTGCCTCCTTCCAGAAAGAGGATGTGATTGGCCTGCTCCAC
GGAACTAAGACGCTGGGTGATGAGAAGCACAGACCGGGAGTACCGCTCAGGGCTTTCATACAGGAGCGACTCCACC
TGAGAAAAAAACACAGACTCTGTCAGAGCTGGGGGCCACTCCCGGAAGAGCTGGGACAGACCTCGCCAGGATCACT
GCCACTTCTGCCAGGAACCCCAAAATCAAAGCTTCTCATTCTGAGTGCTTCTCTGTCAAACTTTTGATCTGTTAAG
GACGGTTTACATGAGGGGGCAAGAGCGTGTCCTATGGTGAAACTCATAAGTATGAAGGGTATTGAGTAGCCTCTCC
TCTCTAATTTTTATATTCTCTTTCAAGGAGACATAAGTGAGTAGTAAAGAGAATGAATATTCGAGTCAGGCAGACT
CGAATTTGGGTCCAGGCTCTGCTATTCAACATTGAGCTGAATGCTATCGAGTGCGTTGTTCAGCCTCTCTTAGCCT
GCATTTTAGCATCTGTTCGATGAAGATAACAACAGCCAGCTCACAAGCATTCACGATGAATAATTAAATGAGAGAG
TACATGGAAAGGGCCTGTTAACATTTCTGGCACATGGTAAGATTTCAACTAATATTGGTATGATGGGATCTTTTCT
TTTGTTTGGCTTCACAGATTCAGAGTCTGAGGATCGTCTCTTTTAACTGACTCTAGGCATGTTGGGGAGAAGCGAA
GGGGAACTGAGAATTGCAAAGACTGGTTTGGATGATTATGATGTTAGTACAATAACAAAGGATGAGTGAAGGAAGG
AGGACTGGGTGGGTTACAGGCATTAAGAAGATGACTCTCTCACCCGTGCTTGACTGTTTGCATCCAGGGCACTGGT
AGCATCATCCAGGATGAGTACCCGTGGTTTCCGGATCAAGGCTCGAGCCAAGGCCACTGCCTGCCGCTGACCCCCT
GATAGCTGGCTCCCAGCCTCACCTACCTCTGCAGAGACAAGTGCCCAGGTAAGAGCTGGATAAACACATGTGCATC
CATGTGCTTGCATGCACGCGCGAGCGTGTGTGCACATGTGCACGCACGCACGCGCGTGCACACACACACACACACA
CACACACACACACTCGGACTAACAGATACAGCTGGATAGGGAAGGTTCTGGGAAGGTGAAGGAGTTCTGAGGATAT
GAGGATGAAAGAGCCATAGAAACAAGCTCTTACAACTTCATACTGATGAATAAAGGCAAGACTATTGGATTTCAAC
AAAGGTAAAGATGTCTGAGCCATAAAATAAAATTTAAAAAAAAAAAGAGTTCCTGCTGTGGCACAGTGGGTTAAGG
ATGCAACTGCAGGAGTTCCTGACATGACTCAGTGGTTTATGAACCCAACTAGTATCCACGTGGACTCGGGTTAGAT
CCCTGGCCTTGCTCAGTGGGTTAAGGATCCAGCATTGCCATGAGCTGTGGTGTAGGTCAGCAGCTGTAGCTCCGAT
TCGACCCCTAGCCTGGGAATGTCCATATGCTGTGGTGCAGCTCCAAAAAAAAGCAAAAAAAAACAAAACAAAACAA
AACCCGAATGCTGTGGCTCAGGTCGCCTTGGAGGTGCAGTTCAATCCCTGGCCTGGTGCAGTGGGTTAAAGGATCT
GGCGTTGCTGCAGCTGCTGCATAGGTTGCATCCGAGGCTTGGATTCAGACTATGGGTGTGGCCATAAAAAACTAGC
CCCCCCAAAAAAGATGCCTGGGTGGTGATATGAGAGGAGAGAGCACCTGTGTCGTAGCCTTGCGGGAGCTTGGAGA
TGAAGCTATGGGCTCCGGACTCCACGGCGGCAGCTATGACTTCCTCCATTGCTGGCTTCTGGCTCAGGCCATAGGC
AATGTTTTCTTGAAAACTTCTTCCAAAGAGCTGTGGCTCTTGCCCCACCGCAGCCACCTGGGACAAAGCATGATGA
GAGAACGAGGAACACAGGAGTATGATGATCTGGAGACTGAAGACTGAAAATCTTTATTGTGAACAAATCATGAAAT
CACACAGCCTCTCTCCTGAACACACCCCCCGCCCCCCCAGGATCTCCTGTCATTCCCAGCACTCCTTTCAGAGTGC
CCAGTGAGCATGGTCTTCTTACTCGCAGCTCCCTGCCCTCCCCTGTGCCACCTTCTTGCTCACCTGTCTGTGCAGG
TAGCGGTGCTCATATTCAGGAAGGGGCTTCTCACCCAGCAGCACCTGCCCCTCCGTGGGCTGGTACAGGTTCTGCA
GCAGGGCAGCCACGGTGCTCTTCCCAGACCCATTGGGCCCCACGAGGGCGGTCACCTCACCAGGACGTAGAGTGAA
CGTGAGGCCCTGGAGGCCAGAGAATCACACACTAAGAGGCAGATCAAGGCCCCTAACCTTAAGAGCGTCATGGACT
TGGCCCATTGTTTTGTCAGTGTCTCACCCCAGAGAAGAAAAGAGGAAAGTGGAGAAACACAGCAACTCCTACCCTC
CCACATGCACAGACTTCTGCTCCTCAGCGATGCCACCTCCCCGTGGACTAGAGATGGAAGAAGAGACAAAGACCAG
GGCAAAGACCATGCCGCACACTCAATCTCAGAGACCAGGAGAAAAAAAGAAAAAAAAAATCACATTTGAAATCACA
AATGGAAAGAAAAAGGAGGAGTTCCTGTTGTGGCTCAGGAGGTTAAGACCCTGACATAGTGTCCGTGAGGATACAG
GTTCAATCCTTGGCTTCGCCCAGTGGGTTAAGGATCTGGTGTGGCTGCAGCTGCCCCGTTCAGTCACAGAAGTGGC
TCAGAGCCGGTGTTGCTGTGGCTGTGATGCAGGCGTTCAGCTCCTGGCCCAGTGTGACCATTAAAAAAAGGAAGAA
AAAAGGCAAGAAAAAGGAAAGATGGAAGACCAGATGGATACACAGATTTTGCAGCAGTTCCTTAGGATATGACAGC
CTTCTCCCTGAAAGCCTCCTTTCCTGTCCTCCCTGGAAATCCAAACTAGGTCTTGAGTTTGGGGCAATTTTATGGA
ACAGATGATGCTCATCTTTGCCTCTGAAGGGTAAAGAAGGATCTAGCTACACCTGATGTTAAGCAGACTGAAGGCA
GGAAGACGATTCAGATCGAGCTGAGAGGAAGATTGGTGGAGTGCAGGGGTTGGTGGGTTGTACCTGCAGCACTGGG
ACCTCTGGTCGGTTCGGGTAGGCAAAGGAGACATTCTGGAACTTGACAAGCCCCTCTGACTTTAAGGAAGTCAACG
ATCCACTGGCCGGGCAGCGAGGGATTCGGTCCAGATACTCAAATATTTCCTTTGAGGAGCCCACAGCCTTCTGTAC
CCTGGGGTAGGTGGACAGCAGTACCTGGAGGGGAGGTATGAATAGTGAGATGGGAGGAGGTAGTGGGGGAGGGACC
TAATCTGCCTGCCAGGATTATGTGATGTGAGAAGGGCAAAGCATGGAAGGAAGGTGACTCAGATGGTGATGGGACA
GGGGAGGGAAAAGCCCTGGGATGTGAGAATGGAAGGACCTCACCTGAACAGCTTCGGTGAACTGGATCTGGTAGAG
AACAAATGTGACGAGGTTTCCGCTGCTTATAGCCCCACCTGCCACCAGCTTCCCGCCAACATACAGGATTCCCACC
TTCAGCAACATCCCTGAGATCTGTGGAGAGACCACACAGAAAAGGGACTTTTGTAGAAAAATCTAGAGGGGCTGCA
GAGAAGCAGAATCATTAGCATTAAGGAGATAAGAAGTTCTTGGAGTTCCCGTCGTGGCTCAGTGGTTAACGAATCC
AACTAGGAACCAGGAGGTTGCGGGTTCGATCTCTGGCCTCGCTCAGTGGGTTAAGGATCGGGTGTTGCCATGAGCT
GTGGTGTAGGTCAAAGATGTGGCTCGGATCTAGTGTTGCTGTGGCTGTAGCTCTAGGGTAGGCTGGCAGCCGTAGC
TCCGACTGGACCCCTTGCCAGGGAAACTCCAAATGCCTCAGGTACAGCCCTAAAAAGCAAAAACAAACAAATAAAC
AAAAAAAAGGAATGAACCATAGCAATGCCACGGAGTGCTCACTCAGTTATACAGAAAAGAAGCCAATCGTTATTACC
ATCACCATTATCACCTTGTCTGGGAAGCATTTACTCTGCACAAAAGGCTTTCATGAATGTAATGTCATCTAATAGT
CGCATCAAAAGCCCCATAAACAAGGTTAGGTCACTGCCATTTTTAAAACTGAGAAAACAGTCTCAGAGAAGTGAAG
TCACCAGCCCCTGGTCACAGAGCCGGAAAATGGCAGCATCGTGATAGGAACTTGATGGCTGGTCGTGTTCGCTTTC
GGTTACATCACAGGTGCCCCTCATCCTTGCTTCTGCTACTCCCAGGACTCTCACTAGCATCCATGTAGTGTCAGCA TABLE 9-continued

| lists sequences for the disclosure |
|---|
| TGAAACGGGACAGGGTGCCAGAATTTATAGTCCTCTGAGCACCCCCTTGAGGCAAAAGAAGGCCTTGGAAAACACT<br>TCCCTAAAGAGAGGGTTGGGTGGATTTTTGTGTACCGTAGTGAAAGGAAGCCATCTAGCACGCCTAAAAAGGGGGG<br>AGGGGGTTAGGAACAGTGAGTAGGGTGACTGAGCCTCCGGTTGTTAGAATATGGCCACTGAACCAACCACTGGGCA<br>GTGGAGGAAGAGTGTGGAGCAGGGTCATGGGAAAGGGAATGGCATTGAGGCATCTTGGGGACAAGGGACTAGGCAG<br>TCATCTGCAGGTGCTCACACTGGTGGTCCAGAGGTCGACCGCATAGGCCAGGGCCTCCTTCTGGTTGAGTGTCTTC<br>ATGTCCTGCAGCTTTTGCTTGAACTTCTGGGCCTCACCCTCTTCATTGGCAAAGCTCCGGACAGTAGGCATAGCTG<br>ACAGAACCTCAATGGCCACCTGGCTTGACTTTGCCAGAGATTCCTGCACCTGTGCTGCCAGCACCTGTGGAGACGT<br>GGACCAGAGATGCCACACATGATTGTTGACAAACCATAGGGGACACTAGTACCTGAGTTATCCGATTAGAGTTTAA<br>AGGTGAGACGTGGCAGAGGGAAGGCAAGGGGACAAAGGGACACAGCCAGGCCCCCAGATACTAAAGGATACAGAGA<br>AGAGGAAAATGACTTAGAAGCGTCGTAGGGGAGCATATTCTTGAGATGGGTGATCATGTTCTTAAAGACAGATTGT<br>GGGCAGGCATTAGAAGAGAAGACACAAGGGATGTGAAGATCAACACTGAGCAATCTGGGAACATGGACGACAGGGA<br>CAAGGAGTCCCACAAAGAGGAGAACCAGTGAAGGTGCCAGGAAAGGGATCTGAGCCCACCAAGTCTGGGATGAGGG<br>TCAGTGTAGGTTGAGGCAACTCCCTAGACATACCTGGTGCCATTTCCCCAGCTTCTCAGGCAGAAGGAAAAGCAGT<br>GGCAAGGCGGCCAGGGTGACCATGGTGAGGGGAGGTGACCCCCAGAGCATGAGCCCTAAGAGACACAGTCCCCGTG<br>CGAGGTACCACAGCAAGAGGCTCAGCTCCGAACTCAGAGACACACTCACAGTGGATGTGTCCTCTGTTACCCGAGA<br>TGTGATGGCACCTGCCAAGGGTTCAAGAGAAGAGAGTGGAGTGAACAGGAGGCTCAGAGTGATGGGAGCGACGAGC<br>AATGAGCCAGGTGCCACAGCGAAGGGCATCAACACAGTGTTCTAAGAAGGTCAGGAAAAGGAGTTCCCGTCGCGGC<br>GCAGTGGTTAACGAATCCGACTAGGAACCATGAGGTTGCGGGTTCGATCCCTGCCCTTGCTCAGTGGGTTAACGAT<br>CCGGCGTTGCTGTGAGCTGTGATGTAGGTTGCAGACTTGGCTCGGATCCGCGTTGCTGTGGCTCTGGCGTAGGCCG<br>GTGGCTACAGCTCCAATTCGACCCCTAGCCTGGGAACCTCCATATGCCGCGGGAGCGGCCCAAGAAATAGCGGGGA<br>AAAAAAAAAAAAAAAAGACAAAGAAGGTCAGGAAAACAAGGTCTGTGGTTGGGGGAGGACTGAAACATAATGCAAG<br>AAAAATGTGTTAGAGTGGAAAAGCCTGGCCAAAGACCTTCGTTTTAACTATAAAGAAATTGATGCCCAGAGTTCCC<br>ACTGTGGCTCAGCGGTTAAGGACCTGACGCCGTCTCTGTGAGGTTGCAGGCTGGAACCCTGGCTTCGCTCAGTGGG<br>TTAAGGACCAGCTGTTGCCACAAGCTGTGGCGTAGGTCACAGATGCTGGATCAGGTGTTGCCATGACTGGCACAGG<br>CCTCACCTGTAGCTCTGATTCAACCCCTGGCCCAGGAACTTCCATATGCCACAGGTGCAGTCATAAAAGAAAAAAA<br>AATTTTTAAAGAAATGGATGCCCATGTGAACTTCTGTTTCTCTGACAGGTGTCTGTTCCTTAAAGAACTTGTATAT<br>ACCATGCTCATAGGTAGGAAGAACTTAAGCTGGTCATACAAGAGCTGGAGAAAAATGGAGAGACTACTAGAGAGCA<br>GTCCAGGAAACCACAGCAAGCACTGGATTGGGAATCAAGACATGGGTTCTGCTCTCAAGTTTGTCTTCATCCATGT<br>GCATCCATGCAAATGTTGGCATTTAGGTCTAGACCTCATTTCACTTCTCTGTAAAATGAGTCAGCTAGACTCTCTA<br>ATCTCAAAATTTCCAGGTTTGAAATTCTACCTAAATACACTTATAGGGATAGTTTATGGAAAAATCTTGGGTGGAA<br>ACAGTAGGTTAATCATTTTTTTTTTTGTTTTATTGTGTTTTTGGTTTTGTCTTTTTTTTTTTTTTTTTTTTTTTTT<br>TTTTTGCCCTTCCCACAGCATGCAGAATTTCCCTGGCCAGATGGAACCTCGCCATAGAAGCAAACTGAGTCACAGC<br>AGCGATCTGAGCCACAGCAGCCACAGAACTACAGCAGTGGCAACACCAGATCCTTAACCCGCTGAGCCACCGGCGA<br>ACTCCAACAGTAGGCTTTTCTAAAGGTAAAGAGCATATCTTGCTCTTGAAGTACATCAAGAATAAAAAGGGACACC<br>ATTTGTGTGTGTGTGAGAGAAAGATCAAGATTATAAGTAAAAGATGAAGTGTGGGGATACAAATAGAAAACAGACG<br>GATAATGAAAGAGGTTCATAAGACACCTGTTTGATTCTTCTGAAAAAACTCTGTTTCTTGGCGCAGGACAGACCGA<br>AACACCTCTCCCTGCAGGTGGCTGTGCACGCGGCCCATGGTGCTGTTATAGATCCCGTCGCACACGAACTCCAGCA<br>CCGAGCTAGAGGGAGACAAAGAAGGAGGGCCGGTCGGTCAGGGACCCCGTAGAAGTGCACTTTGGAGGGCGGCCCC<br>AACTTCCAACTGCGCCCTTTTCAGGGTCCCCCGTCCCCAGCCTTCCAAGCTCAGCAGTCAGACCTGGCTATGATGA<br>GGATGGACATGAGAGTTAGGTTCTGCGTGAAGGCAGCACCTGCCCCATCTCGTAGAATCCAGTCAGTGAGCCGGCC<br>TGTGAAGAACGGAATGGCCATCTCCCCTGGGGAGGGAGAGGAGAGATGGGCGGGTCAGAAAGAGCAAGTCTAAGCA<br>GCCTAAGCAGCTCAGCTCTAACCAGGCTGCACCTCCCGCCCATCCTCCCTTCACCCTTGCCCATTATCCTGCAGAA<br>ACAGCGCACACTCTCGGCACTGGAATGGGCCCCCGGGGAACTCGTAATCCTGTGGCCTCACCAGACCTTTAGAGGG<br>TTAATTAAGAAGCCTAGGATGGTAGGAGGAAAGAGCTCGCCCAAGGTGGCCAGTGAAGCAACACCTGAGCAGCACT<br>GGAGTCCAGGACTCCTGACTCCCACCCAGTCCAGGGCTCTTTCCTCTCCACCAAGTGGACCTGAGCGGGGTGGGCT<br>TGCTCTTATCCACATTTCCGAGAACTCACACCTGTCTATCTCACTGACCGTTAGGCTTGATTCCTACCCAGCCCTC<br>TAGCCTCCCTCTCCCTCCCCCCGCATCCCCCTTACCAAGGCTGGAGAGGACCACCAGGGTCAGAAGGAGCCAGAGG<br>TGGCGGATCTCTGAGCCCAGGCAGCCGAGAAGCCGGCTCACTGTCACTCCAGAGCCTCTGTGACTTCCTTGCACCC<br>AAAGGCTGCTAAGCTTATGCCACAGGGCGGCCGCGGGCAATGCCGCCGCATAGCTGAGGGCGAAGGCATCGAGGCG<br>ACTCCCCCAGTGCAGTAGCCGCGTGCTGTCAGCCGCTCCCGAGCCCAACTCTCGGAACAAGGCAAGTCCCGGCAGA<br>GCCAAGCCCAGAGCCGCCGCCAGCGGCTCCAAAGCTGCCAGCCATCCCCGAAGTCCTGTGCTTTTCTCCCGGAAGC<br>CAACCGTCGCCCTGAGGACGCTGCGGGCCCCCAACCACAGCACAGCCCAACGGCTCAGGCCCACCACCCAGACCCG<br>GAGCAGCGGCAGCGCTGGGGGCAGCAGCAGGGAGGATATCCGGGGCAGCGCCGGCCGGAGCAGCACCCAGTCGGCG<br>AGAAGCAGCAGCGCTGCCCCCAGCCAAGGGAGGGAAGCTCGGGAGACGCAGAGACACCCGCAGGGAGCGGAGGACC<br>CCGAGCTGGCCATTGGCCGTACGAGGTCGACCC |
| SEQ ID NO: 11 TAP1 cDNA Sequence<br>GCCCTTGGGTCGACCTCGTACGCCAATGGCCAGCTCGGGGTCCTCCGCTCCCTGCGGGTGTCTCTGCGTCTCCCGA<br>GCTTCCCTCCCTTGGCTGGGGGCAGCGCTGCTGCTTCTCGCCGACTGGGTGCTGCTCCGGCCGGCGCTGCCCCGGA<br>TATCCTCCCTGCTGCTGCCCCCAGCGCTGCCGCTGCTCCGGGTCTGGGTGGTGGGCCTGAGCCGTTGGGCTGTGCT<br>GTGGTTGGGGGCCCGCAGCGTCCTCAGGGCGACGGTTGGCTTCCGGGAGAAAAGCACAGGACTTCGGGGATGGCTG<br>GCAGCTTTGGAGCCGCTGGCGGCGGCTCTGGGCTTGGCTCTGCCGGGACTTGCCTTGTTCCGAGAGTTGGGCTCGG<br>GAGCGGCTGACAGCACGCGGCTACTGCACTGGGGGAGTCGCCTCGATGCCTTCGCCCTCAGCTATGCAGCGGCATT<br>GCCCGCGGCCGCCCTGTGGCATAAGCTTAGCAGCCTTTGGGTGCAAGGAAGTCACAGAGGCTCTGGAGTGACAGTG<br>AGCCGGCTTCTCGGCTGCCTGGGCTCAGAGATCCGCCACCTCTGGCTCCTTCTGACCCTGGTGGTCCTCTCCAGCC<br>TTGGGGAGATGGCCATTCCGTTCTTCACAGGCCGGCTCACTGACTGGATTCTACGAGATGGGGCAGGTGCTGCCTT<br>CACGCAGAACCTAACTCTCATGTCCATCCTCATCATAGCCAGCTCGGTGCTGGAGTTCGTGTGCGACGGAATCTAT<br>AACAGCACCATGGGCCGCGTGCACAGCCACCTGCAGGGAGAGGTGTTTCGGTCTGTCCTGCGCCAAGAAACAGAGT<br>TTTTTCAGAAGAATCAAACAGGTACCATCACATCTCGGGTAACAGAGGACACATCCACTGTGAGTGTGTCTCTGAG<br>TTCGGAGCTGAGCCTCTTGCTGTGGTACCTCGCACGGGGACTGTGTCTCTTAGGGCTCATGCTCTGGGGGTCACCT<br>CCCCTCACCATGGTCACCCTGGCCGCCTTGCCACTGCTTTTCCTTCTGCCTGAGAAGCTGGGGAAATGGCACCAGG<br>TGCTGGCAGCACAGGTGCAGGAATCTCTGGCAAAGTCAAGCCAGGTGGCCATTGAGGTTCTGTCAGCTATGCCTAC<br>TGTCCGGAGCTTTGCCAATGAAGAGGGTGAGGCCCAGAAATTCAAGCAAAAGCTGCAGGACATGAAGACACTCAAC<br>CAGAAGGAGGCCCTGGCCTATGCGGTCGACCTCTGGACCACCAGTATCTCAGGGATGTTGCTGAAGGTGGGAATCC<br>TGTATGTTGGCGGGAAGCTGGTGGCAGGTGGGGCTATAAGCAGCGGAAACCTCGTCACATTTGTTCTCTACCAGAT<br>CCAGTTCACCGAAGCTGTTCAGGTACTGCTGTCCACCTACCCCAGGGTACAGAAGGCTGTGGGCTCCTCAAAGGAA<br>ATATTTGAGTATCTGGACCGAATCCCTCGCTGCCCGGCCAGTGGATCGTTGACTTCCTTAAAGTCAGAGGGGCTTG<br>TCAAGTTCCAGAATGTCTCCTTTGCCTACCCGAACCGACCAGAGGTCCCAGTGCTGCAGGGCCTCACGTTCACTCT |

TABLE 9-continued

| lists sequences for the disclosure |
|---|
| ACGTCCTGGTGAGGTGACCGCCCTCGTGGGGCCCAATGGGTCTGGGAAGAGCACCGTGGCTGCCCTGCTGCAGAAC<br>CTGTACCAGCCCACGGAGGGGCAGGTGCTGCTGGGTGAGAAGCCCCTTCCTGAATATGAGCACCGCTACCTGCACA<br>GACAGGTGGCTGCGGTGGGGCAAGAGCCACAGCTCTTTGGAAGAAGTTTTCAAGAAAACATTGCCTATGGCCTGAG<br>CCAGAAGCCAGCAATGGAGGAAGTCATAGCTGCCGCCATGGAGTCCGGAGCCCATAGCTTCATCTCCAAGCTCCCG<br>CAAGGCTACGACACAGAGGTAGGTGAGGCTGGGAGCCAGCTATCAGGGGGTCAGCGACAGGCAGTGGCCTTGGCTC<br>GAGCCTTGATCCGGAAACCACGGGTACTCATCCTGGATGATGCTACCAGTGCCCTGGATGCAAACAGTCAAGCACG<br>GGTGGAGTCGCTCCTGTATGAAAGCCCTGAGCGGTACTCCCGGTCTGTGCTTCTCATCACCCAGCGTCTTAGTTCC<br>GTGGAGCAGGCCAATCACATCCTCTTTCTGGAAGGAGGCACCATTGTTGAGGAGGGAACCCACCAGCAGCTCATGG<br>CTAATAAGGGGCGCTATTGGACCATGTTGCAGGCTCCTGGTGGGTCAGATGCTCCTGAGTGAAGCTCTTCTCAGAC |
| SEQ ID NO: 12 TAP1 Protein Sequence<br>MASSGSSAPCGCLCVSRASLPWLGAALLLLADWVLLRPALPRISSLLLPPALPLLRVWVVGLSRWAVLWLGARSVL<br>RATVGFREKSTGLRGWLAALEPLAAALGLALPGLALFRELGSGAADSTRLLHWGSRLDAFALSYAALPAAALWHK<br>LSSLWVQGSHRGSGVTVSRLLGCLGSEIRHLWLLLTLVVLSSLGEMAIPFFTGRLTDWILRDGAGAAFTQNLTLMS<br>ILIIASSVLEFVCDGIYNSTMGRVHSHLQGEVERSVLRQETEFFQKNQTGTITSRVTEDTSTVSVSLSSELSLLLW<br>YLARGLCLLGLMLWGSPPLTMVTLAALPLLFLLPEKLGKWHQVLAAQVQESLAKSSQVAIEVLSAMPTVRSFANEE<br>GEAQKFKQKLQDMKTLNQKEALAYAVDLWTTSISGMLLKVGILYVGGKLVAGGAISSGNLVTFVLYQIQFTEAVQV<br>LLSTYPRVQKAVGSSKEIFEYLDRIPRCPASGSLTSLKSEGLVKFQNVSFAYPNRPEVPVLOGLTFTLRPGEVTAL<br>VGPNGSGKSTVAALLONLYQPTEGQVLLGEKPLPEYEHRYLHRQVAAVGQEPQLFGRSFQENIAYGLSQKPAMEEV<br>IAAAMESGAHSFISKLPQGYDTEVGEAGSQLSGGQRQAVALARALIRKPRVLILDDATSALDANSQARVESLLYES<br>PERYSRSVLLITQRLSSVEQANHILFLEGGTIVEEGTHQQLMANKGRYWTMLQAPGGSDAPE |
| SEQ ID NO: 13 GGTA1 Genomic Sequence<br>ACTGAGAAAATAATTTATTTAATTTTAAATCAGGAATTTTTATTTTTTAATATTGAACTATTAATAAGATCTTGAA<br>TTTGTCCATTTGAAATTTAAATTTAAATGATTTTTTTTAAAAAATCAAGATTCCTTCAAAAGGAAATATCAGTCC<br>TTTTCTTTAATCTTTGAGAACGAATCATTTCTGTAGTTTGGAACTTGCACCATGAAGTCTCTGCACTCCAGAATGG<br>ATTCCATAAACTTGCGTTATAGAGAAACAAGAGTCCTAATTGACTTGTGATTTCCTTTTTCTTTTACAAGACTACT<br>TCTCCAGGATTTTTGTTGAGTTATTTTGTTGGGTTATTTTGTTGAGTTATTTTGCTGGGTTGCAAAAATTTTTAGC<br>AAGAATTGAAGAGTAGGAGGCCCAGGGAAACAGTAGAGAAAATGTAGGTTTCATTTTATCAAAGAAGCCCATCGTG<br>CTGAACATCAAGTCAGTGCAATGGCTCTTCAAGTAAATCATTTGAAAATGGACACAAATGACCTAAACTGGAACAC<br>AAGCAAAAGTATATCACATACCTGCAGATGTAAATATTGCCTCCTAACTTCCTTTACACCAAACTGCTTAACTTTA<br>AATTACATGTAAGATCTCATAGCTTTTCTTAGAGAAAGGGATTGAAAAGCTGTTTAGTCATGAGGACTGGGTCTCC<br>CATTGCCATCCTCTCTACTTTGATATAAAATCAATTAACCACTTTATTAAACATGTCCGGCAGTTACACTTCAGTA<br>GTGCAGCTGGGGCAGGGGAAATGAGAGGTTCCCTGATAAGCAGGCTTTTCCTCTAGTCCACTCCTTGACGGTGGCT<br>CTCAAGTTGCCCATGATGGGCTGAGGGACTCTGAGAGTTAGAGCAGGTGGCAGCAGGACTTGCTGATGCCTGATTG<br>TCATGAAGCCAAGATCTAGGAAGTCACTTCAACCCACTGTAGGCCTCTGTCCACTCTGACATCATCCACTTCCTCT<br>GAGCAAGGATTTGTAGACACAAATTCCAGAGTCTGGCAGACTGAATATGACTTGGCCAAAGCAAGAAGCATCTTCT<br>AAGACAGTGCTGCTCTAGTTGTCATATGGTTGAGGAGGCTGGAGCCACTCTCATTGCCTCCCATTCAGTGCCTGGA<br>TCCAAGCTGTATGTACATGCCAACTCCATGCCCTGTGTCTCTTAGAAATGGCATTGCCCCACAGTGATCAGCCCCC<br>TCTCTTTCCAATCTGTCTTCGCTATTTCATGGCAAACTTACTTAGAAGCTGTGCTTTTATTTCGTGCTGAGCTCCC<br>ATTGGTTCATTCGGATTCCCTGTAACTCCCAACATTCACCATTGGGAATCTTGATCAGTATCTGCGCAGAAGCCAA<br>ACAAAACCCTGATGCGAAAAGGACATGGACTTCAAATAACCTGAAGTCCTCTGCTGTTGAAATCATCTGAGGATTG<br>CTAAGGTAGACTCTGATCTCCTGCTGCAAAGCAACTCTGTTGCTTTAGACTTAGCAGAGACAGGAAGACGCTAAAA<br>TCAAGAGGACGACCCCTCCCAATCTTATTTGTTGCCAAACACTTCCCCTTTGCATACTTTTCTCCAGTATGACATG<br>TAGAGTGTCTCTGACTTTTTCTTTGCCTATGACAATTTTTTTTTTTGGTTCAGTTAATAGTATATACCCCCTCAAC<br>CCAGAACAGATAAGAAATCATTGGGAATTTACATCTGATTACTACAGAGTCATTCTCCCATTTGACAAGGCTCAAA<br>GTTGCAAGGAAGAATAATATGTACTTACTGTGTTGGTATTTTGTTAGTATTTTTTTAAAAGTTAAAATTAAGTGCT<br>ACTTCTCTGAGGAAGTAGCCAGAGTAATACTCTTTCAAATTCAGAAAACTGCTGGCACAATTTAAAGTCAGATGTT<br>ATTTCTAACCAAATTATACTCTTTTTTCTGCCAAGCTATCTTGACAATCCTAATATCCACAGACATGCCTATATGA<br>TAATCCCAGCAGTATTCTGGGGATAAGATTTTAGTGGGTTTGTTGAGAAGGAAATACTTGTTTAGATGGCTTTCAT<br>CATGCCACTCGGCTTCTATGTCATTTTCCTTGTCCTGGAGGATTCCCTTGAAGCACTCCTGAGTGATGTTTAGAAC<br>CTGAGTGGGTGTTCCCCCAAAAATGGCTGCGTGGTAATAAAAATCCCCCTGGCCAAACGGAATGTAGGCTGCGGAC<br>TCCTTCCGCCTCTCGTAGGTGAACTCGTCAGGATGTGCCTTGTACCACCAGGCCTGTAGCTGAGCCACCGACTGGC<br>CCAGGGTCTCCACCCCAAAGTTGTTTTGGAAGACCTGATCCACGTCCATGCAGAAGAGGAAGTCCACCTCGTGCTG<br>GATGTGGGCCAGGATGTGCTCCCCGATGGTCTTCATGCGCATCATGCTGATGTCTTGCCACCTCTTCTCGGACTTG<br>ATCTCAAACACTTTAAAGGAACGCAGAGGACCCAGCTCTATCAAAGGCATCCTGGAGATATCATCCACCATGATGT<br>AAAAGATGACTTTGTGGCCAACCATGAAGTATGTATTTGCAGATATTAAGAACTCCTCCAAGTAATGCTCAATGTA<br>TCTGAAATAAAGAAGAATGGGGTAAATGTAACCTCTGGGATTTCTAGAGGAGACAATATGCTATTATCATCTAGTC<br>TGTATTTTGCAGTTTAGGAAAGGAATGATTTTTCCCCATCCTGGATGAGAGACGTCTGTTGCTGTAACATTCCCAG<br>CTACTCTCCACCATTCAGTCATTCAGCTTTGGGGAGGTGGAGTGGCTTACCTGACTGGTGATTCTGGCAGGGTGGC<br>TGGGCATGCTCAGCCCTGCTCCTTCCTCTCTCACTCTTGGAAGCCAACCAGGCAGAGAGAACATGTGTTTTCAGCT<br>GCTCTGGGCCTTGCAGTGGTACCTTAGTGGCACAGGCCCTGCTCCCACATCCAGAGGCCTGCAGTTACTTGTGCTG<br>TATGTGCCTGGATGCCTAAGTCTTTCTAATTCTGTGGTTCAAGATTTGGAAGCCCAGGGCCTGCAGTTATAAGCCA<br>CATACTCCAACACCAGCTTTAACTGTAATGAAGGTGATAACTCATTACCATCTGCCTTAATTAGTCTTTATCCCCT<br>TGTCCTTATCAATCAGTTCAGATGCTAGTTCTTCCTTTTTTCCTGCATTATTCAGATATAACTGACATATATCATT<br>GTGTAAGTTTAAGGTGTGCAAAGTGTTGATGTGATGCACTTATTTTTAATTTTTATTTTTTGTCTTTTTAGGGCCA<br>CATCCGCAGCATATGGAGGTTCCCAGACTAGGGGTCTAATTGCAGTTGCAGCTGCTGGCCCATGCCACAGCCACAG<br>CAACACCAGATCTGAGCTTTGTCTATGACCTACACCGCAGCTGGTGGCAATGCTTGATCCTTTAACCCACTGAGCA<br>AGGCCAGGGATCGAACCCAAATCCTCATGGTTACTAGTCAGATTCTTAACCCACTGAGTGACAACGGAAACTCCCT<br>GGTACACTCATATATTAGAAATGATTACCACTGTGGCATTACTTGACACCTTCATCATATCACATAATTACCATTT<br>TTTTGTGGCAAGAAGACTTAGGACTTATTCTCTGACCAACCTTAAAGTATATATTACAGTATGATTAAAAACAATC<br>ACCATGCTGTACATTAGATCCCAGAGCTTATTCATCTTATAACTGCAAGTTTGTACCCTTTGATTACCATCAGGGG<br>GCACTAGTTCTTAGCTCTTCCTCAAAAACCCCAGCCTATATTCCAATACTTTTACTGACCTACCAGATGCAAGCGT<br>GATGTGCAAGGGTCATTAAGCCTAACCATCGCCACTCTCTTATCCTTCTCTGGGACCCAAACAATGGATTATGGAA<br>TATGGATATTCTTCCATCTTACTGATTTACCCTGTGAGTTTCCCGCTGGTCACCCCAAACACCAGCCCATTATCCA<br>GACACCATCATTATAAAACCCATCCAAATATGAGAGCAAACGACCTCTGATTCAACCTTACTTTAACTATCTCGTT<br>TCATTTAAAAAAATAGATTTTAGTTTTTAGAACATGTTTAGGCTCACAGCAAAATTGAGCTGAAAGTGCAGAATTC<br>CCCCCGCTCCCCCCACTCCCACTCCCAGCTTCTCCCACCATCAACATCCAGCACCAGGGTAGCACGTGTTGCAACT |

TABLE 9-continued

| lists sequences for the disclosure |
| --- |
| GATGAAACTACACTGACACATCATTATCACACCAAGCCCGTAGTTTACACTAAGGTTCACTCTTGGTGGCAGACTT |
| TCTATGAATCTGAACAATGTAAAATGACATTTATCTATCACTATGTATGGTACCATACAGAGTATTTTCACTGCC |
| CTAAAAAATCCTGTGTTCTGTCTATTCATCCATTCTCCCACACCATCGCCTGGCATCTACTGATATTTTTACTGTC |
| TCCATGGATCAGTACCTTTGACCTTTTCCAGAATGTCATATAGTTGGAACCATATAGTAGGTAGTCTTTGCAGATG |
| GTTTCTTGGTAACGAACATTTGAGGTTCCTCCATGTCTTTTCATGGATTGATTTTTTTTTTTAAAGCACTGCTAAT |
| ACTCCACTGTCTGAATGTGCTACAATTTATCAATTAATTTGCCTACTAAAGGACCTGTTACTTCCAAGTTTTGGGC |
| AATTATGAATAAAAGTGCTATAAACGGAGTTCCTTTCGTGGCTCAGTGGTCAACAAACCCCACCTAGTTGCAGGTTC |
| AATCCCTGGCCTCGCTCAGGGGGTTAAGGATCCAGTGTGGCCATGAGCTGTGGTGTAGGTCGCAGATGTGGCTCAG |
| ATCTCGGGTTACTGTGGCTGTGGCATAGGCCGGCAGCTGTAGCTCTGATTCAACCCTTAGCCTGGGAACCTCCATA |
| TGCCGCAGGTGTGGCCCAAAAAAAACAAAAAAAGAAAAAACCAAAACCCACCCCCCCCAAAAAAAAAATACCTGCTA |
| TAAACATCTGTATGCAAGTTTTTGTGTAGACATAAAGTTTCAGCTTTTGAGGGTAAATACTAAGGTGTGCCATCGC |
| TGGATTGTATGGTAAGAGTATGTTTAGTTTTGTAAGAATCTGCCAAACTGTCTTACAAATTGGTTGTATCATTTCG |
| CATTGCCAGCAGCAGTGAATAAGCTTTCCTATCGCTCTACATTTTCATCAGCAGCTGGTATTGTCAGTGTTTGGGA |
| TTTGGGTCATTCTAATAGATGTGTAGTGGTATTTAGCTATTTACCTATTCATTCAAAAACCATCATGTTCAGGAA |
| GAAAAGGAAAGGGGGGAGTTCCCATTGTGGCAGTGGCACAGTGGGTTAAAGATCCAGTGTTGCTGCAGCTATGGAG |
| AAGGTCACAGCTGTGGCTCAGAACTTCCATACGCCACAGGTGCAGCTGAAAAAGAAAAAGAGAAAAAAAAAAACCC |
| ATCACATTCCTGTCTTCTGTAAGCCAAGATACAGGCTATTCTGTGAAGCCATGGGGATGATAGAGAAGGGAAGAAG |
| TAGTTGGCTGGCTTAACACAACCCACGTCACCACCCAGACTCATGCCCAGTGACTGTGCACTGAATTTAATTTGTT |
| GATCACATTATCAGCCAATGATGACATTTTGTAATAATGACTGGCACTTCCTTTTGTTTTTTGGTTGCTGCTTGGA |
| TTCCCTTTGATTACTACAAACATAAACTGTGCTTTCAATGCTGGTCTCTGGAAACCCCAGGTTTATAGTATTGATT |
| CTTTAAACGGAGAGAATATCTCAGCAATACAAGGAGGGACTTCAACATGGCTCTGGGGCTAATGGCCAGGAAATTC |
| TTCTGCACTCTGGAACTTTAAGAAAAAATCTATTGTGCCCTGAAGCTTGGGAGGTGATCCTAGGGGCGAGGGAGGA |
| AACCTTTGTGAGGTTTAACATTGTTTAGAGATTAAAGCGCTGCAGTTGGTGCTGTGCACTGTCATTTGAAAATAAA |
| CCAAACATCACACCTCCTAAAAGTCCAAATCCACTCTTGGGAGGATTTATTGCTGCTGAGTACAAACAGTCCTCAC |
| TCGCCTCAGAGCAGAGTGCGCGGGTTTCACCAGGACATGCCAAGTACAGTTTAGTTCTCTAAAGCTGCAACAAGAT |
| GGCTAGAGCCAATGTGGAGCCGTTCTTTTTGGAAACACCAAGGTTAAATCAATCTGCAGTATGGCTGGCTGGTCTC |
| CTCTTATACCAAAGGATTAGGTGAGCTGGGAATCTTTCCCAACTCCTAACAGAACATATTCTTCTAGTCGAAAGGT |
| CAAAACTCCAGAGTCACCCTTCTCTATTAGAGATGCCACCCAGGCCCCTGGGATCAGTACATTCAGGGACATTAGG |
| ACTTGATTAGTACAGTGACAGTGATACCTTCTGGGCTCTAGGTTGGAGAAGGTCTCAGGAGGACGCTTAAATCTTC |
| ACTCAGATCAACCTTGACCTTCACTTCTCTTTGTACAGGCAACAGGTCAACTAACTTCTTTTCTTTTCTTTTCTTT |
| TCTTTCTTTCTTTCTTTCTTTCTTTCTTTCTTTCTTTCTTTCTTTCTTTCTTTCTTTCTTTCTTTCTTTCTTTCTT |
| TCCTTCCTTCCTTCCTTCCTTCCTTCCTTCCTTCCTTCCTTCCTTCTTTCTTTCTTTCTTCCTTCCTTTCTTTCTT |
| TCTTTCTTCCTTTCTTTCTTCCTTTCTTCCTTTCTCCCTTTCTCTCTTTCTCTCTTTCTCTTTCTCTTTCCCTTCC |
| TTCCTTTTCTTTCTTCCTTCCTTCCTTCCTTTCCTGCTTTTTTAGGGCTGCACCCTCCCAGGCTAGGGGTCCAATC |
| GAAGCTGTGATGATGGCCTGCGTCAGAGCCACAGCAATGCGGGATTCGAAATGCATCTGTGACCACACCANNNNNN |
| NNNNNNNNNNNNNNNNNNNNNNNNNNNNNNNNNNNNNNNNNNNNNNNNNNNNNNNNNNNNNNNNNNNNNNNNNNNN |
| NNNNNNNNNNNNNNNNNNNTTTCCTTTCTTCTCTTCGGATTTTTTTTAAGTTTGGTGAAAGTATAGTGTCTTACA |
| ATGTTGTGATAATTTTTCTGTATACAAAGTGATTTCAGTTTCTTTGTGGCTTCAGAAAAGGTACAGATGGAAAGGC |
| CCATGGATGTGGGGGAGGGAAGGGGCACGGAGGTGAACAGGAAAATTGAACTTTTGCTTTTGTTTTGGAAAAAAAG |
| GGGGGGGGATTCTCTAAAAAAGAAAACTGGGTTATATTTTAAACGAACATTACAGCTACTACTTTTAAGTAAGAAT |
| GTTTACAGTTTGGGGAGAAAAGTTCCAAACAAGGAAACGGGGGCTGAAACAGGAACCTATCCAACCTCTGGAAGAG |
| GAAGTTCTGAGCAGCCTAATCTCCCCGGGCCAAACCCTCCAGGAGGAATAGGCAGAAGGCACAGAGGAGTGGTCAG |
| CCATGCGGACGTGGAAAACCACTCCACTTAGGACACTTCTGTCTTTGGTCCTTGGTCTGGGGTCTCGAGAGCATAG |
| GAGAAACGACGCACACACAGGCCATCTAACAATTGCCATTTTTGGAATTTCCACAGAGGGCCGTGGAGGTCAGGGC |
| GGAGGTGGCTGTGGGTGTACTGTCGACTCTGGGTGCAGTGGGTATAGCAGATCTTCTTCCCTGCAACCCAAGCCCC |
| TCACCCTGAGGTGGGAAAGAGTTGACCCTCTGACTAGTTTTATTCTTAGCCTTTGGGGACCTCAGCAGAAGGGAGT |
| CTAAAATGGCCCTGTGACACCATTCTCCTCTCCACTAATTCAGACATGACATGAACAGCCTCTGTAAACCCAGGGG |
| CCCCTCACCCATCCTCTGATAGTGGAAGGGGAAAAACTCAAGGCCAGTTTTATTAGCAACACCTACCTTCCGACAG |
| CAAAAACCGTCAAGCCCACGGTAATTTTCTGTTTGGCATAATAATTATCTAAGACGGCTCTGTTGTAAGTGCCTTC |
| CCATACCACTGGAGCCTTCCATCTGGTTATGGTCACGACCTCTGGGCGTTTCCTGGTGACAAAACATAGAGTCAGG |
| ATGGCTTTGCTAAGGTACGACAGTCTGGGGGAACATGGGTCAGTCATGGCTTGTGGTGACTGGCCTTGAATCCTGA |
| CTGTATTTTAGCCCCAGTCAGCTGGTGGTGTGACATTGCAGCATCTTCTGGGGGAGGGACAGGAGGCTCTGGCCCA |
| GGTGCCTCTGCGGGCTGCCCTGGTGGCCCCTTTGGGGATCGTACCTGTACAACGTGTATGTACCTTCCGTCCCCCT |
| GTTCTGCTGTCCTCGTCCTCAATCTTCCTTCCAAACCCCTTCGCCTATCTCCCCAGGCCCTTCCTAAGCTGCCAGC |
| GACATCTTTGGGTGTTGCTTATCCCAGTGGGTGCCACCTGACCCTGAGAAAGCCCTATGGCTTGACTAGCGGGATG |
| AGAGAGTGACATTTGAGCTGAAAGAGGAAGAAGCTGTCTCAGTTTGCCTTCTGCCAGAAAGCAATTTCTGGGTAGG |
| AACCTGGTTATCGGACAAAAAGGGCCCCAGACTAAGGGGACCTGGTGTTGTGGTTCATTTTACGAAGAAGGAGACA |
| GTCACCCAGAAAAGAAGGGACCCGGCGGGCTAACTGTGGCCATGGGTGACACACAGGGCTCGGGCTCAGACCTCTC |
| TCAGATCATGTCACCTCTTGACTAGAAGCACAAAAGCGGGAGGGGAGGGGGCATGTTCTCTGCACCCAGAACACTT |
| GAAAGGGACTTAGCAAAGCCAACACAAACACAGGAAGCCACGGAAGAGCAACGGACAAATTGTAAAGAGTAAATGC |
| GGGAAGTCTGGGTAGCAGCTGGGGCCCCCCAGAGGCAGGAGGGAGCTGAGAAGACTTGGCTCAAACCCCATTTGCT |
| CTGGAAGTGGCTGCACTTCCCCGTCGGAAACAGACTGAAACGTGGTCATTTAGATTCAACCCCCAACACAACATGA |
| GAGGGCCTGGCCCCTGCTAGCTGTGTGCTTGTATTTCAGCCACTGCAGGGAGAAGGCCAGTGGTTGGGGCAACGTC |
| TTGGGGGTCCCATCGGGCCCCTGCTGGCTGCCTGGGTATGGCCCTGGTGAGGCTGTCTAGGAGATGTTAGCCCAGC |
| GAGAACATACCCCCACCCTCATACGCGGGTGGAGGAAGGGTTTCACAAACCTGCCCCTCCCCCATGGGAGAAACC |
| ATGTTTCCCTGCGAGATTGGGCAAGGCTGGGTCACCCCCACTTCTTGCTCATGCCTTCTGTCCCTCGTCACCAAGC |
| TCTGCACCCGTATTCTGGAGCTGCCTCTGCCCTCCCACCCCCACCCCATGCCCTGCTTCAAGCCTGCTTCCTTCCT |
| CCCCTAAGAGTAATTCTGCAGAGATGGAGGGGACATGGCTAGGCTGCTCAAACCCCACACCCCCAGCTCTGCCTTC |
| ACACCCCAGGTATGACCGCCCCTTGGGGACACCTGCTCTTGGTTTCCAACAATCATGAAAGAAGCTGTTTTGGACT |
| CTGTACCAACTTGTGCCAGGTACTTTCACATACACTTTCTCTCATTTAGTCCTTGCAAAAGCTTGGCCATGTAGTA |
| TGCTCAATGTACAGATATGAAAATCAAGGCTCAGGAAGGCTTGTTAACTTGACCAAGGCCAAACAGCAGATGATGG |
| TAACTAACACACACTGGCTCCTTCCTATGGGACCAGGCACAGTGCCAAGAGCTTCACCCTTTTGTGGGGGTGGGGT |
| TGCTATATTTTGATTCCCATTTTATCTGTGAGGAAACTGTAGCACAGAGTGGTGAAATAACTTGTCTGAGGTCACA |
| CAGCTAGTAAGGAGCCAAGCTGGGATTTGAACCCAGATAGTCTGACTGTGGTCTGTGCTCTGAACCACTACCCTCT |
| ATGGCTTCTTGGCTATTTACTTGCTGTACCAATGAACTGGAGTTAAAACCCAGGTATGTCATCATTTCCACTCATT |
| TGAGCTACTTCAGCATTTTTATCAGGGCAGAATAAAAAAAAATGATGAGCTTTTTTTTTGTTTGTTTTGTTTTGTT |
| TTTAGAAACTTATGTGATGCTTTTCTCACATAAAAGCCCCAGCTTTGTTGAATGACTGGATTTCAAACCAAAAAAA |
| CCACACACACACACACACACACACACACACACACACACACACACACAGCTTAGGCTTATCATTCTATAACCGTT |

TABLE 9-continued

| lists sequences for the disclosure |
|---|
| TCCCATGCACTGTCACTTCATTCATTCCTGTCCTTAGTGTAGCCTGTCAAGGATCTCTTAGCAGTTCAGACCCCAG<br>CCTATCAGTTAAGCCATGCAGCTGTGTGTGAGCTGAACATCTGGCAAGCAGGCAATATTATCTTTAAGCAAAGAAA<br>AGGAAGAGAAAGAGAAGGAGGAAGAGGAGGAAAGGAAGGTATTCTTATTTACTAGTCGCAAGCACTGGGGTTAAGT<br>ACCGGACTTTTATTCTCTCATTGAATCCTTACAACCACGTTCAAGAGTGGGTGCTATCATCACCTCCATTTCACAA<br>ATAAAGAAAGTCGGGGGTGAGAGAGAAGGAAACTATGTTTTTAGCCATTCAACCAATAGGAGGGGCCACACCAGGG<br>CATCACCTCCTCGATGCACATCTGCCAAGTCCCTGCTCCATCTGCCGGGGCCCAGGGCTAAAGACGGAGATCAGAC<br>CCATCCTACCCCTTGAGAACTTCCCATCCCTGACAGGTGGTCAGCCTGCCGCACACTCCTCAGCCGCACAACCCCT<br>CAGACTACACCTTCTAGAAAGACCGATTCAGAACACCAGTGTCCAGTTTGGTTACTTGGCTGGGAAGATTCCTTTT<br>AAGCAGGGGGGAGAAAAGTAGCAATATTAAAAATTAACGTCGAATTAAAAATTAAAATGCTCTATTTCCCAGCTG<br>TTAATTATTAAATTCCACTGGCAATTCCAACATGTCAGCAACCCTGACTAGGAAGCCATATGACAGGCTGAAAACA<br>CTGGCCGTGGGCAGGAGGAGGAGGTGGGAGGATGATTGAGATCAGCTTCCTGGATGAACCTCTGCTCAAACCCCAC<br>CCCCACCCCGGCCCACAGAAAAAGAAGAAGTAACAGCAGGCAGGCCAAGTATGTGTAAGAGCAAGAGCTGCCCAAC<br>GTCATCAAGAGAGGGCTCGAAAAGGAGGGAAAAGTCCAGGAAACACTGGAAACTGCTCAGTTTTTTAAGCCGGGCA<br>CCCACTGCGTTACTTCGGCATGTGGGGTTCCACCAGTGCAAACCAAAGACTTCCACAAAATAAAAGGGTCTCCAAA<br>ATCCAAACGCACCACCTACCTAGGTAGTTGGTAGCTTTTCAATTTTATGTACTTATTTATGGGTACACTGTGGTCC<br>TGAAGGGCTGGGCAGAGGAAGTGTTAAAATTCTATGAATCATACAGCAGGTGGAAAAAAATGAGGAATGCAACAAT<br>GTGTTACTTACTGGATTCCTTCCAGGCAGCAGGACGTACACAGTGATCCAGCAAAGAGCTAATGATGCCATGGACA<br>AGGGTGATGGAGAGAGGGAGATGACGTGGGAAGAATGAACAGAACATGTAGATGAATTAGACTGTGGGCTGGATGA<br>AGGAAGGATGAACAGTGAATCATGGAGGTCTCCTGACTCTTGCTTGAGATGGGAAATGAGAAGAATGAGGGTGGGG<br>TGGAATCAAAAACTCCCTCTGGGAGTTCCCGTCATGGCTCAGTGGGAACAAATCTGACTAGCATCCATGAGGATGC<br>AGGTTCGACCCCTGGCCTTGCTCAGTGGGTTAAGGATCTGGCGTTACCGTGAGCTGTGGTGTAGGTCACAGACACG<br>GCTTGGATCTGGTGTTGCTGTGGCTACAGTGCAGGCCGGCAGCTAGAGCTCCAATTCAACCCCTAGCCTGGGAAAC<br>TCCCTATGCCTCAGGTACGGCCTAAAAAGACAAAAAACAAAAAAACAAACAAAAAAACCCAAACTCCATCTGAGTC<br>ATGCGAGACCTGCAGTGATGTCAGGCAAGAGTTAGACACAACTGGGTGCTCAGAGAAAACCTTTGGGCTAAAGATA<br>TAAATGCAGTAGTCATTGTCCCATGAATGGTATCTAATGCCACAGAAATGGATGAAGACAGTGTATAAAGAAAAGA<br>GATGAGGATAATGGACTCAACCTCCAGAAACTCTAACACTTCCTGGCTGAGAAGAGGGAGGGGCCCCAATCAAGGA<br>GACTGACAAGGGAGCTGGAGAAGTCGGAGGAAAACTAAGAGGATGTGGTGCTACAGAGGCTGAGAGATCTTGATGT<br>AAAAATGTATACAGAATACACTTAATATGTTTCAGGTAGAATACAGAGGACACATTTCTATAAATATATCTATAAT<br>ATATTTCTATAAATATATTAATTCAGTGGCTCATCTTTCCTGCATTTATGCAAGCAATTTACTTTGGTGCCCTGAG<br>AAGGCTTAGATTAGTGCTACTACATATCAATATTCTTTAAATATCTGCTCAGCATTCATTTGGAGGAGAAACTGAG<br>CCATGCATGGGGGAAAGTGGAAAGAGTGACAGTGGGTGGCTGTGGTCTTTCACCTCTGACCCCAGTGATTCAGCCC<br>TGGCTCCACCTCTCAAGTCCCACTCAGTAAAGCACAAGTACCACGGTCAGTGTGCCACTCTCTCTTGAAGGGAGCT<br>TGGTGACTGTCTCTAGCTGATCTATCTGGCCCCTGGGGAGTCTCACACCTCCCCACATGCACACACATCTAAGGGG<br>CTTATCAAAGCTCTGGTGGGAGTTCCCGTCATGGCACAGCAGACATGAATCCAACTAGTATCCATGAGGTCGCCAG<br>TTCGATCCCTGGCCTCACTCAGTGGGTTGGGGATCCTGCGTTGCTGTGGCTGTGGTGTAGGCCAGCTGCTGCAGCT<br>CCGATTAGACCCCTAGCCTGGGAACTTCCATATGCTGCAGGTGTGCCCCCTCAAAAGAAAAAAAGTTATAGTGCT<br>TCCACATTCTTCCACTTCCAGGAGTAGCTTAGCATTCCATAGATGGCTACCCTGTGCCCAGCTCCTCAAATAACAC<br>ATGGGGAGGCCAAAATTCCCATTCTTTCACACTGACATGGACCTCCCATCCTAAAACAGTAAGAAACTTGCCAGAA<br>CATACTCAGTCCTTCCAGAGTCCAAGACCCCTCATGCTGGAATAGATGCTATTCTCCTCGGATCCTCCTCCTACCT<br>CTACTGCTGCTCCCACTCCGTTTCAGACTTCTTTTCCTCCCTCCCCTGACCCTTTAAGTGCTGATGTCAGATAAGA<br>CTCAGCTCTGCTCCTCTGCCTGGACTCTGATGGCTCCTCTTCCAATGTCTCTACCACATATCTTCTGCCAGCTTAA<br>AGGCCCTGCTGTACACTGACGATTATGTCTCCCCCAAATTCGTGTGTTGAAACCCACCCTCAATGTAATGGTATTA<br>AGGGGTGGGGCATTGGGGTGATTAGATCCTGAGGGTGGAACCCTCAGGAATGGGATGGGTGCCCTTAGAAAAGAAG<br>CCCTGGAGAGCTCCCTCTCCCCTTCCATGGCCTAAGAACACAATGAGAAGACGGGCATGTACAAACTAGAAAGTGG<br>GTTCTCACCAGACACCACATCTGCTGGTGCCTTGATCTTGGACTTCCCAGCCTCCAGAACGGTACAAAATACATTT<br>TTGTTGTTTATAAGCCACCCCGTCTATGGTATTCTGTTACAGTAGTCTGAAGGTCTAAGATAGGCTCTCCATGAAC<br>TCTATCCAAATGCCCCACAGGTACCTGAATCCACCTACATCCTTAATCAAGCTCATCACCTCCCCTATTCCTAGAC<br>CTGTATCTCCTCCTCCAGTCCCTTTCCTGGTCAACGGCACCAGCATGCACCAGTCTCTCAGGCCTCCCAGTCATCC<br>CGGACAGCCCCCACCTTCTCACTCCCTTCCACATCCTTTCAAGTCAGGTTAATCACACCGCCTTACCAATCTTGGC<br>AAATGCTAGTTTCACATCTAGTGCCCCTATAGGACTGTAAACTTCTTGAATATAAGTGTATTGATTAATTTCTCCT<br>GTCTGTCTCCTGTGCCTAACACAATGTCTAGTACCGTGACTCATAGTGAAATATATCCTACGTCACAAACACATGC<br>ACATACACATATGGAAGCAAAAATGCCACTAAACAATACTTATCCTTACTTCATGAGATGCCTTCTGATTTCCTAT<br>TTGGTTTCAATTTTTGACCCTTAAGCCAGTTTCTAAACACATTAATGGATCAAATAATAGTCTGACACACATGGGC<br>TAGCATATCATAGGTGTTTTAATGAACATTGTTGTATGCTTGCTTAGAGTGTGTGCATGGCCTTGTAAGGTTTTTT<br>AATCATCACTGCCATTTTATTTTATTTTTATTTTTTTAGGGCCACAGGTGCAGCCTATGGAAGTTCCCAGTCTAGG<br>GGTTGAATCGGAGCTGTAATTGCCAGTCTGCACCACAGCCACAGCAACACCAGATCTGAGCCTCGTCTTTGACCTA<br>CACCACAGCTTGCAGCAATGCCAGATCCTTAACCCACTGAGTGGGGCCGGGGATAGAATGGATACTAGTTGGGTTT<br>GTTTCCACTGAACCACAATGGGAACTCGCGTCATTGCCATTTTACAGAGGAGTTAACCGAACCTAAGAATTTTCTT<br>TATCTGATTCTAGATTCTGTGGCTTTCCACAGCACCCCATGGGCTATAGGACCTCTCCTAGCCCCAGTATTTTTTT<br>GCTTTTTAGGGGCTGCACCCGCAGCATATGGAGGTTCCCAGGCTAGGGGTCAAACTGGAGCTACAGCTGCCGGCCT<br>ACCACAGCAACGCCAGATCCGAGCCACGTCTGCAACCTACACCACCGGTCATGGCAACGCGGGATCCTTAGCCCAC<br>TGAGTGAGGCCAGGGATCCAACGTGAAACCTCACAGTTCCTAGTTGGACTCATTTCCGCTGTGCCACCACGGGAAC<br>TGCTAGCCCCAGTATTTTGTGATTCATCTGTTGCCATTGGCTAATTGCTGTCAGAATCACTATGTTGTTGCGCAAA<br>CATTTGAGTCAAAACATCCAGACTCCCCACCTCCCGGGATGCCACGCCAGTCACTCACACACACACACACACACAC<br>ACAAAATCCGGACCCTGTTTTAAGGGTCTAATAGATGCTAAAACTCTGTCTCCCCTGTCGGGAATGTTCTCATGGC<br>CCTGTTGCCTACACAGCCCCTGCCACCTCCTGCTGAGCTGTGGATTTACTGAAATAGGGCAACGCTTCTTTTCTTA<br>CTCAGGATTAAACCAGTCCACTAGCGGAAGCTCTCCTCTGTTGTCTTCTTTTCTTTGTTCCTTTTCGTTGCCTATA<br>GCGTCTTCTTCTTCGTGGTAACTGTGAGTCCTACGTACAAACGGAAAACAAGCTGAGGAAGGCAGGGAGGGTGACC<br>CATGTGCCAGAATGAGAGTGAGGATCTTGTGAAAACAGATTCCAAGGCAGAGAACACGTGCGCCAAGCAAATGTCT<br>ACAGAAGGCTTGTGATACTAAACATTTATTCGTAAAGACGTCCGTCTGATGAAAAGGTTCAGTGCTCCCCTTTTTC<br>ATCATCCTTCCAGACCAGCACAGTTAGCAATGTAATGACCCAGCAATTCTCAGGTTCTGTCAGGAGCAGGGAAACC<br>TGATAAAACAGTCCTTATCAGCGTATGTAAGCTCATGACAGCCTTTCCTGCAGCCTCAACTTCAGCCTGAGCCTCA<br>CTCACTCCCACATCAAATGGGAAAAAACAAAACCTTGAAAACCAAACTTAATGCCCATCCCCACCACGCAACAGAG<br>TCCTTGCATGATTCCAATAAGCCAGAAGGACGAGGCGACTGAGAAGGTCATGGCTGTGAAACCATTTTATTTGGAC<br>TCTACAGCCTTGAGCAGATACACAGATGGCCGTTTCCCAGTCTTACCCATTGTTAAACCAGCTCGGAAACCACCAG<br>CCCCTCTGAGCACTGCTGCCAACTTCTGGGTTTCTAAGAAATGAAAAAGATGACAAACATTTTTTAGAAAATGAGG<br>CAGTCCCAAACTGGGGCAGGGGGTGGGGGGTGTTCCAAACTCTTTTATGGCAGATCACTTAAAATCATTTTTTAA<br>AAAATCACTAATTCGTAAAATGAACAGAAATGAAGCTGCTCCAGCTGAATGACTGAGGATGGACCCGACACTCCCC |

TABLE 9-continued

| lists sequences for the disclosure |
|---|
| AGATCTCCCCTCCCTTGGGTGGCCCCCGGCACTCCGCTGGTCCAGGGAGCCCTCGCAGGAAGAGAAGGGGAGAAGA |
| AGAATGACAAGGGGGAGGGCACTAATCCATAAATCCAAGTCCTGGATCTGCCCCTTTCCTGTTGTGTAACCCTGAT |
| AGGACATTTTTCCTCTCTGAATCGCCATTGCCTCCTCTGGAAAGTTAGAGAACAATGACAGCACCAAACCTACCAT |
| GAAGATGGATGGCTTCGAAGACTAAACAAAGTAGCCTACGTAAAAGAGCTTTATAAGCTGAAAATTACTGTAGTAA |
| GTTGTAGTCTTAAAAAAGAAAAGCCCACATTTCCAAGAATGATCTCTTGCTAAATGAGGAGAACTGGAGTTGCTAC |
| AAAGGTCAGCAGTGACAGATTCAGGAAACCTGAGGGTTTCTAAACCCGAAGCTCAGCAAACTGTAATCAGAAGCCG |
| TTTTTCTCCACACACATGCTCAGATGTCCACACTCACTGTGAGAGTCTCTCCAAGGCGTGGACCGTCTAGAGGAGG |
| GACAAGAGGGGGAAAGCCAGGAGCTGCCATGCCCTTTGGTTGGACAAATGAGGTGGTGAGGCAGGAATAGGCATAG |
| TAGTAAGAAACTTACTTTATTTTACTTTATTATTTTATTTTTTTTGTTTTTTTAGGGCCGCACCCGTGGCATATGG |
| AGGTTCCCAGGCTAGGGGTCTAATTGGAGCTGTAGCTGCCGGCCTACGCCACAGCCACAGCAACTTGGAATCTGAG |
| CCGCCTCTGTGACCTACACCACAGGTCACAGCAGCACCAGATCCTTAACCCACTGAGCAAGGCCAGGGATCGAAGA |
| TGCATCCTCATGGATACTAGTCAGATTTGTTTGCACTGCGCCACAACTGGAAGTCCAAGAAACTTAAAGTCCATCT |
| ACTTTCAGGAAGTGCTTGAAATGGCTTATGAAGAAAGTGTGGTTACGATAAATAGGAAAACAATACAAGAATCAAA |
| ACAAAACAAAACGAAACAGAGAAACATTTTAGTCACTCGGGTGTTTTCACATGACTTTGGTCATCCCAGCCACTCT |
| GTGAGAACAAAATCTTTAACTTTATTTTTACTTCATAGCTAAGATATTGGCAAAATGAGTTTGAGCAAATTGCCAA |
| GATCCCATGGCATCTAACAAAAGCCAGGATTTAACACCAGGGGATAAATCATATCAGATGAAGGCTACTATAAATC |
| AGCTATACTTTAATAAGAAAAAATGTTTTAAAAAAAATGAAGGCCAAGGAAAATGCAAGCATTTAAGCACAATACT |
| TTGCTCTAAGCTTCCTAGCAACCAAGTCGAAGATAGGAAAAAAAAAAAAAGAAAAATGAAGGCTTAGAGTCCTTAAT |
| CACCAGTAATAGTAATAATAATAAATAATAATAATACACACACTAGTTTATCAGGACACCCAGCCTTTCTTCCTAA |
| TCCTTTGTCTTGGCAAAATTTCTGGCAAGGGTCTTTATACCACATGTAGTAGGTAGCATAATGGATAATATCTACT |
| CTGATTCTTTTTTATGAGCAAGGCAGGAATGTTCTCCAAACAACATCACTTAAAGAGATAGATACTTGATGAGAAG |
| CAAAGGAAAAACACAACTCATGCTCTAGAAAGGCAAGTCTAGGGGCTGGAGAAGTACAGCTCAGACCCCTGGAACC |
| CCATCCCTCTCCTCCACCTAGGACCACAAGTGTGTCACCACCTGCCATGTTAAGAATGGACTGTAGGGCCACCAGG |
| GTCACATGGAAGGTGACCTAGAGATATCTGGAATTCAAAGCACTTACTTTGACTGGTATATCCAGAACAAAGAACC |
| TTCTGGGCTAAAAGCAAATGGAAATAAAAACATATCATGTTACTTGGAATGCAGAGAAAAGCTATTTTGCAATCAT |
| TATCATTGAAACCCTAGGCTGAGCTGAGAGCCTGGGTTGTGGCTACTCCCAGGTTTCCACCTTCGAGATCGAAAAA |
| ATGATATCACGGGACTCTCGTCATTTCAGAATTACTCAGATCAAACGGTGGGAGGGAGGTCTCTGGAAAATATCAA |
| ATCTTAGTTTAAAGAAAAAAAAAATAGATGGCAGCTCTTATTGTCCAAGGTGGCTTTGCTGAGGGAGAGAGGCTCC |
| AGAGATGGGTCCCAGGAAGACCACAGCCCACCCATCCCTCACCCAGGATTTATCTTCCTCCAGAAAAACAGGTCTT |
| GCCTCGCTGGCTCAAAGCTGTCTACAGAGTAGCCTCAAAGGGCACTTCTAGGAGTTCCTGCTGTGGCATAGTGGGT |
| TAAGAATCTGACTGCAGGAGTTCCCATCATGGCTCAGTGGTTAACGAATCCAACTAAGAACCATGAGGTTGCGGGT |
| TCAATCCCTGGCCTCGCTCAGCGGGTTAAGGATCCAGCGTTGCCGTGAGCTGTGGTGTAGGTCACAGACAAGGCTT |
| GGATCCTGTGTTGCTGTGGCCGTGGTTTAGGCCGGCGTCTACAGCTCTGATTCGACACCTAGCCTGGGAACCTCCA |
| TATGCCGCACCTAGAAAAGGCAAAAAGCCAAAAAAAAAAAAAAAAAAAAAAAAAAGAAAAGAAAGAAAGAAAGGCAGA |
| AAAAGAATCTGACTGCCGTGGCTTGGGTCGCTGTAGATGCACAGGTATGATCCCTGGCCCAGCACAGTGGGTTAAA |
| AGATGTGGTGTTGCCGCAACTGCAGCTCAGGTTGCACCTGTGGCTTGGATTCAATCCCTGACCCAGGAATTTCCTT |
| CTTTCTTTCTTTCTTTCTTCCTTCCTTCGTGGAATTTCTATATGCCATGGGTGTGGCCATTAAAAAAAAAAAAAAA |
| AAAGGTACTTCTTAAGCTAACAAAAGCAGTGAGACCATCCTACAAGACGGGATCAGTAAATATATGACGACTCTAG |
| CAGACCGCCTCCATTCATTCAACAAATACCTGCTGAGCATGCGTTACATGTCAAGTGCCAGACATACAGTGTTGAC |
| TGAAACAGACACCATGTGTCTGTGGTGTAGAGAAGCTGGCAGGGAGGGTGGACCCTATTTTGATAAACACATCATT |
| ATAGGACTTCAAAACTCCAAGAAAGCATAGGAGCACTTAACAGGAAGACCTCGAAGGCTCCCCAGGGGAGGGGATG |
| ATGTTTTAGCTGAGTTCTGAAGGATACATAGGAGGCCCAGTGAAGAGGGATTAGCAAGAGTGTGCCTAACAGAGAG |
| AAAAACATGCAAAGGCCCCAAGAAAGGAAGGTCGCATATTTATTTATTTATTCATTTATCTTTTGGGGTTGCACCT |
| GCGGCATGTGGAAGTTCCCAGGCTAGGGGTTGAATTGGAGCTACAGCTGCTAGCCTACACCACAGCCACAGCAATG |
| CCAGATCTGAGCTGTGTCTGTGACCTACACCACAACTCACGGCAATGCCGGATCCTTAACTCACTGAGTGAGTCCA |
| GGGATGGAACCTGCATCCTCATGGATACTAGTCAGATTCGTTTCCACTGCGCCACATCGGAAACGCCTGCCCTCAT |
| CTCTTAAAACAGAAACAAAAAACCACTAACCACTAATATTTGTTTGAGATTCTGCCAAAGCCCCGATCTCCTCCCT |
| CTGCCTTCTGCCCCAGCTGGGAGTCCACATCTCCTGGTAGGAATGAAATACATGCCTTCCTACCACCTATGGTTTC |
| CCCTCTAAGCTCAGTACCCATGGACCCAGCTCTAAAGTCCCTTGTTTCTAAATCTGTCTATTGATCTGATAATATT |
| CATAATAGCTAATAGTTGGCTGGGGACCTTTCTAAGCAACTGACATGTATTAGCTCATTAAATTCTAATAACAGTC |
| AATGAAGGAGGTTCTATTCCTCCTCAGAGGGACAGAGGCAATAAATTATTTTGCCCAAGGTCATACTGCTAAGGGA |
| AGAAACAGTATTTGAACCTGGGGAATCTGACTTCAGATCCTACAAGAGGGGGAAGGGAAAGGGGCAAGAGGAGGGG |
| GAGGGCCCGTGCCACCCAGCACTCAGGAGCCCCACCCTCCTGCCGAGGCACTCAGGGCATCAATTTATAGATTTGG |
| ATTTGCCACCTCGTCCCATCTTTTTAGTAACCCCTCCCTCTTCCTCATCTCACCCTCCTTTCCCAGAAGCCTTCAA |
| CACCTCAGGTCACAGCAACAACCACCCTGAAGTGTACGGCATTTAACACATATTCATCCTTCAAGGCACAGCTCGG |
| ATGCCATCTCTTCTGAGCCTTCTTTGGTATGAACCTAGCACAATGCCTGGCATACAGTAGGTGCTCAATAAATATT |
| TCTAAATGAGGGAGTTCCCGTCGTGGCGCAGTGCTTAACGAATCTGACTAGGAACCATGAGGTTGCAGGTTCGGTC |
| CCTGCCCTTGCTCAGTGGGTTAACGATCTGGCGTTGCCGTGAGCTGTGGTGAAGGTTGCAGACGTGGCTCAGATCC |
| TGCGTTGCTGTGGCTCTGGCATAGGCTGGTGGCTGCGGCTCCAATTAGACCCCTAGCCTGGGAACCTCCATATGCC |
| TCGGGAGCAGCCCAAGAAGTAGCAAAAAGACCCCCCCCAAAAAAATAAATGCAAAACATAGATCCATCTCCAAGC |
| CAAACATAATCTTGCCCTCCCTGAACTCTCACGTTCCTTTGCTCTCTCTCTCTGACATCCTCCTTCTAGCCTGTGT |
| TGTTGGGCTTTCATGGGTACCTCTGCCTGCTCCATCTACAGCATAACCCCTTGAGGGTAGGGATTCTCCTTGGCGC |
| ACACTGTACCCCTCGCAGCATTTGGCATGAACAACCAGCTCCAGAAGGAGCCCCAGATGATGAATCAGAAGATCTG |
| AGTTCTAATTAGAAGTTAGACATAAGTTCACTGTTAAGGCATTTCACCTACTTGTCCATCGCCTGAACAATGGAAA |
| CCTTGACTAAAGGAAGGGTTACCCAGGTTACCCAAGTCAGACAGCCCTGGACCTAAATCTTCCTAAAAATGTGACC |
| TTGAACGTTCACATTTAATATTGTGGAAACTCAGTATTCCTCATCTAGAAATGTGGACTAACACTGACCTTCCAGG |
| GCTGTTTTAAAAACAGGAGGGAATGAACAGTGGAGTTCCTGGCACAAGCAAACACTCAATAACTAGTAGCCGCTAA |
| CATCAAAATCACCATCACCATCATTACTTTATTATAGCTCTTAAAGTTTCTTCCACCTCTAAAATTCTAAGCTTGT |
| GGCTCAGTGGCTTAAGAACCCAACTAGCATCCATGAGAATGTGGGTTCAATTCCTGGCCTCACTCAGTGGATTAAG |
| GATCCAGTGTTTGCCATGAGCTGTGGTGTAGGTCACAGACGGGGCTTGGATCTGGCGTGGCTATGGCTGTGGTGTA |
| GGCAGCTCTGATTCCACCCCTAGCCCAGGCATTTCCATAGGCCACAGGTCTGGCCCTAAAAAGAAAAAATAAATAA |
| ATAAAATTCTAAGATTTTTTTTTTTTTTTCATCTAGCCTTTAACCAAATGCTGTCCTGGATGACATTCTTAAACAG |
| CTGTATGTGTTTGATGGAGTTATTTTGTAAATCTCTTTTTTTTTTTTTTTCAAGGGCCTTACCTACAGCACATGGA |
| AGTTCCCAGGCTAGGGGTCAAATCAGAGCTGAAGCTGCCAGCCTACACCACAGCCACAGCAACACCGGATACCTGA |
| CCCACTGAGCGAGGCCAGGGATCGAACCTGAATCCTCATGGATACTAGTTGGATTTGTTACCACTAAGCCACAACA |
| GGAACTCCTGTAATCCTCTTTAGCTACAGTGCTACCCACCTGTCTAAGGTTAGTGCCCTCAGCTCACCTCAGACCA |
| ATTCACAAGGTGGCAAAGAATCTCCTGCCTTTTAAACCCCTTGCAGATGTTCAAATAGATTCCTCACATTGAAGAA |
| TGATGTGGCTGCAGTCTGGGTGCCAGACTACGGCCCTGAAGAGCAGCCAGAATCTGCTCCAGTTACTGTGAAGAGA |

TABLE 9-continued

| lists sequences for the disclosure |
|---|
| GAGTGTGCCCAGCACTGCAAAACAACCCTCTTTATGGGAGGCCAGCACCAATATGCACTTCTGGGCCTTTGGCTTC<br>TGTGTTTTAATTTTGTGAAGTACCCAAAATATGGAAGTATAACTCTGGCTGCAATTCAAAACAATCAAGAGTTCAG<br>AGCTTGAAGGTTGCCTACACAAGCATCTCAACTCAGGTCAGGAACCCCATGGGGAACTTGCTCTTCTGTTAGATTC<br>TTTCAGCCCCTAGAATTTTTTCTTTTTCTTTTTCTTTTTTCTTTGTAGGGCCAAACCTGTGGCATACGGAAATTCC<br>CAGGCTAGGGGTAGAATCCGAGCTACAGCTGCCAGCTTACACCACAGCCATAGCAACTCCAGATCCTAGCCATGTC<br>TGCAATCTACACCACAGCTCATGGCAACACTGGATCCTTAACCCACTGAGCGAGGCGCGGGATTGAACCCGAAATC<br>TCCTAGTTCCTAGTTGGATTCATTTCCCCTGCACCACAACGGGAACTCCTAGAACTCTTCCTTCTATTTGCCAAAA<br>TCTCCTGTCCTATGCTGCCCTCCGGACAGATGGTGATAGTGGTGGTGGTGATGGCAGCCAGCGCTTACTAAGTACG<br>TTGCCCTTAGTGCTTTATTCACAACTTATTTTATCCAACAACCCTATGAAGCAGGTACTACTATCATCCCCATTTT<br>TAAAGATAGGGAAACTTGCCCAAAGTCACAGAGGAGGGAAGTGGTGGCACAGGACCAACCCCAGGCAGCCTAGCTC<br>CAGCCTCCACTGAGAATATCTCCTCAGTCCTCAAGTACCTAAGGGAGCCCCAGGGTCTCTGCATCCAACGCTGTCA<br>TCTTTTCTTCAGAGGAAGTACCACAGTTTCCTCAATTCGAAAAGGTTGGTTTGTAGACATTTGTTCACTCTCTAGC<br>TCGTCTTGTTTTTCTTAAAATGAGTTCTTCAGAATGAGAGGGAATAACTGTTCCAGAAGTGGTTAGATCTATGAAG<br>CATCCAAAGGAATGACAGCTTCTTATTCTAGGGAATCCACCTCCTCCTTTTTTTTTTTTTTTTTTTTTTTTTTTGG<br>CTGCACCTGCAGCATGCAGAAATTCCTGGGCCAGGGATCAAAGCCAAGCCATAGCAGTCACCTGAGCTGCTGTAGG<br>GACAAGACTGAATTCTTGAACCCGCTGAGCTAAGAGAGAACTCCCTAGAGAATCCTCCTTCTACTGATGGACCTGA<br>AGATGCAGTTCCTTTCTAAGTGGCCAAAATGGTCCTGCTGGCTCATCAAGTCTTAGAATTTAAGAGACATTCTAAC<br>GTTAATCCAGGCCATCATCCTGAACTTGAGGGGCTACTAAAACACTACCCATCAAAATATCAATGGTGATGACATA<br>GCTCTCCAGGCCAAGTTGTTTTTTGGTTTTTTGTTTGTTTGTTGTCTTTTTTCCTTTTAGGGCCACACCTGTGGCA<br>TATGGAGGTTCCCAGACTAGGGGTCCAAGTGGAGCTGTAGCTGCCGGCCTACACCAAAGCCACAGCAACACCAGAT<br>CCAAGCTGCGTCTGCAATCTACACCACAGCTTACTTCAACACCCGATCCTTAAGCCACTGAGCAAGGCCAGGGATT<br>GAACCCACAACCTCGGGGTTCCTAGTCAGATTCATTTTCCGCTGCACCACCACGGGAATGCCTTCAGGCCAAGTTG<br>TAAGGTGGCCTTTTTGAAAGAAAGTCCAAGCGGTATCAATACCTCTTAAGTCAAAGCCATCATGCATTTTGGTAGC<br>TGCTTGCAGACATTTCTTTCTGTCAGAAGCGTCTCCAGCTGGAATCTCCAAGGCATCGTAGTTTCCAAAAGCAAAG<br>AAGCAGCGTCAAATATTTGGGGTGAATCCACTGATGAATTTGAAAACTCAGAAATGTTTAATTCATTTTGCTTTCC<br>AGAGTTAAAAAAAAAAGACAAAACACCCAAAAGTTTAGCCAGGCACAAATGAATCACCAGCGACTCAGTGTGTTTT<br>GCAGCAAAAGTCAACAACTTGAGTTGTTCCTTTAAACTCTGCAAATATTTTAGGATTGCAAAAATCAGGGTGTATT<br>TCTCATGGAATTCCTGTCTGAAAGTTCTCAAGGTAACTTCCATATCTGGTCATATAAATAATTTAATATTATATCT<br>TGGTCTTAACATGACCTTATTATTTCTGGCTCTAGCCTACCCAGAACTGCAGAGGTATAAAAATCAGGACAATGGC<br>AACATGGCAGGAAGGAAGATAATTAATTAGCTGGAAGGTACTTGAAGATCTAATGACTTTAAAGACGGTATTTAAG<br>GGCTCAGGGATACAGGAAGGGTAGAATATTTTCTTTCTTTCTTTGCTTTTTAGGGCCGCAAGTGTGGGATATGGAA<br>GTTCCCAGGCTAGGGGTCAAACTGGAGCTGAAGCCACCAGCCTACGCCACAGCCACAGCAATGCCAGATCCGAGCT<br>GCATCTGCAACCTACACCACAGGTCACGGCAATGCCGGATCCTTAAGCCAAAGAGCAAGGCCAGGGATCAAACCCA<br>CCTCCTCTTGGATCCTAATTGGGTTTGCTGCCCCTGAGCCACAACGGCAACTCTCTGGAATGCTTTCTTTACGGTG<br>TCAGTGAATCCTACTTTTAATGCAAGCTGGTGACTTGGCTGATAACTAGGAGATTAGAGGAGACTTTCATCAACAT<br>CATTTCATCATGTTTCATAATTACCTGTTGATGTATTCCCAAAACACAACCATTACAGTTGAGACAAGCAGCATTG<br>ACAGAACCACTCTTCCTTTGACATTCATTATTTTCTCCTGGGAAAAGAAAAGGAGAAGGGAAAATTAGATTAAATA<br>CACCCAGAGTGGAATATGGTTTTTTAAGAAGTGCTTATACCAATATCTTTTCTAAAAGGAAAAGTTGATGAATAGT<br>CAACGAGCGCTAAGGAGTGCGTTCTACCTTAATTTGCATAGGCCTACACTGGCAAATTAGCCAAGTCAATGAACTG<br>ACAGGGCCGTCTGGGTTGGGAAGGATACTAAGGCCATTTTGAGGCTCAAAGGGGAAGCATCCTGACTGATCCCAAG<br>GTCCACCGAGATGTGGGAGAGTGACGGGTTTAGTTAATGGTCCCTAAGGGCTCCAGCCGCCCCCAACTCAGATGCC<br>CCACCTCGCATCACAGACTAGAGGAAGCATCCGTTTCCTAGGTCTACTGTCCCTGATATACTGACTATGTACCTTA<br>TCCTCAAAGAAAAATATACCCTGGTCCTTTATTTAATTTCATTTAAATTTTAGGGCCACACTCACAGCATATAGAG<br>ATTCCCAGGCTAGGGGTCGAATCAGAGCTGTAGCCACTAGCCTATGCCACAGCCACAGCCACACTAAGTCCACGCC<br>TTGTCTGCGAACTACACCACAACTCACGGACAGCAACGCCAGATCCTTAACCCACTGATTGAGGCCAGGGATCAAA<br>CCTTCGTCCTCATGGATGCTAGTCAGATTCATTTCAGCTGAGCCACAATGGGAACTCTCACCCTGGTCCTTTATAA<br>TCTAGGCTCTGCCACTTCCCACCCAGCTTTTCCCCAATGCACCCACACAAGTGGCAAACAGTCGGTACATTCGTAT<br>TTCTTGATCGCTGCATGAAATTGTAGTTGAAGAGGGAAGGGATGCTGGGTGGAATAACAGGTTGCGGAGTACTTTA<br>ATTTGGGTGGAGATAGAAAGATATTTATTTCAAATGGAAAGGACAAGAAAAGTGTGGCAGCTAGCCACATATCAGC<br>AATACTCATAAACAAAGAATGTAACAAAAGATAAAGTAGGGCATTACATAATAACAAAGGGATCAATACCAGAGGA<br>AGACATAACATTGGTTAACATATATGCACACGATATCAGAGCACCTACATCTAGAACGCAAATATTAACAGACATA<br>AAAGGAAAACTTGCACAATTACATAATACTAGTAGAGGACTGATTCGCAACATTTTGTGGGTCTTGTGATTTTTTT<br>CTTTTTAGGTCTATTTGTCTTTTTAGGGCCGCTCCCGCGGCATATGGAGGTTCCCAGGCTAGGGGTCGAATCGGAG<br>CTGTAGCCACCGGCCTACACCAGAGCCACAGCAACGCGGGATCCAAGCCTCATTGGCTACCTACACCACAGCTCAC<br>GGCAACACCGGATCCTTAACCCACTGAGCAAGGGCAGGAATTGAACCTGCAACCTCATGGTTCCTAGTCGGATTCG<br>TTTCCACTGTGCCGTGACGGGAACGCCAACATTTTGTGTTTTAGATGTCATAGTTTACATCTTCACAGCTATCCTT<br>CAACTATATAATTTAGTCTTTTAACATCTGTACTAGTTTATTTAAGTGTTTGATGCAACACCTTCACTATATATTT<br>GACTTTTCTAGTCTTATTATTTCCTTTCTGTATTTTCTCATATCTTGTTACAGTTTTTTCTTTTTCATTTAATGAA<br>GACACAAACATTTCTTGCAAGTCAGTGTAGTAGTTGGAAACTCAGTTTTTCCTTCTGGGAAACTCTTTAGTCACCC<br>TTCAATTTGGGGAGATGACTTTAGAGCTTCCCAAGGGATGAAGATAGGATGGGAAAGGATGACAAGGGCCGTGAGA<br>AGGGATGAGAATATTTTGGAAACAGCATCTATACCAGGCAGACAAGAGAAAGAGCTGCTCGTGTTTGAAAAAAACA<br>AAAGCAAAAAACCTGGACAAGAAAAAAATAGTGACTGACACTGTCCCCCTTGAGTGGCTGGTGCTAGGCAGTCAGA<br>AGGGGGGCAGAGGCAGTCAGAACCTGGAAAGGTATGGAAAGTAGGGTGGGGAATCCCAAAAAGCATCTAAAGCTGG<br>AGAATCCCCTGATCCAACTTCACCTAGAGAGACCCATCTGGGTGCTGAGTGTGGAGAATGGAGAAAAGGACAAGGG<br>CAGACCGTTCTCATGACCATAAAGAGGAGGTGGCCTGGCTCAAAGGGTGGCTTGATTCAAAATATACTTTGGGAGT<br>TCCCGTCGTGGCGCAGTGGTTAACGAATCCGACTAGGAACCATGAGGTTGCGGGTTCGGTCCCTGCCCTTGCTCAG<br>TGGGTTAAGGATCCAGCGTTGCCGTGAGCTGTGGTGTAGGTTGCAGACGCGGCTCGGATCCCGCGTTGCTGTGGCT<br>CTGGCGTAGGCCGGTGGCTACAGCTCCGATTCAACTCCTAGCCTGGGAACCTCCATATGCCGCGGGAGCGGCCCAA<br>GTAATAGCAACAACAACAACAACAACAACAACAAAAAAAAAAAAAGACAAAAGACAAAAAGACAAAGAAAAATAAAA<br>TATATACTTTGACAAATACCATATGATATCACTTATAACTGGAATCTAATATCCAGCACAAATGACCATCTCCACA<br>GAAAAGAAAATCATGGACTTGGAGAATAGACTTGTGGCTGCCCGACAGGAGAGGGAGGGAGTGGGAGGGATCGGGA<br>GCTTGGGGTTATCAGATACAACTTAGATTTACAAGGAGATCCTGCTGAGTAGCATTGAGAACTATGTCTAGATACT<br>CATATTGCAACGGAACAAAGGGTGGGGGGAAAATATACATGTAAGAATAACTTGATCCCCATGCTGTACAGCGGGA<br>AAAAATTAAAAAAAAATATATATATATATACTTTGGAGAGAGAATTGATAGGACGTGGTTGGTAATTTTGTTATCA<br>GAGATGAGACAAGGAAGACCCAAGATTTCTGCTTAAGCAGGGGGGTTGTAGTATTTTCTCAGATGGGCTGGAGGAG<br>GAACAGGCTTGGAGGATAATAATCATGAATTCCCTTTTGGACGTGTGAATGTCGGGGAGTGTGCGAATACCTAAAA<br>GGGGACAGGGAGACAAGTGGACATTCAAGTCTAAAGTTCATCAGAGAGATGTAGGCAGACCATGCAATCGGAGAAG<br>TTGTTCATGGACCAAGGAACGTATCGGATCTGACGTGAAGGGAACGAATTTGATTACCCAGGAGAGAATGCAGAGA |

TABLE 9-continued

| lists sequences for the disclosure |
|---|
| GAGAAAGAGGAAGAGGAGGATGCTGGGCTGAAGCTTTAGAGGTAGGATAGAGGAGGGCCCAGAAGGAGAGGACCAG<br>AAGGTAGCAGAGACAGAAGAGTGGACACCTGGGAGCCAATGTCACTGCCTTTGTGAAGCCACTTCCCACCCCCACC<br>CTGACCACGGCTGAAGCCCTTTTCTCTCCTCCGGCCCCCATCCCTCTATTCCTTTGCTGTACACATCGCCCTGGGA<br>GTCGGCTCACCGGATAAGACCTGCATTTTGCTCTGCCTCCTCTACCTGCTTGTTTGAGCTTCCTGAGGGCAGGAGG<br>GATGACTTCTTCGTCACCCCTGAATTCCCAGTGCCCCACAGAGAGCAGAGAAGGCCGTCAATAAATAATGAGTGGT<br>TTGAGCTTCCTGAGGGCAGGAGGGATGACTTCTTGATCACCCCTGAATTCCCAGTGCCCCACAGAGAGCAGAGAAG<br>GCCGTCAATAAATAATGTGTGGGAGTTCCCGTTGTGGCTCTGTGGTTAACGAATCTGACTAGGAAACATGAGGTTG<br>TGGGTTCCATCCCTGGCCTTGCTCAGTGGCTTAAGGATCCGGCGTTGCCGTGAGCTGTGGTGTAGGTTGCAGACGC<br>GGCTCAGATCCCGTGTGGCTCTGGCTCTGGCGTAGGCCTGCAGCTACGGCTCCAATTAGACCCTTAGCCTGGGAAC<br>CTCCATATGCCGCAGGACTGGCCCAAGAAATGGCAAAAAGACAAAAAAAAAAAAAAAAAAAAAAAAAATGACGTGTG<br>AATGAAATGAGAATGGCACTGAGATGTGTCCTTTCAGGGGACGGGTTATTCTCCAAATATTTGCAGAGAGGGTTCT<br>GAGGTGACTCCAGGCTTAGATCTCAGGTGCTCCATCACCTCTGTTGTGAAATCCAGTTAAAGAAGAGAAAGTATGG<br>GATTATCAGCCATGTCACTCTATTCCTTCTTGCTTGGAAAGTGAGCTCTGTTTGGAAACCTCTGATTCAATCGCCA<br>CCTTTCGGATACAATCATGATAGGTGGTGTTCCAGAGACGGTGAGAAGATGGGGAGATGGAGCTTCTTTCCTGTGA<br>GCACCTCAGGTCCTGGCACAAACAGCCCGGGGCCCAGGGCAAAGTTACGAAATGCACGGGGCTACATGCAGCTCGG<br>CCCAGATGCTGGAAAAAGCCACTTGACTCCTACACCAACAGCATTAGCACTGAGTGCGAGGAAAGGCCTGGGTTTG<br>GGAGCAGACAGATCGGGGTGGAGACTGTGGCCACTGTGGCCATGCCTCTCTGCCGTTGTCTTCACTCCCAGAGAAG<br>TGTGGGTGGTGAGAGAGCTTGGGAAGGAGGTGGGGTCTGGAGACACCCACAGACTGGGTAACCCTGAACATGGAGC<br>AGTTTCTCAGACCCTCATCCAACTCCAAGCTCTGAAAACCAAAAGCCTGTTTATAATTCAGTTGGCATCCAGGCCC<br>TGACACGAGGCTATTTATAATCTTTATCACTTAGTGAGACTGTTTAAACATTTCTTTGCATAAATATTGATGTACA<br>TTGTTATGTGCTGTTGCTGCACTGGAGGCGTTACATAATATAGGATAAATATTCTGCATTTGAAAAATTCTAAATT<br>CCAACATATCTGGCCTTAGGCATTCAGGAAAGGGATGGTGGACCTCTAATTGATCACATTAGATGGGTCTCCTCAT<br>CTTTAAAATGGGAATTAAAATGGTGATGACTGCAAGAGATGGTGTCCATAAAATATTTAGCATCATGCCCAGCATC<br>ATATAAAAGCTCAAAAACTGCTAGTTTGTATTACTGGTATCCATAAAACAGGCTGTTGGGAGGATCCAGTGAAGAC<br>AGCACAGCGCCTGGTACTTAGCAAGAGCTCAAAACGTATCGGAGGGAAAGGAATAAGCATTTTGGAATAAGAATGT<br>GTTAAACAATAAAGTACAAATTGATGCAAATTAGGGCCTCTAAAGGTTTATCCATCTGTTCTATGCTGCAGACTGA<br>CTAAAAGCTCCTGGGAAATGCCACGCAACTTTGATTTTCTTTGATCAAGCCCAGGCCATCCAAAGCCTTGTCATCC<br>CCACCTGCTGAGGATCAAACCCTGTGTAAGAAATGCGAAAGAGAGAAACACAAACTCCTGGCAGAGAACGGATCAG<br>GGAGAAGCTGGTATAAAATCAGACACACCTCCTAATCCTTTCTCCAAAGGCAAGTGTTTTTCTGTTTGTTTTGGTT<br>TCAGGGTTTGTTTGGGTTTTTTTGTTTTTTGGTTTCTTTTGGTCTTTTTAAGGCCACACTGGGAGTTCCCCTCCTA<br>GCTCAGAGGTTAACAAACCTGACTTGTATCTGTGACCATTCAGGTTCGATCCCTGGACCCGCTCAATGGGTTAAGG<br>ATCCAGTGTTGCCATGGCTGTGGTGTAGGTCGCAGATGCGGCTTGGATCCAGCATTGCTGTTGCTGTGGCGTAGGC<br>TGGTAACTACAGCTCTGATTCAACCCCTAGCCTGGGAACCTCCATATGCCAAGCATGTGGCACTTAAAAGATTAAA<br>AAAAAAAAAAATTAAGGCCACACCCAAGGCATATGGAAGTTCCCAGGTTAGAGGTCAAACTGGAGCTATAGCTTCT<br>GGCCTATGCCACAGCCACAGCAACGCCAGATTCAAGCTGAGTCTGTGACCTCCACCACAACTCATCACAACATCAG<br>ATCCTTAATCCGCTGAGTAGGGCCAGGGATTGAACCCTTGTCCTCACGGATACTAGTAGGGCTCATTACCACTGAG<br>CCACAATGGGAACTCCTTTGTTTCATTTGTTTTGATTTTTTTTTTTTTTTTTTTTGGTCTTTTCTAGGGCCGCA<br>TCCACGGCTTATGGAGGTTCCCAGGCAACGCCGCATCCTTAACTCACTGAACGAGGCCAGGGATCAAACCCGCCAC<br>ATCACGGTTCCTAGTCGGATTCGTTAACCACTGAGCCATGACAGGAACTCCTGTTTTTTTAATTTCAGAAATTAGC<br>ATCAGAGACAACTCTTGAAGCCCCCCCCCCCTTTTCTTTTCCTCTGGACCGTAAACATGGCTTGAATCTGCTTACT<br>TTTCGCTGTGGCCAGGCATCACTCTTAGAGACTTACAGTTGGAAGCCACCCAAATGAGCCAATATTGCCTCCTTTT<br>GAAAAGCACTGGGAAGGGGTATATGCAAGCTTTCTGGAATCTGGAACCCTAGTGTCTCAGGAAAGAAGGGTTGCCA<br>GAATGGCCAAAGGGTTTTTAAAACATTTTTTTTTTTTCTCTGGATTAAAATGAGGCATTTGGCAGCCCATGTGGTC<br>TAAAGCCCTTCACGGATGTGTTTGTCACAGAATTTTCTAACTCTCTAATTCTCAAGATTGGTGGTTGACTATCTTA<br>CCCACCAAATAGGAAAAGTGGGGGTTGCTTCTACATTTCTCATGGAAGAGGGAGAGCACAGGATTAGAGCCTAGAG<br>AGCACTAGCACCCTGTCTTATAAGGGAGAGTGTAACCACCTCAGCACCACCTGGGCCCCAGCCCTCAGAGGATCAG<br>GTGAACCCAGCGGGCCCAGTTCCACCTGAGCCCTCCCACCATCCCACAGGCCCTCCTGCCAAGGCGTTTGCCATTT<br>CTCTCTGCTCCTGGGCCACTCCCACAACTCAGCCCCTGCAGCGGTTTCCAAAAGAAACCACTTGCACCCCCACTCC<br>CGGGCCTCGTGCAGACTGTGCTAAAACCCAGTGCATTTCCCAAGGCAGGGCCACGCTGGAAAGCCTGTCATTTCTC<br>CACCTTCCTCCTCCTCCTCCTCCTCCTCTTCGGCTTCTCCATCCCTGGGGTATCAGACTCTTCCCCAAGGCCCATA<br>AATTAATCCTTCCTGACCCACCCCTAACTTGTCCCACACAGAACGGTACACACACCCCCTCCACTTCAGAGAAGCT<br>CATGGTTTCACCGCAACTGGTCCAAGTCAAGGTTTTCCTTCCAGACAGAGTTCCACTCTGAAAGGAATTCTAGTGG<br>CCCTGTTTTTCTCCACCTCGTGTCAGGGGGAAAGGTGAGCACCTCAGCTGAATCACAGAGCTCTCAGAAGCCCTGG<br>AAAAGCCATTATCTTGAGAGAGCAGCGAGCAAGCAGTGACAGAGGAAACCAAAGCTTCCAGCAGACTAAAGAATCT<br>TCCTCTCTGCCTGTGACTCTTGCCCTGCCCCTGGAACCCATCCTGCCCTGCTAGCTCCACAGGACCCTGGCAAGGG<br>TCAAGAAAGTCAGGTAGTGATAAGTGCAGCAAATGAAACACAGTGCGGGGGAGGGAGCCAAGGTGGGGAAGCCGCA<br>GGAACTGACTGGGTGTTACTCACCCTGGACAAAAACCTCCTATTTTTAGGCCTAACATTTAGATCCAGCATTCCAG<br>GCAGAAATTAGGCCGGTGCTGGGACTGGAATCTGCAGCCCTACATGCACTTGCCCTGGGCAAGTCCTCTGGCTCTG<br>AGCCTCTACTTACACAGACCAAACGGAGCTTCAAACACCCTCCTCCAGGGCTCTTGAAAGGACAAAAGGAGACCCC<br>GTCTATGAAGCATGTTGTGCCTGATGCTCAGTAAATGCTCCACAAATGCAGCCAGAACAAGGGCGATGCTTTTTAC<br>GGGGAGAGATTCAGAAATGTGTGGCTCTGACGGCCGAGCTGTGGCTCTGTCTGAGAGGAGTCTGGGCCCTCCAGGG<br>CAGCACCACACAGAAGGGTCCAGGGCGAGCCCCCCACGCTGTTGTGACTGTTGTTGGGGCCAGCTCAGGGTCCCCA<br>AGCGCATCTCGTTTGCCTCTATCGCCTGGCGCGCATGTTGGGCAGGGAAGGAAAGTCAGGCTCCAGGGTCACCCCA<br>GCACCCACACAGAGCGGGTTTGTGAACCACACGCAGCTTTCTCTGGCCTCAGTCTCCCCGTCCTTTGAAACATGTC<br>CTGTGGGCTTAACTTCCCTGAATGAGCCAAGACCTGTATGAGAAGGCAGCCACAGAGCTGGAAGGCTCCTTTTATG<br>AGGACAGGTTCACTGGAGCTCAACTTGCTGCAGTGGCCACAGATTCCTAGAAGTGGTGATCAAAAGATAGGATTGC<br>CAGAGTTTCCGTCATGACGCAACGGAAATGAATCTGACTAGGAACCATGAGGTTGCGGGTTCGATCCCTGGCCTCG<br>CTCAGTGGGTTAAGGATCCGGCATTGCCATGAGCTGTGGTGTAGGTCACAGACGCGGCTTGGATCCTGTGTTGCTG<br>TGGCTGTGGTGTAGGCTGGCAGCTGTAGCTCCGATTTGACCCCTAGCCAGGAAACTTCTATATGCAGCGGGTACGG<br>CCCTAAAAAGCAAAAAATAAAAAAATAAAAATAAAAAAAGAGATAGGATTGCCCACAAAATGTGTTGAGCCCTCAG<br>GCCACTTCACCCAGAAGCCTCCGGGTCAGGCCCCCAGGCAGGCCTGGGGTGTGGAGTGGGCAAGGCCCAAATGCTT<br>CCTCCAGGTGAGGTGCTGCCCCTGCCTGGGGGAATCGTTCCAGCCTGGGTGCCTGTCCTGGGGCTGCAGGTGGAGC<br>CCAGGTACTGACCCTGCTCCCCGCACCTACCTGGGTCCTAGGAGCAACCTGCCCCATCCAGGTAGACCTTGCTGAG<br>CTCCTTGGAGCCTCTCACTTTGATCCCAAGGAGAAGGAGCTGAACATGATGCTACTTGGCTCCCTGCTCACAGGTC<br>ACGATCCAGACCTCACAATCACCTGGTGGTGCACCCCCCACTCCAGCCAGGATCAAAGAGCTGAATTCTCCAGGAC<br>TCTGGCTGGACCCACCTGAGCAAGAAACTGCCAAAAGATGGGGCGTTTGAAGGACCTGGAGCACCTACACACCCCA<br>AGCTTTCCTCATGGTTTCAGTTACAAGATCTGTGTTTGGAGACCTCCCCTTGGGGGCAGGGACCATGGAAAAGTTC<br>CAGCTGCAAGCAGACCAGCTGGGAGTGGAAATCATCTCCTCGGGCTGCACCATCACGGCCCTGGAGGTCAAAGACA |

TABLE 9-continued

| lists sequences for the disclosure |
|---|
| GGCAAGGCAGAGCCTCAGATGTGGTGCTTGGCTTTGCTGAATTGGAAGGGTACCTCCAAAAGCATCCCTACTTTGG |
| AGCAGTGGTTGGCAGGGTGGCAAAGCAAATTGCCAAAGGAACATCACGTTGGATGGGAAGGAGTATAAGCTGGCCA |
| ACAGCCTGCACAGAGGAGTCAGAGGATTTGATAAGGTCCTCTGGACCCCTTGGGTGCTCTCAAATGGCATCAAGTT |
| CTCGAGGGTCAGTCCAGATGGTGAGTTAAAAGTCTGGGTGACATACACGCTAGATGGCAGGGAGCTCATGGTCAAC |
| TCTCAAGCACAGGCCAGTCGGACCGCCCCAGTCAATCTGACCAGCCATTCTTATTTCAACCTCGTGGGCCAGGGTT |
| CCCCGAATATATATGACCATGAAGTCACTATAGAAGCTGATGCTTTTTTGCCTGCAGATGAAAACCTAATCCCTAC |
| AGGAGAAGTTGCTCCAATGCAAGGAGCTGCATTTGATCTGAGGAAACCAGCAGAGCTTGGAAAACACCTGCAGGAG |
| TTCCACATCAATGGCTTTGACCACACGTTCCGTCTGAAGGGATCTAAAGAAAAGCAATTTCGTGTACGGGTCCATC |
| ATGCTGGAAGCGGGAGGGTACTGGAAGTGTATACCACCCAGCCTGGGATCCAGTTTTACACGGGCAACTTCCTGGG |
| TGGCACGCTGAAAGGCCAGACTGGAGCAGTCTGTCCCAAGCACTCTGGTTTCTGCCTCGAGACCCAGAACTGGCCC |
| GATACAGTCAATCAGCCCCACTTCCCGTCTGTGAGTTCAAACACACCCCTTGGTTCTAGTTTTCTGTGGCCTAAGG |
| AAATGTAAAGATATGACCTGTTCCAGGGTCAGGCTGGAAGCCCCTTCAGGAACCTGTCTCCTACGCAGAGATAAGA |
| TGAAGATTTAGAGGTTTTAAAAGTGATCCTGTGTATTACTCAGCCATTAAAAGGAAAGAAAGAACGGCATTTTTAG |
| CAACAGGGATGGACCTAGAAATTATCATGCTAAGTGAAGTCAGTCAGACAATGAGACACCAACATCAAATGCTATC |
| ACTTACATGTGGAATCTGAAAAAAGGACACAATGAACTTCTTTGCAGAACAGATACTGACTCAGAGACTTTGAAAA |
| ACGTATGCTTTCCAAATGAGACAGGTTGAGGGGTGGGGGGATGCACTGGGGTTTTGGGATGATCATGCTATAAAAT |
| TGCATTGGGATGACTGTTGTACATCTATAAATGTAGTAAAACTCATTAAGTAATAAAGAAAAGAATGTAAAAAAAT |
| TAAGAAACAGAAAAAAAAGTGATCCTGTGAATTAAAATTACACAAATGGTAGTTGTCATGATAATCTGAATATTGA |
| TTTCTTTCACAATGACTGGCTCCAGGCCAAGTCTAATGGTCAGCTCTATTCTCTGTGTAGTGAAAAAGACCCAACC |
| ATCAATGTCATCTTCTAAGCCCTGACCCTAATCCAGAAGTGGTACCCAGATCCTTGTGTTGGCTCTGTCTCTCCAC |
| TCTGCTTCTTTTCACTCCTTCTTTCTTTGATCCTACTCATTCCTTTTTCCCTTCCTCTTCTACCTCATACCACCTT |
| GATCTGTGCAGCACTTTGGAGTTTTCAGAGGTCACTGAGCTCATTCAACCTGGTGGTAGAGGGACCTCTCTGCCTC |
| AGTAAAAGAATAGATGATGAAGTGAGCCACCTGAGAATTAGGGGAGGTAAATGACCCACCTAAAGGCGCACAGCCA |
| GGAAAAATTTAGCCTGGATTCAAGATCAGGTCATGCAAATTCAAGTCCTTCTTTGCCTCCACTTCAGTCTTCCAGA |
| GCATTCCTGGAGTCATTAATGGGAAAAGGGGGGGTCTGACCCTTACTCTGTTAAAGCCAGACCTTCTTTCCAGATA |
| TCACTTTTATAAGAAGCCCTAGTCAGAGTTTAAATGTATCTCTGAGCCTTATAAATAGTGTGACTTAAAATACAAG |
| ATCTAAATATCCAGAAAAAAAAAAATCTGTGAATTTGATTCTCCGCCTTTGGGGTTACTAAGAAAGCCCAGCCTAGC |
| CAAGACATGGGAAGGAAGCCGCTGGAGACAAGAGCTGTGTGAGTTCGAGGAGAGGGCCTTGCTGGGACTGCACGCT |
| GCACCGAGAGCAGACTGTATTTGGTATACGAGGCGGAGTTCCCTCCTCTCCTAAACAATTGAATCACGAGTGATGG |
| GTTTGTGTTGATGGTTTTTAAAGAAATGTTATCTTATACTCCTCTACACTAATAATCAGTTGAAATAAAACCAAAA |
| TGTGCACCCTCAGAAAAAAAAAAAAAAGAATAAAAAGAAACTGCCAAAAGACTGACAGCACTAATAACAAGTTATGA |
| AGCTGAAAGAAGCTTCTCAAAACTCCCAGGAATAAAAAGCAACCACTGATTAACCATGCTAGAGGCAGAACTGATT |
| TGTCTTCCTTTTTGTCTCTCTTAAAAATGATACTACAGGAGTTCCCGTCATGGCACAGCGGAAACAAATCCAACTA |
| GGAACCATGAGGTTGCGAGTTCAATCCCTAGCCTCGCTCAGTGGGTTAAGGAGCCAGGGTTGCTGTGATCTATGGT |
| AGGTCACAGACACAGCTCAGATCTGGCGTTGCTATGGCTGTGGCGTAGGCTGGCAGCTACAGGTCTGATTAGACCC |
| CTAGCCTGGGAACCTCCATATGCCATGGGTGTGGTCCTAAAAAGACAAAAAGAAATAAAAATGATACTACAAAAAT |
| CATCAGATAAAGAGATAGTTCAAAGTATGCAGCCAAAATATGAGAGGTACATCAGACAGCTGAGTAATACTAATTA |
| TTTTTATATTATTTTCACGTGTTATGGTTGTTTTTCTGAATTTGGTCCTATTTAGAGTATTGGTCAGTCTGTGTTA |
| GCTGTTGGGATGGCACCTCATATTCTAAATGCAGTCAGCCTTCTGTATCCATGGGTCTTACATCCACAAATTCAAC |
| TAACCACGGATGGAAAATACTCCAAAACATCACATTCCAGAAAGTTCCAAAAAGCAAAACTTAAATTTGCTGCATA |
| CAGGCAACTATTTGCGTGGCATTTACATTGTATTAGGAATTATAAGTAATTGCAAGGTGATTTAAAGTATATGGGA |
| GGGGAGTTCCTCCGTGGGCTAGCTGGTTAAGGATCCAGTGTTGTCACTGCTGTGGCAAGGGTTCGATCCCTGGCCC |
| ATCAACTTCTGTATGCCATGGGCACCGCCAAAAAATAAATAAATAAAATATATGGGAGGCTGTGGGTTATGTGCAA |
| ATACGATGCCCTTTTGTGTAAAGGACTTGAGCGTCCTGGGATCTGGTATCCGTGGGGTCCTGGAACCAATCCCCTG |
| TGGATACCCAAAGACGACTGCATTCAATCCCCAGCCAAATCATGTGTCTGCAAATTTGTGTTCCCTTTTCTTAAAG |
| CAGGCCCTCGATATTGAATAAGCTTCCTGCAGCACTTGGATGCCCCCCAGCTGAACCAGACCAGGCCTCAGGCTAA |
| ACGCTTTACCAGAGGTTTCTCAGATAAGTCTCACAACGTCCTGTGAAGTCATTCTAGTGTTATCTCCACTTTACAG |
| ACATGCAAATGGAAGCTCAGAAAGGTGAAGTGACTTGCCCAGTGTGTCACACAGCATAAAGTGATGGAGCTGATAT |
| TCAGGTCCAGAGAGCTGGCCTCAGGGCCCACCCTTTTAACTATTCTCAGTAAACATGAAGACTCACCCATGGACTA |
| ATCACCCAGGGATCTTTGGCACATCCTCTCATTTTGCCTTTCACGATGATCACTTAGCAATTGACCCAAAGCTAGC |
| CAATCATGGGCTAGACTCAGCAGGGGCCAGCTTCTCCTCGGCCCAGCTGGCGAGCATTGGCTCAACTCCTCTGCCA |
| TTTCCAGGAGCCTCCTGCGTGCCTGGTGTGAGCCTTCCCCATGCACGCCATCCTATTCACCCCTCATCATGGTCAG |
| TGCGGGGGCTTTTTAGCTGAGGAGACCGAGCTTTAGCAAAAGCTGAGATCGCTGGGCTCCCCCACAAGGGGGGCGC |
| TGAGTTTGAAAAGCAGACCCTCTGCCTCCCAGGCCCAGCTCTTGGCCGGGGGATGGTGCTGGGGGGAAGGAGGGAG |
| AGTCCTGCTTTATCTAAAACCTCTTTAAATTGGCTTGCATTACAGGGAAATGCTCCCTGTTGGAAGAAACATGGTA |
| TAATTTGGGGGGCAGGGGTGGGGGGGGAGTAGTGCACGGAAGGCTGTTTCCAGTTATGTTTTTCATTATAAGGGTC |
| AAAGCAAACACAGACGCAGGAAGCTAAGAGACAAGCCTCAGACTAAACATACGACCAGCTGTCGCTCCAGCCATCA |
| CAGACCTGTTCTCGGAGGGACATCTTGTAGGCCCCTTTCTTGAATCCCCTTCAAAAATCTGAAGCCTGGATCCAGC |
| CAGCTTCTCCTTGCTGCCTGGCTCAGAAATCATGGTGCAAGAGTTTTTCCAAGAGAAATAGGGCGAGGTACATGAA |
| GGATCGGTGCTGCCCTGAGAGGGCACTATGTCCGCCCCCAGCACAGGTCCCGGGCCTGAGACTCGTCCTCCTGGCC |
| CCACAATGGCACTGTGTGGCCCACACAGAGAACCCCAGGCTGTAGCCACACCCCGTGAGGTCCTGCCGGGCAGCCA |
| ACGAAAGCAGAACCAACAGTGACTGAGCCAGCATCCTGCCAGCTCCCACTCCTAGATCCGATGCCGGGGACTGGAG |
| GACTTTGTCTTCTTTCAGAACAACTGGGGGGAGCAGCAAGAAGTCAGGGGGAGAGGGGGGCTCCTCTCTCCACGCT |
| GCAGCCAGCTCATGATACCCACCCCCCCGGTGACCCCAGCAAAGCGGAGGCAAATCATTTCAACGTTTCACGTACC |
| TCATCCTCTGCTTCTCTCCCCCCAGAGTAAAAGGCGAAGCAAGTTCTAGTGAGCTCTGCTCTGCAGAAGGAGGCAG |
| GGCTGGGAGGAAGGGAAGGTGCTGCGTTCCAACTCCTGTCAAAAGAATAAACAGCGGTTTCACGAAGAGGAGCGCA |
| GACGGATCCCACAGCAGCCAGGGGCCTTGTTCCTCCTTGCTCGCCCTGGGAAGTGGGCTGTTTATCAGGCCTGTTG |
| ACTCAGAGCTGCATGCCAAGGCAGAGACGTCTCTCTCCGGCCCAGGATCGGCCCGGCCTCCTTCACTAAGCGAAAC |
| TACAGGTCCAAACTAGGCCTGGTGGTGGAGGAGGGACAGCCACCACCCTTGGGAGAGACACACAGGCCGCCCACAT |
| CACCCACTCCTCGGCGAAAATGAGAACCATTCTGAACCCAAACCACCCCAAATGACAACTAGCAGGGACAGCCAAT |
| GGAGAATTTAAAAAGAAGGGGGCAGAAAATGGAGAGGGGTGGCTAAAGGAGAGCATCCTCAAAACTCCCGTTGAAA |
| TGCTACCTTCCGAGCCTCTTGTTCGCATCCTTTAGGCTTCAGAAGTTGTTCTGTTTGAACACTATTTTTATAGAAT |
| GTTCTGAGATCTCCTGCATGGCAAGCCAAGCTATAAGAACTTCAAAAGGTCACTGAGGCCCAACCCAACTCTTTGG |
| CTGAATAATGCTTAACCCTCCCCACACCCACCTCCTGCTCCCAAAATAGAATTTCCTAGCTGGAAGAGACCTCACA |
| GCAGTGGATTTGTAAATGTCGCAACAGCTAAAGCTTTAAAAAAAAAAAAAAAAAAAAATGAAGTCATTCTCAGAACC |
| CCACTATGTAAAACAGAGGACACAGGGGGCTTTGGCTGAAGGAGGGAAATGAAGTAAGTAGGGGCTCAGAGCCCCC |
| CCACCCATTCTTCCCAAGTGGCCCCAGACACTTCCTGGGAGTAGAGCCTAGAAACCCCAGACTAAGGAGAAGGGGC |
| CGAAACCTGACAGAAAGGAGCCAAGAACTGCCCCCTCAGCTTCCAGCGGATGGATGCCTAATTTAGCTTCTCACTC |

TABLE 9-continued

| lists sequences for the disclosure |
|---|
| CTGTTCTGGGGAAGAAATTCACCGCCCCCTCCTCTGGGGCATGAGCTAGTTGACCACAGTCTTCAAGATCTGCTTA ATAAACTACTGAAATCCTCCCTGCTGGCATCTACTAAAGCTGAACCAACCACACCTCATGTTCCAGTCATTCCGCC CCAGATTAATACCTGAAAGCAAGTGCATTTAAGTTCAAACAGAGACGTGACCTGGGACCAAAAGCTGGAAAAACCC CAAGGCCCATCATCAGCCAGATCAGGTGTGGTCCAGGTGAGGGTCACACACATCCGTGAGAAGGAACCAGCCACAG CTGCTGACATCAACAGGGTAAATCTCACACATGGTACTGAGTCAAAGCAGCCCTGGATGCTTGCATTTATTTAACG TTCAAAAATAGACAAAACCGGGAGTTCCCGTCGTGGCGCAGTGGTTAACGAATCCGACTAAGAACCATGAGGTTGC GGGTTCGGTCCCTGGCCTTGCTCAGTGGGTTAAGGGATCTGGCGTTGCCGTGAGCTGTGGTGTAGGTTGCAGACTC GGCTCGGATCCCACGTTGCTGTGGCTCTGGCGTAGGCTGGTGGCTACAGCTCCGATTCGACCCCTAGCCTGGGAAC CTCCATATGCCGCAAGAGCGGCCCAAGAAATGGCAAAAAAGCCAAAAAAAAAAAAAAAAAAATAGACAAACCCAGGG AGTTCCCATGGTGGCTCAGCAGAAACAAATCTGACCAGTATCTACGAGAATGCAAGTTCGATCCCTGGCCTCACTC AGTGGGTTAAGGATCCAGTATTGCCACCAGCTGTGGTGTAGGTTGCAGATGCGGCTCGGATCCCATGTTGCTGTGG CTGTGGTGTAGGCCAACAGCCACAGCTCCAATTGGACCCCTAGCCTGGGAACTTCCATATGCCCCAAGTGTAGCCC TAAAAAGACAAAAAAAAAAAAAAAAAAAGACAAAACCAATCTGTGGTGCCAGAAGTCAGAGTGGGAGTGGTAGAGAC TGGGAAGGGGAGGCTCAGAGAGCTGCTGGGGGAGGGGGGGGGCTTGTCATGTTGTTTCTCGAGCCAGGTAGTGGTT ATGCAGGTGTGTCCACCTTGGGAAAATGCCTCACAAACATTCCCTTTCAGTGTGTGTGTTAAAAACAAAGATGCAC AGAAATCTTCCTGCTGGAAGCTGCCTTCTCTTGGGAATTCTGACTTCCCCTGAGTCTACAGGGTCTCAGGGCCACA GGGTCATGGATAGACCCCGTTTTTTCCTTCTCTTGGGTTCAACGCCCCAATACCAAGCACCACAGAGCACCTAAGT ACGGACTCAGGGAAGATCTTTCACATTAAATGATGCAGGCAGCTGGACTGTGGTCAACTGGGAGGGAAAGTTCACA GCATTTGGAGGCTCAGGAACTGGGCTAAGATAAACTGGTCCTTTCAAGAAGCAAGCACCCAGGAGTTCCCATCGTG GCTCAGTGGTTAACAAATCTGACTAGGAACCATGAGGTTGCGGGTCCAATCCCTGGCCTCGCTCAGTGGGTTAAGG ATCCAGTGTTGCCGTGAACTGCGGTGTAGGTTGCAGACGCGGCTCAGATCCCACGTTGCTGTGGCTCTGGCGTAGG CTGGCAGCTACAGCTCCAACTTGACCCCTAGCCTGCTGGGAACCTCCATATGCTGCAGGAGCGGCCCTAGAAAAGG CAAAAAGACAAAAAAACAAAACAACAACAACAAAAAAAAGCAAGCACCCATCATGGTTGCCACCTTCCAGTTTACA AAGCAGCCTCTCTCCTTTAACTCAGCAAATCCTCAGGCTCACCCGCCCCGGGTCAGGGAAGGGAGGGAGGCACTGG GAGCCTCTGTGACTTGCTCAAAGTTGCCGGCTGGTGGGTCTGATGCTGCCCTTCCTCCTGAGCTGCCTCTGGGGAA CACCCTACAGGTTCGTGGAATTAGAGGCTCCAGGCTCATGAATCAGAGCACGACAGAGTATGCAAACTTGGAAGGC AGAAAATTCAACTTCCAGAGGATCCGACATGACCTTCCTCCTTCTCCGACATACCCTGATGCCCAGACTCTCAAAA CAAGGAAGCATGTACTTCCGGTCATTCCTTCATGGAGAGGCAGGGAACTGTAGCAAGTGAGCCTCAGGTCTGCTGA TCAAAGGAGGCCAGTGGCCATCCAGGTAGGAGTTTGGCACGTTTCCCAGCCCAGCCAGGCCGACTAATCTCATCAC TCAATGTTCCCCAAGGCCCCTTCCAGCCCTAACAGTCCATAGGCCTGTCAGATGACAGCCAGCATTCAGAGCCTGT CCATCTGCCATGTCCCCTGCAGAGGAGTGCAGGGCCTTGGAGCTGCGGCTCAGCAGCTGCAGCCCAGGTGTGAAGG GTCCCGGCTTCATGCCCCAGACCCCTTCCACCTGAGAAACACAAAGGTCCGGATTCCCACCCTGTGGGAGAGGGAG AATTAAGTGTTCTTGGCAAAAAGTGCTACAGATACAAAGATTGCAGCTGTCACTTTTAATCCTAAATACGTTTAGG GCAGGTATAAGACATTCTTGCTGTCACTTGTGAGTGATGGAGCAGTTTAGTTGGTTTCCTCTTCCGTGTGGTGAGG ATAATTATAATCCCCACCGCTCGGGGTGGGTGAGGGGCCTAGAGCACCGTGGTTATGAATGTGGACTCTGGGCCCA GGCTGCCGGAGTTCGAGTCCCAGGCCTGCCCATGTGCGATCCTGGGCAATGTGCTTAACCTCTCTGTGTCTCTGTT TCTATGGCTGCACAATGGGAACAACAGCAGCTGGATGGTAGCTGGCACATGGTAAGTGTCTAGAGATACGTATTAC CCGATATTGCAAGAATTAAGGAGACACGCCCGGAAAAGTGCTTGAGGTGCTCAATCATTGTCCGTCTCTGCTGTTC TATTAATCCGAGGCTGCAGCTCCTTGGAGTTTACATTTGTGTATCAAATAGTCATTTTGACCACGTAACCCTGCAG GTGGGGAAAGGTACGGAGGGAAGGGTTCCTGGCACGACGTTTCCGTTACTGTTAAGTACTGCCCCCCACACACGCC TGTGAGTATCAGAGCTGAAACGATCTTGGCAAAAGCCCACATAATAAATAACGGCAGTCAAGAGAGGTTGCATCTA TAAGTCTATTTCCTTGAGAAGAGCTGGAAAAATGAAATCATGATGACTCTTCCCAGGCCAGTACATTGCTAATCAT CTTGAGATCTGCCTCTGCCCCAGGTAACTCCAGGACAGACTCCACCAAAGCCATGCTGAAGCACTCCTGCCTCTGC AAGCATCCATCCTGAGCCTCAGCCCTCCTCCTGCACACCAGGAAGTCCCTCTCTGGGGCTCATGTCAGTCCTTCAA GCTCTATAGGTCAGACTCTTCCTAGAGAAGAAAGAAGCTGGCTTTGTTGACAGCTGGGGAGATGTGAGGCGCTCCC ACGGAAGGGCGAGGCCCGGGTACTGATGACACCCTGGGCTTGAGCACCAGCACAGGTGGCTGGAGGATTTCCCCAC CCAAGGAAACCGCTCTATTCCTACCCTCTCTTGGTCCTTCTCACCCCTTCCTCAGGCCAAGGACCCCAGATGGAGG TGAGAAAGAAGCACCTGCTCCTTATTCACAATTGGGCAGTAGGTGCCAGGGGGTACCCTTGCCCCCGACCCCCCAC AGAAGTTCTCACTCTTTCCTCAGTAGAGAGAACCTCAAAGTCAGGTAAGTCAGCTCCCTGCCTCAAAGCAGGACTG CTTTTTGAACACGTGATAAGCTCATCTTCCGTCAAGGTCACACCCACGCCCCGTTTAGAGCCCACTGCCATCCACA AAAGCCACATAACATAGAGGCTAAGTAGGAGAAATATTACAAGCCCAAGTTATAAGAAAGGGAACTGAAGATCAGG GAAGAAACTTACAGAGTCGTATGGTCTGAGTCAGCAGCCCTGGAATGGAAGACAAGTTTGGGGTCTTTCTGTGAGT CTGTCCCACCTCAGCCTCGTACACCCCTGGTGGTGGTGAAGCCAGACCAAGCTGGGGATGCTAACGGAAGCAGAAC AAGAAGAGGGTCATGAACCAGATTCCACTAGAACCCAAGTTCTTTGGGGGGTGGGAGGGAGCACTTGTCTTCTGTC TTGGTCACTTCTGGGCTTTCCTGGTACCTGGAACAGTATTTGACATCTATCAGACGTTCAGTAGATATTTGCTGAA TTAATGCTGAGTGAAAGCCTACAGGAGCCAGGCAGGCAGCAGAAGTATGTGAATTTGACCAGGTAAGGATGGACTG TGATAAACTAGCCAAATCAGATCAAAATCAGATTTTAAAAAGAAAACAGGTTTCCCATTGTGGCTTAGCAGAAACG AATCTGACTAGTATCCATGAGGTCTTGGGTTCGATCCCTGGCCTCGCTCAGTGGGTTAAGGATCCAGTATTGCCAC CAGCTGTGGTGTAGGTCACAGACACGTCTTGGATCTGGTGTTGCTGTGGCTGTGGCTGTGGTGTAGGCCGCAGCTA CAGCTCCAATTCAACCCCTAGCCTGGGAACCTCCATATGCCATGGGTACGGTCCTTAAAAGACATAAATAAATAAA TGAAAAAAGAAGTACCCTTCTTTGATTACAGAATGTGATATACTGGCCATAGATGACTCCTCTTTTAAGGGAAATT GTTTTGTGCCAGAAGCGAAAAGTATTGTTTGAACCCTTGCTCCCCAACCTAGGGGATGTAGGCGTGTCTGTCCCTT CTCTGTGCGTCTGTTTTCTCATCTGTGAAGTGCAAGGTCCCTCCCATTTCCACTCCATCCTGCCTGGGCCTGAGTC TGAGGGTAGAGTTGTGAACTGGGCTCCTATAGCAGTCTGACTGGGGGACTCAGAAGGCTTCATGGAGGAGGGGATG TGACCAGACCTTTCCAGATGGGCTTCCCCTGCCTCCCAGGGATCTGGCATATCAGCCTGCACAGCCACTCACCCTT CTCTTCCTTCTCACTGAAGACAGGCTGAAAAACTAACCTGCCGGGGGAGGCAGGCAGCCCCACACTTCAGAATTTA TAAATCCTCCTCTGCTCAGGCTCAGGCCCAGTCCATCCTGGGAGGTGCTGGAGGTCATTTTATGAACCAACCACCT TCGGCTTTCGGGGCGTAGGGATGGGGCAGGATGCCACAGAATCACCAGCCCACTCACGAGCCCCCCTGAACCCTTC CCAGGGTGACAGAAAAGAGGAAATGGAGCACAATTCCGGCCCCAAGACAAAGAAACTCGGCCAAGCAAAGAGAAGG GAAACAGCTTCCTGAGTCAGGGGACTTGGAATCTGCTAGGGCCACAGGGAACCTTCCCCCCATCATGGTGAGGCTG AGGTGTGGACTCAAGCAACTGAGAAGATAAGGACAGGTGGGTCCGCCCCCACCCAGCTCAGCCCAGAAGCATTTCT TTCCAAAGCGCCCGTGGAAAGGAGTGGTTTGCAGTGAAGAACATTTTTCAAAAAAATCGAAGTCTAATACTAATAA TATAACCAGATAAAAGAAAGGCCAAGAAAGTGCCATATAAATCCAAAGACACGGTTCCACAGGCCACGTGGCCACA GGCACATTTTTCCCCTCCTGGGCCTCACGCCCCGTGTGGGCACTGACGGAGTCGAAGTGGAACATTCCCAGGACCC ACCTGGGCTCGGTGGCTGTGAAGAGCCTGTTGTTACTTGCTCTGCAAACCTGGCTGATGAACATGCAGCCTTCAGA GCGCAAGGTCACCTCCTCCAAGATCTGCCTCCTGGCACAAGTGGATTCTCACAGCCCTGGTGTGGCCTGCTGGTTT CACGGCACCTAGAGCGCAGGTTCTTGGACATATGTCCATCTCACTCTCTGCACGCACATTCTCAAGGGCAGCAGGG AAGTCTGCTTTAGGTCAAGGTCCCTGGTGGTCCTCACCACAGGGTCTGGTAGAGAGGAGGTCTTGAGGATCAGTAG |

TABLE 9-continued

| lists sequences for the disclosure |
|---|
| GCTGGTGACAGATGGACAGATGGACTTGCTGGGGCTACTGTAATAAAGCACCACAAAGTGGGTGGCTTAACACAGC<br>AGAAGTTTATCCTCTTATACTTCTGGAGGCCAGAAGTCCAAAGTCAAGGTGTTAGCAGAGCTGGTTCCTTCTGAAG<br>GTCATGAAAAGGAATTCTACAGGCTTCTCTCCTGGCTTCTGGTGGTTGCCAGCCACCCTTGGCATTCCTTGGGGCA<br>GCATAACCCAACACCGTCTGCATCATCACACAGTGTTCTCCGTGTGTGTCAGCCTCCAAATTTCCCTCTCTTTAGA<br>AGGACAACAGTCACTGGATTGGAGCCCACCCGAATCCAGCATGACCTCATCTTAATTTGAGTCATCTGACAAGAAT<br>CTATTTCCAAAAAAACTCATATTCATAAGCACTGGGGATTCGGACGTGAACCCATTTTTTTTTTTTGGAAGACACA<br>ATTCTACCCACTAGAGACCGTTTCCCAAATGCCTATTGGCTGGGAGCGTGTAAACACTAGCAGAACCACCTGTGAG<br>GGTGGAAACGCTGCATATAATTACGGAGTTGAAAGCGAAAGTTTGGAGGCAGGCGGGGAGGTAGGGGTGGTCTTGA<br>GAAAGAGGAAAACATCTTAGAGCATCTCTACTTGGCCAGGATTATAGGAAGAAGAGAAATGCCTCCCCGGGACAGG<br>CATCTGTGGGATGTCCCGCCGAAATGCTGCCGGTCTGTCAATACTCAGCTCTGGGCATCACAGAGCCATGAATGGG<br>TAAGCTTCCTCCCAAGAGGAGCAGGATGTGAAAGAAGAGGGGGCCCTGGGGCAGCTGGAACCAAGAACCTATGGAA<br>GCACAGAGCTGGGCACCAGATTGCAGTGGGTCAAGGAATGAAGGTCAGGTGAGAAAGTGACGTGCAAGGACCTCTC<br>GCCAGCAGCTTGCCTTGGGAAGGGCTGGAGGGAGGGTGCCAGCTAGAGACACATGGAGCAAAAAGGAAATACCCTT<br>GAGTACACTGCTGATAATGAAAAGCCCTTAATGAGACAGAGCCGAGGAGAGGAGGGTTTGAAGATTCAGAGGAGGG<br>AGAGGATGGGGGCTGAAGAGCATCTCTTGGCGGGGAGATGGGGGTGCCACCAAGACAGGCTGAAAGTGCTCCCCCT<br>TTTTGAAAGGAGCAGGAGACAGAATGGGTGGGTTGGCAAGTCTGGGGATAAAGCGGGTAGGTGACAGGCTCCAATC<br>CAGAGCAGCTGAAGCGAGGAGGGAGAAGGGGGCCAGGAGGCAGAGAAGCTGGAGAGCTGTGCAGAATCTCATCACC<br>AGGAACCTTGAACTTGCACCTGAAAAATGGGCATTTCATCCTGAAAGTACTAGAGAATCCTTGAATGCCACTAGGC<br>AAAGAAAGTTACACGATTTGCTTTTTAGAAGACTTCCTTGGCTGAAGGATGAGGGAGCCCAGCCAGGAGGCTGCTG<br>GCCAATGTCAGAGGAAAGAGTAGAGACCTAACCCCACAGGTAGAGCTGGAAGACAAGAAAGAAGTGGCATCTTGAG<br>ACATAGGGTTACATCTATCTTACTTTCTTTCTTTCATTTTTTTTTTTTTTTTTGCTTTTTAGGGCCACACCCACAG<br>CACATGCAAGTTCCCAGGCTAGGGGTTGAATCGAAACTGTAGCTGCCAGCCCACGCCACAGCCACAACAATGCCAA<br>AGCCGCATCTTCGACCTACACTACAGCTCACGGCAACGCCAGATACTTAACCCACCGAGCAAGGCTGGGGATCGAA<br>CCCGCAACCTCAAGGTTACTAGTCGGATTCCTGAGCCACAATAGGAACTACCGGGTCACGTCTTTGAAAATCTGCT<br>TCAGTGTTACTTTAGAGAAACTGTCCTGGATTTAAAATTACTTTCCTTTTGTAGTTATCTATCTTTCAATTTTATT<br>TCTTCTTCTACCAGAGTGTCAACTCTGTGGGCAGATATTTTTGTGCGTTTGGTACCTGTGTGGAAACATCTGTCTA<br>TTACAGCCCCTGGTGCTCCGTACAGCTTTGTAGGCTAAAATGCATGCCTGGTACAGTGCTTGGCACCTGTGTGTTC<br>AATAAACATGAACTATGGTGATAACAACAGCAAGAATAACAGTGAGCAATGGGATGAAGGGAGTGAGGCAGAAATG<br>AGACTAGTTTGGTGGGACTCAAAGTGTGGACTGAGCAACCGGTAGCATCAGCATCACCTGGGAGCTTGTTAAGAAA<br>TGCAGAGCAGCAGGCCCACAGCCCAGGAACCTGTGTCTGCATGAGGTCTGCAGGTGGTCTGGGAATGGGGCTGGTT<br>CCCAGGTTTCTGGTTGAAGGAGGAGAGTGGGTGGCATCGCTGCTGACTGACATGGAGCGGCGGGGCTGAGAGGAGG<br>GGGAGTCAGTGAGTTCTGCTCAAGAGGTGCTGAGTTTGAAGAACCTGCAGAAGTCAATTCAGCAATGTTGTCCCAG<br>AGAGAGAGCCCGGGGAGAGCCCAGTTTCGGAGCTGCCAGCCCAGCGTGCAGGCAGGAGTCGGCAGGTCTTCTGTGT<br>GCCAAGGGAAAGGAGCACGGAGAGCAGAATGGGGCCTCCTTAATGGGCACCGCCTTGAAATCTGAGGGGCAGGGCC<br>GAGAGGCAGGAGGAGAAACAAGAACAAAAGTTGTTGCTGGGAGAAACCCCATCTGAATTCTCAGCTCAGCTCCACC<br>CGTGACCGCCTCTGGCCCTGCTTCCCCTGGAAGAGGGAAGGCCACGGACAATTGCTCGGGCAAGGTTGCTGCTGTT<br>TGAGAATCCCAAGGAGCGGGACTGTCAGGCAAACAGAGGGGTGGCAACAGAGAGGGGTCCCGTTTCCAGCTGTACC<br>TCCAACTCCGGCAACTCCCTGCGTGCCTGGTTGATTCCCGCCCCCTTCGGATGACAAGGTGGGGCCGGGGTCTCTG<br>ACCATGTTGCCTGCCAGCTCTCTGGGCTCACCCCTCATGTCCGGCCACAGACTCTAGGGGAAGACCCCAGCAGAGC<br>ATAATGGCAGCTGCCTTCAGAGCACGTGAGGAGGCTCCAGAGGCCAGACCAAGAGGTGAGGGAAGGGCACGCAGGG<br>TAGGAAGCCAGGATTCCCGAGCCAACAGGTGTGCTCTACCTGGCTCCCATCAGTACAGCTGAGAGTCAAGGTCTAA<br>AGAAGCCTCTCTGTCCCTCAGCCAAAAAGGGAGGCCCAGGAACCAGCAAGGGCCACTCTCTGCATTTATCAGGTCC<br>TAGTCTGGCGAGAGGGACACGTGCTGACTGCAGACCGCAGCTACTGCAGTTGTGTTCAGTGGGCTGGGGCTGGCAG<br>AGTGGGGCTGCACAGGTGTCCCCCGGAGGAAGTCCCAGCTCCTCCCTGCCCCATCACCTGTTGTATTTTGCTTTAC<br>CACCCTCCCATTTTTGCCATTTGTGCTTGGCCTTGTCACAGCAACCCCTCCTGGTGCAGGTAGTTTCCCAGGGCCT<br>CTAAAATCAAGGTGCTTCCCCTAGAACAGTTCTGATTTATACTTGTTATGGCTCAATGTTTTAGTACCTCCTTTCA<br>CTTTCAAAGGTGTGCAGGTGTGGAGGACAAATCATGTTGCCTGTCACCCTACATAAAAACGGTTCAATAAAATAGA<br>GTTCGATGAAGTCCCCTTCAAGACGCCTCTCGGCTTGGACCCTCCAGGAGTCAGGGCTTGTGTTTACCAACAGCCG<br>GTGCCGTGACCTCCCCCTCTCCAGCATCCTTCCTGCTACTGCCTGTGGTACAAGAGGTGGTAAAAGCCTTTCTGCC<br>ACCCCTCCCCTAACCTGTCCCCTTCAGTGCCTGTTGCTGGGATCATCTCAGCTCCCCCTGCCTCCCTGTGTAGGCT<br>GGGAGGAATTAAAAGTCTAAGAATTTACTGGAAAATCCTAAGGTTGTTTTGTCTTGGGCTTTTTTCCCCCCTCACT<br>AGATTTTTTTCTTGTAACAAGTTGACGAGCATAAAAGACCTTCCAAGAATTAATCTCTAATCATGAGAGATTTCCT<br>TCCTAGTGGAAAGCTAAAAATAACAAAGACAACAACAACAACACCCCAAAACCTCTTAACTGAGCCCACAATGGAG<br>ATGGCTTTTCCTCTGCCTGTTCTTTGTCTTTTGCCATTTTTTTTTTTTTTTTTTAAGGGCCGCATCAGCGGCATGTG<br>GAGGTTCCCAGGCTAGGGGTCTAATTGGAGCGACAGCTGCCGGTCTACACCACAGAACAGCAACGCCAGATCCGAG<br>CCACGTCTGCGACCTATACCACAGCTCACGGCAATGCCAGATCCTTAACCCCCTGAGCCAGGCCAGGGCTCGAACC<br>CGCAACCTCATGGTTCCTAGTCGGATTTGTTCTGCTGCGCCACGATGGGAACTCCTTTGCCCGTTCTTGGAAAGAG<br>CCAGGCCCCAGTTCAAATGCCAGTGGCGCCCCACCCCCACCCCCCACTTTCTTGCTGCGAAGCCCTGGCTCAGTCA<br>CTTCACATTCCGAGCCTCAGTTTACTCATCTGTTAAAGAGGGATGATAATTCCTTACTCCTTGAATTGTTGACAAG<br>ATGAACAGTCTGTAAAGCTCCTGGTAGGTACTTGGGAAAAAAGCAACTTGTATTATTATCGCTGGTCCCTAAGAGA<br>CAAGCACTGTCCCCACCTCATCACAGTGACAGGAGGCAGTATGCCCAGAGATTAGAGCTTGCACTTGAGCAAGACA<br>GGCCTGGGAACTGACTAAATGCGTGACCTTGGGCAAGTCACTGGACCTTCTAGGACTTGCTTTTTCTCCTCTGTAA<br>AATGAGAATAACAGTGACTCACCATCGGTGAGATGACGCACATCAAGCTTGGCATGACCCCTGATGTTGCAGCAAG<br>TGCCCAATAGATGGTAGTTTCTCAATTCCCAATAGTGATTATTGCAGAACTCTCCACCTCACAGGCTCTGGCACCA<br>CCTGCTCTGTATCTCCAGGGTCCACTATGTTCCCCTGTCCCCAAAACAACAGCCCTTCCTGTGCAGGGGGCATTTA<br>CAAATCCACCTTTCCCCTTCCGCTGGAGTCTGAGCTGCAGCCCGTGAGTCAGGCTGGGTCTCCACGTGCGGAGGAG<br>GAGGTGGAGGAGGAGGAGTCTGGTAACTCCCCAAGGGGGGCTCAGCTGGGACTGGAAGCTGGGTTTGGGTGCAGCC<br>AAGAATTTCTTCAGCCCCTTCCTGTCCCACAGGGAGCCTGATTCAGAGTTGAAGGGAATTACGTGTTTGTTTATTT<br>ATTCATTAAATAAATATTTAACACCAGGGAGTTCCCATCCTGGCTCAGCGGTTAGCAAACCCAACTAGCATCCATG<br>AAGACATGGATTCCATCCTTGGCCTCGCTCAGTGGTTTAAGGATCTGGCGTTCCTGTGAGCTGTGGTGTAGGTTGC<br>AGATGCAGCTCAGATCCCGAGTTGCTGTAGCTGTGGTATAGGCCAGTGGCTACAGCTCCAATAAGACCCCTAGCCT<br>GGGAACCTCCATATGCTGCAGGTGTGGCCTTAAAAAGACAAAAGAAGACCCCTCCCCCCCAAAACTTAACACCAAT<br>GTTGATACCTACCACGTGCCAGGCACCATTCAGGCTGCTAGGTCAATAAGGATTAGCCTATTCTGTGCCTTTCTCA<br>CAGAGCTAGTGGGAAGTGGAGCCCTTCCTGGTGGGAAGCTGAGCCCGGACAGCAACACTTCTACATCCTGAAGCCA<br>AGGTGAGTGTCCTGTGACAGCAATGAGTCAGCCCCTCTCTGGGCTCCATGGACTTCTGGAAGACTCGGAGAGCAAG<br>CTCACCTGCCTCCTTGCCCGTGTGGCTACAGGAACATGTTTACCACCCAGGGTCACTCTCTCTCAAGCATGGCCCC<br>AATCTTCTGAGCTGCCTCACTTTCCAGATGAGAAAACTGAGGCACCAAGGCAGGGAAGTAACTTATCCAGGGCCAC<br>TTGGTGATGAGGTGAAGAGGCCAGGGCTAGTACCCAGGTATCTGGCATCTCTCTAGGCTGAGACGCCTATTAGCCA |

TABLE 9-continued

| lists sequences for the disclosure |
|---|
| CAGCACCAGAAATCAAGAGCTTAGAGACGGGGCGAAGGGCTGCAGTCAATGGTCTTCTTCTAGAGTTTTCTTATTA |
| ATGCCCAGGAAAACCTCTGATGGGACATAGAAATGCCACTGGGAAAAGGGGAGCATCGTGTGTTTACTGGAGACAA |
| GTGAGGCACCCAATTCAAAAAGAAGATCCCTCTCAAACATAAAATAGTTCAGCAATGGAGTAAAAAACACCTAAAT |
| ATGTGTTCCACTTACAAAGCATCCTATGGGCTGTGATGAAGAATGTGGTTTGGAAACTCCGATTCCACCCCATTGC |
| CTCTGCCTTCACCTCCCACCCCAGTGTTTAGCACCAGGAGCTCCCAGCACATATCACCTACCCTTTTCCTGGCTGC |
| TGTCTTCTTCAATGAGCTTCTGCTTTTGATTCCCCTAGAGAGGCTGGCAGTTTCGGGCACCTTTTTGTTCCTCTGC |
| TTAGCAGTTGGGGCGGAGAAGAAGTGGCTTTGGGGTTTTTCTTCTCTGGGTGTGGTTTCCTAGCCCTCACAAAGGA |
| AAGCCTACAGCCTGCTCTGTCTGCACCACCAGCCTGGTTGCCTCAGCTGGCAGAGCTGATTAGCATGCGAGGTGCA |
| GAAGGGAACAGCCTGCCTGGGGTACTCAGGATACTGTTCTACTAAATGTTTCCTGCTCTCCACCTTCATAGTAGGA |
| TTTCATTTCCTGGTCCCCTTGCAGTTGAGTAGGGCCATGTGACTAGTCTGACCAATAAGATGTGAGTTGGCCCAAG |
| TATTTAATTGCTGGTCAAAGACCCTCCAGGGCTCTCTTTCTCTGTGCCATGAAGTATATTCAAGGACGTAACTGCT |
| CCATCAGCCTGGCTCCTTGAATGAGGAGCACAGCCCCTAGCTGACCCACGGGGCTCATGTTAATTAGAGTAAGACA |
| TAAACCGTTATGGGTTTGGCCCCAAAGATTTAGGGGCTGTTTGTTACTGTAGCATAACCTACACCATCCTGACTGA |
| TACACTGCCCATCTCACACAGAGTGAGATATTCCCTAGTTAAGTCTACCATCTTCCCAATGTTGCTCTTTCAGCCA |
| GAAGCCATTTCACTTCCTCTGAGCTCCCCTTGGCCTCCTGTCACACTTCTGTTCTGCACTCTGACTTCTACTTTTA |
| GTCCCTTATATATAATTACATACAGCCAATTTCACATTGTGAGCGCCTGAAGAGCAGGAATCTGTACCTTATATTA |
| TGATGATGATAATAATAATAATAATAAACAGAGGCAGCAAATGCTACTATTTATTGAATGCTGGGCTGGGTTCTAA |
| GCACTTGACATTCATTCAGTTCTCACTAAGCTCTGAGAGGTCAGTACTGGAACTACCCCCACTTTACAGATGAGGA |
| AGCATCTCAGTTTGGTTCAGCTGAAATTGAACCCCTAATAATATATATATATATATATATATATATATATATATAT |
| ATGCATTTTTTTTTTTTTTGGTCTTTTCCTAGGGCCACACCCGCAGCATATGGAGGTCCCCAGGCTAGGGATCTAA |
| TCAGAACTATAGCTGCTGGCCTACACCACAGCCACAGCAACACCAGATCTGCAACCTACACCACAGCTCACGGCAA |
| CTCCAGATCCTTAAACCACTGAATGAAACCAGGGATCAAACCGGCAACTTCATGGTTCCTGGTCGGATTTGTTAAC |
| CACTGAGCCACGACGGGAACTCTTAATATTTTTTAATAAATATAGTTCAACTTAAGTCATTCCCTCTATAATCCT |
| AGTCACTTATTTTTCACATTTAAAACATTCCCAGAAGGGGTCTATAGGCTCCCCCAGATGCCAAAAGAGTCCATGG |
| CACAATAAAGGTTAAGGTCCCCTGTAGAAGCAGATACCAGGGTTACAGTGACAGGGTTCTGTCCCCTGTTCTCCTG |
| GAACCCAGAGTTTCTGGCTGGTGGAGGGTAAGGGACCCTACACCAAATTCATGCCACAGTGGGGAGTGAACAGGAG |
| CTACTTTATTGTATTCACATAGCATAAACATAAATATCGTAGGTTTGGCATATGGAACTCCCTGTCATGAATATTT |
| TGATTTCAGCAGTGTCAGCCCAAGTATAACATTCATCACAGTAAAGAAGTCACTTGTTTCCCCAGTAAAAAAACAA |
| AACAAGGGCGTTCCCTTCATGGCTCAGCGGTTAACAAACCTGACTAGGATCCGTGAGGATGCAGGTTCGATCCCTA |
| GCCCCACTCAGTGGGTTAAGGAACTGGCGTGTAGGCCGGCAGCTGTAGCTCCGATTCAACCCCTAGCCTGGGAACG |
| TCCATAAGTCGCAAGAGTGGCCCTAAAAGGCAAAAAACAAAACAAAACAAAACAATTCCTAACATCCAGTGTGCTA |
| ATTAGAAAAGCATCAGCTCTTGATCACAAATTGGGATAACAGGACAGCAGCCATCTCTGGTCAGTCCCACTCCCAG |
| ACGATGCATCCTTGAGGGCAGATGGGCCGACCACCCACGATGAGACTTGCTTTCTTAGCTTCTGAGCACTGGCTTG |
| GTCCAAGTAGCACTCACATAATCTCCCATATTGTATATGCTGAAGTTTTATACTTTATTGAACCAGAATTTACTTT |
| AAATTCCAGGCATCCAAACATATACACTGAATCCAGGTGAATCCAAGCAGAACTCTCTGGATTTCAGAAATCCTGG |
| GTGATTACAAGACTCAGGGATAAGGTAGCAGAGCCAATGCTCTGTGCCTCCTTGCCAGCTGGCCAGTAGTGAGGGC |
| TGAGCCCCAGGACAACCGGGTGGCAGTCTGGCACTGCCCTGGTGGGCTGGATGACCTTCCGCAAATTACAGGCTCA |
| GTTTTCGTATCCTCCAAATATGGAGCCATACTAGATCCAAGTCCAGGCAAGAAACAATCACAAGGCACCCGCGCTA |
| CGCCTAGTACTGTGGGGAAAACAGAAATTACACAAACTCCATAAGGAGCTTACATTCTAGTTGGGGAGCCAGGCCT |
| GGAAACAATTTAACTATTGTGCACGACAGAAAGAAGTAAGTATGAAGGTGGTGGAAGCCCCCTCTTGTGCTCTGGG |
| ACCACAGAGGAAGCACGAAGCCAGGCTGCATAGGCCTGCGCAGCTCGGTTTCAAAGAGGAAGGGGCTATGCTTGAA |
| CTGGGCTTCAGAGGGTGAGTAGGAGTCTGATGGGTGAGGAAGGGCATACAGGTGGAAGGGCAAGGATCTGCAAACT |
| CGGGGTCTGGAATGGGAAGCCCCACCCCCAGCCCAGATCCCAGCCCAGGGGTTCCAGTCCTGCTCTCTCCACACAT |
| CCGCTGCTTTGGAATCTGGAAGAGTCCTGGAAACCTGTATTTTGAACAAGCTCCCACAGTCATTCTCACAAGCAGG |
| CAGTGAGTGTTATAGATTGAGAAAAATGAATGAACAAATGAATGAATGAATACAAAAATGAACCTGAGAAGTTCCT |
| GTTGTGGCTCAGCAGAAACGAATCCGACTAGCATCCACAAGGACGCAGGTTCAATCCCTGGACTTGCTCAGTGGGT |
| TAAGGATCTGGCATTGCTGTGAGCTGTGGTATAGGCTGCAGGCTCAGCTTGGATCCCACGTTGCTGTGGCTGTGGT |
| GGAGGCTTTCAGCTGTATCTCTGACTCAACCCCTAGCCTGGGAACTTCCATATGCTGAGGGTGCAGCCCTAAAAAG |
| ACAAAAAAAAAAAAAAAAAAAAGAACTTGACTTCCGGTAAGTCCCTTTCTCTCTTAGGATGTCCACACTACATTAA |
| GGAGCTAAAGAGCTTCAGTTGTGGCTCAGCAGTATCCATGAGGATGCAGGTTCGATTCTGGGCCTCGCCCAGTGGG |
| TTAAAGGATCCAGTGTTGCTGTGAGCTGCAGTGTAGGTCACAGACAAGGCTCAGATCCTGTGCTGCTGTGGCTGCA |
| GCTCCGATTTGACTCCTAGCCTGGGAACTTCCATAGGCCACACCTGCGGCCCTTAAAAAAGACAAAAATGAAAAAA |
| TAAAAAGCAAAATAAAAGTGCTGAATTGGCCTGGTGGCTTTCAAACTGTGTTCCAGAAAAACCCCAGAATCTCCCT |
| GAAGTCCCTCAGGGACACAGAGGAACTGGGGAGGCTGAGAGAGCCGGACTCTGGGCCCCATCCACCCTTCTCAGAT |
| TACCTCTCCTTTTATCTCTTTGCTCTTTTTTTTGCAATAAAGGGTTCTTGGCTACAAAGAACTCTTAAAGCCACTG |
| AATTGAATAATCCTAGAATTCCCAAGGAGTCAGAGTTCCCATTGTGGCTCAGTGGTTAACAAATCTGACTAGCATC |
| CGTGAGGACGCGGGTTTGATCCCTGGCCTCACTCAGTAGGTTAAGGATCTGGCGTTGCCGTGAGCTGTGGTGTAGG |
| TCGCAGACGCGGCTCCGATGCTGTGGCTGTGGCCAGCAGCTACAGCTCCTATTCAACCCCTAGCCTGGGAACCTCC |
| ATATACCACCAGTGCGGCCCTAGAAGACAAAAAAAAAAGAATCCCCAAGGAGAAATTTAAAAATTTCTTGAGGGCA |
| GCAGCTTACCTTTGGCAAGTATGAAGAGAGCATAAGGGTCTTTTTCAGAAGCAAGTTATTTAATCATCACATTTTA |
| AAAACCTTTTGCTGTGGCCCAGAAATTAGTGAGTGAAGGAAAAAAGCAATGTGGTATAATAATGCAAGGGAATATT |
| ATGCAACCTTTAAAGAACACTTTTGAGGAATGGTTAATACAATGGAAAATAAAGTGAGGAAGTCAGATACAAAATT |
| TCATACAGACTGTGATTTACGGTATGGATTTTTTTTTTTTTTTTTTTGGCTACACACATGAAAGTTCCCAGGCCA |
| GGAATTGAACCTGCCACAGCAGTGACCTGAGCCACAGCACTGACAACTCTGGATCCTTAACCCCCTGCACCAGCGC |
| TATGGATCTTATACATCAAAATTATTGGACATGGATGTTAGTAGGCCGGTAGCTGCAGCTCCGATTTGGACCCCTA |
| GCCTGGGAACCTCCATATGCCTCGGATGCAGCCCTAAAAAACAAAACAAAACAAAACAAAAAAAAGAAGAATGCAA |
| TTCTGACATGTTTCAGCACAGATAAAGGTTGAAAACATTACGCTAAGTGAAATAAGCCAGACACAAAAGGACAAAT |
| AGTGTGTGATTTTACTGAGATCAAGCACCCAGAGTTGTCACATTCACCGAGACAGAAAGTAGAAGAGCGGTTACGG |
| GGGTGGGGGGGATGGGGGTGGGCAGTGGGAAATTACTGCTTAAGCAGCACAGAGCTTCTGTCTGGGATGATGGAAA |
| AATTCAGATGGTTGACACTGGGGATGGCTGCCCAACGTGTGAATGTGCTTAGTGGTACCGAACTATGCCCTCAAAA |
| AGCATTAGAATGGTTTATGCTATGTATCTTTTACCACAATAAAAGGGGAAAAAAAAGCCAGAACTAGGTGCATAGG |
| TTATAGTGGTGAATACTATGCGACAAGCTTGTGGGCAGCGTGGTCACTTTATTCTTTGCATTTCTCTGCATTTTTC |
| AAACGTCCTATGATGAGCATACATTTCTTTTTAAAACCAGACAGAAGAGCGAGTTAATTAAACAAATCTCGTGGTT |
| CTCTGACACTTTTGCCCAAATGCGTTACTGTCTTTTGCGTAAATGTAAGGTGTGTTCCCTGTCCTTCGTTAATAAA |
| AGGAGCCGAGCCCAAGGATGCCAACGAAAGGATACACCGAGGTGCTCAAGTCAACGACAGGCACAGCGGCCCTCCT |
| TTCTAAGACTCGTTGCTCTCGTCTATATTTAATAAGTTCCAAATAAAAACAGAACCCAAACAAATCCTCTAATGAA |
| CTTCCTAAGAAGCTGTCTGGCTTGGAAAAGCTCAAAGGCGAACTGAAGAGAAAGGGGGAACAGCTGCTGTGTTTTT |
| AGGGCATTAACTCACTGCAGCTGGGACAGTGCCTTTGTCAGTAGATTTCTATCCCTTCTTGCTTCTGGGAAATGTT |

TABLE 9-continued

| lists sequences for the disclosure |
|---|
| CTTGGGCAGAATGAATTCAGAAACCAGGAGAGGCTCCCCAGTGGTATTCCCTGCCAATCCATCTGCTCCAGTACCC TCTCCCCACCCCAGAAACATGCTGAACAAAGATTTAAAGACTCTTGGTGTGAAGGGCAGCCACGTGTCTGCCTGCC AGGGTGCCCTCCACCCCAGGCCGCCTGGGTCCACTTGCCCGGCTCCTGGGCCCTCTGCTCAGGGGTGGCACAAGGG CAGAAGGTAGCTGCCACGATAAGCAGACCGGGGCTACCCCTGGAGTGGCCCCTCCCTGGCTACGTGACCTCTGCCT TTTTCAAATGTTCTATGATGAGCATACGTTTCTTTTTAAAACCAGACAGAAGAGCGAGTAATTAANNNNNNNNNNN NNNNNNNNNNNNNNNNNNNNNNNNNNNNNNNNNNNNNNNNNNNNNNNNNNNNNNNNNNNNNNNNNNNNNNNNNNNN NNNNNNNNNNNNNCGTATATGGACCATACCACCTTCCCCTGGCCCCAGGTTCTCACCTATGTGACTGAGGGAGGTG GACTGGGGCACCTCTTAGATCTCTGCCAGCTCACACATCCTATGATTGCATCATCTCAAAAAGAAAAAGAAAAACC AACAATACCTAAACCAAACTAAACCCTAAAACCAAAACCAAAAGCAGGGTGCCTTCTAGGAATCTAGGCCAGGTTC TTACGTTTGGGGGGGCCTTGGGGTCCCTATCTACAAAATGAGGCACGGAGTTTCCACCATGGCACAGTGAAAATGA ATTTGACTAGTAACCACGAGGACGCAAGTTCAATCCATGGCCTCGCTCAGTGGGTTAAGGATCTGGGGTTGCTGTA AGCTGTGGTGTAGGTCGAAGACGAGGCTCGGATCTGGCGTTGCTGTGGCTGTGGTGTAGGCCAGTGCCTAGAGCTC CAATTGGACCCCTAGCCTGGGAATTTCCACATGCCACGGGTGTGGCACTAAAAAGACCAAAAAAAAAAAAAAGGGA AAAGAAAAAATTTGGCACAACCTTCCAGCTCGTTCCATGTCCAACATCTGTAATTCCTGAAAGGAAGGCCCCATCC TCCCCTTGCCCTCCACCACGTCCTCTACCTCAGGCCAGGCTCACAAACAGGAAATATGACATTCGAGAGCAGCAGA AGCACTGCTTGCTTCTCGACAGCATAGGGGCCGATGGAGAACAAAGAGTTTCTGAGCTTTTCCAGCAACAACCAGG GCTCCATGCCCAAGACCTTCCCCAAGCAGTGCAGGCAGAGGACACTGCTGGGATGGGCTGGCCTCCCATGCCATCC CCGCCCCGGTGTGTTCCCAGGGGCCCCCGGCAGCGCAGAATCAGCAGATAAGCTGTCTGGCCGTAATTACACGCTG ATGCTTGACCAAAGGTGGTAAAACCCTAAACAGGCGGAAGGCAGGGTGCAGGATTCCTGGACTCCAGTGCAGGAGT GGAGTGACCCTAGAGAGGCCCTACCCCTCTCTGGGCCTGAGTTTCCCCATCTATTTTTTTTTTTTTTTTTTTTTT TTGTGTGAGTGCGTGTGTGTGTGTGTGTATGTCCCCCTCTATTTGAATGAAAGGGCTAGAATGGGGCCTAATGGCA GCTCTTTGCTTGCTCCGAGGTCTTCGGTTTTTCTTTTTTCATTCCATTTTTTTTTTTTTTTTTATGGCCACACCCA CGGCATATGGAAGTTCCCAGGCTAGGGGTTGAATTGGAGCTACAGCTGCCGGCCTACACCACAGCCACAGCAACAC CAGACCCCAGCTGCCAGATCCCTGACCATAGCGGATCCTTAACCTTACACCACAGCGGATTCTTAACCCACTGAGT GAGGCCAGGGATCAAACCCGCACCCTCATGGATCCTAGTCGGGTTTGTTACAGCTGAGCCACGACGGGAACGCCTG ATGTCTTCTTTCTGAAGGCAGTGTGTGGCCTTGATGAAAGGCCCCATCATCTTGCCTGTGTCTGCGTCCCAAATCT CTCCCTCACCACGTGACCCTGAGAAACTGCTAAATCTTTCTGTGTTTCGTTTGCTCATTTGTAAAACTGGGGTTGC TGGGTGATGAAAAGGCAGAGCTCCTGTAAAGCTCCTAGGACAGCTTCTGGAGTTAGCGCCCAGGAAGCGTGCGCTC TTGCTGTTTTATGATTTCTCTGGTTTCAGAATCGCTCCCCTTGCCCTGTTTGCCATCTGAAGAAGGAGCAAGCATG GCCCAGAGAGCCATACTGGCCCTGCAGTCCACGTCTAGCCCTCTCCCTCCAAGAAAGCACATGTGAATCTTGGTCA GCCAAGCACAGTGGGAAGAGGGAACTATGGGAGAAAAGGCAGAAAATCCTACGATGCTGCCCCACAGCAGATGGGC TCGGGTGTCAGCTGCTCCCAGGGGTTGCTGGGCACTAGAGAAGGCCTCCAGCTGCACCCAGAGTCAGTAGCGGAGG GAGGGTCCTGGGCTCATCTCCAGCTTGATCCCCGAATGGGGAGGAGAATGACCCCGTGGGAAGGAGGGTGATGAGA TGCAGAAGATGCAGCCGGGTTTATCTCTGTTCCTACTTTGCCGGGACCATTCAGGGAAGAGGAGGCCACATTCAGT CATCTCAGCCCCGAGGGGAACAGGGAACAGAGAGGGGTGAGGATGACAGCACTGGTGGTCTCTCCCCTGGGGACAT GGAGGTGTGGCCTCCCTCTGCCACAGGGAGGGTCCCAAACCTGCCTGTCCTCAGTGTTCTCACCTGCCAAGGGAGG AGACGCAAATGCCTGTTTCCACCAGGCGCTCTAGGGTCTCAAATTGTGGCTGCGGACGGATGCATCGAGGAGGCAC AGAAATTGAGAGTGTTTTACTAAAGGACCAGTCCACAGGGGATTAGAAATAAAGGAAGAAAGGCCTGATCTTCTAC CACACTGTCCTAGGACATAAAGCATGATGCGGGAGACAGGCAGGACCCCTGTTCCGCCTCCTGGGGCTACCCCGCT TGGCTCCAGTGAGCTCTGTGGTCCAGGTGGAATTGTGGGCTCCCATCTGGCTGGGACGACTCACCCAGACAGACTG CCCTCCTGATCCGAGAGCATTTCACTCGGCAGCAAATTCAACCCACCTCAAAATATCAGCTGCCCCTGATCAGGCA GGGCCTGGCTCCCTCTCTGCCAAGCCCCACAGGGCTGGGCTGGGATCAGTCATGGCAGCTCAAGGGAAGTCACGCT GCACCCAGAGGTAAAAGCTGTCCTGGCAGAGAAAGAGAAAACTGATGGTCCTAAGAACAAGCACACTGGCTTTCAC CCTTGAGGACGCTCAGTTGAGAATCTCGGTTTGGGAGTTCCCATCGTGGTTGTAGATGGCTCTGGTGTAGGCCAGT GGCTACAGCTCCAATTAGACCCCTAGCCAGGGAACCTCCATATGCCGTGAGTGCGGCCCTAAAAAGACAACAAAAA GAATCTCTGTTTGGCTGCCCTGTGTGGCAGGTATGCATTTATCAGGTATAGAGACATTTTACAGATGAAGGGAGCC CAGGGGATCTTTGCTCAAACTCTTTTTTTTTTTAGCTTTTTAGGGCCACACCCGTGGCATATGGAGGTTCCAAGG CTAGGAGTCGAATCAGAGTTTTAGCTGCTGCCCTATGCCACAGCCACAGCAATGCTAAATCCGAGCCACATCTGAG ACCTACACCACAGCTCACGCCAAAGCTGGATCCTTAACCCACTGGGCGATGCCAGGGATCAAACCTGCAACCTCAG GGTTCCTAGTGAGATTCATCTCCACTGAGCCACGATGGGAACTCCCAAACTCTTTTCTTTTACAGATAAAGAGGCT CAAGGAAAGGAGCACCTTGTCGCAGAAGCAGGATTTGAACCCTCCAAGGCTCCTAGCCCCATCTGCATTCAGCCTG CCAATCCACGGTTAGGAGGGCCAACTGCACACATGCGCAGTGTGGGATGTGGTGAGGAACCACACAGGAAAAGCCC TCAGTTCTCACAGAGCTCACATTCTAAACAAACAACAAAATCAGTCATTATAATTAACAAATCATTAAAGACATAA TTTCAGGTGGGGGAGAGGGTTATAAAGCAAATTTAAAACCTGGCGTGTTTGAGAGTGTTTTGGGGTGGGGGCAGCT GCTGTTTGGGAATGGCCTCTTTGCACTGGATCCTCTCAGGTCCTCCCAAGCCAGTAGAATGCTGGAGCTGGCTCCT GCTGGCTTGCAAGGGCCACGTCTCATTAGGAATTTGGCGAGCAAGTTGTTCACCACAGCCATTATTAAAAATTAAA TTACATAAACTTAGAACTAAATGAATTATAGTACGACGGAAGGTAATCATCAAAAGTCATCACTCCCTCGGGTTCC CAGGTGGCCTAGCAGTTAAGGGTTTGGTTTGTCCCTGCTGTGGCTCAGGTTCGATCCCAGACCTGGGAACTTTCCA AGGCCACAGGCACGTGACCAAAAAGAAAAAGAAAAAAAAACTTCATTAATTTCCTCTTTGTATGACCACATACTAT ACTCTTGAAGTTGTTTATATCTATTGAATCTAGACGTAATAGATACTCCCAGTTCCTCCAGTAGTAGCTAGAAACT GGTCATGGTAGAAATATGTCTACTATGGAAACTGGCAAATACCCTCTACGAGGGCTTTCACTTTTCAAAGAGCTGG TGGTGAAATATTTACCAGCACAGCCTTCAGCTCTAATCCAGGCCTTCTATGCCTGTGGGAGTCTGGGTTCTTCCAA GGAGAGGGTGTGGTGGTATAGTCTAACTCTCCTGGGGCTGGGGGCGAGGGGAGGTGGTGGGCAGTGCCTCCAGCCC TGTCCTCTTCTTCTTCTGTGTGTGTGTGTGTGTGTGTGTGTGTGTGTGTGTGTGTGTGTGTGTGTGTGTGTGTGTG TGCTTTTCAGGGCTACTCCCTGGAAAGTTCTCAGGCTACATGTTAAATCGTAGCTGCAGCTGCCGGCCTATACCAC AGCTCATGACAACACTGGATCCTTAACCCACTGAGTGAGGCCAGGGGTCAAACCTGAGTCCTCATGGATACTAGTC GGGTTCCTTACTGCTAAGCCATAATGGGAACTCGGGCAGTCAGATTCTTAACCCACTGCACCACAGCAGGGACCTT CTTCAAAAGTGTTTTTCAACAGGGATCTGTAAGAGGGTGATTCATTCCTTCCTTTGTTATTTATTTTTGATAAATG AAATCCTATCATAAGCATACCAATATAAATTTAAAGGAACCCTGCCGAGAATCTCTTTGTATAAATGCCTGCAGTC ACTTCTGAGTTCCCCTAGATTTTCATAGGTGGAGGGACTTCCTTAGAGAATATAACTGTTCTCATTAACAGCAGAC TGAAGTTACTATTACCTCTACTAATAACAATGACAACTGTAGCTGTCTTTTACTGGCACCACCTCAGGCACTAGGC ACATATATTATCTCTAAAGTCTACATCAACCCATTTTACACATAAGAACGTTGAGGTTCAAGGGTTCAATAACTTG ACCTGAGGCCAGCCTGCTGCTCTGAAAGTTTCACAGAAGGCTTTTTCCTTCTGTAGCGACAGCCCTGCGACTCTCC TTAGACCTGCAGGATTCTGTGGTCCTACAGGACCCCCCATCTCTGGTGGTTTGGGAGAATTTCGTCACGTCTCAGC TTAGTGTAAGGAACTCCCTTCCATCAGCAGAACAGAATGAGCCAGACGCTCCCCCTGGACTTTCTTTTTTTTTTTT TTTTTTTTGTCTTTTTGCTACGTCTTTGGGTCGCTCCCGAGGCATATGGAGGTTCCCAGGCTAGGGGTCCAATTGG AGCTGTAGCCACTGGCCTACGCCAGAGCCATAGCAACGCAGGATCCGAGCCACGTCTGCGACCTACACCACAGCTC ACGGCAATGCCAGATCCTTAACCCACTGAGCAAAGCCAGGGATTGAACCCGCAACCTCATGGTTCCTAGTTGGATT |

TABLE 9-continued

| lists sequences for the disclosure |
|---|
| CGTTATCCGCTGAGCCACGATGGGAACTCCTCCCCCTGGACTTTCACCTGCAATGCAGGAAAGTGACCCAGGCCTG |
| GTCACTTAGCAGCTTCCCACCCAAAAGAAGTAGCACTCAGGTTCTGATACCAGTGAAATGTTAACAGCGGCTCCAG |
| TGCCAGCAAGAGCTAGAATTAACTCCTGTTGGGAGACCCTAACTGTGTTAGGTCTGTTGCCTGACCTCTCCTGGTT |
| CTGAGCAGCTTGGTTTTCAAGCTCCCCCAGGAATACCATGAGCAACAACCAAAAAATCCTTCCAAGGCACATACCT |
| CTTCTGCCTCGGTGAGCTAGAATCTCCATCGGTTGCTTGTAACCACAATTTCTGACCCGTACCTCATCTCAAGCGC |
| TTCTCAATATATCAGCCGCAAACATTCGCTGAGCCTTTCATGCCAGAGAAGGAGCTCCTAAGCACTCAATTAGTTT |
| GCACAGAGGAATAGTAATCGTGCCTTTCTGTGCACAGCTCTGGCATAACCTATGAAAACGGAGTTTGCCACACAAA |
| ATAGCAATCTGCAAACAACCACAGCTCAACTGAGAGCAAATCCAGGCCCAGTCCCTGCTCCCCGGGAGCCATATTC |
| CCCCTAAAGAAAACCCCTTCCTTGATTTTGTCAACGGTCTTGTCTTTCCCCACAGATGCCAGGCAAGTTCCTCTTG |
| GGGACAGCTGGCCGGCCACTTGAGGACTTGCGATTTCCCTGACGTAGGAGAAAGGACAGCTGGGTTTCTGCACACA |
| GATGCTGCCAAGCCCAACGTCACCCTTCTGGGCAGCTGACCCATTGCCCCGGGCTTGCTCCCTCCCCTGTGCCCCT |
| CCAGACACCAGGGCCATCTGGATTCTGGAACAGCCATGGGGAAGATCAGGATGACTGGTTCTCAGGACCCCTTTCC |
| TTTGCCTGAAACGCTCTTCCTTTTTCACCCTCTACATCCTGCGGGCCTCAGTTTAAAGATCACTTCCTCAGGGAAG |
| CCCTCCCTGACCACTTCCCCAGACAAGTTCAGGGCCCCAGGACCCTGCCCTGTTTATCTCCTCCATGTCTCTGTCT |
| GTGCAGTTCATTGTTTACTGACTATCTCCCCAGCTGAATTCTAGCCTCTGCACAGGAAGGGATTGCACCTCTGTTC |
| ACCGAATCTCAGGTTATCTAGCACAGCATGTAGTTCCATAAATCCTGAACGCTTTAAAGATGAGTGAAGGACATTC |
| TGGCGGCTCAGTGAGCGCTGAATGAGTATCTGATTTAAAGCATGCATCTCAGCAACAGGTGCATCTTTTAGGACCA |
| CCGTTTTCTGGTGCCCAAACTCACAAGGGCAGGGTGAAAATTTAGCCATCCCTACTTCTCCCCGGGTCGTTTTTAG |
| TTTGAAGGTTTGTTTCCTGTGGGTTGGGACTGGCCCGATTTTTGTTTAACAGCAGCTATTGCTCAGAGAGGAGTTT |
| GCTAGATGCCAGCCTTATACCACCTGGTTGATGGGGAAACTGAGGCCCCTACCACTGGCTGCACCAGCACCGGCGG |
| GGCGAGACCAGCTCTCTTTCAGCCCAGAGCTCATTTCAGGGTCCTTCGCCCCACATGGGGCCAAGTCCAGGGCATG |
| CGAAGCAAGGCTCGGGAAGATAAGGGCACCCAGACGGGGATGGAGTTTGAAACTTTTATTAAGAACGAATCAAGAG |
| GGAATTCCCTTCATGGCTCAGTGGTTAACGAACCCGACTAGGATCCATAAGGACAAGGGTTTGATCCCTGGCCTCG |
| CTCAGTGGGTTAAGGATCCAGCATTGCCGTGTAGGTCACAGAGGCGGCTCCCATCTGTGTTGCTGTGGTGTTGCTG |
| TGGCTGAGATGTAGTCTGACAGCTACAGCTCCGATTCGACCCCTACCCGGGGAACTTCCACATGCCATGGGTGCAG |
| CCCTAAAAAGCAGAAGAAAAAAAGAAGAAGAAATCAAGAGACCTGGCCTCTCTCTCTGCCCAGCCTCTTCCAGCTG |
| CTACCTTCCACTCTCTCCGGCTAGTTTCAGGTTGAGCAAGGCCAGGCAGGAGCCCTCTCGGGGGCTGAGCATGGAT |
| CTGGGCCCCAGCAGCGCCCCCAACCTTCAGATTCACCTTCACTCTCCTTGCTCAGGGCCCACCAGGGTCTCCAAGC |
| CAAACTATGTTTGAAGTCAAGACCAGGCTTTCATGCTTTGGTTCTGCCACTTCACTCTTGAGAGATGGTGGCCAAA |
| CAATTAAAACGCTGAGCCTCAATTTCCCTGCCTGTAAAGTGAGGAGGCGGGGGGATAATTCCTGCTTTGCTGACTT |
| CATAGGGCTTTTGTGAGGCTCAGGCGAGGTAGATATATGTACTCACTCGTCTAACTGTCCACTAGCTTAGAGAACT |
| CTAACAACAACTCTAGGAGTTCTGGCAGTGGGTTGAGAATCCGACTGCAGCTGCTCAGGTCACTACAGTGGCACGA |
| GTTCGATCCCTGGCCCTGTGCAGTGGGCTAAAGATCTAGATAGAGTTGCGGCAGTGATGGCATAGGTTGCAGCTGT |
| GGCTTGGATTCAATCCCTGGCCCGAGAACTTCCATATGACGTGGTGCAGCCGTAAGGGAAAAAAAAAAAAAAAAAA |
| AAGATACTGTTTTTCTGGTCCCATTAGGGTCTTGCGATCAACGTGTAGCCAGCCCATGTCCTCCAGGGCCCAATCC |
| TCCACCCAACCTCTCAGCCAGGCTCTCCTCTTGACCACATCCTTCTAGAAATCCTTTCTGCCTCTGCCTTCCTGGA |
| TGTGCTCCCTCTGGGCTCTCCTCCATCTCAGGTCACTCATTCTCCCAGTTAGGACCTGGCCCACCTGGCAGCTCCG |
| TGCTTTTTCCTGCCATTCACGTCAGCCAACCACACAGGGCCTGGGACAGGAACTGCAGGGAACACATACCAACACT |
| CAGATCCCTGGATAAGGCTTGCGTGCGCATTCCCTGGGGCACAAAACATGCGCACAAAGCATTGTGTCCCCACCCC |
| ACTGCCCTCACCACCCCTCCTTTGCTGGGGCATAGGGCAGAACCCACAGCAGACGGAAATTCCCAGGCTAGGGGTC |
| TAATTGGAGCTACAACTGCCGGCCTACATCACAGCCACAGCAACGCCAGATCCAAGCCACATCCACGAAGTACAGC |
| ACAGCTCACAGCAACGCCGGATCCTTAACCCACTGCGCGAGGCCAGGGATTGAACCAGCAACCTCATGGATACTTG |
| TCAGATTCATTTCCACTGTACCCCGACAGGAACTCCACCACTCCTCCTTTAAGAGACTCTATTTGGCAATAAAGCC |
| AGAGCCAAGGCTCTGGCAAGAGTTGCAGCCAGGTCTGATCATAGGCAGCCAAGGTCTGTGGCCCTCCAAGCCGGGC |
| TGGGACAAGCCAAGCAGATCAGCTCCTCGGCTGGAGATTTCAATGACATATTTTTAGGTCAGCCTCTCTTTAGAAT |
| TGCAAGGACTTTTATAAATAATTCTGGGTTAAGTATATTCCACATGATGACCCTTCTGCCTTCAGTCCACAGTCCA |
| AATCTACATCACTCTCTGGTGTCCCAGACTGACCCACCTGGCTTCCCTCTCTCAAGACTAAGGCTGAAGCTTTTAT |
| CAGCAGACCTTGCAGCCCAGGGCAGGGGGTTGGGCAGGGGGGAAACGACTTTGCCCCAGTTGCCCTTGGGAGGCCA |
| CTTACCCACAAGTGTGGGTTAAGTAAAGGGCACTGCGGTCACATGCCCAGTGTGCCATCTGGCTTCAGCAGCCACC |
| GTCAAAGAGGGAAGAAAAAGTGACATGCAACAGAATGTAACCGGGGCATGGCCTGCAGGATGCCCAGGGACCTGGG |
| GGGCAGAGGGGTGCCAAATTCATGGGGGGCTTCTCAGAGAGGGTGGTGATTAAGATGGGCCTTGAAGGATGTGTAG |
| GAGTCTGTGGGAGGGTTTGGGGAGGAGGTGGGAGGGTGTCCTGGGCATGGGGAAAAGTCCAGAGCCATCGAACCAG |
| GAGAGGGTTTCAGGAATTGCAGCAGTTCCCTCAGGCTGGAGCAGAAGTTCCAAAGGATGGAGTGGTGAGGGTGGTG |
| AGGGCTTCAGAGGGCTGTCTGTATGGGACCTTGGAGGTCACCCAAAGGAATGTGTGCTTTATCCTGAGAGCAGAGG |
| GAGCCTTGGAAAAGATGGAAAACTCCAATCAATTAGGTGTTTGGAAATGAGACTTAGGCTGCAGGGAGAGGGTGTA |
| TAGGAACAAAGAACAGGGAGCATGCAGCAGCAGGGGCTGGGCTGAAGAGGGCTGCCCACCAGCACAGCAGGGGCAG |
| GGGGGCTGGAAGGAAAGGGTCTCTTTTTTTTTAGGGCCACACCTGCGGCATATGGAGGTTCCCAGGCTAGGGGTCG |
| ACTTGGAGCTGTAGCCACTAGTCTACACCACAGCCATAGCAATGCCAGATCCTTAACCCCCTGAGCAAGGCCAGGG |
| ATCGAACTCATGTCCTCATGGATGTTAATTGGGTTTGTTAACTGCTGAGCCATGACAGGAACTCCTAAAGGGACAC |
| TTTGGAGAGCTGGTAAAGGGGTGGGATTGACTGAACTAGATTAGACTGGAGGGGAATGTTTGTTATGCAGCATAAC |
| TGCAGCCAAAGCTAACAGAGGGGCCACATGAGCAAATATATAGAGACAGAAAGGCCACTGCCATGCTTGAAGAAGC |
| GGAACGATGGTGCTGATGGTACCAAAGAGCAGGCTGTGTGATGGGCATTAGTTTGGAGAGAGAAAGATAGGTGGGG |
| ACCTGCACGAGGGAGTTTCTAACAAATATATGAAGTTGATTGGATTGTTGTTCCCAAGTATCTATTCTGGGCCAAT |
| AGGCAGAGCTTATCGCAGTCCCATTGACTTTAGACTCAGTCACATGACCAGCTTTGACCAATGGAATATGGATAGA |
| AGTGACCATGTGCCAATTCAGAGATTTAATTTTTTTTTTTTTTTTTTTGTCTTTTGTCTTTTGTTGTTGTTGTTG |
| TTGCTATTTCTTGGGCTGCTCCCGCGGCATATGGAGGTTCCCAGGCTAGGGGTTGAATCGGAGCTGTAGCCACCGG |
| CCTACGCCAGACCCACAGCAACGCGGGATCCGAGCCGCGTCTGCAACCTACATACACCACAGCTCACGGCAACGCT |
| GGATCGTTAACCCACTGAGCAAGGGCAGGGACCGAACCCGCAACCTCATGGTTCCTAGTCAGATTCGTTAACCACT |
| GCGCCACGACGGGAATTCCTTATTTTTTTTATTTTTTTGTCTTTTTGTCTTTTTAGGGTCTCACCCACGGCATATG |
| GAGGTTCCCAGGCTAGGGGTCCAATCAGAACTGCAGCCGCCAGCCTATACTAGAGGCACAGTGGATCCAAGCTGCA |
| TCTGTGACACTGGATCGTCAACCCACTGAGCAAGGCCAGGGATCGAACCTGCAAACTCATAGTTCCTGATCAGACT |
| CGTTTCCACTGTGCCACAACAGGAACTCCCTCAGAGATTTTATGTTATTTATTTATTTATTTATTTGGTCATGTAG |
| CAGTTTGATGTGGGATCTCAGTTGCCAGAACAGGGATTGAACCTGGGCTGCATCAGTGAAAGCACCCCAAGTCCCA |
| ACCACTAGACTACCAGGGAACTCTCAGAAACTTTAAGAAGCATTGAATTATCTCTTTCTTCCTCCAGCTCTCAGCA |
| TCAAAATGACACATTCTAGGTAGAAGGAGCAGCTTCAGCCTGGGTCCTGGGAGGAGAAGATACATGCTGCAGATAT |
| TCTATCCTGCTGCCACCTGGAGCAGATCTACAAAACCATGCAGTTGCAACTGCCTTCTGGCTGACAAGCAGTGTGA |
| GCAATAAATAAACCTTTGTGGTCGTAAACTAAGATGGGGGGATGTTTGTTATGCAGCATAAGCTAACTGATACAC |
| ACTATATATGTGAGATGATAAGGATGCAGATGGTGAAGAACATCACATGTCACGATTAGTTGTTGTACACATGGTG |

TABLE 9-continued

| lists sequences for the disclosure |
| --- |
| AGTCAACAAAGAATTTTGTAATTGATGAACCTTCTCCACCTTTCCTTTAAAGCCAACCCTCTCCACTCCCTTCTGC<br>TCCTCCTAGCCCCTTGCTCTATCAGCCACCCCTTCCCTCGCATGGACTGAATCCTTCCCCTGAAACTATATCTCAC<br>TTGTCTCTTCCATCCTAAAATCCTTTTCTTTACTCTGTCTTCCTCCAACTCTAGCTCAGTCTCTTCCTCGACCATC<br>TCAAACAAACTTCTTCTTCTTCTTTTTTTTTTTTTTTGTCTTTTTAGGGCCACACTTATGGCATATAGAGGTTCC<br>CAGTGTGTGACCTACACCACAGCTCATGGCAACGCCGGATGCTTAAGCCACTGAGCAAGACCAGGGATCCAACCCA<br>TGTCCTCATGGATGCTAGTTGGGTTTGTTAACCACTGAGCCACAATGGGAACTTCTTCAAACAAACTTCTTAAACG<br>AGTTGATTCTCCTCATTATCTCCACTTCTTTCTCCCTCACCTCCAAGCAATCTAGTTTACCTTCCCTCCACCCCAC<br>CAAAACCATTCCCAGTATATTTCAGCAATCTAATAGTCCAGTGCAATCCAGTCCTTATCTTCCTAGACTGTTCCAC<br>ATCATTTAGCTTGGAACTAAATTCATTTTCTCCCTGCCCAACCTCAAATATTCTTCTTTCCATGGAGTTCCTGTCA<br>TGGCTTGGTGGTAACAAACACGACTAGTATTCTTAAGGACTCCGGTTCCATCCCTGGCCTCGATCAGTGGGTTAAG<br>GATCCGGCATTGCTGTGAGCTGTGGTGTAGGTTACAGACTCGGCTCAGATCCCTCGTTGCTGTGGCTCTGGTGTAG<br>GCTGGCAGCTGCAGCTCCAGTAAGACCCCCAGCCTGGGAACGTCCATATGCCACAGTTGCGGCCCTAAAAAGAAAA<br>AGAAAAAAAAAAATTCCTCTTTCCATATTCTCTCAGCTAGTGGCACCATCATTCATCCAGTGACTCATGACAGAAAG<br>CCAGCATGACACAGTGAATTCTGCTCTGTAGTTGTCCAGTCTGCGGTGCCTTTGAGACATCCAAGAGGAGATGTCC<br>CAAGGGCAGCAGCTAAACATGTGAATTGGGGGCTGACAACAGAGATCTGAAGTGGAGATACCGATGACTGTTAGAG<br>GCAGCATTTAAAGCCATGTGCATGCGTCAACTTGTCTATTTATAAAGTACAAGGACCTGGTGATACATAGAGCGCT<br>CTCCTGAGCCTATACATTCCCCCTCCTAAGACCACAATTCCAGGTACCACTTAGTTCCTTCCTTCCCAAGTCACGG<br>CTCACAGGGGCCTCCATATCACCACCTTATTTCATATTCTCCCCCCCCAACATGTTGCCTTCTCCAACAACTCTTA<br>AAATTCATAAAAACAGAAGATATAAGATACCACTACCCAGGCACTAAAATGCCTAAAAAACAAAACAAAACGCACC<br>AATGTGCTATCACTCACATGTGGAATCTTTTTTTTTTTTTTGGCTTTATTTAGGGCTGCACCCAGGCGGCATATGG<br>AGGAGGTTCCCAGGTTAGGGGTCTAATCAGAGCTGCAGCTGCCGGCCTACACCACGGCCACAGCATCATCAGATCT<br>GAGCCGCATCTGTGACCTACCCCACAGCTCACGGCAACGCCAGATCCTTAACCCACTGAGCGAGGCCAGGGATCGA<br>ACCCGCATCCTCATGGATCCTAGTCGGATTCCTTTCCACTGCGCCATGACGGGAACCCCCGCATGTGGAATCTTTA<br>AAAAAAAGGACACAATGAACTTCTTTACAGAACAGAAACTGACTCACAGACTTTGAAAAACTTTCAGTTTCCAAGG<br>GAGACAGGTTGGGGGTGGCGGGGTGGGTGAGGGTTTGGGATAGAGATACTATAAAATTGGGTTGTGATGATTGTTG<br>TACAAATATAAATGTAATAAAATTCATTGAGTTAAAAAAAAATGAACAGGAGTTCCCTTCATGGCTCAGTGATTAA<br>CAAACACGACTAGGATCTATGAGGATGCAGGTTCAATCCCTGGCCTTGCTCAGTGTATTAAGGATCTGGCGCTGTG<br>GTGTAGGTCGCACACAGAACTCGGATCCTGCGTGGCTGTGGCTGTGGCGCAGGCTGGCAGCTGTAGCTCTGACTGG<br>ACCCCTAGCCTGGGAACCTCTACATGCCGTGGGTGAGGCAAAAAATTAAAAAAAAAAAAGAATTAATTATAAAATA<br>AATAAATAAATGAACAAATGTAGATGTTAAACACTTATCATGGAACACTCCTGGAAATAAAAGAAGATTAGAACTA<br>AAAAAAAAAAATGGACAATACGCAAACACTGTCGAGGATGTGGAATAATCGTGTTTTATACATTGCTGGGGAATCT<br>AAAACGGTACACCCTATGACCCAACAATTTCAATCCTAGGTGATAACAAAGGTCCACAAAAGACTTCTACAAGAAA<br>TAATAGCCCAACTTAGAAATAACCCAAAGGTTCATCGAGACGAGAATAAATATGCAAATGATGGTATAGCCTTAGA<br>ATAGAATACTACTCAGCACTAAAAAGAAAGACACAGATGAATTTCACAACATACACAACAACACAGGTGAGCTTCA<br>CAAACTATATATATATTACATGGAGGGAAATAAGCCAGATACACAAGAGAAATACAGTGTGATTCCATTTATGTGA<br>AGTCCAAGAGCAGGCAAAATTAATCAATGTTGAATAAAGTGAGAAAATGGTTGCTTGGAAGAGGCGAAGGAAAATT<br>GATAGGAAATGGGAACTTTCCTAGGATGACGCAAAGATTTCATATCTTATTTCGGGTGGCCACTTCAAAGGTGCAA<br>ACAACAGCTAAAACTTGTGGAACCCAACCCTCACCACCTGCGTATTTTATTGTTTGGAAATTATACTTCAGTTAAA<br>ACATTAGGAAAAGAAAATAATTTTGTGAAGTATCAATAAAATAACGAAAATGAAGAGACTCTAAAGGGCAAAAACA<br>CATTCAGTTCAAATATATAAATTATATTTGTGCTATGTATGCATCTATACGAATGTCCAGCCCCCCTTAATGTAGC<br>CCCCTTTCAGCCATTCTCCGCTCACCCTTGCCCCCATCCTGATGGCCTCTGTCCATAGCCATTTTCTAGCTGTCAT<br>CAGAAATGATGCAGTGAAAGAGCAAAAGCCTTAGAGCCAGATAGAGCTGCATTTAAATTCCAGCTGCTGAGCACCC<br>ATAATCGAGTTACTCGGCCTCTCTGAACGTTCATTTCCTCAACTACAAAATGGGTTGATGAGACACAATCAACCCT<br>GTTGGGCTGGACTAAGAGAGAGGCAGTGTGCTGATTAGTTTCTGGGAAACCTAATTCTTTTGACCTCAGCCTGTGA<br>AACCAACTTGGTTGTGCAAGGCCCACTGCCGGCCTGGAAAAGCCCAGAGGATGAGACTCACGGGCTACTTCTCCCT<br>GAAGGATAGGGAGGTGGTCCTGGGAACCCAGAGTCTTTGTGGGCTGGTGCTAAGAGTCGAGTCGCTAACTCAGAGC<br>CATCAGGGCCAGGAAAACCTATGACCTATGACAAAGGAGACAAGTTTCCTGCCAAGGGTTGGCCACCTCAGGATCT<br>TGCCCAAATCACTTTGCACACCCCTAGATTCCATTTATCCACCAAAAATGGCCAGAGGAGCCTGGATCTGAAGAAT<br>TTGATACTAAAAACAGCTTCTGGAATTCCCATAGTGGCTCAGCAGAAACGAATCCGACTAGGAACCATGAGGTTGG<br>GGGTTCGACCCCTGACCTCGCTCAGTGGGCTAAGGATCCAGTGTGGCTGTGAGCTGTGGTGTAGGTCGCAGATGCA<br>GTTTGGATCTGGCGTTGCTGTGGCTGTGGTGTAGGCCAGAGGCTACAGCTCCGATTAGACCCCTAGCCTGGGAACC<br>TCCATATGCCTCGTGTGTGGCCCTAAAAAGTCAAGAGTTAAAAAAAAAAAAAAGAGTTAAAAACAGCTACTATGTCT<br>TGGGAGCATTGCGATGCAAGTTTGTTCTCAGCCAGGCACAGGGTTAAGGGTCTGGCATTGCCACAGCTGCGGCTTC<br>GGTGGCAACTACAGCTCGGATCTGATCCCTGGCCTGCTCCATGTGCTGCGGAGTGGTCAAAAAAAAAAAAAAAAAA<br>AAAAAAAAAACCCAAACAAATAGCCTCTGGTGTTTCCCAATCTATAGAAGAGATCAAGGCAGGACCAAACTGGTTC<br>TGTCCGAAAGAAGGAACGGAAGAGTCAGAGTCGGAGCCCTGCCGGCTAGCTCCCCTCCTCCACCTTGGCGTTTCCT<br>GAGCCAGGATCCTAGGTCTCCCAGGGGCAAAGTTTGAAATCTCCCTGACCAGGTAAACCCTAGGGCCTCTTTTAGC<br>TCAGTCTTATCCAGTCGTGGTGCATCTGTCAAGTGTAATAATAAAGAGGATCTGCACCTGCCCCCCCACCCCATCT<br>GGTAGGGGAGGCAAGGTGCACCCAGAAATAACTCCGAGCAAGGTACAAAGTGCTTAGTGTAGCCAAAGAAGCACAT<br>AAGTCCAATAAAGCATCCACATTCCCCCCCACCACACACACACACACAACCTCTTCGCACTTGGCATTTCCTT<br>ACTTCCAGCAGTCTCTCTATTTCAGGTTTGTGGAAACGGGTTCTCCCTGGAAAAGGGTTTCCCAGCTAGGAGGCGG<br>CCCGGCCCCGACTCCCCCTCTCCCCCACCACCCCCGGTCCCCGCACGTCCAGCGCTCCGAGACCCACCCATTTCCA<br>AGCACAAGAACAAGGCGACAAGGCCCGCTCAGGGGCCAAGAGGAGGGCAAACGACGACAAGCAAAGCCACAAAAGC<br>AACCGTCCGGGTCTCTTGTCTTTCCTGGGGGGAGGAGCGGCGCCCGCAGACGGTCTCCGCGCCTCCCTCCCTCCCG<br>GGCCAGCGGGAAGATAGGGGAATCTCAAGTCGCTCTGCTTTCTCTCTTCGCGCACTGACATTTTCCCCCACTTTAC<br>TGTTTCTTGGACGCCTTTCAAGAGTTTGTGCAACCAGTCTGTTTAGCTGCTTTTCTGCCATTTTCAAACGCGGGGT<br>GGTGTCCCTTTCGAGTGGGAACGTGGTGGCTTAAAGTCTGGAAGGGACCCCTTCGCCTCCCGTCACCCCGCTGCAG<br>CGGGCCTCTTCGCCGCCAAAGTTTCGGCGTTCCAAAGTTTCCCCCGGCCGGGTTTCGGGCTCGGTCCTCCGCTCTC<br>TGAGCTCCCCGACTTCTCCCTCTCTGTGCGCTCAGGGGTTTCTGTGCCCCTCACTTCACTCTCAGGTTCCCTCTTG<br>CGGAGGCATCCTCTTCCCACCTAGTCCCGGGCGAGGGAGGCCTCCGCCTCCCCTGCCCCACATTGGGAGACAGACC<br>CCTCCCTCCTTTCGAGACTTCCCGGGCAGTCCTCCTCCTCTGCGCGCCCCGAGCCTCCCCTCTCCCGCCTCCATCC<br>GGCGGACCCCGTGGAAGCCCGCAGCCCCTCAGGCCCGACAAGATGGGGACAGAGACGGGGTCAGAGTTGAGCACAG<br>AGGTAACGACGAGAACAAAAGCGGGGACACGGCAGGGCAGCAACAGGGCAGGGCCGGCGCGGTGGCCTGTCCTCTC<br>CCCGCGCTGCCTCCACGGCGCCCGCAGCCCCGGGCCGGGCGGGACTCGCGGCCTCCAGGGGCTCGGGCAGCGCCCA<br>GCGGGACCCACCTGATCGGCAGAAGCTGGGTGCGCTCGGGGATGGCCCACACCTCGGCTCCCGGCCCCCCGGCGGC<br>GTCCTCGGCTGAGGGAACAGTGGCGCGCGGCGTGCTCCTGAGCTCGGCAGGGCGTGCCGGGGGGGGGTGTGCCGCC<br>TGCGCTCCGGCCCGCCGGCCGCTGTGTGCTCCTCCGGGGTGGCGGGCAGGGGCGCGAGGAAGCCGGCGGGCACTGG<br>GCGGCGGGCGGCGAGCTCCCCGCTCCACCCGGCCCGCGGCTGTTTGTGCAGAGCGGGTCCCGCCCCAGACACGGCC |

TABLE 9-continued lists sequences for the disclosure

GCTAGGAGGCCGAGGGCGCGAGTGCGCGAGTGCCGGTGCGCGTGTGTGTCTGGTGGCCGGGAGGCGCAGGGGGTGT
TTGTTTCATTTTCACTCAGGCAGAAAAAAGCCTGAAACCAGCAAAAAAAGAAAAGAAATTCCCTGGTGAGGGTGGC
TGGGCCTCTTTGCCTTCTCCGGCCTGCACGTGGTGGGGGTGGAGGGACCCGGAGGGTGGGGTGGGGTCTATCACCC
AGTACTGCAGGGAGGGGCCCCGGAG

SEQ ID NO: 14 GGTA1 cDNA Sequence
ATGAATGTCAAAGGAAGAGTGGTTCTGTCAATGCTGCTTGTCTCAACTGTAATGGTTGTGTTTTGGGAATACATCA
ACAGCCCAGAAGGTTCTTTGTTCTGGATATACCAGTCAAAAAACCCAGAAGTTGGCAGCAGTGCTCAGAGGGGCTG
GTGGTTTCCGAGCTGGTTTAACAATGGGACTCACAGTTACCACGAAGAAGAAGACGCTATAGGCAACGAAAAGGAA
CAAAGAAAAGAAGACAACAGAGGAGAGCTTCCGCTAGTGGACTGGTTTAATCCTGAGAAACGCCCAGAGGTCGTGA
CCATAACCAGATGGAAGGCTCCAGTGGTATGGGAAGGCACTTACAACAGAGCCGTCTTAGATAATTATTATGCCAA
ACAGAAAATTACCGTGGGCTTGACGGTTTTTGCTGTCGGAAGATACATTGAGCATTACTTGGAGGAGTTCTTAATA
TCTGCAAATACATACTTCATGGTTGGCCACAAAGTCATCTTTTACATCATGGTGGATGATATCTCCAGGATGCCTT
TGATAGAGCTGGGTCCTCTGCGTTCCTTTAAAGTGTTTGAGATCAAGTCCGAGAAGAGGTGGCAAGACATCAGCAT
GATGCGCATGAAGACCATCGGGGAGCACATCCTGGCCCACATCCAGCACGAGGTGGACTTCCTCTTCTGCATGGAC
GTGGATCAGGTCTTCCAAAACAACTTTGGGGTGGAGACCCTGGGCCAGTCGGTGGCTCAGCTACAGGCCTGGTGGT
ACAAGGCACATCCTGACGAGTTCACCTACGAGAGGCGGAAGGAGTCCGCAGCCTACATTCCGTTTGGCCAGGGGGA
TTTTTATTACCACGCAGCCATTTTTGGGGGAACACCCACTCAGGTTCTAAACATCACTCAGGAGTGCTTCAAGGGA
ATCCTCCAGGACAAGGAAAATGACATAGAAGCCGAGTGGCATGATGAAAGCCATCTAAACAAGTATTTCCTTCTCA
ACAAACCCACTAAAATCTTATCCCCAGAATACTGCTGGGATTATCATATAGGCATGTCTGTGGATATTAGGATTGT
CAAGATAGCTTGGCAGAAAAAAGAGTATAATTTGGTTAGAAATAACATCTGA SEQ ID NO: 15 GGTA1 Protein Sequence
MNVKGRVVLSMLLVSTVMVVFWEYINSPEGSLFWIYQSKNPEVGSSAQRGWWFPSWENNGTHSYHEEEDAIGNEKE
QRKEDNRGELPLVDWENPEKRPEVVTITRWKAPVVWEGTYNRAVLDNYYAKQKITVGLTVFAVGRYIEHYLEEFLI
SANTYFMVGHKVIFYIMVDDISRMPLIELGPLRSFKVFEIKSEKRWQDISMMRMKTIGEHILAHIQHEVDFLFCMD
VDQVFQNNFGVETLGQSVAQLQAWWYKAHPDEFTYERRKESAAYIPFGQGDFYYHAAIFGGTPTQVLNITQECEKG
ILQDKENDIEAEWHDESHLNKYFLLNKPTKILSPEYCWDYHIGMSVDIRIVKIAWQKKEYNLVRNNI SEQ ID NO: 16 CMAH Genomic Sequence
CTACCCAGAGCACATCAGGAAGGACTTCCAGTCAGGTGGTGTGAGGGGGAGTTTTATTTGAAAATGATTCCAAAAC
CTGTAAGAGATAAAGTAGAAAAACATGTTTTGGAAACTTCCATGCCTGCTGTATTTGCCAAAATCTGTTCAGTACC
TGGTACTCAGCTTTCCCTGAAAGATAGCGTTTCTGTACTGTTTCAGATGTTCATTTAACTTAGCATTTTTGATACA
GAATGCAGTCCTTAAACATGACAATTGTGTCTTCCTTCTATTTTTCTGTGACATGCCTTGCTTTAAGGAATTCTTG
TATGTAAAAATATAGAATCTGTACACAAAAACATTAGGACCTAGTATTGGTGAGAGGGCAAGTAAATGGGTTATAT
GTTATTTCTGAGAAGGCGAGTTGGCTTCCTGAAGATCAGTCTGGCAGAGTATAGATTATTCTAAGAAATCATTATG
AATTTATCCTAAGAAATTTATCCTAAGAAATCATTATGAAAGTGTGCAAGACACACCTACATATTTCTTTGCCAAA
ACATCATTTCAAATAATGAAAAGTTAGAAACTTACAGGGTAGATCAAAGACTGTTCAGTAATCATGCAGGTGTACA
GACGTATGTATAGTATTATCCCATTTTCATTTTTTGAAAAAGTGCTTGTGGTATATGTGCTTGTAAACAGAAAAAG
AAAGATGAACTAGACACCAAAGTACAAATTGCTCTCTGGATGGTGGGATCATTTGTGGTTTAACTGTTTTTTGAAT
TTAAAAGTTTTTTTTTTTCCAAATTTTCTGCGGTAGATCTGTGTTATTTTTATGATCAGAAAAATATTTAGTAAAC
TAAATCTCATTTTAAAAGCAACAAAGATATATTGGGCTATGACTGCTTCCCAAGATTCATCACAGGATCCTTTCAC
ATTTATGAACTTTGCTATCAAAACAGTATATAGAAAAATAGTCTTCAGAATCAATAGCCCAGAAGTTTCCAAGATG
TAATTTTTTTTAAAAGAAAAGTTATCTTTGAATCTTTCTCACTCAAATTTGCTCCATTTCCTTTTTTCCAGAACAG
AAGTCAGCTACGAACTCTGTTGAAAATGAACAAAATGTTTTCATTTTGCTTTACAAATGAAATGGTTTCCAAATGG
AATGTTTTACAGACATTAAAATAGTTGAGGTTGGAGTTCCCATCATGACTCAGTGGTTAATGAACATGACTAGGAT
CCATGAGGATGTGTGTTCGATCCCTGGCCTCGTTCAGTGGTTAAGGATCCGGTGTTGCCATGAGCTGTGCTTGTAG
GTCACAGACACGGCTTGGATCTGACGTTGCTATGGCTATGACGTAGGCTGGTGGCTACAGCTCTGATTAGACTCCT
AGCTTGGGAACGTCCATATGCTGCAGGTGTGGCCCTAGAAAGACAAAAAGACAAAAAAAAAAAACCCAAAAACTGAG
GTTGACCTGTGTGTCCCAACACTAGAAATACCAAAGATATTAATGAATAAAAAATGCAAATTACAGATGTACCAGG
ATTACATTAAAAAAAAAAACAAAACAAAACCCAGGAATGATAACCTCCCCTCCTCAACTATAAGGGATGTTTTATT
GAGAAAAAATACATTTCTTGAAATGCTGATATGCTCAAAAATAGGCCTGGGGTGATACAACTATGCTGTTACCAAG
TGTTACCCTGGAGAGTGGGTGGAGAAAGGCAGGAAACAGGGTTTTGTGGGAGGTGTGGGGTTATTTCCTTTTTATT
TTATATAATTCTACATTCTTTAAATATTTTTAAAGCAATTTCAAGATATTCAAAAAGAAATCTATAAAGAAGAAAT
GTCAAGACAGGCCTGTGCGTGCAAGCTCATGGCAGAAGCGGGGTAGGAGGCTTGCCTGCTTCAGACTAAATTCCTG
ACCTTTTCAGAGGGTCAGTGGTCATGAAAGAATGCATTCTCCCCTCTTGCTGATTATTTTGCAAATACAAAAATGG
CAAATGGGGCTTTCCAGCATTTCAGCACAAATATTCCAACTAAAGCCCTAAGGACCTATACGGTTTTGCTATGAGA
AACTTACGTGGTTTTTGAAGCTCAACCAGGGAGAAACTTGGAGGATCATCCCCTTAACCAACTAGTTCACCAAATT
CATGCTCAGAGTTGGGCAACATGGGAGATGAATGTCTTCCAGGATCACAACTTTGCCATATCACCCCATCCTCATT
CTTGTCATAGTGATTCTTAGTAATTTTGCAGTGTCTTCAGATAAATTCTGAGGAGTGGAGCTGCTGGATCCAAACA
CACCCTCTCCCTTTCATAATGTCCTTCCCTTCCCTGTACTCTAAACTACTTGTATACAGGATTGAAGCACATGGGC
ATGAATGTCCAAATGGTGACTCTTTGAAAGTTATCTTCCTAACCAGATTTGCCTTTCAAGGTTAACAAAGAAAAAA
GCTCTAACGGTGGAATCTCCATGGCCATCAACACTGCAGGGCACAGTCAGTCACTGACTCTGCTTATATAGCCCTG
GCCTCCTCTGCAGCAGCCTAGGGCACACACGACAGGCATTTTCGGACTTACAGATGATGGTATATATCAGGATCCC
GCTGAAGCCGGGTTTGGAATCCTATGTACAAGTCATCCCAGAGCAGACCATTCTTTACCACGTGTCTGATGACATC
AACCCGGCTCCGAATCTGAAACAGAGGAGGAATCACGAGTTAGGCGCAACCCAGCCAGTAGAGAGTGTCAGTATGG
ACCCCTCGTGTCCCGGAGAGAAGCAGCTGCCTGTAAGGGCAGGGATGGAGGAATCAAGGAGAAAAGCCTACTGAAG
CAGATCTCACAGGCCGAGGGGGAGAGGGGCCCCTGAGTGCAGCAGAAATCGAGGGATGGAAACAGGAAGTGGATCA
GGAGCTGGGGGTGCAGAGTGGCAGAGAGTACAGACAGAGTTGGATGGCTGGGTATGAACCCCCAATATAGCTGTGT
GACCTTGGCAACCATTCTGTGCCTCAAGTTCCTCATCTATACAGTGGAGGTAATAGAACATTCCTCCTGGGGCTGT
TGTGAGGATTACCTGAGCCAGTGTACTTAAAATACTGAAAACAAGGCCTGCCACAGAGCAAGATTACCTTAATTCG
GTGGTCAAGGCCCTTACCTTCAAAGAATCCCAACTCCTGACACAGGATCTGTTGAATAGTCAGAGGTGCACAGGGT
TAGGAGACAAGCAGAGATGGTTTTGAGTTTCAGCCCAGCACTTACTAATCATGTGACCTTAACCTTGCTAAGCCTC
GGTCTCCTCTGTGACTGTTGTGAGAAAAAAAAAAAAGAGATAATTCATAAAAAAAAAAAAAAAAAAAAGAGCATGAAGT
AGCATGAAGGGAAGTCACTCTAAGATTGGACTGGCTTCAACATTTTATCGGTACCCATGTTCATGTTTACCAGGAG
CTTTTCAGTATCTGGCATCATATTTTTTTTTTCCTGAGAAGTATTGTGCTAATGCCAGTAGAGGAAACTTTATCAT
AAATGACAGGCTATTAAATGACATAGAATGATCAGGAGTTTGGCATTAGGGATTTACTTCTTTTTCGTTCACCATT
CCTATAAAACAATTACATCCACTGTGATCTGAGATCGCAACACAGGTCAAAGGCACTCTCATTTTGCCAGTAGAGA TABLE 9-continued

| lists sequences for the disclosure |
|---|
| TTTAGAAACACTGCACAGTTTGTCAGGTCGAGGACTGCCCAGCTCAGGGGCAGTATCAAGATCTATTTCCTCACAG<br>TGGAGGGAAGATGGCCTTTCTTGACCTTTCAATATAGAGGAGAGCACGTGGAAGAACTAGGGGATGTTTTGAGCAA<br>CATTTAGGGTGTAAACTGGGAAGGGCTTGGAGACTCATTAGGTTTAGGGATGGAGAAGGAAAGATTGAAGATTAAG<br>CCCTTGTTTCTAGCTTGGCTCACTGCTGGGGGTAGGGGAAAGGCATGGATGTTGCCAATAATCAAGATGGAAAAGG<br>AGAAAGAACAGTTGTAAGAGGATTTTGAACACGCTGAAAGTGAGATACCAAAGGACTTAGACATCCAGGGAATGAT<br>ATCTCTGGGGGGATTAGCTCTACATCTAAAGCTGGACAGTGTTGGAGAGAGGTGGGCAAAGGCCGGGCAGGACCTA<br>TGGATTTTTGGAGTCTTTAGCAGAGAAGTGGTGCCAGCAGATGTGTTCACCCAGCCACAGATTTAAGAAGAAGAGT<br>GGGTTGAGCACGGAACCCCGGGAAAAGAAGAGATTTAGGTGGTGGCTGGAGAAAGAGATATCTTGGAAGGATGCAG<br>AGGAAGAAGAGTCAGGAAGTAAAGGAGATGAGGACTTGTCTCTGGGCTGAGAAAGGACTTCTAGTTCAAAATGATG<br>GACCGCTCTCGTGCATAACCCATGCACATCTTCCAGACTCAACTGAAGTGTTGACAAAACAACTGTACTGGGCTGA<br>ACTGCCTCAGAGAAGAAGAAATGAAGTGAGTCACTGACGGCAGTAGATTTGGACTAACTAATGTGAATCTGGAAAG<br>CTGGCAGGTAAGAGGTGTCTGAGGAACAGGGCAGAGGCTGCAGAATCCCAGAGAGTCTGTGGGGGGACATTCAGAT<br>GCAGGAGGAGGAGAGGTAGGTATCCTGGACGACAGCAGGGACACACAGCACAAAACGATGCCATGAAACCGTGGAC<br>CCCTTCCCTATGCCTCAGCACGGCTCTGGGCCAAATGCATTCAGACAGTGCACTGAAGAAATGGGATCAATTTTGT<br>AGGAAAAGTGTTTGAATGAGACCAGGGAGTGTACTTGTGATGCCCCAGAGCAAGGACCTCCCCGTCTCAGTATTTA<br>GGGGTCCCTCAGCCCAATAGCTGAACGCTCAACTACACAGCTTAAACTGATGACCCCTTGTCCAAATACAACCTAG<br>ATCTTAGTTCATTGCCTATAGTCCCTTTAAAAAAAAATGAATTAGCTTTCCACATCTATAAATCTGGGTATTACAT<br>ATGAAAAATCCAGATTTCTGAGTTTTCTAGAAAATTCAGAAGTACAGCTGGAGCTCAGTAAGGGCCACTCCCTTCC<br>CATCTGGCATTTCCTGGCCACATGACACGGTCCCCACCCAGCTCCACCCAATTATGAGATCTTTCTGTGGTCCGTT<br>TATGAGCACTTGAGGATATGACCCCTGCCTTCAAGTAAAGCCTGCTGGATAACCACTCCAAACATATACAGAAAGC<br>CCTACCTCAGCTTGAAAAGGTCTTTGTTGTTGTTGTTGTAGATATAGATTAATCCCTTAATTCTTAAAAGTCACCT<br>ACAGTGGAAGAAAGATCAGCCTGGGATAAGCAACACTGCATGCAACTAGAAGCCAAAGGAGCAACGCCTTCGGGTG<br>TCCATGGAAAGTAACAGCCACCCAGCATCATGGGCTCAGCCAAGCTATCGTGCAAGACCAGGCAGGAAAGTACCTC<br>CAGTTTAGCTCACGTGCAAATTTTCTTCCTCAGATTCTTAAGCAGAAGGTTCCACAAAGGAGGAAAGCGAAGAAAG<br>TGAAGCCATGGTGGGGTCTGGAAGTGGGTCAAGGATGTCTCTGGGTGGCAGATTGGCGGCAGACCCAGAGAGGAGC<br>CCACCCAAATTGGAGCAGGAGGATGGAGAACTCCAGGAGCCATGCGTCTAAGGAAGATGGAGACTTGTGTACTAGA<br>AAATATATTTATGAGTTTGAAAGGCAATTCACGTCCCTCCTCAAAAAGGGAATATGAGAAGGCTCCAGGTAGCAAG<br>AAAAGAGCTCTTCCAAGTACCGGCATAACCTCTTTAAACAAACCTCAACAACTAGAAATCTCACAAAATTCCTGGG<br>CAATAAAAGCACTGAGAGTCAAAGTAAGGACCACCATGTACGTGACAGGCATGATGCTTTGCCCCAGGGTGTATCA<br>AGTCTGCAAGAGAGCTGTGGCTTACTTTATCCTACAGATGTATTATCAAAAGCTATGGAAAAGTGACTTACTTTCA<br>ATGAAACATTTTATAGGAACTCGTGGTTTTAAAAATTCCAAAGATTATGGTTAACAGATAATTTAGAAGTTTTATA<br>AATTTAAATTTGAAAGTAAAACAGTGGCTAAATACACAGACTCTGGAGATAGACTGCGTGTGGTCAAACCCCTGCA<br>CCATGATTTACTTGCTATAAGACCTCGGGAAAGTTATTTAATCTCTTGGTTAAATATGGCATTTTCCTTATCTGTA<br>AATGGGAAGTACAGTAATATCTGTTCATAAGGTGGCTGCTGTATTAAATGACTTAATATTTATGAAGCTGAGCTTG<br>GCAAGAGCAAGTTATCATGTATTTGGTGAACAAACCAAGACATTTATGATTCTTTTTTTTTTTTCTTTTTATTTTT<br>AACAGCCGAATCTGTGGCATATTCTGGGCTGTGGAAGTTTCTGGGCTAGGAGATGAATCGGAGCTGCAGTTTGTGG<br>CAACACCAGATCCTTAACCCATCGAGTGAGGCCAGGGATCAAACTCACATTCTCATAGAGACAATGTCAGGTCCTT<br>AACCAGTTGAGGCACAACAGGAACTCCTTATCAGATGCATTTTGCTCTAAATGAGTGTTTCACACAGGGTGTTCCT<br>GTGTGTGAAAACCCAGGGATTTTTTTAACTCAGAAAGCTGGCAGTGGATTATTGGTTTCACTGAACTTTTGGCAT<br>AGGCTTTTCTTCAACAGCAAGTGCTAACATACCAATGATTAAAATGTAGTTTAGGAACACATCTATTATAGGAAGC<br>TACATTTACACCTCTACAATTAAGTCGCCACACATTCATGTGACACATGTAATATGCTTAAAGGTGGACTATATAT<br>CCTCCTAATTTATTTAGTGATTCATTTATATAGAATTAAAAATTACAATGTATGCTCACATATATCATGTCATTTG<br>ACTGTCATAAAAAAAACTGATAAGGTGGCAAGAAGCTCAATAGAATGGAAAAAAACAACCTTTGGACAGGGATTCA<br>AAGCCTCATTATTGGTTATCTGAATCAGTCGGGGTGAGGCACCCTTCTTGGTCTTGACCTTGTGTCCAAAGCCCTA<br>GTTCTTAACATCATGCCTCTCTGCCGTAGGTGAGGGATTTGCTCAAAATTGGAGCTCAACAAAATATGTGTTGGTT<br>TATGTTGACTTAACTCCCTTTCCAGAGCCACACTGGGTTTGTTTGGGGAAGGAGACACCACTGGAGAGAAGGCAAG<br>GAGGGCAGAGATCAGTGCTTGCAGGTCTGAGAACAGCATAAGCAGGCCAGCTGTTTGGAAGGAAGCAGGTCAAGAA<br>GCCAGTCTTTGCAAATGACTCAAAAAGAAGCAAGTACGGAGTTAATAGTAATGTTTCAGTATCAGAGTATTGGTTG<br>TAACAAATGTACCCCAGTAAAGTAAGATATTAACAATAATTTGGAGTTCCCATTGTGGCAAAGCGGAAACGAATCC<br>AACTAGGAACCACGAGGATGCAGGTTCAATCCCTGGCCTTGCTCAGTGGGTTAAGAATCCAGCTGTGAGCTTTGGT<br>GTAGGTCACAGACGTGGCCCAGATCCTGCATTGCTGTGGCTATGGCACAGACTGGCAGCTGTAGCTCCAGTTCAAC<br>CCCTAGACTGGGAACCTCCATATGCCACAGGTGTGGTCATAAAAAGCAAAAAAAAATTTATATATATATATAAACA<br>CTACTGTCTGTAATATCCTTGCAACTTTTCTGTAACTCTAAAGTTGTTCCAAAATAAAAAAGTTTATTTAGGAAGG<br>AAGGAAGAAAGGGGCACTTCCACTGGTATTCCTGCTTACTTCCTCATATGGATGTTCCCGGCTTGGTCTTTCTTTT<br>GGAAAGGATAAATCCAGAAAGTCAACCAAATAGTCATATCCTCCAGGCAAAGGGCTGAAGTCCTCATCTGTCTCAA<br>TCATCTGTTCAAATGACAACATGGTAAAGGGAAGAAGCATATCAATCTGGCGGTCAAGGTCCTTAGAAAATTCTAG<br>AATGTGCAAGACCCAAGTGCCCTTAAATGATAGCAATGAAGCAGAATTAATACAAAAACTGTCTCTCCTCTTTGCT<br>CTCTCCCACTGCCCCATCCCTCTACCCATCCCTCTCCCTCCCTCCCTCTCTTCTTTCTTGAACTGAATTCAAATCC<br>TAGCCTTCTACACTAGCAAAACCACTTCATAACACTAACTTAAATAAAATTTATAGAGAAAATTATCATTATCTTA<br>GTAATGAGATATCAAATTGGCTAAAAAATAATAAAATGTGGACTGTTTCTCATCATCACATAGTAGCTAAATATAA<br>AAGAGTATCATTAGGAGTTCCCGTCGTGGCGCAGTGGTTAACGAATCCGACTAGGAACCATGAGGTTGCGGGTTCG<br>GTCCCTGCCCTTGCTCAGTGGGTTAACGATCCGGCATTGCCGTGAGCTGTGGTGTAGGCTGCAGATGCGGCTTGGA<br>TCCCGTGTTGCTGTGGCTCTGGCGTGGGCCGGTGGCTAAAGCTCCGATTCGACCCCTGGCCTGGGAACCTCCATAT<br>GCTGCAGAAGCGGCCCAAAGAAATAGCAAAAAGACCAAAAAACAAAAAAAATTCTTCCACCTACTATCCTTTTATT<br>TTATGAAAGGAAAGATGTTTTCACACCTCAAAAATAGAAAGGACCTAATCTTGGAATAATGACAATTCGTCCAAAG<br>GAAAGAGAGTTGACATCTTGGTGACCATACTCAGATGTGTGCTCATACTTATTTCGTTACTGACCAGCAAAAACTT<br>TGTCACAGACTGTCACTGACCCCCAGGTTGAATTTTAGGATTCATTGATTTTGAGGATGGCAAGTGTTGCCTGGTA<br>CCCAGTACTAATGTTCAGGGGTTGAAATTTAAACTTGGAAATAGTCTTTACCCTGGAGGTAACTGATCTTTGTTCC<br>TAAGGGTATGAATACTGTGCATTTCCCGATGCTTTCCCTAAACTTTGCTCTCCAGGCACACATTCAGGCACTAAAT<br>ATAAGTAGGATAAAATATAAGTATGGCAGGGATTCCCAGACCATTTTAGGCCTCCTCTTTCTCTTGCATCCCGCTG<br>CCTGTTGCTACTTATTTTGCTTTTGTGGACATCCTCAGTTTCAGTGACCAGCTTATAAGCTGAACCACTTAGCTGG<br>TGAGCTCTGTGTGTCTATGTCAGGGCTAACTTAAGTTCTAGATCTAGGCTTACTTCCCAGTTGGTGCAATTCAGTC<br>CTTACCCAGCTGCAGTCCTTACCTTACCTGCTTCCAGGCTGCTACAGGACACCAGCTCTGCAGTGGAGCCACCTGT<br>CTGTCCCACAATTTATTATTATTTTTATTTTTTTATTTTTTTGCCTCTTAAGGCCACACCTGCAGCATATGGATGTT<br>CCCAGGCTAGGGGTTGAATCGGAGCTTCAGCTGCCAGCCTACGCCACAGCCACAGCAATGCAGGATCTGGGCTGCA<br>TCTGCGACCTACATCACAGCTGACAGCAACGCTGGATTCTTAACCCACTGAGCAAGGCCAGGGATCGAACCTACAT<br>CCTCATGGATCCTAGCTGGGTTTGTTAACTGCTGAGCCATGAAGGGAACTCCCCGTTTCACAGTTTATTTACTTA<br>TTTATTTATTTATTTATTTATTTTGTCTTTTTGCTATTTCTTTGGGCCGCTCCTGCGGCATATGGAGGTTCCCAGG |

TABLE 9-continued

| lists sequences for the disclosure |
| --- |
| CTAGGGGTCTAATCGGAGCTGTAGCCGCTGGCCTACGCTAGAGCCACAGCAACGCGGGATCCGAGCCGCGTCTGCA |
| ACCTACACCACAGCTCACGGCAACGCCGGATCGTTAACCCACTGAGCAAGGGCAGGGACCGAACCCGCAACCTCAT |
| GGTTCCTAGTCGGATTCGTTAACCACTGCGCCACGACGGGAACTCCCCCGTTTCACAGTTTAAATAGCTGTCACTG |
| CCATAACCAACACAACACAATACAACACCCACAAAAACCCAAAACAAACAAGAACCAAGACACGGTGATGGAGGAA |
| AAAGAATCCTCCAAAAGAAAAACAGAGCTGGATCTACATTTCATTCCCTACATTTTCAACATTCCCTACATTTTCA |
| ACAAAGGATTGTTTCAGCACATAGTCCAATACGCCCTCCGTCTGACAGTCAGTAAGGCTCAATGAATGCTTATTGA |
| GAAACCAACTGGAATACTAAGAGGTTTTCATATAGCTCTGTAATATAAGAAAACAAAAACAAATAATAACTTCATA |
| GCATACCCTGACCACCAGGTTATAATCCTTAAATCCAGCCCAAGTGAAGTATTCTTTTATCCAGGATGAGTGACGA |
| AATATTTCATCTCCTATAGCAGCATTCAAGATATTCAAATATGGGCCAAAATCCCAGGAATCCTTGTAAATCTTAG |
| TCCCTTCTGGAGGCTCTACGATGCCCTTGCTTAAAGACACAAAGGGGAGAGAACAATGAAAAAAGAAAGCAACAAA |
| TAAGGAAGGCAGAAGTTTGCACTTCTACATCAACAGTCAACTGGATGAGCAGCTCTAAGGCTGCTCAGATAGATGA |
| TGCCCAGGGGTCCCACAGATGTGCCTCAGGGAACATTGAGGAGTAGGGCCCCACCCCAGCCTAAACCAGGTCAGCT |
| CCTGTTAATTGCTTAGTGTGATAGCTCTCCAAGTCAGAATACATTTAAAGACGAAGTCTGGAGTTCCCGTTGTGGC |
| TCAGAGGGTGAAGAACATGACATAGTGTTCATAAGGAGACGGGTTCCATCCCTGGCCTCATTCAGTGGGTTCAGAA |
| TCTGGTGTTACCTCAGCTGCGGTGTATGTCACAGATGCAGCTCAGATCCCACCTTGCTGTGGCTGTGGTGTAGACC |
| AGGCAGCTGCAACTCCCATTCAACCCCTGGCCTGGGAACTTCCATATGCCGCAGGTCTGGCCGCAAAAAAGAAAAA |
| AAAAAAAAAGATAAAGATCCATGTCCGGGGAAAAAAAAAGTTGGAATACCACGGATGTGGACCCTTTGGGCTCAAA |
| TAACTAAATTATGAAAATGTTGAATATAAGTGGTCTTACTGATTTTGTGGACATCCGCTTATTCCTGCCCTGCCCC |
| CACCTCCATTAGACTACAAGTATGATGAAAGCAGCAACCATGACAGTACACAGAAGGGGTCCCATAAATATTTGTT |
| GTACATAGGAATAACTCTAGCCTATCTTTGAGCTACACCTAGAATTTTGTGTCTCTCATATACAGCCCTCTTATTA |
| TACTAATAATACCACAGCTGATAGACAGATGGGCTGACAGGAGACCCAGTCAGCAGTATGGACAAGAGTGTGCTCT |
| GACATCCCTAGAGCTGTCCATCCAGTGTGAAGATGGATCACTGCATGCAAGGTGGAATCTTGAGTCCTGGCAATAG |
| AATAGGACGTGATCTGGAGAAAGGAAATATGAGGAGGGAAATAGGCATCTGTGTAGTAAAGATTTGGCAGGTAATG |
| GTAGGTCCCTACATTCCACTTCTCCAAACACTGTTGGCCCAAAGCCGGAGATGCACTGGTTTTGGTGATAAATTAT |
| GTGTCAGATCCTAAAATGTCTAACTTCTAAATGAATCTCATATCTGCTTCTCTAAATCCTTGCTCCATCTCAGCCA |
| GCAGCCTCACTTATCTCCTCCTGGAAAAAAGCACAGTCTCCCAGCTGGCCCCCCTGACTCTAGGAGTTCTTCCCCA |
| GGACATGGTTTTTCTAAAACACAATGCAGTAATATTCCTTCTTTGCTTTATCGCTTTCTCAAGCTCTCCTTACTCA |
| CAGGCAAGTTCCTTGCCCTCCAGGCAAGGTCTTATAAGGACTTTCTGACCCTGGTCCAACACGGCATCCCTGTCTC |
| ATCCTTTTCCTTTACCTTCATTTACTGAAGGGGATGAATGACTTCATAAGGGAAGGACCTCTTCACAGCTGTTTCC |
| CCTGTACTTAGCATGATGCCCAAAGGAGCTCAATAAATCATTTCTGGAAGAATGGCATACATCTATGCACTTATTC |
| AAAGTAATTGTACTCACTAAGAGCATTGTAAATCAACTATATTTCAATAAAAATATTAAAAACTCAAAGTATCTGC |
| ACTCACCAAACCTATGACATTATTTTCACCCCCTTTCTCCAGCATATCCCTCTGACTGGAACCTCAATCTCTTAAT |
| CACTCTATTGGTAACCTTCTCCTGACCTCTAAGACATAGCTCAAATGCCTAAGATTGGAGGTTGAGCATTCCCTGT |
| CCACATCTCCTGTTCTCTCTAGCCCTCTCCCTACCTCACAAGGCAGAGCTGAGCACTCAGTCTCCCGGAATCTCTT |
| ATACTTTGTCTTACTACTGAGAACCTAACATCAACTCTCATTACCCAGAATGCTTTGGTGTGACACAATGATGCAT |
| ATGCAGATTCCAGGGCTCTGCTTCAGATCTACTGAATCAGAATCTCAGGGGGTGGAGCCCAGGGAGCTGCATTTAC |
| CCAGTTTCCTTGGGTTACTCTGACGCTCACTCTAGTTTGCGAATTTCTACCATAGGATGCGTCTGGGGAACTAGAG |
| AGGGATAATGGAGAGAGTTCAGCAAATGCCAGGTGCCAGACTCTTGAATTCCCCACTAAAACGTGAAATAATTAAA |
| ATCTTCTCTCACCTTGAACTAGAGAATGAAAACTGCCTTTATCCTAGAGGCACTGGAGAGATCCTATGGAATTTTA |
| AACAGGGAAGGGAACGGGAAGAGTTTTGCACTTAAAAATCATTTCTTTGGCAGCAGTGCAGAGTTGGAGCTTTCAA |
| ACTTCTTGCCTAAGATCCCAGGAAGAATATATTTTACATCAGGACTCTAGGGGTCCATATGCCAAGAGTATCTGTG |
| AAACCAGAGTTTCCTGAAATAATACTTACCCTTGTTATATGTGCTCAGGCAACATACTCAGGGTTGTTCTATACAA |
| TTTTGTTCTACTTCTTTTTATTTTATTTTATTTTTGTCTTTTTTTTTTTTTTTTTTTTTTTTTTTTTTTTTTTTTTTAGGG |
| CTGCACTTGCAGCATATGGAGGCTCCCAGGATAGGGGTCTAATTGGAGCTGATGCTGCAGGCCTACGCCAGAGCCA |
| CAGCAATGCCGGATCAGAGCCACGTCTGTGACTTACAAAACAGCCCACAGCAATGCCGGATCCTTAACCCACTGAA |
| CAAGGCCAGGGATTGAACCCGCAACCTTATGGTTCCTAGTCGGATTTATTTCTGCTGTGCCACGACGGGAACGCCT |
| ATTTCCTTTTTCTAAATGCTAGTTGTGATGCCATTGATTTCCTAACCCATCAATGAATCGTGACCAGCAGATTGAA |
| AAAGGCTGGCATGGAGGATGGATCAGAGGACAGCGGGGCTGGGAGCACAGAGGCAAGTCAGGGGCCACTGCCAGAA |
| TTCTGGTTAAAAAAAAATTGTGAGAGGCTGAATCAAGGCCACAGCAGAAGAGGCTGGAGGTGAGTGATGGATTTTT |
| AAGAGATTTGTGAAGGAGAATTGACCAGATTTGAGCTGTGGGAAGTTAGTAAAAGGGTATAATCAGCTGACTGTGT |
| CCCAGACCCCAGCTTTGCAAAGGTAAGGCCAGGAGAAGGGTGTGCTTTTGGTAACCGTGTGCCCTGATCTCCAACA |
| GAGTCACAGTCCACTTCTAAATAATGGTGAGGAATGATGGTTCCATCCGGCTCAAGACAAGTACTTATAAAAATAC |
| AGGTCTGGAACATCCACATTAATGTTTCTGAACTGTACTCCCAGGGCACCGTTAATTGTTCAAATGGACTGTCTGG |
| GGATTGGCGAGGAGGTAATATTTACACTGATAGGAACACTAACTCTCAGGCTTATTGCTTTCTACTTGCTGAAGAC |
| AACTTATTTTTGAGCTGTAATAATGGCCCTTCATAAAAAAAACTTTCTCACTCTTTATCCTGAAGTAAGGTTCTGA |
| GACAAGGAAAACATTTGAGTAATTATCTTATTTATTTATTTTTTTTTCAAGGCCACACCCACAGCATATGGAAGTT |
| CCCAGGCTAAGGGTCTAATCAGAGCTGGAGCTGCTGGCCTATGCCACAGCCACAGTAACGTGGGATCTGAGCCGTG |
| TCTGCCACCTACACCACAGCTCACGGCAATGCCAGATCCTTAACCCACTGAGGGGGGCCAGGAATCGAACCCGCAT |
| CCTCATCGATACTAGTCGGGTTTGTTATTGCTGAGCCACTACGGGAACTCCTAATTATTTTATAGGATAAGAAAAT |
| TATTATATAGGACTGTGAAAAAACTCAGTCTCCCCCCCACCCCAGAGTTGAAAGATACTTATTTAATAGTTTATTT |
| TATACAGTAAGACTCCCACTTTAAAGGGTGGTGTGTAGATCTTAATGCATGACAAGCTCAGGATGCTAGTCAAGAA |
| AAACTTAATATTCCTACAAACAGGGACCTGCCAAGAGGCCATAGGTATGCCCTTTATTTTCTCATAAACATGAAAA |
| AATTCAGAAATCATTTTTGTTCCCTGTAAATATTCAAGTCAAACCTGTCTGTTGGGTCCTTTAGCATCCTACCCAG |
| ATCAAGAGTGGCTCCAGGTCTTGGGGTCCAGGTTACCACCTCAGAATTCTTCTTGATAAGATTGTTGAGTTCATTT |
| GGGTCATTTTTGATGTTTGTTTCCTTAATATACCTGACAAATAAGAGCATTCCCATGTAAGGCAGTTTATTTTCAG |
| ATGACATTCTTATTTGAACAATGACAGAATTATTTTTTATTTCTTTGCATTCCTACTTCCCAATCCTTCTTTTCTT |
| ACCCCAGGAAAAATAAAGACTATACTTGAGCTAATGTCCCTGACTAGGGAAGAGCTGTTAGTCAAAGAAGGTTGAC |
| TCTATACTTCGTTTTTTAGTATAAGCATATAGTGTTTGGAATTGAAGTTAGATGTACAAGACTATTATACATAATT |
| GGTAATAGCACACTCTTGTATTTAATTTTTTTTATTCATACTCTCTGTTTTCAGGCTGCTTGTTAAAATAAGCTCC |
| AGACCCCTACTAATCATTCTTTCTCATTTCATGTTGTTTCACAGCTAAATCACTCATTCAGCATATATTAACTTAT |
| GCGTAAACACGTTATATAAAATATCCAGCCATACTTGTCTGCTGGGTGGGATTCCACGAAATACCCAGCAAAGGGG |
| CAGTAAATTCTGGGTTGTAGGTCCTTCACCAGCCGAGCCTTGTAGTTCAGGAGTTTCTTCCTTTCTGTTTTAATGA |
| ATTGGGCTTTCCATTCCTCTGGAATGACAGGGTTTGGATTAGTCTTCTCTGTTCAGAAATCACAGAAAAACAAAAG |
| TTCTAGTAGATTAGAAGTCTTGCAAGAGATAAAAATTGACAGTTGAGTGATGCAGAAGTAGAACAAAGCTCCTTGT |
| CATTAGTGGCTTTATTTTGCAAAGTTGGTTACTAGGAAAATATCCCAAACTAGTCAAAGACATTGAATCCCCTCTT |
| TGTTTACGGCAATTCATTTGGATCCAACTGAAAACACAGGGCAGCATGCATAGTTGTACCCTGGGTGCATGCATAT |
| TTTAAGGGCACTGTCGATTAACTCTCTACTAACATGGGCATGGCTTTGTTATTTTGGTGGAATATAAAAGTAAAGT |
| ATGTTCATTACACTCTGGAGATGCACAGTGGTCAAGAGCATGGATGTTGGAGTCAGTCAAGATCAAAATGCAGCTC |

TABLE 9-continued

| lists sequences for the disclosure |
|---|
| CACCACTTCAATTCTTTAAGTCTGTTTTTCTCCTCTGTTGAATGGAATCATGATGCCTACCTCACGTGTTGTTCAT<br>TTGTTCGTTTGCTCATTCTTTCATTTGATCGATATTTATTGAGCACCTACTATGTGCCAGACGTAGTTCTAGGCAC<br>TGAGAATACAGTGGCGAGCAAGATAAAGCAGGTCCCTGCTCTCATGGAGCATTCATTCTAGTGAAAGAAGCAAATA<br>ATGAATAAGTAAATAAGTTCATTTCAAAGAGTGATGAGCTAGGAAGAAAATAAAACAGAGCCACCAAATAGAGAGT<br>GGCTGGGGTAAGGATGAGGACGGGTGGGATGGAAGGGCATATTAGAAGGGTAGTTAGTGAAGATGACATCTGGAAT<br>CATAGACCATAGACACAGACACAGAAGAGAAGTTGCTGACCACGTGGTGGTCAGGGGCAATAGCACTCTAAGCAGT<br>AGAAATAGCACATACAAAGACCCAGGGCATGGAGCTACATGGTGTACTGAGTCTGAGGAACGAAAAACAAGCCAGT<br>ATGGACTTATGCTTGTCAAGCAATGGGGGTATGGGCAATAAAGGAAATTGAGAAATTAGGCAGGGCCCAGAGCATG<br>TATGGTACCATGTCAGGTACTCCTTCTACCATTACTGTTATGAAAATTTGATAAACACAAACAAGGATACAGGGGA<br>AAAAATGTTACCTATAAGCTAGGTGTAACCACTATGAACATGTTAGTATATTACAGACCTTTTAAAATGTATGTGC<br>ATGTGCACATACTCACACACATACACATACTCACATAAGAACTGAATTATGCTACCACCCTTTAGTAGGTATGTTT<br>TGCCTCCCTAGTCACACTGTTAACCCCATAAGGACAGCACCTTCCCTCATCTCTCACATGGTGATGCATTCTGGGA<br>GGCAATGAAATCAGACTTACAGAAAAAAGGAAGGAACTGGACAGGTTTTCTTCTTATTGCAAGTAGGGCATTTTTG<br>ACACATTACTAAACAGAGATTACTTACTAAAAACATTAATTTATTAAGCAGACATATATTGAACACTTACAATGAT<br>AGTACTGAGCAAAGGTATGAAAAAAATATACCACTTAACCATCCTCCCCATCCCAGCCCCAGAACCACCCTTAGAC<br>ACAGAGCAGAAGAGCTTCTGCCTTGGTCCCCACATTTTTCTAGCTTTGAGATATAACTGACATCTAGTATTACAT<br>AACTTTAAGGTGTACAACATGGTGATTTCATGACATGCATGTATGGCTAAATGATGACCACAATAAAGTTAGTTAA<br>CACCGCCATCACCTCACATAATTACCATTTCTGTTTGTGTGCACGTGTGTGTGTGGTGTGTGTGTGTGGTGTGT<br>GTGTGTGTGTGTGTGTGTGTGTGTGTGGTTAGAACATGTAAGATCTACTCTCAGCAACTTCCAAGTATATAGTA<br>CAATATGCTATCTATAGTTGCCATGCTGTTTATTATACCCCTAGAATTTATTCATCTTGTAACTGGAAGTTTATAC<br>TCTTTGACCACTATTTTCCCTACCACCCCCCCAACCTCTCGTAATCCCACACTTTAGAGGGGCTTCCTTAGCCTCA<br>TCCCTCCCCCGTATGAGCTTTCCACGAGGTCAAGGGTATGTATCCCCCTCAGGCTGCCCACACTCTGTTCTGAACC<br>ACATACAAAGAGCACTTAAGCCTGGATTACCAATGTCAGACTCTTTCTGATCAGCTCTATGTTCTATGTCAGGAAT<br>CCATTTGATCCAAATTATTCTTGATTTTTCCTGAGATTCTCCCTAGTCTCCTTAGTGTTTCATGCTCCATCAGCAT<br>ATTCTCAGCTGGAAACTTTAGTCTATATTTGTGACTTGCAAGTATGATTTCCCAATAAGATTGCACACCTCTTGTG<br>AGGAAGAACCATGTCCTAATTATCTTTGTATTGATTCACACAGCATTTAGCAAAGTGCCATGCCAACTCCTTGGCA<br>TCATTTTGATATAAAGAATTACCAGTAAATTTTCCACCACTGAAAGTCATTGGAAAGCCTGAAGCTCCTCCAGCAA<br>AATCACTCATCATTAATGCAACCTTCATAGGCAGCCTTCCTCCATTGGGTCTGGTGCAATCCACTGTATTGAGTAT<br>TTTATGACCTGTGGGAAAACAAAATGGCATCGGACTCAAGGTGAAATCTTGAACACCATAGTTTGAATTCTCAGGC<br>CAACAGTCTTCCATGTAAGTCTATATAATCTGCCTCATTCAATTATCGAAGAATTGCTCACATCCAAGGAAAAGAG<br>AGAGTAAGATTTGAAAATTTATACTCTTGAGTGACACATTTTGAACTTTCAAGGAAATAAATTCATTCTGTCTGAT<br>TCAGTGGGTTCTGAATGAGGACACTTAGCCTGATTCCACTCCAGGATCATAAACAGACTACTTTCCTTAGCAAACT<br>ATATTCAAAGGTTAAGCTCAAAGGATGCAGAGGAAAGTAATCAGATCAACACAACTCTCTCAACCTTTTGGAAATT<br>CTTTTCGATGATTATTGGGGTAAAGTGTATGATTCCATAACATAATAATATTCAAGATGAAAGTAAAACATTTATT<br>CAATAATGTCAGTTTTAAGGAAATTACAATAGGTGAAATATAGGATATTTTTATCTGTTGCCTTCAAAAAAAACCT<br>TTGCACCTGTCACGGCATAGAGTACATTACTAATTGATTCTCTGTAAGATTATATGAATGACAGTCCATTTTCCTA<br>AGACAGAGATAGAATATACTGTACTCTATGGAAAATGAAGAGGGAAGAAACAGATGAACATAGGATGATGTTTTGG<br>ATAACTATTATTATCCTTTCTACCAAGAGCAATTTTCATTGCTGATGAGGGTAAGAAAATACCTTTGTATTCCACA<br>ATAATGCAAGTGTCCATCTCAGGATGAACGCCATCCATCAAGATCATGAATCGAAGATTTTTGTCTACCTGGAATT<br>CAACAATAAAACCAACAACGGTTTACATCTATTTTGCTTTTAATTCAATATTTGAAGAAACTGTCCTCTCTTCTGG<br>AAAGAAATCCCCTTTTTTCAGAACTGGATTTGTTATCCATCAGAGTCATACCATGGATAATTGGAGAGGAAGACCA<br>TCTTATTTCAGCTCAAATAGAGATTTACACAGGACCATGTACAGAAAAAGTAGGCCATTGTTTCTTTAGTCTTAAA<br>ATTTCTATCTCGCCTCAAATTTATCCCAGAAAGGATAACCCAAACATGTGGAAAGAACACAGACCTGCTGCCATAT<br>TCCAAATGGCACTACATTGATATTAGTCAACTGGACGCCACTCTGATTCAGATTCCAAAATACAGGTCTTTCCGTG<br>TTGCCAACATAAATGGGAACATCTGGTCTTCTCTCAGCAAGCTTCTTCAGTGTTGGGTAACTAGGGTCAGAAAGAT<br>ATACAGGTTGAAAGGTGAAAAAATAGAATAATCTAGTATAAGAGAGAGTGTGATCCTTACACCAACACGTTGACCG<br>AGAAGCAAGGAACTGAAAAACTAGACTCTCCCCAGAGTCCAAAAGAAGAGCTCTTTCCTCAAGGCTGACTATAACA<br>GTGAGGAGGATTTCCTGGGAGAGTCCTCTTTATTGTTAGAACATCCCATATACCACGGCATGTATATCAAACCAGG<br>TGTGCAAATTCCGTCTTCCACACTGATGCTGCTTTGTGCAAGGGTAGTTCTAACAGAAAGTACAGAGTGGAGAAGT<br>TACGCCAAAGAGGTTTCTGGTTTCATCTTGATTTTCCTTTTTTTTCTCATTCCTCAGTGCAGCTCCCTCCCAGTGA<br>GAGAAAGGTCTCGGCCATATATCTAAGAGAACGGATGGGTGCCCACCCTGGGGCAGTTTTTCAAACTTCGAAGGTT<br>GATAGCCACACATGGTATACAGAATGAACTCCTTGTCCTTAAAGAGAGTTAGTCACTAACTAAGCAAGACAATAAA<br>GTTTAGCACAGAGGAAAATGACATTTACCTCTTGTAGCAATCCCAAGTCAGTACACAATGAACCATCCAAGCATTT<br>TTGAGTACTTACATAAGTTGCCAACTTTCATTTATTAGAATTTATTACATAAAAGGATTATATACTACTGTGTGGG<br>TGGCAAAACATGAACAATAAACAAATAAATGGCTCTGTAGGTATATTTCAATCATAGTGTTACACACTTTCACATG<br>TTATTGTATTTGATTCTCAACAAAAGACCCTTTCATCTTTTAGTGTGCTTTTAATAAATGAGGAAACACACTCAGA<br>AATATATGACTAACAAATAGTAAATTGGTATTCAAATTCAGGCTTTCTGATCCTAAACTTGGTGCTTCTTCTATTG<br>AAAGGAAATTCTGGAGTTCCTGTTCTGGCTCAGTGGGTTAAGGACCCGACGTTGTCTCTATAAGGATGCAAGTTCC<br>ATCCCTGGCTTCACTCAGTGGATCTGGCGTTGCCCTGAGCTGCAGCATAGGTTGCAGATGCAGCTCGGATCTGCTG<br>TTACTACGGCTGTAATGTAGGGTGGCAGCTGCAGCTTAGATTCAACCCCTAGCCTGGGAACTTTCATATGTTGCAG<br>GTGCAACTGTAAAAAAAAAAAAAAAAAAAAAAAAAAAAAAGGCAATTCCAACTCTAATGAATGTGCTATCAGGTTTAAG<br>AATCATATTTGTACATAGACTATAATGTCTGGTGATATAGGATATTTACTCATAAGAAAAATATAAACAAAATCAG<br>CATATCAGCACTTATTAACCATACTAATATTCAAGTTCCAAAACTATATTTAATATGTAGAATCCAGAGGGGGAAA<br>ATCATTAGGTTTTCTTCTCTAAAAACAAGGGATTCAAAAAAAAATCAAGGATTCTTTGAACATGTCTTTAATCTCT<br>GGGTTAACATCTAAATCTTCCACTTTAAAGGGCTTTGGGAGTTAGGATAAATGATTCTAACATGGATGTATTTTAA<br>TTTGTGATTTTTAAATTATTGACAATTCTTGCTGGTGTCTATTAATAACACTATTATAATACTCATATATTTACAT<br>AATAAAATCACATTTCTTTGACTAAAGACAGTTTTCTAAAGCATGCTGGCCCCCTCCCCCTTTGTTTTTGTGAACC<br>AATAAGGCATTATTCAGTAAATAAAGGTCAGACAAGAGCAATGGAGATAAATGACTCTGGTGTTTATTAGTTGAGC<br>AGGTAAGAGTCAAAAAACTCAGGGTCAATTCTGTCAAGGAAATAAACTCAAAGGAGTGAAAACTGCAAGGCTTGGT<br>AACTTTTCAGCCATAAGCTATCTGCAATACACTACCCAACTAAAGCATTGTGATACTACAGTTGAGAAGTGGCTTT<br>TTAATGCCTGGCAACTTTGCCCACACAAGCCCCTGAAATCAAAATGAAATTGGTTTTCAGGACAGTGGTTGGGAAA<br>TGACCAGACTGAATGCCATAAAAAGTTCTTATCCTCACTAAAATGTAGTATACTCCCATAGAATATCTCTTGCTAG<br>GACAATGGCAATAGCATCTTGTGACAGGCACTATAAAGCAATCGCCTCCTTATCTTGACACTGTTCTCTCTAAGCA<br>AGCTGTACAAATTGACTACCACACAACATAGTTATTACACAATGCATGAACTCAGGGCTCTCATAATCCTGAAATT<br>ACAAGTTTGGTTCCAGAACCTCCTGTGGGACAAAGATATCATGTAGTAGACAAGTAGATTTTTAATCGTAGCACAA<br>TACTCCAGTGGGTGGTATTCGGTTTTTAAGTGTGTTACAGGTAATTTGTTACTAAAGCTGTTAATTACTTAAGTTT<br>TTAAACCCTTTCCTTAAAAAGCGAGAGAACACACCTGTGCCTTCGAGATCTCATGGACTTTCAATAGAAAAATCCA<br>GGGGCCAGTCAACCAACAAACAATGTATTTTCCCTAACCATGGACATTACTATCAAAGTATATCCTTCATGTGAAC |

TABLE 9-continued

| lists sequences for the disclosure |
| --- |
| TTGTCATGTAAAGTCACAGGAAAAAAAAATAAAGTTGAAATTGCTTCATTTTAGAACACCATGGGCACTGCTGGGT<br>ATTGGCAACCTGGCAGTAGCAATACAAATTTCTCAATAAGGATGAACACATAGGACCCTGTAATGAAGCCAGGGGG<br>TTGGGAATAGGAGCATTCACAAATATTTGTAACAGTCCATTCACAAATATTTGTGGTTTTTGTCAATGAAAGTTCC<br>TCTTTCTCCCTCCTATTTGATCGCCTGGATTCAGGAAGTTTCCGTTTCTATCCTTAGTATCATATGGCTCTGGTTT<br>CACTGAAGGATGTGGTGGACTCAGGGTTCAAAAGTTGAGAGCTCAGTGTTGTCGAAATGCTACAGATCAGGAGTTG<br>GCAAAACACAGCGACCTGCTGCTGAATGCTAGGAAGGGCTTTTACCTTTTTTTAAAGGGTTGAAAGGGAAATCAAA<br>AGGCAATCATGTTTGGTGACACAGGAAACTGTTTGTGATATTCACACGTCATTGCCTATAAAGCTGAAGGCAATCA<br>GGCTCCTTAGGACCGACTATGGCTGCTTTTGTGCTATAATAGTAGAGTTAAGTAGTTGCAATGCCAACCATATGTC<br>TTGTAAAACTCCAAACAGTTTACACTCTGGTCCTTTGTAGAAAATGTGTGCTGATTCCCACCATAAATGTTAAACT<br>AAAAAAGGAAGTCAACTTTGATGATCCTTAAACTCAGAGTTTTACCAACTAGCCTGAGGGTAGGACGTGAGAGGGT<br>CCAGGGTTATTAACCCCATGCTCCTTTCCACAATAGCTCTTCTCACATCCCAATGGTATAAAACAGGAAGGCACTT<br>TAAAAAGGAGGCTATGCATGTTGCTATGGCAGTGGCGTAGGCCCGGGGCTACAGCTCTGATTCGACCCCTAGCCTG<br>GGAACCTCCATATGCCACAGGTTCAGCCCTGAAAAGACAAAAAAAAAAAAAAAAAAAAAAGTTTTTAAAAAAAGAGG<br>CTATGCAAATGCAAGCATTTATCTGAATTAGTTCTCTTTTTATCAGCCCAAGCGAATCTACCTCAGAATGAGCAGT<br>GATTACAAAAAAAGCTGAAAACCAACAGTGCTTTTATTGCAGCATTTTCTTCGGAGTTGAGGGCTCACCCTTCCTT<br>ACCTCAGGTGGTCTGAGTGCATGTGACTGATGTAAATTAAATCTGCGCGGCTCAGCCTCTCCAGCCAATCAGATGG<br>AGGCTCGTGTAGTAACCACCATCCTCGCGCAAAAGCAGGACCGATTAACCAAGGATCGAACACCATCCTCTTGTCT<br>CCCAGCTTGAGGTCCATGCAGGCGTGAGTAAGGTACGTGATCTGTTGGAAGACAGTGAGATTCAGATGATCGGATC<br>ATTACCAGCCAGAAAAAGGAACTGGGCTGGTTAGCAGACAAGCCACATGGGGGACCTTTGCTCCTAAGCATGTTCA<br>ATGACACAGGACTCAAGAAAGACACAGCAGGAGCATTTCCGTAGAACACAATTCCCAGCACAGGCATTACTTTATT<br>AGAACAGAAATGCTCATGGTGGGTTTTAGGGGTCAAACCAGTTGATTTACCCAACTCAAATCACCTCCAAGGTATT<br>TAATTATGCTCTGTACCACAGAATATCTTTTGTTACCAGTCTTTTAGAACACAATTTACAAGGAAAGGGAGTTACA<br>GATGTTATGGCAGACCTCTGGGGATTTAAATGGTAGGGTGGCTGTGAATAGGTATAAGAATGACTGGTTCCAGTGG<br>GTGGACACAGTCATGCAGCCTGGCTGCACTGGCTTCTAAGGCTTTCTCACCTAAATTACTTGCGGACTCACTCAGG<br>ATGTCAAGGTCCTTTGAGAAGGGTGAAAAACAATGACTTAGAGACAGGCAGAGACTACAGGATTCTAAATCAACGC<br>CTTACTCCCTTCCCATAGTCTGGCACGTCCACAGGAAAAATGAAAACACCAAGGAGCAGAGATAAGGTCACAGAAA<br>TCCAAATGTGAAAAGCCAGCAAAGAAGGTAGGGAGAGGTCAAGAAATCAAATGCAGGTGATTGTGCCTCTTCTGGG<br>TAGGTTCCCATTTGTCTCCTCAAAAAAGTAAGAGCCCATTTTTACAAGCTTCCCGAATACTCCAGAAAAATTAATT<br>TTTGGTTGTTTACCTCTCCCAAACTACCAAAGTGTTTTCTCTGGAGGAAATTCTCTCTCTCTCTCTTTTTTTTTTT<br>TTTTTTAGGGCCATACCTGCGGCATATGGAGGTTCCCAGGCTAGGGGTCCAATCTGAGCTGTAGCCGCCAGCCTAC<br>GCCACAGCCACAGCAATGCCAGATTCTTAACCCACTGAGTGAGGCCAGGGCTCGAACCCCTGTCCCCATGGATACT<br>AGTTGGGTTCGTTAACCACTGAGCAACAACAGGAACCCCGAAATTTTCTTTTAAAAGTGGAAAAATGCACAGAAAA<br>GTTTGTAAAGATCTTAGGGCAATGTGCAGAAACATGTAGCTGGCCATTTTATCTGACAGTGATCTGGTAGCAAGGG<br>CAGTTTCTGAACTTCCTCCCATAGCTGTGCATGACTCTCCTTTGGGACCTCTGCTAAAAGATTTTTTTTTAATCT<br>AGATATATTTCCTTGTAATCCTTGCCAAGTTCCTGAGGTTCCTAAATAATGTGCTCAAGAATTTAGAATAGGGAGT<br>TCCCTGGTGGTCTAGTGGCTAGGACTTGGTGCTTTCACCACTGCGGCTCAGGTTCAGTGCCTGGTCTGGGAGCTGA<br>GATCCACATCAAGCCACTGCTCACCATGGAAAAAGAAAAAAAAAAAAGACTTCAGAATAACTTTATTATATGTCCTA<br>ACTAGCCACTTCCAAGAATACTCAAGGTAATATAAGATGTAAAAAAAAAAAAAAAAAATATATATATATATATATAT<br>AAATTGATATGTTAGCTTTATTTGTGTTTTTAAGAATATTATAATTTAACATTTCCTTACCTGCACTTCCCCAAAA<br>GCCAAATCTTCAGGAGATCTGGGTTCTGAATCCCACGGGTTAGGAGGATTTAGTTCTAGAAGCAAAACTCCATTTT<br>CTTCATCCTTTTCTACAACTAGAAGCAAAGGTGGACAAATCTGGATAATCAACCAAAAAAATGACTTTTAAAAAGC<br>ATCGCTAAGACAGAAATGCATGGCTCAAGTACATGGAGTAGACAAATCAAAGCAAAATCAAAATAAAAGGCAACGC<br>TCATTTGGGTCAAGCAACATCTGCAGAGATGAGGGCTGAAGACCAATACTGTTCATCTCGCTATTCACATTCCACG<br>TAAGGAACTCATGAGATCGCAGATGTGTCAGAGACACAGGCACACCACCACCAACTTCATTACAATCAAATGAATG<br>ATTGATAGAGATGAGTTCAAGGTGCTGTGGAAGTGTCTCGGAAGGAAAACCTTGTTTGGTTGTAAGAGTCAAAGCT<br>GATTTCAAATAGGAGGTAATCCTCCAGCTGAACTTGAAAGACAAAGTATTTGGGGGCTGACAAAAGAGATGTGATG<br>ATGGGATATCTCTTTTGGATAAAAGATAAAAGGACAACATAAAAGATAAAAGAACAGCATGTGCAAAGGCATGGAG<br>GCATGGGAGAGCTGGATGTTCACAAATGACTGGAATTTTATGACCAAGGAGAATGGTGTCTGAACCAGGTGGGAGA<br>GACAGGTAGGTCAGAGTGGGTCATGAAGGACCCTAGATTCCCAACTAAGGAGGCGTCTGGATTTCATCCTGTGGCA<br>ATGAGGGGTCAATGAAGAATTTTAAGCAATTGTGGCAGGCATGCTGGTGGCTTGCGCAAAACCTATTCTCTCCTTC<br>TCCCTTACTATTAGCATCCTAATTGTGTGATGGTACACCTATTTAAAGATTTCCCAGCCCCCTGGCAGTTATGAGT<br>GGCTATGTAGACCTAGCACTATGTGCAGTTTACATAGTTCTGGCGGGTGAGACGTAAGCAGACGTCTACTTCAGAA<br>GTCTCACGGGACTTGCAGGAACACATTTATTTCCCCGACAAAGAGGGACAACTCAAGAGACCAGCACTGTCTCCCC<br>TTCATCCCTTCATATTTCCCCCTCTTGTGTGGAATTTGACTGCCATGCTTGGAGGAGCACAAGCCATCTTGAGATG<br>CTGAAGAATAGAGCCAGACACTGAGGATAGAACAGGAGGTGATAGGGAATTTGGCTCCTTGATAAACACAGAACAA<br>CCATAATGCCCAGGATTACCTGCTTGGGATCTAAGAAAAACAACCTCCTATATGATTGAGCAACTTTTGCCTGGTT<br>TTTCTATTGCACTGGCTGAAAGCAATACCTAAGTGCTATAGCAAGGGAGAATTAAAATCAGAACTTAATTTTAGAA<br>AGACCCGCTGTGAGGCACATGGAGAGGATCAATTGGAGGGAGGCAAGACCATGTTTGAGAGTCCTCTCTGTTGTTC<br>TGGAAGGCTATCAGCAAACCACTAATGGACATGTGCTTGGGAGACAGATGGCCTGTTTCTAGCCCTCACTCTCCCA<br>CTTAATAGCTTATTAGCTAGAGGACCTTGAGCAACTTATTTGACTTCTCCAGTGTTTTTATCTCTAACCCTGGCTA<br>TCTCCACACACAGTTAATCCTATTACTGCCAGCAATTTTATTCATTACTAAATGAAAGCAGATGAGGTCCCAAGCC<br>AAAGCAAACCTTGTGGAAATGGCATTGCCGCCCTGCCCTCAAAGACGAGCACTTTCCTACTTTATTCAAAGGACAT<br>TAAAAAATGTTTTGTGGGAGTTCCCACTGTAGTGCAGTGGGTTAAGAATCCAACTGCAATGGCTCGGGTAGCTGTG<br>GAAATGCAGGTTTGATCCCTAGCCGGGCACAGTGGGTTAAAGGATCCAGCATTGCCACAGCTGCAGTGTAGGGCAC<br>AGCTGCAACTTGGAGCCTGGATTCAACCCCTGGCCCAGAAACTTTCATATGCTGTGGGCATGGCCCTTTAAAAAAT<br>GTTTTGCTTACATTTTCCAAATGAATATTAATTATACTCACTTTAAGACAACTGCTAGTGGAAGAAACTGAAGTAA<br>AAATTACCCGTAAAATGAAAAATGGCACAAATGAAACTTTCCCCAGAAAAGAAAATCATGGACATGGAGAACAGAC<br>TTGTGGTTGCCAAGAGGGAGGAGGAGGGAGTGGGATGGACTGGGAGTTTGGGGTTAATAGAGCAAACTATTGCATT<br>TAGGGAGTTCCCATCGTGGCTCAGTGGTTAATGAATCCGACTAGGAACCATGAGGTTGCCGGTTTGATCTCTGGCC<br>TCACTCAGTGGGTTAAGGATCCGGTGTTGCCGTGAGCTTTGGTGTAGGTTGCAGATGAGGCTTGGATCCCGAGTTG<br>CTGTGGCTGTGGTGTAGGCTGGCAGCTGCAGCTTCAATTTGACCCCTAGCCTGGGAACCTACCTATGCCAAGGGTG<br>AGGCCCCAGAAAAGACAAAAAAAAAAAAAAAAAAAAGACAAAAAAACCCCAAAACACATATACAATAGATGCAAACTA<br>TTGCATTTGGAATGGAAAAGCAATGAGACCCTGCTGAATAGCAGAGGGACTATATCTAGTCACTTGTGATGGATGC<br>ATATTATCTGCATCCTGGGCTGCAATTTCCTGATCTGTCAAATAGGATTATGATACATACTTTGCAGAGTTGTTGT<br>AGGGATTAAGTGATATAATAAATCCTAAAGTGTCACTATGCCTAGCACAGAGAAGGCACGTAATAAATGATAGTAT<br>TATTATGGCAATTATTTCACCCTCAAGGAATAAAGAATTAAAAAGGAGGTTCAAGACTGAACAAACAGGAGTTACT<br>ATCATGGCTCAGTGGTTAACGAAACTGACTGGAAACTCAGGTTCGATCCCTGGCCCCGCTCAGTGGGTTAAGGATC<br>CGGCATTGCCACGAACTGTCATATAAGTTGGACCCCGCTTTGCTGCAGTTGTTGTGTAGGCTGGCAGCTGTAGCTC |

TABLE 9-continued

| lists sequences for the disclosure |
| --- |
| CAATTTGACCTCTAGCCTGGGAACCTCCATATGCTGTGGGTGCAGCCTTAAAAAGACAAGAGACAAAAAAAAAAAA |
| AAAAAAAAAAAAACCCACAAAGATTCAAGAAACAAAATTATATGCTAGCACATAACCAGTTCAAAAATACAAGGAA |
| TTGGGAATTCCCATTGTGGCTCAGCAGAAACGAATCTGACTAGTGTCCATGAGGTCCATGAGGAGACAGATTCGAT |
| CTCTGGCATTGCTCAGTGGGTTAACAATCTGGCATTACCAAGAGCTGTGGTTAAGTCACAGATGCAGCTTGGATCC |
| CATGTTGCTGTGGCTGTGGAGTAGGCTGGCAGCTGTAGCTCCAGTTGGACCCCTAGCCTGGAACTTCCATATGCCA |
| CAGGTGCAGCCCTAAAAGCAAAACAAAACAAAACAAACAAACAAAAACCCAAAAAAACCGACCAACAAACAACAAC |
| AAAAATCCCAAGGAATTACAGGAGACTTTCAGAAAACTACATCGATATCCATGCTTAAGGATTTTCCTTCTTTAGA |
| AGTGTTCTTTTTCAAGAAAAGCAGGAAAAACTGAGTCTGCAGTTCTTAACTATTATTTCAAAGCCAATACCATAAA |
| AGTTTTTATGCCCCTTGCTCAAAGATAAATTGCATTTATGCACTGAAGAAAATCATGACATCTGCCAACTGCCTGC |
| ATCTTTATAGAATGTGGTATCCTTACTTTGACCACATAAACTAATGACATCTAAGTTATTTGGATTATGACTTAAT |
| ATTTAACCAGAAGAACAAACAAATGGAATTCATTAAAATTTTTAATAGGGAGGAATAATGAAGAGGAATTATAATA |
| AAAACATATTAGAAAACTATAATAATTAAATCATAGATAATTGGCATAAGGACGAAGAGAGGATCCTAATTAAATA |
| ACAGTTTAATATAGTCTAAGAGAAGGACCATAAATTAGTGGAAGAGGAAGGGCTGCCTGATACACAGTGCTGTGCA |
| ATGGTTAGTTAAGTATTCCAGGTGCTTAAAGACACAAAGAAAAGCAACCAAGTGCTTAAAAAGTATGAAAAAAATG |
| GCATATCACAGGGGGGACTTCTAAGTTTAATAGCAATGGAAATAATTCCAATGGAAAATCTTAGTAGATAGAAAAG |
| TAAAATGAAAAATTTCTACCACCTAAGAAAATGGGCAAACACACTTGGAATATATAAGCATCGTATTTGAAAAACA |
| AGTATAATTTAAAACAATGATGCTATTTTTGGTTCAAATGAGGAACGTTTGAAAAACTAGAATGCCCTGAGCTGAT |
| AAGGAATGAGGAGAAAAGGCAGGCTGATTAAGTAGTTAATGGGAACAAAAATTGGTTGGGTTCTAAAAAAATGGAT |
| TATAATGCAATACACATTAAAGAATGGGTAAATGAATAGTGGACTCATTCATTCATTTAGGACCTCAAGTTAAGAG |
| GATTATGTTAACCATATTTCTCAGTTCATGACACATTATATTCAGTCCAGGCAGAGCTACTTACTTACTCCCTTTA |
| TCTTTGTTTTCTACTCTTCTTTACTCTCCTCCCCTGTAGGCAACCATTTGAAAGTTCATGCAAAATATTTACTACA |
| TTGTATGTGTGCATCTTTAATTTTTATAAATGGTATTGGGTTTCCAGGCTGTTTCTTACTCTTTTTCATTCAAATC |
| TATGTTTCTAAGATACATTCATGTTGCCATGTGGACATCTCATCTCTAACTGGAGTTTCACATACCCTGGTGCCAC |
| ATTTTATTGATTCATGCTCCCAGGGGTGGACCCATAGATTCTGCCACAACAGGATTTCTTTGGTACATAAACAGGC |
| GTGGGATTGATGGGCCACAGTGTATTCATAAACCTGCTCTGCCTAACCACTGTCAGATTACTTTCCCACATGACTG |
| CACCGGCCATACTCCCACCACAGGCATGACGATTTTTATATCCTTTATCCCTGACATTTGATATCACCTTTGTTTC |
| TAACTTTTTATCAGTCAAAAAGATGTAAAGTAAAGCACCTCATTGCTTCAGTCTGTAGTTTTCTAATAATTAATAG |
| GTTTGAGCATATTTTCATGTGCTTATTGACTTTTGGAGATTTTTCTTTTGTAAAATGCTAGTTCATATCCTTTCTT |
| AATTTTTGTATTTTCTTAATTTTTATATTGGGTTTCCTATCTTTTTCTTGTCGATTTGCATTACTTCCTCCTATAA |
| GCTGGATAATATTCCCTCATTGGTTGTAAATATTGCAAAATAATCACTCAAACTATCATATGTTCTTTAACTTTGT |
| CCATGGGGTCTTCCAGTTCATAGAAATCTGTAGTGTATCGATGATATCTTATTCACTAGGTTTGTGTATATGTGTG |
| TTTCTTTTTTCTTTCTTTTTTCCCTTTGGGCTGTACTTTTGAAGTATTGTTTGAAAAGTCAAGAAGTATCAGTAAT |
| CTCTAGGTCACAAAAATAGTCTACATTTCTTCCATTACTTTCATAGTCTTACCTTCCTCATTTGAGCTATCAGTCC |
| ATGTGAAGCCCATCTTTATGTTAAAGTATGAGGTGTTAAAAAAAATGGGCGGGAGTTCCCGTCGTGGCACAGTGGT |
| TAACAAATCCGACTAGGAACCATGAGGTTGCGGGTTCGATCCCTGGCCTTGCTCAGTGGGTTAACGATCCGGCGTT |
| GCCCTGAGCTGTGGTGTAGGTTGCAGACACGGCTCGGATCCAGCGTTGCTGTGGCTCTGGCGTAGGCCGGTGGCTA |
| CAGCTCCAATTCGACCCCTAGCCTGGGAACCTCCATATGCTGTGAGAGCGGCCCAAGAAAATGGCAAAAAGCCAAA |
| AAAAAAAAAAAAAAAAAAAAATGGGCGAAAGCATGAGTTAGTCATATCCTTTTGCCAGTAATTCATTTGTCTCACAG |
| AAACAACTCCAAACACAAAGCAGCTCTTACGCACAATGATCACAGTTTCGTTTTGATGGAAAAAAAAAAATTATGAA |
| CAGTCTAAATTTCAACAACAGAAAAATGGCTAAATAAATCATGTAAGTTAATATTTAATGTAAACATACTTTATAA |
| TTGTGTATATATGGAATCTGACCTAACATGACTACTATAATAATTTTAACAAGACAAAAAACAGGATAAAAAAAGT |
| AATATATAAAATAATTACAATTGACTGGAACAACTAGATAGAAGATGAACAAGGAAATAGAAGACTCGAACAGCAC |
| TATAAACTAACTAGACCTAACAGACAAAAAAAGCACATTCCACCAGCAGCAGAATACACATTCTTCTCAAGTACAT |
| TTGGAATATTCTCCAGCATAAACTATGTTATATAAACGTTTCAATAAATTTTAAAAGATCAGTCATACAAAGTATG |
| TTCTCTGACCACAATGAAATGAAATTAGATACTAATAAGAGAAGAAAGTTGGAAAATTCACAAATATGTGGAAATT |
| AAACAACATACTTCTAAATACAAACAGTTTAGGAAAGAAATCACAACAGAAATTACAAAATGCTTTGATACAAATA |
| CAAATAAAAACATAACATGCTGAAACATAGAATGCAGCTAAAACAATGCAGTGCATAGAAGGAAATTTATATCTGT |
| ACACACCTATAATAAAAAGAAAGATCTCAAATAAAAAAACTAAACTTCCACCTTAAGAAATTAGAAAAAGAAGATC |
| AAACTAAACACAAAGCAAACAGAAGGAAGGAAATAAGAAAAAAAATTAGAGCTAAATGGAATTTAGACCGGGAAAA |
| CAAGAGAAAATCAATGAAGATAAATGTTTGTTTTTTGAGGGAGTTCTCGTCATGGTGCTTCAGAAATGAATCCGAC |
| TAGGAACCTGAGGTTGCAGGTGTGATCCCTGGCCGAGCTGTGGTGTAGGTCACAGATGCAGCTTGGATCTGGCATT |
| GCTATGGTTGTGGTATAGGCCAGCAGCTGTAGCTCCGATTAGACCTCTAGCCTGAGAACTTCCATATGCCTCAGGT |
| GCAGCCTTAAAAAGCAAAAAAAAAAACCAAAAAACAAACAAAACAAAAAAGTTAGTTATTTGAAAAGATTAATACA |
| ATTACAAACCTTTAGCTAAACTGACCAAGAAAAAAGAGAAAAGACCCAAATTACTACAGCCAGGAATTAAAAGGGG |
| GATATTACTATCAATCTAAATAATCCAAATGAAATGGAGAAAGTCCTAGGAAGAAACAAATGAACAAAACTGACTC |
| AAGAAGAACTAGAACGTCTGAGGAGCAGACCCATAACAAATTAAAGAGATTTAATTAGTAATCAAAAAACTTTTCA |
| CAAAGATTAGCCATGGCCCAGATGGCTTCACTGGTGAATCTGACCAAATGTTTAAAGAAGAATCAATACCAATATA |
| CTTCACAAACTCTTCCAATAAATAGAAAAGGAGGGAACACTTCTCAATTCATTCTATGAGAGCAGTAATTATTACT |
| CTGATCCCCAAACCAGACAAAGATATCACACAAAGAGAAAACTACAGACCAATATTCCTTATGAATATGGACATAG |
| AAATCCTTAATTGAATATTAGCAAATATAATTTAGCACTATAAAAAAGAATTATGACCATGAGCAAGTGGGGTTTA |
| TGCTAGCTTGATTCAATATAGGAACATCCATGGAGACAGTAAGTAGATTAGTGGTTGCCAGGGGCTGAGGGAAGAA |
| GGGAATGGACTGCTAATAGTTAGAAGGTTTCTTTGGGGGATGATGTGAATGACCTGGAATTATATAGTGATAGTAA |
| TAGCACAACATGTGAAAATACTAAAAACCATTGAGTCAAACACTCTAAAAGGGTAAATTTTATGGTACCTGAATTG |
| TATTCCAATAAAAGGAGAAGGAGGAAGAAGAGGAGGCAGGGGAGAGGCGGGGAAGGGGACCAAGGTGACAACTGGC |
| AGATACCAAAACACTGATGGAAATGTAGGTGAGAGTCTTCTTCCTTCTACTTTCCTAACATCTACCTTTTTTAATG |
| ATGACCATACAATGTTATTTATTTAACAATAAAACCAAATAATCTCAGCTCACATGGGATTGAGCCATCCTTTTCT |
| TTCTTGGGATGTGGTATGAAATCACTACAGTATTGGTAGCACTGTACTGAAAAGTGGGTTCTGTTAACAAAATTTT |
| CTACTCTCACAACATTACCTTACTGGAGCAGAGGCTGAAAACTGCAGTGGGTCTTGTTATTTCCAGTCCTCCACTG |
| ACCCTACTGACAACTCTGGCCCTGCCCTTCACCTGCCGTGGCAGTGAACATCAACGCTTTGCATCATTTCCTGGCC |
| TCAGTCTATTTTCCAGTTTACCCAACTTTCTGCTGGGTGGGAAATCCCTCCTTCCTGCTCCACAGGACCCAGTCAC |
| AAGGCATATGGCAGACTATTTGAGTCATACATATACAAGCAAATCATTACTCTGTACTCTGTCGTAACACGTTCTG |
| AACATTTAACAGATGTTCTTTCAACAACCCAGTAAAATCACTACTACCAATATTATCTCCCATTGAGGAAACTAAA |
| GAACAGAGACTAACCCACCTAAAGTCATTTAATTGCATGTTTGAGCATCAGGATATGAACCCACGCTAGTGAGCCC |
| CATTCACTCTTAACCATTTTGCTAAAAGGTCTCACTATAGGTCTTATCCAAAAGACTTAGCTCCCTTAAGGAGCTA |
| TAAGTTTCTGGGTTACATACTCATAAAGTAGATGGTCAATTGTCCTCTCACCTACACAAACAGTTTAAGACAGTCA |
| AACTTTTGCTTCTTATCTCTTTTTTTTTTTAATCAGATGAATTAAATAGTATTTGTACAGCACATGTAACCAGTTC |
| CTGCTAACAATGTGATCTGAAGATTTCCTAGGCTAGGTCAACAGACAAAGGGTGGGGGCTTTCTGGCAAAAGAAGG |
| AAATGGTTCAGGCATCCCTTTGAGGGGCAAGGTGAGAATTAGTCAATATTTCCAAAAGTCATTTAATTGTGTTAGA |

TABLE 9-continued

| lists sequences for the disclosure |
|---|
| TCAAATCTACTTTTTTATTTATATAACAGTCATTCTAAAACAGTGTGTAAAAGCAGTTTTAAGAATCTTCCCAAGT |
| AACTTTTTATACTGATAAAGACATTTTTAATCACTTAGAACAGAGACAAATTTATTCCTATGATTAAGCCCTTCTT |
| ACTCATATTTCTATAGGCTTTCTTGAGTAGGAAGAAGGAAAAAGTAGAAGTGGAGCCAGCATGAGAATCACACAGA |
| AGCTGTAGCCTCTAACGTGTGCCAGAAAGAGTCATGGAATTTGAAGGACTTTATTTCCCAACTGGAATTGTGAGTT |
| TCATTATAACGTCTCATTATATCATCTCATTTACGCCGACTCTATCTTATCCATCTTTGTATTTCTTAATACCTAG |
| TGCAATGTTTACACATGGTAAGGTCTCATCAAATACTTACTGAACAAATGAATGAATGAAGGGATTTTTTAGAGAA |
| AACTTGCCTAGAATTTTCAGTGATGGTTACTTTTAAAATACCTCAGTTTAAAATCAGAATGCATCCAAGGCTTCTA |
| ATGAGATTGGAAACAAGTTGACAAGAGGGACCCCAATGACAGTAACAGCAGAAAACATTGATCAGTATTGATGGTA |
| TTTACCCAGTTCGTCTTGACAGAAGCTTCCAGGAGGATTGATATACTTCATGCTGCTTACATCTAACTTCCAGTTG |
| TGTTTTGTGCATTTAACAGACCTGGATGGAAAATTGTACTTAGGTTTATGAAATGGTGAAAATAAATATTAATCTA |
| TTTAAGGCTTAAATGCATTATTCTGTGATCAAAGTAAACGACTGTAGTTGGTTGAACACAAAACTCATGAAAGGAA |
| AAAAATAGCTAATATTCAAATATCCAAGGAAATATAAACTCATCATCAGTAGGTGATTTTGAAAGTGAAGATATTT |
| TTTCCTTGTATTTGATTTTTGTCAGTTTGATTTGTATGTGACTTTGCACATTTCTCCTTGGGTTTATCCTGTATGA |
| GACTCTTCGTGTTTCCCTGACTTGAGTAAAGTGAAGATAAACACCATGGCACAAAATAACGTGTTAGAGATCAGCA |
| GAGCCATCAGAATAAAGTCTGCTTTGGAGTTCCAACTGTGGCTCAGCAGGTTAGGAACCTGAGCAGTATCCATGAG |
| GATGTGTGTTCAATCCCTGGCATTGTTCAATGGGTTAAGGATCCAGCATTGCTGCAAGCTGCAGTGTAGGTCACAG |
| ATGCAGCTCAGATCTGGCATTGCTGTGGCTGTGGCATAGGCTGGCAGCTGCAGCTCTAATTTGACCGCTAGCCTAG |
| GAACTTCTATATGCTATGGGTGCAGCCCTTAAAATTTGTTTTTTTTTTTAAAGAATAAAGTCATCTTTAAGGATGA |
| CTCTCATACAAAAGCTAAGCTGAGTAAGATCCAAGTGGGGCCAGTATAAGGAAATAATGTAGTAATAAAGATTATC |
| TGTGATTTAATAGTCACACTATAACCCTTGGCCCCTAGTATAGTGTACTAAACCTAAGATCAACTCAAATTTTCAT |
| TTGTCTAAGAAAAAAGACTTCCTGATTGTTTAAAGATTTCTGATCATGGTTGCCAGATAAAATACAGGAAAAATAT |
| AAATTTCAGATAAATAAAAAATAATTTTAAAATGTCTTACACAATATTGAACATATATTGGAAATTTGTTTATCTG |
| TAATTCAAATTTAACTACTCAGCTTTGCATTTTTATTTGTTAACTCTGGCAACACTGCTTCAGAATGAGAATCAGA |
| TTAATTGTAGCAACAAAGGAGGCTTAGTAATATTTTTTCCATTTCTTACCAGACGGTGATAGGGATGTGATAGTTG |
| GAGATAGGGCCTAAAAGTTCCATTTCCTCTCCATATTTGGTAGTCTGTCTGGCTGTCTTTCTTTCTTTCTTTTTGC |
| TTTTTAGGGCTGCACCTTTCTTTTTGCTTTTTAGGGTGGCATATGGGGGTTCCCAGGAGAGGGGTTGAATCGGAGC |
| TGCAGCAACACCATATCCTTAACCCACTTAGCGAGGCCAGGCATCAAACCTGTGTCCTCATGGATACTAGTTAGAT |
| TCATTTCTGCTGTGTCCCAGTAGGAACTCCCATATTTGGTAGTGTTTCCAGTCAAGTTTTTTTTTAAACAGTTCA |
| AGATTTTTTTTTTTTTTAACAGACAAATATGTCTTCAACCAGAAATATCAGATTGTTTAAGCTAACAATGTCTATT |
| TTCACTTATATATCAGTAAACTATGCTGATTTTTTCCAAGCTTCATTACAATCAAGAATTTTTAATGCTCTTTTCT |
| AGTAACAAGGCAGAAAACATATTCAAACTTCGACTTATGGAGGATATTTTGTGACACTTCCTTTCTCATCAATGAG |
| TAACTAACAACTATCATGGCTCAGAGGTTAACGAATCTGACTCGTATCTATGAGGACGAGAGTTTGATCCCTGGCC |
| TCGATCAGTGGGTTAAGAATCCAGTGTTGCCGTGAGCTCTGGTGTAGGTCAAAGATTGGCTCGAATTGTGCATTGC |
| TGTGGCTGTGGTGTAGGCCAGCAGCTACAGCTCACATTGGATCCCTAGCCTGGGAACCTCCATATGCCATGGGTGC |
| GGCCCTAAAAAAAAAAAAAAAAAAAAAAAAAAAAAAAAAAAAAAAAAAGATGAAATAAATAAATTAACAAAAATTGAAA |
| ACATTCCAAATGCAGCTATTCAGCAGGCTGGGTCGTTAAAGGAGAAATGTGGCAGTGTCACAACTGCTCATGGGCA |
| GTAGGCAGAAAGGAGAGAGAGGACAGCTTCATGTGCCAAGAGGCTGTGAAATTAGATTGACAAAATGAGGACCACA |
| GCTTATGAGAGTTCCTGATCTTGATTATGTACAAAGAAGAAAAATGGCTGAGGAAGGGAAGGTGGAACAGGTAGGT |
| CACTGCCCTTGACTGTATCGTGGAAGAGATATTTCAGGTGAATTGCTGCACAGAGAGCCTAAGTAGAAGCAGCCAA |
| ATTTGGAGAGATGGATGGGGGAGTGTACCATGTAAACTGCTCTTGGGATGGAGTTTCAGCATATAAATGCTTGGGG |
| AGCTGTATCTGGGAGCAAAGCTGGGTGAATCTGGCTCCCCACCTGCAGCAGAGCTAAGATGGTGCCATCTCCATGT |
| TAGCCTGCCAACAGAATAGGTTGAAACTGGGATCGTTCACCCCCTAAGGCTTTGGGTGAAGGAGAGGAAGACCAGT |
| CTGTGGCAAAGCAATTACCATATTAAGCTGAGCAAGCCAGATTCAAGAACAGCCTGAATTCCTGTAAAGAACCTCT |
| GTTCCTAAGCTACGCAAGATCATGGCAGAGTAATAATAATAGCAAATGTAAGTGACATTTATTGAGCATGTATCAT |
| ATGCCAGACATTATTTTAAGTGCTTTAGTGTATGAAATCACTCCATCCTCTCAGTAGCCAGACAGAGAAGGCTTTG |
| TCTACTTTCATTTTCACTTTATGAGGAAGAAGAGCGAGGCCCAGAAAGGCTAAGAAATGTGTCCGAGGTCACAGAG |
| CTGCTAAGTGGTGGAGCCAGGCTTCTAAACCAAGCAGTTTGCAAGGAAAGACCATGCTCTTAATCATAAAGCTGCA |
| ACACTCCCTTAAACAACTGGCTAAGACAACACCACAGGACATGGCCCACTAAGGAGAAAAAAGGACAGAGAAAAAG |
| CAGAGTCCCCGGGCCACAAGTCGGAAGACCTCAAGGCCTGCACGTGCCTGCAGAAGCTTCTTGGTGACAGAACAAC |
| CTATGGCTGAGGTCTCCCTAACTTGAAACCACCCAGAAGATGCAAGGGACTCAAAAGCAGTCTGTCAGCAAACAAC |
| CAAGAGGTTCTTCCAGAGTAGGCTGCCTACCAAAAGTATGTCCCATGCAGTGCCTGAAACATATCTAACTAAAAAT |
| ATATTCGTTGTTTATCTGAAATGCAAATTTGACTGGGCACCCTCTATTTGCCTAATCTAGCAACCCTATCTGCAGA |
| GCCAAGCAAGCTACAGGTATGACAGCACTTAACCTGGGAGCTGGGCCCTGAAGCTAAGTATGCAGTGATGCAAGTC |
| TGTGGGCCAGTGTAAGAAGATTCCAGACTTGGGTGGTGATCTTCTATACAGTTAGAGCAGGGAGTTCTTGGACAGC |
| TACCAGTTACCTCTGAGTCCATTCGCACTAAACTGCCCACAGATGACCTGAGAAATAAGATTGACGACACGACACG |
| GTGGAAGACAAGCCTAATATGGAAACGGCTGAAACACTACGAGAGTCAAGTTAGGCTGAAGCAAAGCTTGAAAGAT |
| GGGGTCAATCCCTCATTCATTATCAGTGGTGAGCATCAGGCTGACAAAACACCTCCACCCAGAACTCCCCCTGGCT |
| CTGCAAGCTGTGCTAGCTCTTTGTCAATCACTGAAAAGAAAGCCCAACCATCCTATCCTAGAATTGCTCCTGAGAT |
| GGGGAGGTAAGCGATATGCAGGTTTAATCAAGGGGCTGGGGAAAAGGCGTACCAGCACTCGTTCTTCCAAGAAATG |
| ATCAGAAGAGCCGCTGTTGAGGCCAGGTGCAGCTAGAGCTCTGCCATTTTTCGGGTTTTCATCAGGGAAAGTCTCT |
| CTGTTCTAGGGCAGTGTTTGGACAAGCACTCACCTCACACACACACACTTCTGAGAGAGCAGGAAAGGAAATCCAA |
| AAGAGGCTTGAGTCTTTGAATATAAAAGCTGGTAAACACACACACACACACACACACACACACACACACACTCCTT |
| AGAAGTTTCACTGTTTATCAACTAGGAATACATTTTAAACAATAGTTCTTCAGAGAGGATGGGAAATTAAGTCAAG |
| GTCATAAATCAAAATCAGAGAGCTGCCGTAAAGGAGCTTAAGAAAAAGTTAGGCATGTGCTGGGGGAAATAGCATG |
| TTGATTGGATCATTTAAAATTTCTCAATGAGCACATTTCCTGCCAAACCTAATTGGGAGAAAGGATCGCCAGGGAG |
| AAAGCAAAGGATTCTCAGTACCTTCCATTTAGATCCTCAATGTCTTTAATGAAGAGGCCTCCTTGGTGCTTGCACA |
| TGTTCTTACATGCCTTCAGGCGGCTCTTATTCTTAAATAAGATGTAATCCTTGCCAGTGCTCTTATTTCGAACAAA |
| ATTGATTCCTTCCTTGAGATTGGCAGCTTCGGCAGGTGAGAGGCACAACAGGATCTCCGTCGTTTGTTCGATG |
| |
| SEQ ID NO: 17 CMAH CDNA Sequence |
| ATGAGCAGCATCGAACAAACGACGGAGATCCTGTTGTGCCTCTCACCTGCCGAAGCTGCCAATCTCAAGGAAGGAA |
| TCAATTTTGTTCGAAATAAGAGCACTGGCAAGGACTACATCTTATTTAAGAATAAGAGCCGCCTGAAGGCATGTAA |
| GAACATGTGCAAGCACCAAGGAGGCCTCTTCATTAAAGACATTGAGGATCTAAATGGAAGGTCTGTTAAATGCACA |
| AAACACAACTGGAAGTTAGATGTAAGCAGCATGAAGTATATCAATCCTCCTGGAAGCTTCTGTCAAGACGAACTGG |
| TTGTAGAAAAGGATGAAGAAAATGGAGTTTTGCTTCTAGAACTAAATCCTCCTAACCCGTGGGATTCAGAACCCAG |
| ATCTCCTGAAGATTTGGCTTTTGGGGAAGTGCAGATCACGTACCTTACTCACGCCTGCATGGACCTCAAGCTGGGA |
| GACAAGAGGATGGTGTTCGATCCTTGGTTAATCGGTCCTGCTTTTGCGCGAGGATGGTGGTTACTACACGAGCCTC |
| CATCTGATTGGCTGGAGAGGCTGAGCCTTGCAGATTTAATTTACATCAGTCACATGCACTCAGACCACCTGAGTTA |

TABLE 9-continued lists sequences for the disclosure

CCCAACACTGAAGAAGCTTGCTGAGAGAAGACCAGATGTTCCCATTTATGTTGGCAACACGGAAAGACCTGTATTT
TGGAATCTGAATCAGAGTGGCGTCCAGTTGACTAATATCAATGTAGTGCCATTTGGAATATGGCAGCAGGTAGACA
AAAATCTTCGATTCATGATCTTGATGGATGGCGTTCATCCTGAGATGGACACCTGCATTATTGTGGAATACAAAGG
TCATAAAATACTCCATACAGTGGATTGCACCAGACCCAATGGAGGAAGGCTGCCTATGAAGGTTGCATTAATGATG
AGTGATTTTGCTGGAGGAGCTTCAGGCTTTCCAATGACTTTCAGTGGTGGAAAATTTACTGAGGAATGGAAAGCCC
AATTCATTAAAACAGAAAGGAAGAAACTCCTGAACTACAAGGCTCGGCTGGTGAAGGACCTACAACCCAGAATTTA
CTGCCCCTTTGCTGGGTATTTCGTGGAATCCCACCCAGCAGACAAGTATATTAAGGAAACAAACATCAAAAATGAC
CCAAATGAACTCAACAATCTTATCAAGAAGAATTCTGAGGTGGTAACCTGGACCCCAAGACCTGGAGCCACTCTTG
ATCTGGGTAGGATGCTAAAGGACCCAACAGACAGCAAGGGCATCGTAGAGCCTCCAGAAGGGACTAAGATTTACAA
GGATTCCTGGGATTTTGGCCCATATTTGAATATCTTGAATGCTGCTATAGGAGATGAAATATTTCGTCACTCATCC
TGGATAAAAGAATACTTCACTTGGGCTGGATTTAAGGATTATAACCTGGTGGTCAGGATGATTGAGACAGATGAGG
ACTTCAGCCCTTTGCCTGGAGGATATGACTATTTGGTTGACTTTCTGGATTTATCCTTTCCAAAAGAAAGACCAAG
TCGGGAACATCCATATGAGGAAATTCGGAGCCGGGTTGATGTCATCAGACACGTGGTAAAGAATGGTCTGCTCTGG
GATGACTTGTACATAGGATTCCAAACCCGGCTTCAGCGGGATCCTGATATATACCATCATCTGTTTTGGAATCATT
TTCAAATAAAACTCCCCCTCACACCACCTGACTGGAAGTCCTTCCTGATGTGCTCTGGGTAG

SEQ ID NO: 18 CMAH Protein Sequence
MSSIEQTTEILLCLSPAEAANLKEGINFVRNKSTGKDYILFKNKSRLKACKNMCKHQGGLFIKDIEDLNGRSVKCT
KHNWKLDVSSMKYINPPGSFCQDELVVEKDEENGVLLLELNPPNPWDSEPRSPEDLAFGEVQITYLTHACMDLKLG
DKRMVFDPWLIGPAFARGWWLLHEPPSDWLERLSLADLIYISHMHSDHLSYPTLKKLAERRPDVPIYVGNTERPVF
WNLNQSGVQLTNINVVPFGIWQQVDKNLRFMILMDGVHPEMDTCIIVEYKGHKILHTVDCTRPNGGRLPMKVALMM
SDFAGGASGFPMTFSGGKFTEEWKAQFIKTERKKLLNYKARLVKDLQPRIYCPFAGYFVESHPADKYIKETNIKND
PNELNNLIKKNSEVVTWTPRPGATLDLGRMLKDPTDSKGIVEPPEGTKIYKDSWDFGPYLNILNAAIGDEIFRHSS
WIKEYFTWAGFKDYNLVVRMIETDEDFSPLPGGYDYLVDFLDLSFPKERPSREHPYEEIRSRVDVIRHVVKNGLLW
DDLYIGFQTRLQRDPDIYHHLFWNHFQIKLPLTPPDWKSFLMCSG SEQ ID NO: 19 CXCL10 Genomic Sequence
CTTATAGTAACTTTATTACCTTTTTTGTCTGAACAGTTAGTCTTTCTTAATGTTTCTAGGAGAGAACATTAGTTTT
ATTTTGAAGAGCACCCACTCAGCGTATTTGTCTTACATAACATGCAGAACATGTATCCACATTTAAAAATTTATCT
CATTGTAGTACATACTTTTACAAGGTATTCCATAAACACTGAAAACTATAAGAAACATATACATCTAAGAATCCTA
CTTTATATAGTCTTTCACTAAATAATACTATTTTCATATACATTTTCAGGTATTTCTAGCTTCTCCTGTGTATTTA
GAATTATGTATGTAATCACCAAGAGAATATGGGCCCCTTGGAAGGAAAGCAGTAGAAGCCCACGGAGTAAAGATCT
TTCTTTAAAAAGCAGGTTTTATTATTGTTTTAAATACCTCTTGGTTATTTGAGATTCTAAGAACTTCGATTAAGTC
CCAAAGTGGAATGATCCCTTAATAACCAGACGATAGGAAAGGTGAGGAAAGTGTCAGTAGCAGGGCCAGGACTTGG
CACATTCACTAAGAATGTAGCACCTCAGTGTAGCTTATAGTATAGTGCCTGGGCAGAGTTACTGCTCAACAGCTCG
GGATGATGAACCATCTGCTGCCCTGCAAGTGTGGGAGCAGCTAACTTGGTGACTGCAATCCATGGACAGTTAGGGC
TTGATGTATGGTGTATGTAGAGAGATGATGGCAGAGGTAGATTCTCTCCGGCCCATCCTTATCAGTAGTGCCGTGA
TTATGCTTCTCTCTGTGTTCGAGGAGATCTTTTAGACCTGTAAGAAGAGAGGGAGAGTGTGAAAGACTCTGGTTTC
AGTCTGAGTTCTGCTTGGAACACACTGAATTCATAGATAATCCCAAGTTCTCAGGTGAAGTGTGGTGAGATTTCCT
GCTACACAATCATTGTGTGTTACAGGGGATCCTTTTTAAAAAAGGCCAGGAAAGGCTTGTGGGAAATTTGGTATCT
TTGCTTGGATAGTTATAACTCTGCCTCAAGGTTGAAATGACCTATTGACACTTCTAGATAGGGAATCAGGTGACTT
GATATACCACATAAGATGACATCTCAGTATATAAGCACATGAAGGTAATGGCACAGTGGTGGTAACACTCTTTTAA
GCCAAAGATTCCCAGGAAGGCCCAATGCAAATATTTCTAACTTCCCAAAATTGACATTTCTTAAAGAGAAATACTT
CTGCAAGCAGTAGCAAACCTACCTTTCTTTGCTAATTGCTTTCAGTAAATTCTTGATGGTCTTAGACTCTGGATTC
AGACATCTTTTCTCCCCATTCTTTTTCATTGTGGCA SEQ ID NO: 20 CXCL10 cDNA Sequence
ACGCGGGGGAGACACTCTTCAACTGCTCATTCTGAGCCTACTGCAGAAGAATCTTCAGCTGCAGCACCATGAACCA
AAGTGCTGTTCTTATTTTCTGCCTTATTCTTCTGACTCTGAGTGGAACTCAAGGAATACCTCTCTCCAGAACTGTT
CGCTGTACCTGCATCAAGATCAGTGACAGACCTGTTAATCCGAGGTCCTTAGAAAAACTTGAAATGATTCCTGCAA
GTCAATCTTGCCCACATGTTGAGATCATTGCCACAATGAAAAAGAATGGGGAGAAAAGATGTCTGAATCCAGAGTC
TAAGACCATCAAGAATTTACTGAAAGCAATTAGCAAAGAAAGGTCTAAAAGATCTCCTCGAACACAGAGAGAAGCA
TAATCACGGCACTACTGATAAGGATGGGCCGGAGAGAATCTACCTCTGCCATCATCTCTCTACATACACCATACAT
CAAGCCCTAACTGTCCATGGATTGCAGTCACCAAGTTAGCTGCTCCCACACTTGCAGGGCAGCAGATGGTTCATCA
TCCCGAGCTGTTGAGCAGTAACTCTGCCCAGGCACTATACTATAAGCTACACTGAGGTGCTACATTCTTAGTGAAT
GTGCCAAGTCCTGGCCCTGCTACTGACACTTTCCTCACCTTTCCTATCGTCTGGTTATTAAGGGATCATTCCACTT
TGGGACTTAATCGAAGTTCTTAGAATCTCAAATAACCAAGAGGTATTTAAAACAATAATAAAACCTGCTTTTTAAA
GAAAGATCTTTACTCCGTGGGCTTCTACTGCTTTCCTTCCAAGGGGCCCATATTCTCTTGGTGATTACATACATAA
TTCTAAATACACAGGAGAAGCTAGAAATCCCTGAAAATGTATATGAAAATAGTATTATTTAGTGAAAGACTATATA
AAGTAGGATTCTTAGATGTATATGTTTCTTATAGTTTTCAGTGTTTATGGAATACCTTGTAAAAGTATGTACTACA
ATGAGATAAATTTTTAAATGTGGATACATGTTCTGCATGTTATGTAAGACAAATACGCTGAGTGGGTGCTCTTCAA
AATAAAACTAATGTTCTCTCCTAGAAACATTAAGAAAGACTAACTGTTCAGACAAAAAAGGTAATAAAGTTACTAT
AAGCCAAAAAAAAAAAAAAAAAAAAAAAAAAAAA SEQ ID NO: 21 CXCL10 Protein Sequence
MNQSAVLIFCLILLTLSGTQGIPLSRTVRCTCIKISDRPVNPRSLEKLEMIPASQSCPHVEIIATMKKNGEKRCLN
PESKTIKNLLKAISKERSKRSPRTQREA SEQ ID NO: 22 CIITA Genomic Sequence
GCAGTGGACAGTGCGCCACCATGGAGTTGGGGCCTCTGGAGGGTGGGTACTTGGAGCTTCTCAACAGCAGTGCCGA
CCCTCTGCAGCTCTACCACCTCTATGACCGGATGGACCTGGCTGGAGAAGAAGAGATCGAGCTCTGCTCAGGTGGG
CCCTCCTCCCTCTGGCCCTTTTCAAGTCCTTCCCCAGCCCTCTGCCTGCCATGGAGCGCTGCTCAGCACCACGGAC
AGCTCCAGAGCCCGCCCCCCGGGGGCGGGCTCCTCGTGGGGACATCTCCCAGCCTGCCCGGCTACCCCCTCCTTCC
CCACCAGCCCTCTTTCCTGGCTCTTTCCTGCTTCATCCAAGTGGCTTTTCCTCCCAGAACCTGACACGGACACCAT
CAACTGCGAACAGTTCAGCAGGCTGTTGTGCGACATGGAAGCAGATGAAGAAACCAGGGAAACTTACGCCAGTATC
GGTGAGGAAGCATTCTGAGCCAGAAAAAGGACAAGCGAGGGGAAGAGGCTTCTTTTCTCTTTGGTTAATCTCACCC
ACTCACCAGGAGCCAGCAGGCCCTACCTCAGAAATCTGGGCCAGGGGGATGGGGAGTGAGGGCTGGAAGGACGGAG
AATCAGGGAAGAAGAGAGATGGAGAAGGGGAGGGAAATAGACCCCTTCACCAATGAACACCAGGCAATTAAGTCGC TABLE 9-continued

| lists sequences for the disclosure |
| --- |
| ACTTTTACAGAGCTCCCATTGTGGCTCAGTGGTAACAACCCTGACGAGTAACCACGAGGGTGTGGGTTCGATCCCT<br>GGCATCGCTCAGTGGGGTTAAGGATCTGCTATTGCCCTGAACTGTGGTGTAGGTCGCAGGTGTGGCCTGGATCCTA<br>CATTGCCGTGGCTGTGGTATAGACCAGCAGCTGTAGCTCTGATTTGACCCCTGGCCCAGGGACTTCCACACATTTT<br>ACATGGGGCCCTTTAAAAAAGACAAATCTCACTTTTACATCCTCTGCCTCTATTTCTACATCTTTTTCTATTAGTT<br>GCTCTTCTTTCCTTCCTTCCCACAAAGCCTATGTCATACACCGCTCCCTCTCTCCCAAGCTCCCAAGCTAAACTAC<br>TCTAGTATTTGTAGTAACTACCATTTGGGGAGCATTTGCAGCCTGCTAATCGCTGTGCGTGTCTTATCACATTGAA<br>TCCTTACAAAGACAAAGGAAGTAGATATTCTTAGTATTTTCACTTTACAGATGAGGCAACTGAGGTTTAGCGAGAT<br>AAAGCAATTCACCCATGTCTGCGTTAGAGACAGTAATGGGCATGTCTGAAATTCTAACTGAGGTCTTATTTTTAAC<br>CACAAAAACCAAAGTACCTAGGGTGGGGAGGTTTGCTAAGGCTTAATCTAAGAGGCTGGTTTGCAGCTTTATTGTT<br>TTTTTTTTTCTTTTTAGGGCCACACCTGCAGCATATGGACGTTCCCAGGCTAGGGGTCAAATCAGAGCTGCAGCAG<br>CCAGCCTGCACCACAGCTCATGGCAACACCAGATCCTTAACCCACAGGGCGAGCCCAGGGATCGAAGTCGCATCCT<br>CATGGATACTAGTCGGGTTTACTGCTGCCGAGCCACAGTGGGAATTCCTTGTTTGTAGCTTTAAAAAGAGCGACAC<br>GGATCCCACGTTGCTGTGGCTGTGGCATAGGCTGGCAGCTGCAGCTCTGATTTGACCGCTAGCCTAGGAACCCCCA<br>TATGATACAGGTATGGCCCTAAAAAGACAAAAAAAAATTAAGAGCTGCATTATAAACTACAACAGAAAAAAATGTT<br>AAAGACTACATATGTACAACTGAATCATTCTGCTCTACACTTGAAACTAAAACAATATTGTAAATCAACTATACTT<br>CAATTTTTAAAAAGAGCCTCAGCTTTCAGTCAAGGGTAGAACTCTTTGGGGAGAAAAGTTTCTGTTCTGTTGTGTT<br>TTTTGCGGGGTAGGATGGGGTAAAGGCTCTCTCCTTACCAGGGACATCGCTCTCTTATACAGAGGCTTTGTTCAAA<br>TATAAAAAGATGCTCCTTCTTCTGGAGGATGGAGCCCCCATTAAGAAGTAACAGCTTGGGAGTTCCCGTCGTGGCG<br>CAGTGGTTAACAAATCCGACTAGGAACCATGAGGTTGCGGGTTCCGTCCCTGCCCTTGCTCAGTGGGTTAACGATC<br>CGGCGTTGCCGTGAGCTGTGGTGTAGGTTGCAGATGCGGCTCGGATCCCATGTTGCTGTGGCTCTGGCATAGGCCA<br>GAGGCTACAGCTCCGATTTGACCCCTAGCCTGGGTACCTCCATATGCCACGGGAGCGGCCCAAGAAATAGCAAAAA<br>GACAAAAAGNCCAAAAAAAAAAAAAAAAAAAAAAAAAGTAACAGCTTGGCTATCAAAGTGCAGTCTGGATTTCTGCC<br>CCTTTTGCCCTCTTGGCTAGGCCCCCTTGTACAGTGAACAACCTTCACAACTGTTTTTAGTGGCCCTTTTCCTGGC<br>AACCCAGGAACGACATCCCTTAGGAGGTCTGGCATAAATGTGGCCAGTCTTTCCACAGCACAGAGGGCAGAAAATG<br>GAGAGGAACAGTAACCGTACGTGTCTCAAAAATTGCAGAACTGAGAGCCTGCCTGTTTCCTTTCCTTTCTGGGAAT<br>TTACTTGCTGGAAGGAGAAATATTTGGGCCTGAGGGTATTCACAGTTCCTCACAACTGGAGGTAGTAACGAAGGAT<br>TTGGGCTTTTTCCCAAGTCACTTAGGAGGGGGGACTTTTTCCCTTTAGAGGCATCTACACAGGAAGCGGGAGCATG<br>TGGAGGAGGCAGCTTCGCCCAAGTCCGTTCCTCAAACCTGTGCTCCTAGAATCTCTGGCCAGGTAGTCATTTGAGC<br>AACCTTGGCTTCTATAGAGATAAACTGGGAATAATAATCCCACCTGCCTCGTGGAATGACTGTTTCTGTGCATAAA<br>GTGATTAGAACAGGATTTTGCAAAGAGTGAGCACTCAGTAAGTGTCAGGTTCCACCCCACCACGACCACCAACACC<br>GTCATGTCATCATTATCATGTTTGTCATCGTCTTCATCACCATTATATCTTCCCTCCATTTCCTCAGCACAGAAGC<br>CTTGTATGGCTCCCCACTGCCTATAAAATCAAGTCCAAACTTTCCCCGACATGAAACTTTTAACTGCAGATACCAG<br>TCTCTAAGAGTTTCCCAAACGGCTTTCCTCCCTCTGTCCCCACCACCCAGAAAGCCCTCCTCTTTCCTCCTCGCAG<br>ACTCTGCCCCATCTTTCTTTCTTTCTTTCTTTTTTTTTTTTTTTTTTTTTTTTTTTGGTCTTTTTGCCTTTTCTAG<br>GGCCGCTCCCACGGCATATGGAGGTTCCCAGGCTAGGGGTCTAATCAGAGCTGTAGCTGCCAGCCTACACCACAGC<br>CACAGCAACACGGGATCTTTAACCCACTGAGCGAGGTCAGGGATCGAACCCGCAACCTCATGGTTCCTAGTCGGAT<br>TCATTAACCATTGCGCCTCAATGGGAACTCCTGCCCCATTTTTCAAAGTCTAGCTCCAGGACGTCCTTCTCTGGGA<br>CATCCTCCCTGATTGCCCCATCCCACTTTACACCCTCTCCTGTATCTCCTGCCATGATAACTGTCATCCTGTTGGC<br>TCCAAGCCAGGTTCCACTTCATACAGTTTACAACTGCTTACTGAGTGTCAGCTGTGTACTGACTACTGTGTTGACT<br>GCTGGAAAGGCAAAGCCTATACGCCTCACCATCCATCCCTGAATTGTAGGCATTACTTGTTCTCATCACGTAGAGG<br>AGGAAACGGGGACCTAACTGGCCTAAGTTTGTACGGCTAGTAGGGTGAGTGAGGGGTAGAGCTGAAATTTAAACTC<br>AAACCCAAGACAGCTCTACTATACTACTGGCACTACTTTATAGTACTAGATACACATCATCCCTCTGATTAGGTTA<br>AGAGCCCCTGAAGAGTCAGTGATCATTCATTCAGCAAACCTTTATGGACCCCCATTGTGGGCCAGGTCTGGACAGT<br>CATGACTGCCCAATGCCCAGCCCAAGGCCAGGCACACAATAAGCGTGAGGTGAAAACTCACTGATTGACGGCACTT<br>TTCCTTGTCTGGACAGCGGAACTGGACCAGTATGTTTTTCAAGACTCTCAGCTGGAGGGCCTGGGCAAAGACATTT<br>TCAGTAAGTTGGGGGGTGGGGGGTTCTTGGTTCAGCCTGCATTTCCTTCCTTGTTCCTTAGGGGGCATGGAAATAC<br>CCAGAGGCCACCCTTCAATGAGAAGTCACGTTCCCTTCCCAGTGTAGGGACAATGAGGGCTCATCTCGGACATCCT<br>CTGACTGTGTGTCTTGGTGTCTTTGGTTTTTTCTCTGAAGTTGAGCACATAGGATTGGAAGAAATGATCAGTGAGA<br>GCGTGGAGGTGCTGGAGGACTCAGGGCGGAAAAGTCAGAAAAGATGTGAGTGAGCGTGTTTCCCCCCCGCCCCCTG<br>CCATCCAACCTCTCCTGGCTTCATTCCTGGCCCTGCCCTGGCTCTAAAACCTCCCAGTCGCATTCCTTGTTAAGCC<br>TTGCCTGCTCTGACCTGGCTTTGGGTGTCCCCCCACCTCTCCTCTCACCACTGCTCCCTCGAGACCCAGAGAGGAA<br>GCAAGTGGCCCAGCAGCAGATGGTCCCTCTCCTGGTGGGTCTCTGTTTTTGACTGTCATTTCCAAAAGACCTCTGG<br>GCTCTGGCTTCTCTTTCATCCTTAGTTGTCACCCCTGTATTTAAGGGAGGTCTCTTCAAGGACAGTCTTTCCCCAG<br>CAAGATCTGGGTTTGAATTCCAGATCTGCTATTTAAGGTCTGTGTGACCTTGGGCAAATAATTACACCTCTCTGAG<br>CCTCCTAGTCAGTCTGCCTGCCTCCTCTGTCTGTCCTCACCTGGCAGCCAACATGGGCTTTTGAATGCAAATTCAA<br>TCATTTGGCTGGCCTGCAGACCCTCCAATGGCTCAAAATACATACCACAAGGATCTGTAGGATCTGGCCCTTCCCC<br>CTCTCCAAATTCACGAATGTGAGTCACTATGCTCCATCCAGCCACACTGGCTTCTTTCCATTCCTGTAACTCTTGT<br>ACCCTTTCCAGCCTCAGGGCCTTTGCACTTGCTGTTGGCCCTGTCTGGAATGCCCTTCCCCCGTTTCTTCCCATAG<br>TGGCGCCTCCGAATCTTGTAGGTCTTGGCCAACATGTTGCCTCCTCCCGAAGGCCTTCTTCCATCAACTTTTCCAC<br>ATAAATTAACCTTACTTACTTTCACCTTGTTTGTGTCTCTCCAGCATCACAGCCCTTGTCACAATCTGGACTTGTT<br>TTAGGTATTGGCTTTTGCTTAGTTCCCCCACCATGGGGACAGGGACCTTGTCTTTCTTATGTAATCACTACCTTCC<br>CCAGCACCTGGTACATGCCTGGCATGCGGGAGCATCTCCATAAATATCCACTGAATGGAAATTTCCAGGAGTTCCC<br>ATCGTGGTGCAGCAGAAAGGAATCTGACGAGTATCCATGAGGATTTGGGTTCAATCCCTGGCCTCGGTCAGTGGGT<br>CCAGAAACCAGCACTGCCGTGAGCTGTGGTATAAGTCGAAGATGAGGCTCAGATCCCGTGCTGCTGAGGCCTTGGT<br>GGAGGCCGGCAGCAGCCGATTTGACCCCTAGCCTGGGAATTTCCACATGCCTCAGGTGCAGCCCTAAAGAGCAAAA<br>AAAAAAAAGAAAAAAAAATTTCCACAAAATGGGCATCACAGCTAATTGAATGCTTACTCTAGGCCAAACCATGTGT<br>AAGCCCTGAACCTATTTAATTTGAACAGGTAAACAGATGCATGGCATAAAAATTCAAAAGGTGCGAAGAACAGTCA<br>GTAAAAAAAAAAAAAAAGAAAAAAGAGCTCCTTCCCACTCGTTTCCCAGTCTTTCATTTTCCCTCTCTGAAGACAA<br>TCTATGCTGCCAGTTTCCTTTTTGTCTTATATTTTGCCTAAAAGCCAGCTCTTTAAAACAATGTTGCCCCACAAGT<br>GGCATTTCACCCACCGTCTCGGGCACCTGGCTTTCTTCGTTTACCACGTCAGGACGGCGATTTCCACACCACGATG<br>GAAAACACGTGGTCCTCCCGCCCAGGAATTTCCCTTTCCTTTCCTTCTTTTTTTCCTTCCTTCCCCCTTTCTTCTT<br>TCTTTTCATTTCATAAGCATTTTCCCCCAATATTTTACCATGTGGTGTAGGGTGCAGACTACAAAATTTCTGTCTT<br>TTTTTGCGTGTCTTTTAGACCCCAGGCTAGGGGTTGAGTCCGAGTGTAGGTGCCGGCCTACACCACAGCCACAGCA<br>ATGCAGAGTCTGAGCCTCGTCTGCAACCTACACCACAGCTCACAGCAATGCCAGATCCTTAACCCGCTGAGCGAGG<br>CCAGGGAGCGAACCTGCGTCCTCATGGATGCTAGTCGGGTTCGTTAACCCCTGAGCCACAACGGGAACTCCGAAAA<br>ATTTCAGCATATAGTAGAGGTGACAGAATTGTACTACAAGCAACCACATACCCACTGCTGACAACCTACCATCAGT<br>GTTGGGCTATATTTGCCTTAACACATCTCTATCCATCTGTCCATCCCTCTATCATCCACCCATCCATCCATTTTCC<br>AGGGGAACGTGTCAAAGGACGTTGCAGACGCCAGTACTGCCCACACATCCTTCCACATCCTTGTTATTTTTAGGGC |

TABLE 9-continued

| lists sequences for the disclosure |
|---|
| TGCATGGTATTTCACTGGGGGATGAATCATCGTTTGTTTCATCAGCCCCTCGCTAAGGACACAGCTGGGTTTTTCT<br>CTGTTGATGTGTGCCGTGCTTGATATGCACTCACTGATTTCCAGTGCATTCCTGCAAAATGGGAATCAACACCCCT<br>GTTTCACAGATGAGAGAACAAAGGCTCAGAGAGGCTGTGTAGCAGAGACAACACGGCCAGGAAGGGCCCAAAAGCA<br>GGTGGTTTGTCTTTGTTTTTTTTGTTTTTTTTGGTGGGAGGTTGTTTTGTTTCTGTAATGGCTGCACCCATGGCA<br>TACGTTTCCAGGGCAGGGATTGAATCTGAGCTGCAGCTGTGGCAATGCCGGATCCTTTCACCCACTGCACCAGGCC<br>AGAGATGGAACCTGTGCCTTCACAGCGACTCGGGCTGCTACAGTCAGGTTCTTAACCCACTGTGCCAGGGTGGGAT<br>CTCCCACAGATGTTTTTTTCATTTTTATTATTATTATTTTTAAACTCAAACTCTTCCTGTGTCTCTTCTATGGTTC<br>TGCCTCTTCCAGTGCCTCACTGCCCTGGGTGCTTCAAGATGGGGTTTGGGCTCAAGCAAAAGAGTGGGGGCAGAAA<br>TGGTCGGAGGAAGAGGAGGGAAAGGGACCCCCAGGCCACTTCCCAGCCATTTAAGGCAAGGCCACAAGGCCTAAC<br>TGGGGTCCACAGGCCCGTCCTGGCTGGGTCTGATGACCGTGTGTTCTCTCTGAAGCTTTCCCGGAGGAGCTGCCTG<br>CGGATCTGAAGCACAGGAAGCTAGGTGAGCAGGGCGGGTGCATCCAGGGAGACTGCCAGGCAGGGAAGCTGGGGTC<br>TCCTCAGGTGTGCATATAAACTAGCATTTAAAAGCTGAGGCTCAGAGAGGTGAAGCCACTTGTTCAACATCACACA<br>GCAAGTGAGAGTTGGAGTTGGGATTCAGACTAAGATCATGAATCCACAGTGCGTGCTCTGCAGTTCAAGGACTGTT<br>GGGAGATTCACCTCTACCCACAAAACCTATTTTGAACTCTGAGTCAGAGCTGAGGACCCCCCCACCCCACCTTGTT<br>CCACTGCCCCTCCAGGCCACAGCTCTCCTTTCGGAAGGCAGCGTCACCTCTGGTCAGCTGGTTACCCGGCGGTTCC<br>CCCCTCCCATGCCTCAATGAGCCTCTTCCCCATGCCTCCATCCCCCCCCACCAGATGCTTCCTCCCCTCCCTTCC<br>TCCCTCCTCCCTGATTCGGTTGTTATTGCAAAGGTGGGGAGGCCAGCTCCCCTGTGAGAAAGAGACTGAGAAATGA<br>AAGCCTCATAGTCTGATGGAGGAAGCCTGGTCTCTACTCCCAGGTCTAATCTGATGGAGAAGACAGGGACCCCAAC<br>CAGGAGGACCCCAGCGTGATGGAGACCCCCAATCTGATAGGGGAGGCGAGTCTCCGCCCTCCTGAGCTCCTGATTC<br>AATGGAGGAGATAAACTCGTGCCCCAGGGAGACAGCAAGTGCTCGAGGTCCCTGGAGGCTATAGAAGGTGGTAGGG<br>GCCTGGGCTAACACCCTCTTCTTAGGTGTGTCCCGCCTGCGCCCGGCTCTCCAAGGCAGGAAGTGCTCAGGGAGGA<br>AGCCGGGGGTGGGGGCTGTGTGACACAGCACAGTTGCTGCTCAGACCAGCTTCACCCAGGACTGAGAAGAGGACAG<br>GAATTCCCTTCCACTGCCAGCAGAGAGTTCCACTCTGCTCCCTGAGCACTCCCCACCCTGGGAAGGACCCTCAGGG<br>CACCCACCCAGATCTTACCAAGCCTCTGACACGGCCCCCTTTCTCATAGCCGAGCCCCTCGCCATGCCCATGGTGA<br>CTGGCACTTTCCTGGTGGGGCCAGTGAGCGACTCCTCAGCTCGACCCTGCCCATCACCTCCTGCTCTGTTCAACAA<br>GGAATCAACACCCAGCCAGGCCCAGCTGGAGGACGCTGTCCCAATGCCGGGTAGGTTAGGGGCTTGGAGGGGCAGG<br>GCTTCCCCTTCCCGCCTCCCCGCAGGTGCCTGAGGAGTGGCTACTTCAGGAGCCACAAGGGACAGGAACTGCTCCC<br>CCTACTACTGTCACCCACTTCCATCCCAGCCAGTCCTACCCCCCAGGGTCCCCCTCGACTCCGTCTGTGCCAGAGA<br>ATGTGCCCTGGGCATCACAGCAGGGAATCCCTGCCAACCAGGGAATTCACTGCCAGCCCTATGCTAGTTCGCTTGC<br>TTTCCTCAGCAGTGAACCGTGCACCCTCTCTGGGCCAGCTGCTCTGCTGGGTGCCAGCAACACTGTGCTGGGCCAG<br>CAGACAAAGCTTTTCAATCTCCTCCAGGCTCTCTCGATTAGAGTCCTTGAGAAGGGAGTCAGATGTTAATTAAGAT<br>GCTCAAGTGCTGGGAGTTTGGAGTTAATAGATGCAAACTATTGCCTTCCTGCGTGGATAAGCAATGAGATCCTGCC<br>GCATAGCACAGGGAACTATATATCTAGTCAGTCACTTGTGGTGGGACATGGTTAAGGATGATGTGAGAAAAAGAAT<br>GCATACATATGTACAGCTGGGCCACTCTGCAGTACAGTAGAAATTGACAGAACACTGTAAATCAACTATAATGGAA<br>AAAAATAAAATCTTTCAAAAAAAAAAAAAACAAAAAACAAAAAAGATGCTAACGGAGAACCCTACCTTACCATCTT<br>GGTCTCTTGCAGCGCCCCCTTCAGGTTCCTTGTTGAGCTGCCTGAGTGTCCCTGCTGGACCTATTCAGATCATCCC<br>CACGCTCTCCACCCTGCCCCAGGGGCTCTGGCACATCTCAGGGGCCGGGACAGGGGTCTCCAGTATACTCATCTAC<br>CAAGGTGAGCGTGGGAAGCCAGGCTCCCCACCCCCTCTGCCTGTGACCTGACTATTCCCTGACGCCATCCTTTTCC<br>CACCCCAGGCATTTAGTGCTTACAGCCCAGCACCTTCTCAGGATCCTCCGTCCCCATTTCCCCAAACTCAAAAGAG<br>AGGAGCAAAGCTCCCGCGTGTTCTAAGCGACCCAAGTGCCTAAGTGACCTTTTTTGGTCACTTTTCTCCACGAAGC<br>CTTAGTTTCTCCCTTTTAAGAAAAATAACTTCATTATACTTTAAAATCCAAATATTTATGTATGCTCATTAAGAAA<br>CCAAAAAATAAGACCTACTTACAAGAGTCACGGAGTCTCCCCATCGCTCTTTTTAGTATACCGTTGTGAATAGTTT<br>GGTATGGATCCTTGCACAGCTTTCTCAAAGTTGTCTTGTTTCCGGGTCTGTAAGAAGGTCCTTGCTGACCTGCCAC<br>ATTGGAGGGTTTTAAATTGTCCAAGGGAAGGCACGTTGGGCTCTCAGGGATGGGAGAGAGAATGAGGCTAAGGAGA<br>TATTTCCACTCAACTCAAGAGCATCCTTTGAGGACTTTCCACTGTGGCACAGCAGAAATGAATCCAACTAGTATCC<br>ATGAGGATGTGGGTTCAATCCTTGGCCTCCCTCACTGGGTTAAGGATCCTGTGATGCTGTGAGCTGCGGTGTAGGT<br>CGCAGACACGGTTCGGATCCTGCGATACTGTGGCTGTGGTGTAGGCCGGCGGCCGTAGCTCCGAATCAACCCCTAG<br>CCTGGGAACCTCCATGTGCCGCGGGCATGGCCCTAAAAAGCAAAAAAAAAAAAAAACAGTAGAACTGCGCTGCCGC<br>TTGGCTCACAGTCTCCGGTTTTACGGGAATGGGGTTAGTTTCTGGGTGGTCTATGGCCAATTGTCTTGCCTGACCC<br>GTGCTTGGTCCGCCTCGCGCGGGGACTTTCTGGGTGGCGCACACACCTCTCAGCCAAGATGGATTCCAGCGCCAAG<br>GATCCTGGGAAGTTGGTGGTCTCCTCCCTCCCCACAGGCCCCTCCCACGGGCCCCTCCCACATCCTCCCGGTTAGTC<br>TTCAGGGCAGCAGCACATTCCTCACGGGGCCTCCTGTTTCGAGACACCTCCTGCTAGTGGTTGTTATCCTGCCTGG<br>CCGAGGTGGACAGTTTCGGCCAGTCGTCCCCTAACAGAAGCACTTGCCCTGCTCCCAAGGAGCTGGTTGTGTCCCT<br>TCACAGATGGGGAAATCAAGGCTCCGGGAGCTCCATGTCACTCCNNNNNNNNNNNNNNNNNNNNNNNNNNNNNNNN<br>NNNNNNNNNNNNNNNNNNNNNNNNNNNNNNNNNNNNNNNNNNNNNNNNNNNNNNNNNNNNNNNNNNNNACGAGAGC<br>CAGAGCTCCAGCAGCTTCCAAGTGGCCAGGTGAGTGGTGGCAGGGTCCCTCTGCCCAGGTGCTGGACGTAGAAGCC<br>CAAATCCGACTTCCCTTCATGCATTCACCCAACACTTGTTCAATCTCTCTTTTGTTGGCTCACTCATTCATTCATT<br>CACTCATTCATTCACATGCTCATTGCATCTTCACATCATCTCATCACTCATTCCTCTGGTTATACCTACATTTAAA<br>GCTACCTTTACCGAGGACCTGCCCCGGGGAAGCCCATGCTGGGCGTCAATATCTTTTTTTTTTTTTTTTTGTCTTT<br>TTTTTTGTTATTTCTTTGGGCCACTCCCGCGGCATATGGAAATTCCCAGGCTAGGGGTCTAATCGGAGCTGTAGCC<br>GCTAGCCTACGCCAGAGCCACAGCAACGCGGGATCCGAGCCACGTCTGCAACCTACACCACAGCTCACGGCAACGC<br>CGGATCGTTAACCCACTGAGCAGGGGCAGGAACCGAACCCGCAACCTCATGGTTCCTAGTCGGATTTGTTAACCGC<br>TAAGCCACGACGGGAACTCCTGGGCATCAATATCTTGTTAGCGAGGCTGAGAGAGTGAATGAAGGGAGCGTGGGTG<br>ACCGAGGGAACTAAGACAGGAGTGGGGATGAAAGGGCAGCTGACTGCTGAGTCTGACTCTGTCCCTGGTACTCCAA<br>CACAGGAGATGTAGTAAATCAGGAAAGTCCCAACCTGACTATGGTCCCCATTTTGTGGAGGAGAAAACTGAGGCAC<br>AGTGGGGTATCGCACATGCTCAAGATAATACTAGTAAGTGGTGGAGCCAGGACTTAAACCAGAAACATGGATTCCA<br>CTATCTTAACCCTCAACACACACACACACACACCTCCCCAGAATGGTCTCCCAATCGTGAGTGAGCAAAAGAAGAA<br>AATCTTGGAGTGGGTAAATGATGGAGAAGATGAGGGAATGAATGAGCGAATGAGGCAGCTAATCCAGAAAGCCATC<br>AGGGAAGACGGGTGAATGGACGAAGAAGCTAGTGATGGTGGCCGGGCTGGCCTCTCGGCTGCCCTCCTGGTAGCCG<br>GTCCTGCCACTAGCATCCTCCCCTCCCCCACTCCCGCCTTTGACCTGTGCAGAGACTGTGGAGCAGTTCCACCACT<br>CACTCCGGGACAGGTACCAAGCCAAGCCCGCAGGCCCGGAAGGCATCCTGGTGGAGGTGGACCTGGTGAGGGTGCG<br>GCTGGAGAGGAGCAGCAGCAAGAGTCAGGAGAGAGAGCTGGCCTCCCTGGACTGGGCAGAGCGGCAGCCAGCCCGA<br>GGGGGTCTGGCGGAGGTGCTGCTGGCCGCTAGCGACCGCCAGGGGCCACGCGAGACGCAGGTGATCGCCGTGCTCG<br>GCAAAGCAGGACAAGGGAAGAGTCACTGGGCCCAGGCCGTGAGCTGGGCCTGGGCTGACGGCCAGCTGCCACAGTA<br>CGACTTTGTCTTCTGCATCCCCTGCCACTGTTTGGACCGGCCGGGGAACACCTACCGCCTGCAGGATCTGCTCTTC<br>TCCCTGGGCCCACAGCCCCTGCCCATGGACGACGAGGTCTTCAGTTACATCTTGAGGCGGCCGGACCGCGTTCTGC<br>TCATCCTGGATGCCTTCGAGGAGCGCGAAGCCCAGGACGGCTTCGTGCACAGCGCGGGCGGACCCCTGTCCTCAGA<br>ACCCCGCTCCCTTCGGGGGCTGCTGGCTGGGCTCCTCCAGCGCAAGCTGCTGCGAGGCTGCACCCTGCTGCTCACG |

TABLE 9-continued

| lists sequences for the disclosure |
|---|
| GCCCGGCCCCGGGGCCGCCTGGCCCAGAGCCTGAGCAAGGCCGACGCCCTGTTTGAGGTGGCCGGCTTCTCCGCAC<br>AGCAGGCCAAGACCTACATGCTGCGCTACTTTGAGTGTCGGGGGGCCCGTGAGCGCCAGAAGAGAGCCCTGGAGCT<br>CCTCCAGGCACAGCCGTTTCTCCTGAGTCACAGCCACAGCCCTTCCGTGTGCCGGGCCGTGTGCCGGCTCTCAGAG<br>ACCCTCCTGGAGCTGGGCGAGGAGGCAGAGCTGCCCTCCACGCTCACCGGCCTCTACGTCGGCCTCCTAGGACCAG<br>CGGCCCGCGAAAGCCCCCGGGTGCCCTGGTGGGACTGGCCAGACTGGCCTGGGAACTGGGCCGCCGTCACCACAG<br>CAGCTTGCAGGAGGGCCAGTTCCCATCGGCAGAGGCCAGGGCCTGGGCTGTGGCCCAAGGCTTGGTGCAGCGTGCC<br>CCGGGGGCCCCGGGGGCCCCTGAGCTGGCCTTCTCCAGCTTCCTCCTGCAGTGCTTCCTGGGGGCCGTGTGGCTGG<br>CTCTGAGCAGCGAGATCAAGGACAAGGAGCTGCCGCAGTATTTGGCATTAACCCCTAGGAAGAAGAGGCCCTATGA<br>CAACTGGCTGGAGGCTGTGCCACGCTTTCTGGTCGGGCTGGTCTTCCAGCCTCGCGCCCGCTGCCTGGGAGCCCTG<br>GCAGGGCTGGTGGCAGCCACCTTGGCGGACCGGAAGCAGAAGGTGCTCAACAGGTACCTGAAGCGGCTGCAGCCCG<br>GGACCCTGCAGGCAGGGCGGCTGCTGGAGCTGCTGCACTGCACGCACGAGGCCCTGGATTCTGGGCTTTGGCAGCA<br>TGTGCTGCAGGGGCTCCCGACCCAACTCTCCTTTCTGGGCACTCGGCTCACGCCTCCGGACACCCACGTGCTGGGC<br>AGCGCCTTGGTGGCTGCAGGCCGAGACTTCTCCCTGGACCTCCGCAGCACTGGCATTGACCCCTCTGGACTGGGGA<br>GCCTCGTGGGACTCAGCTGTGTCACCCATTTCAGGTGGGGGCCGGGGACAGGAGAGAGGGCTTCTTTGCATTGAGC<br>ACCTACTGTGGTTTTGCTGCTGTGCCCAGTGCTGGCTCTGTGGGGTCTCATTCAGTAGGCATGGCAGCCAGATGTG<br>GGCAGAAGTGATTCCACTCATTTGAAGATGAGGAAGCCAAGGCTCAGAGAGGGAGAGTAGCTTGCCCGAGGTCACA<br>CAGCCAGTGAGAGGCAGCATCATTCTTTTAACCACTGTTTGAAAGGGCCATGTTCCAGGCACTGGGCCATGTCTAG<br>AGTCTAAGACTGATCTGGGTTCAAATTCATTTTCTTCTCCATCCCCTGATCAAGTCACCATTTTGTCATGGTTA<br>GATTAAAACCACAGCCTCCCCTGACTTCCCTGCCCCCGTTCTCGCCTCTTCCACTCCATTTTATTTTATTTTATTT<br>TATTGGTTTTTAGGGCTACACCTGTGGAATATGGAAGTTCCCAGGCTAGGGGTTGAATCCGAGCTATAGCTGCTGC<br>CCTACACCACAGCCATAGCAACGCAGGATCCTTAACCCACTGAGGGAGGTCAGGGATTGAACCACATCCTCATGGA<br>TCCTAGTCAGGTTCGTCACCACTGAGCCATGACAGGAACTCCCCCACTCCACTTTATTCTTAACCATCAGAGCAAT<br>CTCCCTAGTAATTGCATCTGATCATCTTTCATCCTTGCTTACAATCTTTTAGAGGCACTCCACCTCCCTCAGGTTG<br>AAGTCAAAGTTCCTTAATTTAAGGAATCTAAATCCTCCTGTGATCTGTTTGATCCCTTAAGCCTTATTTCCAGAGA<br>ATCTCTCCTACCTTCCCTCTAAGCATATTTTACCAGAGCTATAAGGTCTACACCATTGTAATGGTTCAACGGAGAA<br>TTCAGCACTGAGCTTCCTGGTAGCCAAAGCAAAAAGGAAAAGAAAACCCAGGAGAGCTAAGAAAAAGGAGGAATTG<br>ATAAGGGCTTAAGTGGTCATGGAAGGCTTTCTAGAGAAAGTAGGGGGTTAAGCTGAGCAAAGAAAGTACCTGAATA<br>GGTAGGAGGTCCCTTCATGGAGTTGCCCATCCGTTATGGTCTAGCCCGGTCACCATGCCTGGGTCTGAGGCCCTTC<br>CTCCACAGGGCCGCCTTGAGTGACACAGTGGGGCTGTGGGAGTCTCTACAGCAACGTGGGGAGACCAAGCTACTCC<br>AGGCACTGGAGGAGAAATTTACCATTGAGCCTTTCAAGGCCAAGTCCATGAAGGATGTGGAAGACCTGGGCAACCT<br>CGTGCAGATCCAGAGGTGAGGAGGAAAGGGCACGGGAGGTGGTCCAGGCCATGCAGGTCCATTACATTTGTCATTA<br>GCACTTCCAGTGCCTCATCTTTGGGGGATATCCCATGTCCTCCGCTTGGACAGTGGCCACCCAGAATCTCTCACTG<br>TTGTCACCACCCATGCAGAACTCCCAGGATTTATCACTTGGTCCCATTAAAAACTTGCAGTCATGTTCCCAATTTT<br>TTTTTTTCTTTTTTAGGACCACACCTTCAGCTTATGGAAGTTCCCAGATGAGGGGTCAAATCGGAGCTATAGCTTC<br>TGGCCTATGCCACAGCCACAGCCACAGCAATACCAGATCCAAGCCACATCTGTGACCTACACCACAGCTCATGGCA<br>ATGCTTGATTCTTAACTCACTGAGTGAGGCCAGGGATCGAACCCGTGTCCTCGTGTGTACTAGCCAGGTTTGTTAC<br>CCCTGAGTCACAATGGGAATCCCCCTAATTCTTTCTCAGCTAAAGCCAGGGAACTATTCTCTGCTGCTAAGAGTTC<br>ACGAGCTGCCTTCTGCATCTAGTAACAGAAGTGACACTATGGCCACCTTTCAAGGCAGCCAGGACCAGTATCATCC<br>CCATTTTTTTGATGGCAGAGATCTAATGTCTAGTGGGTAGAGGACACTTGACCACAGAACAACTGCCTTTCCCTCA<br>TTCCTTCATCATACATTGTTCGAGCACCTACTATGTGCTGTCTGGGATGGGATGGGTCTCCTCTGAGGCTCTTTTC<br>CATGAAACACACAGGAATATTAGCCTTCATAACATCCTGTTCTGAGGCTTTTCTTTTTAAGAAGGGCATAACAAGG<br>AGTTCCTGTGGTGGCTCAGCAGGTTAAGAACCCAGCTAGTCTCCATGAAGACAGGGGTTCAATCCCTGGCCTTGCT<br>CAGTGGGTTAAGAATCTGGTGTTGTGTGAACTATGGTGTAGGTCGCAGACACAGCTTGGGATCCCACGTTGCTGTG<br>GCTGTGGCGTAGGCCAGCGGCTACAGCTCCAAGTCCCCCCCTAGCCTTGGAACTTCCTTATGCCACAGGTGCAGCC<br>TTAAAAAAAAAAGAAAAAAAAGAAAAAAAAGAAGGGACTAACCATAGCCCGGGAAAGGCAGTCCTTCTGGGGAATT<br>TTGGGAATGTGGCATGCATCTTAGTACATTTAGGAAGGGACTCAGCGACAGGTGAAGGTCCCCTGACATTGCCCAT<br>TCTCTCCATCTCTCCAGGACGAGAAGCTCTTCTGAAGACATGGCTGGGGAACTCCCTGCTGTCCGGGACCTAAAGA<br>AGTTGGAATTTGC |
| SEQ ID NO: 23 CIITA cDNA Sequence<br>TTTTTTCACTTCACGTTTTGGATGCTGCAGGCCGGGTAAGCAGAGATCCCAAGGCTCTGGCCCCCGGGGAAGAGGC<br>CCTGTCTCCGAGCCCTACCATGAACCACTTCCAGACCATCCTGACTCAGGTCCGGATGCTGCTGTCCAGCCATCGG<br>CCGAGTCAAGTGCAGGCGCTCCTGGACAACCTCCTGGCGGAGGAGCTTCTCTCCAGGGAGTACCACTACGCCCTGC<br>TCCAGGAGCCTGACGGTGAGGCTCTGGCCAGGAAGATCTCCTTGACACTGCTGGAGAAAGGAGCCCCAGACCTGGC<br>CCTCTTGGGGTGGGTCTGGAGTGCACTGCAGACCCCAGCAGCCGAGAAGGACCCCGGCTACCAGGAACCTGATGGC<br>AGTGGACAGTGCGCCACCATGGAGTTGGGGCCTCTGGAGGGTGGGTACTTGGAGCTTCTCAACAGCAGTGCCGACC<br>CTCTGCAGCTCTACCACCTCTATGACCGGATGGACCTGGCTGGAGAAGAAGAGATCGAGCTCTGCTCAGAACCTGA<br>CACGGACACCATCAACTGCGAACAGTTCAGCAGGCTGTTGTGCGACATGGAAGCAGATGAAGAAACCAGGGAAACT<br>TACGCCAGTATCGCGGAACTGGACCAGTATGTTTTTCAAGACTCTCAGCTGGAGGGCCTGGGCAAAGACATTTTCA<br>TTGAGCACATAGGATTGGAAGAAATGATCAGTGAGAGCGTGGAGGTGCTGGAGGACTCAGGGCGGAAAAGTCAGAA<br>AAGATCTTTCCCGGAGGAGCTGCCTGCGGATCTGAAGCACAGGAAGCTAGCCGAGCCCCTCGCCATGCCCATGGTG<br>ACTGGCACTTTCCTGGTGGGGCCAGTGAGCGACTCCTCAGCTCGACCCTGCCCATCACCTCCTGCTCTGTTCAACA<br>AGGAATCAACACCCAGCCAGGCCCAGCTGGAGGACGCTGTCCCAATGCCGGCGCCCCCTTCAGGTTCCTTGTTGAG<br>CTGCCTGAGTGTCCCTGCTGGACCTATTCAGATCATCCCCACGCTCTCCACCCTGCCCCAGGGGCTCTGGCACATC<br>TCAGGGGCCGGGACAGGGGTCTCCAGTATACTCATCTACCAAGGTGAGATGACCCAGGCCAGCCAAGCACCCCCTG<br>TCCATAGCCTCCCAAAGTCCCCAGACCGGCCTGGCTCCACCAGTCCCTTCGCCCCGTCAGCAGCTGACCTCCCCAG<br>CATGCCTGAACCAGCCCTGACCTCCCGGGCAAACATGACAGAGGGCAGTGTGTCCCCCACCCAATGCTCAGGTGAT<br>CAAGAGGCCTCCAGCAGGCTTCCCAAGTGGCCAGAGACTGTGGAGCAGTTCCACCACTCACTCCGGGACAGGTACC<br>AAGCCAAGCCCGCAGGCCCGGAAGGCATCCTGGTGGAGGTGGACCTGGTGAGGGTGCGGCTGGAGAGGAGCAGCAG<br>CAAGAGTCAGGAGAGAGAGCTGGCCTCCCTGGACTGGGCAGAGCGGCAGCCAGCCCGAGGGGGTCTGGCGGAGGTG<br>CTGCTGGCCGCTAGCGACCGCCAGGGGCCACGCGAGACGCAGGTGATCGCCGTGCTCGGCAAAGCAGGACAAGGGA<br>AGAGTCACTGGGCCCAGGCCGTGAGCTGGGCCTGGGCTGACGGCCAGCTGCCACAGTACGACTTTGTCTTCTGCAT<br>CCCCTGCCACTGTTTGGACCGGCCGGGGAACACCTACCGCCTGCAGGATCTGCTCTTCTCCCTGGGCCCACAGCCC<br>CTGCCCATGGACGACGAGGTCTTCAGTTACATCTTGAGGCGGCCGGACCGCGTTCTGCTCATCCTGGATGCCTTCG<br>AGGAGCGCGAAGCCCAGGACGGCTTCGTGCACAGCGCGGGCGGACCCCTGTCCTCAGAACCCCGCTCCCTTCGGGG<br>GCTGCTGGCTGGGCTCCTCCAGCGCAAGCTGCTGCGAGGCTGCACCCTGCTGCTCACGGCCCGGCCCCGGGGCCGC<br>CTGGCCCAGAGCCTGAGCAAGGCCGACGCCCTGTTTGAGGTGGCCGGCTTCTCCGCACAGCAGGCCAAGACCTACA<br>TGCTGCGCTACTTTGAGTGTCGGGGGGCCCGTGAGCGCCAGAAGAGAGCCCTGGAGCTCCTCCAGGCACAGCCGTT |

TABLE 9-continued lists sequences for the disclosure

TCTCCTGAGTCACAGCCACAGCCCTTCCGTGTGCCGGGCCGTGTGCCGGCTCTCAGAGACCCTCCTGGAGCTGGGC
GAGGAGGCAGAGCTGCCCTCCACGCTCACCGGCCTCTACGTCGGCCTCCTAGGACCAGCGGCCCGCGAAAGCCCCC
CGGGTGCCCTGGTGGGACTGGCCAGACTGGCCTGGGAACTGGGCCGCCGTCACCACAGCAGCTTGCAGGAGGGCCA
GTTCCCATCGGCAGAGGCCAGGGCCTGGGCTGTGGCCCAAGGCTTGGTGCAGCGTGCCCCGGGGGCCCCGGGGGCC
CCTGAGCTGGCCTTCTCCAGCTTCCTCCTGCAGTGCTTCCTGGGGGCCGTGTGGCTGGCTCTGAGCAGCGAGATCA
AGGACAAGGAGCTGCCGCAGTATTTGGCATTAACCCCTAGGAAGAAGAGGCCCTATGACAACTGGCTGGAGGCTGT
GCCACGCTTTCTGGTCGGGCTGGTCTTCCAGCCTCGCGCCCGCTGCCTGGGAGCCCTGGCAGGGCTGGTGGCAGCC
ACCTTGGCGGACCGGAAGCAGAAGGTGCTCAACAGGTACCTGAAGCGGCTGCAGCCCGGGACCCTGCAGGCAGGGC
GGCTGCTGGAGCTGCTGCACTGCACGCACGAGGCCCTGGATTCTGGGCTTTGGCAGCATGTGCTGCAGGGGCTCCC
GACCCAACTCTCCTTTCTGGGCACTCGGCTCACGCCTCCGGACACCCACGTGCTGGGCAGCGCCTTGGTGGCTGCA
GGCCGAGACTTCTCCCTGGACCTCCGCAGCACTGGCATTGACCCCTCTGGACTGGGGAGCCTCGTGGGACTCAGCT
GTGTCACCCATTTCAGGGCCGCCTTGAGTGACACAGTGGGGCTGTGGGAGTCTCTACAGCAACGTGGGGAGACCAA
GCTACTCCAGGCACTGGAGGAGAAATTTACCATTGAGCCTTTCAAGGCCAAGTCCATGAAGGATGTGGAAGACCTG
GGCAACCTCGTGCAGATCCAGAGGACGAGAAGCTCTTCTGAAGACATGGCTGGGGAACTCCCTGCTGTCCGGGACC
TAAAGAAGTTGGAATTTGCGCTGGGCCCTGTCTTGGGCCCCCAGGCTTTCCCCAAACTGGTGAGGATCCTTGAGGC
CTTTTCTTCCCTGCAGCATCTGGACCTGGACTCGCTGAGTGAGAACAAGATCGGGGACGAGGGTGTCGCCCAGCTC
TCAGCCACCTTCCCTCAACTGAAGGCCCTGGAGACGCTCAACTTGTCCCAGAACAACATCTCCGACGTGGGTGCTT
GCCAGCTGGCCAAGGCCCTGCCCTCGCTGGCCGCGTCCCTCCTCAGGCTGAGCTTGTACAATAACTGCATCTGCGA
TGTGGGAGCCGAGAGCCTGGCGCATGTGCTTCCAGACATGGGGTCCCTCCGGGTGCTAGATGTCCAGTACAACAAG
TTCACAGCCGCCGGGGCCCAGCAGCTCGCCGCCAGCCTGAGAAAGTGCCCTCACATGGAGACGCTGGCGATGTGGA
CACCCACCATCCCGTTTGGTGTCCAGGAACACCTGCAGCAGCAGGACTCAAGGATATCCTGAGATGATCCAGGCTG
CACCCGGGACAAGCACGTTCTCTGAGGACGCTGACCACGCTGGACCCTGACCTGATCATCTGTGGACACAGCTCTT
CTTAGGCTGTGTCCCGTGAGCTTTGGCGATCTGGTGCCCAGCCCTGGTGGCTCAGAGTCAGCCCCCACTCTGCTGG
GGAAAGGACCCACGGCCTGCTCTGTGGACAGACCCCAGGCCCGGCCCCAGGCTCCTTCGGGGCCCAGACTGATGTC
AGCCTTGCTCAGCCGCTGCAGTCCTGGCAGACAGGCGGGCACCCAGTGGCAGSYAGGGKCCACCCGGGAGCCCTGA
AGCACTCCCTGCAGGACACTGCAGACAGTGGTGGCCAGGTCAGAGTGAGGGATGTGGCGGCCACATCACCTGCCCA
GGTCCTGCTGGCCGGGGGAGAAAGCACCTCTCCACACTGCTCCCCTGGTGGGGTAAGCTTGGCGCTCAGAAGATAC
CAGCCAGCACCCCCCAGCGTGTTGATTTCCCAAACGGTGACCGACGGGGTGTCCACGGCAGCTGCCCTCTGCCTCC
GGCACCTGCGGGTTTGCACTCACTTTGTTTGCCGAGGCCAAAGCTGGGCCTGGCCAGACACGCCRGACCTTAGCGG
GGGAAGAGCCGACAGTACACTACGGGMCGAGGYRGGGTGGCGAGGGTCTGGAACCACATCCGCCTTCTTGCCCTCA
CGTCCTGTGTCTTTTTTCACTACATTATACATGGCTTATTCAGTCTCA

SEQ ID NO: 24    CIITA Protein Sequence
MNHFQTILTQVRMLLSSHRPSQVQALLDNLLAEELLSREYHYALLQEPDGEALARKISLTLLEKGAPDLALLGWVW
SALQTPAAEKDPGYQEPDGSGQCATMELGPLEGGYLELLNSSADPLQLYHLYDRMDLAGEEEIELCSEPDTDTINC
EQFSRLLCDMEADEETRETYASIAELDQYVFQDSQLEGLGKDIFIEHIGLEEMISESVEVLEDSGRKSQKRSFPEE
LPADLKHRKLAEPLAMPMVTGTFLVGPVSDSSARPCPSPPALFNKESTPSQAQLEDAVPMPAPPSGSLLSCLSVPA
GPIQIIPTLSTLPQGLWHISGAGTGVSSILIYQGEMTQASQAPPVHSLPKSPDRPGSTSPFAPSAADLPSMPEPAL
TSRANMTEGSVSPTQCSGDQEASSRLPKWPETVEQFHHSLRDRYQAKPAGPEGILVEVDLVRVRLERSSSKSQERE
LASLDWAERQPARGGLAEVLLAASDRQGPRETQVIAVLGKAGQGKSHWAQAVSWAWADGQLPQYDFVFCIPCHCLD
RPGNTYRLQDLLFSLGPQPLPMDDEVESYILRRPDRVLLILDAFEEREAQDGFVHSAGGPLSSEPRSLRGLLAGLL
QRKLLRGCTLLLTARPRGRLAQSLSKADALFEVAGESAQQAKTYMLRYFECRGARERQKRALELLQAQPELLSHSH
SPSVCRAVCRLSETLLELGEEAELPSTLTGLYVGLLGPAARESPPGALVGLARLAWELGRRHHSSLQEGQFPSAEA
RAWAVAQGLVQRAPGAPGAPELAFSSFLLQCFLGAVWLALSSEIKDKELPQYLALTPRKKRPYDNWLEAVPRFLVG
LVFQPRARCLGALAGLVAATLADRKQKVLNRYLKRLQPGTLQAGRLLELLHCTHEALDSGLWQHVLQGLPTQLSFL
GTRLTPPDTHVLGSALVAAGRDFSLDLRSTGIDPSGLGSLVGLSCVTHFRAALSDTVGLWESLQQRGETKLLQALE
EKFTIEPFKAKSMKDVEDLGNLVQIQRTRSSSEDMAGELPAVRDLKKLEFALGPVLGPQAFPKLVRILEAFSSLQH
LDLDSLSENKIGDEGVAQLSATFPQLKALETLNLSQNNISDVGACQLAKALPSLAASLLRLSLYNNCICDVGAESL
AHVLPDMGSLRVLDVQYNKFTAAGAQQLAASLRKCPHMETLAMWTPTIPFGVQEHLQQQDSRIS SEQ ID NO: 25    B4GALNT2 Genomic Sequence
CACATGAACTGGACAGGCCCCAGGTACATAAGAAAAAGGCCCCTAGTCCAGTAGCCAATAGGATTCCTCCTTTCTG
AAAGTCACAGCGCTTTTCCTTCCTGAGCAGAGTGGGGGCGGGGGAATAAAGTTGCGGCCACAGAGTGGACTTGAGC
TCCCCCTGGAGGCCCAAACGATTATTTGCACCAACTTGTCCTGGCTTTTGGAGTTGAGCGGGAAGAATCCGAGGGT
CTTCATTCACCGTCCTGGAAGGATAGTTTTGTCAGTGGTTTTGGTCCAGGCTGCTCGGTTGTGCCTGAAAAGTCAC
GGCTGAAGGGAGCGCTGTGTGACGGTTATTGTTTGTGCCTTGACTTTTGCTTCCAAATCAGCCCAAAAGAAACTCT
GCTTTTTTTTTTTCTTTTCTAGGGCCAAACCCATGGCATATGGAAGTTCCCAGGATAGGGGTCCAATCAGAGCTGT
AGCCGCCGGCCTACACCACAGCCACAGCAACGCCAGATCCAAGCCTCGTGTGGAGACTACACCACAGCTCACGGCA
ACGCCGGGTACTTCACCCACTGAGCAAGGCCAGGGATCGAACCTGCAACCTCATGGTTCCTAGTCGGATTCGTTAA
CCACTGTACCACGACAGGAACTCCACCCTTTCTGTTTTGAAAGGCACACAGACAAAGAAAACAGTCGTATTTATTA
TTCTGGACACTTTGCTTCTAAGTCATAGGAAGCAACTCAGATTAGGTTAAAGAAAAATGGGGAATTATAAGGGCAC
TGTGTTTTATAAAATCCCAGGGCAGGACTGTAGCCAGAGCTCAGGAAAGAACCAGAAGGTTTTCAGAAGTCTCTCA
TTTCAGCTCAGTGGTTAACACCCTCCGAGAGTTCCATTTTAACTTTGCTGTGGTGGCACAGCAGAACCCTCTCCCC
AAGGAAGGTGACAGGAACGTCCTTAAAATGAGGAAGAACCGCATGGCCCAATCACCCTCTCTACACGTATGCACAG
CCCAGACTGTACCCAATAAGACTGCAATAAGGCTATATGTTACCATATAAAGGGGACAAAGGGGTAAAAATAATAT
AAAAGGCATCTCCTCACTGTGCTCAGGGCTCAGCCTTTGGACATGAATCTGTCGAGCCAGTGCCGGCATGAATAAA
TACTGCTTCCTGGAAAAAAGCCTTGGTGGGTGTCCCATCTCTGTACGTAAGTCCTACAACAGTTCCTTCCTGCTAG
AGTAGAAGGTTCCAGATCCTGGGGCAGGGAAGAGGTTCCTAGAACCTACTGATGATAACTACAGCACATCAAAACA
GTCCCTGCTGGGGGATGTTGGAGCATGCAACAACTGCCATGAAAGTGGACAACTCTATCTCCCTGTATCAAGAGTG
CATGTTTCAGGAGTTCCCTAGTGGCTCAGAGGGTTAAGAATCTAACTAATATCTATGAGGATGCAGGTTTGATCCC
TAGAATAGTTCAGTGGGTTAAAGGATCTGGTGTTGCAGTGTAGATCAAGGATGTGCTTGGATCTGGTGTTGCTGTG
GCTGTGGCACACACTGGCAGCTGTAGCTCTGATTCAACCCCTAGCCTGGGAACCTCCATATGCCGAGGGTGCAGCC
CTAAAATGACAAAAACAAGAAAACAGGAATGCAAGTAAGTCAGGAGTTCCCTGGTGGTTCAGTGGGTTAAGGATCT
GGCATTGTTACTGCTGTGGTGAGGGTTTTATTCCTGGCCCAGGAACTTCTGCATGCCACAGGCACAGCCAAAATAA
ATAAATAAATAAATAATAAATTAAGTGGAGTTCCCGTCGTGGCGCAGTGGTTAACGAATCCGACTAGGAGCCATGA
GGTTGCGGGTTCGGTCCCTGCCCTTGCTCAGTGAGTTAATGATCCGGTGTTGCTGTGAGCTGTGGTGTAGGTCGCA
GACGCGGCTCGGATCCCACGTTGCTGTGGCTGTGGCATAGGCCAGTGGCTACAGCTCCGATTGGACCCCTAGCCTG
GGAACCTCCATATGCCGCGGGAGCGGCCCAAGAAATAGCAAAAAGACAAAAAAATAAATAAATTAAATAAATAAAT TABLE 9-continued

| lists sequences for the disclosure |
|---|
| AAATTAAATAAATTAAGTAAAATTTAAAATTTCTAGGAGTTCCCTGATGGTCTGGAAGTTAAGGATTTGGAGTTGT<br>CGCTGCTGTGACTCAGGTTGAATCTCTGGCCTGGGAACTTCTGCAGGCTGTGGGCACAGCCAAAAAAAAAAAAAT<br>TAAGACAAAAAAACAAAGCAAATAATTCATCAGGAAGGCAGAAATTTTTGGAAGCAGACCTAGGAGAAAATAAAT<br>ATTTGTTTAAATATGTAAATGTTTATTTATATTTTAACTATTTTATATATTTAACTTTCCTTTTTTTTTTTTTTT<br>TTTTTTGCTTTTTAGGGCCACACCTGAATTATATGGAAGGTCCCAGGGGAGGGGTCAAATCAGAGCTGCAGCTGCT<br>GGCCTACACCACAGCCACAGCCACTCGAGATCCGAGCCACGTCTGCGACCTACACCACACCACAGCTCACGGCAAC<br>GCCAGATCCTTAACCCATTGAGCAAGGCGAGGGATCGAACCTTCAATATCATGATTCCTAGTCAGATTTGTTAACC<br>ACTGAGCCATGACAGGAACTCCAGTCATCTTTTGTTTTGAGGACATAAAGTAAGAGGTATAGAGAAGCACTTCCCC<br>AGGGGTCTGAACAATGTATAGGCTATTTAGGGAAACAGGTGGTTATTATAACTGGAGGTTTGTACTTTTTTTTTTT<br>GGTCTTTTTGTCTTTTCTAGGGCCAAACCCATGGCATATGGAAGTTCCCAGGATAGGGGTCCAATCAGAGCTGTAG<br>CTGCCGGCCTACACCACAGCCCATAGCAACGCCAGATCCAAGCCGCGTGTGGAGCCTACACCACAGCTCACGGCAT<br>CACCGGATCCTTCACCCACTGAGCGAGGCCAGGGATTGAACCCGAAACCTCATGGTTCTTAGTCAGATTCGTTAAC<br>CACTGAGCCACGATGGGAACTCCAGAAGTTTGTACCTTTTGACCACCTTCAACGAGGGGCTATTTAGGGAAACAGG<br>TTATGTTGTCCCAGTGCTGAGCCCTAGATCCCGAGATGCCCAAATGTTCATCAGTAAATATATGTGTTTTTTTTTT<br>TTTTTTTTGCCACACCAGCAGCACGCAGAAGGTTCTGGGCCAGAGATCCAACCTGATCCACAGCACCGACAATGCC<br>AAACCTTAACCACTAGGCCACCAGAGAACTCCTATGTATTTTTTTCTTCCAGTTTATAATTCACCTACAGCACTGA<br>ATGAGTTGTAGAGCATAATGACTGGACTTGCATACGTCATGAAATGATTACCACAATAAGTTTAGTGAGTGAGTTC<br>CCACTGTGGCTCAGCAGTAACGAACCTGACTGGTATCCATGAAGATGCGGGTTGGATTCCTGGCCTCGCTCAGTGC<br>GTTTAAGGATCTGGCATTGCTATGGCTGTGGTGTAGGCGGGCAGCTGCAGGTCTGATTCAACCCCTAGGCTGGGAA<br>CTTCCATATGCCACAGATGCAGCCTTAAAAAACACATAAAAATAAAAATAAGTAAGTTTAGTGAACATCCATTAGC<br>TCACATAAATAAAAAATTAAATAGAAAAAAATTTTCGTTGTGATGAGAACTTATAGGATTTATTCTCTTAACCACT<br>TTCTTTCTTTCTTTCTTTTTTTTTTTTTTTTTGTCTTTTTGCCATTTCTTGGGCCGCTCCCACGACACATGGAGGTT<br>CCCAGGTTAGGGGTCCAATCAGAGCTATAGCCGCTGACCTACGCCAGAGCCACAGCAACTCGGACGGAATCCGAGC<br>CGAGTCTGCAACCTACACCACAGCTCATGGCAATGCCGGATCCTTAACCCACTGAGCAAGGCCAGGGATCGAACCC<br>ACAACCTCATGGTTCCTAGTCGGATTCGTTAACCACTGAGCCACGACAGGAACTCCAGACTCTTCTTTTTTTTTTT<br>TTTTTTAAGGGCTGAACTCGAGGCATGTGGAGGTTCCCAGGCCAGGGGTCGGATCTGAGCTGTAGCTACCGGCCTA<br>TACCACAGCCACAGCAACACAGGATCCGAGCCACATCTGCGACGCACATCATAGTTCACGGCAACACTGGATCCTT<br>AACCCACTGAGCAAAGCCAGGGATTGAACCTGCGTCCTCATGGATGCTAGTCAGATTCAGTTCTGCTGAACAATGA<br>TGGGAACTCCCCATGCTGACTCTTAAGATAACAGAGAGAGCCTGCCTCATCATGATGGCCAGATTCTGTACTTGAC<br>ATGGGTCTTGAATGGTCAGCAACTGATCTCAAGGCCCTGGAATTTAGTGGCTTAGCCTTACACTGGCACCTCAGCA<br>GAGGGTCCCAGATCAATCCCAGGCATTCTAGTAGGTGTCCTTTTTTTTTTTTTTTTTGGTCTTTTTGCCATTTCTT<br>GGGCCGCTGCTGTGGCATATGGAGGTTCCCAGGCTAGGGGTCCAATTGGAACTGTAGCCGCCGGCCTACCCCACAG<br>TCTCAGCAACGCGGGATCCGAGCCGTGTCTGCGACCTATACCACAGCTCACGGCAATGCCGGATCCTTAACCCACT<br>GAGCAAGGCCAGGAATCGAACCCGCAACCTCATGGTTCCTAGTCGGATTCGTTAACCACTGAGCCACGACGGGAAC<br>TCCTCTTTTTTCTTTTTAATGGCTGCACCCACACCATATGGAAGTGCCCTGGCCAGGGGTCAAACTGGAGCTGCAG<br>CTGCTGGTCTACACCACAGCCACAACAACACTGGATCCAAGCTGTATCTGTGACCTACTCCACAGCTCGCGGCAAC<br>GCCGGATCTTTAACCAACTGAGTGAGACCAGAGATGGAACCCGAATCATCACAGAGACTGTGTGGGGTCTTAATCC<br>ACTGGACCACAATGGGAACTCCGAGAATATGCCTTTATGGTAGGGAGTCTGACGCCTGGGAAACCTTTATTCTGGC<br>AGGGCGTGGTTTACCGCAGTGATCGCCTCCCTCTAATTGCCTGCATCCCATCCCTGTGCCGGGCTCCAGGTGAGCT<br>GACTCCACAGAGCTCTCCTCACCTGCCGGGGCCCTTGTGACTTCTCTCTTCTCTGGTCCCCCAACCCTGCTGCTCA<br>ATCCTACTAGCGGACTGAACCGAACGAGGCTGCCACCTCCTCAAGGCAAGGACCCTGGGTTCTTCACATTATTTGA<br>GTCCACAAGGTAGGACCAAAGGAAAATTTGTGGAGGACAGTGATGCTGGAGATGATCTGTGATATAATTTCCAGCA<br>AGTAACCTTCAAGGACCCAGCAGCCATCTTTTTTTTTTTTTCCACTGTACAGCAAAGGGATCAAGTTATCCTTACAT<br>GTATACATTACAATTACATTTTTTCCCCCACCCTTTGTTCTGTTGCAACTTGAGTATCTAGACATAGTTCTCAATG<br>CTATTCAGCAGGATCTCCTTGTAAATCTATTCTAAGTTGTGTCTGATAAGCCCAAGCTCCCGATCCCTCCCACTCC<br>CTCCCCCTACCATCAGGCAGCCACAAGTCTCTTCTCCAAGTCCATGATTTTCTTTTCTGTGGAGATGTTCATTTGT<br>GCTAGATATTAGATTCCAGTTATAAGTGATATCATATGGTATTTGTCTTTGTCTTTCTGGCTCATTTCACTCAGTA<br>TGAGAGTCTCTAGTTCCATCCATGTTGCTGCAAATGGCATTATGTCATTCTTTTTAATGGCTGAGTAGTATTCCAT<br>TGTGTATATATACCACATCTTCAGAATCCAGTTATCTGTTGATGGACATTTGGGTTGTTTCCATGTCCTGGCTATT<br>GTGAATAGTGCTGCAATGAACATGCGGGTGCATGTGTCTCTTTTAAGTAGAGTTTTGTCCAGATAGATGCCCAAGA<br>GTGGGATTGTGGGGTCATATGGAAGTTCTATGTATAGATTTCTAAGGTATCTCCACACTGTTCTCCATAGTGGCTG<br>TACCAGTTTACATTCCCACCAACAGTGCAGGAGGGTTCCCTTTTCTCCATAGCCCCTCCAGCACTTGTTATTTGTG<br>GATTTATTAATGATGGCCATTCTGACTGATATGAGGTGGTATCTCATGGTAGTTTTGATTTGCATTTTTCTTATAA<br>TCAGCGATGTTGAGCATTTTTTCATGTGTTTGCTGGCCATCTGTATATCTTCTTTGGAGAAATGTCTATTCAGGTC<br>TTTTGCCCATTTTTCCATTGATTGATTGGCTTTTTTGCTGTTGGGTTGTATAAGTTGTTTATATATTCTAGAGATT<br>AAGCCCTTGTCCATTGCATCATTTGAAACTATTTTCTCCCATTCTGAAAGTTGTCTTTTTGTTTTCTTTTTGGTTT<br>CCTTTGCTGTGCAAAAGCTTTTCAGTTTGATGAGGTCCCATGGGTTTATTTTTGCTCTAATTCCTATTGCTCTGGG<br>AGACTGACCTGAGAAAATATTCATGATGTTGATGTCAGAGAGTGTTTTGCCTATGTTTTCTTCTAGGAGTTTGTCC<br>TGTCATATATTTAAGTCTTTCAGCCATTTTGAGTTTATTTTTGTACATGGTGTGAGGGCGTGTTCTAGTTTCATTG<br>CTTTGCATGCAGCTGTCCAGGTTTCCCAGCAACCAGCAGCCATCTTTTTGACTGAAGATACACTCTTCCCAGTGAG<br>ATGGAATCAGATGATGGGAGATACTATATGTACAAATGCTTCCCACATAGTAAGGCATCATAACACAGTAATTTTT<br>GTTTATTCTTTTTTGGTCTTTTTTTTTTTTTATGGCCACACACTTAGCATCTGGAAGTTCCCAGGCTAGGGGGCGCA<br>TCAGAGCTGCAGCTGCCAGCCTATGCCACAGCCACAGCAATGCCAGATCCTTAGCCCACTGAGCAAGGCCAGGGAT<br>CCAACTCGCATCTTCGTGGATAGCAGTCTGGATTGCTACCTCTGAGCCATGATGGAAACTCCGCCGTAATCGTTAT<br>GAATGAAGTCTCCATTGCCCACCTCAGTGACTGGTCCATTTCTAATGACCCTGTACTTTTATTGGTACTTCCAGTA<br>ACGGAGTCAGACCCACCTGCCTACCCTGCTCCCTGGGCATTACAATGCTTATCTTATGAGGAGTTCAAATATTGGT<br>ATCCCAGCCACCGCATCCGCTGACTTAGATACTTGCAACCAGGCAGCTCAGCGCTTTTCCAATGCCCAGATACCTT<br>AGGTGGCACATTGGAGATAGTTCTTGAAGTAGTGGAGAGCCAACTTGAATTTGATCTGGGCTTCGGTGTTGGCCCG<br>ATAACTGGTGTAGTTCCCCTCCAGGGTGGCCAGCTCTGGGTCCATCACTGGTAAATGGGGCTGGTGACCTATGATC<br>ACATGTGGGCAGGACCCCACGAGCAGGCTCCCGAGCCCATCAATAAAGAACTCTGCCAAGAGAGGGAGAGAGCGCG<br>AGAAGGAAACGTGAGCTTCAAACCAGAGACCCGGGCCAATACTGCGACTCTGGGAGGAGGGCTGGGGTGGGGGGG<br>ACATAGCTTCTATTCTGGGGAGGTTCAGTCCCATGGCAAAGCCACTGAGTTGGAAGATCAGACAGATATCAGCAGA<br>GAGACACAGATTAGCAGACCCCAGGACTGGGAGGAATGAGAGGGGAAGAGGTGGGGTGCTGCTCACCAGCTGCAGC<br>TAAACAGAGAAGGATGTCTGGAAAAGGAGGAGCAGGAAATTCCCGTCATGGCGTAGTGGTTAATGAATCCGACTAG<br>GAACCATGAGGTTGTGGGTTCGGTCCCTGGCCTCGTTCAGTGGGTTAAGGATCTGGCGCTGCCCTGAGCTGTGGTG<br>TAGGTCACAGAGGCAGCTCAGATCCCGTGTTGCTGTGGCTCTGGCATAGGCCGGGAGCAAAAGCTCCAATTCGACC<br>CCTAGCCTGGGAACCTCCACATGCCATGGGTGCAGCCCTAAAAAGGCAAAAAAAAAAAAAAAAAAAAAAAAAAAGG<br>CAAAAAAAAGGAGGAGCAGCAGCAAGACAAGGAAAGAGGGAAGGGGCAGAGCTGCAGGGAGAGGAGGTAGAAGGGT |

TABLE 9-continued

| lists sequences for the disclosure |
| --- |
| GTCTCGGAGAAGCAGGAATAGCCTATGGGAGACACGAAGGTGGAGGGAGGCAAGAGAGACCAAGAGCTCCCTAGTT<br>TGGGGAGAAGGGGCTGCTTCCCTGAGCAGCAGGGCCCCGCCCTCCCTCAGAAAGAGACTTCTGAAGCCAGCGCACA<br>GCCCAGCTCGCTTCTTGCCCTTCCAGCCTCCCCACCTGAGTGAGCCACTCGCTGCAGCCGGGGGTCGAAGCCAATT<br>CTTTGGAGTCGCTCTGTGTGAGCCAGGAAGAAGTTGACAACACCACTGGTCACCACGCAGTCGGGGAAGCCATCCA<br>CGGGCCGGAAAAATCCTGGCTGCTGGTGGAGACAGTCGCCATTCTTCCCCTGCTCCAGCAACAGCTTGAACTGGAA<br>TGTGTTTTCAATCACGCTGCCACCTACCTAGCCAGCGGGAGGAGAAATCTGTTAGAGAACAGACTCCATATCCAAG<br>GAGCCTGTGCCAGGAAGCCTTACTGGACTGAACCTCAGTCACGACAAGAATTGCACTCCCTGGAGTTCCCGTTGTG<br>GCTCAGTGGTTAACGAATCTGACTAGGAACCATGTGGTTTCGGGTTCGATCCCTGGCCTCCCTCAGTGGGTGAAGG<br>ATCCGGCGTTGCTGTGAGCTGTGGTGTAGGTCGCAGACGTGGCTCGTGAGCTGTGGCATAGGCTGGTGGCTACAGC<br>TCCAATTGGACCCCTAGCCTGGGAACCTCCATATGCTGCGGGAGTGACCTAAGAAATGGCGAAAAGACCAAAAAAA<br>AAAAGGTAATAATAATAATAAAATAAAATAAAATAAAAAGAAAAAGAATTGTACTCCCTGTCTTATCTACCCTTC<br>ATGTTACACTTCCGCCAAGTCCAAAGGGCAGCAAAGTTTCTGCTGCACTTACCCTCCAGCAAGCTCACTCTTTCCA<br>GAGGGCCACTCCCTCCCCTCCCTTCTGCTACAAGGATCCAGGAGGATCGAGGATGGGGGATCGCGTTTGGGTGCAG<br>GTGAGAGGCAGCCAGCGTGCAGCCGTCCCTACGTGGACTTCCTGAGCAAGCCTTTGTCTCAAGTTGTCTCCCTCCC<br>ATTCTCTGCCCCTGGCTCACTTCTCTGCGCCGTCTGTCCACACACCACACACTCCTGGGAGCTCGCAGCTTTGTGT<br>GAGCCCGAGCACAGCAGGACAAGCAAGTACATCTATTCCTGAACCATCATAATCACCTAGGGAGGCAGAGCAGAAT<br>CTGCCAGTTGCCCCCCACCCCCTCGCCTGTTCTTTCCTTCCTCCTCTTAGGAAATGAGCCCCCTGAGGTGTTTTTT<br>GGTTTTTGTTTTTCCTTTTTCAGCTGCCCCTGCAGTTCCCAGGCCGGGGATGGAATCCAAGCCAGAGCTGCACCCA<br>CCCCACCCCCACGCAGCAACGCTGGATACTTAATTTAACCCACGGCACAGGACTGGGGATTGAATGGGCACCTCCA<br>CAGAGACAAACTGGATCCTTAACCCCCATGCCACAGTGAGAACTCCAAACTCCAAACCCTCTGAGATTTAAGTGGA<br>CTAAATTAAGCGACAATGATCCTACGAAAGATGAAATTTCCCCACTTCTCTGGAGTTCCCAATGTGGCTCAGCGGT<br>AATGAACCTGACCAGTATCCATGTGGACGTGGGTTCACTCCCTGGCCTCCTCGAGTGGGTTAAGGATCCGGCATTG<br>CCGTAAGCTGTGGTGTAGGTCACAAAATCAGCTCAGGTCCCATGTTGCTATGGCTGTGGTATAGACGGGCAGCTGC<br>AGCTCCAACGGGACCCCTAGGTTGGGAACTTCCATGTGCCCTACAAAGAAGAAGGGAGGAAGGAAGGGAAAGAGGG<br>AGGGAGGGAAAGAGGAGAGAGAGGGAGGGAGGAAGGAAGGAAGGCAGGGAGAAATGGCCCACAGCATATGGCTTGA<br>ATCCCAGCTGCAGCTGCAGCAATGCCAAATCCTTTAACCCGCTGGACTGAACCAGCACCTCTGCAGCAACCCGAAA<br>TGCTGCAGTCGGGTTCTTAACCCACTGTGTCACAGTGGGAACTCCCTGAAAGGATGTGATTTAGAACAGATGTCTC<br>CAATTTTTAAAAAGACCACATTCTTCTCATCTTTTCCTTTTTTTTTTTTTTTTTTTTTGGCTTCTTAAGGTTGAAC<br>CCACGGCATAGGGGGTTAGTGGTTAGTTTCCAGGCTAGGAGTCAAATTGGACCCACAGCTGTTGGCCTACACCACA<br>GCCACAGCAACGCCAGATCCAAGCCTCGTCTGTGACCTATACCATAGCTCCCAGCAATGCCAGATCCCTGACCCAC<br>TGAACAAGGCCAGGGATCGAACCCACATCCTCATGGATACTAGTCAGATTCATTTCTGCTGCGCCACGAAGGGAAC<br>TCCCAAGACCACATTCTTAAAGAAAACTGTTGTCTTCTACTCCCTCTCTCCCCCTTTCTTCTGACCGTGCAGCTG<br>AGGGCCACAAAGATGGATGAACAACAGGGAAGGAAGCTGGACCAGGATGACCCTGGAAAGAGACAATAGGGCCAGC<br>TTGCATTCTCTCTTTTTTTTTTTTTTTTTTTTTTTTTTTGGCTTTTTGCTAATTCTTGGGCCGCTCCAGCAGCATATG<br>GAGGTTCCCAGGCTAGGGGTCCAATCGGAGCTGTAGCCGCCGGCCTACGCCAGAGCCACAGCAACGCGGGATCCGA<br>GCCGCGTCTGCAACCCACACCACAGCCCACAGCAACGCCGGATCGTTAACCCACTGAGCAAGGGCAGGGACCGAAC<br>CCGCAACCTCCTGGTTCCTAGTCGGATTCGTTAACCACTGCGCCACGACAAGAACTCCCCAGCTTGCATTCTTACA<br>CGGGTAGGAACTGCACCTTTTTTGTCATTTATGCTATTGTGACTGGGTCTCTAGAAGAGTAGCAAAGAGACATCTT<br>CGTCAATCCAGATGTTTTGGGGGACTGTCCACCTGGAATAAGAGATAACTGTGGTCACGGTGCTACTTATCCACTT<br>TCTTTCCAGGCCGGGATAGAACCAGCACCACAGCAGTGACAATGCTGGATCCTTAACCCTATGAGCCACCAGGGAA<br>CTCCCATCTTTCTTTTTCCAAACAGCTTTATTGAGATATCTTTGATATATTAAAACTGTATGAAGGAGTTCCTGTC<br>GTGTCTCAATGGTTAACAAATCCAACTAGGAACCATGAGGTTGCGGATTCGATCCCTGGCCTTGCTCAGTGGGTTC<br>AGGATCCAGCATTTTTGTGAGCTGTGATGTAGGTTGCAGACGCGGCTCGGATCCTGCGCTGCTGTGTCTCTGGCGT<br>AAGCCGGTGGCTGCAGCTCCGATTGGACCCCTAGCCTGAGAACTTCCATATGCCGCGGGAGCGGCTCAAGAAAATG<br>GCAAAAAGACAAAAAGACAAAAAACAAAACAAAACAAAACAAAACAAAACAAAAAACTGTATGTATTGAAGGTGTA<br>CAGCTTGATTTTTTTTTTTTTTTTTGGTCTGTGGCATGTAGTGGCTTGATGCAGGATCTCAATTCCCAGACCAGGG<br>ACTGAACCTGGGCCACAGTGGGGAAAGCACCAAATCCTAACTACTACACCACCAGGGAACTCCCTGCAGCTTGATG<br>TTTTGATATATGTAGACACTGTGAAAAGATCACCACACGCAAGCTAATTAATGAATTCATCACCTCTACACAGTGT<br>GGGTATCTTCACAAATTTCAAGAACGCAATGCAGTATTATTAACTATTCATCACCTTTTTTCCCCCTTTTCCATGT<br>GTAAATTAACTTTTGATATTTGTGGGGTTTTTTGTTCTGTTTTGTTTTGTCTTTTTAGGGCTGCACCTGCAGCATA<br>TGAAAGTTCCCAGGTTAGCAGTCCAATTGGAGCTGCAGCTGCCAGTCTACGCCACAGTCACTGCCACAGCCACAGA<br>AATGCCAGATCTGAGCCACGTCTGGGACACACACCACAGCTTATGCAACACCAGACCCTTAACCCACTGAGCAAGG<br>CCACGGATTGAGCCCACATCCTCATGGACACTAGTCGGGTTCATTACTGCTAAGCCACGACGGGAACTCCTGTGTT<br>AATTTTTTATTGTCATTAAGGCCACGTGTGCTTTTATAGCTTTGTGCCATTTTCATTTTTGTGATGGTGTGTGACA<br>AAACCAGAGCAGCACTCACATTCCTCTCCAACTCTCACCAGTCCAGAGAGGAAGTTGGAAGTGATGCATACAAAGA<br>AAACCACAGCTTTCAAAAGATACACGCACCCCAACGTTCACGGCAGCACTATTCACAATAGCCAAGACGTGGAAAC<br>AACCTAAATGTCCATCAACAGATGAGTGGTGTACACACACACACACACACACACACACACACAATGGAATATTACT<br>CCCTCATGAAAAGAGTGCAATAATGCCATTTGCAGCAACGCAGATGGACCTAGAGATTATCATACTGAATGAATTC<br>AGAGAAAGACGGATATCATATGATATCCCACATATGTGGATTCAAAAGAGATACAAATGAACTTATTTACCAAAGA<br>GAAACAGACTCATAGATTTAGAAAACAACCTTATGGCTACCAAAGGGGAAAGGTGGCTGGCGTGGGGAGGGGGTGG<br>AGGGATAAATTAGGAAATTGGGATTAATATATACATACTACCATATATAAAATAGATAGGAGTTCCCATTGTGGCT<br>CAGTGAGTTATGAACCCAACTGTGATCCATGAGGATGCAGGTTCAATCCCTGGCTTTGCTCAGTGGGTTAAGGATC<br>CGGTGTTGCTGTGACCTGTGGTGTAGGTCACAGATGCAGCTCAGGTCTGATGCTGCTGTGGCTGTGGTGTAGGCCA<br>GCAGCTACAGCTCCGATTTGACCCCTAACCTGGGAACCTCCATATGCCTCGGATGCAGCCCCAAAAAGACCAAAAA<br>AAAAAAAAAAAAGATAACTGACAAGGACCTACTGTATGGCAAAGGGAAGTACACGCAATTATTCTGTAATTTCCTA<br>CGTGAGGGAAGGAATCTGTAAAAGAATGGGTATAGCTGAATCACTTTGCTGTACACTTGAAACTGATACACCATGG<br>TAAATCAACTCTACTCCAATAGAAAATACAAATTAGGGTTTTATAAATTTTATAAAAATAAAATAAAACCTAGGCC<br>ACCTGGTGGCCTAGAGGTTAAGGATCCAACATTCTCACTGCTGTGGCACAGGCGGGATCAGGCTGGATCCCTGGCC<br>TGGGAACTTCTGCATGACATAGGTGTGGCCAAGCAAAAAAAAAAAAATTCAATTAAAAAAAATGACTGGGAGTTCCC<br>ATTGTGGCTCAGTGATTAAGAAACCCAACTAGTAACCATGAGGTTGCAGGTTTGATCCCTGGCCTCACTCAGTGGG<br>TTAAGGATCTGGCCGGCATTGCTGTAAAGTGTGGTGTAGGCCAGCAGTTACAGTTCCAACTGGACCTCTAGCCTGG<br>GAACCTCCAGATGGGGCAAGTGTGGCACTAAAAAGACAGAAGACAAAAAAAAAAAAAGATTGAAAAAAGTGCCTAAA<br>CACACTTTTTTCTTTTGCCATTTCTTGAGCTGCTCCCTCAGCATATGGAGGTTCCCAGGCTAGGGGTCCAGTCGGA<br>GCTATAGCCGCTGGCCTATGCCAGAGCCACAACAACGGGCAATTCAGCCGCATCTGCAAACTACACCACAGCTCAC<br>AGCAATGCCGGATCCTGAACCCACTGAGCAAGGCCAGGGATCGAACCCACAACCTCATGGTTCCTACTCGGATTCG<br>TTAACCACTGAGCCACGACGGGAACTCCACAACACACTTTAAGGACAGAACAACGGTGAGTCTGGGGAGTGGGGTT<br>GGTGTGATTTGTTCAAAGAAAAGTAAGAATGGAGGCAGAAGCAGAATCCGAGGGTCTCATTTCCGTGCGAGAGTCT<br>CAATCCCAGAGCTGCTCTGCATCACCTCCTGCACGGCCCTTCCCCTTCCGCCTCCCTCTTCCCCCCCCCCCCACCC |

TABLE 9-continued

| lists sequences for the disclosure |
| --- |
| CCGTCCCTTTTCCTCTCCTCTTTCCTCCTGTCCTTTCCTCTCTGCCCTCTCCTCCCCCTCCCCCTCTGGCTCGTCA<br>GATGGCAATGGGGTAGAACTGGCAGCGCTCAGCTCACTTACCACGTCCAGTTCCGTTTTCTCTAGGACGTCCACCA<br>GCGCCTCGATCCTGGTCTTGCTGTTGAAGATGAAGTCATCGTCCACCCAGAGCACATATTTGGTGGTGACCTGAGA<br>TATGGCCAGGTTCCTGCCAGCAAACCAGCCCTGCGAGGGCAGGGAGGTTAGACCCGTGGTTGCCCGCCCCGCTGCC<br>TCCTAGCATCACCTGGGGGCTTTCTCAGCTCCCAAGGGTCAGGCTGCCCCCCAGACAGTGGCTGAGAACCTCTGGG<br>CTAAAGGGAGTCCATGTCTCAGAGACCCTGGAAGAAGGAGAGGGACTCTCTGGAGACGAGAAAGTCCCTCCTTGGC<br>CCTGTGGCTTGAGGGATGGATGCAAGTCCCTTTACACCTGACAGTCTTTGTGGCCCTTTCGCCCTGTGTTGCCTGG<br>AAGATGCTGGAGGGTGGGGCTCTCTGGAAGGGGTAACATCCACTTCCTCCCGGTGTGCTCGAGGGAAGGTGTGGGG<br>CGCGGAGAGAGACACCCCAGCAAGGGTGAAATCATGACAGAGGTTTCTCTGCTGTGGGACCTGCGTATCAGGAAAC<br>CTTAGAGCGTCAGACACCGCCAGTCGCTTACAAGGACCTCCATCAATTTCCACACCAAGCGTGAGGAAAGACAGAT<br>TACCCACCCCGTCACTGCAGGAAAGGGAGAGTGACCTGATTTCTCCGGGAATTTGGAGGCAGCCAGGGGACTCAGA<br>GGAGTCCCCACCCCCCGCCCCCCAAGGATCCTGCTGCCGTGGGAGGGTCCCCCCCAACCCCGAAGCAGCCCCAACC<br>AGGGTACCACTTGACCCTGGGGCCCTCTGGTCCCAAGGTGCCCGTGTCTCCCCCTCTGGGAGGAATATACCTTCCC<br>AAATGGCATGGTGTAATACTCCACGTGGCTGTCAGTGATTTTCAGGGGCTCCTTGCTGTCATCGGCCACGATCACC<br>GTCAGGTCTGGGTAGTACTCACGAACACTCCGGAGCATGGTCATGAGCTTGTGGGGACGGAGGAAGGTTTTGGTGG<br>CAATGGTCACCAGGTCTCGGAGCTTCCTCTCTGGGCAAGAAAGGGTAGGTGTCAGAGCTCTGTCTTCAAGAATCCT<br>CACTGACGTGCATTGCTCTGGAGGTTTCTTTACACGGCGCTGTCTCGAGTGTTTGTGGACCTCATGCCTTTTGTTC<br>ACAGTTGATGTTAGTTGGATCAGAAAATACATTTTATTATTATTATTTTGTCTTTTTGTCTTTTTAGGGCCGCACC<br>TGCAGCATATGGAGGGTCCCAGGCTAGGGGTCAGCTCAGAGCTACAGCTGCCGGCCTACACCACAGCCACACCAAC<br>ACAGGATCCGAGCCTCATCTACACCACAGCTCACGGCAATGCCGGATCCCTAACCCACTGAGCGAGGCCAGGGATC<br>AAACCTGCATCCTCATGGATGCTAGTTAGATTCGTTTCCGCTGAGCCATGGTGGGAACTCCATGAGTCAGATTCTC<br>AACCCACTGAGCCACAACGCGAACTCCCAATTTGTTTAAATGGTTTCTGTCTTCTAGAGTGTCTCCCTTTTTTTTT<br>GGTTTTTTTTTGTTTTTTGCTTGTTTGTTTGTTCTTTTCTTAGTAGCTGCACCTGCAGCATATGTAGGTTCCCAG<br>GCTCCCAGGCTCCCAGTTGAATCAGAGCCGCAGCTGCAGGCCTATACCTCAGCCACATCAGATCTGAGCCGCATCT<br>TTGACCCACATCACAGCTGGCAGCTATGCAGATACTGAACCCACTAAGTGAGGCCAGGGGTTGAACCTGCATCCTC<br>ACAGACACCATGTCAGGTTCTTCACCCACTGAGCCACAACGGGAACTCCTCTCTTCTGGTTCTGTTGGCTCCAGTC<br>TGCTGTTTCCTTCTGTCGAGTGGGATGCTTCAAGTTCTGCCTGCCTATCTGCACTTGGTTTGCAACCGGCTTTCAT<br>GCTGTTACTGGGAATTGAGACGCATAGAGTTTCACCCATCAAGGGATTCAATATGACCAGTCGTGAGGCCCAGGAA<br>GAGGGGAAAAGATTTAAAGACCTGAGACCTGCCCTGTCACAGCTGCAATCCTACAGAGAGACGTGCCTGGCCTGGT<br>TTGTTTTTTTTTTTTTGCTTTTTTTAGGGCCGCACCCACGGCATATGGAGGTTCCCAGGCTAGGGGTCGCATTGTA<br>GCTACAGCTGCTGGCCACAGCCACAGCCACAGCCACAGCGATGCCAGATCCGAGCCGAGTCTGCAGCCTATACCAC<br>AGCTCATAGCAACGCCGGATCCTCAACCCACTGAGCAAAGCCAGGAATCGAACCTGAAACCTCATGGACACTGGTA<br>GGGTTCGTTAACCCCTAAGCCACGACGGGAACTCCTTGTGGTTCTTATCCATGTTCTTTTCTTACTGATTCATAAG<br>TCCTCTGAAGTAAAATTAGACCTTTGACTTTCGTGTGTGTGGTTATTTTTCCCCAGTTTGTCTTTTGTCATTTGAC<br>TTTGCATATGGTAGGCTTCCGTCATTAAAAACATTAAAAATTGTTATATAATTTATGTTTTTAGTCTTTTTCCTTT<br>TAGTCTTTTTCCTAGGTTTTGTGTCTTATTTAGAAAAGTCATACTTTACACAGTTATTTTTAAACTCCAGGCTGAT<br>TCCTAGTACTTAAAACAATTAGATATTTGCTCTACCTGGACTGTACCTTGGTGTGAGCTATGAGATGGATTCAGCT<br>TGTTATTTTCACACAGCTACACAGTTATCTAACACAATCTCTTGAACAATCCATCTTTTTCCCCTTTAATTTGAAA<br>AACTACCTTGATCACACGGTAAAATTCCAAGATGTCTATTTCTGGGTTTCTTTTCTTTTCTTTTTCTTTTTTTTT<br>TTTGTCTTTTCTAGGGCTACACCCGCGGCACATGGAGGTTCCCAGGCTAGGGGTCGAATTGGAGCTGCAGCTGCCA<br>GCCTATGCCAGAGCCATAGCAACATGGGATCCAAGCCGCGTCTGTGACCTACACCACAGCTCATGGCAATGCCGGA<br>TCCTTAACCCACTGAGCAAGGCCAGGGACCGAACCCGCAACCTCATGGTTCCTAGTCGGATTAGTTCGTTAACCAC<br>TGCGCCATGACAAGAATGCCTAGGTATCTAATTTGATTCCACTGACATAGCTCTTCGTGGTCCAATACCATTCTAT<br>TTTTATAATTATTACTTATTAAAATGTCATAAATCATTAGATTTTTTTCAAAATAAATTCAACCGTACAATAAGTT<br>AAACGTAATGAAGCAGTATTAAAAGCGTATTCTAGCATTTTTTTCCTCCAAAAAAGCTTGTTGGAGTTCTCTGGTG<br>GCCTAGTGGACTAAGGATCCAGTGTTGTCACTGCTGTGGCTTGGGTCACTGCTGTGGCACAGGTTCCATCCAAGGC<br>CTGGAAACTTCCACTCTGCGGGCACAACCAAAAAAAAAAAAAAAAAGCTTGTTAACAGGACTCCTATTGGAGTTTTTA<br>TTTCATCGAGTCTCCTCCTCCATCTCAGAGGGGAGCCCTTCTGCATCTCACCCAATAGTCTCCAGGGACCCACCAT<br>GGAGCCCCAGGGACAAGGGTCTTACCTGGTCCAGGGTCATATAACTTGGGCATGACAGGATAGCGGATGGTCACTG<br>GAAACTTGGCCACTGAGGACTTGGACTCCAGACTCACTGGAGGGAGAAATCAGGTCAGGGCTGGTGCACGGTATCT<br>GGGTCACTCCCCACAAGGCCGGGGAAGCCCACGCGATGGGGGAGTGAAGGACTGAGGACCCCACAGAGTCTATGGC<br>ATTCTGGCTCCTACCCTGCTGTGTGTTCCGGAAGCAACCTGCTGACCGCCTCTGAAACGCACATGTCTGCCCCCGT<br>GAGACTCTGTCGGGTGAAGTGGGCTTGGAATCAGAGGGGTAGATTAAGTTTGACTCTGCATCTATAATTTGAAATA<br>CCTTGGGTAAGTCACATCACCTCCACCTCCACCTCCAAAACCAGGGTAACACTACCAGCCCAGTTCACCTCACAGT<br>GCCTTTTTTGTTTTTTTTTTTTTTGAAGGGCTGCAGGTGCAGCATATGGAGGTTCCCAGGCTAGGGGTCAAATCAG<br>AGCTGTAGCTGCCGGCCTACACCACAGCCACAGCCACAGCCACATGGGATCCGAGCCACGTCTACAACCTACACCA<br>GTGCCTGGCAACACCAGATACTTAACTCACGAGTGAGGCCAGGGATTGAACCTGCATCGTCATGGATCCCAGTCAG<br>GCTCGTTTCTGCTGAGCCACAATGGGAAGCCCCTTCATAGGGTCATTCTGTGGTAAGACATGTTTAAAAATCCCAA<br>GGTACAGAGAACTCTCTCTCTAGCTTATGCTCATGGAAAATCTGCCTCACATTCACTGGGGTCCTGGGAAAGCCTC<br>CTGTGTATCTGGTCAAAGCAGAAAAAGGTAAATGTCTTTTTTTTTTTTTTTTTTTCTTTTTACGGCTGCACCTGC<br>TGCATATGGAAGTTCCCGGACTAGGGCTCAAATTGGAGCTGCAGCTGCCGGCCTACGCCACAGCCACAGCCACAGC<br>CAATGGAATCCCAGCCACATCTGCGAATTATGCCGCAGCGAGGCCTGGGAGCAAACCTGCATCCTCATGGATTCTA<br>GTTAGGTTCTTAATCCACTGAGCCACAAGAACTCCGGAAAAGGGTAATTTATTTATGTATGTATTTATTTATTTTT<br>GTCTTTTTCTTTTTAGGGCTGCACCCGTGGCATATGGAGGTTCCCAGGCTAGGAGTCCAGCTGGAGCTATAGCCAC<br>CAGACTACACCACAGCCACAGCAGCTCAGAATCTGAGCCACTTCTGCAGCCTACACCACGGCTCACGCAATGCCGG<br>ACCCTTAACGCCCTGAGCAAGGCCATGGATCAAACCCGTGTCCTCATGGATACTAGTTGGGTTCGTTAACCACTGA<br>GCCACAATGGGAACTCCCGGAAAAGGGTTTTAATTCATCCAGAAAGTAAGTGGGGCTGCCCTGAGGGTGGCAGGAA<br>TTGGTCTCCCATGAATTCTGGGAGTAAGAGTCGGGTTTGGGATGGGAGGGGAGGAGGAAGACAAAGCCACTGCCCT<br>TGGGACTGACAGCTCCCCCACATCCCTCTTTCCCGTAATGCTCAGGACAAGCCACTGACACGTGGACTGTGTTCTC<br>CTCTACTGCAGCTGAAACCTTCAGCTTTTTCTTTTTCTTTTCTTTCCTTTGCTTTTTAGGGCCGCACCCGCAGCAT<br>ATGGAAGTTCCCAGGCTAGGAATCGAATAGGAGCCGCAGCTGCCAGCCTACACCACAGCCACAGCAACGCAGGATG<br>GGATCTGAGCCACGTCTGCGACCTACACCACAGCTCACGGCAACGCCGGATCCCCGACCCACCGGTGAGGCCAGGG<br>ATCGAACCGCCAACCTCGTGAATACTGGTCAGATTCATTTCCACTGCACCACAACCGGAACAGGGAACCTTCAGCT<br>TTGATCACTGATGAGAACGGGAGCAGAAGGGGATGGTTTCCAGGTGCAGAGCATGAATGATCTGTCCTCATGTACA<br>GACAAGCAGGCATTTCACTGTCTTTCTTTCGGGTCCCTCCACGGGCTCAATGGCAACACGGGGATAGTACCAGGTA<br>CACTAAGTGGGAAATTAGAAACAGGAGCCAGGGAAGCAGGCTTCCTGGAGAAGGAAGACCTTGAGAGCCGGGGGCG<br>GGGGCAGTGGTGGTGTTTATGGGGTCCCTCAGCATTTTGCCATCCGAGGACGGACTCACCCACATCCACTCTGTGG<br>AGGTGGTACTCTGTGCTCGTGTATGTCACATGCTGGAGGATGAAATTCAAAAGCTCCCGGCTACTGGTCAAAATGT |

TABLE 9-continued

| lists sequences for the disclosure |
|---|
| TCAGCTGCTTCTGGCCTCTGCCCTTCACCACATTGTCTGGGACGTCAGCAAGGGTGTTCAGTGTCCCCAGAGAAGC<br>TGTCAGGGTGACCTAGGATAAAGGAGGTAGAAAGCCTAAATGCAGAGAGGCACATACCCAGGATGGCCAGCAGGGG<br>GCAGCATGCATAAGGGTGTGAGGAGAAGAACGCTTCATGCTCCCGAAAGCTAGGGTCTGGCCTCTGATGGAGTGTC<br>TGCCCCAGCCCCAAAAGCCTAGGACCTAGGACCTGGTGTGTTCAAGGGCCATTTCTGAAACATTCTTAACTCTTGG<br>CATGCAGAGTTAAGTGGCATCCATTCTTAAAGATTTCTTCTGGAGTTCCTGTTGTGGCTCAGTGATAACGAATCCG<br>ACTAGGAACCATGAGGTTGCAGGTTCGATCCCTGGCCTTGCTCAGTGGATTAAGGACCCAGTGTTGCTTCGAGCTG<br>TGGTGTAGGTTGTAGATGCGGCTTGGATCCGGTGTGGCTGTGGCTCTGGCGTAGGCTGGCAGCTACAGCTCTGATT<br>GGACCCCTAGCCTGGGAAACTCCATGTGCCGCTGGATGCGGCCCTAAAAAGACAAAAGACAAAAAAAAAGAAAGAA<br>AGAAAGAAAGAAAAAGAAAACTGCTGAAAACATTTCAGTCAACAGATCTTTTCTTTTCTTTTCTTTCTTTTTAGGG<br>CCAGACCTGAAGCACATGGAAGTTCCCAGGCTAGGGGTCCAATCAGAGCTACAGCATCTTTGTCTGCCCCATCTTT<br>GTCTCTCTGTCAAACGCTGAGACCAGCCACCATCTCAGGGAAAAGCGCATGGGCAGTGAGCCAAGGACAGGATGCT<br>AAGTGCAAAGTGGGGCTGGGAAGGGGACTCTTGCCTCATAGATGGGAGCATCAGGTCCTTCAAACCGGAGGCCTGG<br>AGGTCACAGGAAAAAGGAGAAAGGAAAAAAAAAAAAAAAAAACATTTGAGAGGATGCCAAGAGTTCCCTGATGCTCT<br>CAGCTCCCTGGCCAATTCCTACACATCCCTCCAGAGCCCCTTCAAGTGTCACCTATCCAGGGTGTTTGCAGACCGC<br>TCGCCTCCCCACTAGAGCTTGCTAGATGGTGTCCAACGGACCTCTGCAAACTCCAGCAAACCAAAGCCTCTGATGC<br>CCTCCCCTAGTTTGGGTTTTTTTTTTTTTTTTTTTTGTCTTGTTGTTGTTGGGTTTTGGGGGGGGGTTGGGGGCTT<br>TTTAGGGCCACACCCTCTGCATAAGGAAGTTCCCAGGCCACGGGTTGAATCAGAGCTGCAGCTGCTGGCCTACGTC<br>ACAATGACAGCAATACAGATTGTCAGCTGAGTCTGCGACCTACACCACAGCTCACAGCAACACCGGATCCCTGCCC<br>CACTGAGCGAGGCCAGGGATACAACCCAAAACCTCATGGTGCCTAGTTGGATTTGTTTCCACTGCACCACCACAGG<br>AACCCCTAAATGGTAAACTTTATGTTACATATATTTTACACACTAGAAAGAGAATTATCCAAAATGGCAAATCATT<br>TTTTAAATGAGTACTTAAAAACACGAGCAACTCAGAGTTCCTGTCATGGCGCAGTGGAAACGAATCCAACTAAGAA<br>CCATGAGGTTGTGGGTTCGATCCCTGGCCTCACTCAATGGGTAAAGGATCCAGCATTGCTGTGCGCTGTGGTGTAG<br>GTCGCAGACGCAGCTCGGATCTGGTGTTGCTGGGGCTCTGCTGTAGGCCAGCAGCTACAACTCCGATTTGACCCCT<br>AGCCTGGGAACCTCCAGGTGCTAAAAAGACAAACGACAAAAACAAAAAACAAAAAACAGAACAAAACAAAAAAAAC<br>CCAAAACACCAGCAACTCATCTCAAATGTTTTTACTTTAAAATCTATCTCTGTTCTTATGACTAATGCAAATTCTC<br>ACTCAAACACATCCTCCTTCTGTGGCCTAAACTTATTTGGGAAATTGGCAAAATAACATTTACCTCACAGGGATGT<br>ATGCTGGACGAGAGGTGTGTGTAAAAACCACTCGTGGAGGAGCTGTAACGGATAGAAATATTCTTTCCATATGCAG<br>TCCCTGGAGATGGGCTGAGGCTTTGCTTGCTCCCTTGATGCTGGCAGACACCAAAAAGCCAATAATGGCCTAAGAT<br>TCCTCGAGGCACCCAGATCTCCGTCCTCTCCTATACGATCCAAGATGCCCAGGGAGGCAACAGCTCCTAAGTGCCA<br>TTCCCAGTGGTGGAAACAGTGAGAATAACATCAAATGAAACCATGTCCAGCTTCATGGATTGTGCTGGGTATCCGG<br>GAAGGATTCAGCGGATAACTGCTCCCTTCTGCTCCCTTCTTTGCTTCAGAAGGACTACGAGAGCTGCCTGGGTCCT<br>GTCCGGGTGGAGATGCACCTACCTGGGATGGGGATGGTGTGTAGAGGCATCACTTCCACCCCGTGGACCGGGTACC<br>CAAAGGGGAGGTTGGGCTGAGCCAGCAGGGGCGGTGGGCGAGGGAGCCCTTCTCTGCAGGGAAACAAAACCATCAG<br>CAGCTGCCTTGATACCTGTCCCTGACTAGCTCTTTTTTGGGGGGGAGGGGGGTGCAACCACACCCACGGCATAGAC<br>GTTCCCAGGCCAGGGATCTCACCCACCCCACGGCAGCGACCTGAGCCAATGCAGTGACCATGCCAGATCCTCCTTA<br>ACGTGCTGAGCCACAAGGGAACTTCCACTGCTCCCACTGGTTTGTTCTTTTTTTTTTCTTTCGTTTTTGGCCTTCC<br>CAGGCCAGGGATCAGACCTGAGCTGTGGCTGCGACCTAAGCTGCAGCTGCAGCAAAAGATCTTTAACCCACTGTGC<br>TAGGCCAGGGGTTGAACCTGCATCCCCGTGCTCCCCAGACACAGCTGATTCCACTGTACCACAGCAGGAGCTCCTC<br>ACTGTCGCCACTGGCTAGTTCTTTTTCTTTTTTTCTTTCTTTTTTTTTGCTTTTTTAGAGCCACTTCCCGCGGCAT<br>ATGGAGGTTCCCAGGCTAGGGGTCCAATCAGAGCTGTAGCTGCCGGCCTACGCCACAGCCACAGCAACGCGGGATT<br>TGAGCCGCGTCTGCGACCCACACCACGGCTCACAGCAATGCTGGATCCTGAACCCACTGAGCAAGGCCAGGGATCG<br>AACCCACATCCTCATGGATACTAGTCAGGTTTGTTAACCACTGAGCCACGACAGGAACTGCTGGCTAGCTCTTAAA<br>GGGGTATCTGTGCCCAGAGCTTTGGGCTGCAAAGGGGGAGAAATCCAAAGTAAATCGTCGGATTGTCATGCATTCT<br>CTCCTCTTCTTTATTCCTGCTCCTCCCTCCAGCCTCGAATTCCACAAAGAAACTGAGGCAGATTACAACAACACAC<br>ATTAAAAATAAAAATCACGGAGTTCCTTTTGTGGCTCAGCCGGTTAAGAATCCAATGCAGCATTCTTGAAGTTGCG<br>GGTTCAATCCCTGGCCTCGCTCAGAGGGTTAAGGATCCAGCGTTGCCCTGAGCTGTGGTGTAGGTCGCAGACGCGG<br>CTCGGATCCCACATGGCTGTGGCTGTGGCTGTGGGGTAGGCTGGCTTCTGTAGCTCCGATTGGACCCCTAGCCTGG<br>GAACCTCCATGTGCCTCGGGTGTGGCCCTAAAAAGTAAATAAATAAATAAAATGAAACATAACATAAAGAGAACAA<br>AGGTAACACCTGCTCACACTCACCACGTTCGAATTATTTTAATACATTTTCAATTGCTGGTTTTCAATGTGAGCCA<br>TTTTAAATAAATCTTTACATGCAATATTAAAAAATATTAAAATATTATCTCTACTCTTGAGGTTATTTGCATCAAT<br>CTCCCTGTGGATGGAGATATTATATAACCGGCATGCAATGATATCTCGTGGGAGACTTGAAATCAGCCACAGTGTG<br>ATTTCTTGTAGGGTTGAGTTTTTTTTTTAATTTTTGAACTTTTTACTAAAGCAGGGTTGATTTACAATGTTGTGTAC<br>AGTGTGATTATTAAACCGTGGAAATTGGCAAACACTACAAGCCACTACCAAAAGCCCATGGTTAAATATTACCACC<br>ACTATTCATATTTCTCCCTCAACGTATAAACACATCTACCCACACTTATACACACAACTATCCCCTCCTCTTTTAA<br>AAACACAAATGTGGAGTTCCCATTGTGGCAGAGTGGAAATGAATCTGACTAGGATCCATGAGGATGCAGATTCGAT<br>CCCTGGCCTCACTCAGTGGGGTAAGGATCCAGCGTTACCGTGAGCTGTGGCGTAGGTCGCAGACGCGGCTCAGATC<br>TGGCATTGCTGTGGCTCTGGCGTAGGCAAGAGTCTACAGCTCCAATCAGACTCCTAGCCTGGGAACCTCCATGTGC<br>CATGGGAAGTGGCCCTAGAAAAGGCAAAATACCAAAAAAAAAAAAAAAAAAAAAAAAAAAAAAGAGGGCATTCCCTCC<br>CCCCTCCTTGGAGCCACACCCTCGGGAATGAGTAGAGAGCTTCCGCTCCATCTCAGGGCGCAAGAGCCCTCAGCAT<br>CTGCAATACCTCCTCTGAAAGTGTTCGAGCTCAGCCTGTCTCCTCAGGTTCACTGCGGGGAGGTCTTGCGGGTCGT<br>AGGCATCCTCCAAGTTATAGCTTTCCTGATGCCCGAAGGCGTCACATTGGCACTGGTTTTTCGGGAACAGCCTAAA<br>ATAAGACAAGGTCAAAGATCACAGATTGGGAAAGTGGGCTGGTAGGTGAGGGGGAGCCGCAAGCTCGGTCCGGTGT<br>ATTTTTTTTTTTTTTTTAACTTTTATTTTCTCTTTTTTTGTCTTTTTAGGGCCGCAAGGTTCCGAGGCTGGGGTC<br>TCATCGGAGCCGTAGCCACCGGCCTACGCCAGAGCCACAGCAACGCAGGATCCGAGCCGCATCTGCGACCTACACC<br>ACAGCTCATAGCAATGCTTGATCCTTAACCCACTGGGCAAGGTCAGGGATCGAACCCTCAACCTCATGGTTCCTAT<br>TCGGATTCATCTCCGCGGAGCCATGATGGGAACTCCCAATCCAGTGTGTTTTTCCCCCTAGGCTTTCCCATACCTA<br>GCGCCAGGGTTGGGTTGAGACCCTGGAATCACAGCAGCGGCCGCTCCCAAAGACACAGGGAAGGAAGGGAAGAGAG<br>GAAGGAAGGAGGGCGAGAAGGCCCCCTCTCTGGAATCAAAGTCCTTTATTTATTATTATTATTATTATTTGCTTTG<br>TAGGGCTGCACCCGCAGCATATGCAGGTTCCCAGGCTAGGGGTCCAATCGGAGCTACAGCTGCCAACCTACACCAC<br>AGCCACAGCAAGATCAGATCCAAGCGGCGTCTGGGACCTACACCACAGTTCACGGCAACCCCGATCCTTAACCCAT<br>GGAGCGAGGCCAGGGATCAAACCCACAACCTCATGCTTCCTAGCCAGATTCGTTTCTGCAGCGACATGACAGGAAC<br>TCCCCAAACTCCTTTAAACTTGAGAGTCACAGGAATCTCAGAGGCATTGCAGCCCCACCCACCAGATGAAAAGGCC<br>AGAGGGCCAGAAAGGCCACATCTTTCCTATAATTTTGTTTAGTTTTGGGGGTTTTAATGTGTTTTTGTTTTTTAGG<br>GCCACATCTGCAGCATATGGAAGTTCTCAGGCTAGCGGTGGAATCGGAGCTACAGCTGCCGGCCTACACCACAGCC<br>ACAGAAACATGGGATCTGAGCTGCGTCTTCAATCTACACCACAGCTCACCGCAACCCTGGATCCCCGACTCACTGA<br>GCGAAGCCAAGGATCAAATCTGCGCATCCTCATGGATCCTAGTTGGGTTTGTCACCACTGAGCCACAACGGGAACT<br>CCTCCTACAGTTTTGGTTAAATAGGCCCTCCAAAGTCCTAAAGAACTTTGCTGGGTGCTATAGAGGCTATGCCCAG<br>CAGACCAAGCCCCTTTCTAGTCCCGCCGTTTGCAGTCAAATGCTCTACCCCTGAGCCATACTCCCACCAGGTCCCG |

TABLE 9-continued

| lists sequences for the disclosure |
|---|
| CAGTCAGGATTCACATTCCCAATCAGCACAGGTGCAGAAAGGTAGGGAACTGGCTGTAAAGTGGGCATAAGAGGAC<br>ACAGTAGGAGTTCCCGTCGTGGCGCAGTGGTTAACCAATCCGACTAGGAACCATGAGGTTGAGGGTTCGATCCCTG<br>GCCTTGCTCAGTGGGTTAAGGAGCCAGTGTTGCTGCGAGCTGTGGTGTAGGTTGCAGATGTGGCTCGGATCCTGCG<br>TTGCTGTGGCTCTGGCGTAGGCCGGTGGCTACAGCTCCGATGGGACCCCTAGCCTGGGAACCTCCATATGCTGCGA<br>GAAGGGCCCAAGAAATAGCAAAAAGACAAAAAAAAAAAAAAAAAAAGAAAAAAGGGCACAGTAAAGCCACAGGAGG<br>AGCCAGGGAAGTGTCAGTGCAAAGTGGTATTCTTGCCATCTCACCCGTTTTCACCGTAGAAATCGGGTTTCTCAGG<br>TAGAAGCTTCAGCGTCTGCGCATCCAGGGTGGGGACGGGATGGGTGAGTTGAGGAGACTGAAGTCTGTATCGAGG<br>AACACGCTTTGGAACATAAAGAGTCCAACGCTCAGGACCAAAGCACCATCAATATCTTGAGGATCGACAGACATC<br>TAGGGCTGTTGGGACACAAGAGAGCAAACGCTGTTAAAATCTTTTCTGAGTATGTTAAAAAAGATTTCATTGTGCG<br>ACATAGATGGGAATAGCAACTTGAGCAAAAATGCAAGTCAAACCTGTTTTGTACACTACGTATCAAAATTGATTTC<br>TTCCCAAGGCAAAAGAGAAAGAAAAGCAAAAATAAACCTAAGCAAACTGACAAGCTTTTGCACAGCAAAGGAAACC<br>ATAAAATAACCCAAAAAGATCCTGCTGGGATCCACTGGGAACGATGTCTGGTCACTTGCGATGGAGCATGATCATG<br>TGAGAAAAAAGAATGTATACATGTGTGTGTGACTGGGTCACCTTGCTGTGCAGTAGAAAATTGACAGAACACTGCA<br>AACCAGCTATAATGGGAATGATAAAAATCATTTAAAAAACTGATTTCAGATAAATAGAAAAGTAAAGAATCAAATC<br>TGCAGAGAGTTCCCTGGTGGCTCATTGGGTTAAGGATCTGGTGTGGTCACTGCTGTGGCTCTGGTCACCACCGCGG<br>CATGACCTCCATCCCTAGCCCAGGAACTTCTGCATACGTGGGCATGGCCAAAAAACTATACTCAGTGGAAAATGTG<br>AAGTTTTTCAAATACGCACTTCTGATCACAAGACCTAAAATTAATAAATGAAGCAATAAAATAAGAGATTTGAAAA<br>TGGACAACAAAATGAACCTACGAAAAGCAGAAACAAGATTTTAGAGATAGCCAAATAGAAAGTGGTGAATTTAAAA<br>AAAAAAAAACTAAAATGGAATCATCGTTAAATCTAAGCACAGAGTAGACAACTGGTTTTTTCTTTTATTTTTTTAA<br>AATTTTATGGCCACAGCCATGGCCTGTGGAAGTTCCCAGGCCAAGGACTGAATCCAATCCATAGCTTCAACCTACA<br>CCTTTAACCACCGCACTGGGCCCAGGGATCAAACCTGCACCTCTCCAGTGACCTGAGCCACTGCAGTCGGATTCTT<br>AACCCACTGTGCCAGGGTGGGAATTCCAGACAACTTTATAACCTCCTTGCTCTAAGACTTTCCTCCTGACCCAGAA<br>GTGACACCTACAAACGAGTCTGGTTATATCACATGACGCTCCCCTGGTCCTGGCTGAGTAAGCGGATGTTCACCTC<br>ATCCGAATGGGGCTAATCAGCCAGAATTTCCTTCCCAGAAATGGGGAACCAGAGATATTGTTCGGCTAATCCTAAT<br>CCCCTGAACTGAGAATAGAGGGGAGGAAAGAAGAGAGAGAAGACAGAAGGTGAGAGAAACAAAGAAGCCTAGAAG<br>GACTTCCCATTGTGGCTCAGTGGGTTAAGACCATGACCAGTGTCCCTAAGGATGCAGGTTCAATCCCCACCCTTGC<br>TCTGGCATTGCCACAAACTGGTGGCAGATGCGGCTTGGATCTGGCGTTGCTGTGCCTGGGGCATAGGCTGGCATCT<br>GTGGATCCAATTCGACCCCTAGCCTGGGAACTTCCATGTGACACAGGTGCGGCCCTAAAAAAAAATCGTTTTTAAT<br>TTAAAATTTTGGGGGCAGTGTCTTTAAGGCATTAGTCTGCTATGGCTCCCTTTGCCTGACAAAGCAATAAAGCTAT<br>CTTTTTCTCCTTCACCTGCTCCTCCCCCCAAAAAAGAGTTCCCATTGTGCCGCAGCAGAAACGAATACAACTAGTA<br>ACCATGAGGTTTCACGTTCGATCCCTGGCCTTGCTGGGTGGGTTATGGATCCAGCATTGCCATGAGCTGTGGTGTA<br>GGTTGCAGATGTGGCTCGGATCCTGCATTGCTGTGGCTGTGGTGTAGGCCTAGCCTTGGAACCTCCGTATACCATG<br>GGTATGGCACTAAAAGCCAAAAAAAAAAAAAAAAAAAAAAAAAAAAAAAATTTAATTTAATTTTTAAAATTAAAAAAT<br>TTTTAATTTAGTTTTTTAACTTAAAAAAATTTTTTTAAATAGAGAAGCCTAGATCCTGAATACCTAGATGAAAGG<br>GATGACTTTCTACAAAAACGCAAATGAATAATGTATTGGGGAAATAAAATAAACAAATAAACAAATAAATAAAAGA<br>ATTCCCACTGAAGCACCGCCCCCCCAAAAAAAAACCCACAAAAGACTTAAACAGACCTGTAAAAATTTAAAAAAAA<br>AAATCAAGGAGTTCCTTTCATGCCTCAGGGGTTAATGAATTCAACTATGAACCATGAGGTTTCGGGTTCAATCCCT<br>GGCCTTGCTCAGTGGGTTAGGGATCCAGCGTTGCCGTGAGCTGTGGCTCTGGCGTAGGCTGACAGCTGTAGCTCCA<br>ATTAGACCCCTAGCCTGGGAACATCCATATGCCACTGGTTCGACCCTACAAAAGCCCAAAAAAAAAAAAAAAAAA<br>AAAAATCCAGGAATTTATCAAAGGTCTATGTACTTTTCAAAGTCCCAAATCCACACTTCACAAGTAACTCCAGACT<br>GGTTTGTAAGAAACCAGCTTTGCAGTGATGCAAATATAGGTACTGACCAATAACGATGTAAATACGCCAAACAAAT<br>ATTAACCAGTGGGACACAACAGTATCTTAAATGAATGAGTCACCGTTAACGAATGCTGTTCTTGGAGTTCCCGTCA<br>TGGCTCAGCAGATACGAATCTGACTAGTATCCATGAGGACACAGGCTCCATCCCTGGCCTTGCTCAGTGGGTCAGG<br>GCTCTGGAATTGCTGTGGCTGTGGTGTAGGTCACAGACGTGGCTCAGATCCCGCATTGCTGTGGCTGTGGTGTAGG<br>CCGGCAGCTGTAGCTCCGATTCCACCCCTAGCCTGGGAACCTCCATGTGCCGCAGGTGCGGCCCTAAAAAGACAAA<br>AACAAAAGCATGTTCCTTCTAGGAGAGCAAGGATAACTCAGTGCCACTGTGGGGCAAAACCACACCGACGCCATGC<br>TGTCAGCTCATCTTAGGCCCACAGTCTCATCTGCTCCCCCTCCTTATTAAAAAAAAAAAAAAAAAAAAAAGAATGAT<br>CACATCCTAAGTTCCTAACACAATTTTCAGACTATCAGATAGAAACAAATCACTGACAACCTGGGTGGGGGGCAGC<br>ATTTGGGGGAAGTGAGTGTGGTCTTGGCCTTTTTGAGGGTTGGGTTTGTTTCCTTTTGCTATTAGGTACTAAAACT<br>TAAAATTGCATCACTTAGTGAAAACAGAACAAAAATAGGGTCGGACTTTCTCTGTGGCTCAACAGGTTAAAGACCC<br>AGTGTTGTCACTGCAGTGGCCCTGGTCGTTGCTGTGCCATGGGTTCCATTCCTGGCCTGAGAACTTCTGTATGCCT<br>CGGGCGTGGCCAAAAAAAACCCAAACAAAAACAAAAACAGAAACATGAGTTCCTGTCGTGGCGCAGTGGTTAACGA<br>ATCCAACTAGGAACCATGAGGTTGTAGGTTCGATCCCTAGCCTCGCTCAGTGAGTTAAGGGTCTAGCGTTGCCATG<br>AGCTGTGGTGTAGGTCACAGACACAGCTCAGATCTGGCCTTGCTGTGGCTCTGCCGTAGGCCAGTGGCCACAGCTC<br>TGTTTCAACACCTAACCTGGGAACCTCCATGTGCGGTGCATTCAGCCTTAAAGAGAAAAGAAAAAAACAAACAAAC<br>AAACAAAAAAAAACAATAGTGAGGAAAAGTGGCATCATTTTACCTTTTTGCCTATTTAATGTTTAGCTTAATAGAT<br>AAAATGAACCATCTGTTAGGACAGGTTGTTTCGCTGAAGAATATGAAGAAAATACAACCCCACACAGGTATGTCAC<br>CAGAAAAGGGAGAAACACTTTAATTGCTTTTTCAATATTGTAGATATTTATCTTTGATACTACACCAAAAATCAAG<br>AAGTTAGTAGCAGGTTATTGTTTTGTTTTGTTTTGCCTGTGGCATGCATTAGCTCGATGTGGGATTTTTTTTTTTT<br>TTTTTTGGCTTTTTTTTTGGCCTTTTGCCATTTCTAGGGCTGCTCCCAGGGCATATGGAGGTTCCTAGGCTAGGGG<br>TCCAATTGGAGCTGTAGCCACCAGCCTATGCCAGAGCCACAGGAAACGGGGGGAGTTGAGCCAGGTCTGCTCACCT<br>TACGCCACAGCTCACAGTAATGCTGGATCCTTAATCCATCTGACCCAGGCCAGGGATCGAACCCTCAACCTCATGG<br>CTCCTAGTCAAATTCATTAACCTCTGAGCCACGACGGGAACTCCTCAATGTGGGATTTCAGTTCCCAGTCCAGAGA<br>CTGAACCTAGGCCACAGAGGAAAAAAGCGTGAACCTGAACCCTTAGTAGCTAGGGAACTTCCAAGAAGTGGTACTT<br>TCTTAAAAAGTTAGTTAAGTGTGGACTCTGAAACCATATCAGTGAAAAAAAAATTTTTTTGCTTTTTTTTTTTTAGG<br>ACCCCACCTGGTGCATATGGAAGTTCCCAGGCTAGGGGTGGAATGAGAGCTACAGCTGCTGGCCTACACCACAGCC<br>ATAGCAACGCCGGATCCTAAACCCACCAAGCAAGGGAACAAATAGAGGGAGTTTCCACTGCGCACAATGGGATCGG<br>TGGCATCACTGCAGCGCCAGGGACACAGGTTTGATCCCTGACAGCATAGGTTGCAACTGTGGCTCAGATCTGATCC<br>CTGGCCCAGGAACTCCATATGCCACTGGCACGGCCCCTCCACCCTGCCAAAAAGAGTTTGGAGGCGTTCCCTGGTG<br>GTTCAGTGGTTATGGATCTACACTCTCACCACTGTGGCCCAGGTTCAATCCCTGGTCTGGGAACTGAGATCCCACA<br>TCAAGCCGCTGCACACCTTGCCCAAAAAACAGGGTTTTTTAACCTTTTTTTTTTTAAACTGTTATTCCCCAATGCG<br>ATTTTTTTCCCCTACTGTACAGTATGGTGACCCAGTTACACATACATGTACACATTCTGTTTTCTCACATTATCAT<br>GCTCCATCATAAGTGACTAGACAGAGTTTCTTTCCTTTTTTCTTTTTTTCTTTATTTTTTAATTACTTCCCCAATA<br>CAATTTGTTAAAAGGGTTTTTTAATCCTGATAATAAACACATAAAATTTAGTACCTTGGAGTTCCCGTTGAGGCTC<br>AGCAGAAACAAACCTGACTGGTATCCATGAGGATGCAGGTTCAATCCCTGGCCTCACTCAGTGGGTTAACGATCCC<br>GCATTTGCCATGAGCTGCGGTGTAGGTCGCAGATGCAGCTCAAATCTGGCATTGCTGTGGCTGTGGTGTAGGCTGG<br>CAGCTATAGCTCCGATTTGACCCCTAGCCTGGGAACCTCCATATGCCATAGGTGTGGCCCTCAATAAAACAAAGAA<br>AGAAAGAAAGAAAGAAAGAAGGAAGGAAGGAAGGAAGGAAAGGAAGGAAGAAGGGAAGGAAAGGAAGGAAAGGAAG |

TABLE 9-continued

| lists sequences for the disclosure |
|---|
| AAAGAAAAAAATTTATCACCTTAACTACTTCTAAGTGTACATATACTTTCATAATGTAGATTGTTCATGTCGTTTTA GAACGGATCTCCAGAACTTTTTTCTGCTTTTTTCTTTGCTTATATTTTTGCATGCAACTATTTTTATCCATTTTTT CTGATTATGAAATTTTTATCTTTTACCCATTGAAGAAAAAAAAAAGTTCCTCTTTACAAAAACAAAACAAAACAAAA CAAATATATGTAGGAGAAATGATAGAATTAGAAAAATCACCACTTTGCTACCAACAATGTAATAAATGATTCTGGC CAGGATTGTCCATCTTTTTTTTTTTTTTTTTCCTCGTTTTTTTGCAATTTCTTGGGCCACTCCTGCGGCATATGGAG GTTCCAAGGCCAGGGGTCCAATCCGAGCTGTAGCCGCCAGCCTATGCCAGAGCCACAGCAACGAGGGATCCAAGCC GCGTCTGCAACCTACACCACAGCTCATGGCAACGCCGGATCGTTAACCCACTGAGCAAGGCCAGGGATCGAACCTA CAACCTCATGGTTCCTAGTTGGATTCGTTAACCACTGAGCCACAATGGGAACTCCAGGATTGTCCATCTGTTCTAA AACATTTGCCAGGTGCAGGATTTTGTTTTGTTTTGTTCTGCTTTTTGTGTTTTTCTTCTTCTTTTTCTTTTTTCTT TTTCTTTTTTTTTTTTTTCTTTTTTGTCTTTTTAGTGCTGCACCCACAGCATATGGAAGTTCCCAGGCTAGGGGTCT AACCACAGCTGCAGCTGCCAGCCTACGCCACAACAGCAACAGCAACGTTGGATCCAAGCTGTGCCTCCAACCTACA CCCCAGCTCACGGCAATGCCAGATCCTTAACCCGCTGAGCGAGGCCAGGGATCAAGCCTGCATCATCATGGATACT AGTCGGGTTCATTAGCCACTGAGCCACGACAGGAACTCCTGGAGGCAGGATATTGAATGGTGCCATTCCGGAGAAC ACTTACTACTTACAAAGAGATAAAAACACATCTTTGCAATGAAAGGATCATGCATCACTACCTTAACCACATGGTC AAATAAACATCCCTAATAGTGAGGCAGCCTGACCAACTGTCCTCCGGATATGATGATAGGAAGCACACAGATCATT TAAAGGAGTATTACTGCCAAAATATTTAACCGAAATGTAATCAAGGATCAGAGACCTCACTGCCAATTTATAGGAA AAAACAGGGGATAAAAATTTAGTAACACCATCAAGAACAATAGACAAATCAGGGACATCAGAATGTTTTCTGCAAG ACAACAGGCCTGAACTCTTGACAAAGGAAAAAAAGTGGGAGTTCCCGCTATGGCACAGTGGGTTAGGAATCGGACT ACAGCAGCTCGGGGCATTGTGGAGGTGCGGGTTTGATCCCTGGCCCGCTATAGTGGGTTAAAGGATCTGGCGCTGT CAAAGCTGCGGCCATTAAAAAAAAAAAAAAAAAAGAAAAGAAAAAAGAAAAAGCAATTGAAAAAAATAAAAAGAATG AGAGTGAATGAGTAACATTTCTAGTAAAGGGTTGCCTGTATCTTGTGCAGAACATACAGAATACATCTTTCAATGA TTTTAGTCAATTTTTTTGCATTTTAAGAAATTTCTTTTTTTTTAATTGTGGTATAGTTAATTTACAATGTTGTGTG AATTTCAAGTACACAGCAATGTGATTCAATTACATATATACATATATACACATACATATCCTTTGCAGATTCTTTT CTATTATAGGTTGTTACAACATTTTTTTTTCTTTTTAAGGCTGCATGTGTGGCATATGGAAGTTTCCAGACTAGG GGTCGAACTGGAGCTATAGCTGCCCGCCTACACCACGGCCACTGCCACAGCAACACGGTTTCCGAGCCATGTCTGC AACCTACACCACAGCTCACAGCACGCTGGATCCTTGACCCACTGGGCGAGGCCAGGGATCCAACCTACACCCTCAT GGATACTAGTCAGATTCCTTTCTGCTGCACCACACAGGAACTCCCTATTATAAGATATTGAGAATAGCTGTCCTGT GGCACAGTGGGTAAAGGATCTGGTGTTGTCACTGTAGTGGCTCAGGTTGCTGCTGTTGCACAAGTATGATCCCTGG CCCAGGAACGCTTGGGATGGCATTAATAGGAATTGTTTGGTAGGAGATTTTTAATAAAATGTTCAACCGCCCAATT TTTAATAGATAACTACAAATGTTCTCCACTGTTAAAACTGCACTTTATGTACTTAAGTGGGGATGTTAAAATTATA TGGGTCCGCCCGCTATTATAGTTGAACCACATTTGAGACACATTCAAAAAAGGGTAAAAATCGGGAGTTCCCACTG CAGCTGCGGGTTCAATCCCTGGCCTCACTCAGTGGGTTAAGGTTCCGGCATTGCCATGAGCGGTGGTGTAGGTCGC AGTCGCGGCTCAAATCTCGTGTTGCTGTGGCTGTGGCATAGGCTGGCAGCTACAGCTCTGATTGGACCCCTAGCCT GGGAACCTCCATATGCCGCAGGTGTGGCCCTAGAAAAGACACACACACAAAAAAAAAGGTTATGTTGAAGTTCCCGT TGTGGCTCAGCAGTAACAAACCGGACTAGTATCCGTGAGGACACGGGTTTGATCCCTGGCCTTGCTCAGTGGGTTA AGGACCCAGTGTTGCCACAAGCTGTGGTTGCAGTGCAGGTCACAGACAAAGCTTAGATCTGACATTGCTGTGGCTG TGACACAGGCCAGCAGCTACAGCTCAAATTCGACCCCTAGCCTAGGAACATCCACCCACAGGGGGCGGCCCTAAAA AAAAAAATATATATATATATATGTGTGTGTATATATATATATATATATATTTTATATATAAAACATTTTATATATA TATATAAAATATATATATATAAAAATATATATATATATAACATTTTATATATATATATAAAATGTTAACATTGAGT AGGTTTAAGGTTATTATTTTAATAACTTTATAAATAAAAATTTTAGATTTTCTCAGCTTTAATTTTTAATTAGGTG TGGAGTTCCCACTGTGGAGCAACAGGATCAGCAGCATCTCTGAAGCGCAGGGATGCAGGTTTGATCTCCAGTCCTG CACAGTGGGTCAAAGATCCAGCATTGCCACAACTGGGGCATAAGTCTCAACTGGGGCTCAGCTCTGATCACTGGCC CAGGAACTCCATATGCATCGGGGCAGCCAAAAAAGAAGAAAAAAAAAAGTGTCTAATATGGTAATAGGAATAGATAC AACCCATGTAAACAAAAGTTTTTTGGGGTCTTCAATAATTTCGAAGAGTGTAAGGGGTCCTGAGACCAAAAAGATC AAGAACGGCTGGTCTACGTTCTAAGCAACTGCTGTGGTTCTTGTTAAGTTTTAATACTGAAGATGAGTTTTTACAA GGACAAACAATATAATACAGGGCATGTAGCCAATATTTCGTAATAACTATAAATGGAATATAGCCTTTAAAAAGGC CAATCATTCTGTGGCACCCTGAAATTTATATGATACATGAACTGTACCTCAATAAAAAAATTTAATAAGATAATAA TAATATAGGTGAGCTTCAATTAGCACATTCTATTACTTATCTTTAATAAAAATTATATTCTGTGTGCAAGGTAATC TGACAAACTCACCAGTACAACTGGTTTCCAACATAGACCTGGCTCAGCTGCAGAGGTTCCTTTCAAGAGTAAACTT GCAGGGCTTTCCCCGCTGTGGCACAGCAGAAATGAATCAGACTAGCATCCATGAGGATTCAGGGCACAGAAACAGC TCAGATTTAGTGTTGCTGTGGCTGTGGCCATGGTGTAGGCCAGCAGCTGCAGCTCCAATTCGACCCCTAGCCTGGG AACTTCCATATGCTGATGTAGGAGAAAATGTCCCAATAAAATGTAGAAAGGAGAGACCCCGGCCATGACGACTAAG CAAAGTCTAGCCAACTGCCCCAACCAGTCCTCCCCCATGCATCTGCTTCTGTAAATTTGTTTCCGCATCTACTACC TTGCCTGACGTCACTCCAGTCCAACTAGCCAAGCTTGGACCTGGAAGACGTAGCCCATAAAAGCCTTGTGAAACCC TTCTTCCGGGCTCAGACTCTGGAGAGTGATCTCGTCTGAGCCCGCCGGCGTAATAAACCTGAGTTCTCCAACTCTC CAAGTGCTCGCTTGGTTTCTCGCCGGGTAAAAGAGCTGCTCCACTATGGCCACAGAGCTACTGGAGCTGGTACGCT ACAGCCACGGGGCTGTCGCCAGAGCTGATACGCTGCAGCGCAGGGCTGCTGGGTATCTGCTGTAACATTTCTGGAG GCCCCAGCGAGATTCCAACCTTTCTGGCCCCTTGAGCCACTGGAACAGAGGTAAGGCCGCCCGGGAGCCGGGGAGC CTCAAACCGAACGAGGCGGCGCACCACCCGACGGTATTCTGGGTCCTCCTTCGTCAGCGGCATTCCTGATTCCCGG GTGACCAAACCCTGACCAGACTCAGTGGAGATGGACCAACTCACCAGAAAGGTATCCGGACAAGGTAAGGCAGC GGGGCCAACCCCAGTCAGGTCCTGCCCCAGTGGGCAGAAGAGGGGACTGATCACCCCCTGAGGGAGACTCTCCCGG TCAGAAGCTGTGCCTGACTGGAGCAGCAGTCCTAGTGCTCCAGATTGGAAGCAGAGGAACCTCTTGCTTGGGTGGA GCAACTGTCAGGTGTAGCCAATTGAAAGTTGTGCTTGATCGAGCTACTAGTTAGGGACTCCCAGGGAGTGGAGGC ATTGTGATAACCTCTGAGTGTGTGTGAGAGTGAATGAGCGGCCTGATTCGCTTGTGCTTCAGGTTCGAGTTTGTGG CTCCACGGTCTTAGTGGCTATGGAGTCTGAGTGGGTCCTAACCTGCAGTTCCGTGGTGACCTCATAGGGCTTATGG CTGCAGCAGACTCTGAGGGTTCTGTTCCCTCCCTGCAAGTCCAATCCAAGTTCGGGGATTATACGAACCAGCCAAT TGCTAAGAGGCACCTAAACTCCCGAGAGGGGGGCAGTCAGGCGGACATCTGAATGGCCACCTTCTGAGAAGGAGGC ACCCTCCCTTGTTTTGTCTGCGACACTGGCACAGGGCGTCCACATGGGGTGGGACCTAACCCAGAAGCCCACGAGC CAGAGACCCCTGTGCTTCCGCCATTTTGGGCCATAAATTCCTCCAAGGAGATGACCTAATTTGATCTTGCCCCTGG GCCTCCAGGAACTCCCGGCCCAGATTCTAAACCAGCCATGGGACTGCCTATTTTGTCAGTTCATGGAGGCCCAGGA TCTGAGTCAGGGAGACAAGCCTGTCATCCCTGGCTCAGTTCAGGGTATAGGGAGGATTGGGTACAAGGTCCCCTGT CCTTTGCCCAAAACATTAGAACTTGTCTGAGAGTGCCTTCCTGAGACCGGGGGTCCAGATGGATTGGAGATACTTG CAATAAAGCAGGTGCTCTTCCCAGTCATAGAGCAAGCTGAGTGGGATCTGTCTTGCTTTCAAGAGTGGTGGAGGCA AAGCTACTGGGGATACCACCCACGAGGCCAGAAAAGGTCTCATAATATCAGGCCATAGAAAAGATCCACATAAAGA CACCATGGGTTCACCCAAGTCTAAACCTGTGGTTGTAGACTGTGTGATCAAAGATTTCAAAAAGGGATTTTCTGAA GATTATGGTATAAAACTAACCTGATCTTTCATCATTTCCTTTGCCATTACCTCAAATAGAGCTGTGGGGGCAAAGG AAACAGACCTCTAGATGTTAAGACCATCCTGAGTTGTTACCAGGCCTGTGGGGGAAAAGGAGTTCATAGCTAGTAT TCATCCAACTTAGGCCAAGTGTTTAGCCTCAGAGCCTCGGCATAGTCAGTTTTGCTTTTTGCTGTTTACTTTCATC |

TABLE 9-continued

| lists sequences for the disclosure |
|---|
| CTGGTTGGAGTAATTGATGGCTGGTTCATCCAATTTACCTGTTAACTGTGGTTTAGAAACTTTCCTAATGTTAATA<br>CAGGGCATGTCAGAGTGAGCATCTTAGGATTTGAAAACTCAGGGCAGGGCCTGTATGCCTGGGTTTTCTTCACCTC<br>TGTCCAGAGACAGGCACTGGGCAGGGATGACGGGAAGAGAGGCTACGCTGGTAAGGAGTGGTTAATTCCAGTCAGC<br>CTGAGGTCGGATGGGACATTTGACCACTAGTGTCTAGCTGCTCCATATAAGAGAGGGGACACCCTCACATAGCCAA<br>GAAAGGACAATAGGCGCTGGATGCTGTTTTTTGTCTTTTTCGGATGGGAGCCACATCCTCAAGCCTGCTGCATGAC<br>TCAATAGCAACCCCTCTGACATGTGCCTTGAAGAACTGGAAAAAGTTTGACCCTGAGATTCTGAAAAAGAAACATT<br>TAATTTTCTTTCGAACAAAAGCCTGGCCGTTATATAATCTGTCAGATGGAGAGTGACAGCCATCTGAAGGCTCACT<br>AGCTTATAATACCATTCTCCAATTAGCCAGAAGTTAGTCAGCCTTCTCCAATACTGCTCAAGGCTCCTTCTCCCCG<br>CAAGCCAGTGCCAAAGTTATATCTCTCTACTCCCTTTACAAGAAGTAGCAAACAGAGAATGGAGGCCAAATACA<br>GGTCTATATACCTATTTCACTTCAGGACTTAGGGCAAATAAAAACAGATTTGGGAAAATTTGCTGATGACCCAGAT<br>ATATTGAGGTTTTCAGGGTCTCATGCAGTCCTTTGAGTTAGCCTTCAAGGACGTCATGTTATTACGGAAACAGACA<br>TTGACTATAAGTGGAAAATTACATAAAGTCTCCAAAACTGCTCAAAGCTGGGGAAGATGAATGGAATGATGCTAAA<br>AATGCCAGAGGCAGATTAGAAGAGGAATGATCAAGATTCCCCACAGGGTGTCAGGCAGTTCCTATGAGCGATCCCA<br>ATTGGTCTGCTGATGAGGGAGATAACAACAATTGGCATAGAAATCATTTTATTACTTGTATAGTTAAGGGATTAAA<br>AGCCCGTTAAAACTATCGGAGGTTTACTAGGGGAACAAGAGTCCATCAGCTTTCTTAAAAAGGCTCAGAAAGGCAT<br>TGAGAAAACATAAAACAGGGAACCCAGAAACAATGGAGGGCCAAATAATTATTTATTTATTTATTTATGTCTTTT<br>TGCTATTTCTTTGGCCGCTCCCGTGGCATATGGAGGTTCCCAGGCTAGGGGTCTAATCAGAGCTGTGGCCACCAGC<br>CTACACCAGAGCCACAGCAATGCAGGATCCGAGCCGAGTCTGCAATCTACACCACAGCTCACGGCAATGCCGGATC<br>GTTAACCCACTGAGCAAGGGCAGGGATCGAACCCTCAACCTCATGGTTCCTAGTCGGATTCGTTAACCACTGCGCC<br>ATGACGGGAACTCCCGAATAATTCTTAAGGATAAATTCATAGCTCAATTGGTGCCAGATATATGGAGAAAGCTCCA<br>AAAATTGGCTTTTGGCCCTGATCAGGACCTGGAGCACCTCCTCAGAGTAGCAACTCAAGTATGTTATAATCTGGGC<br>CAGGAAGAATAAAAGGAGAATGAGAGGAGAGACAGAGAAAAGGCTGAGGCTCTAGTTATGGCACTACAGGGAGTCA<br>ACCTGGAAGTTGCCAAGGTGAGAGGACTAGGGCAGAGACCTATGCCTGCAGCCTGTTTCCTCTGTGGAAAAGAGGG<br>ACCCTTTAAATGGGAATGCCCCAAGCCTCAGACCACAGCACCTAGGCCATGCCCCATATGTTGGGGAGATCACTGG<br>AAGAGGGACTGCCCCTGAAGATGAAGGTCTCTGGGGTTGACCCCTCAGGCCCAGGATCAAGGCTGACAGGACATTT<br>CCATAATGGCTCCTGTCCTTCTCACCACTCAGGAGTCCTGGGTGACTCTAAATGTAGGAAGACAGCCTATTGACTT<br>CCTCCTGAATACGGGAGCCACTTTTCAGTCCTCCTCTCCAATCCTGGGCCCCTCCCTCATGAATCTGCCACATTTA<br>TATTTCCGGCAAGCCGGTTACAAAATTTCTTACACAGCCTTTGAGTTGTGGCTGGGAATCCATTTTCTTCTCTCAT<br>GCCTTTCTGATTGTTCCAGAGAGTCCAACTCCTCTTTTAGAAAGAGATATTTTGTAAGAGGTTAAAGCCTCAATTC<br>ACATGGCAATGGAGCCTAATCAAGGTTTATGCCTGCCTTGGATGGAAGTATATACTGACCCAGAAGTCTGGGCCAT<br>AGGAGGAAACATAGGAAGAGAAAAGAATACTCAACTGGTGGAAATAGGTCTTAAAGACTGGAATTTATTTCTTTGC<br>CAAAAGCAGTATCCTCTGAGACCCAAGGCATGACAGGGACTTGTATCAATTATAGGAAGCGTAAGAGAACAGATTA<br>TTAATTGACTGTATCAGCCCTTGTAACACTCCTATATTGGGAGTGCAAAAACTTAACAGGGATTGGTTCCTAGTAC<br>AAGACCTCCATCTAATAAATGAGACACTGGTCTCATTACATCCAGTGGTGCCCAATCTCTACACTCTTCTTTCACA<br>AATTCCAGAAACAGCAGCATGGGTTACTGTATCATATTTAAAAGATGCCTTTATTCTGCATTTCCTTGACTAAGGC<br>TTTGCATATATAAATTCTCAAAATATGGAAGGTAACTAACTGACCAGAATTAATTTTAGGTTCAAGTCAACTGGGA<br>AATATTCAGTATTAAATTAATATCTTAAATTAGAATTGAAGTTTGCTGATCTAATTAATACACACATGTCGTTACA<br>GCTGTCAACATTAGGTATAATATCTTATCGTACCTAGGTTTAACAGAAGTCAAATGAGACACTGAGACATCAGTTA<br>CTAAACAGAAACTAAAGGTATTTAGAATAATTAATCAATATGATCAGTTTCACCCTGAATGGTCTCCATAAGAAAA<br>ACATGTGTTTTTAGAAATTATAAAGGACAGTCTGTGGTTGCTTTAGAAACGTAGAATCTGTGTGCTTTCAATATAG<br>AAGGAATGAGGGATGGAACTGCATTTTATGAAGGCAAAAGAAAGTCTGTCTTCAGCTGATTGCTCTGGTTGGAAAA<br>TAAGGGACAGACTAATATGGATACAGAAAGTGATACAAGGTGTGTGGGAAGTGGACACTGAGAATTTTGTGCATGG<br>TGGGGACTGTCTATATTTGAGTAAGTTAACTTTAAAAGTAATGTGGTGCCATAAATCATACTGCTCACAAGGACAT<br>AAGGTAGCTTTCAATTACATGTTGACCAAGGCATACAAGTGTTTCATAACCAGCCAGAGAAATCAGAAAAATCATA<br>CAAGTTACCTGTGCTATTATAAAATCTAAATGTTGTATTCTTGATGGTTCACAGAATGTGTCTAATTCCCTGCTAG<br>ATCTTCAACAGTAGATTCATGAGCGGTCCTATCCAGCTCCAGCTTTTGGAGCTGCCCTGTGGAACCAGCCGACCTC<br>CTCCTCCTGGTGAAAATATTTCTTCACCATATCTTTTTATTCAGACCCTGTATAATTAACTGTATTTCTTGCTTCA<br>TTACATCCTGATTAAAAGCCATCAGCCTTAAAATGTTGATAGAAGGGGTACCCAAAGCAATGTATCAAAGCCCACT<br>TGACCGTCCCATGAGTGGAGACCTAACTGCTTTCCCTAATGACGCCCCTTTTCAGCAGGAAGAAGTCAGAGCGGTC<br>ATCGCCCCCTTTCCCCACAGTTAGAGTCTCTAACTCACTGGTGGGATTGAGGCAGAATATTCACTCAGGTAGTCAG<br>TGTAGGAACATGGGCTTCGATACATTCTTTGATGTGGCTATTGGTTAACATTTGTAAAGTAAGGGTTGCACAGCAA<br>CCCCAACTGCTATAAAGGTTACAGGTATTACCCCATGGATCCATCACACCGGAATAAAGAAGGCTGCTCCCGCCAT<br>TGACACAGACACCTGGGAAGCTGTCCGGCACCCTGAGAACCCCCCTCAGGATCAAGTTCCAGAGACATATGGCACT<br>GGAGGATGGCAGGCCCTGCTCTGGTCACACCCAGAAGCTGGCCAGTCTATGCACGGCAGAAACTTGAGGAGTCTAC<br>AGCCCTGCCCCAGCCACATACTGGAGTTGGTTGGTTTGTACAAGTGGAGGCCAGAGGATCTCTATGCAAACTTGAA<br>TTGAACTCATGCTCTGGTGGGGAATATTGGTAATTGAAATTGCCATAGCCCTCATATTTGGAGTGGGGCTATATGC<br>AGTATCCCCTTCAGAATGGGGACAGGGAGCCCAGCTACTCATCTGTGTGATGTATCTCCTGACTGTCAGTATACTA<br>GAATCCCTGTTCATAATGGGTCAGTGAAAAGGATCAAAGGAATCATAGTTCTGTTAACACTCACCCTGCTGCTCAC<br>TCCAGGGGCAACAGACTGGGACAATGATCTATGGGATGGGACGGGATTAACAGATGCTTACCAGTGCCTCCCTGCT<br>AATTGGACAGGGACCTGCACTCTAGCCTTTGTCACTCTTCAAATAGATATTGTCCCTGGGAATCAGTCTCTTATGG<br>TGCCCATAGAGGCACATGGCAGAACAAGACAGCAATGCAAGTTATCCCCTTATTTAGTTGGTTTGGGAATTCCAGC<br>AGGGATAGGAGCAGGAGTGGGAGGAATAGAATCCTCCACTGCTTATTATCATCAATTATCTAAAGAATTCACGGAT<br>GATGTGGAACAAGTAGCCCCTTCCCTAGTAGCCTTACAGGATTAGGTAGACTCTCTGGCAGAAGTGGCCCTTCAAG<br>ACAGGAGAGCACTGGACTTATTCACTGCTGAAAAAGGGGAACTTTGCCTGATGAAGAATGCTGTCTTTATGCCAGC<br>AGATCTGGAATAGTCAGAAACATGGCCCAACAAATAAAAGAACGCATAGCAAAGAGAAGGGAAGACTTAGATAACT<br>CCTGGTTAAATTGGAGCAACTACTGGAGTTGGGTGGCATGGCTCACGCTTTGGTTGGGCCCCTCCTCATGCTCTTC<br>ATGGCCCTCACATTTGGCCCCTGTATCCTGAACTGTCTTGTCAAGTTTGTCTCCTCAGGCCTAGAATCTATAAAGC<br>TACAAACGGTGGTGATGTCCCGGCCACACTTATATCAGCCTCTGGGCCAAGAAGACCAGAAAGGTTGATGCTTGCT<br>CCAAGAATGTGAAAAAGCATCAAGAGGGGGGGATGTAGGAGAAAATGTCCCAATAAAATGTGGAAAGGAGAGACCC<br>CGGCCATGACGACTAAGCAAAGTCTAGCCAACTGCCCCAACCAGTCCTCCCCCATGCATCTGCTTCTGTAAATTTG<br>TTTCCGCATCTACTACCTTGCCTGACGTCACTCCAGTCCAACTACCCAAGCTTGGACCTGGAAGACGTAGCCCATA<br>AAAGCCTTGTGAAACCCTTCTTCCAGGCTCAGACTCTGGAGAGTGATCTCATCTGAGCCCGCCGGCGTAATAAACC<br>TGAGTTCTCCAACTCTCCAAGTGCTTGCTTGGTTTCTCGCCGGGTAAAAGAGCTGCTCCACTATGGCCACAGAGCT<br>ACTGGAGCTGGTACGCTACAGCCACGGGGCTGTCGCCAGAGCTGATACGCTGCAGCGCAGGGCTGCTGGGTATCTG<br>CTGTAACACTGAGGGTGCAGCCCGAAATGGTAAAAAAAAAAAAGAAAAGAAAAAAAAAAATAGTAAACTTGCAACCA<br>CAGTAAGTATATAACGGAGTTCCTGTCATGGCTCAGCAGGAAAGAATCCAAGTAGGAACCATGAGGTTGGGGGTTC<br>GATCCCTGGCCTCGCTCAGTGGGTTAAGGGTCCAGTGTTGCCGTGAACTGTGGTGTAGGTCGCAGACATGGCTTGG<br>ATCTGACATTACTGTGGCTGTGGTGTAGGTCAGAGGCTACAGTCCCAATTAGACCCCTAGCCTGGGAACCTCCATA |

TABLE 9-continued

| lists sequences for the disclosure |
|---|
| TGTCGCGGGAGCGGCCCTAAAAGGACAAAAAGACCAAAGGGAAAAAAAAAAGAATGTATATATATGTATGAGTGAG<br>TCACTTGGCTGTACAGCATAAATTGGCACAACACTGTAAATCAACTATACTTTAACTTTTCAAAAAGATTAAAAAA<br>GAAGCATTGGCGTTATCCTCAAGTACAGCTGGATTCCCATCTGCTCCTTATAATGCTGCCCTTGGGCAACCTCCAT<br>TCTCCATGTTCACAGCTCTGAAGTGGACATAACTCTTCCAAGAGTGTTGCTGGGCGCATTAGAGGCACAATCTAGA<br>ACAGGGCCTGTACGTAACAGATAAGTGCTCCACAGTGGATGAAATGAAATGAATTCACCAACAGGAAGTAACGATC<br>ATTTCCTGGGTTGGTAGGGTGTGTTGTAGTGAAACATCCTTTCTCAGAGGGACAAAGATCAGAAATGCACATTTCA<br>AAATCAGACACTCTTTAATTTAAAAAAAAAAAAAGAAAGAAAGAAAAGAAAACGAAAAAGGCAAATAAACATTTAA<br>AAGAGTAAGTTTCTTCTGAGGAAGAAACCTGTTTCCCAAGGTCACCCAAGCCAGCAGCCTTAAAATCTTAGAGACA<br>TAAACACAGCAACATGGACTTGCCAGAATGTTCGGTTGGCACCAGTTTGGATCCTGGTATCAAGACTCCTGGTCAT<br>TCTCCTCATTCACTAAGGAATGTGGGATGAGATAATTTTGGGGAAGTGCTGGAAGGAAAGCCTTAGAAGGGACTTT<br>AGCTGGTAACGCAAGAGCTACCTCCCTTTGCTGAGTTCTGCCATAGCCTCAGTACAAACGTGTTTCTTGGTTTCCT<br>TATTTGTTTCGGCAGCGCCAGGGCATGAGGAAGTTCCCCGGGTGGCCAAGGATCAAACCCTTGCCACAGGAGGAAA<br>AACGCTGGATCCTTAACCTGCTGCACCATCAGAGAACTCGTATACTTCATTTTAATCCTCATAAAACATCATCTAA<br>CCAACACGGTTCCCCCCCTCCCCTTTTTAAGCCATTTAGGGCCGCAGGTGCCTGTGTATGGAGGTTCCCAGGCTG<br>GAGGTCTAATTGAAGCTGTAGCCATCGGCCTACACCAGAGCCACAGCAACGCGGGATCCGAGCCACGTCTGCGACC<br>TACACCACAGCTCACGGTGACACCGGATCCTTCACCCACTGAGCAAGGCCAGGGATGGAACTTGCAACCTCATAGT<br>TCGTAGTCGGATTCGTTACCCACTGAGCCACGACGGGAACTCCCACAAGACGTATTTCTGATCCTTCTTTCTGTTT<br>ATAAAAATTAAATGAGCTCACCAAGTCCGCACTTCCTCCGTTAATTATTATGCTACTCAGAAGTTTTTTTAGCAC<br>CCCAAACCACAAAACGGACGCTCGCTCCACCGCGAGGCTGTCTTCCGGAGCAGAAAACTGACCTTTTAAAATTTTT<br>TTTTCTTTTGGTCTTTTTGGGGCCGTACCCTAGGGCATATGTAAGTTCCCAGGCTAGGAGGTCTAACCAGAACTGC<br>AGCCGCCGGCCTTACGCTGCAACTAGATGCTACGCCAGGTCCGAGTGCGTCTGCGACCTACACCACAGCTCACAGC<br>AACATACCCACTGAGCGAGGCAAGGGATCGAACCCGCGTCCTCGTGGATACGGGGGGCGGGGAGGGGGCGTAAACCG<br>TTGAGCTAGAACAGGAACTCCTAGAAAACCGACTTCTTCAAAACTCTGCCTCTAAAACCCCCAAGCTGTTATTA<br>ATGCAGCGTAAAGGACGCAGCCTCCGCTTCCCCACAGCCTGGGGCCCCACAGCCTGGGGCCCGCACATCCCCCGAG<br>ACTTACATCCCCAGCCCTGGTCATAACCTCCGAGTTCCGGGCCGCCCCCCGTGCTCTGCGCCACGAGAGGCAACCT<br>CCACGTCGAATGTTCCCCTGGAAAACCAGTGTTCCTTGGGGCGCAGGGCGGGGGAACGAGCAGGAACTCTCAACAG<br>CGTCCCGAGGCGCAGTCTCCTTCTCGCTGTCTCACCGACGTACGGAGCCGGTCGGACTTATTTTGGAGACCCGCCG<br>CCCCCCCTACTCGGCTCCGGGGTCCCGGGACCTGGCCGCTCCCGGGTGGCGCCACTGGCTGGCCAAGTTTGACTTC<br>CCATTTGTCTCTGCTCGAGGGACACGCACCTGTACGAAGTCATCCTTAATCCCGCCGCCTCGGGACATTCTGGGCT<br>GGTGGTGCCACTCCGCGGATTGGACAGCCCTAGCACCAACCCCGGCAAATTCTTCCTGGTAAACCGCGAGAGCTTG<br>GGTCGGACCCGCCCACGTCACCACCAACCCCCGC |
| SEQ ID NO: 26 B4GALNT2 CDNA Sequence<br>TCCGCGGAGTGGCACCACCAGCCCAGAATGTTCCGAGGCGGCGGGATTAAGGATGACTTCGTACAGCCCTAGATGT<br>CTGTCGATCCTCAAGATATTGATGGTGCTTTTGGTCCTGAGCGTTGGACTCTTTATGTTCCAAAGCGTGTTCCTCG<br>ATACAGACTTCAGTCTCCTCAACTCACCCATCCCGTCCCCCACCCTGGATGCGCAGACGCTGAAGCTTCTACCTGA<br>GAAACCCGATTTCTACGGTGAAAACGGGCTGTTCCCGAAAAACCAGTGCCAATGTGACGCCTTCGGGCATCAGGAA<br>AGCTATAACTTGGAGGATGCCTACGACCCGCAAGACCTCCCCGCAGTGAACCTGAGGAGACAGGCTGAGCTCGAAC<br>ACTTTCAGAGGAGAGAAGGGCTCCCTCGCCCACCGCCCCTGCTGGCTCAGCCCAACCTCCCCTTTGGGTACCCGGT<br>CCACGGGGTGGAAGTGATGCCTCTACACACCATCCCCATCCCAGGCCTCCGGTTTGAAGGACCTGATGCTCCCATC<br>TATGAGGTCACCCTGACAGCTTCTCTGGGGACACTGAACACCCTTGCTGACGTCCCAGACAATGTGGTGAAGGGCA<br>GAGGCCAGAAGCAGCTGAACATTTTGACCAGTAGCCGGGAGCTTTTGAATTTCATCCTCCAGCATGTGACATACAC<br>GAGCACAGAGTACCACCTCCACAGAGTGGATGTGGTGAGTCTGGAGTCCAAGTCCTCAGTGGCCAAGTTTCCAGTG<br>ACCATCCGCTATCCTGTCATGCCCAAGTTATATGACCCTGGACCAGAGAGGAAGCTCCGAGACCTGGTGACCATTG<br>CCACCAAAACCTTCCTCCGTCCCCACAAGCTCATGACCATGCTCCGGAGTGTTCGTGAGTACTACCCAGACCTGAC<br>GGTGATCGTGGCCGATGACAGCAAGGAGCCCCTGAAAATCACTGACAGCCACGTGGAGTATTACACCATGCCATTT<br>GGGAAGGGCTGGTTTGCTGGCAGGAACCTGGCCATATCTCAGGTCACCACCAAATATGTGCTCTGGGTGGACGATG<br>ACTTCATCTTCAACAGCAAGACCAGGATCGAGGCGCTGGTGGACGTCCTAGAGAAAACGGAACTGGACGTGGTAGG<br>TGGCAGCGTGATTGAAAACACATTCCAGTTCAAGCTGTTGCTGGAGCAGGGGAAGAATGGCGACTGTCTCCACCAG<br>CAGCCAGGATTTTTCCGGCCCGTGGATGGCTTCCCCGACTGCGTGGTGACCAGTGGTGTTGTCAACTTCTTCCTGG<br>CTCACACAGAGCGACTCCAAAGAATTGGCTTCGACCCCCGGCTGCAGCGAGTGGCTCACTCAGAGTTCTTTATTGA<br>TGGGCTCGGGAGCCTGCTCGTGGGGTCCTGCCCACACGTGATCATAGGTCACCAGCCCCATTTACCAGTGATGGAC<br>CCAGAGCTGGCCACCCTGGAGGGGAACTACACCAGTTATCGGCCAACACCGAAGCCCAGATCAAATTCAAGTTGG<br>CTCTCCACTACTTCAAGAACTATCTCCAATGTGTCACCTAAGGTATCCGGGCATTGGAAAAGCGCTGAGCTGCCTG<br>GTTGCAAGTATCTAAGACAGCGGATGCGGTGGCTGGGATACCAATATTTGAACTCCTCATAAGATAAGCACTGTAA<br>TGCCCAGGGAGCAGGGTAGGCAGGTGGGTCTGACTCCGTTACTGGAAGTACCAATAAAAGTACAGGGTCATTAGAA<br>ATGGACCAGTCACTGAGGTGGGCAATGGAGACTTCATTCATAACGATTACGGCGGTGTTTCCATCATGGCTCAGAG<br>GTAGCAATCCAGACTGCTATCCACGAAGATGCGAGTTGGATCCCTGGCCTTGCTCAGTGGGCTAAGGATCTGGCAT<br>TGCTGTGGCTGTGGCATAGGCTGGCAGCTGCAGCTCTGATGCGCCCCCTAGCCTGGGAACTTCCAGATGCTAAGTG<br>TGTGGCCATAAAAAAAAAAAAAAAAAAAAAAAAAAA |
| SEQ ID NO: 27 B4GALNT2 Protein Sequence<br>MTSYSPRCLSILKILMVLLVLSVGLFMFQSVFLDTDFSLLNSPIPSPTLDAQTLKLLPEKPDFYGENGLFPKNQCQ<br>CDAFGHQESYNLEDAYDPQDLPAVNLRRQAELEHFQRREGLPRPPPLLAQPNLPFGYPVHGVEVMPLHTIPIPGLR<br>FEGPDAPIYEVTLTASLGTLNTLADVPDNVVKGRGQKQLNILTSSRELLNFILQHVTYTSTEYHLHRVDVVSLESK<br>SSVAKFPVTIRYPVMPKLYDPGPERKLRDLVTIATKTFLRPHKLMTMLRSVREYYPDLTVIVADDSKEPLKITDSH<br>VEYYTMPFGKGWFAGRNLAISQVTTKYVLWVDDDFIFNSKTRIEALVDVLEKTELDVVGGSVIENTFQFKLLLEQG<br>KNGDCLHQQPGFFRPVDGFPDCVVTSGVVNFFLAHTERLQRIGFDPRLQRVAHSEFFIDGLGSLLVGSCPHVIIGH<br>QPHLPVMDPELATLEGNYTSYRANTEAQIKFKLALHYFKNYLQCVT |
| SEQ ID NO: 28 C3 Genomic Sequence<br>CTCACTTCCCCCCCCACCCCCGTCCTTTCCCTCTGTCCCTTTGTCCCTCCACCGTCCCTCCATCATGGGGTCCACC<br>TCGGGTCCCAGGCTGCTGCTGCTGCTCCTGACCAGCCTCCCCCTAGCCCTGGGGGATCCCATGTGAGTAATCACAA<br>CCCCAACCCCCAAACAAGGCTGCTTTCTGCATTGGGAGTGGGCACTTGTGAGTATAGGTCTCTGCAGGTTTAGGGTG<br>CATGTACGGTGCTGGTTGATTCTGTGGCTTGTGATGAGGTTGGGGTGAGTCTCAGAAGTTGGGGTTGGGTGAGTCT<br>CAGAAGTTTGGACTCCATAGGATCTGGGAGTTTGTAGTTTTAGCATTTAGGAGTTTCAGAGATGCGGTTTGGATGT<br>ATGTGGCTGAGGGGATGGATTGGGTTGTATTTATAGGTCTGGGGTGCTAGAGGTTTAGGAGGCTGTTTAGGGTGTT<br>CCAGGGTTTGGGTATTTAGAGACTTGAGGTATTTAAAGATTTAGGAGTTCTGACCTTGGAGCAGTGGGTTAAGAAT |

TABLE 9-continued

| lists sequences for the disclosure |
| --- |
| TCGACTGCAGAGGCCAGGGTCGCTGATCCGGTGCGACCATAAAATGATAAAAAATAAATAAACGATTAAAAAAAG<br>ATTGAAGGGTTGAGACTTCTGGAATTTGTGGGTTTGATTGTGGGCTTGGAAGTCCATCGTCTTGGAGGAATTGGTT<br>CTGATTTTGAGGTTCAGGAATTGATGGGATCTGAAGCCCCCAAGCTGTCCTCCAGTCATCGGATCCCCCGCAGGGC<br>TAGGGGCTGGGGCAGAGCGCTGACCCTGGGGGTGCCTAGCATCTCGTGCCCCTGGGATGACAGCTCTACGCCTCGT<br>CCTCCCCTCCCGCAGTTACACCATAATCACCCCCAACGTCCTGCGTCTGGAGAGTGAGGAGATGGTGGTGTTGGAG<br>GCCCACGAAGGGCAAGGGGATATTCGGGTTTCGGTCACCGTCCATGACTTCCCGGCCAAGAGACAGGTGCTGTCCA<br>GCGAGACCACGACGCTGAACAACGCCAACAACTACCTGAGCACCGTCAACATCAAGGTGGGCGCGCTCAACAGCCG<br>GACCGCTGAAGCCCCACCCCTTCTTTGAGTCCTCTTGGTAGCTGAGCCCCTCCTCCCTTTCTGAGCCCCACCCACC<br>CTGCCTGAGCCCCGCCCCTTCTGTCTGAGTGTCTCCATTCTGAACCCCGCCCCTCTGAGTCTCCTCCCCTTCGGAG<br>CCCTTCCCCTTTTGGAGTCCGGGTCACTTTTTGGAGCCCCCTCCCACTCTCTCATCCCGGTCTTTCTCTGAGTGTC<br>CCCACCTTCTGAGCCCTCGTCTTTCTCTCAGCCCGGCCCCCTTCCAAGCCCCACCATGTCTGAGCCCTTCCCCATT<br>TCTGACCCCTCCCCTCCAACCCTCCTCCCTAAGTCCTTTCTTCTTTTAGAACCCGTCCCCTCTCCGAGTCTCCTCC<br>CCTTTCTGAACCCCCTACCCCTTCTGAGCCCTCCTTCCGCTAAGCCCCCTGCCTGAATCCCCCTTCCCATCCCTCC<br>CTCTGACTCCCTACCCCCTCTCTTGCCCTTTGGCCCTTCCCCGAGTACCTCTTCTCTCCCCAAACCTGGGCAAAGC<br>AGGAGGACCAGAAGTGACAAGCAGGCTCTGTTGCGAGGAGGGGGGGTGCGGACCCAGCCGAAGTCCTAGAGGCTG<br>GATGGTGGGCAAGGGGTCTTGGCCCCTAGTGATCCCCTGGTTCCTGCTCAGATCCCGGCCAGCAAGGAGTTCAAAT<br>CAGAGAAGGGGCACAAGTTCGTGACCGTTCAGGCGCTCTTTGGGAACGTCCAGGTGGAGAAGGTGGTGCTGGTCAG<br>CCTTCAGAGCGGGTACCTCTTCATCCAGACGGACAAGACTATCTACACCCCAGGCTCCACGGGTAAGGGGCTGAGG<br>GTGGCTGCAGAGAGCCAGGGGCAGGGCTGGAGGAAGGGGCAGGGCCTCACCCGGCTCTGCTTTTCTCTCCCACCAC<br>TGCTCAGTCCTCTATCGGATCTTCACCGTTGACCACAAGCTGCTGCCCGTGGGCCAGACCATTGTCGTCACCATTG<br>AGGTACCAGCCGACTGGGGCCCCAGACATACCCAGGGCAGGGACTCGGGGAGAGACAAAGAGAGAGAGAGAAACAG<br>AGAAAGGGATTCCGGCAAAGGCCCAGCAGCAGAGACATAAAGGCAAAAAACAAAACCCCAAAAACGTAAGGGCACA<br>CAGAGAGATCGGGAGAGAGGCGGGGACCCAGCGATGCTTACCGTGGATGACGGCTCCAGATAAGTCCCTGGTCACT<br>GTGTGAATCTGGACAGGTCACTTCATCTTTCCAAGCCTCAGTTTCCTCATTTGAAGACTGACACGACAGGTACTAA<br>TTCTATGTAGTCTGTTCCGCCTACTGCCCGCCAGAGGGCGCGTGGGAGCACCTGAGTCAGGTTCCACCCCTCCTCT<br>GCCTGCCGTTTTCCAGGGCTCCCCGCTCCTGGGGTAAATGCCCAAGTCCTCCCCACGGGCCTCAAGGCCCTGCAAG<br>ACCTGCTCCCGCACCCTGCCCACCCTCCTTTCTTCCCTCTCTCTTCCTCCCTCCGCTCCAGCCACGTGGGCCTCGT<br>CACCGTTCTTGCAACAATCCAGGCACAGTCCTGCCCCAAGACCTTTGCAGGGGTTGTTCCCCCTCCCCCCCAAATG<br>CTCTTCCTGCAAATATCCACACAGTTTGCTCCCTCACCTCCTTCAAGTCTTTGCTCAAATGTCACCAGTGTACCAA<br>TTTTACAGTGAGGCTTGTCAGAGCGCCCTGTAAAATTGCAACAGAACACACACACACACACACACACACACACACA<br>CACACACACTCCCTTTTTTGCCTTCCTGCCATCTCTTTTTGGCATCTTATAAATCGGAGTTATTTCCCCCCTCCCT<br>TTTTTGGTCTTTTTATCTTTTTAGGGCCGCACCCGCAGCATATGGAAGTTCCCAGGCTAGGGGTCGATTTGGCCTA<br>GGCCACAGCAATGTGGGATCTGAGTTGCACAGCTCACAGCAACGCAGGATCCTTAACCCAGGGAGCGAGGCCAGGG<br>TTCAAACCCAAGTCCTCATGGATACTTGTTGGGTTCGTTAACCACTGAAGCACGATGGGAAGTTTTTTGGGGTTTT<br>TTTTTGTGGGACCTATTCCTTTGTTAACTGCGCCTTCCCCCAATCTGCACTGAACCTAAGTTCTGTTCAGAAAGGG<br>ATTATCTGTTGGCCCAGAGTTTGGCGGGTAGTAGGGTAAATAAAAACTTACTGGAAGAAGGGAGGGAGGGAAGGAG<br>AGGGGAGTGAGAAGCAGGGAGTGATGGGGAGAGAAAGACAAGTGGAGGAGGAAGGGGAGGAATGGGGCCTGTCCTC<br>CTTGTGGGATCTTTGTATTTATTGAAATCAGGCAAACCTAACAAGGACCAGAGTTTTTGTGTGTGTGTGGTATCAG<br>TATGTGTGTGGGGTTTTTTTGGTTTTTGTTTGTTTGTTTTTTGCTTTTTAGGGCCATACCCTCAGCATATGGAGGT<br>TCCCAGGCTTAGGGTCCAATCAGAGCTACAGCTGCTGGTCTACACCACAGCCACAGAAAGGCAGGATCCAAACCAC<br>ATCTGCGACCTACACCGCAGCTCACAGCAATGCCGGATCCTTAATGCCGGACTGAACATGCAACCTCATGGTTCCT<br>AGTTGGATTCGTTTCCACTGCACTACGATGGGAACTCCAAGGAGCGGGTTCTGAAGGCTGTGTGCTCACTTTAGTG<br>ATGGTGGAAAACAGAGAACACCCTCCTCTAAAGATGTGGCGCTGCCAGACTCCCATTGAACGTCACCTCATGCCAT<br>TGGGAAGAACATATCCACAATTACCTCCACTTGCCAGAGAAGCTAGAGAATCAGATTTCTCTTTGAAGTCTCCTGA<br>TGTTTAGCTATTGGCAACAAATGAAATCATATACTTATTAGGTTGAGCCACACGAAGTTGCTATTCTTGCAGGTCA<br>AAAAGGTGAATGTAGGCAGTGATGTGTGCCTTCTACAAATCAAATGCTCAGCCCAGGGTCCTATATCAAAGGAGGT<br>GATAAATTCTAGTAATTACTAGTCTTCAGAGCGACACAGATCATCACAAGCACTTGCCTACACTAACAGGTCCCAA<br>ACCAGTGACACAGGAGCTGTAGTTATCTCCTTTTTCCAAGAGGTTCACATTGAGCACAAAGAGGTTAAGTAATTTG<br>CCCAAGATCACACAGGCTTGTAAGTGGTGCAGTGGGGACAGGAACCCAGGCTACCTGGTTTGGGTGCCCATTCTTA<br>ACCACTGCCCCTGTAGACACGACACAGAGGAGAACCAAGGGGCTAAGCCTGGTCTCTGAAGAGCCACTTCCCTTCC<br>TGTCTCCTCACAGACCCCTGAAGGCATTGACATCAAACGGGACTCCCTGTCATCCCACAACCAGTTTGGCATCTTG<br>GCTTTGTCTTGGAACATCCCAGAGCTGGTCAAGTAGGTCGGGCCCTCCAGCAGGGGTGGGGTGGAGTGGTCGTGTG<br>TTTTAGGGCTCCCCAGGAGAGGGAGTGGGGGGGCTGCCAGACCTGGCGGACTCACTAGCCTGCCTCCCCCACAGCA<br>TGGGGCAGTGGAAGATCCGAGCCCACTATGAGGATGCTCCCCAGCAAGTCTTCTCTGCTGAGTTTGAGGTGAAGGA<br>ATATGGTAAGAAGAGGAGGGAGCTGGGGGGGGGGGGCGTGCATAATGTTGGACCCAGCGTTGACCCCCCCCACCG<br>AACGAATACCATCTGCTCCCCCCCAATAGTGCTGCCCAGTTTTGAGGTCCAAGTGGAGCCTTCAGAGAAATTCTAC<br>TACATCGATGACCCAAATGGCCTAACTGTCAACATCATTGCCAGGTGAGGGTCTAGGGGGAGGGCCTGGGGAGAGG<br>GAAGGTCAAGGGATAGGGCAGGGATGGAGGGGGAGGGGCTCGTCACGGCCAGTGGACATTTGGGGGAAGACTCCTC<br>TTTTCAGGACCGGGGGAGTCTGAGACCCCTTCCCACTTTGCAGGTTCTTGTACGGGGAGAGTGTGGATGGAACAGC<br>TTTCGTCATCTTTGGGGTCCAGGACGGTGACCAGAGGATTTCATTGTCTCAGTCCCTCACCCGTGTTCCGGTACCT<br>AACAGTGGCCCCCTCTGAGTAACTCTTCCTCTCCCCCTCGGAAGCCCTTCCCCTCCCTGAGCCCTCGCTTTCTCCC<br>CCAGATCATTGATGGGACGGGGGAAGCCACGCTGAGCCAAGGGGTCTTGCTGAATGGAGTACATTATTCCAGTGTC<br>AATGACTTGGTGGGAAAATCCATATATGTATCTGTCACTGTCATTCTGAACTCAGGTGAGGCCCGATCTGAGGGCG<br>GAGGCTCCGTACCACCATGTGGTCCAGCCTGAGAGGGGCAGCTCAGTGGAGGGGAGAGGATCAGAATGAAGGGCGA<br>CCCAGTCTGGTGGGGGGCGGTGTGTCCAGTCTGAGGGAGGAGGTCCAGAATGAAGGCAGGGTCGGGTCTGACAGGG<br>GAGACCTAGGCTGGGACACAAACCCAGTCTGAGGGGGGAGGCCCAGTCAGAGGGGGGAGGCCCAAAATCAAGGTGG<br>GATCCAGTTCATGGGGGAGACCTAGTCTGAGGAAGGTGGGGTCCGTGTTGAGGAGGGCAGTCTGGCCCTCCCTCAT<br>GGCTGGCCCCCCTCAGGCAGCGACATGGTGGAGGCAGAGCGCACCGGGATCCCCATCGTGACCTCCCCCTATCAGA<br>TCCACTTCACCAAGACCCCCAAGTTCTTCAAACCCGCCATCCTTCGACCTCANNNNNNNNNNNNNNNNNNNNNNNN<br>NNNNNNNNNNNNNNNNNNNNNNNNNNNNNNNNNNNNNNNNNNNNNNNNNNNNNNNNNNNNNNNNNNNNNNNNNNNN<br>AGCTGTGGTGTAGGTTGCAGACTCAGCTTAGATCTGGCATTGCTGTGGCTGTGGTGTAGGCCAGAGGCTACAGCTC<br>TGATTTGACCCTTAGCCTAGGAAACTCCATATGCAGTGGGTGTGGCCCTAAAAAAAAAAAAAAAAGTTTTCCCTCCT<br>GCACCAGCTCCAACACCCCAAATAGTTTGGTGTGTGTTTTCTAGAAAAAAAAAAGATACAGGCAGACCTCGGAGTCA<br>GTTCCTGGCCATGTTAATAAAGCAAGTCACATAAATTTTTTAGTTTCCTAGTACATATAAAAGTTATGTTTACACT<br>ATGCTATATTCTATTAACTGTGCAACTGCATTGTTTAAAAAAATGTACATACCTTTATTTTAAAATACTTGATTGC<br>TATCAGAGTTTCCCAGCGGCTCAGCAGATTAAGAATCCAGTATTGTCACTGCTGTGACTCTGGTTACTGCTGTTGA<br>TGGGGGTTCAATCCCCTGGCCTGGAACTTCTGCATGCCGTGGGCATGGCCAAAAAATAAAAGAAGAAAAAAAATTT<br>AAAAATTAAAAAATGCTTTACTGCTATCAACTATACTTCAAAGAAAAAATTGCTAGAGTAAAAAATAAATGCTTTA |

TABLE 9-continued

| lists sequences for the disclosure |
|---|
| TTGCTAACAAAAGTTAACCATCCTCTGATAACGCAGAGGTCACAAGCCTTTGATTTGTTTTTCAAAAATGCAGTAT<br>CTGCAAAACTCAATAAACTGAGGTATGCCTGCATTCTCCTACAAACCCACAGTGCAGTCATTAGAATTAGGACGTC<br>AACATTAATTCATTACTACCCTCAAATCCTCCATCACCATTCAAATTTTGCCAGGGTTTTGTTTTGTTTTGTTTTT<br>TGGTGTTTGGGGTTTTGAGGTTTTGTTTTTGTTTTTGTCGTTTATAGGGAAAGGATCCTGTCCAGAATCACAGGCT<br>GTGTTTTCTGGTTGGGTCTCTTCAGTGTCCTTGGACCTGTCTGACCTTTAGAGCACTTTCTTCTTTCTGTGACTTT<br>CACATCCTTGATGGATACGAAGTACACAGACTGAGATCTTGGGGACTGTCCCACCATCTGGGTCTGCCTGATGCTC<br>CTTCATGACAGCACTCAGGTTTTGCATTTTTGGCAGGACTGTCACGGAAGAGACATCGTGTCCTTCTTGGTGCACC<br>ATTTCAGGTGACAAAGGGTACTGATTTATCCCACTCTTTGGTGATGTGTACCCTGATTGCCTGATTAAGCTAATGT<br>CTGCCGGGTCTCTCCATTGTAAATGTCCTCTTTATTCCTTTTTAGTTATTTTAAAAACTTCTCTTTAACTATCAG<br>ATAGTGGCAAAATTCAAGTCAAGAGAGATTTCCCTCCAAATCAGTGTTCACTTAGCCTTTAAGACAACAGGGGTGG<br>ATTCCTTATATTGTAATGTATGATTTTCAAACACAACCGTACTTTTTTTTTCTTTTCTTTCTTCCTTCCTCCCTCC<br>TTTCATCCCTTCATTCTTCCTTCCTTTCTTCTCTTTTTCTTTCCTTCCTTTTTTTTTTTCCTTACAAAAAAGCACC<br>CACCTCTCAAAGGCAGCCATTGATTGCCAAAATGGGCAAACATTTCTAAATTCCTGTAGTGGAAAGCTAGCAGCCC<br>CTGCAGCCCTCCAAAAAGAAAAAGATTCCCAATACACATGAGCAAAGGATCTTCAGTCTCTTTGCACTTTATAACT<br>AGGCGTGCTGCTTTCTGCTCCAGTGACCCAAGATGTTCTTTTGCAAAGAGGAACGTTTTTTTGCAAGGAGGAAATT<br>TAGACAAAACATCTGATTTAGAGGGGTACAGTTTACACATACGTGGATTTTTTTCAACATTGTGTCATTACTTTAA<br>CCAGTTGGGGGTGAGCCAGAGGATTGATTAAAAGTCAGTACCCCAAAGGCACTTTGATGGATTATTCCAGAGCGCA<br>GATGGATTTAGGCATCTCTGGAATTCCACCTACTTGGTTGTAAGGCAGACCCAGAGCCAAAATAAAATCTGTTCAT<br>CATTTTTTTGAGGAAAGCCCAGCCAGGGTTGAACTCTGTTCCCGCCCAGCTTGCTGATGGTGTCAAGCTGGCTTTT<br>AAAGGCCACCTCCTCTCCAGCAGTCTCCATCAAAGTCCAGGGAATCTTTCAACTCACCCCATTGCTTTCAGGAAGG<br>ACTTTTAACCATCAGACACAGCAGCAGGCATGGTACTCAGGGCCCAGGATGCTTCTGGAGGGTCTTCCGTGCAAAG<br>GTTTCATTCCCTCAAAAACCAAAGAAGGGAAAGAAATCAATACAATTCAGCCTGGATTATTTTTGCCTTTATGCCA<br>ACACAGTTGTAAAATAGGGTTTCCCATATATTTTATGGAAGAAGGAGCCCCCAGAGTCAAATGGGCCTGGGGTCCC<br>TGGAAGTGATCACATGGTCATGGGTGTGTGGCAGCTAGGAATCCCTCCGGGGATTGTAGAGATACGTGTCTAAAAG<br>GGGACAGCGAGAAAGTGAGTCTGTTCCAAACCTGGGTTGTTCCCCTCCTCCCCCTCTTCCCCCAAAAGGTGACCTGG<br>ATGAAGAAATAATCCCAGAGGAAGACATCATTTCCAGAAGCCAGTTCCCCGAGAGCTGGCTGTGGACCATTGAGGA<br>GTTTAAAGAACCAGACAAAAATGGGTAAGGCTGGGATGACCCTGCTTCAACCCCCGCCGCCAGTACCCAGGGACAG<br>CCCCCTCTCATCACACTAGAACTGGACAATGAATTTGCAGGTACCTGGAGTCCCCCTTCTTTTCTTTCTTGGGGGA<br>ATCCCACAACCCAACCTAAAAAAATCAAGCCCTTGGGCTATCAGCCACTGCCCCACACACTACAGTCCGTTCCTTT<br>CGCATCTACTAAAAATTTATCTTGTGTTTGTTTATTCTTCATTCATTATATTTTCTTTCTTTCTCACTGCCTGCGC<br>TGTGACTCCTTTTCTCTCTACATTCTGTTTATCATCATCTTCCACACAACTCATTTCTTATCCTCACCACCACCAC<br>TCTCTGCTCCAAATTTTGAATTTTACACCCAGACTCCTCTCTGCTATGTGAAGCGCCTACACCCCGTCACTAGTGT<br>TACTCTCTTATCGCTGACCTCCCTTGTACCCTCCCATTTATTTCTTTTTTTTTTTTCTTTTGCCCTATCTACCTGC<br>CTCTCTTTCCCATCCCATGTTTGCCATGTTGAATTATGTTTATTTAAGAATATGTTTAGAGAGTGATGTCTCTATT<br>GATGATGACTACCTGCTGTCTCTCATCCGCGCGACATATTCATTATTTATACCATTTGGCGTACTTCACTTGTCTA<br>ACACAATCCTTATCCGTATATAAAGAGATGATGAAGAACCCCCCGCCCGCCCCTGNNNNNNNNNNNNNNNNNNNNN<br>NNNNNNNNNNNNNNNNNNNNNNNNNNNNNNNNNNNNNNNNNNNNNNNNNNNNNNNNNNNNNNNNNNNNNNNNNNNN<br>NNNTAACCCACTGAGCAAGACCAGGGATCCTTAACCCGCTTTGCACAGCAGGAACTCCTGGGCTTTTTTTTTTTT<br>TTTTTTTTTGAGCCCTGAGATTTTTAATCCCCCCCCCCTTTTTTTGGCTTTTCTAGGGCCGCACCCGTGGCATA<br>TGGAGGTTCCCAGGCTAGGGGTCTAATGGGAGCTGTAGCCGCTGGCCTACACCACAGCCACAGCCACAGCCACTCA<br>GGATCCGAGCTGCATCTGCAACCTACACCACAGCTCATGGCAACACCAGATCCTTAACCCACTGAGCAAGGCCAGG<br>GATTGAATCTGCAACCTCATGCTTCCTAGTCAGCTTCGTTAACCACTGAGCCAGGATGGGAACTCCCTTAAATTCC<br>TGACATCTTCTCAACATCAACTCTCTTCTCAAGATCAACTCTCTCTCATCTCATTTTTTTTTTTTTTTTTTTTTTT<br>TTCTTTTCTAGGGACGCTCCCGTGGCATATGGAGGTTCCCAGGCTAGGGGTCGAATCGGAGCTGTAGCCACCAGCC<br>TACAGCAGTGTGGGATCTGAGCCGCATCTGCAACCTACACCACAGCTCAAGGCAACACCAGATCCTTAAGCCACTG<br>AGCAAGGCCAGGGATCGAACCCGAAACCTCATGGTTCCTAGTCGGATTCGTTAACCACTGTGCCACAACGGGAACT<br>CCCAAAATAAGAGATTTTTAAAAACCGTTTTAGGATTCCAGAAACAACTGAGCAAAAAAATATACCAATGGCTGAG<br>TAATAGTCCATCATGTATCTGTACTACATCTTCTTTATCCACTCCTCTGGACACTTAGGTTGCTTCCGTGTCTTGG<br>CTATTGTCAGTAGCACTGCAGTGAACACCTGGTGCATTCAAATTATGGTTTTCTTCAGTCTTTTCCATTTTTAATT<br>CCTTTTTTTCCTTTCAAATAGAGAGCAAGGGGTCTAGCTTTCCTCAGGCAGCATAAGCTAACCAATATTTAACACA<br>ATCATTCTATTTTCCTTGAGGACACTCTATTTATAGCACAAGAACCTGGTTTCTCACCCATGTCCTAAATTAAAT<br>TTAAGTTTAGAAAAATTTATAAAAACAAATAGTAAGTAAGAAATGGTAAGGAGCACCAGTGACTAATCAGACACCC<br>CGAGGGTGATGAGTAAATGACAGTAGGTTGGGAAATAAGGATTTTGTTCAAGCCTCTGATTATAATTTTTTTTTT<br>GCTCTTGAAGAATAAGAACAATGCACAAATCTTAATAGATTTCTTAGTGTAACATTATTAATAATGTGTTAACAGT<br>TTGTGCAGTTTCACTTGCATCAGCACTCTGCTTGCATTTGATCAGGTAATTTTTGTGTCATATATAACATTGTTTT<br>CAGCATCATTTTTGATCAAGGTTGTTATCAAAATTCAACGGAGTAAATTTGAAGATGTAATTGGCTTTATTAAACA<br>ATTCATGAATTGGGCAGCGTCTCATCTGGCAGGCAGAGAGATACTCAGAGGAGTTGTGAAAAATGGAAGGTTTTAA<br>TAGAATGAAGTCTAGGGCAAGAGAGTAATCGCAAGATACAAATTTCATCATTGGAGGAAAATAACAATTCAGGTGG<br>GAGAGGATCTCCTTGGCTGAGCTACAGTATTTTCATTCGCTGGGCTTTTTACTGGGCAGGAAGAAAGTCTTCCTTC<br>CTCCTGCTGCAGTAAATTTCACTTCCTATTTGGGAGTGCAAGGTACTTCTCTTTCCTTTGGGGTCTGTAATTGATG<br>CTTCTTCCTGTTGGGATCTGTAATTGACATCTTCCTGTTTGGGGTAATTGACTTGCTTGGTGGAGCATTAGAGCTC<br>CCTCTACAGGCCTTCCCTACTTCAATTTAGTTAAGGTTTACTTTTACTAATTTTTACAATGTAAATCAGTGCTGTC<br>CATTAGAAATATAATGCAGGTTGTAAACGTCATTTAAAATTTTCTGATAGCCCTGTAAAAAAGGGATAGGTGAGTG<br>AGTTCCCTTGTGGCACAGTGGGTTAGGGATCCTGCATCATCACTGCAGCAGCCCATCCCTGCTGTGGTGTGGGTTT<br>GATCCCTGGCCCAGGAACTTCCACATGCTGTAGGGGCAGCCAAAAAGAAGGGATGGTAGGTGAAATCAATTTTAAT<br>AATACATTTTATTTAATCCAAATATATCCTAGGAGTTCTCATTGTGGCTCAGTGGGTTATGAACCCAACTTAGTGT<br>TGTGAGGATGTGGGCTGGATTCCTGGCCTTGCTCAGTGTGTTAAGGATCCGGCACTACCTCAAGCTTTGCATAGGT<br>CGCAGATGGGGCTGGAAGCTGGTGTTGCTGTGACTGTAGTGTAGGCTGGCAGTGACAGCTCAGATTCAGCCCCTAG<br>CCTGGGAACTTCCACATGCTGCAGGTGCAGCCCTAAAGAGAAAACAAACAAATATATCCAAAATATTATTATTTCA<br>ACATTTTGTAAAAACTTGCAAAACCACTATCACACTGATACTGTTACAATAATAAATCCATTAATATTTTAAAATA<br>AGCTATTAATAATCTCAAAATTGTGATATCTTTTAGTTTTATTTGTACTAAGCCTTCAAAATCTGCCATGTATTTT<br>ATACTTACTGATATCTCAATTAGAATGTTAGCTTTTCATTAGAAATACTTTGATCTGTAATTACCATCCATAAAAT<br>TTACAGTTAAAAAGGAAAGTGTACCCAAGTTGTTGTAAATATTCTTTTTTCTTTCTTTTTTTTTGTATTTTTGACT<br>TTTCTAGGGCCACTTCTGCGGCATATGGAGATTCCCAGGCTAGGGGTCTAATTGGAGCTGTAGCCACCGGCCTACG<br>CCAGAGCCATGTCTGCAATCTACACCACAGCTCACAGCAATGCCAGATCCTTAACCCACTGAGCAAGGACAGGGAT<br>TGAACCCGCAACCTCATGGTTCTTAGTCGGATTCGTTAACCACTGTGCCACAATGGGAACTCTGTAAATATTCTTT<br>AAAAAGTTATCCAGTCACTGAATCAAGCATCCTTTTAAAAATTGAGATACAGGAGTTCTCTGGTAGCCTAGCAGTT<br>AAGGATCCATTGTGCCACTGCTGTGGCTCAGGTCGCTGCTGTGATATGGGTTCAATCCCTGGCCCAAGAACTTTCA |

TABLE 9-continued

| lists sequences for the disclosure |
|---|
| CATGCCATATGCACAGCCAAAAAAGTGTAAAATAAAACAAAATTGTGATCTAATTCACATACCACAAAAGTCACCC<br>TTTGAAAGTGTACAATTCAGCGGTTTTTAGTATATTCACGATGCACATTGTTTTTGTTTTTTGGTATTTTTTTTTT<br>TAGGGCTGCACCCACGGCATATGGAGGCTCCCAGGCTAGGGGTTGAATCAGAGCTGCAGCTGCTGGCCTATACCAC<br>AGCCACAGCAACACCAGATCTGAGCCATGTCTGTGACCTACACTGCAGCTTGAGGAAATGCCACATCCTTAACCCA<br>CTAAGCAAGGCCAGGGATCGAATCCATATCTTCATGGATACTAATTGCATTTGTAACCACTGAGCCGCAATGGGAA<br>CTCCTGCACAGTGTTTTTTCTTTTCTTTTTTTTTTTTTTTTTCTTGTCTTTTTGTCTTCTCTAGGGCCGCTCCTGCA<br>GCCTATGGAGGTTCCCAGGCTAGGGATCCAGTTGGAGCTATAGCCACTGGCCTACGCCACAGCCACAGCAACACCA<br>GATCCGAGCTGCATCTGTGACCTACACCACCGTTCATGGCAACACCGGATCCTTAACCCACTGAGCGAGGCCAGGG<br>ATTGAACCCGCAACCTCATGGTTCCTAGTCGGATTCGTTAACCACTGAGCCACGACGGGAACTCCTGGTTTTTAAG<br>TTGAAATCTGAGTTAACTAAAACGAAATAAAAGTAGGAATCCAGTTCTCAACTGAGCTAGCCACATTTCAAGTGCC<br>CAGGGTCCACTTACAGTCATCATTTTGGAGAGCACAGATCAGAACCTTCAGTTATGCTTGCCTTCTTCCCTTCTGC<br>ATATTTACCTATGAATAACATTACAAAGAAAATGAGAATTTCTCTCACAGCAACTCCCATCCACCACCACCACCTG<br>TAAGATATCACTATTAATGATGTGTCTCTGGGCTCTGCCAGGGCAGGCGGAGCTTGGGACAGCTCTTGTGGTCAGG<br>GGTGAGCCCTGAGATATTGGCAGGGTCAGGAACTTGGACCTGAACTTGGATCCAGCCCACCCTCCCTGCCCCCTAC<br>CACCGACGCTGTGTTCTGTTTCCACCTGGGCAGGGATCTGCGTGGCTGACCCCTATGAGGTTGTGGTGAAGCAAGA<br>TTTCTTCATCGATCTGCGTCTCCCCTACTCCGTTGTGCGCAATGAGCAGGTGGAGATCCGAGCTATCCTCTATAAC<br>TACAGGGAGGCAGAGGATCTCAAGGTGAGCCTCTAGTGTGACAGGCATGATGGGGAGCTTGGAGGGAGGGTCCATG<br>GCACACTCTCCTGACTTGATACTCCCTCTTCCTGGCAGGTCAGGGTGGAACTGCTCTACAATCCAGCTTTCTGCAG<br>CCTGGCCACCGCCAAGAAGCGCCACCAACAGACTCTAACGGTCCCAGCCAAGTCCTCAGTGCCCGTGCCTTACATC<br>ATTGTGCCCTTGAAGACTGGCCTCCAGGAGGTGGAGGTCAAGGCCGCCGTCTACAACCACTTCATCAGTGATGGTG<br>TCAAGAAGACCCTGAAGGTCGTGGTGAGTCTTTGGGGATACCTGCTGCCCCTTGTCCTTCAGGAAAGACTCCTGTC<br>TTCCTGTGCTGTGAACCCAGGTTGGAGACCCAGGCTAAGAATACGGAGTACTTCTCAGAAAATTTAGGAGTTCCGG<br>AAGTTTGGAAGCAGGGCTGGGATTAGGGTGAGGCAAGTGAGGCATTCTCCTTGGGCATGGAATTTCAGGGGACACT<br>CCAAAGCTTAGTAACAGAGATCAATGATATTTTTTCGTTAAAATATAGTTTAATGTCAAATATGACATTTCGTAAC<br>ACATTTCAGCAGAGGAGTTTTCTCTTGACTAAAAATCTTGGGAGGAGTTCCCATTGTGGCTCAGTGGTTAACGAAT<br>CCGACTTGGAACCATGAGGTTTTGGGTTCGGTCCCTGGCCTCGCTCAGTGGGTTAAGGATCCAGCGTTGCCATGAG<br>CTGTGGTGTAGGTCGCAGACACCGCTCGCATCCCACATTGCTATGGCTCTGGTGTAGGCCAGCGACTGTGGCTCCA<br>ATTAGACCCCTAGCCTGGGAACCTCCATGTGCCGAGGGAGCGGCCCTAGAAAAAGGCAAAAAAAAAAAAAAAAAAA<br>ATCTTGGGAAAGCATATTTCACAGAACAAATATTATAAAGCCATAACATACAATGCTAGAACAGAGGAAACGTCTA<br>TTTCTACCTATGATTCTTACCTTAAAATATGCATTAACAGTTACTTTTCCATGTCCTATGATTAAACATATAATAG<br>ATAAAATCAACAATAAAAATAAAAGTATTATCATCTTTTAGTAACGTTTTAAAGCAAAATGTGAGATCATAAACAA<br>GATCAAAAATATTTAATTCAAGAGTACCTGTTGTGGCTTAGCGGTAACAAAAATATTTAATTCAAGAGTTCCTGTT<br>GTGGCTCTGACTAGAATCCATGAGGATGTGGGCTTGATCCCTGACCCTGCTCAGTGGGTTAAGGATCTGGCATTGC<br>CATGAGCTGTGGTGTAGGTCATAGAAGCAGCTTGGATCTGGCATTACTGTGGTTATGGTGTAGCCAGCAGCTGCTG<br>CTCCAATTCAACTCCTACCCTGGGAACTTCCATGTGCTGTAAGTGCAGCCCTAAAAAGACAAAAAAAGTAATGCAA<br>TATATTAAGAAATCAAAATTAATGCCCCAAACCCTCACAACAAACAAAATATCAAAATTTTAAATAGAGACAGGAT<br>CTGACAGTGTCAAGGCAAACCATATTGGAGCCTGAAGCAGAAGAAAAATGAGTTGCTCCATAAATGTGCCTGTATG<br>TATTTTTAAATGGTTAATTTTCCCCAAAAACATTACAGTAGCTGAAAAAATATTGAAACATTGAAAACCAAGTGTA<br>TTAAAATTGACAGAGTGATTTTCCATTGAAGTATTTTGTTTATACCCAAACCAGAATTTATTATAATTTTTCTTTA<br>TTGGCTTTAATAAAAGCAAACTCATATTTTTTTCAACTACTTTACTGTTCTGGAATAAAATTAACCATTAAAAATA<br>TGTGAAAGTATATATTTTGGGGCACATATTTTTCTTTCTTTTCTTTCTTTTTTGGGGGGTGTCTTTTTAGGGCCGC<br>ACCATCAGCATATGGAGGTTCCCAGGCTGGGGGTCGAATTGGAGCCATTGGCCTATGTCACAGCCACAGCAACGCC<br>ATTTCTGAGCCAAGTTTGTGACCTACACCACAGCTCATGGCAATGCCAGATCCTTAACCCACTGAGTGAGGTCAGG<br>GATAGAACCTGCATCCTCATGGATACTGGTCAGATTGGTTTTCACTGAGCCACGATGGGAACTCCACACACATTTG<br>TCCTTTTGCCTTGAGTTTCTATATGGCTCAGCTTGGGCACTGGTGAGAAGAAAGCCAGGATTTTGTTAGAGTTTAT<br>ATTGCCCAGCTCCCAAAAGCCAGTGTGCCCATCACTTCACAATTCTGTACTCACTGTGGCTGGTAGCTTGAAAATC<br>ACCATGTTGGGAATATTTACACCAAGGAAATTGGCAGCACTACAAATTAGGAACTTTTCTTCCTGAAAAGCTGGAT<br>GTTATATATTTACCAACACACCATTGGAGGCATCTTAGTCTGCAAAGGAAAATCTGGGAATTACTACCAGGTGAAA<br>GGAGAATGAGTTCTAGGAAGACAAAAACAGCCACCGTCCACCATGGAGATTTATGTGTAGACACATAAGGGCTTGT<br>AGTGGGCCTTTGATCCTAATTAAGACAGTTCTGATTTTAACTGAGCCCTTACTATGTGCTAGGCACTATGTTAAAT<br>ACTTGTGTGAATCCTTTCATTTCTTTTGTGAGAGGGGGGTCTTTTTAGGACCACACCTGTAGCATGTGGGAGTTCC<br>CAGGCTAGAAGCTGAACGGGAGCTTCAGCTGCCAGCCTTCGCCTCTGCCACAGCAACGCCAGATCCGAACCACATC<br>TGCAACGCCACACCACAGCCCATAGCAATGCCGTATCTTTAACCCACTGAGCAGGGCCAGGGATCAAACTCGGGTC<br>CTCATGGATACTAGTCAGGTTCATTACCCTGAGTCACAACAGGAACTCCTCATTTCTTTTTTCTTTACTATTTATT<br>CTCATTTGTTTATTTGAAAATGTTGTTTTACTTTTAAATTATTTGTTTTATTTTACAATTTTTATTTTTATTTTAG<br>TTAGCCTATTGAGAGGCACTGGGTTAAAAACAGACTCTGGAACCAGACTCTCAGGTTCAAATCCACACTGTGTTCT<br>ACTAGCTATGTGACCTTGGGCAAATGACTTCATCCATCTGTACCCCAGTTCCCCCATCTTGAAAATGGAAGTGATA<br>ATAGCAGTATCCACCCCATTGAGTCGTTGTGAGGATTAAATGAATTAACCCCAGTAAAGAAATCTTTTAGGCACAT<br>AGGAAGATTTCTATAGATTTTGTTAGGTCATTATTAACTTATAATTTTATTATTAATCTATACAACAATGGGTACG<br>AGGTAGATGTTTATATTATGTCTTTATAAGGAAGAGAGCTGAGGCACAGACAGGTGAAGTAAGTGACTTCCAGTCA<br>CACAGCTAAGATCTAGTGGATGCCATCGTGCATATGCTACAGTAATCCCCAGAACAATGCCTCGCTGACCAGCTGT<br>CTGTCTGTCTGTCCTTTTCTTCACGGGACTCCCCCTGCCCCCAACACTATCCAGCCAGAAGGAATGAGAGTCAACA<br>AAACTGTGGTCACTCGCACACTGGATCCAGAACATAAGGGCCAACGTGAGTCAGCCACAGAAGGGGTGAGGGCTGG<br>GTGGTTGAGGCAGGGTAGGGTGGGAGGGGGGTGGTTGAGGCAGGGTAAGAGTGGGAGGGGGCTGGTGCAATGGGTG<br>TCTCCCATTCTCCCGGCAGAGGGAGTGCAACGAGAGGAAATCCCACCTGCGGATCTCAGCGACCAAGTCCCAGACA<br>CGGAGTCAGAGACCAAGATCCTCCTGCAAGGTGAGAGGCCCTTGGCTTCGACCCCAGGGGACCCAGAACTGTGTTG<br>GGGGGGCATGAGCCCAGTTCCATCTCATCCCTCCTCCTCTTCAGCTAGAATTTCTCTTTGATCTGCTTCAGGAAGG<br>CTCCAGGCACTATTTAGTTCAGCCAATAGCTTTTGCTGATGAAGAAATTTATTATTTTTTAATGAATTTATTATAT<br>TTATAGTTGTACGACGACCACCACAACCCAATTTTATAGGCTTTCCATTCCTAACCCCCAGCACATCCCCTCTCCT<br>CCCACCCTGCCTCATTTGGAAACCATACGTTTTTCAAAGTCTGTGAGTCAGTATCTGTTCTGCAAAGAAGATAGAT<br>CATTGTAGCTCTGATAAAGAAATTTAAATAAGAAGCAGTATAGTTCCAGAGCAGAAATTCTGGATCTGATTGCCCT<br>GGATGGGGAACTCGGGCAAGAAGGGACAAGATAGATCTGAAAAGGCACCTTGCAACCTGTAAGGTGTAAAGTTTTG<br>GGAGGAGACCCTTGGTTCCCTCATCTGTGACGGGGGCAAATAACAGTATGGTTACCTAAGGGTTGTTGGGTGGGAT<br>TAAATGAGATACTATACAGTGTTCTCTTAGAATAGAGCCTAGCAAATAGCATTAAGCACGATATAAATATTCCTGA<br>CTATTGTTACTGGAATTATGTTACCACTGGTGTGTAACGAGAGGAACCAGGGACTGGAAATCCCCTGTGAAGCACA<br>AGCTCACCCCCACCACTCCGCAAATGCAGAATCCCCCTCCAGCTGCTCAGCTCCTCCCATCACATACCCTCCAGCT<br>GTCCCTGACTCCTTTGGCCCTGGCTGGTCAGAGTCTGGAAATGCTGGGGGCAGCCCTGGTCTTGAATGCCATCTTA<br>CCGTCTGGCTGCAGGGACCCCGGTGGCCCAGATGGTAGAGGATGCCATCGACGGGGACCGGCTGAAGCACCTCATC |

TABLE 9-continued

| lists sequences for the disclosure |
|---|
| CAAACCCCCTCCGGCTGTGGGGAGCAGAACATGATCGGCATGACGCCCACAGTCATCGCTGTGCACTACCTGGACA<br>GCACCGAACAATGGGAGAAGTTCGGCCTGGAGAAGAGGCAGGAAGCCTTGGAGCTCATCAAGAAGGGTATATGCCG<br>CACCTCCTCCTCTGAGCTGTCTAGGCCCCTGAGACCCCGCCCCTCCGAGCCCCCTCCAACCAGAGGCCCCTCCCCT<br>CTAGAGGCCCCACCTCTCTGAGCCCTCTCCAACCAGAGACTCCGCCCCTCTATAGGCACCACCCCTCTGAGCCCCT<br>CCCAACCAGGGGCCCCGCCCCTCCTCTGAGACCACCCCCTTGCTCCTCTCNNNNNNNNNNNNNNNNNNNNNNNNNN<br>NNNNNNNNNNNNNNNNNNNNNNNNNNNNNNNNNNNNNNNNNNNNNNNNNNNNNNNNNNNNNNNNNNNNNNNNNNCC<br>TCTATCTGATCCTCCCACTTTCTACTTTAAGCTCCCCTTCCCCACCCCAAACTTGTCCCCTGCTCAGAACCCTCTC<br>TTTCTTCTCTGTACCCCTGTCCCACCTCTCACAGAATCTTTATCCTCTTTCTAAGCCCCTCCCCTCCCTGGCCTAC<br>CCATGGTAGCCACCCCCTCCACTCAGCCTCTGTTGACACTTCTCCCTTCTCGGCAGGGTACACCCAGCAACTGGCC<br>TTCAGACAAAAGAACTCAGCCTTTGCCGCCTTCCAGGACCGGCTGTCCAGCACCTGGTGAGTCTCCAAGATCTGCT<br>TGCCCATCCTTAGCCTTGCACCTCCCTGAGCAGGGCCTGGATCCCGGCCTCAGGTGGTCTAGGTTGGCCTCGCCCA<br>CACAGCCCTGTGCGACTTGACCCCTCTACTCACGAAGTCAAAACACCAGCCAGATGAGTGGCCTGCATGCCACACC<br>GGGTCCTGAGTTTGGGGAAGAGAAACTGGGCGGACCAGGCCAGGCCCCGCCTCTCTCTGTTCATTGCTTGGCTGGG<br>ATGCAGTCTTCGGATCCCAGAGCCAATTGGCTCATGCTCTGTGTCCGCAGGCTGACAGCCTATGTGGTCAAGGTCT<br>TCGCTATGGCAGCCAACCTCATCGCCATCGACTCCCAGGTCCTCTGTGGGGCCGTCAAATGGCTGATCCTGGAGAA<br>GCAGAAGCCTGATGGAGTCTTCGAGGAGAATGGGCCCGTGATACACCAAGAAATGATTGTAAGAGGAAGGGACTCA<br>GAGCAGGCAGGGGGAGAGGGGCATCTGAGCATCACAGGTTAGCGGGGTGGGGGGGTGGAGGAAGACTCCACCATC<br>CACCCATGGCCCAATCCATTGTGCCAGGGGACAGGGGATAAGGGAGCTGGGAGTGCCACTCCTCCATTGCAAAAAA<br>CAAAGACTTGCAGGATCCGGTGCAAAAGGAAAGTTCCCAGGTCACAGAGCTGCTTAGAGCCGTGGTCCTCAAAGTG<br>TGGTCCCCAAGCCAGCAGCATCAGCACCACCTGCAAACTTGTTAAAAATACACATTTTCAGGATGGACTCCAGAGG<br>CACTGAATCAGAAACAATAGGGGCAACGTCTAGAAATTGGAGCTTTAACGCACATATACACACATCTCTGCTGATG<br>CTGGTGTGTGCTGAAGTTGGAGAGTTGCTGCCTTAGCCTGACCTTGCTGGCTTTCACACAGCTTTCTCCTGCCCCC<br>CTTCACACTCTACCTGGACTGCTAGAAGCCTTGCTCTGTCCAGCCACAGGGCCTTTGAACATGCTGTTTCTGCTGC<br>CTGCCCTGCTAACCCCTGCCCTCTTTGAGAGTTGACTCCTACTCACTCTTCAGATTGTGGTTCCATCTGTCACCCC<br>TCAGAGACACTTTTCCACGACTGAGTCACTCTTCCACTGTCCATTCTCAATGCCATCTCCACTTCTCCTGCACAGC<br>ACTCATCAGTTTGTAATTATATATCTGTGGATGACCTGGTTGGCTCATGTCTGTCTCCCCTACTAGACAGGGAGCT<br>CCATGAGGGCTGGGCTGGGGTCTGGTTTTCTCCCACCATCTTATCCACAGCTCCATCAACATTTGCAGAATGAATG<br>AATGGATACTAAAGAGCTTGGCCCTCTTGGGGAGACCCTGGGGAGAGACCCAGCCCTGCCTTGACCTGCTGATCCT<br>ACAGGGGGGTGGTGGGCATGTGGGGACATGATGTTCACCCGCTCCGGGCTTCCTGCTTCCCCTCTAGGGTGGCTTC<br>AAGAACACTGAGGAGAAAGACGTGTCCCTGACAGCCTTTGTTCTCATCGCGCTGCAGGAGGCTAAAGACATCTGTG<br>AACCACAGGTCAATGTAAGTGTCCCTTGCCTCTCCCTCCTCCCCTCCCCTGCTCAGGACACATCAGGTGAGGTATG<br>GATTTGGGGCCATTTCCAGTCCTCCCAGTGTGACAACCACCATCACAGTGGCCATAAGAGTACCTAACATTTATCG<br>AGCCATTAACTAAGATACTCACCTAAAAGCTTCACATGTTTAAGTCCTGTAATCCTTGTAGCAGCCCAAGAGACAG<br>GCTACCCTTATTATCCCCAGTTTTTAGAAGAGAAAACTGGAGCTCCCATCATGGCTCAGCATAAATGAATCTGACT<br>AGTAGCCATGGGGACACAGGTCTGATCCCTGGCCTTGCTCAGTGGGTTAAGGATCTGGCGTTGCTGTGAGCTGTGG<br>TGTAGATCACAGACGAGGCTCGGATCCTGTGTTGCTGTGGTATAGGCTGGCAACTATAGCTCCTATTTAACCCCTA<br>GCCTGGGAACCTCCATATGCTGTAGGTGCAGCCCTAAAAAGACAAAAAAAAAAAAAAAAAAAAAAGAGAGAGAGA<br>GAGAGAGAAAATTGAGGCACAGAGAGATCAAAGATCAGGTCCTTTCCGCCTGTTCTCCCATTTCTAGAGAGTCATA<br>GCCAATTTCAGCAGAAGTCCTCTCAGTTTGCTTTCCACAGCACTCCTCCACATGCCTCCTTGCTGCTTCCCTAGAG<br>AAAACTCAAGACACAGAGCTTAAAAAGAGGAGAAAAAAAATCCTCAAGACCATTTCCTTAGTTTAGAGGGTCTTTC<br>AGGGTATTTTTTTAAAGGAGTCCATGATCCCAAAAGGGAAGGGATTTAAAATGTTGACTATTCACTGTCCCCTTTT<br>CCTCTGGCTTTGGTTCTGAAGCAGAGAAGTTTGAAAAGACAGGCTCTGGAGAATCTGTAATCACTCCATCTGCTTT<br>GCCCTGGGATTTTGAGGCTGGGTTGCTTGACTTTAGCTTCCCTACAGGGGAACCTCAGGCTCTCATCTTCAGCCAG<br>CTGCTTCTACCTCCTCAGAACCCCAGAAAAGGGATGGAGGGGAGGGGCCGTTGCCTTTAATGCCCAAAAGGGCCCA<br>GGCCTTCCTGGTTCCAACCTGGAAGATTTGAGAGAAATTATAGTAGAAATGAGACAACACTAGGACTAGGCACGGG<br>GTAGGGGTGGGGATGTCAGAGAGAAGTGACTTCAAAGCCTGACTCTCAGGCACTTCCCCTTCAAGGCCTTAATGTG<br>TGCATCTGTAAAACGGGTATGGTGGTCTTTGTATTGTTTAGGACTCTCTGCATTGTCCTAGATGGAACACAAGTGT<br>GACCCAGATTATGCAAAAATAGGGTATTTATTTTAGGGATCCAAGAATTTATCAAGTGCAACGATAAAAGAGTCCT<br>CAGGGACTCTGCCAGAATGCTTCGTTTTTCACGTCCTCCCATATCTTTCCTTCCCTTCTTGCCTAATAATTCAACT<br>TTCCTGGCCATCCGGCCTGCCTGGCCAAACTGTCTTCCTTGGGGAAATAGACCAAAGCACCAGCAGCAGAATCTCA<br>GTGACAGATTCTGATTGGCTCACCGTGGGTCAGGTGATCACCTGTGGACCAATCAGCTGAGGGAGGCAGTAGGTCT<br>TAGTGGGCAACTATGTGCGCTTCTGGTGCGGCCTTGTGAGTGGAAGTGAGGTGTTCTAACAACAGTCATCGACAGG<br>TGTAGAAGAGATTCCTGGGCAGGCAAAAGGATCATTTCTACTGTAATATAACATTTTTTACTATACATATTATAAT<br>GAAGTATGGCATAGGCTGTGGAACCCGACTGCTGGCATTTAAATCAGGAGTATGCTGAACCCATCCGTGTAAAATC<br>TGTAAAACCAGTTGTTAAATTTCCAGGAATTTGCAAGCTGGCTGTTAAACACGATCGTGATTAAATTAAATTATAA<br>ACTTACAGTGAAAAACTGTAAACATTAAACAGTAAAAACAGGCGTTCCCGTCGTGACGTAGCGGAAACTAATCTGA<br>CTAGGAACCATGAGGTTTCGGGTTCGATCCCTGGCCTGGCTCAGTGGGTTAAGAATCCAGCGTTGCCATGAGCTGT<br>GGTGTAGGTCGCAGATGCGGCTCAGATCTGGCGGTGCTGTGGCTGTGGTGTAGACCGGCAGCTGTAGCTCCAATTA<br>GACCCCTGGCCTGGGAACCTCCATAAGCCTCAGGTGCAGCCCTAAAAAGACAAAAAAGATTTTTAAAAAAAGGACA<br>AAAAAAGGAGTTCCGTGGTGGCGCAGTGGTTAACGAATCCGACTAGGAACCATGAGGTTGCGGGTTCGGTCCCTGC<br>CCTTGCTCAGTGGGTTAACGATTCGGCTTGCCGTGAGCTGTGGTGTAGGTTGCAGACGCGGCTCGGATCCCGCGTT<br>GCTGTGGCTCTGGCGTAGGCTGGTGGCTACAGCTCCGATTAGACCCCTAGCCTGGGAACCTCCATATGCCGCGGGA<br>GCCGCCCAAGAAATAGCAACACCACCAAAAGCCAAAAGCCAAAAAAAAAAAAAAAAAAAAAAAAAAAAAGACAAAAA<br>AAAAAGTAAAAACGCAGGTAGTAAACACTTAAAATGTATCACTTCCTAAACATTTTGCTATCTTTTATCATGGTTC<br>TTTTGAGAATTTATGTGTATTGTACTTGTATAGTGGAAATATTATGTAATGTTGAACTACTGCCCATCTCTTCCCA<br>AATCTACATTCAATGATGTGGGTTGATTGATGGATTGAAAGCAGCCATGATAATATTGACATCATAGAAATGACAA<br>ACCCTTCAAATTATGTTTTCCCCCAACCCCTATCTTTCTGGGTCACAGCATTTTTCTCTGACAGGAGGATAATGAT<br>GAAAATAATACCTACCTCATAGTATATTATGAGATTAAGTGAGCAAGTATATGCCTGGGACATAGTAAGAGCTAGC<br>TATGATGGGGATTACTCTCAGATAAGAAGTGTTCCCTTGGTGAGCTGAATCTGGCTCACACTAGCTCACGAGTGCC<br>TACGGGGGGCATCTCTACCCCACTCCATGTTCAGGGACTTCACATTGGTAGCTTAAAACTGACCATGGTAGAATTT<br>TTACACCACAGTAATTGGTGATGCATAAAGGAGCACCCCTCCCCCAACCCCATGCCTCCATTGGAGAGCTGATTGT<br>TAAACATTCACCAGCACACCATGGGGTATACAGACTGCCCCCCCCATCCCCGCTGCCAGCACATAGTAGGTACTCA<br>GCAACAAAGCAGCTCACAATGAGAAAACTTCAAAAGTAGGTAGTAGATCCAAGGCAGGTCCCAAGGACAGATACCA<br>TCCTGGCGCCCAGGAAGTGATGCTTGTGTGATCCTTACTAGTTCTCTGTGGCAGCAACGCCCACTTGATCAGAATA<br>CCCAATCCTCTTTCTCATAGAGCCTGTTGCGCAGCATCAATAAGGCAAGAGACTTCCTCGCAGACTACTACCTAGA<br>ATTAAAAAGACCATATACTGTGGCCATTGCTGGTTATGCCCTGGCTCTATCTGACAAGCTGGATGAGCCCTTCCTC<br>AACAAACTTCTGAGCACAGCCAAAGGTAAGAGGCAGCCTGGAGAGATAAAGAAGGGGGTGCATGGCTAGGGTTTGA<br>GGGTGGTCCTCTCAAGCTGGGATGCATGCCTCTAAGCTGCACTGGGATGTGCATCTCCAAGTGGAGCTGGGCTGGA |

TABLE 9-continued lists sequences for the disclosure

TGGCTCTACAGGTGAAAAGCTCTCATTGTAAACCACACAGGAAGGCTCACTGCATAATTCATGACAGCAGTGAGG
TGTCATTAAGAACATGGGCTCTGACCTCAGGCAGACTGAAACCGAAACCCCACTCAGCCACTTTCTCACTGCCTGA
CCTTGGACAAGTCATTTAACTTCTCTGGACCTTAGTTTCCTCATCTTAATACCTACATCGCAGGGTGGTCATGAAG
ATTAAATGTATAATGCAAGTAGAAGAGAGTCTAGCACACAGTAAGAGCTCTGTCACTGATACCATTAGTGCCTTTA
ATTTTATTTTAATTTTTGTCTTTTTAGGGCCACACCTGCCGCATATGGAAGTTCCCAGGCTAGGGGTTAAATTGGA
GCCACTGCTGCTGGCCTATGCCACAGCACAGCAATGCAGGATCCGAGCCATATATGCAACCTAGCTCACGGAAATG
CCAGATCCTTAACCCACTGAGCAAGGCTAGGGATTGAACCCGCATCCTCATGGATCCTAGTCAGATTCATTAACTG
CTGAGCCACAAAGGGAATCCACCTTCAATATTGTTAAAAATATTATCATTATCTGAAAGCATAGGGAACTTAGCAC
AGTGCCTAGCACAGAGTGAGTGCTTAATTTTTGGTCCCAGCTGATGACACTGTATCATGTTTGCACTCACTGATGT
GACATATCTCAAGTAATGGAATGTAACATATACAAAAGTCATTTAACACAAGAATAATTTATTGGTGGTGGCCGGC
TCTCCTCCACACAGAGATGCAGAGATCTAGGCCTCTATCTTTTCATAGCTCTGCCGCTCAGAATCCATCCATGTAA
GCTGAGGGGGAAATAGTCAGGAAGACTGTGCAAGGGAGGTGGACCAAACATGGAAGGGGTCCCATCATTGCTGTGC
ACATTCCATTGGTCAAAGCTTAGTTATGTGGCCATACCTACCTGCAAAGGCATCTGGGAGATGTAGTCCAACTCTG
TGCCCAGGAAGAGGAGGGTATGATTCTTAGTGACAGCCTCTGCCATCAGTATTTTCTTAGGCACTTGTGACATACA
GTGAATACAGTGCAGCCCTTCCCATTATGGCCTCACACCTCAGTTGAGGAGGGAAAATGAATTAATAGATTACTGT
AGAACATTATAGCATTGGGATAGTAGAAGCACAGGATGCTTTAACGGACAGGAGGAAGAAGGGCCTCACTTCCTCT
TAGGGTGCCATTGAAGCTGAATTGTGCGGGGTGAGAATTAACCACAGGTAGATGGAGAAAAATTGCTCCAAGTAGA
GGGAACAGAATATGCAAAGGCTCATAGGTTTAAAAAAAAAAAGAGCAAGTTTAGGGAATCTCCTGCAGTGGGGCTG
CAGTTGAGAATTCAAATGGAGGAGTGAGGGTTGATGAGGGAAGAGAGCAAGGCAGAAGACAGCAGATTGAGGGTCT
TGAATGTGGGCCAGGACACTTGAAAACCAAGTCCAGTATGAGTCTTTTTTTTTTTTTCTGAGCTTTCTCTGAGCTA
TTTACAGGCTGAACAGAGCATTGAGAGTGGGGGTTCTCTCTGCAGAAAGGAACCGCTGGGAGGAACCTGGCCAGAA
GCTCTACAATGTGGAGGCCACATCCTACGCCCTCTTGGCTCTGCTGGTAGTCAAAGACTTTGACTCTGTCCCTCCT
ATTGTGCGCTGGCTCAATGAGCAGAGATACTACGGAGGTGGCTATGGATCTACCCAGGCAAGTAGCCCCACCCCCA
CCCCACCTCCACCCCAGGCACCTGCATCCCAACCTCTTCTGGCCTCCCACTAGCCTTCTGGAGTAGGCACTGAGAC
CAAGAGAGGTAGGTCTTCTGTCCCATAAGCCAGGATGGTTGGAATGAAGTTGAGAAATCTTTTTTTCCCCCCTTAT
AAACCCATCTCTGGATCTAGACTACATTCTGAGTGCTCCAAGCTGTGTTCTGAGCCTCTCTTTCCCTCTTGACATC
TAGGTCATGTTCTCAGGGCTCAGGTTCAGATGTGAGCCTCTCTCTCCCCCTGGTTCCCCAGTTCCACCAGATTCCC
TATCTTATCCTGTCTCACTGGTAGGTTCTAGATCCTGTTCATCTCACCAGACCCCCAATATTACCTTGTCTCATTG
GTAGGTTCTAGACTGGATTTTTAGTTGTTCTGGGCCATTATCCAAGCTTCTTTCTCTCACTTGTGGGATCTAGACC
ATGTTCTCAGCTCCTTCAGGCTCTCAATATTACCCTGTCTTACTGTGAGTTCTAGAAAAGGGTCTCAGCTATTCTA
GCCCCCAGTAGGTTCTAGACCATGGGTTCTTTAGCCCCCTTTATTTCTAGTGGGCTCTCAATCACATTCTCAGTGT
TTGGGATTCCAAATCAGATGCTCAGTGTTCCCAACTTTACTCTTTTTAATGAGTGGGTTCTAGACATATTCCCAG
CACTTCTAGACTCTTGTCTTAGATGCTCTCCTCTAGATGGGTCTAGACTACTTTCTCACTGTGGCTAGACTTTCAG
TCTTATGTCTGCCCTTTCTGGTGAATTCTAGACATGTTCCCCATGTCTCCAAGCTCTTGTCTGAACCCCTCTCACT
CAGAGAGTTCTAGAACATGTCCTCAGTAGCCAACAACCCTCGATCTTGTTCTTGAAGGCCACAATGGGTGGGTTCA
AGGCCACAGTTTCAGGGCCCCAGCTCTGATCTGAGACTCTTCATCCCTCAGTGGGGTCTAACAACTTTCTTGTTGC
CCAGATTCANNNNNNNNNNNNNNNNNNNNNNNNNNNNNNNNNNNNNNNNNNNNNNNNNNNNNNNNNNNNNNNNNN
NNNNNNNNNNNNNNNNNNNNNNNNNNNNNNNNAAGGTAGCTGCGGGAAACTTTCCCAGGGAAACGGTATTCCGGT
GTGAAATGGTATGGACAAGAAAAGCTATTTCTGTGTGAAATTGTTATCCGCAATCCAGGCTCTGGACCCCTTCCAT
GAATTTTCTGCAGTCCTCATAGTAGTGCTTCGAGGTAGGGTGACCAAGCTATTCTGCCATTCCTGAGACTCTCTCA
GTGTTCGCACTCCAAGTACTGCATCCTGGGAAAAACCCCTTCCCCCAAGACGGGACCTGGGACCCTTGGCTGCGGG
GCTTGCACCTGGGAAATGTCTCCTTGAGCAACAACATACAAAGAAACCAAATGGGACTAAAAATAGCTGCATGGGC
GTTCCCGTCGTGGCGAAGTGTTTAACGAATCCAACTAGGAACCATGAGGTTGTGGGTTCGGTCCCTGCCCTTGCTC
AGTGGGTTAACGATCCGGCGTTGCCATGAGCTGTGGTGTAGGTTGCAGATGCAGCTCGGATCCTGCATTGCTGTGG
CTCTGGCGTGGGCCGGTGGCTGCAGCTCTGATTCGACCCCTAGCCTGGGAACCTCCATATGCGGCGGGAGCGGCCC
AAGAAATGGAAAAAAGACAAAAAAAAAAAAAATAGCAGCATGCTTGCACAGTTGGGGCAGATTATGGACAGCAAGA
TATAAAAAGACCAAAAACCCAGCTGCCATATCTGAGGAGCCAGGAGCAAAAGCTGGGTGCTGTGCATGCCCTCTGC
ACACAGCCCCACCAAGGGGGCAGGCAGACCACCTAAGCCACCCCTCTGGCACCCCTACCCTCACCCCACTTAAGGA
ACCAGCTACACACACACACACACACACACACACACACACACACACACACACCTGCCCCAAGTAAGGGACACACACG
CACATCTGCCCCCAGCAAGGGAATACTTGTTTTCCTTTCTTCCTGCTGCAGCAGGAGCTAAATAAAGCCTTGCCTG
AATTTCTTATCGGGCCTCTTACTCAATTTCTGTTGACTGGGAAAGCCAAGAAGCCTCATGGTTAACACCCCCAGTC
TGGGGCAAGCCGGAATGGTCAGTCACTCTACTTCAAGGTAGACATTAGGACTCCCTTTTCCAGATGCAGAAAAGAG
TGCCCAAGAGAGGTTGCCTAACTGTTCCAGGTCAGCCCCCAAGTCAGAACACAGGAGGAGAGCCAAGCAGACCAGA
CCACGCTGGGAAGGAGTTCAGGAGATTTGCTCATCATTCTGGCTGTACCCCTCATGGGCTACCAGCTTTGACCCAG
CTGCAGCGGAGCCTATAAGAACCAGTGAATTTGTGATTCTCAGAGGAGGAAAGGGGGAGGGGGAAAGGACAGAAGA
AGAGGGAGGGGAGGAGGAGGGAGAAGGGGAGGAGGAAGAGATGGGGGGAGAGGAAAAGGAAGAGGGGGAGGGAAGG
GAGGCGCAGGGGAGGAGGATGGGGAAGGAGGAGAGGGGAGAAGGCTAACATATTACACTTATGATGTTCCAAGTAT
CTACTAAGCACTGCCTATATCTTACCTCGTTTAATCCTCATCAAACCCCTATGGGATTAACTCCTCTTACTCTCAT
TTCCATGGAACCAAAGTCATGGGGCATGGATTGGAACAGCCGAGGTCCCCATGTCAATGAACCCTGGAACCAAGAT
TTGAACCTAGGCAGTGCGACTCCAGAGCCTATCTCATAACAACTCCCCATGGAGTTGAATCCTCAGAACTTAATCC
CATCAGGTAGGCAGGGGTTCATCACCCTACCGGATAATCAGGTGACAAAACCAAGAGATGAAGGCATGTCCCCAAG
GTCTAATTGCCTTCAAGCTGGGGAAGTCTCTTACCAAAATCTGACCACGATCGCCATGGCCACTCACCTGCAAGCA
AAGAGAAGTCTACAGATCCCTTTGATTTTTCTTTCCTCTCTTTTATGGCTGCACCCGCAGCCCATGGAAGCTCCCG
GGCTAGGGGTCAAATCTGAGCAGCAGCTTCCAGCCTACAGCACAGCCATAGCAAAACAGGATCTGAGCCACATCTG
TAATCTGCGCCACAGATCCTTAACCCACTGAAGGAGGCCAGGGATTGAACCTGCATTCTCATGGACACTATGTCAT
GTTCGTAACTCACTGAGCCACAATGGGAAGTCCCTATAGATCCCTCTGAGATCTGGCCATAAGCCATCCTTTCACA
ACCAGGTACCCTGTCTCCCTGGGTACCAGTGATCACAGTGGTGAGTTATGAAAGTGGGAACGGGATGTGAAGAGGA
AAACCCAGTCTCTTTCTGGGGATTTACCTCTATCAGCTCACGAGTTCTTCACACTTTGCCAGGTAAGAAAGGATGG
GATACCAATGTTCATTGCCGCCCTACACACAGTAGCCAAGACGTGGAAGCAACCTATGCATCCATATGCAGAGGAA
TGGATAAAGAAGATGTGGTATATACATACAGTGGAATATTATTCAGCCATAAAAAAGAAGGAAATCATGCCATCTA
CAGCAACATGGATGGACCTAGAGATTATCATACTAAGTGAAGTAAGTCATACAAATTTACAGTTAACCAAGGGGAT
AGCAGGGGGTGGGGAAAGATAAATTAGGATTTGGGGATTAGCAGATACCCACTGCCATATACACAAGGACCTACTA
TATAGCATGGGGAGCTATATTCAATATCTTGTAATAACTTATAATGGAAAATAATCTAAAAGTAAACATGTATGTG
TGTGTGTGTGTTCACTTTGCTATACACCAGAAACTAAAACACCATTGTAAATCAGCTATAATTTTTTTTAAGGGTT
TGGGAGTTCCCTGGTGGTCTAGTGGTAAGGACTCAGCACTTTCTCCATTGCTGCCCAGGTTCAATCCCTGATCTAG
GAACCGAAATCCCACATCAAGCTGCTGCACACCACAGCCAAAAAAATGAAAAAAAAAAAATTTTTTTTGTCTTTTTG
CTATTTCTTGGGCTGCTCCAGCAGCATATGGAGGTTACCAGGCTAGGGGTCAAATCAGAGCTGTAGCCACCGGCCT
ATGCCAGAGCCACAGCAACACAAGATCCGAGCCGCGTCTGCAGCCTACACCACAGCTCACGGCAACGCTGGGTCGT

TABLE 9-continued

| lists sequences for the disclosure |
| --- |
| TAACCCACTGGGCAAGGGCAGGGATCGAACCCACAACCTCATGGTTCCTAGTCGGATTCGTTAACCACTGCGCCAC |
| GACGGGAACTCCAAAAATGAAAATTTTTTAAAATTTTTAATGGTTAAAAGAGGGGGGAATATCAGCCACTCTTG |
| GCCCCACCCGCATCCACCTTGCCAGGTTAGCATCCTATCCCCCGCTGTCTCACTAGCCTTGAAGCACTGCCTGACA |
| CATCCAGGCATGTAACAGCACAGCCTCCGAGCAGGTGAACCTCTGTGGTATAATTCACACTCCAGAGCTCCTCCTG |
| GGACCAGGCTGCGGCTGAAAATCTCCTGAAACACCTTCTGAGTGGCCATTTCCTCCTCCTGCCCCATCCTGCTTCC |
| CTCCCTGCAAGGGTCTCCTGAGAGCCCTCCCTCAACAAATGAGTCACATAAAATCCTCATCTCAGGCTTTGCTTCT |
| CCAGAAATGAATGAAAAACAAGTGGCGATCCTTATTTTTGTGTTTCAGTTTTGTTTTGTTTTTTCAAATTTTGAAG |
| GTCTCCTGTGGTGCAGTGGATTAAGGATCCTGTGCTGTCACTGCAGCGGCTCAGGTTGCTGCTGCAGTTGGGGAGT |
| TCAAACCCTGACCCAGGAACTTCCGCATGCCATGCATGTGGCTAAAAAATAAAATGTTAATTGAAGGCACAAGGGA |
| AAGAGCCAGGGTGGGAACCAAGAGACCTGATGTTATCCCTTGTTCGGCCACCATCTCCTAGCAAGTGGCCAGCTGT |
| GGTTCAACCTCCTGGGACACAAGTCTCCTCCCCACCACATTGGGCATATGCATTTTCCTCGTGCAACTTACACTGT |
| GCCATTGACTCCAACGGAGATAACGTGAATATTACCCAGCTGTAGAAACCACAACACCCTGTCGGAAAGAAAAGGA |
| AAACACCATGAAACATCAAGAAGCTCTTTAGATTCAACCTGAAAAATTACTTCTGGCACGGCTTCATGGAAACAGG |
| TTTGGGGAGCCTAGATGAAAGCTGCAGCTGAGTGATATACGTTGTTCAATATAATCTGCACAACAACCATTCCTGC |
| TTTTCTGCATGTCACTTCTGTTTTTCATTCTGTTTATATTATCTTCATTTTCTTTTCAAAGAGTTCTAGCTGATTT |
| TCAAAAATATGCATTTAAGTATGCGTCCTCAAAGGGAACGACATCTCTCCTAAAAGGGCAAAACTGGAGTTCCCGT |
| CATGGCGCAGTGGTTAACGAATTGGACTAGGATCCATGAGGTTGCAGGTTCGATCCCTGGCCTTGCTCAGTGGGTT |
| AACGATCTGGCGTTGCCGTGAGCTCTGGTGTAGGTCACAGACATGGCTCGGATCCCGCGTTGCTGTGGCTCTGGCG |
| TAGGCCAGCGGCTACAGCTCTGATTAGACCCCTAGCCTGGGAACCTCCATATGCGGCAGGATCGGCCCTATAAGGG |
| CAACACGACAAAAAATCAGAGAAAAAAAAAAGGGCAAAACTTGGTTCTTGGGGAAAGATGAAAAACATTGTACTCT |
| TTTATATACAAGACACATAGATATACATATACCATATAAATAAATACACACTATATCTGTAGTATTATTTTTTTTG |
| GTCTTTTGTCTATTTAGGGCCGCACCCACGGCATTTGGAGGTTCCCAGGATAGGGGCTGAATCAGCTACAGCTGCT |
| GGCCTCCACCACAGCCACAGCAACACCAGATCTGAGCTGCAACTGTGACCTACACCACAGTTCACGGTAATGCCGG |
| CCCCTTAACCCACTGAGCGAGGCCAGGGATCGAACCCGCGTCCTCATGGATGCTAGTCTTGTTCATGATGCTAGTC |
| TTGTTCATTAACCACTGAGCCACGATGGGAACTCCTGTAGTATTAATTTTTTTGGGGAGAGTAAGACAATTCATTT |
| TTTTTAATGTCTAAAAGGCAGCCCAGTCCCCCGTATTTAGTTCCTCTCCAACTACATCATCATCATCACCCTCATC |
| ATCACCATCATCTTCAGCATCACCATCACCAGTCTCACCAGCATCTTCACCACCACCATCATCATCCCCATCATTA |
| TCATCACTGCTATCAACCTCATCATTATCTTCAGCATCACCATCATCACCACCACCATCATCATTATCCCCATCAT |
| CATCATCACCATCACCAGTGTCATCACCACCACTCTTTGTTTCTTGCGGGCAGAATAAAGAGTGCTAATGGCAGGG |
| AGTTCCCGTGGCGCAGTGGTTAACGAATCTAACTAGGAACCATGAGATTGCAGGTTCGATCCCTGGGCTTGCTCAG |
| CGGGTTAAGGATCCGCGTTGCTGTGAGCTGTGGTGTAGGTGGCAGATGCAGCTCAGATCCCACATTGCTGTGGCTC |
| TGGCGTAGGCCGGTGGCTACAGCTCCGATTTGACCCCTGTCCTGGGAACCTCCATATGCCGTGGGAGCAGCCCAAG |
| AAATGGTAAAAAGACAAAAAAAAAAAGAGTGCTAATGGCTAATCCCAGTGCTGACACCCCCAAAGAAACAAGGCCA |
| CAATTCAGGATTTGGGGTCCACAGTCACCTGCTCTTTCTAATGAAACCTGCCACTCAACAAGTCTCACAAACCTAA |
| ACTTCCAACTTCCCTCAGTATCACTAATTGAAATTTCTCTTGCTCTTTAGTTATTTTAGAGGCAACAGAGCATCAT |
| GTTTAAGCATATCAACTCTGACATCACATGTTTGGTGTCAAAATCTAGCTTCACCAATTACAGACTGTGCGGCCTT |
| GGGAAAGTTACTTAATTTCTTTGTGCCTATGTTTTCTCTTATGTGTAATAAGGGAAACAAATCCACTGTACAACAG |
| CTGAGGAAACCCACACTTGTTGCTTAGAAAAGGTCTCCTATTCTTAGATTTGAACCAATGATGAAAACTCACAAGA |
| CCCATGAAGGGAACAATGACATGAAAAAAGCAAGACCAAGAAAAACTGACACCTGAAGAAAAAGAAATAAAAGAAC |
| AGGAAAGGAGTTCTCATCTTGGAGCAGCAGAAATGAATCTGACTAGTGTACATGAGGACGTGAGTTTGATCCCTGG |
| CCTCGCTCAGTGGGTTAAGGATCCAGCGTTGCTGGGAGCTGTAGTGTTGGTCACAGATGCAGCTTGGATCCTGCAT |
| TGCTGTGGCTGTGGTGTAGGCCAGCAGCTGTTGCTCTGATTCAACCTCTGGCCTGGGAACTTCCATAAGCTGTGGG |
| TGCAGCCCTAAAAAGAAAAGAAAGAAAGAAAGAAAGAAAAGAAATACCTTCCCTGGTTTCCTCCTTCTATATAACC |
| CCCGATCACACTATACGACAGCTTCTTTCATAGCTCTTATCACCCCTGGAATGCCCCGTTTTATATATTCTTCGGA |
| GCAGCATAGTTTAGGAATAAAACATACAGACTCTGGAACCAGGCTGGCTTTAAAACCCTGGCTCTACTCCCTTATT |
| ACATAAGTGGTCTTGGGCAAGTTATTCAATTTCTTTTACCTCATTTTTTTCTCCTTTGTAAAATGGGACTGTTTCA |
| GGACCCAATATCAGAGGAATTTAGTGAAGACTGAATATGTTCTCTATTTGAGGAACTTAGAACAGTGCTAAGTGAG |
| TGGTTGCTATTACCGTTAGTGGCTTCCTTTCTGCCTACCTCTTCCTGCTGGTAAGTCAGCCTCACAGGGCAGGAAC |
| TTTGTCTGTTCACTGCTCTATCCTCAGTGCCTAGAACGGCAGCTGGTACACGGTGGGTGCTCAGAAAATACATGCC |
| AAATGAAGGACTATAAAGAAATTCTTTCTTGGCAGATGAATTCCCTGATTTTTATCAAAGCTTTCCTGATGAAGAT |
| GTTTGCAGTGTCCAGTCTAGAATTATGATCTCTTGGCTGGATAGCCCAAGGCCCTCCCTTTTCCCTGCAGCCTATA |
| TCCAGTGTAATCTTCCCCCGGACTCCCTAGTCAGCCTCATACTCACCCCAAAAGAGAAGGAAACTGAAGCTCCACA |
| TCTTGCTGTGTTTCTGTCATTCGAAGAGGAGAATCTTTTCTCTGTTCCCAGAGTTTTTAATAACAGAGGGTGTGGA |
| GAGAGGGGAAGGGCAGAGCCAGCATTGCTCAATGCAACCAGAGCATCACAGCCCTTTTTGCTGAGTTGCCACCACT |
| CGGAAAGGACAGTGTAGCAAACCCCTAATTTTCTCCTTTCTCCACAGTGTAGAGAGGTTGGTCTGGCTGGTGGGTC |
| AGTGTGTGGATCCATCTCCCTCTCTCTCTCTCTTTCCTTCCTGCTGGATTCTTTCTTTCTTTTTTTTTTTTTTTTT |
| TAATTGCAGCATAGTTAATTTACAATGTATACACATATATATTCTTTTTCAGCCTTTCCATTACAGGTTATTATAA |
| GATACTGAGTATAATTTACTGTGCTATATAGTAGGTCCTTGTTGTTTATCTCTTTTATATACAGTAGTGTGTATAT |
| GTTAATCCCAAACTCCTCATTTATCTCCCCCTTCCACTTTGTTCTTTCCCCACCAACATCTATCTCCCATTTCTCA |
| TCATCTTATTTTATTGCACCCAGTAATAAATGAGCTTCCACCATCTATCCCCAATGAAGCAAGAGCAAAACTCAAG |
| GGTCCTTTCCCAGTTTTCCCCGTACAATAACCACCATAAACCTCAAGTACCAGGCACTGTGCTAAATATGTTTCCA |
| AGAAAATTTAATTTCATCGCCATGTCAGCATCATCAAGTAGGGATTCCTACCCCTACCTATCTCATTTAAAAATAC |
| AATAGAATGGAAATTGCAACTACCAACCCCAAGCTCCCTGTCAACTATTACATTTAGAATGGATGAGCTAAGCAAT |
| GGGGTCCTGGCTGCACAGCACAAGGAAATATGTCCAGTCTCTTGGAATAGAACATGACGGAAGACAGTATGAAAAA |
| AAGAATGTATATACATGTATGTTTGGGTCACTATGCTGTGCAGCAGAAATTGATACAACGCTGTAAATCAACTACA |
| CTCTAATAAAAAATAAAGAAAGAAAAGTTAAAAATAAAGATGCTAGAAACAAAAAAGAAAAAAGGAAACTGAGGCT |
| TGGAGAGAAGATGTGTCTTGTCCAAGACTACCTGGACTTGAGATTTGAATCCAGGACCCTCTGACCCCAAAGACTA |
| GAACTTTCACCATTTTGTTTGCCTTCAGCTCCCCATAATATCTGATCACTGTCGGTGACACTCCCACTCCATCCCC |
| CCTCCCCAAGCCCAACCGAAGACACACATACACATGCAACTTCTCATAAACAGGGTGGCCTAGGAATATCTTAGTT |
| AGGGTCTCCCAGATGCAGAGGCTGAGACAAGGCGTCTAGTGAAAGCAGTTCATCAGGGAGGTGACCCCAAAAACGC |
| TCCAGCTGAGGATGGGAGAAGTGAGAGAAGGAAGGAAAAGAGCCCACAATGAATGTTATCCAGTAAGTTACCCAGT |
| AAAAAACTGAAACTGAAACAGAGGTTGAGGACATCTGTGCTATGTAGTAGGTCCTTGTTGTTTCTCTCGTTTATAT |
| GTAATTGTGTGTATATGTTAATCCCAAACTACCTAAGAGACAGCCTAAAGCACCCTCTTCAGACTTATCCCAAACG |
| AGGCGGGTGAGGGAGCTGGGGTATTTATCCACCAGATGCTGTCGGTCACTGATTGAGGCTTGTGTTAACTTAAGAC |
| CTGGCCTCCAAGCAGATAGAATGCGCTCCAGACCATAGCCCTGTTGATGACAAAATGCAGTGGCTGGCAGATGTCA |
| GGCTAGGGCACCCAAATCCTGTGCTCCAAGATAAAACAGAAGGGCAAAGCCCAGCCCTGAGGTCTTGGGAAGAAGA |
| GCCCCATTTGTTTTCATATTCTCCTTTTCGCTCTGGGCAAGGCAAAATACCTACCCTGGAATTATGGTCACCGAA |
| GAAGATTCATCAACAGCTCCATCTGTGGATCAAGAGACCCTATCCAGTGAAGCTGCAGCTAAGAACGAGCACGAAA |

TABLE 9-continued

| lists sequences for the disclosure |
|---|
| ATACAGCAAAGCCCTCCAAGAAGGAGGATAAACAGAGCTGTGTTACATTTAAGAGACACACTGGTGGATCAACACA |
| GACCCTAGCACCAGATCGCAGGGGATTTAAATCCCGACTCCACCACTTGCTAGTCATATGCGGTCCTGGGCAACTT |
| CTTAATGTCTCTATGCCTCAACATTCCCATCTGTAAAATGGGGCTGATAAAAGGAGAATCTATTTCATGGAGTTAA |
| GATGAGCATCAGAGGAGTGGGTATATATCTCACGCTTAGAACCAAGCCTGGCACATAGAGAAAACTCCAAGATGTG |
| GCTATTACTCAAATTCTTTGATATTTCTCCCTTCCAGAGGGGGAACCCAGTTTTTCTCTCCTTGAATATGAGCTGG |
| ACTCAGTGACTTGCTTCCAAGGAACAGGAAAAGGAAGATGTGACGTGTGGCCTCTGAAACATCTGAAAGTCATTGT |
| GGCTTCCCCCTCGCTCTTACTTTCCAGGATCATTCAGTTGGGGGAAGCTAGTTATCGTATTGTGAGTTCACTCAAG |
| CAGCGTGATAGAGAAGCCCTCATGAGGAGGAACTGAGATTCCAGCCAAAACCTTGACTGTGACCTCATAAGACACT |
| CTGATCCAGCCCCACCCAGCTAAGCCACCTCTAGATTCCTGACCCTCAGAAACTGTAAGAAAATAAAAGTTTGTTG |
| TTTGAAGCTGTTACATTTGGAGGAGAGATGTGTTACACTGCAGGAGATAACTGATACGCTTAGAACCAATTGTCCT |
| TGTCAATTAAAAAAAGGATAACAATAACATCATAAGAGTTTGAGGTTTGCTGGAATAAAACCTTAAAGTTCTACCT |
| GGCAAAATAATGCCCACTAATATCAGTAATTCTTGTTATTATTATTATCCCATTAGGCTAAGTGGTCACAGCTACT |
| CATTGGCATCTGTTCCTGGGTACCAGCAAGGACAGAAGTCAGCAACCCATTTCATGCAAGACCATCTAATGTGGGT |
| GAGAAAGTTTAGACTTTCTCTGCTGGGCAATAAAGGGATTTCAGCAAAGGAGTAACCATCCTGTTGGTAGTTTACA |
| ACACTCGTGTTGTGTAGACAGGATGTGGTCATGGGTGGGGAGATGGGGAGAAGAACATAGCGACAAGCTCGTCTAG |
| GGCACGGGTTGTGGAGACAGAGAGGAATTTAGGAAGCAGGAAAAGCAGAATGGGGGGAATGCATGCATGTGGGTGG |
| GGGAGTCTAAAGCAGAAGGAGGAATTGACCTCTGGACATTGGGCTACAGAATTGAAAGTTCTTCCCATCCGGCCCA |
| GGCTCCTTCTCGGGGTGGGATGGGATGGGATGAAATGGTGGAGGAGTTTTCCCGCTACTGCCAAAACAAATCGCCA |
| CAAACATATGGCTTGAAACAATACAAATGCAATACACGACAGGTCGGGAGGTCAGGGTCCCCGATGAGTCTTAGGA |
| GGCTGAAATCAAGATATCCATGGGGGCTCCTAGAGGCTCTGGGGAGAAGTCCATTCCCTGTCTTTGACAGCTTCTG |
| GAGGATGCCCATATTCCTTCGCATTCCAAAGCCCCTTCCTCCATCTGCACAGGCGGTGTAGTATCTCAAAATCTCT |
| CTCCTCTCCCTCTCTCTCTCCTTCTCCCTCTTTCTCCCTCTCTTTCACTCTCTCTCCCTTCCTCCCTCCTTCCCTC |
| TCTCCCTCTCTTTCTCTCCCTCCCTCCCTCCTCTCCCTCTCTCACACATACACACATACAAACACACACACATTTG |
| CTCCATGGATGGATGGATGGATAGGTAGGTGGATTGGTGGGTGGGTAAGATATAGATGGATCAATGGATGAATAAA |
| CAGGTAAGTAGATGTGTGTATTATGCTTTGATAGAGAGAGAGAGAGATTGCTCTCATTCTCTAGATACATTTCTCT |
| CATTCTCTCTATCCTCAATTTCTCTCTCTCCCCCACCTCTCCCTCCCCTTTCCTCTCTGACCCTCCCTCCGCTCCC |
| TTAAAAGGACTTTGTGATTCCATTAGACCTACTCAGATAATCCGCAATAATCTCCTATCTCAAAATCTTTAACTTC |
| ACTGCACTTGCAAAGCCCCCTTGGCAGTGTAAGGTATATATGTACAGCTTTCCAGGAGTGGGATATGGACAACCTG |
| GTGGGAATTAGGGGGAATTTCATTATTCTACCTACTGAAGGTGGGGTCTGGGGTCCTGGTGCGTGACTGAGGATGG |
| CAAGATGCCAGTCACCCTTCAAATCCAAAAGAGGTGACCAAGGCTATGAACTCTGGACCACAGAGATCCTCCAGGA |
| TGAGGGCAGGTAGCAGGCGTGAGGGGAGAAAAAAGGGAAGGAAATGCACAATTGGAGCCACATGGCTTGCAGAAGC |
| CTAACCCCTTGTGACTTTCCCAGCAAAGAGGAAATTGAGAGATACTCAAGAAGTCATCTGAGGGTGTAATAGGAAA |
| GAACAAATCTGACTCCATATTAGACCTGTTCCTTTTACTTTAACCTTTGTGTCCTGTTGTTTTCCCTGAAAGAATG |
| TTACCTAGAGCCTGAAATTCATCCCCCAGCCTGCATAGTCTCAAGCCTCTGACCTTTAAGAGTATAACACGTTTCC |
| ATTCACATAGAGATAAAAAGTTGCAGAACAGAGAATTACATTTGTTTTGTTGGAACCTTACAGGAACATCGGTGAC |
| CTGACCTATGCAGACAAAGGACTCCTGTACCAAGAAGGCTGCGACAACCAACCTGCCCTGCCCCACTTCCCCTGGC |
| CTTTAAAAATGCTCTGCTGGGTATTCCCATTGTGGCTCAGTGGTAGCAAACGTAACTAGTATCCTTGAGGACTCTG |
| GGGTTCGATCCCCCAGGCCTCACTTAGTGTGTTAAAGGATCCAGCGTTGCTGTGAGCTGTGGGATAGGTTGCAGAT |
| GCAGCTCAGATCCTGCGTTGTTGTGGCAAAGGCTGGCTGCTATAGCTTGGATTCAACTCCTAGCCTGGGAACTTCC |
| ATGTGCCCTGGGTTCCGCCTGTGGAAAGTAACATAATGTCTTTTCTATCAAAGGAAATCTTGGTTACTCCATTTTG |
| CTCAGGTTTCACCTTCCTGCGACCCCCCCCACCCCTCCCCTTTCCCTCTTCTCCCAATAACAATTTGTTTCAAATT |
| AGCCAGCCGGGAAGAATGTGCACCCTGACCTGACCAATGGGAAGGGGACAGGTACATCACCTGCGTTAGGGATAAA |
| TAGGGGAGGGTCCTTTGTTCGGGGCGCACACTTTTTGGAGTGGCTGTGCCCTTCTGCAGAAGTAAAGAGCCTTGTC |
| GAGATTTCTCCTTGTCCATGTGTCTCACTTTCTGACACTGACGACCCAGCCCGAGCTAGAGTTATTGGAATTTCCA |
| ACAGGCCTTAAAAAAAAAAAAAAAAAAAAAAAAAAAAAGACAATAAACATGCTTTGCTGAAACCCTTTGGGAAGTTCC |
| GGGTTTGGCAGTGGCGGGGGGAGGTGCATGAGGGCCCTTCCCCTCCAGCCCCCGCCCAAGTCTCCTTGCACAGCCC |
| TGCAATAAACCTCTCTCTGCTCCCAACTCCCCTGTTTTGTATAGTTTGGCCGCACTGAGCAACAGGCACATGATCT |
| GAGTTCGGTAACAGAGAAGCCCGGCCCCAGAGCATCCCTGGGTTCATGCTTAATGAGGGTGTTGGAGGAAGGGCGG |
| CTCCTGGGAAGCCCTCCCTACCCAACTGGACCGTGTTCCTCTCTCGTTCCCTCTAAACCCTCCCCTGGCTCCCTGT |
| GACCTTCGGGATGAAGTCCAGTCTCATTAATACGACACTCAAGACCTCACTGAGTCTTATACTGGTGCCCTTCTTC |
| CTTATTGCCCCCCCTCACAAGTCCCAGTCATCCCAAATGAACCTGCAGTGCACACTGTCGCTGACCTGTCCAGCCA |
| TCCTTCAGCTACTGGAGCACCATCCCCCCGCTGCTGCGGGTGTTGCCTGCTAACAGTTCACAGCTTCCCCTTCTCC |
| AGAGAACGTTCCAGTTCAATGCCTGCATAAACCCTCAGGCCCATCCTGCAGCCAATAAGCAATGGGCACAGGGGTC |
| AAAAGCCAGCGTTCACCCCAAGGTGACTTCAACTTAGTGGTGTTATTCAGGCTCCGGGTGTTGGAAATTACAGTAA |
| CTCTGGCTCCGGTTGTCAGTGTTGGAAAGTGAGACACATGGACAAGGAGAAATCTCGACAAGGCTCTTTACTTCTG |
| CAGAAGGGCACAGCCACTCCAAAAAGTGTGCGCCCCGAACAAAGGACCCTCCCCTATTTATCCCTAACGCAGGTGA |
| TGTACCTGTCCCCTTCCCATTGGTCAGGTCAGGGTGCACATTCTTCCCGGCTGGCTAATTTGAAACAAATTGTTAT |
| TGGGAGAAGAGGGAAAGGGGAGGGGTGGGGGGGGTCGCAGGAAGGTGAAACCTGAGCAAAATGGAGTAACCAAGAT |
| TTCCTTTGATAGAAAAGACATTATGTTACTTTCCACACTACCCTTCCTCATCCTCTGCTAAATGTCCTCTCTCAAT |
| AAACCCTGAAACAAACATCCTCAGGGCAGAGTCTGTTTCCAGGGGGACCTAAGAATCCCTCCCAGCCATTAAACTC |
| TAAGCTGTCTCTTGACCTCAGGTTGCACATGGGTACTCACTCCATATTGTAGGCTTCCTTCCCATGTCAATATCAC |
| CTCCTCTTCCGTGCCTTCCTTTGTCAATCTCACCGCCTCTAGGAAGCCTTCCCACAAAAATATCACCTCCCCCAGG |
| GAGCCTTCCCATGTAAAATCACCTCCTCCAGGAAGCCTTCCCATAGAAATATCACCTCCAGAAAGCCCTCCCTGAC |
| CTCTCCTTCAGGATTAGGGACTTCTTCTATGCTTTCCTAATCCCAACACTTAATATGATCTTTGCTTGTTTCTGGA |
| TTTGGGGGTGGGGGTATGCTTGCTTTTGGTTTTTTCTGGGGTTTTTGGCCGCACCTGCTGCATACGGAAGTTCTCA |
| AGCTAGGGGTCAAATCAGGGCTGCAGCTGTCAGCCTACACCACAGCCACAGCAACGCCAGATCCGAGCCACATCTG |
| CGACCTACACCACAGCTCATGGCAACACCAGATCCTTAACCCACTGAACGAGGCCAGGGATTGAACCTGCAGCCTC |
| ATGGATGCTAGTTGGATTTGTTTCCTCTGGGCCACAACAGGAACTCCTGAAAAAACTAAAAATCTTAAAAAAAAAA |
| AAAAAGAAAGAAAGAAAGAACCAATGAGGAAAAAGAAGAAGGAACTGAAGAATCTCCTGACATCCCCCCCTAAGCC |
| CTCAGAACCAAGACCAAGAATGTAAGGGGATGGCCGATGGGCAGCCACTGCCCTCCCCCTGGAAGGAAGGAACACG |
| AGTTCTGCAAGGGGCAGCACTTGCTGAGGGGCAGAGTCCCAGCTTGCTGGGAAGGATGCATAGTTATCCAGGCTCC |
| TAAGACCCCTGGCAAGTGGAGAGGGGGGGTTGTTGAAATTCCCCTAGAACCACACCCAGGTCAAAGATTCCCCAGG |
| ATGGCTACACAACTCAGTGCATAGCCATCCTCAGGCTGCTTTATTACAGCGAAAAGATACAAAGCAAAGACACAGA |
| GGAAACCAAAAATGAGGAAAGGGTTGAAATACATACAAGCTTCCAGCGGAGAGGTTCCCAGGAGAATGGAAGAAGC |
| AGCCCCCATCCATCAATTCCTTTTGCTGCGCTGATCTCGGTATGAGACTCCGACCCCAACCATCCTCTCCCGTTGT |
| GTGATTTTTTTCCTTTCCCCTATAATTTTCCCTGCCATGCCACCCCTCCCCCAAATTGTGTGACCTTCCTTTCATT |
| GTCCTTGCCACAAGTTCCCACCATGACCCTTTACAAGAGTAACATCTCAGGCGTTCCCGTCGTGGCTCAGTGGCTA |
| ACGAATCCGACTAGGAACCATGAGGTTGAGGGTTTGATCCCTGGTCTTGCCCAGTGGGTTAAGGATCCGGCGTTGC |

TABLE 9-continued

| lists sequences for the disclosure |
| --- |
| CGTGAACTGTGGTGTAGGTTGCAGACGCAGCTCAGATCCTGCGTTGCTGTGGCTGTGGTGTAGGCTGGCGGCTATA<br>GCTCCGATGCAACCCTTAGCCTAGGAACCTCCATATGCCGCGGGAGCAGCCCTGAAATGACAAAAAGAAAAACACT<br>AAAGTCTCCTCACAGTTGGAGCTGCTACTCTCTTGAGCTCAGCCCTTTGGTTCCGGAGGCCCTAATAAATCTCTCT<br>TCTTGACTGACTTGGCCTTGGGCGTTCTTCCTTCGAGCAAACCTAACACCAGGGTGGCCTGGAACCAGAGGGGCAG<br>GGCGGGAGGGATCACAAGAGAGCTCCAGAAAATTTAGGGAAACAATGGAAATGTTCCGTATCTTGAGTGTGGCCAA<br>GGTTGCCAAACTCATCCAATTTTTACACTGAGAAACGAAGCAGTTTGTTGTATGTAAGTCACCCTCTCGTAAAATG<br>GATAAGCTTGGCTCCAAAATAAAAGAGGACCCAGCATTCCATCAAATTATTTTCTTGTGCGTGCCACATGAAAGGA<br>CCCAGTTGTGTTATTGTGCAGGCAATATATAAAGGGACCAGTTTATTTTATGCTATATAAAAGGGAACAAAAGATG<br>GGCATTTTGAGTTTCTCCAGGGAGGTGTGGGCTCTTTTACATTTAAACATTTGGGTTTTTTCGTTTTGTTTTTTTT<br>TTTTTTTTGCTTTTCAGGGCCACACCGGCGGCATATGGAGGTTCCCAGGCTAGGGGTTATTTCAGAGCTACAGCTG<br>CCAGCCTACACCACAGCCACAGCAACACCAGATCCGAGCCGCATCTGCGATCTACACCCGACAGCTCACAGCAACA<br>CTGGATCCTTAACCCACTGAGTGAGGCCAGGGATTGAACCCACGACCTCATGTTTCCTAGTCGGATTCGTTTCCAC<br>TGCACCATGATGGGAACTCCTAAACATTTGTTTAAATGGATAGCTTATCTTATTCCACAATAATAAATACATTTGA<br>CCTTAAGAAGCTTAGGAATGATCTAAATCTATACTTCCTTCAAAATTAAAATGAAACCAAAAAAAAAAAAAAAACT<br>AGTACAGTTCACATTTCCTAACTGCACCCTGACAGATAAGAAATGTTTCTTAGAATAATGCCATTTGCAGCAATAT<br>GGGTGGACCTAGAGATTATCATACTAAGTGAAGTTAGTCAGAGAAAAACAAATGTCATATGATATCACTTGTGGAA<br>TCTCAAAAAATGATACAGAAAATTCCTTCGTGATTCAGCAGGTTAAGGACCCAGCATTGCCACAGCTCTGGCATGG<br>GTTTGAACCCTAGCCCGGCGAACTCTGCATGCTGTAGTTGCTGCAAAAAAAAAAAAAAAAAAAAAAAAAAAAATTAA<br>TTAAAAGAATATTTTAAATAAAGTGTTAAATGATATAAATTAACTTATTTACAAAGCAGAAATAGACTCACTGACA<br>TAGAAAACAAATTTATAGTTACCAAAGGGGATAGTGGGGGTAGGGGGGAGATAAATTAGAAGTTTAAGGGTTAACA<br>TATACACATCACTATATATAAAATAGATCAGCAACGAAGACCTACTGTATAACTTAAACTATATTCAACATCTTGT<br>CATAACCTATAATGGAACAGAATCTGAAAAAGGATATATAAACATATTATATAAGTGAATCACTTTACTGTACACT<br>TGAGACTAACACAACGTTGCAGATTAACTATACCTCAATATTTTAATTTCACTCACATACCCTGCCCTGGGACTTA<br>CTAACTCTGACGAAGGCATCCACAGGTGATATTGGTGGACATATTTCAAACACAGCCAGGCAGATATGGCATTGAA<br>TCAAACAGGGGCCTTTATAAACATCTCTTTCTCTCTTTATAAACATCTCTTTCTCTCTCTCTCCACCCCCCCAA<br>CACACTCTCAAACACGCGAGAGCGCTTTCCAACGCAGATAGCACCAAAGTAAAGCCAAGCTTGCCCTCTGGTGGAC<br>AGTATCAGTAGTGTCCCAAACTGCTGGGCTGATACTTGGATCCCAGCTTGGTGAAAGAAGTAGAGAGAGAGAGAGA<br>AAGAGAGGGAGAGAGAGAAAGAAAGGTGTATCTGTGCACCTGAGTTTGTTCACAAGCCTATATATATGAGCCCATA<br>TTTGGGCACCATAAAGGGCCCCTGATGCTTATGGCTTTGTAGCATCCTCACACTGCCCAGTGGTATCTCCCATTCA<br>TTCACCCAAAAGCACAGAGAAGGGACTTATAGAGTCATTTCAGAGTCTTGTTGGACACAAGCAGTCATAGCCTCAT<br>GTAGCCAGGATGGGGCAAGAGGTAGAAACACAGAGCTGGAGGAAGCTAGAGGGAGAGTTTGGATCTAAGTCTCTGA<br>AGGGTAAACATGGGCCTATACTGTTGCAAAGGCAGAGAAACCTATTGTAGATGGAGTGGGCTCTACTCAAAGCCTT<br>TTACTGTAGCACAAAGCCTCTTCTTAATTCTTTAATCCCTTCCAGAGGGCTAGGTTTGGGCTGTTGAGTTAGTACT<br>TGGTATCTTCTAGAAGAGAAATGAGTGAGCCAAAGAAATGACTCTCTAATGGTGGAATGACAATGAAGTCAGGCAT<br>AGGGCAGATTTTCTTTCTTTTTAAAAACAGTTTTTTGAGGTAAGACTGAAACATACAAATTGTACATATTGAGTGT<br>ATACATAGCGATAAGTTTGGGGATACACATCCACTTGTGAGACCATCACCACCATCAAGGCCGTAAACATACCCAT<br>CACTTCTCAAAGTTTCCTTCTGCAGTGGATTTTCATTTTGGGGTCCCATCACATTTCATGGGGACTGTTGACTTGA<br>GGAAAGTCTGTTCTCAGGGAGCCAGCACTCCTGTTTGAGTTGCGGGGGAGTGTCTCAGGTCCCATGAAATATTTTC<br>CCCGCTGCCTCCAAACTCATCAGTTTGAAGCTGTGTGCTGCTCTCTAGTGGCCACCGCTCATTTGGCTCTAAGCTT<br>TCCGCATAGATTGTTCTGGGACCAGACTGAAAGCGCAGGCTCCAAGTCAGGCTTACAACTTTGAGCCTTAAATTGC<br>AGGAGGTGGGGAGCCATGGATTAAGGAGACTTAATCAGTGGACAATTTGAGGTTTTAATCAGTGTGGCCATTTCAC<br>ACTTGACCTGGCAGATTTCCATTCATTAGTATCATCACTTGGTCTCCAGTCTCTCCCATTTCCAATCTATTCTGCA<br>AAAGCACAACCCAAGTCATATAGTCCAGGCAGCAGATTGAATCCTTAGGATGACCCACAGGGACTTATGTAATTTG<br>CATCCTCCTCTTGATCTGGCTGCACTGACCTCTGGAAGCAGGAAAGGGCAGAAGAAAAAGCTGAGCAAATATGCGG<br>GCTCAGCTTGAGTTTACTTAGAATTAGTTTCATGGCGAAAATTAGTGTAGAGGAGCAAGGTAGAGAGTATCTTGAT<br>GGTGGTGGGTGGTTATTATTGACTATGTGGTCAGAGAAGCCATCTTGGACATTTGAGCTGAGACCTTGAGTGAATG<br>GAGAGAGTGCCCAGGGAAAAGGGGGGAGGAGAAAATGTGTGTTAAGGCAGAGGGAATAGCAGGTGCCAAGGCTCTG<br>AGGAGGCTGTTGAGTCAGTACCCTGTATTTTCTGGAAGAGAAATTATTTAGCAAAAGAAATGACTCTCTAATAATG<br>GAATTTTGGGCAATGAAGTGAGACAAGGAACAGATTTTCTTTTTCTGTTAAAAACCATTNNNNNNNNNNNNNNNNN<br>NNNNNNNNNNNNNNNNNNNNNNNNNNNNNNNNNNNNNNNNNNNNNNNNNNNNNNNNNNNNNNNNNNNNNNNNNNNNNN<br>NNNNNNNCCAGCCCGCCCCGGGCCCTGGGAGGGGAAGCCACCCGAACGCCTCAAACCTTTGCTCTGGAAGCCCCAG<br>GAATTTTTCCCCCTCTCCTAGCCGGGATATATGACCCCTCCTCTTTCTGGGGTGGTGGTAATCCTGGGTTCCTGGG<br>CGCCCTGGGGTAACTAGATAGCCCCTCGTGCCAACTCTGGGATTTCTTTTGGAGGTGCAGTGGAGTCAGTGAGGGA<br>AACCAAGTCACCCCTCGGGGGGGACCCGCGGAAGCATGGCGACCGGGAGAACCTGGTGCCTGCTCTCTGGCCGTTC<br>TGGGGGCCCCCCAAGCTGCGGGGAACCCTGTCCCTCTGGCCCTGACTCACGCCGGGCCGGCCGGATTTTCCGGAAT<br>CTGGGGGGGATTAGGGGAGCCGGGGCAGGGGGAGTGGCCTTGCCCCATTCCACACCCCTGTTGGACGTCTGGAGAG<br>GGGACACTGTAGTCCGGCTGGGGCCCCGCCCCTGTTCCCTGGCCCTTCCTGGGAAGGGGAGGGGGTTCCCGCCGGT<br>TTCCTGCTTCCCCCCACCCCACGCCGCTCCGGGGGGGGGCCGGGAAGCCACTCCTTCTGGGAGCTCAGAGCTTGGA<br>GGCTCCCCTGGGCCAGGTCAGCGGGCTGTGGGGTCCCAAAGTCTTGATCCCGGTCCTCCCAATCCCCCGCTAGGAT<br>CAGTTTGAGGTGCTTGAGCGGCACACGCAATGGGGTCTGGACCTGTTGGACAGATATGTGAAGTTCGTGAAAGAGC<br>GGACGGAGGTGGAGCAGGCTTATGCAAAGCAGCTGCGGTGAGACCCTAGGGTGGCCGCGCCCTGGGCTTCGGGGGA<br>GCGGTTGGAGGGCTGGGGGCTCAGTCTTCCTGCCTCTCTCCGTAGGAGCCTGGTGAAAAAATATCTGCCCAAGAGA<br>CCTGCCAAAGATGACCCTGAATCCAAGTAAGAATGAAGAGGGGAGGCAGAGTTAGATTTGGGAGGACTGGGGTATT<br>GGATCCTTTTCCTCTCCCTCCATTTGGGCCACCCAAGCACTCCTGGCTTCTCCACCCAGTTCCACTTAGAGGTATG<br>AGCTGGGAACCAGGAACCGTATTACCTGGGTTGGAATTCAAAATCCACTACTTTCTAGCTGAACTGCTTTGGGCAG<br>TTGACTCCAGTTCTCCGCCTCCATTTTTCTTGCCTATTAAATGGGAGAGGCTCCAACAGTTATTAAATGAATGACT<br>CTGAGCAAGTGACTTAAGTTTTGTGCCTCTGTCTTCCTCACTGTGAACTGGGGATGATGATCACAATACTGATCAT<br>AATGATAATGACCTTGTAGGGGCTCATTTGAAGATTAAGATAATGTGTTAAAACAATGCCCAGCCCATTTCACTTT<br>ATTCCAAGCCCCCAGTTCCAGAATCCCCAAAGCTCTAAGAATCAGAAGCTTTTCTGGGCACCTATCCAGAGGCAAC<br>CTCTGACCTGAACTAATTTGACATTAATTACATTAATTGCGTTCTTGGTTTTTATCCCACTGAGTGTGAATGTTAA<br>TACTTATCATTGAGAGTTCCCGTTGTGGCTCAGCAGGTTAAGAATCTGACTAGTATCCATGAGGATATGGGTCAGA<br>TCCCTGACCTTTCTCAGTGGGTTAAAGCCCTGTGTTGCCATGAGCTGTGGTGTAGGTCACAGATGGGGCTTGGATC<br>CTGCATTGCTCTGGCTGGGGTGTAAGGCCTGCAGCTGCAGCTCCAATTTGACCCCTAGCCTGGGAACTTCCATATG<br>CCTCAGGTACAGCCCTAAAAAGAGAAGAAAAAAAATCTCATACAAAAATGTTTATTAGATGCTGCCACTAACACCA<br>CTAGGGTAATGTGAAAAGTGATATAAGCATCATATCCCCCTTCTGAACCCCCCTCAAAATCCTGAGAATTCTGAGT<br>TCCCCCTCAGCGGGTGGGGATAAGGGAGATTGGTTAGAATTTATCATTGCTTCTGGGTGAATGTTTTGGAGCTTAC<br>ACTCTTCTGGGGCATATGGCTTCCAAGGGCCCTGACCCCTAGCCCCTGCCCCCTTCCCCCCACCCCAGGTTCAGCC<br>AGCAGCAGTCCTTTGTGCAGCTTCTCCAGGAGGTGAATGATTTTGCAGGCCAGCGGGAGCTGGTGGCTGAGAACCT |

TABLE 9-continued

| lists sequences for the disclosure |
|---|
| CAGTGTCCAAGTATGTCTCGAGCTGGCCAAGTATTCGCAGGAGATGAAGCAGGAGAGAAAGATGGTAGGTGATGCC<br>CTCCTTGGGACTTCCCCAGGGCCCTGGCCACCAGGCTGAGCCTTATTACCCCCTTCTTTCTGTAGCACTTCCAAGA<br>AGGCCGCCGGGCTCAGCAGCAGCTGGAAAGTGGCTTCAAGCAGCTGGAGAATGTGAGTTTGTGCATGGGGAGAAGA<br>GGGGCACCCCTGAGCAGTGGGGTGAGGGTGGCTGATCCATGGAGGTACCCCCTTGGTCTGGCCTGGTCCCCCACCT<br>TCATTGTGGGTTTCCCCCTCCATGTGCTGGGTGACTTCCCACCTGTCCCTGAAACCTTAGTTGGTGGCTCCTTCAT<br>GCCGGTCCTGTCCTCTACACAGAGTAAGCGTAAATTTGAGCGGGACTGCCGGGAGGCAGAGAAGGCAGCCCAGACA<br>GCTGAGCGGCTGGACCAAGATATCAACGCCACCAAGGCTGATGTGGAAAAGGTGCTTGTGCGGTCTGAGGCAGGCT<br>TGGGGGGGGGGGGGGGGCAGGGCCCGAACCTGGCAGTGACCCCTGCTTTCATATTCCTCAGGCCAAGCAACAAGCCC<br>ACCTTCGGAGTCACATGGCAAAAGAAAGCAAAAATGAGTATGCGGCCCAACTCCAGCGCTTCAACCGAGACCAGGC<br>TCACTTCTATTTTTCCCAAATGCCCCAAATATTCGATGTGAGTATTCAAAACCCACAGCCCCACCTCCTCCCCAAA<br>TTCTAAAATTAACCAACTCCTACACATTTGTTGAAACCCCAGCTGCAATGCCCTAATCTCTAAATTGAAAGAGAAT<br>TAGAAATGAAGAGTCACAGTGCACTCTGCCTTTTCTCAAGCTATTCGTTCTGCCCGGGTTGTCTTTCTTTCCTTTT<br>AAAACTTCCATTTATTCTTTCAAGCCCCATCAATTAACCCCTNNNNNNNNNNNNNNNNNNNNNNNNNNNNNNNNNN<br>NNNNNNNNNNNNNNNNNNNNNNNNNNNNNNNNNNNNNNNNNNNNNNNNNNNNNNNNNNNNNNNNNNNNTTCCTGCCTT<br>CTTTGAAATCACCTCCGTTAACTATACCTGACTCCCATGAGTGATTCTGCCATGCACATGTCCAATCTCTCTCTCT<br>CCCCACAGTAGATAATCAATTCCAGGAGAACAAGTATTTGGGCCTGTATTTCTCACTGCTGCATCCTCCATCCCTA<br>GAATCTGGGCGGGCATACAGTAGGTGCTCAACAAGTATTTTTGAATGAGTGCATGAATGAACGAAGAAATGAATGA<br>ATGATTATTGGCTTCAGCTTTGCAACTGAACTCAGCTGAGACTCACTCGAACGCCTCTCCCACGAATGCTGTCTGT<br>GAAAACAGATAGGACCTGATTCCCCCACAGACCCCTGCACCTACCTCTACACATCTGTCCCGGGCCCTGGACACTC<br>GTCTTTCCCCTGCTGGATTCAAATCCGGGCTTGCAGACACAAGAGTAGCTCCCCACACTGTTTCGGCAAATCGCGT<br>GCTCTGGGCAAGTTTTGGGATTGGCACATTCATTTACATCTAGTGAATGGGAATGAAAACCCGGGTCAAGGCAGAG<br>GAAACAGTGAGGACAGGAAGCTGCGAACAGGACATTCATCTCACCCCACAAGGGTAGGAGCGAAGCATTCGAGGGAC<br>GGAACCCCCGTTACCCTCAATTACTGCCTTATCTACTGCTTAGCTCCTAATAGACCCTCAACAAGAATTCAAATCC<br>AAGTTTCTCTACTTGATAGTTATCTATCCTTATGCAAGGGACTGTACCTCTCTGGGCCTCAATTTAATCATTTCTA<br>AAATCAAGATCATAGACGCTACCCATAAGATCATCACATATTACCTGTACAGATGAAACGACCTTTCTTTCCCAAG<br>ATCCAGTTGTTTCCAGTGGGAGATGAGAAACCAGTCAAACAGCTGCACCTGTACCTCCCTGGCAGGTCTTGCAGAT<br>TGAGTGAGGACCACATACTGGGGGGCTTTGAGAACACTCATCTATATCTGGACAGGAAAAGAGAGTCATAGTTGCC<br>AATATGCTCCTTCATGTACAACAGATTGTATTTTTCAAAGAGCTTGAAACACTGTCTTCCATCCCATGTGACCTGC<br>ATGCAATGTCCTTTAACTGGTACACTTTCCATCAAGCAGTGGGTCTATATTTCCTTCCCTTGAATCTGAGTATGGT<br>GGTGGGGACATTAGGTCATCAAAATACCATGGTAAATCATCAAAATATCATACACTTCCACCTTGTTCTCTTGAGA<br>TGCTCATGCTTGGCTCAGCCGCCATACTGTGAGGAAGCCTTGCAAGTCATGAAAAACCAGCTCACACGGTAAGATT<br>AAGACTTCCCACTCACAGCCCTGGAGCAGCCAACCAATAGCCAGCACCATCTTGAAGCCACAGGAGTGAGCCCCCT<br>TCAAAGAGAATCCTCTAGCCCCCAGTTGAGCCAACACAACTCACACTGTGGGGAACAGAGTTGAGCCATTCTCACC<br>CAACTCAGCCCAAATAGCAGATTTATTTGTGAGCAAAATAAATGATTGTTGCTGTCTTAATGTACCAACACCAATA<br>GATAACCAGAACTTTTGCAAACCCACTTCTAGGAATTTACTCATTGGCGCACCCATAGAATTGTGCAGCCATTGTA<br>CCATGGGGTGGGCCTCCCCAAATCTCCTTCAGCCCTGCTCTGCCAAGTCATCCTAAGTAAACATTTGCTTTGAAGT<br>TGCTGGACAAATACAACTTCAAGGCAAGCGCCCTATAGCTCTCTTCCAGGAAAATGCACCTCTCCAAGAGAGAAAT<br>CTGGACCTGCCACATGCATCAAGATAAGATCACAGGGATATTCTTCCCAGTTTTAAGTAATGGAACATTAAACATC<br>TAAATGTCTGTTGATAATAGGATGATTAAATCAGGAGTTGACATAAAGAATAATGTAGCATGTTCCTTCATTTGAG<br>AAATATCTATTGAATATTCACAGTGTCTTAGGTACCATATTGGGAGTCAAAGACATGCAGTGGACAAGGTCCTTAC<br>CATAGTATCCATCATTTTCTAGTTGGGGCATGTTGATTCTACCTGTATTTTATTTTATTTTTTGCTTTTTATGGCC<br>ACACCCACAGCATATGGAGGTTCCCAGGCTAGGGGTCGAATCAGAGCTACAGCTGCTGGCCTACACCACAGCCACA<br>GCAACGCCAGATCCAAGCCACGTCTGTGACCTACACCACAGCTCACGGCAACACTGGATCCTTCACCCCACTGAGCA<br>AGGCCAGGGATCAAACCCACAACCACATGGTTCCTAGTCATATAATTTCTGCTGTTCCATGACAGGAACTCCTGAT<br>CCTACCTGTATTTTAAAACGAGGGACCAAAAAGACTACTGTGCTCACTGAATAATCCATGAACGATAGCCCAAAGG<br>TTTAAAAAAGGATGTTTGGAGCTCCCTAGGAAATATAGTAATAGATATTAAATCATCTTATTCAGAGATTATCAAA<br>CTACAGCCCAAGTGTGAAATCTGGCCCACTACTTGTTTGTGTAAATAAAGTTTTATTGGAACACAGCCACATCCAT<br>TCATTTATGCATTATCTCTGGATGCTTTTGCATTACAACTGGAGTGTTGAATAATCAAGACCTCCATATCATATGG<br>CCTGCAACCTCCAAAATGTTTACTATCTGGCCCCTTGCAGAAAAATTTTGCGGATCCCTGGTCTTATTCAGAAACA<br>TAGTCAGATCTTCACTGTTAAAAGGAAGTTTGGGTCTAAATATAAGGAATACATATCAAAAACTAGCTCATTCTGG<br>GTATTATTTTAGCTTATATTCTTTATGTTAACTGTAGCTCTTGGCACTCTACATGTGCCAAGCAGGTTGTATACAT<br>TATTGCATTTAATTTTCCCAACTATCATTTAAGGTAAATACTTCTTTCTCTCTCTCTCTCTCCCTCTCGGCCACCC<br>TGTGCCATATGGAGTTCCTTCGTCAGATCCCAGCCACAGTTGCAACTCGCACAGCAGCTGTGCCACACCAGATCCT<br>TAACCCACTGTGCTGGGCTGGGGACTGAATTTGCATCCCAGCCCTGCAGAGACGCTGAAGATCCGGTTGCACCACA<br>GCAGAACCCCTAAGGTAGATACTCACATACACCCATTTTATAGATGGAAATATTGAGGCTTAGAGATATTAATGAT<br>GTTTCTGCAACGCTTTACAACTGCTGTGTGGCAAACAGGTAATGTGGTTTGGAGACCGCCATTAGAGTCGGAAAGT<br>CCCGGGTTTGCATTCCAATTTAACTGCATGACTCTGAACACATCACTTCAGATATCCAAGCCTCAGGCTTCTCATC<br>TGTACAATGGAGGTCCTAGCAATGCCTATGCTCAATGTCATGTGAACAGGCACATAAAGCCCTTCACACAGGGCCT<br>GGCACTCCGTACAGGTTAGGAATTCATATTATTCACATGGAAGGAAATCAATGTCTATTTGGGGATATTGGCAAAT<br>AGCATCTTTTTCTTTTTTTCTAATGCAAGTCTCTAATCGCAAGAATTTTTGCTGGCCAGGTATCATTTCTCATAA<br>TCAAAACGCGTTGTCCCGGGCTAAATGTCTGCACCAGACTGNNNNACCNNNNNNNNNNNNNNNNNNNNNNNNNNNN<br>NNNNNNNNNNNNNNNNNNNNNNNNNNNNNNNNNNNNNNNNNNNNNNNNNNNNNNNNNNNNNNNNNNNNNNNNNAGAA<br>GCCGAGAGCCGGGTCCTAAGCAACCGAGGGGACACCCTGGGCCGGCACACTCGGCCCCCAGACCCCCCAGCCAGCG<br>CCCCGCCAGACAGCAGCAGCAGCAACAACGGATCACAGGATAACAAGGAGAGGTGAGCAGGGAGGCCAGAGTGTGT<br>GTCTGCATCCAGGCCCAGGAGTGATGGGGAGGGGTCCTGTCCTCACCGGCTTTGCCCTCTCCAACCAGCTCTGAAG<br>AGCCCCCTGCAGAGGAGGGTCAGGATGCTCCCATCTACACGGAGTTTGATGAGGATTTTGAAGAGGAGCCCGCATC<br>GCCCATAGGCCACTGTGTGGCCATCTACCACTTTGAAGGTAAGGACAGCCTGGGTGGCGCATCGGTGGCTTCGGGG<br>ATAGCATTTTTGGCTAGGCTCTGTTTAGGTTCACCTTGAGCAGATCTGAGCCCACCGCCACCCCCACCCCATGACA<br>GGGTCCAGCGAGGGCACCATCTCCATGGCCGAGGGCGAGGACCTTAGTCTCATGGAAGAGGACAAAGGTGACGGCT<br>GGACCCGGGTCAGGCGGAAACAGGGAGGTGAGGGCTATGTGCCCACCTCCTACCTCCGTGTCACGCTCAACTGAAC<br>CCTGCCAGAGGCGGGAAGAGGGGGGGCTGTTGGCTGCTGCTTCTGGGCCACGGGGGGCCCAGGACCTACGCACTT<br>TATTTCTGCCCCCGTGGCTTCGGCTGAGACCTGTGTAACCTGCTGCCCTCCCCCCCACCCTGCCCCGGAGCCCCCA<br>CTCAAGGGACCCACTGTGCCTTCCACCATCGATGTACATACTCATGTTTCCCATCTTTTCTTCCTGCCACTCGGCT<br>GGGGCCGTTTTGTTTTATATAAAACAATTATGAAAAGCTCTTACAGTCTGTGTCCTATTACGAGATTCTGATACTG<br>GGGCTGGAGATTCAAACACCACCCTCCCGACAGGTGGCACCAGGAAGGAGGAAGGGAAGGCGAACTTGGGCACACG<br>TTGGCATCCCCTGTCCCTTCCTGGGGGGTTGGGTGTGTTGATAGGGAGGAGGGTGCCAGATGTCACCCCTTTGGTG<br>TTCTGCTATAGCTCACTGAGAACAGGTCACACCTGTTGAGCCCCTACTGTGTGCCAGGCATTTTCCACCCATGATC<br>TCATTCAAACGCTGAGCTTTAATCCCCATGACAACCCCTGGAAAGTACACAGTCTCACTTTTATGTTGAAGGCGGG |

TABLE 9-continued

| lists sequences for the disclosure |
| --- |
| GATAGAGAGAGAGGTCAAGTGATCTGCTGGAAGTCACACAGCATTTAAAATGGATTTAAACTCTGGCCTCTTACAG<br>ATCTGCGAGTTCTCTTTAACATTCAAAGCCTCACATTCACCACTTGTGGGATATGTTGAGGGGGGTGTGGGCATGG<br>GGTGGTGAGAAAGGGCGTTCAGAACCTCCAGATGTCGGGTCTTCTCATATGGGGAAGTAGGCTGCCCTCCCTTAGG<br>ATTCGTGCTCAGTTTTAGGGTGCAGGGTGCGTTCTTGCAAACCAGGACCCGTCCCTTCTGTGAGGCTGGGTGCAGG<br>TCCCACTGCATTTGGCTGCCTGAGGACACTGGGGATCCCTGGAAGACTGGGTATCGCCGCGTGAAGAAGTGGATCT<br>GTGCTTTCAAAGGTCAGGCTCCAGGCGCTGCGACAGGACACTGAGGACGTGCTGGAACTTGTCGAAACGTGTGACC<br>CACGGTGCCCCAGCCCCTCTGCTTCCCCAGAGCAGCCTCCGCAAGAAACCGGTGGTCAGGGCCTCTTTCAGCTCAG<br>GGTTGGGCTGGAATCCTGGGGGCGGAGCCAGGTTAGCTGGAGGCGTGGCCAGGCACCTGCCTTACCCTCTGATAAC<br>TGCCTGGTCCCCTTGGGACTTTGACCCAGCAGGGGCCAGGAGGGATTCTGTCCCAGGTTATCTGAACTGCTGGGCA<br>AGGTTAGCGGGGAGGGGGCTCCTGGGTCTCTGCAGGGAGTGGGGTGGGGGTGGCTAACGGGCCCAGTGGAAGCGGG<br>CTCTGCCAGGAGTGCATGGGAGCAGTCTGCTCCAGGTGCAAGACCTGGTGGCCCCACCTTAGGGCTTGTGCCTGGA<br>GATGGAGCTGCCCCGGGGGGCGGGACTTGGGGTCCAGGCTACCCTACGCGACAAACGCCCAGGGGGTGGGGGTGGA<br>GTTGGGCCTAGTTGGAGGGAGAAGAGTGCTAAGTGAAGGCAGGAACTACCCAGGTGGGAGATTCTGGAAGCTGGGC<br>TGCCCCAGAGAGGTGTGGCTCTGAGCTCAGAGGGAGAGCAGTACCATCAGGTTGAAGGACTGAATCATTTTGGGGG<br>GATCGAGATCCTCTGGGGGCAGGACCTTCCCAAGTGTGAGAGAGTGGGACTCTGCGGGCGTGGCTCTGGGGGGATA<br>GGGCCGCCCTTTAGGGGCGGACGGCACCATCTGGTCTATTGCAGCATGCTTGAGTCGAGAAACACCCACCCAGGGC<br>GGGGCCGTCTCAATTTGGGTGGGGCCCTCAGTTTGGGAGGTGTAGCGGGAGGCTCTAGTCCCTGGGCCGGTGGGTT<br>TGGGGGTGCCGGGCTACAGCATACGGCGTGTTCTTAAAGTCAGGATCCTCTGGCAGCCGGGCGCAGATGGGGCGCT<br>CACCTCGCAGGCGCCGGGCTGTCGCCTCGCGGAATCTGGGCGCGTCCCGGGCCGTCTGACGCGCCCGGTCCAGGGT<br>GCGCAGCAGCCGCTCGCAGCTCTCGTCCAAGGGCCCCGGGACTTCCTCGCCCTCCAGCAGGCGCACCACGGGTGCC<br>ACGTGCGGCAGCGCCACCTCGCCCGGGTCGCAAGGTCCTGTTGGGGTAAGGGTCTGGGCTGGGCTAGGGGCAGAGG<br>GTGGGTCCTAGGGTGAAGAGGGTGCGCCATACATTGGGCCGAAACACCCTAGGACAAAAGCAAGGGGTGGAGTTTG<br>GGTCAGATACGAAGTCTTGAGCAGGACCGAGTCAGGGGAGGGGCCCAGGGAAGGGGCGGAGCCTAGGAGATAGTGA<br>GGGCGGGGCCTAGGGATCTGGTCCTGGACCTAGCTTCGCACAGAGGGCGGGGGCTAGGGCGAGGGGGCGGGGCCTT<br>GGACCCAAACAGCCAGCTGAATGTAGGGCGGAGGTGGAGCAAAGGACAGAAACAAGGGGTGGATTTTGGTTGGAAA<br>GAGACCCAGAGGCCAGAGAGCCTAGCAAAGAGCTGGATGGGAGACAGGGACCAGGCCTAAGGCGCGGAGTGGGGTA<br>CTAAAACCCCCGCGGGGCTTAGAACCGGATTGAGGTCCTGATTAGAGTTACCACTTATCTAAAGATGCCACTCACC<br>GGTGCCCTCATCCAGCGTCCGCATTAGAGGCTTCAGCTCCTGCTCGAAGGCCAGCGCAGCCTCCGTGTGGCTCCTC<br>CGGAGCTGGCGCCACGTGCGTTCCAACCGCGACACCTGGAAGAAGAGACCCGAGCCCGCCTTCTCTCCACTCTTCC<br>CCTTCACTTGCTCTCTGGCCTCGTCCCGCATCCCTGCTTCCTACGCACCTGGGGCATGAGCAAGGCGCCCATGACC<br>GCAGCCAGTCCAGGCAGGTCCCCCGCCGCCCCTGGCCGCAGCGCCAGAGCCAGCTCCACCAGGCCCTTCAGGGCGG<br>CGGCGCGCTCCTCCAGCGGTCCCGCGCAGCCCAGCACTGCCAGCGCCCCCGCCAACGCCAGCGTCTCGAGCCTGCA<br>GAGGCGGAGGGCAAGGTTTTGGAGGCAGTGGCGGGGTTTGCGATGTGGGGGTGAGGAGGGAGAGCAGGTGACACAG<br>CTCATCTCCCCTCCTCCCTGGGGGGCCGTGAATGGGGGGGAGGTTGAGGACCCTAGGGATTTTAGGTGGCTGCCTT<br>ACCTCTCCAGCAGTTCCAACCTCAGGCGATGTCCATGGGGAAGAGTGAGCAGCTCCAGACCAGAGGCAACCCCCAT<br>GGCGCCCCGCTGAGCCTTGGTCACCCCCAGGAGGCCTGTCTCCTGGCAGTGGGGGAGGGGTAAGAGTAGGGAGTTC<br>AGAGGAGCAGAATGAGTAAATGGGTATGAGGTGAGACTGGGCCATGCCCTGGCTTCAGCCCTACCTGGTAGGGGAC<br>CCACCTGGCAGTCCACCAATAGCAGGTGGAGGGCAGTGCTCCCAGGATGGTGCTCCAGGAACAGGCCACGGAGAAT<br>GCGCAGGGCTTTAGGTTCCAGAGGCCGATTCTGGGGGCCCAGCAGGCAGGAGGGGTTGTCAGGGGGACAGAAAGAG<br>ACCTCACCCTGTGGTCTTGCAAAACATCTTTGCTCCTCCTCCTCTTCCTCTTCATTGGCCTCCCACCATGGTGCCT<br>CTGGCTCTGGGCAGCTGTGGCCAGGGGGTGTTCCATGGACCCTAGGCACTCGGGGCACCAGCTCACAGTACGTTGG<br>GGAGCGTCCAGAGGCATCAGGCAGCATCAGTGAAGGTGTTCGAGGTGGCTTGGTTGGTGCCTTGGCATGAAGCTGC<br>CCATCGGAGGCCCTCAGGTTGTCAGCAATGGACCCCAGGAGAGCTGGGGTCTTTAGCAACACAGGGTCACTTCCTG<br>TCCGAGGCAATGCAGATGCGGGCACAGTGGAGGCTCCTGGGGGTCACACAAGAGAGGGTAAAAGAGGTCCACAGAG<br>AAAATAGCTGGTTGGGGCTTTGTGGGGTACCAACCTCCAGGTTCATTCACTCGTTCAGCCAATAACCAGGTACCCC<br>ACCTAACCTGGCGCAGCTTTGGACTTGAACGACTTCACCAAAACTCCTCTAGCCCATATGGAGTTTTGCAAATTCT<br>GAATGCTAAATTTTAAATTTGAATTCTTTGTTCTTGCCCCTCGGTTCCTGCATTGCTATAGCTGTGGCATAAGCCA<br>GCAGCTACAGCTCTGATTCAGCCCCTAGCCTCGGAACCTCCATATGCCGTGGGTGTGGCCCTAAAAAGCAAAAATA<br>AATAAATAAATACTCCCGTCTCCATACTCCTTACTCTGTTCTACTTTAGTTTTTGCCCCAAAGCATACATAATTGA<br>CTAATTTTTGTTGTTCATGGTCCTTCTTCCTCTAAAAGGATGTTGGCTCCACCAGCGCAGGGATCTGTGTCATTCT<br>TGTTCATTGATGTTATCACAGCACTTCATACAGTCTCAGGCATGTCACGAGACTTTGGGTGGAGGGCAGGGCTGAC<br>AAGGCAGTCAGGACACAAAGGGGACTCTTCCTTTATGTAGGATTATCAGGGTCGGCTGCTCTGATGAACTCATGTT<br>AGATGAGAAGGAGTCAGTCAGGTAAAGGTAGGGAATGAGCTTTTTCCAGTGGTGAGAATAGCAAGTGCAAAGGCCC<br>TGAGGCCGGAACATATTCGGCAGGTTCCAGCAACTGTAAAAAAGACTGTGTGATTGACGTGAAGAGGGGATGTAGC<br>AGGAGTTATTAGGTCAGCCATGGTTAGAGCATATAGGGCTCCTTGGAATAATAACAAACCCACATTTTATTTTCTT<br>CTTCTTATTTTTGGCCACACCCACAGCATGCAGAAGTTCTGGGGCCAGGGATGGAACCTGTGCCACAGCAGAGACC<br>TGAGCCGCAGCAGTGACAATGCCAGATCCTTAACTTGAGCCAATAGGGAACTCTGGAACTCCATAAACACATATTT<br>TTTTTTAAATTTTTTTACAAAGTTCCTGTGTGTTTTTAAATTACTGTGACAACATGAAGAGTATTACCATCCCTTT<br>TTTCCAAAAGGTTAAGTCCCCTGCCCAAGGTTCCTTAGGTATAGCCTGGCAGAGCCGTCCCTGAGCTCTGTGCTGC<br>CTGGGAAGCCCCTTACCTGGTCCAGGGTGGTCTTCTGTTGGGTGCCCCACATGCTCC |
| SEQ ID NO: 29    C3 cDNA Sequence<br>CTCACTTCCCCCCCACCCCCGTCCTTTCCCTCTGTCCCTTTGTCCCTCCACCGTCCCTCCATCATGGGGTCCACC<br>TCGGGTCCCAGGCTGCTGCTGCTGCTCCTGACCAGCCTCCCCCTAGCCCTGGGGGATCCCATTTACACCATAATCA<br>CCCCCAACGTCCTGCGTCTGGAGAGTGAGGAGATGGTGGTGTTGGAGGCCCACGAAGGGCAAGGGGATATTCGGGT<br>TTCGGTCACCGTCCATGACTTCCCGGCCAAGAGACAGGTGCTGTCCAGCGAGACCACGACGCTGAACAACGCCAAC<br>AACTACCTGAGCACCGTCAACATCAAGATCCCGGCCAGCAAGGAGTTCAAATCAGAGAAGGGGCACAAGTTCGTGA<br>CCGTTCAGGCGCTCTTTGGGAACGTCCAGGTGGAGAAGGTGGTGCTGGTCAGCCTTCAGAGCGGGTACCTCTTCAT<br>CCAGACGGACAAGACTATCTACACCCCAGGCTCCACGGTCCTCTATCGGATCTTCACCGTTGACCACAAGCTGCTG<br>CCCGTGGGCCAGACCATTGTCGTCACCATTGAGACACCTGAAGGCATTGACATCAAACGGGACTCCCTGTCATCCC<br>ACAACCAGTTTGGCATCTTGGCTTTGTCTTGGAACATCCCAGAGCTGGTCAACATGGGGCAGTGGAAGATCCGAGC<br>CCACTATGAGGATGCTCCCCAGCAAGTCTTCTCTGCTGAGTTTGAGGTGAAGGAATATGTGCTGCCCAGTTTTGAG<br>GTCCAAGTGGAGCCTTCAGAGAAATTCTACTACATCGATGACCCAAATGGCCTAACTGTCAACATCATTGCCAGGT<br>TCTTGTACGGGGAGAGTGTGGATGGAACAGCTTTCGTCATCTTTGGGGTCCAGGACGGTGACCAGAGGATTTCATT<br>GTCTCAGTCCCTCACCCGTGTTCCGATCATTGATGGGACGGGGGAAGCCACGCTGAGCCAAGGGGTCTTGCTGAAT<br>GGAGTACATTATTCCAGTGTCAATGACTTGGTGGGAAAATCCATATATGTATCTGTCACTGTCATTCTGAACTCAG<br>GCAGCGACATGGTGGAGGCAGAGCGCACCGGGATCCCCATCGTGACCTCCCCCTATCAGATCCACTTCACCAAGAC<br>CCCCAAGTTCTTCAAACCCGCCATGCCCTTCGACCTCATGGTGTATGTGACGAACCCCGACGGCTCCCCTGCCCGC |

TABLE 9-continued

| lists sequences for the disclosure |
| --- |
| CACATCCCGGTGGTGACTGAGGACTTCAAAGTGAGGTCCTTAACCCAGGAGGACGGTGTTGCCAAACTGAGCATCA<br>ACACACCCGACAACCGGAATTCCCTGCCCATCACCGTACGCACTGAGAAGGACGGTATCCCAGCTGCACGGCAAGC<br>GTCCAAGACCATGCACGTCCTACCCTACAACACCCAGGGTAACTCCAAGAACTACCTCCACCTCTCGTTGCCCCGC<br>GTGGAGCTCAAGCCAGGGGAGAATCTCAATGTTAACTTCCACCTGCGCACGGACCCCGGCTACCAAGACAAGATCC<br>GATACTTTACCTACCTGATCATGAACAAGGGCAAGCTGTTGAAGGTGGGACGCCAGCCGCGCGAGTCTGGCCAGGT<br>CGTGGTGGTGCTGCCCTTGACCATCACGACGGACTTCATCCCTTCCTTCCGCCTGGTGGCTTATTACACCCTGATT<br>GCTGCCAATGGCCAGAGGGAGGTGGTGGCCGATTCCGTATGGGTGGATGTCAAGGACTCATGTGTGGGCACGCTGG<br>TGGTAAAAGGTGGCGGGAAGCAAGACAAGCAGCATCGGCCTGGGCAACAGATGACCCTGGAGATCCAGGGTGAGCG<br>AGGGGCCCGAGTGGGGCTGGTGGCCGTGGACAAGGGCGTGTTTGTGCTGAATAAGAAAAACAAATTGACCCAGCGT<br>AGGATCTGGGATGTCGTGGAGAAGGCAGACATTGGTTGCACACCAGGCAGTGGAAAGGACTTTGCCGGCGTCTTCA<br>CAGATGCAGGGCTGGCCTTCAAGAGCAGCAAGGGCCTACAGACTCCCCAGAGGGCAGATCTTGAGTGTCCGAAACC<br>AGCCGCCCGCAAACGCCGTTCCGTGCAGCTCATGGAGAAAAGGATGGACAAACTGGGTCAGTACAGCAAGGACGTG<br>CGCAGATGCTGTGAGCATGGCATGCGGGACAACCCCATGAAGTTCTCGTGCCAGCGCCGGGCTCAGTTCATCCAGC<br>ATGGTGATGCCTGCGTGAAGGCCTTCCTGGACTGCTGCGAATACATCGCAAAGTTGCGGCAGCAGCACAGCCGAAA<br>CAAGCCCCTGGGGCTGGCCAGGAGTGACCTGGATGAAGAAATAATCCCAGAGGAAGACATCATTTCCAGAAGCCAG<br>TTCCCCGAGAGCTGGCTGTGGACCATTGAGGAGTTTAAAGAACCAGACAAAAATGGAATCTCCACCAAGACCATGA<br>ATGTGTTTTTAAAAGACTCCATCACCACTTGGGAGATTCTGGCTGTGAGCTTGTCGGACAAGAAAGGGATCTGCGT<br>GGCTGACCCCTATGAGGTTGTGGTGAAGCAAGATTTCTTCATCGATCTGCGTCTCCCCTACTCCGTTGTGCGCAAT<br>GAGCAGGTGGAGATCCGAGCTATCCTCTATAACTACAGGGAGGCAGAGGATCTCAAGGTCAGGGTGGAACTGCTCT<br>ACAATCCAGCTTTCTGCAGCCTGGCCACCGCCAAGAAGCGCCACCAACAGACTCTAACGGTCCCAGCCAAGTCCTC<br>AGTGCCCGTGCCTTACATCATTGTGCCCTTGAAGACTGGCCTCCAGGAGGTGGAGGTCAAGGCCGCCGTCTACAAC<br>CACTTCATCAGTGATGGTGTCAAGAAGACCCTGAAGGTCGTGCCAGAAGGAATGAGAGTCAACAAAACTGTGGTCA<br>CTCGCACACTGGATCCAGAACATAAGGGCCAACAGGGAGTGCAACGAGAGGAAATCCCACCTGCGGATCTCAGCGA<br>CCAAGTCCCAGACACGGAGTCAGAGACCAAGATCCTCCTGCAAGGGACCCCGGTGGCCCAGATGGTAGAGGATGCC<br>ATCGACGGGGACCGGCTGAAGCACCTCATCCAAACCCCCTCCGGCTGTGGGGAGCAGAACATGATCGGCATGACGC<br>CCACAGTCATCGCTGTGCACTACCTGGACAGCACCGAACAATGGGAGAAGTTCGGCCTGGAGAAGAGGCAGGAAGC<br>CTTGGAGCTCATCAAGAAGGGGTACACCCAGCAACTGGCCTTCAGACAAAAGAACTCAGCCTTTGCCGCCTTCCAG<br>GACCGGCTGTCCAGCACCCTGCTGACAGCCTATGTGGTCAAGGTCTTCGCTATGGCAGCCAACCTCATCGCCATCG<br>ACTCCCAGGTCCTCTGTGGGGCCGTCAAATGGCTGATCCTGGAGAAGCAGAAGCCTGATGGAGTCTTCGAGGAGAA<br>TGGGCCCGTGATACACCAAGAAATGATTGGTGGCTTCAAGAACACTGAGGAGAAAGACGTGTCCCTGACAGCCTTT<br>GTTCTCATCGCGCTGCAGGAGGCTAAAGACATCTGTGAACCACAGGTCAATAGCCTGTTGCGCAGCATCAATAAGG<br>CAAGAGACTTCCTCGCAGACTACTACCTAGAATTAAAAAGACCATATACTGTGGCCATTGCTGGTTATGCCCTGGC<br>TCTATCTGACAAGCTGGATGAGCCCTTCCTCAACAAACTTCTGAGCACAGCCAAAGAAAGGAACCGCTGGGAGGAA<br>CCTGGCCAGAAGCTCCACAATGTGGAGGCCACATCCTACGCCCTCTTGGCTCTGCTGGTAGTCAAAGACTTTGACT<br>CTGTCCCTCCTATTGTGCGCTGGCTCAATGAGCAGAGATACTACGGAGGTGGCTATGGATCTACCCAGGCCACTTT<br>CATGGTGTTCCAAGCCTTGGCCCAATACCAGAAGGATGTCCCTGATCACAAGGATCTGAACCTGGATGTGTCCATC<br>CACCTGCCCAGCCGCAGCGCTCCAGTCAGGCATCGTATCCTCTGGGAATCTGCTAGCCTTCTGCGGTCAGAAGAGA<br>CAAAAGAAAATGAGGGATTCACATTAATAGCTGAAGGGAAAGGGCAAGGCACCTTGTCGGTGGTGACCATGTACCA<br>CGGCAAGGCCAAAGGCAAAACCACCTGCAAGAAGTTTGACCTCAAGGTTTCCATACATCCAGCCCCTGAACCAGTG<br>AAGAAGCCTCAGGAAGCCAAGAGCTCCATGGTCCTTGACATCTGTACCAGGTACCTTGGAAACCAGGATGCCACTA<br>TGTCAATCCTGGATATATCCATGATGACTGGCTTCTCTCCTGATACTGAAGACCTCAAACTGCTGAGCACTGGTGT<br>GGACAGATACATCTCTAAGTATGAGCTGAACAAAGCCCTCTCCAACAAAAACACCCTCATCATCTACCTGGACAAG<br>ATCTCACACACCCTGGAGGACTGTATATCCTTCAAAGTTCACCAGTACTTTAATGTGGGGCTTATACAGCCTGGGT<br>CAGTCAAGGTGTACTCCTATTACAACCTGGATGAGTCTTGCACCCGGTTCTACCACCCCGAGAAGGAGGACGGGAT<br>GCTAAACAAACTCTGCCACAAAGAAATGTGTCGCTGTGCTGAGGAGAACTGCTTCATGCACCATGACGAAGAGGAG<br>GTCACCCTGGACGACCGGCTGGAAAGGGCCTGCGAGCCCGGCGTGGACTATGTGTACAAGACCAGACTTCTCAAGA<br>AGGAGCTGTCAGATGACTTTGACGATTACATCATGGTCATCGAGCAGATCATCAAATCAGGCTCCGATGAAGTGCA<br>GGTTGGACAGGAGCGCAGGTTCATCAGCCACATCAAATGCAGAGAAGCCCTCAAACTAAAGGAGGGGGGACACTAC<br>CTTGTGTGGGGAGTCTCCTCCGACCTGTGGGGAGAGAAACCCAACATCAGCTACATCATTGGGAAGGACACCTGGG<br>TGGAGCTGTGGCCTGATGGTGATGTATGCCAAGATGAGGAGAACCAGAAACAGTGCCAGGACCTGGCCAACTTCTC<br>TGAGAACATGGTCGTCTTTGGTTGCCCCAACTGATGCCACTCCCCCACAGTCTACCCAATAAAGCTCCAGTTATCT<br>TTCACATTTAAAAAAAAAAAAAAAAAAAAAAAAAA |
| SEQ ID NO: 30 C3 Protein Sequence<br>MGSTSGPRLLLLLLTSLPLALGDPIYTIITPNVLRLESEEMVVLEAHEGQGDIRVSVTVHDFPAKRQVLSSETTTL<br>NNANNYLSTVNIKIPASKEFKSEKGHKFVTVQALFGNVQVEKVVLVSLQSGYLFIQTDKTIYTPGSTVLYRIFTVD<br>HKLLPVGQTIVVTIETPEGIDIKRDSLSSHNQFGILALSWNIPELVNMGQWKIRAHYEDAPQQVFSAEFEVKEYVL<br>PSFEVQVEPSEKFYYIDDPNGLTVNIIARFLYGESVDGTAFVIFGVQDGDQRISLSQSLTRVPIIDGTGEATLSQG<br>VLLNGVHYSSVNDLVGKSIYVSVTVILNSGSDMVEAERTGIPIVTSPYQIHFTKTPKFFKPAMPFDLMVYVTNPDG<br>SPARHIPVVTEDFKVRSLTQEDGVAKLSINTPDNRNSLPITVRTEKDGIPAARQASKTMHVLPYNTQGNSKNYLHL<br>SLPRVELKPGENLNVNFHLRTDPGYQDKIRYFTYLIMNKGKLLKVGRQPRESGQVVVVLPLTITTDFIPSFRLVAY<br>YTLIAANGQREVVADSVWVDVKDSCVGTLVVKGGGKQDKQHRPGQQMTLEIQGERGARVGLVAVDKGVFVLNKKNK<br>LTQRRIWDVVEKADIGCTPGSGKDFAGVFTDAGLAFKSSKGLQTPQRADLECPKPAARKRRSVQLMEKRMDKLGQY<br>SKDVRRCCEHGMRDNPMKESCQRRAQFIQHGDACVKAFLDCCEYIAKLRQQHSRNKPLGLARSDLDEEIIPEEDII<br>SRSQFPESWLWTIEEFKEPDKNGISTKTMNVELKDSITTWEILAVSLSDKKGICVADPYEVVVKQDFFIDLRLPYS<br>VVRNEQVEIRAILYNYREAEDLKVRVELLYNPAFCSLATAKKRHQQTLTVPAKSSVPVPYIIVPLKTGLQEVEVKA<br>AVYNHFISDGVKKTLKVVPEGMRVNKTVVTRTLDPEHKGQQGVQREEIPPADLSDQVPDTESETKILLQGTPVAQM<br>VEDAIDGDRLKHLIQTPSGCGEQNMIGMTPTVIAVHYLDSTEQWEKFGLEKRQEALELIKKGYTQQLAFRQKNSAF<br>AAFQDRLSSTLLTAYVVKVFAMAANLIAIDSQVLCGAVKWLILEKQKPDGVFEENGPVIHQEMIGGEKNTEEKDVS<br>LTAFVLIALQEAKDICEPQVNSLLRSINKARDFLADYYLELKRPYTVAIAGYALALSDKLDEPFLNKLLSTAKERN<br>RWEEPGQKLHNVEATSYALLALLVVKDFDSVPPIVRWLNEQRYYGGGYGSTQATFMVFQALAQYQKDVPDHKDLNL<br>DVSIHLPSRSAPVRHRILWESASLLRSEETKENEGFTLIAEGKGQGTLSVVTMYHGKAKGKTTCKKFDLKVSIHPA<br>PEPVKKPQEAKSSMVLDICTRYLGNQDATMSILDISMMTGFSPDTEDLKLLSTGVDRYISKYELNKALSNKNTLII<br>YLDKISHTLEDCISFKVHQYFNVGLIQPGSVKVYSYYNLDESCTRFYHPEKEDGMLNKLCHKEMCRCAEENCFMHH<br>DEEEVTLDDRLERACEPGVDYVYKTRLLKKELSDDFDDYIMVIEQIIKSGSDEVQVGQERRFISHIKCREALKLKE<br>GGHYLVWGVSSDLWGEKPNISYIIGKDTWVELWPDGDVCQDEENQKQCQDLANFSENMVVFGCPN |

TABLE 9-continued

| lists sequences for the disclosure |
| --- |
| SEQ ID NO: 31 MICA Genomic Sequence<br>GTATCATTTCAGTGAAGGTCACTCCAGTCTTTCATGGAGGCCAAACTAAGGGTGTAAATTAGGATCCTCACTGAAG<br>TGGCGGGACCCTAAGAGGCTTTTTCCTGGCCCCTTAGTTGTGGGTTTTCCTGCGGGCGGCGCAGCCGGTTTCCATC<br>AGAACCGCCCAGAGGCGGACGCTGCCTTCCTGGGGTGACGGAGCAGCAGGAAGCGTTTTCGGATCCTGGAATACGT<br>GGGCGGCCCGTGGGAGGGGCTGAGGCGCAGTTTCCTACTCACCCGGATCCGAATCCTCCGCGGTGCTGTTTCAAGA<br>GAGCCGGATTCCAGATCACGCTCCAGCCCGGACTCGGAATTCCTGCCCTGCGGGTCTGCATTTTCATAACGGGCAG<br>GTGTGAGTGCCCTGCAGCTGGAGACCAGAAGCCTGAAGGCAGCTCGGCCCTCCCCAGCCCACAGCGCCGTTATTCC<br>GTTTCTATATCAGTAAACACATTTCATTTTCCGTAGACCAGGGGGGGGTGACGGGTGATCCCAGTCCTCGCAGTGA<br>ATTCCGGGCAGCAAAATTCAAAACACATGCGGCCAAGGCCGGGCACGGTGGTTCACGCCTGTAATCCCAGCACTTT<br>GGGAGGTCGAGGCGGGCGATCACCTGAGGTCGGGAGCTCGAGACCAACCTGACCAACATGGGGAAATCCCGTCTCT<br>ACTAAAAATATAAAATTAGACGGGCTTGGTGGTGAATGCCTGTAATCCCAGCTAGTCGGGAGGCTGAGGCAGGAGA<br>ATCGCTTAAACCTTGGAGGCGGAGGTTGCGGTGAGCCGAGATCGCGCCATTGCACTTCAGCCTGGGCAACAAGAGG<br>GAAAACTCCGTCGCAAAAACTTTCGGGGGCGGAGCGGAGCCCCGCCCTGGGTTATGTAAGCGACCGCGCTGGGCCG<br>TTTCTCTTTCTTTTCCGGACCCTGCAGTGGCGCCTAAAGTCTGAGAGAGGGAAGTCGCCTCTGTGCTCGTGAGTGC<br>ATGGGGTATAAGGCAAGTGCTGAGGGAGAAAACGTAGTTGATGGGGTAGAGCAGACGGGGTTGGAGGTGGGGTGGA<br>GGGGGAGGGCTTTGGACAGAAGACCTGGGAGGCTTGGTGGGGGAGGGGCGCCCAGGCCTGGGCACTAAGAAACAAG<br>TCCCCTGGAGCTCAAGACCATCTCGGCCTCCCCTAGCCCAAGAGAGGACTGGCTTCATGACTCCCTGAAACCATTT<br>CTAAATGCCTTAGAACAAACCTTGCATATTCATTATTGTTATTGAACTATTAAAAGTCTTTTTTGGGGGCGAGCTG<br>AATCAGATCCTTTGCTGGAGCTGGCACACGGAGGAAGTCCTGGAGGGAGGGTAGACACCGTGGAGGTAAGGGCTTG<br>GGACCTGTGTCAGGAGAGCTAGGTCCATCTCCCTCCCAGTCTCTCACTAGGCTTATGATCTTTAGCAGTGAAAATA<br>ATCTCTCTAAGGTGGGGAAAGGACCCCGGTCCCTGCTGTGCTCAATAAATTATGAGGATCAAAATAAATTATCAGT<br>GAATGTGAATGGGAAAACTAAGAAATTGTTAAAATTCTCGAATACATTACATTTTCATCCACAGAAAAGTGTAGGC<br>TAGGGATCATGGGGGAATAGTTAGTAATGACAGGGATAGTTGAACTTAAAAAAAAAGTTTGTGAGGCTGACAAAGA<br>AGAAACGGACACATTTCCTGATCTTGGAGGGTTCATAGGGTAGAAGATGGTAGATGACAGCTGGGTGTGGTGGCAC<br>TCGCCTGTAGTCCCAGCTACTCAAGAGGCTGTGGTGGGAGGATTGCTTGAGCCCAGGCATTCAAGGCTGCAGTGAG<br>CTATAATCATGCCACTGCATTCCAACTGAGTGACACAGCAAGACTCCTCTCTTAAAAAAAAAAAAAAAAATTCATGG<br>CAGGGCACAATGAGTACTATCAGGAAGGTTCAAACCACGGGCTAAATCAGTAGTTCTAAAACTTGACTACACATCG<br>GAATCACCTAGGGAACTTTAAAAGATACTAAGATTTAGGTCCAACCTGGGTTTACTGATTTAACAACCTAGGTTGT<br>GGCTGTGGCCTGGGAACATGGATATTAAAAACTCTCCAGGTGGTTCTACGCAGTGGCTAGGTTTGATGACCTCTGC<br>CTAGATGTCCCAACGACTAAGAGATGTGCGTTGGGGACAAGGCAATTCTCTTAGTAGAAAGAGGCTTTCGGGACAG<br>CATTCTTATTATTGAGAATTGAGAATTCATATGCCACACAATTTATCCTTTTAAAGTGTGCAGCTCAGTGGCTTCT<br>AGCGTAATCACAAGGTTGTGCCACCGTCACCACTGTCTACCCTGGAAGATTTTTTTTCCTTTTTTTCTTTTTTCTT<br>TTCTTTTTATTTTAAAGGCTAGTCAAGTGAAACAGTGGGAGTGAAGAAGAAACAAAGACATCTATAACTGGTTGTG<br>ATCAATTAGTTGTAAACACTGCACTCAGACCAGCCTGGGAAGATTTTAAGGATATGGTGTGGTCTGATGGGTTCCA<br>AGGCAGAGGTTACAATAGCCTGGAAGAGGGAGACTGCTTAGGCAGTGGCATCCTGGTGGGATAGGGTGAGGAGATC<br>CCAGAGCCCACGTTTACTGCAACCCTGGGGAGATGTCACCAGAGAAATGGGGGTGGTGCCAGACAGCAGATTGTGG<br>CAGCTGAGGTTTTCCACGGTAGAGTAGAAGCATCCATCATGTGTGACATTCAGCAGATGGGGCGCTGTGGGTGGCT<br>TGGAGCACTCTGGTTGTAACTGAGGCAGGCACCGTGTTTAGGAAGGCTGTGCAGTAATCTAGGCTGAAGGGAGGGG<br>AAAGCCTAGACTAAGATTGTGGCTGTGGGATTGAAATAGCGTTGAAGGAGCTGACTTTGACTCCCGGAGATGATGG<br>GGAAAGAGGAAATCAGAAGGGACCAAGGATGGTGATGTTCTTAAGAGAAACTGAGGAGGAAGAGAGGATGATATGG<br>TGGCAGACGTATAGAGAGTCTTTGTAGATCTCTCACATTGGAGGGGACTATGGTCGGAGGTACAGATGTCCTAAGG<br>CAGGCTGGAAAAGGGAGTCTGGAGAGAGCTTGGTGTTGTAGTGAACCACAGGGAGCCGCCTCCTTGGCCCTGTGAT<br>CACCCAGGGACTGAATAGAGAGGCGGCCCTGGGAGACTTCAGACACTTAGAGGATATAAGGGGGTGAAAGGGGGGC<br>CTGGCTTTGAGTCAAAGGGAGGAGAAGGAGATTATAAAGCTGAAACGTCTAAGAGAGTTTGTGGTCTGAGCGGTTC<br>TACTGCGGCAGGTGCTTCTGAGAGGCAGAGGTGGCTGAGATCTGGAAACAGGTCTGCAAATCTGGTCACTGGTCTC<br>ATTGCCAGTAACGCTGTGCGCGGTTGAGGGAGTGTGTTGGGAGAATAGCCACGCGTTGTCTGTCCTGGAAGGAACA<br>AGCCAGTGAGAGCCGGTTTAATGGGGCGGCCGGCGAAAGGGGCTTGGTGAGGCCCGCGCTCCTCGGGGTGGGGGCG<br>CGGGGATGGGTGGTCGCGATGCCGGGAGGGCAGGCAGGGCCCTGGCCGTGCTTATGAAGTTGGAGCTGTACTCTCA<br>GCTACTCGAAGCTGGTCCCTGCTTTAGGCTGCGCTCCCGCGTGCTCCCCATTTTCTGGGCCCCAGGTCCCGCCTTC<br>TAAATCTCCCCAGGTCTCCAGCCCACTGGAATTTTCTCTTCCAAGCGTGGCCCCGCCCTCTCCGCTCGTGATTGGC<br>CCTAAGTTCCGGGCCCCAGTTTCATTGGATGAGCGGTCGGGGGACCGGGCCAGGTGACTAAGTTTCCGCGGCGCCT<br>TCTCCCCGGCCACTGCTTGAGCCGCTGAGAGGGTGGCGACGTCGGGGCCATGGGGCTGGGCCCGGTCTTTCTGCTT<br>CTGGCTGGCATCTTCCCTTTTGCACCTCCGGGAGCTGCTGCTGGTGAGTGGCGTTCCTGGCGGTCCTCGGCGGAGC<br>GGGAGCAGTGGGACGTTTCCGGGGGTCGGGTGGGTAGCGGCGAGCGCTGTGCGGTCAGGGCGGGGCTCCTGTGCCC<br>TGTCGGTGGCGCAGGGAGCTGGACGCGGCCCGTTACCGCCACACTTCAGCCCTGCTTCCCCGTCACTTTTCAGTCC<br>TCCTCGGGATCGCGCATCACCTGCACTTTCTGGTCTCCTCCTGCTCTTTCTCTCCTCGCGTCTCCTCCGCTTCCTC<br>TCACTTTTCGGACAAACCAGTCCTTCTGAGGCCCATGGGTTCCCGGGCTGCCTCCGGGGCTGCTCCTGTGAATGGC<br>ATTCGAGTGCCCTTCCAGCGCGGCCACTGAAGCAGCCACAACCCCCGGTGCTCGGGGCGGCTCTCAGGTCCCTGAA<br>GTCCTGTCCTCTCCCGGAGCCGACGTGTTCTCAGCTCCTGGGCCGCAGCTCCTGGAGTAGGGGCCCTCCTTTCTCG<br>GGACCCGGAGCTGGTGCTTCCTGCTGCTGTGGGGACTGTGGGGGGTCCTGACTCTCAAGCTGAGGGGTTGGAGTCT<br>GCAGGCTCCGGGCAGAGGATTCTTCCTGCGACTTCTCTCATCCCCAGCTCATTCTCCCCTCGCCTCTGGCTCCGAG<br>GGTCCTCTCCTCTCTCTCATCCCACCCCTACTAATGACCAGTGATCTAAGGACACCAGATTCCCTCTCACCTCCTC<br>CCTGCCCATCTCAGGGCCCGCTGAGTCCTTTTGCCCTCCCAGCTCCCTGCTACCCCTTCCTGTGTGCTGTTCTCTG<br>ATCCATTTCTAGGGTGTCCTCTGCCCTCATCCCCTGTCCCCGCCACCGAAGGTCCCTCCTGCACCCCTTATGGGCC<br>TTTCCTACAAGCAGCCTTCACCCAGTGCTGCCCCTATGCCTCCCCGTTCCCAAATGTCCCTGACTCTAACTTTCTG<br>GTGCTGCCTTTTATCCGGGGGGGTCTTCCCTCCATCCCACTCCCCTCCAGACCCCCAAGGGGAACCCTGATGCTAA<br>TGGCAGTTGGGCCTTAGGCAGGGCGCAGGGCAGCGCAGATGCCCCCTCCCCTCCAGTGCAGATGCCTGCTCTGGAC<br>CCTGCCTCATGGTGGCCCCTTCCCCACTCCTTCATCCTCAGCCTCACCCTCTTGAGGACCCCACCCTCCAGCCCAC<br>AGGTGCTGGACCATCCCTCCCTGGTCCCTCCGCCCCTCTCCACCTTGGGACCTTGTGCTGCTCCTGTCTCTTGCCC<br>AGCTGCCTTGGGCCCTCAGCACGTTCTCATCTTTCAGTGGGAAAGTGGGAGTGCTGGAGCATATGACAGTGCTGAG<br>CATCTTTCCCAAGCCCCACCCTCCCCCAGAGCACCCTCCCCTCCTGTCCTCACCCTACCCCAAGTTCTCCCACAGT<br>CACTCCTGCCCCATGCTCATGCCGCCCTCCAGTTCTTGCTCTGCCCATCTCCCCTCCCCAACCCAGACCTAAAACA<br>GGCTGTTGGGCCAACTGTTCCTTGACCTTCCTTCTTTTCTTTTGGTTCCTTGACCCCAGTGGGCTCTCACTCCCCA<br>CACCGCATATCTAAAATCTGTTTTGCCTGCTCTTGGGGTGCCACTGCTCCCCCTCCAGCATTACTCCTTTTGGCAG<br>GTCCTTCCTCAGGCTGAGAATCTCCCCCTCTACCTTGGTTTTCTCTCTCTGGCCAGCACCCCCACCCCTTGCTTTG<br>TTTTTAATTTTTAACTTTTGTTTGGGTACGTAGTAGATATATATGTATATATTTATGGGGTACATGGGATATTTTG<br>ACACAGGCCTACAATATGTAATAATCACATCAGGGTAAATGGGTTATATCACAACAAGCATTTATCCTTTCTTTGT |

TABLE 9-continued

| lists sequences for the disclosure |
| --- |
| GCTACAAACAATCCCATTATGCTCTTTCAGTTATTTTTAAATGTACAATAAATTATTGTTGACTGTACTCACCCTG |
| CTGTGCTATCTACTAGATCTTATTCATTCTAATTATATTTTTGTACCCATTATTAACCATCCCTGCTCCCCCACTC |
| CCCACTACCCTTCTCAGCCTCTGGTAATCATCATTCTATTGTCTCTCCCCATGAGGTCCATTGTTTTAAATTTTGG |
| CTGCCACAAATAAGTGAGAACATGCAAAGTTTGTCTGTCTGGGCCTGGGGCTTATTTCACTTCACAGGATGACCTC |
| CAGTTCTTTGCAAATGACACGATGGCTGAATAGTTCTCCACATACACATGTACACCACATTTTCTTTATCCATGCG |
| TCTGTTGATGGACACTTAGATTGCTTGCAGATCTTGGCTACTTTGAATAGTGCTGCAATAAACATGGAAAAGTAGA |
| TAGCTCTTTAATATACCGATTTCCTTTCTTTGGAGTATATGCCTAACAGTGGGAGTGCTGGAGCATATGACAGCTC |
| TATTGTATTTTTAGTTTTTGGAAGAACCTCCACATTGTTTCCCATAGTGGTTGTACTAGTTTACGTTCCCACCAAC |
| AGTGTACATCCTCACCAGCATTCCTTATTTCTACATCCTCGCCAGCATTCCTTATTGCCTGTCTTCTGGATAAAAG |
| CCAGTTTATCTGGGGTGGGATGTTATCTCGTAGGAGTTTTGATTTGCCTTCATCTGTTGACGAATGATGTTGAGCA |
| CCTTTTCATATACCTGTTTGCCATTTATATGTCTTCTTTTGAGAAATGACTATTCAGATCTTTTCTCATTTTTAAA |
| TTGGATTATTATATTTTTTTTCCTATAGTTGTTCGAGCTCCTTATATGTTTCAGTTACTGATCCTTTGTCAGATGA |
| ATAGTTTGAAAATATTTTCTCCCATTCTTGGATGGTCTCTTCATTTTGTTTATTGTTTCCTTTGCTGTGCAGAAGC |
| CTTTTTACTTGATATGATCCCATTTATGCAATTTTACTTTGGTTACCTGTGCTTGTGGGGTATTACTTTAAAAATC |
| TTTGCCCAGTCCAATATCCTAGAGAGTTTCCCCAATGTTTTCTTGTATAGTTTCATAGTTTGAGGTCATAGATTTA |
| CATCTTTAATCCACTTTGATTTGATTTTTGTATATGGTGAAAGACAGGGTCTAGTTTCATTCTTCTGCATAAGGAT |
| ATCTAGTTTCCCCAGCACCATTTTTGAAGAGACTCTCCTTTGCCAATGTGTGTTCTTGGTACCTTTGTTGGAAATG |
| AGTTTACTGTAGATGTATGGAATTGTTTCTGGGTTCTCTATTCTGTTTCATTGGTCTGTGTGTCTGTTTTTATGCC |
| AGTATCATGCTGTTTTGGTTACTGTAGCTCTGTAGTATAATTTGAAGTCAGATAATGTGATTCCTCTAGTTTTGTT |
| CATTTTGCTCAGGATAGCTTTATCTATTCTGGTTTTTTTGTGGTTCCATATGCATTTTAGGATTATTTTTATTATT |
| TCTGTGAAGAATGTCATTAGTGTTTTGATAGGGATTGCATTGAATCTGTAGATTACTTTGGGTAGTATGGATATTT |
| CAACAAAACTGATTCTTCCAATCCATGAACGTGGACTATCTTTTCCATTTTTTGTGTCCTTCAATTTTTTGCATCA |
| GTGTTTTTTGTTTTTGGTTTTTGAGATGGAGTTTCACTCTTGTTGCCCAGGCTAGAATGCAAGGGTGTGATCTTGG |
| CTCACCGCAACCTCCGCCTCCCAGGTTCAAGCTATTCTTCTGCCTCAGCCTCCCAAGTAGCTGGGATTACAGGCAT |
| GTGCCACTGTGCCTGGCTAATTTTCTATTTTTATTAGAGATGGGGTTTCTCTATGTTGGCCAGGCTAGTCTTGAAC |
| TCCTGACCTCAGGTGATCCACCTGCCTCGGCCTCCCAAAGTGCTGGGATTACAGGCATGAGCCACCACGCCCAGCC |
| ACATCACTGTTTTATAGTTTTTATTGGAGAGGTCTTTCACTTCTTCAGTTAGGTTTATTCCTCAGTATTTTATTTT |
| ATTTGTAGCTATTGTAAATGGGATTCGTTTCTTGATTTCTTTTTCAGATTATTTGCTGTTAGCACTGATTTTTGCA |
| TGTTGATTTTGTATCCTGCAACTTTACTGAATTTGTTCTTCAGTTCTAATGGTTTTTTGGTGGAGTCTTTAGGTTT |
| TTCCAAATATCAGACCACATGATCTGCAAACAAGGATAATTTGACTTCTTCTTTTCCAGTTTTAATGCCCTTTCTT |
| TCTTTCTCCTGTCTGATTGCTCTAGTTAGGATCTGCAGTACTGTGTTGCATAACTGTGGTAAAATTAGTCATCCTT |
| GTCTTATTCCAGATCTTAGAGAAAAGGCTTTCAGTTTCCCCCATTCAGTATGTTACTAGCTGTGAGTTTGTCATA |
| TATGGCTTTTATTATATTGAGGTCTGTTCCTTGTATACTTAGTTTTTTGAGAGTTTTTATCATGAAGGGATGTTGA |
| ATTTATCAAATGCTTTTTCAGTATCAATTGAATGATACTGGCTTTTGTCCTTTATTCTGTTGATATGACGTATTAC |
| ATTGATTGATTTGTGTATGTTAAATCATCCTTGCATACCTGGAATACATTCCACTTGCTCATAAAGAATGATCTTT |
| TTTAATGTATTGTTGAATGTGGTTTGCTAGTATTTCCTTGACGATTTTTGCATCGGTGTTCATCAGGGATATAGGC |
| CTGTAGTTTTCTTTTTTATGATGTCTTTGCCTGGTTTTTGTATCAGGATATTCCTGGCTTTGTAAAATGAGTTT |
| GGAAGTATTCCCTCCTCCTCTATTTTTCAGAACAGTTTGAATAGGACTGACATATGTTGTTCTTTAAAAGTTTAAT |
| TGTGGTAAATTATACATTACATAAATTTTACTGTTTTAACCACTTTTAAGTGTATACTCGGTGGCATTAGATACAT |
| TCACATTTTTGTGCAACCCAAAACTCTGTGCCCATTAATCGGTAACTCCCCATTCCTCCCTACCTCTGGCCCCTGG |
| TAACCACCATTCTACTTTTTGTTTCTATGAATTTGACCACTCTAGGTACCTCATTTAAGCAGAATCATGTAATGTT |
| TGTCTTTTTGTTTCTGGCTTATTTCACTTATATAATATTTTTGAGGTTCGGTGGGCACAGTGGCTCACGCCTGGATTT |
| CCAGCACTTTGGGAGGCTGAAGCAGGTGGATCACCTGAGTTTCGGAGTTCGAAACCAGCCTGGCCAACATGGTGAA |
| ACCCCATCTCTACTAAAAATAATAAAAGTTAGCCGGGCGTGATGGCGGGTGCCTGTAATCCCAACTACTTGGGAGG |
| CTGAGGCAGGAGAATCGCTTGAATCCGGGAAGTGGAGGTTGCAGTGAGCTGAGATCAGGCCACTGCACTCCAGCCT |
| GGGCAACAAGAGTGAAATTCCATCTCCAAAAAAAAAAATAAAACAATAATAATAATAATATTTTTGAGGTTCATCC |
| AAGTTGTAGTATGGGTCAGAATTTCATTCCTTTTAAGGATGGATAATACTCATTATATGTATGTACCACATCTTGG |
| TTATCCATCCCTCAGACAATGGACACTTGGGTTACTTCTACCTTTTGGATATTGGCAAATATTTCATTTCCTTTGG |
| GTATATATTTATTTCCTTTGGGTATTTCTTTTGGGTATATATCCAGAAATAGAAGCAGTACACAGGGGCTTCATTT |
| TCTCTGTCTCTTTGCCAACCTTGCTCTGTGTGTGTGTGTATGTGTGTGTGTAGGTGTGTGATAACAGCCATCCTGA |
| TTGGTTTCAGGTGGCATCTCATTGTGGTTTGGATTTGCATTTCCTAATGAGTGCTGATATTGAGCATCTTTTCAT |
| GTGTTTGTTGATCATTTGTAATTTTCTTTGAAGAATTGGCCATTTAAGTCTTTTGCCCATTTTTTCCCCCACATAG |
| CTTCTCTTATCAGATATATGACTTGCAATATTTATTTCATTTCGGGGTTGATTGCTTTTTCACTCTGATTGTGCCC |
| TTTGATGCATAGATGTTTTGAATTTTCATCAGTCTACTTTGTCAGTTCTTTCTATTCTATCTGTGCTTTGGTGTCA |
| TATCCATGAAAGCACTGTCAAATCCTATGTCATGAACATTATCCCCAATGTTTGCTTCTAAGAAATTTTTAGGTTT |
| TAGTTCTTGAGTGTAGAGTTTAGGTCTTTGATTCATTTTGAGTTAATTTTTGTATATAGTGCAAATTAAGGGTCCA |
| ATTTTATTTTAACACCCCCTGCCCCCAGAACTATTTGCTGAAAAGATCAACTGACTCTTTGTCACCTGCTCACCCC |
| AGTGGACACTAGCTGTTCCATCCAATTGCTGTCCTGGGGCCTTGTCATGCTACTCTTCCACTTTGAACCCAAGCCC |
| ACACCGTTCGTTGCTCCCCTCTGGGATACTGACCCCACTATAAACTTCTCTGGGGCTACAACCTTCCTACCCTTTG |
| TGCCTCATGACCACCCCTCCCTTGTCCCCGCCATGCCCATGATGAGTCTCTTCTCGAGGCAGCTCCCCTTGCCTC |
| CATCTCACCCTCAGCCTATGCACCACAGCCACACTGGACATGGGTCCCTCTGAGCCTGAGTCCCTTCCCATTCCCA |
| CCATCCCCTCTGGCAAGACCTTCCTTCCACCACCTTCATGCTCCTCCCTTGCCCCTGCAGGGCAGCCTCTCCCCTT |
| GGCCCCTATTCCCTTAGGGGGCTTGTGGCCACCCAGTCCTTGCACCTGGCCTACAAGTTTGCCATCTTCATTCCCC |
| CTTCTTCTGTTCATCAGCCCCCTCCTCTATCCTCCCACCCTCACAGTTTTCTTTGTATATGAAATCCTCGTTCTTG |
| TCCCTTTGCCCGTGTGCATTTCCTGCCCCAGGAAGGTTGGGACAGCAGACCTGTGTGTTAAACATCAATGTGAAGT |
| TACTTCCAGGAAGAAGTTTCACCTGTGATTTCCTCTTCCCCAGAGCCCCACAGTCTTCGTTATAACCTCACGGTGC |
| TGTCCTGGGATGGATCTGTGCAGTCAGGGTTTCTTGCTGAGGTACATCTGGATGGTCAGCCCTTCCTGCGCTATGA |
| CAGGCAGAAATGCAGGGCAAAGCCCCAGGGACAGTGGGCAGAAGATGTCCTGGGAAATAAGACATGGGACAGAGAG |
| ACCAGGGACTTGACAGGGAACGGAAAGGACCTCAGGATGACCCTGGCTCATATCAAGGACCAGAAAGAAGGTGAGA |
| GTCGGCAGGGGCAAGAGTGACTGGAGAGGCCTTTTCCAGAAAAGTTAGGGGCAGAGAGCAGGGACCTGTCTCTTCC |
| CACTGGATCTGGCTCAGGCTGGGGGTGAGGAATGGGGGTCAGTGGAACTCAGCAGGGAGGTGAGCCGGCACTCAGC |
| CCACACAGGGAGGCATGGAGGAGGGCCAGGGAGGCATACCCCCTGGGCTGAGTTCCTCACTTGGGTGGAAAGGTGA |
| TGGGTTCGGGAATGGAGAAGTCACTGCTGGGTGGGGGCAGGCTTGCATTCCCTCCAGGAGATTAGGGTCTGTGAGA |
| TCCATGAAGACAACAGCACCAGGAGCTCCCAGCATTTCTACTACGATGGGGAGCTCTTCCTCTCCCAAAACCTGGA |
| GACTGAGGAATGGACAGTGCCCCAGTCCTCCAGAGCTCAGACCTTGGCCATGAACGTCAGGAATTTCTTGAAGGAA |
| GATGCCATGAAGACCAAGACACACTATCACGCTATGCATGCAGACTGCCTGCAGGAACTACGGCGATATCTAGAAT |
| CCGGCGTAGTCCTGAGGAGAACAGGTACCGACGCTGGCCAGGGGCTCTCCTCTCCCTCCAATTCTGCTAGAGTTGC |
| CTCACCTCCCAGATGTGTCCAGGGAAACCCTCCCTGTGCTATGGATGAAGGCATTTCCTGTTGGCACATCGTGTCC |

TABLE 9-continued

| lists sequences for the disclosure |
|---|
| TGATTTTCCTCTATTGTTAGAGCCACTGGATAAAGACAGAGGGTCAGGGACTGGACCATCCAGTGTTGTAATCAGG<br>GCAAGTAGAGGACCCTCCGACAGAATCCTGAGCCTGTGGTGGGTGTCAGGCAGGAGAGGAAGCCTTCAGGGCCAGG<br>GCTGCCCCCTCTGCCTCCCAGCCTGCCCATCCTGGAGAGTTCCCTCCTGGCCCCACAACCCAGGAGTCCACCCCTG<br>ACATCCCCCTCCTCAGCATCAATGTGGGGATCCCAGAGCCTGAGGCCACAGTCCCAAGGCCCATCCTCCTGCCAGC<br>CTGGAAGAACTGGGCCCCAGAGTGAGGACAGACTTGCAGGTCAGGGGTCCCGGAGGGCTTCAGCCAGAGTGAGAAC<br>AGTGAAGAGAAACAGCCCTGTTCCTCTCCCCTCCTTAGAGGGGAGCAGGGCTTCACTGGCTCTGCCCTTTCTTCTC<br>CAGTGCCCCCCATGGTGAATGTCACCCGCAGCGAGGCCTCAGAGGGCAACATCACCGTGACATGCAGGGCTTCCAG<br>CTTCTATCCCCGGAATATCATACTGACCTGGCGTCAGGATGGGGTATCTTTGAGCCACGACACCCAGCAGTGGGGG<br>GATGTCCTGCCTGATGGGAATGGAACCTACCAGACCTGGGTGGCCACCAGGATTTGCCGAGGAGAGGAGCAGAGGT<br>TCACCTGCTACATGGAACACAGCGGGAATCACAGCACTCACCCTGTGCCCTCTGGTGAGCCTAGGGTGACCCTGGA<br>GAGGGTCAGGCCAGGGTAGGGACAGCAGGGATGGCTGTGGCTCTCTGCCCAGTGTATAACAAGTCCCTTTTTTTCA<br>GGGAAAGTGCTGGTGCTTCAGAGTCATTGGCAGACATTCCATGTTTCTGCTGTTGCTGCTGGCTGCTGCTATTTTT<br>GTTATTATTATTTTCTATGTCCGTTGTTGTAAGAAGAAAACATCAGCTGCAGAGGGTCCAGGTGAGAAAAGCGGGC<br>AGTTTCTGGAGATGGTAAGGCCCCTGTCTGGGCAGTAGGGTCCCCTCATTGCTCCTGCAAAGATAGGCATGTTGGT<br>GACAAGGCTTCCATAACAGGGGATGAAAGTTGGGGAATTTGGGAAGGGAATGGGGGCAGCATCTCCATCTACACCC<br>ATAAGTGCTGCCCAAGCAAGGGTCAAACGCCCAGCTGTGGCATCCTCCTGCTGCAGGTGAGGAGTGGGCAGCAGGG<br>AGGGCTGCGGCGCCTGCTCTGTCCCCATCCCGGTCTCTGTGTCTCTTGAACTCACTAGGGCGCATCCAGGTGGGGT<br>GAGCTGGGAATCACGTGCTGAATGCTAAGGGCCTGGATGATCACGGCCTCAGAGGGAGCAAATAGTAAAGGCAGCT<br>GTGATCTGGGGAGGGCCAGAAACTGGAGAGGAATCTGAGGAGAGGCGGTGCCCCTATTCCCTTCCTCTCTGCATCC<br>CCCTCCCCTGTTTCTCCAGCCATCGGGGCGGACACCGAGAAAAAGACCTATGAGGCCCAGCCTGGGGGCCCTGCCT<br>GTGTAGCCCTTTGGAGACCCCTTGTAACAGGGAGGGTCCTGAGCACACATGGCCATCTCTGTCCACTTTGCAGCTC<br>CCCATGCACCTCCTCCAGGAGCTTTCTTGGGGTTGTCGTGTCCTCTGCACCATTCGAGGCCCTACTCTTTCCAGGT<br>TCCCACGGCCTGGCCTCCCTGAGTTTCTTGCAGATGACATGGATGAGTAGATAAGCAGATGTCCCTGGGCCATTTG<br>AGGAGTGGGGCCCAGCCCCTCATCAGGGCAGCTGTGGTCCCTGTTTTCATCCTACCTCCGAGTGTTTTCTTCTCCA<br>GTCCCTGAGGGACACAGTCCTCAGGGCCCATGTTTTTGGGGATTTAATCTGTGCTCTGTGGCCTCACCTTGCCCTC<br>CCTGAGCCAATTTCCCTTTCTAAAGGTGGTCACTGCCTGGTAAGTTTGGAGTAAGGGACGGTCAGAATCATTTCCC<br>CTACAGTCAGGTTGTTTGATGGGGGATGAAAAGAGACAGCAGGAAGTTTTGTGTTTCTGCAAAGACAGAAGCAGTT<br>CAGGCGACAGTAAGAGGCTGGGGTGTCCAGGAGGATGTGTCTGGCAGTAGGGTCGCTGGTTTCTCATCCTTGAACC<br>TAATTGCACTGTCAATCGGCCCCTCAGGCCTGAGCAGATGGGAAGGTTTGTCCCCTGCCCTGCAGCAAGAGGGCCC<br>TGTCCAGGAGGCACCCACAACAGGGGCAGTGCAGGTCTGTGGTCACTCCTGCTCTCACCTGTGGCGTCTCCCGTAG<br>AGGGATTGTCAGTTCTGGTTCCCTGTGGGCAGGAATGGTTTCCTCATAGGTCACTGGAGTTTTGGCCAGGAAAAGA<br>GTATGAAGTTCATGTGCCAGTTTCTCAAAATTCCTGCTTTCAATGTTGATGTCCAGTAAAGATATTCGTAATTTCA<br>GCTCTATAATCTTAATAGGATTTCCTCTAATATTGTGAAGCATATTATATGAAACAGGAACACAAATTTCTCAAAA<br>TTCCTGCGATGTCCAATAAAGATTTTCATAATTTCAGCTCTGCAATCTTAATAGGATTTCCTAATACTGTAAAGCA<br>TATTAAATGAAACAGGAACTCAAATTTGGAGCCCCCTCTCCAGGAGGTTCTGTGTGGAGATGGTGGCTGTGGCAGT<br>GGCAGTTCCCAGGTGCAGAGGGTGGGCAGAGGCAGCCTCAGGCTAAGGGGTCTCCCCTACTCCACATGGAGAAAAT<br>CCCTTGTAGGTTGCAAGGGCAGTGGCCGGGTGGAATCCCTGCTAGGGACAGAGCAGGAAGGCCTCGCAGCCTCACC<br>AAGCAGCAGCCCTGGGGTGGAGCTGCGTTTCCAGGGTTAAGCGGACCAGGCAGGAGTAGCGGTTACTCAAGAGCAG<br>GTCACAGGCTTGGGTTGTGAGGGTCAGGAGAGGCCAGGCCTCCTCGAGCAAGGTGGGGGTCCCAGGGTCAGGTCAG<br>GTGCAGATCCTGTGGCAGCCACGTCTTTCCATGCTGGGCCTGCTGGGCCCCCCAGGCTTCCTGATGGGGTCCCCAG<br>TTAGGAGCTGCCTGCTCAGGGCTGGGAGGGGAGGAGCACTGAGCTGCAGATAGAGGGCAGAGCCCACAGTGGGCAG<br>GGCCTGCCCTGGTGTGTAGGTGCCTCTGAAGGAGAGGAGGGCCTGGGGACTGAGAGCAAGGGTCAGGGCCTCTCTT<br>TGGGGAGGCCTCTCACTGTAACAGGACTGGTCAGGCCTGAGAGGAGGGCACTGGGTTCCCTCTTGGGTCTTGTCCT<br>TTAGTCTTGGGGCCCTTTCCCTCCCTGCACGATGAGTGGTGGGCACAGGGCACGGGCTGATGTTGATGGAGTGATG<br>GGAGGGAACTGGCAGGGGCTGGGAAAAGCAAGGAGGGAGGAAGAAAAAAGTGGGGGCCTCATCTTCCCTCAGAGAA<br>AGGGCAAATCTGGTTTTGGAGCAACTGAAGAGAGAAAAGTCCCCAGGGAATAAACACAACACTGCACCCAGTGGAG<br>CATTTACCCATTTCCCTCTTTTCTCCAGAGCTCGTGAGCCTGCAGGTCCTGGATCAACACCCAGTTGGGACGAGTG<br>ACCACAGGGATGCCACACAGCTCGGATTTCAGCCTCTGATGTCAGCTCTTGGGTCCACTGGCTCCACTGAGGGCAC<br>CTAGACTCTACAGCCAGGCGGCTGGAATTGAATTCCCTGCCTGGATCTCACAAGCACTTTCCCTCTTGGTGCCTCA<br>GTTTCCTGACCTATGAAACAGAGAAAATAAAAGCACTTATTTATTGTTGTTGGAGGCTGCAAAATGTTAGTAGATA<br>TGAGGCATTTGCAGCTGTGCCATATTAA |
| SEQ ID NO: 32 MICA cDNA Sequence<br>AAGTTTCCGCGGCGCCTTCTCCCCGGCCACTGCTTGAGCCGCTGAGAGGGTGGCGACGTCGGGGCCATGGGGCTGG<br>GCCCGGTCTTCCTGCTTCTGGCTGGCATCTTCCCTTTTGCACCTCCGGGAGCTGCTGCTGAGCCCCACAGTCTTCG<br>TTATAACCTCACGGTGCTGTCCTGGGATGGATCTGTGCAGTCAGGGTTTCTCACTGAGGTACATCTGGATGGTCAG<br>CCCTTCCTGCGCTGTGACAGGCAGAAATGCAGGGCAAAGCCCCAGGGACAGTGGGCAGAAGATGTCCTGGGAAATA<br>AGACATGGGACAGAGAGACCAGAGACTTGACAGGGAACGGAAAGGACCTCAGGATGACCCTGGCTCATATCAAGGA<br>CCAGAAAGAAGGCTTGCATTCCCTCCAGGAGATTAGGGTCTGTGAGATCCATGAAGACAACAGCACCAGGAGCTCC<br>CAGCATTTCTACTACGATGGGGAGCTCTTCCTCTCCCAAAACCTGGAGACTAAGGAATGGACAATGCCCCAGTCCT<br>CCAGAGCTCAGACCTTGGCCATGAACGTCAGGAATTTCTTGAAGGAAGATGCCATGAAGACCAAGACACACTATCA<br>CGCTATGCATGCAGACTGCCTGCAGGAACTACGGCGATATCTAAAATCCGGCGTAGTCCTGAGGAGAACAGTGCCC<br>CCCATGGTGAATGTCACCCGCAGCGAGGCCTCAGAGGGCAACATTACCGTGACATGCAGGGCTTCTGGCTTCTATC<br>CCTGGAATATCACACTGAGCTGGCGTCAGGATGGGGTATCTTTGAGCCACGACACCCAGCAGTGGGGGGATGTCCT<br>GCCTGATGGGAATGGAACCTACCAGACCTGGGTGGCCACCAGGATTTGCCAAGGAGAGGAGCAGAGGTTCACCTGC<br>TACATGGAACACAGCGGGAATCACAGCACTCACCCTGTGCCCTCTGGGAAAGTGCTGGTGCTTCAGAGTCATTGGC<br>AGACATTCCATGTTTCTGCTGTTGCTGCTGCTGCTATTTTTGTTATTATTATTTTCTATGTCCGTTGTTGTAAGAA<br>GAAAACATCAGCTGCAGAGGGTCCAGAGCTCGTGAGCCTGCAGGTCCTGGATCAACACCCAGTTGGGACGAGTGAC<br>CACAGGGATGCCACACAGCTCGGATTTCAGCCTCTGATGTCAGATCTTGGGTCCACTGGCTCCACTGAGGGCGCCT<br>AGACTCTACAGCCAGGCAGCTGGGATTCAATTCCCTGCCTGGATCTCACGAGCACTTTCCCTCTTGGTGCCTCAGT<br>TTCCTGACCTATGAAACAGAGAAAATAAAAGCACTTATTTATTGTTGTTGGAGGCTGCAAAATGTTAGTAGATATG<br>AGGCGTTTGCAGCTGTACCATATTAAAAAAAAAAAAAAAAAA |
| SEQ ID NO: 33 MICA Protein Sequence<br>MGLGPVFLLLAGIFPFAPPGAAAEPHSLRYNLTVLSWDGSVQSGFLTEVHLDGQPFLRCDRQKCRAKPQGQWAEDV<br>LGNKTWDRETRDLTGNGKDLRMTLAHIKDQKEGLHSLQEIRVCEIHEDNSTRSSQHFYYDGELFLSQNLETKEWTM |

TABLE 9-continued lists sequences for the disclosure

PQSSRAQTLAMNVRNFLKEDAMKTKTHYHAMHADCLQELRRYLKSGVVLRRTVPPMVNVTRSEASEGNITVTCRAS
GFYPWNITLSWRQDGVSLSHDTQQWGDVLPDGNGTYQTWVATRICQGEEQRFTCYMEHSGNHSTHPVPSGKVLVLQ
SHWQTFHVSAVAAAAIFVIIIFYVRCCKKKTSAAEGPELVSLQVLDQHPVGTSDHRDATQLGFQPLMSDLGSTGST
EGA

SEQ ID NO: 34 MICB Genomic Sequence
CTGTTTCCAGCGAGTCAGATTCCAGATCGCGCTCCAGCCTGGACTCGGAATTCCTGCCCCGCGGGTCTGCATTTTC
ACAGCGGCAGGTGTGAGTGCCGCGCAGCTGGAGACCAGAAGCCTGAGGCAGCTCGGCCCTCCCCAGCCCAAAGTGC
CGTTATTCCGTTTCTGTATCAGTAAACACGTTTCATTTTCCGTAGACCAGGGAAGGGTGATGGGTGATCCCAGTCC
TCGCAGTGAATTCCGGGCCACAAAATTCAAAACGCTTGCGGGCAAAGCCGTGCGCGGTGGCTCAAGCCTGTAATTC
CAGCACTTTGGGAGGCCGAGGCGGGCGGATCACCTGAGGTCGGGATTTCCAGACCAGCCTGACCAACATAGAGAAA
CCCCGCCTCTACTAAAAATACAAAATTAGCCGGGGGTGGCGCATGCCTGTAATCCCAGCTAGTCGGGAGGCTGAGG
CAGGAGACTCACTTGAACCCGGGAGGCGGAGGTTGCTGTGAGCCGAGATCGCGCCACTGCACTCCAGCCTGGGCAA
CAAGAGCGAAACTCCGTTTCAAAAAAAAACAAAAAACAAAAAGCTTTCGGGCGCCGAGGGCAGCCCCGCCCTGAAT
TTTGTGAGCGACCGCGCTGGGCCGTTTCTCTTTCTTTTCCGGACCCTGCAGTGGCGCCTAAAGTCTGCGAGGAGGA
AGTCGCCTCTGTGCTCGTGAGTCCAGGGATCTAAGGCAAGTGCTGAGGGAGAAAACATAGTTGATGGGGCAGAGCA
GAGGGGGCTGGAGGTGGGGTGGAGGGGGAGGGCTTTGAACAGAAGACCTGGGAGGCTTGGTGGGGGAGGGGACCCA
GGCCTCGGCGCTGAGAAGCAACTCCCCTGGAGCTCAAGACCTTCTTGGCCTCCCCTAGCCCAGGGGAGGACTGGCT
TCATGTCTCCCTGAAACCGCTTCTAAATGCCTTAGAACAAACCTTAAATATTCATTATTATTATTGAACTATTAAA
AGTCTTTTTTGGAGGCGAGCTGAATGAGACCCTTTGCTGGAGCTGGCACACGGAGGAAGTCCTGGAGGGAGGGTAG
ACACCGTGGAGGGAAGGGCTTGGGACCTGTGTCAGGAGAGCTGGGTCCATCTGCCTCTCTGTCTCAAACTATGCTT
ATGATCTTTAGCAGTGAAAATAATCTCTCTAAGGTGGGGACAGGACCCCAGTCCCTGCTGTGCTTAATAAATTATG
AGGATCAAAATAAATTATCAGTGAATGTGTATGGGAAGACTAAGAAATTGTTAAAATTCTCGAATACATTACATTT
TCATCCACAGAAAAGTGTAGGCTAGGGATGATAGGGGAATAGTTAGTAATGACAGGGATAGTTGAACTTAAAAAAA
AAGGTTGTGAGGCCAACAAAAAGAAATGGACACAGTTCCTGATCCTGGAGGGTTCATAGTCTAATGGGGGAGGAG
GGTAGAAGATGGTAGGTGATGGCTGGGTGTGTGGCACTCGCCTGTAGTCCCAGCTACTCAAGAGGCTGTGGTGGGA
GGATTGCTTGAGCCCAGGCATTTGAGGCTGCAGTGAGCTATAATCACACCACTGCATTCCAACTGAGTGACACAGC
AAGACTCCTCTCTTAAAAAAATAAAATAAAGTAAATGAAAAAAATAAGATTCAAGACAGGGCACAGTCGGTACCAT
CAGGAAGGTTCAAACCATGGGCTAGATCAGTAGTTCTAAAACTTGACTACACATCGGAATCACGTAGGGAACTTTA
AAAGATACTAAGGTTTAGGTCCAACCTAGGTTTACTGATTTAACTGGTTGTGGCTGTGGCCTGGGAACATGGATAT
TAAAAACTCTCCAGGTGGTTCTACGCAGTGGCTAGGTTTGAAGACCACTGCCTAGATGTCCCAATGACTAAGAATG
TGCGCTGGGGACAAGCCAATTCTCTTAGTAGAGGCTTTCCAGACAGAATTCTTATTATTGAGAATTGAGAATTCAC
ATGCCACACATAATTTATCGTTTTAAAGTGTACAGATCAGTGGCTTCTAGCATAATCACAAGGTTGTGCCACCGTC
ACCACTATCTACTTGGGAAGATTTTCTTCCTTTTTTTCTTTTTTTTTTTTTTTTTTGAGGCGGAGCCTTGCTCTGT
TGCCCAGGCTGGAGTGCAGTGGCGCAATCTCAGCTCACTGCAAGCTCCGCCTCCCGGGTTGACCCCATTCTCCTGC
CTCAGCCTTCTGAGCAGCTGGGACTACAGGTACCCGCCACCACGCCCAGCTAAGTTTTTTGTATTTTTAGTAGAGA
CGGGGTTTCACTGTGTTAGCAGGATGCTCTCGATCTCCTGACCTCGTGATCTGCCCACCTCGACCTCCCAAAGTGC
TGGGATTACAGGCGTGAGCCACCGTGCCCGGACCCTTTTTCCTTTTTTTTTTTTTTTAAAGGCTAGTCAAGTGAAA
CAGTGGGAGTGAAGATGAAACAAAAACATCTATAACTGGTTGTGATCAATTAGTTGTAAACACCACTGCACTCAGA
CCAGCCTAACTGGGAAGATTTTGAGGATATGCTGTGGTCTGATGGGTTCCAAGGCAGAGGTGACAGTAACCTGGAA
GAGGGAGACTGCTTAGGCAGTGGCATCCTGGTGGGATAGGGTGAGGAGATCCCAGAGCCCACGTTTACTGCAACCC
TGGGGAAATGTCACCAGAGAAATGGGGGTGGTGCCAGACAATAGATTGTGGGAGCTATGGTTTCCATGGTAGAGTA
GAAGCATCCACCATGTGTGACATTCAGCAGATGGGGCGCTGTGGGTGGCTTGGAGCACTCTGGTTGTAACTGAGGC
AGGCACAGTGTTTAGGAAGCCTGTGCAGTAATCCAGACTGAAGGGAGGGGAAAGCCTAGACTAAGACTATGGCTGT
GGGATTGAAATAGCGTTGAAGGAGCTGACTTTGACTCCCGGAGATGAAGGAGAAAGAGGAAATCAGAAGGGACCAA
GGATGGTGAAGTTCTTAAGAGAAACTGAGGAGGAAGAGAGGATGATGTGGTGGGAGACGTGTAGAGAGTCCTTGTA
GATCTGTCATATTGAAGGGGACTATGGTCCCAGAGGTACAGATGTCCTAAAACAGGCTGGAAAAGGGAGTCTGGAG
AGAGCTTGGTGTTGTAATGAACCATGGGGAGCCGCCTCGTTGGCCCTGTGATTACCCAGGAACTGAATAGAGAGGG
GGCCCTGGGAGACCTCAGACACTTAGAGGATATAAGGGGGTGAAAGGGGGGACCTGGCTTTGAGTCGAAGGGAGGA
GAAGGAGATTATATAGCTGAAACGTCTAAGAGAATTTGTGATCTGAGCGTTTCTACTGGGGCAAGTGCTTCTGAAA
GGCAGAGGCGGCTGAGATCTGGAAACAGGTCTGCAAATCTGGTCACTGGTCTCATTGCAGTAACGCTGTGCGCGGT
TGAGGGAGTGTATTGGGAGAAAAACCACGCGTTGTCTGTCCCGGAAGGAACAAGCCAGTGAGAGCCGGCCTGATGG
GAGGACCGGCGAAAGGGGCTTGGTGAAGCCCGCGCTCCTTGGGGGTGGGAATGCGGGGATGGGGTGGTCGCGATGC
AGGGAGGGCGACAGGGTCCAGGTCGTGCTCATAAGTTTGGAGCTGTACTCTCAGCTACTCGGGGCTGGTCCTTGAT
TTTGGCTGCGCTCGCGCACGCTCCCCCTTTTCTGGCCGCCAGGTCCCGCCTTCTAAATTTCCCCAGGTCTCCAGGC
CGCTAGAATTTTCTCTTCTGAACGTGGCCCCGCCCTCTCCACTCATGATTGGCCCTAAGTTCCGGGCCTCAGTTTT
CACTGGATAAGCGGTCGCTGAGCGGGGCGCAGGTGACTAAATTTCGACGGGGTCTTCTCACGGGTTTCATTCAGTT
GGCCACTGCTGAGCAGCTGAGAAGGTGGCGACGTAGGGGCCATGGGGCTGGGCCGGGTCCTGCTGTTTCTGGCCGT
CGCCTTCCCTTTTGCACCCCCGGCAGCCGCCGCTGGTGAGTGGGGTTCCTGGCGGTCCCCGGCGGAGCGGGAGCGG
CGGGGCGTTTCCGGGGGTCCGGGTGGGTTGCCGCGAGCGCTGTGCGGTCAGGGCGGGGCTCAGGTGTGCTGTCTGG
AGTGCAGGGAGCTGGACGCCGCCTGTTCCCGCCACACCTCAGCCCTGCTTTCCCATCTCCCGTCTCTTTTTTTTTT
TTTTTTTTTTTTTTTTTTTTTTTTTTTCTTTCTGAGACGGAGTCTCTGTCGCCTAGGCTGTAGTGCAGTGGCGCGA
TCTTGGCTCACTGCAAGCGCCGCCTCCCGGGTTCACGCCATTCTCCTGCCTCAGCCTCCCTAGTAGCTGGGACTAC
AGGCGCCCGCCACCACGCCCGGCTAATTTTTTGTGTTTTTAGTAGAGATGGGGTTTCACCGTGTTAGTCAGGATGG
TCTCGATCTCCTGACCTCGTGATCCGCCCGCCTCGGCCTCCCAAAGTGCTGGGATTACAGGCGTGAGCCACCGCGC
CCGACCTCCTGTCTCCTTTCAGTCCTCCTCGGGATCGCGCATCACCCGCATTTTCTGGTCTCTCCTGCACTTGCTC
TCCTCGCCTCTCCTCCGTCTCCTCTCACTTTTCGGACAAACCAGTCCTTCTGAGGCCCCTGGGTTCCCGGGCTGCT
CCTGTGAATGGCATTGGAAGGCCGTTCCAGCGCGGCCGCTGAGGCAGCCACTTCCCCCGGTGCTGGGGGCGGATCT
CAGGTCCCTGAAGTCCTGTCCTCTCCCGGAGCCGATGTGTTCTCAGCTCCTGGGCCGCAGCTCCTGGAGTTGGGGC
CCTCCTTTCTTGGGACCCGGAGGTGGTGCTTCTTGCTGCTGTGGGGACTGTGGGGGGTCCTGACTCTCAAGCTGAG
GGGTTGGAGTCTGCAGGCTCCGGGCAGAGGATTCTTCCTGCGACTTCTGTCATCCCCAGCTCATTCTCCCCTCGCC
TCCGGCTCCGGGGGTCCTCTCCTCTCTCGCATCCCACCCCTACTAATGACCAATGATCTAAGGACACCAGATTCCC
TCTCACCTCCTCCCTGCCCATCTTACGGCGCCCTGGGTCCTGTTGCTCTCCCAGCTCCCTGCTACCCCTTCCTGTG
TGCTGTTCTCTGATCCATTTCTAGGGTGTCCTCTGCCTTCATCCCCCGCCCCCGCCACTGAAGGTCCCTCCTGCCT
CCTTTATGGGCCTTTCCTGCAAGCAGCCTTCACTCCGTGCTGCCCCTATGCCTCCCCATTCCCAAATGTCCCTGAC
TCTAACTTTCTGGTGCTGCCTTTTGTCCGGGGGGGTCTTCCCTCCATCCCACTCCCCTCCAGACCCCCAAGGAGAG
CCCTGATGCTAATGGCAGTTGGGCCTTAGGCAGGGCGCAGGGCAGCGCAGATGCCCCCTCCCCTCCAGTGCAGGTG
CCTGCTCTGGGCCCTGCCTCATTGTGGCCCCTTCCCCACTCCTTCATCCTCAGCCTCACCCTCTTGAGGACCCCAC TABLE 9-continued

| lists sequences for the disclosure |
| --- |
| CCTCCAGCCCACAGGTGCTGGACCATCCCTCCCTGGTCCCTCCGCCCCTCTCCACCTTGGGACCTTGTGCTGCTCC<br>TATCTCTTGCCCAGCTGCCTGGGGCCCTCAGCAAGTTCTCATCTTTCAGTGGGAAAGTGGGAGTGCTGGAGCATAT<br>GACAGTGCTGAGAATCTTTCCCAAGCCCCACCCTCCCCCAGAGCACCCTCCCCTCCTGTCCTCACCCTACCCCAAG<br>TTCTCCCACAGTCACTCCTGCCCCATGCTCATGCCGCCCTCCAGTTCTTGCTCTGCCCATCTCCCCTCCCCAACCC<br>AGACCTAAAACAGGCTGTTGGGCCAGCTGTTCCTTGACCTTCCTTCTTTTCTTTTGGTTCCTTGACCCCAGTGGGC<br>TCTCACTCCCCACACCGCATATCTAAAATCTGTTTTGCCTGCTCTTGGGGTGCCACTGCTCCCCCTCCAGCATTAC<br>TCCTTTTGGCAGGTCCTTCCTCAGGCTGAGAATCTCCCCCTCTACCTTGGTTTTCTCTCTCTGGCCAGCACCCCCA<br>CCCCTTGCTTTGTTTTTAATTTTTAACTTTTGTTTGGGTACGTAGTAGATATGTATGTATATATTTATGGGGTACA<br>TGGGATATTTTGACACAGGCCTACAATATGTCATAATCACATCAGGGTAAATGGGTTATCTATCACAACAAGCATT<br>TATCCTTTCTTTGTGCTACAAACAATCCCATTATGCTCTTTCAGTTATTTTTAAATGTACAATAAATTATTGTTGG<br>CTGTACTCACCCTGCTGTGCTATCTACTAGATCTTATTCATTCTAACTATATTTTTGTACCCATTAACCATCCGCA<br>CTCCCCCACTCCCCACTACCCTTCTCAGCCTCTGGTAGTCGTCATTCTATTGTCTCTCCCCATGAGGTCCATTGTT<br>TTAATTTTTGGCTGCCACAAATAAGTGAGAACATGCGAAGTTTGTCTCTCTGGGCCTGGGGCTTATTTCACTTCAC<br>ATGATGACCTCCAGTTCTTTGCAAATGACATGATGGCTGAATAGTACTCCACATACACGTGTGCACCACATTTTCT<br>TTCTCCATTCGTCTGTTGATGGACACTTAGGTCGCTTGCAGATCTTGGCTATTTTGAATAGTGCTGCAATAAACAT<br>GGAAAAGTAGATAGCTCTTTAATATACCGATTTCCTTTCTTTTGGGTATATGCCTAACAGTGGGAGTGCTGGAGCA<br>TATGACAGCTCTATTATATTTTTAGTTTTTGGAAGAACCTCCACATTATTTCCCACAGTGGTTATACTAGTTTACG<br>TTCCCACCAACAGTGTACAAGGGTTCTCTTTTGCTACATCCTCGCCAGGATTCCTTATTGCCTGTCTTCTGGATAA<br>AAGCCAGTTTATCTGGGGTGGGATGATATCTCGTAGGAGTTTTGATTTGCCTTCATCTGATGACGAATGATGTTGA<br>GCACCTTTTGATATACCTGTTTGCCATTTGTATGTCTTCTTTTGAGAAATGACTATTCAGATCTTTTGCTCATTTT<br>TAAGTTGGATTATTAGATATTTTTCCTATAGAGTTGTTTGAGATCCTTATATGTTTTGGTTACTAATCCTTTGTCA<br>GATGAATAGTTTGAAAATATTTTCTCCCATTCTTGGATGGTCTCTTCACTTTGTTTATTGTTTCCTTTGCTGTGCA<br>GAAGCTTTTTAACTTGATATGATCCCATTTATGCATTTTTACTTTGGTTGCCTCTGCTTGTGGGGTATTACTTAAA<br>AAATCTTTGCCAGTCCAATATCTTAGAGAGTTTCCCCAATGTTTTCTTTCATAGTTTTCATAGTTTGAGGTCATAG<br>ATTTACATCTTTAATCCTTTTTGATTGGATTTTTATATGTGGTGAGAGATAGGGTCCAGTTTCATTCTTCTGCATA<br>AGGATATCTAGTTTCCCCAGCACCATTTATTGAAGAGACTCTCCTTTGCCCTGTATGTGTTCTTGGTAACTTTGTT<br>AGAAATAACTTCACTGTAGATATATGGATTTGTTTCTGGGTTCTCTATTCTGTTTCATTGGTCCGTGTGTCTGTTT<br>TTATGCCACTACCGTGCTGTTTTGATTACTCTAGCTCTGTAGTATAATTTGAAGTCAGATAATGTGATTCCGCTAG<br>TTTTGTTCTTTTTGCTCAGGGTAGCTTTATCTATTCTGGGTTTTTTGTGATTCCATATACATTTTAGGATTGTTTT<br>TCTATTTCTGTGAAGAATGTCATTGGTGTTTTGATAGCAATTGCATTGAATTTGTAGATTGCTTTGGGTAGGATGG<br>ATATTTTAACAAAATTGATTCTTCCGGCTGGGCACGGTGGCTCACTCCTGTAATCCCAGCACTTTGGGAGGCCGAG<br>TCAGGTGGATCACTTGAGATCAGGAGTTCAAGACCAGCCTGATCAACATGGGGAAACCCCGCCTCTACTAAAAATA<br>CAAAATTAGCCAGGCGTGGTGGCATATGCCTGTAATCCCAGCTACTCAGGAAAGCTGAGGCAGGAGAATCGCTTGA<br>ACCCAGGAGGCAGAGGTTGTGGTGAGCTGAGATTGCACCATTGCACTCCAGCCTGGGCAACAGGAGCAAAACTCCA<br>TCTCAGAAAATAAAAATAAACATTGATTCTTCCAGTCCGTGAACATGGAATGCCTTTTCCATTTTTTGTGTCCTCT<br>TCAATGTTTTGCATCAGTGCTTTATAGTTTTTATTGGAGAGATCTTTCACTTCTTCAGTTAAGTCTATTCCTAGGT<br>ATTTTATTTTATTTGTAGCTAATGAAAATGGGATTCGTTTCTTGATTTCTTTTTCAGATTATTTGCTGTTAGCACA<br>TAGAAGTGCTATTGTTTTTTGCATGTTGATTTTGTATCCTGCAACTTTACTGAATTTGTTCTTCAGTTCTAATAGT<br>TTTTTGGTGGAGTCTTTAGGTTTTCCAAATATCAGACCACATGATGTGCAAACAAGGATAATTTGACTTCTTCTTT<br>TCCAATTTTGATGCCCTTTATTTCCTTCTCCTGTCAGATTGCTCTAGCTAGGACTTGCAGTATTGTGTTGCATAAC<br>TGTAGTGAAAGTAGTCATCCTTGTCTTGTTCCAGATCTTAAAGAAAAGGCTTTCAGTTTTCCCCCATTCAGTATGT<br>TACTAGCTGTGAGTTGTCATATATGGCTTTTGTTATATTGAGGTCTGTTCCTTGTATACTCAGTTTTTTTAGAGTT<br>TTTATCATGAAGGGATGTTAAACTTATCAAATGCTTTTTCAGTATCAATTGAAATGGTGATATGGCTTTTGTCCTT<br>TATTCTGTTGATACGATGTATTACATTGATTGATTTGTGTATGCATACCTGGAATACATTCCACTTGGTCATGAAG<br>AATGATCTTTTTAATATACTGTTGAATGTGGTTTGCTAGTATTTCATTGATGATATTTGCCTCAATGTTCATCAGG<br>GATATAGGCCTGTAGTTTTCTTTTTTTGATGTGTCTTTGCCTGATTTTGATATCAGGATATTCCTGGCTTTGTAAA<br>ATGAGTTTGGAAGTATTCCCTCCTCCTCTGTTTTTCAGAACAATTTGAATAGGACTGATATTTCTTGTTCTTTAAA<br>CGTTTAATTGTGGTAAATTATACATTACATACATTTTACTGTTTTAACCGCTTTTAAGTGTATACTCGGTGGCATT<br>AGATACATTCACATTTTTGTGCAACCCAAAACTCTGTACCCATTAATCAGTAACTCCCCATTCCTCCCTACCTCTG<br>GCCCCTGGTAACCATCATTCTACTTTTTGTTTCTATGAATTTGACCACTCTAGGTACCTCATTTAAGTAGAATCGT<br>GTAATGTTTGTCTTTTTGATTCTGGCTTATTTCACTTATAATATTTCGAGGTTCATCCAGGTTGTAGTATGGGTCA<br>GATTTTCATTCCTTTTAATGATGAATAATACTCATTATATGTATGTACCACATCTTGGTTATCCATTCCTCAGACA<br>ATGGACACTTGGGTTACTTCTACCTTTTGGATATTGGCAAATATTTCATTTCTCTTGGGTATATATTTATTTCTTT<br>TGAGTATTTCTTTTGGGTATATATCCAGAAATAGAATTGTTGGATCATACGGTATTTCATTTTTTAATTTTTAGAG<br>GAATCACCATAGTGTTTTCCATTGCAGGCGTGCCATTTTGTATTTCTAGAAGCAGTATACAGGGGCTTCAGTTTCT<br>CTACCTCCTTGCCAAACTTGCTGTGTGTGTGTGTGTGTGTGTGTGTGTGTGTGTGTGTGTGATAATAGCCACCCTGAT<br>TGGTTTGAAGTGGTATCTCATTGTGGTTTGGATTTGCATTTTCCTAATGAGTACTGATATTGAGCATCTTTTCATG<br>TGTTTATTGATCATTTGTATATTTTCTTTGAAGAATTGGCCATTGAAGTCTTGCCCATTTTTCTCCCCCACATAGC<br>TTCTCATGGCTATTTTGCCCATTTTTGAGTGGGTTGACTGTTTTGTTGTTTTTGTCAAACTTTTTTGCATATTCTG<br>GAAACTAATCTCTCTCTTTTTCTTTTTTTTTTTTTTTTTTTTTTTGAGATGGAGTCTTGCTCTGTTGCCCAGGCTG<br>GAGTGCAGTGGCACGATCTCAGCTCACTGCAAGCTCCGCCCGCTAGCTTCATGCCATTCTCCCGCCTCAGCCTCCC<br>GAGTAGCTGGGACTACAGGCGCCCGCCACCACACCCGGCTAATTTTTTGTATTTTTAGTAGAGATAGGGTTTCACC<br>ATGTTAGCCAGGATGGTCTCAATCTCCTGACCTGGTGATACACCCGCCTCGGCCTCCCAAAGTGCTGGAACTACAG<br>GCTTGAGCCACCACGCCTGGCCTTCTGGAAACTAATCTCTTATCAGATATATGACTTGCAATATTTATTTCATTTC<br>AGGGGTTGATTGCTTTCTCACTCTGATTGTGCCCTTTGATGCACAGATATTTTGAATTTTTCATGAGTCCAGTTTG<br>TCAGTTCTTTCTATTCTATCTGTGCTTTGGCGTCATATCCATGAAAGCACTGTCAAACCCTATGTCATGAACATTA<br>TACCCAATGTTTTTTTCTAAGATATTTTTATGTTTTAGTTCTTGAGTTTAGAGTTTAGGTCTTTGATTCATTTTGA<br>GTTAATTTTTGTATATAGTACAAATTAAGGGTCCAATTTTATATTATTTGAACATCCAGTTCCCCCAGCACTATTT<br>GCTGAAAAGATGGACTTACTCTTTGAGACCCTGTCACCTGCCCACCCCAGTGGACACTAGCTGGTCCATCCAATTG<br>CTGTCCTGGGGCCTTGTCATGCTACTCTTCCACTTTGGACCCAAGCCCACATCATTGCTCCCCTCTGGGATACTGA<br>CCCCACTATAAACTTCACTGGGGCTACAACCTTCCTACCCCTTGTGCCTCATGACCACCCCCTCCCTTGTCCCCAC<br>CATGCCCATGATGAGTCTTTTCTCAAGGCAGCTCGCCTTGCCTCCATCTCACCCTCACCTGTGCACCACAGCCACA<br>CTGGACATGGGTCCCTCTGAGCCTGAGTCCCTTCCCATTCCCACTGTCCCCTCTGGCAAGACCTTCCTTCCAACAC<br>TGCCTTCATGCTCCTCCCTTGCCCCTGCAGGGCAGCCTCTCCCCTTGGCCCCTATTCCCTTAGGGGGCTTGTGGCC<br>ACCCAGTCCTGGCACCTGACCTACAAGTTTGCCATCTTCATTCCCCCTTCTTCTGTTCATCAGCCCCCTCCTCTAT<br>CCTCCCACCCTCACAGTTTTCCTTGTATATGAAATCTTCGTTCTTGTCCTTTTGCCCATGCGCATTTCCTGCCTCC<br>TCAGGGAGGTCGGGACAGCAGACCTGTGTGTTAAACATCAATGTGAAGTTATTTCCAGGAAGAAGTTTCACCTGTG<br>ATTTCCTCTTCCCCAGAGCCCCACAGTCTTCGTTACAACCTCATGGTGCTGTCCCAGGATGGATCTGTGCAGTCAG |

TABLE 9-continued

| lists sequences for the disclosure |
| --- |

GGTTTCTCGCTGAGGGACATCTGGATGGTCAGCCCTTCCTGCGCTATGACAGGCAGAAACGCAGGGCAAAGCCCCA
GGGACAGTGGGCAGAAAATGTCCTGGGAGCTAAGACCTGGGACACAGAGACCGAGGACTTGACAGAGAATGGGCAA
GACCTCAGGAGGACCCTGACTCATATCAAGGACCAGAAAGGAGGTGAGAGTCGGCAGGGGCAAGAGTAATGGGAGG
CCTTCTCCAGGAAAGTTGGAGACAGAGAGCAGGGACCTGTCTCTTCCCGCTGGATCTGGCTGGGGGTGGGATGAG
GAATAGGGTCAGGGAGGCTCAGCAGGGTGGTGAGCCGGAACTCAGCCCACACAGGGAGGCATGGAGGAGGGCCAGG
GAGGGGTCGCTGCTGGGCTGAGTTCCTCACTTGGGTGGAAAGGTGATGGGTTCGGGAATGGAGAAGTCACTGCTGG
GTGGGGGCAGGCTTGCATTCCCTCCAGGAGATTAGGGTCTGTGAGATCCATGAAGACAGCAGCACCAGGGGCTCCC
GGCATTTCTACTACGATGGGGAGCTCTTCCTCTCCCAAAACCTGGAGACTCAAGAATCGACAGTGCCCCAGTCCTC
CAGAGCTCAGACCTTGGCTATGAACGTCACAAATTTCTGGAAGGAAGATGCCATGAAGACCAAGACACACTATCGC
GCTATGCAGGCAGACTGCCTGCAGAAACTACAGCGATATCTGAAATCCGGGGTGGCCATCAGGAGAACAGGTACCG
ACCCTGGCCAGGGGCTCTACTGTTCCCGCAATTCTGCTAGAGTTGCCTCGCCTCCCAGCTCTGTCCGGGGAAACCC
TCCCTGTGCTATGGATGCAGGCGTTTCCTGTTGGCATATTGTGTCCTGATTTGCCTCTCCTGTTAGAGCCATTGGA
TAAAGACAGTGGGTCTGGGACTGAACTGTCCAGTGTTGTAATCTGGGAAAGCAGTGGGCCCTCTGACAGAAGCCTG
AGCCTGGTGTGGGAGTTAGGCAGGAGAGGAAGCCCTCAGGGCCAGGGCTGCCCCCTCTGCCTCCCGGCCTGCCCAT
CCCGGAGAGTTCCCTCCTGGCCCCATGACCCAGGAGTCCACCCTTGACATCCCCCTCCTCAGCATCAATGTGGGGA
TCCCAGAGCCTGAGGCCACAGTCCCAAGGCCCATCCTCCTGCTAGCCTGGAGGAATTAGGCCCCAGGGTGAGGACA
GACTTACAGAAGGTCCGGTATCTGTGAGGGATTCAGCCAGAGTGAGAACAGTGGAGAGGAGCAGCCCTGTTCCCTG
CATCTCCCTTAGAGGGGAGCAGGGCTTCACTGGCTCTGCCCTTTCTTCTCCAGTGCCCCCCATGGTGAATGTCACC
TGCAGCGAGGTCTCAGAGGGCAACATCACCGTGACATGCAGGGCTTCCAGCTTCTATCCCCGGAATATCACACTGA
CCTGGCGTCAGGATGGGGTATCTTTGAGCCACAACACCCAGCAGTGGGGGGATGTCCTGCCTGATGGGAATGGAAC
CTACCAGACCTGGGTGGCCACCAGGATTCGCCAAGGAGAGGAGCAGAGGTTCACCTGCTACATGGAACACAGCGGG
AATCACGGCACTCACCCTGTGCCCTCTGGTGAGCCTGGGGTGACCCTGGAGAGGGTCAGGCCAGGGTAGGAACAGC
AAGGACGGCTGTGGCTCTCTGCCCAGTGTATAACAAGTCCCTTTTTTTCAGGGAAGGCGCTGGTGCTTCAGAGTCA
ACGGACAGACTTTCCATATGTTTCTGCTGCTATGCCATGTTTTGTTATTATTATTATTCTCTGTGTCCCTTGTTGC
AAGAAGAAAACATCAGCGGCAGAGGGTCCAGGTGAGAAAAGGGGACAGTTTCTGGAGATGGGAAAGCTCCTTTCTA
GGCAGTAGGGTCTCCTCATTGCTCCTGCCCAGACAAGACGTAGGTGACAAGGCTGCTGGGACAGGGGATGGAAGCT
GGGGTATTTGGGAGGGGAATGGGAGCTGCATCTCCATCTACACCCATAAGTGCTTCCCAAGCCAGGGCTGGGGCAA
GGCCTTCGAATATCCAGCTGTGGCCTCCTCCTGCTGCAAGTGAGGAGTGGGCAGCAGGGAGGGCTGTGGCACCTGC
TCTGTCCCCATCCCAGCCTCTCTGTCTCTCGGGCTCACTAGGGTGCGTCCAGGTGGGGTGAGTTGGGAATCACGTG
CTGATTGCTGAGGGCCTGGATGATCATGGTGTCAGAGGGAGGAAATAGTAAAGGTGGCTGTGATCTGGGGAGGGCC
AGAAACTGGAGAGGAATCCAAGGAGAGGCGATGCCCACCCGTGTGCCTCCTCCAGGAGGCACTTTCCAGGTTCCCA
CTACCTGGCCTCCCTGAGTTTCCTTGCAGATGACACAGATGAATAGATAAGCAGATGTCCCTGGGCCATTTGAGGA
GCGGGGCCCAGCCCCTCATCAGGGCAGATGTGGTCCCTGTTTTCATCCTACCTCCAGCGTGTTTTCTTCTGCAGTC
CCTGAGGGACACAGTCCCCAGGCGCCATCTCTTTGAGGCTTTGTTCTGTGCTCTGTGGCCTTACCTTGCCCTCCCT
GAGCCAATTTCCCTTTCTCAAGGTGGTCACTGCCTGGTAAGTTTGGAGTAAGGGACAGTCAGAAGCATTTCCCCCA
CAGTCAGGTTGTTTGATGGGAGATGAAAAGAGACAGCAGAAGTTTTGTGTTTCTGCAAAAACAGAGGCAGTGCAGG
GGACAGTGAGAGGCTGGGGTGTCCAGGAGACCTGAGTCTGGCGGTAGGGGCGCTGGTTTCTCATCCTTGAACCTAG
TTGCACTGTCAGTCGGCCCCTCATGCCTGAGCAGATGGGAAGGTTCGTCCCCTGCCCTGCAGCAAGAGGGCCCCAT
CCAGGAGGCACCCACAGCAGGGGCAGTGCAGGTCTGTGGTCACTCCTGCTCTCACCTGCGGCGTCTCCCGTGGAGG
GATTGTCACTTCTGGTTCCCTGTGGGCAGGAATGGTTTCCTCGTAGGTCACTGGGGTTTTGGCCAGGAAAAGGGTA
TGAAATTCATGTGCCAGTTTCTCAAAATTCCTGCTTTCAATGTTGATGTCCAATAAAGATGTTCGTAATTTCAGCT
CTATAATCTTAATAGGATTTCCTCTAATACTGCTGTTGTAAAGCATATTAAATAAAACAGGAACTCAAATTTGGAG
CCCCCTCTCCAGAAGGGTCTGTGTGGAGATGGTGGCTGTGGCAGCGGCAGTTCCCAGGTGCAGAGGGTGGGCAGAG
GCAGCCTCAGGCTAAGGGGTCTCCCCTACTCCACGTGGAGAAAAGTCCTTGTAGGTTGCAAGGGCAGTGGCCTGGG
TGGAATCCCTGCTAGGGACAGAGCAGGAAGGCCTCACAGCCTCACCAAGCAGCAGCCCTGGGGTGAAGTAAGTGGA
CCAGGAGTAAGTGGACCAGGCAGGAGCAGTAGTGACTCAACAGCAGGTCACAGGCCTAGGTGGGTGCTGAAGGTCA
TGGGAGGCCAGGCCTCCTCGAGCAAGGTGGGGGGTCCCAGGGTCAGGTCAGGTGCAGATCCTGTGGCAGCCACGTC
TTTCCATGCTGGGCCTGCTGGGCCCCCCAGGCTTCCTGATGGGGTCCCCAGTTAGGAGCTGCCTGCTCAGGGCTGG
GAGGGGAGGAGTGCTGAGCTGCAGATAGAGGGCAGGGCCCACAGTGGGCAGGGCCTGCCCTGGTGTGCAGGTGCCT
CTGCAGGAGAGAAGGGCCTGGGGACTGAGAGCAAGGGTCAGGGCCTCTCTTTGGGGAGGCCTCTCACTGTAACAGG
ACTGGTCAGGCCTGAGAGGAGGGCACTGGGTTCCCTCTTGGGTCTTGTCCTTTTGTCTTGGGGCCCTTTCACTCCC
TGCACGGTGAGTGGTGGGCACAGGACAGGGGCTGATGTTGATGGAGTGATGGGAGAGAACTGACAGGGGCTGGGAA
AAGCAAGGAGGGAGGAAGAAAAAAGTGGGGGCCTCATCTTCTCTCAGAGAAAGGGCGAATCTGATTTTGGGGCAAC
TGAAGAGAGAAAAGTCCTTAGGGAATAAACACAACACTGCACCCAGTGGAGCATTTACCCGTTTCCCTCTTCTCCA
GAGCTTGTGAGCCTGCAGGTCCTGGATCAACACCCAGTTGGGACAGGAGACCACAGGGATGCAGCACAGCTGGGAT
TTCAGCCTCTGATGTCAGCTACTGGGTCCACTGGTTCCACTGAGGGCACCTAGACTCTACAGCCAGGCGGCCAGGA
TTCAACTCCCTGCCTGGATCTCACCAGCACTTTCCCTCTGTTTCCTGACCTATGAAACAGAGAAAATAACATCACT
TATTTATTGTTGTTGGATGCTGCAAAGTGTTAGTAGGTATGAGGTGTTTGCTGCTCTGCCACGTAGAGAGCCAGCA
AAGGGATCATGACCAACTCAACATTCCATTGGAGGCTATATGATCAAACAGCAAATTGTTTATCATGAATGCAGGA
TGTGGGCAAACTCACGACTGCTCCTGCCAACAGAAGGTTTGCTGAGGGCATTCACTCCATGGTGCTCATTGGAGTT
ATCTACTGGGTCATCTAGAGCCTATTGTTTGAGGAATGCAGTCTTACAAGCCTACTCTGGACCCAGCAGCTGACTC
CTTCTTCCACCCCTCTTCTTGCTATCTCCTATACCAATAAATACGAAGGGCTGTGGAAGATCAGAGCCCTTGTTCA
CGAGAAGCAAGAAGCCCCCTGACCCCTTGTTCCAAATATACTCTTTTGTCTTTCTCTTTATTCCCACGTTCGCCCT
TTGTTCAGTCCAATACAGGGTTGTGGGGCCCTTAACAGTGCCATATTAATTGGTATCATTATTTCTGTTGTTTTTG
TTTTTGTTTTTGTTTTTGTTTTTGAGACAGAGTCTCACTCTGTCACCCAGGCTGCAGTTCACTGGTGTGATCTCAG
CTCACTGCAACCTCTGCCTCCCAGGTTCAAGCACTTCTCGTACCTCAGACTCCCGAATAGCTGGGATTACAGACAG
GCACCACCACACCCAGCTAATTTTTGTATTTTTTGTAGAGACGGGGTTTCGCCAAGTTGACCAGCCCAGTTTCAAA
CTCCTGACCTCAGGTGATCTGCCTGCCTTGGCATCCCAAAGTGCTGGGATTACAAGAATGAGCCACCGTGCCTGGC
CTATTTTATTATATTGTAATATATTTTATTATATTAGCCACCATGCCTGTCCTATTTTCTTATGTTTTAATATATT
TTAATATATTACATGTGCAGTAATTAGATTATCATGGGTGAACTTTATGAGTGAGTATCTTGGTGATGACTCCTCC
TGACCAGCCCAGGACCAGCTTTCTTGTCACCTTGAGGTCCCCTCGCCCCGTCACACCGTTATGCATTACTCTGTGT
CTACTATTATGTGTGCATAATTTATACCGTAAATGTTTACTCTTTAAATAGA

SEQ ID NO: 35 MICB cDNA Sequence
GAATTTTGTGAGCGACCGCGCTGGGCCGTTTCTCTTTCTTTTCCGGACCCTGCAGTGGCGCCTAAAGTCTGCGAGG
AGGAAGTCGCCTCTGTGCTCGTGAGTCCAGGGATCTAAGAGCCCCACAGTCTTCGTTACAACCTCATGGTGCTGTC
CCAGGATGGATCTGTGCAGTCAGGGTTTCTCGCTGAGGGACATCTGGATGGTCAGCCCTTCCTGCGCTATGACAGG
CAGAAACGCAGGGCAAAGCCCCAGGGACAGTGGGCAGAAAATGTCCTGGGAGCTAAGACCTGGGACACAGAGACCG TABLE 9-continued lists sequences for the disclosure AGGACTTGACAGAGAATGGGCAAGACCTCAGGAGGACCCTGACTCATATCAAGGACCAGAAAGGAGGCTTGCATTC
CCTCCAGGAGATTAGGGTCTGTGAGATCCATGAAGACAGCAGCACCAGGGGCTCCCGGCATTTCTACTACGATGGG
GAGCTCTTCCTCTCCCAAAACCTGGAGACTCAAGAATCGACAGTGCCCCAGTCCTCCAGAGCTCAGACCTTGGCTA
TGAACGTCACAAATTTCTGGAAGGAAGATGCCATGAAGACCAAGACACACTATCGCGCTATGCAGGCAGACTGCCT
GCAGAAACTACAGCGATATCTGAAATCCGGGGTGGCCATCAGGAGAACAGTGCCCCCCATGGTGAATGTCACCTGC
AGCGAGGTCTCAGAGGGCAACATCACCGTGACATGCAGGGCTTCCAGCTTCTATCCCCGGAATATCACACTGACCT
GGCGTCAGGATGGGGTATCTTTGAGCCACAACACCCAGCAGTGGGGGGATGTCCTGCCTGATGGGAATGGAACCTA
CCAGACCTGGGTGGCCACCAGGATTCGCCAAGGAGAGGAGCAGAGGTTCACCTGCTACATGGAACACAGCGGGAAT
CACGGCACTCACCCTGTGCCCTCTGGGAAGGCGCTGGTGCTTCAGAGTCAACGGACAGACTTTCCATATGTTTCTG
CTGCTATGCCATGTTTTGTTATTATTATTATTCTCTGTGTCCCTTGTTGCAAGAAGAAAACATCAGCGGCAGAGGG
TCCAGAGCTTGTGAGCCTGCAGGTCCTGGATCAACACCCAGTTGGGACAGGAGACCACAGGGATGCAGCACAGCTG
GGATTTCAGCCTCTGATGTCAGCTACTGGGTCCACTGGTTCCACTGAGGGCACCTAGACTCTACAGCCAGGCGGCC
AGGATTCAACTCCCTGCCTGGATCTCACCAGCACTTTCCCTCTGTTTCCTGACCTATGAAACAGAGAAAATAACAT
CACTTATTTATTGTTGTTGGATGCTGCAAAGTGTTAGTAGGTATGAGGTGTTTGCTGCTCTGCCACGTAGAGAGCC
AGCAAAGGGATCATGACCAACTCAACATTCCATTGGAGGCTATATGATCAAACAGCAAATTGTTTATCATGAATGC
AGGATGTGGGCAAACTCACGACTGCTCCTGCCAACAGAAGGTTTGCTGAGGGCATTCACTCCATGGTGCTCATTGG
AGTTATCTACTGGGTCATCTAGAGCCTATTGTTTGAGGAATGCAGTCTTACAAGCCTACTCTGGACCCAGCAGCTG
ACTCCTTCTTCCACCCCTCTTCTTGCTATCTCCTATACCAATAAATACGAAGGGCTGTGGAAGATCAGAGCCCTTG
TTCACGAGAAGCAAGAAGCCCCCTGACCCCTTGTTCCAAATATACTCTTTTGTCTTTCTCTTTATTCCCACGTTCG
CCCTTTGTTCAGTCCAATACAGGGTTGTGGGGCCCTTAACAGTGCCATATTAATTGGTATCATTATTTCTGTTGTT
TTTGTTTTTGTTTTTGTTTTTGTTTTTGAGACAGAGTCTCACTCTGTCACCCAGGCTGCAGTTCACTGGTGTGATC
TCAGCTCACTGCAACCTCTGCCTCCCAGGTTCAAGCACTTCTCGTACCTCAGACTCCCGAATAGCTGGGATTACAG
ACAGGCACCACCACACCCAGCTAATTTTTGTATTTTTTGTAGAGACGGGGTTTCGCCAAGTTGACCAGCCCAGTTT
CAAACTCCTGACCTCAGGTGATCTGCCTGCCTTGGCATCCCAAAGTGCTGGGATTACAAGAATGAGCCACCGTGCC
TGGCCTATTTTATTATATTGTAATATATTTTATTATATTAGCCACCATGCCTGTCCTATTTTCTTATGTTTTAATA
TATTTTAATATATTACATGTGCAGTAATTAGATTATCATGGGTGAACTTTATGAGTGAGTATCTTGGTGATGACTC
CTCCTGACCAGCCCAGGACCAGCTTTCTTGTCACCTTGAGGTCCCCTCGCCCCGTCACACCGTTATGCATTACTCT
GTGTCTACTATTATGTGTGCATAATTTATACCGTAAATGTTTACTCTTTAAATAGAAAAAAAAAAAAAAA SEQ ID NO: 36    MICB Protein Sequence
MVLSQDGSVQSGFLAEGHLDGQPFLRYDRQKRRAKPQGQWAENVLGAKTWDTETEDLTENGQDLRRTLTHIKDQKG
GLHSLQEIRVCEIHEDSSTRGSRHFYYDGELFLSQNLETQESTVPQSSRAQTLAMNVTNFWKEDAMKTKTHYRAMQ
ADCLQKLQRYLKSGVAIRRTVPPMVNVTCSEVSEGNITVTCRASSFYPRNITLTWRQDGVSLSHNTQQWGDVLPDG
NGTYQTWVATRIRQGEEQRFTCYMEHSGNHGTHPVPSGKALVLQSQRTDFPYVSAAMPCFVIIIILCVPCCKKKTS
AAEGPELVSLQVLDQHPVGTGDHRDAAQLGFQPLMSATGSTGSTEGT SEQ ID NO: 37    CD46 cDNA Sequence
GGAACTCGGAGAGGTCTCCGCTAGGCTGGTGTCGGGTTACCTGCTCATCTTCCCGAAAATGATGGCGTTTTGCGCG
CTGCGCAAGGCACTTCCCTGCCGTCCCGAGAATCCCTTTTCTTCGAGGTGCTTCGTTGAGATTCTTTGGGTGTCGT
TGGCCCTAGTGTTCCTGCTTCCCATGCCCTCAGATGCCTGTGATGAGCCACCGAAGTTTGAAAGCATGCGGCCCCA
ATTTTTGAATACCACTTACAGACCTGGAGACCGTGTAGAGTATGAATGTCGCCCCGGGTTCCAGCCCATGGTTCCT
GCGCTTCCCACCTTTTCCGTCTGTCAGGACGATAATACGTGGTCACCCCTCCAGGAGGCTTGTCGACGAAAAGCCT
GTTCGAATCTACCAGACCCGTTAAATGGCCAAGTTAGCTACCCAAATGGGGATATGCTGTTTGGTTCAAAGGCTCA
GTTTACCTGTAACACTGGTTTTTACATAATTGGAGCCGAGACTGTGTATTGTCAGGTTTCTGGGAATGTTATGGCC
TGGAGTGAGCCCTCCCCGCTATGTGAGAAGATTTTGTGTAAACCACCTGGCGAAATTCCAAATGGAAAATACACCA
ATAGCCATAAGGATGTATTTGAATACAATGAAGTAGTAACTTACAGTTGTCTTTCTTCAACTGGACCGGATGAATT
TTCACTTGTTGGAGAGAGCAGCCTTTTTTGTATTGGGAAGGACGAGTGGAGTAGTGACCCCCCTGAGTGTAAAGTG
GTCAAATGTCCATATCCAGTAGTCCCAAATGGAGAAATTGTATCAGGATTTGGATCAAAATTTTACTACAAAGCAG
AGGTTGTATTTAAATGCAATGCTGGTTTTACCCTTCATGGCAGAGACACAATTGTCTGCGGTGCAAACAGCACGTG
GGAGCCTGAGATGCCCCAATGTATCAAAGATTCCAAGCCTACTGATCCACCTGCAACCCCAGGACCAAGCCATCCA
GGACCTCCCAGTCCCAGTGATGCATCACCACCTAAAGATGCTGAGAGTTTAGATGGAGGAATCATCGCTGCAATTG
TTGTGGGCGTCTTAGCTGCCATTGCAGTAATTGCTGGTGGTGTATACTTTTTTCATCATAAATACAACAAGAAAAG
GTCGAAGTAAAACTGATGTGCTTAAAGTAAAAGTTGCTGAGAGGACGTGGAATCCAGCCCCTTCCCTCTCCTGTGC
TGCTGCCTGGGTCCCGTTTTGCATGTCATGACTGTGTGCTTCCAAAAAATGCCTTTTGTTCGTATTTTTTTGCCTA
AACGCATGATTTTGTCTCTACTTGAATTAAATCATCACTGAATCCACGC SEQ ID NO: 38    CD55 cDNA Sequence
CGGCACGAGATTTCGTCTTAATCGCGGAGGTCGCAGAGTCCGGGAGCCGCTCGGGGTCCCCGTTCCCGCGCGCCAT
GAGTCCCCTGCCGCGGAGCGCCCCCGCGGTGAGGCGCCTAATGGGCGGACAGACGCCGCCGCCGCTGCTGCTGCTG
CTGCTGCTGCTGTGTATCCCGGCTGCGCAGGGTGACTGCAGCCTTCCACCCGATGTACCTAATGCCCAACCAGATT
TGCGAGGTCTTGCAAGTTTTCCTGAACAAACCACAATAACATACAAATGTAACAAAGGCTTTGTCAAAGTTCCTGG
CATGGCAGACTCAGTGCTCTGTCTTAATGATAAATGGTCAGAAGTTGCAGAATTTTGTAATCGTAGCTGTGATGTT
CCAACCAGGCTACATTTTGCATCTCTTAAAAAGTCTTACAGCAAACAGAATTATTTCCCAGAGGGTTTCACCGTGG
AATATGAGTGCCGTAAGGGCTATAAAAGGGATCTTACTCTATCAGAAAAACTAACTTGCCTTCAGAATTTTACGTG
GTCCAAACCTGATGAATTTTGCAAAAAAAAACAATGTCCGACTCCTGGAGAACTAAAAAATGGTCATGTCAATATA
ACAACTGACTTGTTATTTGGCGCATCCATCTTTTTCTCATGTAACGCAGGGTACAGACTAGTTGGTGCAACTTCTA
GTTACTGTTTTGCCATAGCAAATGATGTTGAGTGGAGTGATCCATTGCCAGAATGCCAAGAAATTTCTCCAACTGT
CAAAGCCATACCAGCTGTTGAGAAACCCATCACAGTAAATTTTCCAGCAACAAAGTATCCAGCTATTCCCAGGGCC
ACAACGAGTTTTCATTCAAGTACATCTAAAAATCGAGGAAACCCTTCTTCAGGCATGAGAATCATGTCGTCTGGTA
CCATGCTACTTATTGCAGGAGGTGTTGCTGTTATTATAATAATTGTTGCCCTAATTCTAGCCAAAGGTTTCTGGCA
CTATGGAAAATCAGGCTCTTACCACACTCATGAGAACAACAAAGCCGTTAATGTTGCATTTTATAATTTACCTGCG
ACTGGCGATGCCGCAGATGTAAGACCTGGTAATTAACAAAAGGACGGTGCATGTGTAACACTGACAGTTTTGCTTA
TGGTGCTAGTAACCATTGGCTAGCTGACTTAGCCAAAGAAGAGTTAAGAAGAAAGTGCACACAAGTACACAGAATA
TTTTCAGTTTCTTAGAACTTTCAGGTGGAGTGGACATAGTTTGTGGATAGTGTTCTTCGTTTTGCATGTTTTCATT
GTCTCTAAGGTACATAGGAATGTCACAGAACCAAAGAGAAACAAATCTATCCTGAAATTACATCCTCAACACTCCT
AAGACTCTTGAAAATAGAACAGCTCATAAGATTGAGAGCAATTACTTTCCAAAAAGGGTGAGAAAATGGAGAGATT
TGTTCATGGTTAGAATATAAGAAAAAAGAAAACAAAAAGGTGATTTTTCCCACCAAATGTGTAATGTTATTTTTAT
TAATAAAGGAAAAAAAAAAAAAAAAAA TABLE 9-continued lists sequences for the disclosure SEQ ID NO: 39 CD59 cDNA Sequence
GAAAAGACGCGCAGGCCGGGCCGCTCTCCCGACGGGGAGTAGCGCTGCAGCCGGACGCAGGGTGCAGTTAGAATCC
ATAGACGGTCACGATGGGAAGCAAAGGAGGGTTCATTTTGCTCTGGCTCCTGTCCATCCTGGCTGTTCTCTGCCAC
TTAGGTCACAGCCTGCAGTGCTATAACTGTATCAACCCAGCTGGTAGCTGCACTACGGCCATGAATTGTTCACATA
ATCAGGATGCCTGTATCTTCGTTGAAGCCGTGCCACCCAAAACTTACTACCAGTGTTGGAGGTTCGATGAATGCAA
TTTCGATTTCATTTCGAGAAACCTAGCGGAGAAGAAGCTGAAGTACAACTGCTGCCGGAAGGACCTGTGTAACAAG
AGTGATGCCACGATTTCATCAGGGAAAACCGCTCTGCTGGTGATCCTGCTGCTGGTAGCAACCTGGCACTTTTGTC
TCTAACTGTACACCAGGAGAGTTTCTCCTCAACTTCCTCTGTCTCTCTGTTCCTATTTCCCATGCTGCGGTGTTCC
AAAGGCTGTGTATGCTCCAGCTTCTTCCTGTTGGGAAGGACTAAACCTAGCTTGAGCACTTTGGATTAGAGAGAGA
AACTTTGAGCGACTTTGAAGACCAGGCCTGTTGGCAGAGAAGACCTGTCAGAGGGGAAACGTTTTAAGAGTGAAGC
ACAGGTGATTTGAGCGAGGCCTATGCGTCTTCCTCTGCTCTTGGCAGGACCAGCTTTGCGGTAACCATTCGATAGA
TTCCACAATCCTT SEQ ID NO: 40 ICP47 cDNA Sequence
TCAAGGGGCCAGCACGCGATCCTGCCGCTCGTTCGATCTAGCACACCCACGGGTCTGCTGTGTGGGATTTCGACTC
GCGGGATCCGATCGCACGTCCGGAGGACACAGCAGCGGGAGCTCCGGGTCGGTCACCGCAGTTCTGGCCGCCTCTC
GGTCCTCCCGTTCCCTTTTATGGATCTCCGCGCAGACATCGCCATACGTCCGGTGTGTGCACCGCGAAGAATCCAG
AAACATGTCCGTCGTTTTCAGGGCCCAAGACAT SEQ ID NO: 41 HLA-G1 cDNA Sequence
AGTGTGGTACTTTGTCTTGAGGAGATGTCCTGGACTCACACGGAAACTTAGGGCTACGGAATGAAGTTCTCACTCC
CATTAGGTGACAGGTTTTTAGAGAAGCCAATCAGCGTCGCCGCGGTCCTGGTTCTAAAGTCCTCGCTCACCCACCC
GGACTCATTCTCCCCAGACGCCAAGGATGGTGGTCATGGCGCCCCGAACCCTCTTCCTGCTGCTCTCGGGGGCCCT
GACCCTGACCGAGACCTGGGCGGGCTCCCACTCCATGAGGTATTTCAGCGCCGCCGTGTCCCGGCCCGGCCGCGGG
GAGCCCCGCTTCATCGCCATGGGCTACGTGGACGACACGCAGTTCGTGCGGTTCGACAGCGACTCGGCGTGTCCGA
GGATGGAGCCGCGGGCGCCGTGGGTGGAGCAGGAGGGGCCGGAGTATTGGGAAGAGGAGACACGGAACACCAAGGC
CCACGCACAGACTGACAGAATGAACCTGCAGACCCTGCGCGGCTACTACAACCAGAGCGAGGCCAGTTCTCACACC
CTCCAGTGGATGATTGGCTGCGACCTGGGGTCCGACGGACGCCTCCTCCGCGGGTATGAACAGTATGCCTACGATG
GCAAGGATTACCTCGCCCTGAACGAGGACCTGCGCTCCTGGACCGCAGCGGACACTGCGGCTCAGATCTCCAAGCG
CAAGTGTGAGGCGGCCAATGTGGCTGAACAAAGGAGAGCCTACCTGGAGGGCACGTGCGTGGAGTGGCTCCACAGA
TACCTGGAGAACGGGAAGGAGATGCTGCAGCGCGCGGACCCCCCCAAGACACACGTGACCCACCACCCTGTCTTTG
ACTATGAGGCCACCCTGAGGTGCTGGGCCCTGGGCTTCTACCCTGCGGAGATCATACTGACCTGGCAGCGGGATGG
GGAGGACCAGACCCAGGACGTGGAGCTCGTGGAGACCAGGCCTGCAGGGGATGGAACCTTCCAGAAGTGGGCAGCT
GTGGTGGTGCCTTCTGGAGAGGAGCAGAGATACACGTGCCATGTGCAGCATGAGGGGCTGCCGGAGCCCCTCATGC
TGAGATGGAAGCAGTCTTCCCTGCCCACCATCCCCATCATGGGTATCGTTGCTGGCCTGGTTGTCCTTGCAGCTGT
AGTCACTGGAGCTGCGGTCGCTGCTGTGCTGTGGAGAAAGAAGAGCTCAGATTGAAAAGGAGGGAGCTACTCTCAG
GCTGCAATGTGAAACAGCTGCCCTGTGTGGGACTGAGTGGCAAGTCCCTTTGTGACTTCAAGAACCCTGACTCCTC
TTTGTGCAGAGACCAGCCCACCCCTGTGCCCACCATGACCCTCTTCCTCATGCTGAACTGCATTCCTTCCCCAATC
ACCTTTCCTGTTCCAGAAAAGGGGCTGGGATGTCTCCGTCTCTGTCTCAAATTTGTGGTCCACTGAGCTATAACTT
ACTTCTGTATTAAAATTAGAATCTGAGTATAAATTTACTTTTTCAAATTATTTCCAAGAGAGATTGATGGGTTAAT
TAAAGGAGAAGATTCCTGAAATTTGAGAGACAAAATAAATGGAAGACATGAGAACTTT SEQ ID NO: 42 HLA-E cDNA Sequence
GCAGACTCAGTTCTCATTCCCAATGGGTGTCGGGTTTCTAGAGAAGCCAATCAGCGTCGCCACGACTCCCGACTAT
AAAGTCCCCATCCGGACTCAAGAAGTTCTCAGGACTCAGAGGCTGGGATCATGGTAGATGGAACCCTCCTTTTACT
CCTCTCGGAGGCCCTGGCCCTTACCCAGACCTGGGCGGGCTCCCACTCCTTGAAGTATTTCCACACTTCCGTGTCC
CGGCCCGGCCGCGGGGAGCCCCGCTTCATCTCTGTGGGCTACGTGGACGACACCCAGTTCGTGCGCTTCGACAACG
ACGCCGCGAGTCCGAGGATGGTGCCGCGGGCGCCGTGGATGGAGCAGGAGGGGTCAGAGTATTGGGACCGGGAGAC
ACGGAGCGCCAGGGACACCGCACAGATTTTCCGAGTGAATCTGCGGACGCTGCGCGGCTACTACAATCAGAGCGAG
GCCGGGTCTCACACCCTGCAGTGGATGCATGGCTGCGAGCTGGGGCCCGACGGGCGCTTCCTCCGCGGGTATGAAC
AGTTCGCCTACGACGGCAAGGATTATCTCACCCTGAATGAGGACCTGCGCTCCTGGACCGCGGTGGACACGGCGGC
TCAGATCTCCGAGCAAAAGTCAAATGATGCCTCTGAGGCGGAGCACCAGAGAGCCTACCTGGAAGACACATGCGTG
GAGTGGCTCCACAAATACCTGGAGAAGGGGAAGGAGACGCTGCTTCACCTGGAGCCCCCAAAGACACACGTGACTC
ACCACCCCATCTCTGACCATGAGGCCACCCTGAGGTGCTGGGCCCTGGGCTTCTACCCTGCGGAGATCACACTGAC
CTGGCAGCAGGATGGGGAGGGCCATACCCAGGACACGGAGCTCGTGGAGACCAGGCCTGCAGGGGATGGAACCTTC
CAGAAGTGGGCAGCTGTGGTGGTGCCTTCTGGAGAGGAGCAGAGATACACGTGCCATGTGCAGCATGAGGGGCTAC
CCGAGCCCGTCACCCTGAGATGGAAGCCGGCTTCCCAGCCCACCATCCCCATCGTGGGCATCATTGCTGGCCTGGT
TCTCCTTGGATCTGTGGTCTCTGGAGCTGTGGTTGCTGCTGTGATATGGAGGAAGAAGAGCTCAGGTGGAAAAGGA
GGGAGCTACTCTAAGGCTGAGTGGAGCGACAGTGCCCAGGGGTCTGAGTCTCACAGCTTGTAAAGCCTGAGACAGC
TGCCTTGTGTGCGACTGAGATGCACAGCTGCCTTGTGTGCGACTGAGATGCAGGATTTCCTCACGCCTCCCCTATG
TGTCTTAGGGGACTCTGGCTTCTCTTTTTGCAAGGGCCTCTGAATCTGTCTGTGTCCCTGTTAGCACAATGTGAGG
AGGTAGAGAAACAGTCCACCTCTGTGTCTACCATGACCCCCTTCCTCACACTGACCTGTGTTCCTTCCCTGTTCTC
TTTTCTATTAAAAATAAGAACCTGGGCAGAGTGCGGCAGCTCATGCCTGTAATCCCAGCACTTAGGGAGGCCGAGG
AGGGCAGATCACGAGGTCAGGAGATCGAAACCATCCTGGCTAACACGGTGAAACCCCGTCTCTACTAAAAAATACA
AAAAATTAGCTGGGCGCAGAGGCACGGGCCTGTAGTCCCAGCTACTCAGGAGGCGGAGGCAGGAGAATGGCGTCAA
CCCGGGAGGCGGAGGTTGCAGTGAGCCAGGATTGTGCGACTGCACTCCAGCCTGGGTGACAGGGTGAAACGCCATC
TCAAAAAATAAAAATTGAAAAATAAAAAAAGAACCTGGATCTCAATTTAATTTTTCATATTCTTGCAATGAAATGG
ACTTGAGGAAGCTAAGATCATAGCTAGAAATACAGATAATTCCACAGCACATCTCTAGCAAATTTAGCCTATTCCT
ATTCTCTAGCCTATTCCTTACCACCTGTAATCTTGACCATATACCTTGGAGTTGAATATTGTTTTCATACTGCTGT
GGTTTGAATGTTCCCTCCAACACTCATGTTGAGACTTAATCCCTAATGTGGCAATACTGAAAGGTGGGGCCTTTGA
GATGTGATTGGATCGTAAGGCTGTGCCTTCATTCATGGGTTAATGGATTAATGGGTTATCACAGGAATGGGACTGG
TGGCTTTATAAGAAGAGGAAAAGAGAACTGAGCTAGCATGCCCAGCCCACAGAGAGCCTCCACTAGAGTGATGCTA
AGTGGAAATGTGAGGTGCAGCTGCCACAGAGGGCCCCCACCAGGGAAATGTCTAGTGTCTAGTGGATCCAGGCCAC
AGGAGAGAGTGCCTTGTGGAGCGCTGGGAGCAGGACCTGACCACCACCAGGACCCCAGAACTGTGGAGTCAGTGGC
AGCATGCAGCGCCCCCTTGGGAAAGCTTTAGGCACCAGCCTGCAACCCATTCGAGCAGCCACGTAGGCTGCACCCA
GCAAAGCCACAGGCACGGGGCTACCTGAGGCCTTGGGGGCCCAATCCCTGCTCCAGTGTGTCCGTGAGGCAGCACA
CGAAGTCAAAAGAGATTATTCTCTTCCCACAGATACCTTTTCTCTCCCATGACCCTTTAACAGCATCTGCTTCATT TABLE 9-continued

| lists sequences for the disclosure |
|---|
| CCCCTCACCTTCCCAGGCTGATCTGAGGTAAACTTTGAAGTAAAATAAAAGCTGTGTTTGAGCATCATTTGTATTT<br>CAAAAAAAAAAAAAAAAA |
| SEQ ID NO: 43 Human β-2-microglobulin cDNA Sequence<br>AATATAAGTGGAGGCGTCGCGCTGGCGGGCATTCCTGAAGCTGACAGCATTCGGGCCGAGATGTCTCGCTCCGTGG<br>CCTTAGCTGTGCTCGCGCTACTCTCTCTTTCTGGCCTGGAGGCTATCCAGCGTACTCCAAAGATTCAGGTTTACTC<br>ACGTCATCCAGCAGAGAATGGAAAGTCAAATTTCCTGAATTGCTATGTGTCTGGGTTTCATCCATCCGACATTGAA<br>GTTGACTTACTGAAGAATGGAGAGAGAATTGAAAAAGTGGAGCATTCAGACTTGTCTTTCAGCAAGGACTGGTCTT<br>TCTATCTCTTGTACTACACTGAATTCACCCCCACTGAAAAAGATGAGTATGCCTGCCGTGTGAACCATGTGACTTT<br>GTCACAGCCCAAGATAGTTAAGTGGGATCGAGACATGTAAGCAGCATCATGGAGGTTTGAAGATGCCGCATTTGGA<br>TTGGATGAATTCCAAATTCTGCTTGCTTGCTTTTTAATATTGATATGCTTATACACTTACACTTTATGCACAAAAT<br>GTAGGGTTATAATAATGTTAACATGGACATGATCTTCTTTATAATTCTACTTTGAGTGCTGTCTCCATGTTTGATG<br>TATCTGAGCAGGTTGCTCCACAGGTAGCTCTAGGAGGGCTGGCAACTTAGAGGTGGGGAGCAGAGAATTCTCTTAT<br>CCAACATCAACATCTTGGTCAGATTTGAACTCTTCAATCTCTTGCACTCAAAGCTTGTTAAGATAGTTAAGCGTGC<br>ATAAGTTAACTTCCAATTTACATACTCTGCTTAGAATTTGGGGGAAAATTTAGAAATATAATTGACAGGATTATTG<br>GAAATTTGTTATAATGAATGAAACATTTTGTCATATAAGATTCATATTTACTTCTTATACATTTGATAAAGTAAGG<br>CATGGTTGTGGTTAATCTGGTTTATTTTTGTTCCACAAGTTAAATAAATCATAAAACTTGATGTGTTATCTCTTA |
| SEQ ID NO: 44 Human PD-L1 cDNA Sequence<br>GGCGCAACGCTGAGCAGCTGGCGCGTCCCGCGCGGCCCCAGTTCTGCGCAGCTTCCCGAGGCTCCGCACCAGCCGC<br>GCTTCTGTCCGCCTGCAGGGCATTCCAGAAAGATGAGGATATTTGCTGTCTTTATATTCATGACCTACTGGCATTT<br>GCTGAACGCCCCATACAACAAAATCAACCAAAGAATTTTGGTTGTGGATCCAGTCACCTCTGAACATGAACTGACA<br>TGTCAGGCTGAGGGCTACCCCAAGGCCGAAGTCATCTGGACAAGCAGTGACCATCAAGTCCTGAGTGGTAAGACCA<br>CCACCACCAATTCCAAGAGAGAGGAGAAGCTTTTCAATGTGACCAGCACACTGAGAATCAACACAACAACTAATGA<br>GATTTTCTACTGCACTTTTAGGAGATTAGATCCTGAGGAAAACCATACAGCTGAATTGGTCATCCCAGAACTACCT<br>CTGGCACATCCTCCAAATGAAAGGACTCACTTGGTAATTCTGGGAGCCATCTTATTATGCCTTGGTGTAGCACTGA<br>CATTCATCTTCCGTTTAAGAAAAGGGAGAATGATGGATGTGAAAAAATGTGGCATCCAAGATACAAACTCAAAGAA<br>GCAAAGTGATACACATTTGGAGGAGACGTAATCCAGCATTGGAACTTCTGATCTTCAAGCAGGGATTCTCAACCTG<br>TGGTTTAGGGGTTCATCGGGGCTGAGCGTGACAAGAGGAAGGAATGGGCCCGTGGGATGCAGGCAATGTGGGACTT<br>AAAAGGCCCAAGCACTGAAAATGGAACCTGGCGAAAGCAGAGGAGGAGAATGAAGAAAGATGGAGTCAAACAGGGA<br>GCCTGGAGGGAGACCTTGATACTTTCAAATGCCTGAGGGGCTCATCGACGCCTGTGACAGGGAGAAAGGATACTTC<br>TGAACAAGGAGCCTCCAAGCAAATCATCCATTGCTCATCCTAGGAAGACGGGTTGAGAATCCCTAATTTGAGGGTC<br>AGTTCCTGCAGAAGTGCCCTTTGCCTCCACTCAATGCCTCAATTTGTTTTCTGCATGACTGAGAGTCTCAGTGTTG<br>GAACGGGACAGTATTTATGTATGAGTTTTTCCTATTTATTTTGAGTCTGTGAGGTCTTCTTGTCATGTGAGTGTGG<br>TTGTGAATGATTTCTTTTGAAGATATATTGTAGTAGATGTTACAATTTTGTCGCCAAACTAAACTTGCTGCTTAAT<br>GATTTGCTCACATCTAGTAAAACATGGAGTATTTGTAAGGTGCTTGGTCTCCTCTATAACTACAAGTATACATTGG<br>AAGCATAAAGATCAAACCGTTGGTTGCATAGGATGTCACCTTTATTTAACCCATTAATACTCTGGTTGACCTAATC<br>TTATTCTCAGACCTCAAGTGTCTGTGCAGTATCTGTTCCATTTAAATATCAGCTTTACAATTATGTGGTAGCCTAC<br>ACACATAATCTCATTTCATCGCTGTAACCACCCTGTTGTGATAACCACTATTATTTTACCCATCGTACAGCTGAGG<br>AAGCAAACAGATTAAGTAACTTGCCCAAACCAGTAAATAGCAGACCTCAGACTGCCACCCACTGTCCTTTTATAAT<br>ACAATTTACAGCTATATTTTACTTTAAGCAATTCTTTTATTCAAAAACCATTTATTAAGTGCCCTTGCAATATCAA<br>TCGCTGTGCCAGGCATTGAATCTACAGATGTGAGCAAGACAAAGTACCTGTCCTCAAGGAGCTCATAGTATAATGA<br>GGAGATTAACAAGAAAATGTATTATTACAATTTAGTCCAGTGTCATAGCATAAGGATGATGCGAGGGGAAAACCCG<br>AGCAGTGTTGCCAAGAGGAGGAAATAGGCCAATGTGGTCTGGGACGGTTGGATATACTTAAACATCTTAATAATCA<br>GAGTAATTTTCATTTACAAAGAGAGGTCGGTACTTAAAATAACCCTGAAAAATAACACTGGAATTCCTTTTCTAGC<br>ATTATATTTATTCCTGATTTGCCTTTGCCATATAATCTAATGCTTGTTTATATAGTGTCTGGTATTGTTTAACAGT<br>TCTGTCTTTTCTATTTAAATGCCACTAAATTTTAAATTCATACCTTTCCATGATTCAAAATTCAAAAGATCCCATG<br>GGAGATGGTTGGAAAATCTCCACTTCATCCTCCAAGCCATTCAAGTTTCCTTTCCAGAAGCAACTGCTACTGCCTT<br>TCATTCATATGTTCTTCTAAAGATAGTCTACATTTGGAAATGTATGTTAAAAGCACGTATTTTTAAAATTTTTTTC<br>CTAAATAGTAACACATTGTATGTCTGCTGTGTACTTTGCTATTTTTATTTATTTTAGTGTTTCTTATATAGCAGAT<br>GGAATGAATTTGAAGTTCCCAGGGCTGAGGATCCATGCCTTCTTTGTTTCTAAGTTATCTTTCCCATAGCTTTTCA<br>TTATCTTTCATATGATCCAGTATATGTTAAATATGTCCTACATATACATTTAGACAACCACCATTTGTTAAGTATT<br>TGCTCTAGGACAGAGTTTGGATTTGTTTATGTTTGCTCAAAAGGAGACCCATGGGCTCTCCAGGGTGCACTGAGTC<br>AATCTAGTCCTAAAAAGCAATCTTATTATTAACTCTGTATGACAGAATCATGTCTGGAACTTTTGTTTTCTGCTTT<br>CTGTCAAGTATAAACTTCACTTTGATGCTGTACTTGCAAAATCACATTTTCTTTCTGGAAATTCCGGCAGTGTACC<br>TTGACTGCTAGCTACCCTGTGCCAGAAAAGCCTCATTCGTTGTGCTTGAACCCTTGAATGCCACCAGCTGTCATCA<br>CTACACAGCCCTCCTAAGAGGCTTCCTGGAGGTTTCGAGATTCAGATGCCCTGGGAGATCCCAGAGTTTCCTTTCC<br>CTCTTGGCCATATTCTGGTGTCAATGACAAGGAGTACCTTGGCTTTGCCACATGTCAAGGCTGAAGAAACAGTGTC<br>TCCAACAGAGCTCCTTGTGTTATCTGTTTGTACATGTGCATTTGTACAGTAATTGGTGTGACAGTGTTCTTTGTGT<br>GAATTACAGGCAAGAATTGTGGCTGAGCAAGGCACATAGTCTACTCAGTCTATTCCTAAGTCCTAACTCCTCCTTG<br>TGGTGTTGGATTTGTAAGGCACTTTATCCCTTTTGTCTCATGTTTCATCGTAAATGGCATAGGCAGAGATGATACC<br>TAATTCTGCATTTGATTGTCACTTTTTGTACCTGCATTAATTTAATAAAATATTCTTATTTATTTTGTTACTTGGT<br>ACACCAGCATGTCCATTTTCTTGTTTATTTTGTGTTTAATAAAATGTTCAGTTTAACATCCCAGTGGAGAAAGTTA<br>AAAAA |
| SEQ ID NO: 45 Human PD-L2 cDNA Sequence<br>GCAAACCTTAAGCTGAATGAACAACTTTTCTTCTCTTGAATATATCTTAACGCCAAATTTTGAGTGCTTTTTTGTT<br>ACCCATCCTCATATGTCCCAGCTAGAAAGAATCCTGGGTTGGAGCTACTGCATGTTGATTGTTTTGTTTTTCCTTT<br>TGGCTGTTCATTTTGGTGGCTACTATAAGGAAATCTAACACAAACAGCAACTGTTTTTTGTTGTTTACTTTTGCAT<br>CTTTACTTGTGGAGCTGTGGCAAGTCCTCATATCAAATACAGAACATGATCTTCCTCCTGCTAATGTTGAGCCTGG<br>AATTGCAGCTTCACCAGATAGCAGCTTTATTCACAGTGACAGTCCCTAAGGAACTGTACATAATAGAGCATGGCAG<br>CAATGTGACCCTGGAATGCAACTTTGACACTGGAAGTCATGTGAACCTTGGAGCAATAACAGCCAGTTTGCAAAAG<br>GTGGAAAATGATACATCCCCACACCGTGAAAGAGCCACTTTGCTGGAGGAGCAGCTGCCCCTAGGGAAGGCCTCGT<br>TCCACATACCTCAAGTCCAAGTGAGGGACGAAGGACAGTACCAATGCATAATCATCTATGGGGTCGCCTGGGACTA<br>CAAGTACCTGACTCTGAAAGTCAAAGCTTCCTACAGGAAAATAAACACTCACATCCTAAAGGTTCCAGAAACAGAT<br>GAGGTAGAGCTCACCTGCCAGGCTACAGGTTATCCTCTGGCAGAAGTATCCTGGCCAAACGTCAGCGTTCCTGCCA<br>ACACCAGCCACTCCAGGACCCCTGAAGGCCTCTACCAGGTCACCAGTGTTCTGCGCCTAAAGCCACCCCCTGGCAG<br>AAACTTCAGCTGTGTGTTCTGGAATACTCACGTGAGGGAACTTACTTTGGCCAGCATTGACCTTCAAAGTCAGATG |

TABLE 9-continued

| lists sequences for the disclosure |
| --- |
| GAACCCAGGACCCATCCAACTTGGCTGCTTCACATTTTCATCCCCTTCTGCATCATTGCTTTCATTTTCATAGCCA<br>CAGTGATAGCCCTAAGAAAACAACTCTGTCAAAAGCTGTATTCTTCAAAAGACACAACAAAAAGACCTGTCACCAC<br>AACAAAGAGGGAAGTGAACAGTGCTATCTGAACCTGTGGTCTTGGGAGCCAGGGTGACCTGATATGACATCTAAAG<br>AAGCTTCTGGACTCTGAACAAGAATTCGGTGGCCTGCAGAGCTTGCCATTTGCACTTTTCAAATGCCTTTGGATGA<br>CCCAGCACTTTAATCTGAAACCTGCAACAAGACTAGCCAACACCTGGCCATGAAACTTGCCCCTTCACTGATCTGG<br>ACTCACCTCTGGAGCCTATGGCTTTAAGCAAGCACTACTGCACTTTACAGAATTACCCCACTGGATCCTGGACCCA<br>CAGAATTCCTTCAGGATCCTTCTTGCTGCCAGACTGAAAGCAAAAGGAATTATTTCCCCTCAAGTTTTCTAAGTGA<br>TTTCCAAAAGCAGAGGTGTGTGGAAATTTCCAGTAACAGAAACAGATGGGTTGCCAATAGAGTTATTTTTTATCTA<br>TAGCTTCCTCTGGGTACTAGAAGAGGCTATTGAGACTATGAGCTCACAGACAGGGCTTCGCACAAACTCAAATCAT<br>AATTGACATGTTTTATGGATTACTGGAATCTTGATAGCATAATGAAGTTGTTCTAATTAACAGAGAGCATTTAAAT<br>ATACACTAAGTGCACAAATTGTGGAGTAAAGTCATCAAGCTCTGTTTTTGAGGTCTAAGTCACAAAGCATTTGTTT<br>TAACCTGTAATGGCACCATGTTTAATGGTGGTTTTTTTTTTGAACTACATCTTTCCTTTAAAAATTATTGGTTTCT<br>TTTTATTTGTTTTTACCTTAGAAATCAATTATATACAGTCAAAAATATTTGATATGCTCATACGTTGTATCTGCAG<br>CAATTTCAGATAAGTAGCTAAAATGGCCAAAGCCCCAAACTAAGCCTCCTTTTCTGGCCCTCAATATGACTTTAAA<br>TTTGACTTTTCAGTGCCTCAGTTTGCACATCTGTAATACAGCAATGCTAAGTAGTCAAGGCCTTTGATAATTGGCA<br>CTATGGAAATCCTGCAAGATCCCACTACATATGTGTGGAGCAGAAGGGTAACTCGGCTACAGTAACAGCTTAATTT<br>TGTTAAATTTGTTCTTTATACTGGAGCCATGAAGCTCAGAGCATTAGCTGACCCTTGAACTATTCAAATGGGCACA<br>TTAGCTAGTATAACAGACTTACATAGGTGGGCCTAAAGCAAGCTCCTTAACTGAGCAAAATTTGGGGCTTATGAGA<br>ATGAAAGGGTGTGAAATTGACTAACAGACAAATCATACATCTCAGTTTCTCAATTCTCATGTAAATCAGAGAATGC<br>CTTTAAAGAATAAAACTCAATTGTTATTCTTCAACGTTCTTTATATATTCTACTTTTGGGTA |
| SEQ ID NO: 46 Human Spi9 cDNA Sequence<br>AGCGGGAGTCCGCGGCGAGCGCAGCAGCAGGGCCGGGTCCTGCGCCTCGGGGGTCGGCGTCCAGGCTCGGAGCGCG<br>GCACGGAGACGGCGGCAGCGCTGGACTAGGTGGCAGGCCCTGCATCATGGAAACTCTTTCTAATGCAAGTGGTACT<br>TTTGCCATACGCCTTTTAAAGATACTGTGTCAAGATAACCCTTCGCACAACGTGTTCTGTTCTCCTGTGAGCATCT<br>CCTCTGCCCTGGCCATGGTTCTCCTAGGGGCAAAGGGAAACACCGCAACCCAGATGGCCCAGGCACTGTCTTTAAA<br>CACAGAGGAAGACATTCATCGGGCTTTCCAGTCGCTTCTCACTGAAGTGAACAAGGCTGGCACACAGTACCTGCTG<br>AGAACGGCCAACAGGCTCTTTGGAGAGAAAACTTGTCAGTTCCTCTCAACGTTTAAGGAATCCTGTCTTCAATTCT<br>ACCATGCTGAGCTGAAGGAGCTTTCCTTTATCAGAGCTGCAGAAGAGTCCAGGAAACACATCAACACCTGGGTCTC<br>AAAAAAGACCGAAGGTAAAATTGAAGAGTTGTTGCCGGGTAGCTCAATTGATGCAGAAACCAGGCTGGTTCTTGTC<br>AATGCCATCTACTTCAAAGGAAAGTGGAATGAACCGTTTGACGAAACATACACAAGGGAAATGCCCTTTAAAATAA<br>ACCAGGAGGAGCAAAGGCCAGTGCAGATGATGTATCAGGAGGCCACGTTTAAGCTCGCCCACGTGGGCGAGGTGCG<br>CGCGCAGCTGCTGGAGCTGCCCTACGCCAGGAAGGAGCTGAGCCTGCTGGTGCTGCTGCCTGACGACGGCGTGGAG<br>CTCAGCACGGTGGAAAAAAGTCTCACTTTTGAGAAACTCACAGCCTGGACCAAGCCAGACTGTATGAAGAGTACTG<br>AGGTTGAAGTTCTCCTTCCAAAATTTAAACTACAAGAGGATTATGACATGGAATCTGTGCTTCGGCATTTGGGAAT<br>TGTTGATGCCTTCCAACAGGGCAAGGCTGACTTGTCGGCAATGTCAGCGGAGAGAGACCTGTGTCTGTCCAAGTTC<br>GTGCACAAGAGTTTTGTGGAGGTGAATGAAGAAGGCACCGAGGCAGCGGCAGCGTCGAGCTGCTTTGTAGTTGCAG<br>AGTGCTGCATGGAATCTGGCCCCAGGTTCTGTGCTGACCACCCTTTCCTTTTCTTCATCAGGCACAACAGAGCCAA<br>CAGCATTCTGTTCTGTGGCAGGTTCTCATCGCCATAAAGGGTGCACTTACCGTGCACTCGGCCATTTCCCTCTTCC<br>TGTGTCCCCAGATCCCCACTACAGCTCCAAGAGGATGGGCCTAGAAAGCCAAGTGCAAAGATGAGGGCAGATTCTT<br>TACCTGTCTGCCCTCATGATTTGCCAGCATGAATTCATGATGCTCCACACTCGCTTATGCTACTTAATCAGAATCT<br>TGAGAAAATAGACCATAATGATTCCCTGTTGTATTAAAATTGCAGTCCAAATCCCATAGGATGGCAAGCAAAGTTC<br>TTCTAGAATTCCACATGCAATTCACTCTGGCGACCCTGTGCTTTCCTGACACTGCGAATACATTCCTTAACCCGCT<br>GCCTCAGTGGTAATAAATGGTGCTAGATATTGCTACTATTTTATAGATTTCCTGGTGCTTAGCCTTATAAAAAAGG<br>TTGTAAAATGTACATTTATATTTATCTTTTTTTTTTTTTTTTTTCTGAGACGCAGTCTGGCTCTCTGTCGCCCAG<br>GCTGGAGTGCAGTGGCTCGATCTCGGCTCACTGCAAGCTCCGCCTCCCGGGTTCACGCCATTCTCCTGCCTCAGCC<br>TCCCGAGTAGCTGGGACTACAGGCGCCCGCCACCACGCCCGGCTAATTTTTTGTATTTTTAGTAGAGACGGGGTTT<br>CACCGTGTTAGCCAGGATGGTGTCGATCTCCTGACCTCGTGATCCACCCGCCTCGGCCTCCCAAAGTGCTGGGATT<br>ACAGGCTTGAGCCACCGCGCCCGGCTATATTTATCTTTTATCTTTTTCTTTGACATTTACCAATCACCAAGCATG<br>CACCAAACACTGCTTTAGGCACTGGGGACACAAAGGGGACAGAGCCATCCTCCTTTGACACCTGGTCTTCAGTTCT<br>GTGCCCAACGTATATAGTTTTGACAATGACCAGGTTGGACTGTTTAATGTCTTTCAACTTACCACGTAATCCTCTT<br>GTAGGGATCACATCTTTCTTTATGATATTGTATTTCTCTACCTCTAACAGTAAAAATTCCATTCAACCCTTAAAGC<br>TCACTTCAAATTCTTCTTTGAGAAGTTTTTCCTTTCTCCGCAACCAGATGTACATATTTGAACTCTCTTTGTACTT<br>GGAGGGCACTTCTTTCGTGGTAGTTCTTTTATTTTTATTAATCTCTGTATCCTTAGATAGTCCTCCAACAACCAAA<br>GGTTGGGACTCTGTCTTACATATCTGGGTGCCCCTCATAGTGCAGTAATAAGTAAGTTGATTATATACGAGCTATG<br>TAACTTATATTTTTTAATGGTTGGATATCACTGAGTTTTTTTTTTTAAGAATTTTTTTATTGAGGTAAACTTCACA<br>TAACATAAAATTAACTATTTTAAAGTGAGAAGTTCAGTGCCACTTAGTATTGTTAACAATGTTGCATAACCACCAC<br>CTTTATTTAAAGTTCCAAAAAAAATGTTCTCCTCTAAAAGGAAACCCCATCCCATTAAGCAGATACTCTCCATTCC<br>TTCCTTCCTCCAGCCCCCAGCAACCACCAATCTGCTTTCTGTCTCTATGGATTTATCTATTCTTGCTATTTTATAT<br>AAATTGAATTGTATGAGACCTTTTGTGTCTGGCTTCTTTCACTTAGTACAAGTTTTTGAGATTTATTTACATAGTA<br>GCATGTATCAACACTTCATTTTTATGGCCAAATAAAATTGTATTATGTGTTTATAGCACAATTTATTTATCCACTC<br>ATTCATTGATGGACTTTGGGTTGTTTCTGACTTTTGGCTATTGGGAATAGTGCTGCTATGAATGTTTGTGTACCTG<br>TATTTGTTTGAATGCCTATTTTGCATTCTCTTGGGTATATATCTAGGAGTGGAACTGCTGGGTCATATGTTAATTC<br>TATGTTTAGCTTTTTGAGGAACAGACAAACTGTTTTCCACAGCAGTTGAACCATTCCACATTCCCACCAGCAATGT<br>ATGAGAATTCCAATTTCTGTCCACTTCCTCACCAACACTTATTATTTTCCTTTTCCTTTTTTTAAAAAAAATAAGT<br>TATGGCCATCTTAGTGGGTGTGAAGTGGTATCTCATTGTGTTTTTTATTTGCATTTCCTATGTAATGAGCTAGAAA<br>CTAAAGTACAAACTAGATGGGACATCCAGTCCCTTTGATAGATAATGCTGAGTAAAAAATGAGATGAAAGACATTT<br>GTTTGTTTTTAGAACACGAGTGACAGTTTGTTAAAAAGCTTTAGAGGAGGAATGAAAACAAAGTGAAGTACACTTA<br>GAAAAGGGCCAAGTGGACATCTTGGATGTCAAGTGCCTAGTTCAGTATCTTTTTTTTTTTTTTTTTTTTTTTTGAG<br>ACAGTGCCTCACTCTGTCACCCAGGCTGGAGTGTAGTGGCATGATCTGGGCTCACTGCAACCTCCTCCTCCTGGAT<br>TCAAGCAATTCTCTTGCTTCAGCCTCCCAAGTAGCTGAGACTACAAGCACCCACCATCACACCCAGCTAATTTTGT<br>ATTTTTCAGTAGAGACGGGGTTTCGCCACATTGGCCGTGTTGGTCTTGAACTCCTGGCCTCAAGCGATCCGCCTAC<br>CTCAGCCTCCCAAAGTGCTAGGATTACAGGCATAAGCCACTGAGCCCAGCCCTAGTTCAGTATCTTTTATGTAAAT<br>TACAAACATCTGCAACATTATGTATCATATGCAGATACTTATTGCATTTCTTTTATTAGTGGTGAAAGTGTTCTAT<br>GCATTTATTGGCTCTTGAATTTCCTCATCTATGAATTGTCATTCATACACCTACTTTTCTGCTTCGTTTTTACATA<br>TGTCTTTGCCTATTAAAGATATTATCCCTCTGTTTTATATTTTCTCTCATTCTTGTATTGCCTTTTAAATTTTGTT<br>ATGATGTTTCATTAATAAACAGTGTTTTGTTTTCCTCTATAATCAAAAAAAAAAAAAAAAAA |

TABLE 9-continued

| lists sequences for the disclosure |
|---|
| SEQ ID NO: 47 Human CD47 cDNA Sequence<br>GGGGAGCAGGCGGGGGAGCGGGCGGGAAGCAGTGGGAGCGCGCGTGCGCGCGGCCGTGCAGCCTGGGCAGTGGGTC<br>CTGCCTGTGACGCGCGGCGGCGGTCGGTCCTGCCTGTAACGGCGGCGGCGGCTGCTGCTCCAGACACCTGCGGCGG<br>CGGCGGCGACCCCGCGGCGGGCGCGGAGATGTGGCCCCTGGTAGCGGCGCTGTTGCTGGGCTCGGCGTGCTGCGGA<br>TCAGCTCAGCTACTATTTAATAAAACAAAATCTGTAGAATTCACGTTTTGTAATGACACTGTCGTCATTCCATGCT<br>TTGTTACTAATATGGAGGCACAAAACACTACTGAAGTATACGTAAAGTGGAAATTTAAAGGAAGAGATATTTACAC<br>CTTTGATGGAGCTCTAAACAAGTCCACTGTCCCCACTGACTTTAGTAGTGCAAAAATTGAAGTCTCACAATTACTA<br>AAAGGAGATGCCTCTTTGAAGATGGATAAGAGTGATGCTGTCTCACACACAGGAAACTACACTTGTGAAGTAACAG<br>AATTAACCAGAGAAGGTGAAACGATCATCGAGCTAAAATATCGTGTTGTTTCATGGTTTTCTCCAAATGAAAATAT<br>TCTTATTGTTATTTTCCCAATTTTTGCTATACTCCTGTTCTGGGGACAGTTTGGTATTAAAACACTTAAATATAGA<br>TCCGGTGGTATGGATGAGAAAACAATTGCTTTACTTGTTGCTGGACTAGTGATCACTGTCATTGTCATTGTTGGAG<br>CCATTCTTTTCGTCCCAGGTGAATATTCATTAAAGAATGCTACTGGCCTTGGTTTAATTGTGACTTCTACAGGGAT<br>ATTAATATTACTTCACTACTATGTGTTTAGTACAGCGATTGGATTAACCTCCTTCGTCATTGCCATATTGGTTATT<br>CAGGTGATAGCCTATATCCTCGCTGTGGTTGGACTGAGTCTCTGTATTGCGGCGTGTATACCAATGCATGGCCCTC<br>TTCTGATTTCAGGTTTGAGTATCTTAGCTCTAGCACAATTACTTGGACTAGTTTATATGAAATTTGTGGCTTCCAA<br>TCAGAAGACTATACAACCTCCTAGGAAAGCTGTAGAGGAACCCCTTAATGCATTCAAAGAATCAAAAGGAATGATG<br>AATGATGAATAACTGAAGTGAAGTGATGGACTCCGATTTGGAGAGTAGTAAGACGTGAAAGGAATACACTTGTGTT<br>TAAGCACCATGGCCTTGATGATTCACTGTTGGGGAGAAGAAACAAGAAAAGTAACTGGTTGTCACCTATGAGACCC<br>TTACGTGATTGTTAGTTAAGTTTTTATTCAAAGCAGCTGTAATTTAGTTAATAAAATAATTATGATCTATGTTGTT<br>TGCCCAATTGAGATCCAGTTTTTTGTTGTTATTTTTAATCAATTAGGGGCAATAGTAGAATGGACAATTTCCAAGA<br>ATGATGCCTTTCAGGTCCTAGGGCCTCTGGCCTCTAGGTAACCAGTTTAAATTGGTTCAGGGTGATAACTACTTAG<br>CACTGCCCTGGTGATTACCCAGAGATATCTATGAAAACCAGTGGCTTCCATCAAACCTTTGCCAACTCAGGTTCAC<br>AGCAGCTTTGGGCAGTTATGGCAGTATGGCATTAGCTGAGAGGTGTCTGCCACTTCTGGGTCAATGGAATAATAAA<br>TTAAGTACAGGCAGGAATTTGGTTGGGAGCATCTTGTATGATCTCCGTATGATGTGATATTGATGGAGATAGTGGT<br>CCTCATTCTTGGGGGTTGCCATTCCCACATTCCCCCTTCAACAAACAGTGTAACAGGTCCTTCCCAGATTTAGGGT<br>ACTTTTATTGATGGATATGTTTTCCTTTTATTCACATAACCCCTTGAAACCCTGTCTTGTCCTCCTGTTACTTGCT<br>TCTGCTGTACAAGATGTAGCACCTTTTCTCCTCTTTGAACATGGTCTAGTGACACGGTAGCACCAGTTGCAGGAAG<br>GAGCCAGACTTGTTCTCAGAGCACTGTGTTCACACTTTTCAGCAAAAATAGCTATGGTTGTAACATATGTATTCCC<br>TTCCTCTGATTTGAAGGCAAAAATCTACAGTGTTTCTTCACTTCTTTTCTGATCTGGGGCATGAAAAAAGCAAGAT<br>TGAAATTTGAACTATGAGTCTCCTGCATGGCAACAAAATGTGTGTCACCATCAGGCCAACAGGCCAGCCCTTGAAT<br>GGGGATTTATTACTGTTGTATCTATGTTGCATGATAAACATTCATCACCTTCCTCCTGTAGTCCTGCCTCGTACTC<br>CCCTTCCCCTATGATTGAAAAGTAAACAAAACCCACATTTCCTATCCTGGTTAGAAGAAAATTAATGTTCTGACAG<br>TTGTGATCGCCTGGAGTACTTTTAGACTTTTAGCATTCGTTTTTTACCTGTTTGTGGATGTGTGTTTGTATGTGCA<br>TACGTATGAGATAGGCACATGCATCTTCTGTATGGACAAAGGTGGGGTACCTACAGGAGAGCAAAGGTTAATTTTG<br>TGCTTTTAGTAAAAACATTTAAATACAAAGTTCTTTATTGGGTGGAATTATATTTGATGCAAATATTTGATCACTT<br>AAAACTTTTAAAACTTCTAGGTAATTTGCCACGCTTTTTGACTGCTCACCAATACCCTGTAAAAATACGTAATTCT<br>TCCTGTTTGTGTAATAAGATATTCATATTTGTAGTTGCATTAATAATAGTTATTTCTTAGTCCATCAGATGTTCCC<br>GTGTGCCTCTTTTATGCCAAATTGATTGTCATATTTCATGTTGGGACCAAGTAGTTTGCCCATGGCAAACCTAAAT<br>TTATGACCTGCTGAGGCCTCTCAGAAAACTGAGCATACTAGCAAGACAGCTCTTCTTGAAAAAAAAAAATATGTATA<br>CACAAATATATACGTATATCTATATATACGTATGTATATACACACATGTATATTCTTCCTTGATTGTGTAGCTGTC<br>CAAAATAATAACATATATAGAGGGAGCTGTATTCCTTTATACAAATCTGATGGCTCCTGCAGCACTTTTTCCTTCT<br>GAAAATATTTACATTTTGCTAACCTAGTTTGTTACTTTAAAAATCAGTTTTGATGAAAGGAGGGAAAAGCAGATGG<br>ACTTGAAAAAGATCCAAGCTCCTATTAGAAAAGGTATGAAAATCTTTATAGTAAAATTTTTTATAAACTAAAGTTG<br>TACCTTTTAATATGTAGTAAACTCTCATTTATTTGGGGTTCGCTCTTGGATCTCATCCATCCATTGTGTTCTCTTT<br>AATGCTGCCTGCCTTTTGAGGCATTCACTGCCCTAGACAATGCCACCAGAGATAGTGGGGGAAATGCCAGATGAAA<br>CCAACTCTTGCTCTCACTAGTTGTCAGCTTCTCTGGATAAGTGACCACAGAAGCAGGAGTCCTCCTGCTTGGGCAT<br>CATTGGGCCAGTTCCTTCTCTTTAAATCAGATTTGTAATGGCTCCCAAATTCCATCACATCACATTTAAATTGCAG<br>ACAGTGTTTTGCACATCATGTATCTGTTTTGTCCCATAATATGCTTTTTACTCCCTGATCCCAGTTTCTGCTGTTG<br>ACTCTTCCATTCAGTTTTATTTATTGTGTGTTCTCACAGTGACACCATTTGTCCTTTTCTGCAACAACCTTTCCAG<br>CTACTTTTGCCAAATTCTATTTGTCTTCTCCTTCAAAACATTCTCCTTTGCAGTTCCTCTTCATCTGTGTAGCTGC<br>TCTTTTGTCTCTTAACTTACCATTCCTATAGTACTTTATGCATCTCTGCTTAGTTCTATTAGTTTTTTGGCCTTGC<br>TCTTCTCCTTGATTTTAAAATTCCTTCTATAGCTAGAGCTTTTCTTTCTTTCATTCTCTCTTCCTGCAGTGTTTTG<br>CATACATCAGAAGCTAGGTACATAAGTTAAATGATTGAGAGTTGGCTGTATTTAGATTTATCACTTTTTAATAGGG<br>TGAGCTTGAGAGTTTTCTTTCTTTCTGTTTTTTTTTTTTTGTTTTTTTTTTTTTTTTTTTTTTTTTTTTTTTGACT<br>AATTTCACATGCTCTAAAAACCTTCAAAGGTGATTATTTTTCTCCTGGAAACTCCAGGTCCATTCTGTTTAAATCC<br>CTAAGAATGTCAGAATTAAAATAACAGGGCTATCCCGTAATTGGAAATATTTCTTTTTTCAGGATGCTATAGTCAA<br>TTTAGTAAGTGACCACCAAATTGTTATTTGCACTAACAAAGCTCAAAACACGATAAGTTTACTCCTCCATCTCAGT<br>AATAAAAATTAAGCTGTAATCAACCTTCTAGGTTTCTCTTGTCTTAAAATGGGTATTCAAAAATGGGGATCTGTGG<br>TGTATGTATGGAAACACATACTCCTTAATTTACCTGTTGTTGGAAACTGGAGAAATGATTGTCGGGCAACCGTTTA<br>TTTTTTATTGTATTTTATTTGGTTGAGGGATTTTTTTATAAACAGTTTTACTTGTGTCATATTTTAAAATTACTAA<br>CTGCCATCACCTGCTGGGGTCCTTTGTTAGGTCATTTTCAGTGACTAATAGGGATAATCCAGGTAACTTTGAAGAG<br>ATGAGCAGTGAGTGACCAGGCAGTTTTTCTGCCTTTAGCTTTGACAGTTCTTAATTAAGATCATTGAAGACCAGCT<br>TTCTCATAAATTTCTCTTTTTGAAAAAAAGAAAGCATTTGTACTAAGCTCCTCTGTAAGACAACATCTTAAATCTT<br>AAAAGTGTTGTTATCATGACTGGTGAGAGAAGAAAACATTTTGTTTTTATTAAATGGAGCATTATTTACAAAAAGC<br>CATTGTTGAGAATTAGATCCCACATCGTATAAATATCTATTAACCATTCTAAATAAAGAGAACTCCAGTGTTGCTA<br>TGTGCAAGATCCTCTCTTGGAGCTTTTTTGCATAGCAATTAAAGGTGTGCTATTTGTCAGTAGCCATTTTTTTGCA<br>GTGATTTGAAGACCAAAGTTGTTTTACAGCTGTGTTACCGTTAAAGGTTTTTTTTTTTATATGTATTAAATCAATT<br>TATCACTGTTTAAAGCTTTGAATATCTGCAATCTTTGCCAAGGTACTTTTTTATTTAAAAAAAAACATAACTTTGT<br>AAATATTACCCTGTAATATTATATATACTTAATAAAACATTTTAAGCTATTTTGTTGGGCTATTTCTATTGCTGCT<br>ACAGCAGACCACAAGCACATTTCTGAAAAATTTAATTTATTAATGTATTTTTAAGTTGCTTATATTCTAGGTAACA<br>ATGTAAAGAATGATTTAAAATATTAATTATGAATTTTTTGAGTATAATACCCAATAAGCTTTTAATTAGAGCAGAG<br>TTTTAATTAAAAGTTTTAAATCAGTC |
| SEQ ID NO: 48 Human galectin-9 cDNA Sequence<br>TCCCCATTGAATAACAGCCAAGTTGCTTTGGTTTCTATTTCTTTGTTAAGTCGTTCCCTCTACAAAGGACTTCCTA<br>GTGGGTGTGAAAGGCAGCGGTGGCCACAGAGGCGGCGGAGAGATGGCCTTCAGCGGTTCCCAGGCTCCCTACCTGA<br>GTCCAGCTGTCCCCTTTTCTGGGACTATTCAAGGAGGTCTCCAGGACGGACTTCAGATCACTGTCAATGGGACCGT<br>TCTCAGCTCCAGTGGAACCAGGTTTGCTGTGAACTTTCAGACTGGCTTCAGTGGAAATGACATTGCCTTCCACTTC |

TABLE 9-continued

| lists sequences for the disclosure |
|---|
| AACCCTCGGTTTGAAGATGGAGGGTACGTGGTGTGCAACACGAGGCAGAACGGAAGCTGGGGGCCCGAGGAGAGGA<br>AGACACACATGCCTTTCCAGAAGGGGATGCCCTTTGACCTCTGCTTCCTGGTGCAGAGCTCAGATTTCAAGGTGAT<br>GGTGAACGGGATCCTCTTCGTGCAGTACTTCCACCGCGTGCCCTTCCACCGTGTGGACACCATCTCCGTCAATGGC<br>TCTGTGCAGCTGTCCTACATCAGCTTCCAGAACCCCCGCACAGTCCCTGTTCAGCCTGCCTTCTCCACGGTGCCGT<br>TCTCCCAGCCTGTCTGTTTCCCACCCAGGCCCAGGGGGCGCAGACAAAAACCTCCCGGCGTGTGGCCTGCCAACCC<br>GGCTCCCATTACCCAGACAGTCATCCACACAGTGCAGAGCGCCCCTGGACAGATGTTCTCTACTCCCGCCATCCCA<br>CCTATGATGTACCCCCACCCCGCCTATCCGATGCCTTTCATCACCACCATTCTGGGAGGGCTGTACCCATCCAAGT<br>CCATCCTCCTGTCAGGCACTGTCCTGCCCAGTGCTCAGAGGTTCCACATCAACCTGTGCTCTGGGAACCACATCGC<br>CTTCCACCTGAACCCCCGTTTTGATGAGAATGCTGTGGTCCGCAACACCCAGATCGACAACTCCTGGGGGTCTGAG<br>GAGCGAAGTCTGCCCCGAAAAATGCCCTTCGTCCGTGGCCAGAGCTTCTCAGTGTGGATCTTGTGTGAAGCTCACT<br>GCCTCAAGGTGGCCGTGGATGGTCAGCACCTGTTTGAATACTACCATCGCCTGAGGAACCTGCCCACCATCAACAG<br>ACTGGAAGTGGGGGGCGACATCCAGCTGACCCATGTGCAGACATAGGCGGCTTCCTGGCCCTGGGGCCGGGGGCTG<br>GGGTGTGGGGCAGTCTGGGTCCTCTCATCATCCCCACTTCCCAGGCCCAGCCTTTCCAACCCTGCCTGGGATCTGG<br>GCTTTAATGCAGAGGCCATGTCCTTGTCTGGTCCTGCTTCTGGCTACAGCCACCCTGGAACGGAGAAGGCAGCTGA<br>CGGGGATTGCCTTCCTCAGCCGCAGCAGCACCTGGGGCTCCAGCTGCTGGAATCCTACCATCCCAGGAGGCAGGCA<br>CAGCCAGGGAGAGGGGAGGAGTGGGCAGTGAAGATGAAGCCCCATGCTCAGTCCCCTCCCATCCCCCACGCAGCTC<br>CACCCCAGTCCCAAGCCACCAGCTGTCTGCTCCTGGTGGGAGGTGGCCTCCTCAGCCCCTCCTCTCTGACCTTTAA<br>CCTCACTCTCACCTTGCACCGTGCACCAACCCTTCACCCCTCCTGGAAAGCAGGCCTGATGGCTTCCCACTGGCCT<br>CCACCACCTGACCAGAGTGTTCTCTTCAGAGGACTGGCTCCTTTCCCAGTGTCCTTAAAATAAAGAAATGAAAATG<br>CTTGTTGGCACATTCAAAAAAAAAAAAAAAAAAAAAAAAAAAAAAAAAAAAAAAAAAAAAAAAAAAAAAAAAAAAA<br>AAAAAAAAAAA |
| SEQ ID NO: 49 CD46 Protein Sequence<br>MMAFCALRKALPCRPENPFSSRCFVEILWVSLALVFLLPMPSDACDEPPKFESMRPQFLNTTYRPGDRVEYECRPG<br>FQPMVPALPTFSVCQDDNTWSPLQEACRRKACSNLPDPLNGQVSYPNGDMLFGSKAQFTCNTGFYIIGAETVYCQV<br>SGNVMAWSEPSPLCEKILCKPPGEIPNGKYTNSHKDVFEYNEVVTYSCLSSTGPDEFSLVGESSLFCIGKDEWSSD<br>PPECKVVKCPYPVVPNGEIVSGFGSKFYYKAEVVFKCNAGFTLHGRDTIVCGANSTWEPEMPQCIKDSKPTDPPAT<br>PGPSHPGPPSPSDASPPKDAESLDGGIIAAIVVGVLAAIAVIAGGVYFFHHKYNKKRSK |
| SEQ ID NO: 50 CD55 Protein Sequence<br>MSPLPRSAPAVRRLMGGQTPPPLLLLLLLLCIPAAQGDCSLPPDVPNAQPDLRGLASFPEQTTITYKCNKGFVKVP<br>GMADSVLCLNDKWSEVAEFCNRSCDVPTRLHFASLKKSYSKQNYFPEGFTVEYECRKGYKRDLTLSEKLTCLQNFT<br>WSKPDEFCKKKQCPTPGELKNGHVNITTDLLFGASIFFSCNAGYRLVGATSSYCFAIANDVEWSDPLPECQEISPT<br>VKAIPAVEKPITVNFPATKYPAIPRATTSFHSSTSKNRGNPSSGMRIMSSGTMLLIAGGVAVIIIIVALILAKGFW<br>HYGKSGSYHTHENNKAVNVAFYNLPATGDAADVRPGN |
| SEQ ID NO: 51 CD59 Protein Sequence<br>MGSKGGFILLWLLSILAVLCHLGHSLQCYNCINPAGSCTTAMNCSHNQDACIFVEAVPPKTYYQCWRFDECNFDFI<br>SRNLAEKKLKYNCCRKDLCNKSDATISSGKTALLVILLLVATWHFCL |
| SEQ ID NO: 52 ICP47 Protein Sequence<br>MSWALKTTDMFLDSSRCTHRTYGDVCAEIHKREREDREAARTAVTDPELPLLCPPDVRSDPASRNPTQQTRGCARS<br>NERQDRVLAP |
| SEQ ID NO: 53 HLA-G1 Protein Sequence<br>MVVMAPRTLFLLLSGALTLTETWAGSHSMRYFSAAVSRPGRGEPRFIAMGYVDDTQFVRFDSDSACPRMEPRAPWV<br>EQEGPEYWEEETRNTKAHAQTDRMNLQTLRGYYNQSEASSHTLQWMIGCDLGSDGRLLRGYEQYAYDGKDYLALNE<br>DLRSWTAADTAAQISKRKCEAANVAEQRRAYLEGTCVEWLHRYLENGKEMLQRADPPKTHVTHHPVFDYEATLRCW<br>ALGFYPAEIILTWQRDGEDQTQDVELVETRPAGDGTFQKWAAVVVPSGEEQRYTCHVQHEGLPEPLMLRWKQSSLP<br>TIPIMGIVAGLVVLAAVVTGAAVAAVLWRKKSSD |
| SEQ ID NO: 54 HLA-E Protein Sequence<br>MVDGTLLLLLSEALALTQTWAGSHSLKYFHTSVSRPGRGEPRFISVGYVDDTQFVRFDNDAASPRMVPRAPWMEQE<br>GSEYWDRETRSARDTAQIFRVNLRTLRGYYNQSEAGSHTLQWMHGCELGPDGRFLRGYEQFAYDGKDYLTLNEDLR<br>SWTAVDTAAQISEQKSNDASEAEHQRAYLEDTCVEWLHKYLEKGKETLLHLEPPKTHVTHHPISDHEATLRCWALG<br>FYPAEITLTWQQDGEGHTQDTELVETRPAGDGTFQKWAAVVVPSGEEQRYTCHVQHEGLPEPVTLRWKPASQPTIP<br>IVGIIAGLVLLGSVVSGAVVAAVIWRKKSSGGKGGSYSKAEWSDSAQGSESHSL |
| SEQ ID NO: 55 Human β-2-microglobulin Protein Sequence<br>MSRSVALAVLALLSLSGLEAIQRTPKIQVYSRHPAENGKSNFLNCYVSGFHPSDIEVDLLKNGERIEKVEHSDLSF<br>SKDWSFYLLYYTEFTPTEKDEYACRVNHVTLSQPKIVKWDRDM |
| SEQ ID NO: 56 Human PD-L1 Protein Sequence<br>MRIFAVFIFMTYWHLLNAPYNKINQRILVVDPVTSEHELTCQAEGYPKAEVIWTSSDHQVLSGKTTTTNSKREEKL<br>FNVTSTLRINTTTNEIFYCTFRRLDPEENHTAELVIPELPLAHPPNERTHLVILGAILLCLGVALTFIFRLRKGRM<br>MDVKKCGIQDTNSKKQSDTHLEET |
| SEQ ID NO: 57 Human PD-L2 Protein Sequence<br>MIFLLLMLSLELQLHQIAALFTVTVPKELYIIEHGSNVTLECNFDTGSHVNLGAITASLQKVENDTSPHRERATLL<br>EEQLPLGKASFHIPQVQVRDEGQYQCIIIYGVAWDYKYLTLKVKASYRKINTHILKVPETDEVELTCQATGYPLAE<br>VSWPNVSVPANTSHSRTPEGLYQVTSVLRLKPPPGRNFSCVFWNTHVRELTLASIDLQSQMEPRTHPTWLLHIFIP<br>FCIIAFIFIATVIALRKQLCQKLYSSKDTTKRPVTTTKREVNSAI |
| SEQ ID NO: 58 Human Spi9 Protein Sequence<br>METLSNASGTFAIRLLKILCQDNPSHNVFCSPVSISSALAMVLLGAKGNTATQMAQALSLNTEEDIHRAFQSLLTE<br>VNKAGTQYLLRTANRLFGEKTCQFLSTFKESCLQFYHAELKELSFIRAAEESRKHINTWVSKKTEGKIEELLPGSS |

TABLE 9-continued lists sequences for the disclosure

IDAETRLVLVNAIYFKGKWNEPFDETYTREMPFKINQEEQRPVQMMYQEATFKLAHVGEVRAQLLELPYARKELSL
LVLLPDDGVELSTVEKSLTFEKLTAWTKPDCMKSTEVEVLLPKFKLQEDYDMESVLRHLGIVDAFQQGKADLSAMS
AERDLCLSKFVHKSFVEVNEEGTEAAAASSCFVVAECCMESGPRFCADHPFLFFIRHNRANSILFCGRFSSP

SEQ ID NO: 59 Human CD47 Protein Sequence
MWPLVAALLLGSACCGSAQLLENKTKSVEFTFCNDTVVIPCFVTNMEAQNTTEVYVKWKFKGRDIYTFDGALNKST
VPTDESSAKIEVSQLLKGDASLKMDKSDAVSHTGNYTCEVTELTREGETIIELKYRVVSWFSPNENILIVIFPIFA
ILLFWGQFGIKTLKYRSGGMDEKTIALLVAGLVITVIVIVGAILFVPGEYSLKNATGLGLIVTSTGILILLHYYVF
STAIGLTSFVIAILVIQVIAYILAVVGLSLCIAACIPMHGPLLISGLSILALAQLLGLVYMKFVASNQKTIQPPRK
AVEEPLNAFKESKGMMNDE SEQ ID NO: 60 Human galectin-9 Protein Sequence
MAFSGSQAPYLSPAVPFSGTIQGGLQDGLQITVNGTVLSSSGTRFAVNFQTGFSGNDIAFHFNPRFEDGGYVVCNT
RQNGSWGPEERKTHMPFQKGMPFDLCFLVQSSDFKVMVNGILFVQYFHRVPFHRVDTISVNGSVQLSYISFQNPRT
VPVQPAFSTVPFSQPVCFPPRPRGRRQKPPGVWPANPAPITQTVIHTVQSAPGQMFSTPAIPPMMYPHPAYPMPFI
TTILGGLYPSKSILLSGTVLPSAQRFHINLCSGNHIAFHLNPRFDENAVVRNTQIDNSWGSEERSLPRKMPFVRGQ
SFSVWILCEAHCLKVAVDGQHLFEYYHRLRNLPTINRLEVGGDIQLTHVQT

What is claimed is:

1. A genetically modified pig comprising:

an exogenous nucleic acid inserted into a genome of the genetically modified pig, wherein the exogenous nucleic acid is at least 95% identical to SEQ ID NO. 3 or SEQ ID NO. 4.

2. The genetically modified pig of claim 1, further comprising a regulatory sequence operatively linked to the exogenous nucleic acid.

3. The genetically modified pig of claim 1, wherein the exogenous nucleic acid is inserted into an insertion site, wherein the insertion site is located in a safe harbor site, or the insertion site is located in a gene encoding for a NOD-like receptor family CARD domain containing 5 (NLRC5), a putative cytidine monophosphatase-N-acetylneuraminic acid hydroxylase-like protein (CMAH), a beta-1,4-N-acetylgalactosaminyltransferase (B4GALNT2), GGTA1, cytidine monophospho-N-acetylneuraminic acid (CMP-N-NeuAc) hydrolase, or a porcine endogenous retrovirus (PERV) in the genetically modified pig's genome.

4. The genetically modified pig of claim 3, wherein the safe harbor site is in a ROSA26 gene.

5. The genetically modified pig of claim 3, further comprising a disruption in one or more genes, wherein the one or more genes encode for a NOD-like receptor family CARD domain containing 5 (NLRC5), a glycoprotein galactosyltransferase alpha 1,3 (GGTA1), a putative cytidine monophosphatase-N-acetylneuraminic acid hydroxylase-like protein (CMAH), a beta-1,4-N-acetylgalactosaminyltransferase (B4GALNT2), cytidine monophospho-N-acetylneuraminic acid (CMP-N-NeuAc) hydrolase, a porcine endogenous retrovirus (PERV) genomic region, or a combination thereof.

6. The genetically modified pig of claim 1, further comprising an exogenous polynucleotide encoding for a human leukocyte antigen E (HLA-E), a human leukocyte antigen G (HLA-G), or a β-2-microglobulin (B2M).

7. The genetically modified pig of claim 1, wherein the genetically modified animal pig is a fetal pig.

8. A genetically modified cell, tissue, or organ isolated from said genetically modified pig of claim 1.

9. The genetically modified cell, tissue, or organ of claim 8, further comprising one or more transgenes encoding ICP47, CD46, CD55, CD59, HLA-E, HLA-G, B2M, PD-L1, PD-L2, CD47, Spi9, galectin 9, or any combination thereof.

* * * * *

SEQUENCE LISTING

<160> NUMBER OF SEQ ID NOS: 96

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 1

Gly Thr Gly Ser Gly Ser Gly Ser Gly Ser Gly Ser Gly Ser Gly Ser
1 5 10 15

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 2

Gly Gly Gly Gly Ser Gly Gly Gly Gly
1 5

<210> SEQ ID NO 3
<211> LENGTH: 1503
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 3
atggtgtgcc tgagactgcc aggcggatca tgcatggctg tgctgaccgt gacactgatg 60
gtgctgtcct ctccactggc tctggccagc agccaccaca acctgctcgt gtgtagcgtg 120
tccggattct acccaggtgg taccggcagc ggatcaggtt ccggaagtgg tagcggatct 180
ggaagcggaa gcggagatac aagaccccgc ttcctggaat actctaccag cgagtgccac 240
ttcttcaacg gcacagagag agtgcgctac ctggaccgct acttccacaa tcaagaggaa 300
aacgtgcgct tcgacagcga cgtgggagag tttagagccg tgacagaact gggacgccca 360
gacgccgaat actggaactc ccagaaggac ctgctggaac agaaacgagg ccgcgtggac 420
aactactgca ggcacaatta tggcgtggtg gaatccttca ccgtgcagag gcgagtgcac 480
cccaaagtga cagtgtaccc cagcaagacc cagccactgc agcaccacaa tctgctcgtg 540
tgtagcgtgt ccggcttcta cccaggctct atcgaagtgc gctggttccg caacggccaa 600
gaagagaaaa caggcgtcgt gtccaccgga ctgatccaca acggcgactg gacctttcag 660
accctcgtga tgctcgaaac agtgcccaga tccggcgagg tgtacacatg ccaggtggaa 720
cacccaagcg tgacaagccc actgaccgtc gagtggagag ctcggagtga aagcgcccag 780
tctaaaggcg gcggaggatc tggtggcggc ggaatcaaag aggagcacgt catcatccag 840
gccgaattct atctgaaccc cgaccagagc ggcgagttca tgttcgactt cgacggggac 900
gaaatctttc acgtggacat ggccaaaaaa gaaaccgtgt ggcgcctgga agagttcgga 960
agattcgcct ctttcgaggc ccaaggcgcc ctggccaata tcgctgtgga caaagccaac 1020
ctggaaatca tgaccaagcg cagcaactac accccaatca ccaacgtgcc acctgaagtg 1080
accgtgctga caaacagccc agtggaactg cgcgagccca acgtgctgat ctgcttcatc 1140
gacaagttca ccccaccagt ggtcaacgtg acctggctga gaaacggcaa gccagtgaca 1200
accggcgtgt ccgagacagt gtttctgcca agagaggacc acctgttccg caagttccac 1260
tacctgccat ttctgccgtc gactgaggat gtgtacgact gcagagtcga gcactgggga 1320
ctcgacgagc cactgctgaa gcactgggag tttgacgccc catctccact gccagaaacc 1380
accgagaatg tcgtgtgtgc cctgggcctg acagtgggac tcgtgggaat catcatcggc 1440
accatcttca tcatcaaggg cctgcgcaaa agcaacgccg ctgaaagaag aggcccactc 1500
tga 1503

<210> SEQ ID NO 4
<211> LENGTH: 4132
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 4
tgcaataggg accctaggac gagaggaaaa gcgtccagga acattcttgg agggggggaga 60 tcgagggccc cagagcgacc agagttgtca caaggccgcg cgaacggggg tgggggtggg 120
gtttggggag gggaaaaaaa agtgtgctgt gtattttgag gagggcggcg agaggcctat 180
tctcaagtaa aaggtaaacg tggagtaggc agttcacagg aaaaggggtg aagaggcgtg 240
gggggagggg aaacgtcctg acccaggaaa gacatgaaaa gggtagtggg gtcgactaga 300
ttaaggaggg ggcctctccg cctgggaaag aggggtacag tggtgtgggg gggcgagggg 360
ggatgggaag gggcagcatc ctcctgctga gagccggggg agggccaggc ccacgtcccg 420
agagcaagcg cgaggagacg gaggaggtga cccttccctc ccccggggcc cggtggtgag 480
gggaggtctc tcttttctgt cgcaccctta ccttgtccca ggcctgggcc cgggctgcgg 540
cgcacggcac tcccggtagg cagcaggact cgagttaggc ccagcgcggc gccacggcgt 600
ttcctggccg ggaatggccc gtgcccgtga ggtgggggtg gggggcaaaa aggcggagcg 660
agccaaaggc ggtgaggggg gagggccagg gaaggagggg ggggccggca ctactgtgtt 720
ggcggactgg cgggactggg gctgcgtgag tctctgagcg caggcgggcg gcggccgccc 780
ctcccccggc ggcggcggcg gcggcggcgg cggcggcagc agctcactca gcccgctgcc 840
cgagcggaaa cgccactgac cgcacgggga ttcccagcgc cggcgccagg ggcacccggg 900

```
acacgccccc tcccgccgcg ccattggccc ctccgcccac cgtctcgcac ccattgccag    960
ctccccgcca atcagcggaa gccgccgggg ccgcctagag atcgatgacg tcgcggccgc   1020
atcgatcacg agactagcct cgagaagctt gatatcgaat tccacggggt tggacgcgtc   1080
ttaattaagg atccaaggtc aggaacagag aaacaggaga atatgggcca aacaggatat   1140
ctgtggtaag cagttcctgc cccggctcag ggccaagaac agttggaaca gcagaatatg   1200
ggccaaacag gatatctgtg gtaagcagtt cctgccccgg ctcagggcca agaacagatg   1260
gtccccagat gcggtcccgc cctcagcagt ttctagagaa ccatcagatg tttccagggt   1320
gccccaagga cctgaaatga ccctgtgcct tatttgaact aaccaatcag ttcgcttctc   1380
gcttctgttc gcgcgcttct gctccccgag ctctatataa gcagagctcg tttagtgaac   1440
cgtcagatcg cctggagacg ccatccacgc tgttttgacc tccatagaag acaccgactc   1500
tagaggatcg atcccccggg ctgcaggaat tcaagcgaga agacaagggc agaaaggcca   1560
ccatggtgtg cctgagactg ccaggcggat catgcatggc tgtgctgacc gtgacactga   1620
tggtgctgtc ctctccactg gctctggcca gcagccacca caacctgctc gtgtgtagcg   1680
tgtccggatt ctacccaggt ggtaccggca gcggatcagg ttccggaagt ggtagcggat   1740
ctggaagcgg aagcggagat acaagacccc gcttcctgga atactctacc agcgagtgcc   1800
acttcttcaa cggcacagag agagtgcgct acctggaccg ctacttccac aatcaagagg   1860
aaaacgtgcg cttcgacagc gacgtgggag agtttagagc cgtgacagaa ctgggacgcc   1920
cagacgccga atactggaac tcccagaagg acctgctgga acagaaacga ggccgcgtgg   1980
acaactactg caggcacaat tatggcgtgg tggaatcctt caccgtgcag aggcgagtgc   2040
accccaaagt gacagtgtac cccagcaaga cccagccact gcagcaccac aatctgctcg   2100
tgtgtagcgt gtccggcttc tacccaggct ctatcgaagt gcgctggttc cgcaacggcc   2160
aagaagagaa aacaggcgtc gtgtccaccg gactgatcca caacggcgac tggacctttc   2220
agaccctcgt gatgctcgaa acagtgccca gatccggcga ggtgtacaca tgccaggtgg   2280
aacacccaag cgtgacaagc ccactgaccg tcgagtggag agctcggagt gaaagcgccc   2340
agtctaaagg cggcggagga tctggtggcg gcggaatcaa agaggagcac gtcatcatcc   2400
aggccgaatt ctatctgaac cccgaccaga gcggcgagtt catgttcgac ttcgacgggg   2460
acgaaatctt tcacgtggac atggccaaaa aagaaaccgt gtggcgcctg gaagagttcg   2520
gaagattcgc ctctttcgag gcccaaggcg ccctggccaa tatcgctgtg gacaaagcca   2580
acctggaaat catgaccaag cgcagcaact acaccccaat caccaacgtg ccacctgaag   2640
tgaccgtgct gacaaacagc ccagtggaac tgcgcgagcc caacgtgctg atctgcttca   2700
tcgacaagtt caccccacca gtggtcaacg tgacctggct gagaaacggc aagccagtga   2760
caaccggcgt gtccgagaca gtgtttctgc caagagagga ccacctgttc cgcaagttcc   2820
actacctgcc atttctgccg tcgactgagg atgtgtacga ctgcagagtc gagcactggg   2880
gactcgacga gccactgctg aagcactggg agtttgacgc cccatctcca ctgccagaaa   2940
ccaccgagaa tgtcgtgtgt gccctgggcc tgacagtggg actcgtggga atcatcatcg   3000
gcaccatctt catcatcaag ggcctgcgca aaagcaacgc cgctgaaaga agaggcccac   3060
tctgaacgcg ttctagaaat aaaagatcct tattttcatt ggatctgtgt gttggttttt   3120
tgtgtggcta gcaagaggct gtgctctggg gctccggctc ctcagagagc ctcggctagg   3180
taggggagcg ggactctggt ttgggggagg gccggcggtt tggcggggga tgggtgcttg   3240
```

```
aggtggtctg accggtagcg ggggtcgcct tccctagcgg gaagtcggga gcatatcgtt   3300

tgttacgctg gaaggggaag aggtggtgag aggcaggcgg gagtgcggcc cgccctgcgg   3360

caaccggagg gggagggaga agggagcgga aaagcctgga atacggacgg agccattgct   3420

cccgcagagg gaggagcgct tcctgctctt ctcttgtcac tgattggccg cttctcctcc   3480

cgccgtgtgt gaaaacacaa atggcgtgtt ttggttggag taaagctcct gtcagttaca   3540

gcctcgggag tgcgcagcct cccaggaact ctcgcattgc cccctgggtg ggtaggtagg   3600

tggggtggag agagctgcac aggcgggcgc tgtcggcctc ctgcgggggg aggggagggt   3660

cagtgaaagt ggctcccgcg cgggcgtcct gccaccctcc cctccggggg agtcggttta   3720

cccgccgcct gctcggcttt ggtatctgat tggctgctga agtcctggga acggcccctt   3780

gttattggct tgggtcccaa atgagcgaaa ccactacgcg agtcggcagg gaggcggtct   3840

ttggtacggc cctccccgag gccagcgccg cagtgtctgg cccctcgccc ctgcgcaacg   3900

tggcaggaag cgcgcgcagg aggcgggggc gggctgccgg gccgaggctt ctgggtggtg   3960

gtgactgcgg ctccgccctg ggcgtccgcc gcctgaagga cgagactagc tctctacctg   4020

ctctcggacc cgtgggggtg gggggtggag gaaggagtgg ggggtcggtc ctgctggctt   4080

gtgggtggga ggcgcatgtt ctccaaaaac ccgcgcgagc tgcaatcctg ag           4132
```

<210> SEQ ID NO 5
<211> LENGTH: 1001
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 5

```
tgcaataggg accctaggac gagaggaaaa gcgtccagga acattcttgg aggggggaga     60

tcgagggccc cagagcgacc agagttgtca caaggccgcg cgaacggggg tgggggtggg    120

gtttggggag gggaaaaaaa agtgtgctgt gtattttgag gagggcggcg agaggcctat    180

tctcaagtaa aaggtaaacg tggagtaggc agttcacagg aaaaggggtg aagaggcgtg    240

gggggagggg aaacgtcctg acccaggaaa gacatgaaaa gggtagtggg gtcgactaga    300

ttaaggaggg ggcctctccg cctgggaaag aggggtacag tggtgtgggg gggcgagggg    360

ggatgggaag gggcagcatc ctcctgctga gagccggggg agggccaggc ccacgtcccg    420

agagcaagcg cgaggagacg gaggaggtga cccttccctc ccccggggcc cggtggtgag    480

gggaggtctc tcttttctgt cgcaccctta ccttgtccca ggcctgggcc cgggctgcgg    540

cgcacggcac tcccggtagg cagcaggact cgagttaggc ccagcgcggc gccacggcgt    600

ttcctggccg ggaatggccc gtgcccgtga ggtgggggtg gggggcaaaa aggcggagcg    660

agccaaaggc ggtgaggggg gagggccagg gaaggagggg ggggccggca ctactgtgtt    720

ggcggactgg cgggactggg gctgcgtgag tctctgagcg caggcgggcg gcggccgccc    780

ctccccccggc ggcggcggcg gcggcggcgg cggcggcagc agctcactca gcccgctgcc    840

cgagcggaaa cgccactgac cgcacgggga ttcccagcgc cggcgccagg ggcacccggg    900

acacgccccc tcccgccgcg ccattggccc ctccgcccac cgtctcgcac ccattggcca    960

gctccccgcc aatcagcgga agccgccggg gccgcctaga g                       1001
```

<210> SEQ ID NO 6
<211> LENGTH: 1000
<212> TYPE: DNA

<213> ORGANISM: Artificial Sequence
<220> FEATURE:
<223> OTHER INFORMATION: Description of Artificial Sequence: Synthetic
polynucleotide

<400> SEQUENCE: 6
aagaggctgt gctctggggc tccggctcct cagagagcct cggctaggta ggggagcggg 60
actctggttt gggggagggc cggcggtttg gcgggggatg ggtgcttgag gtggtctgac 120
cggtagcggg ggtcgccttc cctagcggga agtcgggagc atatcgtttg ttacgctgga 180
aggggaagag gtggtgagag gcaggcggga gtgcggcccg ccctgcggca accggagggg 240
gagggagaag ggagcggaaa agcctggaat acggacggag ccattgctcc cgcagaggga 300
ggagcgcttc ctgctcttct cttgtcactg attggccgct tctcctcccg ccgtgtgtga 360
aaacacaaat ggcgtgtttt ggttggagta aagctcctgt cagttacagc ctcgggagtg 420
cgcagcctcc caggaactct cgcattgccc cctgggtggg taggtaggtg gggtggagag 480
agctgcacag gcgggcgctg tcggcctcct gcggggggag gggagggtca gtgaaagtgg 540
ctcccgcgcg ggcgtcctgc caccctcccc tccgggggag tcggtttacc cgccgcctgc 600
tcggctttgg tatctgattg gctgctgaag tcctgggaac ggccccttgt tattggcttg 660
ggtcccaaat gagcgaaacc actacgcgag tcggcaggga ggcggtcttt ggtacggccc 720
tccccgaggc cagcgccgca gtgtctggcc cctcgcccct gcgcaacgtg gcaggaagcg 780
cgcgcaggag gcgggggcgg gctgccgggc cgaggcttct gggtggtggt gactgcggct 840
ccgccctggg cgtccgccgc ctgaaggacg agactagctc tctacctgct ctcggacccg 900
tgggggtggg gggtggagga aggagtgggg ggtcggtcct gctggcttgt gggtgggagg 960
cgcatgttct ccaaaaaccc gcgcgagctg caatcctgag 1000

<210> SEQ ID NO 7
<211> LENGTH: 2662
<212> TYPE: DNA
<213> ORGANISM: Sus scrofa
<220> FEATURE:
<221> NAME/KEY: modified_base
<222> LOCATION: (616)..(715)
<223> OTHER INFORMATION: a, c, t, g, unknown or other
<220> FEATURE:
<221> NAME/KEY: modified_base
<222> LOCATION: (800)..(899)
<223> OTHER INFORMATION: a, c, t, g, unknown or other
<220> FEATURE:
<221> NAME/KEY: modified_base
<222> LOCATION: (1792)..(1792)
<223> OTHER INFORMATION: a, c, t, g, unknown or other

<400> SEQUENCE: 7
tggaaacaac atgaacactg tgagctcccg ggagttcagt cagatccact gaggtagtgg 60
ccgggtccag cggccttgcc taacttggca gtccccaccc gctgcatcct tagatctggc 120
tttgtccctt acacaggaca gcccaggcct gtgatcccca aggtcaggct aacgctacct 180
ggacctgggc tctaagacct gggaagctac aggaggggtg agccagttcc cagattggga 240
aaactgaggc ttgaggcgag aggatagtca tccacaagcc tcgtggctaa atccctggct 300
tggcccaggg ccctggacct caggccactg ggctgatcag tgcttgtatg ctttcctcat 360
cgcacttgtt tggaagacat tccctggttt agctgctctg ggatggtaat ctataaatac 420
atactttgtt taaaaaatta ataaattaaa tcttggacca gcatgagggc atctggccag 480
ccacatggca tatgacatgg acatttgcca cgtctcaaat atggactgcc catcacatgt 540
agtgctagga cccatgccaa caacccacag gccacactgc aggtttcatg caatgtcaca 600
tggaacgctg ccacgnnnnn nnnnnnnnnn nnnnnnnnnn nnnnnnnnnn nnnnnnnnnn 660
nnnnnnnnnn nnnnnnnnnn nnnnnnnnnn nnnnnnnnnn nnnnnnnnnn nnnnntcacg 720
ccacgacatc ctcactgtgc tgcatattcc cgactggtca tgcatgtcat gtgtgatgga 780
gggtggtctg ttggccatan nnnnnnnnnn nnnnnnnnnn nnnnnnnnnn nnnnnnnnnn 840
nnnnnnnnnn nnnnnnnnnn nnnnnnnnnn nnnnnnnnnn nnnnnnnnnn nnnnnnnnnt 900
ctgaagaccg tgcctggaaa acggcgtctc tccctcccgg aacagtgtgc cgggacagcc 960
agctgaggct cttttcctga gccctctatc ctgggggatg gaagcggaca tcacttggct 1020
gtattggaag ggtcttgcgg gggccgtcaa gcatcccagg ggacctgtgg ctgatggtcg 1080
aagaaagcaa agtccagcct gggctcccgg ctctgcagat gctgggccgt gtcctggggg 1140
atggggttat tccacaggct gcggggcaca gagacagaca ttcagcactg ggagctgttc 1200
acttgtcctt gtctctaccc tctgtccaac ccacagatgg ggaaactgag gccccaaagg 1260
ggaagagctg ttcccagagt tacctggcag gtaggagcag gtgttagacc agcatggcta 1320
ccttagggag atggtatccc ccatgcccac cccaacttct tccactcact cttcttccct 1380
ggaagctagt gatgccagct gggccatgct catatgacac attgtgcaaa taaggagaaa 1440
gcccccccct ttatttcttt ttgttttttt ttttttttacc atttcttggg ccgctcccgc 1500
ggcatatgga gattcccagg ctaggggtcg aatcggagct gtagccgcca gcctacgcca 1560
gagccacagc aactcgggat ccgagctgca tctgcgacct gcaccacagc tcatggcaac 1620
gccggatcgt taacccactg agcagggcca gggatcgaac ccgcaacctc atggttccta 1680
gttggattca ttaaccactg tgccacgatg ggaactctga aagctccccc tttttagaca 1740
ctttatttct atcttctgaa actgtcatac tgagttttat agagcgagac cnccccccttt 1800 ttaagacact ttatttctat cttctgaaac tgtcgtaata tactgagttt tatagagcga 1860
gacccttcac tactaccaga aacctaacac gtcaacggtg tgaacagtgt cctttagatg 1920
caaggccttg gtacagtgtg cagcctgtgc aactgtacgt ggtggctgtg attacagtta 1980
tcattttaag cacttgctat gtgccaggca ttgtactcag tgctttgtag aatcatttag 2040
tctgcagagc gcccatctaa ggctgatatg atcattgtct ccagtttaca aatgaggaaa 2100
ccgaggttca gggaggttga gttactgagg caaagttaca cagtcagcaa ccagtagagc 2160
tgggatttga tccaggtctg ctggctgcca cattcctggt ggagtgggcc aaatctcctt 2220
tgataatccc caatccagga gttcctgttg tggcgcagca gaaatgaatc cgactagtaa 2280
ccataaggtt gcaggttcaa tccctggtct tgctcagtgg gttaaggatc tggcgttgct 2340
atgagctgtg gtgtaggttg aagatgcacc tcagatccca caatgctgtg gctatggcgt 2400
aggctggcgg atgtagctct gattggaccc ctagcctggg aatctccata tgctgcaggt 2460
gcggccctaa aaaagcaata aataagtaaa tagataaccc tcaacccagg tcctgcctcc 2520
tcctacagaa agttcctttg cattgtagag gctgctgtgg cccccacctc ccaccatcct 2580
cgcccctgca agtcctgtta ccgaatgact tggatgccag agccctgagc cagcccttca 2640
gccaggagcc aggctccatg ag 2662

<210> SEQ ID NO 8
<211> LENGTH: 6638
<212> TYPE: DNA
<213> ORGANISM: Sus scrofa

<400> SEQUENCE: 8

```
gggcctgtcc tatggaaaga acctgcaagt ccagcacagg ggcttggccg ggaacccatg     60
agaccccctc tggggacatc ctaggacatc tgtgatgaat caggaagcag ggctggctcc    120
tcatggaccc cattagtcgc cacctgggca ccaagaacct gtggggatgg ctcgtgaggc    180
tgctctgcaa acactcagaa tggctgagtg ccaaggtgaa gttcttcctc cccaacatgg    240
acctgggtgc caggaacgag gcctcagacc ccacacagag ggtcgtccta caactcagaa    300
aactgcgtac ccagagtcag atcacctggc aggcgttcat ccactgtgtg tgcatggagc    360
tggacgtgcc gctggacctg gaggtactgc tgctgagcac ctggggccac ggagaagggc    420
tccccagtca gctggaagct gatgaggagc acccacctga gtctcagccc cactctggcc    480
tcaagcggcc acatcagagc tgtgggccct cccctcgccc aaagcagtgc aggaagcagc    540
agcgagaact ggccaagagg tacctgcagc tgctgagaac gtttgcccag cagcgttacg    600
acagcaggag ccctgggcca ggacagccgg tcgcctgcca ccgaacctac atcccgccca    660
tcttgcaatg gaaccgagcc tctgtgccct tcgacactca ggaggggact gttgcagggg    720
gccccaaggc agaagatggc acggatgtga gcattcggga cctcttcagt gccaaagcca    780
acaagggccc gagagtcacg gtgcttctgg gaaaggcggg catgggcaag accacgctgg    840
cccaccggct ctgccaagag tgggccgatg gtcagctgga gcgcttccag gccctgttcc    900
ttttcgaatt ccgccagctc aacctgatca caaacttcct gatgctgcca cagctccttt    960
ttgatctgta cctgaggccc gaggcgggcc cagaggcagt cttccagtac ctggaggaga   1020
atgctaataa aatcctgctc atctttgatg ggctggacga ggtcctccac cccggctcca   1080
gcaaggaggc tgcagatcct gaggcctcgg cgtcagccct caccctcttc tcccgcctct   1140
gccatgggac cctcctgccc ggctgctggg tcatgaccac ctcccgtcca gggaagctgc   1200
ccgcctgcct gcccacagag gtggtcacgg tcagcatgtg gggctttgac ggaccacggg   1260
tggaggagta cgtgagccgc ttcttcagcg accagccagt ccaggaggcg gccctcgcgg   1320
agctgcgggc cagctggcat ctctggagca tgtgtgtggt gcccgcgctg tgccaggtcg   1380
cctgcctctg cctccaccat ctgctcccag gccgctctcc aggccagtct gcagccctcc   1440
tgcccaccgt gacccagagc tacgtgcaga tggtgctttc cctcagcccc caagggttcc   1500
tgcctgccga gtccctgatg ggcctcgggg aggtggccct gtggggcctg gagacgggga   1560
aggttgtctt cactgcagga gacatccctc cacccacgat ggccttcgcg gcggccctcg   1620
gcctgctcac ctccttctgt gtgtacacgg aacccgggca ccaggagaca ggctacgtct   1680
tcacccacct cagcctgcag cagtttttgg ctgccctgca cctgatggcc agccccaagg   1740
tggacagaga cacacttgcc caacatgtca ccctcaattc tcgctgggtg ctgcggacca   1800
aagctaggct gggcctctta gaccaccacc ttcccacctt tctggccggc ctggcctcct   1860
gcgcctgcca ccccttcctc acacccctgg cacagcagga ggaggtgtgg gtgcgtgcca   1920
ggcaggcggc agtcatgcaa gccttggaga agttggccac tcgcaagctg acggggccaa   1980
agctgataga gctatgtcac tgcgtggctg agacacagaa gccggagctg gccagcctcg   2040
tggcccagag cctcccccat cacctctcct tccgcaactt tctgctgacc tatgccgacc   2100
tggctgccct gaccaacatc ctcgggcaca gggatgcccc catccacctg gattttgagg   2160
gctgcccctt ggagccacac tgtcctgaag ccctggcagg ctgcgagcag gtggagaatc   2220
tcagctttaa gagcaggaag tgtggggatg cctttgctga agccctctcc aggagtttgc   2280
caacaatggg gagcctgaag aagctggggt tgtcaggaag taggatcact gcccgaggca   2340
```

-continued

```
tcagccacct ggtgcgggct ttgcccctct gtccacagct ggaagaggtc agctttcagg   2400
acaaccagct caaggacggg gaggtcctga acatcgtgga aatacttccc cacctgccgc   2460
agctccggat gcttgacctg agccgcaaca gtgtctccgt gtcaactctc ctctccttga   2520
caaaggtggc agtcacgtac cctaccatta ggaagctgca ggtcagggag acagacctcg   2580
tcttccttct ctccccacct acagagatga ccacagagct acaaagagac ccagacctac   2640
aggaaaatgc cagccagagg aaagaggctc agaggagaag cctggagctc aggctccaga   2700
agtgtcagct cagtgtctat gatgtgaagc tgctcctcgc ccagctccgg atgggtccac   2760
agctggatga agtggacctc tcagggaacc agctggaaga tgaaggctgt caactggtgg   2820
cagaggctgc gccccagctg cacattgcca ggaagctgga cctcagcgac aatgggcttt   2880
ctgtggctgg gatgcaacgt gtgctgagtg cagtgagaac ctgccggacc ctggcagagc   2940
tacacatcag tctgctgcac aaaaccgtgg tgctcatgtt tgccccagaa ccagaggagc   3000
aggaggggat ccagaagagg ctgacacatt gtggcctgca agcccagcac cttgagcagc   3060
tctgcaaagc gctgggagga agttgccacc tcaagtacct cgatttatca ggcaatgctc   3120
tgggggacga aggtgtggcc ctgctggctc agctgctccc cgggcttggt gccctgcagc   3180
tgctgaacct cagtgagaac ggtttgtccc tggatgctgt gttcagtttg acccagtgct   3240
tctctacagt gcggtggctt cagcgcttgg acttcagctc tgagagccag cacgtcatcc   3300
tgagcggtga cagcagaggc aggcatctct tggctggcgg atctttgcca gagtttcaag   3360
ctggagccca gttcttgggg ttccgtcagc gccgcatccc caggagcttc tgcctcaagg   3420
agtgtcagct ggagcccccg agcctctccc gcctctgtga gactctggag aagtgcccgg   3480
ggcctctgga agtcgaattg ttctgcaagg tcctgagtga ccagagcctg gagaccctgc   3540
tgcatcacct tccccggctc ccccaactaa gcctgctgca gctgagccag acgggactgt   3600
cccaaaggag ccccctcctg ctggccgacc tcttcagcct gtacccacgg gttcagaagg   3660
tggatctcag gtccctccat cacatgactc tgcacttcag gtttagcgag gagcaggaag   3720
gcggatgctg tggcaggttc acaggctgtg gcctcagcca ggagcacatg gagccgctgt   3780
gttggtcgct gagcaagtgt gaggacctca gccaactgga cctctccgcc aacctgctgg   3840
gtgatgacgg gctcaggtcc ctcctggaat gtctccctca ggtgcccatc tccggttcgc   3900
ttgatctgag tcacaacggc atctctcagg aaagtgccct ccgcctggtg gaaacccttc   3960
cctcctgccc acgtgtccgg gaggcctcgg tgaacccggg ctccaagcag accttctgga   4020
ttcacttctc ccgaaaggag gaggctagga agacactaag gctgagtgag tgcagcttca   4080
ggccagagca cgtgcccaga ctggccaccg gcctgagcca ggccctgcag ctgacagagc   4140
tcacgttgaa ccagggctgc ctgggcctgg agcagctgac tatcctcctg ggcctgctga   4200
agtggccggc ggggctgctg actctcaggg tagaggagcc gtgggtgggc agagccggag   4260
tgctcaccct gctggaagtc cgtgcccacg cctcaggcaa cgtcactgaa ataagcatct   4320
ctgagaccca ggagcagctc tgtatgcagc tggaatttcc ccatcaggag aacccagaag   4380
ccgtggccct caggttggct cattgtgatc tcgggaccca ccacagcctc cttgtcaggg   4440
agctaatgga gacatgcgcc aggctgcggc agctcagctt gtcccaggtg aagctctgca   4500
aggccagctc tctgctgctg caaagcctcc tgctgtccct ctctgagctg aagaacttcc   4560
ggctgacctc cagctgtgtg agctctgatg ggctagccca cctgacattt ggtctgagcc   4620
attgtcacca cctggaggag ctggacttgt ctaacaatca atttggcaag gaggacacca   4680
aggtgctgat gggagccctt gagggcaaat gctggctgaa gaggcttgac ctcagccact   4740
```

```
tgcctctgag cagctccacc ctggccgcgc tcattcaagg actgagccac atgagcctcc   4800

tgcagagcct ccgtctaagc aggagcggcg ttgatgacat cggctgctgc cacctctccg   4860

aggcgctcag agctgccacc agcttggtgg agctgggctt gagccacaac cagatcggag   4920

acgccggtgc ccagcactta gctgccatcc tgccagggct gcctgagctc aggaagatag   4980

acctctcagc caatggcatc ggcccggcag ggggagtgcg gttggcggag tccctcaccc   5040

tttgcgagca cctggaggag ctgatgcttg actacaatgc tctgggagat ctcacagccc   5100

tggggctggc ccgagggttg cctcagcacc tgagggtcct gcacctgcgg tccagccacc   5160

tgggcccaga gggggcgctg agcctgggcc aggcactgga tggatgccca tacgtggaag   5220

agatcaactt ggccgagaac agcctggctg gagggatccc acatttctgt caggggctcc   5280

cgatgctccg gcagatagac ctgatgtcat gtgagattga caaccagact gccaagcccc   5340

tcgccgccag cttcgtgctc tgcccagccc tggaagaaat catgctgtcc tggaatctgc   5400

tcggtgacga ggcagctgct gagctggccc aggtcctgcc gcggatgggc cgactgaaga   5460

gagtggacct ggagaagaat cggatcacag ctcacggagc ctggctcctg gctgaagggc   5520

tggctcaggg ctctggcatc caagtcattc gcctgtggaa taaccccatc ccccaggaca   5580

cggcccagca tctgcagagc cgggagccca ggctggactt tgctttcttc gaccatcagc   5640

cacaggtccc ctgggatgct tgacggcccc cgcaagaccc ttccaataca gccaagtgat   5700

gtccgcttcc atcccccagg atagagggct caggaaaaga gcctcagctg gctgtcccgg   5760

cacactgttc cgggagggag agacgccgtt ttccaggcac ggtcttcaga atggacttta   5820

tgggcgacaa agagcctacc atggccaaca gaccaccctc catcacacat gacatgcatg   5880

accagtcggg aatatgcagc acagtgagga tgtcgtggcg tgatgcaaga cacagaaggt   5940

tgcacgtggc agcgttccat gtgacattgc atgaaacctg cagtgtggcc tgtgggttgt   6000

tggcgtgggt cctagcacta catgtgatgg gcagtccata tttgagacgt ggcaaatgtc   6060

cgtgtcatat gccatgtggc tggccagatg ccctcatgct ggtccaagat ttaatttatt   6120

aatttttaa acaaagtatg tatttataga ttacctttcc agagcagcta aaccagggaa   6180

tgtcttccaa acaagtgcga tgaggaaagc atacaagcac tgatcagccc agtggcctga   6240

ggtccagggc cctgggccaa gccagggatt tagccacgag gcttgtggat gactatcctc   6300

tcgcctcaag cctcagtttt cccaatctgg gaactggctc acccctcccg tagcttccca   6360

ggtcttagag cccaggtcca ggtagcgtta gcctgacctt ggggatcaca ggcctgggct   6420

gtcctgtgta agggacaaag ccagatctaa ggatgcagcg ggtggggact gccaagttag   6480

gcaaggccgc tggacccggc cactacctca gtggatctga ctgaactccc gggagctcac   6540

agtgttcatg ttgtttccaa gaaggcccaa ggattgtgag ccaagtttga tcaataaatg   6600

tgagtgatct tccggcctct aaaaaaaaaa aaaaaaaa                          6638
```

```
<210> SEQ ID NO 9
<211> LENGTH: 1846
<212> TYPE: PRT
<213> ORGANISM: Sus scrofa

<400> SEQUENCE: 9

Met Asp Pro Ile Ser Arg His Leu Gly Thr Lys Asn Leu Trp Gly Trp
1               5                   10                  15

Leu Val Arg Leu Leu Cys Lys His Ser Glu Trp Leu Ser Ala Lys Val
            20                  25                  30
```

```
Lys Phe Phe Leu Pro Asn Met Asp Leu Gly Ala Arg Asn Glu Ala Ser
        35                  40                  45

Asp Pro Thr Gln Arg Val Val Leu Gln Leu Arg Lys Leu Arg Thr Gln
    50                  55                  60

Ser Gln Ile Thr Trp Gln Ala Phe Ile His Cys Val Cys Met Glu Leu
65                  70                  75                  80

Asp Val Pro Leu Asp Leu Glu Val Leu Leu Leu Ser Thr Trp Gly His
                85                  90                  95

Gly Glu Gly Leu Pro Ser Gln Leu Glu Ala Asp Glu Glu His Pro Pro
            100                 105                 110

Glu Ser Gln Pro His Ser Gly Leu Lys Arg Pro His Gln Ser Cys Gly
        115                 120                 125

Pro Ser Pro Arg Pro Lys Gln Cys Arg Lys Gln Gln Arg Glu Leu Ala
    130                 135                 140

Lys Arg Tyr Leu Gln Leu Leu Arg Thr Phe Ala Gln Gln Arg Tyr Asp
145                 150                 155                 160

Ser Arg Ser Pro Gly Pro Gly Gln Pro Val Ala Cys His Arg Thr Tyr
                165                 170                 175

Ile Pro Pro Ile Leu Gln Trp Asn Arg Ala Ser Val Pro Phe Asp Thr
            180                 185                 190

Gln Glu Gly Thr Val Ala Gly Gly Pro Lys Ala Glu Asp Gly Thr Asp
        195                 200                 205

Val Ser Ile Arg Asp Leu Phe Ser Ala Lys Ala Asn Lys Gly Pro Arg
    210                 215                 220

Val Thr Val Leu Leu Gly Lys Ala Gly Met Gly Lys Thr Thr Leu Ala
225                 230                 235                 240

His Arg Leu Cys Gln Glu Trp Ala Asp Gly Gln Leu Glu Arg Phe Gln
                245                 250                 255

Ala Leu Phe Leu Phe Glu Phe Arg Gln Leu Asn Leu Ile Thr Asn Phe
            260                 265                 270

Leu Met Leu Pro Gln Leu Leu Phe Asp Leu Tyr Leu Arg Pro Glu Ala
        275                 280                 285

Gly Pro Glu Ala Val Phe Gln Tyr Leu Glu Glu Asn Ala Asn Lys Ile
    290                 295                 300

Leu Leu Ile Phe Asp Gly Leu Asp Glu Val Leu His Pro Gly Ser Ser
305                 310                 315                 320

Lys Glu Ala Ala Asp Pro Glu Ala Ser Ala Ser Ala Leu Thr Leu Phe
                325                 330                 335

Ser Arg Leu Cys His Gly Thr Leu Leu Pro Gly Cys Trp Val Met Thr
            340                 345                 350

Thr Ser Arg Pro Gly Lys Leu Pro Ala Cys Leu Pro Thr Glu Val Val
        355                 360                 365

Thr Val Ser Met Trp Gly Phe Asp Gly Pro Arg Val Glu Glu Tyr Val
    370                 375                 380

Ser Arg Phe Phe Ser Asp Gln Pro Val Gln Glu Ala Ala Leu Ala Glu
385                 390                 395                 400

Leu Arg Ala Ser Trp His Leu Trp Ser Met Cys Val Val Pro Ala Leu
                405                 410                 415

Cys Gln Val Ala Cys Leu Cys Leu His His Leu Leu Pro Gly Arg Ser
            420                 425                 430

Pro Gly Gln Ser Ala Ala Leu Leu Pro Thr Val Thr Gln Ser Tyr Val
        435                 440                 445

Gln Met Val Leu Ser Leu Ser Pro Gln Gly Phe Leu Pro Ala Glu Ser
```

```
    450                 455                 460

Leu Met Gly Leu Gly Glu Val Ala Leu Trp Gly Leu Glu Thr Gly Lys
465                 470                 475                 480

Val Val Phe Thr Ala Gly Asp Ile Pro Pro Pro Thr Met Ala Phe Ala
                485                 490                 495

Ala Ala Leu Gly Leu Leu Thr Ser Phe Cys Val Tyr Thr Glu Pro Gly
            500                 505                 510

His Gln Glu Thr Gly Tyr Val Phe Thr His Leu Ser Leu Gln Gln Phe
        515                 520                 525

Leu Ala Ala Leu His Leu Met Ala Ser Pro Lys Val Asp Arg Asp Thr
    530                 535                 540

Leu Ala Gln His Val Thr Leu Asn Ser Arg Trp Val Leu Arg Thr Lys
545                 550                 555                 560

Ala Arg Leu Gly Leu Leu Asp His His Leu Pro Thr Phe Leu Ala Gly
                565                 570                 575

Leu Ala Ser Cys Ala Cys His Pro Phe Leu Thr Pro Leu Ala Gln Gln
            580                 585                 590

Glu Glu Val Trp Val Arg Ala Arg Gln Ala Ala Val Met Gln Ala Leu
        595                 600                 605

Glu Lys Leu Ala Thr Arg Lys Leu Thr Gly Pro Lys Leu Ile Glu Leu
    610                 615                 620

Cys His Cys Val Ala Glu Thr Gln Lys Pro Glu Leu Ala Ser Leu Val
625                 630                 635                 640

Ala Gln Ser Leu Pro His His Leu Ser Phe Arg Asn Phe Leu Leu Thr
                645                 650                 655

Tyr Ala Asp Leu Ala Ala Leu Thr Asn Ile Leu Gly His Arg Asp Ala
            660                 665                 670

Pro Ile His Leu Asp Phe Glu Gly Cys Pro Leu Glu Pro His Cys Pro
        675                 680                 685

Glu Ala Leu Ala Gly Cys Glu Gln Val Glu Asn Leu Ser Phe Lys Ser
    690                 695                 700

Arg Lys Cys Gly Asp Ala Phe Ala Glu Ala Leu Ser Arg Ser Leu Pro
705                 710                 715                 720

Thr Met Gly Ser Leu Lys Lys Leu Gly Leu Ser Gly Ser Arg Ile Thr
                725                 730                 735

Ala Arg Gly Ile Ser His Leu Val Arg Ala Leu Pro Leu Cys Pro Gln
            740                 745                 750

Leu Glu Glu Val Ser Phe Gln Asp Asn Gln Leu Lys Asp Gly Glu Val
        755                 760                 765

Leu Asn Ile Val Glu Ile Leu Pro His Leu Pro Gln Leu Arg Met Leu
    770                 775                 780

Asp Leu Ser Arg Asn Ser Val Ser Val Ser Thr Leu Leu Ser Leu Thr
785                 790                 795                 800

Lys Val Ala Val Thr Tyr Pro Thr Ile Arg Lys Leu Gln Val Arg Glu
                805                 810                 815

Thr Asp Leu Val Phe Leu Leu Ser Pro Pro Thr Glu Met Thr Thr Glu
            820                 825                 830

Leu Gln Arg Asp Pro Asp Leu Gln Glu Asn Ala Ser Gln Arg Lys Glu
        835                 840                 845

Ala Gln Arg Arg Ser Leu Glu Leu Arg Leu Gln Lys Cys Gln Leu Ser
    850                 855                 860

Val Tyr Asp Val Lys Leu Leu Leu Ala Gln Leu Arg Met Gly Pro Gln
865                 870                 875                 880
```

```
Leu Asp Glu Val Asp Leu Ser Gly Asn Gln Leu Glu Asp Glu Gly Cys
                885                 890                 895

Gln Leu Val Ala Glu Ala Ala Pro Gln Leu His Ile Ala Arg Lys Leu
            900                 905                 910

Asp Leu Ser Asp Asn Gly Leu Ser Val Ala Gly Met Gln Arg Val Leu
        915                 920                 925

Ser Ala Val Arg Thr Cys Arg Thr Leu Ala Glu Leu His Ile Ser Leu
    930                 935                 940

Leu His Lys Thr Val Val Leu Met Phe Ala Pro Glu Pro Glu Glu Gln
945                 950                 955                 960

Glu Gly Ile Gln Lys Arg Leu Thr His Cys Gly Leu Gln Ala Gln His
                965                 970                 975

Leu Glu Gln Leu Cys Lys Ala Leu Gly Gly Ser Cys His Leu Lys Tyr
            980                 985                 990

Leu Asp Leu Ser Gly Asn Ala Leu  Gly Asp Glu Gly Val  Ala Leu Leu
        995                 1000                1005

Ala Gln  Leu Leu Pro Gly Leu  Gly Ala Leu Gln Leu  Leu Asn Leu
    1010                1015                1020

Ser Glu  Asn Gly Leu Ser Leu  Asp Ala Val Phe Ser  Leu Thr Gln
    1025                1030                1035

Cys Phe  Ser Thr Val Arg Trp  Leu Gln Arg Leu Asp  Phe Ser Ser
    1040                1045                1050

Glu Ser  Gln His Val Ile Leu  Ser Gly Asp Ser Arg  Gly Arg His
    1055                1060                1065

Leu Leu  Ala Gly Gly Ser Leu  Pro Glu Phe Gln Ala  Gly Ala Gln
    1070                1075                1080

Phe Leu  Gly Phe Arg Gln Arg  Arg Ile Pro Arg Ser  Phe Cys Leu
    1085                1090                1095

Lys Glu  Cys Gln Leu Glu Pro  Pro Ser Leu Ser Arg  Leu Cys Glu
    1100                1105                1110

Thr Leu  Glu Lys Cys Pro Gly  Pro Leu Glu Val Glu  Leu Phe Cys
    1115                1120                1125

Lys Val  Leu Ser Asp Gln Ser  Leu Glu Thr Leu Leu  His His Leu
    1130                1135                1140

Pro Arg  Leu Pro Gln Leu Ser  Leu Leu Gln Leu Ser  Gln Thr Gly
    1145                1150                1155

Leu Ser  Gln Arg Ser Pro Leu  Leu Leu Ala Asp Leu  Phe Ser Leu
    1160                1165                1170

Tyr Pro  Arg Val Gln Lys Val  Asp Leu Arg Ser Leu  His His Met
    1175                1180                1185

Thr Leu  His Phe Arg Phe Ser  Glu Glu Gln Glu Gly  Gly Cys Cys
    1190                1195                1200

Gly Arg  Phe Thr Gly Cys Gly  Leu Ser Gln Glu His  Met Glu Pro
    1205                1210                1215

Leu Cys  Trp Ser Leu Ser Lys  Cys Glu Asp Leu Ser  Gln Leu Asp
    1220                1225                1230

Leu Ser  Ala Asn Leu Leu Gly  Asp Asp Gly Leu Arg  Ser Leu Leu
    1235                1240                1245

Glu Cys  Leu Pro Gln Val Pro  Ile Ser Gly Ser Leu  Asp Leu Ser
    1250                1255                1260

His Asn  Gly Ile Ser Gln Glu  Ser Ala Leu Arg Leu  Val Glu Thr
    1265                1270                1275
```

```
Leu Pro  Ser Cys Pro Arg Val  Arg Glu Ala Ser Val  Asn Pro Gly
    1280                 1285                 1290

Ser Lys  Gln Thr Phe Trp Ile  His Phe Ser Arg Lys  Glu Glu Ala
    1295                 1300                 1305

Arg Lys  Thr Leu Arg Leu Ser  Glu Cys Ser Phe Arg  Pro Glu His
    1310                 1315                 1320

Val Pro  Arg Leu Ala Thr Gly  Leu Ser Gln Ala Leu  Gln Leu Thr
    1325                 1330                 1335

Glu Leu  Thr Leu Asn Gln Gly  Cys Leu Gly Leu Glu  Gln Leu Thr
    1340                 1345                 1350

Ile Leu  Leu Gly Leu Leu Lys  Trp Pro Ala Gly Leu  Leu Thr Leu
    1355                 1360                 1365

Arg Val  Glu Glu Pro Trp Val  Gly Arg Ala Gly Val  Leu Thr Leu
    1370                 1375                 1380

Leu Glu  Val Arg Ala His Ala  Ser Gly Asn Val Thr  Glu Ile Ser
    1385                 1390                 1395

Ile Ser  Glu Thr Gln Glu Gln  Leu Cys Met Gln Leu  Glu Phe Pro
    1400                 1405                 1410

His Gln  Glu Asn Pro Glu Ala  Val Ala Leu Arg Leu  Ala His Cys
    1415                 1420                 1425

Asp Leu  Gly Thr His His Ser  Leu Leu Val Arg Glu  Leu Met Glu
    1430                 1435                 1440

Thr Cys  Ala Arg Leu Arg Gln  Leu Ser Leu Ser Gln  Val Lys Leu
    1445                 1450                 1455

Cys Lys  Ala Ser Ser Leu Leu  Leu Gln Ser Leu Leu  Leu Ser Leu
    1460                 1465                 1470

Ser Glu  Leu Lys Asn Phe Arg  Leu Thr Ser Ser Cys  Val Ser Ser
    1475                 1480                 1485

Asp Gly  Leu Ala His Leu Thr  Phe Gly Leu Ser His  Cys His His
    1490                 1495                 1500

Leu Glu  Glu Leu Asp Leu Ser  Asn Asn Gln Phe Gly  Lys Glu Asp
    1505                 1510                 1515

Thr Lys  Val Leu Met Gly Ala  Leu Glu Gly Lys Cys  Trp Leu Lys
    1520                 1525                 1530

Arg Leu  Asp Leu Ser His Leu  Pro Leu Ser Ser Ser  Thr Leu Ala
    1535                 1540                 1545

Ala Leu  Ile Gln Gly Leu Ser  His Met Ser Leu Leu  Gln Ser Leu
    1550                 1555                 1560

Arg Leu  Ser Arg Ser Gly Val  Asp Asp Ile Gly Cys  Cys His Leu
    1565                 1570                 1575

Ser Glu  Ala Leu Arg Ala Ala  Thr Ser Leu Val Glu  Leu Gly Leu
    1580                 1585                 1590

Ser His  Asn Gln Ile Gly Asp  Ala Gly Ala Gln His  Leu Ala Ala
    1595                 1600                 1605

Ile Leu  Pro Gly Leu Pro Glu  Leu Arg Lys Ile Asp  Leu Ser Ala
    1610                 1615                 1620

Asn Gly  Ile Gly Pro Ala Gly  Gly Val Arg Leu Ala  Glu Ser Leu
    1625                 1630                 1635

Thr Leu  Cys Glu His Leu Glu  Glu Leu Met Leu Asp  Tyr Asn Ala
    1640                 1645                 1650

Leu Gly  Asp Leu Thr Ala Leu  Gly Leu Ala Arg Gly  Leu Pro Gln
    1655                 1660                 1665

His Leu  Arg Val Leu His Leu  Arg Ser Ser His Leu  Gly Pro Glu
```

```
    1670                1675                1680

Gly Ala  Leu Ser Leu Gly Gln  Ala Leu Asp Gly Cys  Pro Tyr Val
    1685                1690                1695

Glu Glu  Ile Asn Leu Ala Glu  Asn Ser Leu Ala Gly  Gly Ile Pro
    1700                1705                1710

His Phe  Cys Gln Gly Leu Pro  Met Leu Arg Gln Ile  Asp Leu Met
    1715                1720                1725

Ser Cys  Glu Ile Asp Asn Gln  Thr Ala Lys Pro Leu  Ala Ala Ser
    1730                1735                1740

Phe Val  Leu Cys Pro Ala Leu  Glu Glu Ile Met Leu  Ser Trp Asn
    1745                1750                1755

Leu Leu  Gly Asp Glu Ala Ala  Ala Glu Leu Ala Gln  Val Leu Pro
    1760                1765                1770

Arg Met  Gly Arg Leu Lys Arg  Val Asp Leu Glu Lys  Asn Arg Ile
    1775                1780                1785

Thr Ala  His Gly Ala Trp Leu  Leu Ala Glu Gly Leu  Ala Gln Gly
    1790                1795                1800

Ser Gly  Ile Gln Val Ile Arg  Leu Trp Asn Asn Pro  Ile Pro Gln
    1805                1810                1815

Asp Thr  Ala Gln His Leu Gln  Ser Arg Glu Pro Arg  Leu Asp Phe
    1820                1825                1830

Ala Phe  Phe Asp His Gln Pro  Gln Val Pro Trp Asp  Ala
    1835                1840                1845


<210> SEQ ID NO 10
<211> LENGTH: 8621
<212> TYPE: DNA
<213> ORGANISM: Sus scrofa

<400> SEQUENCE: 10

gtctgagaag agcttcactc aggagcatct gacccaccag gagcctgcaa catggtccaa      60

tagcgcccct tattagccat gagctgctgg tgggttccct cctcaacaat ggtgcctcct     120

tccagaaaga ggatgtgatt ggcctgctcc acggaactaa gacgctgggt gatgagaagc     180

acagaccggg agtaccgctc agggctttca tacaggagcg actccacctg agaaaaaaac     240

acagactctg tcagagctgg gggccactcc cggaagagct gggacagacc tcgccaggat     300

cactgccact tctgccagga accccaaaat caaagcttct cattctgagt gcttctctgt     360

caaacttttg atctgttaag gacggtttac atgagggggc aagagcgtgt cctatggtga     420

aactcataag tatgaagggt attgagtagc ctctcctctc taatttttat attctctttc     480

aaggagacat aagtgagtag taaagagaat gaatattcga gtcaggcaga ctcgaatttg     540

ggtccaggct ctgctattca acattgagct gaatgctatc gagtgcgttg ttcagcctct     600

cttagcctgc attttagcat ctgttcgatg aagataacaa cagccagctc acaagcattc     660

acgatgaata attaaatgag agagtacatg gaaagggcct gttaacattt ctggcacatg     720

gtaagatttc aactaatatt ggtatgatgg gatcttttct tttgtttggc ttcacagatt     780

cagagtctga ggatcgtctc ttttaactga ctctaggcat gttggggaga agcgaagggg     840

aactgagaat tgcaaagact ggtttggatg attatgatgt tagtacaata acaaaggatg     900

agtgaaggaa ggaggactgg gtgggttaca ggcattaaga agatgactct ctcacccgtg     960

cttgactgtt tgcatccagg gcactggtag catcatccag gatgagtacc cgtggtttcc    1020

ggatcaaggc tcgagccaag gccactgcct gccgctgacc ccctgatagc tggctcccag    1080
```

```
cctcacctac ctctgcagag acaagtgccc aggtaagagc tggataaaca catgtgcatc   1140
catgtgcttg catgcacgcg cgagcgtgtg tgcacatgtg cacgcacgca cgcgcgtgca   1200
cacacacaca cacacacaca cacacacact cggactaaca gatacagctg gatagggaag   1260
gttctgggaa ggtgaaggag ttctgaggat atgaggatga aagagccata gaaacaagct   1320
cttacaactt catactgatg aataaaggca agactattgg atttcaacaa aggtaaagat   1380
gtctgagcca taaaataaaa tttaaaaaaa aaaagagttc ctgctgtggc acagtgggtt   1440
aaggatgcaa ctgcaggagt tcctgacatg actcagtggt ttatgaaccc aactagtatc   1500
cacgtggact cgggttagat ccctggcctt gctcagtggg ttaaggatcc agcattgcca   1560
tgagctgtgg tgtaggtcag cagctgtagc tccgattcga cccctagcct gggaatgtcc   1620
atatgctgtg gtgcagctcc aaaaaaaagc aaaaaaaaac aaaacaaaac aaaacccgaa   1680
tgctgtggct caggtcgcct tggaggtgca gttcaatccc tggcctggtg cagtgggtta   1740
aaggatctgg cgttgctgca gctgctgcat aggttgcatc cgaggcttgg attcagacta   1800
tgggtgtggc cataaaaaac tagccccccc aaaaaagatg cctgggtggt gatatgagag   1860
gagagagcac ctgtgtcgta gccttgcggg agcttggaga tgaagctatg ggctccggac   1920
tccacggcgg cagctatgac ttcctccatt gctggcttct ggctcaggcc ataggcaatg   1980
ttttcttgaa aacttcttcc aaagagctgt ggctcttgcc ccaccgcagc cacctgggac   2040
aaagcatgat gagagaacga ggaacacagg agtatgatga tctggagact gaagactgaa   2100
aatctttatt gtgaacaaat catgaaatca cacagcctct ctcctgaaca caccccccgc   2160
ccccccagga tctcctgtca ttcccagcac tcctttcaga gtgcccagtg agcatggtct   2220
tcttactcgc agctccctgc cctcccctgt gccaccttct tgctcacctg tctgtgcagg   2280
tagcggtgct catattcagg aaggggcttc tcacccagca gcacctgccc ctccgtgggc   2340
tggtacaggt tctgcagcag ggcagccacg gtgctcttcc cagacccatt gggccccacg   2400
agggcggtca cctcaccagg acgtagagtg aacgtgaggc cctggaggcc agagaatcac   2460
acactaagag gcagatcaag gcccctaacc ttaagagcgt catggacttg gcccattgtt   2520
ttgtcagtgt ctcaccccag agaagaaaag aggaaagtgg agaaacacag caactcctac   2580
cctcccacat gcacagactt ctgctcctca gcgatgccac ctccccgtgg actagagatg   2640
gaagaagaga caaagaccag ggcaaagacc atgccgcaca ctcaatctca gagaccagga   2700
gaaaaaaaga aaaaaaaaat cacatttgaa atcacaaatg gaaagaaaaa ggaggagttc   2760
ctgttgtggc tcaggaggtt aagaccctga catagtgtcc gtgaggatac aggttcaatc   2820
cttggcttcg cccagtgggt taaggatctg gtgtggctgc agctgccccg ttcagtcaca   2880
gaagtggctc agagccggtg ttgctgtggc tgtgatgcag gcgttcagct cctggcccag   2940
tgtgaccatt aaaaaaagga agaaaaaagg caagaaaaag gaaagatgga agaccagatg   3000
gatacacaga ttttgcagca gttccttagg atatgacagc cttctccctg aaagcctcct   3060
ttcctgtcct ccctggaaat ccaaactagg tcttgagttt ggggcaattt tatggaacag   3120
atgatgctca tctttgcctc tgaagggtaa agaaggatct agctacacct gatgttaagc   3180
agactgaagg caggaagacg attcagatcg agctgagagg aagattggtg gagtgcaggg   3240
gttggtgggt tgtacctgca gcactgggac ctctggtcgg ttcgggtagg caaaggagac   3300
attctggaac ttgacaagcc cctctgactt taaggaagtc aacgatccac tggccgggca   3360
gcgagggatt cggtccagat actcaaatat ttcctttgag gagcccacag ccttctgtac   3420
cctggggtag gtggacagca gtacctggag gggaggtatg aatagtgaga tgggaggagg   3480
```

tagtggggga gggacctaat ctgcctgcca ggattatgtg atgtgagaag ggcaaagcat 3540
ggaaggaagg tgactcagat ggtgatggga caggggaggg aaaagccctg ggatgtgaga 3600
atggaaggac ctcacctgaa cagcttcggt gaactggatc tggtagagaa caaatgtgac 3660
gaggtttccg ctgcttatag ccccacctgc caccagcttc ccgccaacat acaggattcc 3720
caccttcagc aacatccctg agatctgtgg agagaccaca cagaaaaggg acttttgtag 3780
aaaaatctag aggggctgca gagaagcaga atcattagca ttaaggagat aagaagttct 3840
tggagttccc gtcgtggctc agtggttaac gaatccaact aggaaccagg aggttgcggg 3900
ttcgatctct ggcctcgctc agtgggttaa ggatcgggtg ttgccatgag ctgtggtgta 3960
ggtcaaagat gtggctcgga tctagtgttg ctgtggctgt agctctaggg taggctggca 4020
gccgtagctc cgactggacc ccttgccagg gaaactccaa atgcctcagg tacagcccta 4080
aaaagcaaaa acaaacaaat aaacaaaaaa aaggaatgaa ccatagcaat gccacggagt 4140
ctcactcagt tatacagaaa agaagccaat cgttattacc atcaccatta tcaccttgtc 4200
tgggaagcat ttactctgca caaaaggctt tcatgaatgt aatgtcatct aatagtcgca 4260
tcaaaagccc cataaacaag gttaggtcac tgccattttt aaaactgaga aaacagtctc 4320
agagaagtga agtcaccagc ccctggtcac agagccggaa aatggcagca tcgtgatagg 4380
aacttgatgg ctggtcgtgt tcgctttcgg ttacatcaca ggtgcccctc atccttgctt 4440
ctgctactcc caggactctc actagcatcc atgtagtgtc agcatgaaac gggacagggt 4500
gccagaattt atagtcctct gagcaccccc ttgaggcaaa agaaggcctt ggaaaacact 4560
tccctaaaga gagggttggg tggatttttg tgtaccgtag tgaaaggaag ccatctagca 4620
cgcctaaaaa ggggggaggg ggttaggaac agtgagtagg gtgactgagc ctccggttgt 4680
tagaatatgg ccactgaacc aaccactggg cagtggagga agagtgtgga gcagggtcat 4740
gggaaaggga atggcattga ggcatcttgg ggacaaggga ctaggcagtc atctgcaggt 4800
gctcacactg gtggtccaga ggtcgaccgc ataggccagg gcctccttct ggttgagtgt 4860
cttcatgtcc tgcagctttt gcttgaactt ctgggcctca ccctcttcat tggcaaagct 4920
ccggacagta ggcatagctg acagaacctc aatggccacc tggcttgact ttgccagaga 4980
ttcctgcacc tgtgctgcca gcacctgtgg agacgtggac cagagatgcc acacatgatt 5040
gttgacaaac catagggac actagtacct gagttatccg attagagttt aaaggtgaga 5100
cgtggcagag ggaaggcaag gggacaaagg gacacagcca ggcccccaga tactaaagga 5160
tacagagaag aggaaaatga cttagaagcg tcgtagggga gcatattctt gagatgggtg 5220
atcatgttct taaagacaga ttgtgggcag gcattagaag agaagacaca agggatgtga 5280
agatcaacac tgagcaatct gggaacatgg acgacaggga caaggagtcc cacaaagagg 5340
agaaccagtg aaggtgccag gaaagggatc tgagcccacc aagtctggga tgagggtcag 5400
tgtaggttga ggcaactccc tagacatacc tggtgccatt tccccagctt ctcaggcaga 5460
aggaaaagca gtggcaaggc ggccagggtg accatggtga ggggaggtga cccccagagc 5520
atgagcccta agagacacag tccccgtgcg aggtaccaca gcaagaggct cagctccgaa 5580
ctcagagaca cactcacagt ggatgtgtcc tctgttaccc gagatgtgat ggcacctgcc 5640
aagggttcaa gagaagagag tggagtgaac aggaggctca gagtgatggg agcgacgagc 5700
aatgagccag gtgccacagc gaagggcatc aacacagtgt tctaagaagg tcaggaaaag 5760
gagttcccgt cgcggcgcag tggttaacga atccgactag gaaccatgag gttgcgggtt 5820
cgatccctgc ccttgctcag tgggttaacg atccggcgtt gctgtgagct gtgatgtagg 5880
ttgcagactt ggctcggatc cgcgttgctg tggctctggc gtaggccggt ggctacagct 5940
ccaattcgac ccctagcctg ggaacctcca tatgccgcgg gagcggccca agaaatagcg 6000
gggaaaaaaa aaaaaaaaaa gacaaagaag gtcaggaaaa caaggtctgt ggttggggga 6060
ggactgaaac ataatgcaag aaaaatgtgt tagagtggaa aagcctggcc aaagaccttc 6120
gttttaacta taaagaaatt gatgcccaga gttcccactg tggctcagcg gttaaggacc 6180
tgacgccgtc tctgtgaggt tgcaggctgg aaccctggct tcgctcagtg ggttaaggac 6240
cagctgttgc cacaagctgt ggcgtaggtc acagatgctg gatcaggtgt tgccatgact 6300
ggcacaggcc tcacctgtag ctctgattca acccctggcc caggaacttc catatgccac 6360
aggtgcagtc ataaaagaaa aaaaaatttt taaagaaatg gatgcccatg tgaacttctg 6420
tttctctgac aggtgtctgt tccttaaaga acttgtatat accatgctca taggtaggaa 6480
gaacttaagc tggtcataca agagctggag aaaaatggag agactactag agagcagtcc 6540
aggaaaccac agcaagcact ggattgggaa tcaagacatg ggttctgctc tcaagtttgt 6600
cttcatccat gtgcatccat gcaaatgttg gcatttaggt ctagacctca tttcacttct 6660
ctgtaaaatg agtcagctag actctctaat ctcaaaattt ccaggtttga aattctacct 6720
aaatacactt atagggatag tttatggaaa aatcttgggt ggaaacagta ggttaatcat 6780
tttttttttt gttttattgt gtttttggtt ttgtcttttt tttttttttt tttttttttt 6840
tttttgccct tcccacagca tgcagaattt ccctggccag atggaacctc gccatagaag 6900
caaactgagt cacagcagcg atctgagcca cagcagccac agaactacag cagtggcaac 6960
accagatcct taacccgctg agccaccggc gaactccaac agtaggcttt tctaaaggta 7020
aagagcatat cttgctcttg aagtacatca agaataaaaa gggacaccat ttgtgtgtgt 7080
gtgagagaaa gatcaagatt ataagtaaaa gatgaagtgt ggggatacaa atagaaaaca 7140
gacggataat gaaagaggtt cataagacac ctgtttgatt cttctgaaaa aactctgttt 7200
cttggcgcag gacagaccga aacacctctc cctgcaggtg gctgtgcacg cggcccatgg 7260
tgctgttata gatcccgtcg cacacgaact ccagcaccga gctagaggga gacaaagaag 7320
gagggccggt cggtcaggga ccccgtagaa gtgcactttg gagggcggcc ccaacttcca 7380
actgcgccct tttcagggtc ccccgtcccc agccttccaa gctcagcagt cagacctggc 7440
tatgatgagg atggacatga gagttaggtt ctgcgtgaag gcagcacctg ccccatctcg 7500
tagaatccag tcagtgagcc ggcctgtgaa gaacggaatg gccatctccc ctggggaggg 7560
agaggagaga tgggcgggtc agaaagagca agtctaagca gcctaagcag ctcagctcta 7620
accaggctgc acctcccgcc catcctccct tcacccttgc ccattatcct gcagaaacag 7680
cgcacactct cggcactgga atgggccccc ggggaactcg taatcctgtg gcctcaccag 7740
acctttagag ggttaattaa gaagcctagg atggtaggag gaaagagctc gcccaaggtg 7800
gccagtgaag caacacctga gcagcactgg agtccaggac tcctgactcc cacccagtcc 7860
agggctcttt cctctccacc aagtggacct gagcggggtg ggcttgctct tatccacatt 7920
tccgagaact cacacctgtc tatctcactg accgttaggc ttgattccta cccagccctc 7980
tagcctccct ctccctcccc ccgcatcccc cttaccaagg ctggagagga ccaccagggt 8040
cagaaggagc cagaggtggc ggatctctga gcccaggcag ccgagaagcc ggctcactgt 8100
cactccagag cctctgtgac ttccttgcac ccaaaggctg ctaagcttat gccacagggc 8160
ggccgcgggc aatgccgccg catagctgag ggcgaaggca tcgaggcgac tcccccagtg 8220
cagtagccgc gtgctgtcag ccgctcccga gcccaactct cggaacaagg caagtcccgg 8280
cagagccaag cccagagccg ccgccagcgg ctccaaagct gccagccatc cccgaagtcc 8340
tgtgcttttc tcccggaagc caaccgtcgc cctgaggacg ctgcgggccc ccaaccacag 8400
cacagcccaa cggctcaggc ccaccaccca gacccggagc agcggcagcg ctgggggcag 8460
cagcagggag gatatccggg gcagcgccgg ccggagcagc acccagtcgg cgagaagcag 8520
cagcgctgcc cccagccaag ggagggaagc tcgggagacg cagagacacc cgcagggagc 8580
ggaggacccc gagctggcca ttggccgtac gaggtcgacc c 8621

<210> SEQ ID NO 11
<211> LENGTH: 2280
<212> TYPE: DNA
<213> ORGANISM: Sus scrofa

<400> SEQUENCE: 11
gcccttgggt cgacctcgta cgccaatggc cagctcgggg tcctccgctc cctgcgggtg 60
tctctgcgtc tcccgagctt ccctcccttg gctgggggca gcgctgctgc ttctcgccga 120
ctgggtgctg ctccggccgg cgctgccccg gatatcctcc ctgctgctgc ccccagcgct 180
gccgctgctc cgggtctggg tggtgggcct gagccgttgg gctgtgctgt ggttgggggc 240
ccgcagcgtc ctcagggcga cggttggctt ccgggagaaa agcacaggac ttcggggatg 300
gctggcagct ttggagccgc tggcggcggc tctgggcttg gctctgccgg gacttgcctt 360
gttccgagag ttgggctcgg gagcggctga cagcacgcgg ctactgcact gggggagtcg 420
cctcgatgcc ttcgccctca gctatgcagc ggcattgccc gcggccgccc tgtggcataa 480
gcttagcagc ctttgggtgc aaggaagtca cagaggctct ggagtgacag tgagccggct 540
tctcggctgc ctgggctcag agatccgcca cctctggctc cttctgaccc tggtggtcct 600
ctccagcctt ggggagatgg ccattccgtt cttcacaggc cggctcactg actggattct 660
acgagatggg gcaggtgctg ccttcacgca gaacctaact ctcatgtcca tcctcatcat 720
agccagctcg gtgctggagt tcgtgtgcga cggaatctat aacagcacca tgggccgcgt 780
gcacagccac ctgcagggag aggtgtttcg gtctgtcctg cgccaagaaa cagagttttt 840
tcagaagaat caaacaggta ccatcacatc tcgggtaaca gaggacacat ccactgtgag 900
tgtgtctctg agttcggagc tgagcctctt gctgtggtac ctcgcacggg gactgtgtct 960
cttagggctc atgctctggg ggtcacctcc cctcaccatg gtcaccctgg ccgccttgcc 1020
actgcttttc cttctgcctg agaagctggg gaaatggcac caggtgctgg cagcacaggt 1080
gcaggaatct ctggcaaagt caagccaggt ggccattgag gttctgtcag ctatgcctac 1140
tgtccggagc tttgccaatg aagagggtga ggcccagaaa ttcaagcaaa agctgcagga 1200
catgaagaca ctcaaccaga aggaggccct ggcctatgcg gtcgacctct ggaccaccag 1260
tatctcaggg atgttgctga aggtgggaat cctgtatgtt ggcgggaagc tggtggcagg 1320
tggggctata agcagcggaa acctcgtcac atttgttctc taccagatcc agttcaccga 1380
agctgttcag gtactgctgt ccacctaccc cagggtacag aaggctgtgg gctcctcaaa 1440
ggaaatattt gagtatctgg accgaatccc tcgctgcccg gccagtggat cgttgacttc 1500
cttaaagtca gaggggcttg tcaagttcca gaatgtctcc tttgcctacc cgaaccgacc 1560
agaggtccca gtgctgcagg gcctcacgtt cactctacgt cctggtgagg tgaccgccct 1620
cgtggggccc aatgggtctg ggaagagcac cgtggctgcc ctgctgcaga acctgtacca 1680
gcccacggag gggcaggtgc tgctgggtga gaagcccctt cctgaatatg agcaccgcta 1740
cctgcacaga caggtggctg cggtggggca agagccacag ctctttggaa gaagttttca 1800
agaaaacatt gcctatggcc tgagccagaa gccagcaatg gaggaagtca tagctgccgc 1860
catggagtcc ggagcccata gcttcatctc caagctcccg caaggctacg acacagaggt 1920
aggtgaggct gggagccagc tatcaggggg tcagcgacag gcagtggcct tggctcgagc 1980
cttgatccgg aaaccacggg tactcatcct ggatgatgct accagtgccc tggatgcaaa 2040
cagtcaagca cgggtggagt cgctcctgta tgaaagccct gagcggtact cccggtctgt 2100
gcttctcatc acccagcgtc ttagttccgt ggagcaggcc aatcacatcc tctttctgga 2160
aggaggcacc attgttgagg agggaaccca ccagcagctc atggctaata aggggcgcta 2220
ttggaccatg ttgcaggctc ctggtgggtc agatgctcct gagtgaagct cttctcagac 2280

<210> SEQ ID NO 12
<211> LENGTH: 746
<212> TYPE: PRT
<213> ORGANISM: Sus scrofa

<400> SEQUENCE: 12

Met Ala Ser Ser Gly Ser Ser Ala Pro Cys Gly Cys Leu Cys Val Ser
1               5                   10                  15

Arg Ala Ser Leu Pro Trp Leu Gly Ala Ala Leu Leu Leu Leu Ala Asp
            20                  25                  30

Trp Val Leu Leu Arg Pro Ala Leu Pro Arg Ile Ser Ser Leu Leu Leu
        35                  40                  45

Pro Pro Ala Leu Pro Leu Leu Arg Val Trp Val Val Gly Leu Ser Arg
    50                  55                  60

Trp Ala Val Leu Trp Leu Gly Ala Arg Ser Val Leu Arg Ala Thr Val
65                  70                  75                  80

Gly Phe Arg Glu Lys Ser Thr Gly Leu Arg Gly Trp Leu Ala Ala Leu
                85                  90                  95

Glu Pro Leu Ala Ala Ala Leu Gly Leu Ala Leu Pro Gly Leu Ala Leu
            100                 105                 110

Phe Arg Glu Leu Gly Ser Gly Ala Ala Asp Ser Thr Arg Leu Leu His
        115                 120                 125

Trp Gly Ser Arg Leu Asp Ala Phe Ala Leu Ser Tyr Ala Ala Ala Leu
    130                 135                 140

Pro Ala Ala Ala Leu Trp His Lys Leu Ser Ser Leu Trp Val Gln Gly
145                 150                 155                 160

Ser His Arg Gly Ser Gly Val Thr Val Ser Arg Leu Leu Gly Cys Leu
                165                 170                 175

Gly Ser Glu Ile Arg His Leu Trp Leu Leu Leu Thr Leu Val Val Leu
            180                 185                 190

Ser Ser Leu Gly Glu Met Ala Ile Pro Phe Phe Thr Gly Arg Leu Thr
        195                 200                 205

Asp Trp Ile Leu Arg Asp Gly Ala Gly Ala Ala Phe Thr Gln Asn Leu
    210                 215                 220

Thr Leu Met Ser Ile Leu Ile Ile Ala Ser Ser Val Leu Glu Phe Val
225                 230                 235                 240

Cys Asp Gly Ile Tyr Asn Ser Thr Met Gly Arg Val His Ser His Leu
                245                 250                 255

Gln Gly Glu Val Phe Arg Ser Val Leu Arg Gln Glu Thr Glu Phe Phe
            260                 265                 270

```
Gln Lys Asn Gln Thr Gly Thr Ile Thr Ser Arg Val Thr Glu Asp Thr
        275                 280                 285

Ser Thr Val Ser Val Ser Leu Ser Ser Glu Leu Ser Leu Leu Leu Trp
    290                 295                 300

Tyr Leu Ala Arg Gly Leu Cys Leu Leu Gly Leu Met Leu Trp Gly Ser
305                 310                 315                 320

Pro Pro Leu Thr Met Val Thr Leu Ala Ala Leu Pro Leu Leu Phe Leu
                325                 330                 335

Leu Pro Glu Lys Leu Gly Lys Trp His Gln Val Leu Ala Ala Gln Val
            340                 345                 350

Gln Glu Ser Leu Ala Lys Ser Ser Gln Val Ala Ile Glu Val Leu Ser
        355                 360                 365

Ala Met Pro Thr Val Arg Ser Phe Ala Asn Glu Glu Gly Glu Ala Gln
    370                 375                 380

Lys Phe Lys Gln Lys Leu Gln Asp Met Lys Thr Leu Asn Gln Lys Glu
385                 390                 395                 400

Ala Leu Ala Tyr Ala Val Asp Leu Trp Thr Thr Ser Ile Ser Gly Met
                405                 410                 415

Leu Leu Lys Val Gly Ile Leu Tyr Val Gly Gly Lys Leu Val Ala Gly
            420                 425                 430

Gly Ala Ile Ser Ser Gly Asn Leu Val Thr Phe Val Leu Tyr Gln Ile
        435                 440                 445

Gln Phe Thr Glu Ala Val Gln Val Leu Leu Ser Thr Tyr Pro Arg Val
    450                 455                 460

Gln Lys Ala Val Gly Ser Ser Lys Glu Ile Phe Glu Tyr Leu Asp Arg
465                 470                 475                 480

Ile Pro Arg Cys Pro Ala Ser Gly Ser Leu Thr Ser Leu Lys Ser Glu
                485                 490                 495

Gly Leu Val Lys Phe Gln Asn Val Ser Phe Ala Tyr Pro Asn Arg Pro
            500                 505                 510

Glu Val Pro Val Leu Gln Gly Leu Thr Phe Thr Leu Arg Pro Gly Glu
        515                 520                 525

Val Thr Ala Leu Val Gly Pro Asn Gly Ser Gly Lys Ser Thr Val Ala
    530                 535                 540

Ala Leu Leu Gln Asn Leu Tyr Gln Pro Thr Glu Gly Gln Val Leu Leu
545                 550                 555                 560

Gly Glu Lys Pro Leu Pro Glu Tyr Glu His Arg Tyr Leu His Arg Gln
                565                 570                 575

Val Ala Ala Val Gly Gln Glu Pro Gln Leu Phe Gly Arg Ser Phe Gln
            580                 585                 590

Glu Asn Ile Ala Tyr Gly Leu Ser Gln Lys Pro Ala Met Glu Glu Val
        595                 600                 605

Ile Ala Ala Ala Met Glu Ser Gly Ala His Ser Phe Ile Ser Lys Leu
    610                 615                 620

Pro Gln Gly Tyr Asp Thr Glu Val Gly Glu Ala Gly Ser Gln Leu Ser
625                 630                 635                 640

Gly Gly Gln Arg Gln Ala Val Ala Leu Ala Arg Ala Leu Ile Arg Lys
                645                 650                 655

Pro Arg Val Leu Ile Leu Asp Asp Ala Thr Ser Ala Leu Asp Ala Asn
            660                 665                 670

Ser Gln Ala Arg Val Glu Ser Leu Leu Tyr Glu Ser Pro Glu Arg Tyr
        675                 680                 685

Ser Arg Ser Val Leu Leu Ile Thr Gln Arg Leu Ser Ser Val Glu Gln
```

```
    690                 695                 700

Ala Asn His Ile Leu Phe Leu Glu Gly Gly Thr Ile Val Glu Glu Gly
705                 710                 715                 720

Thr His Gln Gln Leu Met Ala Asn Lys Gly Arg Tyr Trp Thr Met Leu
                725                 730                 735

Gln Ala Pro Gly Gly Ser Asp Ala Pro Glu
            740                 745


<210> SEQ ID NO 13
<211> LENGTH: 75569
<212> TYPE: DNA
<213> ORGANISM: Sus scrofa
<220> FEATURE:
<221> NAME/KEY: modified_base
<222> LOCATION: (6835)..(6934)
<223> OTHER INFORMATION: a, c, t, g, unknown or other
<220> FEATURE:
<221> NAME/KEY: modified_base
<222> LOCATION: (57902)..(58001)
<223> OTHER INFORMATION: a, c, t, g, unknown or other

<400> SEQUENCE: 13

actgagaaaa taatttattt aattttaaat caggaatttt tattttttaa tattgaacta     60

ttaataagat cttgaatttg tccatttgaa atttaaattt aaatgatttt tttttaaaaa    120

atcaagattc cttcaaaagg aaatatcagt ccttttcttt aatctttgag aacgaatcat    180

ttctgtagtt tggaacttgc accatgaagt ctctgcactc cagaatggat tccataaact    240

tgcgttatag agaaacaaga gtcctaattg acttgtgatt tcctttttct tttacaagac    300

tacttctcca ggatttttgt tgagttattt tgttgggtta ttttgttgag ttattttgct    360

gggttgcaaa aatttttagc aagaattgaa gagtaggagg cccagggaaa cagtagagaa    420

aatgtaggtt tcattttatc aaagaagccc atcgtgctga acatcaagtc agtgcaatgg    480

ctcttcaagt aaatcatttg aaaatggaca caaatgacct aaactggaac acaagcaaaa    540

gtatatcaca tacctgcaga tgtaaatatt gcctcctaac ttcctttaca ccaaactgct    600

taactttaaa ttacatgtaa gatctcatag cttttcttag agaaagggat tgaaaagctg    660

tttagtcatg aggactgggt ctcccattgc catcctctct actttgatat aaaatcaatt    720

aaccacttta ttaaacatgt ccggcagtta cacttcagta gtgcagctgg ggcaggggaa    780

atgagaggtt ccctgataag caggcttttc ctctagtcca ctccttgacg gtggctctca    840

agttgcccat gatgggctga gggactctga gagttagagc aggtggcagc aggacttgct    900

gatgcctgat tgtcatgaag ccaagatcta ggaagtcact tcaacccact gtaggcctct    960

gtccactctg acatcatcca cttcctctga gcaaggattt gtagacacaa attccagagt   1020

ctggcagact gaatatgact tggccaaagc aagaagcatc ttctaagaca gtgctgctct   1080

agttgtcata tggttgagga ggctggagcc actctcattg cctcccattc agtgcctgga   1140

tccaagctgt atgtacatgc caactccatg ccctgtgtct cttagaaatg gcattgcccc   1200

acagtgatca gccccctctc tttccaatct gtcttcgcta tttcatggca aacttactta   1260

gaagctgtgc ttttatttcg tgctgagctc ccattggttc attcggattc cctgtaactc   1320

ccaacattca ccattgggaa tcttgatcag tatctgcgca gaagccaaac aaaaccctga   1380

tgcgaaaagg acatggactt caaataacct gaagtcctct gctgttgaaa tcatctgagg   1440

attgctaagg tagactctga tctcctgctg caaagcaact ctgttgcttt agacttagca   1500

gagacaggaa gacgctaaaa tcaagaggac gacccctccc aatcttattt tgttgccaaa   1560
```

-continued

```
cacttccctt tgcatacttt tctccagtat gacatgtaga gtgtctctga ctttttcttt   1620
gcctatgaca attttttttt ttggttcagt taatagtata taccccctca acccagaaca   1680
gataagaaat cattgggaat ttacatctga ttactacaga gtcattctcc catttgacaa   1740
ggctcaaagt tgcaaggaag aataatatgt acttactgtg ttggtatttt gttagtattt   1800
ttttaaaagt taaaattaag tgctacttct ctgaggaagt agccagagta atactctttc   1860
aaattcagaa aactgctggc acaatttaaa gtcagatgtt atttctaacc aaattatact   1920
ctttttttctg ccaagctatc ttgacaatcc taatatccac agacatgcct atatgataat   1980
cccagcagta ttctggggat aagattttag tgggtttgtt gagaaggaaa tacttgttta   2040
gatggctttc atcatgccac tcggcttcta tgtcattttc cttgtcctgg aggattccct   2100
tgaagcactc ctgagtgatg tttagaacct gagtgggtgt tcccccaaaa atggctgcgt   2160
ggtaataaaa atccccctgg ccaaacggaa tgtaggctgc ggactccttc cgcctctcgt   2220
aggtgaactc gtcaggatgt gccttgtacc accaggcctg tagctgagcc accgactggc   2280
ccagggtctc caccccaaag ttgttttgga agacctgatc cacgtccatg cagaagagga   2340
agtccacctc gtgctggatg tgggccagga tgtgctcccc gatggtcttc atgcgcatca   2400
tgctgatgtc ttgccacctc ttctcggact tgatctcaaa cactttaaag gaacgcagag   2460
gacccagctc tatcaaaggc atcctggaga tatcatccac catgatgtaa aagatgactt   2520
tgtggccaac catgaagtat gtatttgcag atattaagaa ctcctccaag taatgctcaa   2580
tgtatctgaa ataaagaaga atggggtaaa tgtaacctct gggatttcta gaggagacaa   2640
tatgctatta tcatctagtc tgtattttgc agtttaggaa aggaatgatt tttccccatc   2700
ctggatgaga gacgtctgtt gctgtaacat tcccagctac tctccaccat tcagtcattc   2760
agctttgggg aggtggagtg gcttacctga ctggtgattc tggcagggtg gctgggcatg   2820
ctcagccctg ctccttcctc tctcactctt ggaagccaac caggcagaga gaacatgtgt   2880
tttcagctgc tctgggcctt gcagtggtac cttagtggca caggccctgc tcccacatcc   2940
agaggcctgc agttacttgt gctgtatgtg cctggatgcc taagtctttc taattctgtg   3000
gttcaagatt tggaagccca gggcctgcag ttataagcca catactccaa caccagcttt   3060
aactgtaatg aaggtgataa ctcattacca tctgccttaa ttagtcttta tccccttgtc   3120
cttatcaatc agttcagatg ctagttcttc cttttttcct gcattattca gatataactg   3180
acatatatca ttgtgtaagt ttaaggtgtg caaagtgttg atgtgatgca cttattttta   3240
atttttattt tttgtctttt tagggccaca tccgcagcat atggaggttc ccagactagg   3300
ggtctaattg cagttgcagc tgctggccca tgccacagcc acagcaacac cagatctgag   3360
ctttgtctat gacctacacc gcagctggtg gcaatgcttg atcctttaac ccactgagca   3420
aggccaggga tcgaacccaa atcctcatgg ttactagtca gattcttaac ccactgagtg   3480
acaacggaaa ctccctggta cactcatata ttagaaatga ttaccactgt ggcattactt   3540
gacaccttca tcatatcaca taattaccat ttttttgtgg caagaagact taggacttat   3600
tctctgacca accttaaagt atatattaca gtatgattaa aaacaatcac catgctgtac   3660
attagatccc agagcttatt catcttataa ctgcaagttt gtaccctttg attaccatca   3720
gggggcacta gttcttagct cttcctcaaa aaccccagcc tatattccaa tacttttact   3780
gacctaccag atgcaagcgt gatgtgcaag ggtcattaag cctaaccatc gccactctct   3840
tatccttctc tgggacccaa acaatggatt atggaatatg gatattcttc catcttactg   3900
atttaccctg tgagtttccc gctggtcacc ccaaacacca gcccattatc cagacaccat   3960
```

```
cattataaaa cccatccaaa tatgagagca aacgacctct gattcaacct tactttaact   4020
atctcgtttc atttaaaaaa atagatttta gtttttagaa catgtttagg ctcacagcaa   4080
aattgagctg aaagtgcaga attccccccg ctcccccac tcccactccc agcttctccc    4140
accatcaaca tccagcacca gggtagcacg tgttgcaact gatgaaacta cactgacaca   4200
tcattatcac accaagcccg tagtttacac taaggttcac tcttggtggc agactttcta   4260
tgaatctgaa caaatgtaaa atgacattta tctatcacta tgtatggtac catacagagt   4320
attttcactg ccctaaaaaa tcctgtgttc tgtctattca tccattctcc cacaccatcg   4380
cctggcatct actgatattt ttactgtctc catggatcag tacctttgac cttttccaga   4440
atgtcatata gttggaacca tatagtaggt agtctttgca gatggtttct tggtaacgaa   4500
catttgaggt tcctccatgt cttttcatgg attgattttt tttttaaag cactgctaat    4560
actccactgt ctgaatgtgc tacaatttat caattaattt gcctactaaa ggacctgtta   4620
cttccaagtt ttgggcaatt atgaataaaa gtgctataaa cggagttcct ttcgtggctc   4680
agtggtcaac aaacccacct agttgcaggt tcaatccctg gcctcgctca gggggttaag   4740
gatccagtgt ggccatgagc tgtggtgtag gtcgcagatg tggctcagat ctcgggttac   4800
tgtggctgtg gcataggccg gcagctgtag ctctgattca acccttagcc tgggaacctc   4860
catatgccgc aggtgtggcc caaaaaaaac aaaaaaagaa aaaaccaaaa cccaccccc    4920
ccaaaaaaaa atacctgcta taaacatctg tatgcaagtt tttgtgtaga cataaagttt   4980
cagcttttga gggtaaatac taaggtgtgc catcgctgga ttgtatggta agagtatgtt   5040
tagttttgta agaatctgcc aaactgtctt acaaattggt tgtatcattt cgcattgcca   5100
gcagcagtga ataagctttc ctatcgctct acattttcat cagcagctgg tattgtcagt   5160
gtttgggatt tgggtcattc taatagatgt gtagtggtat tttagctatt tacctattca   5220
ttcaaaaacc atcatgttca ggaagaaaag gaaagggggg agttcccatt gtggcagtgg   5280
cacagtgggt taaagatcca gtgttgctgc agctatggag aaggtcacag ctgtggctca   5340
gaacttccat acgccacagg tgcagctgaa aaagaaaaag agaaaaaaaa aaacccatca   5400
cattcctgtc ttctgtaagc caagatacag gctattctgt gaagccatgg ggatgataga   5460
gaagggaaga agtagttggc tggcttaaca caacccacgt caccacccag actcatgccc   5520
agtgactgtg cactgaattt aatttgttga tcacattatc agccaatgat gacattttgt   5580
aataatgact ggcacttcct tttgtttttt ggttgctgct tggattccct ttgattacta   5640
caaacataaa ctgtgctttc aatgctggtc tctggaaacc ccaggtttat agtattgatt   5700
ctttaaacgg agagaatatc tcagcaatac aaggagggac ttcaacatgg ctctggggct   5760
aatggccagg aaattcttct gcactctgga actttaagaa aaaatctatt gtgccctgaa   5820
gcttgggagg tgatcctagg ggcgagggag gaaacctttg tgaggtttaa cattgtttag   5880
agattaaagc gctgcagttg gtgctgtgca ctgtcatttg aaaataaacc aaacatcaca   5940
cctcctaaaa gtccaaatcc actcttggga ggatttattg ctgctgagta caaacagtcc   6000
tcactcgcct cagagcagag tgcgcgggtt tcaccaggac atgccaagta cagtttagtt   6060
ctctaaagct gcaacaagat ggctagagcc aatgtggagc cgttcttttt ggaaacacca   6120
aggttaaatc aatctgcagt atggctggct ggtctcctct tataccaaag gattaggtga   6180
gctgggaatc tttcccaact cctaacagaa catattcttc tagtcgaaag gtcaaaactc   6240
cagagtcacc cttctctatt agagatgcca cccaggcccc tgggatcagt acattcaggg   6300
```

```
acattaggac ttgattagta cagtgacagt gataccttct gggctctagg ttggagaagg   6360
tctcaggagg acgcttaaat cttcactcag atcaaccttg accttcactt ctctttgtac   6420
aggcaacagg tcaactaact tcttttcttt tcttttcttt tctttctttc tttctttctt   6480
tctttctttc tttctttctt tctttctttc tttctttctt tctttctttc tttctttcct   6540
tccttccttc cttccttcct tccttccttc cttccttcct tccttctttc tttctttctt   6600
cctttctttc tttctttctt cctttctttc ttcctttctt cctttctccc tttctctctt   6660
tctctctttc tctttctctt tcccttcctt ccttttcttt cttccttcct tccttccttt   6720
cctgcttttt tagggctgca ccctcccagg ctaggggtcc aatcgaagct gtgatgatgg   6780
cctgcgtcag agccacagca atgcgggatt cgaaatgcat ctgtgaccac accannnnnn   6840
nnnnnnnnnn nnnnnnnnnn nnnnnnnnnn nnnnnnnnnn nnnnnnnnnn nnnnnnnnnn   6900
nnnnnnnnnn nnnnnnnnnn nnnnnnnnnn nnnntttcct ttcttctctt tcggattttt   6960
ttttaagttt ggtgaaagta tagtgtctta caatgttgtg ataatttttc tgtatacaaa   7020
gtgatttcag tttctttgtg gcttcagaaa aggtacagat ggaaaggccc atggatgtgg   7080
gggagggaag gggcacggag gtgaacagga aaattgaact tttgcttttg ttttggaaaa   7140
aaagggggggg ggattctcta aaaaagaaaa ctgggttata ttttaaacga acattacagc   7200
tactactttt aagtaagaat gtttacagtt tggggagaaa agttccaaac aaggaaacgg   7260
gggctgaaac aggaacctat ccaacctctg gaagaggaag ttctgagcag cctaatctcc   7320
ccgggccaaa ccctccagga ggaataggca gaaggcacag aggagtggtc agccatgcgg   7380
acgtggaaaa ccactccact taggacactt ctgtctttgg tccttggtct ggggtctcga   7440
gagcatagga gaaacgacgc acacacaggc catctaacaa ttgccatttt tggaatttcc   7500
acagagggcc gtggaggtca gggcggaggt ggctgtgggt gtactgtcga ctctgggtgc   7560
agtgggtata gcagatcttc ttccctgcaa cccaagcccc tcaccctgag gtgggaaaga   7620
gttgaccctc tgactagttt tattcttagc ctttggggac ctcagcagaa gggagtctaa   7680
aatggccctg tgacaccatt ctcctctcca ctaattcaga catgacatga acagcctctg   7740
taaacccagg ggcccctcac ccatcctctg atagtggaag gggaaaaact caaggccagt   7800
tttattagca acacctacct tccgacagca aaaaccgtca agcccacggt aattttctgt   7860
ttggcataat aattatctaa gacggctctg ttgtaagtgc cttcccatac cactggagcc   7920
ttccatctgg ttatggtcac gacctctggg cgtttcctgg tgacaaaaca tagagtcagg   7980
atggctttgc taaggtacga cagtctgggg gaacatgggt cagtcatggc ttgtggtgac   8040
tggccttgaa tcctgactgt attttagccc cagtcagctg gtggtgtgac attgcagcat   8100
cttctggggg agggacagga ggctctggcc caggtgcctc tgcgggctgc cctggtggcc   8160
cctttgggga tcgtacctgt acaacgtgta tgtaccttcc gtccccctgt tctgctgtcc   8220
tcgtcctcaa tcttccttcc aaacccccttc gcctatctcc ccaggccctt cctaagctgc   8280
cagcgacatc tttgggtgtt gcttatccca gtgggtgcca cctgaccctg agaaagccct   8340
atggcttgac tagcgggatg agagagtgac atttgagctg aaagaggaag aagctgtctc   8400
agtttgcctt ctgccagaaa gcaatttctg ggtaggaacc tggttatcgg acaaaaaggg   8460
ccccagacta aggggacctg gtgttgtggt tcattttacg aagaaggaga cagtcaccca   8520
gaaaagaagg gacccggcgg gctaactgtg gccatgggtg acacacaggg ctcgggctca   8580
gacctctctc agatcatgtc acctcttgac tagaagcaca aaagcgggag gggagggggc   8640
atgttctctg cacccagaac acttgaaagg gacttagcaa agccaacaca aacacaggaa   8700
```

```
gccacggaag agcaacggac aaattgtaaa gagtaaatgc gggaagtctg ggtagcagct   8760
ggggcccccc agaggcagga gggagctgag aagacttggc tcaaacccca tttgctctgg   8820
aagtggctgc acttccccgt cggaaacaga ctgaaacgtg gtcatttaga ttcaaccccc   8880
aacacaacat gagagggcct ggcccctgct agctgtgtgc ttgtatttca gccactgcag   8940
ggagaaggcc agtggttggg gcaacgtctt gggggtccca tcgggcccct gctggctgcc   9000
tgggtatggc cctggtgagg ctgtctagga gatgttagcc cagcgagaac atacccccac   9060
cctcatacgc gggtggagga agggttttca caaacctgcc cctcccccat gggagaaacc   9120
atgtttccct gcgagattgg gcaaggctgg gtcaccccca cttcttgctc atgccttctg   9180
tccctcgtca ccaagctctg cacccgtatt ctggagctgc ctctgccctc ccacccccac   9240
cccatgccct gcttcaagcc tgcttccttc ctcccctaag agtaattctg cagagatgga   9300
ggggacatgg ctaggctgct caaaccccac acccccagct ctgccttcac accccaggta   9360
tgaccgcccc ttggggacac ctgctcttgg tttccaacaa tcatgaaaga agctgttttg   9420
gactctgtac caacttgtgc caggtacttt cacatacact ttctctcatt tagtccttgc   9480
aaaagcttgg ccatgtagta tgctcaatgt acagatatga aaatcaaggc tcaggaaggc   9540
ttgttaactt gaccaaggcc aaacagcaga tgatggtaac taacacacac tggctccttc   9600
ctatgggacc aggcacagtg ccaagagctt caccctttttg tgggggtggg gttgctatat   9660
tttgattccc attttatctg tgaggaaact gtagcacaga gtggtgaaat aacttgtctg   9720
aggtcacaca gctagtaagg agccaagctg ggatttgaac ccagatagtc tgactgtggt   9780
ctgtgctctg aaccactacc ctctatggct tcttggctat ttacttgctg taccaatgaa   9840
ctggagttaa aacccaggta tgtcatcatt tccactcatt tgagctactt cagcattttt   9900
atcagggcag aataaaaaaa aatgatgagc tttttttttg tttgttttgt tttgttttta   9960
gaaacttatg tgatgctttt ctcacataaa agccccagct ttgttgaatg actggatttc  10020
aaaccaaaaa aaccacacac acacacacac acacacacac acacacacac acacacacac  10080
agcttaggct tatcattcta taaccgtttc ccatgcactg tcacttcatt cattcctgtc  10140
cttagtgtag cctgtcaagg atctcttagc agttcagacc ccagcctatc agttaagcca  10200
tgcagctgtg tgtgagctga acatctggca agcaggcaat attatcttta agcaaagaaa  10260
aggaagagaa agagaaggag gaagaggagg aaaggaaggt attcttattt actagtcgca  10320
agcactgggg ttaagtaccg gacttttatt ctctcattga atccttacaa ccacgttcaa  10380
gagtgggtgc tatcatcacc tccatttcac aaataaagaa agtcgggggt gagagagaag  10440
gaaactatgt ttttagccat tcaaccaata ggaggggcca caccagggca tcacctcctc  10500
gatgcacatc tgccaagtcc ctgctccatc tgccggggcc cagggctaaa gacggagatc  10560
agacccatcc taccccttga gaacttccca tccctgacag gtggtcagcc tgccgcacac  10620
tcctcagccg cacaacccct cagactacac cttctagaaa gaccgattca gaacaccagt  10680
gtccagtttg gttacttggc tgggaagatt ccttttaagc aggggggaga aaaagtagca  10740
atattaaaaa ttaacgtcga attaaaaatt aaaatgctct atttcccagc tgttaattat  10800
taaattccac tggcaattcc aacatgtcag caaccctgac taggaagcca tatgacaggc  10860
tgaaaacact ggccgtgggc aggaggagga ggtgggagga tgattgagat cagcttcctg  10920
gatgaacctc tgctcaaacc ccaccccccac cccggcccac agaaaaagaa gaagtaacag  10980
caggcaggcc aagtatgtgt aagagcaaga gctgcccaac gtcatcaaga gagggctcga  11040
```

```
aaaggaggga aaagtccagg aaacactgga aactgctcag ttttttaagc cgggcaccca  11100
ctgcgttact tcggcatgtg gggttccacc agtgcaaacc aaagacttcc acaaaataaa  11160
agggtctcca aaatccaaac gcaccaccta cctaggtagt tggtagcttt tcaattttat  11220
gtacttattt atgggtacac tgtggtcctg aagggctggg cagaggaagt gttaaaattc  11280
tatgaatcat acagcaggtg gaaaaaaatg aggaatgcaa caatgtgtta cttactggat  11340
tccttccagg cagcaggacg tacacagtga tccagcaaag agctaatgat gccatggaca  11400
agggtgatgg agagagggag atgacgtggg aagaatgaac agaacatgta gatgaattag  11460
actgtgggct ggatgaagga aggatgaaca gtgaatcatg gaggtctcct gactcttgct  11520
tgagatggga aatgagaaga atgagggtgg ggtggaatca aaaactccct ctgggagttc  11580
ccgtcatggc tcagtgggaa caaatctgac tagcatccat gaggatgcag gttcgacccc  11640
tggccttgct cagtgggtta aggatctggc gttaccgtga gctgtggtgt aggtcacaga  11700
cacggcttgg atctggtgtt gctgtggcta cagtgcaggc cggcagctag agctccaatt  11760
caacccctag cctgggaaac tccctatgcc tcaggtacgg cctaaaaaga caaaaaaacaa  11820
aaaaacaaac aaaaaaaccc aaactccatc tgagtcatgc gagacctgca gtgatgtcag  11880
gcaagagtta gacacaactg ggtgctcaga gaaaaccttt gggctaaaga tataaatgca  11940
gtagtcattg tcccatgaat ggtatctaat gccacagaaa tggatgaaga cagtgtataa  12000
agaaaagaga tgaggataat ggactcaacc tccagaaact ctaacacttc ctggctgaga  12060
agagggaggg gccccaatca aggagactga caagggagct ggagaagtcg gaggaaaact  12120
aagaggatgt ggtgctacag aggctgagag atcttgatgt aaaaatgtat acagaataca  12180
cttaatatgt ttcaggtaga atacagagga cacatttcta taaatatatc tataatatat  12240
ttctataaat atattaattc agtggctcat ctttcctgca tttatgcaag caatttactt  12300
tggtgccctg agaaggctta gattagtgct actacatatc aatattcttt aaatatctgc  12360
tcagcattca tttggaggag aaactgagcc atgcatgggg gaaagtggaa agagtgacag  12420
tgggtggctg tggtctttca cctctgaccc cagtgattca gccctggctc cacctctcaa  12480
gtcccactca gtaaagcaca agtaccacgg tcagtgtgcc actctctctt gaagggagct  12540
tggtgactgt ctctagctga tctatctggc ccctggggag tctcacacct ccccacatgc  12600
acacacatct aaggggctta tcaaagctct ggtgggagtt cccgtcatgg cacagcagac  12660
atgaatccaa ctagtatcca tgaggtcgcc agttcgatcc ctggcctcac tcagtgggtt  12720
ggggatcctg cgttgctgtg gctgtggtgt aggccagctg ctgcagctcc gattagaccc  12780
ctagcctggg aacttccata tgctgcaggt gtgccccctc aaaagaaaaa aaagttatag  12840
tgcttccaca ttcttccact tccaggagta gcttagcatt ccatagatgg ctaccctgtg  12900
cccagctcct caaataacac atggggaggc caaaattccc attctttcac actgacatgg  12960
acctcccatc ctaaaacagt aagaaacttg ccagaacata ctcagtcctt ccagagtcca  13020
agacccctca tgctggaata gatgctattc tcctcggatc ctcctcctac ctctactgct  13080
gctcccactc cgtttcagac ttcttttcct ccctcccctg accctttaag tgctgatgtc  13140
agataagact cagctctgct cctctgcctg gactctgatg gctcctcttc caatgtctct  13200
accacatatc ttctgccagc ttaaaggccc tgctgtacac tgacgattat gtctcccccca  13260
aattcgtgtg ttgaaaccca ccctcaatgt aatggtatta aggggtgggg cattggggtg  13320
attagatcct gagggtggaa ccctcaggaa tgggatgggt gcccttagaa aagaagccct  13380
ggagagctcc ctctcccctt ccatggccta agaacacaat gagaagacgg gcatgtacaa  13440
```

actagaaagt gggttctcac cagacaccac atctgctggt gccttgatct tggacttccc 13500
agcctccaga acggtacaaa atacattttt gttgtttata agccaccccg tctatggtat 13560
tctgttacag tagtctgaag gtctaagata ggctctccat gaactctatc caaatgcccc 13620
acaggtacct gaatccacct acatccttaa tcaagctcat cacctcccct attcctagac 13680
ctgtatctcc tcctccagtc cctttcctgg tcaacggcac cagcatgcac cagtctctca 13740
ggcctcccag tcatcccgga cagcccccac cttctcactc ccttccacat cctttcaagt 13800
caggttaatc acaccgcctt accaatcttg gcaaatgcta gtttcacatc tagtgcccct 13860
ataggactgt aaacttcttg aatataagtg tattgattaa tttctcctgt ctgtctcctg 13920
tgcctaacac aatgtctagt accgtgactc atagtgaaat atatcctacg tcacaaacac 13980
atgcacatac acatatggaa gcaaaaatgc cactaaacaa tacttatcct tacttcatga 14040
gatgccttct gatttcctat ttggtttcaa tttttgaccc ttaagccagt ttctaaacac 14100
attaatggat caaataatag tctgacacac atgggctagc atatcatagg tgttttaatg 14160
aacattgttg tatgcttgct tagagtgtgt gcatggcctt gtaaggtttt ttaatcatca 14220
ctgccatttt attttatttt tatttttta gggccacagg tgcagcctat ggaagttccc 14280
agtctagggg ttgaatcgga gctgtaattg ccagtctgca ccacagccac agcaacacca 14340
gatctgagcc tcgtctttga cctacaccac agcttgcagc aatgccagat ccttaaccca 14400
ctgagtgggg ccggggatag aatggatact agttgggttt gtttccactg aaccacaatg 14460
ggaactcgcg tcattgccat tttacagagg agttaaccga acctaagaat tttctttatc 14520
tgattctaga ttctgtggct ttccacagca ccccatgggc tataggacct ctcctagccc 14580
cagtattttt ttgcttttta ggggctgcac ccgcagcata tggaggttcc caggctaggg 14640
gtcaaactgg agctacagct gccggcctac cacagcaacg ccagatccga gccacgtctg 14700
caacctacac caccggtcat ggcaacgcgg gatccttagc ccactgagtg aggccaggga 14760
tccaacgtga aacctcacag ttcctagttg gactcatttc cgctgtgcca ccacgggaac 14820
tgctagcccc agtattttgt gattcatctg ttgccattgg ctaattgctg tcagaatcac 14880
tatgttgttg cgcaaacatt tgagtcaaaa catccagact ccccacctcc cgggatgcca 14940
cgccagtcac tcacacacac acacacacac acacaaaatc cggaccctgt tttaagggtc 15000
taatagatgc taaaactctg tctcccctgt cgggaatgtt ctcatggccc tgttgcctac 15060
acagcccctg ccacctcctg ctgagctgtg gatttactga aatagggcaa cgcttctttt 15120
cttactcagg attaaaccag tccactagcg gaagctctcc tctgttgtct tcttttcttt 15180
gttccttttc gttgcctata gcgtcttctt cttcgtggta actgtgagtc ctacgtacaa 15240
acggaaaaca agctgaggaa ggcagggagg gtgacccatg tgccagaatg agagtgagga 15300
tcttgtgaaa acagattcca aggcagagaa cacgtgcgcc aagcaaatgt ctacagaagg 15360
cttgtgatac taaacattta ttcgtaaaga cgtccgtctg atgaaaaggt tcagtgctcc 15420
ccttttttcat catccttcca gaccagcaca gttagcaatg taatgaccca gcaattctca 15480
ggttctgtca ggagcaggga aacctgataa aacagtcctt atcagcgtat gtaagctcat 15540
gacagccttt cctgcagcct caacttcagc ctgagcctca ctcactccca catcaaatgg 15600
gaaaaaacaa aaccttgaaa accaaactta atgcccatcc ccaccacgca acagagtcct 15660
tgcatgattc caataagcca gaaggacgag gcgactgaga aggtcatggc tgtgaaacca 15720
ttttatttgg actctacagc cttgagcaga tacacagatg gccgtttccc agtcttaccc 15780

```
attgttaaac cagctcggaa accaccagcc cctctgagca ctgctgccaa cttctgggtt  15840
tctaagaaat gaaaaagatg acaaacattt tttagaaaat gaggcagtcc caaactgggg  15900
cagggggtgg ggggtgttcc aaactctttt tatggcagat cacttaaaat cattttttaa  15960
aaaatcacta attcgtaaaa tgaacagaaa tgaagctgct ccagctgaat gactgaggat  16020
ggacccgaca ctccccagat ctcccctccc ttgggtggcc cccggcactc cgctggtcca  16080
gggagccctc gcaggaagag aaggggagaa gaagaatgac aagggggagg gcactaatcc  16140
ataaatccaa gtcctggatc tgcccctttc ctgttgtgta accctgatag gacatttttc  16200
ctctctgaat cgccattgcc tcctctggaa agttagagaa caatgacagc accaaaccta  16260
ccatgaagat ggatggcttc gaagactaaa caaagtagcc tacgtaaaag agctttataa  16320
gctgaaaatt actgtagtaa gttgtagtct taaaaaagaa aagcccacat ttccaagaat  16380
gatctcttgc taaatgagga gaactggagt tgctacaaag gtcagcagtg acagattcag  16440
gaaacctgag ggtttctaaa cccgaagctc agcaaactgt aatcagaagc cgtttttctc  16500
cacacacatg ctcagatgtc cacactcact gtgagagtct ctccaaggcg tggaccgtct  16560
agaggaggga caagaggggg aaagccagga gctgccatgc cctttggttg gacaaatgag  16620
gtggtgaggc aggaataggc atagtagtaa gaaacttact ttattttact ttattatttt  16680
atttttttg tttttttagg gccgcacccg tggcatatgg aggttcccag gctaggggtc  16740
taattggagc tgtagctgcc ggcctacgcc acagccacag caacttggaa tctgagccgc  16800
ctctgtgacc tacaccacag gtcacagcag caccagatcc ttaacccact gagcaaggcc  16860
agggatcgaa gatgcatcct catggatact agtcagattt gtttgcactg cgccacaact  16920
ggaagtccaa gaaacttaaa gtccatctac tttcaggaag tgcttgaaat ggcttatgaa  16980
gaaagtgtgg ttacgataaa taggaaaaca atacaagaat caaaacaaaa caaaacgaaa  17040
cagagaaaca ttttagtcac tcgggtgttt tcacatgact ttggtcatcc cagccactct  17100
gtgagaacaa aatctttaac tttattttta cttcatagct aagatattgg caaaatgagt  17160
ttgagcaaat tgccaagatc ccatggcatc taacaaaagc caggatttaa caccagggga  17220
taaatcatat cagatgaagg ctactataaa tcagctatac tttaataaga aaaaatgttt  17280
taaaaaaaat gaaggccaag gaaaatgcaa gcatttaagc acaatacttt gctctaagct  17340
tcctagcaac caagtcgaag ataggaaaaa aaaaaaagaa aaatgaaggc ttagagtcct  17400
taatcaccag taatagtaat aataataaat aataataata cacacactag tttatcagga  17460
cacccagcct ttcttcctaa tcctttgtct tggcaaaatt tctggcaagg gtctttatac  17520
cacatgtagt aggtagcata atggataata tctactctga ttctttttta tgagcaaggc  17580
aggaatgttc tccaaacaac atcacttaaa gagatagata cttgatgaga agcaaaggaa  17640
aaacacaact catgctctag aaaggcaagt ctaggggctg gagaagtaca gctcagaccc  17700
ctggaacccc atccctctcc tccacctagg accacaagtg tgtcaccacc tgccatgtta  17760
agaatggact gtagggccac cagggtcaca tggaaggtga cctagagata tctggaattc  17820
aaagcactta ctttgactgg tatatccaga acaaagaacc ttctgggcta aaagcaaatg  17880
gaaataaaaa catatcatgt tacttggaat gcagagaaaa gctattttgc aatcattatc  17940
attgaaaccc taggctgagc tgagagcctg ggttgtggct actcccaggt ttccaccttc  18000
gagatcgaaa aaatgatatc acgggactct cgtcatttca gaattactca gatcaaacgg  18060
tgggagggag gtctctggaa aatatcaaat cttagtttaa agaaaaaaaa aatagatggc  18120
agctcttatt gtccaaggtg gctttgctga gggagagagg ctccagagat gggtcccagg  18180
```

```
aagaccacag cccacccatc cctcacccag gatttatctt cctccagaaa aacaggtctt  18240
gcctcgctgg ctcaaagctg tctacagagt agcctcaaag ggcacttcta ggagttcctg  18300
ctgtggcata gtgggttaag aatctgactg caggagttcc catcatggct cagtggttaa  18360
cgaatccaac taagaaccat gaggttgcgg gttcaatccc tggcctcgct cagcgggtta  18420
aggatccagc gttgccgtga gctgtggtgt aggtcacaga caaggcttgg atcctgtgtt  18480
gctgtggccg tggtttaggc cggcgtctac agctctgatt cgacacctag cctgggaacc  18540
tccatatgcc gcacctagaa aaggcaaaaa gccaaaaaaa aaaaaaaaaa aaaaaaagaa  18600
aagaaagaaa gaaaggcaga aaaagaatct gactgccgtg gcttgggtcg ctgtagatgc  18660
acaggtatga tccctggccc agcacagtgg gttaaaagat gtggtgttgc cgcaactgca  18720
gctcaggttg cacctgtggc ttggattcaa tccctgaccc aggaatttcc ttctttcttt  18780
ctttctttct tccttccttc gtggaatttc tatatgccat gggtgtggcc attaaaaaaa  18840
aaaaaaaaaa aggtacttct taagctaaca aaagcagtga gaccatccta caagacggga  18900
tcagtaaata tatgacgact ctagcagacc gcctccattc attcaacaaa tacctgctga  18960
gcatgcgtta catgtcaagt gccagacata cagtgttgac tgaaacagac accatgtgtc  19020
tgtggtgtag agaagctggc agggagggtg gaccctattt tgataaacac atcattatag  19080
gacttcaaaa ctccaagaaa gcataggagc acttaacagg aagacctcga aggctcccca  19140
ggggagggga tgatgtttta gctgagttct gaaggataca taggaggccc agtgaagagg  19200
gattagcaag agtgtgccta acagagagaa aaacatgcaa aggccccaag aaaggaaggt  19260
cgcatattta tttatttatt catttatctt ttggggttgc acctgcggca tgtggaagtt  19320
cccaggctag ggttgaattg ggagctacag ctgctagcct acaccacagc cacagcaatg  19380
ccagatctga gctgtgtctg tgacctacac cacaactcac ggcaatgccg gatccttaac  19440
tcactgagtg agtccaggga tggaacctgc atcctcatgg atactagtca gattcgtttc  19500
cactgcgcca catcggaaac gcctgccctc atctcttaaa acagaaacaa aaaaccacta  19560
accactaata tttgtttgag attctgccaa agccccgatc tcctccctct gccttctgcc  19620
ccagctggga gtccacatct cctggtagga atgaaataca tgccttccta ccacctatgg  19680
tttcccctct aagctcagta cccatggacc cagctctaaa gtcccttgtt tctaaatctg  19740
tctattgatc tgataatatt cataatagct aatagttggc tggggacctt tctaagcaac  19800
tgacatgtat tagctcatta aattctaata acagtcaatg aaggaggttc tattcctcct  19860
cagagggaca gaggcaataa attattttgc ccaaggtcat actgctaagg gaagaaacag  19920
tatttgaacc tggggaatct gacttcagat cctacaagag ggggaaggga aaggggcaag  19980
aggaggggga gggcccgtgc cacccagcac tcaggagccc caccctcctg ccgaggcact  20040
cagggcatca atttatagat ttggatttgc cacctcgtcc catcttttta gtaacccctc  20100
cctcttcctc atctcaccct cctttcccag aagccttcaa cacctcaggt cacagcaaca  20160
accaccctga agtgtacggc atttaacaca tattcatcct tcaaggcaca gctcggatgc  20220
catctcttct gagccttctt tggtatgaac ctagcacaat gcctggcata cagtaggtgc  20280
tcaataaata tttctaaatg agggagttcc cgtcgtggcg cagtgcttaa cgaatctgac  20340
taggaaccat gaggttgcag gttcggtccc tgcccttgct cagtgggtta acgatctggc  20400
gttgccgtga gctgtggtga aggttgcaga cgtggctcag atcctgcgtt gctgtggctc  20460
tggcataggc tggtggctgc ggctccaatt agacccctag cctgggaacc tccatatgcc  20520
```

tcgggagcag cccaagaagt agcaaaaaga cccccccccca aaaaaataaa tgcaaaacat 20580
agatccatct ccaagccaaa cataatcttg ccctccctga actctcacgt tcctttgctc 20640
tctctctctg acatcctcct tctagcctgt gttgttgggc tttcatgggt acctctgcct 20700
gctccatcta cagcataacc ccttgagggt agggattctc cttggcgcac actgtacccc 20760
tcgcagcatt tggcatgaac aaccagctcc agaaggagcc ccagatgatg aatcagaaga 20820
tctgagttct aattagaagt tagacataag ttcactgtta aggcatttca cctacttgtc 20880
catcgcctga acaatggaaa ccttgactaa aggaagggtt acccaggtta cccaagtcag 20940
acagccctgg acctaaatct tcctaaaaat gtgaccttga acgttcacat ttaatattgt 21000
ggaaactcag tattcctcat ctagaaatgt ggactaacac tgaccttcca gggctgtttt 21060
aaaaacagga gggaatgaac agtggagttc ctggcacaag caaacactca ataactagta 21120
gccgctaaca tcaaaatcac catcaccatc attactttat tatagctctt aaagtttctt 21180
ccacctctaa aattctaagc ttgtggctca gtggcttaag aacccaacta gcatccatga 21240
gaatgtgggt tcaattcctg gcctcactca gtggattaag gatccagtgt ttgccatgag 21300
ctgtggtgta ggtcacagac ggggcttgga tctggcgtgg ctatggctgt ggtgtaggca 21360
gctctgattc cacccctagc ccaggcattt ccataggcca caggtctggc cctaaaaaga 21420
aaaaataaat aaataaaatt ctaagatttt tttttttttt tcatctagcc tttaaccaaa 21480
tgctgtcctg gatgacattc ttaaacagct gtatgtgttt gatggagtta ttttgtaaat 21540
ctcttttttt ttttttttca agggccttac ctacagcaca tggaagttcc caggctaggg 21600
gtcaaatcag agctgaagct gccagcctac accacagcca cagcaacacc ggatacctga 21660
cccactgagc gaggccaggg atcgaacctg aatcctcatg gatactagtt ggatttgtta 21720
ccactaagcc acaacaggaa ctcctgtaat cctctttagc tacagtgcta cccacctgtc 21780
taaggttagt gccctcagct cacctcagac caattcacaa ggtggcaaag aatctcctgc 21840
cttttaaacc ccttgcagat gttcaaatag attcctcaca ttgaagaatg atgtggctgc 21900
agtctgggtg ccagactacg gccctgaaga gcagccagaa tctgctccag ttactgtgaa 21960
gagagagtgt gcccagcact gcaaaacaac cctctttatg ggaggccagc accaatatgc 22020
acttctgggc ctttggcttc tgtgttttaa ttttgtgaag tacccaaaat atggaagtat 22080
aactctggct gcaattcaaa acaatcaaga gttcagagct tgaaggttgc ctacacaagc 22140
atctcaactc aggtcaggaa ccccatgggg aacttgctct tctgttagat tctttcagcc 22200
cctagaattt tttctttttc tttttctttt ttctttgtag ggccaaacct gtggcatacg 22260
gaaattccca ggctaggggt agaatccgag ctacagctgc cagcttacac cacagccata 22320
gcaactccag atcctagcca tgtctgcaat ctacaccaca gctcatggca acactggatc 22380
cttaacccac tgagcgaggc gcgggattga acccgaaatc tcctagttcc tagttggatt 22440
catttcccct gcaccacaac gggaactcct agaactcttc cttctatttg ccaaaatctc 22500
ctgtcctatg ctgccctccg gacagatggt gatagtggtg gtggtgatgg cagccagcgc 22560
ttactaagta cgttgccctt agtgctttat tcacaactta ttttatccaa caaccctatg 22620
aagcaggtac tactatcatc cccattttta aagataggga aacttgccca aagtcacaga 22680
ggagggaagt ggtggcacag gaccaacccc aggcagccta gctccagcct ccactgagaa 22740
tatctcctca gtcctcaagt acctaaggga gccccagggt ctctgcatcc aacgctgtca 22800
tcttttcttc agaggaagta ccacagtttc ctcaattcga aaaggttggt ttgtagacat 22860
ttgttcactc tctagctcgt cttgtttttc ttaaaatgag ttcttcagaa tgagagggaa 22920

```
taactgttcc agaagtggtt agatctatga agcatccaaa ggaatgacag cttcttattc  22980
tagggaatcc acctcctcct tttttttttt tttttttttt ttttttggct gcacctgcag  23040
catgcagaaa ttcctgggcc agggatcaaa gccaagccat agcagtcacc tgagctgctg  23100
tagggacaag actgaattct tgaacccgct gagctaagag agaactccct agagaatcct  23160
ccttctactg atggacctga agatgcagtt cctttctaag tggccaaaat ggtcctgctg  23220
gctcatcaag tcttagaatt taagagacat tctaacgtta atccaggcca tcatcctgaa  23280
cttgaggggc tactaaaaca ctacccatca aaatatcaat ggtgatgaca tagctctcca  23340
ggccaagttg ttttttggtt ttttgtttgt ttgttgtctt ttttcctttt agggccacac  23400
ctgtggcata tggaggttcc cagactaggg gtccaagtgg agctgtagct gccggcctac  23460
accaaagcca cagcaacacc agatccaagc tgcgtctgca atctacacca cagcttactt  23520
caacacccga tccttaagcc actgagcaag gccagggatt gaacccacaa cctcggggtt  23580
cctagtcaga ttcattttcc gctgcaccac cacgggaatg ccttcaggcc aagttgtaag  23640
gtggcctttt tgaaagaaag tccaagcggt atcaatacct cttaagtcaa agccatcatg  23700
cattttggta gctgcttgca gacatttctt tctgtcagaa gcgtctccag ctggaatctc  23760
caaggcatcg tagtttccaa aagcaaagaa gcagcgtcaa atatttgggg tgaatccact  23820
gatgaatttg aaaactcaga aatgtttaat tcattttgct ttccagagtt aaaaaaaaaa  23880
gacaaaacac ccaaaagttt agccaggcac aaatgaatca ccagcgactc agtgtgtttt  23940
gcagcaaaag tcaacaactt gagttgttcc tttaaactct gcaaatattt taggattgca  24000
aaaatcaggg tgtatttctc atggaattcc tgtctgaaag ttctcaaggt aacttccata  24060
tctggtcata taaataattt aatattatat cttggtctta acatgacctt attatttctg  24120
gctctagcct acccagaact gcagaggtat aaaaatcagg acaatggcaa catggcagga  24180
aggaagataa ttaattagct ggaaggtact tgaagatcta atgactttaa agacggtatt  24240
taagggctca gggatacagg aagggtagaa tattttcttt ctttctttgc tttttagggc  24300
cgcaagtgtg ggatatggaa gttcccaggc taggggtcaa actggagctg aagccaccag  24360
cctacgccac agccacagca atgccagatc cgagctgcat ctgcaaccta caccacaggt  24420
cacggcaatg ccggatcctt aagccaaaga gcaaggccag ggatcaaacc cacctcctct  24480
tggatcctaa ttgggtttgc tgcccctgag ccacaacggc aactctctgg aatgctttct  24540
ttacggtgtc agtgaatcct acttttaatg caagctggtg acttggctga taactaggag  24600
attagaggag actttcatca acatcatttc atcatgtttc ataattacct gttgatgtat  24660
tcccaaaaca caaccattac agttgagaca agcagcattg acagaaccac tcttcctttg  24720
acattcatta ttttctcctg ggaaaagaaa aggagaaggg aaaattagat taaatacacc  24780
cagagtggaa tatggttttt taagaagtgc ttataccaat atcttttcta aaaggaaaag  24840
ttgatgaata gtcaacgagc gctaaggagt gcgttctacc ttaatttgca taggcctaca  24900
ctggcaaatt agccaagtca atgaactgac agggccgtct gggttgggaa ggatactaag  24960
gccattttga ggctcaaagg ggaagcatcc tgactgatcc caaggtccac cgagatgtgg  25020
gagagtgacg ggtttagtta atggtcccta agggctccag ccgcccccaa ctcagatgcc  25080
ccacctcgca tcacagacta gaggaagcat ccgtttccta ggtctactgt ccctgatata  25140
ctgactatgt accttatcct caaagaaaaa tataccctgg tcctttattt aatttcattt  25200
aaattttagg gccacactca cagcatatag agattcccag gctaggggtc gaatcagagc  25260
```

```
tgtagccact agcctatgcc acagccacag ccacactaag tccacgcctt gtctgcgaac  25320
tacaccacaa ctcacggaca gcaacgccag atccttaacc cactgattga ggccagggat  25380
caaaccttcg tcctcatgga tgctagtcag attcatttca gctgagccac aatgggaact  25440
ctcaccctgg tcctttataa tctaggctct gccacttccc acccagcttt tccccaatgc  25500
acccacacaa gtggcaaaca gtcggtacat tcgtatttct tgatcgctgc atgaaattgt  25560
agttgaagag ggaagggatg ctgggtggaa taacaggttg cggagtactt taatttgggt  25620
ggagatagaa agatatttat ttcaaatgga aaggacaaga aaagtgtggc agctagccac  25680
atatcagcaa tactcataaa caaagaatgt aacaaaagat aaagtagggc attacataat  25740
aacaaaggga tcaataccag aggaagacat aacattggtt aacatatatg cacacgatat  25800
cagagcacct acatctagaa cgcaaatatt aacagacata aaaggaaaac ttgcacaatt  25860
acataatact agtagaggac tgattcgcaa cattttgtgg gtcttgtgat tttttttcttt  25920
ttaggtctat ttgtcttttt agggccgctc ccgcggcata tggaggttcc caggctaggg  25980
gtcgaatcgg agctgtagcc accggcctac accagagcca cagcaacgcg ggatccaagc  26040
ctcattggct acctacacca cagctcacgg caacaccgga tccttaaccc actgagcaag  26100
ggcaggaatt gaacctgcaa cctcatggtt cctagtcgga ttcgtttcca ctgtgccgtg  26160
acgggaacgc caacattttg tgttttagat gtcatagttt acatcttcac agctatcctt  26220
caactatata atttagtctt ttaacatctg tactagttta tttaagtgtt tgatgcaaca  26280
ccttcactat atatttgact tttctagtct tattatttcc tttctgtatt ttctcatatc  26340
ttgttacagt tttttctttt tcatttaatg aagacacaaa catttcttgc aagtcagtgt  26400
agtagttgga aactcagttt ttccttctgg gaaactcttt agtcaccctt caatttgggg  26460
agatgacttt agagcttccc aagggatgaa gataggatgg gaaaggatga caagggccgt  26520
gagaagggat gagaatattt tggaaacagc atctatacca ggcagacaag agaaagagct  26580
gctcgtgttt gaaaaaaaca aaagcaaaaa acctggacaa gaaaaaaata gtgactgaca  26640
ctgtccccct tgagtggctg gtgctaggca gtcagaaggg gggcagaggc agtcagaacc  26700
tggaaaggta tggaaagtag ggtggggaat cccaaaaagc atctaaagct ggagaatccc  26760
ctgatccaac ttcacctaga gagacccatc tgggtgctga gtgtggagaa tggagaaaag  26820
gacaagggca gaccgttctc atgaccataa agaggaggtg gcctggctca aagggtggct  26880
tgattcaaaa tatactttgg gagttcccgt cgtggcgcag tggttaacga atccgactag  26940
gaaccatgag gttgcgggtt cggtccctgc ccttgctcag tgggttaagg atccagcgtt  27000
gccgtgagct gtggtgtagg ttgcagacgc ggctcggatc ccgcgttgct gtggctctgg  27060
cgtaggccgg tggctacagc tccgattcaa ctcctagcct gggaacctcc atatgccgcg  27120
ggagcggccc aagtaatagc aacaacaaca acaacaacaa caacaaaaaa aaaaaagaca  27180
aaagacaaaa agacaaagaa aaataaaata tatactttga caaataccat atgatatcac  27240
ttataactgg aatctaatat ccagcacaaa tgaccatctc cacagaaaag aaaatcatgg  27300
acttggagaa tagacttgtg gctgcccgac aggagaggga gggagtggga gggatcggga  27360
gcttggggtt atcagataca acttagattt acaaggagat cctgctgagt agcattgaga  27420
actatgtcta gatactcata ttgcaacgga acaaagggtg gggggaaaat atacatgtaa  27480
gaataacttg atccccatgc tgtacagcgg gaaaaaatta aaaaaaaata tatatatata  27540
tactttggag agagaattga taggacgtgg ttggtaattt tgttatcaga gatgagacaa  27600
ggaagaccca agatttctgc ttaagcaggg gggttgtagt attttctcag atggctggaa  27660
```

ggaggaacag gcttggagga taataatcat gaattccctt ttggacgtgt gaatgtcggg 27720
gagtgtgcga atacctaaaa ggggacaggg agacaagtgg acattcaagt ctaaagttca 27780
tcagagagat gtaggcagac catgcaatcg gagaagttgt tcatggacca aggaacgtat 27840
cggatctgac gtgaagggaa cgaatttgat tacccaggag agaatgcaga gagagaaaga 27900
ggaagaggag gatgctgggc tgaagcttta gaggtaggat agaggagggc ccagaaggag 27960
aggaccagaa ggtagcagag acagaagagt ggacacctgg gagccaatgt cactgccttt 28020
gtgaagccac ttcccacccc caccctgacc acggctgaag cccttttctc tcctccggcc 28080
cccatccctc tattcctttg ctgtacacat cgccctggga gtcggctcac cggataagac 28140
ctgcattttg ctctgcctcc tctacctgct tgtttgagct tcctgagggc aggagggatg 28200
acttcttcgt caccoctgaa ttcccagtgc cccacagaga gcagagaagg ccgtcaataa 28260
ataatgagtg gtttgagctt cctgagggca ggagggatga cttcttgatc accoctgaat 28320
tcccagtgcc ccacagagag cagagaaggc cgtcaataaa taatgtgtgg gagttcccgt 28380
tgtggctctg tggttaacga atctgactag gaaacatgag gttgtgggtt ccatccctgg 28440
ccttgctcag tggcttaagg atccggcgtt gccgtgagct gtggtgtagg ttgcagacgc 28500
ggctcagatc ccgtgtggct ctggctctgg cgtaggcctg cagctacggc tccaattaga 28560
cccttagcct gggaacctcc atatgccgca ggactggccc aagaaatggc aaaaagacaa 28620
aaaaaaaaaa aaaaaaaaaa aaatgacgtg tgaatgaaat gagaatggca ctgagatgtg 28680
tcctttcagg ggacgggtta ttctccaaat atttgcagag agggttctga ggtgactcca 28740
ggcttagatc tcaggtgctc catcacctct gttgtgaaat ccagttaaag aagagaaagt 28800
atgggattat cagccatgtc actctattcc ttcttgcttg gaaagtgagc tctgtttgga 28860
aacctctgat tcaatcgcca cctttcggat acaatcatga taggtggtgt tccagagacg 28920
gtgagaagat ggggagatgg agcttctttc ctgtgagcac ctcaggtcct ggcacaaaca 28980
gcccggggcc cagggcaaag ttacgaaatg cacggggcta catgcagctc ggcccagatg 29040
ctggaaaaag ccacttgact cctacaccaa cagcattagc actgagtgcg aggaaaggcc 29100
tgggtttggg agcagacaga tcggggtgga gactgtggcc actgtggcca tgcctctctg 29160
ccgttgtctt cactcccaga gaagtgtggg tggtgagaga gcttgggaag gaggtggggt 29220
ctggagacac ccacagactg ggtaaccctg aacatggagc agtttctcag accctcatcc 29280
aactccaagc tctgaaaacc aaaagcctgt ttataattca gttggcatcc aggccctgac 29340
acgaggctat ttataatctt tatcacttag tgagactgtt taaacatttc tttgcataaa 29400
tattgatgta cattgttatg tgctgttgct gcactggagg cgttacataa tataggataa 29460
atattctgca tttgaaaaat tctaaattcc aacatatctg gccttaggca ttcaggaaag 29520
ggatggtgga cctctaattg atcacattag atgggtctcc tcatctttaa aatgggaatt 29580
aaaatggtga tgactgcaag agatggtgtc cataaaatat ttagcatcat gcccagcatc 29640
atataaaagc tcaaaaactg ctagtttgta ttactggtat ccataaaaca ggctgttggg 29700
aggatccagt gaagacagca cagcgcctgg tacttagcaa gagctcaaaa cgtatcggag 29760
ggaaaggaat aagcattttg gaataagaat gtgttaaaca ataaagtaca aattgatgca 29820
aattagggcc tctaaaggtt tatccatctg ttctatgctg cagactgact aaaagctcct 29880
gggaaatgcc acgcaacttt gattttcttt gatcaagccc aggccatcca aagccttgtc 29940
atccccacct gctgaggatc aaaccctgtg taagaaatgc gaaagagaga aacacaaact 30000

```
cctggcagag aacggatcag ggagaagctg gtataaaatc agacacacct cctaatcctt  30060
tctccaaagg caagtgtttt tctgtttgtt ttggtttcag ggtttgtttg ggttttttg  30120
ttttttggtt tcttttggtc tttttaaggc cacactggga gttcccctcc tagctcagag  30180
gttaacaaac ctgacttgta tctgtgacca ttcaggttcg atccctggac ccgctcaatg  30240
ggttaaggat ccagtgttgc catggctgtg gtgtaggtcg cagatgcggc ttggatccag  30300
cattgctgtt gctgtggcgt aggctggtaa ctacagctct gattcaaccc ctagcctggg  30360
aacctccata tgccaagcat gtggcactta aaagattaaa aaaaaaaaaa attaaggcca  30420
cacccaaggc atatggaagt tcccaggtta gaggtcaaac tggagctata gcttctggcc  30480
tatgccacag ccacagcaac gccagattca agctgagtct gtgacctcca ccacaactca  30540
tcacaacatc agatccttaa tccgctgagt agggccaggg attgaaccct tgtcctcacg  30600
gatactagta gggctcatta ccactgagcc acaatgggaa ctcctttgtt tcatttgttt  30660
ttgatttttt tttttttttt tttttggtct tttctagggc cgcatccacg gcttatggag  30720
gttcccaggc aacgccgcat ccttaactca ctgaacgagg ccagggatca aacccgccac  30780
atcacggttc ctagtcggat tcgttaacca ctgagccatg acaggaactc ctgttttttt  30840
aatttcagaa attagcatca gagacaactc ttgaagcccc ccccccccttt tcttttcctc  30900
tggaccgtaa acatggcttg aatctgctta cttttcgctg tggccaggca tcactcttag  30960
agacttacag ttggaagcca cccaaatgag ccaatattgc ctccttttga aaagcactgg  31020
gaaggggtat atgcaagctt tctggaatct ggaaccctag tgtctcagga aagaagggtt  31080
gccagaatgg ccaaagggtt tttaaaacat tttttttttt tctctggatt aaaatgaggc  31140
atttggcagc ccatgtggtc taaagccctt cacggatgtg tttgtcacag aatttctaa  31200
ctctctaatt ctcaagattg gtggttgact atcttaccca ccaaatagga aaagtggggg  31260
ttgcttctac atttctcatg gaagagggag agcacaggat tagagcctag agagcactag  31320
caccctgtct tataagggag agtgtaacca cctcagcacc acctgggccc cagccctcag  31380
aggatcaggt gaacccagcg ggcccagttc cacctgagcc ctcccaccat cccacaggcc  31440
ctcctgccaa ggcgtttgcc atttctctct gctcctgggc cactcccaca actcagcccc  31500
tgcagcggtt tccaaaagaa accacttgca cccccactcc cgggcctcgt gcagactgtg  31560
ctaaaaccca gtgcatttcc caaggcaggg ccacgctgga aagcctgtca tttctccacc  31620
ttcctcctcc tcctcctcct cctcttcggc ttctccatcc ctggggtatc agactcttcc  31680
ccaaggccca taaattaatc cttcctgacc cacccctaac ttgtcccaca cagaacggta  31740
cacacacccc ctccacttca gagaagctca tggtttcacc gcaactggtc caagtcaagg  31800
ttttccttcc agacagagtt ccactctgaa aggaattcta gtggccctgt ttttctccac  31860
ctcgtgtcag gggaaaggt gagcacctca gctgaatcac agagctctca gaagccctgg  31920
aaaagccatt atcttgagag agcagcgagc aagcagtgac agaggaaacc aaagcttcca  31980
gcagactaaa gaatcttcct ctctgcctgt gactcttgcc ctgcccctgg aacccatcct  32040
gccctgctag ctccacagga ccctggcaag ggtcaagaaa gtcaggtagt gataagtgca  32100
gcaaatgaaa cacagtgcgg gggagggagc caaggtgggg aagccgcagg aactgactgg  32160
gtgttactca ccctggacaa aaacctccta tttttaggcc taacatttag atccagcatt  32220
ccaggcagaa attaggccgg tgctgggact ggaatctgca gccctacatg cacttgccct  32280
gggcaagtcc tctggctctg agcctctact tacacagacc aaacggagct tcaaacaccc  32340
tcctccaggg ctcttgaaag gacaaaagga gaccccgtct atgaagcatg ttgtgcctga  32400
```

tgctcagtaa atgctccaca aatgcagcca gaacaagggc gatgcttttt acggggagag 32460
attcagaaat gtgtggctct gacggccgag ctgtggctct gtctgagagg agtctgggcc 32520
ctccagggca gcaccacaca gaagggtcca gggcgagccc cccacgctgt tgtgactgtt 32580
gttggggcca gctcagggtc cccaagcgca tctcgtttgc ctctatcgcc tggcgcgcat 32640
gttgggcagg gaaggaaagt caggctccag ggtcacccca gcacccacac agagcgggtt 32700
tgtgaaccac acgcagcttt ctctggcctc agtctccccg tcctttgaaa catgtcctgt 32760
gggcttaact tccctgaatg agccaagacc tgtatgagaa ggcagccaca gagctggaag 32820
gctcctttta tgaggacagg ttcactggag ctcaacttgc tgcagtggcc acagattcct 32880
agaagtggtg atcaaaagat aggattgcca gagtttccgt catgacgcaa cggaaatgaa 32940
tctgactagg aaccatgagg ttgcgggttc gatccctggc ctcgctcagt gggttaagga 33000
tccggcattg ccatgagctg tggtgtaggt cacagacgcg gcttggatcc tgtgttgctg 33060
tggctgtggt gtaggctggc agctgtagct ccgatttgac ccctagccag gaaacttcta 33120
tatgcagcgg gtacggccct aaaaagcaaa aaataaaaaa ataaaaataa aaaaagagat 33180
aggattgccc acaaaatgtg ttgagccctc aggccacttc acccagaagc ctccgggtca 33240
ggcccccagg caggcctggg gtgtggagtg ggcaaggccc aaatgcttcc tccaggtgag 33300
gtgctgcccc tgcctggggg aatcgttcca gcctgggtgc ctgtcctggg gctgcaggtg 33360
gagcccaggt actgaccctg ctccccgcac ctacctgggt cctaggagca acctgcccca 33420
tccaggtaga ccttgctgag ctccttggag cctctcactt tgatcccaag gagaaggagc 33480
tgaacatgat gctacttggc tccctgctca caggtcacga tccagacctc acaatcacct 33540
ggtggtgcac cccccactcc agccaggatc aaagagctga attctccagg actctggctg 33600
gacccacctg agcaagaaac tgccaaaaga tggggcgttt gaaggacctg gagcacctac 33660
acaccccaag ctttcctcat ggtttcagtt acaagatctg tgtttggaga cctccccttg 33720
ggggcaggga ccatggaaaa gttccagctg caagcagacc agctgggagt ggaaatcatc 33780
tcctcgggct gcaccatcac ggccctggag gtcaaagaca ggcaaggcag agcctcagat 33840
gtggtgcttg gctttgctga attggaaggg tacctccaaa agcatcccta ctttggagca 33900
gtggttggca gggtggcaaa gcaaattgcc aaaggaacat cacgttggat gggaaggagt 33960
ataagctggc caacagcctg cacagaggag tcagaggatt tgataaggtc ctctggaccc 34020
cttgggtgct ctcaaatggc atcaagttct cgagggtcag tccagatggt gagttaaaag 34080
tctgggtgac atacacgcta gatggcaggg agctcatggt caactctcaa gcacaggcca 34140
gtcggaccgc cccagtcaat ctgaccagcc attcttattt caacctcgtg ggccagggtt 34200
ccccgaatat atatgaccat gaagtcacta tagaagctga tgcttttttg cctgcagatg 34260
aaaacctaat ccctacagga gaagttgctc caatgcaagg agctgcattt gatctgagga 34320
aaccagcaga gcttggaaaa cacctgcagg agttccacat caatggcttt gaccacacgt 34380
tccgtctgaa gggatctaaa gaaaagcaat ttcgtgtacg ggtccatcat gctggaagcg 34440
ggagggtact ggaagtgtat accacccagc ctgggatcca gttttacacg ggcaacttcc 34500
tgggtggcac gctgaaaggc cagactggag cagtctgtcc caagcactct ggtttctgcc 34560
tcgagaccca gaactggccc gatacagtca atcagcccca cttcccgtct gtgagttcaa 34620
acacacccct tggttctagt tttctgtggc ctaaggaaat gtaaagatat gacctgttcc 34680
agggtcaggc tggaagcccc ttcaggaacc tgtctcctac gcagagataa gatgaagatt 34740
tagaggtttt aaaagtgatc ctgtgtatta ctcagccatt aaaaggaaag aaagaacggc 34800
atttttagca acagggatgg acctagaaat tatcatgcta agtgaagtca gtcagacaat 34860
gagacaccaa catcaaatgc tatcacttac atgtggaatc tgaaaaaagg acacaatgaa 34920
cttctttgca gaacagatac tgactcagag actttgaaaa acgtatgctt tccaaatgag 34980
acaggttgag ggtgggggg atgcactggg gttttgggat gatcatgcta taaaattgca 35040
ttgggatgac tgttgtacat ctataaatgt agtaaaactc attaagtaat aaagaaaaga 35100
atgtaaaaaa attaagaaac agaaaaaaaa gtgatcctgt gaattaaaat tacacaaatg 35160
gtagttgtca tgataatctg aatattgatt tctttcacaa tgactggctc caggccaagt 35220
ctaatggtca gctctattct ctgtgtagtg aaaaagaccc aaccatcaat gtcatcttct 35280
aagccctgac cctaatccag aagtggtacc cagatccttg tgttggctct gtctctccac 35340
tctgcttctt ttcactcctt ctttctttga tcctactcat tcctttttcc cttcctcttc 35400
tacctcatac caccttgatc tgtgcagcac tttggagttt tcagaggtca ctgagctcat 35460
tcaacctggt ggtagaggga cctctctgcc tcagtaaaag aatagatgat gaagtgagcc 35520
acctgagaat taggggaggt aaatgaccca cctaaaggcg cacagccagg aaaaatttag 35580
cctggattca agatcaggtc atgcaaattc aagtccttct ttgcctccac ttcagtcttc 35640
cagagcattc ctggagtcat taatgggaaa aggggggtc tgacccttac tctgttaaag 35700
ccagaccttc tttccagata tcacttttat aagaagccct agtcagagtt taaatgtatc 35760
tctgagcctt ataaatagtg tgacttaaaa tacaagatct aaatatccag aaaaaaaaaa 35820
tctgtgaatt tgattctccg cctttggggt tactaagaaa gcccagccta gccaagacat 35880
gggaaggaag ccgctggaga caagagctgt gtgagttcga ggagagggcc ttgctgggac 35940
tgcacgctgc accgagagca gactgtattt ggtatacgag gcggagttcc ctcctctcct 36000
aaacaattga atcacgagtg atgggtttgt gttgatggtt tttaaagaaa tgttatctta 36060
tactcctcta cactaataat cagttgaaat aaaaccaaaa tgtgcaccct cagaaaaaaa 36120
aaaaaagaat aaaaagaaac tgccaaaaga ctgacagcac taataacaag ttatgaagct 36180
gaaagaagct tctcaaaact cccaggaata aaaagcaacc actgattaac catgctagag 36240
gcagaactga tttgtcttcc tttttgtctc tcttaaaaat gatactacag gagttcccgt 36300
catggcacag cggaaacaaa tccaactagg aaccatgagg ttgcgagttc aatccctagc 36360
ctcgctcagt gggttaagga gccagggttg ctgtgatcta tggtaggtca cagacacagc 36420
tcagatctgg cgttgctatg gctgtggcgt aggctggcag ctacaggtct gattagaccc 36480
ctagcctggg aacctccata tgccatgggt gtggtcctaa aaagacaaaa agaaataaaa 36540
atgatactac aaaaatcatc agataaagag atagttcaaa gtatgcagcc aaaatatgag 36600
aggtacatca gacagctgag taatactaat tatttttata ttattttcac gtgttatggt 36660
tgtttttctg aatttggtcc tatttagagt attggtcagt ctgtgttagc tgttgggatg 36720
gcacctcata ttctaaatgc agtcagcctt ctgtatccat gggtcttaca tccacaaatt 36780
caactaacca cggatggaaa atactccaaa acatcacatt ccagaaagtt ccaaaaagca 36840
aaacttaaat ttgctgcata caggcaacta tttgcgtggc atttacattg tattaggaat 36900
tataagtaat tgcaaggtga tttaaagtat atgggagggg agttcctccg tgggctagct 36960
ggttaaggat ccagtgttgt cactgctgtg gcaagggttc gatccctggc ccatcaactt 37020
ctgtatgcca tgggcaccgc caaaaaataa ataaataaaa tatatgggag gctgtgggtt 37080
atgtgcaaat acgatgccct tttgtgtaaa ggacttgagc gtcctgggat ctggtatccg 37140
tggggtcctg gaaccaatcc cctgtggata cccaaagacg actgcattca atccccagcc 37200
aaatcatgtg tctgcaaatt tgtgttccct tttcttaaag caggccctcg atattgaata 37260
agcttcctgc agcacttgga tgccccccag ctgaaccaga ccaggcctca ggctaaacgc 37320
tttaccagag gtttctcaga taagtctcac aacgtcctgt gaagtcattc tagtgttatc 37380
tccactttac agacatgcaa atggaagctc agaaaggtga agtgacttgc ccagtgtgtc 37440
acacagcata aagtgatgga gctgatattc aggtccagag agctggcctc agggcccacc 37500
cttttaacta ttctcagtaa acatgaagac tcacccatgg actaatcacc cagggatctt 37560
tggcacatcc tctcattttg cctttcacga tgatcactta gcaattgacc caaagctagc 37620
caatcatggg ctagactcag caggggccag cttctcctcg gcccagctgg cgagcattgg 37680
ctcaactcct ctgccatttc caggagcctc ctgcgtgcct ggtgtgagcc ttccccatgc 37740
acgccatcct attcacccct catcatggtc agtgcggggg ctttttagct gaggagaccg 37800
agctttagca aaagctgaga tcgctgggct cccccacaag gggggcgctg agtttgaaaa 37860
gcagaccctc tgcctcccag gcccagctct tggccggggg atggtgctgg ggggaaggag 37920
ggagagtcct gctttatcta aaacctcttt aaattggctt gcattacagg gaaatgctcc 37980
ctgttggaag aaacatggta taatttgggg ggcaggggtg gggggggagt agtgcacgga 38040
aggctgtttc cagttatgtt tttcattata agggtcaaag caaacacaga cgcaggaagc 38100
taagagacaa gcctcagact aaacatacga ccagctgtcg ctccagccat cacagacctg 38160
ttctcggagg gacatcttgt aggccccttt cttgaatccc cttcaaaaat ctgaagcctg 38220
gatccagcca gcttctcctt gctgcctggc tcagaaatca tggtgcaaga gtttttccaa 38280
gagaaatagg gcgaggtaca tgaaggatcg gtgctgccct gagagggcac tatgtccgcc 38340
cccagcacag gtcccgggcc tgagactcgt cctcctggcc ccacaatggc actgtgtggc 38400
ccacacagag aaccccaggc tgtagccaca ccccgtgagg tcctgccggg cagccaacga 38460
aagcagaacc aacagtgact gagccagcat cctgccagct cccactccta gatccgatgc 38520
cggggactgg aggactttgt cttctttcag aacaactggg gggagcagca agaagtcagg 38580
gggagagggg ggctcctctc tccacgctgc agccagctca tgatacccac ccccccggtg 38640
accccagcaa agcggaggca aatcatttca acgtttcacg tacctcatcc tctgcttctc 38700
tccccccaga gtaaaaggcg aagcaagttc tagtgagctc tgctctgcag aaggaggcag 38760
ggctgggagg aagggaaggt gctgcgttcc aactcctgtc aaaagaataa acagcggttt 38820
cacgaagagg agcgcagacg gatcccacag cagccagggg ccttgttcct ccttgctcgc 38880
cctgggaagt gggctgttta tcaggcctgt tgactcagag ctgcatgcca aggcagagac 38940
gtctctctcc ggcccaggat cggcccggcc tccttcacta agcgaaacta caggtccaaa 39000
ctaggcctgg tggtggagga gggacagcca ccacccttgg gagagacaca caggccgccc 39060
acatcaccca ctcctcggcg aaaatgagaa ccattctgaa cccaaaccac cccaaatgac 39120
aactagcagg gacagccaat ggagaattta aaaagaaggg ggcagaaaat ggagaggggt 39180
ggctaaagga gagcatcctc aaaactcccg ttgaaatgct accttccgag cctcttgttc 39240
gcatccttta ggcttcagaa gttgttctgt ttgaacacta tttttataga atgttctgag 39300
atctcctgca tggcaagcca agctataaga acttcaaaag gtcactgagg cccaacccaa 39360
ctctttggct gaataatgct taaccctccc cacacccacc tcctgctccc aaaatagaat 39420
ttcctagctg gaagagacct cacagcagtg gatttgtaaa tgtcgcaaca gctaaagctt 39480

-continued

```
taaaaaaaaa aaaaaaaaaa atgaagtcat tctcagaacc ccactatgta aaacagagga  39540
cacagggggc tttggctgaa ggagggaaat gaagtaagta ggggctcaga gccccccccac  39600
ccattcttcc caagtggccc cagacacttc ctgggagtag agcctagaaa ccccagacta  39660
aggagaaggg gccgaaacct gacagaaagg agccaagaac tgccccctca gcttccagcg  39720
gatggatgcc taatttagct tctcactcct gttctgggga agaaattcac cgccccctcc  39780
tctggggcat gagctagttg accacagtct tcaagatctg cttaataaac tactgaaatc  39840
ctccctgctg gcatctacta aagctgaacc aaccacacct catgttccag tcattccgcc  39900
ccagattaat acctgaaagc aagtgcattt aagttcaaac agagacgtga cctgggacca  39960
aaagctggaa aaaccccaag gcccatcatc agccagatca ggtgtggtcc aggtgagggt  40020
cacacacatc cgtgagaagg aaccagccac agctgctgac atcaacaggg taaatctcac  40080
acatggtact gagtcaaagc agccctggat gcttgcattt atttaacgtt caaaaataga  40140
caaaaccggg agttcccgtc gtggcgcagt ggttaacgaa tccgactaag aaccatgagg  40200
ttgcgggttc ggtccctggc cttgctcagt gggttaaggg atctggcgtt gccgtgagct  40260
gtggtgtagg ttgcagactc ggctcggatc ccacgttgct gtggctctgg cgtaggctgg  40320
tggctacagc tccgattcga cccctagcct gggaacctcc atatgccgca agagcggccc  40380
aagaaatggc aaaaaagcca aaaaaaaaaa aaaaaaatag acaaacccag ggagttccca  40440
tggtggctca gcagaaacaa atctgaccag tatctacgag aatgcaagtt cgatccctgg  40500
cctcactcag tgggttaagg atccagtatt gccaccagct gtggtgtagg ttgcagatgc  40560
ggctcggatc ccatgttgct gtggctgtgg tgtaggccaa cagccacagc tccaattgga  40620
cccctagcct gggaacttcc atatgcccca agtgtagccc taaaaagaca aaaaaaaaaa  40680
aaaaaaagac aaaaccaatc tgtggtgcca gaagtcagag tgggagtggt agagactggg  40740
aaggggaggc tcagagagct gctgggggag gggggggct tgtcatgttg tttctcgagc  40800
caggtagtgg ttatgcaggt gtgtccacct tgggaaaatg cctcacaaac attccctttc  40860
agtgtgtgtg ttaaaaacaa agatgcacag aaatcttcct gctggaagct gccttctctt  40920
gggaattctg acttcccctg agtctacagg gtctcagggc cacagggtca tggatagacc  40980
ccgtttttc cttctcttgg gttcaacgcc ccaataccaa gcaccacaga gcacctaagt  41040
acggactcag ggaagatctt tcacattaaa tgatgcaggc agctggactg tggtcaactg  41100
ggagggaaag ttcacagcat ttggaggctc aggaactggg ctaagataaa ctggtccttt  41160
caagaagcaa gcacccagga gttcccatcg tggctcagtg gttaacaaat ctgactagga  41220
accatgaggt tgcgggtcca atccctggcc tcgctcagtg ggttaaggat ccagtgttgc  41280
cgtgaactgc ggtgtaggtt gcagacgcgg ctcagatccc acgttgctgt ggctctggcg  41340
taggctggca gctacagctc caacttgacc cctagcctgc tgggaacctc catatgctgc  41400
aggagcggcc ctagaaaagg caaaaagaca aaaaaacaaa acaacaacaa caaaaaaaag  41460
caagcaccca tcatggttgc caccttccag tttacaaagc agcctctctc ctttaactca  41520
gcaaatcctc aggctcaccc gccccgggtc agggaaggga gggaggcact gggagcctct  41580
gtgacttgct caaagttgcc ggctggtggg tctgatgctg cccttcctcc tgagctgcct  41640
ctggggaaca ccctacaggt tcgtggaatt agaggctcca ggctcatgaa tcagagcacg  41700
acagagtatg caaacttgga aggcagaaaa ttcaacttcc agaggatccg acatgacctt  41760
cctccttctc cgacataccc tgatgcccag actctcaaaa caaggaagca tgtacttccg  41820
gtcattcctt catggagagg cagggaactg tagcaagtga gcctcaggtc tgctgatcaa  41880
```

aggaggccag tggccatcca ggtaggagtt tggcacgttt cccagcccag ccaggccgac 41940
taatctcatc actcaatgtt ccccaaggcc ccttccagcc ctaacagtcc ataggcctgt 42000
cagatgacag ccagcattca gagcctgtcc atctgccatg tcccctgcag aggagtgcag 42060
ggccttggag ctgcggctca gcagctgcag cccaggtgtg aagggtcccg gcttcatgcc 42120
ccagacccct tccacctgag aaacacaaag gtccggattc ccaccctgtg ggagagggag 42180
aattaagtgt tcttggcaaa aagtgctaca gatacaaaga ttgcagctgt cacttttaat 42240
cctaaatacg tttagggcag gtataagaca ttcttgctgt cacttgtgag tgatggagca 42300
gtttagttgg tttcctcttc cgtgtggtga ggataattat aatccccacc gctcggggtg 42360
ggtgaggggc ctagagcacc gtggttatga atgtggactc tgggcccagg ctgccggagt 42420
tcgagtccca ggcctgccca tgtgcgatcc tgggcaatgt gcttaacctc tctgtgtctc 42480
tgtttctatg gctgcacaat gggaacaaca gcagctggat ggtagctggc acatggtaag 42540
tgtctagaga tacgtattac ccgatattgc aagaattaag gagacacgcc cggaaaagtg 42600
cttgaggtgc tcaatcattg tccgtctctg ctgttctatt aatccgaggc tgcagctcct 42660
tggagtttac atttgtgtat caaatagtca ttttgaccac gtaaccctgc aggtggggaa 42720
aggtacggag ggaagggttc ctggcacgac gtttccgtta ctgttaagta ctgcccccca 42780
cacacgcctg tgagtatcag agctgaaacg atcttggcaa aagcccacat aataaataac 42840
ggcagtcaag agaggttgca tctataagtc tatttccttg agaagagctg gaaaaatgaa 42900
atcatgatga ctcttcccag gccagtacat tgctaatcat cttgagatct gcctctgccc 42960
caggtaactc caggacagac tccaccaaag ccatgctgaa gcactcctgc ctctgcaagc 43020
atccatcctg agcctcagcc ctcctcctgc acaccaggaa gtccctctct ggggctcatg 43080
tcagtccttc aagctctata ggtcagactc ttcctagaga agaaagaagc tggctttgtt 43140
gacagctggg gagatgtgag gcgctcccac ggaagggcga ggcccgggta ctgatgacac 43200
cctgggcttg agcaccagca caggtggctg gaggatttcc ccacccaagg aaaccgctct 43260
attcctaccc tctcttggtc cttctcaccc cttcctcagg ccaaggaccc cagatggagg 43320
tgagaaagaa gcacctgctc cttattcaca attgggcagt aggtgccagg gggtacccct 43380
gcccccgacc ccccacagaa gttctcactc tttcctcagt agagagaacc tcaaagtcag 43440
gtaagtcagc tccctgcctc aaagcaggac tgctttttga acacgtgata agctcatctt 43500
ccgtcaaggt cacacccacg ccccgtttag agcccactgc catccacaaa agccacataa 43560
catagaggct aagtaggaga aatattacaa gcccaagtta taagaaaggg aactgaagat 43620
cagggaagaa acttacagag tcgtatggtc tgagtcagca gccctggaat ggaagacaag 43680
tttggggtct ttctgtgagt ctgtcccacc tcagcctcgt acacccctgg tggtggtgaa 43740
gccagaccaa gctggggatg ctaacggaag cagaacaaga agagggtcat gaaccagatt 43800
ccactagaac ccaagttctt tggggggtgg gagggagcac ttgtcttctg tcttggtcac 43860
ttctgggctt tcctggtacc tggaacagta tttgacatct atcagacgtt cagtagatat 43920
ttgctgaatt aatgctgagt gaaagcctac aggagccagg caggcagcag aagtatgtga 43980
atttgaccag gtaaggatgg actgtgataa actagccaaa tcagatcaaa atcagatttt 44040
aaaaagaaaa caggtttccc attgtggctt agcagaaacg aatctgacta gtatccatga 44100
ggtcttgggt tcgatccctg gcctcgctca gtgggttaag gatccagtat tgccaccagc 44160
tgtggtgtag gtcacagaca cgtcttggat ctggtgttgc tgtggctgtg gctgtggtgt 44220

```
aggccgcagc tacagctcca attcaacccc tagcctggga acctccatat gccatgggta  44280
cggtccttaa aagacataaa taaataaatg aaaaaagaag tacccttctt tgattacaga  44340
atgtgatata ctggccatag atgactcctc ttttaaggga aattgttttg tgccagaagc  44400
gaaaagtatt gtttgaaccc ttgctcccca acctagggga tgtaggcgtg tctgtccctt  44460
ctctgtgcgt ctgttttctc atctgtgaag tgcaaggtcc ctcccatttc cactccatcc  44520
tgcctgggcc tgagtctgag ggtagagttg tgaactgggc tcctatagca gtctgactgg  44580
gggactcaga aggcttcatg gaggagggga tgtgaccaga cctttccaga tgggcttccc  44640
ctgcctccca gggatctggc atatcagcct gcacagccac tcacccttct cttccttctc  44700
actgaagaca ggctgaaaaa ctaacctgcc gggggaggca ggcagcccca cacttcagaa  44760
tttataaatc ctcctctgct caggctcagg cccagtccat cctgggaggt gctggaggtc  44820
attttatgaa ccaaccacct tcggctttcg gggcgtaggg atggggcagg atgccacaga  44880
atcaccagcc cactcacgag ccccccctgaa cccttcccag ggtgacagaa aagaggaaat  44940
ggagcacaat tccggcccca agacaaagaa actcggccaa gcaaagagaa gggaaacagc  45000
ttcctgagtc aggggacttg gaatctgcta gggccacagg gaaccttccc cccatcatgg  45060
tgaggctgag gtgtggactc aagcaactga gaagataagg acaggtgggt ccgccccccac  45120
ccagctcagc ccagaagcat ttctttccaa agcgcccgtg gaaaggagtg gtttgcagtg  45180
aagaacattt ttcaaaaaaa tcgaagtcta atactaataa tataaccaga taaaagaaag  45240
gccaagaaag tgccatataa atccaaagac acggttccac aggccacgtg gccacaggca  45300
catttttccc ctcctgggcc tcacgccccg tgtgggcact gacggagtcg aagtggaaca  45360
ttcccaggac ccacctgggc tcggtggctg tgaagagcct gttgttactt gctctgcaaa  45420
cctggctgat gaacatgcag ccttcagagc gcaaggtcac ctcctccaag atctgcctcc  45480
tggcacaagt ggattctcac agccctggtg tggcctgctg gtttcacggc acctagagcg  45540
caggttcttg gacatatgtc catctcactc tctgcacgca cattctcaag ggcagcaggg  45600
aagtctgctt taggtcaagg tccctggtgg tcctcaccac agggtctggt agagaggagg  45660
tcttgaggat cagtaggctg gtgacagatg gacagatgga cttgctgggg ctactgtaat  45720
aaagcaccac aaagtgggtg gcttaacaca gcagaagttt atcctcttat acttctggag  45780
gccagaagtc caaagtcaag gtgttagcag agctggttcc ttctgaaggt catgaaaagg  45840
aattctacag gcttctctcc tggcttctgg tggttgccag ccacccttgg cattccttgg  45900
ggcagcataa cccaacaccg tctgcatcat cacacagtgt tctccgtgtg tgtcagcctc  45960
caaatttccc tctctttaga aggacaacag tcactggatt ggagcccacc cgaatccagc  46020
atgacctcat cttaatttga gtcatctgac aagaatctat ttccaaaaaa actcatattc  46080
ataagcactg gggattcgga cgtgaaccca ttttttttt ttggaagaca caattctacc  46140
cactagagac cgtttcccaa atgcctattg gctgggagcg tgtaaacact agcagaacca  46200
cctgtgaggg tggaaacgct gcatataatt acggagttga aagcgaaagt ttggaggcag  46260
gcggggaggt aggggtggtc ttgagaaaga ggaaaacatc ttagagcatc tctacttggc  46320
caggattata ggaagaagag aaatgcctcc ccgggacagg catctgtggg atgtcccgcc  46380
gaaatgctgc cggtctgtca atactcagct ctgggcatca cagagccatg aatgggtaag  46440
cttcctccca agaggagcag gatgtgaaag aagagggggc cctggggcag ctggaaccaa  46500
gaacctatgg aagcacagag ctgggcacca gattgcagtg ggtcaaggaa tgaaggtcag  46560
gtgagaaagt gacgtgcaag gacctctcgc cagcagcttg ccttgggaag ggctggaggg  46620
```

agggtgccag ctagagacac atggagcaaa aaggaaatac ccttgagtac actgctgata 46680
atgaaaagcc cttaatgaga cagagccgag gagaggaggg tttgaagatt cagaggaggg 46740
agaggatggg ggctgaagag catctcttgg cggggagatg ggggtgccac caagacaggc 46800
tgaaagtgct ccccctttt gaaaggagca ggagacagaa tgggtgggtt ggcaagtctg 46860
gggataaagc gggtaggtga caggctccaa tccagagcag ctgaagcgag gagggagaag 46920
ggggccagga ggcagagaag ctggagagct gtgcagaatc tcatcaccag gaaccttgaa 46980
cttgcacctg aaaaatgggc atttcatcct gaaagtacta gagaatcctt gaatgccact 47040
aggcaaagaa agttacacga tttgcttttt agaagacttc cttggctgaa ggatgaggga 47100
gcccagccag gaggctgctg gccaatgtca gaggaaagag tagagaccta accccacagg 47160
tagagctgga agacaagaaa gaagtggcat cttgagacat agggttacat ctatcttact 47220
ttctttcttt catttttttt ttttttttg ctttttaggg ccacacccac agcacatgca 47280
agttcccagg ctaggggttg aatcgaaact gtagctgcca gcccacgcca cagccacaac 47340
aatgccaaag ccgcatcttc gacctacact acagctcacg gcaacgccag atacttaacc 47400
caccgagcaa ggctggggat cgaacccgca acctcaaggt tactagtcgg attcctgagc 47460
cacaatagga actaccgggt cacgtctttg aaaatctgct tcagtgttac tttagagaaa 47520
ctgtcctgga tttaaaatta ctttcctttt gtagttatct atctttcaat tttatttctt 47580
cttctaccag agtgtcaact ctgtgggcag atatttttgt gcgtttggta cctgtgtgga 47640
aacatctgtc tattacagcc cctggtgctc cgtacagctt tgtaggctaa aatgcatgcc 47700
tggtacagtg cttggcacct gtgtgttcaa taaacatgaa ctatggtgat aacaacagca 47760
agaataacag tgagcaatgg gatgaaggga gtgaggcaga aatgagacta gtttggtggg 47820
actcaaagtg tggactgagc aaccggtagc atcagcatca cctgggagct tgttaagaaa 47880
tgcagagcag caggcccaca gcccaggaac ctgtgtctgc atgaggtctg caggtggtct 47940
gggaatgggg ctggttccca ggtttctggt tgaaggagga gagtgggtgg catcgctgct 48000
gactgacatg gagcggcggg gctgagagga gggggagtca gtgagttctg ctcaagaggt 48060
gctgagtttg aagaacctgc agaagtcaat tcagcaatgt tgtcccagag agagagcccg 48120
gggagagccc agtttcggag ctgccagccc agcgtgcagg caggagtcgg caggtcttct 48180
gtgtgccaag ggaaaggagc acggagagca gaatggggcc tccttaatgg gcaccgcctt 48240
gaaatctgag ggcagggcc gagaggcagg aggagaaaca agaacaaaag ttgttgctgg 48300
gagaaacccc atctgaattc tcagctcagc tccacccgtg accgcctctg gccctgcttc 48360
ccctggaaga gggaaggcca cggacaattg ctcgggcaag gttgctgctg tttgagaatc 48420
ccaaggagcg ggactgtcag gcaaacagag gggtggcaac agagaggggt cccgtttcca 48480
gctgtacctc caactccggc aactccctgc gtgcctggtt gattcccgcc cccttcggat 48540
gacaaggtgg ggccggggtc tctgaccatg ttgcctgcca gctctctggg ctcacccctc 48600
atgtccggcc acagactcta ggggaagacc ccagcagagc ataatggcag ctgccttcag 48660
agcacgtgag gaggctccag aggccagacc aagaggtgag ggaagggcac gcagggtagg 48720
aagccaggat tcccgagcca acaggtgtgc tctacctggc tcccatcagt acagctgaga 48780
gtcaaggtct aaagaagcct ctctgtccct cagccaaaaa gggaggccca ggaaccagca 48840
agggccactc tctgcattta tcaggtccta gtctggcgag agggacacgt gctgactgca 48900
gaccgcagct actgcagttg tgttcagtgg gctggggctg gcagagtggg gctgcacagg 48960

```
tgtcccccgg aggaagtccc agctcctccc tgccccatca cctgttgtat tttgctttac  49020
caccctccca tttttgccat ttgtgcttgg ccttgtcaca gcaacccctc ctggtgcagg  49080
tagtttccca gggcctctaa aatcaaggtg cttcccctag aacagttctg atttatactt  49140
gttatggctc aatgttttag tacctccttt cactttcaaa ggtgtgcagg tgtggaggac  49200
aaatcatgtt gcctgtcacc ctacataaaa acggttcaat aaaatagagt tcgatgaagt  49260
ccccttcaag acgcctctcg gcttggaccc tccaggagtc agggcttgtg tttaccaaca  49320
gccggtgccg tgacctcccc ctctccagca tccttcctgc tactgcctgt ggtacaagag  49380
gtggtaaaag cctttctgcc acccctcccc taacctgtcc ccttcagtgc ctgttgctgg  49440
gatcatctca gctccccctg cctccctgtg taggctggga ggaattaaaa gtctaagaat  49500
ttactggaaa atcctaaggt tgttttgtct tgggcttttt tccccccctca ctagattttt  49560
ttcttgtaac aagttgacga gcataaaaga ccttccaaga attaatctct aatcatgaga  49620
gatttccttc ctagtggaaa gctaaaaata acaaagacaa caacaacaac accccaaaac  49680
ctcttaactg agcccacaat ggagatggct tttcctctgc ctgttctttg tcttttgcca  49740
tttttttttt ttttttaag ggccgcatca gcggcatgtg gaggttccca ggctaggggt  49800
ctaattggag cgacagctgc cggtctacac cacagaacag caacgccaga tccgagccac  49860
gtctgcgacc tataccacag ctcacggcaa tgccagatcc ttaacccccct gagccaggcc  49920
agggctcgaa cccgcaacct catggttcct agtcggattt gttctgctgc gccacgatgg  49980
gaactccttt gcccgttctt ggaaagagcc aggccccagt tcaaatgcca gtggcgcccc  50040
acccccaccc cccactttct tgctgcgaag ccctggctca gtcacttcac attccgagcc  50100
tcagtttact catctgttaa agagggatga taattcctta ctccttgaat tgttgacaag  50160
atgaacagtc tgtaaagctc ctggtaggta cttgggaaaa aagcaacttg tattattatc  50220
gctggtccct aagagacaag cactgtcccc acctcatcac agtgacagga ggcagtatgc  50280
ccagagatta gagcttgcac ttgagcaaga caggcctggg aactgactaa atgcgtgacc  50340
ttgggcaagt cactggacct tctaggactt gctttttctc ctctgtaaaa tgagaataac  50400
agtgactcac catcggtgag atgacgcaca tcaagcttgg catgacccct gatgttgcag  50460
caagtgccca atagatggta gtttctcaat tcccaatagt gattattgca gaactctcca  50520
cctcacaggc tctggcacca cctgctctgt atctccaggg tccactatgt tcccctgtcc  50580
ccaaaacaac agcccttcct gtgcaggggg catttacaaa tccacctttc cccttccgct  50640
ggagtctgag ctgcagcccg tgagtcaggc tgggtctcca cgtgcggagg aggaggtgga  50700
ggaggaggag tctggtaact ccccaagggg ggctcagctg ggactggaag ctgggtttgg  50760
gtgcagccaa gaatttcttc agccccttcc tgtcccacag ggagcctgat tcagagttga  50820
agggaattac gtgtttgttt atttattcat taaataaata tttaacacca gggagttccc  50880
atcctggctc agcggttagc aaacccaact agcatccatg aagacatgga ttccatcctt  50940
ggcctcgctc agtggtttaa ggatctggcg ttcctgtgag ctgtggtgta ggttgcagat  51000
gcagctcaga tcccgagttg ctgtagctgt ggtataggcc agtggctaca gctccaataa  51060
gacccctagc ctgggaacct ccatatgctg caggtgtggc cttaaaaaga caaaagaaga  51120
cccctccccc ccaaaactta acaccaatgt tgatacctac cacgtgccag gcaccattca  51180
ggctgctagg tcaataagga ttagcctatt ctgtgccttt ctcacagagc tagtgggaag  51240
tggagccctt cctggtggga agctgagccc ggacagcaac acttctacat cctgaagcca  51300
aggtgagtgt cctgtgacag caatgagtca gcccctctct gggctccatg gacttctgga  51360
```

```
agactcggag agcaagctca cctgcctcct tgcccgtgtg gctacaggaa catgtttacc  51420
acccagggtc actctctctc aagcatggcc ccaatcttct gagctgcctc actttccaga  51480
tgagaaaact gaggcaccaa ggcagggaag taacttatcc agggccactt ggtgatgagg  51540
tgaagaggcc agggctagta cccaggtatc tggcatctct ctaggctgag acgcctatta  51600
gccacagcac cagaaatcaa gagcttagag acggggcgaa gggctgcagt caatggtctt  51660
cttctagagt tttcttatta atgcccagga aaacctctga tgggacatag aaatgccact  51720
gggaaaaggg gagcatcgtg tgtttactgg agacaagtga ggcacccaat tcaaaaagaa  51780
gatccctctc aaacataaaa tagttcagca atggagtaaa aaacacctaa atatgtgttc  51840
cacttacaaa gcatcctatg ggctgtgatg aagaatgtgg tttggaaact ccgattccac  51900
cccattgcct ctgccttcac ctcccacccc agtgtttagc accaggagct cccagcacat  51960
atcacctacc cttttcctgg ctgctgtctt cttcaatgag cttctgcttt tgattcccct  52020
agagaggctg gcagtttcgg gcaccttttt gttcctctgc ttagcagttg gggcggagaa  52080
gaagtggctt tggggttttt cttctctggg tgtggtttcc tagccctcac aaaggaaagc  52140
ctacagcctg ctctgtctgc accaccagcc tggttgcctc agctggcaga gctgattagc  52200
atgcgaggtg cagaagggaa cagcctgcct ggggtactca ggatactgtt ctactaaatg  52260
tttcctgctc tccaccttca tagtaggatt tcatttcctg gtccccttgc agttgagtag  52320
ggccatgtga ctagtctgac caataagatg tgagttggcc caagtattta attgctggtc  52380
aaagaccctc cagggctctc tttctctgtg ccatgaagta tattcaagga cgtaactgct  52440
ccatcagcct ggctccttga atgaggagca cagcccctag ctgacccacg gggctcatgt  52500
taattagagt aagacataaa ccgttatggg tttggcccca aagatttagg ggctgtttgt  52560
tactgtagca taacctacac catcctgact gatacactgc ccatctcaca cagagtgaga  52620
tattccctag ttaagtctac catcttccca atgttgctct ttcagccaga agccatttca  52680
cttcctctga gctccccttg gcctcctgtc acacttctgt tctgcactct gacttctact  52740
tttagtccct tatatataat tacatacagc caatttcaca ttgtgagcgc ctgaagagca  52800
ggaatctgta ccttatatta tgatgatgat aataataata ataataaaca gaggcagcaa  52860
atgctactat ttattgaatg ctgggctggg ttctaagcac ttgacattca ttcagttctc  52920
actaagctct gagaggtcag tactggaact acccccactt tacagatgag gaagcatctc  52980
agtttggttc agctgaaatt gaacccctaa taatatatat atatatatat atatatatat  53040
atatatatat gcattttttt ttttttggt cttttcctag ggccacaccc gcagcatatg  53100
gaggtcccca ggctagggat ctaatcagaa ctatagctgc tggcctacac cacagccaca  53160
gcaacaccag atctgcaacc tacaccacag ctcacggcaa ctccagatcc ttaaaccact  53220
gaatgaaacc agggatcaaa ccggcaactt catggttcct ggtcggattt gttaaccact  53280
gagccacgac gggaactctt aatatttttt taataaatat agttcaactt aagtcattcc  53340
ctctataatc ctagtcactt atttttcaca tttaaaacat tcccagaagg ggtctatagg  53400
ctcccccaga tgccaaaaga gtccatggca caataaaggt taaggtcccc tgtagaagca  53460
gataccaggg ttacagtgac agggttctgt cccctgttct cctggaaccc agagtttctg  53520
gctggtggag ggtaagggac cctacaccaa attcatgcca cagtggggag tgaacaggag  53580
ctactttatt gtattcacat agcataaaca taaatatcgt aggtttggca tatggaactc  53640
cctgtcatga atattttgat ttcagcagtg tcagcccaag tataacattc atcacagtaa  53700
```

agaagtcact tgtttcccca gtaaaaaaac aaaacaaggg cgttcccttc atggctcagc 53760
ggttaacaaa cctgactagg atccgtgagg atgcaggttc gatccctagc cccactcagt 53820
gggttaagga actggcgtgt aggccggcag ctgtagctcc gattcaaccc ctagcctggg 53880
aacgtccata agtcgcaaga gtggccctaa aaggcaaaaa acaaaacaaa acaaaacaat 53940
tcctaacatc cagtgtgcta attagaaaag catcagctct tgatcacaaa ttgggataac 54000
aggacagcag ccatctctgg tcagtcccac tcccagacga tgcatccttg agggcagatg 54060
ggccgaccac ccacgatgag acttgctttc ttagcttctg agcactggct tggtccaagt 54120
agcactcaca taatctccca tattgtatat gctgaagttt tatactttat tgaaccagaa 54180
tttactttaa attccaggca tccaaacata tacactgaat ccaggtgaat ccaagcagaa 54240
ctctctggat ttcagaaatc ctgggtgatt acaagactca gggataaggt agcagagcca 54300
atgctctgtg cctccttgcc agctggccag tagtgagggc tgagccccag gacaaccggg 54360
tggcagtctg gcactgccct ggtgggctgg atgaccttcc gcaaattaca ggctcagttt 54420
tcgtatcctc caaatatgga gccatactag atccaagtcc aggcaagaaa caatcacaag 54480
gcacccgcgc tacgcctagt actgtgggga aaacagaaat tacacaaact ccataaggag 54540
cttacattct agttggggag ccaggcctgg aaacaattta actattgtgc acgacagaaa 54600
gaagtaagta tgaaggtggt ggaagccccc tcttgtgctc tgggaccaca gaggaagcac 54660
gaagccaggc tgcataggcc tgcgcagctc ggtttcaaag aggaaggggc tatgcttgaa 54720
ctgggcttca gagggtgagt aggagtctga tgggtgagga agggcataca ggtggaaggg 54780
caaggatctg caaactcggg gtctggaatg ggaagcccca cccccagccc agatcccagc 54840
ccaggggttc cagtcctgct ctctccacac atccgctgct ttggaatctg gaagagtcct 54900
ggaaacctgt attttgaaca agctcccaca gtcattctca caagcaggca gtgagtgtta 54960
tagattgaga aaaatgaatg aacaaatgaa tgaatgaata caaaaatgaa cctgagaagt 55020
tcctgttgtg gctcagcaga aacgaatccg actagcatcc acaaggacgc aggttcaatc 55080
cctggacttg ctcagtgggt taaggatctg gcattgctgt gagctgtggt ataggctgca 55140
ggctcagctt ggatcccacg ttgctgtggc tgtggtggag gctttcagct gtatctctga 55200
ctcaacccct agcctgggaa cttccatatg ctgagggtgc agccctaaaa agacaaaaaa 55260
aaaaaaaaaa aaaagaactt gacttccggt aagtcccttt ctctcttagg atgtccacac 55320
tacattaagg agctaaagag cttcagttgt ggctcagcag tatccatgag gatgcaggtt 55380
cgattctggg cctcgcccag tgggttaaag gatccagtgt tgctgtgagc tgcagtgtag 55440
gtcacagaca aggctcagat cctgtgctgc tgtggctgca gctccgattt gactcctagc 55500
ctgggaactt ccataggcca cacctgcggc ccttaaaaaa gacaaaaatg aaaaaataaa 55560
aagcaaaata aaagtgctga attggcctgg tggctttcaa actgtgttcc agaaaaaccc 55620
cagaatctcc ctgaagtccc tcagggacac agaggaactg gggaggctga gagagccgga 55680
ctctgggccc catccaccct tctcagatta cctctccttt tatctctttg ctcttttttt 55740
tgcaataaag ggttcttggc tacaaagaac tcttaaagcc actgaattga ataatcctag 55800
aattcccaag gagtcagagt tcccattgtg gctcagtggt taacaaatct gactagcatc 55860
cgtgaggacg cgggtttgat ccctggcctc actcagtagg ttaaggatct ggcgttgccg 55920
tgagctgtgg tgtaggtcgc agacgcggct ccgatgctgt ggctgtggcc agcagctaca 55980
gctcctattc aacccctagc ctgggaacct ccatatacca ccagtgcggc cctagaagac 56040
aaaaaaaaaa gaatccccaa ggagaaattt aaaaatttct tgagggcagc agcttacctt 56100
tggcaagtat gaagagagca taagggtctt tttcagaagc aagttattta atcatcacat 56160
tttaaaaacc ttttgctgtg gcccagaaat tagtgagtga aggaaaaaag caatgtggta 56220
taataatgca agggaatatt atgcaacctt taaagaacac ttttgaggaa tggttaatac 56280
aatggaaaat aaagtgagga agtcagatac aaaatttcat acagactgtg atttacggta 56340
tggatttttt tttttttttt ttttggctac acacatgaaa gttcccaggc caggaattga 56400
acctgccaca gcagtgacct gagccacagc actgacaact ctggatcctt aaccccctgc 56460
accagcgcta tggatcttat acatcaaaat tattggacat ggatgttagt aggccggtag 56520
ctgcagctcc gatttggacc cctagcctgg gaacctccat atgcctcgga tgcagcccta 56580
aaaaacaaaa caaaacaaaa caaaaaaaag aagaatgcaa ttctgacatg tttcagcaca 56640
gataaaggtt gaaaacatta cgctaagtga aataagccag acacaaaagg acaaatagtg 56700
tgtgatttta ctgagatcaa gcacccagag ttgtcacatt caccgagaca gaaagtagaa 56760
gagcggttac gggggtgggg gggatggggg tgggcagtgg gaaattactg cttaagcagc 56820
acagagcttc tgtctgggat gatggaaaaa ttcagatggt tgacactggg gatggctgcc 56880
caacgtgtga atgtgcttag tggtaccgaa ctatgccctc aaaaagcatt agaatggttt 56940
atgctatgta tcttttacca caataaaagg ggaaaaaaaa gccagaacta ggtgcatagg 57000
ttatagtggt gaatactatg cgacaagctt gtgggcagcg tggtcacttt attctttgca 57060
tttctctgca tttttcaaac gtcctatgat gagcatacat ttctttttaa aaccagacag 57120
aagagcgagt taattaaaca aatctcgtgg ttctctgaca cttttgccca aatgcgttac 57180
tgtcttttgc gtaaatgtaa ggtgtgttcc ctgtccttcg ttaataaaag gagccgagcc 57240
caaggatgcc aacgaaagga tacaccgagg tgctcaagtc aacgacaggc acagcggccc 57300
tcctttctaa gactcgttgc tctcgtctat atttaataag ttccaaataa aaacagaacc 57360
caaacaaatc ctctaatgaa cttcctaaga agctgtctgg cttggaaaag ctcaaaggcg 57420
aactgaagag aaagggggaa cagctgctgt gtttttaggg cattaactca ctgcagctgg 57480
gacagtgcct ttgtcagtag atttctatcc cttcttgctt ctgggaaatg ttcttgggca 57540
gaatgaattc agaaaccagg agaggctccc cagtggtatt ccctgccaat ccatctgctc 57600
cagtaccctc tccccacccc agaaacatgc tgaacaaaga tttaaagact cttggtgtga 57660
agggcagcca cgtgtctgcc tgccagggtg ccctccaccc caggccgcct gggtccactt 57720
gcccggctcc tgggccctct gctcaggggt ggcacaaggg cagaaggtag ctgccacgat 57780
aagcagaccg gggctacccc tggagtggcc cctccctggc tacgtgacct ctgccttttt 57840
caaatgttct atgatgagca tacgtttctt tttaaaacca gacagaagag cgagtaatta 57900
annnnnnnnn nnnnnnnnnn nnnnnnnnnn nnnnnnnnnn nnnnnnnnnn nnnnnnnnnn 57960
nnnnnnnnnn nnnnnnnnnn nnnnnnnnnn nnnnnnnnnn ncgtatatgg accataccac 58020
cttcccctgg ccccaggttc tcacctatgt gactgaggga ggtggactgg ggcacctctt 58080
agatctctgc cagctcacac atcctatgat tgcatcatct caaaaagaaa aagaaaaacc 58140
aacaatacct aaaccaaact aaaccctaaa accaaaacca aaagcagggt gccttctagg 58200
aatctaggcc aggttcttac gtttgggggg gccttggggt ccctatctac aaaatgaggc 58260
acggagtttc caccatggca cagtgaaaat gaatttgact agtaaccacg aggacgcaag 58320
ttcaatccat ggcctcgctc agtgggttaa ggatctgggg ttgctgtaag ctgtggtgta 58380
ggtcgaagac gaggctcgga tctggcgttg ctgtggctgt ggtgtaggcc agtgcctaga 58440
gctccaattg gacccctagc ctgggaattt ccacatgcca cgggtgtggc actaaaaaga 58500
ccaaaaaaaa aaaaaaggga aaagaaaaaa tttggcacaa ccttccagct cgttccatgt 58560
ccaacatctg taattcctga aaggaaggcc ccatcctccc cttgccctcc accacgtcct 58620
ctacctcagg ccaggctcac aaacaggaaa tatgacattc gagagcagca gaagcactgc 58680
ttgcttctcg acagcatagg ggccgatgga gaacaaagag tttctgagct tttccagcaa 58740
caaccagggc tccatgccca agaccttccc caagcagtgc aggcagagga cactgctggg 58800
atgggctggc ctcccatgcc atccccgccc cggtgtgttc ccaggggccc ccggcagcgc 58860
agaatcagca gataagctgt ctggccgtaa ttacacgctg atgcttgacc aaaggtggta 58920
aaaccctaaa caggcggaag gcagggtgca ggattcctgg actccagtgc aggagtggag 58980
tgaccctaga gaggccctac ccctctctgg gcctgagttt ccccatctat tttttttttt 59040
tttttttttt ttttgtgtga gtgcgtgtgt gtgtgtgtgt atgtccccct ctatttgaat 59100
gaaagggcta gaatggggcc taatggcagc tctttgcttg ctccgaggtc ttcggttttt 59160 ctttttttcat tccatttttt tttttttttt tatggccaca cccacggcat atggaagttc 59220
ccaggctagg ggttgaattg gagctacagc tgccggccta caccacagcc acagcaacac 59280
cagaccccag ctgccagatc cctgaccata gcggatcctt aaccttacac cacagcggat 59340
tcttaaccca ctgagtgagg ccagggatca aacccgcacc ctcatggatc ctagtcgggt 59400
ttgttacagc tgagccacga cgggaacgcc tgatgtcttc tttctgaagg cagtgtgtgg 59460
ccttgatgaa aggccccatc atcttgcctg tgtctgcgtc ccaaatctct ccctcaccac 59520
gtgaccctga gaaactgcta aatctttctg tgtttcgttt gctcatttgt aaaactgggg 59580
ttgctgggtg atgaaaaggc agagctcctg taaagctcct aggacagctt ctggagttag 59640
cgcccaggaa gcgtgcgctc ttgctgtttt atgatttctc tggtttcaga atcgctcccc 59700
ttgccctgtt tgccatctga agaaggagca agcatggccc agagagccat actggccctg 59760
cagtccacgt ctagccctct ccctccaaga aagcacatgt gaatcttggt cagccaagca 59820
cagtgggaag agggaactat gggagaaaag gcagaaaatc ctacgatgct gccccacagc 59880
agatgggctc gggtgtcagc tgctcccagg ggttgctggg cactagagaa ggcctccagc 59940
tgcacccaga gtcagtagcg gagggagggt cctgggctca tctccagctt gatccccgaa 60000
tggggaggag aatgaccccg tgggaaggag ggtgatgaga tgcagaagat gcagccgggt 60060
ttatctctgt tcctactttg ccgggaccat tcagggaaga ggaggccaca ttcagtcatc 60120
tcagccccga ggggaacagg gaacagagag gggtgaggat gacagcactg gtggtctctc 60180
ccctggggac atggaggtgt ggcctccctc tgccacaggg agggtcccaa acctgcctgt 60240
cctcagtgtt ctcacctgcc aagggaggag acgcaaatgc ctgtttccac caggcgctct 60300
agggtctcaa attgtggctg cggacggatg catcgaggag gcacagaaat tgagagtgtt 60360
ttactaaagg accagtccac aggggattag aaataaagga agaaaggcct gatcttctac 60420
cacactgtcc taggacataa agcatgatgc gggagacagg caggacccct gttccgcctc 60480
ctggggctac cccgcttggc tccagtgagc tctgtggtcc aggtggaatt gtgggctccc 60540
atctggctgg gacgactcac ccagacagac tgccctcctg atccgagagc atttcactcg 60600
gcagcaaatt caacccacct caaaatatca gctgcccctg atcaggcagg gcctggctcc 60660
ctctctgcca agccccacag ggctgggctg ggatcagtca tggcagctca agggaagtca 60720
cgctgcaccc agaggtaaaa gctgtcctgg cagagaaaga gaaaactgat ggtcctaaga 60780
acaagcacac tggctttcac ccttgaggac gctcagttga gaatctcggt ttgggagttc 60840
ccatcgtggt tgtagatggc tctggtgtag gccagtggct acagctccaa ttagacccct 60900
agccagggaa cctccatatg ccgtgagtgc ggccctaaaa agacaacaaa aagaatctct 60960
gtttggctgc cctgtgtggc aggtatgcat ttatcaggta tagagacatt ttacagatga 61020
agggagccca ggggatcttt gctcaaactc tttttttttt ttagcttttt agggccacac 61080
ccgtggcata tggaggttcc aaggctagga gtcgaatcag agttttagct gctgccctat 61140
gccacagcca cagcaatgct aaatccgagc cacatctgag acctacacca cagctcacgc 61200
caaagctgga tccttaaccc actgggcgat gccagggatc aaacctgcaa cctcagggtt 61260
cctagtgaga ttcatctcca ctgagccacg atgggaactc ccaaactctt ttcttttaca 61320
gataaagagg ctcaaggaaa ggagcacctt gtcgcagaag caggatttga accctccaag 61380
gctcctagcc ccatctgcat tcagcctgcc aatccacggt taggagggcc aactgcacac 61440
atgcgcagtg tgggatgtgg tgaggaacca cacaggaaaa gccctcagtt ctcacagagc 61500
tcacattcta aacaaacaac aaaatcagtc attataatta acaaatcatt aaagacataa 61560
tttcaggtgg gggagagggt tataaagcaa atttaaaacc tggcgtgttt gagagtgttt 61620
tggggtgggg gcagctgctg tttgggaatg gcctctttgc actggatcct ctcaggtcct 61680
cccaagccag tagaatgctg gagctggctc ctgctggctt gcaagggcca cgtctcatta 61740
ggaatttggc gagcaagttg ttcaccacag ccattattaa aaattaaatt acataaactt 61800
agaactaaat gaattatagt acgacggaag gtaatcatca aaagtcatca ctccctcggg 61860
ttcccaggtg gcctagcagt taagggtttg gtttgtccct gctgtggctc aggttcgatc 61920
ccagacctgg gaactttcca aggccacagg cacgtgacca aaaagaaaaa gaaaaaaaaa 61980
cttcattaat ttcctctttg tatgaccaca tactatactc ttgaagttgt ttatatctat 62040
tgaatctaga cgtaatagat actcccagtt cctccagtag tagctagaaa ctggtcatgg 62100
tagaaatatg tctactatgg aaactggcaa ataccctcta cgagggcttt cacttttcaa 62160
agagctggtg gtgaaatatt taccagcaca gccttcagct ctaatccagg ccttctatgc 62220
ctgtgggagt ctgggttctt ccaaggagag ggtgtggtgg tatagtctaa ctctcctggg 62280
gctgggggcg aggggaggtg gtgggcagtg cctccagccc tgtcctcttc ttcttctgtg 62340
tgtgtgtgtg tgtgtgtgtg tgtgtgtgtg tgtgtgtgtg tgtgtgtgtg tgtgtgtgct 62400
tttcagggct actccctgga aagttctcag gctacatgtt aaatcgtagc tgcagctgcc 62460
ggcctatacc acagctcatg acaacactgg atccttaacc cactgagtga ggccaggggt 62520
caaacctgag tcctcatgga tactagtcgg gttccttact gctaagccat aatgggaact 62580
cgggcagtca gattcttaac ccactgcacc acagcaggga ccttcttcaa aagtgttttt 62640
caacagggat ctgtaagagg gtgattcatt ccttcctttg ttatttattt ttgataaatg 62700
aaatcctatc ataagcatac caatataaat ttaaaggaac cctgccgaga atctctttgt 62760
ataaatgcct gcagtcactt ctgagttccc ctagattttc ataggtggag ggacttcctt 62820
agagaatata actgttctca ttaacagcag actgaagtta ctattacctc tactaataac 62880
aatgacaact gtagctgtct tttactggca ccacctcagg cactaggcac atatattatc 62940
tctaaagtct acatcaaccc attttacaca taagaacgtt gaggttcaag ggttcaataa 63000
cttgacctga ggccagcctg ctgctctgaa agtttcacag aaggcttttt ccttctgtag 63060
cgacagccct gcgactctcc ttagacctgc aggattctgt ggtcctacag gaccccccat 63120
ctctggtggt ttgggagaat ttcgtcacgt ctcagcttag tgtaaggaac tcccttccat 63180
cagcagaaca gaatgagcca gacgctcccc ctggactttc tttttttttt tttttttttt 63240
gtctttttgc tacgtctttg ggtcgctccc gaggcatatg gaggttccca ggctaggggt 63300
ccaattggag ctgtagccac tggcctacgc cagagccata gcaacgcagg atccgagcca 63360
cgtctgcgac ctacaccaca gctcacggca atgccagatc cttaacccac tgagcaaagc 63420
cagggattga acccgcaacc tcatggttcc tagttggatt cgttatccgc tgagccacga 63480
tgggaactcc tccccctgga ctttcacctg caatgcagga aagtgaccca ggcctggtca 63540
cttagcagct tcccacccaa aagaagtagc actcaggttc tgataccagt gaaatgttaa 63600
cagcggctcc agtgccagca agagctagaa ttaactcctg ttgggagacc ctaactgtgt 63660
taggtctgtt gcctgacctc tcctggttct gagcagcttg gttttcaagc tcccccagga 63720
ataccatgag caacaaccaa aaaatccttc caaggcacat acctcttctg cctcggtgag 63780
ctagaatctc catcggttgc ttgtaaccac aatttctgac ccgtacctca tctcaagcgc 63840
ttctcaatat atcagccgca aacattcgct gagcctttca tgccagagaa ggagctccta 63900
agcactcaat tagtttgcac agaggaatag taatcgtgcc tttctgtgca cagctctggc 63960
ataacctatg aaaacggagt ttgccacaca aaatagcaat ctgcaaacaa ccacagctca 64020
actgagagca aatccaggcc cagtccctgc tccccgggag ccatattccc cctaaagaaa 64080
accccttcct tgattttgtc aacggtcttg tctttcccca cagatgccag gcaagttcct 64140
cttggggaca gctggccggc cacttgagga cttgcgattt ccctgacgta ggagaaagga 64200
cagctgggtt tctgcacaca gatgctgcca agcccaacgt cacccttctg ggcagctgac 64260
ccattgcccc gggcttgctc cctcccctgt gcccctccag acaccagggc catctggatt 64320
ctggaacagc catggggaag atcaggatga ctggttctca ggaccccttt cctttgcctg 64380
aaacgctctt cctttttcac cctctacatc ctgcgggcct cagtttaaag atcacttcct 64440
cagggaagcc ctccctgacc acttccccag acaagttcag ggccccagga ccctgccctg 64500
tttatctcct ccatgtctct gtctgtgcag ttcattgttt actgactatc tccccagctg 64560
aattctagcc tctgcacagg aagggattgc acctctgttc accgaatctc aggttatcta 64620
gcacagcatg tagttccata aatcctgaac gctttaaaga tgagtgaagg acattctggc 64680
ggctcagtga gcgctgaatg agtatctgat ttaaagcatg catctcagca acaggtgcat 64740
cttttaggac caccgttttc tggtgcccaa actcacaagg gcagggtgaa aatttagcca 64800
tccctacttc tccccgggtc gtttttagtt tgaaggtttg tttcctgtgg gttgggactg 64860
gcccgatttt tgtttaacag cagctattgc tcagagagga gtttgctaga tgccagcctt 64920
ataccacctg gttgatgggg aaactgaggc ccctaccact ggctgcacca gcaccggcgg 64980
ggcgagacca gctctctttc agcccagagc tcatttcagg gtccttcgcc ccacatgggg 65040
ccaagtccag ggcatgcgaa gcaaggctcg ggaagataag ggcacccaga cggggatgga 65100
gtttgaaact tttattaaga acgaatcaag agggaattcc cttcatggct cagtggttaa 65160
cgaacccgac taggatccat aaggacaagg gtttgatccc tggcctcgct cagtgggtta 65220
aggatccagc attgccgtgt aggtcacaga ggcggctccc atctgtgttg ctgtggtgtt 65280
gctgtggctg agatgtagtc tgacagctac agctccgatt cgacccctac ccggggaact 65340
tccacatgcc atgggtgcag ccctaaaaag cagaagaaaa aaagaagaag aaatcaagag 65400
acctggcctc tctctctgcc cagcctcttc cagctgctac cttccactct ctccggctag 65460
tttcaggttg agcaaggcca ggcaggagcc ctctcggggg ctgagcatgg atctgggccc 65520
cagcagcgcc cccaaccttc agattcacct tcactctcct tgctcagggc ccaccagggt 65580

```
ctccaagcca aactatgttt gaagtcaaga ccaggctttc atgctttggt tctgccactt  65640
cactcttgag agatggtggc caaacaatta aaacgctgag cctcaatttc cctgcctgta  65700
aagtgaggag gcggggggat aattcctgct ttgctgactt catagggctt ttgtgaggct  65760
caggcgaggt agatatatgt actcactcgt ctaactgtcc actagcttag agaactctaa  65820
caacaactct aggagttctg gcagtgggtt gagaatccga ctgcagctgc tcaggtcact  65880
acagtggcac gagttcgatc cctggccctg tgcagtgggc taaagatcta gatagagttg  65940
cggcagtgat ggcataggtt gcagctgtgg cttggattca atccctggcc cgagaacttc  66000
catatgacgt ggtgcagccg taagggaaaa aaaaaaaaaa aaaaaagata ctgtttttct  66060
ggtcccatta gggtcttgcg atcaacgtgt agccagccca tgtcctccag ggcccaatcc  66120
tccacccaac ctctcagcca ggctctcctc ttgaccacat ccttctagaa atcctttctg  66180
cctctgcctt cctggatgtg ctccctctgg gctctcctcc atctcaggtc actcattctc  66240
ccagttagga cctggcccac ctggcagctc cgtgcttttt cctgccattc acgtcagcca  66300
accacacagg gcctgggaca ggaactgcag ggaacacata ccaacactca gatccctgga  66360
taaggcttgc gtgcgcattc cctggggcac aaaacatgcg cacaaagcat tgtgtcccca  66420
ccccactgcc ctcaccaccc ctcctttgct ggggcatagg gcagaaccca cagcagacgg  66480
aaattcccag gctaggggtc taattggagc tacaactgcc ggcctacatc acagccacag  66540
caacgccaga tccaagccac atccacgaag tacagcacag ctcacagcaa cgccggatcc  66600
ttaacccact gcgcgaggcc agggattgaa ccagcaacct catggatact tgtcagattc  66660
atttccactg taccccgaca ggaactccac cactcctcct ttaagagact ctatttggca  66720
ataaagccag agccaaggct ctggcaagag ttgcagccag gtctgatcat aggcagccaa  66780
ggtctgtggc cctccaagcc gggctgggac aagccaagca gatcagctcc tcggctggag  66840
atttcaatga catattttta ggtcagcctc tctttagaat tgcaaggact tttataaata  66900
attctgggtt aagtatattc cacatgatga cccttctgcc ttcagtccac agtccaaatc  66960
tacatcactc tctggtgtcc cagactgacc cacctggctt ccctctctca agactaaggc  67020
tgaagctttt atcagcagac cttgcagccc agggcagggg gttgggcagg ggggaaacga  67080
ctttgcccca gttgcccttg ggaggccact tacccacaag tgtgggttaa gtaaagggca  67140
ctgcggtcac atgcccagtg tgccatctgg cttcagcagc caccgtcaaa gagggaagaa  67200
aaagtgacat gcaacagaat gtaaccgggg catggcctgc aggatgccca gggacctggg  67260
gggcagaggg gtgccaaatt catgggggc ttctcagaga gggtggtgat taagatgggc  67320
cttgaaggat gtgtaggagt ctgtgggagg gtttggggag gaggtgggag ggtgtcctgg  67380
gcatggggaa aagtccagag ccatcgaacc aggagagggt ttcaggaatt gcagcagttc  67440
cctcaggctg gagcagaagt tccaaaggat ggagtggtga gggtggtgag ggcttcagag  67500
ggctgtctgt atgggacctt ggaggtcacc caaaggaatg tgtgctttat cctgagagca  67560
gagggagcct tggaaaagat ggaaaactcc aatcaattag gtgtttggaa atgagactta  67620
ggctgcaggg agagggtgta taggaacaaa gaacagggag catgcagcag caggggctgg  67680
gctgaagagg gctgcccacc agcacagcag gggcaggggg gctggaagga aagggtctct  67740
tttttttag ggccacacct gcggcatatg gaggttccca ggctaggggt cgacttggag  67800
ctgtagccac tagtctacac cacagccata gcaatgccag atccttaacc ccctgagcaa  67860
ggccagggat cgaactcatg tcctcatgga tgttaattgg gtttgttaac tgctgagcca  67920
```

```
tgacaggaac tcctaaaggg acactttgga gagctggtaa aggggtggga ttgactgaac  67980
tagattagac tggaggggaa tgtttgttat gcagcataac tgcagccaaa gctaacagag  68040
gggccacatg agcaaatata tagagacaga aaggccactg ccatgcttga agaagcggaa  68100
cgatggtgct gatggtacca aagagcaggc tgtgtgatgg gcattagttt ggagagagaa  68160
agataggtgg ggacctgcac gagggagttt ctaacaaata tatgaagttg attggattgt  68220
tgttcccaag tatctattct gggccaatag gcagagctta tcgcagtccc attgacttta  68280
gactcagtca catgaccagc tttgaccaat ggaatatgga tagaagtgac catgtgccaa  68340
ttcagagatt taattttttt ttttttttt tttgtctttt gtcttttgtt gttgttgttg  68400
ttgctatttc ttgggctgct cccgcggcat atggaggttc ccaggctagg ggttgaatcg  68460
gagctgtagc caccggccta cgccagaccc acagcaacgc gggatccgag ccgcgtctgc  68520
aacctacata caccacagct cacggcaacg ctggatcgtt aacccactga gcaagggcag  68580
ggaccgaacc cgcaacctca tggttcctag tcagattcgt taaccactgc gccacgacgg  68640
gaattcctta ttttttttat tttttgtctt ttttgtcttt ttagggtctc acccacggca  68700
tatggaggtt cccaggctag ggtccaatc agaactgcag ccgccagcct atactagagg  68760
cacagtggat ccaagctgca tctgtgacac tggatcgtca acccactgag caaggccagg  68820
gatcgaacct gcaaactcat agttcctgat cagactcgtt tccactgtgc cacaacagga  68880
actccctcag agattttatg ttatttattt atttatttat ttggtcatgt agcagtttga  68940
tgtgggatct cagttgccag aacagggatt gaacctgggc tgcatcagtg aaagcacccc  69000
aagtcccaac cactagacta ccagggaact ctcagaaact ttaagaagca ttgaattatc  69060
tctttcttcc tccagctctc agcatcaaaa tgacacattc taggtagaag gagcagcttc  69120
agcctgggtc ctgggaggag aagatacatg ctgcagatat tctatcctgc tgccacctgg  69180
agcagatcta caaaaccatg cagttgcaac tgccttctgg ctgacaagca gtgtgagcaa  69240
taaataaacc tttgtggtcg taaactaaga tgggggggat gtttgttatg cagcataagc  69300
taactgatac acactatata tgtgagatga taaggatgca gatggtgaag aacatcacat  69360
gtcacgatta gttgttgtac acatggtgag tcaacaaaga attttgtaat tgatgaacct  69420
tctccacctt tcctttaaag ccaaccctct ccactccctt ctgctcctcc tagcccccttg  69480
ctctatcagc cacccccttcc ctcgcatgga ctgaatcctt cccctgaaac tatatctcac  69540
ttgtctcttc catcctaaaa tccttttctt tactctgtct tcctccaact ctagctcagt  69600
ctcttcctcg accatctcaa acaaacttct tcttcttctt tttttttttt ttttgtcttt  69660
ttagggccac acttatggca tatagaggtt cccagtgtgt gacctacacc acagctcatg  69720
gcaacgccgg atgcttaagc cactgagcaa gaccagggat ccaacccatg tcctcatgga  69780
tgctagttgg gtttgttaac cactgagcca caatgggaac ttcttcaaac aaacttctta  69840
aacgagttga ttctcctcat tatctccact tctttctccc tcacctccaa gcaatctagt  69900
ttaccttccc tccaccccac caaaaccatt cccagtatat ttcagcaatc taatagtcca  69960
gtgcaatcca gtccttatct tcctagactg ttccacatca tttagcttgg aactaaattc  70020
attttctccc tgcccaacct caaatattct tctttccatg gagttcctgt catggcttgg  70080
tggtaacaaa cacgactagt attcttaagg actccggttc catccctggc ctcgatcagt  70140
gggttaagga tccggcattg ctgtgagctg tggtgtaggt tacagactcg gctcagatcc  70200
ctcgttgctg tggctctggt gtaggctggc agctgcagct ccagtaagac cccccagcctg  70260
ggaacgtcca tatgccacag ttgcggccct aaaaagaaaa agaaaaaaaa aattcctctt  70320
```

tccatattct ctcagctagt ggcaccatca ttcatccagt gactcatgac agaaagccag 70380
catgacacag tgaattctgc tctgtagttg tccagtctgc ggtgcctttg agacatccaa 70440
gaggagatgt cccaagggca gcagctaaac atgtgaattg gggctgaca acagagatct 70500
gaagtggaga taccgatgac tgttagaggc agcatttaaa gccatgtgca tgcgtcaact 70560
tgtctattta taaagtacaa ggacctggtg atacatagag cgctctcctg agcctataca 70620
ttccccctcc taagaccaca attccaggta ccacttagtt ccttccttcc caagtcacgg 70680
ctcacagggg cctccatatc accaccttat ttcatattct cccccccaa catgttgcct 70740
tctccaacaa ctcttaaaat tcataaaaac agaagatata agataccact acccaggcac 70800
taaaatgcct aaaaaacaaa acaaaacgca ccaatgtgct atcactcaca tgtggaatct 70860
ttttttttt tttggcttta tttagggctg cacccaggcg gcatatggag gaggttccca 70920
ggttaggggt ctaatcagag ctgcagctgc cggcctacac cacggccaca gcatcatcag 70980
atctgagccg catctgtgac ctaccccaca gctcacggca acgccagatc cttaacccac 71040
tgagcgaggc cagggatcga acccgcatcc tcatggatcc tagtcggatt cctttccact 71100
gcgccatgac gggaaccccc gcatgtggaa tctttaaaaa aaaggacaca atgaacttct 71160
ttacagaaca gaaactgact cacagacttt gaaaaacttt cagtttccaa gggagacagg 71220
ttgggggtgg cggggtgggt gagggtttgg gatagagata ctataaaatt gggttgtgat 71280
gattgttgta caaatataaa tgtaataaaa ttcattgagt taaaaaaaaa tgaacaggag 71340
ttcccttcat ggctcagtga ttaacaaaca cgactaggat ctatgaggat gcaggttcaa 71400
tccctggcct tgctcagtgt attaaggatc tggcgctgtg gtgtaggtcg cacacagaac 71460
tcggatcctg cgtggctgtg gctgtggcgc aggctggcag ctgtagctct gactggaccc 71520
ctagcctggg aacctctaca tgccgtgggt gaggcaaaaa attaaaaaaa aaaaagaatt 71580
aattataaaa taaataaata aatgaacaaa tgtagatgtt aaacacttat catggaacac 71640
tcctggaaat aaaagaagat tagaactaaa aaaaaaaaat ggacaatacg caaacactgt 71700
cgaggatgtg gaataatcgt gttttataca ttgctgggga atctaaaacg gtacacccta 71760
tgacccaaca atttcaatcc taggtgataa caaaggtcca caaaagactt ctacaagaaa 71820
taatagccca acttagaaat aacccaaagg ttcatcgaga cgagaataaa tatgcaaatg 71880
atggtatagc cttagaatag aatactactc agcactaaaa agaaagacac agatgaattt 71940
cacaacatac acaacaacac aggtgagctt cacaaactat atatatatta catggaggga 72000
aataagccag atacacaaga gaaatacagt gtgattccat ttatgtgaag tccaagagca 72060
ggcaaaatta atcaatgttg aataaagtga gaaaatggtt gcttggaaga ggcgaaggaa 72120
aattgatagg aaatgggaac tttcctagga tgacgcaaag atttcatatc ttatttcggg 72180
tggccacttc aaaggtgcaa acaacagcta aaacttgtgg aacccaaccc tcaccacctg 72240
cgtattttat tgtttggaaa ttatacttca gttaaaacat taggaaaaga aaataatttt 72300
gtgaagtatc aataaaataa cgaaaatgaa gagactctaa agggcaaaaa cacattcagt 72360
tcaaatatat aaattatatt tgtgctatgt atgcatctat acgaatgtcc agcccccctt 72420
aatgtagccc cctttcagcc attctccgct caccccttgcc cccatcctga tggcctctgt 72480
ccatagccat tttctagctg tcatcagaaa tgatgcagtg aaagagcaaa agccttagag 72540
ccagatagag ctgcatttaa attccagctg ctgagcaccc ataatcgagt tactcggcct 72600
ctctgaacgt tcatttcctc aactacaaaa tgggttgatg agacacaatc aaccctgttg 72660
ggctggacta agagagaggc agtgtgctga ttagtttctg ggaaacctaa ttcttttgac 72720
ctcagcctgt gaaaccaact tggttgtgca aggcccactg ccggcctgga aaagcccaga 72780
ggatgagact cacgggctac ttctccctga aggataggga ggtggtcctg ggaacccaga 72840
gtctttgtgg gctggtgcta agagtcgagt cgctaactca gagccatcag ggccaggaaa 72900
acctatgacc tatgacaaag gagacaagtt tcctgccaag ggttggccac ctcaggatct 72960
tgcccaaatc actttgcaca cccctagatt ccatttatcc accaaaaatg gccagaggag 73020
cctggatctg aagaatttga tactaaaaac agcttctgga attcccatag tggctcagca 73080
gaaacgaatc cgactaggaa ccatgaggtt gggggttcga cccctgacct cgctcagtgg 73140
gctaaggatc cagtgtggct gtgagctgtg gtgtaggtcg cagatgcagt ttggatctgg 73200
cgttgctgtg gctgtggtgt aggccagagg ctacagctcc gattagaccc ctagcctggg 73260
aacctccata tgcctcgtgt gtggccctaa aaagtcaaga gttaaaaaaa aaaaaagagt 73320
taaaaacagc tactatgtct tgggagcatt gcgatgcaag tttgttctca gccaggcaca 73380
gggttaaggg tctggcattg ccacagctgc ggcttcggtg gcaactacag ctcggatctg 73440
atccctggcc tgctccatgt gctgcggagt ggtcaaaaaa aaaaaaaaaa aaaaaaaaaa 73500
aacccaaaca aatagcctct ggtgtttccc aatctataga agagatcaag gcaggaccaa 73560
actggttctg tccgaaagaa ggaacggaag agtcagagtc ggagccctgc cggctagctc 73620
ccctcctcca ccttggcgtt tcctgagcca ggatcctagg tctcccaggg gcaaagtttg 73680
aaatctccct gaccaggtaa accctagggc ctcttttagc tcagtcttat ccagtcgtgg 73740
tgcatctgtc aagtgtaata ataaagagga tctgcacctg cccccccacc ccatctggta 73800
ggggaggcaa ggtgcaccca gaaataactc cgagcaaggt acaaagtgct tagtgtagcc 73860
aaagaagcac ataagtccaa taaagcatcc acattccccc cccaccacac acacacacac 73920
acaacctctt cgcacttggc atttccttac ttccagcagt ctctctattt caggtttgtg 73980
gaaacgggtt ctccctggaa aagggtttcc cagctaggag gcggcccggc cccgactccc 74040
cctctccccc accacccccg gtccccgcac gtccagcgct ccgagaccca cccatttcca 74100
agcacaagaa caaggcgaca aggcccgctc aggggccaag aggagggcaa acgacgacaa 74160
gcaaagccac aaaagcaacc gtccgggtct cttgtctttc ctggggggag gagcggcgcc 74220
cgcagacggt ctccgcgcct ccctccctcc cgggccagcg ggaagatagg ggaatctcaa 74280
gtcgctctgc tttctctctt cgcgcactga cattttcccc cactttactg tttcttggac 74340
gcctttcaag agtttgtgca accagtctgt ttagctgctt ttctgccatt ttcaaacgcg 74400
gggtggtgtc cctttcgagt gggaacgtgg tggcttaaag tctggaaggg accccttcgc 74460
ctcccgtcac cccgctgcag cgggcctctt cgccgccaaa gtttcggcgt tccaaagttt 74520
cccccggccg ggtttcgggc tcggtcctcc gctctctgag ctccccgact tctccctctc 74580
tgtgcgctca ggggtttctg tgcccctcac ttcactctca ggttccctct tgcggaggca 74640
tcctcttccc acctagtccc gggcgaggga ggcctccgcc tcccctgccc cacattggga 74700
gacagacccc tccctccttt cgagacttcc cgggcagtcc tcctcctctg cgcgccccga 74760
gcctcccctc tcccgcctcc atccggcgga ccccgtggaa gcccgcagcc cctcaggccc 74820
gacaagatgg ggacagagac ggggtcagag ttgagcacag aggtaacgac gagaacaaaa 74880
gcggggacac ggcagggcag caacagggca gggccggcgc ggtggcctgt cctctccccg 74940
cgctgcctcc acggcgcccg cagccccggg ccgggcggga ctcgcggcct ccaggggctc 75000
gggcagcgcc cagcgggacc cacctgatcg gcagaagctg ggtgcgctcg gggatggccc 75060

```
acacctcggc tcccggcccc ccggcggcgt cctcggctga gggaacagtg gcgcgcggcg  75120

tgctcctgag ctcggcaggg cgtgccgggg cggggtgtgc cgcctgcgct ccggcccgcc  75180

ggccgctgtg tgctcctccg gggtggcggg caggggcgcg aggaagccgg cgggcactgg  75240

gcggcgggcg gcgagctccc cgctccaccc ggcccgcggc tgtttgtgca gagcgggtcc  75300

cgccccagac acggccgcta ggaggccgag ggcgcgagtg cgcgagtgcc ggtgcgcgtg  75360

tgtgtctggt ggccgggagg cgcagggggt gtttgtttca ttttcactca ggcagaaaaa  75420

agcctgaaac cagcaaaaaa agaaaagaaa ttccctggtg agggtggctg ggcctctttg  75480

ccttctccgg cctgcacgtg gtgggggtgg agggacccgg agggtggggt ggggtctatc  75540

acccagtact gcagggaggg gccccggag                                     75569
```

<210> SEQ ID NO 14
<211> LENGTH: 1116
<212> TYPE: DNA
<213> ORGANISM: Sus scrofa

<400> SEQUENCE: 14

```
atgaatgtca aaggaagagt ggttctgtca atgctgcttg tctcaactgt aatggttgtg     60

ttttgggaat acatcaacag cccagaaggt tctttgttct ggatatacca gtcaaaaaac    120

ccagaagttg gcagcagtgc tcagaggggc tggtggtttc cgagctggtt taacaatggg    180

actcacagtt accacgaaga agaagacgct ataggcaacg aaaaggaaca aagaaaagaa    240

gacaacagag gagagcttcc gctagtggac tggtttaatc ctgagaaacg cccagaggtc    300

gtgaccataa ccagatggaa ggctccagtg gtatgggaag gcacttacaa cagagccgtc    360

ttagataatt attatgccaa acagaaaatt accgtgggct tgacggtttt tgctgtcgga    420

agatacattg agcattactt ggaggagttc ttaatatctg caaatacata cttcatggtt    480

ggccacaaag tcatctttta catcatggtg gatgatatct ccaggatgcc tttgatagag    540

ctgggtcctc tgcgttcctt taaagtgttt gagatcaagt ccgagaagag gtggcaagac    600

atcagcatga tgcgcatgaa gaccatcggg gagcacatcc tggcccacat ccagcacgag    660

gtggacttcc tcttctgcat ggacgtggat caggtcttcc aaaacaactt tggggtggag    720

accctgggcc agtcggtggc tcagctacag gcctggtggt acaaggcaca tcctgacgag    780

ttcacctacg agaggcggaa ggagtccgca gcctacattc cgtttggcca gggggatttt    840

tattaccacg cagccatttt tggggggaaca cccactcagg ttctaaacat cactcaggag    900

tgcttcaagg gaatcctcca ggacaaggaa aatgacatag aagccgagtg gcatgatgaa    960

agccatctaa acaagtattt ccttctcaac aaacccacta aaatcttatc cccagaatac   1020

tgctgggatt atcatatagg catgtctgtg gatattagga ttgtcaagat agcttggcag   1080

aaaaaagagt ataatttggt tagaaataac atctga                             1116
```

<210> SEQ ID NO 15
<211> LENGTH: 371
<212> TYPE: PRT
<213> ORGANISM: Sus scrofa

<400> SEQUENCE: 15

```
Met Asn Val Lys Gly Arg Val Val Leu Ser Met Leu Leu Val Ser Thr
1               5                   10                  15

Val Met Val Val Phe Trp Glu Tyr Ile Asn Ser Pro Glu Gly Ser Leu
            20                  25                  30
```

```
Phe Trp Ile Tyr Gln Ser Lys Asn Pro Glu Val Gly Ser Ser Ala Gln
        35                  40                  45

Arg Gly Trp Trp Phe Pro Ser Trp Phe Asn Asn Gly Thr His Ser Tyr
    50                  55                  60

His Glu Glu Glu Asp Ala Ile Gly Asn Glu Lys Glu Gln Arg Lys Glu
65                  70                  75                  80

Asp Asn Arg Gly Glu Leu Pro Leu Val Asp Trp Phe Asn Pro Glu Lys
                85                  90                  95

Arg Pro Glu Val Val Thr Ile Thr Arg Trp Lys Ala Pro Val Val Trp
            100                 105                 110

Glu Gly Thr Tyr Asn Arg Ala Val Leu Asp Asn Tyr Tyr Ala Lys Gln
        115                 120                 125

Lys Ile Thr Val Gly Leu Thr Val Phe Ala Val Gly Arg Tyr Ile Glu
    130                 135                 140

His Tyr Leu Glu Glu Phe Leu Ile Ser Ala Asn Thr Tyr Phe Met Val
145                 150                 155                 160

Gly His Lys Val Ile Phe Tyr Ile Met Val Asp Asp Ile Ser Arg Met
                165                 170                 175

Pro Leu Ile Glu Leu Gly Pro Leu Arg Ser Phe Lys Val Phe Glu Ile
            180                 185                 190

Lys Ser Glu Lys Arg Trp Gln Asp Ile Ser Met Met Arg Met Lys Thr
        195                 200                 205

Ile Gly Glu His Ile Leu Ala His Ile Gln His Glu Val Asp Phe Leu
    210                 215                 220

Phe Cys Met Asp Val Asp Gln Val Phe Gln Asn Asn Phe Gly Val Glu
225                 230                 235                 240

Thr Leu Gly Gln Ser Val Ala Gln Leu Gln Ala Trp Trp Tyr Lys Ala
                245                 250                 255

His Pro Asp Glu Phe Thr Tyr Glu Arg Arg Lys Glu Ser Ala Ala Tyr
            260                 265                 270

Ile Pro Phe Gly Gln Gly Asp Phe Tyr Tyr His Ala Ala Ile Phe Gly
        275                 280                 285

Gly Thr Pro Thr Gln Val Leu Asn Ile Thr Gln Glu Cys Phe Lys Gly
    290                 295                 300

Ile Leu Gln Asp Lys Glu Asn Asp Ile Glu Ala Glu Trp His Asp Glu
305                 310                 315                 320

Ser His Leu Asn Lys Tyr Phe Leu Leu Asn Lys Pro Thr Lys Ile Leu
                325                 330                 335

Ser Pro Glu Tyr Cys Trp Asp Tyr His Ile Gly Met Ser Val Asp Ile
            340                 345                 350

Arg Ile Val Lys Ile Ala Trp Gln Lys Lys Glu Tyr Asn Leu Val Arg
        355                 360                 365

Asn Asn Ile
    370
```

<210> SEQ ID NO 16
<211> LENGTH: 38453
<212> TYPE: DNA
<213> ORGANISM: Sus scrofa

<400> SEQUENCE: 16

```
ctacccagag cacatcagga aggacttcca gtcaggtggt gtgaggggga gttttatttg      60

aaaatgattc caaaacctgt aagagataaa gtagaaaaac atgttttgga aacttccatg     120

cctgctgtat ttgccaaaat ctgttcagta cctggtactc agctttccct gaaagatagc     180
```

```
gtttctgtac tgtttcagat gttcatttaa cttagcattt ttgatacaga atgcagtcct    240
taaacatgac aattgtgtct tccttctatt tttctgtgac atgccttgct ttaaggaatt    300
cttgtatgta aaaatataga atctgtacac aaaaacatta ggacctagta ttggtgagag    360
ggcaagtaaa tgggttatat gttatttctg agaaggcgag ttggcttcct gaagatcagt    420
ctggcagagt atagattatt ctaagaaatc attatgaatt tatcctaaga aatttatcct    480
aagaaatcat tatgaaagtg tgcaagacac acctacatat ttctttgcca aaacatcatt    540
tcaaataatg aaaagttaga aacttacagg gtagatcaaa gactgttcag taatcatgca    600
ggtgtacaga cgtatgtata gtattatccc attttcattt tttgaaaaag tgcttgtggt    660
atatgtgctt gtaaacagaa aaagaaagat gaactagaca ccaaagtaca aattgctctc    720
tggatggtgg gatcatttgt ggtttaactg tttttgaat ttaaaagttt ttttttttcc    780
aaattttctg cggtagatct gtgttatttt tatgatcaga aaaatattta gtaaactaaa    840
tctcatttta aaagcaacaa agatatattg ggctatgact gcttcccaag attcatcaca    900
ggatcctttc acatttatga actttgctat caaaacagta tatagaaaaa tagtcttcag    960
aatcaatagc ccagaagttt ccaagatgta attttttta aaagaaaagt tatctttgaa   1020
tctttctcac tcaaatttgc tccatttcct tttttccaga acagaagtca gctacgaact   1080
ctgttgaaaa tgaacaaaat gttttcattt tgctttacaa atgaaatggt ttccaaatgg   1140
aatgttttac agacattaaa atagttgagg ttggagttcc catcatgact cagtggttaa   1200
tgaacatgac taggatccat gaggatgtgt gttcgatccc tggcctcgtt cagtggttaa   1260
ggatccggtg ttgccatgag ctgtgcttgt aggtcacaga cacggcttgg atctgacgtt   1320
gctatggcta tgacgtaggc tggtggctac agctctgatt agactcctag cttgggaacg   1380
tccatatgct gcaggtgtgg ccctagaaag acaaaaagac aaaaaaaaaa acccaaaaac   1440
tgaggttgac ctgtgtgtcc caacactaga aataccaaag atattaatga ataaaaaatg   1500
caaattacag atgtaccagg attacattaa aaaaaaaaac aaaacaaaac ccaggaatga   1560
taacctcccc tcctcaacta taagggatgt tttattgaga aaaaatacat ttcttgaaat   1620
gctgatatgc tcaaaaatag gcctggggtg atacaactat gctgttacca agtgttaccc   1680
tggagagtgg gtggagaaag gcaggaaaca gggttttgtg ggaggtgtgg ggttatttcc   1740
tttttatttt atataattct acattcttta aatattttta aagcaatttc aagatattca   1800
aaaagaaatc tataaagaag aaatgtcaag acaggcctgt gcgtgcaagc tcatggcaga   1860
agcggggtag gaggcttgcc tgcttcagac taaattcctg accttttcag agggtcagtg   1920
gtcatgaaag aatgcattct cccctcttgc tgattatttt gcaaatacaa aaatggcaaa   1980
tggggctttc cagcatttca gcacaaatat tccaactaaa gccctaagga cctatacggt   2040
tttgctatga gaaacttacg tggtttttga agctcaacca gggagaaact tggaggatca   2100
tccccttaac caactagttc accaaattca tgctcagagt tgggcaacat gggagatgaa   2160
tgtcttccag gatcacaact ttgccatatc accccatcct cattcttgtc atagtgattc   2220
ttagtaattt tgcagtgtct tcagataaat tctgaggagt ggagctgctg gatccaaaca   2280
caccctctcc ctttcataat gtccttccct tccctgtact ctaaactact tgtatacagg   2340
attgaagcac atgggcatga atgtccaaat ggtgactctt tgaaagttat cttcctaacc   2400
agatttgcct ttcaaggtta acaaagaaaa aagctctaac ggtggaatct ccatggccat   2460
caacactgca gggcacagtc agtcactgac tctgcttata tagccctggc ctcctctgca   2520
```

```
gcagcctagg gcacacacga caggcatttt cggacttaca gatgatggta tatatcagga   2580
tcccgctgaa gccgggtttg gaatcctatg tacaagtcat cccagagcag accattcttt   2640
accacgtgtc tgatgacatc aacccggctc cgaatctgaa acagaggagg aatcacgagt   2700
taggcgcaac ccagccagta gagagtgtca gtatggaccc ctcgtgtccc ggagagaagc   2760
agctgcctgt aagggcaggg atggaggaat caaggagaaa agcctactga agcagatctc   2820
acaggccgag ggggagaggg gcccctgagt gcagcagaaa tcgagggatg gaaacaggaa   2880
gtggatcagg agctgggggt gcagagtggc agagagtaca gacagagttg gatggctggg   2940
tatgaacccc caatatagct gtgtgacctt ggcaaccatt ctgtgcctca agttcctcat   3000
ctatacagtg gaggtaatag aacattcctc ctggggctgt tgtgaggatt acctgagcca   3060
gtgtacttaa aatactgaaa acaaggcctg ccacagagca agattacctt aattcggtgg   3120
tcaaggccct taccttcaaa gaatcccaac tcctgacaca ggatctgttg aatagtcaga   3180
ggtgcacagg gttaggagac aagcagagat ggttttgagt ttcagcccag cacttactaa   3240
tcatgtgacc ttaaccttgc taagcctcgg tctcctctgt gactgttgtg agaaaaaaaa   3300
aaagagataa ttcataaaaa aaaaaaaaaa aaagagcatg aagtagcatg aagggaagtc   3360
actctaagat tggactggct tcaacatttt atcggtaccc atgttcatgt ttaccaggag   3420
cttttcagta tctggcatca tatttttttt ttcctgagaa gtattgtgct aatgccagta   3480
gaggaaactt tatcataaat gacaggctat taaatgacat agaatgatca ggagtttggc   3540
attagggatt tacttctttt tcgttcacca ttcctataaa acaattacat ccactgtgat   3600
ctgagatcgc aacacaggtc aaaggcactc tcattttgcc agtagagatt tagaaacact   3660
gcacagtttg tcaggtcgag gactgcccag ctcaggggca gtatcaagat ctatttcctc   3720
acagtggagg gaagatggcc tttcttgacc tttcaatata gaggagagca cgtggaagaa   3780
ctaggggatg ttttgagcaa catttagggt gtaaactggg aagggcttgg agactcatta   3840
ggtttaggga tggagaagga aagattgaag attaagccct tgtttctagc ttggctcact   3900
gctgggggta ggggaaaggc atggatgttg ccaataatca agatggaaaa ggagaaagaa   3960
cagttgtaag aggattttga acacgctgaa agtgagatac caaaggactt agacatccag   4020
ggaatgatat ctctgggggg attagctcta catctaaagc tggacagtgt tggagagagg   4080
tgggcaaagg ccgggcagga cctatggatt tttggagtct ttagcagaga agtggtgcca   4140
gcagatgtgt tcacccagcc acagatttaa gaagaagagt gggttgagca cggaaccccg   4200
ggaaaagaag agatttaggt ggtggctgga gaaagagata tcttggaagg atgcagagga   4260
agaagagtca ggaagtaaag gagatgagga cttgtctctg ggctgagaaa ggacttctag   4320
ttcaaaatga tggaccgctc tcgtgcataa cccatgcaca tcttccagac tcaactgaag   4380
tgttgacaaa acaactgtac tgggctgaac tgcctcagag aagaagaaat gaagtgagtc   4440
actgacggca gtagatttgg actaactaat gtgaatctgg aaagctggca ggtaagaggt   4500
gtctgaggaa cagggcagag gctgcagaat cccagagagt ctgtgggggg acattcagat   4560
gcaggaggag gagaggtagg tatcctggac gacagcaggg acacacagca caaaacgatg   4620
ccatgaaacc gtggacccct tccctatgcc tcagcacggc tctgggccaa atgcattcag   4680
acagtgcact gaagaaatgg gatcaatttt gtaggaaaag tgtttgaatg agaccaggga   4740
gtgtacttgt gatgccccag agcaaggacc tccccgtctc agtatttagg ggtccctcag   4800
cccaatagct gaacgctcaa ctacacagct taaactgatg accccttgtc caaatacaac   4860
ctagatctta gttcattgcc tatagtccct ttaaaaaaaa atgaattagc tttccacatc   4920
```

```
tataaatctg ggtattacat atgaaaaatc cagatttctg agttttctag aaaattcaga   4980
agtacagctg gagctcagta agggccactc ccttcccatc tggcatttcc tggccacatg   5040
acacggtccc cacccagctc cacccaatta tgagatcttt ctgtggtccg tttatgagca   5100
cttgaggata tgacccctgc cttcaagtaa agcctgctgg ataaccactc caaacatata   5160
cagaaagccc tacctcagct tgaaaaggtc tttgttgttg ttgttgtaga tatagattaa   5220
tcccttaatt cttaaaagtc acctacagtg gaagaaagat cagcctggga taagcaacac   5280
tgcatgcaac tagaagccaa aggagcaacg ccttcgggtg tccatggaaa gtaacagcca   5340
cccagcatca tgggctcagc caagctatcg tgcaagacca ggcaggaaag tacctccagt   5400
ttagctcacg tgcaaatttt cttcctcaga ttcttaagca gaaggttcca caaaggagga   5460
aagcgaagaa agtgaagcca tggtggggtc tggaagtggg tcaaggatgt ctctgggtgg   5520
cagattggcg gcagacccag agaggagccc acccaaattg gagcaggagg atggagaact   5580
ccaggagcca tgcgtctaag gaagatggag acttgtgtac tagaaaatat atttatgagt   5640
ttgaaaggca attcacgtcc ctcctcaaaa agggaatatg agaaggctcc aggtagcaag   5700
aaaagagctc ttccaagtac cggcataacc tctttaaaca aacctcaaca actagaaatc   5760
tcacaaaatt cctgggcaat aaaagcactg agagtcaaag taaggaccac catgtacgtg   5820
acaggcatga tgctttgccc cagggtgtat caagtctgca agagagctgt ggcttacttt   5880
atcctacaga tgtattatca aaagctatgg aaaagtgact tactttcaat gaaacatttt   5940
ataggaactc gtggttttaa aaattccaaa gattatggtt aacagataat ttagaagttt   6000
tataaattta aatttgaaag taaaacagtg gctaaataca cagactctgg agatagactg   6060
cgtgtggtca aacccctgca ccatgattta cttgctataa gacctcggga aagttattta   6120
atctcttggt taaatatggc attttcctta tctgtaaatg ggaagtacag taatatctgt   6180
tcataaggtg gctgctgtat taaatgactt aatatttatg aagctgagct tggcaagagc   6240
aagttatcat gtatttggtg aacaaaccaa gacatttatg attctttttt tttttctttt   6300
ttatttttaa cagccgaatc tgtggcatat tctgggctgt ggaagtttct gggctaggag   6360
atgaatcgga gctgcagttt gtggcaacac cagatcctta acccatcgag tgaggccagg   6420
gatcaaactc acattctcat agagacaatg tcaggtcctt aaccagttga ggcacaacag   6480
gaactcctta tcagatgcat tttgctctaa atgagtgttt cacacagggt gttcctgtgt   6540
gtgaaaaccc agggattttt tttaactcag aaagctggca gtggattatt ggtttcactg   6600
aacttttggc ataggctttt cttcaacagc aagtgctaac ataccaatga ttaaaatgta   6660
gtttaggaac acatctatta taggaagcta catttacacc tctacaatta agtcgccaca   6720
cattcatgtg acacatgtaa tatgcttaaa ggtggactat atatcctcct aatttattta   6780
gtgattcatt tatatagaat taaaaattac aatgtatgct cacatatatc atgtcatttg   6840
actgtcataa aaaaaactga taaggtggca agaagctcaa tagaatggaa aaaaacaacc   6900
tttggacagg gattcaaagc ctcattattg gttatctgaa tcagtcgggg tgaggcaccc   6960
ttcttggtct tgaccttgtg tccaaagccc tagttcttaa catcatgcct ctctgccgta   7020
ggtgagggat ttgctcaaaa ttggagctca acaaaatatg tgttggttta tgttgactta   7080
actccctttc cagagccaca ctgggtttgt ttggggaagg agacaccact ggagagaagg   7140
caaggagggc agagatcagt gcttgcaggt ctgagaacag cataagcagg ccagctgttt   7200
ggaaggaagc aggtcaagaa gccagtcttt gcaaatgact caaaaagaag caagtacgga   7260
```

```
gttaatagta atgtttcagt atcagagtat tggttgtaac aaatgtaccc cagtaaagta   7320
agatattaac aataatttgg agttcccatt gtggcaaagc ggaaacgaat ccaactagga   7380
accacgagga tgcaggttca atccctggcc ttgctcagtg ggttaagaat ccagctgtga   7440
gctttggtgt aggtcacaga cgtggcccag atcctgcatt gctgtggcta tggcacagac   7500
tggcagctgt agctccagtt caacccctag actgggaacc tccatatgcc acaggtgtgg   7560
tcataaaaag caaaaaaaaa tttatatata tatataaaca ctactgtctg taatatcctt   7620
gcaacttttc tgtaactcta aagttgttcc aaaataaaaa agtttattta ggaaggaagg   7680
aagaaagggg cacttccact ggtattcctg cttacttcct catatggatg ttcccggctt   7740
ggtctttctt ttggaaagga taaatccaga aagtcaacca aatagtcata tcctccaggc   7800
aaagggctga agtcctcatc tgtctcaatc atctgttcaa atgacaacat ggtaaaggga   7860
agaagcatat caatctggcg gtcaaggtcc ttagaaaatt ctagaatgtg caagacccaa   7920
gtgcccttaa atgatagcaa tgaagcagaa ttaatacaaa aactgtctct cctctttgct   7980
ctctcccact gccccatccc tctacccatc cctctccctc cctccctctc ttctttcttg   8040
aactgaattc aaatcctagc cttctacact agcaaaacca cttcataaca ctaacttaaa   8100
taaaatttat agagaaaatt atcattatct tagtaatgag atatcaaatt ggctaaaaaa   8160
taataaaatg tggactgttt ctcatcatca catagtagct aaatataaaa gagtatcatt   8220
aggagttccc gtcgtggcgc agtggttaac gaatccgact aggaaccatg aggttgcggg   8280
ttcggtccct gcccttgctc agtgggttaa cgatccggca ttgccgtgag ctgtggtgta   8340
ggctgcagat gcggcttgga tcccgtgttg ctgtggctct ggcgtgggcc ggtggctaaa   8400
gctccgattc gacccctggc ctgggaacct ccatatgctg cagaagcggc ccaaagaaat   8460
agcaaaaaga ccaaaaaaca aaaaaaattc ttccacctac tatcctttta ttttatgaaa   8520
ggaaagatgt tttcacacct caaaaataga aaggacctaa tcttggaata atgacaattc   8580
gtccaaagga aagagagttg acatcttggt gaccatactc agatgtgtgc tcatacttat   8640
ttcgttactg accagcaaaa actttgtcac agactgtcac tgacccccag gttgaatttt   8700
aggattcatt gattttgagg atggcaagtg ttgcctggta cccagtacta atgttcaggg   8760
gttgaaattt aaacttggaa atagtcttta ccctggaggt aactgatctt tgttcctaag   8820
ggtatgaata ctgtgcattt cccgatgctt tccctaaact ttgctctcca ggcacacatt   8880
caggcactaa atataagtag gataaaatat aagtatggca gggattccca gaccatttta   8940
ggcctcctct ttctcttgca tcccgctgcc tgttgctact tattttgctt ttgtggacat   9000
cctcagtttc agtgaccagc ttataagctg aaccacttag ctggtgagct ctgtgtgtct   9060
atgtcagggc taacttaagt tctagatcta ggcttacttc ccagttggtg caattcagtc   9120
cttacccagc tgcagtcctt accttacctg cttccaggct gctacaggac accagctctg   9180
cagtggagcc acctgtctgt cccacaattt atttattttt tattttttta tttttttgcc   9240
tcttaaggcc acacctgcag catatggatg ttcccaggct aggggttgaa tcggagcttc   9300
agctgccagc ctacgccaca gccacagcaa tgcaggatct gggctgcatc tgcgacctac   9360
atcacagctg acagcaacgc tggattctta acccactgag caaggccagg gatcgaacct   9420
acatcctcat ggatcctagc tgggtttgtt aactgctgag ccatgaaggg aactccccgt   9480
ttcacagttt attttactta tttatttatt tatttattta ttttgtcttt ttgctatttc   9540
tttgggccgc tcctgcggca tatggaggtt cccaggctag ggtctaatc ggagctgtag   9600
ccgctggcct acgctagagc cacagcaacg cgggatccga gccgcgtctg caacctacac   9660
```

```
cacagctcac ggcaacgccg gatcgttaac ccactgagca agggcaggga ccgaacccgc   9720
aacctcatgg ttcctagtcg gattcgttaa ccactgcgcc acgacgggaa ctcccccgtt   9780
tcacagttta aatagctgtc actgccataa ccaacacaac acaatacaac acccacaaaa   9840
acccaaaaca aacaagaacc aagacacggt gatggaggaa aaagaatcct ccaaaagaaa   9900
aacagagctg gatctacatt tcattcccta cattttcaac attccctaca ttttcaacaa   9960
aggattgttt cagcacatag tccaatacgc cctccgtctg acagtcagta aggctcaatg  10020
aatgcttatt gagaaaccaa ctggaatact aagaggtttt catatagctc tgtaatataa  10080
gaaaacaaaa acaaataata acttcatagc ataccctgac caccaggtta taatccttaa  10140
atccagccca agtgaagtat tcttttatcc aggatgagtg acgaaatatt tcatctccta  10200
tagcagcatt caagatattc aaatatgggc caaaatccca ggaatccttg taaatcttag  10260
tcccttctgg aggctctacg atgcccttgc ttaaagacac aaaggggaga gaacaatgaa  10320
aaaagaaagc aacaaataag gaaggcagaa gtttgcactt ctacatcaac agtcaactgg  10380
atgagcagct ctaaggctgc tcagatagat gatgcccagg ggtcccacag atgtgcctca  10440
gggaacattg aggagtaggg ccccacccca gcctaaacca ggtcagctcc tgttaattgc  10500
ttagtgtgat agctctccaa gtcagaatac atttaaagac gaagtctgga gttcccgttg  10560
tggctcagag ggtgaagaac atgacatagt gttcataagg agacgggttc catccctggc  10620
ctcattcagt gggttcagaa tctggtgtta cctcagctgc ggtgtatgtc acagatgcag  10680
ctcagatccc accttgctgt ggctgtggtg tagaccaggc agctgcaact cccattcaac  10740
ccctggcctg ggaacttcca tatgccgcag gtctggccgc aaaaaagaaa aaaaaaaaaa  10800
agataaagat ccatgtccgg ggaaaaaaaa agttggaata ccacggatgt ggaccctttg  10860
ggctcaaata actaaattat gaaaatgttg aatataagtg gtcttactga ttttgtggac  10920
atccgcttat tcctgccctg cccccacctc cattagacta caagtatgat gaaagcagca  10980
accatgacag tacacagaag ggtcccata aatatttgtt gtacatagga ataactctag  11040
cctatctttg agctacacct agaattttgt gtctctcata tacagccctc ttattatact  11100
aataatacca cagctgatag acagatgggc tgacaggaga cccagtcagc agtatggaca  11160
agagtgtgct ctgacatccc tagagctgtc catccagtgt gaagatggat cactgcatgc  11220
aaggtggaat cttgagtcct ggcaatagaa taggacgtga tctggagaaa ggaaatatga  11280
ggagggaaat aggcatctgt gtagtaaaga tttggcaggt aatggtaggt ccctacattc  11340
cacttctcca aacactgttg gcccaaagcc ggagatgcac tggttttggt gataaattat  11400
gtgtcagatc ctaaaatgtc taacttctaa atgaatctca tatctgcttc tctaaatcct  11460
tgctccatct cagccagcag cctcacttat ctcctcctgg aaaaaagcac agtctcccag  11520
ctggcccccc tgactctagg agttcttccc caggacatgg tttttctaaa acacaatgca  11580
gtaatattcc ttctttgctt tatcgctttc tcaagctctc cttactcaca ggcaagttcc  11640
ttgccctcca ggcaaggtct tataaggact ttctgaccct ggtccaacac ggcatccctg  11700
tctcatcctt ttcctttacc ttcatttact gaaggggatg aatgacttca taagggaagg  11760
acctcttcac agctgtttcc cctgtactta gcatgatgcc caaaggagct caataaatca  11820
tttctggaag aatggcatac atctatgcac ttattcaaag taattgtact cactaagagc  11880
attgtaaatc aactatattt caataaaaat attaaaaact caaagtatct gcactcacca  11940
aacctatgac attattttca ccccctttct ccagcatatc cctctgactg gaacctcaat  12000
```

```
ctcttaatca ctctattggt aaccttctcc tgacctctaa gacatagctc aaatgcctaa  12060
gattggaggt tgagcattcc ctgtccacat ctcctgttct ctctagccct ctccctacct  12120
cacaaggcag agctgagcac tcagtctccc ggaatctctt atactttgtc ttactactga  12180
gaacctaaca tcaactctca ttacccagaa tgctttggtg tgacacaatg atgcatatgc  12240
agattccagg gctctgcttc agatctactg aatcagaatc tcagggggtg gagcccaggg  12300
agctgcattt acccagtttc cttgggttac tctgacgctc actctagttt gcgaatttct  12360
accataggat gcgtctgggg aactagagag ggataatgga gagagttcag caaatgccag  12420
gtgccagact cttgaattcc ccactaaaac gtgaaataat taaaatcttc tctcaccttg  12480
aactagagaa tgaaaactgc ctttatccta gaggcactgg agagatccta tggaatttta  12540
aacagggaag ggaacgggaa gagttttgca cttaaaaatc atttctttgg cagcagtgca  12600
gagttggagc tttcaaactt cttgcctaag atcccaggaa gaatatattt tacatcagga  12660
ctctaggggt ccatatgcca agagtatctg tgaaaccaga gtttcctgaa ataatactta  12720
cccttgttat atgtgctcag gcaacatact cagggttgtt ctatacaatt ttgttctact  12780
tctttttatt ttattttatt tttgtctttt tttttttttt tttttttttt tttttttttt  12840
agggctgcac ttgcagcata tggaggctcc caggataggg gtctaattgg agctgatgct  12900
gcaggcctac gccagagcca cagcaatgcc ggatcagagc cacgtctgtg acttacaaaa  12960
cagcccacag caatgccgga tccttaaccc actgaacaag gccagggatt gaacccgcaa  13020
ccttatggtt cctagtcgga tttatttctg ctgtgccacg acgggaacgc ctatttcctt  13080
tttctaaatg ctagttgtga tgccattgat ttcctaaccc atcaatgaat cgtgaccagc  13140
agattgaaaa aggctggcat ggaggatgga tcagaggaca gcggggctgg gagcacagag  13200
gcaagtcagg ggccactgcc agaattctgg ttaaaaaaaa attgtgagag gctgaatcaa  13260
ggccacagca gaagaggctg gaggtgagtg atggattttt aagagatttg tgaaggagaa  13320
ttgaccagat ttgagctgtg ggaagttagt aaaagggtat aatcagctga ctgtgtccca  13380
gaccccagct ttgcaaaggt aaggccagga gaagggtgtg cttttggtaa ccgtgtgccc  13440
tgatctccaa cagagtcaca gtccacttct aaataatggt gaggaatgat ggttccatcc  13500
ggctcaagac aagtacttat aaaaatacag gtctggaaca tccacattaa tgtttctgaa  13560
ctgtactccc agggcaccgt taattgttca aatggactgt ctggggattg gcgaggaggt  13620
aatatttaca ctgataggaa cactaactct caggcttatt gctttctact tgctgaagac  13680
aacttatttt tgagctgtaa taatggccct tcataaaaaa aactttctca ctctttatcc  13740
tgaagtaagg ttctgagaca aggaaaacat ttgagtaatt atcttattta tttatttttt  13800
tttcaaggcc acacccacag catatggaag ttcccaggct aagggtctaa tcagagctgg  13860
agctgctggc ctatgccaca gccacagtaa cgtgggatct gagccgtgtc tgccacctac  13920
accacagctc acggcaatgc cagatcctta acccactgag gggggccagg aatcgaaccc  13980
gcatcctcat cgatactagt cgggtttgtt attgctgagc cactacggga actcctaatt  14040
attttatagg ataagaaaat tattatatag gactgtgaaa aaactcagtc tcccccccac  14100
cccagagttg aaagatactt atttaatagt ttattttata cagtaagact cccactttaa  14160
agggtggtgt gtagatctta atgcatgaca agctcaggat gctagtcaag aaaaacttaa  14220
tattcctaca aacagggacc tgccaagagg ccataggtat gccctttatt ttctcataaa  14280
catgaaaaaa ttcagaaatc atttttgttc cctgtaaata ttcaagtcaa acctgtctgt  14340
tgggtccttt agcatcctac ccagatcaag agtggctcca ggtcttgggg tccaggttac  14400
```

```
cacctcagaa ttcttcttga taagattgtt gagttcattt gggtcatttt tgatgtttgt  14460
ttccttaata tacctgacaa ataagagcat tcccatgtaa ggcagtttat tttcagatga  14520
cattcttatt tgaacaatga cagaattatt ttttatttct ttgcattcct acttcccaat  14580
ccttcttttc ttaccccagg aaaaataaag actatacttg agctaatgtc cctgactagg  14640
gaagagctgt tagtcaaaga aggttgactc tatacttcgt tttttagtat aagcatatag  14700
tgtttggaat tgaagttaga tgtacaagac tattatacat aattggtaat agcacactct  14760
tgtatttaat ttttttttatt catactctct gttttcaggc tgcttgttaa aataagctcc  14820
agacccctac taatcattct ttctcatttc atgttgtttc acagctaaat cactcattca  14880
gcatatatta acttatgcgt aaacacgtta tataaaatat ccagccatac ttgtctgctg  14940
ggtgggattc cacgaaatac ccagcaaagg ggcagtaaat tctgggttgt aggtccttca  15000
ccagccgagc cttgtagttc aggagtttct tcctttctgt tttaatgaat tgggctttcc  15060
attcctctgg aatgacaggg tttggattag tcttctctgt tcagaaatca cagaaaaaca  15120
aaagttctag tagattagaa gtcttgcaag agataaaaat tgacagttga gtgatgcaga  15180
agtagaacaa agctccttgt cattagtggc tttattttgc aaagttggtt actaggaaaa  15240
tatcccaaac tagtcaaaga cattgaatcc cctctttgtt tacggcaatt catttggatc  15300
caactgaaaa cacagggcag catgcatagt tgtaccctgg gtgcatgcat attttaaggg  15360
cactgtcgat taactctcta ctaacatggg catggctttg ttattttggt ggaatataaa  15420
agtaaagtat gttcattaca ctctggagat gcacagtggt caagagcatg gatgttggag  15480
tcagtcaaga tcaaaatgca gctccaccac ttcaattctt taagtctgtt tttctcctct  15540
gttgaatgga atcatgatgc ctacctcacg tgttgttcat ttgttcgttt gctcattctt  15600
tcatttgatc gatatttatt gagcacctac tatgtgccag acgtagttct aggcactgag  15660
aatacagtgg cgagcaagat aaagcaggtc cctgctctca tggagcattc attctagtga  15720
aagaagcaaa taatgaataa gtaaataagt tcatttcaaa gagtgatgag ctaggaagaa  15780
aataaaacag agccaccaaa tagagagtgg ctggggtaag gatgaggacg ggtgggatgg  15840
aagggcatat tagaagggta gttagtgaag atgacatctg gaatcataga ccatagacac  15900
agacacagaa gagaagttgc tgaccacgtg gtggtcaggg gcaatagcac tctaagcagt  15960
agaaatagca catacaaaga cccagggcat ggagctacat ggtgtactga gtctgaggaa  16020
cgaaaaacaa gccagtatgg acttatgctt gtcaagcaat gggggtatgg gcaataaagg  16080
aaattgagaa attaggcagg gcccagagca tgtatggtac catgtcaggt actccttcta  16140
ccattactgt tatgaaaatt tgataaacac aaacaaggat acaggggaaa aaatgttacc  16200
tataagctag gtgtaaccac tatgaacatg ttagtatatt acagaccttt taaaatgtat  16260
gtgcatgtgc acatactcac acacatacac atactcacat aagaactgaa ttatgctacc  16320
accctttagt aggtatgttt tgcctcccta gtcacactgt taaccccata aggacagcac  16380
cttccctcat ctctcacatg gtgatgcatt ctgggaggca atgaaatcag acttacagaa  16440
aaaaggaagg aactggacag gttttcttct tattgcaagt agggcatttt tgacacatta  16500
ctaaacagag attacttact aaaaacatta atttattaag cagacatata ttgaacactt  16560
acaatgatag tactgagcaa aggtatgaaa aaaatatacc acttaaccat cctccccatc  16620
ccagccccag aaccaccctt agacacagag cagaagagct tctgccttgg tccccacatt  16680
ttttctagct ttgagatata actgacatct agtattacat aactttaagg tgtacaacat  16740
```

```
ggtgatttca tgacatgcat gtatggctaa atgatgacca caataaagtt agttaacacc  16800
gccatcacct cacataatta ccatttctgt ttgtgtgcac gtgtgtgtgt gtggtgtgtg  16860
tgtgtggtgt gtgtgtgtgt gtgtgtgtgt gtgtgtgtgt ggttagaaca tgtaagatct  16920
actctcagca acttccaagt atatagtaca atatgctatc tatagttgcc atgctgttta  16980
ttataccccct agaatttatt catcttgtaa ctggaagttt atactctttg accactattt  17040
tccctaccac ccccccaacc tctcgtaatc ccacacttta gaggggcttc cttagcctca  17100
tccctccccc gtatgagctt tccacgaggt caagggtatg tatccccctc aggctgccca  17160
cactctgttc tgaaccacat acaaagagca cttaagcctg gattaccaat gtcagactct  17220
ttctgatcag ctctatgttc tatgtcagga atccatttga tccaaattat tcttgatttt  17280
tcctgagatt ctccctagtc tccttagtgt ttcatgctcc atcagcatat tctcagctgg  17340
aaactttagt ctatatttgt gacttgcaag tatgatttcc caataagatt gcacacctct  17400
tgtgaggaag aaccatgtcc taattatctt tgtattgatt cacacagcat ttagcaaagt  17460
gccatgccaa ctccttggca tcattttgat ataaagaatt accagtaaat tttccaccac  17520
tgaaagtcat tggaaagcct gaagctcctc cagcaaaatc actcatcatt aatgcaacct  17580
tcataggcag ccttcctcca ttgggtctgg tgcaatccac tgtattgagt attttatgac  17640
ctgtgggaaa acaaaatggc atcggactca aggtgaaatc ttgaacacca tagtttgaat  17700
tctcaggcca acagtcttcc atgtaagtct atataatctg cctcattcaa ttatcgaaga  17760
attgctcaca tccaaggaaa agagagagta agatttgaaa atttatactc ttgagtgaca  17820
cattttgaac tttcaaggaa ataaattcat tctgtctgat tcagtgggtt ctgaatgagg  17880
acacttagcc tgattccact ccaggatcat aaacagacta ctttccttag caaactatat  17940
tcaaaggtta agctcaaagg atgcagagga aagtaatcag atcaacacaa ctctctcaac  18000
cttttggaaa ttcttttcga tgattattgg ggtaaagtgt atgattccat aacataataa  18060
tattcaagat gaaagtaaaa catttattca ataatgtcag ttttaaggaa attacaatag  18120
gtgaaatata ggatattttt atctgttgcc ttcaaaaaaa acctttgcac ctgtcacggc  18180
atagagtaca ttactaattg attctctgta agattatatg aatgacagtc cattttccta  18240
agacagagat agaatatact gtactctatg gaaaatgaag agggaagaaa cagatgaaca  18300
taggatgatg ttttggataa ctattattat cctttctacc aagagcaatt ttcattgctg  18360
atgagggtaa gaaaatacct ttgtattcca caataatgca agtgtccatc tcaggatgaa  18420
cgccatccat caagatcatg aatcgaagat ttttgtctac ctggaattca acaataaaac  18480
caacaacggt ttacatctat tttgctttta attcaatatt tgaagaaact gtcctctctt  18540
ctggaaagaa atccccttt ttcagaactg gatttgttat ccatcagagt cataccatgg  18600
ataattggag aggaagacca tcttatttca gctcaaatag agatttacac aggaccatgt  18660
acagaaaaag taggccattg tttctttagt cttaaaattt ctatctcgcc tcaaatttat  18720
cccagaaagg ataacccaaa catgtggaaa gaacacagac ctgctgccat attccaaatg  18780
gcactacatt gatattagtc aactggacgc cactctgatt cagattccaa aatacaggtc  18840
tttccgtgtt gccaacataa atgggaacat ctggtcttct ctcagcaagc ttcttcagtg  18900
ttgggtaact agggtcagaa agatatacag gttgaaaggt gaaaaaatag aataatctag  18960
tataagagag agtgtgatcc ttacaccaac acgttgaccg agaagcaagg aactgaaaaa  19020
ctagactctc cccagagtcc aaaagaagag ctctttcctc aaggctgact ataacagtga  19080
ggaggatttc ctgggagagt cctctttatt gttagaacat cccatatacc acggcatgta  19140
```

```
tatcaaacca ggtgtgcaaa ttccgtcttc cacactgatg ctgctttgtg caagggtagt  19200
tctaacagaa agtacagagt ggagaagtta cgccaaagag gtttctggtt tcatcttgat  19260
tttccttttt tttctcattc ctcagtgcag ctccctccca gtgagagaaa ggtctcggcc  19320
atatatctaa gagaacggat gggtgcccac cctggggcag tttttcaaac ttcgaaggtt  19380
gatagccaca catggtatac agaatgaact ccttgtcctt aaagagagtt agtcactaac  19440
taagcaagac aataaagttt agcacagagg aaaatgacat ttacctcttg tagcaatccc  19500
aagtcagtac acaatgaacc atccaagcat ttttgagtac ttacataagt tgccaacttt  19560
catttattag aatttattac ataaaaggat tatatactac tgtgtgggtg gcaaaacatg  19620
aacaataaac aaataaatgg ctctgtaggt atatttcaat catagtgtta cacactttca  19680
catgttattg tatttgattc tcaacaaaag accctttcat cttttagtgt gcttttaata  19740
aatgaggaaa cacactcaga aatatatgac taacaaatag taaattggta ttcaaattca  19800
ggctttctga tcctaaactt ggtgcttctt ctattgaaag gaaattctgg agttcctgtt  19860
ctggctcagt gggttaagga cccgacgttg tctctataag gatgcaagtt ccatccctgg  19920
cttcactcag tggatctggc gttgccctga gctgcagcat aggttgcaga tgcagctcgg  19980
atctgctgtt actacggctg taatgtaggg tggcagctgc agcttagatt caacccctag  20040
cctgggaact ttcatatgtt gcaggtgcaa ctgtaaaaaa aaaaaaaaaa aaaaaaaaaa  20100
aggcaattcc aactctaatg aatgtgctat caggtttaag aatcatattt gtacatagac  20160
tataatgtct ggtgatatag gatatttact cataagaaaa atataaacaa aatcagcata  20220
tcagcactta ttaaccatac taatattcaa gttccaaaac tatatttaat atgtagaatc  20280
cagaggggga aaatcattag gttttcttct ctaaaaacaa gggattcaaa aaaaaatcaa  20340
ggattctttg aacatgtctt taatctctgg gttaacatct aaatcttcca ctttaaaggg  20400
ctttgggagt taggataaat gattctaaca tggatgtatt ttaatttgtg atttttaaat  20460
tattgacaat tcttgctggt gtctattaat aacactatta taatactcat atatttacat  20520
aataaaatca catttctttg actaaagaca gttttctaaa gcatgctggc cccctccccc  20580
tttgtttttg tgaaccaata aggcattatt cagtaaataa aggtcagaca agagcaatgg  20640
agataaatga ctctggtgtt tattagttga gcaggtaaga gtcaaaaaac tcagggtcaa  20700
ttctgtcaag gaaataaact caaaggagtg aaaactgcaa ggcttggtaa cttttcagcc  20760
ataagctatc tgcaatacac tacccaacta aagcattgtg atactacagt tgagaagtgg  20820
ctttttaatg cctggcaact ttgcccacac aagcccctga aatcaaaatg aaattggttt  20880
tcaggacagt ggttgggaaa tgaccagact gaatgccata aaaagttctt atcctcacta  20940
aaatgtagta tactcccata gaatatctct tgctaggaca atggcaatag catcttgtga  21000
caggcactat aaagcaatcg cctccttatc ttgacactgt tctctctaag caagctgtac  21060
aaattgacta ccacacaaca tagttattac acaatgcatg aactcagggc tctcataatc  21120
ctgaaattac aagtttggtt ccagaacctc ctgtgggaca aagatatcat gtagtagaca  21180
agtagatttt taatcgtagc acaatactcc agtgggtggt attcggtttt taagtgtgtt  21240
acaggtaatt tgttactaaa gctgttaatt acttaagttt ttaaaccctt tccttaaaaa  21300
gcgagagaac acacctgtgc cttcgagatc tcatggactt tcaatagaaa aatccagggg  21360
ccagtcaacc aacaaacaat gtattttccc taaccatgga cattactatc aaagtatatc  21420
cttcatgtga acttgtcatg taaagtcaca ggaaaaaaaa ataaagttga aattgcttca  21480
```

```
ttttagaaca ccatgggcac tgctgggtat tggcaacctg gcagtagcaa tacaaatttc  21540
tcaataagga tgaacacata ggaccctgta atgaagccag ggggttggga ataggagcat  21600
tcacaaatat ttgtaacagt ccattcacaa atatttgtgg tttttgtcaa tgaaagttcc  21660
tctttctccc tcctatttga tcgcctggat tcaggaagtt tccgtttcta tccttagtat  21720
catatggctc tggtttcact gaaggatgtg gtggactcag ggttcaaaag ttgagagctc  21780
agtgttgtcg aaatgctaca gatcaggagt tggcaaaaca cagcgacctg ctgctgaatg  21840
ctaggaaggg cttttacctt tttttaaagg gttgaaaggg aaatcaaaag gcaatcatgt  21900
ttggtgacac aggaaactgt ttgtgatatt cacacgtcat tgcctataaa gctgaaggca  21960
atcaggctcc ttaggaccga ctatggctgc ttttgtgcta taatagtaga gttaagtagt  22020
tgcaatgcca accatatgtc ttgtaaaact ccaaacagtt tacactctgg tcctttgtag  22080
aaaatgtgtg ctgattccca ccataaatgt taaactaaaa aaggaagtca actttgatga  22140
tccttaaact cagagtttta ccaactagcc tgagggtagg acgtgagagg gtccagggtt  22200
attaacccca tgctcctttc cacaatagct cttctcacat cccaatggta taaaacagga  22260
aggcacttta aaaaggaggc tatgcatgtt gctatggcag tggcgtaggc ccggggctac  22320
agctctgatt cgacccctag cctgggaacc tccatatgcc acaggttcag ccctgaaaag  22380
acaaaaaaaa aaaaaaaaaa aaagttttta aaaaaagagg ctatgcaaat gcaagcattt  22440
atctgaatta gttctctttt tatcagccca agcgaatcta cctcagaatg agcagtgatt  22500
acaaaaaaag ctgaaaacca acagtgcttt tattgcagca ttttcttcgg agttgagggc  22560
tcacccttcc ttacctcagg tggtctgagt gcatgtgact gatgtaaatt aaatctgcgc  22620
ggctcagcct ctccagccaa tcagatggag gctcgtgtag taaccaccat cctcgcgcaa  22680
aagcaggacc gattaaccaa ggatcgaaca ccatcctctt gtctcccagc ttgaggtcca  22740
tgcaggcgtg agtaaggtac gtgatctgtt ggaagacagt gagattcaga tgatcggatc  22800
attaccagcc agaaaaagga actgggctgg ttagcagaca agccacatgg gggacctttg  22860
ctcctaagca tgttcaatga cacaggactc aagaaagaca cagcaggagc atttccgtag  22920
aacacaattc ccagcacagg cattacttta ttagaacaga aatgctcatg gtgggtttta  22980
ggggtcaaac cagttgattt acccaactca aatcacctcc aaggtattta attatgctct  23040
gtaccacaga atatcttttg ttaccagtct tttagaacac aatttacaag gaaagggagt  23100
tacagatgtt atggcagacc tctggggatt taaatggtag ggtggctgtg aataggtata  23160
agaatgactg gttccagtgg gtggacacag tcatgcagcc tggctgcact ggcttctaag  23220
gctttctcac ctaaattact tgcggactca ctcaggatgt caaggtcctt tgagaagggt  23280
gaaaaacaat gacttagaga caggcagaga ctacaggatt ctaaatcaac gccttactcc  23340
cttcccatag tctggcacgt ccacaggaaa aatgaaaaca ccaaggagca gagataaggt  23400
cacagaaatc caaatgtgaa aagccagcaa agaaggtagg gagaggtcaa gaaatcaaat  23460
gcaggtgatt gtgcctcttc tgggtaggtt cccatttgtc tcctcaaaaa agtaagagcc  23520
catttttaca agcttcccga atactccaga aaaattaatt tttggttgtt tacctctccc  23580
aaactaccaa agtgttttct ctggaggaaa ttctctctct ctctcttttt tttttttttt  23640
ttagggccat acctgcggca tatggaggtt cccaggctag ggtccaatc tgagctgtag  23700
ccgccagcct acgccacagc cacagcaatg ccagattctt aacccactga gtgaggccag  23760
ggctcgaacc cctgtcccca tggatactag ttgggttcgt taaccactga gcaacaacag  23820
gaaccccgaa attttctttt aaaagtggaa aaatgcacag aaaagtttgt aaagatctta  23880
```

gggcaatgtg cagaaacatg tagctggcca ttttatctga cagtgatctg gtagcaaggg 23940
cagtttctga acttcctccc atagctgtgc atgactctcc tttgggacct ctgctaaaag 24000
attttttttt taatctagat atatttcctt gtaatccttg ccaagttcct gaggttccta 24060
aataatgtgc tcaagaattt agaataggga gttccctggt ggtctagtgg ctaggacttg 24120
gtgctttcac cactgcggct caggttcagt gcctggtctg ggagctgaga tccacatcaa 24180
gccactgctc accatggaaa aagaaaaaaa aaaagacttc agaataactt tattatatgt 24240
cctaactagc cacttccaag aatactcaag gtaatataag atgtaaaaaa aaaaaaaaaa 24300
atatatatat atatatatat aaattgatat gttagcttta tttgtgtttt taagaatatt 24360
ataatttaac atttccttac ctgcacttcc ccaaaagcca aatcttcagg agatctgggt 24420
tctgaatccc acgggttagg aggatttagt tctagaagca aaactccatt ttcttcatcc 24480
ttttctacaa ctagaagcaa aggtggacaa atctggataa tcaaccaaaa aaatgacttt 24540
taaaaagcat cgctaagaca gaaatgcatg gctcaagtac atggagtaga caaatcaaag 24600
caaaatcaaa ataaaaggca acgctcattt gggtcaagca acatctgcag agatgagggc 24660
tgaagaccaa tactgttcat ctcgctattc acattccacg taaggaactc atgagatcgc 24720
agatgtgtca gagacacagg cacaccacca ccaacttcat tacaatcaaa tgaatgattg 24780
atagagatga gttcaaggtg ctgtggaagt gtctcggaag gaaaaccttg tttggttgta 24840
agagtcaaag ctgatttcaa ataggaggta atcctccagc tgaacttgaa agacaaagta 24900
tttgggggct gacaaaagag atgtgatgat gggatatctc ttttggataa aagataaaag 24960
gacaacataa aagataaaag aacagcatgt gcaaaggcat ggaggcatgg gagagctgga 25020
tgttcacaaa tgactggaat tttatgacca aggagaatgg tgtctgaacc aggtgggaga 25080
gacaggtagg tcagagtggg tcatgaagga ccctagattc ccaactaagg aggcgtctgg 25140
atttcatcct gtggcaatga ggggtcaatg aagaatttta agcaattgtg gcaggcatgc 25200
tggtggcttg cgcaaaacct attctctcct tctcccttac tattagcatc ctaattgtgt 25260
gatggtacac ctatttaaag atttcccagc cccctggcag ttatgagtgg ctatgtagac 25320
ctagcactat gtgcagttta catagttctg gcgggtgaga cgtaagcaga cgtctacttc 25380
agaagtctca cgggacttgc aggaacacat ttatttcccc gacaaagagg gacaactcaa 25440
gagaccagca ctgtctcccc ttcatccctt catatttccc cctcttgtgt ggaatttgac 25500
tgccatgctt ggaggagcac aagccatctt gagatgctga agaatagagc cagacactga 25560
ggatagaaca ggaggtgata gggaatttgg ctccttgata aacacagaac aaccataatg 25620
cccaggatta cctgcttggg atctaagaaa aacaacctcc tatatgattg agcaactttt 25680
gcctggtttt tctattgcac tggctgaaag caatacctaa gtgctatagc aagggagaat 25740
taaaatcaga acttaatttt agaaagaccc gctgtgaggc acatggagag gatcaattgg 25800
agggaggcaa gaccatgttt gagagtcctc tctgttgttc tggaaggcta tcagcaaacc 25860
actaatggac atgtgcttgg gagacagatg gcctgtttct agccctcact ctcccactta 25920
atagcttatt agctagagga ccttgagcaa cttatttgac ttctccagtg tttttatctc 25980
taaccctggc tatctccaca cacagttaat cctattactg ccagcaattt tattcattac 26040
taaatgaaag cagatgaggt cccaagccaa agcaaacctt gtggaaatgg cattgccgcc 26100
ctgccctcaa agacgagcac tttcctactt tattcaaagg acattaaaaa atgttttgtg 26160
ggagttccca ctgtagtgca gtgggttaag aatccaactg caatggctcg ggtagctgtg 26220

```
gaaatgcagg tttgatccct agccgggcac agtgggttaa aggatccagc attgccacag  26280
ctgcagtgta gggcacagct gcaacttgga gcctggattc aacccctggc ccagaaactt  26340
tcatatgctg tgggcatggc cctttaaaaa atgttttgct tacattttcc aaatgaatat  26400
taattatact cactttaaga caactgctag tggaagaaac tgaagtaaaa attacccgta  26460
aaatgaaaaa tggcacaaat gaaactttcc ccagaaaaga aaatcatgga catggagaac  26520
agacttgtgg ttgccaagag ggaggaggag ggagtgggat ggactgggag tttggggtta  26580
atagagcaaa ctattgcatt tagggagttc ccatcgtggc tcagtggtta atgaatccga  26640
ctaggaacca tgaggttgcc ggtttgatct ctggcctcac tcagtgggtt aaggatccgg  26700
tgttgccgtg agctttggtg taggttgcag atgaggcttg gatcccgagt tgctgtggct  26760
gtggtgtagg ctggcagctg cagcttcaat ttgaccccta gcctgggaac ctacctatgc  26820
caagggtgag gccccagaaa agacaaaaaa aaaaaaaaaa aagacaaaaa aaccccaaaa  26880
cacatataca atagatgcaa actattgcat ttggaatgga aaagcaatga gaccctgctg  26940
aatagcagag ggactatatc tagtcacttg tgatggatgc atattatctg catcctgggc  27000
tgcaatttcc tgatctgtca aataggatta tgatacatac tttgcagagt tgttgtaggg  27060
attaagtgat ataataaatc ctaaagtgtc actatgccta gcacagagaa ggcacgtaat  27120
aaatgatagt attattatgg caattatttc accctcaagg aataaagaat taaaaaggag  27180
gttcaagact gaacaaacag gagttactat catggctcag tggttaacga aactgactgg  27240
aaactcaggt tcgatccctg gccccgctca gtgggttaag gatccggcat tgccacgaac  27300
tgtcatataa gttggacccc gctttgctgc agttgttgtg taggctggca gctgtagctc  27360
caatttgacc tctagcctgg gaacctccat atgctgtggg tgcagcctta aaaagacaag  27420
agacaaaaaa aaaaaaaaaa aaaaaaaaac ccacaaagat tcaagaaaca aaattatatg  27480
ctagcacata accagttcaa aaatacaagg aattgggaat tcccattgtg gctcagcaga  27540
aacgaatctg actagtgtcc atgaggtcca tgaggagaca gattcgatct ctggcattgc  27600
tcagtgggtt aacaatctgg cattaccaag agctgtggtt aagtcacaga tgcagcttgg  27660
atcccatgtt gctgtggctg tggagtaggc tggcagctgt agctccagtt ggacccctag  27720
cctggaactt ccatatgcca caggtgcagc cctaaaagca aaacaaaaca aaacaaacaa  27780
acaaaaaccc aaaaaaaccg accaacaaac aacaacaaaa atcccaagga attacaggag  27840
actttcagaa aactacatcg atatccatgc ttaaggattt tccttcttta gaagtgttct  27900
ttttcaagaa aagcaggaaa aactgagtct gcagttctta actattattt caaagccaat  27960
accataaaag tttttatgcc ccttgctcaa agataaattg catttatgca ctgaagaaaa  28020
tcatgacatc tgccaactgc ctgcatcttt atagaatgtg gtatccttac tttgaccaca  28080
taaactaatg acatctaagt tatttggatt atgacttaat atttaaccag aagaacaaac  28140
aaatggaatt cattaaaatt tttaataggg aggaataatg aagaggaatt ataataaaaa  28200
catattagaa aactataata attaaatcat agataattgg cataaggacg aagagaggat  28260
cctaattaaa taacagttta atatagtcta agagaaggac cataaattag tggaagagga  28320
agggctgcct gatacacagt gctgtgcaat ggttagttaa gtattccagg tgcttaaaga  28380
cacaaagaaa agcaaccaag tgcttaaaaa gtatgaaaaa aatggcatat cacagggggg  28440
acttctaagt ttaatagcaa tggaaataat tccaatggaa aatcttagta gatagaaaag  28500
taaaatgaaa aatttctacc acctaagaaa atgggcaaac acacttggaa tatataagca  28560
tcgtatttga aaaacaagta taatttaaaa caatgatgct atttttggtt caaatgagga  28620
```

acgtttgaaa aactagaatg ccctgagctg ataaggaatg aggagaaaag gcaggctgat 28680
taagtagtta atgggaacaa aaattggttg ggttctaaaa aaatggatta taatgcaata 28740
cacattaaag aatgggtaaa tgaatagtgg actcattcat tcatttagga cctcaagtta 28800
agaggattat gttaaccata tttctcagtt catgacacat tatattcagt ccaggcagag 28860
ctacttactt actcccttta tctttgtttt ctactcttct ttactctcct cccctgtagg 28920
caaccatttg aaagttcatg caaaatattt actacattgt atgtgtgcat ctttaatttt 28980
tataaatggt attgggtttc caggctgttt cttactcttt ttcattcaaa tctatgtttc 29040
taagatacat tcatgttgcc atgtggacat ctcatctcta actggagttt cacataccct 29100
ggtgccacat tttattgatt catgctccca ggggtggacc catagattct gccacaacag 29160
gatttctttg gtacataaac aggcgtggga ttgatgggcc acagtgtatt cataaacctg 29220
ctctgcctaa ccactgtcag attactttcc cacatgactg caccggccat actcccacca 29280
caggcatgac gatttttata tcctttatcc ctgacatttg atatcacctt tgtttctaac 29340
tttttatcag tcaaaaagat gtaaagtaaa gcacctcatt gcttcagtct gtagttttct 29400
aataattaat aggtttgagc atattttcat gtgcttattg acttttggag atttttcttt 29460
tgtaaaatgc tagttcatat cctttcttaa tttttgtatt ttcttaattt ttatattggg 29520
tttcctatct ttttcttgtc gatttgcatt acttcctcct ataagctgga taatattccc 29580
tcattggttg taaatattgc aaaataatca ctcaaactat catatgttct ttaactttgt 29640
ccatggggtc ttccagttca tagaaatctg tagtgtatcg atgatatctt attcactagg 29700
tttgtgtata tgtgtgtttc tttttttcttt ctttttttccc tttgggctgt acttttgaag 29760
tattgtttga aaagtcaaga agtatcagta atctctaggt cacaaaaata gtctacattt 29820
cttccattac tttcatagtc ttaccttcct catttgagct atcagtccat gtgaagccca 29880
tctttatgtt aaagtatgag gtgttaaaaa aaatgggcgg gagttcccgt cgtggcacag 29940
tggttaacaa atccgactag gaaccatgag gttgcgggtt cgatccctgg ccttgctcag 30000
tgggttaacg atccggcgtt gccctgagct gtggtgtagg ttgcagacac ggctcggatc 30060
cagcgttgct gtggctctgg cgtaggccgg tggctacagc tccaattcga cccctagcct 30120
gggaacctcc atatgctgtg agagcggccc aagaaaatgg caaaaagcca aaaaaaaaaa 30180
aaaaaaaaaa aatgggcgaa agcatgagtt agtcatatcc ttttgccagt aattcatttg 30240
tctcacagaa acaactccaa acacaaagca gctcttacgc acaatgatca cagtttcgtt 30300
ttgatggaaa aaaaaaatta tgaacagtct aaatttcaac aacagaaaaa tggctaaata 30360
aatcatgtaa gttaatattt aatgtaaaca tactttataa ttgtgtatat atggaatctg 30420
acctaacatg actactataa taattttaac aagacaaaaa acaggataaa aaaagtaata 30480
tataaaataa ttacaattga ctggaacaac tagatagaag atgaacaagg aaatagaaga 30540
ctcgaacagc actataaact aactagacct aacagacaaa aaaagcacat tccaccagca 30600
gcagaataca cattcttctc aagtacattt ggaatattct ccagcataaa ctatgttata 30660
taaacgtttc aataaatttt aaaagatcag tcatacaaag tatgttctct gaccacaatg 30720
aaatgaaatt agatactaat aagagaagaa agttggaaaa ttcacaaata tgtggaaatt 30780
aaacaacata cttctaaata caaacagttt aggaaagaaa tcacaacaga aattacaaaa 30840
tgctttgata caaatacaaa taaaaacata acatgctgaa acatagaatg cagctaaaac 30900
aatgcagtgc atagaaggaa atttatatct gtacacacct ataataaaaa gaaagatctc 30960

```
aaataaaaaa actaaacttc caccttaaga aattagaaaa agaagatcaa actaaacaca  31020
aagcaaacag aaggaaggaa ataagaaaaa aaattagagc taaatggaat ttagaccggg  31080
aaaacaagag aaaatcaatg aagataaatg tttgtttttt gagggagttc tcgtcatggt  31140
gcttcagaaa tgaatccgac taggaacctg aggttgcagg tgtgatccct ggccgagctg  31200
tggtgtaggt cacagatgca gcttggatct ggcattgcta tggttgtggt ataggccagc  31260
agctgtagct ccgattagac ctctagcctg agaacttcca tatgcctcag gtgcagcctt  31320
aaaaagcaaa aaaaaaaacc aaaaaacaaa caaaacaaaa aagttagtta tttgaaaaga  31380
ttaatacaat tacaaacctt tagctaaact gaccaagaaa aaagagaaaa gacccaaatt  31440
actacagcca ggaattaaaa gggggatatt actatcaatc taaataatcc aaatgaaatg  31500
gagaaagtcc taggaagaaa caaatgaaca aaactgactc aagaagaact agaacgtctg  31560
aggagcagac ccataacaaa ttaaagagat ttaattagta atcaaaaaac ttttcacaaa  31620
gattagccat ggcccagatg gcttcactgg tgaatctgac caaatgttta aagaagaatc  31680
aataccaata tacttcacaa actcttccaa taaatagaaa aggagggaac acttctcaat  31740
tcattctatg agagcagtaa ttattactct gatccccaaa ccagacaaag atatcacaca  31800
aagagaaaac tacagaccaa tattccttat gaatatggac atagaaatcc ttaattgaat  31860
attagcaaat ataatttagc actataaaaa agaattatga ccatgagcaa gtggggttta  31920
tgctagcttg attcaatata ggaacatcca tggagacagt aagtagatta gtggttgcca  31980
ggggctgagg gaagaaggga atggactgct aatagttaga aggtttcttt gggggatgat  32040
gtgaatgacc tggaattata tagtgatagt aatagcacaa catgtgaaaa tactaaaaac  32100
cattgagtca aacactctaa aagggtaaat tttatggtac ctgaattgta ttccaataaa  32160
aggagaagga ggaagaagag gaggcagggg agaggcgggg aaggggacca aggtgacaac  32220
tggcagatac caaaacactg atggaaatgt aggtgagagt cttcttcctt ctactttcct  32280
aacatctacc ttttttaatg atgaccatac aatgttattt atttaacaat aaaaccaaat  32340
aatctcagct cacatgggat tgagccatcc ttttctttct tgggatgtgg tatgaaatca  32400
ctacagtatt ggtagcactg tactgaaaag tgggttctgt taacaaaatt ttctactctc  32460
acaacattac cttactggag cagaggctga aaactgcagt gggtcttgtt atttccagtc  32520
ctccactgac cctactgaca actctggccc tgcccttcac ctgccgtggc agtgaacatc  32580
aacgctttgc atcatttcct ggcctcagtc tattttccag tttacccaac tttctgctgg  32640
gtgggaaatc cctccttcct gctccacagg acccagtcac aaggcatatg gcagactatt  32700
tgagtcatac atatacaagc aaatcattac tctgtactct gtcgtaacac gttctgaaca  32760
tttaacagat gttctttcaa caacccagta aaatcactac taccaatatt atctcccatt  32820
gaggaaacta aagaacagag actaacccac ctaaagtcat ttaattgcat gtttgagcat  32880
caggatatga acccacgcta gtgagcccca ttcactctta accattttgc taaaaggtct  32940
cactataggt cttatccaaa agacttagct cccttaagga gctataagtt tctgggttac  33000
atactcataa agtagatggt caattgtcct ctcacctaca caaacagttt aagacagtca  33060
aacttttgct tcttatctct tttttttttt aatcagatga attaaatagt atttgtacag  33120
cacatgtaac cagttcctgc taacaatgtg atctgaagat ttcctaggct aggtcaacag  33180
acaaagggtg ggggctttct ggcaaaagaa ggaaatggtt caggcatccc tttgaggggc  33240
aaggtgagaa ttagtcaata tttccaaaag tcatttaatt gtgttagatc aaatctactt  33300
ttttatttat ataacagtca ttctaaaaca gtgtgtaaaa gcagttttaa gaatcttccc  33360
```

aagtaacttt ttatactgat aaagacattt ttaatcactt agaacagaga caaatttatt 33420
cctatgatta agcccttctt actcatattt ctataggctt tcttgagtag gaagaaggaa 33480
aaagtagaag tggagccagc atgagaatca cacagaagct gtagcctcta acgtgtgcca 33540
gaaagagtca tggaatttga aggactttat ttcccaactg gaattgtgag tttcattata 33600
acgtctcatt atatcatctc atttacgccg actctatctt atccatcttt gtatttctta 33660
atacctagtg caatgtttac acatggtaag gtctcatcaa atacttactg aacaaatgaa 33720
tgaatgaagg gattttttag agaaaacttg cctagaattt tcagtgatgg ttacttttaa 33780
aatacctcag tttaaaatca gaatgcatcc aaggcttcta atgagattgg aaacaagttg 33840
acaagaggga ccccaatgac agtaacagca gaaaacattg atcagtattg atggtattta 33900
cccagttcgt cttgacagaa gcttccagga ggattgatat acttcatgct gcttacatct 33960
aacttccagt tgtgttttgt gcatttaaca gacctggatg gaaaattgta cttaggttta 34020
tgaaatggtg aaaataaata ttaatctatt taaggcttaa atgcattatt ctgtgatcaa 34080
agtaaacgac tgtagttggt tgaacacaaa actcatgaaa ggaaaaaaat agctaatatt 34140
caaatatcca aggaaatata aactcatcat cagtaggtga ttttgaaagt gaagatattt 34200
tttccttgta tttgattttt gtcagtttga tttgtatgtg actttgcaca tttctccttg 34260
ggtttatcct gtatgagact cttcgtgttt ccctgacttg agtaaagtga agataaacac 34320
catggcacaa aataacgtgt tagagatcag cagagccatc agaataaagt ctgctttgga 34380
gttccaactg tggctcagca ggttaggaac ctgagcagta tccatgagga tgtgtgttca 34440
atccctggca ttgttcaatg ggttaaggat ccagcattgc tgcaagctgc agtgtaggtc 34500
acagatgcag ctcagatctg gcattgctgt ggctgtggca taggctggca gctgcagctc 34560
taatttgacc gctagcctag gaacttctat atgctatggg tgcagccctt aaaatttgtt 34620
ttttttttta aagaataaag tcatctttaa ggatgactct catacaaaag ctaagctgag 34680
taagatccaa gtggggccag tataaggaaa taatgtagta ataaagatta tctgtgattt 34740
aatagtcaca ctataaccct tggcccctag tatagtgtac taaacctaag atcaactcaa 34800
attttcattt gtctaagaaa aaagacttcc tgattgttta aagatttctg atcatggttg 34860
ccagataaaa tacaggaaaa atataaattt cagataaata aaaaataatt ttaaaatgtc 34920
ttacacaata ttgaacatat attggaaatt tgtttatctg taattcaaat ttaactactc 34980
agctttgcat ttttatttgt taactctggc aacactgctt cagaatgaga atcagattaa 35040
ttgtagcaac aaaggaggct tagtaatatt ttttccattt cttaccagac ggtgataggg 35100
atgtgatagt tggagatagg gcctaaaagt tccatttcct ctccatattt ggtagtctgt 35160
ctggctgtct ttctttcttt ctttttgctt tttagggctg cacctttctt tttgcttttt 35220
agggtggcat atgggggttc ccaggagagg ggttgaatcg gagctgcagc aacaccatat 35280
ccttaaccca cttagcgagg ccaggcatca aacctgtgtc ctcatggata ctagttagat 35340
tcatttctgc tgtgtcccag taggaactcc catattttgg tagtgtttcc agtcaagttt 35400
tttttaaac agttcaagat tttttttttt tttaacagac aaatatgtct tcaaccagaa 35460
atatcagatt gtttaagcta acaatgtcta ttttcactta tatatcagta aactatgctg 35520
attttttcca agcttcatta caatcaagaa tttttaatgc tcttttctag taacaaggca 35580
gaaaacatat tcaaacttcg acttatggag gatattttgt gacacttcct ttctcatcaa 35640
tgagtaacta acaactatca tggctcagag gttaacgaat ctgactcgta tctatgagga 35700
cgagagtttg atccctggcc tcgatcagtg ggttaagaat ccagtgttgc cgtgagctct 35760
ggtgtaggtc aaagattggc tcgaattgtg cattgctgtg gctgtggtgt aggccagcag 35820
ctacagctca cattggatcc ctagcctggg aacctccata tgccatgggt gcggccctaa 35880
aaaaaaaaaa aaaaaaaaaa aaaaaaaaaa aaaaaaagat gaaataaata aattaacaaa 35940
aattgaaaac attccaaatg cagctattca gcaggctggg tcgttaaagg agaaatgtgg 36000
cagtgtcaca actgctcatg ggcagtaggc agaaaggaga gagaggacag cttcatgtgc 36060
caagaggctg tgaaattaga ttgacaaaat gaggaccaca gcttatgaga gttcctgatc 36120
ttgattatgt acaaagaaga aaaatggctg aggaagggaa ggtggaacag gtaggtcact 36180
gcccttgact gtatcgtgga agagatattt caggtgaatt gctgcacaga gagcctaagt 36240
agaagcagcc aaatttggag agatggatgg gggagtgtac catgtaaact gctcttggga 36300
tggagtttca gcatataaat gcttggggag ctgtatctgg gagcaaagct gggtgaatct 36360
ggctccccac ctgcagcaga gctaagatgg tgccatctcc atgttagcct gccaacagaa 36420
taggttgaaa ctgggatcgt tcacccccta aggctttggg tgaaggagag gaagaccagt 36480
ctgtggcaaa gcaattacca tattaagctg agcaagccag attcaagaac agcctgaatt 36540
cctgtaaaga acctctgttc ctaagctacg caagatcatg gcagagtaat aataatagca 36600
aatgtaagtg acatttattg agcatgtatc atatgccaga cattatttta agtgctttag 36660
tgtatgaaat cactccatcc tctcagtagc cagacagaga aggctttgtc tactttcatt 36720
ttcactttat gaggaagaag agcgaggccc agaaaggcta agaaatgtgt ccgaggtcac 36780
agagctgcta agtggtggag ccaggcttct aaaccaagca gtttgcaagg aaagaccatg 36840
ctcttaatca taaagctgca acactccctt aaacaactgg ctaagacaac accacaggac 36900
atggcccact aaggagaaaa aaggacagag aaaaagcaga gtccccgggc cacaagtcgg 36960
aagacctcaa ggcctgcacg tgcctgcaga agcttcttgg tgacagaaca acctatggct 37020
gaggtctccc taacttgaaa ccacccagaa gatgcaaggg actcaaaagc agtctgtcag 37080
caaacaacca agaggttctt ccagagtagg ctgcctacca aaagtatgtc ccatgcagtg 37140
cctgaaacat atctaactaa aaatatattc gttgtttatc tgaaatgcaa atttgactgg 37200
gcaccctcta tttgcctaat ctagcaaccc tatctgcaga gccaagcaag ctacaggtat 37260
gacagcactt aacctgggag ctgggccctg aagctaagta tgcagtgatg caagtctgtg 37320
ggccagtgta agaagattcc agacttgggt ggtgatcttc tatacagtta gagcagggag 37380
ttcttggaca gctaccagtt acctctgagt ccattcgcac taaactgccc acagatgacc 37440
tgagaaataa gattgacgac acgacacggt ggaagacaag cctaatatgg aaacggctga 37500
aacactacga gagtcaagtt aggctgaagc aaagcttgaa agatggggtc aatccctcat 37560
tcattatcag tggtgagcat caggctgaca aaacacctcc acccagaact ccccctggct 37620
ctgcaagctg tgctagctct ttgtcaatca ctgaaaagaa agcccaacca tcctatccta 37680
gaattgctcc tgagatgggg aggtaagcga tatgcaggtt taatcaaggg gctggggaaa 37740
aggcgtacca gcactcgttc ttccaagaaa tgatcagaag agccgctgtt gaggccaggt 37800
gcagctagag ctctgccatt tttcgggttt tcatcaggga aagtctctct gttctagggc 37860
agtgtttgga caagcactca cctcacacac acacacttct gagagagcag gaaaggaaat 37920
ccaaaagagg cttgagtctt tgaatataaa agctggtaaa cacacacaca cacacacaca 37980
cacacacaca cacactcctt agaagtttca ctgtttatca actaggaata cattttaaac 38040
aatagttctt cagagaggat gggaaattaa gtcaaggtca taaatcaaaa tcagagagct 38100

```
gccgtaaagg agcttaagaa aaagttaggc atgtgctggg ggaaatagca tgttgattgg  38160

atcatttaaa atttctcaat gagcacattt cctgccaaac ctaattggga gaaaggatcg  38220

ccagggagaa agcaaaggat tctcagtacc ttccatttag atcctcaatg tctttaatga  38280

agaggcctcc ttggtgcttg cacatgttct tacatgcctt caggcggctc ttattcttaa  38340

ataagatgta atccttgcca gtgctcttat ttcgaacaaa attgattcct tccttgagat  38400

tggcagcttc ggcaggtgag aggcacaaca ggatctccgt cgtttgttcg atg         38453
```

<210> SEQ ID NO 17
<211> LENGTH: 1734
<212> TYPE: DNA
<213> ORGANISM: Sus scrofa

<400> SEQUENCE: 17

```
atgagcagca tcgaacaaac gacggagatc ctgttgtgcc tctcacctgc cgaagctgcc     60

aatctcaagg aaggaatcaa ttttgttcga aataagagca ctggcaagga ctacatctta    120

tttaagaata agagccgcct gaaggcatgt aagaacatgt gcaagcacca aggaggcctc    180

ttcattaaag acattgagga tctaaatgga aggtctgtta aatgcacaaa acacaactgg    240

aagttagatg taagcagcat gaagtatatc aatcctcctg gaagcttctg tcaagacgaa    300

ctggttgtag aaaaggatga agaaaatgga gttttgcttc tagaactaaa tcctcctaac    360

ccgtgggatt cagaacccag atctcctgaa gatttggctt ttggggaagt gcagatcacg    420

taccttactc acgcctgcat ggacctcaag ctgggagaca agaggatggt gttcgatcct    480

tggttaatcg gtcctgcttt tgcgcgagga tggtggttac tacacgagcc tccatctgat    540

tggctggaga ggctgagcct tgcagattta atttacatca gtcacatgca ctcagaccac    600

ctgagttacc caacactgaa gaagcttgct gagagaagac cagatgttcc catttatgtt    660

ggcaacacgg aaagacctgt attttggaat ctgaatcaga gtggcgtcca gttgactaat    720

atcaatgtag tgccatttgg aatatggcag caggtagaca aaaatcttcg attcatgatc    780

ttgatggatg gcgttcatcc tgagatggac acctgcatta ttgtggaata caaaggtcat    840

aaaatactcc atacagtgga ttgcaccaga cccaatggag gaaggctgcc tatgaaggtt    900

gcattaatga tgagtgattt tgctggagga gcttcaggct ttccaatgac tttcagtggt    960

ggaaaattta ctgaggaatg gaaagcccaa ttcattaaaa cagaaaggaa gaaactcctg   1020

aactacaagg ctcggctggt gaaggaccta caacccagaa tttactgccc ctttgctggg   1080

tatttcgtgg aatcccaccc agcagacaag tatattaagg aaacaaacat caaaaatgac   1140

ccaaatgaac tcaacaatct tatcaagaag aattctgagg tggtaacctg gaccccaaga   1200

cctggagcca ctcttgatct gggtaggatg ctaaaggacc caacagacag caagggcatc   1260

gtagagcctc cagaagggac taagatttac aaggattcct gggattttgg cccatatttg   1320

aatatcttga atgctgctat aggagatgaa atatttcgtc actcatcctg gataaaagaa   1380

tacttcactt gggctggatt taaggattat aacctggtgg tcaggatgat tgagacagat   1440

gaggacttca gccctttgcc tggaggatat gactatttgg ttgactttct ggatttatcc   1500

tttccaaaag aaagaccaag tcgggaacat ccatatgagg aaattcggag ccgggttgat   1560

gtcatcagac acgtggtaaa gaatggtctg ctctgggatg acttgtacat aggattccaa   1620

acccggcttc agcgggatcc tgatatatac catcatctgt tttggaatca ttttcaaata   1680

aaactccccc tcacaccacc tgactggaag tccttcctga tgtgctctgg gtag         1734
```

<210> SEQ ID NO 18
<211> LENGTH: 577
<212> TYPE: PRT
<213> ORGANISM: Sus scrofa

<400> SEQUENCE: 18

```
Met Ser Ser Ile Glu Gln Thr Thr Glu Ile Leu Leu Cys Leu Ser Pro
1               5                   10                  15

Ala Glu Ala Ala Asn Leu Lys Glu Gly Ile Asn Phe Val Arg Asn Lys
            20                  25                  30

Ser Thr Gly Lys Asp Tyr Ile Leu Phe Lys Asn Lys Ser Arg Leu Lys
        35                  40                  45

Ala Cys Lys Asn Met Cys Lys His Gln Gly Gly Leu Phe Ile Lys Asp
    50                  55                  60

Ile Glu Asp Leu Asn Gly Arg Ser Val Lys Cys Thr Lys His Asn Trp
65                  70                  75                  80

Lys Leu Asp Val Ser Ser Met Lys Tyr Ile Asn Pro Pro Gly Ser Phe
                85                  90                  95

Cys Gln Asp Glu Leu Val Val Glu Lys Asp Glu Glu Asn Gly Val Leu
            100                 105                 110

Leu Leu Glu Leu Asn Pro Pro Asn Pro Trp Asp Ser Glu Pro Arg Ser
        115                 120                 125

Pro Glu Asp Leu Ala Phe Gly Glu Val Gln Ile Thr Tyr Leu Thr His
    130                 135                 140

Ala Cys Met Asp Leu Lys Leu Gly Asp Lys Arg Met Val Phe Asp Pro
145                 150                 155                 160

Trp Leu Ile Gly Pro Ala Phe Ala Arg Gly Trp Trp Leu Leu His Glu
                165                 170                 175

Pro Pro Ser Asp Trp Leu Glu Arg Leu Ser Leu Ala Asp Leu Ile Tyr
            180                 185                 190

Ile Ser His Met His Ser Asp His Leu Ser Tyr Pro Thr Leu Lys Lys
        195                 200                 205

Leu Ala Glu Arg Arg Pro Asp Val Pro Ile Tyr Val Gly Asn Thr Glu
    210                 215                 220

Arg Pro Val Phe Trp Asn Leu Asn Gln Ser Gly Val Gln Leu Thr Asn
225                 230                 235                 240

Ile Asn Val Val Pro Phe Gly Ile Trp Gln Gln Val Asp Lys Asn Leu
                245                 250                 255

Arg Phe Met Ile Leu Met Asp Gly Val His Pro Glu Met Asp Thr Cys
            260                 265                 270

Ile Ile Val Glu Tyr Lys Gly His Lys Ile Leu His Thr Val Asp Cys
        275                 280                 285

Thr Arg Pro Asn Gly Gly Arg Leu Pro Met Lys Val Ala Leu Met Met
    290                 295                 300

Ser Asp Phe Ala Gly Gly Ala Ser Gly Phe Pro Met Thr Phe Ser Gly
305                 310                 315                 320

Gly Lys Phe Thr Glu Glu Trp Lys Ala Gln Phe Ile Lys Thr Glu Arg
                325                 330                 335

Lys Lys Leu Leu Asn Tyr Lys Ala Arg Leu Val Lys Asp Leu Gln Pro
            340                 345                 350

Arg Ile Tyr Cys Pro Phe Ala Gly Tyr Phe Val Glu Ser His Pro Ala
        355                 360                 365

Asp Lys Tyr Ile Lys Glu Thr Asn Ile Lys Asn Asp Pro Asn Glu Leu
    370                 375                 380
```

Asn Asn Leu Ile Lys Lys Asn Ser Glu Val Val Thr Trp Thr Pro Arg
385 390 395 400

Pro Gly Ala Thr Leu Asp Leu Gly Arg Met Leu Lys Asp Pro Thr Asp
405 410 415

Ser Lys Gly Ile Val Glu Pro Pro Glu Gly Thr Lys Ile Tyr Lys Asp
420 425 430

Ser Trp Asp Phe Gly Pro Tyr Leu Asn Ile Leu Asn Ala Ala Ile Gly
435 440 445

Asp Glu Ile Phe Arg His Ser Ser Trp Ile Lys Glu Tyr Phe Thr Trp
450 455 460

Ala Gly Phe Lys Asp Tyr Asn Leu Val Val Arg Met Ile Glu Thr Asp
465 470 475 480

Glu Asp Phe Ser Pro Leu Pro Gly Gly Tyr Asp Tyr Leu Val Asp Phe
485 490 495

Leu Asp Leu Ser Phe Pro Lys Glu Arg Pro Ser Arg Glu His Pro Tyr
500 505 510

Glu Glu Ile Arg Ser Arg Val Asp Val Ile Arg His Val Val Lys Asn
515 520 525

Gly Leu Leu Trp Asp Asp Leu Tyr Ile Gly Phe Gln Thr Arg Leu Gln
530 535 540

Arg Asp Pro Asp Ile Tyr His His Leu Phe Trp Asn His Phe Gln Ile
545 550 555 560

Lys Leu Pro Leu Thr Pro Pro Asp Trp Lys Ser Phe Leu Met Cys Ser
565 570 575

Gly

<210> SEQ ID NO 19
<211> LENGTH: 1328
<212> TYPE: DNA
<213> ORGANISM: Sus scrofa

<400> SEQUENCE: 19
cttatagtaa ctttattacc ttttttgtct gaacagttag tctttcttaa tgtttctagg 60
agagaacatt agttttattt tgaagagcac ccactcagcg tatttgtctt acataacatg 120
cagaacatgt atccacattt aaaaatttat ctcattgtag tacatacttt tacaaggtat 180
tccataaaca ctgaaaacta taagaaacat atacatctaa gaatcctact ttatatagtc 240
tttcactaaa taatactatt ttcatataca ttttcaggta tttctagctt ctcctgtgta 300
tttagaatta tgtatgtaat caccaagaga atatgggccc cttggaagga aagcagtaga 360
agcccacgga gtaaagatct ttctttaaaa agcaggtttt attattgttt taaatacctc 420
ttggttattt gagattctaa gaacttcgat taagtcccaa agtggaatga tcccttaata 480
accagacgat aggaaaggtg aggaaagtgt cagtagcagg gccaggactt ggcacattca 540
ctaagaatgt agcacctcag tgtagcttat agtatagtgc ctgggcagag ttactgctca 600
acagctcggg atgatgaacc atctgctgcc ctgcaagtgt gggagcagct aacttggtga 660
ctgcaatcca tggacagtta gggcttgatg tatggtgtat gtagagagat gatggcagag 720
gtagattctc tccggcccat ccttatcagt agtgccgtga ttatgcttct ctctgtgttc 780
gaggagatct tttagacctg taagaagaga gggagagtgt gaaagactct ggtttcagtc 840
tgagttctgc ttggaacaca ctgaattcat agataatccc aagttctcag gtgaagtgtg 900
gtgagatttc ctgctacaca atcattgtgt gttacagggg atcctttttta aaaaaggcca 960 ggaaaggctt gtgggaaatt tggtatcttt gcttggatag ttataactct gcctcaaggt 1020
tgaaatgacc tattgacact tctagatagg gaatcaggtg acttgatata ccacataaga 1080
tgacatctca gtatataagc acatgaaggt aatggcacag tggtggtaac actcttttaa 1140
gccaaagatt cccaggaagg cccaatgcaa atatttctaa cttcccaaaa ttgacatttc 1200
ttaaagagaa atacttctgc aagcagtagc aaacctacct ttctttgcta attgctttca 1260
gtaaattctt gatggtctta gactctggat tcagacatct tttctcccca ttctttttca 1320
ttgtggca 1328

<210> SEQ ID NO 20
<211> LENGTH: 1173
<212> TYPE: DNA
<213> ORGANISM: Sus scrofa

<400> SEQUENCE: 20
acgcggggga gacactcttc aactgctcat tctgagccta ctgcagaaga atcttcagct 60
gcagcaccat gaaccaaagt gctgttctta ttttctgcct tattcttctg actctgagtg 120
gaactcaagg aatacctctc tccagaactg ttcgctgtac ctgcatcaag atcagtgaca 180
gacctgttaa tccgaggtcc ttagaaaaac ttgaaatgat tcctgcaagt caatcttgcc 240
cacatgttga gatcattgcc acaatgaaaa agaatgggga gaaaagatgt ctgaatccag 300
agtctaagac catcaagaat ttactgaaag caattagcaa agaaaggtct aaaagatctc 360
ctcgaacaca gagagaagca taatcacggc actactgata aggatgggcc ggagagaatc 420
tacctctgcc atcatctctc tacatacacc atacatcaag ccctaactgt ccatggattg 480
cagtcaccaa gttagctgct cccacacttg cagggcagca gatggttcat catcccgagc 540
tgttgagcag taactctgcc caggcactat actataagct acactgaggt gctacattct 600
tagtgaatgt gccaagtcct ggccctgcta ctgacacttt cctcaccttt cctatcgtct 660
ggttattaag ggatcattcc actttgggac ttaatcgaag ttcttagaat ctcaaataac 720
caagaggtat ttaaaacaat aataaaacct gctttttaaa gaaagatctt tactccgtgg 780
gcttctactg ctttccttcc aaggggccca tattctcttg gtgattacat acataattct 840
aaatacacag gagaagctag aaatccctga aaatgtatat gaaaatagta ttatttagtg 900
aaagactata taaagtagga ttcttagatg tatatgtttc ttatagtttt cagtgtttat 960
ggaatacctt gtaaaagtat gtactacaat gagataaatt tttaaatgtg gatacatgtt 1020
ctgcatgtta tgtaagacaa atacgctgag tgggtgctct tcaaaataaa actaatgttc 1080
tctcctagaa acattaagaa agactaactg ttcagacaaa aaaggtaata aagttactat 1140
aagccaaaaa aaaaaaaaaa aaaaaaaaaa aaa 1173

<210> SEQ ID NO 21
<211> LENGTH: 104
<212> TYPE: PRT
<213> ORGANISM: Sus scrofa

<400> SEQUENCE: 21

Met Asn Gln Ser Ala Val Leu Ile Phe Cys Leu Ile Leu Leu Thr Leu
1               5                   10                  15

Ser Gly Thr Gln Gly Ile Pro Leu Ser Arg Thr Val Arg Cys Thr Cys
            20                  25                  30

Ile Lys Ile Ser Asp Arg Pro Val Asn Pro Arg Ser Leu Glu Lys Leu
        35                  40                  45

```
Glu Met Ile Pro Ala Ser Gln Ser Cys Pro His Val Glu Ile Ile Ala
    50                  55                  60

Thr Met Lys Lys Asn Gly Glu Lys Arg Cys Leu Asn Pro Glu Ser Lys
65                  70                  75                  80

Thr Ile Lys Asn Leu Leu Lys Ala Ile Ser Lys Glu Arg Ser Lys Arg
                85                  90                  95

Ser Pro Arg Thr Gln Arg Glu Ala
            100
```

<210> SEQ ID NO 22
<211> LENGTH: 16125
<212> TYPE: DNA
<213> ORGANISM: Sus scrofa
<220> FEATURE:
<221> NAME/KEY: modified_base
<222> LOCATION: (2290)..(2290)
<223> OTHER INFORMATION: a, c, t, g, unknown or other
<220> FEATURE:
<221> NAME/KEY: modified_base
<222> LOCATION: (10685)..(10784)
<223> OTHER INFORMATION: a, c, t, g, unknown or other

<400> SEQUENCE: 22

```
gcagtggaca gtgcgccacc atggagttgg ggcctctgga gggtgggtac ttggagcttc     60
tcaacagcag tgccgaccct ctgcagctct accacctcta tgaccggatg gacctggctg    120
gagaagaaga gatcgagctc tgctcaggtg ggccctcctc cctctggccc ttttcaagtc    180
cttccccagc cctctgcctg ccatggagcg ctgctcagca ccacggacag ctccagagcc    240
cgcccccgg gggcgggctc ctcgtgggga catctcccag cctgcccggc tacccctcc    300
ttccccacca gccctctttc ctggctcttt cctgcttcat ccaagtggct tttcctccca    360
gaacctgaca cggacaccat caactgcgaa cagttcagca ggctgttgtg cgacatggaa    420
gcagatgaag aaaccaggga aacttacgcc agtatcggtg aggaagcatt ctgagccaga    480
aaaaggacaa gcgaggggaa gaggcttctt ttctctttgg ttaatctcac ccactcacca    540
ggagccagca ggccctacct cagaaatctg ggccaggggg atggggagtg agggctggaa    600
ggacggagaa tcagggaaga agagagatgg agaaggggag ggaaatagac cccttcacca    660
atgaacacca ggcaattaag tcgcactttt acagagctcc cattgtggct cagtggtaac    720
aaccctgacg agtaaccacg agggtgtggg ttcgatccct ggcatcgctc agtggggtta    780
aggatctgct attgccctga actgtggtgt aggtcgcagg tgtggcctgg atcctacatt    840
gccgtggctg tggtatagac cagcagctgt agctctgatt tgacccctgg cccagggact    900
tccacacatt ttacatgggg ccctttaaaa aagacaaatc tcacttttac atcctctgcc    960
tctatttcta catctttttc tattagttgc tcttctttcc ttccttccca caaagcctat   1020
gtcatacacc gctccctctc tcccaagctc ccaagctaaa ctactctagt atttgtagta   1080
actaccattt ggggagcatt tgcagcctgc taatcgctgt gcgtgtctta tcacattgaa   1140
tccttacaaa gacaaaggaa gtagatattc ttagtatttt cactttacag atgaggcaac   1200
tgaggtttag cgagataaag caattcaccc atgtctgcgt tagagacagt aatgggcatg   1260
tctgaaattc taactgaggt cttattttta accacaaaaa ccaaagtacc tagggtgggg   1320
aggtttgcta aggcttaatc taagaggctg gtttgcagct ttattgtttt ttttttcttt   1380
tttagggcca cacctgcagc atatggacgt tcccaggcta ggggtcaaat cagagctgca   1440
gcagccagcc tgcaccacag ctcatggcaa caccagatcc ttaacccaca gggcgagccc   1500
agggatcgaa gtcgcatcct catggatact agtcgggttt actgctgccg agccacagtg   1560
```

```
ggaattcctt gtttgtagct ttaaaaagag cgacacggat cccacgttgc tgtggctgtg   1620
gcataggctg gcagctgcag ctctgatttg accgctagcc taggaacccc catatgatac   1680
aggtatggcc ctaaaaagac aaaaaaaaat taagagctgc attataaact acaacagaaa   1740
aaaatgttaa agactacata tgtacaactg aatcattctg ctctacactt gaaactaaaa   1800
caatattgta aatcaactat acttcaattt ttaaaaagag cctcagcttt cagtcaaggg   1860
tagaactctt tggggagaaa agtttctgtt ctgttgtgtt ttttgcgggg taggatgggg   1920
taaaggctct ctccttacca gggacatcgc tctcttatac agaggctttg ttcaaatata   1980
aaaagatgct ccttcttctg gaggatggag cccccattaa gaagtaacag cttgggagtt   2040
cccgtcgtgg cgcagtggtt aacaaatccg actaggaacc atgaggttgc gggttccgtc   2100
cctgcccttg ctcagtgggt taacgatccg gcgttgccgt gagctgtggt gtaggttgca   2160
gatgcggctc ggatcccatg ttgctgtggc tctggcatag gccagaggct acagctccga   2220
tttgacccct agcctgggta cctccatatg ccacgggagc ggcccaagaa atagcaaaaa   2280
gacaaaaagn ccaaaaaaaa aaaaaaaaaa aaaaaagtaa cagcttggct atcaaagtgc   2340
agtctggatt tctgcccctt ttgccctctt ggctaggccc ccttgtacag tgaacaacct   2400
tcacaactgt ttttagtggc ccttttcctg gcaacccagg aacgacatcc cttaggaggt   2460
ctggcataaa tgtggccagt ctttccacag cacagagggc agaaaatgga gaggaacagt   2520
aaccgtacgt gtctcaaaaa ttgcagaact gagagcctgc ctgtttcctt tcctttctgg   2580
gaatttactt gctggaagga gaaatatttg ggcctgaggg tattcacagt tcctcacaac   2640
tggaggtagt aacgaaggat ttgggctttt tcccaagtca cttaggaggg gggacttttt   2700
ccctttagag gcatctacac aggaagcggg agcatgtgga ggaggcagct tcgcccaagt   2760
ccgttcctca aacctgtgct cctagaatct ctggccaggt agtcatttga gcaaccttgg   2820
cttctataga gataaactgg gaataataat cccacctgcc tcgtggaatg actgtttctg   2880
tgcataaagt gattagaaca ggattttgca aagagtgagc actcagtaag tgtcaggttc   2940
caccccacca cgaccaccaa caccgtcatg tcatcattat catgtttgtc atcgtcttca   3000
tcaccattat atcttccctc catttcctca gcacagaagc cttgtatggc tccccactgc   3060
ctataaaatc aagtccaaac tttccccgac atgaaacttt taactgcaga taccagtctc   3120
taagagtttc ccaaacggct ttcctccctc tgtccccacc acccagaaag ccctcctctt   3180
tcctcctcgc agactctgcc ccatctttct ttctttcttt cttttttttt ttttttttt    3240
tttttttgg tctttttgcc ttttctaggg ccgctcccac ggcatatgga ggttcccagg    3300
ctaggggtct aatcagagct gtagctgcca gcctacacca cagccacagc aacacgggat   3360
ctttaaccca ctgagcgagg tcagggatcg aacccgcaac ctcatggttc ctagtcggat   3420
tcattaacca ttgcgcctca atgggaactc ctgccccatt tttcaaagtc tagctccagg   3480
acgtccttct ctgggacatc ctccctgatt gccccatccc actttacacc ctctcctgta   3540
tctcctgcca tgataactgt catcctgttg gctccaagcc aggttccact tcatacagtt   3600
tacaactgct tactgagtgt cagctgtgta ctgactactg tgttgactgc tggaaaggca   3660
aagcctatac gcctcaccat ccatccctga attgtaggca ttacttgttc tcatcacgta   3720
gaggaggaaa cggggaccta actggcctaa gtttgtacgg ctagtagggt gagtgagggg   3780
tagagctgaa atttaaactc aaacccaaga cagctctact atactactgg cactacttta   3840
tagtactaga tacacatcat ccctctgatt aggttaagag cccctgaaga gtcagtgatc   3900
```

```
attcattcag caaacccttta tggacccccca ttgtgggcca ggtctggaca gtcatgactg   3960
cccaatgccc agcccaaggc caggcacaca ataagcgtga ggtgaaaact cactgattga   4020
cggcactttt ccttgtctgg acagcggaac tggaccagta tgtttttcaa gactctcagc   4080
tggagggcct gggcaaagac attttcagta agttgggggg tggggggttc ttggttcagc   4140
ctgcatttcc ttccttgttc cttagggggc atggaaatac ccagaggcca cccttcaatg   4200
agaagtcacg ttcccttccc agtgtaggga caatgagggc tcatctcgga catcctctga   4260
ctgtgtgtct tggtgtcttt ggtttttct ctgaagttga gcacatagga ttggaagaaa   4320
tgatcagtga gagcgtggag gtgctggagg actcagggcg gaaaagtcag aaaagatgtg   4380
agtgagcgtg tttcccccc gccccctgcc atccaacctc tcctggcttc attcctggcc   4440
ctgccctggc tctaaaacct cccagtcgca ttccttgtta agccttgcct gctctgacct   4500
ggctttgggt gtccccccac ctctcctctc accactgctc cctcgagacc cagagaggaa   4560
gcaagtggcc cagcagcaga tggtccctct cctggtgggt ctctgttttt gactgtcatt   4620
tccaaaagac ctctgggctc tggcttctct ttcatcctta gttgtcaccc ctgtatttaa   4680
gggaggtctc ttcaaggaca gtctttcccc agcaagatct gggtttgaat tccagatctg   4740
ctatttaagg tctgtgtgac cttgggcaaa taattacacc tctctgagcc tcctagtcag   4800
tctgcctgcc tcctctgtct gtcctcacct ggcagccaac atgggctttt gaatgcaaat   4860
tcaatcattt ggctggcctg cagaccctcc aatggctcaa aatacatacc acaaggatct   4920
gtaggatctg gcccttcccc ctctccaaat tcacgaatgt gagtcactat gctccatcca   4980
gccacactgg cttctttcca ttcctgtaac tcttgtaccc tttccagcct cagggccttt   5040
gcacttgctg ttggccctgt ctggaatgcc cttccccccgt ttcttcccat agtggcgcct   5100
ccgaatcttg taggtcttgg ccaacatgtt gcctcctccc gaaggccttc ttccatcaac   5160
ttttccacat aaattaacct tacttacttt caccttgttt gtgtctctcc agcatcacag   5220
cccttgtcac aatctggact tgttttaggt attggctttt gcttagttcc cccaccatgg   5280
ggacagggac cttgtctttc ttatgtaatc actaccttcc ccagcacctg gtacatgcct   5340
ggcatgcggg agcatctcca taaatatcca ctgaatggaa atttccagga gttcccatcg   5400
tggtgcagca gaaaggaatc tgacgagtat ccatgaggat ttgggttcaa tccctggcct   5460
cggtcagtgg gtccagaaac cagcactgcc gtgagctgtg gtataagtcg aagatgaggc   5520
tcagatcccg tgctgctgag gccttggtgg aggccggcag cagccgattt gacccctagc   5580
ctgggaattt ccacatgcct caggtgcagc cctaaagagc aaaaaaaaaa aagaaaaaaa   5640
aatttccaca aaatgggcat cacagctaat tgaatgctta ctctaggcca aaccatgtgt   5700
aagccctgaa cctatttaat ttgaacaggt aaacagatgc atggcataaa aattcaaaag   5760
gtgcgaagaa cagtcagtaa aaaaaaaaaa aaagaaaaaa gagctccttc ccactcgttt   5820
cccagtcttt cattttccct ctctgaagac aatctatgct gccagtttcc tttttgtctt   5880
atattttgcc taaaagccag ctctttaaaa caatgttgcc ccacaagtgg catttcaccc   5940
accgtctcgg gcacctggct ttcttcgttt accacgtcag gacggcgatt tccacaccac   6000
gatggaaaac acgtggtcct cccgcccagg aatttccctt tcctttcctt cttttttcc   6060
ttccttcccc ctttcttctt tcttttcatt tcataagcat tttcccccaa tattttacca   6120
tgtggtgtag ggtgcagact acaaaatttc tgtctttttt tgcgtgtctt ttagacccca   6180
ggctaggggt tgagtccgag tgtaggtgcc ggcctacacc acagccacag caatgcagag   6240
tctgagcctc gtctgcaacc tacaccacag ctcacagcaa tgccagatcc ttaacccgct   6300
```

gagcgaggcc agggagcgaa cctgcgtcct catggatgct agtcgggttc gttaacccct 6360
gagccacaac gggaactccg aaaaatttca gcatatagta gaggtgacag aattgtacta 6420
caagcaacca catacccact gctgacaacc taccatcagt gttgggctat atttgcctta 6480
acacatctct atccatctgt ccatccctct atcatccacc catccatcca ttttccaggg 6540
gaacgtgtca aaggacgttg cagacgccag tactgcccac acatccttcc acatccttgt 6600
tatttttagg gctgcatggt atttcactgg gggatgaatc atcgtttgtt tcatcagccc 6660
ctcgctaagg acacagctgg gtttttctct gttgatgtgt gccgtgcttg atatgcactc 6720
actgatttcc agtgcattcc tgcaaaatgg gaatcaacac ccctgtttca cagatgagag 6780
aacaaaggct cagagaggct gtgtagcaga gacaacacgg ccaggaaggg cccaaaagca 6840
ggtggtttgt ctttgttttt tttgtttttt ttggtgggag gttgtttttg tttctgtaat 6900
ggctgcaccc atggcatacg tttccagggc agggattgaa tctgagctgc agctgtggca 6960
atgccggatc ctttcaccca ctgcaccagg ccagagatgg aacctgtgcc ttcacagcga 7020
ctcgggctgc tacagtcagg ttcttaaccc actgtgccag ggtgggatct cccacagatg 7080
ttttttttcat ttttattatt attattttta aactcaaact cttcctgtgt ctcttctatg 7140
gttctgcctc ttccagtgcc tcactgccct gggtgcttca agatggggtt tgggctcaag 7200
caaaagagtg gggcagaaa tggtcggagg aagaggaggg aaagggaccc cccaggccac 7260
ttcccagcca tttaaggcaa ggccacaagg cctaactggg gtccacaggc ccgtcctggc 7320
tgggtctgat gaccgtgtgt tctctctgaa gctttcccgg aggagctgcc tgcggatctg 7380
aagcacagga agctaggtga gcagggcggg tgcatccagg gagactgcca ggcagggaag 7440
ctggggtctc ctcaggtgtg catataaact agcatttaaa agctgaggct cagagaggtg 7500
aagccacttg ttcaacatca cacagcaagt gagagttgga gttgggattc agactaagat 7560
catgaatcca cagtgcgtgc tctgcagttc aaggactgtt gggagattca cctctaccca 7620
caaaacctat tttgaactct gagtcagagc tgaggacccc cccaccccac cttgttccac 7680
tgcccctcca ggccacagct ctcctttcgg aaggcagcgt cacctctggt cagctggtta 7740
cccggcggtt ccccccctccc atgcctcaat gagcctcttc cccatgcctc catccccccc 7800
ccaccagatg cttcctcccc tcccttcctc cctcctccct gattcggttg ttattgcaaa 7860
ggtggggagg ccagctcccc tgtgagaaag agactgagaa atgaaagcct catagtctga 7920
tggaggaagc ctggtctcta ctcccaggtc taatctgatg gagaagacag ggaccccaac 7980
caggaggacc ccagcgtgat ggagaccccc aatctgatag gggaggcgag tctccgccct 8040
cctgagctcc tgattcaatg gaggagataa actcgtgccc cagggagaca gcaagtgctc 8100
gaggtccctg gaggctatag aaggtggtag ggcctgggc taacaccctc ttcttaggtg 8160
tgtcccgcct gcgcccggct ctccaaggca ggaagtgctc agggaggaag ccgggggtgg 8220
gggctgtgtg acacagcaca gttgctgctc agaccagctt cacccaggac tgagaagagg 8280
acaggaattc ccttccactg ccagcagaga gttccactct gctccctgag cactccccac 8340
cctgggaagg accctcaggg cacccaccca gatcttacca agcctctgac acggccccct 8400
ttctcatagc cgagcccctc gccatgccca tggtgactgg cactttcctg gtggggccag 8460
tgagcgactc ctcagctcga ccctgcccat cacctcctgc tctgttcaac aaggaatcaa 8520
cacccagcca ggcccagctg gaggacgctg tcccaatgcc gggtaggtta ggggcttgga 8580
ggggcagggc ttccccttcc cgcctccccg caggtgcctg aggagtggct acttcaggag 8640
ccacaaggga caggaactgc tccccctact actgtcaccc acttccatcc cagccagtcc 8700
taccccccag ggtccccctc gactccgtct gtgccagaga atgtgccctg ggcatcacag 8760
cagggaatcc ctgccaacca gggaattcac tgccagccct atgctagttc gcttgctttc 8820
ctcagcagtg aaccgtgcac cctctctggg ccagctgctc tgctgggtgc cagcaacact 8880
gtgctgggcc agcagacaaa gcttttcaat ctcctccagg ctctctcgat tagagtcctt 8940
gagaagggag tcagatgtta attaagatgc tcaagtgctg ggagtttgga gttaatagat 9000
gcaaactatt gccttcctgc gtggataagc aatgagatcc tgccgcatag cacagggaac 9060
tatatatcta gtcagtcact tgtggtggga catggttaag gatgatgtga gaaaaagaat 9120
gcatacatat gtacagctgg gccactctgc agtacagtag aaattgacag aacactgtaa 9180
atcaactata atggaaaaaa ataaaatctt tcaaaaaaaa aaaaaacaaa aaacaaaaaa 9240
gatgctaacg gagaacccta ccttaccatc ttggtctctt gcagcgcccc cttcaggttc 9300
cttgttgagc tgcctgagtg tccctgctgg acctattcag atcatcccca cgctctccac 9360
cctgccccag gggctctggc acatctcagg ggccgggaca ggggtctcca gtatactcat 9420
ctaccaaggt gagcgtggga agccaggctc cccacccccct ctgcctgtga cctgactatt 9480
ccctgacgcc atcctttcc caccccaggc atttagtgct tacagcccag caccttctca 9540
ggatcctccg tccccatttc cccaaactca aaagagagga gcaaagctcc cgcgtgttct 9600
aagcgaccca agtgcctaag tgaccttttt tggtcacttt tctccacgaa gccttagttt 9660
ctccctttta agaaaaataa cttcattata ctttaaaatc caaatattta tgtatgctca 9720
ttaagaaacc aaaaaataag acctacttac aagagtcacg gagtctcccc atcgctcttt 9780
ttagtatacc gttgtgaata gtttggtatg gatccttgca cagctttctc aaagttgtct 9840
tgtttccggg tctgtaagaa ggtccttgct gacctgccac attggagggt tttaaattgt 9900
ccaagggaag gcacgttggg ctctcaggga tgggagagag aatgaggcta aggagatatt 9960
tccactcaac tcaagagcat cctttgagga ctttccactg tggcacagca gaaatgaatc 10020
caactagtat ccatgaggat gtgggttcaa tccttggcct ccctcactgg gttaaggatc 10080
ctgtgatgct gtgagctgcg gtgtaggtcg cagacacggt tcggatcctg cgatactgtg 10140
gctgtggtgt aggccggcgg ccgtagctcc gaatcaaccc ctagcctggg aacctccatg 10200
tgccgcgggc atggccctaa aaagcaaaaa aaaaaaaaaa cagtagaact gcgctgccgc 10260
ttggctcaca gtctccggtt ttacgggaat ggggttagtt tctgggtggt ctatggccaa 10320
ttgtcttgcc tgacccgtgc ttggtccgcc tcgcgcgggg actttctggg tggcgcacac 10380
acctctcagc caagatggat tccagcgcca aggatcctgg gaagttggtg gtctcctccc 10440
tcccacaggc ccctcccacg ggcccctccc acatcctccc ggttagtctt cagggcagca 10500
gcacattcct cacggggcct cctgtttcga gacacctcct gctagtggtt gttatcctgc 10560
ctggccgagg tggacagttt cggccagtcg tcccctaaca gaagcacttg ccctgctccc 10620
aaggagctgg ttgtgtccct tcacagatgg ggaaatcaag gctccgggag ctccatgtca 10680
ctccnnnnnn nnnnnnnnnn nnnnnnnnnn nnnnnnnnnn nnnnnnnnnn nnnnnnnnnn 10740
nnnnnnnnnn nnnnnnnnnn nnnnnnnnnn nnnnnnnnnn nnnnacgaga gccagagctc 10800
cagcagcttc caagtggcca ggtgagtggt ggcagggtcc ctctgcccag gtgctggacg 10860
tagaagccca aatccgactt cccttcatgc attcacccaa cacttgttca atctctcttt 10920
tgttggctca ctcattcatt cattcactca ttcattcaca tgctcattgc atcttcacat 10980
catctcatca ctcattcctc tggttatacc tacatttaaa gctaccttta ccgaggacct 11040
gccccgggga agcccatgct gggcgtcaat atcttttttt tttttttttt gtcttttttt 11100
ttgttatttc tttgggccac tcccgcggca tatggaaatt cccaggctag gggtctaatc 11160
ggagctgtag ccgctagcct acgccagagc cacagcaacg cgggatccga gccacgtctg 11220
caacctacac cacagctcac ggcaacgccg gatcgttaac ccactgagca ggggcaggaa 11280
ccgaacccgc aacctcatgg ttcctagtcg gatttgttaa ccgctaagcc acgacgggaa 11340
ctcctgggca tcaatatctt gttagcgagg ctgagagagt gaatgaaggg agcgtgggtg 11400
accgagggaa ctaagacagg agtggggatg aaagggcagc tgactgctga gtctgactct 11460
gtccctggta ctccaacaca ggagatgtag taaatcagga aagtcccaac ctgactatgg 11520
tccccatttt gtggaggaga aaactgaggc acagtggggt atcgcacatg ctcaagataa 11580
tactagtaag tggtggagcc aggacttaaa ccagaaacat ggattccact atcttaaccc 11640
tcaacacaca cacacacaca cctccccaga atggtctccc aatcgtgagt gagcaaaaga 11700
agaaaatctt ggagtgggta aatgatggag aagatgaggg aatgaatgag cgaatgaggc 11760
agctaatcca gaaagccatc agggaagacg ggtgaatgga cgaagaagct agtgatggtg 11820
gccgggctgg cctctcggct gccctcctgg tagccggtcc tgccactagc atcctcccct 11880
cccccactcc cgcctttgac ctgtgcagag actgtggagc agttccacca ctcactccgg 11940
gacaggtacc aagccaagcc cgcaggcccg gaaggcatcc tggtggaggt ggacctggtg 12000
agggtgcggc tggagaggag cagcagcaag agtcaggaga gagagctggc ctccctggac 12060
tgggcagagc ggcagccagc ccgagggggt ctggcggagg tgctgctggc cgctagcgac 12120
cgccaggggc cacgcgagac gcaggtgatc gccgtgctcg gcaaagcagg acaagggaag 12180
agtcactggg cccaggccgt gagctgggcc tgggctgacg gccagctgcc acagtacgac 12240
tttgtcttct gcatcccctg ccactgtttg gaccggccgg ggaacaccta ccgcctgcag 12300
gatctgctct tctccctggg cccacagccc ctgcccatgg acgacgaggt cttcagttac 12360
atcttgaggc ggccggaccg cgttctgctc atcctggatg ccttcgagga gcgcgaagcc 12420
caggacggct tcgtgcacag cgcgggcgga cccctgtcct cagaaccccg ctcccttcgg 12480
gggctgctgg ctgggctcct ccagcgcaag ctgctgcgag gctgcaccct gctgctcacg 12540
gcccggcccc ggggccgcct ggcccagagc ctgagcaagg ccgacgccct gtttgaggtg 12600
gccggcttct ccgcacagca ggccaagacc tacatgctgc gctactttga gtgtcggggg 12660
gcccgtgagc gccagaagag agccctggag ctcctccagg cacagccgtt tctcctgagt 12720
cacagccaca gcccttccgt gtgccgggcc gtgtgccggc tctcagagac cctcctggag 12780
ctgggcgagg aggcagagct gccctccacg ctcaccggcc tctacgtcgg cctcctagga 12840
ccagcggccc gcgaaagccc cccgggtgcc ctggtgggac tggccagact ggcctgggaa 12900
ctgggccgcc gtcaccacag cagcttgcag gagggccagt tcccatcggc agaggccagg 12960
gcctgggctg tggcccaagg cttggtgcag cgtgccccgg gggcccgggg ggcccctgag 13020
ctggccttct ccagcttcct cctgcagtgc ttcctggggg ccgtgtggct ggctctgagc 13080
agcgagatca aggacaagga gctgccgcag tatttggcat taacccctag gaagaagagg 13140
ccctatgaca actggctgga ggctgtgcca cgctttctgg tcgggctggt cttccagcct 13200
cgcgcccgct gcctgggagc cctggcaggg ctggtggcag ccaccttggc ggaccggaag 13260
cagaaggtgc tcaacaggta cctgaagcgg ctgcagcccg ggaccctgca ggcagggcgg 13320
ctgctggagc tgctgcactg cacgcacgag gccctggatt ctgggctttg gcagcatgtg 13380
ctgcaggggc tcccgaccca actctccttt ctgggcactc ggctcacgcc tccggacacc 13440
cacgtgctgg gcagcgcctt ggtggctgca ggccgagact tctccctgga cctccgcagc 13500
actggcattg accccctctgg actggggagc ctcgtgggac tcagctgtgt cacccatttc 13560
aggtgggggc cggggacagg agagagggct tctttgcatt gagcacctac tgtggttttg 13620
ctgctgtgcc cagtgctggc tctgtggggt ctcattcagt aggcatggca gccagatgtg 13680
ggcagaagtg attccactca tttgaagatg aggaagccaa ggctcagaga gggagagtag 13740
cttgcccgag gtcacacagc cagtgagagg cagcatcatt cttttaacca ctgtttgaaa 13800
gggccatgtt ccaggcactg ggccatgtct agagtctaag actgatctgg gttcaaattc 13860
attttcttct ctccatcccc tgatcaagtc accattttgt catggttaga ttaaaaccac 13920
agcctcccct gacttccctg cccccgttct cgcctcttcc actccatttt attttatttt 13980
attttattgg tttttagggc tacacctgtg gaatatggaa gttcccaggc taggggttga 14040
atccgagcta tagctgctgc cctacaccac agccatagca acgcaggatc cttaacccac 14100
tgagggaggt cagggattga accacatcct catggatcct agtcaggttc gtcaccactg 14160
agccatgaca ggaactcccc cactccactt tattcttaac catcagagca atctccctag 14220
taattgcatc tgatcatctt tcatccttgc ttacaatctt ttagaggcac tccacctccc 14280
tcaggttgaa gtcaaagttc cttaatttaa ggaatctaaa tcctcctgtg atctgtttga 14340
tcccttaagc cttatttcca gagaatctct cctaccttcc ctctaagcat attttaccag 14400
agctataagg tctacaccat tgtaatggtt caacggagaa ttcagcactg agcttcctgg 14460
tagccaaagc aaaaaggaaa agaaaaccca ggagagctaa gaaaaaggag gaattgataa 14520
gggcttaagt ggtcatggaa ggctttctag agaaagtagg gggttaagct gagcaaagaa 14580
agtacctgaa taggtaggag gtcccttcat ggagttgccc atccgttatg gtctagcccg 14640
gtcaccatgc ctgggtctga ggcccttcct ccacagggcc gccttgagtg acacagtggg 14700
gctgtgggag tctctacagc aacgtgggga gaccaagcta ctccaggcac tggaggagaa 14760
atttaccatt gagcctttca aggccaagtc catgaaggat gtggaagacc tgggcaacct 14820
cgtgcagatc cagaggtgag gaggaaaggg cacgggaggt ggtccaggcc atgcaggtcc 14880
attacatttg tcattagcac ttccagtgcc tcatctttgg gggatatccc atgtcctccg 14940
cttggacagt ggccacccag aatctctcac tgttgtcacc acccatgcag aactcccagg 15000
atttatcact tggtcccatt aaaaacttgc agtcatgttc ccaatttttt tttttctttt 15060
ttaggaccac accttcagct tatggaagtt cccagatgag ggtcaaatc ggagctatag 15120
cttctggcct atgccacagc cacagccaca gcaataccag atccaagcca catctgtgac 15180
ctacaccaca gctcatggca atgcttgatt cttaactcac tgagtgaggc cagggatcga 15240
acccgtgtcc tcgtgtgtac tagccaggtt tgttacccct gagtcacaat gggaatcccc 15300
ctaattcttt ctcagctaaa gccagggaac tattctctgc tgctaagagt tcacgagctg 15360
ccttctgcat ctagtaacag aagtgacact atggccacct ttcaaggcag ccaggaccag 15420
tatcatcccc attttttttga tggcagagat ctaatgtcta gtgggtagag gacacttgac 15480
cacagaacaa ctgcctttcc ctcattcctt catcatacat tgttcgagca cctactatgt 15540
gctgtctggg atgggatggg tctcctctga ggctcttttc catgaaacac acaggaatat 15600
tagccttcat aacatcctgt tctgaggctt ttctttttaa gaagggcata acaaggagtt 15660
cctgtggtgg ctcagcaggt taagaaccca gctagtctcc atgaagacag ggggttcaatc 15720
cctggccttg ctcagtgggt taagaatctg gtgttgtgtg aactatggtg taggtcgcag 15780
acacagcttg ggatcccacg ttgctgtggc tgtggcgtag gccagcggct acagctccaa 15840
gtccccccct agccttggaa cttccttatg ccacaggtgc agccttaaaa aaaaaagaaa 15900
aaaaagaaaa aaaagaaggg actaaccata gcccgggaaa ggcagtcctt ctggggaatt 15960
ttgggaatgt ggcatgcatc ttagtacatt taggaaggga ctcagcgaca ggtgaaggtc 16020
ccctgacatt gcccattctc tccatctctc caggacgaga agctcttctg aagacatggc 16080
tggggaactc cctgctgtcc gggacctaaa gaagttggaa tttgc 16125

<210> SEQ ID NO 23
<211> LENGTH: 4456
<212> TYPE: DNA
<213> ORGANISM: Sus scrofa

<400> SEQUENCE: 23 tttttcact tcacgttttg gatgctgcag gccgggtaag cagagatccc aaggctctgg 60
cccccgggga agaggccctg tctccgagcc ctaccatgaa ccacttccag accatcctga 120
ctcaggtccg gatgctgctg tccagccatc ggccgagtca agtgcaggcg ctcctggaca 180
acctcctggc ggaggagctt ctctccaggg agtaccacta cgccctgctc caggagcctg 240
acggtgaggc tctggccagg aagatctcct tgacactgct ggagaaagga gccccagacc 300
tggccctctt ggggtgggtc tggagtgcac tgcagacccc agcagccgag aaggaccccg 360
gctaccagga acctgatggc agtggacagt gcgccaccat ggagttgggg cctctggagg 420
gtgggtactt ggagcttctc aacagcagtg ccgaccctct gcagctctac cacctctatg 480
accggatgga cctggctgga gaagaagaga tcgagctctg ctcagaacct gacacggaca 540
ccatcaactg cgaacagttc agcaggctgt tgtgcgacat ggaagcagat gaagaaacca 600
gggaaactta cgccagtatc gcggaactgg accagtatgt ttttcaagac tctcagctgg 660
agggcctggg caaagacatt ttcattgagc acataggatt ggaagaaatg atcagtgaga 720
gcgtggaggt gctggaggac tcagggcgga aaagtcagaa aagatctttc ccggaggagc 780
tgcctgcgga tctgaagcac aggaagctag ccgagcccct cgccatgccc atggtgactg 840
gcactttcct ggtggggcca gtgagcgact cctcagctcg accctgccca tcacctcctg 900
ctctgttcaa caaggaatca acacccagcc aggcccagct ggaggacgct gtcccaatgc 960
cggcgccccc ttcaggttcc ttgttgagct gcctgagtgt ccctgctgga cctattcaga 1020
tcatccccac gctctccacc ctgccccagg ggctctggca catctcaggg gccgggacag 1080
gggtctccag tatactcatc taccaaggtg agatgaccca ggccagccaa gcacccccctg 1140 tccatagcct cccaaagtcc ccagaccggc ctggctccac cagtcccttc gccccgtcag 1200
cagctgacct ccccagcatg cctgaaccag ccctgacctc ccgggcaaac atgacagagg 1260
gcagtgtgtc ccccacccaa tgctcaggtg atcaagaggc ctccagcagg cttcccaagt 1320
ggccagagac tgtggagcag ttccaccact cactccggga caggtaccaa gccaagcccg 1380
caggcccgga aggcatcctg gtggaggtgg acctggtgag ggtgcggctg gagaggagca 1440
gcagcaagag tcaggagaga gagctggcct ccctggactg ggcagagcgg cagccagccc 1500
gagggggtct ggcggaggtg ctgctggccg ctagcgaccg ccaggggcca cgcgagacgc 1560
aggtgatcgc cgtgctcggc aaagcaggac aagggaagag tcactgggcc caggccgtga 1620
gctgggcctg ggctgacggc cagctgccac agtacgactt tgtcttctgc atcccctgcc 1680
actgtttgga ccggccgggg aacacctacc gcctgcagga tctgctcttc tccctgggcc 1740
cacagcccct gcccatggac gacgaggtct tcagttacat cttgaggcgg ccggaccgcg 1800
ttctgctcat cctggatgcc ttcgaggagc gcgaagccca ggacggcttc gtgcacagcg 1860
cgggcggacc cctgtcctca gaaccccgct cccttcgggg gctgctggct gggctcctcc 1920
agcgcaagct gctgcgaggc tgcaccctgc tgctcacggc ccggccccgg ggccgcctgg 1980
cccagagcct gagcaaggcc gacgccctgt ttgaggtggc cggcttctcc gcacagcagg 2040
ccaagaccta catgctgcgc tactttgagt gtcgggggc ccgtgagcgc cagaagagag 2100
ccctggagct cctccaggca cagccgtttc tcctgagtca cagccacagc ccttccgtgt 2160
gccgggccgt gtgccggctc tcagagaccc tcctggagct gggcgaggag gcagagctgc 2220
cctccacgct caccggcctc tacgtcggcc tcctaggacc agcggcccgc gaaagccccc 2280
cgggtgccct ggtgggactg gccagactgg cctgggaact gggccgccgt caccacagca 2340
gcttgcagga gggccagttc ccatcggcag aggccagggc ctgggctgtg gcccaaggct 2400
tggtgcagcg tgccccgggg gccccggggg cccctgagct ggccttctcc agcttcctcc 2460
tgcagtgctt cctgggggcc gtgtggctgg ctctgagcag cgagatcaag gacaaggagc 2520
tgccgcagta tttggcatta acccctagga agaagaggcc ctatgacaac tggctggagg 2580
ctgtgccacg ctttctggtc gggctggtct tccagcctcg cgcccgctgc ctgggagccc 2640
tggcagggct ggtggcagcc accttggcgg accggaagca gaaggtgctc aacaggtacc 2700
tgaagcggct gcagcccggg accctgcagg cagggcggct gctggagctg ctgcactgca 2760
cgcacgaggc cctggattct gggctttggc agcatgtgct gcaggggctc ccgacccaac 2820
tctcctttct gggcactcgg ctcacgcctc cggacaccca cgtgctgggc agcgccttgg 2880
tggctgcagg ccgagacttc tccctggacc tccgcagcac tggcattgac ccctctggac 2940
tggggagcct cgtgggactc agctgtgtca cccatttcag ggccgccttg agtgacacag 3000
tggggctgtg ggagtctcta cagcaacgtg gggagaccaa gctactccag gcactggagg 3060
agaaatttac cattgagcct ttcaaggcca agtccatgaa ggatgtggaa gacctgggca 3120
acctcgtgca gatccagagg acgagaagct cttctgaaga catggctggg gaactccctg 3180
ctgtccggga cctaaagaag ttggaatttg cgctgggccc tgtcttgggc ccccaggctt 3240
tccccaaact ggtgaggatc cttgaggcct tttcttccct gcagcatctg gacctggact 3300
cgctgagtga gaacaagatc ggggacgagg gtgtcgccca gctctcagcc accttccctc 3360
aactgaaggc cctggagacg ctcaacttgt cccagaacaa catctccgac gtgggtgctt 3420
gccagctggc caaggccctg ccctcgctgg ccgcgtccct cctcaggctg agcttgtaca 3480
ataactgcat ctgcgatgtg ggagccgaga gcctggcgca tgtgcttcca gacatggggt 3540
ccctccgggt gctagatgtc cagtacaaca agttcacagc cgccggggcc cagcagctcg 3600
ccgccagcct gagaaagtgc cctcacatgg agacgctggc gatgtggaca cccaccatcc 3660
cgtttggtgt ccaggaacac ctgcagcagc aggactcaag gatatcctga gatgatccag 3720
gctgcacccg ggacaagcac gttctctgag gacgctgacc acgctggacc ctgacctgat 3780
catctgtgga cacagctctt cttaggctgt gtcccgtgag ctttggcgat ctggtgccca 3840
gccctggtgg ctcagagtca gcccccactc tgctggggaa aggacccacg gcctgctctg 3900
tggacagacc ccaggcccgg ccccaggctc cttcggggcc cagactgatg tcagccttgc 3960
tcagccgctg cagtcctggc agacaggcgg gcacccagtg gcagsyaggg kccacccggg 4020
agccctgaag cactccctgc aggacactgc agacagtggt ggccaggtca gagtgaggga 4080
tgtggcggcc acatcacctg cccaggtcct gctggccggg ggagaaagca cctctccaca 4140
ctgctcccct ggtggggtaa gcttggcgct cagaagatac cagccagcac cccccagcgt 4200
gttgatttcc caaacggtga ccgacggggt gtccacggca gctgccctct gcctccggca 4260
cctgcgggtt tgcactcact ttgtttgccg aggccaaagc tgggcctggc cagacacgcc 4320
rgaccttagc gggggaagag ccgacagtac actacgggmc gaggyrgggt ggcgagggtc 4380
tggaaccaca tccgccttct tgccctcacg tcctgtgtct tttttcacta cattatacat 4440
ggcttattca gtctca 4456

<210> SEQ ID NO 24
<211> LENGTH: 1204
<212> TYPE: PRT
<213> ORGANISM: Sus scrofa

<400> SEQUENCE: 24

Met Asn His Phe Gln Thr Ile Leu Thr Gln Val Arg Met Leu Leu Ser
1 5 10 15

Ser His Arg Pro Ser Gln Val Gln Ala Leu Leu Asp Asn Leu Leu Ala
20 25 30

Glu Glu Leu Leu Ser Arg Glu Tyr His Tyr Ala Leu Leu Gln Glu Pro
35 40 45

Asp Gly Glu Ala Leu Ala Arg Lys Ile Ser Leu Thr Leu Leu Glu Lys
50 55 60

Gly Ala Pro Asp Leu Ala Leu Leu Gly Trp Val Trp Ser Ala Leu Gln
65 70 75 80

Thr Pro Ala Ala Glu Lys Asp Pro Gly Tyr Gln Glu Pro Asp Gly Ser
85 90 95

Gly Gln Cys Ala Thr Met Glu Leu Gly Pro Leu Glu Gly Gly Tyr Leu
100 105 110

Glu Leu Leu Asn Ser Ser Ala Asp Pro Leu Gln Leu Tyr His Leu Tyr
115 120 125

Asp Arg Met Asp Leu Ala Gly Glu Glu Glu Ile Glu Leu Cys Ser Glu
130 135 140

Pro Asp Thr Asp Thr Ile Asn Cys Glu Gln Phe Ser Arg Leu Leu Cys
145 150 155 160

Asp Met Glu Ala Asp Glu Glu Thr Arg Glu Thr Tyr Ala Ser Ile Ala
165 170 175

Glu Leu Asp Gln Tyr Val Phe Gln Asp Ser Gln Leu Glu Gly Leu Gly
180 185 190

Lys Asp Ile Phe Ile Glu His Ile Gly Leu Glu Glu Met Ile Ser Glu
195 200 205

Ser Val Glu Val Leu Glu Asp Ser Gly Arg Lys Ser Gln Lys Arg Ser
210 215 220

Phe Pro Glu Glu Leu Pro Ala Asp Leu Lys His Arg Lys Leu Ala Glu
225 230 235 240

Pro Leu Ala Met Pro Met Val Thr Gly Thr Phe Leu Val Gly Pro Val
245 250 255

Ser Asp Ser Ser Ala Arg Pro Cys Pro Ser Pro Pro Ala Leu Phe Asn
260 265 270

Lys Glu Ser Thr Pro Ser Gln Ala Gln Leu Glu Asp Ala Val Pro Met
275 280 285

Pro Ala Pro Pro Ser Gly Ser Leu Leu Ser Cys Leu Ser Val Pro Ala
290 295 300

Gly Pro Ile Gln Ile Ile Pro Thr Leu Ser Thr Leu Pro Gln Gly Leu

```
305                 310                 315                 320

Trp His Ile Ser Gly Ala Gly Thr Gly Val Ser Ser Ile Leu Ile Tyr
                325                 330                 335

Gln Gly Glu Met Thr Gln Ala Ser Gln Ala Pro Pro Val His Ser Leu
            340                 345                 350

Pro Lys Ser Pro Asp Arg Pro Gly Ser Thr Ser Pro Phe Ala Pro Ser
        355                 360                 365

Ala Ala Asp Leu Pro Ser Met Pro Glu Pro Ala Leu Thr Ser Arg Ala
    370                 375                 380

Asn Met Thr Glu Gly Ser Val Ser Pro Thr Gln Cys Ser Gly Asp Gln
385                 390                 395                 400

Glu Ala Ser Ser Arg Leu Pro Lys Trp Pro Glu Thr Val Glu Gln Phe
                405                 410                 415

His His Ser Leu Arg Asp Arg Tyr Gln Ala Lys Pro Ala Gly Pro Glu
            420                 425                 430

Gly Ile Leu Val Glu Val Asp Leu Val Arg Val Arg Leu Glu Arg Ser
        435                 440                 445

Ser Ser Lys Ser Gln Glu Arg Glu Leu Ala Ser Leu Asp Trp Ala Glu
    450                 455                 460

Arg Gln Pro Ala Arg Gly Gly Leu Ala Glu Val Leu Leu Ala Ala Ser
465                 470                 475                 480

Asp Arg Gln Gly Pro Arg Glu Thr Gln Val Ile Ala Val Leu Gly Lys
                485                 490                 495

Ala Gly Gln Gly Lys Ser His Trp Ala Gln Ala Val Ser Trp Ala Trp
            500                 505                 510

Ala Asp Gly Gln Leu Pro Gln Tyr Asp Phe Val Phe Cys Ile Pro Cys
        515                 520                 525

His Cys Leu Asp Arg Pro Gly Asn Thr Tyr Arg Leu Gln Asp Leu Leu
    530                 535                 540

Phe Ser Leu Gly Pro Gln Pro Leu Pro Met Asp Asp Glu Val Phe Ser
545                 550                 555                 560

Tyr Ile Leu Arg Arg Pro Asp Arg Val Leu Leu Ile Leu Asp Ala Phe
                565                 570                 575

Glu Glu Arg Glu Ala Gln Asp Gly Phe Val His Ser Ala Gly Gly Pro
            580                 585                 590

Leu Ser Ser Glu Pro Arg Ser Leu Arg Gly Leu Leu Ala Gly Leu Leu
        595                 600                 605

Gln Arg Lys Leu Leu Arg Gly Cys Thr Leu Leu Leu Thr Ala Arg Pro
    610                 615                 620

Arg Gly Arg Leu Ala Gln Ser Leu Ser Lys Ala Asp Ala Leu Phe Glu
625                 630                 635                 640

Val Ala Gly Phe Ser Ala Gln Gln Ala Lys Thr Tyr Met Leu Arg Tyr
                645                 650                 655

Phe Glu Cys Arg Gly Ala Arg Glu Arg Gln Lys Arg Ala Leu Glu Leu
            660                 665                 670

Leu Gln Ala Gln Pro Phe Leu Leu Ser His Ser His Ser Pro Ser Val
        675                 680                 685

Cys Arg Ala Val Cys Arg Leu Ser Glu Thr Leu Leu Glu Leu Gly Glu
    690                 695                 700

Glu Ala Glu Leu Pro Ser Thr Leu Thr Gly Leu Tyr Val Gly Leu Leu
705                 710                 715                 720

Gly Pro Ala Ala Arg Glu Ser Pro Pro Gly Ala Leu Val Gly Leu Ala
                725                 730                 735
```

```
Arg Leu Ala Trp Glu Leu Gly Arg Arg His His Ser Ser Leu Gln Glu
            740                 745                 750

Gly Gln Phe Pro Ser Ala Glu Ala Arg Ala Trp Ala Val Ala Gln Gly
        755                 760                 765

Leu Val Gln Arg Ala Pro Gly Ala Pro Gly Ala Pro Glu Leu Ala Phe
    770                 775                 780

Ser Ser Phe Leu Leu Gln Cys Phe Leu Gly Ala Val Trp Leu Ala Leu
785                 790                 795                 800

Ser Ser Glu Ile Lys Asp Lys Glu Leu Pro Gln Tyr Leu Ala Leu Thr
                805                 810                 815

Pro Arg Lys Lys Arg Pro Tyr Asp Asn Trp Leu Glu Ala Val Pro Arg
            820                 825                 830

Phe Leu Val Gly Leu Val Phe Gln Pro Arg Ala Arg Cys Leu Gly Ala
        835                 840                 845

Leu Ala Gly Leu Val Ala Ala Thr Leu Ala Asp Arg Lys Gln Lys Val
    850                 855                 860

Leu Asn Arg Tyr Leu Lys Arg Leu Gln Pro Gly Thr Leu Gln Ala Gly
865                 870                 875                 880

Arg Leu Leu Glu Leu Leu His Cys Thr His Glu Ala Leu Asp Ser Gly
                885                 890                 895

Leu Trp Gln His Val Leu Gln Gly Leu Pro Thr Gln Leu Ser Phe Leu
            900                 905                 910

Gly Thr Arg Leu Thr Pro Pro Asp Thr His Val Leu Gly Ser Ala Leu
        915                 920                 925

Val Ala Ala Gly Arg Asp Phe Ser Leu Asp Leu Arg Ser Thr Gly Ile
    930                 935                 940

Asp Pro Ser Gly Leu Gly Ser Leu Val Gly Leu Ser Cys Val Thr His
945                 950                 955                 960

Phe Arg Ala Ala Leu Ser Asp Thr Val Gly Leu Trp Glu Ser Leu Gln
                965                 970                 975

Gln Arg Gly Glu Thr Lys Leu Leu Gln Ala Leu Glu Glu Lys Phe Thr
            980                 985                 990

Ile Glu Pro Phe Lys Ala Lys Ser  Met Lys Asp Val Glu  Asp Leu Gly
        995                 1000                 1005

Asn Leu  Val Gln Ile Gln Arg  Thr Arg Ser Ser Ser  Glu Asp Met
    1010                 1015                 1020

Ala Gly  Glu Leu Pro Ala Val  Arg Asp Leu Lys Lys  Leu Glu Phe
    1025                 1030                 1035

Ala Leu  Gly Pro Val Leu Gly  Pro Gln Ala Phe Pro  Lys Leu Val
    1040                 1045                 1050

Arg Ile  Leu Glu Ala Phe Ser  Ser Leu Gln His Leu  Asp Leu Asp
    1055                 1060                 1065

Ser Leu  Ser Glu Asn Lys Ile  Gly Asp Glu Gly Val  Ala Gln Leu
    1070                 1075                 1080

Ser Ala  Thr Phe Pro Gln Leu  Lys Ala Leu Glu Thr  Leu Asn Leu
    1085                 1090                 1095

Ser Gln  Asn Asn Ile Ser Asp  Val Gly Ala Cys Gln  Leu Ala Lys
    1100                 1105                 1110

Ala Leu  Pro Ser Leu Ala Ala  Ser Leu Leu Arg Leu  Ser Leu Tyr
    1115                 1120                 1125

Asn Asn  Cys Ile Cys Asp Val  Gly Ala Glu Ser Leu  Ala His Val
    1130                 1135                 1140
```

Leu Pro Asp Met Gly Ser Leu Arg Val Leu Asp Val Gln Tyr Asn
    1145                1150                1155

Lys Phe Thr Ala Ala Gly Ala Gln Gln Leu Ala Ala Ser Leu Arg
    1160                1165                1170

Lys Cys Pro His Met Glu Thr Leu Ala Met Trp Thr Pro Thr Ile
    1175                1180                1185

Pro Phe Gly Val Gln Glu His Leu Gln Gln Gln Asp Ser Arg Ile
    1190                1195                1200

Ser

<210> SEQ ID NO 25
<211> LENGTH: 45862
<212> TYPE: DNA
<213> ORGANISM: Sus scrofa

<400> SEQUENCE: 25
cacatgaact ggacaggccc caggtacata agaaaaaggc ccctagtcca gtagccaata 60
ggattcctcc tttctgaaag tcacagcgct tttccttcct gagcagagtg ggggcggggg 120
aataaagttg cggccacaga gtggacttga gctccccctg gaggcccaaa cgattatttg 180
caccaacttg tcctggcttt tggagttgag cgggaagaat ccgagggtct tcattcaccg 240
tcctggaagg atagttttgt cagtggtttt ggtccaggct gctcggttgt gcctgaaaag 300
tcacggctga agggagcgct gtgtgacggt tattgtttgt gccttgactt ttgcttccaa 360
atcagcccaa aagaaactct gctttttttt tttcttttct agggccaaac ccatggcata 420
tggaagttcc caggataggg gtccaatcag agctgtagcc gccggcctac accacagcca 480
cagcaacgcc agatccaagc ctcgtgtgga gactacacca cagctcacgg caacgccggg 540
tacttcaccc actgagcaag gccagggatc gaacctgcaa cctcatggtt cctagtcgga 600
ttcgttaacc actgtaccac gacaggaact ccaccctttc tgttttgaaa ggcacacaga 660
caaagaaaac agtcgtattt attattctgg acactttgct tctaagtcat aggaagcaac 720
tcagattagg ttaaagaaaa atggggaatt ataagggcac tgtgttttat aaaatcccag 780
ggcaggactg tagccagagc tcaggaaaga accagaaggt tttcagaagt ctctcatttc 840
agctcagtgg ttaacaccct ccgagagttc cattttaact ttgctgtggt ggcacagcag 900
aaccctctcc ccaaggaagg tgacaggaac gtccttaaaa tgaggaagaa ccgcatggcc 960
caatcaccct ctctacacgt atgcacagcc cagactgtac ccaataagac tgcaataagg 1020
ctatatgtta ccatataaag gggacaaagg ggtaaaaata atataaaagg catctcctca 1080
ctgtgctcag ggctcagcct ttggacatga atctgtcgag ccagtgccgg catgaataaa 1140
tactgcttcc tggaaaaaag ccttggtggg tgtcccatct ctgtacgtaa gtcctacaac 1200
agttccttcc tgctagagta gaaggttcca gatcctgggg cagggaagag gttcctagaa 1260
cctactgatg ataactacag cacatcaaaa cagtccctgc tgggggatgt tggagcatgc 1320
aacaactgcc atgaaagtgg acaactctat ctccctgtat caagagtgca tgtttcagga 1380
gttccctagt ggctcagagg gttaagaatc taactaatat ctatgaggat gcaggtttga 1440
tccctagaat agttcagtgg gttaaaggat ctggtgttgc agtgtagatc aaggatgtgc 1500
ttggatctgg tgttgctgtg gctgtggcac acactggcag ctgtagctct gattcaaccc 1560
ctagcctggg aacctccata tgccgagggt gcagccctaa aatgacaaaa acaagaaaac 1620
aggaatgcaa gtaagtcagg agttccctgg tggttcagtg ggttaaggat ctggcattgt 1680
tactgctgtg gtgaggggttt tattcctggc ccaggaactt ctgcatgcca caggcacagc 1740

```
caaaataaat aaataaataa ataataaatt aagtggagtt cccgtcgtgg cgcagtggtt   1800
aacgaatccg actaggagcc atgaggttgc gggttcggtc cctgcccttg ctcagtgagt   1860
taatgatccg gtgttgctgt gagctgtggt gtaggtcgca gacgcggctc ggatcccacg   1920
ttgctgtggc tgtggcatag gccagtggct acagctccga ttggacccct agcctgggaa   1980
cctccatatg ccgcgggagc ggcccaagaa atagcaaaaa gacaaaaaaa taaataaatt   2040
aaataaataa ataaattaaa taaattaagt aaaatttaaa atttctagga gttccctgat   2100
ggtctggaag ttaaggattt ggagttgtcg ctgctgtgac tcaggttgaa tctctggcct   2160
gggaacttct gcaggctgtg ggcacagcca aaaaaaaaaa aaattaagac aaaaaaacaa   2220
agcaaataat tcatcaggaa ggcagaaatt ttttggaagc agacctagga gaaaataaat   2280
atttgtttaa atatgtaaat gtttatttat attttaacta ttttatatat ttaactttcc   2340
ttttttttt ttttttttt ttgcttttta gggccacacc tgaattatat ggaaggtccc   2400
aggggagggg tcaaatcaga gctgcagctg ctggcctaca ccacagccac agccactcga   2460
gatccgagcc acgtctgcga cctacaccac accacagctc acggcaacgc cagatcctta   2520
acccattgag caaggcgagg gatcgaacct tcaatatcat gattcctagt cagatttgtt   2580
aaccactgag ccatgacagg aactccagtc atcttttgtt ttgaggacat aaagtaagag   2640
gtatagagaa gcacttcccc aggggtctga acaatgtata ggctatttag ggaaacaggt   2700
ggttattata actggaggtt tgtacttttt ttttttggtc tttttgtctt ttctagggcc   2760
aaacccatgg catatggaag ttcccaggat aggggtccaa tcagagctgt agctgccggc   2820
ctacaccaca gcccatagca acgccagatc caagccgcgt gtggagccta caccacagct   2880
cacggcatca ccggatcctt cacccactga gcgaggccag ggattgaacc cgaaacctca   2940
tggttcttag tcagattcgt taaccactga gccacgatgg gaactccaga agtttgtacc   3000
ttttgaccac cttcaacgag gggctattta gggaaacagg ttatgttgtc ccagtgctga   3060
gccctagatc ccgagatgcc caaatgttca tcagtaaata tatgtgtttt ttttttttt    3120
ttttgccaca ccagcagcac gcagaaggtt ctgggccaga gatccaacct gatccacagc   3180
accgacaatg ccaaacctta accactaggc caccagagaa ctcctatgta ttttttttctt  3240
ccagtttata attcacctac agcactgaat gagttgtaga gcataatgac tggacttgca   3300
tacgtcatga aatgattacc acaataagtt tagtgagtga gttcccactg tggctcagca   3360
gtaacgaacc tgactggtat ccatgaagat gcgggttgga ttcctggcct cgctcagtgc   3420
gtttaaggat ctggcattgc tatggctgtg gtgtaggcgg gcagctgcag gtctgattca   3480
accccctaggc tgggaacttc catatgccac agatgcagcc ttaaaaaaca cataaaaata  3540
aaaataagta agtttagtga acatccatta gctcacataa ataaaaaatt aaatagaaaa   3600
aaattttcgt tgtgatgaga acttatagga tttattctct taaccacttt ctttctttct   3660
ttcttttttt tttttttttg tctttttgcc atttcttggg ccgctcccac gacacatgga   3720
ggttcccagg ttaggggtcc aatcagagct atagccgctg acctacgcca gagccacagc   3780
aactcggacg gaatccgagc cgagtctgca acctacacca cagctcatgg caatgccgga   3840
tccttaaccc actgagcaag gccagggatc gaacccacaa cctcatggtt cctagtcgga   3900
ttcgttaacc actgagccac gacaggaact ccagactctt cttttttttt ttttttttaa   3960
gggctgaact cgaggcatgt ggaggttccc aggccagggg tcggatctga gctgtagcta   4020
ccggcctata ccacagccac agcaacacag gatccgagcc acatctgcga cgcacatcat   4080
```

-continued

```
agttcacggc aacactggat ccttaaccca ctgagcaaag ccagggattg aacctgcgtc   4140
ctcatggatg ctagtcagat tcagttctgc tgaacaatga tgggaactcc ccatgctgac   4200
tcttaagata acagagagag cctgcctcat catgatggcc agattctgta cttgacatgg   4260
gtcttgaatg gtcagcaact gatctcaagg ccctggaatt tagtggctta gccttacact   4320
ggcacctcag cagagggtcc cagatcaatc ccaggcattc tagtaggtgt cctttttttt   4380
tttttttttg gtctttttgc catttcttgg gccgctgctg tggcatatgg aggttcccag   4440
gctaggggtc caattggaac tgtagccgcc ggcctacccc acagtctcag caacgcggga   4500
tccgagccgt gtctgcgacc tataccacag ctcacggcaa tgccggatcc ttaacccact   4560
gagcaaggcc aggaatcgaa cccgcaacct catggttcct agtcggattc gttaaccact   4620
gagccacgac gggaactcct ctttttttctt tttaatggct gcacccacac catatggaag   4680
tgccctggcc aggggtcaaa ctggagctgc agctgctggt ctacaccaca gccacaacaa   4740
cactggatcc aagctgtatc tgtgacctac tccacagctc gcggcaacgc cggatcttta   4800
accaactgag tgagaccaga gatggaaccc gaatcatcac agagactgtg tggggtctta   4860
atccactgga ccacaatggg aactccgaga atatgccttt atggtaggga gtctgacgcc   4920
tgggaaacct ttattctggc agggcgtggt ttaccgcagt gatcgcctcc ctctaattgc   4980
ctgcatccca tccctgtgcc gggctccagg tgagctgact ccacagagct ctcctcacct   5040
gccggggccc ttgtgacttc tctcttctct ggtcccccaa ccctgctgct caatcctact   5100
agcggactga accgaacgag gctgccacct cctcaaggca aggaccctgg gttcttcaca   5160
ttatttgagt ccacaaggta ggaccaaagg aaaatttgtg gaggacagtg atgctggaga   5220
tgatctgtga tataatttcc agcaagtaac cttcaaggac ccagcagcca tctttttttt   5280
ttttccactg tacagcaaag ggatcaagtt atccttacat gtatacatta caattacatt   5340
ttttcccccca ccctttgttc tgttgcaact tgagtatcta gacatagttc tcaatgctat   5400
tcagcaggat ctccttgtaa atctattcta agttgtgtct gataagccca agctcccgat   5460
ccctcccact ccctccccct accatcaggc agccacaagt ctcttctcca agtccatgat   5520
tttcttttct gtggagatgt tcatttgtgc tagatattag attccagtta taagtgatat   5580
catatggtat ttgtctttgt ctttctggct catttcactc agtatgagag tctctagttc   5640
catccatgtt gctgcaaatg gcattatgtc attcttttta atggctgagt agtattccat   5700
tgtgtatata taccacatct tcagaatcca gttatctgtt gatggacatt tgggttgttt   5760
ccatgtcctg gctattgtga atagtgctgc aatgaacatg cgggtgcatg tgtctctttt   5820
aagtagagtt ttgtccagat agatgcccaa gagtgggatt gtggggtcat atggaagttc   5880
tatgtataga tttctaaggt atctccacac tgttctccat agtggctgta ccagtttaca   5940
ttcccaccaa cagtgcagga gggttccctt ttctccatag cccctccagc acttgttatt   6000
tgtggattta ttaatgatgg ccattctgac tgatatgagg tggtatctca tggtagtttt   6060
gatttgcatt tttcttataa tcagcgatgt tgagcatttt ttcatgtgtt tgctggccat   6120
ctgtatatct tctttggaga aatgtctatt caggtctttt gcccattttt ccattgattg   6180
attggctttt ttgctgttgg gttgtataag ttgtttatat attctagaga ttaagccctt   6240
gtccattgca tcatttgaaa ctattttctc ccattctgaa agttgtcttt ttgttttctt   6300
tttggtttcc tttgctgtgc aaaagctttt cagtttgatg aggtcccatg ggtttatttt   6360
tgctctaatt cctattgctc tgggagactg acctgagaaa atattcatga tgttgatgtc   6420
agagagtgtt ttgcctatgt tttcttctag gagtttgtcc tgtcatatat ttaagtcttt   6480
```

```
cagccatttt gagtttattt ttgtacatgg tgtgagggcg tgttctagtt tcattgcttt   6540
gcatgcagct gtccaggttt cccagcaacc agcagccatc tttttgactg aagatacact   6600
cttcccagtg agatggaatc agatgatggg agatactata tgtacaaatg cttcccacat   6660
agtaaggcat cataacacag taatttttgt ttattctttt ttggtctttt ttttttttat   6720
ggccacacac ttagcatctg gaagttccca ggctaggggg cgcatcagag ctgcagctgc   6780
cagcctatgc cacagccaca gcaatgccag atccttagcc cactgagcaa ggccagggat   6840
ccaactcgca tcttcgtgga tagcagtctg gattgctacc tctgagccat gatggaaact   6900
ccgccgtaat cgttatgaat gaagtctcca ttgcccacct cagtgactgg tccatttcta   6960
atgaccctgt acttttattg gtacttccag taacggagtc agacccacct gcctaccctg   7020
ctccctgggc attacaatgc ttatcttatg aggagttcaa atattggtat cccagccacc   7080
gcatccgctg acttagatac ttgcaaccag gcagctcagc gcttttccaa tgcccagata   7140
ccttaggtgg cacattggag atagttcttg aagtagtgga gagccaactt gaatttgatc   7200
tgggcttcgg tgttggcccg ataactggtg tagttcccct ccagggtggc cagctctggg   7260
tccatcactg gtaaatgggg ctggtgacct atgatcacat gtgggcagga ccccacgagc   7320
aggctcccga gcccatcaat aaagaactct gccaagagag ggagagagcg cgagaaggaa   7380
acgtgagctt caaaccagag acccgggcca atactgcgac tctgggagga gggctggggt   7440
ggggggggac atagcttcta ttctggggag gttcagtccc atggcaaagc cactgagttg   7500
gaagatcaga cagatatcag cagagagaca cagattagca gaccccagga ctgggaggaa   7560
tgagagggga agaggtgggg tgctgctcac cagctgcagc taaacagaga aggatgtctg   7620
gaaaaggagg agcaggaaat tcccgtcatg gcgtagtggt taatgaatcc gactaggaac   7680
catgaggttg tgggttcggt ccctggcctc gttcagtggg ttaaggatct ggcgctgccc   7740
tgagctgtgg tgtaggtcac agaggcagct cagatcccgt gttgctgtgg ctctggcata   7800
ggccgggagc aaaagctcca attcgacccc tagcctggga acctccacat gccatgggtg   7860
cagccctaaa aaggcaaaaa aaaaaaaaaa aaaaaaaaaa aaggcaaaaa aaaggaggag   7920
cagcagcaag acaaggaaag agggaagggg cagagctgca gggagaggag gtagaagggt   7980
gtctcggaga agcaggaata gcctatggga gacacgaagg tggagggagg caagagagac   8040
caagagctcc ctagtttggg gagaaggggc tgcttccctg agcagcaggg ccccgccctc   8100
cctcagaaag agacttctga agccagcgca cagcccagct cgcttcttgc ccttccagcc   8160
tccccacctg agtgagccac tcgctgcagc cgggggtcga agccaattct ttggagtcgc   8220
tctgtgtgag ccaggaagaa gttgacaaca ccactggtca ccacgcagtc ggggaagcca   8280
tccacgggcc ggaaaaatcc tggctgctgg tggagacagt cgccattctt cccctgctcc   8340
agcaacagct tgaactggaa tgtgttttca atcacgctgc cacctaccta gccagcggga   8400
ggagaaatct gttagagaac agactccata tccaaggagc ctgtgccagg aagccttact   8460
ggactgaacc tcagtcacga caagaattgc actccctgga gttcccgttg tggctcagtg   8520
gttaacgaat ctgactagga accatgtggt ttcgggttcg atccctggcc tccctcagtg   8580
ggtgaaggat ccggcgttgc tgtgagctgt ggtgtaggtc gcagacgtgg ctcgtgagct   8640
gtggcatagg ctggtggcta cagctccaat tggaccccta gcctgggaac ctccatatgc   8700
tgcgggagtg acctaagaaa tggcgaaaag accaaaaaaa aaaaggtaat aataataata   8760
aaataaaata aaataaaaaa gaaaaagaat tgtactccct gtcttatcta cccttcatgt   8820
```

```
tacacttccg ccaagtccaa agggcagcaa agtttctgct gcacttaccc tccagcaagc   8880
tcactctttc cagagggcca ctccctcccc tcccttctgc tacaaggatc caggaggatc   8940
gaggatgggg gatcgcgttt gggtgcaggt gagaggcagc cagcgtgcag ccgtccctac   9000
gtggacttcc tgagcaagcc tttgtctcaa gttgtctccc tcccattctc tgcccctggc   9060
tcacttctct gcgccgtctg tccacacacc acacactcct gggagctcgc agctttgtgt   9120
gagcccgagc acagcaggac aagcaagtac atctattcct gaaccatcat aatcacctag   9180
ggaggcagag cagaatctgc cagttgcccc ccaccccctc gcctgttctt tccttcctcc   9240
tcttaggaaa tgagccccct gaggtgtttt ttggtttttg tttttccttt ttcagctgcc   9300
cctgcagttc ccaggccggg gatggaatcc aagccagagc tgcacccacc ccacccccac   9360
gcagcaacgc tggatactta atttaaccca cggcacagga ctggggattg aatgggcacc   9420
tccacagaga caaactggat ccttaacccc catgccacag tgagaactcc aaactccaaa   9480
ccctctgaga tttaagtgga ctaaattaag cgacaatgat cctacgaaag atgaaatttc   9540
cccacttctc tggagttccc aatgtggctc agcggtaatg aacctgacca gtatccatgt   9600
ggacgtgggt tcactccctg gcctcctcga gtgggttaag gatccggcat tgccgtaagc   9660
tgtggtgtag gtcacaaaat cagctcaggt cccatgttgc tatggctgtg gtatagacgg   9720
gcagctgcag ctccaacggg acccctaggt tgggaacttc catgtgccct acaaagaaga   9780
agggaggaag gaagggaaag agggagggag ggaaagagga gagagaggga gggaggaagg   9840
aaggaaggca gggagaaatg gcccacagca tatggcttga atcccagctg cagctgcagc   9900
aatgccaaat cctttaaccc gctggactga accagcacct ctgcagcaac ccgaaatgct   9960
gcagtcgggt tcttaaccca ctgtgtcaca gtgggaactc cctgaaagga tgtgatttag  10020
aacagatgtc tccaattttt aaaaagacca cattcttctc atcttttcct ttttttttt   10080
ttttttttt ggcttcttaa ggttgaaccc acggcatagg gggttagtgg ttagtttcca  10140
ggctaggagt caaattggac ccacagctgt tggcctacac cacagccaca gcaacgccag  10200
atccaagcct cgtctgtgac ctataccata gctcccagca atgccagatc cctgacccac  10260
tgaacaaggc cagggatcga acccacatcc tcatggatac tagtcagatt catttctgct  10320
gcgccacgaa gggaactccc aagaccacat tcttaaaaga aaactgttgt cttctactcc  10380
ctctctcccc ctttcttctg accgtgcagc tgagggccac aaagatggat gaacaacagg  10440
gaaggaagct ggaccaggat gaccctggaa agagacaata gggccagctt gcattctctc  10500
ttttttttt ttttttttt tttttggctt tttgctaatt cttgggccgc tccagcagca  10560
tatggaggtt cccaggctag gggtccaatc ggagctgtag ccgccggcct acgccagagc  10620
cacagcaacg cgggatccga gccgcgtctg caacccacac cacagcccac agcaacgccg  10680
gatcgttaac ccactgagca agggcaggga ccgaacccgc aacctcctgg ttcctagtcg  10740
gattcgttaa ccactgcgcc acgacaagaa ctccccagct tgcattctta cacgggtagg  10800
aactgcacct tttttgtcat ttatgctatt gtgactgggt ctctagaaga gtagcaaaga  10860
gacatcttcg tcaatccaga tgttttgggg gactgtccac ctggaataag agataactgt  10920
ggtcacggtg ctacttatcc actttctttc caggccggga tagaaccagc accacagcag  10980
tgacaatgct ggatccttaa ccctatgagc caccagggaa ctcccatctt tctttttcca  11040
aacagcttta ttgagatatc tttgatatat taaaactgta tgaaggagtt cctgtcgtgt  11100
ctcaatggtt aacaaatcca actaggaacc atgaggttgc ggattcgatc cctggccttg  11160
ctcagtgggt tcaggatcca gcatttttgt gagctgtgat gtaggttgca gacgcggctc  11220
```

ggatcctgcg ctgctgtgtc tctggcgtaa gccggtggct gcagctccga ttggacccct 11280
agcctgagaa cttccatatg ccgcgggagc ggctcaagaa aatggcaaaa agacaaaaag 11340
acaaaaaaca aaacaaaaca aaacaaaaca aaacaaaaaa ctgtatgtat tgaaggtgta 11400
cagcttgatt tttttttttt tttttggtct gtggcatgta gtggcttgat gcaggatctc 11460
aattcccaga ccagggactg aacctgggcc acagtgggga aagcaccaaa tcctaactac 11520
tacaccacca gggaactccc tgcagcttga tgttttgata tatgtagaca ctgtgaaaag 11580
atcaccacac gcaagctaat taatgaattc atcacctcta cacagtgtgg gtatcttcac 11640
aaatttcaag aacgcaatgc agtattatta actattcatc acctttttc cccttttcc 11700
atgtgtaaat taacttttga tatttgtggg gtttttttgtt ctgttttgtt ttgtcttttt 11760
agggctgcac ctgcagcata tgaaagttcc caggttagca gtccaattgg agctgcagct 11820
gccagtctac gccacagtca ctgccacagc cacagaaatg ccagatctga gccacgtctg 11880
ggacacacac cacagcttat gcaacaccag acccttaacc cactgagcaa ggccacggat 11940
tgagcccaca tcctcatgga cactagtcgg gttcattact gctaagccac gacgggaact 12000
cctgtgttaa ttttttattg tcattaaggc cacgtgtgct tttatagctt tgtgccattt 12060
tcatttttgt gatggtgtgt gacaaaacca gagcagcact cacattcctc tccaactctc 12120
accagtccag agaggaagtt ggaagtgatg catacaaaga aaaccacagc tttcaaaaga 12180
tacacgcacc ccaacgttca cggcagcact attcacaata gccaagacgt ggaaacaacc 12240
taaatgtcca tcaacagatg agtggtgtac acacacacac acacacacac acacacacaa 12300
tggaatatta ctccctcatg aaaagagtgc aataatgcca tttgcagcaa cgcagatgga 12360
cctagagatt atcatactga atgaattcag agaaagacgg atatcatatg atatcccaca 12420
tatgtggatt caaaagagat acaaatgaac ttatttacca aagagaaaca gactcataga 12480
tttagaaaac aaccttatgg ctaccaaagg ggaaaggtgg ctggcgtggg gagggggtgg 12540
agggataaat taggaaattg ggattaatat atacatacta ccatatataa aatagatagg 12600
agttcccatt gtggctcagt gagttatgaa cccaactgtg atccatgagg atgcaggttc 12660
aatccctggc tttgctcagt gggttaagga tccggtgttg ctgtgacctg tggtgtaggt 12720
cacagatgca gctcaggtct gatgctgctg tggctgtggt gtaggccagc agctacagct 12780
ccgatttgac ccctaacctg ggaacctcca tatgcctcgg atgcagcccc aaaaagacca 12840
aaaaaaaaaa aaaaaagata actgacaagg acctactgta tggcaaaggg aagtacacgc 12900
aattattctg taatttccta cgtgagggaa ggaatctgta aaagaatggg tatagctgaa 12960
tcactttgct gtacacttga aactgataca ccatggtaaa tcaactctac tccaatagaa 13020
aatacaaatt agggttttat aaattttata aaaataaaat aaaacctagg ccacctggtg 13080
gcctagaggt taaggatcca acattctcac tgctgtggca caggcgggat caggctggat 13140
ccctggcctg ggaacttctg catgacatag gtgtggccaa gcaaaaaaaa aaaattcaat 13200
taaaaaaaat gactgggagt tcccattgtg gctcagtgat taagaaaccc aactagtaac 13260
catgaggttg caggtttgat ccctggcctc actcagtggg ttaaggatct ggccggcatt 13320
gctgtaaagt gtggtgtagg ccagcagtta cagttccaac tggacctcta gcctgggaac 13380
ctccagatgg ggcaagtgtg gcactaaaaa gacagaagac aaaaaaaaaa aagattgaaa 13440
aaagtgccta aacacacttt tttcttttgc catttcttga gctgctccct cagcatatgg 13500
aggttcccag gctaggggtc cagtcggagc tatagccgct ggcctatgcc agagccacaa 13560

```
caacgggcaa ttcagccgca tctgcaaact acaccacagc tcacagcaat gccggatcct  13620
gaacccactg agcaaggcca gggatcgaac ccacaacctc atggttccta ctcggattcg  13680
ttaaccactg agccacgacg ggaactccac aacacacttt aaggacagaa caacggtgag  13740
tctggggagt ggggttggtg tgatttgttc aaagaaaagt aagaatggag gcagaagcag  13800
aatccgaggg tctcatttcc gtgcgagagt ctcaatccca gagctgctct gcatcacctc  13860
ctgcacggcc cttccccttc cgcctccctc ttcccccccc ccccaccccc gtcccttttc  13920
ctctcctctt tcctcctgtc ctttcctctc tgccctctcc tccccctccc cctctggctc  13980
gtcagatggc aatggggtag aactggcagc gctcagctca cttaccacgt ccagttccgt  14040
tttctctagg acgtccacca gcgcctcgat cctggtcttg ctgttgaaga tgaagtcatc  14100
gtccacccag agcacatatt tggtggtgac ctgagatatg gccaggttcc tgccagcaaa  14160
ccagccctgc gagggcaggg aggttagacc cgtggttgcc cgccccgctg cctcctagca  14220
tcacctgggg gctttctcag ctcccaaggg tcaggctgcc ccccagacag tggctgagaa  14280
cctctgggct aaagggagtc catgtctcag agaccctgga agaaggagag ggactctctg  14340
gagacgagaa agtccctcct tggccctgtg gcttgaggga tggatgcaag tccctttaca  14400
cctgacagtc tttgtggccc tttcgccctg tgttgcctgg aagatgctgg agggtggggc  14460
tctctggaag ggtaacatc cacttcctcc cggtgtgctc gagggaaggt gtggggcgcg  14520
gagagagaca ccccagcaag ggtgaaatca tgacagaggt ttctctgctg tgggacctgc  14580
gtatcaggaa accttagagc gtcagacacc gccagtcgct tacaaggacc tccatcaatt  14640
tccacaccaa gcgtgaggaa agacagatta cccaccccgt cactgcagga aagggagagt  14700
gacctgattt ctccgggaat ttggaggcag ccaggggact cagaggagtc cccaccccc  14760
gccccccaag gatcctgctg ccgtgggagg gtcccccca accccgaagc agccccaacc  14820
agggtaccac ttgaccctgg ggccctctgg tcccaaggtg cccgtgtctc cccctctggg  14880
aggaatatac cttcccaaat ggcatggtgt aatactccac gtggctgtca gtgattttca  14940
ggggctcctt gctgtcatcg gccacgatca ccgtcaggtc tgggtagtac tcacgaacac  15000
tccggagcat ggtcatgagc ttgtggggac ggaggaaggt tttggtggca atggtcacca  15060
ggtctcggag cttcctctct gggcaagaaa gggtaggtgt cagagctctg tcttcaagaa  15120
tcctcactga cgtgcattgc tctggaggtt tctttacacg gcgctgtctc gagtgtttgt  15180
ggacctcatg ccttttgttc acagttgatg ttagttggat cagaaaatac attttattat  15240
tattattttg tctttttgtc tttttagggc cgcacctgca gcatatggag ggtcccaggc  15300
taggggtcag ctcagagcta cagctgccgg cctacaccac agccacacca acacaggatc  15360
cgagcctcat ctacaccaca gctcacggca atgccggatc cctaacccac tgagcgaggc  15420
cagggatcaa acctgcatcc tcatggatgc tagttagatt cgtttccgct gagccatggt  15480
gggaactcca tgagtcagat tctcaaccca ctgagccaca acgcgaactc ccaatttgtt  15540
taaatggttt ctgtcttcta gagtgtctcc cttttttttt ggtttttttt ttgtttttttg  15600
cttgtttgtt tgttcttttc ttagtagctg cacctgcagc atatgtaggt tcccaggctc  15660
ccaggctccc agttgaatca gagccgcagc tgcaggccta tacctcagcc acatcagatc  15720
tgagccgcat ctttgaccca catcacagct ggcagctatg cagatactga acccactaag  15780
tgaggccagg ggttgaacct gcatcctcac agacaccatg tcaggttctt cacccactga  15840
gccacaacgg gaactcctct cttctggttc tgttggctcc agtctgctgt ttccttctgt  15900
cgagtgggat gcttcaagtt ctgcctgcct atctgcactt ggtttgcaac cggctttcat  15960
```

gctgttactg ggaattgaga cgcatagagt ttcacccatc aagggattca atatgaccag 16020
tcgtgaggcc caggaagagg ggaaaagatt taaagacctg agacctgccc tgtcacagct 16080
gcaatcctac agagagacgt gcctggcctg gtttgttttt tttttttgc tttttttagg 16140 gccgcaccca cggcatatgg aggttcccag gctaggggtc gcattgtagc tacagctgct 16200
ggccacagcc acagccacag ccacagcgat gccagatccg agccgagtct gcagcctata 16260
ccacagctca tagcaacgcc ggatcctcaa cccactgagc aaagccagga atcgaacctg 16320
aaacctcatg gacactggta gggttcgtta acccctaagc cacgacggga actccttgtg 16380
gttcttatcc atgttctttt cttactgatt cataagtcct ctgaagtaaa attagacctt 16440
tgactttcgt gtgtgtggtt atttttcccc agtttgtctt ttgtcatttg actttgcata 16500
tggtaggctt ccgtcattaa aaacattaaa aattgttata taatttatgt ttttagtctt 16560
tttcctttta gtctttttcc taggttttgt gtcttattta gaaaagtcat actttacaca 16620
gttattttta aactccaggc tgattcctag tacttaaaac aattagatat ttgctctacc 16680
tggactgtac cttggtgtga gctatgagat ggattcagct tgttattttc acacagctac 16740
acagttatct aacacaatct cttgaacaat ccatcttttt cccctttaat ttgaaaaact 16800
accttgatca cacggtaaaa ttccaagatg tctatttctg ggtttctttt cttttctttt 16860
tctttttttt tttttgtctt ttctagggct acacccgcgg cacatggagg ttcccaggct 16920
aggggtcgaa ttggagctgc agctgccagc ctatgccaga gccatagcaa catgggatcc 16980
aagccgcgtc tgtgacctac accacagctc atggcaatgc cggatcctta acccactgag 17040
caaggccagg gaccgaaccc gcaacctcat ggttcctagt cggattagtt cgttaaccac 17100
tgcgccatga caagaatgcc taggtatcta atttgattcc actgacatag ctcttcgtgg 17160
tccaatacca ttctattttt ataattatta cttattaaaa tgtcataaat cattagattt 17220
ttttcaaaat aaattcaacc gtacaataag ttaaacgtaa tgaagcagta ttaaaagcgt 17280
attctagcat ttttttcctc caaaaaagct tgttggagtt ctctggtggc ctagtggact 17340
aaggatccag tgttgtcact gctgtggctt gggtcactgc tgtggcacag gttccatcca 17400
aggcctggaa acttccactc tgcgggcaca accaaaaaaa aaaaaaaagc ttgttaacag 17460
gactcctatt ggagttttta tttcatcgag tctcctcctc catctcagag gggagccctt 17520
ctgcatctca cccaatagtc tccagggacc caccatggag ccccagggac aagggtctta 17580
cctggtccag ggtcatataa cttgggcatg acaggatagc ggatggtcac tggaaacttg 17640
gccactgagg acttggactc cagactcact ggagggagaa atcaggtcag ggctggtgca 17700
cggtatctgg gtcactcccc acaaggccgg ggaagcccac gcgatggggg agtgaaggac 17760
tgaggacccc acagagtcta tggcattctg gctcctaccc tgctgtgtgt tccggaagca 17820
acctgctgac cgcctctgaa acgcacatgt ctgccccgt gagactctgt cgggtgaagt 17880
gggcttggaa tcagaggggt agattaagtt tgactctgca tctataattt gaaatacctt 17940
gggtaagtca catcacctcc acctccacct ccaaaaccag ggtaacacta ccagcccagt 18000
tcacctcaca gtgccttttt tgtttttttt ttttttgaag ggctgcaggt gcagcatatg 18060
gaggttccca ggctaggggt caaatcagag ctgtagctgc cggcctacac cacagccaca 18120
gccacagcca catgggatcc gagccacgtc tacaacctac accagtgcct ggcaacacca 18180
gatacttaac tcacgagtga ggccagggat tgaacctgca tcgtcatgga tcccagtcag 18240
gctcgtttct gctgagccac aatgggaagc cccttcatag ggtcattctg tggtaagaca 18300

```
tgtttaaaaa tcccaaggta cagagaactc tctctctagc ttatgctcat ggaaaatctg  18360
cctcacattc actggggtcc tgggaaagcc tcctgtgtat ctggtcaaag cagaaaaagg  18420
taaatgtctt tttttttttt ttttttttct ttttacggct gcacctgctg catatggaag  18480
ttcccggact agggctcaaa ttggagctgc agctgccggc ctacgccaca gccacagcca  18540
cagccaatgg aatcccagcc acatctgcga attatgccgc agcgaggcct gggagcaaac  18600
ctgcatcctc atggattcta gttaggttct taatccactg agccacaaga actccggaaa  18660
agggtaattt atttatgtat gtatttattt atttttgtct ttttcttttt agggctgcac  18720
ccgtggcata tggaggttcc caggctagga gtccagctgg agctatagcc accagactac  18780
accacagcca cagcagctca gaatctgagc cacttctgca gcctacacca cggctcacgc  18840
aatgccggac ccttaacgcc ctgagcaagg ccatggatca aacccgtgtc ctcatggata  18900
ctagttgggt tcgttaacca ctgagccaca atgggaactc ccggaaaagg gttttaattc  18960
atccagaaag taagtggggc tgccctgagg gtggcaggaa ttggtctccc atgaattctg  19020
ggagtaagag tcgggtttgg gatgggaggg gaggaggaag acaaagccac tgcccttggg  19080
actgacagct cccccacatc cctctttccc gtaatgctca ggacaagcca ctgacacgtg  19140
gactgtgttc tcctctactg cagctgaaac cttcagcttt ttctttttct tttctttcct  19200
ttgcttttta gggccgcacc cgcagcatat ggaagttccc aggctaggaa tcgaatagga  19260
gccgcagctg ccagcctaca ccacagccac agcaacgcag gatgggatct gagccacgtc  19320
tgcgacctac accacagctc acggcaacgc cggatccccg acccaccggt gaggccaggg  19380
atcgaaccgc caacctcgtg aatactggtc agattcattt ccactgcacc acaaccggaa  19440
cagggaacct tcagctttga tcactgatga gaacgggagc agaaggggat ggtttccagg  19500
tgcagagcat gaatgatctg tcctcatgta cagacaagca ggcatttcac tgtctttctt  19560
tcgggtccct ccacgggctc aatggcaaca cggggatagt accaggtaca ctaagtggga  19620
aattagaaac aggagccagg gaagcaggct tcctggagaa ggaagacctt gagagccggg  19680
ggcgggggca gtggtggtgt ttatggggtc cctcagcatt ttgccatccg aggacggact  19740
cacccacatc cactctgtgg aggtggtact ctgtgctcgt gtatgtcaca tgctggagga  19800
tgaaattcaa aagctcccgg ctactggtca aaatgttcag ctgcttctgg cctctgccct  19860
tcaccacatt gtctgggacg tcagcaaggg tgttcagtgt ccccagagaa gctgtcaggg  19920
tgacctagga taaaggaggt agaaagccta aatgcagaga ggcacatacc caggatggcc  19980
agcagggggc agcatgcata agggtgtgag gagaagaacg cttcatgctc ccgaaagcta  20040
gggtctggcc tctgatggag tgtctgcccc agccccaaaa gcctaggacc taggacctgg  20100
tgtgttcaag ggccatttct gaaacattct taactcttgg catgcagagt taagtggcat  20160
ccattcttaa agatttcttc tggagttcct gttgtggctc agtgataacg aatccgacta  20220
ggaaccatga ggttgcaggt tcgatccctg gccttgctca gtggattaag gacccagtgt  20280
tgcttcgagc tgtggtgtag gttgtagatg cggcttggat ccggtgtggc tgtggctctg  20340
gcgtaggctg gcagctacag ctctgattgg acccctagcc tgggaaactc catgtgccgc  20400
tggatgcggc cctaaaaaga caaaagacaa aaaaaaagaa agaaagaaag aaagaaaaag  20460
aaaactgctg aaaacatttc agtcaacaga tcttttcttt tcttttcttt ctttttaggg  20520
ccagacctga agcacatgga agttcccagg ctaggggtcc aatcagagct acagcatctt  20580
tgtctgcccc atctttgtct ctctgtcaaa cgctgagacc agccaccatc tcagggaaaa  20640
gcgcatgggc agtgagccaa ggacaggatg ctaagtgcaa agtggggctg ggaaggggac  20700
```

```
tcttgcctca tagatgggag catcaggtcc ttcaaaccgg aggcctggag gtcacaggaa  20760
aaaggagaaa ggaaaaaaaa aaaaaaaaac atttgagagg atgccaagag ttccctgatg  20820
ctctcagctc cctggccaat tcctacacat ccctccagag ccccttcaag tgtcacctat  20880
ccagggtgtt tgcagaccgc tcgcctcccc actagagctt gctagatggt gtccaacgga  20940
cctctgcaaa ctccagcaaa ccaaagcctc tgatgccctc ccctagtttg ggtttttttt  21000
tttttttttt ttgtcttgtt gttgttgggt tttggggggg ggttgggggc tttttagggc  21060
cacaccctct gcataaggaa gttcccaggc cacgggttga atcagagctg cagctgctgg  21120
cctacgtcac aatgacagca atacagattg tcagctgagt ctgcgaccta caccacagct  21180
cacagcaaca ccggatccct gccccactga gcgaggccag ggatacaacc caaaacctca  21240
tggtgcctag ttggatttgt ttccactgca ccaccacagg aacccctaaa tggtaaactt  21300
tatgttacat atattttaca cactagaaag agaattatcc aaaatggcaa atcatttttt  21360
aaatgagtac ttaaaaacac gagcaactca gagttcctgt catggcgcag tggaaacgaa  21420
tccaactaag aaccatgagg ttgtgggttc gatccctggc ctcactcaat gggtaaagga  21480
tccagcattg ctgtgcgctg tggtgtaggt cgcagacgca gctcggatct ggtgttgctg  21540
gggctctgct gtaggccagc agctacaact ccgatttgac ccctagcctg ggaacctcca  21600
ggtgctaaaa agacaaacga caaaaacaaa aaacaaaaaa cagaacaaaa caaaaaaaac  21660
ccaaaacacc agcaactcat ctcaaatgtt tttactttaa aatctatctc tgttcttatg  21720
actaatgcaa attctcactc aaacacatcc tccttctgtg gcctaaactt atttgggaaa  21780
ttggcaaaat aacatttacc tcacagggat gtatgctgga cgagaggtgt gtgtaaaaac  21840
cactcgtgga ggagctgtaa cggatagaaa tattctttcc atatgcagtc cctggagatg  21900
ggctgaggct ttgcttgctc ccttgatgct ggcagacacc aaaaagccaa taatggccta  21960
agattcctcg aggcacccag atctccgtcc tctcctatac gatccaagat gcccagggag  22020
gcaacagctc ctaagtgcca ttcccagtgg tggaaacagt gagaataaca tcaaatgaaa  22080
ccatgtccag cttcatggat tgtgctgggt atccgggaag gattcagcgg ataactgctc  22140
ccttctgctc ccttctttgc ttcagaagga ctacgagagc tgcctgggtc ctgtccgggt  22200
ggagatgcac ctacctggga tggggatggt gtgtagaggc atcacttcca ccccgtggac  22260
cgggtaccca aaggggaggt tgggctgagc cagcaggggc ggtgggcgag ggagcccttc  22320
tctgcaggga aacaaaacca tcagcagctg ccttgatacc tgtccctgac tagctctttt  22380
ttgggggggga gggggtgca accacaccca cggcatagac gttcccaggc cagggatctc  22440
acccacccca cggcagcgac ctgagccaat gcagtgacca tgccagatcc tccttaacgt  22500
gctgagccac aagggaactt ccactgctcc cactggtttg ttcttttttt tttctttcgt  22560
ttttggcctt cccaggccag ggatcagacc tgagctgtgg ctgcgaccta agctgcagct  22620
gcagcaaaag atctttaacc cactgtgcta ggccaggggt tgaacctgca tccccgtgct  22680
ccccagacac agctgattcc actgtaccac agcaggagct cctcactgtc gccactggct  22740
agttcttttt ctttttttct ttcttttttt ttgctttttt agagccactt cccgcggcat  22800
atggaggttc ccaggctagg ggtccaatca gagctgtagc tgccggccta cgccacagcc  22860
acagcaacgc gggatttgag ccgcgtctgc gacccacacc acggctcaca gcaatgctgg  22920
atcctgaacc cactgagcaa ggccagggat cgaacccaca tcctcatgga tactagtcag  22980
gtttgttaac cactgagcca cgacaggaac tgctggctag ctcttaaagg ggtatctgtg  23040
```

-continued

```
cccagagctt tgggctgcaa agggggagaa atccaaagta aatcgtcgga ttgtcatgca  23100
ttctctcctc ttctttattc ctgctcctcc ctccagcctc gaattccaca aagaaactga  23160
ggcagattac aacaacacac attaaaaata aaaatcacgg agttcctttt gtggctcagc  23220
cggttaagaa tccaatgcag cattcttgaa gttgcgggtt caatccctgg cctcgctcag  23280
agggttaagg atccagcgtt gccctgagct gtggtgtagg tcgcagacgc ggctcggatc  23340
ccacatggct gtggctgtgg ctgtggggta ggctggcttc tgtagctccg attggacccc  23400
tagcctggga acctccatgt gcctcgggtg tggccctaaa aagtaaataa ataaataaaa  23460
tgaaacataa cataaagaga acaaaggtaa cacctgctca cactcaccac gttcgaatta  23520
ttttaataca ttttcaattg ctggttttca atgtgagcca ttttaaataa atctttacat  23580
gcaatattaa aaaatattaa aatattatct ctactcttga ggttatttgc atcaatctcc  23640
ctgtggatgg agatattata taaccggcat gcaatgatat ctcgtgggag acttgaaatc  23700
agccacagtg tgatttcttg tagggttgag ttttttttta atttttgaac tttttactaa  23760
agcagggttg atttacaatg ttgtgtacag tgtgattatt aaaccgtgga aattggcaaa  23820
cactacaagc cactaccaaa agcccatggt taaatattac caccactatt catatttctc  23880
cctcaacgta taaacacatc tacccacact tatacacaca actatcccct cctcttttaa  23940
aaacacaaat gtggagttcc cattgtggca gagtggaaat gaatctgact aggatccatg  24000
aggatgcaga ttcgatccct ggcctcactc agtggggtaa ggatccagcg ttaccgtgag  24060
ctgtggcgta ggtcgcagac gcggctcaga tctggcattg ctgtggctct ggcgtaggca  24120
agagtctaca gctccaatca gactcctagc ctgggaacct ccatgtgcca tgggaagtgg  24180
ccctagaaaa ggcaaaatac caaaaaaaaa aaaaaaaaaa aaaaaaaaag agggcattcc  24240
ctccccccctc cttggagcca caccctcggg aatgagtaga gagcttccgc tccatctcag  24300
ggcgcaagag ccctcagcat ctgcaatacc tcctctgaaa gtgttcgagc tcagcctgtc  24360
tcctcaggtt cactgcgggg aggtcttgcg ggtcgtaggc atcctccaag ttatagcttt  24420
cctgatgccc gaaggcgtca cattggcact ggtttttcgg gaacagccta aaataagaca  24480
aggtcaaaga tcacagattg ggaaagtggg ctggtaggtg agggggagcc gcaagctcgg  24540
tccggtgtat tttttttttt tttttaactt tttattttct cttttttttgt ctttttaggg  24600
ccgcaaggtt ccgaggctgg ggtctcatcg gagccgtagc caccggccta cgccagagcc  24660
acagcaacgc aggatccgag ccgcatctgc gacctacacc acagctcata gcaatgcttg  24720
atccttaacc cactgggcaa ggtcagggat cgaaccctca acctcatggt tcctattcgg  24780
attcatctcc gcggagccat gatgggaact cccaatccag tgtgtttttc cccctaggct  24840
ttcccatacc tagcgccagg gttgggttga gaccctggaa tcacagcagc ggccgctccc  24900
aaagacacag ggaaggaagg gaagagagga aggaaggagg gcgagaaggc cccctctctg  24960
gaatcaaagt cctttattta ttattattat tattatttgc tttgtagggc tgcacccgca  25020
gcatatgcag gttcccaggc taggggtcca atcggagcta cagctgccaa cctacaccac  25080
agccacagca agatcagatc caagcggcgt ctgggaccta caccacagtt cacggcaacc  25140
ccgatcctta acccatggag cgaggccagg gatcaaaccc acaacctcat gcttcctagc  25200
cagattcgtt tctgcagcga catgacagga actccccaaa ctcctttaaa cttgagagtc  25260
acaggaatct cagaggcatt gcagccccac ccaccagatg aaaaggccag agggccagaa  25320
aggccacatc tttcctataa ttttgtttag ttttgggggt tttaatgtgt ttttgttttt  25380
tagggccaca tctgcagcat atggaagttc tcaggctagc ggtggaatcg gagctacagc  25440
```

tgccggccta caccacagcc acagaaacat gggatctgag ctgcgtcttc aatctacacc 25500
acagctcacc gcaaccctgg atccccgact cactgagcga agccaaggat caaatctgcg 25560
catcctcatg gatcctagtt gggtttgtca ccactgagcc acaacgggaa ctcctcctac 25620
agttttggtt aaataggccc tccaaagtcc taaagaactt tgctgggtgc tatagaggct 25680
atgcccagca gaccaagccc ctttctagtc ccgccgtttg cagtcaaatg ctctacccct 25740
gagccatact cccaccaggt cccgcagtca ggattcacat tcccaatcag cacaggtgca 25800
gaaaggtagg gaactggctg taaagtgggc ataagaggac acagtaggag ttcccgtcgt 25860
ggcgcagtgg ttaaccaatc cgactaggaa ccatgaggtt gagggttcga tccctggcct 25920
tgctcagtgg gttaaggagc cagtgttgct gcgagctgtg gtgtaggttg cagatgtggc 25980
tcggatcctg cgttgctgtg gctctggcgt aggccggtgg ctacagctcc gatgggaccc 26040
ctagcctggg aacctccata tgctgcgaga agggcccaag aaatagcaaa aagacaaaaa 26100
aaaaaaaaaa aaaagaaaaa agggcacagt aaagccacag gaggagccag ggaagtgtca 26160
gtgcaaagtg gtattcttgc catctcaccc gttttcaccg tagaaatcgg gtttctcagg 26220
tagaagcttc agcgtctgcg catccagggt gggggacggg atgggtgagt tgaggagact 26280
gaagtctgta tcgaggaaca cgctttggaa cataaagagt ccaacgctca ggaccaaaag 26340
caccatcaat atcttgagga tcgacagaca tctagggctg ttgggacaca agagagcaaa 26400
cgctgttaaa atcttttctg agtatgttaa aaaagatttc attgtgcgac atagatggga 26460
atagcaactt gagcaaaaat gcaagtcaaa cctgttttgt acactacgta tcaaaattga 26520
tttcttccca aggcaaaaga gaaagaaaag caaaaataaa cctaagcaaa ctgacaagct 26580
tttgcacagc aaaggaaacc ataaaataac ccaaaaagat cctgctggga tccactggga 26640
acgatgtctg gtcacttgcg atggagcatg atcatgtgag aaaaaagaat gtatacatgt 26700
gtgtgtgact gggtcacctt gctgtgcagt agaaaattga cagaacactg caaaccagct 26760
ataatgggaa tgataaaaat catttaaaaa actgatttca gataaataga aaagtaaaga 26820
atcaaatctg cagagagttc cctggtggct cattgggtta aggatctggt gtggtcactg 26880
ctgtggctct ggtcaccacc gcggcatgac ctccatccct agcccaggaa cttctgcata 26940
cgtgggcatg gccaaaaaac tatactcagt ggaaaatgtg aagtttttca aatacgcact 27000
tctgatcaca agacctaaaa ttaataaatg aagcaataaa ataagagatt tgaaaatgga 27060
caacaaaatg aacctacgaa aagcagaaac aagattttag agatagccaa atagaaagtg 27120
gtgaatttaa aaaaaaaaaa actaaaatgg aatcatcgtt aaatctaagc acagagtaga 27180
caactggttt tttcttttat ttttttaaaa ttttatggcc acagccatgg cctgtggaag 27240
ttcccaggcc aaggactgaa tccaatccat agcttcaacc tacaccttta accaccgcac 27300
tgggcccagg gatcaaacct gcacctctcc agtgacctga gccactgcag tcggattctt 27360
aacccactgt gccagggtgg gaattccaga caactttata acctccttgc tctaagactt 27420
tcctcctgac ccagaagtga cacctacaaa cgagtctggt tatatcacat gacgctcccc 27480
tggtcctggc tgagtaagcg gatgttcacc tcatccgaat ggggctaatc agccagaatt 27540
tccttcccag aaatggggaa ccagagatat tgttcggcta atcctaatcc cctgaactga 27600
gaatagaggg gaggaaagaa gagagagaag acagaaggtg agagaaacaa aagaagccta 27660
gaaggacttc ccattgtggc tcagtgggtt aagaccatga ccagtgtccc taaggatgca 27720
ggttcaatcc ccacccttgc tctggcattg ccacaaactg gtggcagatg cggcttggat 27780
ctggcgttgc tgtgcctggg gcataggctg gcatctgtgg atccaattcg acccctagcc 27840
tgggaacttc catgtgacac aggtgcggcc ctaaaaaaaa atcgttttta atttaaaatt 27900
ttgggggcag tgtctttaag gcattagtct gctatggctc cctttgcctg acaaagcaat 27960
aaagctatct ttttctcctt cacctgctcc tccccccaaa aaagagttcc cattgtgccg 28020
cagcagaaac gaatacaact agtaaccatg aggtttcacg ttcgatccct ggccttgctg 28080
ggtgggttat ggatccagca ttgccatgag ctgtggtgta ggttgcagat gtggctcgga 28140
tcctgcattg ctgtggctgt ggtgtaggcc tagccttgga acctccgtat accatgggta 28200
tggcactaaa agccaaaaaa aaaaaaaaaa aaaaaaaaaa aaaatttaat ttaattttta 28260
aaattaaaaa atttttaatt tagttttttt aacttaaaaa aatttttttta aatagagaag 28320
cctagatcct gaatacctag atgaaaggga tgactttcta caaaaacgca aatgaataat 28380
gtattgggga aataaaataa acaaataaac aaataaataa aagaattccc actgaagcac 28440
cgccccccca aaaaaaaacc cacaaaagac ttaaacagac ctgtaaaaat ttaaaaaaaa 28500
aaatcaagga gttcctttca tgcctcaggg gttaatgaat tcaactatga accatgaggt 28560
ttcgggttca atccctggcc ttgctcagtg ggttagggat ccagcgttgc cgtgagctgt 28620
ggctctggcg taggctgaca gctgtagctc caattagacc cctagcctgg gaacatccat 28680
atgccactgg ttcgacccta caaaagccca aaaaaaaaaa aaaaaaaaaa aaatccagga 28740
atttatcaaa ggtctatgta cttttcaaag tcccaaatcc acacttcaca agtaactcca 28800
gactggtttg taagaaacca gctttgcagt gatgcaaata taggtactga ccaataacga 28860
tgtaaatacg ccaaacaaat attaaccagt gggacacaac agtatcttaa atgaatgagt 28920
caccgttaac gaatgctgtt cttggagttc ccgtcatggc tcagcagata cgaatctgac 28980
tagtatccat gaggacacag gctccatccc tggccttgct cagtgggtca gggctctgga 29040
attgctgtgg ctgtggtgta ggtcacagac gtggctcaga tcccgcattg ctgtggctgt 29100
ggtgtaggcc ggcagctgta gctccgattc cacccctagc ctgggaacct ccatgtgccg 29160
caggtgcggc cctaaaaaga caaaaacaaa agcatgttcc ttctaggaga gcaaggataa 29220
ctcagtgcca ctgtggggca aaaccacacc gacgccatgc tgtcagctca tcttaggccc 29280
acagtctcat ctgctccccc tccttattaa aaaaaaaaaa aaaaaaaaag aatgatcaca 29340
tcctaagttc ctaacacaat tttcagacta tcagatagaa acaaatcact gacaacctgg 29400
gtgggggggca gcatttgggg gaagtgagtg tggtcttggc ctttttgagg gttgggtttg 29460
tttcctttttg ctattaggta ctaaaactta aaattgcatc acttagtgaa aacagaacaa 29520
aaatagggtc ggactttctc tgtggctcaa caggttaaag acccagtgtt gtcactgcag 29580
tggccctggt cgttgctgtg ccatgggttc cattcctggc ctgagaactt ctgtatgcct 29640
cgggcgtggc caaaaaaaac ccaaacaaaa acaaaaacag aaacatgagt tcctgtcgtg 29700
gcgcagtggt taacgaatcc aactaggaac catgaggttg taggttcgat ccctagcctc 29760
gctcagtgag ttaagggtct agcgttgcca tgagctgtgg tgtaggtcac agacacagct 29820
cagatctggc cttgctgtgg ctctgccgta ggccagtggc cacagctctg tttcaacacc 29880
taacctggga acctccatgt gcggtgcatt cagccttaaa gagaaaagaa aaaaacaaac 29940
aaacaaacaa aaaaaaacaa tagtgaggaa aagtggcatc attttacctt tttgcctatt 30000
taatgtttag cttaatagat aaaatgaacc atctgttagg acaggttgtt tcgctgaaga 30060
atatgaagaa aatacaaccc cacacaggta tgtcaccaga aaagggagaa acactttaat 30120
tgctttttca atattgtaga tatttatctt tgatactaca ccaaaaatca agaagttagt 30180
agcaggttat tgttttgttt tgttttgcct gtggcatgca ttagctcgat gtgggatttt 30240
ttttttttt ttttggcttt ttttttggcc ttttgccatt tctagggctg ctcccagggc 30300
atatggaggt tcctaggcta ggggtccaat tggagctgta gccaccagcc tatgccagag 30360
ccacaggaaa cggggggagt tgagccaggt ctgctcacct tacgccacag ctcacagtaa 30420
tgctggatcc ttaatccatc tgacccaggc cagggatcga accctcaacc tcatggctcc 30480
tagtcaaatt cattaacctc tgagccacga cgggaactcc tcaatgtggg atttcagttc 30540
ccagtccaga gactgaacct aggccacaga ggaaaaaagc gtgaacctga acccttagta 30600
gctagggaac ttccaagaag tggtactttc ttaaaaagtt agttaagtgt ggactctgaa 30660
accatatcag tgaaaaaaaa attttttttgc ttttttttt taggacccca cctggtgcat 30720
atggaagttc ccaggctagg ggtggaatga gagctacagc tgctggccta caccacagcc 30780
atagcaacgc cggatcctaa acccaccaag caagggaaca aatagaggga gtttccactg 30840
cgcacaatgg gatcggtggc atcactgcag cgccagggac acaggtttga tccctgacag 30900
cataggttgc aactgtggct cagatctgat ccctggccca ggaactccat atgccactgg 30960
cacggcccct ccaccctgcc aaaaagagtt tggaggcgtt ccctggtggt tcagtggtta 31020
tggatctaca ctctcaccac tgtggcccag gttcaatccc tggtctggga actgagatcc 31080
cacatcaagc cgctgcacac cttgcccaaa aaacagggtt ttttaacctt tttttttta 31140
aactgttatt ccccaatgcg attttttttcc cctactgtac agtatggtga cccagttaca 31200
catacatgta cacattctgt tttctcacat tatcatgctc catcataagt gactagacag 31260
agtttctttc cttttttctt tttttcttta tttttttaatt acttccccaa tacaatttgt 31320
taaaagggtt ttttaatcct gataataaac acataaaatt tagtaccttg gagttcccgt 31380
tgaggctcag cagaaacaaa cctgactggt atccatgagg atgcaggttc aatccctggc 31440
ctcactcagt gggttaacga tcccgcattt gccatgagct gcggtgtagg tcgcagatgc 31500
agctcaaatc tggcattgct gtggctgtgg tgtaggctgg cagctatagc tccgatttga 31560
cccctagcct gggaacctcc atatgccata ggtgtggccc tcaataaaac aaagaaagaa 31620
agaaagaaag aaagaaggaa ggaaggaagg aaggaaagga aggaagaagg gaaggaaagg 31680
aaggaaagga agaaagaaaa aatttatcac cttaactact tctaagtgta catatacttt 31740
cataatgtag attgttcatg tcgttttaga acggatctcc agaacttttt tctgcttttt 31800
tctttgctta tatttttgca tgcaactatt tttatccatt ttttctgatt atgaaatttt 31860
tatcttttac ccattgaaga aaaaaaaagt tcctctttac aaaaacaaaa caaaacaaaa 31920
caaatatatg taggagaaat gatagaatta gaaaaatcac cactttgcta ccaacaatgt 31980
aataaatgat tctggccagg attgtccatc ttttttttt tttttcctc gtttttttgc 32040
aatttcttgg gccactcctg cggcatatgg aggttccaag gccaggggtc caatccgagc 32100
tgtagccgcc agcctatgcc agagccacag caacgaggga tccaagccgc gtctgcaacc 32160
tacaccacag ctcatggcaa cgccggatcg ttaacccact gagcaaggcc agggatcgaa 32220
cctacaacct catggttcct agttggattc gttaaccact gagccacaat gggaactcca 32280
ggattgtcca tctgttctaa aacatttgcc aggtgcagga ttttgttttg ttttgttctg 32340
ctttttgtgt ttttcttctt ctttttcttt tttctttttc ttttttttt tttctttttt 32400
gtctttttag tgctgcaccc acagcatatg gaagttccca ggctaggggt ctaaccacag 32460
ctgcagctgc cagcctacgc cacaacagca acagcaacgt tggatccaag ctgtgcctcc 32520
aacctacacc ccagctcacg gcaatgccag atccttaacc cgctgagcga ggccagggat 32580
caagcctgca tcatcatgga tactagtcgg gttcattagc cactgagcca cgacaggaac 32640
tcctggaggc aggatattga atggtgccat tccggagaac acttactact tacaaagaga 32700
taaaaacaca tctttgcaat gaaaggatca tgcatcacta ccttaaccac atggtcaaat 32760
aaacatccct aatagtgagg cagcctgacc aactgtcctc cggatatgat gataggaagc 32820
acacagatca tttaaaggag tattactgcc aaaatattta accgaaatgt aatcaaggat 32880
cagagacctc actgccaatt tataggaaaa aacaggggat aaaaatttag taacaccatc 32940
aagaacaata gacaaatcag ggacatcaga atgttttctg caagacaaca ggcctgaact 33000
cttgacaaag gaaaaaaagt gggagttccc gctatggcac agtgggttag gaatcggact 33060
acagcagctc ggggcattgt ggaggtgcgg gtttgatccc tggcccgcta tagtgggtta 33120
aaggatctgg cgctgtcaaa gctgcggcca ttaaaaaaaa aaaaaaaaag aaaagaaaaa 33180
agaaaaagca attgaaaaaa ataaaaagaa tgagagtgaa tgagtaacat ttctagtaaa 33240
gggttgcctg tatcttgtgc agaacataca gaatacatct ttcaatgatt ttagtcaatt 33300
tttttgcatt ttaagaaatt tctttttttt taattgtggt atagttaatt tacaatgttg 33360
tgtgaatttc aagtacacag caatgtgatt caattacata tatacatata tacacataca 33420
tatcctttgc agattctttt ctattatagg ttgttacaac attttttttt tctttttaag 33480
gctgcatgtg tggcatatgg aagtttccag actaggggtc gaactggagc tatagctgcc 33540
cgcctacacc acggccactg ccacagcaac acggtttccg agccatgtct gcaacctaca 33600
ccacagctca cagcacgctg gatccttgac ccactgggcg aggccaggga tccaacctac 33660
accctcatgg atactagtca gattcctttc tgctgcacca cacaggaact ccctattata 33720
agatattgag aatagctgtc ctgtggcaca gtgggtaaag gatctggtgt tgtcactgta 33780
gtggctcagg ttgctgctgt tgcacaagta tgatccctgg cccaggaacg cttgggatgg 33840
cattaatagg aattgtttgg taggagattt ttaataaaat gttcaaccgc ccaattttta 33900
atagataact acaaatgttc tccactgtta aaactgcact ttatgtactt aagtggggat 33960
gttaaaatta tatgggtccg cccgctatta tagttgaacc acatttgaga cacattcaaa 34020
aaagggtaaa aatcgggagt tcccactgca gctgcgggtt caatccctgg cctcactcag 34080
tgggttaagg ttccggcatt gccatgagcg gtggtgtagg tcgcagtcgc ggctcaaatc 34140
tcgtgttgct gtggctgtgg cataggctgg cagctacagc tctgattgga cccctagcct 34200
gggaacctcc atatgccgca ggtgtggccc tagaaaagac acacacacaa aaaaaaggtt 34260
atgttgaagt tcccgttgtg gctcagcagt aacaaaccgg actagtatcc gtgaggacac 34320
gggtttgatc cctggccttg ctcagtgggt taaggaccca gtgttgccac aagctgtggt 34380
tgcagtgcag gtcacagaca aagcttagat ctgacattgc tgtggctgtg acacaggcca 34440
gcagctacag ctcaaattcg acccctagcc taggaacatc cacccacagg gggcggccct 34500
aaaaaaaaaa atatatatat atatatgtgt gtgtatatat atatatatat atattttata 34560
tataaaacat tttatatata tatataaaat atatatatat aaaaatatat atatatataa 34620
cattttatat atatatataa aatgttaaca ttgagtaggt ttaaggttat tattttaata 34680
actttataaa taaaaatttt agattttctc agctttaatt tttaattagg tgtggagttc 34740
ccactgtgga gcaacaggat cagcagcatc tctgaagcgc agggatgcag gtttgatctc 34800
cagtcctgca cagtgggtca aagatccagc attgccacaa ctggggcata agtctcaact 34860
ggggctcagc tctgatcact ggcccaggaa ctccatatgc atcggggcag ccaaaaaaga 34920
agaaaaaaaa agtgtctaat atggtaatag gaatagatac aacccatgta aacaaaagtt 34980
ttttggggtc ttcaataatt tcgaagagtg taaggggtcc tgagaccaaa aagatcaaga 35040
acggctggtc tacgttctaa gcaactgctg tggttcttgt taagttttaa tactgaagat 35100
gagtttttac aaggacaaac aatataatac agggcatgta gccaatattt cgtaataact 35160
ataaatggaa tatagccttt aaaaaggcca atcattctgt ggcaccctga aatttatatg 35220
atacatgaac tgtacctcaa taaaaaaatt taataagata ataataatat aggtgagctt 35280
caattagcac attctattac ttatctttaa taaaaattat attctgtgtg caaggtaatc 35340
tgacaaactc accagtacaa ctggtttcca acatagacct ggctcagctg cagaggttcc 35400
tttcaagagt aaacttgcag ggctttcccc gctgtggcac agcagaaatg aatcagacta 35460
gcatccatga ggattcaggg cacagaaaca gctcagattt agtgttgctg tggctgtggc 35520
catggtgtag gccagcagct gcagctccaa ttcgacccct agcctgggaa cttccatatg 35580
ctgatgtagg agaaaatgtc ccaataaaat gtagaaagga gagaccccgg ccatgacgac 35640
taagcaaagt ctagccaact gccccaacca gtcctccccc atgcatctgc ttctgtaaat 35700
ttgtttccgc atctactacc ttgcctgacg tcactccagt ccaactagcc aagcttggac 35760
ctggaagacg tagcccataa aagccttgtg aaacccttct tccgggctca gactctggag 35820
agtgatctcg tctgagcccg ccggcgtaat aaacctgagt tctccaactc tccaagtgct 35880
cgcttggttt ctcgccgggt aaaagagctg ctccactatg gccacagagc tactggagct 35940
ggtacgctac agccacgggg ctgtcgccag agctgatacg ctgcagcgca gggctgctgg 36000
gtatctgctg taacatttct ggaggcccca gcgagattcc aacctttctg gccccttgag 36060
ccactggaac agaggtaagg ccgcccggga gccggggagc ctcaaaccga acgaggcggc 36120
gcaccacccg acggtattct gggtcctcct tcgtcagcgg cattcctgat tcccgggtga 36180
ccaaaccctg accagactca gtggagagat ggaccaactc accagaaagg tatccggaca 36240
aggtaaggca gcggggccaa ccccagtcag gtcctgcccc agtgggcaga agaggggact 36300
gatcaccccc tgagggagac tctcccggtc agaagctgtg cctgactgga gcagcagtcc 36360
tagtgctcca gattggaagc agaggaacct cttgcttggg tggagcaact gtcaggtgta 36420
gccaattgaa agttgtgctt gatcgagcta ctagttaggg actcccaggg agtgggaggc 36480
attgtgataa cctctgagtg tgtgtgagag tgaatgagcg gcctgattcg cttgtgcttc 36540
aggttcgagt ttgtggctcc acggtcttag tggctatgga gtctgagtgg gtcctaacct 36600
gcagttccgt ggtgacctca tagggcttat ggctgcagca gactctgagg gttctgttcc 36660
ctccctgcaa gtccaatcca agttcgggga ttatacgaac cagccaattg ctaagaggca 36720
cctaaactcc cgagaggggg gcagtcaggc ggacatctga atggccacct tctgagaagg 36780
aggcaccctc ccttgttttg tctgcgacac tggcacaggg cgtccacatg gggtgggacc 36840
taacccagaa gcccacgagc cagagacccc tgtgcttccg ccattttggg ccataaattc 36900
ctccaaggag atgacctaat ttgatcttgc ccctgggcct ccaggaactc ccggcccaga 36960
ttctaaacca gccatgggac tgcctatttt gtcagttcat ggaggcccag gatctgagtc 37020
agggagacaa gcctgtcatc cctggctcag ttcagggtat agggaggatt gggtacaagg 37080
tcccctgtcc tttgcccaaa acattagaac ttgtctgaga gtgccttcct gagaccgggg 37140
gtccagatgg attggagata cttgcaataa agcaggtgct cttcccagtc atagagcaag 37200
ctgagtggga tctgtcttgc tttcaagagt ggtggaggca aagctactgg ggataccacc 37260

```
cacgaggcca gaaaaggtct cataatatca ggccatagaa aagatccaca taaagacacc  37320
atgggttcac ccaagtctaa acctgtggtt gtagactgtg tgatcaaaga tttcaaaaag  37380
ggattttctg aagattatgg tataaaacta acctgatctt tcatcatttc ctttgccatt  37440
acctcaaata gagctgtggg ggcaaaggaa acagacctct agatgttaag accatcctga  37500
gttgttacca ggcctgtggg ggaaaaggag ttcatagcta gtattcatcc aacttaggcc  37560
aagtgtttag cctcagagcc tcggcatagt cagttttgct ttttgctgtt tactttcatc  37620
ctggttggag taattgatgg ctggttcatc caatttacct gttaactgtg gtttagaaac  37680
tttcctaatg ttaatacagg gcatgtcaga gtgagcatct taggatttga aaactcaggg  37740
cagggcctgt atgcctgggt tttcttcacc tctgtccaga gacaggcact gggcagggat  37800
gacgggaaga gaggctacgc tggtaaggag tggttaattc cagtcagcct gaggtcggat  37860
gggacatttg accactagtg tctagctgct ccatataaga gaggggacac cctcacatag  37920
ccaagaaagg acaataggcg ctggatgctg ttttttgtct ttttcggatg ggagccacat  37980
cctcaagcct gctgcatgac tcaatagcaa cccctctgac atgtgccttg aagaactgga  38040
aaaagtttga ccctgagatt ctgaaaaaga aacatttaat tttctttcga acaaaagcct  38100
ggccgttata taatctgtca gatggagagt gacagccatc tgaaggctca ctagcttata  38160
ataccattct ccaattagcc agaagttagt cagccttctc caatactgct caaggctcct  38220
tctccccgca agccagtgcc aaagttatat ctctctctac tccctttaca agaagtagca  38280
aacagagaat ggaggccaaa tacaggtcta tatacctatt tcacttcagg acttagggca  38340
aataaaaaca gatttgggaa aatttgctga tgacccagat atattgaggt tttcagggtc  38400
tcatgcagtc ctttgagtta gccttcaagg acgtcatgtt attacggaaa cagacattga  38460
ctataagtgg aaaattacat aaagtctcca aaactgctca aagctgggga agatgaatgg  38520
aatgatgcta aaaatgccag aggcagatta gaagaggaat gatcaagatt ccccacaggg  38580
tgtcaggcag ttcctatgag cgatcccaat tggtctgctg atgagggaga taacaacaat  38640
tggcatagaa atcattttat tacttgtata gttaagggat taaaagcccg ttaaaactat  38700
cggaggttta ctaggggaac aagagtccat cagctttctt aaaaaggctc agaaaggcat  38760
tgagaaaaca taaaacaggg aacccagaaa caatggaggg ccaaataatt atttatttat  38820
ttatttattg tctttttgct atttctttgg ccgctcccgt ggcatatgga ggttcccagg  38880
ctaggggtct aatcagagct gtggccacca gcctacacca gagccacagc aatgcaggat  38940
ccgagccgag tctgcaatct acaccacagc tcacggcaat gccggatcgt taacccactg  39000
agcaagggca gggatcgaac cctcaacctc atggttccta gtcggattcg ttaaccactg  39060
cgccatgacg ggaactcccg aataattctt aaggataaat tcatagctca attggtgcca  39120
gatatatgga gaaagctcca aaaattggct tttggccctg atcaggacct ggagcacctc  39180
ctcagagtag caactcaagt atgttataat ctgggccagg aagaataaaa ggagaatgag  39240
aggagagaca gagaaaaggc tgaggctcta gttatggcac tacagggagt caacctggaa  39300
gttgccaagg tgagaggact agggcagaga cctatgcctg cagcctgttt cctctgtgga  39360
aaagagggac cctttaaatg ggaatgcccc aagcctcaga ccacagcacc taggccatgc  39420
cccatatgtt ggggagatca ctggaagagg gactgcccct gaagatgaag gtctctgggg  39480
ttgacccctc aggcccagga tcaaggctga caggacattt ccataatggc tcctgtcctt  39540
ctcaccactc aggagtcctg ggtgactcta aatgtaggaa gacagcctat tgacttcctc  39600
ctgaatacgg gagccacttt tcagtcctcc tctccaatcc tgggcccctc cctcatgaat  39660
```

ctgccacatt tatatttccg gcaagccggt tacaaaattt cttacacagc ctttgagttg 39720
tggctgggaa tccattttct tctctcatgc ctttctgatt gttccagaga gtccaactcc 39780
tcttttagaa agagatattt tgtaagaggt taaagcctca attcacatgg caatggagcc 39840
taatcaaggt ttatgcctgc cttggatgga agtatatact gacccagaag tctgggccat 39900
aggaggaaac ataggaagag aaaagaatac tcaactggtg gaaataggtc ttaaagactg 39960
gaatttattt ctttgccaaa agcagtatcc tctgagaccc aaggcatgac agggacttgt 40020
atcaattata ggaagcgtaa gagaacagat tattaattga ctgtatcagc ccttgtaaca 40080
ctcctatatt gggagtgcaa aaacttaaca gggattggtt cctagtacaa gacctccatc 40140
taataaatga gacactggtc tcattacatc cagtggtgcc caatctctac actcttcttt 40200
cacaaattcc agaaacagca gcatgggtta ctgtatcata tttaaaagat gcctttattc 40260
tgcatttcct tgactaaggc tttgcatata taaattctca aaatatggaa ggtaactaac 40320
tgaccagaat taattttagg ttcaagtcaa ctgggaaata ttcagtatta aattaatatc 40380
ttaaattaga attgaagttt gctgatctaa ttaatacaca catgtcgtta cagctgtcaa 40440
cattaggtat aatatcttat cgtacctagg tttaacagaa gtcaaatgag acactgagac 40500
atcagttact aaacagaaac taaaggtatt tagaataatt aatcaatatg atcagtttca 40560
ccctgaatgg tctccataag aaaaacatgt gtttttagaa attataaagg acagtctgtg 40620
gttgctttag aaacgtagaa tctgtgtgct ttcaatatag aaggaatgag ggatggaact 40680
gcattttatg aaggcaaaag aaagtctgtc ttcagctgat tgctctggtt ggaaaataag 40740
ggacagacta atatggatac agaaagtgat acaaggtgtg tgggaagtgg acactgagaa 40800
ttttgtgcat ggtggggact gtctatattt gagtaagtta actttaaaag taatgtggtg 40860
ccataaatca tactgctcac aaggacataa ggtagctttc aattacatgt tgaccaaggc 40920
atacaagtgt ttcataacca gccagagaaa tcagaaaaat catacaagtt acctgtgcta 40980
ttataaaatc taaatgttgt attcttgatg gttcacagaa tgtgtctaat tccctgctag 41040
atcttcaaca gtagattcat gagcggtcct atccagctcc agcttttgga gctgccctgt 41100
ggaaccagcc gacctcctcc tcctggtgaa aatatttctt caccatatct ttttattcag 41160
accctgtata attaactgta tttcttgctt cattacatcc tgattaaaag ccatcagcct 41220
taaaatgttg atagaagggg tacccaaagc aatgtatcaa agcccacttg accgtcccat 41280
gagtggagac ctaactgctt tccctaatga cgcccctttt cagcaggaag aagtcagagc 41340
ggtcatcgcc ccctttcccc acagttagag tctctaactc actggtggga ttgaggcaga 41400
atattcactc aggtagtcag tgtaggaaca tgggcttcga tacattcttt gatgtggcta 41460
ttggttaaca tttgtaaagt aagggttgca cagcaacccc aactgctata aaggttacag 41520
gtattacccc atggatccat cacaccggaa taaagaaggc tgctcccgcc attgacacag 41580
acacctggga agctgtccgg caccctgaga acccccctca ggatcaagtt ccagagacat 41640
atggcactgg aggatggcag gccctgctct ggtcacaccc agaagctggc cagtctatgc 41700
acggcagaaa cttgaggagt ctacagccct gccccagcca catactggag ttggttggtt 41760
tgtacaagtg gaggccagag gatctctatg caaacttgaa ttgaactcat gctctggtgg 41820
ggaatattgg taattgaaat tgccatagcc ctcatatttg gagtggggct atatgcagta 41880
tccccttcag aatggggaca gggagcccag ctactcatct gtgtgatgta tctcctgact 41940
gtcagtatac tagaatccct gttcataatg ggtcagtgaa aaggatcaaa ggaatcatag 42000

```
ttctgttaac actcaccctg ctgctcactc caggggcaac agactgggac aatgatctat  42060
gggatgggac gggattaaca gatgcttacc agtgcctccc tgctaattgg acagggacct  42120
gcactctagc ctttgtcact cttcaaatag atattgtccc tgggaatcag tctcttatgg  42180
tgcccataga ggcacatggc agaacaagac agcaatgcaa gttatcccct tatttagttg  42240
gtttgggaat tccagcaggg ataggagcag gagtgggagg aatagaatcc tccactgctt  42300
attatcatca attatctaaa gaattcacgg atgatgtgga acaagtagcc ccttccctag  42360
tagccttaca ggattaggta gactctctgg cagaagtggc ccttcaagac aggagagcac  42420
tggacttatt cactgctgaa aaaggggaac tttgcctgat gaagaatgct gtctttatgc  42480
cagcagatct ggaatagtca gaaacatggc ccaacaaata aaagaacgca tagcaaagag  42540
aagggaagac ttagataact cctggttaaa ttggagcaac tactggagtt gggtggcatg  42600
gctcacgctt tggttgggcc cctcctcatg ctcttcatgg ccctcacatt tggcccctgt  42660
atcctgaact gtcttgtcaa gtttgtctcc tcaggcctag aatctataaa gctacaaacg  42720
gtggtgatgt cccggccaca cttatatcag cctctgggcc aagaagacca gaaaggttga  42780
tgcttgctcc aagaatgtga aaaagcatca agagggggg atgtaggaga aaatgtccca  42840
ataaaatgtg gaaaggagag accccggcca tgacgactaa gcaaagtcta gccaactgcc  42900
ccaaccagtc ctcccccatg catctgcttc tgtaaatttg tttccgcatc tactaccttg  42960
cctgacgtca ctccagtcca actacccaag cttggacctg gaagacgtag cccataaaag  43020
ccttgtgaaa cccttcttcc aggctcagac tctggagagt gatctcatct gagcccgccg  43080
gcgtaataaa cctgagttct ccaactctcc aagtgcttgc ttggtttctc gccgggtaaa  43140
agagctgctc cactatggcc acagagctac tggagctggt acgctacagc cacggggctg  43200
tcgccagagc tgatacgctg cagcgcaggg ctgctgggta tctgctgtaa cactgagggt  43260
gcagcccgaa atggtaaaaa aaaaaaagaa aagaaaaaaa aaatagtaaa cttgcaacca  43320
cagtaagtat ataacggagt tcctgtcatg gctcagcagg aaagaatcca agtaggaacc  43380
atgaggttgg gggttcgatc cctggcctcg ctcagtgggt taagggtcca gtgttgccgt  43440
gaactgtggt gtaggtcgca gacatggctt ggatctgaca ttactgtggc tgtggtgtag  43500
gtcagaggct acagtcccaa ttagacccct agcctgggaa cctccatatg tcgcgggagc  43560
ggccctaaaa ggacaaaaag accaaaggga aaaaaaaaag aatgtatata tatgtatgag  43620
tgagtcactt ggctgtacag cataaattgg cacaacactg taaatcaact atactttaac  43680
ttttcaaaaa gattaaaaaa gaagcattgg cgttatcctc aagtacagct ggattcccat  43740
ctgctcctta taatgctgcc cttgggcaac ctccattctc catgttcaca gctctgaagt  43800
ggacataact cttccaagag tgttgctggg cgcattagag gcacaatcta gaacagggcc  43860
tgtacgtaac agataagtgc tccacagtgg atgaaatgaa atgaattcac caacaggaag  43920
taacgatcat ttcctgggtt ggtagggtgt gttgtagtga aacatccttt ctcagaggga  43980
caaagatcag aaatgcacat ttcaaaatca gacactcttt aatttaaaaa aaaaaaaaga  44040
aagaaagaaa agaaaacgaa aaaggcaaat aaacatttaa aagagtaagt ttcttctgag  44100
gaagaaacct gtttcccaag gtcacccaag ccagcagcct taaaatctta gagacataaa  44160
cacagcaaca tggacttgcc agaatgttcg gttggcacca gtttggatcc tggtatcaag  44220
actcctggtc attctcctca ttcactaagg aatgtgggat gagataattt tggggaagtg  44280
ctggaaggaa agccttagaa gggactttag ctggtaacgc aagagctacc tccctttgct  44340
gagttctgcc atagcctcag tacaaacgtg tttcttggtt tccttatttg tttcggcagc  44400
```

gccagggcat gaggaagttc cccgggtggc caaggatcaa acccttgcca caggaggaaa 44460
aacgctggat ccttaacctg ctgcaccatc agagaactcg tatacttcat tttaatcctc 44520
ataaaacatc atctaaccaa cacggttccc cccctcccct tttttaagcc atttagggcc 44580
gcaggtgcct gtgtatggag gttcccaggc tggaggtcta attgaagctg tagccatcgg 44640
cctacaccag agccacagca acgcgggatc cgagccacgt ctgcgaccta caccacagct 44700
cacggtgaca ccggatcctt cacccactga gcaaggccag ggatggaact tgcaacctca 44760
tagttcgtag tcggattcgt tacccactga gccacgacgg gaactcccac aagacgtatt 44820
tctgatcctt ctttctgttt ataaaaatta aatgagctca ccaagtccgc acttcctccg 44880
ttaattatta tgctactcag aagttttttt tagcacccca aaccacaaaa cggacgctcg 44940
ctccaccgcg aggctgtctt ccggagcaga aaactgacct tttaaaattt tttttctttt 45000
tggtcttttt ggggccgtac cctagggcat atgtaagttc ccaggctagg aggtctaacc 45060
agaactgcag ccgccggcct tacgctgcaa ctagatgcta cgccaggtcc gagtgcgtct 45120
gcgacctaca ccacagctca cagcaacata cccactgagc gaggcaaggg atcgaacccg 45180
cgtcctcgtg gatacggggg gcggggaggg gcgtaaaccg ttgagctaga acaggaactc 45240
ctagaaaacc gacttcttca aaaactctgc ctctaaaacc cccaagctgt tatttaatgc 45300
agcgtaaagg acgcagcctc cgcttcccca cagcctgggg ccccacagcc tggggcccgc 45360 acatccccg agacttacat ccccagccct ggtcataacc tccgagttcc gggccgcccc 45420
ccgtgctctg cgccacgaga ggcaacctcc acgtcgaatg ttcccctgga aaaccagtgt 45480
tccttggggc gcagggcggg ggaacgagca ggaactctca acagcgtccc gaggcgcagt 45540
ctccttctcg ctgtctcacc gacgtacgga gccggtcgga cttattttgg agacccgccg 45600
ccccccctac tcggctccgg ggtcccggga cctggccgct cccgggtggc gccactggct 45660
ggccaagttt gacttcccat ttgtctctgc tcgagggaca cgcacctgta cgaagtcatc 45720
cttaatcccg ccgcctcggg acattctggg ctggtggtgc cactccgcgg attggacagc 45780
cctagcacca accccggcaa attcttcctg gtaaaccgcg agagcttggg tcggacccgc 45840
ccacgtcacc accaaccccc gc 45862

<210> SEQ ID NO 26
<211> LENGTH: 2012
<212> TYPE: DNA
<213> ORGANISM: Sus scrofa

<400> SEQUENCE: 26
tccgcggagt ggcaccacca gcccagaatg ttccgaggcg gcgggattaa ggatgacttc 60
gtacagccct agatgtctgt cgatcctcaa gatattgatg gtgcttttgg tcctgagcgt 120
tggactcttt atgttccaaa gcgtgttcct cgatacagac ttcagtctcc tcaactcacc 180
catcccgtcc cccaccctgg atgcgcagac gctgaagctt ctacctgaga aacccgattt 240
ctacggtgaa aacgggctgt tcccgaaaaa ccagtgccaa tgtgacgcct tcgggcatca 300
ggaaagctat aacttggagg atgcctacga cccgcaagac ctccccgcag tgaacctgag 360
gagacaggct gagctcgaac actttcagag gagagaaggg ctccctcgcc caccgcccct 420
gctggctcag cccaacctcc cctttgggta cccggtccac ggggtggaag tgatgcctct 480
acacaccatc cccatcccag gcctccggtt tgaaggacct gatgctccca tctatgaggt 540
caccctgaca gcttctctgg ggacactgaa cacccttgct gacgtcccag acaatgtggt 600

```
gaagggcaga ggccagaagc agctgaacat tttgaccagt agccgggagc ttttgaattt    660

catcctccag catgtgacat acacgagcac agagtaccac ctccacagag tggatgtggt    720

gagtctggag tccaagtcct cagtggccaa gtttccagtg accatccgct atcctgtcat    780

gcccaagtta tatgaccctg gaccagagag gaagctccga gacctggtga ccattgccac    840

caaaaccttc ctccgtcccc acaagctcat gaccatgctc cggagtgttc gtgagtacta    900

cccagacctg acggtgatcg tggccgatga cagcaaggag cccctgaaaa tcactgacag    960

ccacgtggag tattacacca tgccatttgg gaagggctgg tttgctggca ggaacctggc   1020

catatctcag gtcaccacca aatatgtgct ctgggtggac gatgacttca tcttcaacag   1080

caagaccagg atcgaggcgc tggtggacgt cctagagaaa acggaactgg acgtggtagg   1140

tggcagcgtg attgaaaaca cattccagtt caagctgttg ctggagcagg ggaagaatgg   1200

cgactgtctc caccagcagc caggattttt ccggcccgtg gatggcttcc ccgactgcgt   1260

ggtgaccagt ggtgttgtca acttcttcct ggctcacaca gagcgactcc aaagaattgg   1320

cttcgacccc cggctgcagc gagtggctca ctcagagttc tttattgatg ggctcgggag   1380

cctgctcgtg gggtcctgcc cacacgtgat cataggtcac cagccccatt taccagtgat   1440

ggacccagag ctggccaccc tggaggggaa ctacaccagt tatcgggcca acaccgaagc   1500

ccagatcaaa ttcaagttgg ctctccacta cttcaagaac tatctccaat gtgtcaccta   1560

aggtatccgg gcattggaaa agcgctgagc tgcctggttg caagtatcta agacagcgga   1620

tgcggtggct gggataccaa tatttgaact cctcataaga taagcactgt aatgcccagg   1680

gagcagggta ggcaggtggg tctgactccg ttactggaag taccaataaa agtacagggt   1740

cattagaaat ggaccagtca ctgaggtggg caatggagac ttcattcata acgattacgg   1800

cggtgtttcc atcatggctc agaggtagca atccagactg ctatccacga agatgcgagt   1860

tggatccctg gccttgctca gtgggctaag gatctggcat tgctgtggct gtggcatagg   1920

ctggcagctg cagctctgat gcgcccccta gcctgggaac ttccagatgc taagtgtgtg   1980

gccataaaaa aaaaaaaaaa aaaaaaaaaa aa                                 2012
```

<210> SEQ ID NO 27
<211> LENGTH: 502
<212> TYPE: PRT
<213> ORGANISM: Sus scrofa

<400> SEQUENCE: 27

```
Met Thr Ser Tyr Ser Pro Arg Cys Leu Ser Ile Leu Lys Ile Leu Met
1               5                   10                  15

Val Leu Leu Val Leu Ser Val Gly Leu Phe Met Phe Gln Ser Val Phe
            20                  25                  30

Leu Asp Thr Asp Phe Ser Leu Leu Asn Ser Pro Ile Pro Ser Pro Thr
        35                  40                  45

Leu Asp Ala Gln Thr Leu Lys Leu Leu Pro Glu Lys Pro Asp Phe Tyr
    50                  55                  60

Gly Glu Asn Gly Leu Phe Pro Lys Asn Gln Cys Gln Cys Asp Ala Phe
65                  70                  75                  80

Gly His Gln Glu Ser Tyr Asn Leu Glu Asp Ala Tyr Asp Pro Gln Asp
                85                  90                  95

Leu Pro Ala Val Asn Leu Arg Arg Gln Ala Glu Leu Glu His Phe Gln
            100                 105                 110

Arg Arg Glu Gly Leu Pro Arg Pro Pro Pro Leu Leu Ala Gln Pro Asn
        115                 120                 125
```

```
Leu Pro Phe Gly Tyr Pro Val His Gly Val Glu Val Met Pro Leu His
    130                 135                 140

Thr Ile Pro Ile Pro Gly Leu Arg Phe Glu Gly Pro Asp Ala Pro Ile
145                 150                 155                 160

Tyr Glu Val Thr Leu Thr Ala Ser Leu Gly Thr Leu Asn Thr Leu Ala
                165                 170                 175

Asp Val Pro Asp Asn Val Val Lys Gly Arg Gly Gln Lys Gln Leu Asn
            180                 185                 190

Ile Leu Thr Ser Ser Arg Glu Leu Leu Asn Phe Ile Leu Gln His Val
        195                 200                 205

Thr Tyr Thr Ser Thr Glu Tyr His Leu His Arg Val Asp Val Val Ser
    210                 215                 220

Leu Glu Ser Lys Ser Ser Val Ala Lys Phe Pro Val Thr Ile Arg Tyr
225                 230                 235                 240

Pro Val Met Pro Lys Leu Tyr Asp Pro Gly Pro Glu Arg Lys Leu Arg
                245                 250                 255

Asp Leu Val Thr Ile Ala Thr Lys Thr Phe Leu Arg Pro His Lys Leu
            260                 265                 270

Met Thr Met Leu Arg Ser Val Arg Glu Tyr Tyr Pro Asp Leu Thr Val
        275                 280                 285

Ile Val Ala Asp Asp Ser Lys Glu Pro Leu Lys Ile Thr Asp Ser His
    290                 295                 300

Val Glu Tyr Tyr Thr Met Pro Phe Gly Lys Gly Trp Phe Ala Gly Arg
305                 310                 315                 320

Asn Leu Ala Ile Ser Gln Val Thr Thr Lys Tyr Val Leu Trp Val Asp
                325                 330                 335

Asp Asp Phe Ile Phe Asn Ser Lys Thr Arg Ile Glu Ala Leu Val Asp
            340                 345                 350

Val Leu Glu Lys Thr Glu Leu Asp Val Val Gly Gly Ser Val Ile Glu
        355                 360                 365

Asn Thr Phe Gln Phe Lys Leu Leu Leu Glu Gln Gly Lys Asn Gly Asp
    370                 375                 380

Cys Leu His Gln Gln Pro Gly Phe Phe Arg Pro Val Asp Gly Phe Pro
385                 390                 395                 400

Asp Cys Val Val Thr Ser Gly Val Val Asn Phe Phe Leu Ala His Thr
                405                 410                 415

Glu Arg Leu Gln Arg Ile Gly Phe Asp Pro Arg Leu Gln Arg Val Ala
            420                 425                 430

His Ser Glu Phe Phe Ile Asp Gly Leu Gly Ser Leu Leu Val Gly Ser
        435                 440                 445

Cys Pro His Val Ile Ile Gly His Gln Pro His Leu Pro Val Met Asp
    450                 455                 460

Pro Glu Leu Ala Thr Leu Glu Gly Asn Tyr Thr Ser Tyr Arg Ala Asn
465                 470                 475                 480

Thr Glu Ala Gln Ile Lys Phe Lys Leu Ala Leu His Tyr Phe Lys Asn
                485                 490                 495

Tyr Leu Gln Cys Val Thr
            500
```

<210> SEQ ID NO 28
<211> LENGTH: 58425
<212> TYPE: DNA
<213> ORGANISM: Sus scrofa
<220> FEATURE:

<221> NAME/KEY: modified_base
<222> LOCATION: (5753)..(5852)
<223> OTHER INFORMATION: a, c, t, g, unknown or other
<220> FEATURE:
<221> NAME/KEY: modified_base
<222> LOCATION: (9176)..(9275)
<223> OTHER INFORMATION: a, c, t, g, unknown or other
<220> FEATURE:
<221> NAME/KEY: modified_base
<222> LOCATION: (18671)..(18770)
<223> OTHER INFORMATION: a, c, t, g, unknown or other
<220> FEATURE:
<221> NAME/KEY: modified_base
<222> LOCATION: (26990)..(27089)
<223> OTHER INFORMATION: a, c, t, g, unknown or other
<220> FEATURE:
<221> NAME/KEY: modified_base
<222> LOCATION: (45736)..(45835)
<223> OTHER INFORMATION: a, c, t, g, unknown or other
<220> FEATURE:
<221> NAME/KEY: modified_base
<222> LOCATION: (48911)..(49010)
<223> OTHER INFORMATION: a, c, t, g, unknown or other
<220> FEATURE:
<221> NAME/KEY: modified_base
<222> LOCATION: (52558)..(52561)
<223> OTHER INFORMATION: a, c, t, g, unknown or other
<220> FEATURE:
<221> NAME/KEY: modified_base
<222> LOCATION: (52565)..(52664)
<223> OTHER INFORMATION: a, c, t, g, unknown or other

<400> SEQUENCE: 28
ctcacttccc cccccacccc cgtcctttcc ctctgtccct ttgtccctcc accgtccctc 60
catcatgggg tccacctcgg gtcccaggct gctgctgctg ctcctgacca gcctcccccct 120 agccctgggg gatcccatgt gagtaatcac aaccccaacc cccaaacaag gctgcttctg 180
cattgggagt gggcacttgt gagtataggt ctctgcaggt ttagggtgca tgtacggtgc 240
tggttgattc tgtggcttgt gatgaggttg gggtgagtct cagaagttgg ggttgggtga 300
gtctcagaag tttggactcc ataggatctg ggagtttgta gttttagcat ttaggagttt 360
cagagatgcg gtttggatgt atgtggctga ggggatggat tgggttgtat ttataggtct 420
ggggtgctag aggtttagga ggctgtttag ggtgttccag ggtttgggta tttagagact 480
tgaggtattt aaagatttag gagttctgac cttggagcag tgggttaaga attcgactgc 540
agaggccagg gtcgctgatc cggtgcgacc ataaaatgat aaaaaataaa taaacgatta 600
aaaaaaagat tgaagggttg agacttctgg aatttgtggg tttgattgtg ggcttggaag 660
tccatcgtct tggaggaatt ggttctgatt ttgaggttca ggaattgatg ggatctgaag 720
cccccaagct gtcctccagt catcggatcc cccgcagggc taggggctgg ggcagagcgc 780
tgaccctggg ggtgcctagc atctcgtgcc cctgggatga cagctctacg cctcgtcctc 840
ccctcccgca gttacaccat aatcaccccc aacgtcctgc gtctggagag tgaggagatg 900
gtggtgttgg aggcccacga agggcaaggg gatattcggg tttcggtcac cgtccatgac 960
ttcccggcca agagacaggt gctgtccagc gagaccacga cgctgaacaa cgccaacaac 1020
tacctgagca ccgtcaacat caaggtgggc gcgctcaaca gccggaccgc tgaagcccca 1080
ccccttcttt gagtcctctt ggtagctgag cccctcctcc ctttctgagc cccacccacc 1140
ctgcctgagc cccgcccctt ctgtctgagt gtctccattc tgaaccccgc ccctctgagt 1200
ctcctcccct tcggagccct tccccttttg gagtccgggt cactttttgg agccccctcc 1260
cactctctca tcccggtctt tctctgagtg tccccacctt ctgagccctc gtctttctct 1320
cagcccggcc cccttccaag ccccaccatg tctgagccct tccccatttc tgacccctcc 1380

```
cctccaaccc tcctccctaa gtcctttctt cttttagaac ccgtcccctc tccgagtctc   1440
ctccccttttc tgaaccccct accccttctg agccctcctt ccgctaagcc ccctgcctga   1500
atcccccttc ccatccctcc ctctgactcc ctaccccctc tcttgccctt tggcccttcc   1560
ccgagtacct cttctctccc caaacctggg caaagcagga ggaccagaag tgacaagcag   1620
gctctgttgc gaggaggggc gggtgcggac ccagccgaag tcctagaggc tggatggtgg   1680
gcaaggggtc ttggccccta gtgatcccct ggttcctgct cagatcccgg ccagcaagga   1740
gttcaaatca gagaaggggc acaagttcgt gaccgttcag gcgctctttg ggaacgtcca   1800
ggtggagaag gtggtgctgg tcagccttca gagcgggtac ctcttcatcc agacggacaa   1860
gactatctac accccaggct ccacgggtaa ggggctgagg gtggctgcag agagccaggg   1920
gcagggctgg aggaaggggc agggcctcac ccggctctgc ttttctctcc caccactgct   1980
cagtcctcta tcggatcttc accgttgacc acaagctgct gcccgtgggc cagaccattg   2040
tcgtcaccat tgaggtacca gccgactggg gccccagaca tacccagggc agggactcgg   2100
ggagagacaa agagagagag agaaacagag aaagggattc cggcaaaggc ccagcagcag   2160
agacataaag gcaaaaaaca aaaccccaaa aacgtaaggg cacacagaga gatcgggaga   2220
gaggcgggga cccagcgatg cttaccgtgg atgacggctc cagataagtc cctggtcact   2280
gtgtgaatct ggacaggtca cttcatcttt ccaagcctca gtttcctcat ttgaagactg   2340
acacgacagg tactaattct atgtagtctg ttccgcctac tgcccgccag agggcgcgtg   2400
ggagcacctg agtcaggttc cacccctcct ctgcctgccg ttttccaggg ctccccgctc   2460
ctggggtaaa tgcccaagtc ctccccacgg gcctcaaggc cctgcaagac ctgctcccgc   2520
accctgccca ccctcctttc ttccctctct cttcctccct ccgctccagc cacgtgggcc   2580
tcgtcaccgt tcttgcaaca atccaggcac agtcctgccc caagaccttt gcaggggttg   2640
ttccccctcc cccccaaatg ctcttcctgc aaatatccac acagtttgct ccctcacctc   2700
cttcaagtct ttgctcaaat gtcaccagtg taccaatttt acagtgaggc ttgtcagagc   2760
gccctgtaaa attgcaacag aacacacaca cacacacaca cacacacaca cacacacaca   2820
ctcccttttt tgccttcctg ccatctcttt ttggcatctt ataaatcgga gttatttccc   2880
ccctcccttt tttggtcttt ttatcttttt agggccgcac ccgcagcata tggaagttcc   2940
caggctaggg gtcgatttgg cctaggccac agcaatgtgg gatctgagtt gcacagctca   3000
cagcaacgca ggatccttaa cccagggagc gaggccaggg ttcaaaccca agtcctcatg   3060
gatacttgtt gggttcgtta accactgaag cacgatggga agttttttgg ggtttttttt   3120
tgtgggacct attcctttgt taactgcgcc ttcccccaat ctgcactgaa cctaagttct   3180
gttcagaaag ggattatctg ttggcccaga gtttggcggg tagtagggta aataaaaact   3240
tactggaaga agggagggag ggaaggagag gggagtgaga agcagggagt gatggggaga   3300
gaaagacaag tggaggagga aggggaggaa tggggcctgt cctccttgtg ggatctttgt   3360
atttattgaa atcaggcaaa cctaacaagg accagagttt ttgtgtgtgt gtggtatcag   3420
tatgtgtgtg gggttttttt ggtttttgtt tgtttgtttt ttgcttttta gggccatacc   3480
ctcagcatat ggaggttccc aggcttaggg tccaatcaga gctacagctg ctggtctaca   3540
ccacagccac agaaaggcag gatccaaacc acatctgcga cctacaccgc agctcacagc   3600
aatgccggat ccttaatgcc ggactgaaca tgcaacctca tggttcctag ttggattcgt   3660
ttccactgca ctacgatggg aactccaagg agcgggttct gaaggctgtg tgctcacttt   3720
```

```
agtgatggtg gaaaacagag aacaccctcc tctaaagatg tggcgctgcc agactcccat   3780
tgaacgtcac ctcatgccat tgggaagaac atatccacaa ttacctccac ttgccagaga   3840
agctagagaa tcagatttct ctttgaagtc tcctgatgtt tagctattgg caacaaatga   3900
aatcatatac ttattaggtt gagccacacg aagttgctat tcttgcaggt caaaaaggtg   3960
aatgtaggca gtgatgtgtg ccttctacaa atcaaatgct cagcccaggg tcctatatca   4020
aaggaggtga taaattctag taattactag tcttcagagc gacacagatc atcacaagca   4080
cttgcctaca ctaacaggtc ccaaaccagt gacacaggag ctgtagttat ctcctttttc   4140
caagaggttc acattgagca caaagaggtt aagtaatttg cccaagatca cacaggcttg   4200
taagtggtgc agtggggaca ggaacccagg ctacctggtt tgggtgccca ttcttaacca   4260
ctgcccctgt agacacgaca cagaggagaa ccaaggggct aagcctggtc tctgaagagc   4320
cacttccctt cctgtctcct cacagacccc tgaaggcatt gacatcaaac gggactccct   4380
gtcatcccac aaccagtttg gcatcttggc tttgtcttgg aacatcccag agctggtcaa   4440
gtaggtcggg ccctccagca ggggtggggt ggagtggtcg tgtgttttag ggctccccag   4500
gagagggagt ggggggcctg ccagacctgg cggactcact agcctgcctc ccccacagca   4560
tggggcagtg gaagatccga gcccactatg aggatgctcc ccagcaagtc ttctctgctg   4620
agtttgaggt gaaggaatat ggtaagaaga ggagggagct gggggggggg gggcgtgcat   4680
aatgttggac ccagcgttga ccccccccac cgaacgaata ccatctgctc ccccccaata   4740
gtgctgccca gttttgaggt ccaagtggag ccttcagaga aattctacta catcgatgac   4800
ccaaatggcc taactgtcaa catcattgcc aggtgagggt ctagggggag ggcctgggga   4860
gagggaaggt caagggatag ggcagggatg gagggggagg ggctcgtcac ggccagtgga   4920
catttggggg aagactcctc ttttcaggac cgggggagtc tgagacccct tcccactttg   4980
caggttcttg tacggggaga gtgtggatgg aacagctttc gtcatctttg gggtccagga   5040
cggtgaccag aggatttcat tgtctcagtc cctcacccgt gttccggtac ctaacagtgg   5100
ccccctctga gtaactcttc ctctccccct cggaagccct tcccctccct gagccctcgc   5160
tttctccccc agatcattga tgggacgggg gaagccacgc tgagccaagg ggtcttgctg   5220
aatggagtac attattccag tgtcaatgac ttggtgggaa aatccatata tgtatctgtc   5280
actgtcattc tgaactcagg tgaggcccga tctgagggcg gaggctccgt accaccatgt   5340
ggtccagcct gagaggggca gctcagtgga ggggagagga tcagaatgaa gggcgaccca   5400
gtctggtggg gggcggtgtg tccagtctga gggaggaggt ccagaatgaa ggcagggtcg   5460
ggtctgacag gggagaccta ggctgggaca caaacccagt ctgagggggg aggcccagtc   5520
agagggggga ggcccaaaat caaggtggga tccagttcat gggggagacc tagtctgagg   5580
aaggtggggt ccgtgttgag gagggcagtc tggccctccc tcatggctgg ccccccctcag  5640
gcagcgacat ggtggaggca gagcgcaccg ggatccccat cgtgacctcc ccctatcaga   5700
tccacttcac caagaccccc aagttcttca aacccgccat ccttcgacct cannnnnnnn   5760
nnnnnnnnnn nnnnnnnnnn nnnnnnnnnn nnnnnnnnnn nnnnnnnnnn nnnnnnnnnn   5820
nnnnnnnnnn nnnnnnnnnn nnnnnnnnnn nnagctgtgg tgtaggttgc agactcagct   5880
tagatctggc attgctgtgg ctgtggtgta ggccagaggc tacagctctg atttgaccct   5940
tagcctagga aactccatat gcagtgggtg tggccctaaa aaaaaaaaaa aagttttccc   6000
tcctgcacca gctccaacac cccaaatagt ttggtgtgtg ttttctagaa aaaaaaagat   6060
acaggcagac ctcggagtca gttcctggcc atgttaataa agcaagtcac ataaattttt   6120
```

```
tagtttccta gtacatataa aagttatgtt tacactatgc tatattctat taactgtgca   6180
actgcattgt ttaaaaaaat gtacatacct ttattttaaa atacttgatt gctatcagag   6240
tttcccagcg gctcagcaga ttaagaatcc agtattgtca ctgctgtgac tctggttact   6300
gctgttgatg ggggttcaat cccctggcct ggaacttctg catgccgtgg gcatggccaa   6360
aaaataaaag aagaaaaaaa atttaaaaat taaaaaatgc tttactgcta tcaactatac   6420
ttcaaagaaa aaattgctag agtaaaaaat aaatgcttta ttgctaacaa aagttaacca   6480
tcctctgata acgcagaggt cacaagcctt tgatttgttt ttcaaaaatg cagtatctgc   6540
aaaactcaat aaactgaggt atgcctgcat tctcctacaa acccacagtg cagtcattag   6600
aattaggacg tcaacattaa ttcattacta ccctcaaatc ctccatcacc attcaaattt   6660
tgccagggtt ttgttttgtt ttgttttttg gtgtttgggg ttttgaggtt ttgtttttgt   6720
ttttgtcgtt tatagggaaa ggatcctgtc cagaatcaca ggctgtgttt tctggttggg   6780
tctcttcagt gtccttggac ctgtctgacc tttagagcac tttcttcttt ctgtgacttt   6840
cacatccttg atggatacga agtacacaga ctgagatctt ggggactgtc ccaccatctg   6900
ggtctgcctg atgctccttc atgacagcac tcaggttttg catttttggc aggactgtca   6960
cggaagagac atcgtgtcct tcttggtgca ccatttcagg tgacaaaggg tactgattta   7020
tcccactctt tggtgatgtg taccctgatt gcctgattaa gctaatgtct gccgggtctc   7080
tccattgtaa atgtcctctt tattcctttt tagttatttt taaaaacttc tctttaacta   7140
tcagatagtg gcaaaattca agtcaagaga gatttccctc caaatcagtg ttcacttagc   7200
ctttaagaca acaggggtgg attccttata ttgtaatgta tgattttcaa acacaaccgt   7260
actttttttt tcttttcttt cttccttcct ccctcctttc atcccttcat tcttccttcc   7320
tttcttctct ttttctttcc ttcctttttt tttttcctta caaaaaagca cccacctctc   7380
aaaggcagcc attgattgcc aaaatgggca aacatttcta aattcctgta gtggaaagct   7440
agcagcccct gcagccctcc aaaaagaaaa agattcccaa tacacatgag caaaggatct   7500
tcagtctctt tgcactttat aactaggcgt gctgctttct gctccagtga cccaagatgt   7560
tcttttgcaa agaggaacgt ttttttgcaa ggaggaaatt tagacaaaac atctgattta   7620
gaggggtaca gtttacacat acgtggattt ttttcaacat tgtgtcatta ctttaaccag   7680
ttgggggtga gccagaggat tgattaaaag tcagtacccc aaaggcactt tgatggatta   7740
ttccagagcg cagatggatt taggcatctc tggaattcca cctacttggt tgtaaggcag   7800
acccagagcc aaaataaaat ctgttcatca tttttttgag gaaagcccag ccagggttga   7860
actctgttcc cgcccagctt gctgatggtg tcaagctggc ttttaaaggc cacctcctct   7920
ccagcagtct ccatcaaagt ccagggaatc tttcaactca ccccattgct ttcaggaagg   7980
acttttaacc atcagacaca gcagcaggca tggtactcag ggcccaggat gcttctggag   8040
ggtcttccgt gcaaaggttt cattccctca aaaaccaaag aagggaaaga aatcaataca   8100
attcagcctg gattattttt gcctttatgc caacacagtt gtaaaatagg gtttcccata   8160
tattttatgg aagaaggagc ccccagagtc aaatgggcct ggggtccctg gaagtgatca   8220
catggtcatg ggtgtgtggc agctaggaat ccctccgggg attgtagaga tacgtgtcta   8280
aaaggggaca gcgagaaagt gagtctgttc caaacctggg ttgttcccct cctcccctct   8340
tcccccaaaa ggtgacctgg atgaagaaat aatcccagag gaagacatca tttccagaag   8400
ccagttcccc gagagctggc tgtggaccat tgaggagttt aaagaaccag acaaaaatgg   8460
```

```
gtaaggctgg gatgaccctg cttcaacccc cgccgccagt acccagggac agccccctct   8520
catcacacta gaactggaca atgaatttgc aggtacctgg agtccccctt cttttctttc   8580
ttgggggaat cccacaaccc aacctaaaaa aatcaagccc ttgggctatc agccactgcc   8640
ccacacacta cagtccgttc ctttcgcatc tactaaaaat ttatcttgtg tttgtttatt   8700
cttcattcat tatattttct ttctttctca ctgcctgcgc tgtgactcct tttctctcta   8760
cattctgttt atcatcatct tccacacaac tcatttctta tcctcaccac caccactctc   8820
tgctccaaat tttgaatttt acacccagac tcctctctgc tatgtgaagc gcctacaccc   8880
cgtcactagt gttactctct tatcgctgac ctcccttgta ccctcccatt tatttctttt   8940
tttttttct tttgccctat ctacctgcct ctctttccca tcccatgttt gccatgttga   9000
attatgttta tttaagaata tgtttagaga gtgatgtctc tattgatgat gactacctgc   9060
tgtctctcat ccgcgcgaca tattcattat ttataccatt tggcgtactt cacttgtcta   9120
acacaatcct tatccgtata taaagagatg atgaagaacc ccccgcccgc ccctgnnnnn   9180
nnnnnnnnnn nnnnnnnnnn nnnnnnnnnn nnnnnnnnnn nnnnnnnnnn nnnnnnnnnn   9240
nnnnnnnnnn nnnnnnnnnn nnnnnnnnnn nnnnntaacc cactgagcaa gaccagggat   9300
ccttaacccg ctttgcacag caggaactcc tgggcttttt tttttttttt ttttttttga   9360
gccctgagat tttttaatcc cccccccctt tttttggctt ttctagggcc gcacccgtgg   9420
catatggagg ttcccaggct aggggtctaa tgggagctgt agccgctggc ctacaccaca   9480
gccacagcca cagccactca ggatccgagc tgcatctgca acctacacca cagctcatgg   9540
caacaccaga tccttaaccc actgagcaag gccagggatt gaatctgcaa cctcatgctt   9600
cctagtcagc ttcgttaacc actgagccag gatgggaact cccttaaatt cctgacatct   9660
tctcaacatc aactctcttc tcaagatcaa ctctctctca tctcattttt tttttttttt   9720
tttttttttt cttttctagg gacgctcccg tggcatatgg aggttcccag gctaggggtc   9780
gaatcggagc tgtagccacc agcctacagc agtgtgggat ctgagccgca tctgcaacct   9840
acaccacagc tcaaggcaac accagatcct taagccactg agcaaggcca gggatcgaac   9900
ccgaaacctc atggttccta gtcggattcg ttaaccactg tgccacaacg ggaactccca   9960
aaataagaga tttttaaaaa ccgttttagg attccagaaa caactgagca aaaaaatata  10020
ccaatggctg agtaatagtc catcatgtat ctgtactaca tcttctttat ccactcctct  10080
ggacacttag gttgcttccg tgtcttggct attgtcagta gcactgcagt gaacacctgg  10140
tgcattcaaa ttatggtttt cttcagtctt ttccattttt aattcctttt tttcctttca  10200
aatagagagc aaggggtcta gctttcctca ggcagcataa gctaaccaat atttaacaca  10260
atcattctat tttccttgag gacactctta tttatagcac aagaacctgg tttctcaccc  10320
atgtcctaaa ttaaatttaa gtttagaaaa atttataaaa acaaatagta agtaagaaat  10380
ggtaaggagc accagtgact aatcagacac cccgagggtg atgagtaaat gacagtaggt  10440
tgggaaataa ggattttgtt caagcctctg attataattt tttttttgc tcttgaagaa  10500
taagaacaat gcacaaatct taatagattt cttagtgtaa cattattaat aatgtgttaa  10560
cagtttgtgc agtttcactt gcatcagcac tctgcttgca tttgatcagg taatttttgt  10620
gtcatatata acattgtttt cagcatcatt tttgatcaag gttgttatca aaattcaacg  10680
gagtaaattt gaagatgtaa ttggctttat taaacaattc atgaattggg cagcgtctca  10740
tctggcaggc agagagatac tcagaggagt tgtgaaaaat ggaaggtttt aatagaatga  10800
agtctagggc aagagagtaa tcgcaagata caaatttcat cattggagga aaataacaat  10860
```

```
tcaggtggga gaggatctcc ttggctgagc tacagtattt tcattcgctg ggctttttac  10920
tgggcaggaa gaaagtcttc cttcctcctg ctgcagtaaa tttcacttcc tatttgggag  10980
tgcaaggtac ttctctttcc tttggggtct gtaattgatg cttcttcctg ttgggatctg  11040
taattgacat cttcctgttt ggggtaattg acttgcttgg tggagcatta gagctccctc  11100
tacaggcctt ccctacttca atttagttaa ggtttacttt tactaatttt tacaatgtaa  11160
atcagtgctg tccattagaa atataatgca ggttgtaaac gtcatttaaa attttctgat  11220
agccctgtaa aaaagggata ggtgagtgag ttcccttgtg gcacagtggg ttagggatcc  11280
tgcatcatca ctgcagcagc ccatccctgc tgtggtgtgg gtttgatccc tggcccagga  11340
acttccacat gctgtagggg cagccaaaaa gaagggatgg taggtgaaat caattttaat  11400
aatacatttt atttaatcca aatatatcct aggagttctc attgtggctc agtgggttat  11460
gaacccaact tagtgttgtg aggatgtggg ctggattcct ggccttgctc agtgtgttaa  11520
ggatccggca ctacctcaag ctttgcatag gtcgcagatg gggctggaag ctggtgttgc  11580
tgtgactgta gtgtaggctg gcagtgacag ctcagattca gcccctagcc tgggaacttc  11640
cacatgctgc aggtgcagcc ctaaagagaa aacaaacaaa tatatccaaa atattattat  11700
ttcaacattt tgtaaaaact tgcaaaacca ctatcacact gatactgtta caataataaa  11760
tccattaata ttttaaaata agctattaat aatctcaaaa ttgtgatatc ttttagtttt  11820
atttgtacta agccttcaaa atctgccatg tattttatac ttactgatat ctcaattaga  11880
atgttagctt ttcattagaa atactttgat ctgtaattac catccataaa atttacagtt  11940
aaaaaggaaa gtgtacccaa gttgttgtaa atattctttt ttctttcttt tttttgtat  12000
ttttgacttt tctagggcca cttctgcggc atatggagat tcccaggcta ggggtctaat  12060
tggagctgta gccaccggcc tacgccagag ccatgtctgc aatctacacc acagctcaca  12120
gcaatgccag atccttaacc cactgagcaa ggacagggat tgaacccgca acctcatggt  12180
tcttagtcgg attcgttaac cactgtgcca caatgggaac tctgtaaata ttctttaaaa  12240
agttatccag tcactgaatc aagcatcctt ttaaaaattg agatacagga gttctctggt  12300
agcctagcag ttaaggatcc attgtgccac tgctgtggct caggtcgctg ctgtgatatg  12360
ggttcaatcc ctggcccaag aactttcaca tgccatatgc acagccaaaa aagtgtaaaa  12420
taaaacaaaa ttgtgatcta attcacatac cacaaaagtc accctttgaa agtgtacaat  12480
tcagcggttt ttagtatatt cacgatgcac attgtttttg ttttttggta ttttttttt  12540
tagggctgca cccacggcat atggaggctc ccaggctagg ggttgaatca gagctgcagc  12600
tgctggccta taccacagcc acagcaacac cagatctgag ccatgtctgt gacctacact  12660
gcagcttgag gaaatgccac atccttaacc cactaagcaa ggccagggat cgaatccata  12720
tcttcatgga tactaattgc atttgtaacc actgagccgc aatgggaact cctgcacagt  12780
gtttttcttt ttctttttt ttttttttc ttgtcttttt gtcttctcta gggccgctcc  12840
tgcagcctat ggaggttccc aggctaggga tccagttgga gctatagcca ctggcctacg  12900
ccacagccac agcaacacca gatccgagct gcatctgtga cctacaccac cgttcatggc  12960
aacaccggat ccttaaccca ctgagcgagg ccagggattg aacccgcaac ctcatggttc  13020
ctagtcggat tcgttaacca ctgagccacg acgggaactc ctggttttta agttgaaatc  13080
tgagttaact aaaacgaaat aaaagtagga atccagttct caactgagct agccacattt  13140
caagtgccca gggtccactt acagtcatca ttttggagag cacagatcag aaccttcagt  13200
```

```
tatgcttgcc ttcttccctt ctgcatattt acctatgaat aacattacaa agaaaatgag  13260
aatttctctc acagcaactc ccatccacca ccaccacctg taagatatca ctattaatga  13320
tgtgtctctg ggctctgcca gggcaggcgg agcttgggac agctcttgtg gtcaggggtg  13380
agccctgaga tattggcagg gtcaggaact tggacctgaa cttggatcca gcccaccctc  13440
cctgccccct accaccgacg ctgtgttctg tttccacctg ggcagggatc tgcgtggctg  13500
acccctatga ggttgtggtg aagcaagatt tcttcatcga tctgcgtctc ccctactccg  13560
ttgtgcgcaa tgagcaggtg gagatccgag ctatcctcta taactacagg gaggcagagg  13620
atctcaaggt gagcctctag tgtgacaggc atgatgggga gcttggaggg agggtccatg  13680
gcacactctc ctgacttgat actccctctt cctggcaggt cagggtggaa ctgctctaca  13740
atccagcttt ctgcagcctg gccaccgcca agaagcgcca ccaacagact ctaacggtcc  13800
cagccaagtc ctcagtgccc gtgccttaca tcattgtgcc cttgaagact ggcctccagg  13860
aggtggaggt caaggccgcc gtctacaacc acttcatcag tgatggtgtc aagaagaccc  13920
tgaaggtcgt ggtgagtctt tggggatacc tgctgcccct tgtccttcag gaaagactcc  13980
tgtcttcctg tgctgtgaac ccaggttgga gacccaggct aagaatacgg agtacttctc  14040
agaaaattta ggagttccgg aagtttggaa gcagggctgg gattagggtg aggcaagtga  14100
ggcattctcc ttgggcatgg aatttcaggg gacactccaa agcttagtaa cagagatcaa  14160
tgatattttt tcgttaaaat atagtttaat gtcaaatatg acatttcgta acacatttca  14220
gcagaggagt tttctcttga ctaaaaatct tgggaggagt tcccattgtg gctcagtggt  14280
taacgaatcc gacttggaac catgaggttt tgggttcggt ccctggcctc gctcagtggg  14340
ttaaggatcc agcgttgcca tgagctgtgg tgtaggtcgc agacaccgct cgcatcccac  14400
attgctatgg ctctggtgta ggccagcgac tgtggctcca attagacccc tagcctggga  14460
acctccatgt gccgagggag cggccctaga aaaaggcaaa aaaaaaaaaa aaaaaaatct  14520
tgggaaagca tatttcacag aacaaatatt ataaagccat aacatacaat gctagaacag  14580
aggaaacgtc tatttctacc tatgattctt accttaaaat atgcattaac agttactttt  14640
ccatgtccta tgattaaaca tataatagat aaaatcaaca ataaaaaataa aagtattatc  14700
atcttttagt aacgttttaa agcaaaatgt gagatcataa acaagatcaa aaatatttaa  14760
ttcaagagta cctgttgtgg cttagcggta acaaaaatat ttaattcaag agttcctgtt  14820
gtggctctga ctagaatcca tgaggatgtg ggcttgatcc ctgaccctgc tcagtgggtt  14880
aaggatctgg cattgccatg agctgtggtg taggtcatag aagcagcttg gatctggcat  14940
tactgtggtt atggtgtagc cagcagctgc tgctccaatt caactcctac cctgggaact  15000
tccatgtgct gtaagtgcag ccctaaaaag acaaaaaaag taatgcaata tattaagaaa  15060
tcaaaattaa tgccccaaac cctcacaaca aacaaaatat caaaatttta aatagagaca  15120
ggatctgaca gtgtcaaggc aaaccatatt ggagcctgaa gcagaagaaa aatgagttgc  15180
tccataaatg tgcctgtatg tatttttaaa tggttaattt tccccaaaaa cattacagta  15240
gctgaaaaaa tattgaaaca ttgaaaacca agtgtattaa aattgacaga gtgattttcc  15300
attgaagtat tttgtttata cccaaaccag aatttattat aatttttctt tattggcttt  15360
aataaaagca aactcatatt tttttcaact actttactgt tctggaataa aattaaccat  15420
taaaaatatg tgaaagtata tattttgggg cacatatttt tctttctttt ctttcttttt  15480
tggggggtgt ctttttaggg ccgcaccatc agcatatgga ggttcccagg ctgggggtcg  15540
aattggagcc attggcctat gtcacagcca cagcaacgcc atttctgagc caagtttgtg  15600
```

acctacacca cagctcatgg caatgccaga tccttaaccc actgagtgag gtcagggata 15660
gaacctgcat cctcatggat actggtcaga ttggttttca ctgagccacg atgggaactc 15720
cacacacatt tgtccttttg ccttgagttt ctatatggct cagcttgggc actggtgaga 15780
agaaagccag gattttgtta gagtttatat tgcccagctc ccaaaagcca gtgtgcccat 15840
cacttcacaa ttctgtactc actgtggctg gtagcttgaa aatcaccatg ttgggaatat 15900
ttacaccaag gaaattggca gcactacaaa ttaggaactt ttcttcctga aaagctggat 15960
gttatatatt taccaacaca ccattggagg catcttagtc tgcaaaggaa aatctgggaa 16020
ttactaccag gtgaaaggag aatgagttct aggaagacaa aaacagccac cgtccaccat 16080
ggagatttat gtgtagacac ataagggctt gtagtgggcc tttgatccta attaagacag 16140
ttctgatttt aactgagccc ttactatgtg ctaggcacta tgttaaatac ttgtgtgaat 16200
cctttcattt cttttgtgag aggggggtct ttttaggacc acacctgtag catgtgggag 16260
ttcccaggct agaagctgaa cgggagcttc agctgccagc cttcgcctct gccacagcaa 16320
cgccagatcc gaaccacatc tgcaacgcca caccacagcc catagcaatg ccgtatcttt 16380
aacccactga gcagggccag ggatcaaact cgggtcctca tggatactag tcaggttcat 16440
taccctgagt cacaacagga actcctcatt tctttttct ttactattta ttctcatttg 16500
tttatttgaa aatgttgttt tacttttaaa ttatttgttt tattttacaa tttttatttt 16560
tattttagtt agcctattga gaggcactgg gttaaaaaca gactctggaa ccagactctc 16620
aggttcaaat ccacactgtg ttctactagc tatgtgacct tgggcaaatg acttcatcca 16680
tctgtacccc agttccccca tcttgaaaat ggaagtgata atagcagtat ccaccccatt 16740
gagtcgttgt gaggattaaa tgaattaacc ccagtaaaga aatcttttag gcacatagga 16800
agatttctat agattttgtt aggtcattat taacttataa ttttattatt aatctataca 16860
acaatgggta cgaggtagat gtttatatta tgtctttata aggaagagag ctgaggcaca 16920
gacaggtgaa gtaagtgact tccagtcaca cagctaagat ctagtggatg ccatcgtgca 16980
tatgctacag taatccccag aacaatgcct cgctgaccag ctgtctgtct gtctgtcctt 17040
ttcttcacgg gactccccct gcccccaaca ctatccagcc agaaggaatg agagtcaaca 17100
aaactgtggt cactcgcaca ctggatccag aacataaggg ccaacgtgag tcagccacag 17160
aaggggtgag ggctgggtgg ttgaggcagg gtagggtggg aggggggtgg ttgaggcagg 17220
gtaagagtgg gagggggctg gtgcaatggg tgtctcccat tctcccggca gagggagtgc 17280
aacgagagga aatcccacct gcggatctca gcgaccaagt cccagacacg gagtcagaga 17340
ccaagatcct cctgcaaggt gagaggccct tggcttcgac cccaggggac ccagaactgt 17400
gttggggggg catgagccca gttccatctc atccctcctc ctcttcagct agaatttctc 17460
tttgatctgc ttcaggaagg ctccaggcac tatttagttc agccaatagc ttttgctgat 17520
gaagaaattt attatttttt aatgaattta ttatatttat agttgtacga cgaccaccac 17580
aacccaattt tataggcttt ccattcctaa cccccagcac atcccctctc ctcccaccct 17640
gcctcatttg gaaaccatac gtttttcaaa gtctgtgagt cagtatctgt tctgcaaaga 17700
agatagatca ttgtagctct gataaagaaa tttaaataag aagcagtata gttccagagc 17760
agaaattctg gatctgattg ccctggatgg ggaactcggg caagaaggga caagatagat 17820
ctgaaaaggc accttgcaac ctgtaaggtg taaagttttg ggaggagacc cttggttccc 17880
tcatctgtga cgggggcaaa taacagtatg gttacctaag ggttgttggg tgggattaaa 17940
tgagatacta tacagtgttc tcttagaata gagcctagca aatagcatta agcacgatat 18000
aaatattcct gactattgtt actggaatta tgttaccact ggtgtgtaac gagaggaacc 18060
agggactgga aatcccctgt gaagcacaag ctcaccccca ccactccgca aatgcagaat 18120
ccccctccag ctgctcagct cctcccatca catacccctcc agctgtccct gactcctttg 18180
gccctggctg gtcagagtct ggaaatgctg gggcagccc tggtcttgaa tgccatctta 18240
ccgtctggct gcagggaccc cggtggccca gatggtagag gatgccatcg acggggaccg 18300
gctgaagcac ctcatccaaa ccccctccgg ctgtggggag cagaacatga tcggcatgac 18360
gcccacagtc atcgctgtgc actacctgga cagcaccgaa caatgggaga agttcggcct 18420
ggagaagagg caggaagcct tggagctcat caagaagggt atatgccgca cctcctcctc 18480
tgagctgtct aggcccctga gaccccgccc ctccgagccc cctccaacca gaggcccctc 18540
ccctctagag gccccacctc tctgagccct ctccaaccag agactccgcc cctctatagg 18600
caccacccct ctgagcccct cccaaccagg ggccccgccc ctcctctgag accacccct 18660 tgctcctctc nnnnnnnnnn nnnnnnnnnn nnnnnnnnnn nnnnnnnnnn nnnnnnnnnn 18720
nnnnnnnnnn nnnnnnnnnn nnnnnnnnnn nnnnnnnnnn nnnnnnnnnn cctctatctg 18780
atcctcccac tttctacttt aagctcccct tccccacccc aaacttgtcc cctgctcaga 18840
accctctctt tcttctctgt accccctgtcc cacctctcac agaatcttta tcctctttct 18900
aagcccctcc cctccctggc ctacccatgg tagccacccc ctccactcag cctctgttga 18960
cacttctccc ttctcggcag ggtacaccca gcaactggcc ttcagacaaa agaactcagc 19020
ctttgccgcc ttccaggacc ggctgtccag cacctggtga gtctccaaga tctgcttgcc 19080
catccttagc cttgcacctc cctgagcagg gcctggatcc cggcctcagg tggtctaggt 19140
tggcctcgcc cacacagccc tgtgcgactt gacccctcta ctcacgaagt caaaacacca 19200
gccagatgag tggcctgcat gccacaccgg gtcctgagtt tggggaagag aaactgggcg 19260
gaccaggcca ggccccgcct ctctctgttc attgcttggc tgggatgcag tcttcggatc 19320
ccagagccaa ttggctcatg ctctgtgtcc gcaggctgac agcctatgtg gtcaaggtct 19380
tcgctatggc agccaacctc atcgccatcg actcccaggt cctctgtggg gccgtcaaat 19440
ggctgatcct ggagaagcag aagcctgatg gagtcttcga ggagaatggg cccgtgatac 19500
accaagaaat gattgtaaga ggaagggact cagagcaggc agggggagag gggcatctga 19560
gcatcacagg ttagcggggt gggggggtgg gaggaagact ccaccatcca cccatggccc 19620
aatccattgt gccaggggac aggggataag ggagctggga gtgccactcc tccattgcaa 19680
aaaacaaaga cttgcaggat ccggtgcaaa aggaaagttc ccaggtcaca gagctgctta 19740
gagccgtggt cctcaaagtg tggtccccaa gccagcagca tcagcaccac ctgcaaactt 19800
gttaaaaata cacattttca ggatggactc cagaggcact gaatcagaaa caataggggc 19860
aacgtctaga aattggagct ttaacgcaca tatacacaca tctctgctga tgctggtgtg 19920
tgctgaagtt ggagagttgc tgccttagcc tgaccttgct ggctttcaca cagctttctc 19980
ctgcccccct tcacactcta cctggactgc tagaagcctt gctctgtcca gccacagggc 20040
ctttgaacat gctgtttctg ctgcctgccc tgctaacccc tgccctcttt gagagttgac 20100
tcctactcac tcttcagatt gtggttccat ctgtcacccc tcagagacac ttttccacga 20160
ctgagtcact cttccactgt ccattctcaa tgccatctcc acttctcctg cacagcactc 20220
atcagtttgt aattatatat ctgtggatga cctggttggc tcatgtctgt ctcccctact 20280
agacagggag ctccatgagg gctgggctgg ggtctggttt tctcccacca tcttatccac 20340
agctccatca acatttgcag aatgaatgaa tggatactaa agagcttggc cctcttgggg 20400
agaccctggg gagagaccca gccctgcctt gacctgctga tcctacaggg gggtggtggg 20460
catgtgggga catgatgttc acccgctccg ggcttcctgc ttcccctcta gggtggcttc 20520
aagaacactg aggagaaaga cgtgtccctg acagcctttg ttctcatcgc gctgcaggag 20580
gctaaagaca tctgtgaacc acaggtcaat gtaagtgtcc cttgcctctc cctcctcccc 20640
tcccctgctc aggacacatc aggtgaggta tggatttggg gccatttcca gtcctcccag 20700
tgtgacaacc accatcacag tggccataag agtacctaac atttatcgag ccattaacta 20760
agatactcac ctaaaagctt cacatgttta agtcctgtaa tccttgtagc agcccaagag 20820
acaggctacc cttattatcc ccagtttttta gaagagaaaa ctggagctcc catcatggct 20880
cagcataaat gaatctgact agtagccatg gggacacagg tctgatccct ggccttgctc 20940
agtgggttaa ggatctggcg ttgctgtgag ctgtggtgta gatcacagac gaggctcgga 21000
tcctgtgttg ctgtggtata ggctggcaac tatagctcct atttaacccc tagcctggga 21060
acctccatat gctgtaggtg cagccctaaa aagacaaaaa aaaaaaaaaa aaaaaaaaga 21120
gagagagaga gagagaaaat tgaggcacag agagatcaaa gatcaggtcc tttccgcctg 21180
ttctcccatt tctagagagt catagccaat ttcagcagaa gtcctctcag tttgctttcc 21240
acagcactcc tccacatgcc tccttgctgc ttccctagag aaaactcaag acacagagct 21300
taaaaagagg agaaaaaaaa tcctcaagac catttcctta gtttagaggg tctttcaggg 21360
tattttttta aaggagtcca tgatcccaaa agggaaggga tttaaaatgt tgactattca 21420
ctgtcccctt ttcctctggc tttggttctg aagcagagaa gtttgaaaag acaggctctg 21480
gagaatctgt aatcactcca tctgctttgc cctgggattt tgaggctggg ttgcttgact 21540
ttagcttccc tacaggggaa cctcaggctc tcatcttcag ccagctgctt ctacctcctc 21600
agaaccccag aaaagggatg gaggggaggg gccgttgcct ttaatgccca aaagggccca 21660
ggccttcctg gttccaacct ggaagatttg agagaaatta tagtagaaat gagacaacac 21720
taggactagg cacggggtag gggtggggat gtcagagaga agtgacttca aagcctgact 21780
ctcaggcact tccccttcaa ggccttaatg tgtgcatctg taaaacgggt atggtggtct 21840
ttgtattgtt taggactctc tgcattgtcc tagatggaac acaagtgtga cccagattat 21900
gcaaaaatag ggtatttatt ttagggatcc aagaatttat caagtgcaac gataaaagag 21960
tcctcaggga ctctgccaga atgcttcgtt tttcacgtcc tcccatatct ttccttccct 22020
tcttgcctaa taattcaact ttcctggcca tccggcctgc ctggccaaac tgtcttcctt 22080
ggggaaatag accaaagcac cagcagcaga atctcagtga cagattctga ttggctcacc 22140
gtgggtcagg tgatcacctg tggaccaatc agctgaggga ggcagtaggt cttagtgggc 22200
aactatgtgc gcttctggtg cggccttgtg agtggaagtg aggtgttcta acaacagtca 22260
tcgacaggtg tagaagagat tcctgggcag gcaaaaggat catttctact gtaatataac 22320
attttttact atacatatta taatgaagta tggcataggc tgtggaaccc gactgctggc 22380
atttaaatca ggagtatgct gaacccatcc gtgtaaaatc tgtaaaacca gttgttaaat 22440
ttccaggaat ttgcaagctg gctgttaaac acgatcgtga ttaaattaaa ttataaactt 22500
acagtgaaaa actgtaaaca ttaaacagta aaaacaggcg ttcccgtcgt gacgtagcgg 22560
aaactaatct gactaggaac catgaggttt cgggttcgat ccctggcctg gctcagtggg 22620
ttaagaatcc agcgttgcca tgagctgtgg tgtaggtcgc agatgcggct cagatctggc 22680
ggtgctgtgg ctgtggtgta gaccggcagc tgtagctcca attagacccc tggcctggga 22740
acctccataa gcctcaggtg cagccctaaa aagacaaaaa agatttttaa aaaaaggaca 22800
aaaaaaggag ttccgtggtg gcgcagtggt taacgaatcc gactaggaac catgaggttg 22860
cgggttcggt ccctgccctt gctcagtggg ttaacgattc ggcttgccgt gagctgtggt 22920
gtaggttgca gacgcggctc ggatcccgcg ttgctgtggc tctggcgtag gctggtggct 22980
acagctccga ttagacccct agcctgggaa cctccatatg ccgcgggagc cgcccaagaa 23040
atagcaacac caccaaaagc caaaagccaa aaaaaaaaaa aaaaaaaaaa aaaaaagaca 23100
aaaaaaaaag taaaaacgca ggtagtaaac acttaaaatg tatcacttcc taaacatttt 23160
gctatctttt atcatggttc ttttgagaat ttatgtgtat tgtacttgta tagtggaaat 23220
attatgtaat gttgaactac tgcccatctc ttcccaaatc tacattcaat gatgtgggtt 23280
gattgatgga ttgaaagcag ccatgataat attgacatca tagaaatgac aaacccttca 23340
aattatgttt tcccccaacc cctatctttc tgggtcacag catttttctc tgacaggagg 23400
ataatgatga aaataatacc tacctcatag tatattatga gattaagtga gcaagtatat 23460
gcctgggaca tagtaagagc tagctatgat ggggattact ctcagataag aagtgttccc 23520
ttggtgagct gaatctggct cacactagct cacgagtgcc tacggggggc atctctaccc 23580
cactccatgt tcagggactt cacattggta gcttaaaact gaccatggta gaatttttac 23640
accacagtaa ttggtgatgc ataaaggagc acccctcccc caaccccatg cctccattgg 23700
agagctgatt gttaaacatt caccagcaca ccatggggta tacagactgc ccccccccatc 23760
cccgctgcca gcacatagta ggtactcagc aacaaagcag ctcacaatga gaaaacttca 23820
aaagtaggta gtagatccaa ggcaggtccc aaggacagat accatcctgg cgcccaggaa 23880
gtgatgcttg tgtgatcctt actagttctc tgtggcagca acgcccactt gatcagaata 23940
cccaatcctc tttctcatag agcctgttgc gcagcatcaa taaggcaaga gacttcctcg 24000
cagactacta cctagaatta aaaagaccat atactgtggc cattgctggt tatgccctgg 24060
ctctatctga caagctggat gagcccttcc tcaacaaact tctgagcaca gccaaaggta 24120
agaggcagcc tggagagata aagaaggggg tgcatggcta gggtttgagg gtggtcctct 24180
caagctggga tgcatgcctc taagctgcac tgggatgtgc atctccaagt ggagctgggc 24240
tggatggctc tacaaggtga aaagctctca ttgtaaacca cacaggaagg ctcactgcat 24300
aattcatgac agcagtgagg tgtcattaag aacatgggct ctgacctcag gcagactgaa 24360
accgaaaccc cactcagcca ctttctcact gcctgacctt ggacaagtca tttaacttct 24420
ctggacctta gtttcctcat cttaatacct acatcgcagg gtggtcatga agattaaatg 24480
tataatgcaa gtagaagaga gtctagcaca cagtaagagc tctgtcactg ataccattag 24540
tgcctttaat tttattttaa tttttgtctt tttagggcca cacctgccgc atatggaagt 24600
tcccaggcta ggggttaaat tggagccact gctgctggcc tatgccacag cacagcaatg 24660
caggatccga gccatatatg caacctagct cacggaaatg ccagatcctt aacccactga 24720
gcaaggctag ggattgaacc cgcatcctca tggatcctag tcagattcat taactgctga 24780
gccacaaagg gaatccacct tcaatattgt taaaaatatt atcattatct gaaagcatag 24840
ggaacttagc acagtgccta gcacagagtg agtgcttaat ttttggtccc agctgatgac 24900
actgtatcat gtttgcactc actgatgtga catatctcaa gtaatggaat gtaacatata 24960
caaaagtcat ttaacacaag aataatttat tggtggtggc cggctctcct ccacacagag 25020
atgcagagat ctaggcctct atcttttcat agctctgccg ctcagaatcc atccatgtaa 25080
gctgaggggg aaatagtcag gaagactgtg caagggaggt ggaccaaaca tggaaggggt 25140
cccatcattg ctgtgcacat tccattggtc aaagcttagt tatgtggcca tacctacctg 25200
caaaggcatc tgggagatgt agtccaactc tgtgcccagg aagaggaggg tatgattctt 25260
agtgacagcc tctgccatca gtattttctt aggcacttgt gacatacagt gaatacagtg 25320
cagcccttcc cattatggcc tcacacctca gttgaggagg gaaaatgaat taatagatta 25380
ctgtagaaca ttatagcatt gggatagtag aagcacagga tgctttaacg gacaggagga 25440
agaagggcct cacttcctct tagggtgcca ttgaagctga attgtgcggg gtgagaatta 25500
accacaggta gatggagaaa aattgctcca agtagaggga acagaatatg caaaggctca 25560
taggtttaaa aaaaaaaaga gcaagtttag ggaatctcct gcagtggggc tgcagttgag 25620
aattcaaatg gaggagtgag ggttgatgag ggaagagagc aaggcagaag acagcagatt 25680
gagggtcttg aatgtgggcc aggacacttg aaaaccaagt ccagtatgag tctttttttt 25740
tttttctgag ctttctctga gctatttaca ggctgaacag agcattgaga gtgggggttc 25800
tctctgcaga aaggaaccgc tgggaggaac ctggccagaa gctctacaat gtggaggcca 25860
catcctacgc cctcttggct ctgctggtag tcaaagactt tgactctgtc cctcctattg 25920
tgcgctggct caatgagcag agatactacg gaggtggcta tggatctacc caggcaagta 25980
gccccacccc caccccacct ccaccccagg cacctgcatc ccaacctctt ctggcctccc 26040
actagccttc tggagtaggc actgagacca agagaggtag gtcttctgtc ccataagcca 26100
ggatggttgg aatgaagttg agaaatcttt ttttcccccc ttataaaccc atctctggat 26160
ctagactaca ttctgagtgc tccaagctgt gttctgagcc tctctttccc tcttgacatc 26220
taggtcatgt tctcagggct caggttcaga tgtgagcctc tctctccccc tggttcccca 26280
gttccaccag attccctatc ttatcctgtc tcactggtag gttctagatc ctgttcatct 26340
caccagaccc ccaatattac cttgtctcat tggtaggttc tagactggat ttttagttgt 26400
tctgggccat tatccaagct tctttctctc acttgtggga tctagaccat gttctcagct 26460
ccttcaggct ctcaatatta ccctgtctta ctgtgagttc tagaaaaggg tctcagctat 26520
tctagccccc agtaggttct agaccatggg ttctttagcc ccctttattt ctagtgggct 26580
ctcaatcaca ttctcagtgt ttgggattcc aaatcagatg ctcagtgttc ccaactttac 26640
tctttttttaa tgagtgggtt ctagacatat tcccagcact tctagactct tgtcttagat 26700
gctctcctct agatgggtct agactacttt ctcactgtgg ctagactttc agtcttatgt 26760
ctgccctttc tggtgaattc tagacatgtt ccccatgtct ccaagctctt gtctgaaccc 26820
ctctcactca gagagttcta gaacatgtcc tcagtagcca acaaccctcg atcttgttct 26880
tgaaggccac aatgggtggg ttcaaggcca cagtttcagg gccccagctc tgatctgaga 26940
ctcttcatcc ctcagtgggg tctaacaact ttcttgttgc ccagattcan nnnnnnnnnn 27000
nnnnnnnnnn nnnnnnnnnn nnnnnnnnnn nnnnnnnnnn nnnnnnnnnn nnnnnnnnnn 27060
nnnnnnnnnn nnnnnnnnnn nnnnnnnnna aggtagctgc gggaaacttt cccagggaaa 27120
cggtattccg gtgtgaaatg gtatggacaa gaaaagctat ttctgtgtga aattgttatc 27180
cgcaatccag gctctggacc ccttccatga attttctgca gtcctcatag tagtgcttcg 27240
aggtagggtg accaagctat tctgccattc ctgagactct ctcagtgttc gcactccaag 27300
tactgcatcc tgggaaaaac cccttccccc aagacgggac ctgggaccct tggctgcggg 27360
gcttgcacct gggaaatgtc tccttgagca acaacataca aagaaaccaa atgggactaa 27420

```
aaatagctgc atgggcgttc ccgtcgtggc gaagtgttta acgaatccaa ctaggaacca  27480
tgaggttgtg ggttcggtcc ctgcccttgc tcagtgggtt aacgatccgg cgttgccatg  27540
agctgtggtg taggttgcag atgcagctcg gatcctgcat tgctgtggct ctggcgtggg  27600
ccggtggctg cagctctgat tcgaccccta gcctgggaac ctccatatgc ggcgggagcg  27660
gcccaagaaa tggaaaaaag acaaaaaaaa aaaaaatagc agcatgcttg cacagttggg  27720
gcagattatg gacagcaaga tataaaaaga ccaaaaaccc agctgccata tctgaggagc  27780
caggagcaaa agctgggtgc tgtgcatgcc ctctgcacac agccccacca agggggcagg  27840
cagaccacct aagccacccc tctggcaccc ctaccctcac cccacttaag gaaccagcta  27900
cacacacaca cacacacaca cacacacaca cacacacaca cacctgcccc aagtaaggga  27960
cacacacgca catctgcccc cagcaaggga atacttgttt tcctttcttc ctgctgcagc  28020
aggagctaaa taaagccttg cctgaatttc ttatcgggcc tcttactcaa tttctgttga  28080
ctgggaaagc caagaagcct catggttaac acccccagtc tggggcaagc cggaatggtc  28140
agtcactcta cttcaaggta gacattagga ctcccttttc cagatgcaga aaagagtgcc  28200
caagagaggt tgcctaactg ttccaggtca gcccccaagt cagaacacag gaggagagcc  28260
aagcagacca gaccacgctg ggaaggagtt caggagattt gctcatcatt ctggctgtac  28320
ccctcatggg ctaccagctt tgacccagct gcagcggagc ctataagaac cagtgaattt  28380
gtgattctca gaggaggaaa gggggagggg gaaaggacag aagaagaggg aggggaggag  28440
gagggagaag gggaggagga agagatgggg ggagaggaaa aggaagaggg ggagggaagg  28500
gaggcgcagg ggaggaggat ggggaaggag gagaggggag aaggctaaca tattacactt  28560
atgatgttcc aagtatctac taagcactgc ctatatctta cctcgtttaa tcctcatcaa  28620
acccctatgg gattaactcc tcttactctc atttccatgg aaccaaagtc atggggcatg  28680
gattggaaca gccgaggtcc ccatgtcaat gaaccctgga accaagattt gaacctaggc  28740
agtgcgactc cagagcctat ctcataacaa ctccccatgg agttgaatcc tcagaactta  28800
atcccatcag gtaggcaggg gttcatcacc ctaccggata atcaggtgac aaaaccaaga  28860
gatgaaggca tgtccccaag gtctaattgc cttcaagctg ggaagtctc ttaccaaaat  28920
ctgaccacga tcgccatggc cactcacctg caagcaaaga gaagtctaca gatccctttg  28980
atttttcttt cctctctttt atggctgcac ccgcagccca tggaagctcc cgggctaggg  29040
gtcaaatctg agcagcagct tccagcctac agcacagcca tagcaaaaca ggatctgagc  29100
cacatctgta atctgcgcca cagatcctta acccactgaa ggaggccagg gattgaacct  29160
gcattctcat ggacactatg tcatgttcgt aactcactga gccacaatgg gaagtcccta  29220
tagatccctc tgagatctgg ccataagcca tcctttcaca accaggtacc ctgtctccct  29280
gggtaccagt gatcacagtg gtgagttatg aaagtgggaa cgggatgtga agaggaaaac  29340
ccagtctctt tctggggatt tacctctatc agctcacgag ttcttcacac tttgccaggt  29400
aagaaaggat gggataccaa tgttcattgc cgccctacac acagtagcca agacgtggaa  29460
gcaacctatg catccatatg cagaggaatg gataaagaag atgtggtata tacatacagt  29520
ggaatattat tcagccataa aaaagaagga aatcatgcca tctacagcaa catggatgga  29580
cctagagatt atcatactaa gtgaagtaag tcatacaaat ttacagttaa ccaaggggat  29640
agcagggggt ggggaaagat aaattaggat ttggggatta gcagataccc actgccatat  29700
acacaaggac ctactatata gcatggggag ctatattcaa tatcttgtaa taacttataa  29760
tggaaaataa tctaaaagta aacatgtatg tgtgtgtgtg tgttcacttt gctatacacc  29820
```

agaaactaaa acaccattgt aaatcagcta taattttttt taagggtttg ggagttccct 29880
ggtggtctag tggtaaggac tcagcacttt ctccattgct gcccaggttc aatccctgat 29940
ctaggaaccg aaatcccaca tcaagctgct gcacaccaca gccaaaaaaa tgaaaaaaaa 30000
aaattttttt tgtctttttg ctatttcttg ggctgctcca gcagcatatg gaggttacca 30060
ggctaggggt caaatcagag ctgtagccac cggcctatgc cagagccaca gcaacacaag 30120
atccgagccg cgtctgcagc ctacaccaca gctcacggca acgctgggtc gttaacccac 30180
tgggcaaggg cagggatcga acccacaacc tcatggttcc tagtcggatt cgttaaccac 30240
tgcgccacga cgggaactcc aaaaatgaaa atttttttaa aatttttaat ggttaaaaga 30300
ggggggggaat atcagccact cttggcccca cccgcatcca ccttgccagg ttagcatcct 30360
atcccccgct gtctcactag ccttgaagca ctgcctgaca catccaggca tgtaacagca 30420
cagcctccga gcaggtgaac ctctgtggta taattcacac tccagagctc ctcctgggac 30480
caggctgcgg ctgaaaatct cctgaaacac cttctgagtg gccatttcct cctcctgccc 30540
catcctgctt ccctccctgc aagggtctcc tgagagccct ccctcaacaa atgagtcaca 30600
taaaatcctc atctcaggct ttgcttctcc agaaatgaat gaaaaacaag tggcgatcct 30660
tatttttgtg tttcagtttt gttttgtttt ttcaaatttt gaaggtctcc tgtggtgcag 30720
tggattaagg atcctgtgct gtcactgcag cggctcaggt tgctgctgca gttggggagt 30780
tcaaaccctg acccaggaac ttccgcatgc catgcatgtg gctaaaaaat aaaatgttaa 30840
ttgaaggcac aagggaaaga gccagggtgg gaaccaagag acctgatgtt atcccttgtt 30900
cggccaccat ctcctagcaa gtggccagct gtggttcaac ctcctgggac acaagtctcc 30960
tccccaccac attgggcata tgcattttcc tcgtgcaact tacactgtgc cattgactcc 31020
aacggagata acgtgaatat tacccagctg tagaaaccac aacaccctgt cggaaagaaa 31080
aggaaaacac catgaaacat caagaagctc tttagattca acctgaaaaa ttacttctgg 31140
cacggcttca tggaaacagg tttggggagc ctagatgaaa gctgcagctg agtgatatac 31200
gttgttcaat ataatctgca caacaaccat tcctgctttt ctgcatgtca cttctgtttt 31260
tcattctgtt tatattatct tcattttctt ttcaaagagt tctagctgat tttcaaaaat 31320
atgcatttaa gtatgcgtcc tcaaagggaa cgacatctct cctaaaaggg caaaactgga 31380
gttcccgtca tggcgcagtg gttaacgaat tggactagga tccatgaggt tgcaggttcg 31440
atccctggcc ttgctcagtg ggttaacgat ctggcgttgc cgtgagctct ggtgtaggtc 31500
acagacatgg ctcggatccc gcgttgctgt ggctctggcg taggccagcg gctacagctc 31560
tgattagacc cctagcctgg gaacctccat atgcggcagg atcggcccta taagggcaac 31620
acgacaaaaa atcagagaaa aaaaaaaggg caaaacttgg ttcttgggga aagatgaaaa 31680
acattgtact cttttatata caagacacat agatatacat ataccatata aataaataca 31740
cactatatct gtagtattat ttttttttggt cttttgtcta tttagggccg cacccacggc 31800
atttggaggt tcccaggata ggggctgaat cagctacagc tgctggcctc caccacagcc 31860
acagcaacac cagatctgag ctgcaactgt gacctacacc acagttcacg gtaatgccgg 31920
ccccttaacc cactgagcga ggccagggat cgaacccgcg tcctcatgga tgctagtctt 31980
gttcatgatg ctagtcttgt tcattaacca ctgagccacg atgggaactc ctgtagtatt 32040
aattttttttg gggagagtaa gacaattcat ttttttaat gtctaaaagg cagcccagtc 32100
ccccgtattt agttcctctc caactacatc atcatcatca ccctcatcat caccatcatc 32160

```
ttcagcatca ccatcaccag tctcaccagc atcttcacca ccaccatcat catccccatc  32220
attatcatca ctgctatcaa cctcatcatt atcttcagca tcaccatcat caccaccacc  32280
atcatcatta tccccatcat catcatcacc atcaccagtg tcatcaccac cactctttgt  32340
ttcttgcggg cagaataaag agtgctaatg gcagggagtt cccgtggcgc agtggttaac  32400
gaatctaact aggaaccatg agattgcagg ttcgatccct gggcttgctc agcgggttaa  32460
ggatccgcgt tgctgtgagc tgtggtgtag gtggcagatg cagctcagat cccacattgc  32520
tgtggctctg gcgtaggccg gtggctacag ctccgatttg acccctgtcc tgggaacctc  32580
catatgccgt gggagcagcc caagaaatgg taaaaagaca aaaaaaaaaa gagtgctaat  32640
ggctaatccc agtgctgaca cccccaaaga aacaaggcca caattcagga tttggggtcc  32700
acagtcacct gctctttcta atgaaacctg ccactcaaca agtctcacaa acctaaactt  32760
ccaacttccc tcagtatcac taattgaaat ttctcttgct ctttagttat tttagaggca  32820
acagagcatc atgtttaagc atatcaactc tgacatcaca tgtttggtgt caaaatctag  32880
cttcaccaat tacagactgt gcggccttgg gaaagttact taatttcttt gtgcctatgt  32940
tttctcttat gtgtaataag ggaaacaaat ccactgtaca acagctgagg aaacccacac  33000
ttgttgctta gaaaaggtct cctattctta gatttgaacc aatgatgaaa actcacaaga  33060
cccatgaagg gaacaatgac atgaaaaaag caagaccaag aaaaactgac acctgaagaa  33120
aaagaaataa aagaacagga aaggagttct catcttggag cagcagaaat gaatctgact  33180
agtgtacatg aggacgtgag tttgatccct ggcctcgctc agtgggttaa ggatccagcg  33240
ttgctgggag ctgtagtgtt ggtcacagat gcagcttgga tcctgcattg ctgtggctgt  33300
ggtgtaggcc agcagctgtt gctctgattc aacctctggc ctgggaactt ccataagctg  33360
tgggtgcagc cctaaaaaga aaagaaagaa agaaagaaag aaaagaaata ccttccctgg  33420
tttcctcctt ctatataacc cccgatcaca ctatacgaca gcttctttca tagctcttat  33480
cacccctgga atgccccgtt ttatatattc ttcggagcag catagtttag gaataaaaca  33540
tacagactct ggaaccaggc tggctttaaa accctggctc tactccctta ttacataagt  33600
ggtcttgggc aagttattca atttctttta cctcattttt ttctcctttg taaaatggga  33660
ctgtttcagg acccaatatc agaggaattt agtgaagact gaatatgttc tctatttgag  33720
gaacttagaa cagtgctaag tgagtggttg ctattaccgt tagtggcttc ctttctgcct  33780
acctcttcct gctggtaagt cagcctcaca gggcaggaac tttgtctgtt cactgctcta  33840
tcctcagtgc ctagaacggc agctggtaca cggtgggtgc tcagaaaata catgccaaat  33900
gaaggactat aaagaaattc tttcttggca gatgaattcc ctgattttta tcaaagcttt  33960
cctgatgaag atgtttgcag tgtccagtct agaattatga tctcttggct ggatagccca  34020
aggccctccc ttttccctgc agcctatatc cagtgtaatc ttcccccgga ctccctagtc  34080
agcctcatac tcaccccaaa agagaaggaa actgaagctc cacatcttgc tgtgtttctg  34140
tcattcgaag aggagaatct tttctctgtt cccagagttt ttaataacag agggtgtgga  34200
gagaggggaa gggcagagcc agcattgctc aatgcaacca gagcatcaca gccctttttg  34260
ctgagttgcc accactcgga aaggacagtg tagcaaaccc ctaattttct cctttctcca  34320
cagtgtagag aggttggtct ggctggtggg tcagtgtgtg gatccatctc cctctctctc  34380
tctctctttc cttcctgctg gattctttct ttcttttttt ttttttttta attgcagcat  34440
agttaattta caatgtatac acatatatat tctttttcag cctttccatt acaggttatt  34500
ataagatact gagtataatt tactgtgcta tatagtaggt ccttgttgtt tatctctttt  34560
```

atatacagta gtgtgtatat gttaatccca aactcctcat ttatctcccc cttccacttt 34620
gttctttccc caccaacatc tatctcccat ttctcatcat cttattttat tgcacccagt 34680
aataaatgag cttccaccat ctatccccaa tgaagcaaga gcaaaactca agggtccttt 34740
cccagttttc cccgtacaat aaccaccata aacctcaagt accaggcact gtgctaaata 34800
tgtttccaag aaaatttaat ttcatcgcca tgtcagcatc atcaagtagg gattcctacc 34860
cctacctatc tcatttaaaa atacaataga atggaaattg caactaccaa ccccaagctc 34920
cctgtcaact attacattta gaatggatga gctaagcaat ggggtcctgg ctgcacagca 34980
caaggaaata tgtccagtct cttggaatag aacatgacgg aagacagtat gaaaaaaaga 35040
atgtatatac atgtatgttt gggtcactat gctgtgcagc agaaattgat acaacgctgt 35100
aaatcaacta cactctaata aaaaataaag aaagaaaagt taaaaataaa gatgctagaa 35160
acaaaaaaga aaaaaggaaa ctgaggcttg gagagaagat gtgtcttgtc caagactacc 35220
tggacttgag atttgaatcc aggaccctct gaccccaaag actagaactt tcaccatttt 35280
gtttgccttc agctccccat aatatctgat cactgtcggt gacactccca ctccatcccc 35340
cctccccaag cccaaccgaa gacacacata cacatgcaac ttctcataaa cagggtggcc 35400
taggaatatc ttagttaggg tctcccagat gcagaggctg agacaaggcg tctagtgaaa 35460
gcagttcatc agggaggtga ccccaaaaac gctccagctg aggatgggag aagtgagaga 35520
aggaaggaaa agagcccaca atgaatgtta tccagtaagt tacccagtaa aaaactgaaa 35580
ctgaaacaga ggttgaggac atctgtgcta tgtagtaggt ccttgttgtt tctctcgttt 35640
atatgtaatt gtgtgtatat gttaatccca aactacctaa gagacagcct aaagcaccct 35700
cttcagactt atcccaaacg aggcgggtga gggagctggg gtatttatcc accagatgct 35760
gtcggtcact gattgaggct tgtgttaact taagacctgg cctccaagca gatagaatgc 35820
gctccagacc atagccctgt tgatgacaaa atgcagtggc tggcagatgt caggctaggg 35880
cacccaaatc ctgtgctcca agataaaaca gaagggcaaa gcccagccct gaggtcttgg 35940
gaagaagagc cccatttgtt ttcatattct cctttttcgc tctgggcaag gcaaaatacc 36000
taccctggaa ttatggtcac cgaagaagat tcatcaacag ctccatctgt ggatcaagag 36060
accctatcca gtgaagctgc agctaagaac gagcacgaaa atacagcaaa gccctccaag 36120
aaggaggata aacagagctg tgttacattt aagagacaca ctggtggatc aacacagacc 36180
ctagcaccag atcgcagggg atttaaatcc cgactccacc acttgctagt catatgcggt 36240
cctgggcaac ttcttaatgt ctctatgcct caacattccc atctgtaaaa tggggctgat 36300
aaaaggagaa tctatttcat ggagttaaga tgagcatcag aggagtgggt atatatctca 36360
cgcttagaac caagcctggc acatagagaa aactccaaga tgtggctatt actcaaattc 36420
tttgatattt ctcccttcca gagggggaac ccagtttttc tctccttgaa tatgagctgg 36480
actcagtgac ttgcttccaa ggaacaggaa aaggaagatg tgacgtgtgg cctctgaaac 36540
atctgaaagt cattgtggct tccccctcgc tcttactttc caggatcatt cagttggggg 36600
aagctagtta tcgtattgtg agttcactca agcagcgtga tagagaagcc ctcatgagga 36660
ggaactgaga ttccagccaa aaccttgact gtgacctcat aagacactct gatccagccc 36720
cacccagcta agccacctct agattcctga ccctcagaaa ctgtaagaaa ataaaagttt 36780
gttgtttgaa gctgttacat ttggaggaga gatgtgttac actgcaggag ataactgata 36840
cgcttagaac caattgtcct tgtcaattaa aaaaaggata acaataacat cataagagtt 36900

```
tgaggtttgc tggaataaaa ccttaaagtt ctacctggca aaataatgcc cactaatatc  36960
agtaattctt gttattatta ttatcccatt aggctaagtg gtcacagcta ctcattggca  37020
tctgttcctg ggtaccagca aggacagaag tcagcaaccc atttcatgca agaccatcta  37080
atgtgggtga gaaagtttag actttctctg ctgggcaata aagggatttc agcaaaggag  37140
taaccatcct gttggtagtt tacaacactc gtgttgtgta gacaggatgt ggtcatgggt  37200
ggggagatgg ggagaagaac atagcgacaa gctcgtctag ggcacgggtt gtggagacag  37260
agaggaattt aggaagcagg aaaagcagaa tgggggggaat gcatgcatgt gggtggggga  37320
gtctaaagca gaaggaggaa ttgacctctg gacattgggc tacagaattg aaagttcttc  37380
ccatccggcc caggctcctt ctcggggtgg gatgggatgg gatgaaatgg tggaggagtt  37440
ttcccgctac tgccaaaaca aatcgccaca aacatatggc ttgaaacaat acaaatgcaa  37500
tacacgacag gtcgggaggt cagggtcccc gatgagtctt aggaggctga aatcaagata  37560
tccatggggg ctcctagagg ctctggggag aagtccattc cctgtctttg acagcttctg  37620
gaggatgccc atattccttc gcattccaaa gccccttcct ccatctgcac aggcggtgta  37680
gtatctcaaa atctctctcc tctccctctc tctctccttc tccctctttc tccctctctt  37740
tcactctctc tcccttcctc cctccttccc tctctccctc tctttctctc cctccctccc  37800
tcctctccct ctctcacaca tacacacata caaacacaca cacatttgct ccatggatgg  37860
atggatggat aggtaggtgg attggtgggt gggtaagata tagatggatc aatggatgaa  37920
taaacaggta agtagatgtg tgtattatgc tttgatagag agagagagag attgctctca  37980
ttctctagat acatttctct cattctctct atcctcaatt tctctctctc ccccacctct  38040
ccctcccctt tcctctctga ccctccctcc gctcccttaa aaggactttg tgattccatt  38100
agacctactc agataatccg caataatctc ctatctcaaa atctttaact tcactgcact  38160
tgcaaagccc ccttggcagt gtaaggtata tatgtacagc tttccaggag tgggatatgg  38220
acaacctggt gggaattagg gggaatttca ttattctacc tactgaaggt ggggtctggg  38280
gtcctggtgc gtgactgagg atggcaagat gccagtcacc cttcaaatcc aaaagaggtg  38340
accaaggcta tgaactctgg accacagaga tcctccagga tgagggcagg tagcaggcgt  38400
gaggggagaa aaaagggaag gaaatgcaca attggagcca catggcttgc agaagcctaa  38460
ccccttgtga ctttcccagc aaagaggaaa ttgagagata ctcaagaagt catctgaggg  38520
tgtaatagga aagaacaaat ctgactccat attagacctg ttccttttac tttaaccttt  38580
gtgtcctgtt gttttccctg aaagaatgtt acctagagcc tgaaattcat cccccagcct  38640
gcatagtctc aagcctctga cctttaagag tataacacgt ttccattcac atagagataa  38700
aaagttgcag aacagagaat tacatttgtt ttgttggaac cttacaggaa catcggtgac  38760
ctgacctatg cagacaaagg actcctgtac caagaaggct gcgacaacca acctgccctg  38820
ccccacttcc cctggccttt aaaaatgctc tgctgggtat tcccattgtg gctcagtggt  38880
agcaaacgta actagtatcc ttgaggactc tggggttcga tcccccaggc ctcacttagt  38940
gtgttaaagg atccagcgtt gctgtgagct gtgggatagg ttgcagatgc agctcagatc  39000
ctgcgttgtt gtggcaaagg ctggctgcta tagcttggat tcaactccta gcctgggaac  39060
ttccatgtgc cctgggttcc gcctgtggaa agtaacataa tgtcttttct atcaaaggaa  39120
atcttggtta ctccattttg ctcaggtttc accttcctgc gacccccccc accccctcccc  39180
tttccctctt ctcccaataa caatttgttt caaattagcc agccgggaag aatgtgcacc  39240
ctgacctgac caatgggaag gggacaggta catcacctgc gttagggata aatagggggag  39300
```

ggtcctttgt tcggggcgca cactttttgg agtggctgtg cccttctgca gaagtaaaga 39360
gccttgtcga gatttctcct tgtccatgtg tctcactttc tgacactgac gacccagccc 39420
gagctagagt tattggaatt tccaacaggc cttaaaaaaa aaaaaaaaaa aaaaaaaaaa 39480
gacaataaac atgctttgct gaaacccttt gggaagttcc gggtttggca gtggcggggg 39540
gaggtgcatg agggcccttc ccctccagcc cccgcccaag tctccttgca cagccctgca 39600
ataaacctct ctctgctccc aactcccctg ttttgtatag tttggccgca ctgagcaaca 39660
ggcacatgat ctgagttcgg taacagagaa gcccggcccc agagcatccc tgggttcatg 39720
cttaatgagg gtgttggagg aagggcggct cctgggaagc cctccctacc caactggacc 39780
gtgttcctct ctcgttccct ctaaaccctc ccctggctcc ctgtgacctt cgggatgaag 39840
tccagtctca ttaatacgac actcaagacc tcactgagtc ttatactggt gcccttcttc 39900
cttattgccc cccctcacaa gtcccagtca tcccaaatga acctgcagtg cacactgtcg 39960
ctgacctgtc cagccatcct tcagctactg gagcaccatc cccccgctgc tgcgggtgtt 40020
gcctgctaac agttcacagc ttccccttct ccagagaacg ttccagttca atgcctgcat 40080
aaaccctcag gcccatcctg cagccaataa gcaatgggca caggggtcaa aagccagcgt 40140
tcaccccaag gtgacttcaa cttagtggtg ttattcaggc tccgggtgtt ggaaattaca 40200
gtaactctgg ctccggttgt cagtgttgga aagtgagaca catggacaag gagaaatctc 40260
gacaaggctc tttacttctg cagaagggca cagccactcc aaaaagtgtg cgccccgaac 40320
aaaggaccct cccctattta tccctaacgc aggtgatgta cctgtcccct tcccattggt 40380
caggtcaggg tgcacattct tcccggctgg ctaatttgaa acaaattgtt attgggagaa 40440
gagggaaagg ggaggggtgg ggggggtcgc aggaaggtga aacctgagca aaatggagta 40500
accaagattt cctttgatag aaaagacatt atgttacttt ccacactacc cttcctcatc 40560
ctctgctaaa tgtcctctct caataaaccc tgaaacaaac atcctcaggg cagagtctgt 40620
ttccaggggg acctaagaat ccctcccagc cattaaactc taagctgtct cttgacctca 40680
ggttgcacat gggtactcac tccatattgt aggcttcctt cccatgtcaa tatcacctcc 40740
tcttccgtgc cttcctttgt caatctcacc gcctctagga agccttccca caaaaatatc 40800
acctccccca gggagccttc ccatgtaaaa tcacctcctc caggaagcct tcccatagaa 40860
atatcacctc cagaaagccc tccctgacct ctccttcagg attagggact tcttctatgc 40920
tttcctaatc ccaacactta atatgatctt tgcttgtttc tggatttggg ggtgggggta 40980
tgcttgcttt tggtttttttc tggggttttt ggccgcacct gctgcatacg gaagttctca 41040
agctaggggt caaatcaggg ctgcagctgt cagcctacac cacagccaca gcaacgccag 41100
atccgagcca catctgcgac ctacaccaca gctcatggca acaccagatc cttaacccac 41160
tgaacgaggc cagggattga acctgcagcc tcatggatgc tagttggatt tgtttcctct 41220
gggccacaac aggaactcct gaaaaaacta aaaatcttaa aaaaaaaaaa aaagaaagaa 41280
agaaagaacc aatgaggaaa aagaagaagg aactgaagaa tctcctgaca tcccccccta 41340
agccctcaga accaagacca agaatgtaag gggatggccg atgggcagcc actgccctcc 41400
ccctggaagg aaggaacacg agttctgcaa ggggcagcac ttgctgaggg gcagagtccc 41460
agcttgctgg gaaggatgca tagttatcca ggctcctaag acccctggca agtggagagg 41520
gggggttgtt gaaattcccc tagaaccaca cccaggtcaa agattcccca ggatggctac 41580
acaactcagt gcatagccat cctcaggctg ctttattaca gcgaaaagat acaaagcaaa 41640
gacacagagg aaaccaaaaa tgaggaaagg gttgaaatac atacaagctt ccagcggaga 41700
ggttcccagg agaatggaag aagcagcccc catccatcaa ttccttttgc tgcgctgatc 41760
tcggtatgag actccgaccc caaccatcct ctcccgttgt gtgatttttt tcctttcccc 41820
tataattttc cctgccatgc cacccctccc ccaaattgtg tgaccttcct ttcattgtcc 41880
ttgccacaag ttcccaccat gaccctttac aagagtaaca tctcaggcgt tcccgtcgtg 41940
gctcagtggc taacgaatcc gactaggaac catgaggttg agggtttgat ccctggtctt 42000
gcccagtggg ttaaggatcc ggcgttgccg tgaactgtgg tgtaggttgc agacgcagct 42060
cagatcctgc gttgctgtgg ctgtggtgta ggctggcggc tatagctccg atgcaaccct 42120
tagcctagga acctccatat gccgcgggag cagccctgaa atgacaaaaa gaaaaacact 42180
aaagtctcct cacagttgga gctgctactc tcttgagctc agccctttgg ttccggaggc 42240
cctaataaat ctctcttctt gactgacttg gccttgggcg ttcttccttc gagcaaacct 42300
aacaccaggg tggcctggaa ccagaggggc agggcgggag ggatcacaag agagctccag 42360
aaaatttagg gaaacaatgg aaatgttccg tatcttgagt gtggccaagg ttgccaaact 42420
catccaattt ttacactgag aaacgaagca gtttgttgta tgtaagtcac cctctcgtaa 42480
aatggataag cttggctcca aaataaaaga ggacccagca ttccatcaaa ttattttctt 42540
gtgcgtgcca catgaaagga cccagttgtg ttattgtgca ggcaatatat aaagggacca 42600
gtttatttta tgctatataa aagggaacaa aagatgggca ttttgagttt ctccagggag 42660
gtgtgggctc ttttacattt aaacatttgg gttttttcgt tttgtttttt tttttttttt 42720
gcttttcagg gccacaccgg cggcatatgg aggttcccag gctaggggtt atttcagagc 42780
tacagctgcc agcctacacc acagccacag caacaccaga tccgagccgc atctgcgatc 42840
tacacccgac agctcacagc aacactggat ccttaaccca ctgagtgagg ccagggattg 42900
aacccacgac ctcatgtttc ctagtcggat tcgtttccac tgcaccatga tgggaactcc 42960
taaacatttg tttaaatgga tagcttatct tattccacaa taataaatac atttgacctt 43020
aagaagctta ggaatgatct aaatctatac ttccttcaaa attaaaatga aaccaaaaaa 43080
aaaaaaaaaa ctagtacagt tcacatttcc taactgcacc ctgacagata agaaatgttt 43140
cttagaataa tgccatttgc agcaatatgg gtggacctag agattatcat actaagtgaa 43200
gttagtcaga gaaaaacaaa tgtcatatga tatcacttgt ggaatctcaa aaaatgatac 43260
agaaaattcc ttcgtgattc agcaggttaa ggacccagca ttgccacagc tctggcatgg 43320
gtttgaaccc tagcccggcg aactctgcat gctgtagttg ctgcaaaaaa aaaaaaaaaa 43380
aaaaaaaaaa aattaattaa aagaatattt taaataaagt gttaaatgat ataaattaac 43440
ttatttacaa agcagaaata gactcactga catagaaaac aaatttatag ttaccaaagg 43500
ggatagtggg ggtagggggg agataaatta gaagtttaag ggttaacata tacacatcac 43560
tatatataaa atagatcagc aacgaagacc tactgtataa cttaaactat attcaacatc 43620
ttgtcataac ctataatgga acagaatctg aaaaaggata tataaacata ttatataagt 43680
gaatcacttt actgtacact tgagactaac acaacgttgc agattaacta tacctcaata 43740
ttttaatttc actcacatac cctgccctgg gacttactaa ctctgacgaa ggcatccaca 43800
ggtgatattg gtggacatat ttcaaacaca gccaggcaga tatggcattg aatcaaacag 43860
gggcctttat aaacatctct ttctctcttt ataaacatct ctttctctct ctctctccac 43920
ccccccaaca cactctcaaa cacgcgagag cgctttccaa cgcagatagc accaaagtaa 43980
agccaagctt gccctctggt ggacagtatc agtagtgtcc caaactgctg ggctgatact 44040
tggatcccag cttggtgaaa gaagtagaga gagagagaga aagagaggga gagagagaaa 44100
gaaaggtgta tctgtgcacc tgagtttgtt cacaagccta tatatatgag cccatatttg 44160
ggcaccataa agggcccctg atgcttatgg ctttgtagca tcctcacact gcccagtggt 44220
atctcccatt cattcaccca aaagcacaga gaagggactt atagagtcat ttcagagtct 44280
tgttggacac aagcagtcat agcctcatgt agccaggatg gggcaagagg tagaaacaca 44340
gagctggagg aagctagagg gagagtttgg atctaagtct ctgaagggta aacatgggcc 44400
tatactgttg caaaggcaga gaaacctatt gtagatggag tgggctctac tcaaagcctt 44460
ttactgtagc acaaagcctc ttcttaattc tttaatccct tccagagggc taggtttggg 44520
ctgttgagtt agtacttggt atcttctaga agagaaatga gtgagccaaa gaaatgactc 44580
tctaatggtg gaatgacaat gaagtcaggc atagggcaga ttttctttct ttttaaaaac 44640
agtttttga ggtaagactg aaacatacaa attgtacata ttgagtgtat acatagcgat 44700
aagtttgggg atacacatcc acttgtgaga ccatcaccac catcaaggcc gtaaacatac 44760
ccatcacttc tcaaagtttc cttctgcagt ggattttcat tttggggtcc catcacattt 44820
catggggact gttgacttga ggaaagtctg ttctcaggga gccagcactc ctgtttgagt 44880
tgcgggggag tgtctcaggt cccatgaaat attttccccg ctgcctccaa actcatcagt 44940
ttgaagctgt gtgctgctct ctagtggcca ccgctcattt ggctctaagc tttccgcata 45000
gattgttctg ggaccagact gaaagcgcag gctccaagtc aggcttacaa ctttgagcct 45060
taaattgcag gaggtgggga gccatggatt aaggagactt aatcagtgga caatttgagg 45120
ttttaatcag tgtggccatt tcacacttga cctggcagat ttccattcat tagtatcatc 45180
acttggtctc cagtctctcc catttccaat ctattctgca aaagcacaac ccaagtcata 45240
tagtccaggc agcagattga atccttagga tgacccacag ggacttatgt aatttgcatc 45300
ctcctcttga tctggctgca ctgacctctg gaagcaggaa agggcagaag aaaaagctga 45360
gcaaatatgc gggctcagct tgagtttact tagaattagt ttcatggcga aaattagtgt 45420
agaggagcaa ggtagagagt atcttgatgg tggtgggtgg ttattattga ctatgtggtc 45480
agagaagcca tcttggacat ttgagctgag accttgagtg aatggagaga gtgcccaggg 45540
aaaagggggg aggagaaaat gtgtgttaag gcagagggaa tagcaggtgc caaggctctg 45600
aggaggctgt tgagtcagta ccctgtattt tctggaagag aaattattta gcaaaagaaa 45660
tgactctcta ataatggaat tttgggcaat gaagtgagac aaggaacaga ttttcttttt 45720
ctgttaaaaa ccattnnnnn nnnnnnnnnn nnnnnnnnnn nnnnnnnnnn nnnnnnnnnn 45780
nnnnnnnnnn nnnnnnnnnn nnnnnnnnnn nnnnnnnnnn nnnnnnnnnn nnnnnccagc 45840
ccgccccggg ccctgggagg ggaagccacc cgaacgcctc aaacctttgc tctggaagcc 45900
ccaggaattt ttccccctct cctagccggg atatatgacc cctcctcttt ctggggtggt 45960
ggtaatcctg ggttcctggg cgccctgggg taactagata gcccctcgtg ccaactctgg 46020
gatttctttt ggaggtgcag tggagtcagt gagggaaacc aagtcacccc tcgggggga 46080
cccgcggaag catggcgacc gggagaacct ggtgcctgct ctctggccgt tctgggggcc 46140
ccccaagctg cggggaaccc tgtccctctg gccctgactc acgccgggcc ggccggattt 46200
tccggaatct ggggggatt aggggagccg gggcaggggg agtggccttg ccccattcca 46260
cacccctgtt ggacgtctgg agaggggaca ctgtagtccg gctggggccc cgcccctgtt 46320
ccctggccct tcctgggaag gggagggggt tcccgccggt ttcctgcttc cccccacccc 46380
acgccgctcc ggggcggggc cgggaagcca ctccttctgg gagctcagag cttggaggct 46440
cccctgggcc aggtcagcgg gctgtggggt cccaaagtct tgatcccggt cctcccaatc 46500
ccccgctagg atcagtttga ggtgcttgag cggcacacgc aatggggtct ggacctgttg 46560
gacagatatg tgaagttcgt gaaagagcgg acggaggtgg agcaggctta tgcaaagcag 46620
ctgcggtgag accctagggt ggccgcgccc tgggcttcgg gggagcggtt ggagggctgg 46680
gggctcagtc ttcctgcctc tctccgtagg agcctggtga aaaaatatct gcccaagaga 46740
cctgccaaag atgaccctga atccaagtaa gaatgaagag gggaggcaga gttagatttg 46800
ggaggactgg ggtattggat ccttttcctc tccctccatt tgggccaccc aagcactcct 46860
ggcttctcca cccagttcca cttagaggta tgagctggga accaggaacc gtattacctg 46920
ggttggaatt caaaatccac tactttctag ctgaactgct ttgggcagtt gactccagtt 46980
ctccgcctcc atttttcttg cctattaaat gggagaggct ccaacagtta ttaaatgaat 47040
gactctgagc aagtgactta agttttgtgc ctctgtcttc ctcactgtga actggggatg 47100
atgatcacaa tactgatcat aatgataatg accttgtagg ggctcatttg aagattaaga 47160
taatgtgtta aaacaatgcc cagcccattt cactttattc caagccccca gttccagaat 47220
ccccaaagct ctaagaatca gaagcttttc tgggcaccta tccagaggca acctctgacc 47280
tgaactaatt tgacattaat tacattaatt gcgttcttgg tttttatccc actgagtgtg 47340
aatgttaata cttatcattg agagttcccg ttgtggctca gcaggttaag aatctgacta 47400
gtatccatga ggatatgggt cagatccctg acctttctca gtgggttaaa gccctgtgtt 47460
gccatgagct gtggtgtagg tcacagatgg ggcttggatc ctgcattgct ctggctgggg 47520
tgtaaggcct gcagctgcag ctccaatttg accccctagcc tgggaacttc catatgcctc 47580
aggtacagcc ctaaaaagag aagaaaaaaa atctcataca aaaatgttta ttagatgctg 47640
ccactaacac cactagggta atgtgaaaag tgatataagc atcatatccc ccttctgaac 47700
ccccctcaaa atcctgagaa ttctgagttc cccctcagcg ggtggggata agggagattg 47760
gttagaattt atcattgctt ctgggtgaat gttttggagc ttacactctt ctggggcata 47820
tggcttccaa gggccctgac ccctagcccc tgccccctc cccccacccc aggttcagcc 47880
agcagcagtc ctttgtgcag cttctccagg aggtgaatga ttttgcaggc cagcgggagc 47940
tggtggctga gaacctcagt gtccaagtat gtctcgagct ggccaagtat tcgcaggaga 48000
tgaagcagga gagaaagatg gtaggtgatg ccctccttgg gacttcccca gggccctggc 48060
caccaggctg agccttatta ccccccttctt tctgtagcac ttccaagaag gccgccgggc 48120
tcagcagcag ctggaaagtg gcttcaagca gctggagaat gtgagtttgt gcatggggag 48180
aagaggggca cccctgagca gtggggtgag ggtggctgat ccatggaggt acccccttgg 48240
tctggcctgg tcccccacct tcattgtggg tttccccctc catgtgctgg gtgacttccc 48300
acctgtccct gaaaccttag ttggtggctc cttcatgccg gtcctgtcct ctacacagag 48360
taagcgtaaa tttgagcggg actgccggga ggcagagaag gcagcccaga cagctgagcg 48420
gctggaccaa gatatcaacg ccaccaaggc tgatgtggaa aaggtgcttg tgcggtctga 48480
ggcaggcttg gggggggggg ggggcagggc ccgaacctgg cagtgacccc tgctttcata 48540
ttcctcaggc caagcaacaa gcccaccttc ggagtcacat ggcaaaagaa agcaaaaatg 48600
agtatgcggc ccaactccag cgcttcaacc gagaccaggc tcacttctat ttttcccaaa 48660
tgccccaaat attcgatgtg agtattcaaa acccacagcc ccacctcctc cccaaattct 48720
aaaattaacc aactcctaca catttgttga aaccccagct gcaatgccct aatctctaaa 48780
ttgaaagaga attagaaatg aagagtcaca gtgcactctg ccttttctca agctattcgt 48840
tctgcccggg ttgtctttct ttccttttaa aacttccatt tattctttca agccccatca 48900
attaacccct nnnnnnnnnn nnnnnnnnnn nnnnnnnnnn nnnnnnnnnn nnnnnnnnnn 48960
nnnnnnnnnn nnnnnnnnnn nnnnnnnnnn nnnnnnnnnn nnnnnnnnnn ttcctgcctt 49020
ctttgaaatc acctccgtta actatacctg actcccatga gtgattctgc catgcacatg 49080
tccaatctct ctctctcccc acagtagata atcaattcca ggagaacaag tatttgggcc 49140
tgtatttctc actgctgcat cctccatccc tagaatctgg gcgggcatac agtaggtgct 49200
caacaagtat ttttgaatga gtgcatgaat gaacgaagaa atgaatgaat gattattggc 49260
ttcagctttg caactgaact cagctgagac tcactcgaac gcctctccca cgaatgctgt 49320
ctgtgaaaac agataggacc tgattccccc acagacccct gcacctacct ctacacatct 49380
gtcccgggcc ctggacactc gtctttcccc tgctggattc aaatccgggc ttgcagacac 49440
aagagtagct ccccacactg tttcggcaaa tcgcgtgctc tgggcaagtt ttgggattgg 49500
cacattcatt tacatctagt gaatgggaat gaaaacccgg gtcaaggcag aggaaacagt 49560
gaggacagga agctgcgaac aggacattca tctcacccac aagggtagga gcgaagcatt 49620
cgagggacgg aacccccgtt accctcaatt actgccttat ctactgctta gctcctaata 49680
gaccctcaac aagaattcaa atccaagttt ctctacttga tagttatcta tccttatgca 49740
agggactgta cctctctggg cctcaattta atcatttcta aaatcaagat catagacgct 49800
acccataaga tcatcacata ttacctgtac agatgaaacg acctttcttt cccaagatcc 49860
agttgtttcc agtgggagat gagaaaccag tcaaacagct gcacctgtac ctccctggca 49920
ggtcttgcag attgagtgag gaccacatac tggggggctt tgagaacact catctatatc 49980
tggacaggaa aagagagtca tagttgccaa tatgctcctt catgtacaac agattgtatt 50040
tttcaaagag cttgaaacac tgtcttccat cccatgtgac ctgcatgcaa tgtcctttaa 50100
ctggtacact ttccatcaag cagtgggtct atatttcctt cccttgaatc tgagtatggt 50160
ggtggggaca ttaggtcatc aaaataccat ggtaaatcat caaaatatca tacacttcca 50220
ccttgttctc ttgagatgct catgcttggc tcagccgcca tactgtgagg aagccttgca 50280
agtcatgaaa aaccagctca cacggtaaga ttaagacttc ccactcacag ccctggagca 50340
gccaaccaat agccagcacc atcttgaagc cacaggagtg agccccccttc aaagagaatc 50400 ctctagcccc cagttgagcc aacacaactc acactgtggg gaacagagtt gagccattct 50460
cacccaactc agcccaaata gcagatttat ttgtgagcaa aataaatgat tgttgctgtc 50520
ttaatgtacc aacaccaata gataaccaga acttttgcaa acccacttct aggaatttac 50580
tcattggcgc acccatagaa ttgtgcagcc attgtaccat ggggtgggcc tccccaaatc 50640
tccttcagcc ctgctctgcc aagtcatcct aagtaaacat ttgctttgaa gttgctggac 50700
aaatacaact tcaaggcaag cgccctatag ctctcttcca ggaaaatgca cctctccaag 50760
agagaaatct ggacctgcca catgcatcaa gataagatca cagggatatt cttcccagtt 50820
ttaagtaatg gaacattaaa catctaaatg tctgttgata ataggatgat taaatcagga 50880
gttgacataa agaataatgt agcatgttcc ttcatttgag aaatatctat tgaatattca 50940
cagtgtctta ggtaccatat tgggagtcaa agacatgcag tggacaaggt ccttaccata 51000
gtatccatca ttttctagtt ggggcatgtt gattctacct gtattttatt ttattttttg 51060
ctttttatgg ccacacccac agcatatgga ggttcccagg ctaggggtcg aatcagagct 51120
acagctgctg gcctacacca cagccacagc aacgccagat ccaagccacg tctgtgacct 51180
acaccacagc tcacggcaac actggatcct tcacccactg agcaaggcca gggatcaaac 51240
ccacaaccac atggttccta gtcatataat ttctgctgtt ccatgacagg aactcctgat 51300
cctacctgta ttttaaaacg agggaccaaa aagactactg tgctcactga ataatccatg 51360
aacgatagcc caaaggttta aaaaaggatg tttggagctc cctaggaaat atagtaatag 51420
atattaaatc atcttattca gagattatca aactacagcc caagtgtgaa atctggccca 51480
ctacttgttt gtgtaaataa agttttattg gaacacagcc acatccattc atttatgcat 51540
tatctctgga tgcttttgca ttacaactgg agtgttgaat aatcaagacc tccatatcat 51600
atggcctgca acctccaaaa tgtttactat ctggcccctt gcagaaaaat tttgcggatc 51660
cctggtctta ttcagaaaca tagtcagatc ttcactgtta aaaggaagtt tgggtctaaa 51720
tataaggaat acatatcaaa aactagctca ttctgggtat tattttagct tatattcttt 51780
atgttaactg tagctcttgg cactctacat gtgccaagca ggttgtatac attattgcat 51840
ttaattttcc caactatcat ttaaggtaaa tacttctttc tctctctctc tctccctctc 51900
ggccaccctg tgccatatgg agttccttcg tcagatccca gccacagttg caactcgcac 51960
agcagctgtg ccacaccaga tccttaaccc actgtgctgg gctggggact gaatttgcat 52020
cccagccctg cagagacgct gaagatccgg ttgcaccaca gcagaacccc taaggtagat 52080
actcacatac acccatttta tagatggaaa tattgaggct tagagatatt aatgatgttt 52140
ctgcaacgct ttacaactgc tgtgtggcaa acaggtaatg tggtttggag accgccatta 52200
gagtcggaaa gtcccgggtt tgcattccaa tttaactgca tgactctgaa cacatcactt 52260
cagatatcca agcctcaggc ttctcatctg tacaatggag gtcctagcaa tgcctatgct 52320
caatgtcatg tgaacaggca cataaagccc ttcacacagg gcctggcact ccgtacaggt 52380
taggaattca tattattcac atggaaggaa atcaatgtct atttggggat attggcaaat 52440
agcatctttt tctttttttt ctaatgcaag tctctaatcg caagaatttt tgctggccag 52500
gtatcatttc tcataatcaa aacgcgttgt cccgggctaa atgtctgcac cagactgnnn 52560
naccnnnnnn nnnnnnnnnn nnnnnnnnnn nnnnnnnnnn nnnnnnnnnn nnnnnnnnnn 52620
nnnnnnnnnn nnnnnnnnnn nnnnnnnnnn nnnnnnnnnn nnnnagaagc cgagagccgg 52680
gtcctaagca accgagggga caccctgggc cggcacactc ggcccccaga ccccccagcc 52740
agcgccccgc cagacagcag cagcagcaac aacggatcac aggataacaa ggagaggtga 52800
gcagggaggc cagagtgtgt gtctgcatcc aggcccagga gtgatgggga ggggtcctgt 52860
cctcaccggc tttgccctct ccaaccagct ctgaagagcc ccctgcagag gagggtcagg 52920
atgctcccat ctacacggag tttgatgagg attttgaaga ggagcccgca tcgcccatag 52980
gccactgtgt ggccatctac cactttgaag gtaaggacag cctgggtggc gcatcggtgg 53040
cttcggggat agcatttttg gctaggctct gtttaggttc accttgagca gatctgagcc 53100
caccgccacc cccaccccat gacagggtcc agcgagggca ccatctccat ggccgagggc 53160
gaggacctta gtctcatgga agaggacaaa ggtgacggct ggacccgggt caggcggaaa 53220
cagggaggtg agggctatgt gcccacctcc tacctccgtg tcacgctcaa ctgaaccctg 53280
ccagaggcgg gaagaggggg ggctgttggc tgctgcttct gggccacggg gggccccagg 53340
acctacgcac tttatttctg cccccgtggc ttcggctgag acctgtgtaa cctgctgccc 53400
tccccccac cctgccccgg agcccccact caagggaccc actgtgcctt ccaccatcga 53460
tgtacatact catgtttccc atcttttctt cctgccactc ggctggggcc gttttgtttt 53520
atataaaaca attatgaaaa gctcttacag tctgtgtcct attacgagat tctgatactg 53580
gggctggaga ttcaaacacc accctcccga caggtggcac caggaaggag gaagggaagg 53640
cgaacttggg cacacgttgg catcccctgt cccttcctgg ggggttgggt gtgttgatag 53700
ggaggagggt gccagatgtc accccttttgg tgttctgcta tagctcactg agaacaggtc 53760
acacctgttg agcccctact gtgtgccagg cattttccac ccatgatctc attcaaacgc 53820
tgagctttaa tccccatgac aacccctgga aagtacacag tctcactttt atgttgaagg 53880
cggggataga gagagaggtc aagtgatctg ctggaagtca cacagcattt aaaatggatt 53940
taaactctgg cctcttacag atctgcgagt tctctttaac attcaaagcc tcacattcac 54000
cacttgtggg atatgttgag gggggtgtgg gcatggggtg gtgagaaagg gcgttcagaa 54060
cctccagatg tcgggtcttc tcatatgggg aagtaggctg ccctccctta ggattcgtgc 54120
tcagttttag ggtgcagggt gcgttcttgc aaaccaggac ccgtcccttc tgtgaggctg 54180
ggtgcaggtc ccactgcatt tggctgcctg aggacactgg ggatccctgg aagactgggt 54240
atcgccgcgt gaagaagtgg atctgtgctt tcaaaggtca ggctccaggc gctgcgacag 54300
gacactgagg acgtgctgga acttgtcgaa acgtgtgacc cacggtgccc cagcccctct 54360
gcttccccag agcagcctcc gcaagaaacc ggtggtcagg gcctctttca gctcagggtt 54420
gggctggaat cctgggggcg gagccaggtt agctggaggc gtggccaggc acctgcctta 54480
ccctctgata actgcctggt ccccttggga ctttgaccca gcaggggcca ggagggattc 54540
tgtcccaggt tatctgaact gctgggcaag gttagcgggg agggggctcc tgggtctctg 54600
cagggagtgg ggtgggggtg gctaacgggc ccagtggaag cgggctctgc caggagtgca 54660
tgggagcagt ctgctccagg tgcaagacct ggtggcccca ccttagggct tgtgcctgga 54720
gatggagctg ccccgggggg cgggacttgg ggtccaggct accctacgcg acaaacgccc 54780
agggggtggg ggtggagttg ggcctagttg gagggagaag agtgctaagt gaaggcagga 54840
actacccagg tgggagattc tggaagctgg gctgccccag agaggtgtgg ctctgagctc 54900
agagggagag cagtaccatc aggttgaagg actgaatcat tttgggggga tcgagatcct 54960
ctgggggcag gaccttccca agtgtgagag agtgggactc tgcgggcgtg gctctggggg 55020
gatagggccg ccctttaggg gcggacggca ccatctggtc tattgcagca tgcttgagtc 55080
gagaaacacc cacccagggc ggggccgtct caatttgggt ggggccctca gtttgggagg 55140
tgtagcggga ggctctagtc cctgggccgg tgggtttggg ggtgccgggc tacagcatac 55200
ggcgtgttct taaagtcagg atcctctggc agccgggcgc agatggggcg ctcacctcgc 55260
aggcgccggg ctgtcgcctc gcggaatctg ggcgcgtccc gggccgtctg acgcgcccgg 55320
tccagggtgc gcagcagccg ctcgcagctc tcgtccaagg gccccgggac ttcctcgccc 55380
tccagcaggc gcaccacggg tgccacgtgc ggcagcgcca cctcgcccgg gtcgcaaggt 55440
cctgttgggg taagggtctg ggctgggcta ggggcagagg gtgggtccta gggtgaagag 55500
ggtgcgccat acattgggcc gaaacaccct aggacaaaag caaggggtgg agtttgggtc 55560
agatacgaag tcttgagcag gaccgagtca ggggaggggc ccagggaagg ggcggagcct 55620
aggagatagt gagggcgggg cctagggatc tggtcctgga cctagcttcg cacagagggc 55680
gggggctagg gcgagggggc ggggccttgg acccaaacag ccagctgaat gtagggcgga 55740
ggtggagcaa aggacagaaa caaggggtgg attttggttg gaaagagacc cagaggccag 55800
agagcctagc aaagagctgg atgggagaca gggaccaggc ctaaggcgcg gagtggggta 55860
ctaaaacccc cgcggggctt agaaccggat tgaggtcctg attagagtta ccacttatct 55920
aaagatgcca ctcaccggtg ccctcatcca gcgtccgcat tagaggcttc agctcctgct 55980
cgaaggccag cgcagcctcc gtgtggctcc tccggagctg gcgccacgtg cgttccaacc 56040
gcgacacctg gaagaagaga cccgagcccg ccttctctcc actcttcccc ttcacttgct 56100
ctctggcctc gtcccgcatc cctgcttcct acgcacctgg ggcatgagca aggcgcccat 56160
gaccgcagcc agtccaggca ggtcccccgc cgcccctggc cgcagcgcca gagccagctc 56220
caccaggccc ttcagggcgg cggcgcgctc ctccagcggt cccgcgcagc ccagcactgc 56280
cagcgccccc gccaacgcca gcgtctcgag cctgcagagg cggagggcaa ggttttggag 56340
gcagtggcgg ggtttgcgat gtgggggtga ggagggagag caggtgacac agctcatctc 56400
ccctcctccc tggggggccg tgaatggggg ggaggttgag gaccctaggg attttaggtg 56460
gctgccttac ctctccagca gttccaacct caggcgatgt ccatggggaa gagtgagcag 56520
ctccagacca gaggcaaccc ccatggcgcc ccgctgagcc ttggtcaccc ccaggaggcc 56580
tgtctcctgg cagtggggga ggggtaagag tagggagttc agaggagcag aatgagtaaa 56640
tgggtatgag gtgagactgg gccatgccct ggcttcagcc ctacctggta ggggacccac 56700
ctggcagtcc accaatagca ggtggagggc agtgctccca ggatggtgct ccaggaacag 56760
gccacggaga atgcgcaggg ctttaggttc cagaggccga ttctgggggc ccagcaggca 56820
ggaggggttg tcagggggac agaaagagac ctcaccctgt ggtcttgcaa aacatctttg 56880
ctcctcctcc tcttcctctt cattggcctc ccaccatggt gcctctggct ctgggcagct 56940
gtggccaggg ggtgttccat ggaccctagg cactcggggc accagctcac agtacgttgg 57000
ggagcgtcca gaggcatcag gcagcatcag tgaaggtgtt cgaggtggct tggttggtgc 57060
cttggcatga agctgcccat cggaggccct caggttgtca gcaatggacc ccaggagagc 57120
tggggtcttt agcaacacag ggtcacttcc tgtccgaggc aatgcagatg cgggcacagt 57180
ggaggctcct gggggtcaca caagagaggg taaaagaggt ccacagagaa aatagctggt 57240
tggggctttg tggggtacca acctccaggt tcattcactc gttcagccaa taaccaggta 57300
ccccacctaa cctggcgcag ctttggactt gaacgacttc accaaaactc ctctagccca 57360
tatggagttt tgcaaattct gaatgctaaa ttttaaattt gaattctttg ttcttgcccc 57420
tcggttcctg cattgctata gctgtggcat aagccagcag ctacagctct gattcagccc 57480
ctagcctcgg aacctccata tgccgtgggt gtggccctaa aaagcaaaaa taaataaata 57540
aatactcccg tctccatact ccttactctg ttctacttta gtttttgccc caaagcatac 57600
ataattgact aatttttgtt gttcatggtc cttcttcctc taaaaggatg ttggctccac 57660
cagcgcaggg atctgtgtca ttcttgttca ttgatgttat cacagcactt catacagtct 57720
caggcatgtc acgagacttt gggtggaggg cagggctgac aaggcagtca ggacacaaag 57780
gggactcttc ctttatgtag gattatcagg gtcggctgct ctgatgaact catgttagat 57840
gagaaggagt cagtcaggta aaggtaggga atgagctttt tccagtggtg agaatagcaa 57900
gtgcaaaggc cctgaggccg gaacatattc ggcaggttcc agcaactgta aaaaagactg 57960
tgtgattgac gtgaagaggg gatgtagcag gagttattag gtcagccatg gttagagcat 58020
atagggctcc ttggaataat aacaaaccca cattttattt tcttcttctt atttttggcc 58080
acacccacag catgcagaag ttctggggcc agggatggaa cctgtgccac agcagagacc 58140
tgagccgcag cagtgacaat gccagatcct taacttgagc caatagggaa ctctggaact 58200
ccataaacac atattttttt ttaaattttt ttacaaagtt cctgtgtgtt tttaaattac 58260
tgtgacaaca tgaagagtat taccatccct tttttccaaa aggttaagtc ccctgcccaa 58320
ggttccttag gtatagcctg gcagagccgt ccctgagctc tgtgctgcct gggaagcccc 58380
ttacctggtc cagggtggtc ttctgttggg tgccccacat gctcc 58425

<210> SEQ ID NO 29
<211> LENGTH: 5127
<212> TYPE: DNA
<213> ORGANISM: Sus scrofa

<400> SEQUENCE: 29
ctcacttccc cccccacccc cgtcctttcc ctctgtccct ttgtccctcc accgtccctc 60
catcatgggg tccacctcgg gtcccaggct gctgctgctg ctcctgacca gcctccccct 120
agccctgggg gatcccattt acaccataat cacccccaac gtcctgcgtc tggagagtga 180
ggagatggtg gtgttggagg cccacgaagg gcaaggggat attcgggttt cggtcaccgt 240
ccatgacttc ccggccaaga gacaggtgct gtccagcgag accacgacgc tgaacaacgc 300
caacaactac ctgagcaccg tcaacatcaa gatcccggcc agcaaggagt tcaaatcaga 360
gaaggggcac aagttcgtga ccgttcaggc gctctttggg aacgtccagg tggagaaggt 420
ggtgctggtc agccttcaga gcgggtacct cttcatccag acggacaaga ctatctacac 480
cccaggctcc acggtcctct atcggatctt caccgttgac cacaagctgc tgcccgtggg 540
ccagaccatt gtcgtcacca ttgagacacc tgaaggcatt gacatcaaac gggactccct 600
gtcatcccac aaccagtttg gcatcttggc tttgtcttgg aacatcccag agctggtcaa 660
catggggcag tggaagatcc gagcccacta tgaggatgct ccccagcaag tcttctctgc 720
tgagtttgag gtgaaggaat atgtgctgcc cagttttgag gtccaagtgg agccttcaga 780
gaaattctac tacatcgatg acccaaatgg cctaactgtc aacatcattg ccaggttctt 840
gtacggggag agtgtggatg gaacagcttt cgtcatcttt ggggtccagg acggtgacca 900
gaggatttca ttgtctcagt ccctcacccg tgttccgatc attgatggga cgggggaagc 960
cacgctgagc caaggggtct tgctgaatgg agtacattat tccagtgtca atgacttggt 1020
gggaaaatcc atatatgtat ctgtcactgt cattctgaac tcaggcagcg acatggtgga 1080
ggcagagcgc accgggatcc ccatcgtgac ctccccctat cagatccact tcaccaagac 1140
ccccaagttc ttcaaacccg ccatgccctt cgacctcatg gtgtatgtga cgaaccccga 1200
cggctcccct gcccgccaca tcccggtggt gactgaggac ttcaaagtga ggtccttaac 1260
ccaggaggac ggtgttgcca aactgagcat caacacaccc gacaaccgga attccctgcc 1320
catcaccgta cgcactgaga aggacggtat cccagctgca cggcaagcgt ccaagaccat 1380
gcacgtccta ccctacaaca cccagggtaa ctccaagaac tacctccacc tctcgttgcc 1440
ccgcgtggag ctcaagccag gggagaatct caatgttaac ttccacctgc gcacggaccc 1500
cggctaccaa gacaagatcc gatactttac ctacctgatc atgaacaagg gcaagctgtt 1560
gaaggtggga cgccagccgc gcgagtctgg ccaggtcgtg gtggtgctgc ccttgaccat 1620
cacgacggac ttcatccctt ccttccgcct ggtggcttat tacaccctga ttgctgccaa 1680
tggccagagg gaggtggtgg ccgattccgt atgggtggat gtcaaggact catgtgtggg 1740
cacgctggtg gtaaaaggtg gcgggaagca agacaagcag catcggcctg ggcaacagat 1800
gaccctggag atccagggtg agcgaggggc ccgagtgggg ctggtggccg tggacaaggg 1860
cgtgtttgtg ctgaataaga aaaacaaatt gacccagcgt aggatctggg atgtcgtgga 1920

```
gaaggcagac attggttgca caccaggcag tggaaaggac tttgccggcg tcttcacaga   1980
tgcagggctg gccttcaaga gcagcaaggg cctacagact ccccagaggg cagatcttga   2040
gtgtccgaaa ccagccgccc gcaaacgccg ttccgtgcag ctcatggaga aaaggatgga   2100
caaactgggt cagtacagca aggacgtgcg cagatgctgt gagcatggca tgcgggacaa   2160
ccccatgaag ttctcgtgcc agcgccgggc tcagttcatc cagcatggtg atgcctgcgt   2220
gaaggccttc ctggactgct gcgaatacat cgcaaagttg cggcagcagc acagccgaaa   2280
caagcccctg ggctggccca ggagtgacct ggatgaagaa ataatcccag aggaagacat   2340
catttccaga agccagttcc ccgagagctg gctgtggacc attgaggagt ttaaagaacc   2400
agacaaaaat ggaatctcca ccaagaccat gaatgtgttt ttaaaagact ccatcaccac   2460
ttgggagatt ctggctgtga gcttgtcgga caagaaaggg atctgcgtgg ctgaccccta   2520
tgaggttgtg gtgaagcaag atttcttcat cgatctgcgt ctcccctact ccgttgtgcg   2580
caatgagcag gtggagatcc gagctatcct ctataactac agggaggcag aggatctcaa   2640
ggtcagggtg gaactgctct acaatccagc tttctgcagc ctggccaccg ccaagaagcg   2700
ccaccaacag actctaacgg tcccagccaa gtcctcagtg cccgtgcctt acatcattgt   2760
gcccttgaag actggcctcc aggaggtgga ggtcaaggcc gccgtctaca accacttcat   2820
cagtgatggt gtcaagaaga ccctgaaggt cgtgccagaa ggaatgagag tcaacaaaac   2880
tgtggtcact cgcacactgg atccagaaca taagggccaa cagggagtgc aacgagagga   2940
aatcccacct gcggatctca gcgaccaagt cccagacacg gagtcagaga ccaagatcct   3000
cctgcaaggg accccggtgg cccagatggt agaggatgcc atcgacgggg accggctgaa   3060
gcacctcatc caaacccccct ccggctgtgg ggagcagaac atgatcggca tgacgcccac   3120
agtcatcgct gtgcactacc tggacagcac cgaacaatgg gagaagttcg gcctggagaa   3180
gaggcaggaa gccttggagc tcatcaagaa ggggtacacc cagcaactgg ccttcagaca   3240
aaagaactca gcctttgccg ccttccagga ccggctgtcc agcaccctgc tgacagccta   3300
tgtggtcaag gtcttcgcta tggcagccaa cctcatcgcc atcgactccc aggtcctctg   3360
tggggccgtc aaatggctga tcctggagaa gcagaagcct gatggagtct tcgaggagaa   3420
tgggcccgtg atacaccaag aaatgattgg tggcttcaag aacactgagg agaaagacgt   3480
gtccctgaca gcctttgttc tcatcgcgct gcaggaggct aaagacatct gtgaaccaca   3540
ggtcaatagc ctgttgcgca gcatcaataa ggcaagagac ttcctcgcag actactacct   3600
agaattaaaa agaccatata ctgtggccat tgctggttat gccctggctc tatctgacaa   3660
gctggatgag cccttcctca acaaacttct gagcacagcc aaagaaagga accgctggga   3720
ggaacctggc cagaagctcc acaatgtgga ggccacatcc tacgccctct tggctctgct   3780
ggtagtcaaa gactttgact ctgtccctcc tattgtgcgc tggctcaatg agcagagata   3840
ctacggaggt ggctatggat ctacccaggc cactttcatg gtgttccaag ccttggccca   3900
ataccagaag gatgtccctg atcacaagga tctgaacctg gatgtgtcca tccacctgcc   3960
cagccgcagc gctccagtca ggcatcgtat cctctgggaa tctgctagcc ttctgcggtc   4020
agaagagaca aaagaaaatg agggattcac attaatagct gaagggaaag ggcaaggcac   4080
cttgtcggtg gtgaccatgt accacggcaa ggccaaaggc aaaaccacct gcaagaagtt   4140
tgacctcaag gtttccatac atccagcccc tgaaccagtg aagaagcctc aggaagccaa   4200
gagctccatg gtccttgaca tctgtaccag gtaccttgga aaccaggatg ccactatgtc   4260
aatcctggat atatccatga tgactggctt ctctcctgat actgaagacc tcaaactgct   4320
```

```
gagcactggt gtggacagat acatctctaa gtatgagctg aacaaagccc tctccaacaa   4380

aaacaccctc atcatctacc tggacaagat ctcacacacc ctggaggact gtatatcctt   4440

caaagttcac cagtacttta atgtggggct tatacagcct gggtcagtca aggtgtactc   4500

ctattacaac ctggatgagt cttgcacccg gttctaccac cccgagaagg aggacgggat   4560

gctaaacaaa ctctgccaca aagaaatgtg tcgctgtgct gaggagaact gcttcatgca   4620

ccatgacgaa gaggaggtca ccctggacga ccggctggaa agggcctgcg agcccggcgt   4680

ggactatgtg tacaagacca gacttctcaa gaaggagctg tcagatgact ttgacgatta   4740

catcatggtc atcgagcaga tcatcaaatc aggctccgat gaagtgcagg ttggacagga   4800

gcgcaggttc atcagccaca tcaaatgcag agaagccctc aaactaaagg agggggggaca   4860

ctaccttgtg tggggagtct cctccgacct gtggggagag aaacccaaca tcagctacat   4920

cattgggaag gacacctggg tggagctgtg gcctgatggt gatgtatgcc aagatgagga   4980

gaaccagaaa cagtgccagg acctggccaa cttctctgag aacatggtcg tctttggttg   5040

ccccaactga tgccactccc ccacagtcta cccaataaag ctccagttat ctttcacatt   5100

taaaaaaaaa aaaaaaaaaa aaaaaaa                                       5127
```

```
<210> SEQ ID NO 30
<211> LENGTH: 1661
<212> TYPE: PRT
<213> ORGANISM: Sus scrofa

<400> SEQUENCE: 30

Met Gly Ser Thr Ser Gly Pro Arg Leu Leu Leu Leu Leu Leu Thr Ser
1               5                   10                  15

Leu Pro Leu Ala Leu Gly Asp Pro Ile Tyr Thr Ile Ile Thr Pro Asn
            20                  25                  30

Val Leu Arg Leu Glu Ser Glu Glu Met Val Val Leu Glu Ala His Glu
        35                  40                  45

Gly Gln Gly Asp Ile Arg Val Ser Val Thr Val His Asp Phe Pro Ala
    50                  55                  60

Lys Arg Gln Val Leu Ser Ser Glu Thr Thr Thr Leu Asn Asn Ala Asn
65                  70                  75                  80

Asn Tyr Leu Ser Thr Val Asn Ile Lys Ile Pro Ala Ser Lys Glu Phe
                85                  90                  95

Lys Ser Glu Lys Gly His Lys Phe Val Thr Val Gln Ala Leu Phe Gly
            100                 105                 110

Asn Val Gln Val Glu Lys Val Val Leu Val Ser Leu Gln Ser Gly Tyr
        115                 120                 125

Leu Phe Ile Gln Thr Asp Lys Thr Ile Tyr Thr Pro Gly Ser Thr Val
    130                 135                 140

Leu Tyr Arg Ile Phe Thr Val Asp His Lys Leu Leu Pro Val Gly Gln
145                 150                 155                 160

Thr Ile Val Val Thr Ile Glu Thr Pro Glu Gly Ile Asp Ile Lys Arg
                165                 170                 175

Asp Ser Leu Ser Ser His Asn Gln Phe Gly Ile Leu Ala Leu Ser Trp
            180                 185                 190

Asn Ile Pro Glu Leu Val Asn Met Gly Gln Trp Lys Ile Arg Ala His
        195                 200                 205

Tyr Glu Asp Ala Pro Gln Gln Val Phe Ser Ala Glu Phe Glu Val Lys
    210                 215                 220
```

-continued

```
Glu Tyr Val Leu Pro Ser Phe Glu Val Gln Val Glu Pro Ser Glu Lys
225                 230                 235                 240

Phe Tyr Tyr Ile Asp Asp Pro Asn Gly Leu Thr Val Asn Ile Ile Ala
                245                 250                 255

Arg Phe Leu Tyr Gly Glu Ser Val Asp Gly Thr Ala Phe Val Ile Phe
            260                 265                 270

Gly Val Gln Asp Gly Asp Gln Arg Ile Ser Leu Ser Gln Ser Leu Thr
        275                 280                 285

Arg Val Pro Ile Ile Asp Gly Thr Gly Glu Ala Thr Leu Ser Gln Gly
    290                 295                 300

Val Leu Leu Asn Gly Val His Tyr Ser Ser Val Asn Asp Leu Val Gly
305                 310                 315                 320

Lys Ser Ile Tyr Val Ser Val Thr Val Ile Leu Asn Ser Gly Ser Asp
                325                 330                 335

Met Val Glu Ala Glu Arg Thr Gly Ile Pro Ile Val Thr Ser Pro Tyr
            340                 345                 350

Gln Ile His Phe Thr Lys Thr Pro Lys Phe Phe Lys Pro Ala Met Pro
        355                 360                 365

Phe Asp Leu Met Val Tyr Val Thr Asn Pro Asp Gly Ser Pro Ala Arg
    370                 375                 380

His Ile Pro Val Val Thr Glu Asp Phe Lys Val Arg Ser Leu Thr Gln
385                 390                 395                 400

Glu Asp Gly Val Ala Lys Leu Ser Ile Asn Thr Pro Asp Asn Arg Asn
                405                 410                 415

Ser Leu Pro Ile Thr Val Arg Thr Glu Lys Asp Gly Ile Pro Ala Ala
            420                 425                 430

Arg Gln Ala Ser Lys Thr Met His Val Leu Pro Tyr Asn Thr Gln Gly
        435                 440                 445

Asn Ser Lys Asn Tyr Leu His Leu Ser Leu Pro Arg Val Glu Leu Lys
    450                 455                 460

Pro Gly Glu Asn Leu Asn Val Asn Phe His Leu Arg Thr Asp Pro Gly
465                 470                 475                 480

Tyr Gln Asp Lys Ile Arg Tyr Phe Thr Tyr Leu Ile Met Asn Lys Gly
                485                 490                 495

Lys Leu Leu Lys Val Gly Arg Gln Pro Arg Glu Ser Gly Gln Val Val
            500                 505                 510

Val Val Leu Pro Leu Thr Ile Thr Thr Asp Phe Ile Pro Ser Phe Arg
        515                 520                 525

Leu Val Ala Tyr Tyr Thr Leu Ile Ala Ala Asn Gly Gln Arg Glu Val
    530                 535                 540

Val Ala Asp Ser Val Trp Val Asp Val Lys Asp Ser Cys Val Gly Thr
545                 550                 555                 560

Leu Val Val Lys Gly Gly Gly Lys Gln Asp Lys Gln His Arg Pro Gly
                565                 570                 575

Gln Gln Met Thr Leu Glu Ile Gln Gly Glu Arg Gly Ala Arg Val Gly
            580                 585                 590

Leu Val Ala Val Asp Lys Gly Val Phe Val Leu Asn Lys Lys Asn Lys
        595                 600                 605

Leu Thr Gln Arg Arg Ile Trp Asp Val Val Glu Lys Ala Asp Ile Gly
    610                 615                 620

Cys Thr Pro Gly Ser Gly Lys Asp Phe Ala Gly Val Phe Thr Asp Ala
625                 630                 635                 640

Gly Leu Ala Phe Lys Ser Ser Lys Gly Leu Gln Thr Pro Gln Arg Ala
```

```
                645                 650                 655

Asp Leu Glu Cys Pro Lys Pro Ala Ala Arg Lys Arg Arg Ser Val Gln
            660                 665                 670

Leu Met Glu Lys Arg Met Asp Lys Leu Gly Gln Tyr Ser Lys Asp Val
        675                 680                 685

Arg Arg Cys Cys Glu His Gly Met Arg Asp Asn Pro Met Lys Phe Ser
    690                 695                 700

Cys Gln Arg Arg Ala Gln Phe Ile Gln His Gly Asp Ala Cys Val Lys
705                 710                 715                 720

Ala Phe Leu Asp Cys Cys Glu Tyr Ile Ala Lys Leu Arg Gln Gln His
                725                 730                 735

Ser Arg Asn Lys Pro Leu Gly Leu Ala Arg Ser Asp Leu Asp Glu Glu
            740                 745                 750

Ile Ile Pro Glu Glu Asp Ile Ile Ser Arg Ser Gln Phe Pro Glu Ser
        755                 760                 765

Trp Leu Trp Thr Ile Glu Glu Phe Lys Glu Pro Asp Lys Asn Gly Ile
    770                 775                 780

Ser Thr Lys Thr Met Asn Val Phe Leu Lys Asp Ser Ile Thr Thr Trp
785                 790                 795                 800

Glu Ile Leu Ala Val Ser Leu Ser Asp Lys Lys Gly Ile Cys Val Ala
                805                 810                 815

Asp Pro Tyr Glu Val Val Val Lys Gln Asp Phe Phe Ile Asp Leu Arg
            820                 825                 830

Leu Pro Tyr Ser Val Val Arg Asn Glu Gln Val Glu Ile Arg Ala Ile
        835                 840                 845

Leu Tyr Asn Tyr Arg Glu Ala Glu Asp Leu Lys Val Arg Val Glu Leu
    850                 855                 860

Leu Tyr Asn Pro Ala Phe Cys Ser Leu Ala Thr Ala Lys Lys Arg His
865                 870                 875                 880

Gln Gln Thr Leu Thr Val Pro Ala Lys Ser Ser Val Pro Val Pro Tyr
                885                 890                 895

Ile Ile Val Pro Leu Lys Thr Gly Leu Gln Glu Val Glu Val Lys Ala
            900                 905                 910

Ala Val Tyr Asn His Phe Ile Ser Asp Gly Val Lys Lys Thr Leu Lys
        915                 920                 925

Val Val Pro Glu Gly Met Arg Val Asn Lys Thr Val Val Thr Arg Thr
    930                 935                 940

Leu Asp Pro Glu His Lys Gly Gln Gln Gly Val Gln Arg Glu Glu Ile
945                 950                 955                 960

Pro Pro Ala Asp Leu Ser Asp Gln Val Pro Asp Thr Glu Ser Glu Thr
                965                 970                 975

Lys Ile Leu Leu Gln Gly Thr Pro Val Ala Gln Met Val Glu Asp Ala
            980                 985                 990

Ile Asp Gly Asp Arg Leu Lys His  Leu Ile Gln Thr Pro  Ser Gly Cys
        995                 1000                1005

Gly Glu  Gln Asn Met Ile Gly  Met Thr Pro Thr Val  Ile Ala Val
    1010                1015                1020

His Tyr  Leu Asp Ser Thr Glu  Gln Trp Glu Lys Phe  Gly Leu Glu
    1025                1030                1035

Lys Arg  Gln Glu Ala Leu Glu  Leu Ile Lys Lys Gly  Tyr Thr Gln
    1040                1045                1050

Gln Leu  Ala Phe Arg Gln Lys  Asn Ser Ala Phe Ala  Ala Phe Gln
    1055                1060                1065
```

```
Asp Arg Leu Ser Ser Thr Leu Leu Thr Ala Tyr Val Val Lys Val
    1070                1075                1080

Phe Ala Met Ala Ala Asn Leu Ile Ala Ile Asp Ser Gln Val Leu
    1085                1090                1095

Cys Gly Ala Val Lys Trp Leu Ile Leu Glu Lys Gln Lys Pro Asp
    1100                1105                1110

Gly Val Phe Glu Glu Asn Gly Pro Val Ile His Gln Glu Met Ile
    1115                1120                1125

Gly Gly Phe Lys Asn Thr Glu Glu Lys Asp Val Ser Leu Thr Ala
    1130                1135                1140

Phe Val Leu Ile Ala Leu Gln Glu Ala Lys Asp Ile Cys Glu Pro
    1145                1150                1155

Gln Val Asn Ser Leu Leu Arg Ser Ile Asn Lys Ala Arg Asp Phe
    1160                1165                1170

Leu Ala Asp Tyr Tyr Leu Glu Leu Lys Arg Pro Tyr Thr Val Ala
    1175                1180                1185

Ile Ala Gly Tyr Ala Leu Ala Leu Ser Asp Lys Leu Asp Glu Pro
    1190                1195                1200

Phe Leu Asn Lys Leu Leu Ser Thr Ala Lys Glu Arg Asn Arg Trp
    1205                1210                1215

Glu Glu Pro Gly Gln Lys Leu His Asn Val Glu Ala Thr Ser Tyr
    1220                1225                1230

Ala Leu Leu Ala Leu Leu Val Val Lys Asp Phe Asp Ser Val Pro
    1235                1240                1245

Pro Ile Val Arg Trp Leu Asn Glu Gln Arg Tyr Tyr Gly Gly Gly
    1250                1255                1260

Tyr Gly Ser Thr Gln Ala Thr Phe Met Val Phe Gln Ala Leu Ala
    1265                1270                1275

Gln Tyr Gln Lys Asp Val Pro Asp His Lys Asp Leu Asn Leu Asp
    1280                1285                1290

Val Ser Ile His Leu Pro Ser Arg Ser Ala Pro Val Arg His Arg
    1295                1300                1305

Ile Leu Trp Glu Ser Ala Ser Leu Leu Arg Ser Glu Glu Thr Lys
    1310                1315                1320

Glu Asn Glu Gly Phe Thr Leu Ile Ala Glu Gly Lys Gly Gln Gly
    1325                1330                1335

Thr Leu Ser Val Val Thr Met Tyr His Gly Lys Ala Lys Gly Lys
    1340                1345                1350

Thr Thr Cys Lys Lys Phe Asp Leu Lys Val Ser Ile His Pro Ala
    1355                1360                1365

Pro Glu Pro Val Lys Lys Pro Gln Glu Ala Lys Ser Ser Met Val
    1370                1375                1380

Leu Asp Ile Cys Thr Arg Tyr Leu Gly Asn Gln Asp Ala Thr Met
    1385                1390                1395

Ser Ile Leu Asp Ile Ser Met Met Thr Gly Phe Ser Pro Asp Thr
    1400                1405                1410

Glu Asp Leu Lys Leu Leu Ser Thr Gly Val Asp Arg Tyr Ile Ser
    1415                1420                1425

Lys Tyr Glu Leu Asn Lys Ala Leu Ser Asn Lys Asn Thr Leu Ile
    1430                1435                1440

Ile Tyr Leu Asp Lys Ile Ser His Thr Leu Glu Asp Cys Ile Ser
    1445                1450                1455
```

```
Phe Lys  Val His Gln Tyr Phe  Asn Val Gly Leu Ile  Gln Pro Gly
    1460                 1465                 1470

Ser Val  Lys Val Tyr Ser Tyr  Tyr Asn Leu Asp Glu  Ser Cys Thr
    1475                 1480                 1485

Arg Phe  Tyr His Pro Glu Lys  Glu Asp Gly Met Leu  Asn Lys Leu
    1490                 1495                 1500

Cys His  Lys Glu Met Cys Arg  Cys Ala Glu Glu Asn  Cys Phe Met
    1505                 1510                 1515

His His  Asp Glu Glu Glu Val  Thr Leu Asp Asp Arg  Leu Glu Arg
    1520                 1525                 1530

Ala Cys  Glu Pro Gly Val Asp  Tyr Val Tyr Lys Thr  Arg Leu Leu
    1535                 1540                 1545

Lys Lys  Glu Leu Ser Asp Asp  Phe Asp Asp Tyr Ile  Met Val Ile
    1550                 1555                 1560

Glu Gln  Ile Ile Lys Ser Gly  Ser Asp Glu Val Gln  Val Gly Gln
    1565                 1570                 1575

Glu Arg  Arg Phe Ile Ser His  Ile Lys Cys Arg Glu  Ala Leu Lys
    1580                 1585                 1590

Leu Lys  Glu Gly Gly His Tyr  Leu Val Trp Gly Val  Ser Ser Asp
    1595                 1600                 1605

Leu Trp  Gly Glu Lys Pro Asn  Ile Ser Tyr Ile Ile  Gly Lys Asp
    1610                 1615                 1620

Thr Trp  Val Glu Leu Trp Pro  Asp Gly Asp Val Cys  Gln Asp Glu
    1625                 1630                 1635

Glu Asn  Gln Lys Gln Cys Gln  Asp Leu Ala Asn Phe  Ser Glu Asn
    1640                 1645                 1650

Met Val  Val Phe Gly Cys Pro  Asn
    1655                 1660
```

<210> SEQ ID NO 31
<211> LENGTH: 15532
<212> TYPE: DNA
<213> ORGANISM: Homo sapiens

<400> SEQUENCE: 31

```
gtatcatttc agtgaaggtc actccagtct ttcatggagg ccaaactaag ggtgtaaatt      60

aggatcctca ctgaagtggc gggaccctaa gaggcttttt cctggcccct tagttgtggg     120

ttttcctgcg ggcggcgcag ccggtttcca tcagaaccgc ccagaggcgg acgctgcctt     180

cctggggtga cggagcagca ggaagcgttt tcggatcctg gaatacgtgg gcggcccgtg     240

ggaggggctg aggcgcagtt tcctactcac ccggatccga atcctccgcg gtgctgtttc     300

aagagagccg gattccagat cacgctccag cccggactcg gaattcctgc cctgcgggtc     360

tgcattttca taacgggcag gtgtgagtgc cctgcagctg gagaccagaa gcctgaaggc     420

agctcggccc tccccagccc acagcgccgt tattccgttt ctatatcagt aaacacattt     480

cattttccgt agaccagggc ggggtgacgg gtgatcccag tcctcgcagt gaattccggg     540

cagcaaaatt caaaacacat gcggccaagg ccgggcacgg tggttcacgc ctgtaatccc     600

agcactttgg gaggtcgagg cgggcgatca cctgaggtcg ggagctcgag accaacctga     660

ccaacatggg gaaatcccgt ctctactaaa aatataaaat tagacgggct tggtggtgaa     720

tgcctgtaat cccagctagt cgggaggctg aggcaggaga atcgcttaaa ccttggaggc     780

ggaggttgcg gtgagccgag atcgcgccat tgcacttcag cctgggcaac aagagggaaa     840

actccgtcgc aaaaactttc gggggcggag cggagccccg ccctgggtta tgtaagcgac     900
```

cgcgctgggc cgtttctctt tcttttccgg accctgcagt ggcgcctaaa gtctgagaga 960
gggaagtcgc ctctgtgctc gtgagtgcat ggggtataag gcaagtgctg agggagaaaa 1020
cgtagttgat ggggtagagc agacggggtt ggaggtgggg tggaggggga gggctttgga 1080
cagaagacct gggaggcttg gtgggggagg ggcgcccagg cctgggcact aagaaacaag 1140
tcccctggag ctcaagacca tctcggcctc ccctagccca agagaggact ggcttcatga 1200
ctccctgaaa ccatttctaa atgccttaga acaaaccttg catattcatt attgttattg 1260
aactattaaa agtctttttt gggggcgagc tgaatcagat cctttgctgg agctggcaca 1320
cggaggaagt cctggaggga gggtagacac cgtggaggta agggcttggg acctgtgtca 1380
ggagagctag gtccatctcc ctcccagtct ctcactaggc ttatgatctt tagcagtgaa 1440
aataatctct ctaaggtggg gaaaggaccc cggtccctgc tgtgctcaat aaattatgag 1500
gatcaaaata aattatcagt gaatgtgaat gggaaaacta agaaattgtt aaaattctcg 1560
aatacattac attttcatcc acagaaaagt gtaggctagg gatcatgggg gaatagttag 1620
taatgacagg gatagttgaa cttaaaaaaa aagtttgtga ggctgacaaa gaagaaacgg 1680
acacatttcc tgatcttgga gggttcatag ggtagaagat ggtagatgac agctgggtgt 1740
ggtggcactc gcctgtagtc ccagctactc aagaggctgt ggtgggagga ttgcttgagc 1800
ccaggcattc aaggctgcag tgagctataa tcatgccact gcattccaac tgagtgacac 1860
agcaagactc ctctcttaaa aaaaaaaaaa aaattcatgg cagggcacaa tgagtactat 1920
caggaaggtt caaaccacgg gctaaatcag tagttctaaa acttgactac acatcggaat 1980
cacctaggga actttaaaag atactaagat ttaggtccaa cctgggttta ctgatttaac 2040
aacctaggtt gtggctgtgg cctgggaaca tggatattaa aaactctcca ggtggttcta 2100
cgcagtggct aggtttgatg acctctgcct agatgtccca acgactaaga gatgtgcgtt 2160
ggggacaagg caattctctt agtagaaaga ggctttcggg acagcattct tattattgag 2220
aattgagaat tcatatgcca cacaatttat ccttttaaag tgtgcagctc agtggcttct 2280
agcgtaatca caaggttgtg ccaccgtcac cactgtctac cctggaagat ttttttttcct 2340 ttttttcttt tttcttttct ttttatttta aaggctagtc aagtgaaaca gtgggagtga 2400
agaagaaaca aagacatcta taactggttg tgatcaatta gttgtaaaca ctgcactcag 2460
accagcctgg gaagatttta aggatatggt gtggtctgat gggttccaag gcagaggtta 2520
caatagcctg gaagagggag actgcttagg cagtggcatc ctggtgggat agggtgagga 2580
gatcccagag cccacgttta ctgcaaccct ggggagatgt caccagagaa atgggggtgg 2640
tgccagacag cagattgtgg cagctgaggt tttccacggt agagtagaag catccatcat 2700
gtgtgacatt cagcagatgg ggcgctgtgg gtggcttgga gcactctggt tgtaactgag 2760
gcaggcaccg tgtttaggaa ggctgtgcag taatctaggc tgaagggagg ggaaagccta 2820
gactaagatt gtggctgtgg gattgaaata gcgttgaagg agctgacttt gactcccgga 2880
gatgatgggg aaagaggaaa tcagaaggga ccaaggatgg tgatgttctt aagagaaact 2940
gaggaggaag agaggatgat atggtggcag acgtatagag agtctttgta gatctctcac 3000
attggagggg actatggtcg gaggtacaga tgtcctaagg caggctggaa aagggagtct 3060
ggagagagct tggtgttgta gtgaaccaca gggagccgcc tccttggccc tgtgatcacc 3120
cagggactga atagagaggc ggccctggga gacttcagac acttagagga tataaggggg 3180
tgaaaggggg gcctggcttt gagtcaaagg gaggagaagg agattataaa gctgaaacgt 3240

-continued

```
ctaagagagt ttgtggtctg agcggttcta ctgcggcagg tgcttctgag aggcagaggt   3300
ggctgagatc tggaaacagg tctgcaaatc tggtcactgg tctcattgcc agtaacgctg   3360
tgcgcggttg agggagtgtg ttgggagaat agccacgcgt tgtctgtcct ggaaggaaca   3420
agccagtgag agccggttta atggggcggc cggcgaaagg ggcttggtga ggcccgcgct   3480
cctcggggtg ggggcgcggg gatgggtggt cgcgatgccg ggagggcagg cagggccctg   3540
gccgtgctta tgaagttgga gctgtactct cagctactcg aagctggtcc ctgctttagg   3600
ctgcgctccc gcgtgctccc cattttctgg gccccaggtc ccgccttcta aatctcccca   3660
ggtctccagc ccactggaat ttctcttcc aagcgtggcc ccgccctctc cgctcgtgat   3720
tggccctaag ttccgggccc cagtttcatt ggatgagcgg tcgggggacc gggccaggtg   3780
actaagtttc cgcggcgcct tctccccggc cactgcttga gccgctgaga gggtggcgac   3840
gtcggggcca tggggctggg cccggtcttt ctgcttctgg ctggcatctt cccttttgca   3900
cctccgggag ctgctgctgg tgagtggcgt tcctggcggt cctcggcgga gcgggagcag   3960
tgggacgttt ccgggggtcg ggtgggtagc ggcgagcgct gtgcggtcag ggcggggctc   4020
ctgtgccctg tcggtggcgc agggagctgg acgcggcccg ttaccgccac acttcagccc   4080
tgcttccccg tcacttttca gtcctcctcg ggatcgcgca tcacctgcac tttctggtct   4140
cctcctgctc tttctctcct cgcgtctcct ccgcttcctc tcacttttcg gacaaaccag   4200
tccttctgag gcccatgggt tcccgggctg cctccggggc tgctcctgtg aatggcattc   4260
gagtgccctt ccagcgcggc cactgaagca gccacaaccc ccggtgctcg gggcggctct   4320
caggtccctg aagtcctgtc ctctcccgga gccgacgtgt tctcagctcc tgggccgcag   4380
ctcctggagt aggggccctc ctttctcggg acccggagct ggtgcttcct gctgctgtgg   4440
ggactgtggg gggtcctgac tctcaagctg aggggttgga gtctgcaggc tccgggcaga   4500
ggattcttcc tgcgacttct ctcatcccca gctcattctc ccctcgcctc tggctccgag   4560
ggtcctctcc tctctctcat cccaccccta ctaatgacca gtgatctaag gacaccagat   4620
tccctctcac ctcctccctg cccatctcag ggcccgctga gtccttttgc cctcccagct   4680
ccctgctacc ccttcctgtg tgctgttctc tgatccattt ctagggtgtc ctctgccctc   4740
atcccctgtc cccgccaccg aaggtccctc ctgcacccct tatgggcctt tcctacaagc   4800
agccttcacc cagtgctgcc cctatgcctc cccgttccca aatgtccctg actctaactt   4860
tctggtgctg ccttttatcc ggggggggtct tccctccatc ccactcccct ccagaccccc   4920
aaggggaacc ctgatgctaa tggcagttgg gccttaggca gggcgcaggg cagcgcagat   4980
gccccctccc ctccagtgca gatgcctgct ctggaccctg cctcatggtg gccccttccc   5040
cactccttca tcctcagcct caccctcttg aggaccccac cctccagccc acaggtgctg   5100
gaccatccct ccctggtccc tccgccccctc tccaccttgg gaccttgtgc tgctcctgtc   5160
tcttgcccag ctgccttggg ccctcagcac gttctcatct ttcagtggga aagtgggagt   5220
gctggagcat atgacagtgc tgagcatctt tcccaagccc caccctcccc cagagcaccc   5280
tcccctcctg tcctcaccct accccaagtt ctcccacagt cactcctgcc ccatgctcat   5340
gccgccctcc agttcttgct ctgcccatct cccctcccca acccagacct aaaacaggct   5400
gttgggccaa ctgttccttg accttccttc ttttcttttg gttccttgac cccagtgggc   5460
tctcactccc cacaccgcat atctaaaatc tgttttgcct gctcttgggg tgccactgct   5520
ccccctccag cattactcct tttggcaggt ccttcctcag gctgagaatc tccccctcta   5580
ccttggtttt ctctctctgg ccagcacccc caccccttgc tttgttttta atttttaact   5640
```

```
tttgtttggg tacgtagtag atatatatgt atatatttat ggggtacatg ggatattttg   5700
acacaggcct acaatatgta ataatcacat cagggtaaat gggttatatc acaacaagca   5760
tttatccttt ctttgtgcta caaacaatcc cattatgctc tttcagttat ttttaaatgt   5820
acaataaatt attgttgact gtactcaccc tgctgtgcta tctactagat cttattcatt   5880
ctaattatat ttttgtaccc attattaacc atccctgctc ccccactccc cactaccctt   5940
ctcagcctct ggtaatcatc attctattgt ctctccccat gaggtccatt gttttaaatt   6000
ttggctgcca caaataagtg agaacatgca aagtttgtct gtctgggcct ggggcttatt   6060
tcacttcaca ggatgacctc cagttctttg caaatgacac gatggctgaa tagttctcca   6120
catacacatg tacaccacat tttctttatc catgcgtctg ttgatggaca cttagattgc   6180
ttgcagatct tggctacttt gaatagtgct gcaataaaca tggaaaagta gatagctctt   6240
taatataccg atttcctttc tttggagtat atgcctaaca gtgggagtgc tggagcatat   6300
gacagctcta ttgtattttt agtttttgga agaacctcca cattgtttcc catagtggtt   6360
gtactagttt acgttcccac caacagtgta catcctcacc agcattcctt atttctacat   6420
cctcgccagc attccttatt gcctgtcttc tggataaaag ccagtttatc tggggtggga   6480
tgttatctcg taggagtttt gatttgcctt catctgttga cgaatgatgt tgagcacctt   6540
ttcatatacc tgtttgccat ttatatgtct tcttttgaga aatgactatt cagatctttt   6600
ctcattttta aattggatta ttatattttt tttcctatag ttgttcgagc tccttatatg   6660
tttcagttac tgatcctttg tcagatgaat agtttgaaaa tattttctcc cattcttgga   6720
tggtctcttc attttgttta ttgtttcctt tgctgtgcag aagccttttt acttgatatg   6780
atcccattta tgcaatttta ctttggttac ctgtgcttgt ggggtattac tttaaaaatc   6840
tttgcccagt ccaatatcct agagagtttc cccaatgttt tcttgtatag tttcatagtt   6900
tgaggtcata gatttacatc tttaatccac tttgatttga tttttgtata tggtgaaaga   6960
cagggtctag tttcattctt ctgcataagg atatctagtt tccccagcac catttttgaa   7020
gagactctcc tttgccaatg tgtgttcttg gtacctttgt tggaaatgag tttactgtag   7080
atgtatggaa ttgtttctgg gttctctatt ctgtttcatt ggtctgtgtg tctgttttta   7140
tgccagtatc atgctgtttt ggttactgta gctctgtagt ataatttgaa gtcagataat   7200
gtgattcctc tagttttgtt cattttgctc aggatagctt tatctattct ggtttttttg   7260
tggttccata tgcattttag gattattttt attatttctg tgaagaatgt cattagtgtt   7320
ttgataggga ttgcattgaa tctgtagatt actttgggta gtatggatat ttcaacaaaa   7380
ctgattcttc caatccatga acgtggacta tcttttccat tttttgtgtc cttcaatttt   7440
ttgcatcagt gttttttgtt tttggttttt gagatggagt ttcactcttg ttgcccaggc   7500
tagaatgcaa gggtgtgatc ttggctcacc gcaacctccg cctcccaggt tcaagctatt   7560
cttctgcctc agcctcccaa gtagctggga ttacaggcat gtgccactgt gcctggctaa   7620
ttttctattt ttattagaga tggggtttct ctatgttggc caggctagtc ttgaactcct   7680
gacctcaggt gatccacctg cctcggcctc ccaaagtgct gggattacag gcatgagcca   7740
ccacgcccag ccacatcact gttttatagt ttttattgga gaggtctttc acttcttcag   7800
ttaggtttat tcctcagtat tttattttat ttgtagctat tgtaaatggg attcgtttct   7860
tgatttcttt ttcagattat ttgctgttag cactgatttt tgcatgttga ttttgtatcc   7920
tgcaacttta ctgaatttgt tcttcagttc taatggtttt ttggtggagt ctttaggttt   7980
```

ttccaaatat cagaccacat gatctgcaaa caaggataat ttgacttctt cttttccagt 8040
tttaatgccc tttctttctt tctcctgtct gattgctcta gttaggatct gcagtactgt 8100
gttgcataac tgtggtaaaa ttagtcatcc ttgtcttatt ccagatctta gagaaaaggc 8160
tttcagtttt cccccattca gtatgttact agctgtgagt ttgtcatata tggcttttat 8220
tatattgagg tctgttcctt gtatacttag tttttgaga gtttttatca tgaagggatg 8280
ttgaatttat caaatgcttt ttcagtatca attgaatgat actggctttt gtcctttatt 8340
ctgttgatat gacgtattac attgattgat ttgtgtatgt taaatcatcc ttgcatacct 8400
ggaatacatt ccacttgctc ataaagaatg atctttttta atgtattgtt gaatgtggtt 8460
tgctagtatt tccttgacga tttttgcatc ggtgttcatc agggatatag gcctgtagtt 8520
ttcttttta tgatgtgtct ttgcctggtt tttgtatcag gatattcctg gctttgtaaa 8580
atgagtttgg aagtattccc tcctcctcta tttttcagaa cagtttgaat aggactgaca 8640
tatgttgttc tttaaaagtt taattgtggt aaattataca ttacataaat tttactgttt 8700
taaccacttt taagtgtata ctcggtggca ttagatacat tcacattttt gtgcaaccca 8760
aaactctgtg cccattaatc ggtaactccc cattcctccc tacctctggc ccctggtaac 8820
caccattcta ctttttgttt ctatgaattt gaccactcta ggtacctcat ttaagcagaa 8880
tcatgtaatg tttgtctttt tgtttctggc ttatttcact tataatattt ttgaggttcg 8940
gtgggcacag tggctcacgc ctggatttcc agcactttgg gaggctgaag caggtggatc 9000
acctgagttt cggagttcga aaccagcctg gccaacatgg tgaaacccca tctctactaa 9060
aaataataaa agttagccgg gcgtgatggc gggtgcctgt aatcccaact acttgggagg 9120
ctgaggcagg agaatcgctt gaatccggga agtggaggtt gcagtgagct gagatcaggc 9180
cactgcactc cagcctgggc aacaagagtg aaattccatc tccaaaaaaa aaaataaaac 9240
aataataata ataatatttt tgaggttcat ccaagttgta gtatgggtca gaatttcatt 9300
ccttttaagg atggataata ctcattatat gtatgtacca catcttggtt atccatccct 9360
cagacaatgg acacttgggt tacttctacc ttttggatat tggcaaatat ttcatttcct 9420
ttgggtatat atttatttcc tttgggtatt tcttttgggt atatatccag aaatagaagc 9480
agtacacagg ggcttcattt tctctgtctc tttgccaacc ttgctctgtg tgtgtgtgta 9540
tgtgtgtgtg taggtgtgtg ataacagcca tcctgattgg tttcaggtgg catctcattg 9600
tggtttggat ttgcattttc ctaatgagtg ctgatattga gcatcttttc atgtgtttgt 9660
tgatcatttg taattttctt tgaagaattg gccatttaag tcttttgccc attttttccc 9720
ccacatagct tctcttatca gatatatgac ttgcaatatt tatttcattt cggggttgat 9780
tgctttttca ctctgattgt gccctttgat gcatagatgt tttgaatttt catcagtcta 9840
ctttgtcagt tctttctatt ctatctgtgc tttggtgtca tatccatgaa agcactgtca 9900
aatcctatgt catgaacatt atccccaatg tttgcttcta agaaattttt aggttttagt 9960
tcttgagtgt agagtttagg tctttgattc attttgagtt aatttttgta tatagtgcaa 10020
attaagggtc caattttatt ttaacacccc ctgcccccag aactatttgc tgaaaagatc 10080
aactgactct ttgtcacctg ctcaccccag tggacactag ctgttccatc caattgctgt 10140
cctggggcct tgtcatgcta ctcttccact ttgaacccaa gcccacaccg ttcgttgctc 10200
ccctctggga tactgacccc actataaact tctctggggc tacaaccttc ctaccctttg 10260
tgcctcatga ccaccccctc ccttgtcccc gccatgccca tgatgagtct cttctcgagg 10320
cagctcccct tgcctccatc tcaccctcag cctatgcacc acagccacac tggacatggg 10380

```
tccctctgag cctgagtccc ttcccattcc caccatcccc tctggcaaga ccttccttcc  10440
accaccttca tgctcctccc ttgcccctgc agggcagcct ctccccttgg cccctattcc  10500
cttagggggc ttgtggccac ccagtccttg cacctggcct acaagtttgc catcttcatt  10560
ccccccttctt ctgttcatca gccccctcct ctatcctccc accctcacag ttttctttgt  10620
atatgaaatc ctcgttcttg tccctttgcc cgtgtgcatt tcctgcccca ggaaggttgg  10680
gacagcagac ctgtgtgtta aacatcaatg tgaagttact tccaggaaga agtttcacct  10740
gtgatttcct cttccccaga gccccacagt cttcgttata acctcacggt gctgtcctgg  10800
gatggatctg tgcagtcagg gtttcttgct gaggtacatc tggatggtca gcccttcctg  10860
cgctatgaca ggcagaaatg cagggcaaag ccccagggac agtgggcaga agatgtcctg  10920
ggaaataaga catgggacag agagaccagg gacttgacag ggaacggaaa ggacctcagg  10980
atgaccctgg ctcatatcaa ggaccagaaa gaaggtgaga gtcggcaggg gcaagagtga  11040
ctggagaggc cttttccaga aaagttaggg gcagagagca gggacctgtc tcttcccact  11100
ggatctggct caggctgggg gtgaggaatg ggggtcagtg gaactcagca gggaggtgag  11160
ccggcactca gcccacacag ggaggcatgg aggagggcca gggaggcata ccccctgggc  11220
tgagttcctc acttgggtgg aaaggtgatg ggttcgggaa tggagaagtc actgctgggt  11280
gggggcaggc ttgcattccc tccaggagat tagggtctgt gagatccatg aagacaacag  11340
caccaggagc tcccagcatt tctactacga tggggagctc ttcctctccc aaaacctgga  11400
gactgaggaa tggacagtgc cccagtcctc cagagctcag accttggcca tgaacgtcag  11460
gaatttcttg aaggaagatg ccatgaagac caagacacac tatcacgcta tgcatgcaga  11520
ctgcctgcag gaactacggc gatatctaga atccggcgta gtcctgagga gaacaggtac  11580
cgacgctggc caggggctct cctctccctc caattctgct agagttgcct cacctcccag  11640
atgtgtccag ggaaaccctc cctgtgctat ggatgaaggc atttcctgtt ggcacatcgt  11700
gtcctgattt tcctctattg ttagagccac tggataaaga cagagggtca gggactggac  11760
catccagtgt tgtaatcagg gcaagtagag gaccctccga cagaatcctg agcctgtggt  11820
gggtgtcagg caggagagga agccttcagg gccagggctg ccccctctgc ctcccagcct  11880
gcccatcctg gagagttccc tcctggcccc acaacccagg agtccacccc tgacatcccc  11940
ctcctcagca tcaatgtggg gatcccagag cctgaggcca cagtcccaag gcccatcctc  12000
ctgccagcct ggaagaactg ggccccagag tgaggacaga cttgcaggtc aggggtcccg  12060
gagggcttca gccagagtga gaacagtgaa gagaaacagc cctgttcctc tcccctcctt  12120
agaggggagc agggcttcac tggctctgcc ctttcttctc cagtgccccc catggtgaat  12180
gtcacccgca gcgaggcctc agagggcaac atcaccgtga catgcagggc ttccagcttc  12240
tatccccgga atatcatact gacctggcgt caggatgggg tatctttgag ccacgacacc  12300
cagcagtggg gggatgtcct gcctgatggg aatggaacct accagacctg ggtggccacc  12360
aggatttgcc gaggagagga gcagaggttc acctgctaca tggaacacag cgggaatcac  12420
agcactcacc ctgtgccctc tggtgagcct agggtgaccc tggagagggt caggccaggg  12480
tagggacagc agggatggct gtggctctct gcccagtgta taacaagtcc ctttttttca  12540
gggaaagtgc tggtgcttca gagtcattgg cagacattcc atgtttctgc tgttgctgct  12600
ggctgctgct atttttgtta ttattatttt ctatgtccgt tgttgtaaga agaaaacatc  12660
agctgcagag ggtccaggtg agaaaagcgg gcagtttctg gagatggtaa ggcccctgtc  12720
```

tgggcagtag ggtcccctca ttgctcctgc aaagataggc atgttggtga caaggcttcc 12780
ataacagggg atgaaagttg gggaatttgg gaagggaatg ggggcagcat ctccatctac 12840
acccataagt gctgcccaag caagggtcaa acgcccagct gtggcatcct cctgctgcag 12900
gtgaggagtg ggcagcaggg agggctgcgg cgcctgctct gtccccatcc cggtctctgt 12960
gtctcttgaa ctcactaggg cgcatccagg tggggtgagc tgggaatcac gtgctgaatg 13020
ctaagggcct ggatgatcac ggcctcagag ggagcaaata gtaaaggcag ctgtgatctg 13080
gggagggcca gaaactggag aggaatctga ggagaggcgg tgcccctatt cccttcctct 13140
ctgcatcccc ctcccctgtt tctccagcca tcggggcgga caccgagaaa aagacctatg 13200
aggcccagcc tgggggccct gcctgtgtag ccctttggag accccttgta acagggaggg 13260
tcctgagcac acatggccat ctctgtccac tttgcagctc cccatgcacc tcctccagga 13320
gctttcttgg ggttgtcgtg tcctctgcac cattcgaggc cctactcttt ccaggttccc 13380
acggcctggc ctccctgagt ttcttgcaga tgacatggat gagtagataa gcagatgtcc 13440
ctgggccatt tgaggagtgg ggcccagccc ctcatcaggg cagctgtggt ccctgttttc 13500
atcctacctc cgagtgtttt cttctccagt ccctgaggga cacagtcctc agggcccatg 13560
tttttgggga tttaatctgt gctctgtggc ctcaccttgc cctccctgag ccaatttccc 13620
tttctaaagg tggtcactgc ctggtaagtt tggagtaagg gacggtcaga atcatttccc 13680
ctacagtcag gttgtttgat gggggatgaa aagagacagc aggaagtttt gtgtttctgc 13740
aaagacagaa gcagttcagg cgacagtaag aggctggggt gtccaggagg atgtgtctgg 13800
cagtagggtc gctggtttct catccttgaa cctaattgca ctgtcaatcg gcccctcagg 13860
cctgagcaga tgggaaggtt tgtcccctgc cctgcagcaa gagggccctg tccaggaggc 13920
acccacaaca ggggcagtgc aggtctgtgg tcactcctgc tctcacctgt ggcgtctccc 13980
gtagagggat tgtcagttct ggttccctgt gggcaggaat ggtttcctca taggtcactg 14040
gagttttggc caggaaaaga gtatgaagtt catgtgccag tttctcaaaa ttcctgcttt 14100
caatgttgat gtccagtaaa gatattcgta atttcagctc tataatctta ataggatttc 14160
ctctaatatt gtgaagcata ttatatgaaa caggaacaca aatttctcaa aattcctgcg 14220
atgtccaata aagattttca taatttcagc tctgcaatct taataggatt tcctaatact 14280
gtaaagcata ttaaatgaaa caggaactca aatttggagc cccctctcca ggaggttctg 14340
tgtggagatg gtggctgtgg cagtggcagt tcccaggtgc agagggtggg cagaggcagc 14400
ctcaggctaa ggggtctccc ctactccaca tggagaaaat cccttgtagg ttgcaagggc 14460
agtggccggg tggaatccct gctagggaca gagcaggaag gcctcgcagc ctcaccaagc 14520
agcagccctg gggtggagct gcgtttccag ggttaagcgg accaggcagg agtagcggtt 14580
actcaagagc aggtcacagg cttgggttgt gagggtcagg agaggccagg cctcctcgag 14640
caaggtgggg gtcccagggt caggtcaggt gcagatcctg tggcagccac gtctttccat 14700
gctgggcctg ctgggccccc caggcttcct gatggggtcc ccagttagga gctgcctgct 14760
cagggctggg aggggaggag cactgagctg cagatagagg gcagagccca cagtgggcag 14820
ggcctgccct ggtgtgtagg tgcctctgaa ggagaggagg gcctggggac tgagagcaag 14880
ggtcagggcc tctctttggg gaggcctctc actgtaacag gactggtcag gcctgagagg 14940
agggcactgg gttccctctt gggtcttgtc ctttagtctt ggggcccttt ccctccctgc 15000
acgatgagtg gtgggcacag ggcacgggct gatgttgatg gagtgatggg agggaactgg 15060
caggggctgg gaaaagcaag gagggaggaa gaaaaaagtg ggggcctcat cttccctcag 15120
agaaagggca aatctggttt tggagcaact gaagagagaa aagtccccag ggaataaaca 15180
caacactgca cccagtggag catttaccca tttccctctt ttctccagag ctcgtgagcc 15240
tgcaggtcct ggatcaacac ccagttggga cgagtgacca cagggatgcc acacagctcg 15300
gatttcagcc tctgatgtca gctcttgggt ccactggctc cactgagggc acctagactc 15360
tacagccagg cggctggaat tgaattccct gcctggatct cacaagcact ttccctcttg 15420
gtgcctcagt ttcctgacct atgaaacaga gaaaataaaa gcacttattt attgttgttg 15480
gaggctgcaa aatgttagta gatatgaggc atttgcagct gtgccatatt aa 15532

<210> SEQ ID NO 32
<211> LENGTH: 1410
<212> TYPE: DNA
<213> ORGANISM: Homo sapiens

<400> SEQUENCE: 32
aagtttccgc ggcgccttct ccccggccac tgcttgagcc gctgagaggg tggcgacgtc 60
ggggccatgg ggctgggccc ggtcttcctg cttctggctg gcatcttccc ttttgcacct 120
ccgggagctg ctgctgagcc ccacagtctt cgttataacc tcacggtgct gtcctgggat 180
ggatctgtgc agtcagggtt tctcactgag gtacatctgg atggtcagcc cttcctgcgc 240
tgtgacaggc agaaatgcag ggcaaagccc cagggacagt gggcagaaga tgtcctggga 300
aataagacat gggacagaga gaccagagac ttgacaggga acggaaagga cctcaggatg 360
accctggctc atatcaagga ccagaaagaa ggcttgcatt ccctccagga gattagggtc 420
tgtgagatcc atgaagacaa cagcaccagg agctcccagc atttctacta cgatggggag 480
ctcttcctct cccaaaacct ggagactaag gaatggacaa tgccccagtc ctccagagct 540
cagaccttgg ccatgaacgt caggaatttc ttgaaggaag atgccatgaa gaccaagaca 600
cactatcacg ctatgcatgc agactgcctg caggaactac ggcgatatct aaaatccggc 660
gtagtcctga ggagaacagt gccccccatg gtgaatgtca cccgcagcga ggcctcagag 720
ggcaacatta ccgtgacatg cagggcttct ggcttctatc cctggaatat cacactgagc 780
tggcgtcagg atggggtatc tttgagccac gacacccagc agtgggggga tgtcctgcct 840
gatgggaatg gaacctacca gacctgggtg gccaccagga tttgccaagg agaggagcag 900
aggttcacct gctacatgga acacagcggg aatcacagca ctcaccctgt gccctctggg 960
aaagtgctgg tgcttcagag tcattggcag acattccatg tttctgctgt tgctgctgct 1020
gctatttttg ttattattat tttctatgtc cgttgttgta agaagaaaac atcagctgca 1080
gagggtccag agctcgtgag cctgcaggtc ctggatcaac acccagttgg gacgagtgac 1140
cacagggatg ccacacagct cggatttcag cctctgatgt cagatcttgg gtccactggc 1200
tccactgagg gcgcctagac tctacagcca ggcagctggg attcaattcc ctgcctggat 1260
ctcacgagca ctttccctct tggtgcctca gtttcctgac ctatgaaaca gagaaaataa 1320
aagcacttat ttattgttgt tggaggctgc aaaatgttag tagatatgag gcgtttgcag 1380
ctgtaccata ttaaaaaaaa aaaaaaaaaa 1410

<210> SEQ ID NO 33
<211> LENGTH: 383
<212> TYPE: PRT
<213> ORGANISM: Homo sapiens

<400> SEQUENCE: 33

```
Met Gly Leu Gly Pro Val Phe Leu Leu Leu Ala Gly Ile Phe Pro Phe
1               5                   10                  15

Ala Pro Pro Gly Ala Ala Ala Glu Pro His Ser Leu Arg Tyr Asn Leu
            20                  25                  30

Thr Val Leu Ser Trp Asp Gly Ser Val Gln Ser Gly Phe Leu Thr Glu
        35                  40                  45

Val His Leu Asp Gly Gln Pro Phe Leu Arg Cys Asp Arg Gln Lys Cys
    50                  55                  60

Arg Ala Lys Pro Gln Gly Gln Trp Ala Glu Asp Val Leu Gly Asn Lys
65                  70                  75                  80

Thr Trp Asp Arg Glu Thr Arg Asp Leu Thr Gly Asn Gly Lys Asp Leu
                85                  90                  95

Arg Met Thr Leu Ala His Ile Lys Asp Gln Lys Glu Gly Leu His Ser
            100                 105                 110

Leu Gln Glu Ile Arg Val Cys Glu Ile His Glu Asp Asn Ser Thr Arg
        115                 120                 125

Ser Ser Gln His Phe Tyr Tyr Asp Gly Glu Leu Phe Leu Ser Gln Asn
    130                 135                 140

Leu Glu Thr Lys Glu Trp Thr Met Pro Gln Ser Ser Arg Ala Gln Thr
145                 150                 155                 160

Leu Ala Met Asn Val Arg Asn Phe Leu Lys Glu Asp Ala Met Lys Thr
                165                 170                 175

Lys Thr His Tyr His Ala Met His Ala Asp Cys Leu Gln Glu Leu Arg
            180                 185                 190

Arg Tyr Leu Lys Ser Gly Val Val Leu Arg Arg Thr Val Pro Pro Met
        195                 200                 205

Val Asn Val Thr Arg Ser Glu Ala Ser Glu Gly Asn Ile Thr Val Thr
    210                 215                 220

Cys Arg Ala Ser Gly Phe Tyr Pro Trp Asn Ile Thr Leu Ser Trp Arg
225                 230                 235                 240

Gln Asp Gly Val Ser Leu Ser His Asp Thr Gln Gln Trp Gly Asp Val
                245                 250                 255

Leu Pro Asp Gly Asn Gly Thr Tyr Gln Thr Trp Val Ala Thr Arg Ile
            260                 265                 270

Cys Gln Gly Glu Glu Gln Arg Phe Thr Cys Tyr Met Glu His Ser Gly
        275                 280                 285

Asn His Ser Thr His Pro Val Pro Ser Gly Lys Val Leu Val Leu Gln
    290                 295                 300

Ser His Trp Gln Thr Phe His Val Ser Ala Val Ala Ala Ala Ala Ile
305                 310                 315                 320

Phe Val Ile Ile Ile Phe Tyr Val Arg Cys Cys Lys Lys Lys Thr Ser
                325                 330                 335

Ala Ala Glu Gly Pro Glu Leu Val Ser Leu Gln Val Leu Asp Gln His
            340                 345                 350

Pro Val Gly Thr Ser Asp His Arg Asp Ala Thr Gln Leu Gly Phe Gln
        355                 360                 365

Pro Leu Met Ser Asp Leu Gly Ser Thr Gly Ser Thr Glu Gly Ala
    370                 375                 380
```

<210> SEQ ID NO 34
<211> LENGTH: 16848
<212> TYPE: DNA
<213> ORGANISM: Homo sapiens

<400> SEQUENCE: 34
ctgtttccag cgagtcagat tccagatcgc gctccagcct ggactcggaa ttcctgcccc 60
gcgggtctgc attttcacag cggcaggtgt gagtgccgcg cagctggaga ccagaagcct 120
gaggcagctc ggccctcccc agcccaaagt gccgttattc cgtttctgta tcagtaaaca 180
cgtttcattt tccgtagacc agggaagggt gatgggtgat cccagtcctc gcagtgaatt 240
ccgggccaca aaattcaaaa cgcttgcggg caaagccgtg cgcggtggct caagcctgta 300
attccagcac tttgggaggc cgaggcgggc ggatcacctg aggtcgggat ttccagacca 360
gcctgaccaa catagagaaa ccccgcctct actaaaaata caaaattagc cgggggtggc 420
gcatgcctgt aatcccagct agtcgggagg ctgaggcagg agactcactt gaacccggga 480
ggcggaggtt gctgtgagcc gagatcgcgc cactgcactc cagcctgggc aacaagagcg 540
aaactccgtt tcaaaaaaaa acaaaaaaca aaaagctttc gggcgccgag ggcagccccg 600
ccctgaattt tgtgagcgac cgcgctgggc cgtttctctt tcttttccgg accctgcagt 660
ggcgcctaaa gtctgcgagg aggaagtcgc ctctgtgctc gtgagtccag ggatctaagg 720
caagtgctga gggagaaaac atagttgatg gggcagagca gagggggctg gaggtggggt 780
ggagggggag ggctttgaac agaagacctg ggaggcttgg tgggggaggg gacccaggcc 840
tcggcgctga gaagcaactc ccctggagct caagaccttc ttggcctccc ctagcccagg 900
ggaggactgg cttcatgtct ccctgaaacc gcttctaaat gccttagaac aaaccttaaa 960
tattcattat tattattgaa ctattaaaag tcttttttgg aggcgagctg aatgagaccc 1020
tttgctggag ctggcacacg gaggaagtcc tggagggagg gtagacaccg tggagggaag 1080
ggcttgggac ctgtgtcagg agagctgggt ccatctgcct ctctgtctca aactatgctt 1140
atgatcttta gcagtgaaaa taatctctct aaggtgggga caggacccca gtccctgctg 1200
tgcttaataa attatgagga tcaaaataaa ttatcagtga atgtgtatgg gaagactaag 1260
aaattgttaa aattctcgaa tacattacat tttcatccac agaaaagtgt aggctaggga 1320
tgatagggga atagttagta atgacaggga tagttgaact taaaaaaaaa ggttgtgagg 1380
ccaacaaaaa agaaatggac acagttcctg atcctggagg gttcatagtc taatggggga 1440
ggagggtaga agatggtagg tgatggctgg gtgtgtggca ctcgcctgta gtcccagcta 1500
ctcaagaggc tgtggtggga ggattgcttg agcccaggca tttgaggctg cagtgagcta 1560
taatcacacc actgcattcc aactgagtga cacagcaaga ctcctctctt aaaaaaataa 1620
aataaagtaa atgaaaaaaa taagattcaa gacagggcac agtcggtacc atcaggaagg 1680
ttcaaaccat gggctagatc agtagttcta aaacttgact acacatcgga atcacgtagg 1740
gaactttaaa agatactaag gtttaggtcc aacctaggtt tactgattta actggttgtg 1800
gctgtggcct gggaacatgg atattaaaaa ctctccaggt ggttctacgc agtggctagg 1860
tttgaagacc actgcctaga tgtcccaatg actaagaatg tgcgctgggg acaagccaat 1920
tctcttagta gaggctttcc agacagaatt cttattattg agaattgaga attcacatgc 1980
cacacataat ttatcgtttt aaagtgtaca gatcagtggc ttctagcata atcacaaggt 2040
tgtgccaccg tcaccactat ctacttggga agattttctt cctttttttc tttttttttt 2100
tttttttgga ggcggagcct tgctctgttg cccaggctgg agtgcagtgg cgcaatctca 2160
gctcactgca agctccgcct cccgggttga ccccattctc ctgcctcagc cttctgagca 2220
gctgggacta caggtacccg ccaccacgcc cagctaagtt ttttgtattt ttagtagaga 2280
cggggtttca ctgtgttagc aggatgctct cgatctcctg acctcgtgat ctgcccacct 2340
cgacctccca aagtgctggg attacaggcg tgagccaccg tgcccggacc ctttttcctt 2400
tttttttttt tttaaaggct agtcaagtga aacagtggga gtgaagatga aacaaaaaca 2460
tctataactg gttgtgatca attagttgta aacaccactg cactcagacc agcctaactg 2520
ggaagatttt gaggatatgc tgtggtctga tgggttccaa ggcagaggtg acagtaacct 2580
ggaagaggga gactgcttag gcagtggcat cctggtggga tagggtgagg agatcccaga 2640
gcccacgttt actgcaaccc tggggaaatg tcaccagaga aatgggggtg gtgccagaca 2700
atagattgtg ggagctatgg tttccatggt agagtagaag catccaccat gtgtgacatt 2760
cagcagatgg ggcgctgtgg gtggcttgga gcactctggt tgtaactgag gcaggcacag 2820
tgtttaggaa gcctgtgcag taatccagac tgaagggagg ggaaagccta gactaagact 2880
atggctgtgg gattgaaata gcgttgaagg agctgacttt gactcccgga gatgaaggag 2940
aaagaggaaa tcagaaggga ccaaggatgg tgaagttctt aagagaaact gaggaggaag 3000
agaggatgat gtggtgggag acgtgtagag agtccttgta gatctgtcat attgaagggg 3060
actatggtcc cagaggtaca gatgtcctaa aacaggctgg aaaagggagt ctggagagag 3120
cttggtgttg taatgaacca tggggagccg cctcgttggc cctgtgatta cccaggaact 3180
gaatagagag gggcccctgg gagacctcag acacttagag gatataaggg ggtgaaaggg 3240
gggacctggc tttgagtcga agggaggaga aggagattat atagctgaaa cgtctaagag 3300
aatttgtgat ctgagcgttt ctactggggc aagtgcttct gaaaggcaga ggcggctgag 3360
atctggaaac aggtctgcaa atctggtcac tggtctcatt gcagtaacgc tgtgcgcggt 3420
tgagggagtg tattgggaga aaaaccacgc gttgtctgtc ccggaaggaa caagccagtg 3480
agagccggcc tgatgggagg accggcgaaa ggggcttggt gaagcccgcg ctccttgggg 3540
gtgggaatgc ggggatgggg tggtcgcgat gcagggaggg cgacagggtc caggtcgtgc 3600
tcataagttt ggagctgtac tctcagctac tcggggctgg tccttgattt tggctgcgct 3660
cgcgcacgct ccccctttc tggccgccag gtcccgcctt ctaaatttcc ccaggtctcc 3720
aggccgctag aattttctct tctgaacgtg gccccgccct ctccactcat gattggccct 3780
aagttccggg cctcagtttt cactggataa gcggtcgctg agcggggcgc aggtgactaa 3840
atttcgacgg ggtcttctca cgggtttcat tcagttggcc actgctgagc agctgagaag 3900
gtggcgacgt aggggccatg ggctgggcc gggtcctgct gtttctggcc gtcgccttcc 3960
cttttgcacc cccggcagcc gccgctggtg agtggggttc ctggcggtcc ccggcggagc 4020
gggagcggcg gggcgtttcc gggggtccgg gtgggttgcc gcgagcgctg tgcggtcagg 4080
gcggggctca ggtgtgctgt ctggagtgca gggagctgga cgccgcctgt tcccgccaca 4140
cctcagccct gctttcccat ctcccgtctc tttttttttt tttttttttt tttttttttt 4200
ttttttcttt tctgagacgg agtctctgtc gcctaggctg tagtgcagtg gcgcgatctt 4260
ggctcactgc aagcgccgcc tcccgggttc acgccattct cctgcctcag cctccctagt 4320
agctgggact acaggcgccc gccaccacgc ccggctaatt ttttgtgttt ttagtagaga 4380
tggggtttca ccgtgttagt caggatggtc tcgatctcct gacctcgtga tccgcccgcc 4440
tcggcctccc aaagtgctgg gattacaggc gtgagccacc gcgcccgacc tcctgtctcc 4500
tttcagtcct cctcgggatc gcgcatcacc cgcattttct ggtctctcct gcacttgctc 4560
tcctcgcctc tcctccgtct cctctcactt ttcggacaaa ccagtccttc tgaggcccct 4620
gggttcccgg gctgctcctg tgaatggcat tggaaggccg ttccagcgcg gccgctgagg 4680
cagccacttc cccggtgct gggggcggat ctcaggtccc tgaagtcctg tcctctcccg 4740
gagccgatgt gttctcagct cctgggccgc agctcctgga gttggggccc tcctttcttg 4800
ggacccggag gtggtgcttc ttgctgctgt ggggactgtg gggggtcctg actctcaagc 4860
tgaggggttg gagtctgcag gctccgggca gaggattctt cctgcgactt ctgtcatccc 4920
cagctcattc tcccctcgcc tccggctccg gggtcctct cctctctcgc atcccacccc 4980
tactaatgac caatgatcta aggacaccag attccctctc acctcctccc tgcccatctt 5040
acggcgccct gggtcctgtt gctctcccag ctccctgcta ccccttcctg tgtgctgttc 5100
tctgatccat ttctagggtg tcctctgcct tcatccccg cccccgccac tgaaggtccc 5160
tcctgcctcc tttatgggcc tttcctgcaa gcagccttca ctccgtgctg cccctatgcc 5220
tccccattcc caaatgtccc tgactctaac tttctggtgc tgccttttgt ccgggggggt 5280
cttccctcca tcccactccc ctccagaccc ccaaggagag ccctgatgct aatggcagtt 5340
gggccttagg cagggcgcag ggcagcgcag atgccccctc ccctccagtg caggtgcctg 5400
ctctgggccc tgcctcattg tggccccttc cccactcctt catcctcagc ctcaccctct 5460
tgaggacccc accctccagc ccacaggtgc tggaccatcc ctccctggtc cctccgcccc 5520
tctccacctt gggaccttgt gctgctccta tctcttgccc agctgcctgg ggccctcagc 5580
aagttctcat ctttcagtgg gaaagtggga gtgctggagc atatgacagt gctgagaatc 5640
tttcccaagc cccaccctcc cccagagcac cctcccctcc tgtcctcacc ctaccccaag 5700
ttctcccaca gtcactcctg ccccatgctc atgccgccct ccagttcttg ctctgcccat 5760
ctcccctccc caacccagac ctaaaacagg ctgttgggcc agctgttcct tgaccttcct 5820
tcttttcttt tggttccttg accccagtgg gctctcactc cccacaccgc atatctaaaa 5880
tctgttttgc ctgctcttgg ggtgccactg ctccccctcc agcattactc cttttggcag 5940
gtccttcctc aggctgagaa tctccccctc taccttggtt ttctctctct ggccagcacc 6000
cccacccctt gctttgtttt taatttttaa cttttgtttg ggtacgtagt agatatgtat 6060
gtatatattt atggggtaca tgggatattt tgacacaggc ctacaatatg tcataatcac 6120
atcagggtaa atgggttatc tatcacaaca agcatttatc ctttctttgt gctacaaaca 6180
atcccattat gctctttcag ttatttttaa atgtacaata aattattgtt ggctgtactc 6240
accctgctgt gctatctact agatcttatt cattctaact atatttttgt acccattaac 6300
catccgcact cccccactcc ccactaccct tctcagcctc tggtagtcgt cattctattg 6360
tctctcccca tgaggtccat tgttttaatt tttggctgcc acaaataagt gagaacatgc 6420
gaagtttgtc tctctgggcc tggggcttat ttcacttcac atgatgacct ccagttcttt 6480
gcaaatgaca tgatggctga atagtactcc acatacacgt gtgcaccaca ttttctttct 6540
ccattcgtct gttgatggac acttaggtcg cttgcagatc ttggctattt tgaatagtgc 6600
tgcaataaac atggaaaagt agatagctct ttaatatacc gatttccttt cttttgggta 6660
tatgcctaac agtgggagtg ctggagcata tgacagctct attatatttt tagtttttgg 6720
aagaacctcc acattatttc ccacagtggt tatactagtt tacgttccca ccaacagtgt 6780
acaagggttc tcttttgcta catcctcgcc aggattcctt attgcctgtc ttctggataa 6840
aagccagttt atctggggtg ggatgatatc tcgtaggagt tttgatttgc cttcatctga 6900
tgacgaatga tgttgagcac cttttgatat acctgtttgc catttgtatg tcttcttttg 6960
agaaatgact attcagatct tttgctcatt tttaagttgg attattagat atttttccta 7020
tagagttgtt tgagatcctt atatgttttg gttactaatc ctttgtcaga tgaatagttt 7080
gaaaatattt tctcccattc ttggatggtc tcttcacttt gtttattgtt tcctttgctg 7140
tgcagaagct ttttaacttg atatgatccc atttatgcat ttttactttg gttgcctctg 7200
cttgtggggt attacttaaa aaatctttgc cagtccaata tcttagagag tttccccaat 7260
gttttctttc atagttttca tagtttgagg tcatagattt acatctttaa tcctttttga 7320
ttggattttt atatgtggtg agagataggg tccagtttca ttcttctgca taaggatatc 7380
tagtttcccc agcaccattt attgaagaga ctctcctttg ccctgtatgt gttcttggta 7440
actttgttag aaataacttc actgtagata tatggatttg tttctgggtt ctctattctg 7500
tttcattggt ccgtgtgtct gtttttatgc cactaccgtg ctgttttgat tactctagct 7560
ctgtagtata atttgaagtc agataatgtg attccgctag ttttgttctt tttgctcagg 7620
gtagctttat ctattctggg ttttttgtga ttccatatac attttaggat tgtttttcta 7680
tttctgtgaa gaatgtcatt ggtgttttga tagcaattgc attgaatttg tagattgctt 7740
tgggtaggat ggatatttta acaaaattga ttcttccggc tgggcacggt ggctcactcc 7800
tgtaatccca gcactttggg aggccgagtc aggtggatca cttgagatca ggagttcaag 7860
accagcctga tcaacatggg gaaaccccgc ctctactaaa aatacaaaat tagccaggcg 7920
tggtggcata tgcctgtaat cccagctact caggaaagct gaggcaggag aatcgcttga 7980
acccaggagg cagaggttgt ggtgagctga gattgcacca ttgcactcca gcctgggcaa 8040
caggagcaaa actccatctc agaaaataaa aataaacatt gattcttcca gtccgtgaac 8100
atggaatgcc ttttccattt tttgtgtcct cttcaatgtt ttgcatcagt gctttatagt 8160
ttttattgga gagatctttc acttcttcag ttaagtctat tcctaggtat tttattttat 8220
ttgtagctaa tgaaaatggg attcgtttct tgatttcttt ttcagattat ttgctgttag 8280
cacatagaag tgctattgtt ttttgcatgt tgattttgta tcctgcaact ttactgaatt 8340
tgttcttcag ttctaatagt tttttggtgg agtctttagg ttttccaaat atcagaccac 8400
atgatgtgca aacaaggata atttgacttc ttcttttcca attttgatgc cctttatttc 8460
cttctcctgt cagattgctc tagctaggac ttgcagtatt gtgttgcata actgtagtga 8520
aagtagtcat ccttgtcttg ttccagatct taaagaaaag gctttcagtt ttcccccatt 8580
cagtatgtta ctagctgtga gttgtcatat atggcttttg ttatattgag gtctgttcct 8640
tgtatactca gttttttttag agtttttatc atgaagggat gttaaactta tcaaatgctt 8700
tttcagtatc aattgaaatg gtgatatggc ttttgtcctt tattctgttg atacgatgta 8760
ttacattgat tgatttgtgt atgcatacct ggaatacatt ccacttggtc atgaagaatg 8820
atctttttaa tatactgttg aatgtggttt gctagtattt cattgatgat atttgcctca 8880
atgttcatca gggatatagg cctgtagttt tcttttttttg atgtgtcttt gcctgatttt 8940
gatatcagga tattcctggc tttgtaaaat gagtttggaa gtattccctc ctcctctgtt 9000
tttcagaaca atttgaatag gactgatatt tcttgttctt taaacgttta attgtggtaa 9060
attatacatt acatacattt tactgtttta accgctttta agtgtatact cggtggcatt 9120
agatacattc acatttttgt gcaacccaaa actctgtacc cattaatcag taactcccca 9180
ttcctcccta cctctggccc ctggtaacca tcattctact ttttgtttct atgaatttga 9240
ccactctagg tacctcattt aagtagaatc gtgtaatgtt tgtctttttg attctggctt 9300
atttcactta taatatttcg aggttcatcc aggttgtagt atgggtcaga ttttcattcc 9360
ttttaatgat gaataatact cattatatgt atgtaccaca tcttggttat ccattcctca 9420
gacaatggac acttgggtta cttctacctt ttggatattg gcaaatattt catttctctt 9480

```
gggtatatat ttatttcttt tgagtatttc ttttgggtat atatccagaa atagaattgt   9540
tggatcatac ggtatttcat tttttaattt ttagaggaat caccatagtg ttttccattg   9600
caggcgtgcc attttgtatt tctagaagca gtatacaggg gcttcagttt ctctacctcc   9660
ttgccaaact tgctgtgtgt gtgtgtgtgt gtgtgtgtgt gtgtgtgtgt gataatagcc   9720
accctgattg gtttgaagtg gtatctcatt gtggtttgga tttgcatttt cctaatgagt   9780
actgatattg agcatctttt catgtgttta ttgatcattt gtatattttc tttgaagaat   9840
tggccattga agtcttgccc atttttctcc cccacatagc ttctcatggc tattttgccc   9900
atttttgagt gggttgactg ttttgttgtt tttgtcaaac ttttttgcat attctggaaa   9960
ctaatctctc tctttttctt tttttttttt tttttttttt tgagatggag tcttgctctg  10020
ttgcccaggc tggagtgcag tggcacgatc tcagctcact gcaagctccg cccgctagct  10080
tcatgccatt ctcccgcctc agcctcccga gtagctggga ctacaggcgc ccgccaccac  10140
acccggctaa tttttttgtat ttttagtaga gatagggttt caccatgtta gccaggatgg  10200
tctcaatctc ctgacctggt gatacacccg cctcggcctc ccaaagtgct ggaactacag  10260
gcttgagcca ccacgcctgg ccttctggaa actaatctct tatcagatat atgacttgca  10320
atatttattt catttcaggg gttgattgct ttctcactct gattgtgccc tttgatgcac  10380
agatattttg aatttttcat gagtccagtt tgtcagttct ttctattcta tctgtgcttt  10440
ggcgtcatat ccatgaaagc actgtcaaac cctatgtcat gaacattata cccaatgttt  10500
ttttctaaga tatttttatg ttttagttct tgagtttaga gtttaggtct ttgattcatt  10560
ttgagttaat ttttgtatat agtacaaatt aagggtccaa ttttatatta tttgaacatc  10620
cagttccccc agcactattt gctgaaaaga tggacttact ctttgagacc ctgtcacctg  10680
cccaccccag tggacactag ctggtccatc caattgctgt cctggggcct tgtcatgcta  10740
ctcttccact ttggacccaa gcccacatca ttgctcccct ctgggatact gaccccacta  10800
taaacttcac tggggctaca accttcctac cccttgtgcc tcatgaccac cccctccctt  10860
gtccccacca tgcccatgat gagtcttttc tcaaggcagc tcgccttgcc tccatctcac  10920
cctcacctgt gcaccacagc cacactggac atgggtccct ctgagcctga gtcccttccc  10980
attcccactg tcccctctgg caagaccttc cttccaacac tgccttcatg ctcctccctt  11040
gcccctgcag ggcagcctct ccccttggcc cctattccct tagggggctt gtggccaccc  11100
agtcctggca cctgacctac aagtttgcca tcttcattcc cccttcttct gttcatcagc  11160
cccctcctct atcctcccac cctcacagtt ttccttgtat atgaaatctt cgttcttgtc  11220
cttttgccca tgcgcatttc ctgcctcctc agggaggtcg ggacagcaga cctgtgtgtt  11280
aaacatcaat gtgaagttat ttccaggaag aagtttcacc tgtgatttcc tcttccccag  11340
agccccacag tcttcgttac aacctcatgg tgctgtccca ggatggatct gtgcagtcag  11400
ggtttctcgc tgagggacat ctggatggtc agcccttcct gcgctatgac aggcagaaac  11460
gcagggcaaa gccccaggga cagtgggcag aaaatgtcct gggagctaag acctgggaca  11520
cagagaccga ggacttgaca gagaatgggc aagacctcag gaggaccctg actcatatca  11580
aggaccagaa aggaggtgag agtcggcagg ggcaagagta atgggaggcc ttctccagga  11640
aagttggaga cagagagcag ggacctgtct cttcccgctg gatctggctg gggtgggga  11700
tgaggaatag ggtcagggag gctcagcagg gtggtgagcc ggaactcagc ccacacaggg  11760
aggcatggag gagggccagg gaggggtcgc tgctgggctg agttcctcac ttgggtggaa  11820
```

aggtgatggg ttcgggaatg gagaagtcac tgctgggtgg gggcaggctt gcattccctc 11880
caggagatta gggtctgtga gatccatgaa gacagcagca ccaggggctc ccggcatttc 11940
tactacgatg gggagctctt cctctcccaa aacctggaga ctcaagaatc gacagtgccc 12000
cagtcctcca gagctcagac cttggctatg aacgtcacaa atttctggaa ggaagatgcc 12060
atgaagacca agacacacta tcgcgctatg caggcagact gcctgcagaa actacagcga 12120
tatctgaaat ccggggtggc catcaggaga acaggtaccg accctggcca ggggctctac 12180
tgttcccgca attctgctag agttgcctcg cctcccagct ctgtccgggg aaaccctccc 12240
tgtgctatgg atgcaggcgt ttcctgttgg catattgtgt cctgatttgc ctctcctgtt 12300
agagccattg gataaagaca gtgggtctgg gactgaactg tccagtgttg taatctggga 12360
aagcagtggg ccctctgaca gaagcctgag cctggtgtgg gagttaggca ggagaggaag 12420
ccctcagggc cagggctgcc ccctctgcct cccggcctgc ccatcccgga gagttccctc 12480
ctggccccat gacccaggag tccacccttg acatccccct cctcagcatc aatgtgggga 12540
tcccagagcc tgaggccaca gtcccaaggc ccatcctcct gctagcctgg aggaattagg 12600
ccccagggtg aggacagact tacagaaggt ccggtatctg tgagggattc agccagagtg 12660
agaacagtgg agaggagcag ccctgttccc tgcatctccc ttagagggga gcagggcttc 12720
actggctctg ccctttcttc tccagtgccc cccatggtga atgtcacctg cagcgaggtc 12780
tcagagggca acatcaccgt gacatgcagg gcttccagct tctatccccg gaatatcaca 12840
ctgacctggc gtcaggatgg ggtatctttg agccacaaca cccagcagtg gggggatgtc 12900
ctgcctgatg ggaatggaac ctaccagacc tgggtggcca ccaggattcg ccaaggagag 12960
gagcagaggt tcacctgcta catggaacac agcgggaatc acggcactca ccctgtgccc 13020
tctggtgagc ctggggtgac cctggagagg gtcaggccag ggtaggaaca gcaaggacgg 13080
ctgtggctct ctgcccagtg tataacaagt ccctttttt cagggaaggc gctggtgctt 13140
cagagtcaac ggacagactt tccatatgtt tctgctgcta tgccatgttt tgttattatt 13200
attattctct gtgtcccttg ttgcaagaag aaaacatcag cggcagaggg tccaggtgag 13260
aaaaggggac agtttctgga gatgggaaag ctcctttcta ggcagtaggg tctcctcatt 13320
gctcctgccc agacaagacg taggtgacaa ggctgctggg acaggggatg gaagctgggg 13380
tatttgggag gggaatggga gctgcatctc catctacacc cataagtgct tcccaagcca 13440
gggctggggc aaggccttcg aatatccagc tgtggcctcc tcctgctgca agtgaggagt 13500
gggcagcagg gagggctgtg gcacctgctc tgtccccatc ccagcctctc tgtctctcgg 13560
gctcactagg gtgcgtccag gtggggtgag ttgggaatca cgtgctgatt gctgagggcc 13620
tggatgatca tggtgtcaga gggaggaaat agtaaaggtg gctgtgatct ggggagggcc 13680
agaaactgga gaggaatcca aggagaggcg atgcccaccc gtgtgcctcc tccaggaggc 13740
actttccagg ttcccactac ctggcctccc tgagtttcct tgcagatgac acagatgaat 13800
agataagcag atgtccctgg gccatttgag gagcggggcc cagcccctca tcagggcaga 13860
tgtggtccct gttttcatcc tacctccagc gtgttttctt ctgcagtccc tgagggacac 13920
agtccccagg cgccatctct ttgaggcttt gttctgtgct ctgtggcctt accttgccct 13980
ccctgagcca atttcccttt ctcaaggtgg tcactgcctg gtaagtttgg agtaagggac 14040
agtcagaagc atttccccca cagtcaggtt gtttgatggg agatgaaaag agacagcaga 14100
agttttgtgt ttctgcaaaa acagaggcag tgcaggggac agtgagaggc tggggtgtcc 14160
aggagacctg agtctggcgg taggggcgct ggtttctcat ccttgaacct agttgcactg 14220
tcagtcggcc cctcatgcct gagcagatgg gaaggttcgt cccctgccct gcagcaagag 14280
ggccccatcc aggaggcacc cacagcaggg gcagtgcagg tctgtggtca ctcctgctct 14340
cacctgcggc gtctcccgtg gagggattgt cacttctggt tccctgtggg caggaatggt 14400
ttcctcgtag gtcactgggg ttttggccag gaaaagggta tgaaattcat gtgccagttt 14460
ctcaaaattc ctgctttcaa tgttgatgtc caataaagat gttcgtaatt tcagctctat 14520
aatcttaata ggatttcctc taatactgct gttgtaaagc atattaaata aaacaggaac 14580
tcaaatttgg agccccctct ccagaagggt ctgtgtggag atggtggctg tggcagcggc 14640
agttcccagg tgcagagggt gggcagaggc agcctcaggc taaggggtct cccctactcc 14700
acgtggagaa aagtccttgt aggttgcaag ggcagtggcc tgggtggaat ccctgctagg 14760
gacagagcag gaaggcctca cagcctcacc aagcagcagc cctggggtga agtaagtgga 14820
ccaggagtaa gtggaccagg caggagcagt agtgactcaa cagcaggtca caggcctagg 14880
tgggtgctga aggtcatggg aggccaggcc tcctcgagca aggtgggggg tcccagggtc 14940
aggtcaggtg cagatcctgt ggcagccacg tctttccatg ctgggcctgc tgggcccccc 15000
aggcttcctg atggggtccc cagttaggag ctgcctgctc agggctggga ggggaggagt 15060
gctgagctgc agatagaggg cagggcccac agtgggcagg gcctgccctg gtgtgcaggt 15120
gcctctgcag gagagaaggg cctggggact gagagcaagg gtcagggcct ctctttgggg 15180
aggcctctca ctgtaacagg actggtcagg cctgagagga gggcactggg ttccctcttg 15240
ggtcttgtcc ttttgtcttg gggccctttc actccctgca cggtgagtgg tgggcacagg 15300
acaggggctg atgttgatgg agtgatggga gagaactgac aggggctggg aaaagcaagg 15360
agggaggaag aaaaaagtgg gggcctcatc ttctctcaga gaaagggcga atctgatttt 15420
ggggcaactg aagagagaaa agtccttagg gaataaacac aacactgcac ccagtggagc 15480
atttacccgt ttccctcttc tccagagctt gtgagcctgc aggtcctgga tcaacaccca 15540
gttgggacag gagaccacag ggatgcagca cagctgggat ttcagcctct gatgtcagct 15600
actgggtcca ctggttccac tgagggcacc tagactctac agccaggcgg ccaggattca 15660
actccctgcc tggatctcac cagcactttc cctctgtttc ctgacctatg aaacagagaa 15720
aataacatca cttatttatt gttgttggat gctgcaaagt gttagtaggt atgaggtgtt 15780
tgctgctctg ccacgtagag agccagcaaa gggatcatga ccaactcaac attccattgg 15840
aggctatatg atcaaacagc aaattgttta tcatgaatgc aggatgtggg caaactcacg 15900
actgctcctg ccaacagaag gtttgctgag ggcattcact ccatggtgct cattggagtt 15960
atctactggg tcatctagag cctattgttt gaggaatgca gtcttacaag cctactctgg 16020
acccagcagc tgactccttc ttccacccct cttcttgcta tctcctatac caataaatac 16080
gaagggctgt ggaagatcag agcccttgtt cacgagaagc aagaagcccc ctgacccctt 16140
gttccaaata tactcttttg tctttctctt tattcccacg ttcgcccttt gttcagtcca 16200
atacagggtt gtggggccct taacagtgcc atattaattg gtatcattat ttctgttgtt 16260
tttgtttttg tttttgtttt tgtttttgag acagagtctc actctgtcac ccaggctgca 16320
gttcactggt gtgatctcag ctcactgcaa cctctgcctc ccaggttcaa gcacttctcg 16380
tacctcagac tcccgaatag ctgggattac agacaggcac caccacaccc agctaatttt 16440
tgtatttttt gtagagacgg ggtttcgcca agttgaccag cccagtttca aactcctgac 16500
ctcaggtgat ctgcctgcct tggcatccca aagtgctggg attacaagaa tgagccaccg 16560
tgcctggcct attttattat attgtaatat attttattat attagccacc atgcctgtcc 16620
tattttctta tgttttaata tattttaata tattacatgt gcagtaatta gattatcatg 16680
ggtgaacttt atgagtgagt atcttggtga tgactcctcc tgaccagccc aggaccagct 16740
ttcttgtcac cttgaggtcc cctcgccccg tcacaccgtt atgcattact ctgtgtctac 16800
tattatgtgt gcataattta taccgtaaat gtttactctt taaataga 16848

<210> SEQ ID NO 35
<211> LENGTH: 2426
<212> TYPE: DNA
<213> ORGANISM: Homo sapiens

<400> SEQUENCE: 35
gaattttgtg agcgaccgcg ctgggccgtt tctctttctt ttccggaccc tgcagtggcg 60
cctaaagtct gcgaggagga agtcgcctct gtgctcgtga gtccagggat ctaagagccc 120
cacagtcttc gttacaacct catggtgctg tcccaggatg gatctgtgca gtcagggttt 180
ctcgctgagg gacatctgga tggtcagccc ttcctgcgct atgacaggca gaaacgcagg 240
gcaaagcccc agggacagtg ggcagaaaat gtcctgggag ctaagacctg ggacacagag 300
accgaggact tgacagagaa tgggcaagac ctcaggagga ccctgactca tatcaaggac 360
cagaaaggag gcttgcattc cctccaggag attagggtct gtgagatcca tgaagacagc 420
agcaccaggg gctcccggca tttctactac gatggggagc tcttcctctc ccaaaacctg 480
gagactcaag aatcgacagt gccccagtcc tccagagctc agaccttggc tatgaacgtc 540
acaaatttct ggaaggaaga tgccatgaag accaagacac actatcgcgc tatgcaggca 600
gactgcctgc agaaactaca gcgatatctg aaatccgggg tggccatcag gagaacagtg 660
ccccccatgg tgaatgtcac ctgcagcgag gtctcagagg gcaacatcac cgtgacatgc 720
agggcttcca gcttctatcc ccggaatatc acactgacct ggcgtcagga tggggtatct 780
ttgagccaca acacccagca gtggggggat gtcctgcctg atgggaatgg aacctaccag 840
acctgggtgg ccaccaggat tcgccaagga gaggagcaga ggttcacctg ctacatggaa 900
cacagcggga atcacggcac tcaccctgtg ccctctggga aggcgctggt gcttcagagt 960
caacggacag actttccata tgtttctgct gctatgccat gttttgttat tattattatt 1020
ctctgtgtcc cttgttgcaa gaagaaaaca tcagcggcag agggtccaga gcttgtgagc 1080
ctgcaggtcc tggatcaaca cccagttggg acaggagacc acagggatgc agcacagctg 1140
ggatttcagc ctctgatgtc agctactggg tccactggtt ccactgaggg cacctagact 1200
ctacagccag gcggccagga ttcaactccc tgcctggatc tcaccagcac tttccctctg 1260
tttcctgacc tatgaaacag agaaaataac atcacttatt tattgttgtt ggatgctgca 1320
aagtgttagt aggtatgagg tgtttgctgc tctgccacgt agagagccag caaagggatc 1380
atgaccaact caacattcca ttggaggcta tatgatcaaa cagcaaattg tttatcatga 1440
atgcaggatg tgggcaaact cacgactgct cctgccaaca gaaggtttgc tgagggcatt 1500
cactccatgg tgctcattgg agttatctac tgggtcatct agagcctatt gtttgaggaa 1560
tgcagtctta caagcctact ctggacccag cagctgactc cttcttccac ccctcttctt 1620
gctatctcct ataccaataa atacgaaggg ctgtggaaga tcagagccct tgttcacgag 1680
aagcaagaag ccccctgacc ccttgttcca aatatactct tttgtctttc tctttattcc 1740
cacgttcgcc ctttgttcag tccaatacag ggttgtgggg cccttaacag tgccatatta 1800
attggtatca ttatttctgt tgtttttgtt tttgtttttg tttttgtttt tgagacagag 1860
tctcactctg tcacccaggc tgcagttcac tggtgtgatc tcagctcact gcaacctctg 1920
cctcccaggt tcaagcactt ctcgtacctc agactcccga atagctggga ttacagacag 1980
gcaccaccac acccagctaa tttttgtatt ttttgtagag acggggtttc gccaagttga 2040
ccagcccagt ttcaaactcc tgacctcagg tgatctgcct gccttggcat cccaaagtgc 2100
tgggattaca agaatgagcc accgtgcctg gcctatttta ttatattgta atatatttta 2160
ttatattagc caccatgcct gtcctatttt cttatgtttt aatatatttt aatatattac 2220
atgtgcagta attagattat catgggtgaa ctttatgagt gagtatcttg gtgatgactc 2280
ctcctgacca gcccaggacc agctttcttg tcaccttgag gtcccctcgc cccgtcacac 2340
cgttatgcat tactctgtgt ctactattat gtgtgcataa tttataccgt aaatgtttac 2400
tctttaaata gaaaaaaaaa aaaaaa 2426

<210> SEQ ID NO 36
<211> LENGTH: 351
<212> TYPE: PRT
<213> ORGANISM: Homo sapiens

<400> SEQUENCE: 36

Met Val Leu Ser Gln Asp Gly Ser Val Gln Ser Gly Phe Leu Ala Glu
1 5 10 15

Gly His Leu Asp Gly Gln Pro Phe Leu Arg Tyr Asp Arg Gln Lys Arg
20 25 30

Arg Ala Lys Pro Gln Gly Gln Trp Ala Glu Asn Val Leu Gly Ala Lys
35 40 45

Thr Trp Asp Thr Glu Thr Glu Asp Leu Thr Glu Asn Gly Gln Asp Leu
50 55 60

Arg Arg Thr Leu Thr His Ile Lys Asp Gln Lys Gly Gly Leu His Ser
65 70 75 80

Leu Gln Glu Ile Arg Val Cys Glu Ile His Glu Asp Ser Ser Thr Arg
85 90 95

Gly Ser Arg His Phe Tyr Tyr Asp Gly Glu Leu Phe Leu Ser Gln Asn
100 105 110

Leu Glu Thr Gln Glu Ser Thr Val Pro Gln Ser Ser Arg Ala Gln Thr
115 120 125

Leu Ala Met Asn Val Thr Asn Phe Trp Lys Glu Asp Ala Met Lys Thr
130 135 140

Lys Thr His Tyr Arg Ala Met Gln Ala Asp Cys Leu Gln Lys Leu Gln
145 150 155 160

Arg Tyr Leu Lys Ser Gly Val Ala Ile Arg Arg Thr Val Pro Pro Met
165 170 175

Val Asn Val Thr Cys Ser Glu Val Ser Glu Gly Asn Ile Thr Val Thr
180 185 190

Cys Arg Ala Ser Ser Phe Tyr Pro Arg Asn Ile Thr Leu Thr Trp Arg
195 200 205

Gln Asp Gly Val Ser Leu Ser His Asn Thr Gln Gln Trp Gly Asp Val
210 215 220

Leu Pro Asp Gly Asn Gly Thr Tyr Gln Thr Trp Val Ala Thr Arg Ile
225 230 235 240

Arg Gln Gly Glu Glu Gln Arg Phe Thr Cys Tyr Met Glu His Ser Gly
245 250 255

Asn His Gly Thr His Pro Val Pro Ser Gly Lys Ala Leu Val Leu Gln
260 265 270

```
Ser Gln Arg Thr Asp Phe Pro Tyr Val Ser Ala Ala Met Pro Cys Phe
        275                 280                 285

Val Ile Ile Ile Ile Leu Cys Val Pro Cys Cys Lys Lys Lys Thr Ser
    290                 295                 300

Ala Ala Glu Gly Pro Glu Leu Val Ser Leu Gln Val Leu Asp Gln His
305                 310                 315                 320

Pro Val Gly Thr Gly Asp His Arg Asp Ala Ala Gln Leu Gly Phe Gln
                325                 330                 335

Pro Leu Met Ser Ala Thr Gly Ser Thr Gly Ser Thr Glu Gly Thr
            340                 345                 350
```

<210> SEQ ID NO 37
<211> LENGTH: 1341
<212> TYPE: DNA
<213> ORGANISM: Sus scrofa

<400> SEQUENCE: 37

```
ggaactcgga gaggtctccg ctaggctggt gtcgggttac ctgctcatct tcccgaaaat     60
gatggcgttt tgcgcgctgc gcaaggcact tccctgccgt cccgagaatc ccttttcttc    120
gaggtgcttc gttgagattc tttgggtgtc gttggcccta gtgttcctgc ttcccatgcc    180
ctcagatgcc tgtgatgagc caccgaagtt tgaaagcatg cggccccaat tttgaatac     240
cacttacaga cctggagacc gtgtagagta tgaatgtcgc cccgggttcc agcccatggt    300
tcctgcgctt cccacctttt ccgtctgtca ggacgataat acgtggtcac ccctccagga    360
ggcttgtcga cgaaaagcct gttcgaatct accagacccg ttaaatggcc aagttagcta    420
cccaaatggg gatatgctgt ttggttcaaa ggctcagttt acctgtaaca ctggttttta    480
cataattgga gccgagactg tgtattgtca ggtttctggg aatgttatgg cctggagtga    540
gccctccccg ctatgtgaga agattttgtg taaaccacct ggcgaaattc caaatggaaa    600
atacaccaat agccataagg atgtatttga atacaatgaa gtagtaactt acagttgtct    660
ttcttcaact ggaccggatg aattttcact tgttggagag agcagccttt tttgtattgg    720
gaaggacgag tggagtagtg accccccctga gtgtaaagtg gtcaaatgtc catatccagt    780
agtcccaaat ggagaaattg tatcaggatt tggatcaaaa ttttactaca aagcagaggt    840
tgtatttaaa tgcaatgctg gttttaccct tcatggcaga gacacaattg tctgcggtgc    900
aaacagcacg tgggagcctg agatgcccca atgtatcaaa gattccaagc ctactgatcc    960
acctgcaacc ccaggaccaa gccatccagg acctcccagt cccagtgatg catcaccacc   1020
taaagatgct gagagtttag atggaggaat catcgctgca attgttgtgg gcgtcttagc   1080
tgccattgca gtaattgctg gtggtgtata ctttttttcat cataaataca acaagaaaag   1140
gtcgaagtaa aactgatgtg cttaaagtaa aagttgctga gaggacgtgg aatccagccc   1200
cttccctctc ctgtgctgct gcctgggtcc cgttttgcat gtcatgactg tgtgcttcca   1260
aaaaatgcct tttgttcgta tttttttgcc taaacgcatg attttgtctc tacttgaatt   1320
aaatcatcac tgaatccacg c                                             1341
```

<210> SEQ ID NO 38
<211> LENGTH: 1546
<212> TYPE: DNA
<213> ORGANISM: Sus scrofa

<400> SEQUENCE: 38

```
cggcacgaga tttcgtctta atcgcggagg tcgcagagtc cgggagccgc tcggggtccc     60
```

```
cgttcccgcg cgccatgagt cccctgccgc ggagcgcccc cgcggtgagg cgcctaatgg    120
gcggacagac gccgccgccg ctgctgctgc tgctgctgct gctgtgtatc ccggctgcgc    180
agggtgactg cagccttcca cccgatgtac ctaatgccca accagatttg cgaggtcttg    240
caagttttcc tgaacaaacc acaataacat acaaatgtaa caaaggcttt gtcaaagttc    300
ctggcatggc agactcagtg ctctgtctta atgataaatg gtcagaagtt gcagaatttt    360
gtaatcgtag ctgtgatgtt ccaaccaggc tacattttgc atctcttaaa aagtcttaca    420
gcaaacagaa ttatttccca gagggtttca ccgtggaata tgagtgccgt aagggctata    480
aaagggatct tactctatca gaaaaactaa cttgccttca gaattttacg tggtccaaac    540
ctgatgaatt ttgcaaaaaa aaacaatgtc cgactcctgg agaactaaaa aatggtcatg    600
tcaatataac aactgacttg ttatttggcg catccatctt tttctcatgt aacgcagggt    660
acagactagt tggtgcaact tctagttact gttttgccat agcaaatgat gttgagtgga    720
gtgatccatt gccagaatgc caagaaattt ctccaactgt caaagccata ccagctgttg    780
agaaacccat cacagtaaat tttccagcaa caaagtatcc agctattccc agggccacaa    840
cgagttttca ttcaagtaca tctaaaaatc gaggaaaccc ttcttcaggc atgagaatca    900
tgtcgtctgg taccatgcta cttattgcag gaggtgttgc tgttattata ataattgttg    960
ccctaattct agccaaaggt ttctggcact atggaaaatc aggctcttac cacactcatg   1020
agaacaacaa agccgttaat gttgcatttt ataatttacc tgcgactggc gatgccgcag   1080
atgtaagacc tggtaattaa caaaaggacg gtgcatgtgt aacactgaca gttttgctta   1140
tggtgctagt aaccattggc tagctgactt agccaaagaa gagttaagaa gaaagtgcac   1200
acaagtacac agaatatttt cagtttctta gaactttcag gtggagtgga catagtttgt   1260
ggatagtgtt cttcgttttg catgttttca ttgtctctaa ggtacatagg aatgtcacag   1320
aaccaaagag aaacaaatct atcctgaaat tacatcctca acactcctaa gactcttgaa   1380
aatagaacag ctcataagat tgagagcaat tactttccaa aaagggtgag aaaatggaga   1440
gatttgttca tggttagaat ataagaaaaa agaaaacaaa aaggtgattt ttcccaccaa   1500
atgtgtaatg ttatttttat taataaagga aaaaaaaaaa aaaaaa                  1546
```

<210> SEQ ID NO 39
<211> LENGTH: 773
<212> TYPE: DNA
<213> ORGANISM: Sus scrofa

<400> SEQUENCE: 39

```
gaaaagacgc gcaggccggg ccgctctccc gacggggagt agcgctgcag ccggacgcag     60
ggtgcagtta gaatccatag acggtcacga tgggaagcaa aggagggttc attttgctct    120
ggctcctgtc catcctggct gttctctgcc acttaggtca cagcctgcag tgctataact    180
gtatcaaccc agctggtagc tgcactacgg ccatgaattg ttcacataat caggatgcct    240
gtatcttcgt tgaagccgtg ccacccaaaa cttactacca gtgttggagg ttcgatgaat    300
gcaatttcga tttcatttcg agaaacctag cggagaagaa gctgaagtac aactgctgcc    360
ggaaggacct gtgtaacaag agtgatgcca cgatttcatc agggaaaacc gctctgctgg    420
tgatcctgct gctggtagca acctggcact tttgtctcta actgtacacc aggagagttt    480
ctcctcaact tcctctgtct ctctgttcct atttcccatg ctgcggtgtt ccaaaggctg    540
tgtatgctcc agcttcttcc tgttgggaag gactaaacct agcttgagca ctttggatta    600
```

gagagagaaa ctttgagcga ctttgaagac caggcctgtt ggcagagaag acctgtcaga 660
ggggaaacgt tttaagagtg aagcacaggt gatttgagcg aggcctatgc gtcttcctct 720
gctcttggca ggaccagctt tgcggtaacc attcgataga ttccacaatc ctt 773

<210> SEQ ID NO 40
<211> LENGTH: 261
<212> TYPE: DNA
<213> ORGANISM: Human alphaherpesvirus 2

<400> SEQUENCE: 40
tcaaggggcc agcacgcgat cctgccgctc gttcgatcta gcacacccac gggtctgctg 60
tgtgggattt cgactcgcgg gatccgatcg cacgtccgga ggacacagca gcgggagctc 120
cgggtcggtc accgcagttc tggccgcctc tcggtcctcc cgttcccttt tatggatctc 180
cgcgcagaca tcgccatacg tccggtgtgt gcaccgcgaa gaatccagaa acatgtccgt 240
cgttttcagg gcccaagaca t 261

<210> SEQ ID NO 41
<211> LENGTH: 1578
<212> TYPE: DNA
<213> ORGANISM: Homo sapiens

<400> SEQUENCE: 41
agtgtggtac tttgtcttga ggagatgtcc tggactcaca cggaaactta gggctacgga 60
atgaagttct cactcccatt aggtgacagg tttttagaga agccaatcag cgtcgccgcg 120
gtcctggttc taaagtcctc gctcacccac ccggactcat tctccccaga cgccaaggat 180
ggtggtcatg gcgccccgaa ccctcttcct gctgctctcg ggggccctga ccctgaccga 240
gacctgggcg ggctcccact ccatgaggta tttcagcgcc gccgtgtccc ggcccggccg 300
cggggagccc cgcttcatcg ccatgggcta cgtggacgac acgcagttcg tgcggttcga 360
cagcgactcg gcgtgtccga ggatggagcc gcgggcgccg tgggtggagc aggaggggcc 420
ggagtattgg gaagaggaga cacggaacac caaggcccac gcacagactg acagaatgaa 480
cctgcagacc ctgcgcggct actacaacca gagcgaggcc agttctcaca ccctccagtg 540
gatgattggc tgcgacctgg ggtccgacgg acgcctcctc cgcgggtatg aacagtatgc 600
ctacgatggc aaggattacc tcgccctgaa cgaggacctg cgctcctgga ccgcagcgga 660
cactgcggct cagatctcca agcgcaagtg tgaggcggcc aatgtggctg aacaaaggag 720
agcctacctg gagggcacgt gcgtggagtg gctccacaga tacctggaga acgggaagga 780
gatgctgcag cgcgcggacc cccccaagac acacgtgacc caccaccctg tctttgacta 840
tgaggccacc ctgaggtgct gggccctggg cttctaccct gcggagatca tactgacctg 900
gcagcgggat ggggaggacc agacccagga cgtggagctc gtggagacca ggcctgcagg 960
ggatggaacc ttccagaagt gggcagctgt ggtggtgcct tctggagagg agcagagata 1020
cacgtgccat gtgcagcatg aggggctgcc ggagcccctc atgctgagat ggaagcagtc 1080
ttccctgccc accatcccca tcatgggtat cgttgctggc ctggttgtcc ttgcagctgt 1140
agtcactgga gctgcggtcg ctgctgtgct gtggagaaag aagagctcag attgaaaagg 1200
agggagctac tctcaggctg caatgtgaaa cagctgccct gtgtgggact gagtggcaag 1260
tccctttgtg acttcaagaa ccctgactcc tctttgtgca gagaccagcc cacccctgtg 1320
cccaccatga ccctcttcct catgctgaac tgcattcctt ccccaatcac ctttcctgtt 1380
ccagaaaagg ggctgggatg tctccgtctc tgtctcaaat ttgtggtcca ctgagctata 1440

```
acttacttct gtattaaaat tagaatctga gtataaattt actttttcaa attatttcca   1500

agagagattg atgggttaat taaaggagaa gattcctgaa atttgagaga caaaataaat   1560

ggaagacatg agaacttt                                                 1578
```

<210> SEQ ID NO 42
<211> LENGTH: 2679
<212> TYPE: DNA
<213> ORGANISM: Homo sapiens

<400> SEQUENCE: 42

```
gcagactcag ttctcattcc caatgggtgt cgggtttcta gagaagccaa tcagcgtcgc     60

cacgactccc gactataaag tccccatccg gactcaagaa gttctcagga ctcagaggct    120

gggatcatgg tagatggaac cctcctttta ctcctctcgg aggccctggc ccttacccag    180

acctgggcgg gctcccactc cttgaagtat ttccacactt ccgtgtcccg gcccggccgc    240

ggggagcccc gcttcatctc tgtgggctac gtggacgaca cccagttcgt gcgcttcgac    300

aacgacgccg cgagtccgag gatggtgccg cgggcgccgt ggatggagca ggaggggtca    360

gagtattggg accgggagac acggagcgcc agggacaccg cacagatttt ccgagtgaat    420

ctgcggacgc tgcgcggcta ctacaatcag agcgaggccg ggtctcacac cctgcagtgg    480

atgcatggct gcgagctggg gcccgacggg cgcttcctcc gcgggtatga acagttcgcc    540

tacgacggca aggattatct caccctgaat gaggacctgc gctcctggac cgcggtggac    600

acggcggctc agatctccga gcaaaagtca aatgatgcct ctgaggcgga gcaccagaga    660

gcctacctgg aagacacatg cgtggagtgg ctccacaaat acctggagaa ggggaaggag    720

acgctgcttc acctggagcc cccaaagaca cacgtgactc accaccccat ctctgaccat    780

gaggccaccc tgaggtgctg ggccctgggc ttctaccctg cggagatcac actgacctgg    840

cagcaggatg gggagggcca tacccaggac acggagctcg tggagaccag gcctgcaggg    900

gatggaacct tccagaagtg ggcagctgtg gtggtgcctt ctggagagga gcagagatac    960

acgtgccatg tgcagcatga ggggctaccc gagcccgtca ccctgagatg gaagccggct   1020

tcccagccca ccatccccat cgtgggcatc attgctggcc tggttctcct tggatctgtg   1080

gtctctggag ctgtggttgc tgctgtgata tggaggaaga agagctcagg tggaaaagga   1140

gggagctact ctaaggctga gtggagcgac agtgcccagg ggtctgagtc tcacagcttg   1200

taaagcctga gacagctgcc ttgtgtgcga ctgagatgca cagctgcctt gtgtgcgact   1260

gagatgcagg atttcctcac gcctccccta tgtgtcttag gggactctgg cttctctttt   1320

tgcaagggcc tctgaatctg tctgtgtccc tgttagcaca atgtgaggag gtagagaaac   1380

agtccacctc tgtgtctacc atgacccccct tcctcacact gacctgtgtt ccttccctgt   1440

tctcttttct attaaaaata agaacctggg cagagtgcgg cagctcatgc ctgtaatccc   1500

agcacttagg gaggccgagg agggcagatc acgaggtcag gagatcgaaa ccatcctggc   1560

taacacggtg aaaccccgtc tctactaaaa aatacaaaaa attagctggg cgcagaggca   1620

cgggcctgta gtcccagcta ctcaggaggc ggaggcagga gaatggcgtc aacccgggag   1680

gcggaggttg cagtgagcca ggattgtgcg actgcactcc agcctgggtg acagggtgaa   1740

acgccatctc aaaaaataaa aattgaaaaa taaaaaaaga acctggatct caatttaatt   1800

tttcatattc ttgcaatgaa atggacttga ggaagctaag atcatagcta gaaatacaga   1860

taattccaca gcacatctct agcaaattta gcctattcct attctctagc ctattcctta   1920
```

ccacctgtaa tcttgaccat ataccttgga gttgaatatt gttttcatac tgctgtggtt 1980
tgaatgttcc ctccaacact catgttgaga cttaatccct aatgtggcaa tactgaaagg 2040
tggggccttt gagatgtgat tggatcgtaa ggctgtgcct tcattcatgg gttaatggat 2100
taatgggtta tcacaggaat gggactggtg gctttataag aagaggaaaa gagaactgag 2160
ctagcatgcc cagcccacag agagcctcca ctagagtgat gctaagtgga aatgtgaggt 2220
gcagctgcca cagagggccc ccaccaggga aatgtctagt gtctagtgga tccaggccac 2280
aggagagagt gccttgtgga gcgctgggag caggacctga ccaccaccag gaccccagaa 2340
ctgtggagtc agtggcagca tgcagcgccc ccttgggaaa gctttaggca ccagcctgca 2400
acccattcga gcagccacgt aggctgcacc cagcaaagcc acaggcacgg ggctacctga 2460
ggccttgggg gcccaatccc tgctccagtg tgtccgtgag gcagcacacg aagtcaaaag 2520
agattattct cttcccacag atacctttc tctcccatga ccctttaaca gcatctgctt 2580
cattcccctc accttcccag gctgatctga ggtaaacttt gaagtaaaat aaaagctgtg 2640
tttgagcatc atttgtattt caaaaaaaaa aaaaaaaaa 2679

<210> SEQ ID NO 43
<211> LENGTH: 987
<212> TYPE: DNA
<213> ORGANISM: Homo sapiens

<400> SEQUENCE: 43
aatataagtg gaggcgtcgc gctggcgggc attcctgaag ctgacagcat tcgggccgag 60
atgtctcgct ccgtggcctt agctgtgctc gcgctactct ctctttctgg cctggaggct 120
atccagcgta ctccaaagat tcaggtttac tcacgtcatc cagcagagaa tggaaagtca 180
aatttcctga attgctatgt gtctgggttt catccatccg acattgaagt tgacttactg 240
aagaatggag agagaattga aaaagtggag cattcagact tgtctttcag caaggactgg 300
tctttctatc tcttgtacta cactgaattc acccccactg aaaaagatga gtatgcctgc 360
cgtgtgaacc atgtgacttt gtcacagccc aagatagtta agtgggatcg agacatgtaa 420
gcagcatcat ggaggtttga agatgccgca tttggattgg atgaattcca aattctgctt 480
gcttgctttt taatattgat atgcttatac acttacactt tatgcacaaa atgtagggtt 540
ataataatgt taacatggac atgatcttct ttataattct actttgagtg ctgtctccat 600
gtttgatgta tctgagcagg ttgctccaca ggtagctcta ggagggctgg caacttagag 660
gtggggagca gagaattctc ttatccaaca tcaacatctt ggtcagattt gaactcttca 720
atctcttgca ctcaaagctt gttaagatag ttaagcgtgc ataagttaac ttccaattta 780
catactctgc ttagaatttg ggggaaaatt tagaaatata attgacagga ttattggaaa 840
tttgttataa tgaatgaaac attttgtcat ataagattca tatttacttc ttatacattt 900
gataaagtaa ggcatggttg tggttaatct ggtttatttt tgttccacaa gttaaataaa 960
tcataaaact tgatgtgtta tctctta 987

<210> SEQ ID NO 44
<211> LENGTH: 3349
<212> TYPE: DNA
<213> ORGANISM: Homo sapiens

<400> SEQUENCE: 44
ggcgcaacgc tgagcagctg gcgcgtcccg cgcggcccca gttctgcgca gcttcccgag 60
gctccgcacc agccgcgctt ctgtccgcct gcagggcatt ccagaaagat gaggatattt 120

```
gctgtcttta tattcatgac ctactggcat ttgctgaacg ccccatacaa caaaatcaac    180
caaagaattt tggttgtgga tccagtcacc tctgaacatg aactgacatg tcaggctgag    240
ggctacccca aggccgaagt catctggaca agcagtgacc atcaagtcct gagtggtaag    300
accaccacca ccaattccaa gagagaggag aagcttttca atgtgaccag cacactgaga    360
atcaacacaa caactaatga gattttctac tgcactttta ggagattaga tcctgaggaa    420
aaccatacag ctgaattggt catcccagaa ctacctctgg cacatcctcc aaatgaaagg    480
actcacttgg taattctggg agccatctta ttatgccttg gtgtagcact gacattcatc    540
ttccgtttaa gaaaagggag aatgatggat gtgaaaaaat gtggcatcca agatacaaac    600
tcaaagaagc aaagtgatac acatttggag gagacgtaat ccagcattgg aacttctgat    660
cttcaagcag ggattctcaa cctgtggttt aggggttcat cggggctgag cgtgacaaga    720
ggaaggaatg ggcccgtggg atgcaggcaa tgtgggactt aaaaggccca agcactgaaa    780
atggaacctg gcgaaagcag aggaggagaa tgaagaaaga tggagtcaaa cagggagcct    840
ggagggagac cttgatactt tcaaatgcct gaggggctca tcgacgcctg tgacagggag    900
aaaggatact tctgaacaag gagcctccaa gcaaatcatc cattgctcat cctaggaaga    960
cgggttgaga atccctaatt tgagggtcag ttcctgcaga agtgcccttt gcctccactc   1020
aatgcctcaa tttgttttct gcatgactga gagtctcagt gttggaacgg gacagtattt   1080
atgtatgagt ttttcctatt tattttgagt ctgtgaggtc ttcttgtcat gtgagtgtgg   1140
ttgtgaatga tttcttttga agatatattg tagtagatgt tacaattttg tcgccaaact   1200
aaacttgctg cttaatgatt tgctcacatc tagtaaaaca tggagtattt gtaaggtgct   1260
tggtctcctc tataactaca agtatacatt ggaagcataa agatcaaacc gttggttgca   1320
taggatgtca cctttattta acccattaat actctggttg acctaatctt attctcagac   1380
ctcaagtgtc tgtgcagtat ctgttccatt taaatatcag ctttacaatt atgtggtagc   1440
ctacacacat aatctcattt catcgctgta accaccctgt tgtgataacc actattattt   1500
tacccatcgt acagctgagg aagcaaacag attaagtaac ttgcccaaac cagtaaatag   1560
cagacctcag actgccaccc actgtccttt tataatacaa tttacagcta tattttactt   1620
taagcaattc ttttattcaa aaaccattta ttaagtgccc ttgcaatatc aatcgctgtg   1680
ccaggcattg aatctacaga tgtgagcaag acaaagtacc tgtcctcaag gagctcatag   1740
tataatgagg agattaacaa gaaaatgtat tattacaatt tagtccagtg tcatagcata   1800
aggatgatgc gaggggaaaa cccgagcagt gttgccaaga ggaggaaata ggccaatgtg   1860
gtctgggacg gttggatata cttaaacatc ttaataatca gagtaatttt catttacaaa   1920
gagaggtcgg tacttaaaat aaccctgaaa aataacactg gaattccttt tctagcatta   1980
tatttattcc tgatttgcct ttgccatata atctaatgct tgtttatata gtgtctggta   2040
ttgtttaaca gttctgtctt ttctatttaa atgccactaa attttaaatt catacctttc   2100
catgattcaa aattcaaaag atcccatggg agatggttgg aaaatctcca cttcatcctc   2160
caagccattc aagtttcctt tccagaagca actgctactg cctttcattc atatgttctt   2220
ctaaagatag tctacatttg gaaatgtatg ttaaaagcac gtatttttaa aattttttc    2280
ctaaatagta acacattgta tgtctgctgt gtactttgct atttttattt attttagtgt   2340
ttcttatata gcagatggaa tgaatttgaa gttcccaggg ctgaggatcc atgccttctt   2400
tgtttctaag ttatctttcc catagctttt cattatcttt catatgatcc agtatatgtt   2460
```

aaatatgtcc tacatataca tttagacaac caccatttgt taagtatttg ctctaggaca 2520
gagtttggat ttgtttatgt ttgctcaaaa ggagacccat gggctctcca gggtgcactg 2580
agtcaatcta gtcctaaaaa gcaatcttat tattaactct gtatgacaga atcatgtctg 2640
gaacttttgt tttctgcttt ctgtcaagta taaacttcac tttgatgctg tacttgcaaa 2700
atcacatttt ctttctggaa attccggcag tgtaccttga ctgctagcta ccctgtgcca 2760
gaaaagcctc attcgttgtg cttgaaccct tgaatgccac cagctgtcat cactacacag 2820
ccctcctaag aggcttcctg gaggtttcga gattcagatg ccctgggaga tcccagagtt 2880
tcctttccct cttggccata ttctggtgtc aatgacaagg agtaccttgg ctttgccaca 2940
tgtcaaggct gaagaaacag tgtctccaac agagctcctt gtgttatctg tttgtacatg 3000
tgcatttgta cagtaattgg tgtgacagtg ttctttgtgt gaattacagg caagaattgt 3060
ggctgagcaa ggcacatagt ctactcagtc tattcctaag tcctaactcc tccttgtggt 3120
gttggatttg taaggcactt tatccctttt gtctcatgtt tcatcgtaaa tggcataggc 3180
agagatgata cctaattctg catttgattg tcacttttttg tacctgcatt aatttaataa 3240
aatattctta tttattttgt tacttggtac accagcatgt ccatttttctt gtttattttg 3300 tgtttaataa aatgttcagt ttaacatccc agtggagaaa gttaaaaaa 3349

<210> SEQ ID NO 45
<211> LENGTH: 2418
<212> TYPE: DNA
<213> ORGANISM: Homo sapiens

<400> SEQUENCE: 45
gcaaacctta agctgaatga acaacttttc ttctcttgaa tatatcttaa cgccaaattt 60
tgagtgcttt tttgttaccc atcctcatat gtcccagcta gaaagaatcc tgggttggag 120
ctactgcatg ttgattgttt tgtttttcct tttggctgtt cattttggtg gctactataa 180
ggaaatctaa cacaaacagc aactgttttt tgttgtttac ttttgcatct ttacttgtgg 240
agctgtggca agtcctcata tcaaatacag aacatgatct tcctcctgct aatgttgagc 300
ctggaattgc agcttcacca gatagcagct ttattcacag tgacagtccc taaggaactg 360
tacataatag agcatggcag caatgtgacc ctggaatgca actttgacac tggaagtcat 420
gtgaaccttg gagcaataac agccagtttg caaaaggtgg aaaatgatac atccccacac 480
cgtgaaagag ccactttgct ggaggagcag ctgcccctag ggaaggcctc gttccacata 540
cctcaagtcc aagtgaggga cgaaggacag taccaatgca taatcatcta tggggtcgcc 600
tgggactaca agtacctgac tctgaaagtc aaagcttcct acaggaaaat aaacactcac 660
atcctaaagg ttccagaaac agatgaggta gagctcacct gccaggctac aggttatcct 720
ctggcagaag tatcctggcc aaacgtcagc gttcctgcca acaccagcca ctccaggacc 780
cctgaaggcc tctaccaggt caccagtgtt ctgcgcctaa agccaccccc tggcagaaac 840
ttcagctgtg tgttctggaa tactcacgtg agggaactta ctttggccag cattgacctt 900
caaagtcaga tggaacccag gacccatcca acttggctgc ttcacatttt catccccttc 960
tgcatcattg ctttcatttt catagccaca gtgatagccc taagaaaaca actctgtcaa 1020
aagctgtatt cttcaaaaga cacaacaaaa agacctgtca ccacaacaaa gagggaagtg 1080
aacagtgcta tctgaacctg tggtcttggg agccagggtg acctgatatg acatctaaag 1140
aagcttctgg actctgaaca agaattcggt ggcctgcaga gcttgccatt tgcacttttc 1200
aaatgccttt ggatgaccca gcactttaat ctgaaacctg caacaagact agccaacacc 1260

```
tggccatgaa acttgcccct tcactgatct ggactcacct ctggagccta tggctttaag   1320
caagcactac tgcactttac agaattaccc cactggatcc tggacccaca gaattccttc   1380
aggatccttc ttgctgccag actgaaagca aaaggaatta tttcccctca agttttctaa   1440
gtgatttcca aaagcagagg tgtgtggaaa tttccagtaa cagaaacaga tgggttgcca   1500
atagagttat tttttatcta tagcttcctc tgggtactag aagaggctat tgagactatg   1560
agctcacaga cagggcttcg cacaaactca aatcataatt gacatgtttt atggattact   1620
ggaatcttga tagcataatg aagttgttct aattaacaga gagcatttaa atatacacta   1680
agtgcacaaa ttgtggagta aagtcatcaa gctctgtttt tgaggtctaa gtcacaaagc   1740
atttgtttta acctgtaatg gcaccatgtt taatggtggt tttttttttg aactacatct   1800
ttcctttaaa aattattggt ttctttttat ttgtttttac cttagaaatc aattatatac   1860
agtcaaaaat atttgatatg ctcatacgtt gtatctgcag caatttcaga taagtagcta   1920
aaatggccaa agccccaaac taagcctcct tttctggccc tcaatatgac tttaaatttg   1980
acttttcagt gcctcagttt gcacatctgt aatacagcaa tgctaagtag tcaaggcctt   2040
tgataattgg cactatggaa atcctgcaag atcccactac atatgtgtgg agcagaaggg   2100
taactcggct acagtaacag cttaattttg ttaaatttgt tctttatact ggagccatga   2160
agctcagagc attagctgac ccttgaacta ttcaaatggg cacattagct agtataacag   2220
acttacatag gtgggcctaa agcaagctcc ttaactgagc aaaatttggg gcttatgaga   2280
atgaaagggt gtgaaattga ctaacagaca aatcatacat ctcagtttct caattctcat   2340
gtaaatcaga gaatgccttt aaagaataaa actcaattgt tattcttcaa cgttctttat   2400
atattctact tttgggta                                                 2418
```

<210> SEQ ID NO 46
<211> LENGTH: 4167
<212> TYPE: DNA
<213> ORGANISM: Homo sapiens

<400> SEQUENCE: 46

```
agcgggagtc cgcggcgagc gcagcagcag ggccgggtcc tgcgcctcgg gggtcggcgt     60
ccaggctcgg agcgcggcac ggagacggcg gcagcgctgg actaggtggc aggccctgca    120
tcatggaaac tctttctaat gcaagtggta cttttgccat acgcctttta aagatactgt    180
gtcaagataa cccttcgcac aacgtgttct gttctcctgt gagcatctcc tctgccctgg    240
ccatggttct cctaggggca aagggaaaca ccgcaaccca gatggcccag gcactgtctt    300
taaacacaga ggaagacatt catcgggctt tccagtcgct tctcactgaa gtgaacaagg    360
ctggcacaca gtacctgctg agaacggcca acaggctctt tggagagaaa acttgtcagt    420
tcctctcaac gtttaaggaa tcctgtcttc aattctacca tgctgagctg aaggagcttt    480
cctttatcag agctgcagaa gagtccagga aacacatcaa cacctgggtc tcaaaaaaga    540
ccgaaggtaa aattgaagag ttgttgccgg gtagctcaat tgatgcagaa accaggctgg    600
ttcttgtcaa tgccatctac ttcaaaggaa agtggaatga accgtttgac gaaacataca    660
caagggaaat gccctttaaa ataaaccagg aggagcaaag gccagtgcag atgatgtatc    720
aggaggccac gtttaagctc gcccacgtgg gcgaggtgcg cgcgcagctg ctggagctgc    780
cctacgccag gaaggagctg agcctgctgg tgctgctgcc tgacgacggc gtggagctca    840
gcacggtgga aaaaagtctc acttttgaga aactcacagc ctggaccaag ccagactgta    900
```

-continued

```
tgaagagtac tgaggttgaa gttctccttc caaaatttaa actacaagag gattatgaca    960
tggaatctgt gcttcggcat ttgggaattg ttgatgcctt ccaacagggc aaggctgact   1020
tgtcggcaat gtcagcggag agagacctgt gtctgtccaa gttcgtgcac aagagttttg   1080
tggaggtgaa tgaagaaggc accgaggcag cggcagcgtc gagctgcttt gtagttgcag   1140
agtgctgcat ggaatctggc cccaggttct gtgctgacca ccctttcctt ttcttcatca   1200
ggcacaacag agccaacagc attctgttct gtggcaggtt ctcatcgcca taaagggtgc   1260
acttaccgtg cactcggcca tttccctctt cctgtgtccc cagatcccca ctacagctcc   1320
aagaggatgg gcctagaaag ccaagtgcaa agatgagggc agattcttta cctgtctgcc   1380
ctcatgattt gccagcatga attcatgatg ctccacactc gcttatgcta cttaatcaga   1440
atcttgagaa aatagaccat aatgattccc tgttgtatta aaattgcagt ccaaatccca   1500
taggatggca agcaaagttc ttctagaatt ccacatgcaa ttcactctgg cgaccctgtg   1560
ctttcctgac actgcgaata cattccttaa cccgctgcct cagtggtaat aaatggtgct   1620
agatattgct actattttat agatttcctg gtgcttagcc ttataaaaaa ggttgtaaaa   1680
tgtacattta tattttatct tttttttttt ttttttctg agacgcagtc tggctctctg    1740
tcgcccaggc tggagtgcag tggctcgatc tcggctcact gcaagctccg cctcccgggt   1800
tcacgccatt ctcctgcctc agcctcccga gtagctggga ctacaggcgc ccgccaccac   1860
gcccggctaa tttttgtat ttttagtaga gacggggttt caccgtgtta gccaggatgg    1920
tgtcgatctc ctgacctcgt gatccacccg cctcggcctc ccaaagtgct gggattacag   1980
gcttgagcca ccgcgcccgg ctatatttta tcttttatct ttttctttga catttaccaa   2040
tcaccaagca tgcaccaaac actgctttag gcactgggga cacaaagggg acagagccat   2100
cctcctttga cacctggtct tcagttctgt gcccaacgta tatagttttg acaatgacca   2160
ggttggactg tttaatgtct ttcaacttac cacgtaatcc tcttgtaggg atcacatctt   2220
tctttatgat attgtatttc tctacctcta acagtaaaaa ttccattcaa cccttaaagc   2280
tcacttcaaa ttcttctttg agaagttttt cctttctccg caaccagatg tacatatttg   2340
aactctcttt gtacttggag ggcacttctt tcgtggtagt tcttttattt ttattaatct   2400
ctgtatcctt agatagtcct ccaacaacca aaggttggga ctctgtctta catatctggg   2460
tgcccctcat agtgcagtaa taagtaagtt gattatatac gagctatgta acttatattt   2520
tttaatggtt ggatatcact gagttttttt ttttaagaat ttttttattg aggtaaactt   2580
cacataacat aaaattaact attttaaagt gagaagttca gtgccactta gtattgttaa   2640
caatgttgca taaccaccac ctttatttaa agttccaaaa aaaatgttct cctctaaaag   2700
gaaaccccat cccattaagc agatactctc cattccttcc ttcctccagc ccccagcaac   2760
caccaatctg ctttctgtct ctatggattt atctattctt gctattttat ataaattgaa   2820
ttgtatgaga ccttttgtgt ctggcttctt tcacttagta caagtttttg agatttattt   2880
acatagtagc atgtatcaac acttcatttt tatggccaaa taaaattgta ttatgtgttt   2940
atagcacaat ttatttatcc actcattcat tgatggactt tgggttgttt ctgacttttg   3000
gctattggga atagtgctgc tatgaatgtt tgtgtacctg tatttgtttg aatgcctatt   3060
ttgcattctc ttgggtatat atctaggagt ggaactgctg ggtcatatgt taattctatg   3120
tttagctttt tgaggaacag acaaactgtt ttccacagca gttgaaccat tccacattcc   3180
caccagcaat gtatgagaat tccaatttct gtccacttcc tcaccaacac ttattatttt   3240
ccttttcctt tttttaaaaa aaataagtta tggccatctt agtgggtgtg aagtggtatc   3300
```

tcattgtgtt ttttatttgc atttcctatg taatgagcta gaaactaaag tacaaactag 3360
atgggacatc cagtcccttt gatagataat gctgagtaaa aaatgagatg aaagacattt 3420
gtttgttttt agaacacgag tgacagtttg ttaaaaagct ttagaggagg aatgaaaaca 3480
aagtgaagta cacttagaaa agggccaagt ggacatcttg gatgtcaagt gcctagttca 3540
gtatcttttt tttttttttt ttttttttg agacagtgcc tcactctgtc acccaggctg 3600
gagtgtagtg gcatgatctg ggctcactgc aacctcctcc tcctggattc aagcaattct 3660
cttgcttcag cctcccaagt agctgagact acaagcaccc accatcacac ccagctaatt 3720
ttgtattttt cagtagagac ggggtttcgc cacattggcc gtgttggtct tgaactcctg 3780
gcctcaagcg atccgcctac ctcagcctcc caaagtgcta ggattacagg cataagccac 3840
tgagcccagc cctagttcag tatcttttat gtaaattaca aacatctgca acattatgta 3900
tcatatgcag atacttattg catttctttt attagtggtg aaagtgttct atgcatttat 3960
tggctcttga atttcctcat ctatgaattg tcattcatac acctactttt ctgcttcgtt 4020
tttacatatg tctttgccta ttaaagatat tatccctctg ttttatattt tctctcattc 4080
ttgtattgcc ttttaaattt tgttatgatg tttcattaat aaacagtgtt ttgttttcct 4140
ctataatcaa aaaaaaaaaa aaaaaaa 4167

<210> SEQ ID NO 47
<211> LENGTH: 5346
<212> TYPE: DNA
<213> ORGANISM: Homo sapiens

<400> SEQUENCE: 47
ggggagcagg cgggggagcg ggcgggaagc agtgggagcg cgcgtgcgcg cggccgtgca 60
gcctgggcag tgggtcctgc ctgtgacgcg cggcggcggt cggtcctgcc tgtaacggcg 120
gcggcggctg ctgctccaga cacctgcggc ggcggcggcg accccgcggc gggcgcggag 180
atgtggcccc tggtagcggc gctgttgctg ggctcggcgt gctgcggatc agctcagcta 240
ctatttaata aaacaaaatc tgtagaattc acgttttgta atgacactgt cgtcattcca 300
tgctttgtta ctaatatgga ggcacaaaac actactgaag tatacgtaaa gtggaaattt 360
aaaggaagag atatttacac ctttgatgga gctctaaaca agtccactgt ccccactgac 420
tttagtagtg caaaaattga agtctcacaa ttactaaaag gagatgcctc tttgaagatg 480
gataagagtg atgctgtctc acacacagga aactacactt gtgaagtaac agaattaacc 540
agagaaggtg aaacgatcat cgagctaaaa tatcgtgttg tttcatggtt ttctccaaat 600
gaaaatattc ttattgttat tttcccaatt tttgctatac tcctgttctg ggacagtttt 660
ggtattaaaa cacttaaata tagatccggt ggtatggatg agaaaacaat tgctttactt 720
gttgctggac tagtgatcac tgtcattgtc attgttggag ccattctttt cgtcccaggt 780
gaatattcat taaagaatgc tactggcctt ggtttaattg tgacttctac agggatatta 840
atattacttc actactatgt gtttagtaca gcgattggat taacctcctt cgtcattgcc 900
atattggtta ttcaggtgat agcctatatc ctcgctgtgg ttggactgag tctctgtatt 960
gcggcgtgta taccaatgca tggccctctt ctgatttcag gtttgagtat cttagctcta 1020
gcacaattac ttggactagt ttatatgaaa tttgtggctt ccaatcagaa gactatacaa 1080
cctcctagga aagctgtaga ggaacccctt aatgcattca aagaatcaaa aggaatgatg 1140
aatgatgaat aactgaagtg aagtgatgga ctccgatttg gagagtagta agacgtgaaa 1200

-continued

```
ggaatacact tgtgtttaag caccatggcc ttgatgattc actgttgggg agaagaaaca   1260
agaaaagtaa ctggttgtca cctatgagac ccttacgtga ttgttagtta agtttttatt   1320
caaagcagct gtaatttagt taataaaata attatgatct atgttgtttg cccaattgag   1380
atccagtttt ttgttgttat ttttaatcaa ttaggggcaa tagtagaatg gacaatttcc   1440
aagaatgatg cctttcaggt cctagggcct ctggcctcta ggtaaccagt ttaaattggt   1500
tcagggtgat aactacttag cactgccctg gtgattaccc agagatatct atgaaaacca   1560
gtggcttcca tcaaaccttt gccaactcag gttcacagca gctttgggca gttatggcag   1620
tatggcatta gctgagaggt gtctgccact tctgggtcaa tggaataata aattaagtac   1680
aggcaggaat ttggttggga gcatcttgta tgatctccgt atgatgtgat attgatggag   1740
atagtggtcc tcattcttgg gggttgccat tcccacattc cccccttcaac aaacagtgta   1800
acaggtcctt cccagattta gggtactttt attgatggat atgttttcct tttattcaca   1860
taacccccttg aaaccctgtc ttgtcctcct gttacttgct tctgctgtac aagatgtagc   1920
acctttctc ctctttgaac atggtctagt gacacggtag caccagttgc aggaaggagc   1980
cagacttgtt ctcagagcac tgtgttcaca cttttcagca aaaatagcta tggttgtaac   2040
atatgtattc ccttcctctg atttgaaggc aaaaatctac agtgtttctt cacttctttt   2100
ctgatctggg gcatgaaaaa agcaagattg aaatttgaac tatgagtctc ctgcatggca   2160
acaaaatgtg tgtcaccatc aggccaacag gccagccctt gaatggggat ttattactgt   2220
tgtatctatg ttgcatgata aacattcatc accttcctcc tgtagtcctg cctcgtactc   2280
cccttcccct atgattgaaa agtaaacaaa acccacattt cctatcctgg ttagaagaaa   2340
attaatgttc tgacagttgt gatcgcctgg agtactttta gacttttagc attcgttttt   2400
tacctgtttg tggatgtgtg tttgtatgtg catacgtatg agataggcac atgcatcttc   2460
tgtatggaca aaggtggggt acctacagga gagcaaaggt taattttgtg cttttagtaa   2520
aaacatttaa atacaaagtt ctttattggg tggaattata tttgatgcaa atatttgatc   2580
acttaaaact tttaaaactt ctaggtaatt tgccacgctt tttgactgct caccaatacc   2640
ctgtaaaaat acgtaattct tcctgtttgt gtaataagat attcatattt gtagttgcat   2700
taataatagt tatttcttag tccatcagat gttcccgtgt gcctctttta tgccaaattg   2760
attgtcatat ttcatgttgg gaccaagtag tttgcccatg gcaaacctaa atttatgacc   2820
tgctgaggcc tctcagaaaa ctgagcatac tagcaagaca gctcttcttg aaaaaaaaaa   2880
tatgtataca caaatatata cgtatatcta tatatacgta tgtatataca cacatgtata   2940
ttcttccttg attgtgtagc tgtccaaaat aataacatat atagagggag ctgtattcct   3000
ttatacaaat ctgatggctc ctgcagcact ttttccttct gaaaatattt acattttgct   3060
aacctagttt gttactttaa aaatcagttt tgatgaaagg agggaaaagc agatggactt   3120
gaaaaagatc caagctccta ttagaaaagg tatgaaaatc tttatagtaa aattttttat   3180
aaactaaagt tgtacctttt aatatgtagt aaactctcat ttatttgggg ttcgctcttg   3240
gatctcatcc atccattgtg ttctctttaa tgctgcctgc cttttgaggc attcactgcc   3300
ctagacaatg ccaccagaga tagtggggga aatgccagat gaaaccaact cttgctctca   3360
ctagttgtca gcttctctgg ataagtgacc acagaagcag gagtcctcct gcttgggcat   3420
cattgggcca gttccttctc tttaaatcag atttgtaatg gctcccaaat tccatcacat   3480
cacatttaaa ttgcagacag tgttttgcac atcatgtatc tgttttgtcc cataatatgc   3540
tttttactcc ctgatcccag tttctgctgt tgactcttcc attcagtttt atttattgtg   3600
```

```
tgttctcaca gtgacaccat ttgtcctttt ctgcaacaac ctttccagct acttttgcca   3660
aattctattt gtcttctcct tcaaaacatt ctcctttgca gttcctcttc atctgtgtag   3720
ctgctctttt gtctcttaac ttaccattcc tatagtactt tatgcatctc tgcttagttc   3780
tattagtttt ttggccttgc tcttctcctt gattttaaaa ttccttctat agctagagct   3840
tttctttctt tcattctctc ttcctgcagt gttttgcata catcagaagc taggtacata   3900
agttaaatga ttgagagttg gctgtattta gatttatcac tttttaatag ggtgagcttg   3960
agagttttct ttctttctgt tttttttttt tgtttttttt tttttttttt tttttttttt   4020
ttttgactaa tttcacatgc tctaaaaacc ttcaaaggtg attatttttc tcctggaaac   4080
tccaggtcca ttctgtttaa atccctaaga atgtcagaat taaaataaca gggctatccc   4140
gtaattggaa atatttcttt tttcaggatg ctatagtcaa tttagtaagt gaccaccaaa   4200
ttgttatttg cactaacaaa gctcaaaaca cgataagttt actcctccat ctcagtaata   4260
aaaattaagc tgtaatcaac cttctaggtt tctcttgtct taaaatgggt attcaaaaat   4320
ggggatctgt ggtgtatgta tggaaacaca tactccttaa tttacctgtt gttggaaact   4380
ggagaaatga ttgtcgggca accgtttatt ttttattgta ttttatttgg ttgagggatt   4440
tttttataaa cagttttact tgtgtcatat tttaaaatta ctaactgcca tcacctgctg   4500
gggtcctttg ttaggtcatt ttcagtgact aatagggata atccaggtaa ctttgaagag   4560
atgagcagtg agtgaccagg cagtttttct gcctttagct ttgacagttc ttaattaaga   4620
tcattgaaga ccagctttct cataaatttc tctttttgaa aaaaagaaag catttgtact   4680
aagctcctct gtaagacaac atcttaaatc ttaaaagtgt tgttatcatg actggtgaga   4740
gaagaaaaca ttttgttttt attaaatgga gcattattta caaaaagcca ttgttgagaa   4800
ttagatccca catcgtataa atatctatta accattctaa ataaagagaa ctccagtgtt   4860
gctatgtgca agatcctctc ttggagcttt tttgcatagc aattaaaggt gtgctatttg   4920
tcagtagcca ttttttttgca gtgatttgaa gaccaaagtt gttttacagc tgtgttaccg   4980
ttaaaggttt ttttttttat atgtattaaa tcaatttatc actgtttaaa gctttgaata   5040
tctgcaatct ttgccaaggt actttttttat ttaaaaaaaa acataacttt gtaaatatta   5100
ccctgtaata ttatatatac ttaataaaac attttaagct attttgttgg gctatttcta   5160
ttgctgctac agcagaccac aagcacattt ctgaaaaatt taatttatta atgtattttt   5220
aagttgctta tattctaggt aacaatgtaa agaatgattt aaaatattaa ttatgaattt   5280
tttgagtata atacccaata agcttttaat tagagcagag ttttaattaa aagttttaaa   5340
tcagtc                                                              5346
```

<210> SEQ ID NO 48
<211> LENGTH: 1835
<212> TYPE: DNA
<213> ORGANISM: Homo sapiens

<400> SEQUENCE: 48

```
tccccattga ataacagcca agttgctttg gtttctattt ctttgttaag tcgttccctc     60
tacaaaggac ttcctagtgg gtgtgaaagg cagcggtggc cacagaggcg gcggagagat    120
ggccttcagc ggttcccagg ctccctacct gagtccagct gtcccctttt ctgggactat    180
tcaaggaggt ctccaggacg gacttcagat cactgtcaat gggaccgttc tcagctccag    240
tggaaccagg tttgctgtga actttcagac tggcttcagt ggaaatgaca ttgccttcca    300
```

```
cttcaaccct cggtttgaag atggagggta cgtggtgtgc aacacgaggc agaacggaag    360
ctgggggccc gaggagagga agacacacat gcctttccag aaggggatgc cctttgacct    420
ctgcttcctg gtgcagagct cagatttcaa ggtgatggtg aacgggatcc tcttcgtgca    480
gtacttccac cgcgtgccct tccaccgtgt ggacaccatc tccgtcaatg gctctgtgca    540
gctgtcctac atcagcttcc agaacccccg cacagtccct gttcagcctg ccttctccac    600
ggtgccgttc tcccagcctg tctgtttccc acccaggccc agggggcgca gacaaaaacc    660
tcccggcgtg tggcctgcca acccggctcc cattacccag acagtcatcc acacagtgca    720
gagcgcccct ggacagatgt tctctactcc cgccatccca cctatgatgt acccccaccc    780
cgcctatccg atgcctttca tcaccaccat tctgggaggg ctgtacccat ccaagtccat    840
cctcctgtca ggcactgtcc tgcccagtgc tcagaggttc cacatcaacc tgtgctctgg    900
gaaccacatc gccttccacc tgaacccccg ttttgatgag aatgctgtgg tccgcaacac    960
ccagatcgac aactcctggg ggtctgagga gcgaagtctg ccccgaaaaa tgcccttcgt   1020
ccgtggccag agcttctcag tgtggatctt gtgtgaagct cactgcctca aggtggccgt   1080
ggatggtcag cacctgtttg aatactacca tcgcctgagg aacctgccca ccatcaacag   1140
actggaagtg gggggcgaca tccagctgac ccatgtgcag acataggcgg cttcctggcc   1200
ctggggccgg gggctggggt gtggggcagt ctgggtcctc tcatcatccc cacttcccag   1260
gcccagcctt tccaaccctg cctgggatct gggctttaat gcagaggcca tgtccttgtc   1320
tggtcctgct tctggctaca gccaccctgg aacggagaag gcagctgacg gggattgcct   1380
tcctcagccg cagcagcacc tggggctcca gctgctggaa tcctaccatc ccaggaggca   1440
ggcacagcca gggagagggg aggagtgggc agtgaagatg aagccccatg ctcagtcccc   1500
tcccatcccc cacgcagctc caccccagtc ccaagccacc agctgtctgc tcctggtggg   1560
aggtggcctc ctcagcccct cctctctgac ctttaacctc actctcacct tgcaccgtgc   1620
accaaccctt cacccctcct ggaaagcagg cctgatggct tcccactggc ctccaccacc   1680
tgaccagagt gttctcttca gaggactggc tcctttccca gtgtccttaa aataaagaaa   1740
tgaaaatgct tgttggcaca ttcaaaaaaa aaaaaaaaaa aaaaaaaaaa aaaaaaaaaa   1800
aaaaaaaaaa aaaaaaaaaa aaaaaaaaaa aaaaa                              1835
```

<210> SEQ ID NO 49
<211> LENGTH: 363
<212> TYPE: PRT
<213> ORGANISM: Sus scrofa

<400> SEQUENCE: 49

```
Met Met Ala Phe Cys Ala Leu Arg Lys Ala Leu Pro Cys Arg Pro Glu
1               5                   10                  15

Asn Pro Phe Ser Ser Arg Cys Phe Val Glu Ile Leu Trp Val Ser Leu
            20                  25                  30

Ala Leu Val Phe Leu Leu Pro Met Pro Ser Asp Ala Cys Asp Glu Pro
        35                  40                  45

Pro Lys Phe Glu Ser Met Arg Pro Gln Phe Leu Asn Thr Thr Tyr Arg
    50                  55                  60

Pro Gly Asp Arg Val Glu Tyr Glu Cys Arg Pro Gly Phe Gln Pro Met
65                  70                  75                  80

Val Pro Ala Leu Pro Thr Phe Ser Val Cys Gln Asp Asp Asn Thr Trp
                85                  90                  95

Ser Pro Leu Gln Glu Ala Cys Arg Arg Lys Ala Cys Ser Asn Leu Pro
```

```
            100                 105                 110

Asp Pro Leu Asn Gly Gln Val Ser Tyr Pro Asn Gly Asp Met Leu Phe
        115                 120                 125

Gly Ser Lys Ala Gln Phe Thr Cys Asn Thr Gly Phe Tyr Ile Ile Gly
    130                 135                 140

Ala Glu Thr Val Tyr Cys Gln Val Ser Gly Asn Val Met Ala Trp Ser
145                 150                 155                 160

Glu Pro Ser Pro Leu Cys Glu Lys Ile Leu Cys Lys Pro Pro Gly Glu
                165                 170                 175

Ile Pro Asn Gly Lys Tyr Thr Asn Ser His Lys Asp Val Phe Glu Tyr
            180                 185                 190

Asn Glu Val Val Thr Tyr Ser Cys Leu Ser Ser Thr Gly Pro Asp Glu
        195                 200                 205

Phe Ser Leu Val Gly Glu Ser Ser Leu Phe Cys Ile Gly Lys Asp Glu
    210                 215                 220

Trp Ser Ser Asp Pro Pro Glu Cys Lys Val Val Lys Cys Pro Tyr Pro
225                 230                 235                 240

Val Val Pro Asn Gly Glu Ile Val Ser Gly Phe Gly Ser Lys Phe Tyr
                245                 250                 255

Tyr Lys Ala Glu Val Val Phe Lys Cys Asn Ala Gly Phe Thr Leu His
            260                 265                 270

Gly Arg Asp Thr Ile Val Cys Gly Ala Asn Ser Thr Trp Glu Pro Glu
        275                 280                 285

Met Pro Gln Cys Ile Lys Asp Ser Lys Pro Thr Asp Pro Pro Ala Thr
    290                 295                 300

Pro Gly Pro Ser His Pro Gly Pro Pro Ser Pro Ser Asp Ala Ser Pro
305                 310                 315                 320

Pro Lys Asp Ala Glu Ser Leu Asp Gly Gly Ile Ile Ala Ala Ile Val
                325                 330                 335

Val Gly Val Leu Ala Ala Ile Ala Val Ile Ala Gly Gly Val Tyr Phe
            340                 345                 350

Phe His His Lys Tyr Asn Lys Lys Arg Ser Lys
        355                 360
```

<210> SEQ ID NO 50
<211> LENGTH: 341
<212> TYPE: PRT
<213> ORGANISM: Sus scrofa

<400> SEQUENCE: 50

```
Met Ser Pro Leu Pro Arg Ser Ala Pro Ala Val Arg Arg Leu Met Gly
1               5                   10                  15

Gly Gln Thr Pro Pro Pro Leu Leu Leu Leu Leu Leu Leu Leu Cys Ile
            20                  25                  30

Pro Ala Ala Gln Gly Asp Cys Ser Leu Pro Pro Asp Val Pro Asn Ala
        35                  40                  45

Gln Pro Asp Leu Arg Gly Leu Ala Ser Phe Pro Glu Gln Thr Thr Ile
    50                  55                  60

Thr Tyr Lys Cys Asn Lys Gly Phe Val Lys Val Pro Gly Met Ala Asp
65                  70                  75                  80

Ser Val Leu Cys Leu Asn Asp Lys Trp Ser Glu Val Ala Glu Phe Cys
                85                  90                  95

Asn Arg Ser Cys Asp Val Pro Thr Arg Leu His Phe Ala Ser Leu Lys
            100                 105                 110
```

Lys Ser Tyr Ser Lys Gln Asn Tyr Phe Pro Glu Gly Phe Thr Val Glu
115 120 125

Tyr Glu Cys Arg Lys Gly Tyr Lys Arg Asp Leu Thr Leu Ser Glu Lys
130 135 140

Leu Thr Cys Leu Gln Asn Phe Thr Trp Ser Lys Pro Asp Glu Phe Cys
145 150 155 160

Lys Lys Lys Gln Cys Pro Thr Pro Gly Glu Leu Lys Asn Gly His Val
165 170 175

Asn Ile Thr Thr Asp Leu Leu Phe Gly Ala Ser Ile Phe Phe Ser Cys
180 185 190

Asn Ala Gly Tyr Arg Leu Val Gly Ala Thr Ser Ser Tyr Cys Phe Ala
195 200 205

Ile Ala Asn Asp Val Glu Trp Ser Asp Pro Leu Pro Glu Cys Gln Glu
210 215 220

Ile Ser Pro Thr Val Lys Ala Ile Pro Ala Val Glu Lys Pro Ile Thr
225 230 235 240

Val Asn Phe Pro Ala Thr Lys Tyr Pro Ala Ile Pro Arg Ala Thr Thr
245 250 255

Ser Phe His Ser Ser Thr Ser Lys Asn Arg Gly Asn Pro Ser Ser Gly
260 265 270

Met Arg Ile Met Ser Ser Gly Thr Met Leu Leu Ile Ala Gly Gly Val
275 280 285

Ala Val Ile Ile Ile Ile Val Ala Leu Ile Leu Ala Lys Gly Phe Trp
290 295 300

His Tyr Gly Lys Ser Gly Ser Tyr His Thr His Glu Asn Asn Lys Ala
305 310 315 320

Val Asn Val Ala Phe Tyr Asn Leu Pro Ala Thr Gly Asp Ala Ala Asp
325 330 335

Val Arg Pro Gly Asn
340

<210> SEQ ID NO 51
<211> LENGTH: 123
<212> TYPE: PRT
<213> ORGANISM: Sus scrofa

<400> SEQUENCE: 51

Met Gly Ser Lys Gly Gly Phe Ile Leu Leu Trp Leu Leu Ser Ile Leu
1 5 10 15

Ala Val Leu Cys His Leu Gly His Ser Leu Gln Cys Tyr Asn Cys Ile
20 25 30

Asn Pro Ala Gly Ser Cys Thr Thr Ala Met Asn Cys Ser His Asn Gln
35 40 45

Asp Ala Cys Ile Phe Val Glu Ala Val Pro Pro Lys Thr Tyr Tyr Gln
50 55 60

Cys Trp Arg Phe Asp Glu Cys Asn Phe Asp Phe Ile Ser Arg Asn Leu
65 70 75 80

Ala Glu Lys Lys Leu Lys Tyr Asn Cys Cys Arg Lys Asp Leu Cys Asn
85 90 95

Lys Ser Asp Ala Thr Ile Ser Ser Gly Lys Thr Ala Leu Leu Val Ile
100 105 110

Leu Leu Leu Val Ala Thr Trp His Phe Cys Leu
115 120

<210> SEQ ID NO 52

<211> LENGTH: 86
<212> TYPE: PRT
<213> ORGANISM: Human alphaherpesvirus 2

<400> SEQUENCE: 52

Met Ser Trp Ala Leu Lys Thr Thr Asp Met Phe Leu Asp Ser Ser Arg
1               5                   10                  15

Cys Thr His Arg Thr Tyr Gly Asp Val Cys Ala Glu Ile His Lys Arg
            20                  25                  30

Glu Arg Glu Asp Arg Glu Ala Ala Arg Thr Ala Val Thr Asp Pro Glu
        35                  40                  45

Leu Pro Leu Leu Cys Pro Pro Asp Val Arg Ser Asp Pro Ala Ser Arg
    50                  55                  60

Asn Pro Thr Gln Gln Thr Arg Gly Cys Ala Arg Ser Asn Glu Arg Gln
65                  70                  75                  80

Asp Arg Val Leu Ala Pro
                85

<210> SEQ ID NO 53
<211> LENGTH: 338
<212> TYPE: PRT
<213> ORGANISM: Homo sapiens

<400> SEQUENCE: 53

Met Val Val Met Ala Pro Arg Thr Leu Phe Leu Leu Leu Ser Gly Ala
1               5                   10                  15

Leu Thr Leu Thr Glu Thr Trp Ala Gly Ser His Ser Met Arg Tyr Phe
            20                  25                  30

Ser Ala Ala Val Ser Arg Pro Gly Arg Gly Glu Pro Arg Phe Ile Ala
        35                  40                  45

Met Gly Tyr Val Asp Asp Thr Gln Phe Val Arg Phe Asp Ser Asp Ser
    50                  55                  60

Ala Cys Pro Arg Met Glu Pro Arg Ala Pro Trp Val Glu Gln Glu Gly
65                  70                  75                  80

Pro Glu Tyr Trp Glu Glu Glu Thr Arg Asn Thr Lys Ala His Ala Gln
                85                  90                  95

Thr Asp Arg Met Asn Leu Gln Thr Leu Arg Gly Tyr Tyr Asn Gln Ser
            100                 105                 110

Glu Ala Ser Ser His Thr Leu Gln Trp Met Ile Gly Cys Asp Leu Gly
        115                 120                 125

Ser Asp Gly Arg Leu Leu Arg Gly Tyr Glu Gln Tyr Ala Tyr Asp Gly
    130                 135                 140

Lys Asp Tyr Leu Ala Leu Asn Glu Asp Leu Arg Ser Trp Thr Ala Ala
145                 150                 155                 160

Asp Thr Ala Ala Gln Ile Ser Lys Arg Lys Cys Glu Ala Ala Asn Val
                165                 170                 175

Ala Glu Gln Arg Arg Ala Tyr Leu Glu Gly Thr Cys Val Glu Trp Leu
            180                 185                 190

His Arg Tyr Leu Glu Asn Gly Lys Glu Met Leu Gln Arg Ala Asp Pro
        195                 200                 205

Pro Lys Thr His Val Thr His His Pro Val Phe Asp Tyr Glu Ala Thr
    210                 215                 220

Leu Arg Cys Trp Ala Leu Gly Phe Tyr Pro Ala Glu Ile Ile Leu Thr
225                 230                 235                 240

Trp Gln Arg Asp Gly Glu Asp Gln Thr Gln Asp Val Glu Leu Val Glu
                245                 250                 255

```
Thr Arg Pro Ala Gly Asp Gly Thr Phe Gln Lys Trp Ala Ala Val Val
            260                 265                 270

Val Pro Ser Gly Glu Glu Gln Arg Tyr Thr Cys His Val Gln His Glu
        275                 280                 285

Gly Leu Pro Glu Pro Leu Met Leu Arg Trp Lys Gln Ser Ser Leu Pro
    290                 295                 300

Thr Ile Pro Ile Met Gly Ile Val Ala Gly Leu Val Val Leu Ala Ala
305                 310                 315                 320

Val Val Thr Gly Ala Ala Val Ala Ala Val Leu Trp Arg Lys Lys Ser
                325                 330                 335

Ser Asp


<210> SEQ ID NO 54
<211> LENGTH: 358
<212> TYPE: PRT
<213> ORGANISM: Homo sapiens

<400> SEQUENCE: 54

Met Val Asp Gly Thr Leu Leu Leu Leu Leu Ser Glu Ala Leu Ala Leu
1               5                   10                  15

Thr Gln Thr Trp Ala Gly Ser His Ser Leu Lys Tyr Phe His Thr Ser
            20                  25                  30

Val Ser Arg Pro Gly Arg Gly Glu Pro Arg Phe Ile Ser Val Gly Tyr
        35                  40                  45

Val Asp Asp Thr Gln Phe Val Arg Phe Asp Asn Asp Ala Ala Ser Pro
    50                  55                  60

Arg Met Val Pro Arg Ala Pro Trp Met Glu Gln Glu Gly Ser Glu Tyr
65                  70                  75                  80

Trp Asp Arg Glu Thr Arg Ser Ala Arg Asp Thr Ala Gln Ile Phe Arg
                85                  90                  95

Val Asn Leu Arg Thr Leu Arg Gly Tyr Tyr Asn Gln Ser Glu Ala Gly
            100                 105                 110

Ser His Thr Leu Gln Trp Met His Gly Cys Glu Leu Gly Pro Asp Gly
        115                 120                 125

Arg Phe Leu Arg Gly Tyr Glu Gln Phe Ala Tyr Asp Gly Lys Asp Tyr
    130                 135                 140

Leu Thr Leu Asn Glu Asp Leu Arg Ser Trp Thr Ala Val Asp Thr Ala
145                 150                 155                 160

Ala Gln Ile Ser Glu Gln Lys Ser Asn Asp Ala Ser Glu Ala Glu His
                165                 170                 175

Gln Arg Ala Tyr Leu Glu Asp Thr Cys Val Glu Trp Leu His Lys Tyr
            180                 185                 190

Leu Glu Lys Gly Lys Glu Thr Leu Leu His Leu Glu Pro Pro Lys Thr
        195                 200                 205

His Val Thr His His Pro Ile Ser Asp His Glu Ala Thr Leu Arg Cys
    210                 215                 220

Trp Ala Leu Gly Phe Tyr Pro Ala Glu Ile Thr Leu Thr Trp Gln Gln
225                 230                 235                 240

Asp Gly Glu Gly His Thr Gln Asp Thr Glu Leu Val Glu Thr Arg Pro
                245                 250                 255

Ala Gly Asp Gly Thr Phe Gln Lys Trp Ala Ala Val Val Val Pro Ser
            260                 265                 270

Gly Glu Glu Gln Arg Tyr Thr Cys His Val Gln His Glu Gly Leu Pro
        275                 280                 285
```

Glu Pro Val Thr Leu Arg Trp Lys Pro Ala Ser Gln Pro Thr Ile Pro
290 295 300

Ile Val Gly Ile Ile Ala Gly Leu Val Leu Leu Gly Ser Val Val Ser
305 310 315 320

Gly Ala Val Val Ala Ala Val Ile Trp Arg Lys Lys Ser Ser Gly Gly
325 330 335

Lys Gly Gly Ser Tyr Ser Lys Ala Glu Trp Ser Asp Ser Ala Gln Gly
340 345 350

Ser Glu Ser His Ser Leu
355

<210> SEQ ID NO 55
<211> LENGTH: 119
<212> TYPE: PRT
<213> ORGANISM: Homo sapiens

<400> SEQUENCE: 55

Met Ser Arg Ser Val Ala Leu Ala Val Leu Ala Leu Leu Ser Leu Ser
1 5 10 15

Gly Leu Glu Ala Ile Gln Arg Thr Pro Lys Ile Gln Val Tyr Ser Arg
20 25 30

His Pro Ala Glu Asn Gly Lys Ser Asn Phe Leu Asn Cys Tyr Val Ser
35 40 45

Gly Phe His Pro Ser Asp Ile Glu Val Asp Leu Leu Lys Asn Gly Glu
50 55 60

Arg Ile Glu Lys Val Glu His Ser Asp Leu Ser Phe Ser Lys Asp Trp
65 70 75 80

Ser Phe Tyr Leu Leu Tyr Tyr Thr Glu Phe Thr Pro Thr Glu Lys Asp
85 90 95

Glu Tyr Ala Cys Arg Val Asn His Val Thr Leu Ser Gln Pro Lys Ile
100 105 110

Val Lys Trp Asp Arg Asp Met
115

<210> SEQ ID NO 56
<211> LENGTH: 176
<212> TYPE: PRT
<213> ORGANISM: Homo sapiens

<400> SEQUENCE: 56

Met Arg Ile Phe Ala Val Phe Ile Phe Met Thr Tyr Trp His Leu Leu
1 5 10 15

Asn Ala Pro Tyr Asn Lys Ile Asn Gln Arg Ile Leu Val Val Asp Pro
20 25 30

Val Thr Ser Glu His Glu Leu Thr Cys Gln Ala Glu Gly Tyr Pro Lys
35 40 45

Ala Glu Val Ile Trp Thr Ser Ser Asp His Gln Val Leu Ser Gly Lys
50 55 60

Thr Thr Thr Thr Asn Ser Lys Arg Glu Glu Lys Leu Phe Asn Val Thr
65 70 75 80

Ser Thr Leu Arg Ile Asn Thr Thr Thr Asn Glu Ile Phe Tyr Cys Thr
85 90 95

Phe Arg Arg Leu Asp Pro Glu Glu Asn His Thr Ala Glu Leu Val Ile
100 105 110

Pro Glu Leu Pro Leu Ala His Pro Pro Asn Glu Arg Thr His Leu Val
115 120 125

```
Ile Leu Gly Ala Ile Leu Leu Cys Leu Gly Val Ala Leu Thr Phe Ile
    130                 135                 140

Phe Arg Leu Arg Lys Gly Arg Met Met Asp Val Lys Lys Cys Gly Ile
145                 150                 155                 160

Gln Asp Thr Asn Ser Lys Lys Gln Ser Asp Thr His Leu Glu Glu Thr
                165                 170                 175
```

<210> SEQ ID NO 57
<211> LENGTH: 273
<212> TYPE: PRT
<213> ORGANISM: Homo sapiens

<400> SEQUENCE: 57

```
Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
            20                  25                  30

Glu His Gly Ser Asn Val Thr Leu Glu Cys Asn Phe Asp Thr Gly Ser
        35                  40                  45

His Val Asn Leu Gly Ala Ile Thr Ala Ser Leu Gln Lys Val Glu Asn
    50                  55                  60

Asp Thr Ser Pro His Arg Glu Arg Ala Thr Leu Leu Glu Glu Gln Leu
65                  70                  75                  80

Pro Leu Gly Lys Ala Ser Phe His Ile Pro Gln Val Gln Val Arg Asp
                85                  90                  95

Glu Gly Gln Tyr Gln Cys Ile Ile Ile Tyr Gly Val Ala Trp Asp Tyr
            100                 105                 110

Lys Tyr Leu Thr Leu Lys Val Lys Ala Ser Tyr Arg Lys Ile Asn Thr
        115                 120                 125

His Ile Leu Lys Val Pro Glu Thr Asp Glu Val Glu Leu Thr Cys Gln
    130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Pro Gly Arg Asn Phe Ser Cys
            180                 185                 190

Val Phe Trp Asn Thr His Val Arg Glu Leu Thr Leu Ala Ser Ile Asp
        195                 200                 205

Leu Gln Ser Gln Met Glu Pro Arg Thr His Pro Thr Trp Leu Leu His
    210                 215                 220

Ile Phe Ile Pro Phe Cys Ile Ile Ala Phe Ile Phe Ile Ala Thr Val
225                 230                 235                 240

Ile Ala Leu Arg Lys Gln Leu Cys Gln Lys Leu Tyr Ser Ser Lys Asp
                245                 250                 255

Thr Thr Lys Arg Pro Val Thr Thr Thr Lys Arg Glu Val Asn Ser Ala
            260                 265                 270

Ile
```

<210> SEQ ID NO 58
<211> LENGTH: 376
<212> TYPE: PRT
<213> ORGANISM: Homo sapiens

<400> SEQUENCE: 58

```
Met Glu Thr Leu Ser Asn Ala Ser Gly Thr Phe Ala Ile Arg Leu Leu
1               5                   10                  15

Lys Ile Leu Cys Gln Asp Asn Pro Ser His Asn Val Phe Cys Ser Pro
            20                  25                  30

Val Ser Ile Ser Ser Ala Leu Ala Met Val Leu Leu Gly Ala Lys Gly
        35                  40                  45

Asn Thr Ala Thr Gln Met Ala Gln Ala Leu Ser Leu Asn Thr Glu Glu
    50                  55                  60

Asp Ile His Arg Ala Phe Gln Ser Leu Leu Thr Glu Val Asn Lys Ala
65                  70                  75                  80

Gly Thr Gln Tyr Leu Leu Arg Thr Ala Asn Arg Leu Phe Gly Glu Lys
                85                  90                  95

Thr Cys Gln Phe Leu Ser Thr Phe Lys Glu Ser Cys Leu Gln Phe Tyr
            100                 105                 110

His Ala Glu Leu Lys Glu Leu Ser Phe Ile Arg Ala Ala Glu Glu Ser
        115                 120                 125

Arg Lys His Ile Asn Thr Trp Val Ser Lys Lys Thr Glu Gly Lys Ile
    130                 135                 140

Glu Glu Leu Leu Pro Gly Ser Ser Ile Asp Ala Glu Thr Arg Leu Val
145                 150                 155                 160

Leu Val Asn Ala Ile Tyr Phe Lys Gly Lys Trp Asn Glu Pro Phe Asp
                165                 170                 175

Glu Thr Tyr Thr Arg Glu Met Pro Phe Lys Ile Asn Gln Glu Glu Gln
            180                 185                 190

Arg Pro Val Gln Met Met Tyr Gln Glu Ala Thr Phe Lys Leu Ala His
        195                 200                 205

Val Gly Glu Val Arg Ala Gln Leu Leu Glu Leu Pro Tyr Ala Arg Lys
    210                 215                 220

Glu Leu Ser Leu Leu Val Leu Leu Pro Asp Asp Gly Val Glu Leu Ser
225                 230                 235                 240

Thr Val Glu Lys Ser Leu Thr Phe Glu Lys Leu Thr Ala Trp Thr Lys
                245                 250                 255

Pro Asp Cys Met Lys Ser Thr Glu Val Glu Val Leu Leu Pro Lys Phe
            260                 265                 270

Lys Leu Gln Glu Asp Tyr Asp Met Glu Ser Val Leu Arg His Leu Gly
        275                 280                 285

Ile Val Asp Ala Phe Gln Gln Gly Lys Ala Asp Leu Ser Ala Met Ser
    290                 295                 300

Ala Glu Arg Asp Leu Cys Leu Ser Lys Phe Val His Lys Ser Phe Val
305                 310                 315                 320

Glu Val Asn Glu Glu Gly Thr Glu Ala Ala Ala Ala Ser Ser Cys Phe
                325                 330                 335

Val Val Ala Glu Cys Cys Met Glu Ser Gly Pro Arg Phe Cys Ala Asp
            340                 345                 350

His Pro Phe Leu Phe Phe Ile Arg His Asn Arg Ala Asn Ser Ile Leu
        355                 360                 365

Phe Cys Gly Arg Phe Ser Ser Pro
    370                 375
```

```
<210> SEQ ID NO 59
<211> LENGTH: 323
<212> TYPE: PRT
<213> ORGANISM: Homo sapiens

<400> SEQUENCE: 59
```

```
Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
            20                  25                  30

Cys Asn Asp Thr Val Val Ile Pro Cys Phe Val Thr Asn Met Glu Ala
        35                  40                  45

Gln Asn Thr Thr Glu Val Tyr Val Lys Trp Lys Phe Lys Gly Arg Asp
    50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
    130                 135                 140

Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
        195                 200                 205

Gly Leu Gly Leu Ile Val Thr Ser Thr Gly Ile Leu Ile Leu Leu His
    210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Ala Ser Asn Gln Lys Thr Ile Gln Pro Pro Arg Lys
    290                 295                 300

Ala Val Glu Glu Pro Leu Asn Ala Phe Lys Glu Ser Lys Gly Met Met
305                 310                 315                 320

Asn Asp Glu
```

<210> SEQ ID NO 60
<211> LENGTH: 355
<212> TYPE: PRT
<213> ORGANISM: Homo sapiens

<400> SEQUENCE: 60

```
Met Ala Phe Ser Gly Ser Gln Ala Pro Tyr Leu Ser Pro Ala Val Pro
1               5                   10                  15

Phe Ser Gly Thr Ile Gln Gly Gly Leu Gln Asp Gly Leu Gln Ile Thr
            20                  25                  30

Val Asn Gly Thr Val Leu Ser Ser Ser Gly Thr Arg Phe Ala Val Asn
        35                  40                  45
```

Phe Gln Thr Gly Phe Ser Gly Asn Asp Ile Ala Phe His Phe Asn Pro
    50                  55                  60

Arg Phe Glu Asp Gly Gly Tyr Val Val Cys Asn Thr Arg Gln Asn Gly
65                  70                  75                  80

Ser Trp Gly Pro Glu Glu Arg Lys Thr His Met Pro Phe Gln Lys Gly
                85                  90                  95

Met Pro Phe Asp Leu Cys Phe Leu Val Gln Ser Ser Asp Phe Lys Val
            100                 105                 110

Met Val Asn Gly Ile Leu Phe Val Gln Tyr Phe His Arg Val Pro Phe
        115                 120                 125

His Arg Val Asp Thr Ile Ser Val Asn Gly Ser Val Gln Leu Ser Tyr
    130                 135                 140

Ile Ser Phe Gln Asn Pro Arg Thr Val Pro Val Gln Pro Ala Phe Ser
145                 150                 155                 160

Thr Val Pro Phe Ser Gln Pro Val Cys Phe Pro Pro Arg Pro Arg Gly
                165                 170                 175

Arg Arg Gln Lys Pro Pro Gly Val Trp Pro Ala Asn Pro Ala Pro Ile
            180                 185                 190

Thr Gln Thr Val Ile His Thr Val Gln Ser Ala Pro Gly Gln Met Phe
        195                 200                 205

Ser Thr Pro Ala Ile Pro Pro Met Met Tyr Pro His Pro Ala Tyr Pro
    210                 215                 220

Met Pro Phe Ile Thr Thr Ile Leu Gly Gly Leu Tyr Pro Ser Lys Ser
225                 230                 235                 240

Ile Leu Leu Ser Gly Thr Val Leu Pro Ser Ala Gln Arg Phe His Ile
                245                 250                 255

Asn Leu Cys Ser Gly Asn His Ile Ala Phe His Leu Asn Pro Arg Phe
            260                 265                 270

Asp Glu Asn Ala Val Val Arg Asn Thr Gln Ile Asp Asn Ser Trp Gly
        275                 280                 285

Ser Glu Glu Arg Ser Leu Pro Arg Lys Met Pro Phe Val Arg Gly Gln
    290                 295                 300

Ser Phe Ser Val Trp Ile Leu Cys Glu Ala His Cys Leu Lys Val Ala
305                 310                 315                 320

Val Asp Gly Gln His Leu Phe Glu Tyr Tyr His Arg Leu Arg Asn Leu
                325                 330                 335

Pro Thr Ile Asn Arg Leu Glu Val Gly Gly Asp Ile Gln Leu Thr His
            340                 345                 350

Val Gln Thr
        355

<210> SEQ ID NO 61
<211> LENGTH: 100
<212> TYPE: PRT
<213> ORGANISM: Unknown
<220> FEATURE:
<223> OTHER INFORMATION: Description of Unknown:
      CD40 binding epitope sequence

<400> SEQUENCE: 61

Glu Pro Pro Thr Ala Cys Arg Glu Lys Gln Tyr Leu Ile Asn Ser Gln
1               5                   10                  15

Cys Cys Ser Leu Cys Gln Pro Gly Gln Lys Leu Val Ser Asp Cys Thr
            20                  25                  30

Glu Phe Thr Glu Thr Glu Cys Leu Pro Cys Gly Glu Ser Glu Phe Leu

```
        35                  40                  45

Asp Thr Trp Asn Arg Glu Thr His Cys His Gln His Lys Tyr Cys Asp
    50                  55                  60

Pro Asn Leu Gly Leu Arg Val Gln Gln Lys Gly Thr Ser Glu Thr Asp
65                  70                  75                  80

Thr Ile Cys Thr Cys Glu Glu Gly Trp His Cys Thr Ser Glu Ala Cys
                85                  90                  95

Glu Ser Cys Val
            100


<210> SEQ ID NO 62
<211> LENGTH: 33
<212> TYPE: PRT
<213> ORGANISM: Unknown
<220> FEATURE:
<223> OTHER INFORMATION: Description of Unknown:
      CD40 binding epitope sequence

<400> SEQUENCE: 62

Glu Lys Gln Tyr Leu Ile Asn Ser Gln Cys Cys Ser Leu Cys Gln Pro
1               5                   10                  15

Gly Gln Lys Leu Val Ser Asp Cys Thr Glu Phe Thr Glu Thr Glu Cys
            20                  25                  30

Leu


<210> SEQ ID NO 63
<211> LENGTH: 15
<212> TYPE: PRT
<213> ORGANISM: Homo sapiens

<400> SEQUENCE: 63

Trp Thr Phe Gln Thr Leu Val Met Leu Glu Thr Val Pro Arg Ser
1               5                   10                  15


<210> SEQ ID NO 64
<211> LENGTH: 15
<212> TYPE: PRT
<213> ORGANISM: Homo sapiens

<400> SEQUENCE: 64

His His Asn Leu Leu Val Cys Ser Val Ser Gly Phe Tyr Pro Gly
1               5                   10                  15


<210> SEQ ID NO 65
<211> LENGTH: 15
<212> TYPE: PRT
<213> ORGANISM: Homo sapiens

<400> SEQUENCE: 65

Asn Val Arg Phe Asp Ser Asp Val Gly Glu Phe Arg Ala Val Thr
1               5                   10                  15


<210> SEQ ID NO 66
<211> LENGTH: 15
<212> TYPE: PRT
<213> ORGANISM: Homo sapiens

<400> SEQUENCE: 66

His Asn Tyr Gly Val Val Glu Ser Phe Thr Val Gln Arg Arg Val
1               5                   10                  15


<210> SEQ ID NO 67
```

<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 67
gccggggccg cctagagaag 20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 68
gctgcttgtc tcaactgtaa 20

<210> SEQ ID NO 69
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 69
ccttagcgct cgttgactat tc 22

<210> SEQ ID NO 70
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 70
tttctttgct ttttagggcc gc 22

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 71
ccatgggcca aactacccac 20

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 72
ggcatgagct cttggtaatg g 21

<210> SEQ ID NO 73
<211> LENGTH: 19

<212> TYPE: DNA
<213> ORGANISM: Artificial Sequence
<220> FEATURE:
<223> OTHER INFORMATION: Description of Artificial Sequence: Synthetic
primer

<400> SEQUENCE: 73
ccactggcca aggaatagc 19

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 74
caggcatcct tggtggtagg 20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 75
gctcactttg ggggttctct 20

<210> SEQ ID NO 76
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 76
tgaaactgag ctgcaaagc 19

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 77
gttgactttc tctcctacaa g 21

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 78
ggtacctcag ttcaaactca t 21

<210> SEQ ID NO 79
<211> LENGTH: 19
<212> TYPE: DNA

<213> ORGANISM: Artificial Sequence
<220> FEATURE:
<223> OTHER INFORMATION: Description of Artificial Sequence: Synthetic primer

<400> SEQUENCE: 79
actggacagt aacatggag 19

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 80
gtcccaaagt aggagaggag 20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 81
ttctcactgc ctgacgatgt 20

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 82
ccttcacgca ttccttttct g 21

<210> SEQ ID NO 83
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 83
ggcatcgtgg aagagtgct 19

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 84
ctggggaagt tgtccggaag 20

<210> SEQ ID NO 85
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 85
agttcgagat caccttcgag tg 22

<210> SEQ ID NO 86
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 86
actgctctct ggatcttcca gt 22

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 87
agatcgtgcg ggacatcaag 20

<210> SEQ ID NO 88
<211> LENGTH: 17
<212> TYPE: DNA
<213> ORGANISM: Artificial Sequence
<220> FEATURE:
<223> OTHER INFORMATION: Description of Artificial Sequence: Synthetic
primer

<400> SEQUENCE: 88
gcggcagtgg ccatctc 17

<210> SEQ ID NO 89
<211> LENGTH: 80
<212> TYPE: DNA
<213> ORGANISM: Sus scrofa

<400> SEQUENCE: 89
gtattcccaa aacacaacca ttacagttga gacaagcagc attgacagaa ccactcttcc 60
tttgacattc attattttct 80

<210> SEQ ID NO 90
<211> LENGTH: 79
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 90
gtattcccaa aacacaacca ttaagttgag acaagcagca ttgacagaac cactcttcct 60
ttgacattca ttattttct 79

<210> SEQ ID NO 91
<211> LENGTH: 93
<212> TYPE: DNA
<213> ORGANISM: Sus scrofa

<400> SEQUENCE: 91
tacaccacag gtcacggcaa tgccggatcc ttaagccaaa gagcaaggcc agggatcaaa 60
cccacctcct cttggatcct aattgggttt gct 93

<210> SEQ ID NO 92
<211> LENGTH: 94
<212> TYPE: DNA
<213> ORGANISM: Sus scrofa

<400> SEQUENCE: 92
cctacaccac aggtcacggc aatgccggat ccttaagcca aagagcaagg ccagggatca 60
aacccacctc ctcttggatc ctaattgggt ttgc 94

<210> SEQ ID NO 93
<211> LENGTH: 765
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 93
gcggcgagtc atgttcgact tcgacgggga cgaaatcttt cacgtggaca tggccaaaaa 60
agaaaccgtg tggcgcctgg aagagttcgg aagattcgcc tctttcgagg cccaaggcgc 120
cctggccaat atcgctgtgg acaaagccaa cctggaaatc atgaccaagc gcagcaacta 180
caccccaatc accaacgtgc cacctgaagt gaccgtgctg acaaacagcc cagtggaact 240
gcgcgagccc aacgtgctga tctgcttcat cgacaagttc accccaccag tggtcaacgt 300
gacctggctg agaaacggca agccagtgac aaccggcgtg tccgagacag tgtttctgcc 360
aagagaggac cacctgttcc gcaagttcca ctacctgcca tttctgccgt cgactgagga 420
tgtgtacgac tgcagagtcg agcactgggg actcgacgag ccactgctga agcactggga 480
gtttgacgcc ccatctccac tgccagaaac caccgagaat gtcgtgtgtg ccctgggcct 540
gacagtggga ctcgtgggaa tcatcatcgg caccatcttc atcatcaagg gcctgcgcaa 600
aagcaacgcc gctgaaagaa gaggcccact ctgaacgcgt tctagaaata aaagatcctt 660
attttcattg gatctgtgtg ttggtttttt gtgtggctaa caagaggctg tgctctgagg 720
gctgcggctc ctcttataga ctcgagctag gtaagtgagc gggac 765

<210> SEQ ID NO 94
<211> LENGTH: 1073
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 94
cccgaccaag agcggcgagt tcatgttcga cttcgacggg gacgaaatct ttcacgtgga 60
catggccaaa aaaagaaacc cgtgtggcgc tggaagagtt cggaagattc gcctctttcg 120
aggcccaagg cgcctgggcc aatatcgctg tggacaaagc caacctggaa atcatgacca 180
agcggcagca acttacacac cccccatcac caacgtgcca ctgaagtgac cgtgctgaca 240
aacagcccag tggaactgcg cgagcccaac gtgctgatct gcttcatcga caagttcacc 300
ccaccagtgg tcaacgtgac ctggctgaga aacggcaagc cagtgacaac cggcgtgtcc 360

```
gagacagtgt ttctgccaag agaggaccac ctgttccgca agttccacta cctgccattt    420

ctgccgtcga ctgaggatgt gtacgactgc agagtcgagc actggggact cgacgagcca    480

ctgctgaagc actgggagtt tgacgcccca tctccactgc cagaaaccac cgagaatgtc    540

gtgtgtgccc tgggcctgac agtgggactc gtgggaatca tcatcggcac catcttcatc    600

atcaagggcc tgcgcaaaag caacgccgct gaaagaagag gcccactctg aacgcgttct    660

agaaataaaa gatccttatt ttcattggat ctgtgtgttg gtttttttgtg tggctagcaa    720

gaggctgtgc tctggggctc cggctcctca gagagcctcg gctaggtagg ggagcgggac    780

tctggtttgg gggagggccg gcggtttggc gggggatggg tgcttgaggt ggtctgaccg    840

gtagcggggg tcgccttccc tagcgggaag tcgggagcat atcgtttgtt acgctggaag    900

gggaagaggt ggtgagaggc aggcgggagt gcggcccgcc ctgcggcaac cggaggggga    960

gggagaaggg agcggaaaag cctggaatac ggacggagcc attgctcccg cagagggagg   1020

agcgcttcct gctcttctct tgtcactgat tggccgctct cctcccgccg tgt          1073
```

<210> SEQ ID NO 95
<211> LENGTH: 978
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 95

```
ccagggcgcg agtcatgttc gacttcgacg gggacgaaat ctttcacgtg gacatggcca     60

aaaaagaaac cgtgtggcgc ctggaagagt tcggaagatt cgcctctttc gaggcccaag    120

gcgccctggc caatatcgct gtggacaaag ccaacctgga aatcatgacc aagcgcagca    180

actacacccc aatcaccaac gtgccacctg aagtgaccgt gctgacaaac agcccagtgg    240

aactgcgcga gcccaacgtg ctgatctgct tcatcgacaa gttcacccca ccagtggtca    300

acgtgacctg gctgagaaac ggcaagccag tgacaaccgg cgtgtccgag acagtgtttc    360

tgccaagaga ggaccacctg ttccgcaagt tccactacct gccatttctg ccgtcgactg    420

aggatgtgta cgactgcaga gtcgagcact ggggactcga cgagccactg ctgaagcact    480

gggagtttga cgccccatct ccactgccag aaaccaccga gaatgtcgtg tgtgccctgg    540

gcctgacagt gggactcgtg ggaatcatca tcggcaccat cttcatcatc aagggcctgc    600

gcaaaagcaa cgccgctgaa agaagaggcc cactctgaac gcgttctaga aataaaagat    660

ccttattttc attggatctg tgtgttggtt tttttgtgtg gctagcaaga ggctgtgctc    720

tggggctccg gctcctcaga gagcctcggc taggtagggg gagcgggact ctggtttggg    780

gggagggccg gcggtttgcg gggggatggg tgctttgaga ggtggttctg accggtagcc    840

ggggggtcgc cttccctagc gggaagtcgg gagcatatcg tttgttacgc tggaggggaa    900

gagggtgggt ggggaggcag gcgggagtgc ggcccgctct gcggcacgag gggagagggg    960

agaaggagcc gaagcctg                                                  978
```

<210> SEQ ID NO 96
<211> LENGTH: 1072
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 96

-continued

```
cccgaccaag agcggcggag tcatgtcgac tcgacgggga cgaaatcttt cacgtggaca     60
tggccaaaaa agaaaccgtg tggcgctgga agagtcggaa gattcgctct ttcgaggcca    120
agggcgcctg gccaatatcg ctgtggacaa agcccaacct ggaaattcat gaaccagggg    180
cgagacaata tcacaccccc acaatcacaa cgtgccactg aagtgaccgt gctgacaaac    240
agcccagtgg aactgcgcga gcccaacgtg ctgatctgct tcatcgacaa gttcacccca    300
cccagtggtc aacgtgacct ggctgagaaa cggcaagcca gtgacaaccg gcgtgtccga    360
gacagtgttt ctgccaagag aggaccacct gttccgcaag ttccactacc tgccatttct    420
gccgtcgact gaggatgtgt acgactgcag agtcgagcac tggggactcg acgagccact    480
gctgaagcac tgggagtttg acgccccatc tccactgcca gaaaccaccg agaatgtcgt    540
gtgtgccctg ggcctgacag tgggactcgt gggaatcatc atcggcacca tcttcatcat    600
caagggcctg cgcaaaagca acgccgctga aagaagaggc ccactctgaa cgcgttctag    660
aaataaaaga tccttatttt cattggatct gtgtgttggt tttttgtgtg gctagcaaga    720
ggctgtgctc tggggctccg gctcctcaga gagcctcggc taggtagggg agcgggactc    780
tggtttgggg gagggccggc ggtttggcgg gggatgggtg cttgaggtgg tctgaccggt    840
agcgggggtc gccttcccta gcgggaagtc gggagcatat cgtttgttac gctggaaggg    900
gaagaggtgg tgagaggcag gcgggagtgc ggcccgccct gcggcaaccg gagggggagg    960
gagaagggag cggaaaagcc tggaatacgg acggagccat tgctcccgca gagggaggag   1020
cgcttcctgc tcttctcttg tcactgattg gccgctctcc tcccgccgtg tg           1072
```